US008815548B2

(12) United States Patent
Beck et al.

(10) Patent No.: US 8,815,548 B2
(45) Date of Patent: Aug. 26, 2014

(54) INCREASED ISOPRENE PRODUCTION USING THE ARCHAEAL LOWER MEVALONATE PATHWAY

(71) Applicants: Danisco US Inc., Palo Alto, CA (US); The Goodyear Tire & Rubber Company, Akron, OH (US)

(72) Inventors: Zachary Q. Beck, Palo Alto, CA (US); Anthony R. Calabria, Wilmington, DE (US); Michael C. Miller, San Francisco, CA (US); Alex T. Nielsen, Kokkedal (DK); Dmitrii V. Vaviline, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 14 days.

(21) Appl. No.: 13/730,661

(22) Filed: Dec. 28, 2012

(65) Prior Publication Data

US 2013/0280769 A1 Oct. 24, 2013

Related U.S. Application Data

(62) Division of application No. 12/560,390, filed on Sep. 15, 2009, now Pat. No. 8,361,762.

(60) Provisional application No. 61/097,186, filed on Sep. 15, 2008, provisional application No. 61/187,876, filed on Jun. 17, 2009.

(51) Int. Cl.
*C12P 9/00* (2006.01)

(52) U.S. Cl.
USPC ........ 435/131; 435/167; 435/243; 435/252.1; 435/252.5; 435/252.8; 435/253.5; 435/245.1; 435/255.1; 435/255.2; 435/256.1; 435/256.7; 435/289.1

(58) Field of Classification Search
None
See application file for complete search history.

(56) References Cited

U.S. PATENT DOCUMENTS

| | | | |
|---|---|---|---|
| 4,385,151 | A | 5/1983 | Furukawa et al. |
| 4,570,029 | A | 2/1986 | Kulprathipanja et al. |
| 4,683,202 | A | 7/1987 | Mullis |
| 4,703,007 | A | 10/1987 | Mulholland et al. |
| 5,849,970 | A | 12/1998 | Fall et al. |
| 5,874,276 | A | 2/1999 | Fowler et al. |
| 6,022,725 | A | 2/2000 | Fowler et al. |
| 6,106,888 | A | 8/2000 | Dale et al. |
| 6,176,176 | B1 | 1/2001 | Dale et al. |
| 6,268,328 | B1 | 7/2001 | Mitchinson et al. |
| 7,132,527 | B2 | 11/2006 | Payne et al. |
| 7,183,089 | B2 | 2/2007 | Keasling et al. |
| 7,241,587 | B2 | 7/2007 | Dodge et al. |
| 7,262,041 | B2 | 8/2007 | Baldwin et al. |
| 8,173,410 | B2 | 5/2012 | Bott et al. |
| 8,257,957 | B2 | 9/2012 | Keasling et al. |
| 8,361,762 | B2 | 1/2013 | Beck et al. |
| 2005/0287655 | A1 | 12/2005 | Tabata et al. |
| 2006/0079476 | A1 | 4/2006 | Keasling et al. |
| 2009/0203102 | A1 | 8/2009 | Cervin et al. |
| 2010/0048964 | A1 | 2/2010 | Calabria et al. |
| 2010/0184178 | A1 | 7/2010 | Beck et al. |
| 2010/0196977 | A1 | 8/2010 | Chotani et al. |
| 2011/0014672 | A1 | 1/2011 | Chotani et al. |
| 2011/0076743 | A1 | 3/2011 | Beck et al. |
| 2011/0159557 | A1 | 6/2011 | Beck et al. |

FOREIGN PATENT DOCUMENTS

| | | | |
|---|---|---|---|
| DE | 19629568 | C1 | 1/1998 |
| EP | 0 137 280 | B1 | 4/1985 |
| EP | 0 215 594 | A2 | 3/1987 |
| EP | 0 215 594 | A3 | 3/1987 |
| EP | 0 215 594 | B1 | 3/1987 |
| EP | 0 215 594 | B2 | 3/1987 |
| EP | 0 238 023 | A2 | 9/1987 |
| EP | 0 238 023 | A3 | 9/1987 |
| EP | 0 238 023 | B1 | 9/1987 |
| EP | 0 238 023 | B2 | 9/1987 |
| EP | 0 244 234 | A2 | 11/1987 |
| EP | 0 244 234 | A3 | 11/1987 |
| EP | 0 244 234 | B1 | 11/1987 |
| EP | 0 244 234 | B2 | 11/1987 |
| EP | 0 587 354 | A1 | 3/1994 |
| JP | 2008-035831 | A | 2/2008 |
| WO | WO-95/04134 | A1 | 2/1995 |
| WO | WO-96/35796 | A1 | 11/1996 |
| WO | WO-98/02550 | A2 | 1/1998 |
| WO | wo-98/02550 | A3 | 1/1998 |
| WO | WO-2004/033646 | A2 | 4/2004 |
| WO | WO-2004/033646 | A3 | 4/2004 |
| WO | WO-2004/111214 | A1 | 12/2004 |
| WO | WO-2005/001036 | A2 | 1/2005 |
| WO | WO-2005/001036 | C1 | 1/2005 |
| WO | WO-2006/063752 | A1 | 6/2006 |

(Continued)

OTHER PUBLICATIONS

Anderson, M.S. et al. (Nov. 15, 1989). "Isopentenyl Diphosphate: Dimethylallyl Diphosphate Isomerare. An Improved Purification of the Enzyme and Isolation of the Gene From *Saccharomyces cerevisia*," *J. Biol. Chem.* 264(32):19169-19175.

Andreassi, J. et al. (2004). "*Streptococcus pneumonia* Isoprenoid Biosynthesis Is Downregulated by Diphosphomevalonate: An Antimicrobial Target." *Biochemistry*, 43:16461-16466.

Andreassi, J. L. et al. (2007). "Crystal Structure of the *Streptococcus pneumonia* Mevalonate Kinase in Complex with Diphosphomevalonate," *Protein Sci* 16(5):983-989.

(Continued)

*Primary Examiner* — Kade Ariani
(74) *Attorney, Agent, or Firm* — Morrison & Foerster LLP

(57) ABSTRACT

The invention features methods for producing isoprene from cultured cells using a feedback-resistant mevalonate kinase polypeptide, such as an archaeal mevalonate kinase polypeptide. The resulting isoprene compositions may have increased yields and/or purity of isoprene.

20 Claims, 259 Drawing Sheets

(56) References Cited

FOREIGN PATENT DOCUMENTS

| WO | WO-2006/085899 A2 | 8/2006 |
|---|---|---|
| WO | WO-2006/085899 A3 | 8/2006 |
| WO | WO-2008/003078 A2 | 1/2008 |
| WO | WO-2008/003078 A3 | 1/2008 |
| WO | WO-2009/076676 A2 | 6/2009 |
| WO | WO-2009/076676 A3 | 6/2009 |
| WO | WO-2010/031077 A1 | 3/2010 |

OTHER PUBLICATIONS

Ausubel, F. M. et al. eds. (1987). *Current Protocols in Molecular Biology*, John Wiley and Sons, Inc., pp. 1-13. (Table of Contents Only).
Ausubel, F. M. et al. eds. (1994). *Current Protocols in Molecular Biology*, John Wiley and Sons, Inc., pp. 1-7, (Table of Contents Only).
Bellion, E. et al. (1993). "Methylamine Utilization in Yeast and Bacteria: Studies Using in vivo NMR," Chapter 32 in *Microbial Growth $C_1$ Compounds*, Muerrell, J.C. et al. eds, Intercept Ltd: Andover, UK, pp. 415-432.
Bennett, J. W. et al. eds. (1991). "Gene Cloning and Analysis," Chapter 3 in *More Gene Manipulations in Fungi*, Academic Press, San Diego, CA pp. 70-76.
Beytia, E. et al. (1970). "Purification and Mechanism of Action of Hog Liver Mevalonic Kinase." *J. Biol. Chem.* 245(2): 5450 5458.
Boel, E. et al. (1984). "Two Different Types of Intervening Sequences in the Glucoamylase Gene from *Aspergillus niger*," *The EMBO Journal* 3(7):1581-1585.
Bouvier, F. et al. (2005). "Biogenesis, Molecular Regulation and Function of Plant Isoprenoids," *Progress in Lipid Res*. 44:357-429.
Campbell, E. I. et al. (1989). "Improved Transformation Efficiency of *Aspergillus niger* Using the Homologus *nia*D Gene for Nitrate Reductase," *Curr. Genet.* 16:53-56.
Cao, Q.-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Crueger, W. et al. (1989). *Biotechnology: A Textbook of Industrial Microbiology*, Second Edition, Brock, T.D. ed., Sinauer Associates, Inc.: Sunderland, MA, pp. vii-x, (Table of Contents Only).
Cunningham, F. X. et al. (Oct. 2000). "Evidence of a Role for LytB in the Nonmevalonate Pathway of Isoprenoid Biosynthesis," *Journal of Bacteriology* 182(20):5841-5848.
Darnell, J. et al. (1990). *Molecular Cell Biology*, $2^{nd}$ edition, Scientific American Books: New York, NY, p. 51.
Deppenmeier, U. et al (Jul. 2002). "The Genome of Methanosarcina Mazei: Evidence for Lateral Gene Transfer Between Bacteria and Archaea." *J. Mol.Microb. Biotech*. 4(7):453-461.
Dhe-Paganon, S. et al. (1994). "Mechanism of Mevalonate Pyrophosphate Decarboxylase: Evidence for a Carbocationic Transition State," *Biochemistry* 33(45):13355-13362.
Finkelstein, D. B. (1992). "Transformation," Chapter 6 in *Biotechnology of Filamentous Fungi*, Butterworth-Heinemann: Boston, MA, pp. 113-156.
Fu, Z. et al. (2008). "Biochemical and Structural basis for Feedback inhibition of Mevalonate Kinase and Isoprenoid Metabolism." *Biochemistry* 47(12):3715-24.
GenBank Accession No. AY341431, last updated Apr. 16, 2005, located at <http://www.ncbi.nlm.nih.gov/nuccore/AY341431 >, last visited on Feb. 27, 2012, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. CAC35696, last updated Apr. 15, 2005, located at <http://www.ncbi.nlm.nih.gov/protein/CAC35696>, last visited on Nov. 1, 2011, 1 page.
GenBank Accession No. CR936503, last updated Aug. 26, 2009, located at <http://www.ncbi.nlm.nih.gov/nuccore/CR936503>, last visited on Oct. 17, 2011, 351 pages.
GenBank Accession No. NP_633786, last updated on Jun. 10, 2013, located at <http://www.ncbi.nlm.nih.gov/protein/21227864>, last visited on Jul. 16, 2013, two pages.
GenBank Accession No. NC_003901.1, last updated on May 11, 2011, located at <http://www.ncbi.nlm.nih.gov/nuccore/NC_003901.1>, last visited on Oct. 27, 2011, 360 pages.
GenPept Accession No. AAM31458, last updated Nov. 21, 2011, located at http://www.ncbi.nlm.nih.gov/sviewer/viewer.fcgi?db=protein&term=AAM31458&report=genpept last visited on Feb. 28, 2012, 1 page.
Gerhardt, P. et al. eds. (1994). *Methods for General and Molecular Bacteriology*, American Society for Microbiology: Washington, D.C., p. v, (Table of Contents Only).
Goedegebuur, F. et al. (2002, e-pub. May 7, 2002). "Cloning and Relational Analysis of 15 Novel Fungal Endoglucanases form Family 12 Glycosyl Hydrolase," *Curr. Genet*. 41:89-98.
Gottschalk, G. (1986). *Bacterial Metabolism*, Second Edition, Springer Verlag: New York, NY, pp. xi-xiii, (Table of Contents Only).
Grӓwert, T. et al. (2004, e-pub. Sep. 21, 2004). "IspH Protein of *Escherichia coli*: Studies on Iron-Sulfur Cluster Implementation and Catalysis," *J. Am. Chem. Soc*.126(40):12847-12855.
Greenberg, J. P. et al. (1993). "Sub-Parts Per Billion Detection of Isoprene Using a Reduction Gas Detector with a Portable Gas Chormatograph," *Atmos. Environ*. 27A(16):2689-2692.
Harkki, A. et al. (Jun. 1989). "A Novel Fungal Expression System: Secretion of Active Calf Chymosin From the Filamentous Fungus *Trichoderma ressei*," *Bio. Technol*.7:596-603.
Harkki, A. et al. (Mar. 1991). "Genetic Engineering of *Trichoderma* to Produce Strains with Novel Cellulase Profiles," *Enzyme Microb. Technol*. 13:227-233.
Hedl, M. et al. (Apr. 2002). "*Enterococcus faecalis* Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol*. 184(8):2116-2122.
Hoeffler, J.-F. et al. (2002). "Isoprenoid Biosynthesis via the Methylerythritol Phosphate Pathway. Mechanistic Investigations of the 1-Deoxy-$_D$-Xylulose 5-Phosphate Reductiosimerase," *Eur. J. Biochem*. 269:4446-4457.
Huang, K.-X. et al. (1999). "Overexpression, Purification, and Characterization of the Thermostable Mevalonate Kinase from *Methanococcus jannaschii*," *Protein Expression and Purification* 17:33-40.
Hunter, B. K. (1985). "Formaldehyde Metabolism by *Escherichia coli*. Carbon and Solvent Deuterium Incoproration into Glycerol, 1,2-Propanediol, and 1,3-Propanediol," *Biochemistry* 24(15):4148-4155.
Ilmen, M. et al. (Apr. 1997). "Regulation of Cellulase Gene Expression in the Filamentous Fungus *Trichoderma reesei*," *Appl. Environ. Microbiol*. 63(4):1298-1306.
Innis, M. A. et al. (Apr. 5, 1985). "Expression, Glycosylation, and Secretion of an *Aspergillus* Glucoamylase by *Saccharomyces cerevisiae*," *Science* 228:21-26.
Penttila, M. et al. (1987). "A Versatile Transformation System for the Cellulolytic Filamentous Fungus *Trichoderma reesei*," *Gene*61:155-164.
Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

(56) References Cited

OTHER PUBLICATIONS

Rohdich, F. et al. (Jun. 6, 2000). "Biosynthesis of Terpenoids: 4-Diphosphocytidyl-2C-Methyl-$_D$-Erythritol Synthase of *Arabidopsis thaliana*," *PNAS* 97(12):6451-6456.
Sambrook, J. et al. (1989). *Molecular Cloning: A Laboratory Manual*, 2$^{nd}$ edition, Cold Spring Harbor Laboratory Press: New York, NY, pp. xi-xxxviii (Table of Contents Only).
Sauret-Gueto, S. et al. (2006). "A Mutant Pyruvate Dehydrogenase E1 Subunit Allows Survival of *Escherichia coli* Strains Defective in 1-Deoxy-D-Xylulose 5-Phosphate Synthase." *FEBS Letters* 580:736-740.
Sonenshein, A. et al. (1993). *Bacillus subtilis and Other Gram-Positive Bacteria: Biochemistry, Physiology, and Molecular Genetics*, American Society for Microbiology, Washington ,D.C., pp. 9, 939, 941-952.
Stenesh, J. (1989). *Dictionary of Biochemistry and Molecular Biology*, 2$^{nd}$ edition, John Wiley & Sons: New York, NY, p. 97.
Van Den Hondel, C. A. M. J. J. et al. (1991). "Heterologous Gene Expression in Filamentous Fungi," Chapter 18 in *More Gene Manipulations in Fungi*, Bennet, J.W. et al. eds., Academic Press, Inc.: San Diego, CA, pp. 396-428.
Voynova, N. et al. (Jan. 2004). "*Staphylococcus aureus* mevalonate kinase; Isolation and characterization of an enzyme of the isoprenold biosynthetic pathway." *J. Bacteriol.*186(1):61-67.
Ward, M. et al. (Aug. 1993). "Use of *Aspergillus* Overproducing Mutants, Cured for Intergrated Plasmid, to Overproduce Heterologous Proteins," *Appl. Microbiol. Biotechnol.* 39(6):738-743.
Withers, S. T. et al. (Oct. 2007, e-pub. Aug. 10, 2007). "Identification of Isopentenol Biosynthetic from *Bacillus subtilis* by a Screening Method Based on Isorpenoid Precursor Toxicity," *Appl. Environ Microbiol.* 73(19):6277-6283.
Yamada, K. et al. (1989). "Production of Glycerol from Methanol by a Mutant Strain of *Candida boidinii* No. 2201," *Agric. Biol. Chem.* 53(2):541-543.
Yelton, M. M. et al. (Mar. 1984). "Transformation of *Aspergillus nidulans* by Using a *trpC* Plasmid," *PNAS* 81:1470-1474.
Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.
International Search Report mailed on Jan. 27, 2010 for PCT Patent Application No. PCT/US2009/057037, filed on Sep. 15, 2009, 2 pages.
International Search Report mailed on Feb. 3, 2010 for PCT Patent Application No. PCT/US2009/057007, filed on Sep. 15, 2009, 2 pages.
Julsing, M. K. et al. (2007). "Functional Analysis of Genes Involved in the Biosynthesis of Isoprene in *Bacillus subtilis*," *Applied Microbiol. Biotechnol.* 75:1377-1384.
Kelly, J. M. et al. (1985). "Transformation of *Aspergillus niger* by the amdS Gene of *Asperfillus nidulans*," *The EMBO Journal* 4(2):475-479.
Kinghorn, J. R. et al. (1992). *Applied Molecular Genetics of Filamentous Fungi*, Blackie Academic Professional and Chapman and Hall: London, 3 pages, (Table of Contents Only).
Koga, Y. et al. (Mar. 2007). "Biosynthesis of Ether-Type Polar Lipids in Archaea and Evolutionary Considerations," *Microbiology and Molecular Biology Reviews* 71(1):97-120.
Kreigler, M. (1990). *Gene Transfer and Expression: A Laboratory Manual*, W.H. Freeman and Company: New York, NY, pp. vii-x, (Table of Contents Only.).
Ladygina, N. et al. (2006). "A Review on Microbial Synthesis of Hydrocarbons," *Process Biochemistry* 41:1001-1014.
Lüttgen, H. et al. (Feb. 1, 2000). "Biosynthesis of Terpenoids: YchB Protein *Escherichia coli* Phosphorylates the 2-Hydroxy Group of 4-Diphosphocytidyl-2C-Methyl-$_D$-Erythritol," *PNAS* 97(3):1062-1067.
Martin, V. J. J. et al. (2003). "Engineering a Mevalonate Pathway in *Escherichia coli* for Production of Terpenoids," *Nature Biotechnology* 21(7):796-802.
Neidhardt, F. C. et al. (Sep. 1974). "Culture Medium for Enterobacteria," *J. Bacteriology* 119(3):736-747.
Miller, B. et al. (2001, e-pub. May 10, 2001). "First Isolation of an Isoprene Synthase Gene from Poplar and Successful Expression of the Gene in *Escherichia Coli*," *Planta* 213:483-487.
Nevalainen, K. M. H. et al. (1992). "The Molecular Biology of *Trichoderma* and Its Application to the Expression of Both Homologous and Heterologous Genes," Chapter 6 in *Molecular Industrial Mycology, Systems and Applications for Filamentous Fungi*, Leong, S.A. et al. eds., Marcel Dekker Inc.: New York, NY, pp. 129-148.
Nunberg, J. H. et al. (Nov. 1984). "Molecular Cloning and Characterization of the Glucoamylase Gene of *Aspergillus awamori*," *Mol. Cell. Biol.* 4(11):2306-2315.
Oulmouden, A. et al. (1991). "Nucleotide Sequence of the ERG12 Gene of *Saccharomyces cerevisiae* Encoding Mevalonate Kinase," *Curr. Genet.* 19:9-14.
Penttila, M. et al. (1987). "A Versatile Transformation System for the Cellulolytic Filamentous Fungus *Trichoderma reesei*," *Gene* 61:155-164.
Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology:. Washington, D.C., pp. 615-624.
Pourquie, J. et al. (1988). "Scale Up of Cellulase Production and Utilization," in *Biochemistry and Genetics of Cellulose Degradation*, Aubert, J.-P. et al. eds., Academic Press: San Diego, CA, pp. 71-86.
Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidy1-2-*C*-Methylerythritol," *PNAS* 96(21):11758-11763.
Rohdich, F. et al. (Jun. 6, 2000). "Biosynthesis of Terpenoids: 4-Diphosphocytidyl-2CMethyl-$_D$-Erythritol Synthase of *Arabidopsis thaliana*," *PNAS* 97(12):6451-6456.
Sambrook, J. et al. (1982). *Molecular Cloning: A Laboratory Manual*, 2$^{nd}$ edition, Cold Spring Harbor Laboratory Press: New York, NY, pp. xi-xxxviii (Table of Contents Only).
Sambrook, J. et al. (1989). *Molecular Cloning: A Laboratory Manual*, 2$^{nd}$ edition, Cold Spring Harbor Laboratory Press: New York, NY, pp. xi-xxxviii (Table of Contents Only)
Sauret-Gueto, S. et al. (2006). "A Mutant Pyruvate Dehydrogenase El Subunit Allows Survival of *Escherichia coli* Strains Defective in 1-Deoxy-D-Xylulose 5-Phosphate Synthase." *FEBS Letters* 580:736-740.
Schnitzler, J.-P. et al. (2005, e-pub. Jul. 29, 2005). "Biochemical Properties of Isoprene Synthase in Poplar (*Populus x canescens*)," *Planta* 222(5):777-786.
Sharkey, T. D. et al. (Feb. 2005). "Evolution of the Isoprene Biosynthetic Pathway in Kudzu," *Plant Physiology* 137:700-712.
Sheir-Neiss, G. et al. (Jul. 1984). "Characterization of the Secreted Ceullulases of *Trichoderma ressei* Wild Type and Mutants During Controlled Fermentations," *Appl. Microbiol. Biotechnol.* 20(1):46-53.
Silver, G. M. et al. (1991). "Enzymatic Synthesis of Isoprene from Dimethylallyl Diphosphate in Aspen Leaf Extracts," *Plant Physiol.* 97:1588-1591.
Silver, G. M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.
Sonenshein, A. et al. (1993). *Bacillus Subtilis and Other Gram-Positive Bacteria: Biochemistry, Physiology, and Molecular Genetics*, American Society for Microbiology, Washington, D.C., pp. 9, 939, 941-952.
Sprenger, G. A. et al. (Nov. 1997). Identification of a Thiamin-Dependent Synthase in *Escherichia coli* Required for the Formation of the 1-Deoxy-$_D$-Xylulose 5-Phosphate Precursor to Isoprenoids, Thiamin, and Pyridoxol *PNAS* 94:12857-12862.
Stenesh, J. (1989). *Dictionary of Biochemistry and Molecular Biology*, 2$^{nd}$ edition, John.Wiley & Sons: New York, NY, p. 97.

(56) References Cited

OTHER PUBLICATIONS

Sulter, G. J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme a Synthase, an Enzyme of Isopentenyl Diphosphate Biosynthesis," *J. Bacteriol.* 184(15):4065-4070.

Teymouri, F. et al. (2005, e-pub. Feb. 24, 2005). "Optimization of the Ammonia Fiber Explosion (AFEX) Treatment Parameters for Enzymeatic Hydrolysis of Corn Stover," *Bioresource Technology* 96:2014-2018.

Trutko, S. M. et al. (2005). "Occurrence of Nonmevalonate and Mevalonate Pathways for Isoprenoid Biosynthesis in Bacteria of Different Taxonomic Groups," *Microbiology* 74(2):153-158.

Tsay, Y. H. et al. (Feb. 1991). "Cloning and Characterization of *ERG8*, an Essential Gene of *Saccharomyces cerevisiae* That Encodes Phosphomevalonate Kinase," *Mol. Cell Biol.* 11(2):620-631.

Figure 1

1-
*atg*tgtgcgacctcttctcaatttactcagattaccgagcataattcccgtcgttccgcaaact
atcagccaaacctgtggaatttcgaattcctgcaatccctggagaacgacctgaaagtggaaaa
gctggaggagaaagcgaccaaactggaggaagaagttcgctgcatgatcaaccgtgtagacacc
cagccgctgtccctgctggagctgatcgacgatgtgcagcgcctgggtctgacctacaaatttg
aaaaagacatcattaaagccctggaaaacatcgtactgctggacgaaaacaaaaagaacaaatc
tgacctgcacgcaaccgctctgtctttccgtctgctgcgtcagcacggtttcgaggtttctcag
gatgtttttgagcgtttcaaggataaagaaggtggtttcagcggtgaactgaaaggtgacgtcc
aaggcctgctgagcctgtatgaagcgtcttacctgggtttcgagggtgagaacctgctggagga
ggcgcgtaccttttccatcacccacctgaagaacaacctgaaagaaggcattaataccaaggtt
gcagaacaagtgagccacgccctggaactgccatatcaccagcgtctgcaccgtctggaggcac
gttggttcctggataaatacgaaccgaaagaaccgcatcaccagctgctgctggagctggcgaa
gctggattttaacatggtacagaccctgcaccagaaagagctgcaagatctgtcccgctggtgg
accgagatgggcctggctagcaaactggattttgtacgcgaccgcctgatggaagtttatttct
gggcactgggtatggcgccagacccgcagtttggtgaatgtcgcaaagctgttactaaaatgtt
tggtctggtgacgatcatcgatgacgtgtatgacgtttatggcactctggacgaactgcaactg
ttcaccgatgctgtagagcgctgggacgttaacgctattaacaccctgccggactatatgaaac
tgtgtttcctggcactgtacaacaccgttaacgacacgtcctattctattctgaaagagaaagg
tcataacaacctgtcctatctgacgaaaagctggcgtgaactgtgcaaagcctttctgcaagag
gcgaaatggtccaacaacaaaattatcccggctttctccaagtacctggaaaacgccagcgttt
cctcctccggtgtagcgctgctggcgccgtcttacttttccgtatgccagcagcaggaagacat
ctccgaccacgcgctgcgttccctgaccgacttccatggtctggtgcgttctagctgcgttatc
ttccgcctgtgcaacgatctggccacctctgcggcggagctggaacgtggcgagactaccaatt
ctatcattagctacatgcacgaaaacgatggtaccagcgaggaacaggcccgcgaagaactgcg
taaactgatcgacgccgaatggaaaaagatgaatcgtgaacgcgttagcgactccaccctgctg
cctaaagcgttcatggaaatcgcagttaacatggcacgtgtttcccactgcacctaccagtatg
gcgatggtctgggtcgcccagactacgcgactgaaaaccgcatcaaactgctgctgattgaccc
tttcccgattaaccagctgatgtatgtc
taactgcag
(SEQ ID NO:1)

Figure 3A

1- gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccATGtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtc*TAA*ctgca
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg

Figure 3B agggtggcgggcaggacgcccgccataaactgccaggcatcaaattaagcagaaggccatcctg
acggatggcctttttgcgtttctacaaactcttttgtttatttttctaaatacattcaaatat
gtatccgctcatgagacaataaccctgataaatgcttcaataatattgaaaaaggaagagtatg
agtattcaacatttccgtgtcgcccttattcccttttttgcggcattttgccttcctgtttttg
ctcacccagaaacgctggtgaaagtaaaagatgctgaagatcagttgggtgcacgagtgggtta
catcgaactggatctcaacagcggtaagatccttgagagttttcgccccgaagaacgttttcca
atgatgagcacttttaaagttctgctatgtggcgcggtattatcccgtgttgacgccgggcaag
agcaactcggtcgccgcatacactattctcagaatgacttggttgagtactcaccagtcacaga
aaagcatcttacggatggcatgacagtaagagaattatgcagtgctgccataaccatgagtgat
aacactgcggccaacttacttctgacaacgatcggaggaccgaaggagctaaccgcttttttgc
acaacatgggggatcatgtaactcgccttgatcgttgggaaccggagctgaatgaagccatacc
aaacgacgagcgtgacaccacgatgcctgtagcaatggcaacaacgttgcgcaaactattaact
ggcgaactacttactctagcttcccggcaacaattaatagactggatggaggcggataaagttg
caggaccacttctgcgctcggcccttccggctggctggtttattgctgataaatctggagccgg
tgagcgtgggtctcgcggtatcattgcagcactggggccagatggtaagccctcccgtatcgta
gttatctacacgacggggagtcaggcaactatggatgaacgaaatagacagatcgctgagatag
gtgcctcactgattaagcattggtaactgtcagaccaagtttactcatatatactttagattga
tttaaaacttcatttttaatttaaaaggatctaggtgaagatcctttttgataatctcatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct

Figure 3C

Gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
(SEQ ID NO:2)

Figure 5A 1-
ttctcatgtttgacagcttatcatcgataagctttaatgcggtagtttatcacagttaaattgc
taacgcagtcaggcaccgtgtatgaaatctaacaatgcgctcatcgtcatcctcggcaccgtca
ccctggatgctgtaggcataggcttggttatgccggtactgccgggcctcttgcgggatatccg
gatatagttcctcctttcagcaaaaaacccctcaagacccgtttagaggccccaaggggttatg
ctagttattgctcagcggtggcagcagccaactcagcttcctttcgggctttgttagcagccgg
atccctgcagttagacatacatcagctggttaatcgggaaagggtcaatcagcagcagtttgat
gcggttttcagtcgcgtagtctgggcgacccagaccatcgccatactggtaggtgcagtgggaa
acacgtgccatgttaactgcgatttccatgaacgctttaggcagcagggtggagtcgctaacgc
gttcacgattcatctttttccattcggcgtcgatcagtttacgcagttcttcgcgggcctgttc
ctcgctggtaccatcgttttcgtgcatgtagctaatgatagaattggtagtctcgccacgttcc
agctccgccgcagaggtggccagatcgttgcacaggcggaagataacgcagctagaacgcacca
gaccatggaagtcggtcagggaacgcagcgcgtggtcggagatgtcttcctgctgctggcatac
ggaaaagtaagacggcgccagcagcgctacaccggaggaggaaacgctggcgttttccaggtac
ttggagaaagccgggataattttgttgttggaccatttcgcctcttgcagaaaggctttgcaca
gttcacgccagcttttcgtcagataggacaggttgttatgacctttctctttcagaatagaata
ggacgtgtcgttaacggtgttgtacagtgccaggaaacacagtttcatatagtccggcagggtg
ttaatagcgttaacgtcccagcgctctacagcatcggtgaacagttgcagttcgtccagagtgc
cataaacgtcatacacgtcatcgatgatcgtcaccagaccaaacattttagtaacagctttgcg
acattcaccaaactgcgggtctggcgccatacccagtgcccagaaataaacttccatcaggcgg
tcgcgtacaaaatccagtttgctagccaggcccatctcggtccaccagcgggacagatcttgca
gctctttctggtgcagggtctgtaccatgttaaaatccagcttcgccagctccagcagcagctg
gtgatgcggttctttcggttcgtatttatccaggaaccaacgtgcctccagacggtgcagacgc
tggtgatatggcagttccagggcgtggctcacttgttctgcaaccttggtattaatgccttctt
tcaggttgttcttcaggtgggtgatggaaaggtacgcgcctcctccagcaggttctcaccctc
gaaacccaggtaagacgcttcatacaggctcagcaggccttggacgtcacctttcagttcaccg
ctgaaaccaccttctttatccttgaaacgctcaaaaacatcctgagaaacctcgaaaccgtgct
gacgcagcagacggaaagacagagcggttgcgtgcaggtcagatttgttctttttgttttcgtc
cagcagtacgatgttttccagggctttaatgatgtctttttcaaatttgtaggtcagacccagg
cgctgcacatcgtcgatcagctccagcagggacagcggctgggtgtctacacggttgatcatgc
agcgaacttcttcctccagtttggtcgctttctcctccagcttttccactttcaggtcgttctc
cagggattgcaggaattcgaaattccacaggtttggctgatagtttgcggaacgacggaatta
tgctcggtaatctgagtaaattgagaagaggtcgcacacatatgacgaccttcgatatggccgc
tgctgtgatgatgatgatgatgatgatgatgatggcccatggtatatctccttcttaaagttaa
acaaaattatttctagaggggaattgttatccgctcacaattcccctatagtgagtcgtattaa
tttcgcgggatcgagatctcgatcctctacgccggacgcatcgtggccggcatcaccggcgcca
caggtgcggttgctggcgcctatatcgccgacatcaccgatggggaagatcgggctcgccactt
cgggctcatgagcgcttgtttcggcgtgggtatggtggcaggccccgtggccgggggactgttg
ggcgccatctccttgcatgcaccattccttgcggcggcggtgctcaacggcctcaacctactac
tgggctgcttcctaatgcaggagtcgcataagggagagcgtcgagatcccggacaccatcgaat
ggcgcaaaacctttcgcggtatggcatgatagcgcccggaagagagtcaattcagggtggtgaa
tgtgaaaccagtaacgttatacgatgtcgcagagtatgccggtgtctcttatcagaccgtttcc
cgcgtggtgaaccaggccagccacgtttctgcgaaaacgcgggaaaaagtggaagcggcgatgg
cggagctgaattacattcccaaccgcgtggcacaacaactggcgggcaaacagtcgttgctgat
tggcgttgccacctccagtctggccctgcacgcgccgtcgcaaattgtcgcggcgattaaatct

Figure 5B cgcgccgatcaactgggtgccagcgtggtggtgtcgatggtagaacgaagcggcgtcgaagcct
gtaaagcggcggtgcacaatcttctcgcgcaacgcgtcagtgggctgatcattaactatccgct
ggatgaccaggatgccattgctgtggaagctgcctgcactaatgttccggcgttatttcttgat
gtctctgaccagacacccatcaacagtattattttctcccatgaagacggtacgcgactgggcg
tggagcatctggtcgcattgggtcaccagcaaatcgcgctgttagcgggcccattaagttctgt
ctcggcgcgtctgcgtctggctggctggcataaatatctcactcgcaatcaaattcagccgata
gcggaacgggaaggcgactggagtgccatgtccggttttcaacaaaccatgcaaatgctgaatg
agggcatcgttcccactgcgatgctggttgccaacgatcagatggcgctgggcgcaatgcgcgc
cattaccgagtccgggctgcgcgttggtgcggatatctcggtagtgggatacgacgataccgaa
gacagctcatgttatatcccgccgttaaccaccatcaaacaggattttcgcctgctggggcaaa
ccagcgtggaccgcttgctgcaactctctcagggccaggcggtgaagggcaatcagctgttgcc
cgtctcactggtgaaaagaaaaaccaccctggcgcccaatacgcaaaccgcctctccccgcgcg
ttggccgattcattaatgcagctggcacgacaggtttcccgactggaaagcgggcagtgagcgc
aacgcaattaatgtaagttagctcactcattaggcaccgggatctcgaccgatgcccttgagag
ccttcaacccagtcagctccttccggtgggcgcggggcatgactatcgtcgccgcacttatgac
tgtcttctttatcatgcaactcgtaggacaggtgccggcagcgctctgggtcattttcggcgag
gaccgctttcgctggagcgcgacgatgatcggcctgtcgcttgcggtattcggaatcttgcacg
ccctcgctcaagccttcgtcactggtcccgccaccaaacgtttcggcgagaagcaggccattat
cgccggcatggcggccgacgcgctgggctacgtcttgctggcgttcgcgacgcgaggctggatg
gccttccccattatgattcttctcgcttccggcggcatcgggatgcccgcgttgcaggccatgc
tgtccaggcaggtagatgacgaccatcagggacagcttcaaggatcgctcgcggctcttaccag
cctaacttcgatcactggaccgctgatcgtcacggcgatttatgccgcctcggcgagcacatgg
aacgggttggcatggattgtaggcgccgccctataccttgtctgcctccccgcgttgcgtcgcg
gtgcatggagccgggccacctcgacctgaatggaagccggcggcacctcgctaacggattcacc
actccaagaattggagccaatcaattcttgcggagaactgtgaatgcgcaaaccaacccttggc
agaacatatccatcgcgtccgccatctccagcagccgcacgcggcgcatctcgggcagcgttgg
gtcctggccacgggtgcgcatgatcgtgctcctgtcgttgaggacccggctaggctggcggggt
tgccttactggttagcagaatgaatcaccgatacgcgagcgaacgtgaagcgactgctgctgca
aaacgtctgcgacctgagcaacaacatgaatggtcttcggtttccgtgtttcgtaaagtctgga
aacgcggaagtcagcgccctgcaccattatgttccggatctgcatcgcaggatgctgctggcta
ccctgtggaacacctacatctgtattaacgaagcgctggcattgaccctgagtgatttttctct
ggtcccgccgcatccataccgccagttgtttaccctcacaacgttccagtaaccgggcatgttc
atcatcagtaacccgtatcgtgagcatcctctctcgtttcatcggtatcattacccccatgaac
agaaatcccccttacacggaggcatcagtgaccaaacaggaaaaaaccgcccttaacatggccc
gctttatcagaagccagacattaacgcttctggagaaactcaacgagctggacgcggatgaaca
ggcagacatctgtgaatcgcttcacgaccacgctgatgagctttaccgcagctgcctcgcgcgt
ttcggtgatgacggtgaaaacctctgacacatgcagctcccggagacggtcacagcttgtctgt
aagcggatgccgggagcagacaagcccgtcagggcgcgtcagcgggtgttggcgggtgtcgggg
cgcagccatgacccagtcacgtagcgatagcggagtgtatactggcttaactatgcggcatcag
agcagattgtactgagagtgcaccatatatgcggtgtgaaataccgcacagatgcgtaaggaga
aaataccgcatcaggcgctcttccgcttcctcgctcactgactcgctgcgctcggtcgttcggc
tgcggcgagcggtatcagctcactcaaaggcggtaatacggttatccacagaatcaggggataa
cgcaggaaagaacatgtgagcaaaaggccagcaaaaggccaggaaccgtaaaaaggccgcgttg
ctggcgtttttccataggctccgcccccctgacgagcatcacaaaaatcgacgctcaagtcaga

Figure 5C ggtggcgaaacccgacaggactataaagataccaggcgtttccccctggaagctccctcgtgcg
ctctcctgttccgaccctgccgcttaccggatacctgtccgcctttctcccttcgggaagcgtg
gcgctttctcatagctcacgctgtaggtatctcagttcggtgtaggtcgttcgctccaagctgg
gctgtgtgcacgaaccccccgttcagcccgaccgctgcgccttatccggtaactatcgtcttga
gtccaacccggtaagacacgacttatcgccactggcagcagccactggtaacaggattagcaga
gcgaggtatgtaggcggtgctacagagttcttgaagtggtggcctaactacggctacactagaa
ggacagtatttggtatctgcgctctgctgaagccagttaccttcggaaaaagagttggtagctc
ttgatccggcaaacaaaccaccgctggtagcggtggtttttttgtttgcaagcagcagattacg
cgcagaaaaaaaggatctcaagaagatcctttgatcttttctacggggtctgacgctcagtgga
acgaaaactcacgttaagggattttggtcatgagattatcaaaaaggatcttcacctagatcct
tttaaattaaaaatgaagttttaaatcaatctaaagtatatatgagtaaacttggtctgacagt
taccaatgcttaatcagtgaggcacctatctcagcgatctgtctatttcgttcatccatagttg
cctgactccccgtcgtgtagataactacgatacgggagggcttaccatctggccccagtgctgc
aatgataccgcgagacccacgctcaccggctccagatttatcagcaataaaccagccagccgga
agggccgagcgcagaagtggtcctgcaactttatccgcctccatccagtctattaattgttgcc
gggaagctagagtaagtagttcgccagttaatagtttgcgcaacgttgttgccattgctgcagg
catcgtggtgtcacgctcgtcgtttggtatggcttcattcagctccggttcccaacgatcaagg
cgagttacatgatcccccatgttgtgcaaaaaagcggttagctccttcggtcctccgatcgttg
tcagaagtaagttggccgcagtgttatcactcatggttatggcagcactgcataattctcttac
tgtcatgccatccgtaagatgcttttctgtgactggtgagtactcaaccaagtcattctgagaa
tagtgtatgcggcgaccgagttgctcttgcccggcgtcaacacgggataataccgcgccacata
gcagaactttaaaagtgctcatcattggaaaacgttcttcggggcgaaaactctcaaggatctt
accgctgttgagatccagttcgatgtaacccactcgtgcacccaactgatcttcagcatctttt
actttcaccagcgtttctgggtgagcaaaaacaggaaggcaaaatgccgcaaaaaagggaataa
gggcgacacggaaatgttgaatactcatactcttcctttttcaatattattgaagcatttatca
gggttattgtctcatgagcggatacatatttgaatgtatttagaaaaataaacaaataggggtt
ccgcgcacatttccccgaaaagtgccacctgacgtctaagaaaccattattatcatgacattaa
cctataaaaataggcgtatcacgaggccctttcgtcttcaagaa
(SEQ ID NO:5)

Figure 7A 1-
cccgtcttactgtcgggaattcgcgttggccgattcattaatgcagctggcacgacaggtttcc
cgactggaaagcgggcagtgagcgcaacgcaattaatgtgagttagctcactcattaggcaccc
caggctttacactttatgcttccggctcgtatgttgtgtggaattgtgagcggataacaatttc
acacaggaaacagctatgaccatgattacgccaagcttgtatcgattaaataaggaggaataaa
ccatgtgtgcgacctcttctcaatttactcagattaccgagcataattcccgtcgttccgcaaa
ctatcagccaaacctgtggaatttcgaattcctgcaatccctggagaacgacctgaaagtggaa
aagctggaggagaaagcgaccaaactggaggaagaagttcgctgcatgatcaaccgtgtagaca
cccagccgctgtccctgctggagctgatcgacgatgtgcagcgcctgggtctgacctacaaatt
tgaaaaagacatcattaaagccctggaaaacatcgtactgctggacgaaaacaaaaagaacaaa
tctgacctgcacgcaaccgctctgtctttccgtctgctgcgtcagcacggtttcgaggtttctc
aggatgtttttgagcgtttcaaggataaagaaggtggtttcagcggtgaactgaaaggtgacgt
ccaaggcctgctgagcctgtatgaagcgtcttacctgggtttcgagggtgagaacctgctggag
gaggcgcgtacctttttccatcacccacctgaagaacaacctgaaagaaggcattaataccaagg
ttgcagaacaagtgagccacgccctggaactgccatatcaccagcgtctgcaccgtctggaggc
acgttggttcctggataaatacgaaccgaaagaaccgcatcaccagctgctgctggagctggcg
aagctggattttaacatggtacagaccctgcaccagaaagagctgcaagatctgtcccgctggt
ggaccgagatgggcctggctagcaaactggattttgtacgcgaccgcctgatggaagtttattt
ctgggcactgggtatggcgccagacccgcagtttggtgaatgtcgcaaagctgttactaaaatg
tttggtctggtgacgatcatcgatgacgtgtatgacgtttatggcactctggacgaactgcaac
tgttcaccgatgctgtagagcgctgggacgttaacgctattaacaccctgccggactatatgaa
actgtgtttcctggcactgtacaacaccgttaacgacacgtcctattctattctgaaagagaaa
ggtcataacaacctgtcctatctgacgaaaagctggcgtgaactgtgcaaagcctttctgcaag
aggcgaaatggtccaacaacaaaattatcccggctttctccaagtacctggaaaacgccagcgt
ttcctcctccggtgtagcgctgctggcgccgtcttacttttccgtatgccagcagcaggaagac
atctccgaccacgcgctgcgttccctgaccgacttccatggtctggtgcgttctagctgcgtta
tcttccgcctgtgcaacgatctggccacctctgcggcggagctggaacgtggcgagactaccaa
ttctatcattagctacatgcacgaaaacgatggtaccagcgaggaacaggcccgcgaagaactg
cgtaaactgatcgacgccgaatggaaaaagatgaatcgtgaacgcgttagcgactccaccctgc
tgcctaaagcgttcatggaaatcgcagttaacatggcacgtgtttcccactgcacctaccagta
tggcgatggtctgggtcgcccagactacgcgactgaaaaccgcatcaaactgctgctgattgac
cctttcccgattaaccagctgatgtatgtctaactgcaggtcgactctagaggatccccgggta
ccgagctcgaattcactggccgtcgttttacaacgtcgtgactgggaaaaccctggcgttaccc
aacttaatcgccttgcagcacatccccctttcgccagctggcgtaatagcgaagaggcccgcac
cgatcgcccttcccaacagttgcgcagcctgaatggcgaatggcgcctgatgcggtattttctc
cttacgcatctgtgcggtatttcacaccgcatatggtgcactctcagtacaatctgctctgatg
ccgcatagttaagccagccccgacacccgccaacacccgctgacgagcttagtaaagccctcgc
tagattttaatgcggatgttgcgattacttcgccaactattgcgataacaagaaaaagccagcc
tttcatgatatatctcccaatttgtgtagggcttattatgcacgcttaaaaataataaaagcag
acttgacctgatagtttggctgtgagcaattatgtgcttagtgcatctaacgcttgagttaagc
cgcgccgcgaagcggcgtcggcttgaacgaattgttagacattatttgccgactaccttggtga
tctcgcctttcacgtagtggacaaattcttccaactgatctgcgcgcgaggccaagcgatcttc
ttcttgtccaagataagcctgtctagcttcaagtatgacgggctgatactgggccggcaggcgc
tccattgcccagtcggcagcgacatccttcggcgcgattttgccggttactgcgctgtaccaaa
tgcgggacaacgtaagcactacatttcgctcatcgccagcccagtcgggcggcgagttccatag

Figure 7B cgttaaggtttcatttagcgcctcaaatagatcctgttcaggaaccggatcaaagagttcctcc
gccgctggacctaccaaggcaacgctatgttctcttgcttttgtcagcaagatagccagatcaa
tgtcgatcgtggctggctcgaagatacctgcaagaatgtcattgcgctgccattctccaaattg
cagttcgcgcttagctggataacgccacggaatgatgtcgtcgtgcacaacaatggtgacttct
acagcgcggagaatctcgctctctccaggggaagccgaagtttccaaaaggtcgttgatcaaag
ctcgccgcgttgtttcatcaagccttacggtcaccgtaaccagcaaatcaatatcactgtgtgg
cttcaggccgccatccactgcggagccgtacaaatgtacggccagcaacgtcggttcgagatgg
cgctcgatgacgccaactacctctgatagttgagtcgatacttcggcgatcaccgcttccctca
tgatgtttaactttgttttagggcgactgccctgctgcgtaacatcgttgctgctccataacat
caaacatcgacccacggcgtaacgcgcttgctgcttggatgcccgaggcatagactgtacccca
aaaaaacagtcataacaagccatgaaaccgccactgcgccgttaccaccgctgcgttcggtca
aggttctggaccagttgcgtgagcgcatacgctacttgcattacagcttacgaaccgaacaggc
ttatgtccactgggttcgtgccttcatccgtttccacggtgtgcgtcacccggcaaccttgggc
agcagcgaagtcgaggcatttctgtcctggctggcgaacgagcgcaaggtttcggtctccacgc
atcgtcaggcattggcggccttgctgttcttctacggcaaggtgctgtgcacggatctgccctg
gcttcaggagatcggaagacctcggccgtcgcggcgcttgccggtggtgctgaccccggatgaa
gtggttcgcatcctcggttttctggaaggcgagcatcgtttgttcgcccagcttctgtatggaa
cgggcatgcggatcagtgagggtttgcaactgcgggtcaaggatctggatttcgatcacggcac
gatcatcgtgcgggagggcaagggctccaaggatcgggccttgatgttacccgagagcttggca
cccagcctgcgcgagcaggggaattaattcccacgggttttgctgcccgcaaacgggctgttct
ggtgttgctagtttgttatcagaatcgcagatccggcttcagccggtttgccggctgaaagcgc
tatttcttccagaattgccatgattttttccccacgggaggcgtcactggctcccgtgttgtcg
gcagctttgattcgataagcagcatcgcctgtttcaggctgtctatgtgtgactgttgagctgt
aacaagttgtctcaggtgttcaatttcatgttctagttgctttgttttactggtttcacctgtt
ctattaggtgttacatgctgttcatctgttacattgtcgatctgttcatggtgaacagctttga
atgcaccaaaaactcgtaaaagctctgatgtatctatcttttttacaccgttttcatctgtgca
tatggacagttttccctttgatatgtaacggtgaacagttgttctacttttgtttgttagtctt
gatgcttcactgatagatacaagagccataagaacctcagatccttccgtatttagccagtatg
ttctctagtgtggttcgttgtttttgcgtgagccatgagaacgaaccattgagatcatacttac
tttgcatgtcactcaaaaattttgcctcaaaactggtgagctgaatttttgcagttaaagcatc
gtgtagtgtttttcttagtccgttatgtaggtaggaatctgatgtaatggttgttggtatttg
tcaccattcatttttatctggttgttctcaagttcggttacgagatccatttgtctatctagtt
caacttggaaaatcaacgtatcagtcgggcggcctcgcttatcaaccaccaatttcatattgct
gtaagtgtttaaatctttacttattggtttcaaaacccattggttaagccttttaaactcatgg
tagttattttcaagcattaacatgaacttaaattcatcaaggctaatctctatatttgccttgt
gagttttcttttgtgttagttcttttaataaccactcataaatcctcatagagtatttgttttc
aaaagacttaacatgttccagattatattttatgaatttttttaactggaaaagataaggcaat
atctcttcactaaaaactaattctaatttttcgcttgagaacttggcatagtttgtccactgga
aaatctcaaagcctttaaccaaaggattcctgatttccacagttctcgtcatcagctctctggt
tgctttagctaatacaccataagcattttccctactgatgttcatcatctgagcgtattggtta
taagtgaacgataccgtccgttctttccttgtagggttttcaatcgtggggttgagtagtgcca
cacagcataaaattagcttggtttcatgctccgttaagtcatagcgactaatcgctagttcatt
tgctttgaaaacaactaattcagacatacatctcaattggtctaggtgattttaatcactatac
caattgagatgggctagtcaatgataattactagtcctttcctttgagttgtgggtatctgta

Figure 7C

```
Aattctgctagacctttgctggaaaacttgtaaattctgctagaccctctgtaaattccgctag
acctttgtgtgttttttttgtttatattcaagtggttataatttatagaataaagaaagaataa
aaaagataaaaagaatagatcccagccctgtgtataactcactactttagtcagttccgcagt
attacaaaaggatgtcgcaaacgctgtttgctcctctacaaaacagaccttaaaaccctaaagg
cttaagtagcaccctcgcaagctcgggcaaatcgctgaatattccttttgtctccgaccatcag
gcacctgagtcgctgtcttttcgtgacattcagttcgctgcgctcacggctctggcagtgaat
gggggtaaatggcactacaggcgccttttatggattcatgcaaggaaactacccataatacaag
aaaagcccgtcacgggcttctcagggcgttttatggcgggtctgctatgtggtgctatctgact
ttttgctgttcagcagttcctgccctctgattttccagtctgaccacttcggattatcccgtga
caggtcattcagactggctaatgcacccagtaaggcagcggtatcatcaacaggctta
(SEQ ID NO:7)
```

Figure 9
A.
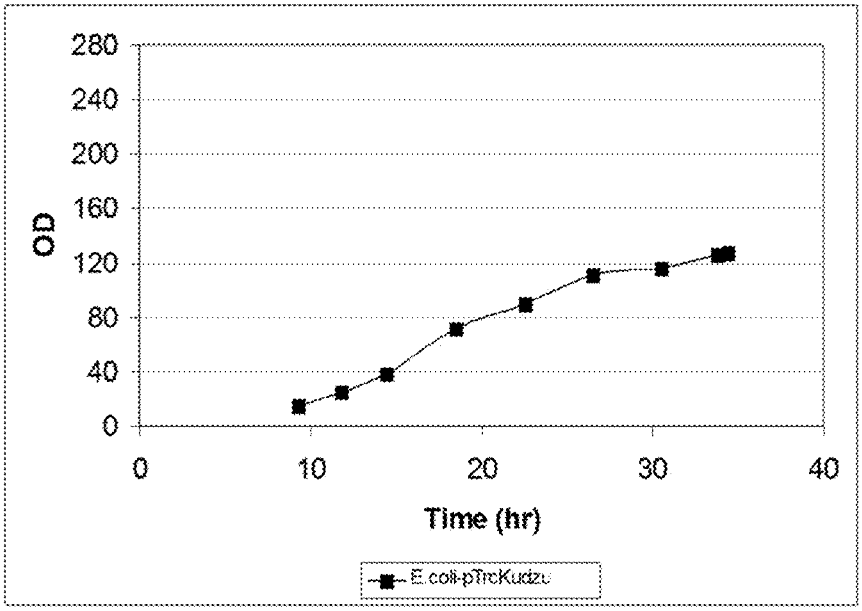
B.
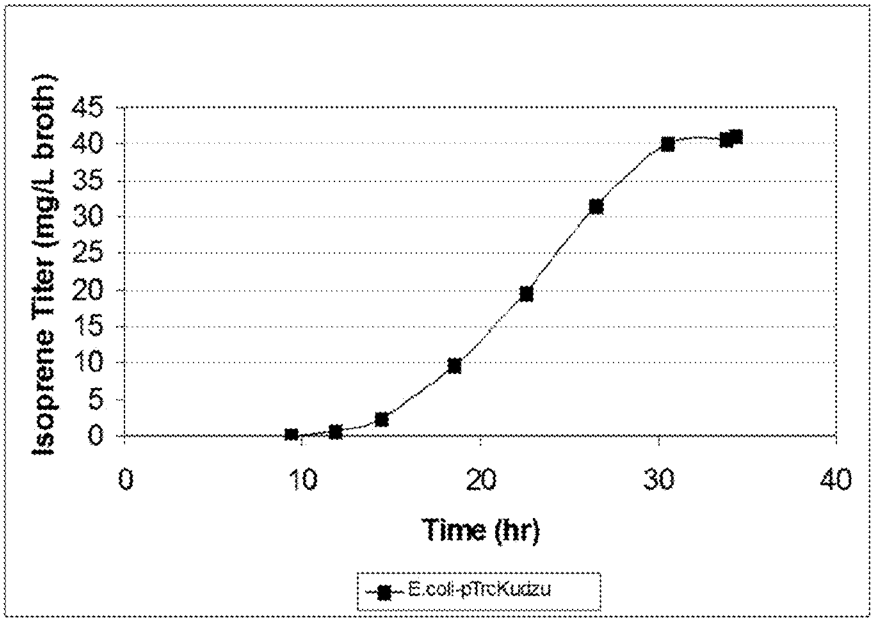

Figure 12A 1-
gaattgctccattttcttctgctatcaaaataacagactcgtgattttccaaacgagctttcaa
aaaagcctctgccccttgcaaatcggatgcctgtctataaaattcccgatattggttaaacagc
ggcgcaatggcggccgcatctgatgtctttgcttggcgaatgttcatcttatttcttcctccct
ctcaataatttttttcattctatccctttttctgtaaagtttatttttcagaatacttttatcatc
atgctttgaaaaaatatcacgataatatccattgttctcacggaagcacacgcaggtcatttga
acgaatttttcgacaggaatttgccgggactcaggagcatttaacctaaaaaagcatgacatt
tcagcataatgaacatttactcatgtctattttcgttcttttctgtatgaaaatagttatttcg
agtctctacggaaatagcgagagatgatatacctaaatagagataaaatcatctcaaaaaaatg
ggtctactaaaatattattccatctattacaataaattcacagaatagtcttttaagtaagtct
actctgaatttttttaaaaggagagggtaaagagtgtgtgcgacctcttctcaatttactcaga
ttaccgagcataattcccgtcgttccgcaaactatcagccaaacctgtggaatttcgaattcct
gcaatccctggagaacgacctgaaagtggaaaagctggaggagaaagcgaccaaactggaggaa
gaagttcgctgcatgatcaaccgtgtagacacccagccgctgtccctgctggagctgatcgacg
atgtgcagcgcctgggtctgacctacaaatttgaaaaagacatcattaaagccctggaaaacat
cgtactgctggacgaaaacaaaaagaacaaatctgacctgcacgcaaccgctctgtctttccgt
ctgctgcgtcagcacggtttcgaggtttctcaggatgtttttgagcgtttcaaggataaagaag
gtggtttcagcggtgaactgaaaggtgacgtccaaggcctgctgagcctgtatgaagcgtctta
cctgggtttcgagggtgagaacctgctggaggaggcgcgtaccttttccatcacccacctgaag
aacaacctgaaagaaggcattaataccaaggttgcagaacaagtgagccacgccctggaactgc
catatcaccagcgtctgcaccgtctggaggcacgttggttcctggataaatacgaaccgaaaga
accgcatcaccagctgctgctggagctggcgaagctggattttaacatggtacagaccctgcac
cagaaagagctgcaagatctgtcccgctggtggaccgagatgggcctggctagcaaactggatt
ttgtacgcgaccgcctgatggaagtttatttctgggcactgggtatggcgccagacccgcagtt
tggtgaatgtcgcaaagctgttactaaaatgtttggtctggtgacgatcatcgatgacgtgtat
gacgtttatggcactctggacgaactgcaactgttcaccgatgctgtagagcgctgggacgtta
acgctattaacaccctgccggactatatgaaactgtgtttcctggcactgtacaacaccgttaa
cgacacgtcctattctattctgaaagagaaaggtcataacaacctgtcctatctgacgaaaagc
tggcgtgaactgtgcaaagcctttctgcaagaggcgaaatggtccaacaacaaaattatcccgg
ctttctccaagtacctggaaaacgccagcgtttcctcctccggtgtagcgctgctggcgccgtc
ttacttttccgtatgccagcagcaggaagacatctccgaccacgcgctgcgttccctgaccgac
ttccatggtctggtgcgttctagctgcgttatcttccgcctgtgcaacgatctggccacctctg
cggcggagctggaacgtggcgagactaccaattctatcattagctacatgcacgaaaacgatgg
taccagcgaggaacaggcccgcgaagaactgcgtaaactgatcgacgccgaatggaaaaagatg
aatcgtgaacgcgttagcgactccaccctgctgcctaaagcgttcatggaaatcgcagttaaca
tggcacgtgtttcccactgcacctaccagtatggcgatggtctgggtcgcccagactacgcgac
tgaaaaccgcatcaaactgctgctgattgaccctttcccgattaaccagctgatgtatgtctaa
aaaaaaccggccttggccccgccggtttttttattatttttcttcctccgcatgttcaatccgct
ccataatcgacggatggctccctctgaaaattttaacgagaaacggcgggttgacccggctcag
tcccgtaacggccaagtcctgaaacgtctcaatcgccgcttcccggtttccggtcagctcaatg
ccgtaacggtcggcggcgtttttcctgataccgggagacggcattcgtaatcggatcctctagag
tcgacctgcaggcatgcaagctttgcctcgcgcgtttcggtgatgacggtgaaaacctctgaca
catgcagctcccggagacggtcacagcttgtctgtaagcggatgccgggagcagacaagcccgt
cagggcgcgtcagcgggtgttggcgggtgtcggggcgcagccatgacccagtcacgtagcgata

Figure 12B gcggagtgtatactggcttaactatgcggcatcagagcagattgtactgagagtgcaccatatg
cggtgtgaaataccgcacagatgcgtaaggagaaaataccgcatcaggcgctcttccgcttcct
cgctcactgactcgctgcgctcggtcgttcggctgcggcgagcggtatcagctcactcaaaggc
ggtaatacggttatccacagaatcaggggataacgcaggaaagaacatgtgagcaaaaggccag
caaaaggccaggaaccgtaaaaaggccgcgttgctggcgtttttccataggctccgcccccctg
acgagcatcacaaaaatcgacgctcaagtcagaggtggcgaaacccgacaggactataaagata
ccaggcgtttccccctggaagctccctcgtgcgctctcctgttccgaccctgccgcttaccgga
tacctgtccgcctttctcccttcgggaagcgtggcgctttctcaatgctcacgctgtaggtatc
tcagttcggtgtaggtcgttcgctccaagctgggctgtgtgcacgaaccccccgttcagcccga
ccgctgcgccttatccggtaactatcgtcttgagtccaacccggtaagacacgacttatcgcca
ctggcagcagccactggtaacaggattagcagagcgaggtatgtaggcggtgctacagagttct
tgaagtggtggcctaactacggctacactagaaggacagtatttggtatctgcgctctgctgaa
gccagttaccttcggaaaaagagttggtagctcttgatccggcaaacaaaccaccgctggtagc
ggtggtttttttgtttgcaagcagcagattacgcgcagaaaaaaaggatctcaagaagatcctt
tgatcttttctacggggtctgacgctcagtggaacgaaaactcacgttaagggattttggtcat
gagattatcaaaaaggatcgaagtcggttcagaaaaagaaggatatggatctggagctgtaata
taaaaaccttcttcaactaacggggcaggttagtgacattagaaaaccgactgtaaaaagtaca
gtcggcattatctcatattataaaagccagtcattaggcctatctgacaattcctgaatagagt
tcataaacaatcctgcatgataaccatcacaaacagaatgatgtacctgtaaagatagcggtaa
atatattgaattacctttattaatgaattttcctgctgtaataatgggtagaaggtaattacta
ttattattgatatttaagttaaacccagtaaatgaagtccatggaataatagaaagagaaaaag
cattttcaggtataggtgttttgggaaacaatttaaaagaaccattatatttctctacatcaga
aaggtataaatcataaaactctttgaagtcattctttacaggagtccaaataccagagaatgtt
ttagatacaccatcaaaaattgtataaagtggctctaacttatcccaataacctaactctccgt
cgctattgtaaccagttctaaaagctgtatttgagtttatcaccccttgtcactaagaaaataaa
tgcagggtaaaatttatatccttcttgttttatgtttcggtataaaacactaatatcaatttct
gtggttatactaaaagtcgtttgttggttcaaataatgattaaatatctcttttctcttccaat
tgtctaaatcaattttattaaagttcatttgatatgcctcctaaatttttatctaaagtgaatt
taggaggcttacttgtctgctttcttcattagaatcaatcctttttttaaagtcaatattactgt
aacataaatatatattttaaaaatatcccactttatccaattttcgtttgttgaactaatgggt
gctttagttgaagaataaagaccacattaaaaaatgtggtcttttgtgtttttttaaaggattt
gagcgtacgcgaaaaatccttttctttctttcttatcttgataataagggtaactattgccggt
tgtccattcatggctgaactctgcttcctctgttgacatgacacacatcatctcaatatccgaa
tagggcccatcagtctgacgaccaagagagccataaacaccaatagccttaacatcatccccat
atttatccaatattcgttccttaatttcatgaacaatcttcattctttcttctctagtcattat
tattggtccattcactattctcattccctttttcagataattttagatttgcttttctaaataag
aatatttggagagcaccgttcttattcagctattaataactcgtcttcctaagcatccttcaat
ccttttaataacaattatagcatctaatcttcaacaaactggcccgtttgttgaactactcttt
aataaaataatttttccgttcccaattccacattgcaataatagaaaatccatcttcatcggct
ttttcgtcatcatctgtatgaatcaaatcgccttcttctgtgtcatcaaggtttaatttttat
gtatttcttttaacaaaccaccataggagattaaccttttacggtgtaaaccttcctccaaatc
agacaaacgtttcaaattcttttcttcatcatcggtcataaaatccgtatcctttacaggatat
tttgcagtttcgtcaattgccgattgtatatccgatttatatttatttttcggtcgaatcattt
gaacttttacatttggatcatagtctaatttcattgcctttttccaaaattgaatccattgttt

Figure 12C ttgattcacgtagttttctgttattctaaaataagttggttccacacataccattacatgcatg
tgctgattataagaattatctttattatttattgtcacatccgttgcacgcataaaaccaacaa
gatttttattaatttttttatattgcatcattcggcgaaatccttgagccatatctgtcaaact
cttatttaattcttcgccatcataaacatttttaactgttaatgtgagaaacaaccaacgaact
gttggcttttgtttaataacttcagcaacaaccttttgtgactgaatgccatgtttcattgctc
tcctccagttgcacattggacaaagcctggatttgcaaaaccacactcgataccactttctttc
gcctgtttcacgattttgtttatactctaatatttcagcacaatcttttactctttcagccttt
ttaaattcaagaatatgcagaagttcaaagtaatcaacattagcgattttcttttctctccatg
gtctcacttttccactttttgtcttgtccactaaacccttgatttttcatctgaataaatgct
actattaggacacataatattaaaagaaacccccatctatttagttatttgtttagtcacttat
aactttaacagatggggtttttctgtgcaaccaattttaagggttttcaatactttaaaacaca
tacataccaacacttcaacgcacctttcagcaactaaaataaaaatgacgttatttctatatgt
atcaagataagaaagaacaagttcaaaaccatcaaaaaaagacaccttttcaggtgcttttttt
attttataaactcattccctgatctcgacttcgttctttttttacctctcggttatgagttagt
tcaaattcgttctttttaggttctaaatcgtgtttttcttggaattgtgctgttttatccttta
ccttgtctacaaaccccttaaaaacgtttttaaaggcttttaagccgtctgtacgttccttaag (SEQ ID NO:57)

Figure 13

ATGTGTGCAACCTCCTCCCAGTTTACTCAGATTACCGAGCATAATTCTCGACGATCTGCTAACT
ACCAGCCGAACCTTTGGAACTTTGAGTTTCTCCAGTCTCTCGAAAATGACCTGAAGGTGGAAAA
GCTCGAGGAGAAGGCGACCAAACTCGAGGAGGAGGTGCGATGTATGATCAACAGAGTTGACACC
CAACCCCTGTCTTTGCTGGAGCTGATCGACGATGTGCAGCGGTTGGGTTTGACTTATAAATTCG
AGAAGGACATTATCAAGGCACTGGAGAACATTGTGCTCCTCGACGAGAACAAGAAGAACAAGTC
TGATCTTCACGCTACCGCTCTCTCTTTCCGACTTCTTCGACAACACGGCTTCGAGGTGTCGCAG
GACGTCTTCGAGAGATTTAAGGACAAGGAGGGAGGATTTAGCGGCGAGCTGAAGGGAGACGTTC
AGGGTCTTCTCTCCTTGTACGAGGCGTCCTACCTGGGATTCGAGGGAGAGAACCTCCTGGAGGA
AGCTCGTACATTTTCCATCACTCACCTTAAGAATAACCTTAAGGAGGGAATTAACACCAAGGTG
GCCGAGCAGGTTTCTCACGCCCTGGAGCTCCCCTACCACCAACGGCTCCATAGACTGGAGGCTC
GTTGGTTCCTGGACAAATATGAGCCAAAGGAGCCTCATCATCAGTTGCTGTTGGAGTTGGCCAA
GCTGGACTTCAATATGGTTCAGACGCTGCACCAAAAGGAGTTGCAGGACCTGTCTCGATGGTGG
ACCGAGATGGGATTGGCCTCGAAGCTGGATTTTGTCCGTGACCGACTTATGGAGGTCTATTTTT
GGGCCCTTGGAATGGCGCCTGACCCCCAGTTCGGAGAGTGCCGGAAGGCGGTGACGAAGATGTT
CGGTCTTGTGACTATCATCGACGACGTCTACGATGTCTACGGCACACTCGACGAGTTGCAGCTG
TTCACTGACGCCGTCGAGCGATGGGATGTGAACGCCATTAATACTCTCCCTGACTATATGAAGC
TGTGCTTCCTGGCTCTGTACAACACTGTCAACGATACCTCGTACTCTATCCTCAAGGAGAAGGG
ACACAACAATCTCTCCTACTTGACCAAATCCTGGCGAGAACTGTGCAAGGCTTTTCTGCAGGAG
GCTAAATGGTCCAATAACAAGATCATTCCTGCTTTTTCTAAATACCTGGAAAATGCCTCGGTGT
CGAGCTCTGGCGTCGCCCTTCTGGCCCCTTCCTACTTCTCCGTCTGCCAGCAGCAGGAGGATAT
TTCCGATCATGCTCTTAGATCGCTGACCGATTTTCACGGCCTCGTGCGATCTTCCTGCGTGATT
TTTCGGTTGTGTAATGACCTTGCGACCTCTGCTGCTGAGCTGGAACGAGGCGAGACTACAAATT
CCATTATTTCTTACATGCACGAAAACGATGGAACATCTGAAGAACAGGCTAGAGAGGAACTGCG
AAAGTTGATCGACGCCGAGTGGAAGAAGATGAACAGAGAGCGGGTGTCCGACTCTACCCTGCTT
CCCAAGGCCTTCATGGAGATCGCCGTGAACATGGCTCGAGTTTCCCATTGTACTTACCAGTACG
GTGACGGCCTGGGTCGTCCGGACTACGCTACAGAGAACCGAATCAAGCTGCTGCTCATCGACCC
CTTCCCTATCAACCAATTGATGTACGTGTAA
(SEQ ID NO:8)

Figure 15A

```
   1 TCGACCGGTG AGAAGAACAG CATCGGGACA AGGGAAGGAA GAACAAAGAC AAAGAAAACA
  61 AAAGAAAGCA ATTGAAAACA AAACAAAACA ATTTTCATTC CTTCTCTTAT CATTCCTTTT
 121 CTTTTCTTTT CTCTCATTCA ACGCACTCCA TCGTATCCGT ATTCCTCTTA TTTTTTCTCT
 181 TTCTCTATAT CCATTTCTTT CTCTCTAGGT GTGTCCTCTC TCTCTCTTCA ATTTCTCTAC
 241 TCCGCATTCC AACGCATCCT TCCCCCAACC TCCCATTTCC TCCTTACGGC CCGATAGCGA
 301 TCGTCTTTCC CTCGCTATCA CTCGCTACCG GCCCCTCCTC TGCACCGTAA CCTCCTACGT
 361 ATTTACCATA TCATAAAGTT TTTTCCGACG CTTATCGCTG ACCCCCTGTC GCCCTCCTAT
 421 TGGCTTCCGG ATTATCTTCT TGTCCATAAG GTGATCCATG CTTCCTGAAG ATTCCCGAAA
 481 TGTGTCCACT TTGGCGGGGA ATCATTCCAT CCACTTCTTT CTCTCTCGCT TTCCTCATTC
 541 GGCGCTCCCC TTCCGCGTCT CATTGGTCTT CCGCTCCGTT TTTGCTTTGC CGATGTTACT
 601 TGGGGAGAGG TGCGATAATC CTTTCGCAAA AACTCGGTTT GACGCCTCCC ATGGTATAAA
 661 TAGTGGGTGG TGGACAGGTG CCTTCGCTTT TCTTTAAGCA AGAGAATCCC ATTGTCTTGA
 721 CTATCACGAA TTCACATACA TTATGAAGAT CACCGCTGTC ATTGCCCTTT TATTCTCACT
 781 TGCTGCTGCC TCACCTATTC CAGTTGCCGA TCCTGGTGTG GTTTCAGTTA GCAAGTCATA
 841 TGCTGATTTC CTTCGTGTTT ACCAAAGTTG GAACACTTTT GCTAATCCTG ATAGACCCAA
 901 CCTTAAGAAG AGAAATGATA CACCTGCAAG TGGATATCAA GTTGAAAAAG TCGTAATTTT
 961 GTCACGTCAC GGTGTTAGGG CCCCTACAAA AATGACTCAA ACCATGCGTG ATGTCACTCC
1021 TAATACATGG CCAGAATGGC CCGTTAAATT AGGATATATT ACACCAAGAG GTGAACACTT
1081 GATATCACTT ATGGGCGGTT TTTACCGTCA AAAATTCCAG CAACAAGGAA TCCTTTCTCA
1141 GGGCTCCTGT CCTACTCCTA ACTCCATATA TGTCTGGGCT GACGTCGATC AGCGTACTTT
1201 AAAAACTGGT GAAGCATTCC TTGCTGGTTT GGCACCACAA TGTGGCTTGA CAATTCATCA
1261 CCAACAAAAT CTTGAGAAAG CTGATCCTCT TTTTCATCCC GTTAAAGCTG GAACCTGCTC
1321 TATGGATAAA ACTCAAGTTC AACAAGCTGT TGAGAAGGAG GCACAAACTC CTATAGATAA
1381 TTTGAATCAA CATTACATCC CCTTTTTAGC TTTAATGAAT ACAACATTAA ATTTTAGTAC
1441 TTCTGCCTGG TGCCAAAAAC ACTCTGCTGA TAAATCCTGT GACCTAGGTT TATCCATGCC
1501 TTCTAAATTG TCCATAAAAG ATAATGGTAA CAAGGTCGCA TTGGATGGAG CTATTGGTCT
1561 ATCCTCTACT TTGGCCGAGA TTTTTCTTCT TGAATATGCT CAAGGCATGC CTCAAGCTGC
1621 TTGGGGTAAC ATCCACTCAG AGCAAGAGTG GGCTTCCTTG CTAAAGTTGC ATAATGTTCA
1681 ATTCGATTTG ATGGCCCGAA CACCTTATAT TGCTCGACAT AACGGTACTC CTTTATTGCA
1741 AGCTATATCA AATGCCCTTA ATCCCAACGC CACTGAATCA AAACTTCCAG ATATTTCACC
1801 TGATAACAAA ATATTGTTCA TTGCAGGTCA TGACACAAAT ATTGCTAATA TAGCCGGCAT
1861 GTTAAATATG CGTTGGACAT TACCAGGTCA ACCAGATAAT ACTCCTCCAG GTGGTGCCCT
1921 AGTATTTGAA CGTCTTGCTG ATAAAAGTGG AAAACAATAT GTTTCTGTAT CTATGGTTTA
1981 TCAAACACTA GAACAACTTC GATCACAGAC TCCCCTTTCT CTAAATCAGC CTGCCGGATC
2041 TGTTCAACTT AAAATTCCAG GTTGCAATGA TCAAACAGCC GAGGGTTACT GTCCTCTTTC
2101 CACTTTTACA AGAGTTGTTT CCCAATCTGT TGAACCTGGA TGCCAACTTC AATAATGAGG
2161 ATCCAAGTAA GCGAATCAGA ATGTGATCCA CTTTTAATTC CTAATGAATA CATGCCTATA
2221 GTTCTTTTCT TTTGTTCTTT ATGTCGTTTT TCGATGGTAC GGCCGTTGTC AATCTCAGTT
2281 TGTGTGCTTG GTTGCAGCTT GGTTTCAAAT CTGTTCATCT CATGAATCTT TTACCATTTC
2341 ACCACACGTT TATACCATTC TCTCATAGAA TCTTCATCAA ACCATCTCGG GGTTAGAGTG
2401 GAAAGAAAGT CTTGTTCTTT TATTTCCTTT TTTCCATCTT CAAGGCTTTT CTTTTCTTCC
2461 TCCTCCTCGT TCATCTTGAG GTTTGACGTG TCTGTTTAGA ATTTTGAGCT GTTGCAGCAT
2521 CTTATTTTTT GTTTTGCGAA AACGAAGCGC TTTACTCTCT TCATCAGTTG GACGATTGTA
2581 CCTTTGAAAA CCAACTACTT TTGCATGTTT TGTATAGAAA TCAATGATAT TAGAATCCCA
2641 TCCTTTAATT TCTTTCAAAG TAGTTGAGCT ATAGTTAAGT GTAAGGGCCC TACTGCGAAA
2701 GCATTTGCCA AGGATGTTTT CATTAATCAA GAACGAAAGT TAGGGGATCG AAGACGATCA
2761 GATACCGTCG TAGTCTTAAC CATAAACTAT GCCGACTAGG GATCGGGCAA TGTTTCATTT
2821 ATCGACTTGC TCGGCACCTT ACGAGAAATC AAAGTCTTTG GGTTCCGGGG GGAGTATGGT
2881 CGCAAGGCTG AAACTTAAAG GAATTGACGG AAGGGCACCA CAATGGAGTG GAGCCTGCGG
2941 CTTAATTTGA CTCAACACGG GGAAACTCAC CAGGTCCAGA CATAGTAAGG ATTGACAGAT
3001 TGAGAGCTCT TTCTTGATTC TATGGGTGGT GGTGCATGGC CGTTCTTAGT TGGTGGAGTG
3061 ATTTGTCTGC TTAATTGCGA TAACGAACGA GACCTTAACC TGCTAAATAG CTGGATCAGC
3121 CATTTTGGCT GATCATTAGC TTCTTAGAGG GACTATTGGC ATAAAGCCAA TGGAAGTTTG
3181 AGGCAATAAC AGGTCTGTGA TGCCCTTAGA TGTTCTGGGC CGCACGCGCG CTACACTGAC
3241 GGAGCCAACG AGTTGAAAAA AATCTTTTGA TTTTTTATCC TTGGCCGGAA GGTCTGGGTA
3301 ATCTTGTTAA ACTCCGTCGT GCTGGGGATA GAGCATTGCA ATTATTGCGG CCGCTCCTCA
3361 ATTCGATGTT GCAGATTTTA CAAGTTTTTA AAATGTATTT CATTATTACT TTTTATATGC
3421 CTAATAAAAA AGCCATAGTT TAATCTATAG ATAACTTTTT TTCCAGTGCA CTAACGGACG
```

Figure 15B

```
3481 TTACATTCCC ATACAAAACT GCGTAGTTAA AGCTAAGGAA AAGTTAATAT CATGTTAATT
3541 AAATACGCTA TTTACAATAA GACATTGAAC TCATTTATAT CGTTGAATAT GAATAACCAA
3601 TTTCAGCGAA TTTTTAACAA ACATCGTTCA CCTCGTTTAA GGATATCTTG TGTATGGGGT
3661 GTTGACTTGC TTTATCGAAT AATTACCGTA CCTGTAATTG GCTTGCTGGA TATAGCGGTA
3721 GTCTAATATC TAGCAAAAAT CTTTTGGGTG AAAAGGCTTG CAATTTCACG ACACCGAACT
3781 ATTTGTCATT TTTTAATAAG GAAGTTTTCC ATAAATTCCT GTAATTCTCG GTTGATCTAA
3841 TTGAAAAGAG TAGTTTTGCA TCACGATGAG GAGGGCTTTT GTAGAAAGAA ATACGAACGA
3901 AACGAAAATC AGCGTTGCCA TCGCTTTGGA CAAAGCTCCC TTACCTGAAG AGTCGAATTT
3961 TATTGATGAA CTTATAACTT CCAAGCATGC AAACCAAAAG GGAGAACAAG TAATCCAAGT
4021 AGACACGGGA ATTGGATTCT TGGATCACAT GTATCATGCA CTGGCTAAAC ATGCAGGCTG
4081 GAGCTTACGA CTTTACTCAA GAGGTGATTT AATCATCGAT GATCATCACA CTGCAGAAGA
4141 TACTGCTATT GCACTTGGTA TTGCATTCAA GCAGGCTATG GGTAACTTTG CCGGCGTTAA
4201 AAGATTTGGA CATGCTTATT GTCCACTTGA CGAAGCTCTT TCTAGAAGCG TAGTTGACTT
4261 GTCGGGACGG CCCTATGCTG TTATCGATTT GGGATTAAAG CGTGAAAAGG TTGGGGAATT
4321 GTCCTGTGAA ATGATCCCTC ACTTACTATA TTCCTTTTCG GTAGCAGCTG GAATTACTTT
4381 GCATCTTACC TGCTTATATG GTAGTAATGA CCATCATCGT GCTGAAAGCG CTTTTAAATC
4441 TCTGGCTGTT GCCATGCGCG CGGCTACTAG TCTTACTGGA AGTTCTGAAG TCCCAAGCAC
4501 GAAGGGAGTG TTGTAAAGAT GAATTGGATT ATGTCAGGAA AAGAACGACA ATTTTGCATC
4561 CAAATTGTCT AAATTTTAGA GTTGCTTGAA AACAATAGAA CCTTACTTGC TTTATAATTA
4621 CGTTAATTAG AAGCGTTATC TCGTGAAGGA ATATAGTACG TAGCCGTATA AATTGAATTG
4681 AATGTTCAGC TTATAGAATA GAGACACTTT GCTGTTCAAT GCGTCGTCAC TTACCATACT
4741 CACTTTATTA TACGACTTTA AGTATAAACT CCGCGGTTAT GGTAAAATTA ATGATGCACA
4801 AACGTCCGAT TCCATATGGG TACACTACAA TTAAATACTT TTAAGCTGAT CCCCCACACA
4861 CCATAGCTTC AAAATGTTTC TACTCCTTTT TTACTCTTCC AGATTTTCTC GGACTCCGCG
4921 CATCGCCGTA CCACTTCAAA ACACCCAAGC ACAGCATACT AAATTTTCCC TCTTTCTTCC
4981 TCTAGGGTGT CGTTAATTAC CCGTACTAAA GGTTTGGAAA AGAAAAAAGA GACCGCCTCG
5041 TTTCTTTTTC TTCGTCGAAA AAGGCAATAA AAATTTTTAT CACGTTTCTT TTTCTTGAAA
5101 TTTTTTTTTT TAGTTTTTTT CTCTTTCAGT GACCTCCATT GATATTTAAG TTAATAAACG
5161 GTCTTCAATT TCTCAAGTTT CAGTTTCATT TTTCTTGTTC TATTACAACT TTTTTTACTT
5221 CTTGTTCATT AGAAAGAAAG CATAGCAATC TAATCTAAGG GCGGTGTTGA CAATTAATCA
5281 TCGGCATAGT ATATCGGCAT AGTATAATAC GACAAGGTGA GGAACTAAAC CATGGCCAAG
5341 TTGACCAGTG CCGTTCCGGT GCTCACCGCG CGCGACGTCG CCGGAGCGGT CGAGTTCTGG
5401 ACCGACCGGC TCGGGTTCTC CCGGGACTTC GTGGAGGACG ACTTCGCCGG TGTGGTCCGG
5461 GACGACGTGA CCCTGTTCAT CAGCGCGGTC CAGGACCAGG TGGTGCCGGA CAACACCCTG
5521 GCCTGGGTGT GGGTGCGCGG CCTGGACGAG CTGTACGCCG AGTGGTCGGA GGTCGTGTCC
5581 ACGAACTTCC GGGACGCCTC CGGGCCGGCC ATGACCGAGA TCGGCGAGCA GCCGTGGGGG
5641 CGGGAGTTCG CCCTGCGCGA CCCGGCCGGC AACTGCGTGC ACTTCGTGGC CGAGGAGCAG
5701 GACTGACACG TCCGACGGCG GCCCACGGGT CCCAGGCCTC GGAGATCCGT CCCCCTTTTC
5761 CTTTGTCGAT ATCATGTAAT TAGTTATGTC ACGCTTACAT TCACGCCCTC CCCCCACATC
5821 CGCTCTAACC GAAAAGGAAG GAGTTAGACA ACCTGAAGTC TAGGTCCCTA TTTATTTTTT
5881 TATAGTTATG TTAGTATTAA GAACGTTATT TATATTTCAA ATTTTTCTTT TTTTTCTGTA
5941 CAGACGCGAG CTTCCCAGTA AATGTGCCAT CTCGTAGGCA GAAAACGGTT CCCCCGTAGG
6001 GTCTCTCTCT TGGCCTCCTT TCTAGGTCGG GCTGATTGCT CTTGAAGCTC TCTAGGGGGG
6061 CTCACACCAT AGGCAGATAA CGTTCCCCAC CGGCTCGCCT CGTAAGCGCA CAAGGACTGC
6121 TCCCAAAGAT CCTAGGCGGG ATTTTGCCGA TTTCGGCCTA AAGGAACCGG AACACGTAGA
6181 AAGCCAGTCC GCAGAAACGG TGCTGACCCC GGATGAATGT CAGCTACTGG GCTATCTGGA
6241 CAAGGGAAAA CGCAAGCGCA AAGAGAAAGC AGGTAGCTTG CAGTGGGCTT ACATGGCGAT
6301 AGCTAGACTG GGCGGTTTTA TGGACAGCAA GCGAACCGGA ATTGCCAGCT GGGGCGCCCT
6361 CTGGTAAGGT TGGGAAGCCC TGCAAAGTAA ACTGGATGGC TTTCTTGCCG CCAAGGATCT
6421 GATGGCGCAG GGGATCAAGA TCTGATCAAG AGACAGGATG AGGATCGTTT CGCATGATTG
6481 AACAAGATGG ATTGCACGCA GGTTCTCCGG CCGCTTGGGT GGAGAGGCTA TTCGGCTATG
6541 ACTGGGCACA ACAGACAATC GGCTGCTCTG ATGCCGCCGT GTTCCGGCTG TCAGCGCAGG
6601 GGCGCCCGGT TCTTTTTGTC AAGACCGACC TGTCCGGTGC CCTGAATGAA CTGCAGGACG
6661 AGGCAGCGCG GCTATCGTGG CTGGCCACGA CGGGCGTTCC TTGCGCAGCT GTGCTCGACG
6721 TTGTCACTGA AGCGGGAAGG GACTGGCTGC TATTGGGCGA AGTGCCGGGG CAGGATCTCC
6781 TGTCATCTCG CCTTGCTCCT GCCGAGAAAG TATCCATCAT GGCTGATGCA ATGCGGCGGC
6841 TGCATACGCT TGATCCGGCT ACCTGCCCAT TCGACCACCA AGCGAAACAT CGCATCGAGC
6901 GAGCACGTAC TCGGATGGAA GCCGGTCTTG TCGATCAGGA TGATCTGGAC GAAGAGCATC
6961 AGGGGCTCGC GCCAGCCGAA CTGTTCGCCA GGCTCAAGGC GCGCATGCCC GACGGCGAGG
```

Figure 15C

```
7021 ATCTCGTCGT GATCCATGGC GATGCCTGCT TGCCGAATAT CATGGTGGAA AATGGCCGCT
7081 TTTCTGGATT CAACGACTGT GGCCGGCTGG GTGTGGCGGA CCGCTATCAG GACATAGCGT
7141 TGGATACCCG TGATATTGCT GAAGAGCTTG GCGGCGAATG GGCTGACCGC TTCCTCGTGC
7201 TTTACGGTAT CGCCGCTCCC GATTCGCAGC GCATCGCCTT CTATCGCCTT CTTGACGAGT
7261 TCTTCTGAAT TGAAAAAGGT ACCAAGTTTA CTCATATATA CTTTAGATTG ATTTAAAACT
7321 TCATTTTTAA TTTAAAAGGA TCTAGGTGAA GATCCTTTTT GATAATCTCA TGACCAAAAT
7381 CCCTTAACGT GAGTTTTCGT TCCACTGAGC GTCAGACCCC GTAGAAAAGA TCAAAGGATC
7441 TTCTTGAGAT CCTTTTTTTC TGCGCGTAAT CTGCTGCTTG CAAACAAAAA AACCACCGCT
7501 ACCAGCGGTG GTTTGTTTGC CGGATCAAGA GCTACCAACT CTTTTTCCGA AGGTAACTGG
7561 CTTCAGCAGA GCGCAGATAC CAAATACTGT CCTTCTAGTG TAGCCGTAGT TAGGCCACCA
7621 CTTCAAGAAC TCTGTAGCAC CGCCTACATA CCTCGCTCTG CTAATCCTGT TACCAGTGGC
7681 TGCTGCCAGT GGCGATAAGT CGTGTCTTAC CGGGTTGGAC TCAAGACGAT AGTTACCGGA
7741 TAAGGCGCAG CGGTCGGGCT GAACGGGGGG TTCGTGCACA CAGCCCAGCT TGGAGCGAAC
7801 GACCTACACC GAACTGAGAT ACCTACAGCG TGAGCATTGA GAAAGCGCCA CGCTTCCCGA
7861 AGGGAGAAAG GCGGACAGGT ATCCGGTAAG CGGCAGGGTC GGAACAGGAG AGCGCACGAG
7921 GGAGCTTCCA GGGGGAAACG CCTGGTATCT TTATAGTCCT GTCGGGTTTC GCCACCTCTG
7981 ACTTGAGCGT CGATTTTTGT GATGCTCGTC AGGGGGGCGG AGCCTATGGA AAAACGCCAG
8041 CAACGCGGCC TTTTTACGGT TCCTGGCCTT TTGCTGGCCT TTTGCTCACA TGTTCTTTCC
8101 TGCGTTATCC CCTGATTCTG TGGATAACCG TATTACCGCC TTTGAGTGAG CTGATACCGC
8161 TCGCCGCAGC CGAACGACCG AGCGCAGCGA G
   (SEQ ID NO:11)
```

Figure 16

```
   1 GAATTCAAAA CAAAATGTGT GCAACCTCCT CCCAGTTTAC TCAGATTACC GAGCATAATT
  61 CTCGACGATC TGCTAACTAC CAGCCGAACC TTTGGAACTT TGAGTTTCTC CAGTCTCTCG
 121 AAAATGACCT GAAGGTGGAA AAGCTCGAGG AGAAGGCGAC CAAACTCGAG GAGGAGGTGC
 181 GATGTATGAT CAACAGAGTT GACACCCAAC CCCTGTCTTT GCTGGAGCTG ATCGACGATG
 241 TGCAGCGGTT GGGTTTGACT TATAAATTCG AGAAGGACAT TATCAAGGCA CTGGAGAACA
 301 TTGTGCTCCT CGACGAGAAC AAGAAGAACA AGTCTGATCT TCACGCTACC GCTCTCTCTT
 361 TCCGACTTCT TCGACAACAC GGCTTCGAGG TGTCGCAGGA CGTCTTCGAG AGATTTAAGG
 421 ACAAGGAGGG AGGATTTAGC GGCGAGCTGA AGGGAGACGT TCAGGGTCTT CTCTCCTTGT
 481 ACGAGGCGTC CTACCTGGGA TTCGAGGGAG AGAACCTCCT GGAGGAAGCT CGTACATTTT
 541 CCATCACTCA CCTTAAGAAT AACCTTAAGG AGGGAATTAA CACCAAGGTG GCCGAGCAGG
 601 TTTCTCACGC CCTGGAGCTC CCCTACCACC AACGGCTCCA TAGACTGGAG GCTCGTTGGT
 661 TCCTGGACAA ATATGAGCCA AAGGAGCCTC ATCATCAGTT GCTGTTGGAG TTGGCCAAGC
 721 TGGACTTCAA TATGGTTCAG ACGCTGCACC AAAAGGAGTT GCAGGACCTG TCTCGATGGT
 781 GGACCGAGAT GGGATTGGCC TCGAAGCTGG ATTTTGTCCG TGACCGACTT ATGGAGGTCT
 841 ATTTTTGGGC CCTTGGAATG GCGCCTGACC CCCAGTTCGG AGAGTGCCGG AAGGCGGTGA
 901 CGAAGATGTT CGGTCTTGTG ACTATCATCG ACGACGTCTA CGATGTCTAC GGCACACTCG
 961 ACGAGTTGCA GCTGTTCACT GACGCCGTCG AGCGATGGGA TGTGAACGCC ATTAATACTC
1021 TCCCTGACTA TATGAAGCTG TGCTTCCTGG CTCTGTACAA CACTGTCAAC GATACCTCGT
1081 ACTCTATCCT CAAGGAGAAG GGACACAACA ATCTCTCCTA CTTGACCAAA TCCTGGCGAG
1141 AACTGTGCAA GGCTTTTCTG CAGGAGGCTA AATGGTCCAA TAACAAGATC ATTCCTGCTT
1201 TTTCTAAATA CCTGGAAAAT GCCTCGGTGT CGAGCTCTGG CGTCGCCCTT CTGGCCCCTT
1261 CCTACTTCTC CGTCTGCCAG CAGCAGGAGG ATATTTCCGA TCATGCTCTT AGATCGCTGA
1321 CCGATTTTCA CGGCCTCGTG CGATCTTCCT GCGTGATTTT TCGGTTGTGT AATGACCTTG
1381 CGACCTCTGC TGCTGAGCTG GAACGAGGCG AGACTACAAA TTCCATTATT TCTTACATGC
1441 ACGAAAACGA TGGAACATCT GAAGAACAGG CTAGAGAGGA ACTGCGAAAG TTGATCGACG
1501 CCGAGTGGAA GAAGATGAAC AGAGAGCGGG TGTCCGACTC TACCCTGCTT CCCAAGGCCT
1561 TCATGGAGAT CGCCGTGAAC ATGGCTCGAG TTTCCCATTG TACTTACCAG TACGGTGACG
1621 GCCTGGGTCG TCCGGACTAC GCTACAGAGA ACCGAATCAA GCTGCTGCTC ATCGACCCCT
1681 TCCCTATCAA CCAATTGATG TACGTGTAAT AGTCTAGAGG ATCC
     (SEQ ID NO:12)
```

Figure 17

```
   1 GAATTCAACA AAAATGTGCT CTGTTTCCAC TGAGAACGTG TCCTTTACTG AGACTGAGAC
  61 TGAAGCACGT AGAAGCGCCA ACTACGAACC CAACTCCTGG GATTATGACT TTCTGCTGTC
 121 TTCTGACACC GACGAGTCGA TCGAGGTTTA TAAGGATAAG GCCAAGAAAC TTGAGGCCGA
 181 GGTCAGACGA GAGATTAACA ACGAGAAGGC CGAGTTCCTG ACCCTTCTTG AGCTGATCGA
 241 CAACGTTCAA CGACTTGGTC TTGGTTACCG TTTCGAATCC GATATCCGAC GTGCATTGGA
 301 TCGATTTGTC TCGTCCGGAG GTTTCGATGG TGTGACTAAG ACGTCGCTGC ACGCCACAGC
 361 TCTTTCCTTC AGACTGTTGC GGCAGCATGG ATTTGAGGTT TCCCAGGAAG CCTTTTCTGG
 421 TTTCAAGGAT CAGAACGGAA ACTTTTTGGA GAATCTCAAG GAGGACACCA AGGCCATCCT
 481 GTCGTTGTAT GAGGCCTCGT TCCTGGCTCT TGAGGGCGAG AATATTCTGG ATGAGGCTCG
 541 GGTTTTCGCT ATTTCGCACC TGAAGGAGTT GTCGGAGGAA AAGATCGGAA AGGAACTGGC
 601 CGAGCAGGTC AACCATGCAC TTGAACTTCC CCTGCATCGA CGTACCCAGC GACTGGAGGC
 661 CGTGTGGAGC ATCGAGGCGT ACAGAAAAAA GGAGGATGCT AATCAGGTTC TGCTCGAACT
 721 CGCTATCCTC GACTATAACA TGATTCAGAG CGTGTACCAG CGTGACTTGC GAGAGACAAG
 781 CCGGTGGTGG CGACGGGTGG GACTGGCCAC GAAGCTCCAC TTTGCTAAAG ATCGATTGAT
 841 TGAGTCGTTC TACTGGGCAG TGGGTGTGGC CTTTGAGCCT CAGTACTCCG ACTGCCGAAA
 901 CTCCGTTGCA AAGATGTTTT CTTTTGTCAC TATCATCGAC GACATCTACG ATGTTTACGG
 961 CACTCTCGAT GAACTCGAAC TCTTCACGGA CGCTGTCGAG CGATGGGATG TGAATGCCAT
1021 TAATGATCTG CCAGATTATA TGAAGTTGTG TTTCTTGGCG CTCTACAACA CAATTAATGA
1081 AATTGCCTAC GACAACCTCA AGGACAAGGG AGAGAACATT CTGCCCTACC TTACTAAAGC
1141 CTGGGCCGAC CTGTGTAACG CCTTTTTGCA GGAAGCCAAG TGGCTCTATA ACAAATCTAC
1201 TCCTACATTT GATGACTACT TCGGCAACGC TTGGAAGTCT TCCAGCGGCC CTCTCCAGTT
1261 GATCTTCGCT TACTTTGCAG TGGTCCAGAA CATCAAGAAA GAGGAGATTG AGAACCTCCA
1321 GAAGTATCAC GACATCATCT CCCGACCTTC GCACATCTTT CGACTGTGCA ATGACCTTGC
1381 CTCCGCATCC GCTGAGATTG CCCGAGGAGA AACAGCCAAT TCTGTGTCGT GTTACATGCG
1441 TACAAAGGGC ATCTCCGAGG AGCTGGCTAC CGAGTCTGTG ATGAACCTGA TCGATGAAAC
1501 CTGTAAGAAG ATGAACAAAG AGAAACTGGG CGGTTCTCTG TTCGCCAAAC CATTTGTTGA
1561 AACCGCGATC AATCTGGCTC GTCAGTCTCA TTGTACTTAC CATAACGGTG ACGCGCACAC
1621 TTCGCCGGAC GAATTGACCC GTAAGCGTGT GCTTTCGGTG ATTACCGAGC CGATCCTGCC
1681 GTTCGAAAGA TAATAGGATC C
     (SEQ ID NO:13)
```

acetyl-CoA acetoacetyl-CoA

HMG-CoA mevalonic acid 5-phosphomevalonic acid isopentenyl-P diphosphomevalonic acid isopentenyl-PP dimethylallyl-PP

Figure 22A 1-
gctggtaccatatgggaattcgaagctttctagaacaaaaactcatctcagaagaggatctgaa
tagcgccgtcgaccatcatcatcatcatcattgagtttaaacggtctccagcttggctgttttg
gcggatgagagaagattttcagcctgatacagattaaatcagaacgcagaagcggtctgataaa
acagaatttgcctggcggcagtagcgcggtggtcccacctgaccccatgccgaactcagaagtg
aaacgccgtagcgccgatggtagtgtggggtctccccatgcgagagtagggaactgccaggcat
caaataaaacgaaaggctcagtcgaaagactgggcctttcgttttatctgttgtttgtcggtga
acgctctcctgagtaggacaaatccgccgggagcggatttgaacgttgcgaagcaacggcccgg
agggtggcgggcaggacgcccgccataaactgccaggcatcaaattaagcagaaggccatcctg
acggatggcctttttgcgtttctacaaactctttttgtttatttttctaaatacattcaaatat
gtatccgcttaaccggaattgccagctggggcgccctctggtaaggttgggaagccctgcaaag
taaactggatggctttctcgccgccaaggatctgatggcgcaggggatcaagctctgatcaaga
gacaggatgaggatcgtttcgcatgattgaacaagatggattgcacgcaggttctccggccgct
tgggtggagaggctattcggctatgactgggcacaacagacaatcggctgctctgatgccgccg
tgttccggctgtcagcgcaggggcgcccggttctttttgtcaagaccgacctgtccggtgccct
gaatgaactgcaagacgaggcagcgcggctatcgtggctggccacgacgggcgttccttgcgca
gctgtgctcgacgttgtcactgaagcgggaagggactggctgctattgggcgaagtgccggggc
aggatctcctgtcatctcaccttgctcctgccgagaaagtatccatcatggctgatgcaatgcg
gcggctgcatacgcttgatccggctacctgcccattcgaccaccaagcgaaacatcgcatcgag
cgagcacgtactcggatggaagccggtcttgtcgatcaggatgatctggacgaagagcatcagg
ggctcgcgccagccgaactgttcgccaggctcaaggcgagcatgcccgacggcgaggatctcgt
cgtgacccatggcgatgcctgcttgccgaatatcatggtggaaaatggccgcttttctggattc
atcgactgtggccggctgggtgtggcggaccgctatcaggacatagcgttggctacccgtgata
ttgctgaagagcttggcggcgaatgggctgaccgcttcctcgtgctttacggtatcgccgctcc
cgattcgcagcgcatcgccttctatcgccttcttgacgagttcttctgacatgaccaaaatccc
ttaacgtgagttttcgttccactgagcgtcagaccccgtagaaaagatcaaaggatcttcttga
gatcctttttttctgcgcgtaatctgctgcttgcaaacaaaaaaaccaccgctaccagcggtgg
tttgtttgccggatcaagagctaccaactctttttccgaaggtaactggcttcagcagagcgca
gataccaaatactgtccttctagtgtagccgtagttaggccaccacttcaagaactctgtagca
ccgcctacatacctcgctctgctaatcctgttaccagtggctgctgccagtggcgataagtcgt
gtcttaccgggttggactcaagacgatagttaccggataaggcgcagcggtcgggctgaacggg
gggttcgtgcacacagcccagcttggagcgaacgacctacaccgaactgagatacctacagcgt
gagctatgagaaagcgccacgcttcccgaagggagaaaggcggacaggtatccggtaagcggca
gggtcggaacaggagagcgcacgagggagcttccagggggaaacgcctggtatctttatagtcc
tgtcgggtttcgccacctctgacttgagcgtcgatttttgtgatgctcgtcaggggggcggagc
ctatggaaaaacgccagcaacgcggcctttttacggttcctggccttttgctggccttttgctc
acatgttctttcctgcgttatcccctgattctgtggataaccgtattaccgcctttgagtgagc
tgataccgctcgccgcagccgaacgaccgagcgcagcgagtcagtgagcgaggaagcggaagag
cgcctgatgcggtattttctccttacgcatctgtgcggtatttcacaccgcatatggtgcactc
tcagtacaatctgctctgatgccgcatagttaagccagtatacactccgctatcgctacgtgac
tgggtcatggctgcgccccgacacccgccaacacccgctgacgcgccctgacgggcttgtctgc
tcccggcatccgcttacagacaagctgtgaccgtctccgggagctgcatgtgtcagaggttttc
accgtcatcaccgaaacgcgcgaggcagcagatcaattcgcgcgcgaaggcgaagcggcatgca
tttacgttgacaccatcgaatggtgcaaacctttcgcggtatggcatgatagcgcccggaaga

Figure 22B gagtcaattcagggtggtgaatgtgaaaccagtaacgttatacgatgtcgcagagtatgccggt
gtctcttatcagaccgtttcccgcgtggtgaaccaggccagccacgtttctgcgaaaacgcggg
aaaaagtggaagcggcgatggcggagctgaattacattcccaaccgcgtggcacaacaactggc
gggcaaacagtcgttgctgattggcgttgccacctccagtctggccctgcacgcgccgtcgcaa
attgtcgcggcgattaaatctcgcgccgatcaactgggtgccagcgtggtggtgtcgatggtag
aacgaagcggcgtcgaagcctgtaaagcggcggtgcacaatcttctcgcgcaacgcgtcagtgg
gctgatcattaactatccgctggatgaccaggatgccattgctgtggaagctgcctgcactaat
gttccggcgttatttcttgatgtctctgaccagacacccatcaacagtattattttctcccatg
aagacggtacgcgactgggcgtggagcatctggtcgcattgggtcaccagcaaatcgcgctgtt
agcgggcccattaagttctgtctcggcgcgtctgcgtctggctggctggcataaatatctcact
cgcaatcaaattcagccgatagcggaacgggaaggcgactggagtgccatgtccggttttcaac
aaaccatgcaaatgctgaatgagggcatcgttcccactgcgatgctggttgccaacgatcagat
ggcgctgggcgcaatgcgcgccattaccgagtccgggctgcgcgttggtgcggatatctcggta
gtgggatacgacgataccgaagacagctcatgttatatcccgccgtcaaccaccatcaaacagg
attttcgcctgctggggcaaaccagcgtggaccgcttgctgcaactctctcagggccaggcggt
gaagggcaatcagctgttgcccgtctcactggtgaaaagaaaaaccaccctggcgcccaatacg
caaaccgcctctccccgcgcgttggccgattcattaatgcagctggcacgacaggtttcccgac
tggaaagcgggcagtgagcgcaacgcaattaatgtgagttagcgcgaattgatctggtttgaca
gcttatcatcgactgcacggtgcaccaatgcttctggcgtcaggcagccatcggaagctgtggt
atggctgtgcaggtcgtaaatcactgcataattcgtgtcgctcaaggcgcactcccgttctgga
taatgttttttgcgccgacatcataacggttctggcaaatattctgaaatgagctgttgacaat
taatcatccggctcgtataatgtgtggaattgtgagcggataacaatttcacacaggaaacagc
gccgctgagaaaaagcgaagcggcactgctctttaacaatttatcagacaatctgtgtgggcac
tcgaccggaattatcgattaactttattattaaaaattaaagaggtatatattaatgtatcgat
taaataaggaggaataaaccatgtgtgcgacctcttctcaatttactcagattaccgagcataa
ttcccgtcgttccgcaaactatcagccaaacctgtggaatttcgaattcctgcaatccctggag
aacgacctgaaagtggaaaagctggaggagaaagcgaccaaactggaggaagaagttcgctgca
tgatcaaccgtgtagacacccagccgctgtccctgctggagctgatcgacgatgtgcagcgcct
gggtctgacctacaaatttgaaaaagacatcattaaagccctggaaaacatcgtactgctggac
gaaaacaaaaagaacaaatctgacctgcacgcaaccgctctgtctttccgtctgctgcgtcagc
acggtttcgaggtttctcaggatgtttttgagcgtttcaaggataaagaaggtggtttcagcgg
tgaactgaaaggtgacgtccaaggcctgctgagcctgtatgaagcgtcttacctgggtttcgag
ggtgagaacctgctggaggaggcgcgtaccttttccatcacccacctgaagaacaacctgaaag
aaggcattaataccaaggttgcagaacaagtgagccacgccctggaactgccatatcaccagcg
tctgcaccgtctggaggcacgttggttcctggataaatacgaaccgaaagaaccgcatcaccag
ctgctgctggagctggcgaagctggattttaacatggtacagaccctgcaccagaaagagctgc
aagatctgtcccgctggtggaccgagatgggcctggctagcaaactggattttgtacgcgaccg
cctgatggaagtttatttctgggcactgggtatggcgccagacccgcagtttggtgaatgtcgc
aaagctgttactaaaatgtttggtctggtgacgatcatcgatgacgtgtatgacgtttatggca
ctctggacgaactgcaactgttcaccgatgctgtagagcgctgggacgttaacgctattaacac
cctgccggactatatgaaactgtgtttcctggcactgtacaacaccgttaacgacacgtcctat
tctattctgaaagagaaaggtcataacaacctgtcctatctgacgaaaagctggcgtgaactgt
gcaaagcctttctgcaagaggcgaaatggtccaacaacaaaattatcccggctttctccaagta
cctggaaaacgccagcgtttcctcctccggtgtagcgctgctggcgccgtcttacttttccgta

Figure 22C tgccagcagcaggaagacatctccgaccacgcgctgcgttccctgaccgacttccatggtctgg
tgcgttctagctgcgttatcttccgcctgtgcaacgatctggccacctctgcggcggagctgga
acgtggcgagactaccaattctatcattagctacatgcacgaaaacgatggtaccagcgaggaa
caggcccgcgaagaactgcgtaaactgatcgacgccgaatggaaaaagatgaatcgtgaacgcg
ttagcgactccaccctgctgcctaaagcgttcatggaaatcgcagttaacatggcacgtgtttc
ccactgcacctaccagtatggcgatggtctgggtcgcccagactacgcgactgaaaaccgcatc
aaactgctgctgattgaccctttcccgattaaccagctgatgtatgtctaactgcatcgccctt
aggaggtaaaaaaaaatgactgccgacaacaatagtatgccccatggtgcagtatctagttacg
ccaaattagtgcaaaaccaaacacctgaagacattttggaagagtttcctgaaattattccatt
acaacaaagacctaatacccgatctagtgagacgtcaaatgacgaaagcggagaaacatgtttt
tctggtcatgatgaggagcaaattaagttaatgaatgaaaattgtattgttttggattgggacg
ataatgctattggtgccggtaccaagaaagtttgtcatttaatggaaaatattgaaaagggttt
actacatcgtgcattctccgtctttattttcaatgaacaaggtgaattacttttacaacaaaga
gccactgaaaaaataactttccctgatctttggactaacacatgctgctctcatccactatgta
ttgatgacgaattaggtttgaagggtaagctagacgataagattaagggcgctattactgcggc
ggtgagaaaactagatcatgaattaggtattccagaagatgaaactaagacaaggggtaagttt
cactttttaaacagaatccattacatggcaccaagcaatgaaccatggggtgaacatgaaattg
attacatcctattttataagatcaacgctaaagaaaacttgactgtcaacccaaacgtcaatga
agttagagacttcaaatgggtttcaccaaatgatttgaaaactatgtttgctgacccaagttac
aagtttacgccttggtttaagattatttgcgagaattacttattcaactggtgggagcaattag
atgacctttctgaagtggaaaatgacaggcaaattcatagaatgctataacaacgcgtcctgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagtttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg

Figure 22D cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgca
(SEQ ID NO:20)

Figure 25A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatggatccgagctcggatccactagtaacggccgcc
agtgtgctggaattcgcccttaggaggtaaaaaaacatgtcattaccgttcttaacttctgcac
cgggaaaggttattattttggtgaacactctgctgtgtacaacaagcctgccgtcgctgctag
tgtgtctgcgttgagaacctacctgctaataagcgagtcatctgcaccagatactattgaattg
gacttcccggacattagctttaatcataagtggtccatcaatgatttcaatgccatcaccgagg
atcaagtaaactcccaaaaattggccaaggctcaacaagccaccgatggcttgtctcaggaact
cgttagtcttttggatccgttgttagctcaactatccgaatccttccactaccatgcagcgttt
tgtttcctgtatatgtttgtttgcctatgcccccatgccaagaatattaagttttctttaaagt
ctactttacccatcggtgctgggttgggctcaagcgcctctatttctgtatcactggccttagc
tatggcctacttgggggggttaataggatctaatgacttggaaaagctgtcagaaaacgataag
catatagtgaatcaatgggccttcataggtgaaaagtgtattcacggtaccccttcaggaatag
ataacgctgtggccacttatggtaatgccctgctatttgaaaaagactcacataatggaacaat
aaacacaaacaattttaagttcttagatgatttcccagccattccaatgatcctaacctatact
agaattccaaggtctacaaaagatcttgttgctcgcgttcgtgtgttggtcaccgagaaatttc
ctgaagttatgaagccaattctagatgccatgggtgaatgtgccctacaaggcttagagatcat
gactaagttaagtaaatgtaaaggcaccgatgacgaggctgtagaaactaataatgaactgtat
gaacaactattggaattgataagaataaatcatggactgcttgtctcaatcggtgtttctcatc
ctggattagaacttattaaaaatctgagcgatgatttgagaattggctccacaaaacttaccgg
tgctggtggcggcggttgctctttgactttgttacgaagagacattactcaagagcaaattgac
agcttcaaaaagaaattgcaagatgattttagttacgagacatttgaaacagacttgggtggga
ctggctgctgtttgttaagcgcaaaaaatttgaataaagatcttaaaatcaaatccctagtatt
ccaattatttgaaaataaaactaccacaaagcaacaaattgacgatctattattgccaggaaac
acgaatttaccatggacttcataagctaatttgcgataggcctgcacccttaaggaggaaaaaa
acatgtcagagttgagagccttcagtgccccagggaaagcgttactagctggtggatatttagt
tttagatacaaaatatgaagcatttgtagtcggattatcggcaagaatgcatgctgtagcccat
ccttacggttcattgcaagggtctgataagtttgaagtgcgtgtgaaaagtaaacaatttaaag
atggggagtggctgtaccatataagtcctaaaagtggcttcattcctgtttcgataggcggatc
taagaaccctttcattgaaaaagttatcgctaacgtatttagctactttaaacctaacatggac
gactactgcaatagaaacttgttcgttattgatattttctctgatgatgcctaccattctcagg
aggatagcgttaccgaacatcgtggcaacagaagattgagttttcattcgcacagaattgaaga
agttcccaaaacagggctgggctcctcggcaggtttagtcacagttttaactacagctttggcc
tcctttttttgtatcggacctggaaaataatgtagacaaatatagagaagttattcataatttag
cacaagttgctcattgtcaagctcagggtaaaattggaagcgggtttgatgtagcggcggcagc
atatggatctatcagatatagaagattcccacccgcattaatctctaatttgccagatattgga
agtgctacttacggcagtaaactggcgcatttggttgatgaagaagactggaatattacgatta
aaagtaaccatttaccttcgggattaactttatggatggcgatattaagaatggttcagaaac
agtaaaactggtccagaaggtaaaaaattggtatgattcgcatatgccagaaagcttgaaata

Figure 25B tatacagaactcgatcatgcaaattctagatttatggatggactatctaaactagatcgcttac
acgagactcatgacgattacagcgatcagatatttgagtctcttgagaggaatgactgtacctg
tcaaaagtatcctgaaatcacagaagttagagatgcagttgccacaattagacgttcctttaga
aaaataactaaagaatctggtgccgatatcgaacctcccgtacaaactagcttattggatgatt
gccagaccttaaaaggagttcttacttgcttaatacctggtgctggtggttatgacgccattgc
agtgattactaagcaagatgttgatcttagggctcaaaccgctaatgacaaaagattttctaag
gttcaatggctggatgtaactcaggctgactggggtgttaggaaagaaaaagatccggaaactt
atcttgataaataacttaaggtagctgcatgcagaattcgcccttaaggaggaaaaaaaatga
ccgtttacacagcatccgttaccgcacccgtcaacatcgcaacccttaagtattgggggaaaag
ggacacgaagttgaatctgcccaccaattcgtccatatcagtgactttatcgcaagatgacctc
agaacgttgacctctgcggctactgcacctgagtttgaacgcgacactttgtggttaaatggag
aaccacacagcatcgacaatgaaagaactcaaaattgtctgcgcgacctacgccaattaagaaa
ggaaatggaatcgaaggacgcctcattgcccacattatctcaatggaaactccacattgtctcc
gaaaataactttcctacagcagctggtttagcttcctccgctgctggctttgctgcattggtct
ctgcaattgctaagttataccaattaccacagtcaacttcagaaatatctagaatagcaagaaa
ggggtctggttcagcttgtagatcgttgtttggcggatacgtggcctgggaaatgggaaaagct
gaagatggtcatgattccatggcagtacaaatcgcagacagctctgactggcctcagatgaaag
cttgtgtcctagttgtcagcgatattaaaaaggatgtgagttccactcagggtatgcaattgac
cgtggcaacctccgaactatttaaagaaagaattgaacatgtcgtaccaaagagatttgaagtc
atgcgtaaagccattgttgaaaaagatttcgccacctttgcaaaggaaacaatgatggattcca
actctttccatgccacatgtttggactctttccctccaatattctacatgaatgacacttccaa
gcgtatcatcagttggtgccacaccattaatcagttttacggagaaacaatcgttgcatacacg
tttgatgcaggtccaaatgctgtgttgtactacttagctgaaaatgagtcgaaactctttgcat
ttatctataaattgtttggctctgttcctggatgggacaagaaatttactactgagcagcttga
ggctttcaaccatcaatttgaatcatctaactttactgcacgtgaattggatcttgagttgcaa
aaggatgttgccagagtgattttaactcaagtcggttcaggcccacaagaaacaaacgaatctt
tgattgacgcaaagactggtctaccaaaggaataagatcaattcgctgcatcgcccttaggagg
taaaaaaaaatgactgccgacaacaatagtatgccccatggtgcagtatctagttacgccaaat
tagtgcaaaaccaaacacctgaagacattttggaagagtttcctgaaattattccattacaaca
aagacctaatacccgatctagtgagacgtcaaatgacgaaagcggagaaacatgtttttctggt
catgatgaggagcaaattaagttaatgaatgaaaattgtattgttttggattgggacgataatg
ctattggtgccggtaccaagaaagtttgtcatttaatggaaaatattgaaaagggtttactaca
tcgtgcattctccgtctttattttcaatgaacaaggtgaattacttttacaacaaagagccact
gaaaaaataactttccctgatctttggactaacacatgctgctctcatccactatgtattgatg
acgaattaggtttgaagggtaagctagacgataagattaagggcgctattactgcggcggtgag
aaaactagatcatgaattaggtattccagaagatgaaactaagacaaggggtaagtttcacttt
ttaaacagaatccattacatggcaccaagcaatgaaccatggggtgaacatgaaattgattaca
tcctattttataagatcaacgctaaagaaaacttgactgtcaacccaaacgtcaatgaagttag
agacttcaaatgggtttcaccaaatgatttgaaaactatgtttgctgacccaagttacaagttt
acgccttggtttaagattatttgcgagaattacttattcaactggtgggagcaattagatgacc
tttctgaagtggaaaatgacaggcaaattcatagaatgctataacaacgcgtcctgcattcgcc
cttaggaggtaaaaaaacatgtgtgcgacctcttctcaatttactcagattaccgagcataatt
cccgtcgttccgcaaactatcagccaaacctgtggaatttcgaattcctgcaatccctggagaa
cgacctgaaagtggaaaagctggaggagaaagcgaccaaactggaggaagaagttcgctgcatg

Figure 25C atcaaccgtgtagacacccagccgctgtccctgctggagctgatcgacgatgtgcagcgcctgg
gtctgacctacaaatttgaaaaagacatcattaaagccctggaaaacatcgtactgctggacga
aaacaaaaagaacaaatctgacctgcacgcaaccgctctgtctttccgtctgctgcgtcagcac
ggtttcgaggtttctcaggatgtttttgagcgtttcaaggataaagaaggtggtttcagcggtg
aactgaaaggtgacgtccaaggcctgctgagcctgtatgaagcgtcttacctgggtttcgaggg
tgagaacctgctggaggaggcgcgtaccttttccatcacccacctgaagaacaacctgaaagaa
ggcattaataccaaggttgcagaacaagtgagccacgccctggaactgccatatcaccagcgtc
tgcaccgtctggaggcacgttggttcctggataaatacgaaccgaaagaaccgcatcaccagct
gctgctggagctggcgaagctggattttaacatggtacagaccctgcaccagaaagagctgcaa
gatctgtcccgctggtggaccgagatgggcctggctagcaaactggattttgtacgcgaccgcc
tgatggaagtttatttctgggcactgggtatggcgccagacccgcagtttggtgaatgtcgcaa
agctgttactaaaatgtttggtctggtgacgatcatcgatgacgtgtatgacgtttatggcact
ctggacgaactgcaactgttcaccgatgctgtagagcgctgggacgttaacgctattaacaccc
tgccggactatatgaaactgtgtttcctggcactgtacaacaccgttaacgacacgtcctattc
tattctgaaagagaaaggtcataacaacctgtcctatctgacgaaaagctggcgtgaactgtgc
aaagcctttctgcaagaggcgaaatggtccaacaacaaaattatcccggctttctccaagtacc
tggaaaacgccagcgtttcctcctccggtgtagcgctgctggcgccgtcttacttttccgtatg
ccagcagcaggaagacatctccgaccacgcgctgcgttccctgaccgacttccatggtctggtg
cgttctagctgcgttatcttccgcctgtgcaacgatctggccacctctgcggcggagctggaac
gtggcgagactaccaattctatcattagctacatgcacgaaaacgatggtaccagcgaggaaca
ggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttccc
actgcacctaccagtatggcgatggtctgggtcgcccagactacgcgactgaaaaccgcatcaa
actgctgctgattgaccctttcccgattaaccagctgatgtatgtctaactgcagctggtacca
tatgggaattcgaagctttctagaacaaaaactcatctcagaagaggatctgaatagcgccgtc
gaccatcatcatcatcatcattgagtttaaacggtctccagcttggctgttttggcggatgaga
gaagattttcagcctgatacagattaaatcagaacgcagaagcggtctgataaaacagaatttg
cctggcggcagtagcgcggtggtcccacctgaccccatgccgaactcagaagtgaaacgccgta
gcgccgatggtagtgtggggtctccccatgcgagagtagggaactgccaggcatcaaataaaac
gaaaggctcagtcgaaagactgggcctttcgttttatctgttgtttgtcggtgaacgctctcct
gagtaggacaaatccgccgggagcggatttgaacgttgcgaagcaacggcccggagggtggcgg
gcaggacgcccgccataaactgccaggcatcaaattaagcagaaggccatcctgacggatggcc
tttttgcgtttctacaaactctttttgtttatttttctaaatacattcaaatatgtatccgctt
aaccggaattgccagctggggcgccctctggtaaggttgggaagccctgcaaagtaaactggat
ggctttctcgccgccaaggatctgatggcgcaggggatcaagctctgatcaagagacaggatga
ggatcgtttcgcatgattgaacaagatggattgcacgcaggttctccggccgcttgggtggaga
ggctattcggctatgactgggcacaacagacaatcggctgctctgatgccgccgtgttccggct
gtcagcgcaggggcgcccggttctttttgtcaagaccgacctgtccggtgccctgaatgaactg
caagacgaggcagcgcggctatcgtggctggccacgacgggcgttccttgcgcagctgtgctcg
acgttgtcactgaagcgggaagggactggctgctattgggcgaagtgccggggcaggatctcct
gtcatctcaccttgctcctgccgagaaagtatccatcatggctgatgcaatgcggcggctgcat
acgcttgatccggctacctgcccattcgaccaccaagcgaaacatcgcatcgagcgagcacgta
ctcggatggaagccggtcttgtcgatcaggatgatctggacgaagagcatcaggggctcgcgcc
agccgaactgttcgccaggctcaaggcgagcatgcccgacggcgaggatctcgtcgtgacccat

Figure 25D ggcgatgcctgcttgccgaatatcatggtggaaaatggccgcttttctggattcatcgactgtg
gccggctgggtgtggcggaccgctatcaggacatagcgttggctacccgtgatattgctgaaga
gcttggcggcgaatgggctgaccgcttcctcgtgctttacggtatcgccgctcccgattcgcag
cgcatcgccttctatcgccttcttgacgagttcttctgacgcatgaccaaaatcccttaacgtg
agttttcgttccactgagcgtcagaccccgtagaaaagatcaaaggatcttcttgagatccttt
ttttctgcgcgtaatctgctgcttgcaaacaaaaaaaccaccgctaccagcggtggtttgtttg
ccggatcaagagctaccaactctttttccgaaggtaactggcttcagcagagcgcagataccaa
atactgtccttctagtgtagccgtagttaggccaccacttcaagaactctgtagcaccgcctac
atacctcgctctgctaatcctgttaccagtggctgctgccagtggcgataagtcgtgtcttacc
gggttggactcaagacgatagttaccggataaggcgcagcggtcgggctgaacggggggttcgt
gcacacagcccagcttggagcgaacgacctacaccgaactgagatacctacagcgtgagctatg
agaaagcgccacgcttcccgaagggagaaaggcggacaggtatccggtaagcggcagggtcgga
acaggagagcgcacgagggagcttccagggggaaacgcctggtatctttatagtcctgtcgggt
ttcgccacctctgacttgagcgtcgatttttgtgatgctcgtcaggggggcggagcctatggaa
aaacgccagcaacgcggcctttttacggttcctggccttttgctggccttttgctcacatgttc
tttcctgcgttatcccctgattctgtggataaccgtattaccgcctttgagtgagctgataccg
ctcgccgcagccgaacgaccgagcgcagcgagtcagtgagcgaggaagcggaagagcgcctgat
gcggtattttctccttacgcatctgtgcggtatttcacaccgcatatggtgcactctcagtaca
atctgctctgatgccgcatagttaagccagtatacactccgctatcgctacgtgactgggtcat
ggctgcgccccgacacccgccaacacccgctgacgcgccctgacgggcttgtctgctcccggca
tccgcttacagacaagctgtgaccgtctccgggagctgcatgtgtcagaggttttcaccgtcat
caccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaat
tcagggtggtgaatgtgaaaccagtaacgttatacgatgtcgcagagtatgccggtgtctctta
tcagaccgtttcccgcgtggtgaaccaggccagccacgtttctgcgaaaacgcgggaaaaagtg
gaagcggcgatggcggagctgaattacattcccaaccgcgtggcacaacaactggcgggcaaac
agtcgttgctgattggcgttgccacctccagtctggccctgcacgcgccgtcgcaaattgtcgc
ggcgattaaatctcgcgccgatcaactgggtgccagcgtggtggtgtcgatggtagaacgaagc
ggcgtcgaagcctgtaaagcggcggtgcacaatcttctcgcgcaacgcgtcagtgggctgatca
ttaactatccgctggatgaccaggatgccattgctgtggaagctgcctgcactaatgttccggc
gttatttcttgatgtctctgaccagacacccatcaacagtattattttctcccatgaagacggt
acgcgactgggcgtggagcatctggtcgcattgggtcaccagcaaatcgcgctgttagcgggcc
cattaagttctgtctcggcgcgtctgcgtctggctggctggcataaatatctcactcgcaatca
aattcagccgatagcggaacgggaaggcgactggagtgccatgtccggttttcaacaaaccatg
caaatgctgaatgagggcatcgttcccactgcgatgctggttgccaacgatcagatggcgctgg
gcgcaatgcgcgccattaccgagtccgggctgcgcgttggtgcggatatctcggtagtgggata
cgacgataccgaagacagctcatgttatatcccgccgtcaaccaccatcaaacaggattttcgc
ctgctggggcaaaccagcgtggaccgcttgctgcaactctctcagggccaggcggtgaagggca
atcagctgttgcccgtctcactggtgaaaagaaaaaccaccctggcgcccaatacgcaaaccgc
ctctccccgcgcgttggccgattcattaatgcagctggcacgacaggtttcccgactggaaagc
gggcagtgagcgcaacgcaattaatgtgagttagcgcgaattgatctg
(SEQ ID NO:33)

Figure 27A

5′-
cccgtcttactgtcgggaattcgcgttggccgattcattaatgcagattctgaaatgagctgtt
gacaattaatcatccggctcgtataatgtgtggaattgtgagcggataacaatttcacacagga
aacagcgccgctgagaaaaagcgaagcggcactgctctttaacaatttatcagacaatctgtgt
gggcactcgaccggaattatcgattaactttattattaaaaattaaagaggtatatattaatgt
atcgattaaataaggaggaataaaccatggatccgagctcaggaggtaaaaaaacatgaaaaca
gtagttattattgatgcattacgaacaccaattggaaaatataaaggcagcttaagtcaagtaa
gtgccgtagacttaggaacacatgttacaacacaacttttaaaaagacattccactatttctga
agaaattgatcaagtaatctttggaaatgttttacaagctggaaatggccaaaatcccgcacga
caaatagcaataaacagcggtttgtctcatgaaattcccgcaatgacggttaatgaggtctgcg
gatcaggaatgaaggccgttattttggcgaaacaattgattcaattaggagaagcggaagtttt
aattgctggcgggattgagaatatgtcccaagcacctaaattacaacgttttaattacgaaaca
gaaagctacgatgcgcctttttctagtatgatgtatgatggattaacggatgcctttagtggtc
aggcaatgggcttaactgctgaaaatgtggccgaaaagtatcatgtaactagagaagagcaaga
tcaattttctgtacattcacaattaaaagcagctcaagcacaagcagaagggatattcgctgac
gaaatagccccattagaagtatcaggaacgcttgtggagaaagatgaagggattcgccctaatt
cgagcgttgagaagctaggaacgcttaaaacagtttttaaagaagacggtactgtaacagcagg
gaatgcatcaaccattaatgatggggcttctgctttgattattgcttcacaagaatatgccgaa
gcacacggtcttccttatttagctattattcgagacagtgtggaagtcggtattgatccagcct
atatgggaatttcgccgattaaagccattcaaaaactgttagcgcgcaatcaacttactacgga
agaaattgatctgtatgaaatcaacgaagcatttgcagcaacttcaatcgtggtccaaagagaa
ctggctttaccagaggaaaaggtcaacatttatggtggcggtatttcattaggtcatgcgattg
gtgccacaggtgctcgtttattaacgagtttaagttatcaattaaatcaaaaagaaaagaaata
tggagtggcttctttatgtatcggcggtggcttaggactcgctatgctactagagagacctcag
caaaaaaaaaacagccgattttatcaaatgagtcctgaggaacgcctggcttctcttcttaatg
aaggccagatttctgctgatacaaaaaaagaatttgaaaatacggctttatcttcgcagattgc
caatcatatgattgaaaatcaaatcagtgaaacagaagtgccgatgggcgttggcttacattta
acagtggacgaaactgattatttggtaccaatggcgacagaagagccctcagttattgcggctt
tgagtaatggtgcaaaaatagcacaaggatttaaaacagtgaatcaacaacgcttaatgcgtgg
acaaatcgtttttttacgatgttgcagatcccgagtcattgattgataaactacaagtaagagaa
gcggaagtttttcaacaagcagagttaagttatccatctatcgttaaacggggcggcggcttaa
gagatttgcaatatcgtacttttgatgaatcatttgtatctgtcgactttttagtagatgttaa
ggatgcaatgggggcaaatatcgttaacgctatgttggaaggtgtggccgagttgttccgtgaa
tggtttgcggagcaaaagattttattcagtattttaagtaattatgccacggagtcggttgtta
cgatgaaaacggctattccagtttcacgtttaagtaaggggagcaatggccgggaaattgctga
aaaaattgttttagcttcacgctatgcttcattagatccttatcgggcagtcacgcataacaaa
ggaatcatgaatggcattgaagctgtagttttagctacaggaaatgatacacgcgctgttagcg
cttcttgtcatgcttttgcggtgaaggaaggtcgctaccaaggcttgactagttggacgctgga
tggcgaacaactaattggtgaaatttcagttccgcttgctttagccacggttggcggtgccaca
aaagtcttacctaaatctcaagcagctgctgatttgttagcagtgacggatgcaaaagaactaa
gtcgagtagtagcggctgttggtttggcacaaaatttagcggcgttacgggccttagtctctga
aggaattcaaaaaggacacatggctctacaagcacgttctttagcgatgacggtcggagctact
ggtaaagaagttgaggcagtcgctcaacaattaaaacgtcaaaaaacgatgaaccaagaccgag
ccatggctattttaaatgatttaagaaaacaataaaggaggtaaaaaaacatgacaattggat

Figure 27B tgataaaattagtttttttgtgccccttattatattgatatgacggcactggctgaagccaga
aatgtagaccctggaaaatttcatattggtattgggcaagaccaaatggcggtgaacccaatca
gccaagatattgtgacatttgcagccaatgccgcagaagcgatcttgaccaaagaagataaaga
ggccattgatatggtgattgtcgggactgagtccagtatcgatgagtcaaaagcggccgcagtt
gtcttacatcgtttaatggggattcaacctttcgctcgctctttcgaaatcaaggaagcttgtt
acggagcaacagcaggcttacagttagctaagaatcacgtagccttacatccagataaaaagt
cttggtcgtagcggcagatattgcaaaatatggcttaaattctggcggtgagcctacacaagga
gctggggcggttgcaatgttagttgctagtgaaccgcgcattttggctttaaaagaggataatg
tgatgctgacgcaagatatctatgacttttggcgtccaacaggccacccgtatcctatggtcga
tggtcctttgtcaaacgaaacctacatccaatcttttgcccaagtctgggatgaacataaaaa
cgaaccggtcttgattttgcagattatgatgctttagcgttccatattccttacacaaaaatgg
gcaaaaaagccttattagcaaaaatctccgaccaaactgaagcagaacaggaacgaattttagc
ccgttatgaagaaagtatcgtctatagtcgtcgcgtaggaaacttgtatacgggttcactttat
ctgggactcatttccctttagaaaatgcaacgactttaaccgcaggcaatcaaattggtttat
tcagttatggttctggtgctgtcgctgaatttttcactggtgaattagtagctggttatcaaaa
tcatttacaaaaagaaactcatttagcactgctggataatcggacagaactttctatcgctgaa
tatgaagccatgtttgcagaaactttagacacagacattgatcaaacgttagaagatgaattaa
aatatagtatttctgctattaataataccgttcgttcttatcgaaactaagagatctgcagctg
gtaccatatgggaattcgaagcttgggcccgaacaaaaactcatctcagaagaggatctgaata
gcgccgtcgaccatcatcatcatcatcattgagtttaaacggtctccagcttggctgttttggc
ggatgagagaagattttcagcctgatacagattaaatcagaacgcagaagcggtctgataaaac
agaatttgcctggcggcagtagcgcggtggtcccacctgaccccatgccgaactcagaagtgaa
acgccgtagcgccgatggtagtgtggggtctccccatgcgagagtagggaactgccaggcatca
aataaaacgaaaggctcagtcgaaagactgggcctttcgttttatctgttgtttgtcggtgaac
gctctcctgagtaggacaaatccgccgggagcggatttgaacgttgcgaagcaacggcccggag
ggtggcgggcaggacgcccgccataaactgccaggcatcaaattaagcagaaggccatcctgac
ggatggcctttttgcgtttctacaaactctttttgtttatttttctaaatacattcaaatatgt
atccgctcatgagacaataaccctgataaatgcttcaataatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc
tgatgccgcatagttaagccagccccgacacccgccaacacccgctgacgagcttagtaaagcc
ctcgctagatttaatgcggatgttgcgattacttcgccaactattgcgataacaagaaaagc
cagcctttcatgatatatctcccaatttgtgtagggcttattatgcacgcttaaaaataataa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat

Figure 27C caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatctttttttacaccgttttcatct
gtgcatatggacagttttccctttgatatgtaacggtgaacagttgttctactttttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaattttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc
cttgtgagttttcttttgtgttagttcttttaataaccactcataaatcctcatagagtatttg
ttttcaaaagacttaacatgttccagattatattttatgaattttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtcctttttcctttgagttgtgggtat
ctgtaaattctgctagacctttgctggaaaacttgtaaattctgctagaccctctgtaaattcc
gctagacctttgtgtgtttttttttgtttatattcaagtggttataatttatagaataaagaaag
aataaaaaaagataaaaagaatagatcccagccctgtgtataactcactactttagtcagttcc
gcagtattacaaaaggatgtcgcaaacgctgtttgctcctctacaaaacagaccttaaaaccct
aaaggcttaagtagcaccctcgcaagctcgggcaaatcgctgaatattccttttgtctccgacc

Figure 27D

Atcaggcacctgagtcgctgtctttttcgtgacattcagttcgctgcgctcacggctctggcag
tgaatgggggtaaatggcactacaggcgccttttatggattcatgcaaggaaactacccataat
acaagaaaagcccgtcacgggcttctcagggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:46)

Lower Pathway Bacillus Cassette 9271 bp

Figure 29A

5'-
tgtaacctttgctttcaaatgagtagaaataatgcacatccatgtttgtatcgtgcaaataaag
tgtttcatccgtaggaaaaaatgactttagtatctgttccgctttttctgatgaaatgtgctcc
ccgacaaaattgaatgaatcatggacatttgctggctttgatacagcgaaagcagccgttccta
tgttatatatcggatttaacagcaggacaaaaaacaccatgacagccatcgtcacccacttatt
cacacgcacataaacctttcctgacttttggaacagatgatagctcatcaaaaatcccgccatt
gccaaataaatcgtatatggcattactgcaccataatcttttgagatttgattgggatatggcg
caagcagcaagacaagcagtccgataatcagcgtataaaataagcctagtaagatcttatccgt
tctccaatacagcttgaaaaacactacattcaacgcaatgggaagagtgatgatgaaaaacaga
aacacgaatgcaatcggctccatcccatccgggtattccttccaatacgaaaagaaactaaaaa
tcatttgtacgatcggcaaactgacaacagcaaggtcgaacgtataaacttaccctttccgcc
atgatcacgcggcatcagcatatagtgaaaagccgtcagcagcacatatccgtataacaaaaaa
tgcagcagcggcagcagttcttttccgtcctctcttaagtaagcgctggtgaagtttgttgatt
gcacctggtgaataagttcaacagacactcccgccagcagcacaatccgcaatataacacccgc
caagaacattgtgcgctgccggtttattttgggatgatgcaccaaaagatataagcccgccaga
acaacaattgaccattgaatcagcagggtgctttgtctgcttaatataaaataacgttcgaaat
gcaatacataatgactgaataactccaacacgaacaacaactccatttcttctgctatcaaaa
taacagactcgtgattttccaaacgagctttcaaaaaagcctctgccccttgcaaatcggatgc
ctgtctataaaattcccgatattggttaaacagcggcgcaatggcggccgcatctgatgtcttt
gcttggcgaatgttcatcttatttcttcctccctctcaataatttttttcattctatccctttc
tgtaaagtttatttttcagaatacttttatcatcatgctttgaaaaaatatcacgataatatcc
attgttctcacggaagcacacgcaggtcatttgaacgaatttttttcgacaggaatttgccgga
ctcaggagcatttaacctaaaaaagcatgacatttcagcataatgaacatttactcatgtctat
tttcgttcttttctgtatgaaaatagttatttcgagtctctacggaaatagcgagagatgatat
acctaaatagagataaaatcatctcaaaaaaatgggtctactaaatattattccatctattac
aataaattcacagaatagtcttttaagtaagtctactctgaatttttttaaaaggagagggtaa
agagtgtcattaccgttcttaacttctgcaccgggaaaggttattatttttggtgaacactctg
ctgtgtacaacaagcctgccgtcgctgctagtgtgtctgcgttgagaacctacctgctaataag
cgagtcatctgcaccagatactattgaattggacttcccggacattagctttaatcataagtgg
tccatcaatgatttcaatgccatcaccgaggatcaagtaaactcccaaaaattggccaaggctc
aacaagccaccgatggcttgtctcaggaactcgttagtcttttggatccgttgttagctcaact
atccgaatccttccactaccatgcagcgttttgtttcctgtatatgtttgtttgcctatgcccc
catgccaagaatattaagttttctttaaagtctactttacccatcggtgctgggttgggctcaa
gcgcctctatttctgtatcactggccttagctatggcctacttggggggttaataggatctaa
tgacttggaaaagctgtcagaaaacgataagcatatagtgaatcaatgggccttcataggtgaa
aagtgtattcacggtaccccttcaggaatagataacgctgtggccacttatggtaatgccctgc
tatttgaaaaagactcacataatggaacaataaacacaaacaattttaagttcttagatgattt
cccagccattccaatgatcctaacctatactagaattccaaggtctacaaaagatcttgttgct
cgcgttcgtgtgttggtcaccgagaaatttcctgaagttatgaagccaattctagatgccatgg
gtgaatgtgccctacaaggcttagagatcatgactaagttaagtaaatgtaaaggcaccgatga
cgaggctgtagaaactaataatgaactgtatgaacaactattggaattgataagaataaatcat
ggactgcttgtctcaatcggtgtttctcatcctggattagaacttattaaaaatctgagcgatg
atttgagaattggctccacaaaacttaccggtgctggtggcggcggttgctctttgactttgtt
acgaagagacattactcaagagcaaattgacagcttcaaaaagaaattgcaagatgattttagt

Figure 29B tacgagacatttgaaacagacttgggtgggactggctgctgtttgttaagcgcaaaaaatttga
ataaagatcttaaaatcaaatccctagtattccaattatttgaaaataaaactaccacaaagca
acaaattgacgatctattattgccaggaaacacgaatttaccatggacttcataaaggagagg
gtgtcagagttgagagccttcagtgccccagggaaagcgttactagctggtggatatttagttt
tagatacaaaatatgaagcatttgtagtcggattatcggcaagaatgcatgctgtagcccatcc
ttacggttcattgcaagggtctgataagtttgaagtgcgtgtgaaaagtaaacaatttaaagat
ggggagtggctgtaccatataagtcctaaaagtggcttcattcctgtttcgataggcggatcta
agaaccctttcattgaaaaagttatcgctaacgtatttagctactttaaacctaacatggacga
ctactgcaatagaaacttgttcgttattgatattttctctgatgatgcctaccattctcaggag
gatagcgttaccgaacatcgtggcaacagaagattgagttttcattcgcacagaattgaagaag
ttcccaaaacagggctgggctcctcggcaggtttagtcacagttttaactacagctttggcctc
ctttttgtatcggacctggaaaataatgtagacaaatatagagaagttattcataatttagca
caagttgctcattgtcaagctcagggtaaaattggaagcgggtttgatgtagcggcggcagcat
atggatctatcagatatagaagattcccacccgcattaatctctaatttgccagatattggaag
tgctacttacggcagtaaactggcgcatttggttgatgaagaagactggaatattacgattaaa
agtaaccatttaccttcgggattaactttatggatgggcgatattaagaatggttcagaaacag
taaaactggtccagaaggtaaaaaattggtatgattcgcatatgccagaaagcttgaaaatata
tacagaactcgatcatgcaaattctagatttatggatggactatctaaactagatcgcttacac
gagactcatgacgattacagcgatcagatatttgagtctcttgagaggaatgactgtacctgtc
aaaagtatcctgaaatcacagaagttagagatgcagttgccacaattagacgttcctttagaaa
aataactaaagaatctggtgccgatatcgaacctcccgtacaaactagcttattggatgattgc
cagaccttaaaaggagttcttacttgcttaatacctggtgctggtggttatgacgccattgcag
tgattactaagcaagatgttgatcttagggctcaaaccgctaatgacaaaagattttctaaggt
tcaatggctggatgtaactcaggctgactggggtgttaggaaagaaaaagatccggaaacttat
cttgataaataaaggagagggtgaccgtttacacagcatccgttaccgcacccgtcaacatcg
caacccttaagtattggggaaaagggacacgaagttgaatctgcccaccaattcgtccatatc
agtgactttatcgcaagatgacctcagaacgttgacctctgcggctactgcacctgagtttgaa
cgcgacactttgtggttaaatggagaaccacacagcatcgacaatgaaagaactcaaaattgtc
tgcgcgacctacgccaattaagaaaggaaatggaatcgaaggacgcctcattgcccacattatc
tcaatggaaactccacattgtctccgaaaataactttcctacagcagctggtttagcttcctcc
gctgctggctttgctgcattggtctctgcaattgctaagttataccaattaccacagtcaactt
cagaaatatctagaatagcaagaaaggggtctggttcagcttgtagatcgttgtttggcggata
cgtggcctgggaaatgggaaaagctgaagatggtcatgattccatggcagtacaaatcgcagac
agctctgactggcctcagatgaaagcttgtgtcctagttgtcagcgatattaaaaaggatgtga
gttccactcagggtatgcaattgaccgtggcaacctccgaactatttaaagaaagaattgaaca
tgtcgtaccaaagagatttgaagtcatgcgtaaagccattgttgaaaaagatttcgccaccttt
gcaaaggaaacaatgatggattccaactctttccatgccacatgtttggactctttccctccaa
tattctacatgaatgacacttccaagcgtatcatcagttggtgccacaccattaatcagtttta
cggagaaacaatcgttgcatacacgtttgatgcaggtccaaatgctgtgttgtactacttagct
gaaaatgagtcgaaactctttgcatttatctataaattgtttggctctgttcctggatgggaca
agaaatttactactgagcagcttgaggctttcaaccatcaatttgaatcatctaactttactgc
acgtgaattggatcttgagttgcaaaaggatgttgccagagtgattttaactcaagtcggttca
ggcccacaagaaacaaacgaatctttgattgacgcaaagactggtctaccaaaggaataaaagg
agagggtgactgccgacaacaatagtatgccccatggtgcagtatctagttacgccaaattagt

Figure 29C gcaaaaccaaacacctgaagacattttggaagagtttcctgaaattattccattacaacaaaga
cctaatacccgatctagtgagacgtcaaatgacgaaagcggagaaacatgtttttctggtcatg
atgaggagcaaattaagttaatgaatgaaaattgtattgttttggattgggacgataatgctat
tggtgccggtaccaagaaagtttgtcatttaatggaaaatattgaaaagggtttactacatcgt
gcattctccgtctttattttcaatgaacaaggtgaattacttttacaacaaagagccactgaaa
aaataactttccctgatctttggactaacacatgctgctctcatccactatgtattgatgacga
attaggtttgaagggtaagctagacgataagattaagggcgctattactgcggcggtgagaaaa
ctagatcatgaattaggtattccagaagatgaaactaagacaaggggtaagtttcactttttaa
acagaatccattacatggcaccaagcaatgaaccatggggtgaacatgaaattgattacatcct
attttataagatcaacgctaaagaaaacttgactgtcaacccaaacgtcaatgaagttagagac
ttcaaatgggtttcaccaaatgatttgaaaactatgtttgctgacccaagttacaagtttacgc
cttggtttaagattatttgcgagaattacttattcaactggtgggagcaattagatgacctttc
tgaagtggaaaatgacaggcaaattcatagaatgctataaaaaaaaccggccttggccccgccg
gtttttattatttttcttcctccgcatgttcaatccgctccataatcgacggatggctccctc
tgaaaattttaacgagaaacggcgggttgacccggctcagtcccgtaacggccaagtcctgaaa
cgtctcaatcgccgcttcccggtttccggtcagctcaatgccgtaacggtcggcggcgttttcc
tgataccgggagacggcattcgtaatttgaatacatacgaacaaattaataaagtgaaaaaaat
acttcggaaacatttaaaaaataaccttattggtacttacatgtttggatcaggagttgagagt
ggactaaaaccaaatagtgatcttgactttttagtcgtcgtatctgaaccattgacagatcaaa
gtaaagaaatacttatacaaaaaattagacctatttcaaaaaaaataggagataaaagcaactt
acgatatattgaattaacaattattattcagcaagaaatggtaccgtggaatcatcctcccaaa
caagaatttatttatggagaatggttacaagagctttatgaacaaggatacattcctcagaagg
aattaaattcagatttaaccataatgctttaccaagcaaaacgaaaaaataaaagaatatacgg
aaattatgacttagaggaattactacctgatattccattttctgatgtgagaagagccattatg
gattcgtcagaggaattaatagataattatcaggatgatgaaaccaactctatattaactttat
gccgtatgattttaactatggacacgggtaaaatcataccaaaagatattgcgggaaatgcagt
ggctgaatcttctccattagaacatagggagagaattttgttagcagttcgtagttatcttgga
gagaatattgaatggactaatgaaaatgtaaatttaactataaactatttaaataacagattaa
aaaaattataatgtaacctttgctttcaaatgagtagaaataatgcacatccatgtttgtatcg
tgcaaataaagtgtttcatccgtaggaaaaaatgactttagtatctgttccgctttttctgatg
aaatgtgctccccgacaaaattgaatgaatcatggacatttgctggctttgatacagcgaaagc
agccgttcctatgttatatatcggatttaacagcaggacaaaaacaccatgacagccatcgtc
acccacttattcacacgcacataaacctttcctgacttttggaacagatgatagctcatcaaaa
atcccgccattgccaaataaatcgtatatggcattactgcaccataatcttttgagatttgatt
gggatatggcgcaagcagcaagacaagcagtccgataatcagcgtataaaataagcctagtaag
atcttatccgttctccaatacagcttgaaaaacactacattcaacgcaatgggaagagtgatga
tgaaaaacagaaacacgaatgcaatcggctccatcccatccgggtattccttccaatacgaaaa
gaaactaaaaatcatttgtacgatcggcaaactgacaacagcaaggtcgaacgtataaaactta
ccctttccgccatgatcacgcggcatcagcatatagtgaaaagccgtcagcagcacatatccgt
ataacaaaaaatgcagcagcggcagcagttcttttccgtcctctcttaagtaagcgctggtgaa
gtttgttgattgcacctggtgaataagttcaacagacactcccgccagcagcacaatccgcaat
ataacacccgccaagaacattgtgcgctgccggtttattttgggatgatgcaccaaaagatata
agcccgccagaacaacaattgaccattgaatcagcagggtgctttgtctgcttaatataaaata
acgttcgaaatgcaatacataatgactgaataactccaacacgaacaacaaaagtgcgcatttt

Figure 29D

Ataaaagctaatgattcagtccacataattgatagacgaattctgctacaggtcacgtggctat
gtgaaggatcgcgcgtccagttaagagcaaaaacattgacaaaaaaatttatttatgctaaaat
ttactattaatatatttgtatgtataataagattctcctggccaggggaatcttatttttttgtg
gaggatcatttcatgaggaaaaatgagtccagcttaacgtctctaatttcagcttttgcccgtg
catatcacagccgatatgacacacctcttatttttgatgattttatcgcaaaagatctcattaa
cgaaaaagagtttatcgacatcagtaaaaatatgattcaagaaatatcgtttttcaacaaagag
atcgccgaacgtcttcaaaatgatcctgaaaaaatattaaaatgggttgcacaaatccagctgt
ctccaacgcccctagcacgtgcttcttattgtgaaaaagtcttgcacaacgaattaatcctggg
ggcaaaacagtatgtcattcttggagcgggactggatactttctgctttcggcatccagaatta
gaaaacagcttacaggttttcgaggttgatcatccggccacacagcaattgaaaaaaaataagc
tgaaggatgcaaatctgacaattccgggtcatcttcattttgttcctatggatttcaccaaaac
gttttcgtatgatcctctcttagatgaaggatttaaaaacacaaaaacattcttcagccttctc
ggagtgtcttattatgtaacacgggaagaaaatgcaagcttgatcagcaatttattttctcatg
tcccgcctggaagctctattgtttttgattatgcggacgaaacactttttacagcaaaagggac
gtcgaatcgagttgaacatatggtgaagatggctgccgcaagcggggaaccgatgaaatcatgt
ttcacttatcaagagattgaacatctg
(SEQ ID NO:47)

Figure 31A

5'-
tagaaaaactcatcgagcatcaaatgaaactgcaatttattcatatcaggattatcaataccat
atttttgaaaaagccgtttctgtaatgaaggagaaaactcaccgaggcagttccataggatggc
aagatcctggtatcggtctgcgattccgactcgtccaacatcaatacaacctattaatttcccc
tcgtcaaaaataaggttatcaagtgagaaatcaccatgagtgacgactgaatccggtgagaatg
gcaaaagtttatgcatttctttccagacttgttcaacaggccagccattacgctcgtcatcaaa
atcactcgcatcaaccaaaccgttattcattcgtgattgcgcctgagcgaggcgaaatacgcga
tcgctgttaaaaggacaattacaaacaggaatcgagtgcaaccggcgcaggaacactgccagcg
catcaacaatattttcacctgaatcaggatattcttctaatacctggaacgctgtttttccggg
gatcgcagtggtgagtaaccatgcatcatcaggagtacggataaaatgcttgatggtcggaagt
ggcataaattccgtcagccagtttagtctgaccatctcatctgtaacatcattggcaacgctac
ctttgccatgtttcagaaacaactctggcgcatcgggcttcccatacaagcgatagattgtcgc
acctgattgcccgacattatcgcgagcccatttatacccatataaatcagcatccatgttggaa
tttaatcgcggcctcgacgtttcccgttgaatatggctcatattcttcctttttcaatattatt
gaagcatttatcagggttattgtctcatgagcggatacatatttgaatgtatttagaaaaataa
acaaataggggtcagtgttacaaccaattaaccaattctgaacattatcgcgagcccatttata
cctgaatatggctcataacaccccttgtttgcctggcggcagtagcgcggtggtcccacctgac
cccatgccgaactcagaagtgaaacgccgtagcgccgatggtagtgtggggactccccatgcga
gagtagggaactgccaggcatcaaataaaacgaaaggctcagtcgaaagactgggcctttcgcc
cgggctaattagggggtgtcgccctttagtcgctgaacatgtgctctgtttctaccgagaacgt
ttccttcactgagacggaaaccgaggcacgtcgtagcgcgaactacgagccgaatagctgggac
tacgatttcctgctgtcttccgatactgacgaatctattgaggtgtacaaagacaaagcaaaga
aactggaggctgaagtgcgccgcgaaattaacaacgagaaagctgaattcctgactctgctgga
gctgatcgataacgtacagcgcctgggtctgggttaccgcttcgaatctgatatccgtcgcgca
ctggatcgtttcgtaagcagcggcggtttcgatggcgtgaccaaaacgagcctgcacgctaccg
cgctgtccttccgtctgctgcgtcagcacggcttcgaagtttctcaggaagcattctccggttt
caaagatcaaaacggtaacttcctggaaaacctgaaagaagacactaaggcgatcctgagcctg
tatgaggcaagctttctggccctggagggtgagaacatcctggatgaggcgcgcgtattcgcca
tctcccatctgaaagagctgtctgaagagaaaatcggtaaggaactggcagagcaggttaatca
cgcactggaactgccgctgcatcgtcgtacccagcgtctggaggcggtttggtccatcgaagcg
taccgcaaaaaggaggatgctaaccaggttctgctggaactggccatcctggactacaacatga
tccagtccgtttaccagcgtgatctgcgtgaaacctcccgttggtggcgccgtgtgggcctggc
gaccaaactgcacttcgctaaggaccgcctgattgagtctttttactgggcagtcggcgttgcg
ttcgaacctcagtattctgactgccgtaacagcgttgcgaaaatgttcagcttcgttactatta
tcgacgacatctacgacgtttacggtactctggacgagctggaactgtttaccgacgctgtcga
acgttgggatgttaacgccatcaacgatctgcctgactacatgaaactgtgcttcctggcactg
tataacacgatcaacgaaattgcatacgacaacctgaaagacaaaggtgaaaacatcctgccgt
acctgactaaagcgtgggcggatctgtgtaacgcttttctgcaagaagcgaaatggctgtataa
caaatccactccgacctttgacgattatttcggcaatgcctggaaatccagctctggcccgctg
caactgatcttcgcttattttgcggttgtccaaaacatcaaaaaggaggaaattgaaaacctgc
aaaaataccacgatatcattagccgtccttctcatatctttcgcctgtgcaacgacctggcaag
cgcgtccgcagagatcgcacgtggcgaaaccgctaactctgtttcctgctacatgcgcaccaag
ggcatttccgaagagctggcaaccgagagcgtaatgaatctgatcgacgaaacctgtaagaaaa
tgaacaaagaaaaactgggtggctccctgttcgctaaaccgttcgtagagactgctattaacct

Figure 31B ggcacgtcagagccactgcacctaccacaatggtgacgcacatactagcccggatgaactgact
cgtaaacgtgtactgtctgttatcaccgaaccgattctgccgttcgaacgttaactgcagcgtc
aatcgaaagggcgacacaaaatttattctaaatgcataataaatactgataacatcttatagtt
tgtattatattttgtattatcgttgacatgtataattttgatatcaaaaactgattttcccttt
attattttcgagatttattttcttaattctctttaacaaactagaaatattgtatatacaaaaa
atcataaataatagatgaatagtttaattataggtgttcatcaatcgaaaaagcaacgtatctt
atttaaagtgcgttgctttttctcatttataaggttaaataattctcatatatcaagcaaagt
gacaggcgcccttaaatattctgacaaatgctctttccctaaactccccccataaaaaaacccg
ccgaagcgggtttttacgttatttgcggattaacgattactcgttatcagaaccgcccagggggg
cccgagcttaagactggccgtcgttttacaacacagaaagagtttgtagaaacgcaaaaaggcc
atccgtcaggggccttctgcttagtttgatgcctggcagttccctactctcgccttccgcttcc
tcgctcactgactcgctgcgctcggtcgttcggctgcggcgagcggtatcagctcactcaaagg
cggtaatacggttatccacagaatcaggggataacgcaggaaagaacatgtgagcaaaaggcca
gcaaaaggccaggaaccgtaaaaaggccgcgttgctggcgtttttccataggctccgcccccct
gacgagcatcacaaaaatcgacgctcaagtcagaggtggcgaaacccgacaggactataaagat
accaggcgtttccccctggaagctccctcgtgcgctctcctgttccgaccctgccgcttaccgg
atacctgtccgcctttctcccttcgggaagcgtggcgctttctcatagctcacgctgtaggtat
ctcagttcggtgtaggtcgttcgctccaagctgggctgtgtgcacgaaccccccgttcagcccg
accgctgcgccttatccggtaactatcgtcttgagtccaacccggtaagacacgacttatcgcc
actggcagcagccactggtaacaggattagcagagcgaggtatgtaggcggtgctacagagttc
ttgaagtggtggcctaactacggctacactagaagaacagtatttggtatctgcgctctgctga
agccagttaccttcggaaaaagagttggtagctcttgatccggcaaacaaaccaccgctggtag
cggtggtttttttgtttgcaagcagcagattacgcgcagaaaaaaaggatctcaagaagatcct
ttgatcttttctacggggtctgacgctcagtggaacgacgcgcgcgtaactcacgttaagggat
tttggtcatgagcttgcgccgtcccgtcaagtcagcgtaatgctctgcttt
(SEQ ID NO:48)

Figure 33A

5'-
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgctctgtttctaccgagaacgtttccttcact
gagacggaaaccgaggcacgtcgtagcgcgaactacgagccgaatagctgggactacgatttcc
tgctgtcttccgatactgacgaatctattgaggtgtacaaagacaaagcaaagaaactggaggc
tgaagtgcgccgcgaaattaacaacgagaaagctgaattcctgactctgctggagctgatcgat
aacgtacagcgcctgggtctgggttaccgcttcgaatctgatatccgtcgcgcactggatcgtt
tcgtaagcagcggcggtttcgatggcgtgaccaaaacgagcctgcacgctaccgcgctgtcctt
ccgtctgctgcgtcagcacggcttcgaagtttctcaggaagcattctccggtttcaaagatcaa
aacggtaacttcctggaaaacctgaaagaagacactaaggcgatcctgagcctgtatgaggcaa
gctttctggccctggagggtgagaacatcctggatgaggcgcgcgtattcgccatctcccatct
gaaagagctgtctgaagagaaaatcggtaaggaactggcagagcaggttaatcacgcactggaa
ctgccgctgcatcgtcgtacccagcgtctggaggcggtttggtccatcgaagcgtaccgcaaaa
aggaggatgctaaccaggttctgctggaactggccatcctggactacaacatgatccagtccgt
ttaccagcgtgatctgcgtgaaacctcccgttggtggcgccgtgtgggcctggcgaccaaactg
cacttcgctaaggaccgcctgattgagtctttttactgggcagtcggcgttgcgttcgaacctc
agtattctgactgccgtaacagcgttgcgaaaatgttcagcttcgttactattatcgacgacat
ctacgacgtttacggtactctggacgagctggaactgtttaccgacgctgtcgaacgttgggat
gttaacgccatcaacgatctgcctgactacatgaaactgtgcttcctggcactgtataacacga
tcaacgaaattgcatacgacaacctgaaagacaaaggtgaaaacatcctgccgtacctgactaa
agcgtgggcggatctgtgtaacgcttttctgcaagaagcgaaatggctgtataacaaatccact
ccgacctttgacgattatttcggcaatgcctggaaatccagctctggcccgctgcaactgatct
tcgcttattttgcggttgtccaaaacatcaaaaaggaggaaattgaaaacctgcaaaaatacca
cgatatcattagccgtccttctcatatctttcgcctgtgcaacgacctggcaagcgcgtccgca
gagatcgcacgtggcgaaaccgctaactctgtttcctgctacatgcgcaccaagggcatttccg
aagagctggcaaccgagagcgtaatgaatctgatcgacgaaacctgtaagaaaatgaacaaaga
aaaactgggtggctccctgttcgctaaaccgttcgtagagactgctattaacctggcacgtcag
agccactgcacctaccacaatggtgacgcacatactagcccggatgaactgactcgtaaacgtg
tactgtctgttatcaccgaaccgattctgccgttcgaacgttaactgcagctggtaccatatgg
gaattcgaagctttctagaacaaaaactcatctcagaagaggatctgaatagcgccgtcgacca
tcatcatcatcatcattgagtttaaacggtctccagcttggctgttttggcggatgagagaaga
ttttcagcctgatacagattaaatcagaacgcagaagcggtctgataaaacagaatttgcctgg
cggcagtagcgcggtggtcccacctgaccccatgccgaactcagaagtgaaacgccgtagcgcc
gatggtagtgtggggtctccccatgcgagagtagggaactgccaggcatcaaataaaacgaaag
gctcagtcgaaagactgggcctttcgttttatctgttgtttgtcggtgaacgctctcctgagta
ggacaaatccgccgggagcggatttgaacgttgcgaagcaacggcccggagggtggcgggcagg
acgcccgccataaactgccaggcatcaaattaagcagaaggccatcctgacggatggcctttttt
gcgtttctacaaactctttttgtttatttttctaaatacattcaaatatgtatccgctcatgag
acaataaccctgataaatgcttcaatagtattgaaaaaggaagagtatgagtattcaacatttc

Figure 33B cgtgtcgcccttattcccttttttgcggcattttgccttcctgtttttgctcacccagaaacgc
tggtgaaagtaaaagatgctgaagatcagttgggtgcacgagtgggttacatcgaactggatct
caacagcggtaagatccttgagagttttcgccccgaagaacgttttccaatgatgagcactttt
aaagttctgctatgtggcgcggtattatcccgtgttgacgccgggcaagagcaactcggtcgcc
gcatacactattctcagaatgacttggttgagtactcaccagtcacagaaaagcatcttacgga
tggcatgacagtaagagaattatgcagtgctgccataaccatgagtgataacactgcggccaac
ttacttctgacaacgatcggaggaccgaaggagctaaccgcttttttgcacaacatgggggatc
atgtaactcgccttgatcgttgggaaccggagctgaatgaagccataccaaacgacgagcgtga
caccacgatgcctgtagcaatggcaacaacgttgcgcaaactattaactggcgaactacttact
ctagcttcccggcaacaattaatagactggatggaggcggataaagttgcaggaccacttctgc
gctcggcccttccggctggctggtttattgctgataaatctggagccggtgagcgtgggtctcg
cggtatcattgcagcactggggccagatggtaagccctcccgtatcgtagttatctacacgacg
gggagtcaggcaactatggatgaacgaaatagacagatcgctgagataggtgcctcactgatta
agcattggtaactgtcagaccaagtttactcatatatactttagattgatttaaaacttcattt
ttaatttaaaaggatctaggtgaagatcctttttgataatctcatgaccaaaatcccttaacgt
gagttttcgttccactgagcgtcagaccccgtagaaaagatcaaaggatcttcttgagatcctt
tttttctgcgcgtaatctgctgcttgcaaacaaaaaaaccaccgctaccagcggtggtttgttt
gccggatcaagagctaccaactctttttccgaaggtaactggcttcagcagagcgcagatacca
aatactgtccttctagtgtagccgtagttaggccaccacttcaagaactctgtagcaccgccta
catacctcgctctgctaatcctgttaccagtggctgctgccagtggcgataagtcgtgtcttac
cgggttggactcaagacgatagttaccggataaggcgcagcggtcgggctgaacggggggttcg
tgcacacagcccagcttggagcgaacgacctacaccgaactgagatacctacagcgtgagctat
gagaaagcgccacgcttcccgaagggagaaaggcggacaggtatccggtaagcggcagggtcgg
aacaggagagcgcacgagggagcttccagggggaaacgcctggtatctttatagtcctgtcggg
tttcgccacctctgacttgagcgtcgatttttgtgatgctcgtcaggggggcggagcctatgga
aaaacgccagcaacgcggcctttttacggttcctggccttttgctggccttttgctcacatgtt
ctttcctgcgttatcccctgattctgtggataaccgtattaccgcctttgagtgagctgatacc
gctcgccgcagccgaacgaccgagcgcagcgagtcagtgagcgaggaagcggaagagcgcctga
tgcggtattttctccttacgcatctgtgcggtatttcacaccgcatatggtgcactctcagtac
aatctgctctgatgccgcatagttaagccagtatacactccgctatcgctacgtgactgggtca
tggctgcgccccgacacccgccaacacccgctgacgcgccctgacgggcttgtctgctcccggc
atccgcttacagacaagctgtgaccgtctccgggagctgcatgtgtcagaggttttcaccgtca
tcaccgaaacgcgcgaggcagcagatcaattcgcgcgcgaaggcgaagcggcatgcatttacgt
tgacaccatcgaatggtgcaaaacctttcgcggtatggcatgatagcgcccggaagagagtcaa
ttcagggtggtgaatgtgaaaccagtaacgttatacgatgtcgcagagtatgccggtgtctctt
atcagaccgtttcccgcgtggtgaaccaggccagccacgtttctgcgaaaacgcgggaaaaagt
ggaagcggcgatggcggagctgaattacattcccaaccgcgtggcacaacaactggcgggcaaa
cagtcgttgctgattggcgttgccacctccagtctggccctgcacgcgccgtcgcaaattgtcg
cggcgattaaatctcgcgccgatcaactgggtgccagcgtggtggtgtcgatggtagaacgaag
cggcgtcgaagcctgtaaagcggcggtgcacaatcttctcgcgcaacgcgtcagtgggctgatc
attaactatccgctggatgaccaggatgccattgctgtggaagctgcctgcactaatgttccgg
cgttatttcttgatgtctctgaccagacacccatcaacagtattattttctcccatgaagacgg
tacgcgactgggcgtggagcatctggtcgcattgggtcaccagcaaatcgcgctgttagcgggc
ccattaagttctgtctcggcgcgtctgcgtctggctggctggcataaatatctcactcgcaatc

Figure 33C aaattcagccgatagcggaacgggaaggcgactggagtgccatgtccggttttcaacaaaccat
gcaaatgctgaatgagggcatcgttcccactgcgatgctggttgccaacgatcagatggcgctg
ggcgcaatgcgcgccattaccgagtccgggctgcgcgttggtgcggatatctcggtagtgggat
acgacgataccgaagacagctcatgttatatcccgccgtcaaccaccatcaaacaggattttcg
cctgctggggcaaaccagcgtggaccgcttgctgcaactctctcagggccaggcggtgaagggc
aatcagctgttgcccgtctcactggtgaaaagaaaaaccaccctggcgcccaatacgcaaaccg
cctctccccgcgcgttggccgattcattaatgcagctggcacgacaggtttcccgactggaaag
cgggcagtgagcgcaacgcaattaatgtgagttagcgcgaattgatctg
(SEQ ID NO:49)

Figure 35A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtaccttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt

Figure 35B ttatggcactctggacgaactgcaactgttcaccgatgctgtagagcgctgggacgttaacgct
attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
tcgcccttaggaggtaaaaaaaaatgactgccgacaacaatagtatgccccatggtgcagtatc
tagttacgccaaattagtgcaaaaccaaacacctgaagacattttggaagagtttcctgaaatt
attccattacaacaaagacctaatacccgatctagtgagacgtcaaatgacgaaagcggagaaa
catgtttttctggtcatgatgaggagcaaattaagttaatgaatgaaaattgtattgttttgga
ttgggacgataatgctattggtgccggtaccaagaaagtttgtcatttaatggaaaatattgaa
aagggtttactacatcgtgcattctccgtctttattttcaatgaacaaggtgaattacttttac
aacaaagagccactgaaaaaataactttccctgatctttggactaacacatgctgctctcatcc
actatgtattgatgacgaattaggtttgaagggtaagctagacgataagattaagggcgctatt
actgcggcggtgagaaaactagatcatgaattaggtattccagaagatgaaactaagacaaggg
gtaagtttcactttttaaacagaatccattacatggcaccaagcaatgaaccatggggtgaaca
tgaaattgattacatcctattttataagatcaacgctaaagaaaacttgactgtcaacccaaac
gtcaatgaagttagagacttcaaatgggtttcaccaaatgatttgaaaactatgtttgctgacc
caagttacaagtttacgccttggtttaagattatttgcgagaattacttattcaactggtggga
gcaattagatgacctttctgaagtggaaaatgacaggcaaattcatagaatgctataacaacgc
gtcctgcagctggtaccatatgggaattcgaagctttctagaacaaaaactcatctcagaagag
gatctgaatagcgccgtcgaccatcatcatcatcatcattgagtttaaacggtctccagcttgg
ctgttttggcggatgagagaagattttcagcctgatacagattaaatcagaacgcagaagcggt
ctgataaaacagaatttgcctggcggcagtagcgcggtggtcccacctgaccccatgccgaact
cagaagtgaaacgccgtagcgccgatggtagtgtggggtctccccatgcgagagtagggaactg
ccaggcatcaaataaaacgaaaggctcagtcgaaagactgggcctttcgttttatctgttgttt
gtcggtgaacgctctcctgagtaggacaaatccgccgggagcggatttgaacgttgcgaagcaa
cggcccggagggtggcgggcaggacgcccgccataaactgccaggcatcaaattaagcagaagg
ccatcctgacggatggcctttttgcgtttctacaaactctttttgtttatttttctaaatacat
tcaaatatgtatccgcttaaccggaattgccagctggggcgccctctggtaaggttgggaagcc
ctgcaaagtaaactggatggctttctcgccgccaaggatctgatggcgcaggggatcaagctct
gatcaagagacaggatgaggatcgtttcgcatgattgaacaagatggattgcacgcaggttctc
cggccgcttgggtggagaggctattcggctatgactgggcacaacagacaatcggctgctctga
tgccgccgtgttccggctgtcagcgcaggggcgcccggttctttttgtcaagaccgacctgtcc
ggtgccctgaatgaactgcaagacgaggcagcgcggctatcgtggctggccacgacgggcgttc
cttgcgcagctgtgctcgacgttgtcactgaagcgggaagggactggctgctattgggcgaagt
gccggggcaggatctcctgtcatctcaccttgctcctgccgagaaagtatccatcatggctgat

Figure 35C gcaatgcggcggctgcatacgcttgatccggctacctgcccattcgaccaccaagcgaaacatc
gcatcgagcgagcacgtactcggatggaagccggtcttgtcgatcaggatgatctggacgaaga
gcatcaggggctcgcgccagccgaactgttcgccaggctcaaggcgagcatgcccgacggcgag
gatctcgtcgtgacccatggcgatgcctgcttgccgaatatcatggtggaaaatggccgctttt
ctggattcatcgactgtggccggctgggtgtggcggaccgctatcaggacatagcgttggctac
ccgtgatattgctgaagagcttggcggcgaatgggctgaccgcttcctcgtgctttacggtatc
gccgctcccgattcgcagcgcatcgccttctatcgccttcttgacgagttcttctgacatgacc
aaaatcccttaacgtgagttttcgttccactgagcgtcagaccccgtagaaaagatcaaaggat
cttcttgagatcctttttttctgcgcgtaatctgctgcttgcaaacaaaaaaaccaccgctacc
agcggtggtttgtttgccggatcaagagctaccaactctttttccgaaggtaactggcttcagc
agagcgcagataccaaatactgtccttctagtgtagccgtagttaggccaccacttcaagaact
ctgtagcaccgcctacatacctcgctctgctaatcctgttaccagtggctgctgccagtggcga
taagtcgtgtcttaccgggttggactcaagacgatagttaccggataaggcgcagcggtcgggc
tgaacggggggttcgtgcacacagcccagcttggagcgaacgacctacaccgaactgagatacc
tacagcgtgagctatgagaaagcgccacgcttcccgaagggagaaaggcggacaggtatccggt
aagcggcagggtcggaacaggagagcgcacgagggagcttccagggggaaacgcctggtatctt
tatagtcctgtcgggtttcgccacctctgacttgagcgtcgatttttgtgatgctcgtcagggg
ggcggagcctatggaaaaacgccagcaacgcggcctttttacggttcctggccttttgctggcc
ttttgctcacatgttctttcctgcgttatcccctgattctgtggataaccgtattaccgccttt
gagtgagctgataccgctcgccgcagccgaacgaccgagcgcagcgagtcagtgagcgaggaag
cggaagagcgcctgatgcggtattttctccttacgcatctgtgcggtatttcacaccgcatatg
gtgcactctcagtacaatctgctctgatgccgcatagttaagccagtatacactccgctatcgc
tacgtgactgggtcatggctgcgccccgacacccgccaacacccgctgacgcgccctgacgggc
(SEQ ID NO:50)

Figure 37A

5'-
ttgtctgctcccggcatccgcttacagacaagctgtgaccgtctccgggagctgcatgtgtcag
aggttttcaccgtcatcaccgaaacgcgcgaggcagcagatcaattcgcgcgcgaaggcgaagc
ggcatgcatttacgttgacaccatcgaatggtgcaaaacctttcgcggtatggcatgatagcgc
ccggaagagagtcaattcagggtggtgaatgtgaaaccagtaacgttatacgatgtcgcagagt
atgccggtgtctcttatcagaccgtttcccgcgtggtgaaccaggccagccacgtttctgcgaa
aacgcgggaaaaagtggaagcggcgatggcggagctgaattacattcccaaccgcgtggcacaa
caactggcgggcaaacagtcgttgctgattggcgttgccacctccagtctggccctgcacgcgc
cgtcgcaaattgtcgcggcgattaaatctcgcgccgatcaactgggtgccagcgtggtggtgtc
gatggtagaacgaagcggcgtcgaagcctgtaaagcggcggtgcacaatcttctcgcgcaacgc
gtcagtgggctgatcattaactatccgctggatgaccaggatgccattgctgtggaagctgcct
gcactaatgttccggcgttatttcttgatgtctctgaccagacacccatcaacagtattatttt
ctcccatgaagacggtacgcgactgggcgtggagcatctggtcgcattgggtcaccagcaaatc
gcgctgttagcgggcccattaagttctgtctcggcgcgtctgcgtctggctggctggcataaat
atctcactcgcaatcaaattcagccgatagcggaacgggaaggcgactggagtgccatgtccgg
ttttcaacaaaccatgcaaatgctgaatgagggcatcgttcccactgcgatgctggttgccaac
gatcagatggcgctgggcgcaatgcgcgccattaccgagtccgggctgcgcgttggtgcggata
tctcggtagtgggatacgacgataccgaagacagctcatgttatatcccgccgtcaaccaccat
caaacaggattttcgcctgctggggcaaaccagcgtggaccgcttgctgcaactctctcagggc
caggcggtgaagggcaatcagctgttgcccgtctcactggtgaaaagaaaaaccaccctggcgc
ccaatacgcaaaccgcctctccccgcgcgttggccgattcattaatgcagctggcacgacaggt
ttcccgactggaaagcgggcagtgagcgcaacgcaattaatgtgagttagcgcgaattgatctg
gtttgacagcttatcatcgactgcacggtgcaccaatgcttctggcgtcaggcagccatcggaa
gctgtggtatggctgtgcaggtcgtaaatcactgcataattcgtgtcgctcaaggcgcactccc
gttctggataatgttttttgcgccgacatcataacggttctggcaaatattctgaaatgagctg
ttgacaattaatcatccggctcgtataatgtgtggaattgtgagcggataacaatttcacacag
gaaacagcgccgctgagaaaaagcgaagcggcactgctctttaacaatttatcagacaatctgt
gtgggcactcgaccggaattatcgattaactttattattaaaaattaaagaggtatatattaat
gtatcgattaaataaggaggaataaaccatgtgtgcgacctcttctcaatttactcagattacc
gagcataattcccgtcgttccgcaaactatcagccaaacctgtggaatttcgaattcctgcaat
ccctggagaacgacctgaaagtggaaaagctggaggagaaagcgaccaaactggaggaagaagt
tcgctgcatgatcaaccgtgtagacacccagccgctgtccctgctggagctgatcgacgatgtg
cagcgcctgggtctgacctacaaatttgaaaaagacatcattaaagccctggaaaacatcgtac
tgctggacgaaaacaaaaagaacaaatctgacctgcacgcaaccgctctgtctttccgtctgct
gcgtcagcacggtttcgaggtttctcaggatgtttttgagcgtttcaaggataaagaaggtggt
ttcagcggtgaactgaaaggtgacgtccaaggcctgctgagcctgtatgaagcgtcttacctgg
gtttcgagggtgagaacctgctggaggaggcgcgtacctttttccatcacccacctgaagaacaa
cctgaaagaaggcattaataccaaggttgcagaacaagtgagccacgccctggaactgccatat
caccagcgtctgcaccgtctggaggcacgttggttcctggataaatacgaaccgaaagaaccgc
atcaccagctgctgctggagctggcgaagctggattttaacatggtacagaccctgcaccagaa
agagctgcaagatctgtcccgctggtggaccgagatgggcctggctagcaaactggattttgta
cgcgaccgcctgatggaagtttatttctgggcactgggtatggcgccagacccgcagtttggtg
aatgtcgcaaagctgttactaaaatgtttggtctggtgacgatcatcgatgacgtgtatgacgt
ttatggcactctggacgaactgcaactgttcaccgatgctgtagagcgctgggacgttaacgct

Figure 37B attaacaccctgccggactatatgaaactgtgtttcctggcactgtacaacaccgttaacgaca
cgtcctattctattctgaaagagaaaggtcataacaacctgtcctatctgacgaaaagctggcg
tgaactgtgcaaagcctttctgcaagaggcgaaatggtccaacaacaaaattatcccggctttc
tccaagtacctggaaaacgccagcgtttcctcctccggtgtagcgctgctggcgccgtcttact
tttccgtatgccagcagcaggaagacatctccgaccacgcgctgcgttccctgaccgacttcca
tggtctggtgcgttctagctgcgttatcttccgcctgtgcaacgatctggccacctctgcggcg
gagctggaacgtggcgagactaccaattctatcattagctacatgcacgaaaacgatggtacca
gcgaggaacaggcccgcgaagaactgcgtaaactgatcgacgccgaatggaaaaagatgaatcg
tgaacgcgttagcgactccaccctgctgcctaaagcgttcatggaaatcgcagttaacatggca
cgtgtttcccactgcacctaccagtatggcgatggtctgggtcgcccagactacgcgactgaaa
accgcatcaaactgctgctgattgaccctttcccgattaaccagctgatgtatgtctaactgca
ttcgcccttaggaggtaaaaaaacatgagttttgatattgccaaatacccgaccctggcactgg
tcgactccacccaggagttacgactgttgccgaaagagagtttaccgaaactctgcgacgaact
gcgccgctatttactcgacagcgtgagccgttccagcgggcacttcgcctccgggctgggcacg
gtcgaactgaccgtggcgctgcactatgtctacaacaccccgtttgaccaattgatttgggatg
tggggcatcaggcttatccgcataaaattttgaccggacgccgcgacaaaatcggcaccatccg
tcagaaaggcggtctgcacccgttcccgtggcgcggcgaaagcgaatatgacgtattaagcgtc
gggcattcatcaacctccatcagtgccggaattggtattgcggttgctgccgaaaaagaaggca
aaaatcgccgcaccgtctgtgtcattggcgatggcgcgattaccgcaggcatggcgtttgaagc
gatgaatcacgcgggcgatatccgtcctgatatgctggtgattctcaacgacaatgaaatgtcg
atttccgaaaatgtcggcgcgctcaacaaccatctggcacagctgctttccggtaagctttact
cttcactgcgcgaaggcgggaaaaaagttttctctggcgtgccgccaattaaagagctgctcaa
acgcaccgaagaacatattaaaggcatggtagtgcctggcacgttgtttgaagagctgggcttt
aactacatcggcccggtggacggtcacgatgtgctggggcttatcaccacgctaaagaacatgc
gcgacctgaaaggcccgcagttcctgcatatcatgaccaaaaaaggtcgtggttatgaaccggc
agaaaaagacccgatcactttccacgccgtgcctaaatttgatccctccagcggttgtttgccg
aaaagtagcggcggtttgccgagctattcaaaaatctttggcgactggttgtgcgaaacggcag
cgaaagacaacaagctgatggcgattactccggcgatgcgtgaaggttccggcatggtcgagtt
ttcacgtaaattcccggatcgctacttcgacgtggcaattgccgagcaacacgcggtgaccttt
gctgcgggtctggcgattggtgggtacaaacccattgtcgcgatttactccactttcctgcaac
gcgcctatgatcaggtgctgcatgacgtggcgattcaaaagcttccggtcctgttcgccatcga
ccgcgcgggcattgttggtgctgacggtcaaacccatcagggtgcttttgatctctcttacctg
cgctgcataccggaaatggtcattatgaccccgagcgatgaaaacgaatgtcgccagatgctct
ataccggctatcactataacgatggcccgtcagcggtgcgctacccgcgtggcaacgcggtcgg
cgtggaactgacgccgctggaaaaactaccaattggcaaaggcattgtgaagcgtcgtggcgag
aaactggcgatccttaactttggtacgctgatgccagaagcggcgaaagtcgccgaatcgctga
acgccacgctggtcgatatgcgttttgtgaaaccgcttgatgaagcgttaattctggaaatggc
cgccagccatgaagcgctggtcaccgtagaagaaaacgccattatgggcggcgcaggcagcggc
gtgaacgaagtgctgatggcccatcgtaaaccagtacccgtgctgaacattggcctgccggact
tctttattccgcaaggaactcaggaagaaatgcgcgccgaactcggcctcgatgccgctggtat
ggaagccaaaatcaaggcctggctggcataactgcagctggtaccatatgggaattcgaagctt
tctagaacaaaaactcatctcagaagaggatctgaatagcgccgtcgaccatcatcatcatcat
cattgagtttaaacggtctccagcttggctgttttggcggatgagagaagattttcagcctgat
acagattaaatcagaacgcagaagcggtctgataaaacagaatttgcctggcggcagtagcgcg

Figure 37C gtggtcccacctgaccccatgccgaactcagaagtgaaacgccgtagcgccgatggtagtgtgg
ggtctccccatgcgagagtagggaactgccaggcatcaaataaaacgaaaggctcagtcgaaag
actgggcctttcgttttatctgttgtttgtcggtgaacgctctcctgagtaggacaaatccgcc
gggagcggatttgaacgttgcgaagcaacggcccggagggtggcgggcaggacgcccgccataa
actgccaggcatcaaattaagcagaaggccatcctgacggatggcctttttgcgtttctacaaa
ctctttttgtttatttttctaaatacattcaaatatgtatccgcttaaccggaattgccagctg
gggcgccctctggtaaggttgggaagccctgcaaagtaaactggatggctttctcgccgccaag
gatctgatggcgcaggggatcaagctctgatcaagagacaggatgaggatcgtttcgcatgatt
gaacaagatggattgcacgcaggttctccggccgcttgggtggagaggctattcggctatgact
gggcacaacagacaatcggctgctctgatgccgccgtgttccggctgtcagcgcaggggcgccc
ggttctttttgtcaagaccgacctgtccggtgccctgaatgaactgcaagacgaggcagcgcgg
ctatcgtggctggccacgacgggcgttccttgcgcagctgtgctcgacgttgtcactgaagcgg
gaagggactggctgctattgggcgaagtgccggggcaggatctcctgtcatctcaccttgctcc
tgccgagaaagtatccatcatggctgatgcaatgcggcggctgcatacgcttgatccggctacc
tgcccattcgaccaccaagcgaaacatcgcatcgagcgagcacgtactcggatggaagccggtc
ttgtcgatcaggatgatctggacgaagagcatcaggggctcgcgccagccgaactgttcgccag
gctcaaggcgagcatgcccgacggcgaggatctcgtcgtgacccatggcgatgcctgcttgccg
aatatcatggtggaaaatggccgcttttctggattcatcgactgtggccggctgggtgtggcgg
accgctatcaggacatagcgttggctacccgtgatattgctgaagagcttggcggcgaatgggc
tgaccgcttcctcgtgctttacggtatcgccgctcccgattcgcagcgcatcgccttctatcgc
cttcttgacgagttcttctgacgcatgaccaaaatcccttaacgtgagttttcgttccactgag
cgtcagaccccgtagaaaagatcaaaggatcttcttgagatcctttttttctgcgcgtaatctg
ctgcttgcaaacaaaaaaaccaccgctaccagcggtggtttgtttgccggatcaagagctacca
actctttttccgaaggtaactggcttcagcagagcgcagataccaaatactgtccttctagtgt
agccgtagttaggccaccacttcaagaactctgtagcaccgcctacatacctcgctctgctaat
cctgttaccagtggctgctgccagtggcgataagtcgtgtcttaccgggttggactcaagacga
tagttaccggataaggcgcagcggtcgggctgaacggggggttcgtgcacacagcccagcttgg
agcgaacgacctacaccgaactgagatacctacagcgtgagctatgagaaagcgccacgcttcc
cgaagggagaaaggcggacaggtatccggtaagcggcagggtcggaacaggagagcgcacgagg
gagcttccagggggaaacgcctggtatctttatagtcctgtcgggtttcgccacctctgacttg
agcgtcgatttttgtgatgctcgtcaggggggcggagcctatggaaaaacgccagcaacgcggc
ctttttacggttcctggccttttgctggccttttgctcacatgttctttcctgcgttatcccct
gattctgtggataaccgtattaccgcctttgagtgagctgataccgctcgccgcagccgaacga
ccgagcgcagcgagtcagtgagcgaggaagcggaagagcgcctgatgcggtattttctccttac
gcatctgtgcggtatttcacaccgcatatggtgcactctcagtacaatctgctctgatgccgca
tagttaagccagtatacactccgctatcgctacgtgactgggtcatggctgcgccccgacaccc
gccaacacccgctgacgcgccctgacgggc
(SEQ ID NO:51)

Figure 39A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctacttttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaaattttgcctcaaaactggt
gagctgaattttttgcagttaaagcatcgtgtagtgtttttcttagtccgttatgtaggtaggaa
tctgatgtaatggttgttggtattttgtcaccattcatttttatctggttgttctcaagttcgg

Figure 39B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
tttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgcctttt atggattc
atgcaaggaaactacccataatacaagaaaagcccgtcacgggcttctcagggcgttttatggc
gggtctgctatgtggtgctatctgactttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtacctttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 39C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcagctggtaccatatgggaattcgaagctttctagaacaaaaactca
tctcagaagaggatctgaatagcgccgtcgaccatcatcatcatcatcattgagtttaaacggt
ctccagcttggctgttttggcggatgagagaagattttcagcctgatacagattaaatcagaac
gcagaagcggtctgataaaacagaatttgcctggcggcagtagcgcggtggtcccacctgaccc
catgccgaactcagaagtgaaacgccgtagcgccgatggtagtgtggggtctccccatgcgaga
gtagggaactgccaggcatcaaataaaacgaaaggctcagtcgaaagactgggcctttcgtttt
atctgttgtttgtcggtgaacgctctcctgagtaggacaaatccgccgggagcggatttgaacg
ttgcgaagcaacggcccggagggtggcgggcaggacgcccgccataaactgccaggcatcaaat
taagcagaaggccatcctgacggatggcctttttgcgtttctacaaactctttttgtttatttt
tctaaatacattcaaatatgtatccgctcatgagacaataaccctgataaatgcttcaataat
(SEQ ID NO:52)

Figure 41A

5′-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttagacatacatcagctggttaatcgggaaagg
gtcaatcagcagcagtttgatgcggttttcagtcgcgtagtctgggcgacccagaccatcgcca
tactggtaggtgcagtgggaaacacgtgccatgttaactgcgatttccatgaacgctttaggca
gcagggtggagtcgctaacgcgttcacgattcatctttttccattcggcgtcgatcagtttacg
cagttcttcgcgggcctgttcctcgctggtaccatcgttttcgtgcatgtagctaatgatagaa
ttggtagtctcgccacgttccagctccgccgcagaggtggccagatcgttgcacaggcggaaga
taacgcagctagaacgcaccagaccatggaagtcggtcagggaacgcagcgcgtggtcggagat
gtcttcctgctgctggcatacggaaaagtaagacggcgccagcagcgctacaccggaggaggaa
acgctggcgttttccaggtacttggagaaagccgggataattttgttgttggaccatttcgcct
cttgcagaaaggctttgcacagttcacgccagcttttcgtcagataggacaggttgttatgacc
tttctctttcagaatagaataggacgtgtcgttaacggtgttgtacagtgccaggaaacacagt
ttcatatagtccggcagggtgttaatagcgttaacgtcccagcgctctacagcatcggtgaaca
gttgcagttcgtccagagtgccataaacgtcatacacgtcatcgatgatcgtcaccagaccaaa
cattttagtaacagctttgcgacattcaccaaactgcgggtctggcgccatacccagtgcccag
aaataaacttccatcaggcggtcgcgtacaaaatccagtttgctagccaggcccatctcggtcc
accagcgggacagatcttgcagctctttctggtgcagggtctgtaccatgttaaaatccagctt
cgccagctccagcagcagctggtgatgcggttctttcggttcgtatttatccaggaaccaacgt
gcctccagacggtgcagacgctggtgatatggcagttccagggcgtggctcacttgttctgcaa
ccttggtattaatgccttctttcaggttgttcttcaggtgggtgatggaaaaggtacgcgcctc
ctccagcaggttctcaccctcgaaacccaggtaagacgcttcatacaggctcagcaggccttgg
acgtcacctttcagttcaccgctgaaaccaccttctttatccttgaaacgctcaaaaacatcct
gagaaacctcgaaaccgtgctgacgcagcagacggaaagacagagcggttgcgtgcaggtcaga
tttgttctttttgttttcgtccagcagtacgatgttttccagggctttaatgatgtcttttca
aatttgtaggtcagacccaggcgctgcacatcgtcgatcagctccagcagggacagcggctggg
tgtctacacggttgatcatgcagcgaacttcttcctccagtttggtcgctttctcctccagctt
ttccactttcaggtcgttctccagggattgcaggaattcgaaattccacaggtttggctgatag
tttgcggaacgacgggaattatgctcggtaatctgagtaaattgagaagaggtcgcacacatgg
tttattcctccttatttaatcgatacattaatatatacctctttaatttttaataataaagtta
atcgataattccggtcgagtgcccacacagattgtctgataaattgttaaagagcagtgccgct
tcgctttttctcagcggcgctgtttcctgtgtgaaattgttatccgctcacaattccacacatt
atacgagccggatgattaattgtcaacagctcatttcagaatctggcgtaatagcgaagaggcc
cgcaccgatcgcccttcccaacagttgcgcagcctgaatggcgaatggcgcctgatgcggtatt
ttctccttacgcatctgtgcggtatttcacaccgcatatggtgcactctcagtacaatctgctc

Figure 41B tgatgccgcatagttaagccagccccgacacccgccaacacccgctgacgagcttagtaaagcc
ctcgctagattttaatgcggatgttgcgattacttcgccaactattgcgataacaagaaaaagc
cagcctttcatgatatatctcccaatttgtgtagggcttattatgcacgcttaaaaataataaa
agcagacttgacctgatagtttggctgtgagcaattatgtgcttagtgcatctaacgcttgagt
taagccgcgccgcgaagcggcgtcggcttgaacgaattgttagacattatttgccgactacctt
ggtgatctcgcctttcacgtagtggacaaattcttccaactgatctgcgcgcgaggccaagcga
tcttcttcttgtccaagataagcctgtctagcttcaagtatgacgggctgatactgggccggca
ggcgctccattgcccagtcggcagcgacatccttcggcgcgattttgccggttactgcgctgta
ccaaatgcgggacaacgtaagcactacatttcgctcatcgccagcccagtcgggcggcgagttc
catagcgttaaggtttcatttagcgcctcaaatagatcctgttcaggaaccggatcaaagagtt
cctccgccgctggacctaccaaggcaacgctatgttctcttgcttttgtcagcaagatagccag
atcaatgtcgatcgtggctggctcgaagatacctgcaagaatgtcattgcgctgccattctcca
aattgcagttcgcgcttagctggataacgccacggaatgatgtcgtcgtgcacaacaatggtga
cttctacagcgcggagaatctcgctctctccaggggaagccgaagtttccaaaaggtcgttgat
caaagctcgccgcgttgtttcatcaagccttacggtcaccgtaaccagcaaatcaatatcactg
tgtggcttcaggccgccatccactgcggagccgtacaaatgtacggccagcaacgtcggttcga
gatggcgctcgatgacgccaactacctctgatagttgagtcgatacttcggcgatcaccgcttc
cctcatgatgtttaactttgttttagggcgactgccctgctgcgtaacatcgttgctgctccat
aacatcaaacatcgacccacggcgtaacgcgcttgctgcttggatgcccgaggcatagactgta
ccccaaaaaaacagtcataacaagccatgaaaaccgccactgcgccgttaccaccgctgcgttc
ggtcaaggttctggaccagttgcgtgagcgcatacgctacttgcattacagcttacgaaccgaa
caggcttatgtccactgggttcgtgccttcatccgtttccacggtgtgcgtcacccggcaacct
tgggcagcagcgaagtcgaggcatttctgtcctggctggcgaacgagcgcaaggtttcggtctc
cacgcatcgtcaggcattggcggccttgctgttcttctacggcaaggtgctgtgcacggatctg
ccctggcttcaggagatcggaagacctcggccgtcgcggcgcttgccggtggtgctgaccccgg
atgaagtggttcgcatcctcggttttctggaaggcgagcatcgtttgttcgcccagcttctgta
tggaacgggcatgcggatcagtgagggtttgcaactgcgggtcaaggatctggatttcgatcac
ggcacgatcatcgtgcgggagggcaagggctccaaggatcgggccttgatgttacccgagagct
tggcacccagcctgcgcgagcaggggaattaattcccacgggttttgctgcccgcaaacgggct
gttctggtgttgctagtttgttatcagaatcgcagatccggcttcagccggtttgccggctgaa
agcgctatttcttccagaattgccatgatttttttccccacgggaggcgtcactggctcccgtgt
tgtcggcagctttgattcgataagcagcatcgcctgtttcaggctgtctatgtgtgactgttga
gctgtaacaagttgtctcaggtgttcaatttcatgttctagttgctttgttttactggtttcac
ctgttctattaggtgttacatgctgttcatctgttacattgtcgatctgttcatggtgaacagc
tttgaatgcaccaaaaactcgtaaaagctctgatgtatctatctttttttacaccgttttcatct
gtgcatatggacagttttccctttgatatgtaacggtgaacagttgttctactttgtttgtta
gtcttgatgcttcactgatagatacaagagccataagaacctcagatccttccgtatttagcca
gtatgttctctagtgtggttcgttgtttttgcgtgagccatgagaacgaaccattgagatcata
cttactttgcatgtcactcaaaaattttgcctcaaaactggtgagctgaattttttgcagttaaa
gcatcgtgtagtgtttttcttagtccgttatgtaggtaggaatctgatgtaatggttgttggta
ttttgtcaccattcatttttatctggttgttctcaagttcggttacgagatccatttgtctatc
tagttcaacttggaaaatcaacgtatcagtcgggcggcctcgcttatcaaccaccaatttcata
ttgctgtaagtgtttaaatctttacttattggtttcaaaacccattggttaagccttttaaact
catggtagttattttcaagcattaacatgaacttaaattcatcaaggctaatctctatatttgc

Figure 41C cttgtgagttttcttttgtgttagttcttttaataaccactcataaatcctcatagagtatttg
ttttcaaaagacttaacatgttccagattatattttatgaatttttttaactggaaaagataag
gcaatatctcttcactaaaaactaattctaatttttcgcttgagaacttggcatagtttgtcca
ctggaaaatctcaaagcctttaaccaaaggattcctgatttccacagttctcgtcatcagctct
ctggttgctttagctaatacaccataagcattttccctactgatgttcatcatctgagcgtatt
ggttataagtgaacgataccgtccgttctttccttgtagggttttcaatcgtggggttgagtag
tgccacacagcataaaattagcttggtttcatgctccgttaagtcatagcgactaatcgctagt
tcatttgctttgaaaacaactaattcagacatacatctcaattggtctaggtgattttaatcac
tataccaattgagatgggctagtcaatgataattactagtccttttcctttgagttgtgggtat
ctgtaaattctgctagacctttgctggaaaacttgtaaattctgctagaccctctgtaaattcc
gctagacctttgtgtgtttttttttgtttatattcaagtggttataatttatagaataaagaaag
aataaaaaaagataaaaagaatagatcccagccctgtgtataactcactactttagtcagttcc
gcagtattacaaaaggatgtcgcaaacgctgtttgctcctctacaaaacagaccttaaaccct
aaaggcttaagtagcaccctcgcaagctcgggcaaatcgctgaatattccttttgtctccgacc
atcaggcacctgagtcgctgtctttttcgtgacattcagttcgctgcgctcacggctctggcag
tgaatgggggtaaatggcactacaggcgccttttatggattcatgcaaggaaactacccataat
acaagaaaagcccgtcacgggcttctcaggcgttttatggcgggtctgctatgtggtgctatc
tgactttttgctgttcagcagttcctgccctctgattttccagtctgaccacttcggattatcc
cgtgacaggtcattcagactggctaatgcacccagtaaggcagcggtatcatcaacaggctta
(SEQ ID NO:53)

Figure 43A

5'-
ctggcgtaatagcgaagaggcccgcaccgatcgcccttcccaacagttgcgcagcctgaatggc
gaatggcgcctgatgcggtattttctccttacgcatctgtgcggtatttcacaccgcatatggt
gcactctcagtacaatctgctctgatgccgcatagttaagccagccccgacacccgccaacacc
cgctgacgagcttagtaaagccctcgctagattttaatgcggatgttgcgattacttcgccaac
tattgcgataacaagaaaaagccagcctttcatgatatatctcccaatttgtgtagggcttatt
atgcacgcttaaaaataataaaagcagacttgacctgatagtttggctgtgagcaattatgtgc
ttagtgcatctaacgcttgagttaagccgcgccgcgaagcggcgtcggcttgaacgaattgtta
gacattatttgccgactaccttggtgatctcgcctttcacgtagtggacaaattcttccaactg
atctgcgcgcgaggccaagcgatcttcttcttgtccaagataagcctgtctagcttcaagtatg
acgggctgatactgggccggcaggcgctccattgcccagtcggcagcgacatccttcggcgcga
ttttgccggttactgcgctgtaccaaatgcgggacaacgtaagcactacatttcgctcatcgcc
agcccagtcgggcggcgagttccatagcgttaaggtttcatttagcgcctcaaatagatcctgt
tcaggaaccggatcaaagagttcctccgccgctggacctaccaaggcaacgctatgttctcttg
cttttgtcagcaagatagccagatcaatgtcgatcgtggctggctcgaagatacctgcaagaat
gtcattgcgctgccattctccaaattgcagttcgcgcttagctggataacgccacggaatgatg
tcgtcgtgcacaacaatggtgacttctacagcgcggagaatctcgctctctccaggggaagccg
aagtttccaaaaggtcgttgatcaaagctcgccgcgttgtttcatcaagccttacggtcaccgt
aaccagcaaatcaatatcactgtgtggcttcaggccgccatccactgcggagccgtacaaatgt
acggccagcaacgtcggttcgagatggcgctcgatgacgccaactacctctgatagttgagtcg
atacttcggcgatcaccgcttccctcatgatgtttaactttgttttagggcgactgccctgctg
cgtaacatcgttgctgctccataacatcaaacatcgacccacggcgtaacgcgcttgctgcttg
gatgcccgaggcatagactgtaccccaaaaaaacagtcataacaagccatgaaaaccgccactg
cgccgttaccaccgctgcgttcggtcaaggttctggaccagttgcgtgagcgcatacgctactt
gcattacagcttacgaaccgaacaggcttatgtccactgggttcgtgccttcatccgtttccac
ggtgtgcgtcacccggcaaccttgggcagcagcgaagtcgaggcatttctgtcctggctggcga
acgagcgcaaggtttcggtctccacgcatcgtcaggcattggcggccttgctgttcttctacgg
caaggtgctgtgcacggatctgccctggcttcaggagatcggaagacctcggccgtcgcggcgc
ttgccggtggtgctgaccccggatgaagtggttcgcatcctcggttttctggaaggcgagcatc
gtttgttcgcccagcttctgtatggaacgggcatgcggatcagtgagggtttgcaactgcgggt
caaggatctggatttcgatcacggcacgatcatcgtgcgggagggcaagggctccaaggatcgg
gccttgatgttacccgagagcttggcacccagcctgcgcgagcaggggaattaattcccacggg
ttttgctgcccgcaaacgggctgttctggtgttgctagtttgttatcagaatcgcagatccggc
ttcagccggtttgccggctgaaagcgctatttcttccagaattgccatgatttttttccccacgg
gaggcgtcactggctcccgtgttgtcggcagctttgattcgataagcagcatcgcctgtttcag
gctgtctatgtgtgactgttgagctgtaacaagttgtctcaggtgttcaatttcatgttctagt
tgctttgttttactggtttcacctgttctattaggtgttacatgctgttcatctgttacattgt
cgatctgttcatggtgaacagctttgaatgcaccaaaaactcgtaaaagctctgatgtatctat
cttttttacaccgttttcatctgtgcatatggacagttttccctttgatatgtaacggtgaaca
gttgttctactttgtttgttagtcttgatgcttcactgatagatacaagagccataagaacct
cagatccttccgtatttagccagtatgttctctagtgtggttcgttgtttttgcgtgagccatg
agaacgaaccattgagatcatacttactttgcatgtcactcaaaaatttgcctcaaaactggt
gagctgaattttttgcagttaaagcatcgtgtagtgtttttcttagtccgttatgtaggtaggaa
tctgatgtaatggttgttggtattttgtcaccattcatttttatctggttgttctcaagttcgg

Figure 43B ttacgagatccatttgtctatctagttcaacttggaaaatcaacgtatcagtcgggcggcctcg
cttatcaaccaccaatttcatattgctgtaagtgtttaaatctttacttattggtttcaaaacc
cattggttaagccttttaaactcatggtagttattttcaagcattaacatgaacttaaattcat
caaggctaatctctatatttgccttgtgagttttcttttgtgttagttcttttaataaccactc
ataaatcctcatagagtatttgttttcaaaagacttaacatgttccagattatattttatgaat
ttttttaactggaaaagataaggcaatatctcttcactaaaaactaattctaatttttcgcttg
agaacttggcatagtttgtccactggaaaatctcaaagcctttaaccaaaggattcctgatttc
cacagttctcgtcatcagctctctggttgctttagctaatacaccataagcattttccctactg
atgttcatcatctgagcgtattggttataagtgaacgataccgtccgttctttccttgtagggt
tttcaatcgtggggttgagtagtgccacacagcataaaattagcttggtttcatgctccgttaa
gtcatagcgactaatcgctagttcatttgctttgaaaacaactaattcagacatacatctcaat
tggtctaggtgattttaatcactataccaattgagatgggctagtcaatgataattactagtcc
ttttcctttgagttgtgggtatctgtaaattctgctagacctttgctggaaaacttgtaaattc
tgctagaccctctgtaaattccgctagacctttgtgtgttttttttgtttatattcaagtggtt
ataatttatagaataaagaaagaataaaaaaagataaaaagaatagatcccagccctgtgtata
actcactactttagtcagttccgcagtattacaaaaggatgtcgcaaacgctgtttgctcctct
acaaaacagaccttaaaaccctaaaggcttaagtagcaccctcgcaagctcgggcaaatcgctg
aatattccttttgtctccgaccatcaggcacctgagtcgctgtctttttcgtgacattcagttc
gctgcgctcacggctctggcagtgaatgggggtaaatggcactacaggcgccttttatggattc
atgcaaggaaactacccataatacaagaaaagcccgtcacgggcttctcagggcgttttatggc
gggtctgctatgtggtgctatctgacttttttgctgttcagcagttcctgccctctgattttcca
gtctgaccacttcggattatcccgtgacaggtcattcagactggctaatgcacccagtaaggca
gcggtatcatcaacaggcttacccgtcttactgtcgggaattcgcgttggccgattcattaatg
cagattctgaaatgagctgttgacaattaatcatccggctcgtataatgtgtggaattgtgagc
ggataacaatttcacacaggaaacagcgccgctgagaaaaagcgaagcggcactgctctttaac
aatttatcagacaatctgtgtgggcactcgaccggaattatcgattaactttattattaaaaat
taaagaggtatatattaatgtatcgattaaataaggaggaataaaccatgtgtgcgacctcttc
tcaatttactcagattaccgagcataattcccgtcgttccgcaaactatcagccaaacctgtgg
aatttcgaattcctgcaatccctggagaacgacctgaaagtggaaaagctggaggagaaagcga
ccaaactggaggaagaagttcgctgcatgatcaaccgtgtagacacccagccgctgtccctgct
ggagctgatcgacgatgtgcagcgcctgggtctgacctacaaatttgaaaaagacatcattaaa
gccctggaaaacatcgtactgctggacgaaaacaaaaagaacaaatctgacctgcacgcaaccg
ctctgtctttccgtctgctgcgtcagcacggtttcgaggtttctcaggatgtttttgagcgttt
caaggataaagaaggtggtttcagcggtgaactgaaaggtgacgtccaaggcctgctgagcctg
tatgaagcgtcttacctgggtttcgagggtgagaacctgctggaggaggcgcgtaccttttcca
tcacccacctgaagaacaacctgaaagaaggcattaataccaaggttgcagaacaagtgagcca
cgccctggaactgccatatcaccagcgtctgcaccgtctggaggcacgttggttcctggataaa
tacgaaccgaaagaaccgcatcaccagctgctgctggagctggcgaagctggattttaacatgg
tacagaccctgcaccagaaagagctgcaagatctgtcccgctggtggaccgagatgggcctggc
tagcaaactggattttgtacgcgaccgcctgatggaagtttatttctgggcactgggtatggcg
ccagacccgcagtttggtgaatgtcgcaaagctgttactaaaatgtttggtctggtgacgatca
tcgatgacgtgtatgacgtttatggcactctggacgaactgcaactgttcaccgatgctgtaga
gcgctgggacgttaacgctattaacaccctgccggactatatgaaactgtgtttcctggcactg
tacaacaccgttaacgacacgtcctattctattctgaaagagaaaggtcataacaacctgtcct

Figure 43C atctgacgaaaagctggcgtgaactgtgcaaagcctttctgcaagaggcgaaatggtccaacaa
caaaattatcccggctttctccaagtacctggaaaacgccagcgtttcctcctccggtgtagcg
ctgctggcgccgtcttacttttccgtatgccagcagcaggaagacatctccgaccacgcgctgc
gttccctgaccgacttccatggtctggtgcgttctagctgcgttatcttccgcctgtgcaacga
tctggccacctctgcggcggagctggaacgtggcgagactaccaattctatcattagctacatg
cacgaaaacgatggtaccagcgaggaacaggcccgcgaagaactgcgtaaactgatcgacgccg
aatggaaaaagatgaatcgtgaacgcgttagcgactccaccctgctgcctaaagcgttcatgga
aatcgcagttaacatggcacgtgtttcccactgcacctaccagtatggcgatggtctgggtcgc
ccagactacgcgactgaaaaccgcatcaaactgctgctgattgaccctttcccgattaaccagc
tgatgtatgtctaactgcatcgcccttaggaggtaaaaaaaaatgactgccgacaacaatagta
tgccccatggtgcagtatctagttacgccaaattagtgcaaaaccaaacacctgaagacatttt
ggaagagtttcctgaaattattccattacaacaaagacctaatacccgatctagtgagacgtca
aatgacgaaagcggagaaacatgtttttctggtcatgatgaggagcaaattaagttaatgaatg
aaaattgtattgttttggattgggacgataatgctattggtgccggtaccaagaaagtttgtca
tttaatggaaaatattgaaaagggtttactacatcgtgcattctccgtctttattttcaatgaa
caaggtgaattacttttacaacaaagagccactgaaaaaataactttccctgatctttggacta
acacatgctgctctcatccactatgtattgatgacgaattaggtttgaagggtaagctagacga
taagattaagggcgctattactgcggcggtgagaaaactagatcatgaattaggtattccagaa
gatgaaactaagacaaggggtaagtttcactttttaaacagaatccattacatggcaccaagca
atgaaccatggggtgaacatgaaattgattacatcctattttataagatcaacgctaaagaaaa
cttgactgtcaacccaaacgtcaatgaagttagagacttcaaatgggtttcaccaaatgatttg
aaaactatgtttgctgacccaagttacaagtttacgccttggtttaagattatttgcgagaatt
acttattcaactggtgggagcaattagatgacctttctgaagtggaaaatgacaggcaaattca
tagaatgctataacgacgcgtcctgcagctggtaccatatgggaattcgaagctttctagaacg
aaaactcatctcagaagaggatctgaatagcgccgtcgaccatcatcatcatcatcattgagtt
taaacggtctccagcttggctgttttggcggatgagagaagattttcagcctgatacagattaa
atcagaacgcagaagcggtctgataaaacagaatttgcctggcggcagtagcgcggtggtccca
cctgaccccatgccgaactcagaagtgaaacgccgtagcgccgatggtagtgtggggtctcccc
atgcgagagtagggaactgccaggcatcaaataaaacgaaaggctcagtcgaaagactgggcct
ttcgttttatctgttgtttgtcggtgaacgctctcctgagtaggacaaatccgccgggagcgga
tttgaacgttgcgaagcaacggcccggagggtggcgggcaggacgcccgccataaactgccagg
catcaaattaagcagaaggccatcctgacggatggcctttttgcgtttctacaaactctttttg
tttatttttctaaatacattcaaatatgtatccgctcatgagacaataaccctgataaatgctt
caataat
(SEQ ID NO:54)

Figure 45A

5'-
cccgtcttactgtcgggaattcgcgttggccgattcattaatgcagattattgaagcatttatc
agggttattgtctcatgagcggatacatatttgaatgtatttagaaaaataaacaaaaagagtt
tgtagaaacgcaaaaaggccatccgtcaggatggccttctgcttaatttgatgcctggcagttt
atggcgggcgtcctgcccgccaccctccgggccgttgcttcgcaacgttcaaatccgctcccgg
cggatttgtcctactcaggagagcgttcaccgacaaacaacagataaaacgaaaggcccagtct
ttcgactgagcctttcgttttatttgatgcctggcagttccctactctcgcatggggagacccc
acactaccatcggcgctacggcgtttcacttctgagttcggcatggggtcaggtgggaccaccg
cgctactgccgccaggcaaattctgttttatcagaccgcttctgcgttctgatttaatctgtat
caggctgaaaatcttctctcatccgccaaaacagccaagctggagaccgtttaaactcaatgat
gatgatgatgatggtcgacggcgctattcagatcctcttctgagatgagtttttgttctagaaa
gcttcgaattcccatatggtaccagctgcagttatgccagccaggccttgattttggcttccat
accagcggcatcgaggccgagttcggcgcgcatttcttcctgagttccttgcggaataaagaag
tccggcaggccaatgttcagcacgggtactggtttacgatgggccatcagcacttcgttcacgc
cgctgcctgcgccgcccataatggcgttttcttctacggtgaccagcgcttcatggctggcggc
catttccagaattaacgcttcatcaagcggtttcacaaaacgcatatcgaccagcgtggcgttc
agcgattcggcgactttcgccgcttctggcatcagcgtaccaaagttaaggatcgccagtttct
cgccacgacgcttcacaatgcctttgccaattggtagtttttccagcggcgtcagttccacgcc
gaccgcgttgccacgcgggtagcgcaccgctgacgggccatcgttatagtgatagccggtatag
agcatctggcgacattcgttttcatcgctcggggtcataatgaccatttccggtatgcagcgca
ggtaagagagatcaaaagcaccctgatgggtttgaccgtcagcaccaacaatgcccgcgcggtc
gatggcgaacaggaccggaagcttttgaatcgccacgtcatgcagcacctgatcataggcgcgt
tgcaggaaagtggagtaaatcgcgacaatgggtttgtacccaccaatcgccagacccgcagcaa
aggtcaccgcgtgttgctcggcaattgccacgtcgaagtagcgatccgggaatttacgtgaaaa
ctcgaccatgccggaaccttcacgcatcgccggagtaatcgccatcagcttgttgtctttcgct
gccgtttcgcacaaccagtcgccaaagattttgaatagctcggcaaaccgccgctactttttcg
gcaaacaaccgctggagggatcaaatttaggcacggcgtggaaagtgatcgggtctttttctgc
cggttcataaccacgacctttttggtcatgatatgcaggaactgcgggcctttcaggtcgcgc
atgttctttagcgtggtgataagccccagcacatcgtgaccgtccaccgggccgatgtagttaa
agcccagctcttcaaacaacgtgccaggcactaccatgcctttaatatgttcttcggtgcgttt
gagcagctctttaattggcggcacgccagagaaactttttcccgccttcgcgcagtgaagag
taaagcttaccggaaagcagctgtgccagatggttgttgagcgcgccgacattttcggaaatcg
acatttcattgtcgttgagaatcaccagcatatcaggacggatatcgcccgcgtgattcatcgc
ttcaaacgccatgcctgcggtaatcgcgccatcgccaatgacacagacggtgcggcgattttg
ccttctttttcggcagcaaccgcaataccaattccggcactgatggaggttgatgaatgcccga
cgcttaatacgtcatattcgctttcgccgcgccacgggaacgggtgcagaccgcctttctgacg
gatggtgccgattttgtcgcggcgtccggtcaaaattttatgcggataagcctgatgccccaca
tcccaaatcaattggtcaaacggggtgttgtagacatagtgcagcgccacggtcagttcgaccg
tgcccagcccggaggcgaagtgcccgctggaacggctcacgctgtcgagtaaatagcggcgcag
ttcgtcgcagagtttcggtaaactctctttcggcaacagtcgtaactcctgggtggagtcgacc
agtgccagggtcgggtatttggcaatatcaaaactcatgtttttttacctcctaagggcgaatg
cagttagacatacatcagctggttaatcgggaaagggtcaatcagcagcagtttgatgcggttt
tcagtcgcgtagtctgggcgacccagaccatcgccatactggtaggtgcagtgggaaacacgtg
ccatgttaactgcgatttccatgaacgctttaggcagcaggtggagtcgctaacgcgttcacg

Figure 45B attcatctttttccattcggcgtcgatcagtttacgcagttcttcgcgggcctgttcctcgctg
gtaccatcgttttcgtgcatgtagctaatgatagaattggtagtctcgccacgttccagctccg
ccgcagaggtggccagatcgttgcacaggcggaagataacgcagctagaacgcaccagaccatg
gaagtcggtcagggaacgcagcgcgtggtcggagatgtcttcctgctgctggcatacggaaaag
taagacggcgccagcagcgctacaccggaggaggaaacgctggcgttttccaggtacttggaga
aagccgggataattttgttgttggaccatttcgcctcttgcagaaaggctttgcacagttcacg
ccagcttttcgtcagataggacaggttgttatgacctttctctttcagaatagaataggacgtg
tcgttaacggtgttgtacagtgccaggaaacacagtttcatatagtccggcagggtgttaatag
cgttaacgtcccagcgctctacagcatcggtgaacagttgcagttcgtccagagtgccataaac
gtcatacacgtcatcgatgatcgtcaccagaccaaacattttagtaacagctttgcgacattca
ccaaactgcgggtctggcgccatacccagtgcccagaaataaacttccatcaggcggtcgcgta
caaaatccagtttgctagccaggcccatctcggtccaccagcgggacagatcttgcagctcttt
ctggtgcagggtctgtaccatgttaaaatccagcttcgccagctccagcagcagctggtgatgc
ggttctttcggttcgtatttatccaggaaccaacgtgcctccagacggtgcagacgctggtgat
atggcagttccagggcgtggctcacttgttctgcaaccttggtattaatgccttctttcaggtt
gttcttcaggtgggtgatggaaaaggtacgcgcctcctccagcaggttctcaccctcgaaaccc
aggtaagacgcttcatacaggctcagcaggccttggacgtcacctttcagttcaccgctgaaac
caccttctttatccttgaaacgctcaaaaacatcctgagaaacctcgaaaccgtgctgacgcag
cagacggaaagacagagcggttgcgtgcaggtcagatttgttctttttgttttcgtccagcagt
acgatgttttccagggctttaatgatgtctttttcaaatttgtaggtcagacccaggcgctgca
catcgtcgatcagctccagcagggacagcggctgggtgtctacacggttgatcatgcagcgaac
ttcttcctccagtttggtcgctttctcctccagcttttccactttcaggtcgttctccagggat
tgcaggaattcgaaattccacaggtttggctgatagtttgcggaacgacgggaattatgctcgg
taatctgagtaaattgagaagaggtcgcacacatggtttattcctccttatttaatcgatacat
taatatatacctctttaatttttaataataaagttaatcgataattccggtcgagtgcccacac
agattgtctgataaattgttaaagagcagtgccgcttcgctttttctcagcggcgctgtttcct
gtgtgaaattgttatccgctcacaattccacacattatacgagccggatgattaattgtcaaca
gctcatttcagaatctggcgtaatagcgaagaggcccgcaccgatcgcccttcccaacagttgc
gcagcctgaatggcgaatggcgcctgatgcggtattttctccttacgcatctgtgcggtatttc
acaccgcatatggtgcactctcagtacaatctgctctgatgccgcatagttaagccagccccga
cacccgccaacacccgctgacgagcttagtaaagccctcgctagattttaatgcggatgttgcg
attacttcgccaactattgcgataacaagaaaaagccagcctttcatgatatatctcccaattt
gtgtagggcttattatgcacgcttaaaaataataaaagcagacttgacctgatagtttggctgt
gagcaattatgtgcttagtgcatctaacgcttgagttaagccgcgccgcgaagcggcgtcggct
tgaacgaattgttagacattatttgccgactaccttggtgatctcgcctttcacgtagtggaca
aattcttccaactgatctgcgcgcgaggccaagcgatcttcttcttgtccaagataagcctgtc
tagcttcaagtatgacgggctgatactgggccggcaggcgctccattgcccagtcggcagcgac
atccttcggcgcgattttgccggttactgcgctgtaccaaatgcgggacaacgtaagcactaca
tttcgctcatcgccagcccagtcgggcggcgagttccatagcgttaaggtttcatttagcgcct
caaatagatcctgttcaggaaccggatcaaagagttcctccgccgctggacctaccaaggcaac
gctatgttctcttgcttttgtcagcaagatagccagatcaatgtcgatcgtggctggctcgaag
atacctgcaagaatgtcattgcgctgccattctccaattgcagttcgcgcttagctggataac
gccacggaatgatgtcgtcgtgcacaacaatggtgacttctacagcgcggagaatctcgctctc
tccaggggaagccgaagtttccaaaaggtcgttgatcaaagctcgccgcgttgtttcatcaagc

Figure 45C cttacggtcaccgtaaccagcaaatcaatatcactgtgtggcttcaggccgccatccactgcgg
agccgtacaaatgtacggccagcaacgtcggttcgagatggcgctcgatgacgccaactacctc
tgatagttgagtcgatacttcggcgatcaccgcttccctcatgatgtttaactttgttttaggg
cgactgccctgctgcgtaacatcgttgctgctccataacatcaaacatcgacccacggcgtaac
gcgcttgctgcttggatgcccgaggcatagactgtaccccaaaaaaacagtcataacaagccat
gaaaaccgccactgcgccgttaccaccgctgcgttcggtcaaggttctggaccagttgcgtgag
cgcatacgctacttgcattacagcttacgaaccgaacaggcttatgtccactgggttcgtgcct
tcatccgtttccacggtgtgcgtcacccggcaaccttgggcagcagcgaagtcgaggcatttct
gtcctggctggcgaacgagcgcaaggtttcggtctccacgcatcgtcaggcattggcggccttg
ctgttcttctacggcaaggtgctgtgcacggatctgccctggcttcaggagatcggaagacctc
ggccgtcgcggcgcttgccggtggtgctgaccccggatgaagtggttcgcatcctcggttttct
ggaaggcgagcatcgtttgttcgcccagcttctgtatggaacgggcatgcggatcagtgagggt
ttgcaactgcgggtcaaggatctggatttcgatcacggcacgatcatcgtgcgggagggcaagg
gctccaaggatcgggccttgatgttacccgagagcttggcacccagcctgcgcgagcaggggaa
ttaattcccacgggttttgctgcccgcaaacgggctgttctggtgttgctagtttgttatcaga
atcgcagatccggcttcagccggtttgccggctgaaagcgctatttcttccagaattgccatga
tttttccccacgggaggcgtcactggctcccgtgttgtcggcagctttgattcgataagcagc
atcgcctgtttcaggctgtctatgtgtgactgttgagctgtaacaagttgtctcaggtgttcaa
tttcatgttctagttgctttgttttactggtttcacctgttctattaggtgttacatgctgttc
atctgttacattgtcgatctgttcatggtgaacagctttgaatgcaccaaaaactcgtaaaagc
tctgatgtatctatctttttacaccgttttcatctgtgcatatggacagttttccctttgata
tgtaacggtgaacagttgttctactttgtttgttagtcttgatgcttcactgatagatacaag
agccataagaacctcagatccttccgtatttagccagtatgttctctagtgtggttcgttgttt
ttgcgtgagccatgagaacgaaccattgagatcatacttactttgcatgtcactcaaaaatttt
gcctcaaaactggtgagctgaattttgcagttaaagcatcgtgtagtgtttttcttagtccgt
tatgtaggtaggaatctgatgtaatggttgttggtattttgtcaccattcatttttatctggtt
gttctcaagttcggttacgagatccatttgtctatctagttcaacttggaaaatcaacgtatca
gtcgggcggcctcgcttatcaaccaccaatttcatattgctgtaagtgtttaaatctttactta
ttggtttcaaaacccattggttaagccttttaaactcatggtagttattttcaagcattaacat
gaacttaaattcatcaaggctaatctctatatttgccttgtgagttttcttttgtgttagttct
tttaataaccactcataaatcctcatagagtatttgttttcaaaagacttaacatgttccagat
tatattttatgaatttttttaactggaaaagataaggcaatatctcttcactaaaaactaattc
taatttttcgcttgagaacttggcatagtttgtccactggaaaatctcaaagcctttaaccaaa
ggattcctgatttccacagttctcgtcatcagctctctggttgctttagctaatacaccataag
cattttccctactgatgttcatcatctgagcgtattggttataagtgaacgataccgtccgttc
tttccttgtagggttttcaatcgtggggttgagtagtgccacacagcataaaattagcttggtt
tcatgctccgttaagtcatagcgactaatcgctagttcatttgctttgaaaacaactaattcag
acatacatctcaattggtctaggtgattttaatcactataccaattgagatgggctagtcaatg
ataattactagtcctttttcctttgagttgtgggtatctgtaaattctgctagacctttgctgga
aaacttgtaaattctgctagaccctctgtaaattccgctagacctttgtgtgtttttttttgttt
atattcaagtggttataatttatagaataaagaaagaataaaaaaagataaaaagaatagatcc
cagccctgtgtataactcactactttagtcagttccgcagtattacaaaaggatgtcgcaaacg
ctgtttgctcctctacaaaacagaccttaaaaccctaaaggcttaagtagcaccctcgcaagct
cgggcaaatcgctgaatattccttttgtctccgaccatcaggcacctgagtcgctgtcttttc

Figure 45D

Gtgacattcagttcgctgcgctcacggctctggcagtgaatgggggtaaatggcactacaggcg
ccttttatggattcatgcaaggaaactacccataatacaagaaaagcccgtcacgggcttctca
gggcgttttatggcgggtctgctatgtggtgctatctgactttttgctgttcagcagttcctgc
cctctgattttccagtctgaccacttcggattatcccgtgacaggtcattcagactggctaatg
cacccagtaaggcagcggtatcatcaacaggctta
(SEQ ID NO:55)

Figure 46B gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcaccccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagcc
tgcaagaaatcgctaaactgggccacgaaatcgaaattaaagtacagggtgccgcgtccccaaccgatacgtatgtttctaccttc
ggcggcgtggttaccatcccggaacgtcgcaaactgaaaactccggactgcggcattgtgattggcgataccggcgttttctcct
ccaccaaagagttagtagctaacgtacgtcagctgcgcgaaagctacccggatttgatcgaaccgctgatgacctctattggcaa
aatctctcgtatcggcgaacaactggttctgtctggcgactacgcatccatcggccgcctgatgaacgtcaaccagggtctcctgg
acgccctgggcgttaacatcttagaactgagccagctgatctattccgctcgtgcggcaggtgcgtttggcgctaaaatcacggg
cgctggcggcggtggctgtatggttgcgctgaccgctccggaaaaatgcaaccaagtggcagaagcggtagcaggcgctggc
ggtaaagtgactatcactaaaccgaccgagcaaggtctgaaagtagattaagccttgacttaatagctgcttatttcgccccttatggt
acctagtaggaggaaaaaaacatggaaatgcgtcaaccggctgtcgcaggtcaattctacccactgcgttgcgagaacctggaa
aacgaactgaaacgctgcttcgaaggcctggagatccgcgaacaagaagtgctgggcgcagtctgtccgcacgccggttatat
gtactctggcaaagttgcggcgcacgtctatgccactctgccggaagctgatacctacgtaatcttcggccccgaaccacaccggc
tacggtagccctgtctctgtgagccgtgaaacttggaagaccccgttgggcaatatcgatgttgacctggaactggcggacggct
tcctgggttccatcgtagatgcggatgaactcggtcacaaatacgaacactctatcgaagttcagctgccgtttctgcaataccgttt
tgaacgcgatttcaaaattctgccaatctgcatgggtatgcaagacgaagaaaccgcggtcgaagtaggtaacctgctggcggat
ctgatcagcgagtccggtaaacgtgctgtgatcatcgcaagctctgatttcacccactatgagacggctgaacgtgccaaagaaa
tcgattccgaagttattgattctatcctgaactttgacatctctggcatgtacgatcgcctgtatcgccgtaacgcctctgtttgcggtta
cggcccgatcaccgctatgctgacggcaagcaaaaagctgggcggctctcgtgcgactttgctgaaatacgcaaacagcggtg
acgtgtccggtgataaagacgctgtggtgggctacgccgccatcatcgttgagtaagctgattaaaggttgaacagataggatttc
gtcatggatcctacaaggaggaaaaaaacatgaatgcttctaatgaaccggtgattctgaaactgggtggctctgctattaccgac
aaaggtgcctacgaaggcgtagttaaggaagctgatttgctgcgcatcgcacaggaagttagcggtttccgtggcaagatgatcg
tggttcatggtgctggtagcttcggccatacgtacgcgaagaaatacggcctggaccgtaccttcgacccagagggcgcaattgt
tactcatgaatctgttaaaaagctcgcctccaaagttgtaggtgctctgaatagcttcggcgtgcgtgctatcgcggtgcatcctatg
gactgcgcagtatgccgtaacggtcgtatcgaaacgatgtatctggactccatcaagttaatgctggaaaaaggtctggtgccggt
tctgcacggcgacgtcgcaatggatattgaactgggcacttgtatcctgtccggtgatcaaatcgttccttacctggccaaagaact
gggtatctcccgcctcggcctgggcagcgcagaggatggtgtgctggatatggagggcaaacctgtaccggaaatcaccccag
aaactttcgaagagttccgccactgcatcggtggttctggttctactgatgtaaccggtggcatgctgggcaaagtgctggaacttc
tggaattgagcaaaaattcttccattactagctacattttcaacgctggtaaagcagacaacatctaccgctttctgaatggtgagtcc
atcggcactcgcatcagcccggacaagcgtgtttaagctagttattaacctaaatgctctaaaccagttatgagctctacaaggag
gaaaaaaacatgattaacactaccagccgccgcaaaattgaacacctgaaactctgcgcagaatccccggttgaagcgcgtca
ggtatctgccggctttgaagacgttactctgatccaccgcgctttaccggagctgaacatggatgaactggacctcagcgttgattt
cctgggtaaacgcatcaaagcgccgttcctgattgcgtctatcacgggtggtcacccagataccatcccggttaacgctgcgctg
gcagctgctgctgaggagctgggtgttggcatcggcgttggctctcagcgcgcggccattgatgatccgagccaggaagacag
cttccgtgtagtgcgtgatgaagccccagatgcgtttgtttatggcaacgtcggcgcagcacagatccgtcagtatggtgttgaag
gtgttgaaaaactgatcgaaatgattgacgcagatgccttggcaatccacctgaactttctgcaagaagcggtccaaccggaagg
tgaccgcgacgcgaccggttgcctggacatgattaccgaaatttgctctcagattaaaactccggtaatcgtgaaagaaaccggt
gcaggcattagccgtgaagatgcgattctgttccagaaagctggcgtgagcgcaatcgacgttggcggcgcgggcggcacctc
ctgggctggcgtcgaggtctaccgtgctaaagaaagccgtgactctgttagcgagcgtttaggtgagctgttttgggatttcggcat
tccgacggtagcttctctgattgaatcccgcgtttccttgccgctgatcgcaaccggcggtatccgtaacggtctggacattgctaa
aagcattgctctcggcgcaagcgctgccagcgccgctctgccgttcgttggtccgtccctggagggcaaagaatccgttgtacgt
gtgctgagctgcatgctggaagaatttaaagcagcaatgtttttgtgcggttgcggcaacatcaaaga

Figure 46C cctgcacaactctccagtagtggtaactggttggacccgcgaatacctggagcagcgcggttttaacgttaaggacctctccctg
ccgggcaacgctctgtaagcttcaacgcgtctacaaataaaaaaggcacgtcagatgacgtgcctttttcttgtctaga
(SEQ ID NO:102)

Figure 47B gtttgacagcttatcatcgactgcacggtgcaccaatgcttctggcgtcaggcagccatcggaagctgtggtatggctgtgcagg
tcgtaaatcactgcataattcgtgtcgctcaaggcgcactcccgttctggataatgttttttgcgccgacatcataacggttctggca
aatattctgaaatgagctgttgacaattaatcatccggctcgtataatgtgtggaattgtgagcggataacaatttcacacaggaaa
cagcgccgctgagaaaaagcgaagcggcactgctctttaacaatttatcagacaatctgtgtgggcactcgaccggaattatcg
attaactttattattaaaaattaaagaggtatatattaatgtatcgattaaataaggaggaataaaccatgtgtgcgacctcttctcaatt
tactcagattaccgagcataattcccgtcgttccgcaaactatcagccaaacctgtggaatttcgaattcctgcaatccctggagaa
cgacctgaaagtggaaaagctggaggagaaagcgaccaaactggaggaagaagttcgctgcatgatcaaccgtgtagacac
ccagccgctgtccctgctggagctgatcgacgatgtgcagcgcctgggtctgacctacaaatttgaaaaagacatcattaaagc
cctggaaaacatcgtactgctggacgaaaacaaaaagaacaaatctgacctgcacgcaaccgctctgtctttccgtctgctgcgt
cagcacggtttcgaggtttctcaggatgtttttgagcgtttcaaggataaagaaggtggtttcagcggtgaactgaaaggtgacgt
ccaaggcctgctgagcctgtatgaagcgtcttacctgggtttcgagggtgagaacctgctggaggaggcgcgtaccttttccatc
acccacctgaagaacaacctgaaagaaggcattaataccaaggttgcagaacaagtgagccacgccctggaactgccatatc
accagcgtctgcaccgtctggaggcacgttggttcctggataaatacgaaccgaaagaaccgcatcaccagctgctgctggag
ctggcgaagctggattttaacatggtacagaccctgcaccagaaagagctgcaagatctgtcccgctggtggaccgagatggg
cctggctagcaaactggattttgtacgcgaccgcctgatggaagtttatttctgggcactgggtatggcgccagacccgcagtttg
gtgaatgtcgcaaagctgttactaaaatgtttggtctggtgacgatcatcgatgacgtgtatgacgtttatggcactctggacgaac
tgcaactgttcaccgatgctgtagagcgctgggacgttaacgctattaacaccctgccggactatatgaaactgtgtttcctggca
ctgtacaacaccgttaacgacacgtcctattctattctgaaagagaaaggtcataacaacctgtcctatctgacgaaaagctggcg
tgaactgtgcaaagcctttctgcaagaggcgaaatggtccaacaacaaaattatcccggctttctccaagtacctggaaaacgcc
agcgtttcctcctccggtgtagcgctgctggcgccgtcttacttttccgtatgccagcagcaggaagacatctccgaccacgcgc
tgcgttccctgaccgacttccatggtctggtgcgttctagctgcgttatcttccgcctgtgcaacgatctggccacctctgcggcgg
agctggaacgtggcgagactaccaattctatcattagctacatgcacgaaaacgatggtaccagcgaggaacaggcccgcga
agaactgcgtaaactgatcgacgccgaatggaaaaagatgaatcgtgaacgcgttagcgactccaccctgctgcctaaagcgtt
catggaaatcgcagttaacatggcacgtgtttcccactgcacctaccagtatggcgatggtctgggtcgcccagactacgcgact
gaaaaccgcatcaaactgctgctgattgaccctttcccgattaaccagctgatgtatgtctaactgcataaaggaggtaaaaaaac
atggtatcctgttctgcgccgggtaagatttacctgttcggtgaacacgccgtagtttatggcgaaactgcaattgcgtgtgcggtg
gaactgcgtacccgtgttcgcgcggaactcaatgactctatcactattcagagccagatcggccgcaccggtctggatttcgaaa
agcacccttatgtgtctgcggtaattgagaaaatgcgcaaatctattcctattaacggtgttttcttgaccgtcgattccgacatcccg
gtgggctccggtctgggtagcagcgcagccgttactatcgcgtctattggtgcgctgaacgagctgttcggctttggcctcagcc
tgcaagaaatcgctaaactgggccacgaaatcgaaattaaagtacagggtgccgcgtccccaaccgatacgtatgtttctacctt
cggcggcgtggttaccatcccggaacgtcgcaaactgaaaactccggactgcggcattgtgattggcgataccggcgttttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcc
tggacgccctgggcgttaacatcttagaactgagccagctgatctattccgctcgtgcggcaggtgcgtttggcgctaaaatcac
gggcgctggcggcggtggctgtatggttgcgctgaccgctccggaaaaatgcaaccaagtggcagaagcggtagcaggcgc
tggcggtaaagtgactatcactaaaccgaccgagcaaggtctgaaagtagattaaagtctagttaaagtttaaacggtctccagct
tggctgttttggcggatgagagaagattttcagcctgatacagattaaatcagaacgcagaagcggtctgataaaacagaatttgc
ctggcggcagtagcgcggtggtcccacctgaccccatgccgaactcagaagtgaaacgccgtagcgccgatggtagtgtgg
ggtctccccatgcgagagtagggaactgccaggcatcaaataaaacgaaaggctcagtcgaaagactgggcctttcgttttatct
gttgtttgtcggtgaacgctctcctgagtaggacaaatccgccgggagcggatttgaacgttgcgaagcaacggcccggaggg
tggcgggcaggacgcccgccataaactgccaggcatcaaattaagcagaaggccatcctgacggatggcctttttgcgtttcta
caaactctttttgtttatttttctaaatacattcaaatatgtatccgcttaaccggaattgccagctggggcgccctctggtaaggttgg
gaagccctgcaaagtaaactggatggctttctcgccgccaaggatctgatggcgcaggggatcaagctctgatcaagagacag
gatgaggatcgtttcgcatgattgaacaagatggattgcacgcaggttctccggccgcttgggtggagaggctattcggctatga
ctgggcacaa

Figure 47C cagacaatcggctgctctgatgccgccgtgttccggctgtcagcgcaggggcgcccggttctttttgtcaagaccgacctgtccg
gtgccctgaatgaactgcaagacgaggcagcgcggctatcgtggctggccacgacgggcgttccttgcgcagctgtgctcgac
gttgtcactgaagcgggaagggactggctgctattgggcgaagtgccggggcaggatctcctgtcatctcaccttgctcctgccg
agaaagtatccatcatggctgatgcaatgcggcggctgcatacgcttgatccggctacctgcccattcgaccaccaagcgaaaca
tcgcatcgagcgagcacgtactcggatggaagccggtcttgtcgatcaggatgatctggacgaagagcatcaggggctcgcgc
cagccgaactgttcgccaggctcaaggcgagcatgcccgacggcgaggatctcgtcgtgacccatggcgatgcctgcttgccg
aatatcatggtggaaaatggccgcttttctggattcatcgactgtggccggctgggtgtggcggaccgctatcaggacatagcgtt
ggctacccgtgatattgctgaagagcttggcggcgaatgggctgaccgcttcctcgtgctttacggtatcgccgctcccgattcgc
agcgcatcgccttctatcgccttcttgacgagttcttctgacgcatgaccaaaatcccttaacgtgagttttcgttccactgagcgtca
gaccccgtagaaaagatcaaaggatcttcttgagatcctttttttctgcgcgtaatctgctgcttgcaaacaaaaaaaccaccgctac
cagcggtggtttgtttgccggatcaagagctaccaactctttttccgaaggtaactggcttcagcagagcgcagataccaaatactg
tccttctagtgtagccgtagttaggccaccacttcaagaactctgtagcaccgcctacatacctcgctctgctaatcctgttaccagtg
gctgctgccagtggcgataagtcgtgtcttaccgggttggactcaagacgatagttaccggataaggcgcagcggtcgggctga
acggggggttcgtgcacacagcccagcttggagcgaacgacctacaccgaactgagatacctacagcgtgagctatgagaaag
cgccacgcttcccgaagggagaaaggcggacaggtatccggtaagcggcagggtcggaacaggagagcgcacgagggag
cttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcct
gcgttatcccctgattctgtggataaccgtattaccgcctttgagtgagctgataccgctcgccgcagccgaacgaccgagcgca
gcgagtcagtgagcgaggaagcggaagagcgcctgatgcggtattttctccttacgcatctgtgcggtatttcacaccgcatatgg
tgcactctcagtacaatctgctctgatgccgcatagttaagccagtatacactccgctatcgctacgtgactgggtcatggctgcgc
cccgacacccgccaacacccgctgacgcgccctgacgggcttgtctgctcccggcatccgcttacagacaagctgtgaccgtct
ccgggagctgcatgtgtcagaggttttcaccgtcatcaccgaaacgcgcgaggcagcagatcaattcgcgcgcgaaggcgaag
cggcatgcatttacgttgacaccatcgaatggtgcaaaacctttcgcggtatggcatgatagcgcccggaagagagtcaattcag
ggtggtgaatgtgaaaccagtaacgttatacgatgtcgcagagtatgccggtgtctcttatcagaccgtttcccgcgtggtgaacca
ggccagccacgtttctgcgaaaacgcgggaaaaagtggaagcggcgatggcggagctgaattacattcccaaccgcgtggca
caacaactggcgggcaaacagtcgttgctgattggcgttgccacctccagtctggccctgcacgcgccgtcgcaaattgtcgcg
gcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagc
tgcctgcactaatgttccggcgttatttcttgatgtctctgaccagacacccatcaacagtattattttctcccatgaagacggtacgcg
actgggcgtggagcatctggtcgcattgggtcaccagcaaatcgcgctgttagcgggcccattaagttctgtctcggcgcgtctgc
gtctggctggctggcataaatatctcactcgcaatcaaattcagccgatagcggaacgggaaggcgactggagtgccatgtccg
gttttcaacaaaccatgcaaatgctgaatgagggcatcgttcccactgcgatgctggttgccaacgatcagatggcgctgggcgc
aatgcgcgccattaccgagtccgggctgcgcgttggtgcggatatctcggtagtgggatacgacgataccgaagacagctcatgt
tatatcccgccgtcaaccaccatcaaacaggattttcgcctgctggggcaaaccagcgtggaccgcttgctgcaactctctcagg
gccaggcggtgaagggcaatcagctgttgcccgtctcactggtgaaaagaaaaaccaccctggcgcccaatacgcaaaccgc
ctctccccgcgcgttggccgattcattaatgcagctggcacgacaggtttcccgactggaaagcgggcagtgagcgcaacgcaa
ttaatgtgagttagcgcgaattgatctg
(SEQ ID NO:103)

Figure 51A

5′-
tcgctgcgctcggtcgttcggctgcggcgagcggtatcagctcactcaaaggcggtaatacggt
tatccacagaatcaggggataacgcaggaaagaacatgtgagcaaaaggccagcaaaaggccag
gaaccgtaaaaaggccgcgttgctggcgtttttccataggctccgcccccctgacgagcatcac
aaaaatcgacgctcaagtcagaggtggcgaaacccgacaggactataaagataccaggcgtttc
cccctggaagctccctcgtgcgctctcctgttccgaccctgccgcttaccggatacctgtccgc
ctttctcccttcgggaagcgtggcgctttctcatagctcacgctgtaggtatctcagttcggtg
taggtcgttcgctccaagctgggctgtgtgcacgaaccccccgttcagcccgaccgctgcgcct
tatccggtaactatcgtcttgagtccaacccggtaagacacgacttatcgccactggcagcagc
cactggtaacaggattagcagagcgaggtatgtaggcggtgctacagagttcttgaagtggtgg
cctaactacggctacactagaagaacagtatttggtatctgcgctctgctgaagccagttacct
tcggaaaaagagttggtagctcttgatccggcaaacaaaccaccgctggtagcggtggtttttt
tgtttgcaagcagcagattacgcgcagaaaaaaaggatctcaagaagatcctttgatcttttct
acggggtctgacgctcagtggaacgaaaactcacgttaagggattttggtcatgagattatcaa
aaaggatcttcacctagatccttttaaattaaaaatgaagttttaaatcaatctaaagtatata
tgagtaaacttggtctgacagttaccaatgcttaatcagtgaggcacctatctcagcgatctgt
ctatttcgttcatccatagttgcctgactccccgtcgtgtagataactacgatacgggagggct
taccatctggccccagtgctgcaatgataccgcgagacccacgctcaccggctccagatttatc
agcaataaaccagccagccggaagggccgagcgcagaagtggtcctgcaactttatccgcctcc
atccagtctattaattgttgccgggaagctagagtaagtagttcgccagttaatagtttgcgca
acgttgttgccattgctacaggcatcgtggtgtcacgctcgtcgtttggtatggcttcattcag
ctccggttcccaacgatcaaggcgagttacatgatcccccatgttgtgcaaaaaagcggttagc
tccttcggtcctccgatcgttgtcagaagtaagttggccgcagtgttatcactcatggttatgg
cagcactgcataattctcttactgtcatgccatccgtaagatgcttttctgtgactggtgagta
ctcaaccaagtcattctgagaatagtgtatgcggcgaccgagttgctcttgcccggcgtcaata
cgggataataccgcgccacatagcagaactttaaaagtgctcatcattggaaaacgttcttcgg
ggcgaaaactctcaaggatcttaccgctgttgagatccagttcgatgtaacccactcgtgcacc
caactgatcttcagcatcttttactttcaccagcgtttctgggtgagcaaaaacaggaaggcaa
aatgccgcaaaaaagggaataagggcgacacggaaatgttgaatactcatactcttcctttttc
aatattattgaagcatttatcagggttattgtctcatgagcggatacatatttgaatgtattta
gaaaaataaacaaataggggttccgcgcacatttccccgaaaagtgccacctgacgtctaagaa
accattattatcatgacattaacctataaaaataggcgtatcacgaggccctttcgtctcgcgc
gtttcggtgatgacggtgaaaacctctgacacatgcagctcccggagacggtcacagcttgtct
gtaagcggatgccgggagcagacaagcccgtcagggcgcgtcagcgggtgttggcgggtgtcgg
ggctggcttaactatgcggcatcagagcagattgtactgagagtgcaccatagatctggagctg
taatataaaaaccttcttcaactaacggggcaggttagtgacattagaaaaccgactgtaaaaa
gtacagtcggcattatctcatattataaaagccagtcattaggcctatctgacaattcctgaat
agagttcataaacaatcctgcatgataaccatcacaaacagaatgatgtacctgtaaagatagc
ggtaaatatattgaattacctttattaatgaattttcctgctgtaataatgggtagaaggtaat
tactattattattgatatttaagttaaacccagtaaatgaagtccatggaataatagaaagaga
aaaagcattttcaggtataggtgttttgggaaacaatttccccgaaccattatatttctctaca
tcagaaaggtataaatcataaaactctttgaagtcattctttacaggagtccaaataccagaga
atgttttagatacaccatcaaaaattgtataaagtggctctaacttatcccaataacctaactc
tccgtcgctattgtaaccagttctaaaagctgtatttgagtttatcaccccttgtcactaagaaa
ataaatgcagggtaaaatttatatccttcttgttttatgtttc

Figure 51B ggtataaaacactaatatcaatttctgtggttatactaaaagtcgtttgttggttcaaataatg
attaaatatctcttttctcttccaattgtctaaatcaattttattaaagttcatttgatatgcc
tcctaaatttttatctaaagtgaatttaggaggcttacttgtctgctttcttcattagaatcaa
tcctttttttaaaagtcaatattactgtaacataaatatatattttaaaaatatcccactttatc
caattttcgtttgttgaactaatgggtgctttagttgaagaataaaagacctatgcggtgtgaa
ataccgcacagatgcgtaaggagaaaataccgcatcaggcgccattcgccattcaggctgcgca
actgttgggaagggcgatcggtgcgggcctcttcgctattacgccagctggcgaaggggggatg
tgctgcaaggcgattaagttgggtaacgccagggttttcccagtcacgacgttgtaaaacgacg
gccagtgccaagcttgcatgcctgcactccatttcttctgctatcaaaataacagactcgtga
ttttccaaacgagctttcaaaaaagcctctgccccttgcaaatcggatgcctgtctataaaatt
cccgatattggttaaacagcggcgcaatggcggccgcatctgatgtctttgcttggcgaatgtt
catcttatttcttcctccctctcaataatttttttcattctatccctttctgtaaagtttattt
ttcagaatacttttatcatcatgctttgaaaaaatatcacgataatatccattgttctcacgga
agcacacgcaggtcatttgaacgaatttttttcgacaggaatttgccgggactcaggagcattta
acctaaaaaagcatgacatttcagcataatgaacatttactcatgtctattttcgttcttttct
gtatgaaaatagttatttcgagtctctacggaaatagcgagagatgatatacctaaatagagat
aaaatcatctcaaaaaaatgggtctactaaaatattattccatctattacaataaattcacaga
atagtcttttaagtaagtctactctgaatttttttaaaaggagagggtaaagagtgaaaacagt
agttattattgatgcattacgaacaccaattggaaaatataaaggcagcttaagtcaagtaagt
gccgtagacttaggaacacatgttacaacacaacttttaaaaagacattccactatttctgaag
aaattgatcaagtaatctttggaaatgttttacaagctggaaatggccaaaatcccgcacgaca
aatagcaataaacagcggtttgtctcatgaaattcccgcaatgacggttaatgaggtctgcgga
tcaggaatgaaggccgttattttggcgaaacaattgattcaattaggagaagcggaagttttaa
ttgctggcgggattgagaatatgtcccaagcacctaaattacaacgttttaattacgaaacaga
aagctacgatgcgcctttttctagtatgatgtatgatggattaacggatgcctttagtggtcag
gcaatgggcttaactgctgaaaatgtggccgaaaagtatcatgtaactagagaagagcaagatc
aattttctgtacattcacaattaaaagcagctcaagcacaagcagaagggatattcgctgacga
aatagccccattagaagtatcaggaacgcttgtggagaaagatgaagggattcgccctaattcg
agcgttgagaagctaggaacgcttaaaacagtttttaaagaagacggtactgtaacagcaggga
atgcatcaaccattaatgatggggcttctgctttgattattgcttcacaagaatatgccgaagc
acacggtcttccttatttagctattattcgagacagtgtggaagtcggtattgatccagcctat
atgggaatttcgccgattaaagccattcaaaaactgttagcgcgcaatcaacttactacggaag
aaattgatctgtatgaaatcaacgaagcatttgcagcaacttcaatcgtggtccaaagagaact
ggctttaccagaggaaaaggtcaacatttatggtggcggtatttcattaggtcatgcgattggt
gccacaggtgctcgtttattaacgagtttaagttatcaattaaatcaaaaagaaaagaaatatg
gagtggcttctttatgtatcggcggtggcttaggactcgctatgctactagagagacctcagca
aaaaaaaaacagccgattttatcaaatgagtcctgaggaacgcctggcttctcttcttaatgaa
ggccagatttctgctgatacaaaaaaagaatttgaaaatacggctttatcttcgcagattgcca
atcatatgattgaaaatcaaatcagtgaaacagaagtgccgatgggcgttggcttacatttaac
agtggacgaaactgattatttggtaccaatggcgacagaagagccctcagttattgcggctttg
agtaatggtgcaaaaatagcacaaggatttaaaacagtgaatcaacaacgcttaatgcgtggac
aaatcgtttttttacgatgttgcagatcccgagtcattgattgataaactacaagtaagagaagc
ggaagtttttcaacaagcagagttaagttatccatctatcgttaaacggggcggcggcttaaga
gatttgcaatatcgtacttttgatgaatcatttgtatctgtcgactttttagtagatgttaagg
atgcaatgggggcaaatatcgttaacgctatgttggaaggtgtg

Figure 51C gccgagttgttccgtgaatggtttgcggagcaaaagattttattcagtattttaagtaattatg
ccacggagtcggttgttacgatgaaaacggctattccagtttcacgtttaagtaaggggagcaa
tggccgggaaattgctgaaaaaattgtttagcttcacgctatgcttcattagatccttatcgg
gcagtcacgcataacaaaggaatcatgaatggcattgaagctgtagttttagctacaggaaatg
atacacgcgctgttagcgcttcttgtcatgcttttgcggtgaaggaaggtcgctaccaaggctt
gactagttggacgctggatggcgaacaactaattggtgaaatttcagttccgcttgctttagcc
acggttggcggtgccacaaaagtcttacctaaatctcaagcagctgctgatttgttagcagtga
cggatgcaaaagaactaagtcgagtagtagcggctgttggtttggcacaaaatttagcggcgtt
acgggccttagtctctgaaggaattcaaaaaggacacatggctctacaagcacgttctttagcg
atgacggtcggagctactggtaaagaagttgaggcagtcgctcaacaattaaaacgtcaaaaa
cgatgaaccaagaccgagccatggctattttaaatgatttaagaaaacaataaaaggagagggt
gacaattgggattgataaaattagtttttttgtgccccttattatattgatatgacggcactg
gctgaagccagaaatgtagaccctggaaaatttcatattggtattgggcaagaccaaatggcgg
tgaacccaatcagccaagatattgtgacatttgcagccaatgccgcagaagcgatcttgaccaa
agaagataaagaggccattgatatggtgattgtcgggactgagtccagtatcgatgagtcaaaa
gcggccgcagttgtcttacatcgtttaatggggattcaacctttcgctcgctctttcgaaatca
aggaagcttgttacggagcaacagcaggcttacagttagctaagaatcacgtagccttacatcc
agataaaaaagtcttggtcgtagcggcagatattgcaaaatatggcttaaattctggcggtgag
cctacacaaggagctggggcggttgcaatgttagttgctagtgaaccgcgcattttggctttaa
aagaggataatgtgatgctgacgcaagatatctatgacttttggcgtccaacaggccacccgta
tcctatggtcgatggtcctttgtcaaacgaaacctacatccaatcttttgcccaagtctgggat
gaacataaaaaacgaaccggtcttgattttgcagattatgatgctttagcgttccatattcctt
acacaaaaatgggcaaaaaagccttattagcaaaaatctccgaccaaactgaagcagaacagga
acgaattttagcccgttatgaagaaagtatcgtctatagtcgtcgcgtaggaaacttgtatacg
ggttcactttatctgggactcattcccttttagaaaatgcaacgactttaaccgcaggcaatc
aaattggtttattcagttatggttctggtgctgtcgctgaatttttcactggtgaattagtagc
tggttatcaaaatcatttacaaaaagaaactcatttagcactgctggataatcggacagaactt
tctatcgctgaatatgaagccatgtttgcagaaactttagacacagacattgatcaaacgttag
aagatgaattaaaatatagtatttctgctattaataataccgttcgttcttatcgaaactaaaa
aaaaccggccttggccccgccggtttttttattatttttcttcctccgcatgttcaatccgctcc
ataatcgacggatggctccctctgaaaattttaacgagaaacggcgggttgacccggctcagtc
ccgtaacggccaagtcctgaaacgtctcaatcgccgcttcccggtttccggtcagctcaatgcc
gtaacggtcggcggcgttttcctgataccgggagacggcattcgtaatcgggatccccgggtac
cgagctcgaattcgtaatcatgtcatagctgtttcctgtgtgaaattgttatccgctcacaatt
ccacacaacatacgagccggaagcataaagtgtaaagcctggggtgcctaatgagtgagctaac
tcacattaattgcgttgcgctcactgcccgctttccagtcgggaaacctgtcgtgccagctgca
ttaatgaatcggccaacgcgcggggagaggcggtttgcgtattgggcgctcttccgcttcctcg
ctcactgac
(SEQ ID NO:56)

MCM376 - MVK from M. mazei archeal Lowerin pET200D
6647 bp

Figure 57B aagggcgagctcaacgatccggctgctaacaaagcccgaaaggaagctgagttggctgctgccaccgctgagcaataactag
cataaccccttggggcctctaaacgggtcttgaggagttttttgctgaaaggaggaactatatccggatatcccgcaagaggccc
ggcagtaccggcataaccaagcctatgcctacagcatccagggtgacggtgccgaggatgacgatgagcgcattgttagatttc
atacacggtgcctgactgcgttagcaatttaactgtgataaactaccgcattaaagcttatcgatgataagctgtcaaacatgagaat
taattcttgaagacgaaagggcctcgtgatacgcctatttttataggttaatgtcatgataataatggtttcttagacgtcaggtggcac
ttttcggggaaatgtgcgcggaacccctatttgtttatttttctaaatacattcaaatatgtatccgctcatgagacaataaccctgataa
atgcttcaataatattgaaaaaggaagagtatgattgaacaagatggattgcacgcaggttctccggccgcttgggtggagaggct
attcggctatgactgggcacaactgacaatcggctgctctgatgccgccgtgttccggctgtcagcgcaggggcgcccggttctt
tttgtcaagaccgacctgtccggtgccctgaatgaactgcaggacgaggcagcgcggctatcgtggctggccacgacgggcgt
tccttgcgcagctgtgctcgacgttgtcactgaagcgggaagggactggctgctattgggcgaagtgccggggcaggatctcct
gtcatctcaccttgctcctgccgagaaagtatccatcatggctgatgcaatgcggcggctgcatacgcttgatccggctacctgcc
cattcgaccaccaagcgaaacatcgcatcgagcgggcacgtactcggatggaagccggtcttgtcgatcaggatgatctggac
gaagagcatcaggggctcgcgccagccgaactgttcgccaggctcaaggcgcgcatgcccgacggcgaggatctcgtcgtg
acacatggcgatgcctgcttgccgaatatcatggtggaaaatggccgcttttctggattcatcgactgtggccggctgggtgtggc
ggaccgctatcaggacatagcgttggctacccgtgatattgctgaagagcttggcggcgaatgggctgaccgcttcctcgtgcttt
acggtatcgccgctcccgattcgcagcgcatcgccttctatcgccttcttgacgagttcttctgagcgggactctggggttcgaaat
gaccgaccaagcgacgcctaactgtcagaccaagtttactcatatatactttagattgatttaaaacttcatttttaatttaaaaggatct
aggtgaagatcctttttgataatctcatgaccaaaatcccttaacgtgagttttcgttccactgagcgtcagaccccgtagaaaagat
caaaggatcttcttgagatcctttttttctgcgcgtaatctgctgcttgcaaacaaaaaaaccaccgctaccagcggtggtttgtttgc
cggatcaagagctaccaactctttttccgaaggtaactggcttcagcagagcgcagataccaaatactgtccttctagtgtagccgt
agttaggccaccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacggggggttcgtgc
acacagcccagcttggagcgaacgacctacaccgaactgagatacctacagcgtgagctatgagaaagcgccacgcttcccg
aagggagaaaggcggacaggtatccggtaagcggcagggtcggaacaggagagcgcacgagggagcttccagggggaaa
cgcctggtatctttatagtcctgtcgggtttcgccacctctgacttgagcgtcgatttttgtgatgctcgtcaggggggcggagcctat
ggaaaaacgccagcaacgcggcctttttacggttcctggccttttgctggccttttgctcacatgttctttcctgcgttatcccctgatt
ctgtggataaccgtattaccgcctttgagtgagctgataccgctcgccgcagccgaacgaccgagcgcagcgagtcagtgagc
gaggaagcggaagagcgcctgatgcggtattttctccttacgcatctgtgcggtatttcacaccgcaatggtgcactctcagtaca
atctgctctgatgccgcatagttaagccagtatacactccgctatcgctacgtgactgggtcatggctgcgccccgacacccgcc
aacacccgctgacgcgccctgacgggcttgtctgctcccggcatccgcttacagacaagctgtgaccgtctccgggagctgcat
gtgtcagaggttttcaccgtcatcaccgaaacgcgcgaggcagctgcggtaaagctcatcagcgtggtcgtgaagcgattcaca
gatgtctgcctgttcatccgcgtccagctcgttgagtttctccagaagcgttaatgtctggcttctgataaagcgggccatgttaagg
gcggtttttttcctgtttggtcactgatgcctccgtgtaagggggatttctgttcatgggggtaatgataccgatgaaacgagagagga
tgctcacgatacgggttactgatgatgaacatgcccggttactggaacgttgtgagggtaaacaactggcggtatggatgcggcg
ggaccagagaaaaatcactcagggtcaatgccagcgcttcgttaatacagatgtaggtgttccacagggtagccagcagcatcc
tgcgatgcagatccggaacataatggtgcagggcgctgacttccgcgtttccagactttacgaaacacggaaaccgaagaccat
tcatgttgttgctcaggtcgcagacgttttgcagcagcagtcgcttcacgttcgctcgcgtatcggtgattcattctgctaaccagtaa
ggcaaccccgccagcctagccgggtcctcaacgacaggagcacgatcatgcgcacccgtggccaggacccaacgctgccc
gagatgcgccgcgtgcggctgctggagatggcggacgcgatggatatgttctgccaagggttggtttgcgcattcacagttctcc
gcaagaattgattggctccaattcttggagtggtgaatccgttagcgaggtgccgccggcttccattcaggtcgaggtggcccgg
ctccatgcaccgcgacgcaacgcggggaggcagacaaggtatagggcggcgcctacaatccatgccaacccgttccatgtgc
tcgccgaggcggcataaatcgccgtgacgatcagcggtccaatgatcgaagttaggctggtaagagccgcgagcgatccttga
agctgtccctgatggtcgtcatctacctgcctggacagcatggcctgcaacgcgggcatcccgatgccgccggaagcgagaag
aatcataatggggaaggccatccagcctcgcgtcgcgaacgccagcaagacgtagcccagcgcg

Figure 57C cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagaggc
ggtttgcgtattgggcgccagggtggtttttcttttcaccagtgagacgggcaacagctgattgcccttcaccgcctggccctgaga
gagttgcagcaagcggtccacgctggtttgccccagcaggcgaaaatcctgtttgatggtggttaacggcgggatataacatgag
ctgtcttcggtatcgtcgtatcccactaccgagatatccgcaccaacgcgcagcccggactcggtaatggcgcgcattgcgccca
gcgccatctgatcgttggcaaccagcatcgcagtgggaacgatgccctcattcagcatttgcatggtttgttgaaaaccggacatg
gcactccagtcgccttcccgttccgctatcggctgaatttgattgcgagtgagatatttatgccagccagccagacgcagacgcgc
cgagacagaacttaatgggcccgctaacagcgcgatttgctggtgacccaatgcgaccagatgctccacgcccagtcgcgtac
cgtcttcatgggagaaaataatactgttgatgggtgtctggtcagagacatcaagaaataacgccggaacattagtgcaggcagc
ttccacagcaatggcatcctggtcatccagcggatagttaatgatcagcccactgacgcgttgcgcgagaagattgtgcaccgcc
gctttacaggcttcgacgccgcttcgttctaccatcgacaccaccacgctggcacccagttgatcggcgcgagatttaatcgccg
cgacaatttgcgacggcgcgtgcagggccagactggaggtggcaacgccaatcagcaacgactgtttgcccgccagttgttgt
gccacgcggttgggaatgtaattcagctccgccatcgccgcttccactttttcccgcgttttcgcagaaacgtggctggcctggttc
accacgcgggaaacggtctgataagagacaccggcatactctgcgacatcgtataacgttactggtttcacattcaccaccctga
attgactctcttccgggcgctatcatgccataccgcgaaaggttttgcgccattcgatggtgtccgggatctcgacgctctcccttat
gcgactcctgcattaggaagcagcccagtagtaggttgaggccgttgagcaccgccgccgcaaggaatggtgcatgcaagga
gatggcgcccaacagtcccccggccacggggcctgccaccatacccacgccgaaacaagcgctcatgagcccgaagtggc
gagcccgatcttccccatcggtgatgtcggcgatataggcgccagcaaccgcacctgtggcgccggtgatgccggccacgatg
cgtccggcgtagaggatcgagatctcgatcccgcgaaattaatacgactcactataggggaattgtgagcggataacaattcccc
tctagaaataattttgtttaactttaagaaggagatatacatatgcggggttctcatcatcatcatcatcatggtatggctagcatgact
ggtggacagcaaatgggtcgggatctgtacgacgatgacgataaggatcatcccttcaccatggtatcctgttctgcgccgggta
agatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaatt
gagaaaatgcgcaaatctattcctattaacggtgttttcttgaccgtcgattccgacatcccggtgggctccggtctgggtagcagc
gcagccgttactatcgcgtctattggtgcgctgaacgagctgttcggctttggcctcagcctgcaagaaatcgctaaactgggcca
cgaaatcgaaattaaagtacagggtgccgcgtccccaaccgatacgtatgtttctaccttcggcggcgtggttaccatcccggaa
cgtcgcaaactgaaaactccggactgcggcattgtgattggcgataccggcgttttctcctccaccaaagagttagtagctaacgt
acgtcagctgcgcgaaagctacccggatttgatcgaaccgctgatgacctctattggcaaaatctctcgtatcggcgaacaactg
gttctgtctggcgactacgcatccatcggccgcctgatgaacgtcaaccagggtctcctggacgccctgggcgttaacatcttaga
actgagccagctgatctattccgctcgtgcggcaggtgcgtttggcgctaaaatcacgggcgctggcggcggtggctgtatggtt
gcgctgaccgctccggaaaaatgcaaccaagtggcagaagcggtagcaggcgctggcggtaaagtgactatcactaaaccga
ccgagcaaggtctgaaagtagattaa
(SEQ ID NO:104)

A

B

C

D

Figure 59B gtttgacagcttatcatcgactgcacggtgcaccaatgcttctggcgtcaggcagccatcggaagctgtggtatggctgtgcagg
tcgtaaatcactgcataattcgtgtcgctcaaggcgcactcccgttctggataatgttttttgcgccgacatcataacggttctggca
aatattctgaaatgagctgttgacaattaatcatccggctcgtataatgtgtggaattgtgagcggataacaatttcacacaggaaa
cagcgccgctgagaaaaagcgaagcggcactgctctttaacaatttatcagacaatctgtgtgggcactcgaccggaattatcg
attaactttattattaaaaattaaagaggtatatattaatgtatcgattaaataaggaggaataaaccatgtgtgcgacctcttctcaatt
tactcagattaccgagcataattcccgtcgttccgcaaactatcagccaaacctgtggaatttcgaattcctgcaatccctggagaa
cgacctgaaagtggaaaagctggaggagaaagcgaccaaactggaggaagaagttcgctgcatgatcaaccgtgtagacac
ccagccgctgtccctgctggagctgatcgacgatgtgcagcgcctgggtctgacctacaaatttgaaaaagacatcattaaagc
cctggaaaacatcgtactgctggacgaaaacaaaaagaacaaatctgacctgcacgcaaccgctctgtctttccgtctgctgcgt
cagcacggtttcgaggtttctcaggatgtttttgagcgtttcaaggataaagaaggtggtttcagcggtgaactgaaaggtgacgt
ccaaggcctgctgagcctgtatgaagcgtcttacctgggtttcgagggtgagaacctgctggaggaggcgcgtaccttttccatc
acccacctgaagaacaacctgaaagaaggcattaataccaaggttgcagaacaagtgagccacgccctggaactgccatatca
ccagcgtctgcaccgtctggaggcacgttggttcctggataaatacgaaccgaaagaaccgcatcaccagctgctgctggagc
tggcgaagctggatttttaacatggtacagaccctgcaccagaaagagctgcaagatctgtcccgctggtggaccgagatgggc
ctggctagcaaactggattttgtacgcgaccgcctgatggaagtttatttctgggcactgggtatggcgccagacccgcagtttgg
tgaatgtcgcaaagctgttactaaaatgtttggtctggtgacgatcatcgatgacgtgtatgacgtttatggcactctggacgaactg
caactgttcaccgatgctgtagagcgctgggacgttaacgctattaacaccctgccggactatatgaaactgtgtttcctggcact
gtacaacaccgttaacgacacgtcctattctattctgaaagagaaaggtcataacaacctgtcctatctgacgaaaagctggcgtg
aactgtgcaaagcctttctgcaagaggcgaaatggtccaacaacaaaattatcccggctttctccaagtacctggaaaacgccag
cgtttcctcctccggtgtagcgctgctggcgccgtcttacttttccgtatgccagcagcaggaagacatctccgaccacgcgctgc
gttccctgaccgacttccatggtctggtgcgttctagctgcgttatcttccgcctgtgcaacgatctggccacctctgcggcggag
ctggaacgtggcgagactaccaattctatcattagctacatgcacgaaaacgatggtaccagcgaggaacaggcccgcgaag
aactgcgtaaactgatcgacgccgaatggaaaaagatgaatcgtgaacgcgttagcgactccaccctgctgcctaaagcgttca
tggaaatcgcagttaacatggcacgtgtttcccactgcacctaccagtatggcgatggtctgggtcgcccagactacgcgactga
aaaccgcatcaaactgctgctgattgaccctttcccgattaaccagctgatgtatgtctaactgcataaaggaggtaaaaaaacat
gtcattaccgttcttaacttctgcaccgggaaaggttattattttggtgaacactctgctgtgtacaacaagcctgccgtcgctgcta
gtgtgtctgcgttgagaacctacctgctaataagcgagtcatctgcaccagatactattgaattggacttcccggacattagcttta
tcataagtggtccatcaatgatttcaatgccatcaccgaggatcaagtaaactcccaaaaattggccaaggctcaacaagccacc
gatggcttgtctcaggaactcgttagtcttttggatccgttgttagctcaactatccgaatccttccactaccatgcagcgttttgtttcc
tgtatatgtttgtttgcctatgcccccatgccaagaatattaagttttctttaaagtctactttacccatcggtgctgggttgggctcaag
cgcctctatttctgtatcactggccttagctatggcctacttgggggggttaataggatctaatgacttggaaaagctgtcagaaaa
cgataagcatatagtgaatcaatgggccttcataggtgaaaagtgtattcacggtaccccttcaggaatagataacgctgtggcca
cttatggtaatgccctgctatttgaaaaagactcacataatggaacaataaacacaaacaattttaagttcttagatgatttcccagcc
attccaatgatcctaacctatactagaattccaaggtctacaaaagatcttgttgctcgcgttcgtgtgttggtcaccgagaaattcc
tgaagttatgaagccaattctagatgccatgggtgaatgtgccctacaaggcttagagatcatgactaagttaagtaaatgtaaag
gcaccgatgacgaggctgtagaaactaataatgaactgtatgaacaactattggaattgataagaataaatcatggactgcttgtct
caatcggtgtttctcatcctggattagaacttattaaaaatctgagcgatgatttgagaattggctccacaaaacttaccggtgctggt
ggcggcggttgctctttgactttgttacgaagagacattactcaagagcaaattgacagcttcaaaaagaaattgcaagatgatttt
agttacgagacatttgaaacagacttgggtgggactggctgctgtttgttaagcgcaaaaaatttgaataaagatcttaaaatcaaa
tccctagtattccaattatttgaaaataaaactaccacaaagcaacaaattgacgatctattattgccaggaaacacgaatttaccat
ggacttcataactgcagagtctagttaaagtttaaacggtctccagcttggctgttttggcggatgagagaagattttcagcctgata
cagattaaatcagaacgcagaagcggtctgataaaacagaatttgcctggcggcagtagcgcggtggtcccacctgaccccat
gccgaactcagaagtgaaacgccgtagcgccgatggtagtgtggggtctccccatgcgagagtagggaactgccaggcatca
aataaaacgaaaggctcagtcgaaagactgggcctttcgttttatctgttgtttgtcggtgaacgctctcctgagtaggacaaatcc
gccgggag

Figure 59C cggatttgaacgttgcgaagcaacggcccggagggtggcgggcaggacgcccgccataaactgccaggcatcaaattaagc
agaaggccatcctgacggatggcctttttgcgtttctacaaactcttttgtttatttttctaaatacattcaaatatgtatccgcttaacc
ggaattgccagctggggcgccctctggtaaggttgggaagccctgcaaagtaaactggatggctttctcgccgccaaggatctg
atggcgcaggggatcaagctctgatcaagagacaggatgaggatcgtttcgcatgattgaacaagatggattgcacgcaggttc
tccggccgcttgggtggagaggctattcggctatgactgggcacaacagacaatcggctgctctgatgccgccgtgttccggct
gtcagcgcaggggcgcccggttctttttgtcaagaccgacctgtccggtgccctgaatgaactgcaagacgaggcagcgcgg
ctatcgtggctggccacgacgggcgttccttgcgcagctgtgctcgacgttgtcactgaagcgggaagggactggctgctattg
ggcgaagtgccggggcaggatctcctgtcatctcaccttgctcctgccgagaaagtatccatcatggctgatgcaatgcggcgg
ctgcatacgcttgatccggctacctgcccattcgaccaccaagcgaaacatcgcatcgagcgagcacgtactcggatggaagc
cggtcttgtcgatcaggatgatctggacgaagagcatcaggggctcgcgccagccgaactgttcgccaggctcaaggcgagc
atgcccgacggcgaggatctcgtcgtgacccatggcgatgcctgcttgccgaatatcatggtggaaaatggccgcttttctggat
tcatcgactgtggccggctgggtgtggcggaccgctatcaggacatagcgttggctacccgtgatattgctgaagagcttggcg
gcgaatgggctgaccgcttcctcgtgctttacggtatcgccgctcccgattcgcagcgcatcgccttctatcgccttcttgacgagt
tcttctgacgcatgaccaaaatcccttaacgtgagttttcgttccactgagcgtcagaccccgtagaaaagatcaaaggatcttctt
gagatcctttttttctgcgcgtaatctgctgcttgcaaacaaaaaaaccaccgctaccagcggtggtttgtttgccggatcaagagc
taccaactctttttccgaaggtaactggcttcagcagagcgcagataccaaatactgtccttctagtgtagccgtagttaggccacc
acttcaagaactctgtagcaccgcctacatacctcgctctgctaatcctgttaccagtggctgctgccagtggcgataagtcgtgt
cttaccgggttggactcaagacgatagttaccggataaggcgcagcggtcgggctgaacggggggttcgtgcacacagccca
gcttggagcgaacgacctacaccgaactgagatacctacagcgtgagctatgagaaagcgccacgcttcccgaagggagaa
aggcggacaggtatccggtaagcggcagggtcggaacaggagagcgcacgagggagcttccagggggaaacgcctggta
tctttatagtcctgtcgggtttcgccacctctgacttgagcgtcgatttttgtgatgctcgtcaggggggcggagcctatggaaaaa
cgccagcaacgcggcctttttacggttcctggccttttgctggccttttgctcacatgttctttcctgcgttatcccctgattctgtggat
aaccgtattaccgcctttgagtgagctgataccgctcgccgcagccgaacgaccgagcgcagcgagtcagtgagcgaggaa
gcggaagagcgcctgatgcggtattttctccttacgcatctgtgcggtatttcacaccgcatatggtgcactctcagtacaatctgc
tctgatgccgcatagttaagccagtatacactccgctatcgctacgtgactgggtcatggctgcgccccgacacccgccaacac
ccgctgacgcgccctgacgggcttgtctgctcccggcatccgcttacagacaagctgtgaccgtctccgggagctgcatgtgtc
agaggttttcaccgtcatcaccgaaacgcgcgaggcagcagatcaattcgcgcgcgaaggcgaagcggcatgcatttacgttg
acaccatcgaatggtgcaaaacctttcgcggtatggcatgatagcgcccggaagagagtcaattcagggtggtgaatgtgaaa
ccagtaacgttatacgatgtcgcagagtatgccggtgtctcttatcagaccgtttcccgcgtggtgaaccaggccagccacgtttc
tgcgaaaacgcgggaaaaagtggaagcggcgatggcggagctgaattacattcccaaccgcgtggcacaacaactggcgg
gcaaacagtcgttgctgattggcgttgccacctccagtctggccctgcacgcgccgtcgcaaattgtcgcggcgattaaatctcg
cgccgatcaactgggtgccagcgtggtggtgtcgatggtagaacgaagcggcgtcgaagcctgtaaagcggcggtgcacaat
cttctcgcgcaacgcgtcagtgggctgatcattaactatccgctggatgaccaggatgccattgctgtggaagctgcctgcacta
atgttccggcgttatttcttgatgtctctgaccagacacccatcaacagtattattttctcccatgaagacggtacgcgactgggcgt
ggagcatctggtcgcattgggtcaccagcaaatcgcgctgttagcgggcccattaagttctgtctcggcgcgtctgcgtctggct
ggctggcataaatatctcactcgcaatcaaattcagccgatagcggaacgggaaggcgactggagtgccatgtccggttttcaa
caaaccatgcaaatgctgaatgagggcatcgttcccactgcgatgctggttgccaacgatcagatggcgctgggcgcaatgcg
cgccattaccgagtccgggctgcgcgttggtgcggatatctcggtagtgggatacgacgataccgaagacagctcatgttatatc
ccgccgtcaaccaccatcaaacaggattttcgcctgctggggcaaaccagcgtggaccgcttgctgcaactctctcagggcca
ggcggtgaagggcaatcagctgttgcccgtctcactggtgaaaagaaaaaccaccctggcgcccaatacgcaaaccgcctct
ccccgcgcgttggccgattcattaatgcagctggcacgacaggtttcccgactggaaagcgggcagtgagcgcaacgcaatta
atgtgagttagcgcgaattgatctg
(SEQ ID NO:105)

| Concentration at Deflagration | | | | | | | | | | | | | | |
|---|---|---|---|---|---|---|---|---|---|---|---|---|---|---|
| | | Fuel Makeup | Oxidizer Makeup | | | Molar Concentration based on 100g of sample | | | | | Volumetric Concentrations based on ideal gas law | | | |
| Fuel Conc. (wt.%) | Oxidizer Conc. (wt.%) | Isoprene (wt. %) | $H_2O$ (wt. %) | $O_2$ (wt. %) | $N_2$ (wt. %) | Isoprene (mole) | $H_2O$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.10 | 96.90 | 100 | 0 | 12 | 88 | 4.56 | 0.00 | 36.34 | 304.54 | 345.44 | 1.32 | 10.52 | 88.16 | 0.00 |
| 3.10 | 96.90 | 100 | 0 | 13 | 87 | 4.56 | 0.00 | 39.37 | 301.08 | 345.01 | 1.32 | 11.41 | 87.27 | 0.00 |
| 3.10 | 96.90 | 100 | 0 | 14 | 86 | 4.56 | 0.00 | 42.39 | 297.62 | 344.57 | 1.32 | 12.30 | 86.37 | 0.00 |
| 3.10 | 96.90 | 100 | 0 | 15 | 85 | 4.56 | 0.00 | 45.42 | 294.16 | 344.14 | 1.32 | 13.20 | 85.48 | 0.00 |
| 3.10 | 96.90 | 100 | 0 | 16 | 84 | 4.56 | 0.00 | 48.45 | 290.70 | 343.71 | 1.33 | 14.10 | 84.58 | 0.00 |
| 3.10 | 96.90 | 100 | 0 | 17 | 83 | 4.56 | 0.00 | 51.48 | 287.24 | 343.28 | 1.33 | 15.00 | 83.68 | 0.00 |
| 3.10 | 96.90 | 100 | 0 | 21 | 79 | 4.56 | 0.00 | 63.59 | 273.40 | 341.55 | 1.33 | 18.62 | 80.05 | 0.00 |
| 3.50 | 96.50 | 100 | 0 | 11.1 | 88.9 | 5.15 | 0.00 | 33.47 | 306.39 | 345.01 | 1.49 | 9.70 | 88.81 | 0.00 |
| 4.40 | 95.60 | 100 | 0 | 12 | 88 | 6.47 | 0.00 | 35.85 | 300.46 | 342.78 | 1.89 | 10.46 | 87.65 | 0.00 |
| 5.50 | 94.50 | 100 | 0 | 13 | 87 | 8.09 | 0.00 | 38.39 | 293.63 | 340.10 | 2.38 | 11.29 | 86.33 | 0.00 |
| 6.60 | 93.40 | 100 | 0 | 14 | 86 | 9.71 | 0.00 | 40.86 | 286.87 | 337.44 | 2.88 | 12.11 | 85.01 | 0.00 |
| 7.60 | 92.40 | 100 | 0 | 15 | 85 | 11.18 | 0.00 | 43.31 | 280.50 | 334.99 | 3.34 | 12.93 | 83.73 | 0.00 |
| 8.50 | 91.50 | 100 | 0 | 16 | 84 | 12.50 | 0.00 | 45.75 | 274.50 | 332.75 | 3.76 | 13.75 | 82.49 | 0.00 |
| 9.60 | 90.40 | 100 | 0 | 17 | 83 | 14.12 | 0.00 | 48.03 | 267.97 | 330.11 | 4.28 | 14.55 | 81.18 | 0.00 |
| 13.50 | 86.50 | 100 | 0 | 21 | 79 | 19.85 | 0.00 | 56.77 | 244.05 | 320.67 | 6.19 | 17.70 | 76.11 | 0.00 |

| Concentration at Deflagration | | | | | | | | | | | | | | | |
|---|---|---|---|---|---|---|---|---|---|---|---|---|---|---|---|
| | | Fuel Makeup | Oxidizer Makeup | | | Molar Concentration based on 100g of sample | | | | | Volumetric Concentrations based on ideal gas law | | | | |
| Fuel Conc. (wt.%) | Oxidizer Conc. (wt.%) | Isoprene (wt. %) | $H_2O$ (wt. %) | $O_2$ (wt. %) | $N_2$ (wt. %) | Isoprene (mole) | $H_20$ (mole) | $O_2$ (mole) | $N_2$ (mole) | Total (mole) | Isoprene (vol. %) | $O_2$ (vol. %) | $N_2$ (vol. %) | $H_2O$ (vol. %) |
| 3.252 | 96.748 | 100 | 4 | 12 | 84 | 4.78 | 21.50 | 36.28 | 290.24 | 352.81 | 1.36 | 10.28 | 82.27 | 6.09 |
| 3.274 | 96.726 | 100 | 4 | 13 | 83 | 4.81 | 21.49 | 39.29 | 286.72 | 352.33 | 1.37 | 11.15 | 81.38 | 6.10 |
| 3.290 | 96.710 | 100 | 4 | 14 | 82 | 4.84 | 21.49 | 42.31 | 283.22 | 351.86 | 1.38 | 12.02 | 80.49 | 6.11 |
| 3.288 | 96.712 | 100 | 4 | 15 | 81 | 4.84 | 21.49 | 45.33 | 279.77 | 351.43 | 1.38 | 12.90 | 79.61 | 6.12 |
| 3.286 | 96.714 | 100 | 4 | 16 | 80 | 4.83 | 21.49 | 48.36 | 276.33 | 351.01 | 1.38 | 13.78 | 78.72 | 6.12 |
| 3.284 | 96.716 | 100 | 4 | 17 | 79 | 4.83 | 21.49 | 51.38 | 272.86 | 350.58 | 1.38 | 14.66 | 77.84 | 6.13 |
| 3.276 | 96.724 | 100 | 4 | 21 | 75 | 4.82 | 21.49 | 63.48 | 259.06 | 348.87 | 1.38 | 18.19 | 74.26 | 6.16 |
| 3.500 | 96.500 | 100 | 4 | 11.5 | 84.5 | 5.15 | 21.44 | 34.68 | 291.22 | 352.49 | 1.46 | 9.84 | 82.62 | 6.08 |
| 4.200 | 95.800 | 100 | 4 | 12 | 84 | 6.18 | 21.29 | 35.93 | 287.40 | 350.79 | 1.76 | 10.24 | 81.93 | 6.07 |
| 5.300 | 94.700 | 100 | 4 | 13 | 83 | 7.79 | 21.04 | 38.47 | 280.72 | 348.03 | 2.24 | 11.05 | 80.66 | 6.05 |
| 6.400 | 93.600 | 100 | 4 | 14 | 82 | 9.41 | 20.80 | 40.95 | 274.11 | 345.28 | 2.73 | 11.86 | 79.39 | 6.02 |
| 7.400 | 92.600 | 100 | 4 | 15 | 81 | 10.88 | 20.58 | 43.41 | 267.88 | 342.74 | 3.18 | 12.66 | 78.16 | 6.00 |
| 8.500 | 91.500 | 100 | 4 | 16 | 80 | 12.50 | 20.33 | 45.75 | 261.43 | 340.01 | 3.68 | 13.46 | 76.89 | 5.98 |
| 9.400 | 90.600 | 100 | 4 | 17 | 79 | 13.82 | 20.13 | 48.13 | 255.62 | 337.71 | 4.09 | 14.25 | 75.69 | 5.96 |
| 13.300 | 86.700 | 100 | 4 | 21 | 75 | 19.56 | 19.27 | 56.90 | 232.23 | 327.95 | 5.96 | 17.35 | 70.81 | 5.87 |

Figure 78B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 1.5 | 21.0 | 1.4 |
| 13.0 | 1.5 | 13.0 | 1.4 |
| 11.0 | 1.6 | 11.0 | 1.5 |
| 10.4 | 1.8 | 10.4 | 1.7 |
| 10.0 | 1.9 | 10.0 | 1.8 |
| 9.8 | 2 | 9.7 | 2 |
| 10.0 | 2.2 | 10.0 | 2.3 |
| 10.4 | 2.5 | 10.4 | 2.6 |
| 11.0 | 2.9 | 11.0 | 3.0 |
| 13.0 | 4.0 | 13.0 | 4.1 |
| 17.7 | 8.0 | 17.6 | 8.0 |
| 21.0 | 11.8 | 21.0 | 11.9 |

Figure 79B

| Explosions | | Non-explosions | |
|---|---|---|---|
| $O_2$ Concentration (vol. %) | $C_5H_8$ Concentration (vol. %) | $O_2$ Concentration (vol. %) | $C_5H_8$ Concentration (vol. %) |
| 21.0 | 11.7 | 21.0 | 11.9 |
| 21.0 | 11.8 | 21.0 | 11.9 |
| 21.0 | 11.8 | 21.0 | 11.9 |
| 21.0 | 1.5 | 21.0 | 1.4 |
| 21.0 | 1.5 | 21.0 | 1.4 |
| 10.2 | 2.0 | 21.0 | 1.4 |
| 10.1 | 2.0 | 9.8 | 2.0 |
| 10.0 | 2.0 | 9.8 | 2.0 |
| 9.9 | 2.0 | 9.8 | 2.0 |

Figure 80A

TEST SERIES 1

| Test | Data File Name | Temp | Initial Pressure | Partial Pressures | | | Concentrations | | | Result | Pex |
|---|---|---|---|---|---|---|---|---|---|---|---|
| | | | | $C_3H_8$ | $N_2$ | $O_2$ | $C_3H_8$ | $N_2$ | $O_2$ | | |
| | | °C | bara | mbar | mbar | mbar | vol. % | vol. % | vol. % | | bara |
| 1 | T11120700 | 40 | 1.012 | 12 | 787 | 213 | 1.2 | 77.8 | 21.0 | Non-Explosion | 1.05 |
| 2 | T11120701 | 40 | 1.016 | 16 | 787 | 213 | 1.6 | 77.5 | 21.0 | Explosion | 5.5 |
| 3 | T11120702 | 40 | 1.015 | 14 | 788 | 213 | 1.4 | 77.6 | 21.0 | Non-Explosion | <1.02 |
| 4 | T11120703 | 40 | 1.014 | 15 | 786 | 213 | 1.5 | 77.5 | 21.0 | Non-Explosion | <1.02 |
| 5 | T11120704 | 40 | 1.014 | 15 | 786 | 213 | 1.5 | 77.5 | 21.0 | Explosion | 4.31 |
| 6 | T11120705 | 40 | 1.017 | 18 | 785 | 214 | 1.8 | 77.2 | 21.0 | Explosion | 5.47 |
| 7 | T11120706 | 40 | 1.014 | 15 | 786 | 213 | 1.5 | 77.5 | 21.0 | Explosion | 4.51 |
| 8 | T11120707 | 40 | 1.014 | 14 | 787 | 213 | 1.4 | 77.6 | 21.0 | Non-Explosion | <1.02 |
| 9 | T11120708 | 40 | 1.014 | 14 | 787 | 213 | 1.4 | 77.6 | 21.0 | Non-Explosion | 1.05 |
| 10 | T11120709 | 40 | 1.015 | 102 | 700 | 213 | 10.0 | 69.0 | 21.0 | Explosion | 1.45 |
| 11 | T11120710 | 40 | 1.014 | 102 | 699 | 213 | 10.1 | 68.9 | 21.0 | Explosion | 1.39 |
| 12 | T11120711 | 40 | 1.014 | 106 | 695 | 213 | 10.5 | 68.5 | 21.0 | Explosion | 1.34 |
| 13 | T11120712 | 40 | 1.014 | 113 | 688 | 213 | 11.1 | 67.9 | 21.0 | Explosion | 1.29 |
| 14 | T11120713 | 40 | 1.014 | 122 | 679 | 213 | 12.0 | 67.0 | 21.0 | Non-Explosion | <1.02 |
| 15 | T11120714 | 40 | 1.014 | 117 | 684 | 213 | 11.5 | 67.5 | 21.0 | Explosion | 1.32 |
| 16 | T11120715 | 40 | 1.014 | 120 | 681 | 213 | 11.8 | 67.2 | 21.0 | Non-Explosion | 1.08 |
| 17 | T11130700 | 40 | 1.014 | 120 | 681 | 213 | 11.8 | 67.2 | 21.0 | Explosion | 1.09 |
| 18 | T11130701 | 40 | 1.014 | 121 | 680 | 213 | 11.9 | 67.1 | 21.0 | Non-Explosion | 1.07 |
| 19 | T11130702 | 40 | 1.015 | 121 | 681 | 213 | 11.9 | 67.1 | 21.0 | Non-Explosion | 1.06 |
| 20 | T11130703 | 40 | 1.015 | 121 | 681 | 213 | 11.9 | 67.1 | 21.0 | Non-Explosion | 1.07 |
| 21 | T11130704 | 40 | 1.015 | 30 | 853 | 132 | 3.0 | 84.0 | 13.0 | Explosion | 1.61 |
| 22 | T11130705 | 40 | 1.014 | 36 | 846 | 132 | 3.6 | 83.4 | 13.0 | Explosion | 1.28 |
| 23 | T11130706 | 40 | 1.014 | 39 | 843 | 132 | 3.8 | 83.1 | 13.0 | Explosion | 1.12 |
| 24 | T11130707 | 40 | 1.015 | 41 | 842 | 132 | 4.0 | 83.0 | 13.0 | Explosion | 1.09 |
| 25 | T11130708 | 40 | 1.014 | 42 | 840 | 132 | 4.1 | 82.8 | 13.0 | Non-Explosion | 1.06 |
| 26 | T11130709 | 40 | 1.015 | 42 | 841 | 132 | 4.1 | 82.9 | 13.0 | Non-Explosion | 1.06 |
| 27 | T11130710 | 40 | 1.014 | 42 | 840 | 132 | 4.1 | 82.8 | 13.0 | Non-Explosion | 1.05 |
| 28 | T11130711 | 40 | 1.014 | 15 | 867 | 132 | 1.5 | 85.5 | 13.0 | Non-Explosion | 1.03 |
| 29 | T11130712 | 40 | 1.014 | 16 | 866 | 132 | 1.6 | 85.4 | 13.0 | Explosion | 4.81 |
| 30 | T11130713 | 40 | 1.014 | 15 | 867 | 132 | 1.5 | 85.5 | 13.0 | Explosion | 4 |
| 31 | T11130714 | 40 | 1.014 | 14 | 868 | 132 | 1.4 | 85.6 | 13.0 | Non-Explosion | 1.03 |
| 32 | T11130715 | 40 | 1.014 | 14 | 868 | 132 | 1.4 | 85.6 | 13.0 | Non-Explosion | <1.02 |
| 33 | T11130716 | 40 | 1.014 | 14 | 868 | 132 | 1.4 | 85.6 | 13.0 | Non-Explosion | 1.03 |
| 34 | T11130717 | 40 | 1.015 | 20 | 883 | 112 | 2.0 | 87.0 | 11.0 | Explosion | 1.7 |
| 35 | T11130718 | 40 | 1.014 | 28 | 874 | 112 | 2.8 | 86.2 | 11.0 | Non-Explosion | 1.08 |
| 36 | T11130719 | 40 | 1.014 | 28 | 874 | 112 | 2.8 | 86.2 | 11.0 | Non-Explosion | 1.08 |
| 37 | T11130720 | 40 | 1.014 | 28 | 874 | 112 | 2.8 | 86.2 | 11.0 | Explosion | 1.13 |
| 38 | T11130721 | 40 | 1.015 | 29 | 874 | 112 | 2.9 | 86.1 | 11.0 | Non-Explosion | 1.08 |
| 39 | T11130722 | 40 | 1.014 | 29 | 873 | 112 | 2.9 | 86.1 | 11.0 | Explosion | 1.1 |

Figure 80B

| Test | Data File Name | Temp | Initial Pressure | Partial Pressures | | | Concentrations | | | Result | Pex |
|---|---|---|---|---|---|---|---|---|---|---|---|
| | | | | $C_3H_8$ | $N_2$ | $O_2$ | $C_3H_8$ | $N_2$ | $O_2$ | | |
| | | °C | bara | mbar | mbar | mbar | vol. % | vol. % | vol. % | | bara |
| 40 | T11130723 | 40 | 1.014 | 30 | 872 | 112 | 3.0 | 86.0 | 11.0 | Non-Explosion | 1.08 |
| 41 | T11130724 | 40 | 1.014 | 30 | 872 | 112 | 3.0 | 86.0 | 11.0 | Non-Explosion | 1.05 |
| 42 | T11130725 | 40 | 1.014 | 30 | 872 | 112 | 3.0 | 86.0 | 11.0 | Non-Explosion | 1.05 |
| 43 | T11130726 | 40 | 1.014 | 15 | 887 | 112 | 1.5 | 87.5 | 11.0 | Non-Explosion | <1.02 |
| 44 | T11130727 | 40 | 1.014 | 15 | 887 | 112 | 1.5 | 87.5 | 11.0 | Non-Explosion | <1.02 |
| 45 | T11140700 | 40 | 1.014 | 16 | 886 | 112 | 1.6 | 87.4 | 11.0 | Non-Explosion | <1.02 |
| 46 | T11140701 | 40 | 1.014 | 17 | 885 | 112 | 1.7 | 87.3 | 11.0 | Explosion | 1.81 |
| 47 | T11140702 | 40 | 1.014 | 16 | 886 | 112 | 1.6 | 87.4 | 11.0 | Explosion | 1.54 |
| 48 | T11140703 | 40 | 1.014 | 15 | 887 | 112 | 1.5 | 87.5 | 11.0 | Non-Explosion | <1.02 |
| 49 | T11140704 | 40 | 1.015 | 20 | 899 | 96 | 2.0 | 88.6 | 9.5 | Non-Explosion | 1.05 |
| 50 | T11140705 | 40 | 1.014 | 20 | 898 | 96 | 2.0 | 88.6 | 9.5 | Non-Explosion | 1.05 |
| 51 | T11140706 | 40 | 1.014 | 23 | 890 | 101 | 2.3 | 87.8 | 10.0 | Non-Explosion | 1.05 |
| 52 | T11140707 | 40 | 1.015 | 23 | 886 | 106 | 2.3 | 87.3 | 10.4 | Explosion | 1.19 |
| 53 | T11140708 | 40 | 1.014 | 25 | 884 | 105 | 2.5 | 87.2 | 10.4 | Explosion | 1.09 |
| 54 | T11140709 | 40 | 1.014 | 26 | 883 | 105 | 2.6 | 87.1 | 10.4 | Non-Explosion | 1.05 |
| 55 | T11140710 | 40 | 1.014 | 26 | 883 | 105 | 2.6 | 87.1 | 10.4 | Non-Explosion | 1.06 |
| 56 | T11140711 | 40 | 1.014 | 26 | 883 | 105 | 2.6 | 87.1 | 10.4 | Non-Explosion | 1.07 |
| 57 | T11140712 | 40 | 1.014 | 20 | 889 | 105 | 2.0 | 87.7 | 10.4 | Explosion | 1.21 |
| 58 | T11140713 | 40 | 1.014 | 17 | 892 | 105 | 1.7 | 88.0 | 10.4 | Non-Explosion | 1.04 |
| 59 | T11140714 | 40 | 1.014 | 18 | 891 | 105 | 1.8 | 87.9 | 10.4 | Explosion | 1.21 |
| 60 | T11140715 | 40 | 1.014 | 17 | 892 | 105 | 1.7 | 88.0 | 10.4 | Non-Explosion | 1.03 |
| 61 | T11140716 | 40 | 1.014 | 17 | 892 | 105 | 1.7 | 88.0 | 10.4 | Non-Explosion | 1.03 |
| 62 | T11140717 | 40 | 1.014 | 21 | 890 | 103 | 2.1 | 87.8 | 10.2 | Explosion | 1.1 |
| 63 | T11140718 | 40 | 1.014 | 21 | 891 | 102 | 2.1 | 87.9 | 10.1 | Explosion | 1.09 |
| 64 | T11140719 | 40 | 1.014 | 21 | 892 | 101 | 2.1 | 88.0 | 10.0 | Explosion | 1.09 |
| 65 | T11140720 | 40 | 1.014 | 22 | 891 | 101 | 2.2 | 87.9 | 10.0 | Explosion | 1.1 |
| 66 | T11140721 | 40 | 1.014 | 23 | 890 | 101 | 2.3 | 87.8 | 10.0 | Non-Explosion | 1.06 |
| 67 | T11140722 | 40 | 1.014 | 23 | 890 | 101 | 2.3 | 87.8 | 10.0 | Non-Explosion | 1.08 |
| 68 | T11140723 | 40 | 1.014 | 19 | 894 | 101 | 1.9 | 88.2 | 10.0 | Explosion | 1.12 |
| 69 | T11140724 | 40 | 1.014 | 18 | 895 | 101 | 1.8 | 88.3 | 10.0 | Non-Explosion | 1.06 |
| 70 | T11140725 | 40 | 1.014 | 18 | 895 | 101 | 1.8 | 88.3 | 10.0 | Non-Explosion | 1.03 |
| 71 | T11140726 | 40 | 1.014 | 18 | 895 | 101 | 1.8 | 88.3 | 10.0 | Non-Explosion | 1.04 |
| 72 | T11140727 | 40 | 1.014 | 20 | 895 | 99 | 2.0 | 88.3 | 9.8 | Non-Explosion | 1.08 |
| 73 | T11140728 | 40 | 1.014 | 20 | 895 | 99 | 2.0 | 88.3 | 9.8 | Explosion | 1.1 |
| 74 | T11140729 | 40 | 1.014 | 20 | 896 | 98 | 2.0 | 88.4 | 9.7 | Non-Explosion | 1.06 |
| 75 | T11140730 | 40 | 1.014 | 20 | 896 | 98 | 2.0 | 88.4 | 9.7 | Non-Explosion | 1.08 |
| 76 | T11140731 | 40 | 1.014 | 20 | 896 | 98 | 2.0 | 88.4 | 9.7 | Non-Explosion | 1.07 |
| 77 | T11140732 | 40 | 1.014 | 81 | 761 | 172 | 8.0 | 75.0 | 17.0 | Non-Explosion | 1.04 |
| 78 | T11140733 | 40 | 1.014 | 81 | 750 | 183 | 8.0 | 74.0 | 18.0 | Explosion | 1.3 |
| 79 | T11140734 | 40 | 1.014 | 81 | 754 | 179 | 8.0 | 74.4 | 17.7 | Explosion | 1.24 |
| 80 | T11140735 | 40 | 1.014 | 81 | 757 | 176 | 8.0 | 74.7 | 17.4 | Non-Explosion | 1.03 |
| 81 | T11140736 | 40 | 1.014 | 81 | 755 | 178 | 8.0 | 74.5 | 17.6 | Non-Explosion | 1.05 |
| 82 | T11140737 | 40 | 1.014 | 81 | 755 | 178 | 8.0 | 74.5 | 17.6 | Non-Explosion | 1.03 |
| 83 | T11140738 | 40 | 1.014 | 81 | 755 | 178 | 8.0 | 74.5 | 17.6 | Non-Explosion | 1.03 |

Figure 81

TEST SERIES 2

| Test | Data File Name | Temp | Initial Pressure | Partial Pressures | | | | Concentrations | | | | Result | Pex |
|---|---|---|---|---|---|---|---|---|---|---|---|---|---|
| | | | | $H_2O$ | $C_3H_8$ | $N_2$ | $O_2$ | $H_2O$ | $C_3H_8$ | $N_2$ | $O_2$ | | |
| | | °C | bara | mbar | mbar | mbar | mbar | vol. % | vol. % | vol. % | vol. % | | bara |
| 1 | T11150700 | 40 | 1.014 | 41 | 119 | 641 | 213 | 4.0 | 11.7 | 63.2 | 21.0 | Explosion | 1.33 |
| 2 | T11150701 | 40 | 1.014 | 40 | 121 | 640 | 213 | 3.9 | 11.9 | 63.1 | 21.0 | Non-explosion | 1.07 |
| 3 | T11150702 | 40 | 1.014 | 41 | 120 | 640 | 213 | 4.0 | 11.8 | 63.1 | 21.0 | Explosion | 1.09 |
| 4 | T11150703 | 40 | 1.014 | 40 | 121 | 640 | 213 | 3.9 | 11.9 | 63.1 | 21.0 | Non-explosion | 1.06 |
| 5 | T11150704 | 40 | 1.014 | 40 | 120 | 641 | 213 | 3.9 | 11.8 | 63.2 | 21.0 | Explosion | 1.09 |
| 6 | T11150705 | 40 | 1.014 | 40 | 121 | 640 | 213 | 3.9 | 11.9 | 63.1 | 21.0 | Non-explosion | 1.08 |
| 7 | T11150706 | 40 | 1.014 | 40 | 15 | 746 | 213 | 3.9 | 1.5 | 73.6 | 21.0 | Explosion | 4.68 |
| 8 | T11150707 | 40 | 1.014 | 41 | 15 | 745 | 213 | 4.0 | 1.5 | 73.5 | 21.0 | Explosion | 5.27 |
| 9 | T11150708 | 40 | 1.014 | 41 | 14 | 746 | 213 | 4.0 | 1.4 | 73.6 | 21.0 | Non-explosion | 1.03 |
| 10 | T11150709 | 40 | 1.014 | 42 | 14 | 745 | 213 | 4.1 | 1.4 | 73.5 | 21.0 | Non-explosion | 1.03 |
| 11 | T11160700 | 40 | 1.014 | 41 | 14 | 746 | 213 | 4.0 | 1.4 | 73.6 | 21.0 | Non-explosion | 1.03 |
| 12 | T11160701 | 40 | 1.014 | 41 | 20 | 850 | 103 | 4.0 | 2.0 | 83.8 | 10.2 | Explosion | 1.11 |
| 13 | T11160702 | 40 | 1.014 | 41 | 20 | 851 | 102 | 4.0 | 2.0 | 83.9 | 10.1 | Explosion | 1.11 |
| 14 | T11160703 | 40 | 1.014 | 41 | 20 | 852 | 101 | 4.0 | 2.0 | 84.0 | 10.0 | Explosion | 1.09 |
| 15 | T11160704 | 40 | 1.014 | 41 | 20 | 853 | 100 | 4.0 | 2.0 | 84.1 | 9.9 | Explosion | 1.09 |
| 16 | T11160705 | 40 | 1.014 | 41 | 20 | 854 | 99 | 4.0 | 2.0 | 84.2 | 9.8 | Non-explosion | 1.07 |
| 17 | T11160706 | 40 | 1.014 | 40 | 20 | 855 | 99 | 3.9 | 2.0 | 84.3 | 9.8 | Non-explosion | 1.06 |
| 18 | T11160707 | 40 | 1.014 | 41 | 20 | 854 | 99 | 4.0 | 2.0 | 84.2 | 9.8 | Non-explosion | 1.08 |

Figure 88A-B
A
B
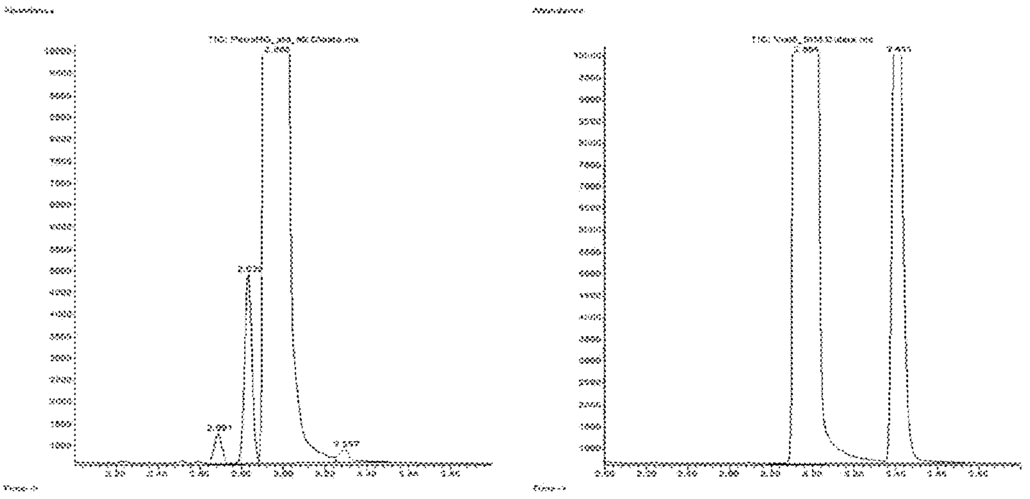
2-methyl-1,3-butadiene standard.
2-methyl-1,3-butadiene from recombinant *E. coli*
Figure 89
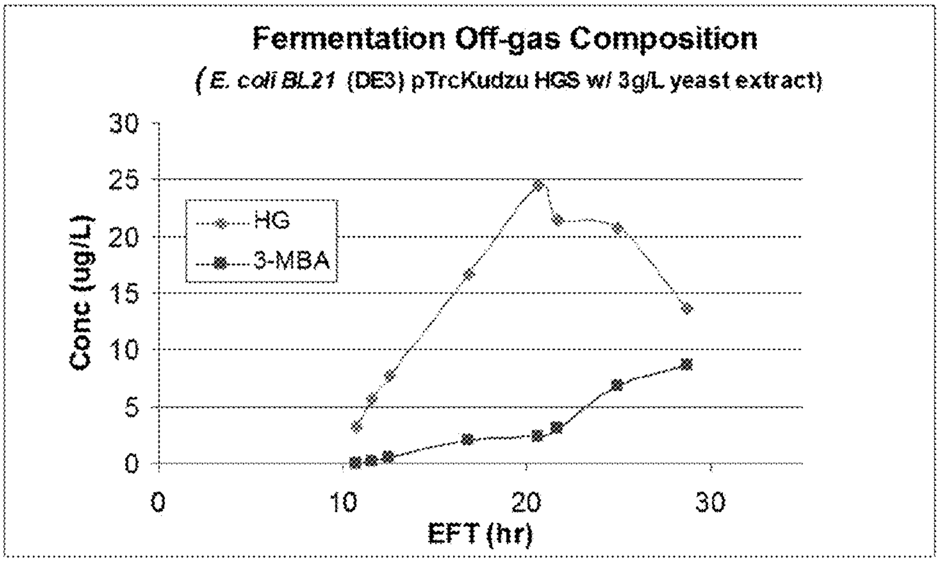

Figure 90
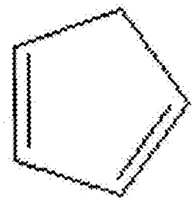
cyclopentadiene
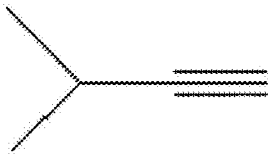
"isopryne" = 3-Me-1-butyne
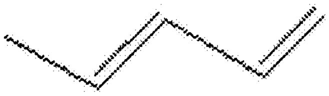
trans-piperylene
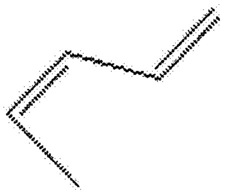
cis-piperylene
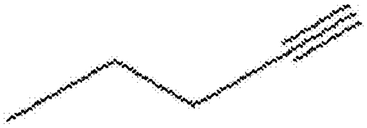
1-pentyne
pent-4-ene-1-yne
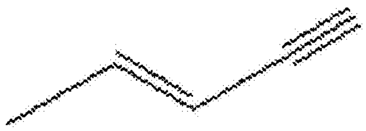
trans-pent-3-ene-1-yne
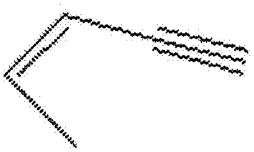
cis-pent-3-ene-1-yne

Figure 92A 1-
gtttgacagcttatcatcgactgcacggtgcaccaatgcttctggcgtcaggcagccatcggaagctgtggtatggctgtgcagg
tcgtaaatcactgcataattcgtgtcgctcaaggcgcactcccgttctggataatgttttttgcgccgacatcataacggttctggca
aatattctgaaatgagctgttgacaattaatcatccggctcgtataatgtgtggaattgtgagcggataacaatttcacacaggaaa
cagcgccgctgagaaaaagcgaagcggcactgctctttaacaatttatcagacaatctgtgtgggcactcgaccggaattatcg
attaactttattattaaaaattaaagaggtatatattaatgtatcgattaaataaggaggaataaaccatggatccgagctcaggagg
taaaaaaacatgaaaacagtagttattattgatgcattacgaacaccaattggaaaatataaaggcagcttaagtcaagtaagtgc
cgtagacttaggaacacatgttacaacacaacttttaaaaagacattccactatttctgaagaaattgatcaagtaatctttggaaat
gttttacaagctggaaatggccaaaatcccgcacgacaaatagcaataaacagcggtttgtctcatgaaattcccgcaatgacgg
ttaatgaggtctgcggatcaggaatgaaggccgttattttggcgaaacaattgattcaattaggagaagcggaagttttaattgctg
gcgggattgagaatatgtcccaagcacctaaattacaacgttttaattacgaaacagaaagctacgatgcgccttttctagtatga
tgtatgatggattaacggatgcctttagtggtcaggcaatgggcttaactgctgaaaatgtggccgaaaagtatcatgtaactaga
gaagagcaagatcaatttctgtacattcacaattaaaagcagctcaagcacaagcagaagggatattcgctgacgaaatagcc
ccattagaagtatcaggaacgcttgtggagaaagatgaagggattcgccctaattcgagcgttgagaagctaggaacgcttaaa
acagttttaaagaagacggtactgtaacagcagggaatgcatcaaccattaatgatggggcttctgctttgattattgcttcacaag
aatatgccgaagcacacggtcttccttatttagctattattcgagacagtgtggaagtcggtattgatccagcctatatgggaatttc
gccgattaaagccattcaaaaactgttagcgcgcaatcaacttactacggaagaaattgatctgtatgaaatcaacgaagcatttg
cagcaacttcaatcgtggtccaaagagaactggctttaccagaggaaaaggtcaacatttatggtggcggtatttcattaggtcat
gcgattggtgccacaggtgctcgtttattaacgagtttaagttatcaattaaatcaaaaagaaaagaaatatggagtggcttctttat
gtatcggcggtggcttaggactcgctatgctactagagagacctcagcaaaaaaaaaacagccgattttatcaaatgagtcctga
ggaacgcctggcttctcttcttaatgaaggccagatttctgctgatacaaaaaaagaatttgaaaatacggctttatcttcgcagatt
gccaatcatatgattgaaaatcaaatcagtgaaacagaagtgccgatgggcgttggcttacatttaacagtggacgaaactgatta
tttggtaccaatggcgacagaagagccctcagttattgcggctttgagtaatggtgcaaaaatagcacaaggatttaaaacagtg
aatcaacaacgcttaatgcgtggacaaatcgtttttacgatgttgcagatcccgagtcattgattgataaactacaagtaagagaa
gcggaagtttttcaacaagcagagttaagttatccatctatcgttaaacggggcggcggcttaagagatttgcaatatcgtactttg
atgaatcatttgtatctgtcgacttttagtagatgttaaggatgcaatgggggcaaatatcgttaacgctatgttggaaggtgtggcc
gagttgttccgtgaatggtttgcggagcaaaagattttattcagtattttaagtaattatgccacggagtcggttgttacgatgaaac
ggctattccagtttcacgtttaagtaaggggagcaatggccgggaaattgctgaaaaaattgttttagcttcacgctatgcttcatta
gatccttatcgggcagtcacgcataacaaaggaatcatgaatggcattgaagctgtagttttagctacaggaaatgatacacgcg
ctgttagcgcttcttgtcatgcttttgcggtgaaggaaggtcgctaccaaggcttgactagttggacgctggatggcgaacaacta
attggtgaaatttcagttccgcttgctttagccacggttggcggtgccacaaaagtcttacctaaatctcaagcagctgctgatttgtt
agcagtgacggatgcaaaagaactaagtcgagtagtagcggctgttggtttggcacaaaatttagcggcgttacgggccttagt
ctctgaaggaattcaaaaaggacacatggctctacaagcacgttctttagcgatgacggtcggagctactggtaaagaagttga
ggcagtcgctcaacaattaaaacgtcaaaaaacgatgaaccaagaccgagccatggctattttaaatgatttaagaaaacaataa
aggaggtaaaaaaacatgacaattgggattgataaaattagtttttttgtgcccccttattatattgatatgacggcactggctgaag
ccagaaatgtagaccctggaaaatttcatattggtattgggcaagaccaaatggcggtgaacccaatcagccaagatattgtgac
atttgcagccaatgccgcagaagcgatcttgaccaaagaagataaagaggccattgatatggtgattgtcgggactgagtccag
tatcgatgagtcaaaagcggccgcagttgtcttacatcgtttaatggggattcaacctttcgctcgctctttcgaaatcaaggaagct
tgttacggagcaacagcaggcttacagttagctaagaatcacgtagccttacatccagataaaaaagtcttggtcgtagcggcag
atattgcaaaatatggcttaaattctggcggtgagcctacacaaggagctggggcggttgcaatgttagttgctagtgaaccgcg
cattttggctttaaaagaggataatgtgatgctgacgcaagatatctatgacttttggcgtccaacaggccacccgtatcctatggtc
gatggtcctttgtcaaacgaaacctacatccaatcttttgcccaagtctgggatgaacataaaaaacgaaccggtcttgattttgca
gattatgatgctttagcgttccatattccttacacaaaaatgggcaaaaaagccttattagcaaaaatctccgaccaaactgaagca
gaacaggaacgaattttagcccgttatgaagaaagtatcgtctatagtcgtcgcgtaggaaacttgtatacgggttcactttatctg
ggactcatttccctttagaaaatgcaacgactttaaccgcaggcaatcaaattggtttattcagttatggttctggtgctgtcgctga
atttttcactggtgaattag

Figure 92B tagctggttatcaaaatcatttacaaaaagaaactcatttagcactgctggataatcggacagaactttctatcgctgaatatgaagc
catgtttgcagaaactttagacacagacattgatcaaacgttagaagatgaattaaaatatagtatttctgctattaataataccgttcg
ttcttatcgaaactaagagatctgcagctggtaccatatgggaattcgaagcttgggcccgaacaaaaactcatctcagaagagg
atctgaatagcgccgtcgaccatcatcatcatcatcattgagtttaaacggtctccagcttggctgttttggcggatgagagaagatt
ttcagcctgatacagattaaatcagaacgcagaagcggtctgataaaacagaatttgcctggcggcagtagcgcggtggtccca
cctgaccccatgccgaactcagaagtgaaacgccgtagcgccgatggtagtgtggggtctccccatgcgagagtagggaactg
ccaggcatcaaataaaacgaaaggctcagtcgaaagactgggcctttcgttttatctgttgtttgtcggtgaacgctctcctgagtag
gacaaatccgccgggagcggatttgaacgttgcgaagcaacggcccggagggtggcgggcaggacgcccgccataaactg
ccaggcatcaaattaagcagaaggccatcctgacggatggcctttttgcgtttctacaaactctttttgtttatttttctaaatacattcaa
atatgtatccgctcatgagacaataaccctgataaatgcttcaataatattgaaaaaggaagagtatgagtattcaacatttccgtgtc
gcccttattcccttttttgcggcattttgccttcctgtttttgctcacccagaaacgctggtgaaagtaaaagatgctgaagatcagttg
ggtgcacgagtgggttacatcgaactggatctcaacagcggtaagatccttgagagttttcgccccgaagaacgttttccaatgat
gagcacttttaaagttctgctatgtggcgcggtattatcccgtgttgacgccgggcaagagcaactcggtcgccgcatacactattc
tcagaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttttgcacaacatg
ggggatcatgtaactcgccttgatcgttgggaaccggagctgaatgaagccataccaaacgacgagcgtgacaccacgatgcc
tgtagcaatggcaacaacgttgcgcaaactattaactggcgaactacttactctagcttcccggcaacaattaatagactggatgg
aggcggataaagttgcaggaccacttctgcgctcggcccttccggctggctggtttattgctgataaatctggagccggtgagcgt
gggtctcgcggtatcattgcagcactggggccagatggtaagccctcccgtatcgtagttatctacacgacggggagtcaggca
actatggatgaacgaaatagacagatcgctgagataggtgcctcactgattaagcattggtaactgtcagaccaagtttactcatat
atactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctgcttg
caaacaaaaaaaccaccgctaccagcggtggtttgtttgccggatcaagagctaccaactctttttccgaaggtaactggcttcag
cagagcgcagataccaaatactgtccttctagtgtagccgtagttaggccaccacttcaagaactctgtagcaccgcctacatacc
tcgctctgctaatcctgttaccagtggctgctgccagtggcgataagtcgtgtcttaccgggttggactcaagacgatagttaccgg
ataaggcgcagcggtcgggctgaacggggggttcgtgcacacagcccagcttggagcgaacgacctacaccgaactgagat
acctacagcgtgagctatgagaaagcgccacgcttcccgaagggagaaaggcggacaggtatccggtaagcggcagggtcg
gaacaggagagcgcacgagggagcttccagggggaaacgcctggtatctttatagtcctgtcgggtttcgccacctctgacttga
gcgtcgatttttgtgatgctcgtcaggggggcggagcctatggaaaaacgccagcaacgcggcctttttacggttcctggccttttg
ctggccttttgctcacatgttctttcctgcgttatcccctgattctgtggataaccgtattaccgcctttgagtgagctgataccgctcgc
cgcagccgaacgaccgagcgcagcgagtcagtgagcgaggaagcggaagagcgcctgatgcggtattttctccttacgcatct
gtgcggtatttcacaccgcatatggtgcactctcagtacaatctgctctgatgccgcatagttaagccagtatacactccgctatcgc
tacgtgactgggtcatggctgcgccccgacacccgccaacacccgctgacgcgccctgacgggcttgtctgctcccggcatcc
gcttacagacaagctgtgaccgtctccgggagctgcatgtgtcagaggttttcaccgtcatcaccgaaacgcgcgaggcagcag
atcaattcgcgcgcgaaggcgaagcggcatgcatttacgttgacaccatcgaatggtgcaaaacctttcgcggtatggcatgata
gcgcccggaagagagtcaattcagggtggtgaatgtgaaaccagtaacgttatacgatgtcgcagagtatgccggtgtctcttatc
agaccgtttcccgcgtggtgaaccaggccagccacgtttctgcgaaaacgcgggaaaaagtggaagcggcgatggcggagct
gaattacattcccaaccgcgtggcacaacaactggcgggcaaacagtcgttgctgattggcgttgccacctccagtctggccctg
cacgcgccgtcgcaaattgtcgcggcgattaaatctcgcgccgatcaactgggtgccagcgtggtggtgtcgatggtagaacga
agcggcgtcgaagcctgtaaagcggcggtgcacaatcttctcgcgcaacgcgtcagtgggctgatcattaactatccgctggat
gaccaggatgccattgctgtggaagctgcctgcactaatgttccggcgttatttcttgatgtctctgaccagacacccatcaacagt
attattttctcccatgaagacggtacgcgactgggcgtggagcatctggtcgcattgggtcaccagcaaatcgcgctgttagcgg
gcccattaagttctgtctcggcgcgtctgcgtctggctggctggcataaatatctcactcgcaatcaaattcagccgatagcggaac
gggaaggcgactggagtgccatgtccggttttcaacaaaccatgcaaatgctgaatgagggcatcg

Figure 92C ttcccactgcgatgctggttgccaacgatcagatggcgctgggcgcaatgcgcgccattaccgagtccgggctgcgcgttggtg
cggatatctcggtagtgggatacgacgataccgaagacagctcatgttatatcccgccgtcaaccaccatcaaacaggattttcg
cctgctggggcaaaccagcgtggaccgcttgctgcaactctctcagggccaggcggtgaagggcaatcagctgttgcccgtct
cactggtgaaaagaaaaaccaccctggcgcccaatacgcaaaccgcctctccccgcgcgttggccgattcattaatgcagctg
gcacgacaggtttcccgactggaaagcgggcagtgagcgcaacgcaattaatgtgagttagcgcgaattgatctg
(SEQ ID NO:86)

A

B

A

B

C

A

B

C

Figure 103A cccgtcttactgtcgggaattcgcgttggccgattcattaatgcagattctgaaatgagctgttgacaattaatcatccggctcgtata
atgtgtggaattgtgagcggataacaatttcacacaggaaacagcgccgctgagaaaagcgaagcggcactgctctttaacaa
tttatcagacaatctgtgtgggcactcgaccggaattatcgattaactttattattaaaaattaaagaggtatatattaatgtatcgatta
aataaggaggaataaaccatggatccgagctcaggaggtaaaaaaacatgaaaacagtagttattattgatgcattacgaacacc
aattggaaaatataaaggcagcttaagtcaagtaagtgccgtagacttaggaacacatgttacaacacaacttttaaaaagacattc
cactatttctgaagaaattgatcaagtaatctttggaaatgttttacaagctggaaatggccaaaatcccgcacgacaaatagcaata
aacagcggtttgtctcatgaaattcccgcaatgacggttaatgaggtctgcggatcaggaatgaaggccgttattttggcgaaaca
attgattcaattaggagaagcggaagttttaattgctggcgggattgagaatatgtcccaagcacctaaattacaacgttttaattacg
aaacagaaagctacgatgcgcctttttctagtatgatgtatgatggattaacggatgcctttagtggtcaggcaatgggcttaactgc
tgaaaatgtggccgaaaagtatcatgtaactagagaagagcaagatcaatttctgtacattcacaattaaaagcagctcaagcac
aagcagaagggatattcgctgacgaaatagccccattagaagtatcaggaacgcttgtggagaaagatgaagggattcgccta
attcgagcgttgagaagctaggaacgcttaaaacagtttttaaagaagacggtactgtaacagcagggaatgcatcaaccattaat
gatggggcttctgctttgattattgcttcacaagaatatgccgaagcacacggtcttccttatttagctattattcgagacagtgtggaa
gtcggtattgatccagcctatatgggaatttcgccgattaaagccattcaaaaactgttagcgcgcaatcaacttactacggaagaa
attgatctgtatgaaatcaacgaagcatttgcagcaacttcaatcgtggtccaaagagaactggctttaccagaggaaaaggtcaa
catttatggtggcggtatttcattaggtcatgcgattggtgccacaggtgctcgtttattaacgagtttaagttatcaattaaatcaaaaa
gaaaagaaatatggagtggcttctttatgtatcggcggtggcttaggactcgctatgctactagagagacctcagcaaaaaaaaa
cagccgattttatcaaatgagtcctgaggaacgcctggcttctcttcttaatgaaggccagatttctgctgatacaaaaaaagaattt
gaaaatacggctttatcttcgcagattgccaatcatatgattgaaaatcaaatcagtgaaacagaagtgccgatgggcgttggctta
catttaacagtggacgaaactgattatttggtaccaatggcgacagaagagccctcagttattgcggctttgagtaatggtgcaaaa
atagcacaaggatttaaaacagtgaatcaacaacgcttaatgcgtggacaaatcgtttttacgatgttgcagatcccgagtcattga
ttgataaactacaagtaagagaagcggaagtttttcaacaagcagagttaagttatccatctatcgttaaacggggcggcggcttaa
gagatttgcaatatcgtacttttgatgaatcatttgtatctgtcgactttttagtagatgttaaggatgcaatgggggcaaatatcgttaa
cgctatgttggaaggtgtggccgagttgttccgtgaatggtttgcggagcaaaagattttattcagtattttaagtaattatgccacgg
agtcggttgttacgatgaaaacggctattccagtttcacgtttaagtaaggggagcaatggccgggaaattgctgaaaaaattgtttt
agcttcacgctatgcttcattagatccttatcgggcagtcacgcataacaaaggaatcatgaatggcattgaagctgtagttttagct
acaggaaatgatacacgcgctgttagcgcttcttgtcatgcttttgcggtgaaggaaggtcgctaccaaggcttgactagttggac
gctggatggcgaacaactaattggtgaaatttcagttccgcttgctttagccacggttggcggtgccacaaaagtcttacctaaatct
caagcagctgctgatttgttagcagtgacggatgcaaaagaactaagtcgagtagtagcggctgttggtttggcacaaaatttagc
ggcgttacgggccttagtctctgaaggaattcaaaaaggacacatggctctacaagcacgttctttagcgatgacggtcggagct
actggtaaagaagttgaggcagtcgctcaacaattaaaacgtcaaaaaacgatgaaccaagaccgagccatggctattttaaatg
atttaagaaaacaataaaggaggtaaaaaaacatgacaattgggattgataaaattagtttttttgtgcccccttattatattgatatga
cggcactggctgaagccagaaatgtagaccctggaaaatttcatattggtattgggcaagaccaaatggcggtgaacccaatca
gccaagatattgtgacatttgcagccaatgccgcagaagcgatcttgaccaaagaagataaagaggccattgatatggtgattgtc
gggactgagtccagtatcgatgagtcaaaagcggccgcagttgtcttacatcgtttaatggggattcaacctttcgctcgctctttcg
aaatcaaggaagcttgttacggagcaacagcaggcttacagttagctaagaatcacgtagccttacatccagataaaaaagtcttg
gtcgtagcggcagatattgcaaaatatggcttaaattctggcggtgagcctacacaaggagctggggcggttgcaatgttagttgc
tagtgaaccgcgcattttggctttaaaagaggataatgtgatgctgacgcaagatatctatgacttttggcgtccaacaggccaccc
gtatcctatggtcgatggtcctttgtcaaacgaaacctacatccaatcttttgcccaagtctgggatgaacataaaaaacgaaccgg
tcttgattttgcagattatgatgctttagcgttccatattccttacacaaaaatgggcaaaaaagccttattagcaaaaatctccgacca
aactgaagcagaacaggaacgaattttagcccgttatgaagaaagtatcgtctatagtcgtcgcgtaggaaacttgtatacgggtt
cactttatctgggactcatttcccttttagaaaatgcaacgactttaaccgcaggcaatcaaattggtttattcagttatggttctggtgc
tgtcgctgaattttcactggtgaattagtagctggttatcaaaatcatttacaaaaagaaactcatttagcactgctggataatcggac
agaactttctatcgctgaatatgaagccatgtttgcagaaactttagacacagacattgatcaaacgtta

Figure 103B gaagatgaattaaaatatagtatttctgctattaataataccgttcgttcttatcgaaactaaagatctgcatcctgcattcgcccttag
gaggtaaaaaaacatgtgtgcgacctcttctcaatttactcagattaccgagcataattcccgtcgttccgcaaactatcagccaaa
cctgtggaatttcgaattcctgcaatccctggagaacgacctgaaagtggaaaagctggaggagaaagcgaccaaactggagg
aagaagttcgctgcatgatcaaccgtgtagacacccagccgctgtccctgctggagctgatcgacgatgtgcagcgcctgggtc
tgacctacaaatttgaaaaagacatcattaaagccctggaaaacatcgtactgctggacgaaaacaaaaagaacaaatctgacct
gcacgcaaccgctctgtctttccgtctgctgcgtcagcacggtttcgaggtttctcaggatgtttttgagcgtttcaaggataaagaa
ggtggtttcagcggtgaactgaaaggtgacgtccaaggcctgctgagcctgtatgaagcgtcttacctgggtttcgagggtgaga
acctgctggaggaggcgcgtacctttccatcacccacctgaagaacaacctgaaagaaggcattaataccaaggttgcagaac
aagtgagccacgccctggaactgccatatcaccagcgtctgcaccgtctggaggcacgttggttcctggataaatacgaaccga
aagaaccgcatcaccagctgctgctggagctggcgaagctggatttaacatggtacagaccctgcaccagaaagagctgcaa
gatctgtcccgctggtggaccgagatgggcctggctagcaaactggatttgtacgcgaccgcctgatggaagtttatttctgggc
actgggtatggcgccagacccgcagtttggtgaatgtcgcaaagctgttactaaaatgtttggtctggtgacgatcatcgatgacg
tgtatgacgtttatggcactctggacgaactgcaactgttcaccgatgctgtagagcgctgggacgttaacgctattaacaccctg
ccggactatatgaaactgtgtttcctggcactgtacaacaccgttaacgacacgtcctattctattctgaaagagaaaggtcataac
aacctgtcctatctgacgaaaagctggcgtgaactgtgcaaagcctttctgcaagaggcgaaatggtccaacaacaaaattatcc
cggctttctccaagtacctggaaaacgccagcgtttcctcctccggtgtagcgctgctggcgccgtcttacttttccgtatgccagc
agcaggaagacatctccgaccacgcgctgcgttccctgaccgacttccatggtctggtgcgttctagctgcgttatcttccgcctg
tgcaacgatctggccacctctgcggcggagctggaacgtggcgagactaccaattctatcattagctacatgcacgaaaacgat
ggtaccagcgaggaacaggcccgcgaagaactgcgtaaactgatcgacgccgaatggaaaaagatgaatcgtgaacgcgtt
agcgactccaccctgctgcctaaagcgttcatggaaatcgcagttaacatggcacgtgtttcccactgcacctaccagtatggcg
atggtctgggtcgcccagactacgcgactgaaaaccgcatcaaactgctgctgattgaccctttcccgattaaccagctgatgtat
gtctaactgcagctggtaccatatgggaattcgaagcttgggcccgaacaaaaactcatctcagaagaggatctgaatagcgcc
gtcgaccatcatcatcatcatcattgagtttaaacggtctccagcttggctgttttggcggatgagagaagattttcagcctgataca
gattaaatcagaacgcagaagcggtctgataaaacagaatttgcctggcggcagtagcgcggtggtcccacctgaccccatgc
cgaactcagaagtgaaacgccgtagcgccgatggtagtgtggggtctccccatgcgagagtagggaactgccaggcatcaaa
taaaacgaaaggctcagtcgaaagactgggcctttcgttttatctgttgtttgtcggtgaacgctctcctgagtaggacaaatccgc
cgggagcggatttgaacgttgcgaagcaacggcccggagggtggcgggcaggacgcccgccataaactgccaggcatcaa
attaagcagaaggccatcctgacggatggcctttttgcgtttctacaaactctttttgtttatttttctaaatacattcaaatatgtatccg
ctcatgagacaataaccctgataaatgcttcaataatctggcgtaatagcgaagaggcccgcaccgatcgcccttcccaacagtt
gcgcagcctgaatggcgaatggcgcctgatgcggtattttctccttacgcatctgtgcggtatttcacaccgcatatggtgcactct
cagtacaatctgctctgatgccgcatagttaagccagccccgacacccgccaacacccgctgacgagcttagtaaagccctcgc
tagattttaatgcggatgttgcgattacttcgccaactattgcgataacaagaaaaagccagcctttcatgatatatctcccaatttgt
gtagggcttattatgcacgcttaaaaataataaaagcagacttgacctgatagtttggctgtgagcaattatgtgcttagtgcatctaa
cgcttgagttaagccgcgccgcgaagcggcgtcggcttgaacgaattgttagacattatttgccgactaccttggtgatctcgcctt
tcacgtagtggacaaattcttccaactgatctgcgcgcgaggccaagcgatcttcttcttgtccagataagcctgtctagcttcaa
gtatgacgggctgatactgggccggcaggcgctccattgcccagtcggcagcgacatccttcggcgcgattttgccggttactg
cgctgtaccaaatgcgggacaacgtaagcactacatttcgctcatcgccagcccagtcgggcggcgagttccatagcgttaagg
tttcatttagcgcctcaaatagatcctgttcaggaaccggatcaaagagttcctccgccgctggacctaccaaggcaacgctatgtt
ctcttgcttttgtcagcaagatagccagatcaatgtcgatcgtggctggctcgaagatacctgcaagaatgtcattgcgctgccatt
ctccaaattgcagttcgcgcttagctggataacgccacggaatgatgtcgtcgtgcacaacaatggtgacttctacagcgcggag
aatctcgctctctccaggggaagccgaagtttccaaaaggtcgttgatcaaagctcgccgcgttgtttcatcaagccttacggtca
ccgtaaccagcaaatcaatatcactgtgtggcttcaggccgccatccactgcggagccgtacaaatgtacggccagcaacgtcg
gttcgagatggcgctcgatgacgccaactacctctgatagttgagtcgatacttcggcgatcaccgcttccctcatgatgtttaactt
tgttttagggcgactgccctgctgcgtaacatcgttgctgctccataacatcaaacatcgacccacggcgtaacgcgcttgctgctt
ggat

Figure 103C gcccgaggcatagactgtaccccaaaaaaacagtcataacaagccatgaaaaccgccactgcgccgttaccaccgctgcgttc
ggtcaaggttctggaccagttgcgtgagcgcatacgctacttgcattacagcttacgaaccgaacaggcttatgtccactgggttc
gtgccttcatccgtttccacggtgtgcgtcacccggcaaccttgggcagcagcgaagtcgaggcatttctgtcctggctggcgaa
cgagcgcaaggtttcggtctccacgcatcgtcaggcattggcggccttgctgttcttctacggcaaggtgctgtgcacggatctgc
cctggcttcaggagatcggaagacctcggccgtcgcggcgcttgccggtggtgctgaccccggatgaagtggttcgcatcctcg
gttttctggaaggcgagcatcgtttgttcgcccagcttctgtatggaacgggcatgcggatcagtgagggtttgcaactgcgggtc
aaggatctggatttcgatcacggcacgatcatcgtgcgggagggcaagggctccaaggatcgggccttgatgttacccgagag
cttggcacccagcctgcgcgagcaggggaattaattcccacgggttttgctgcccgcaaacgggctgttctggtgttgctagtttgt
tatcagaatcgcagatccggcttcagccggtttgccggctgaaagcgctatttcttccagaattgccatgatttttccccacgggag
gcgtcactggctcccgtgttgtcggcagctttgattcgataagcagcatcgcctgtttcaggctgtctatgtgtgactgttgagctgta
acaagttgtctcaggtgttcaatttcatgttctagttgctttgttttactggtttcacctgttctattaggtgttacatgctgttcatctgttac
attgtcgatctgttcatggtgaacagctttgaatgcaccaaaaactcgtaaaagctctgatgtatctatctttttacaccgttttcatctg
tgcatatggacagttttccctttgatatgtaacggtgaacagttgttctacttttgtttgttagtcttgatgcttcactgatagatacaaga
gccataagaacctcagatccttccgtatttagccagtatgttctctagtgtggttcgttgttttgcgtgagccatgagaacgaaccatt
gagatcatacttactttgcatgtcactcaaaaattttgcctcaaaactggtgagctgaattttgcagttaaagcatcgtgtagtgttttc
ttagtccgttatgtaggtaggaatctgatgtaatggttgttggtattttgtcaccattcatttttatctggttgttctcaagttcggttacgag
atccatttgtctatctagttcaacttggaaaatcaacgtatcagtcgggcggcctcgcttatcaaccaccaatttcatattgctgtaagt
gtttaaatctttacttattggtttcaaaacccattggttaagccttttaaactcatggtagttattttcaagcattaacatgaacttaaattca
tcaaggctaatctctatatttgccttgtgagttttcttttgtgttagttcttttaataaccactcataaatcctcatagagtatttgttttcaaaa
gacttaacatgttccagattatattttatgaatttttttaactggaaaagataaggcaatatctcttcactaaaaactaattctaattttcgc
ttgagaacttggcatagtttgtccactggaaaatctcaaagcctttaaccaaaggattcctgatttccacagttctcgtcatcagctctc
tggttgctttagctaatacaccataagcattttccctactgatgttcatcatctgagcgtattggttataagtgaacgataccgtccgttc
tttccttgtagggttttcaatcgtggggttgagtagtgccacacagcataaaattagcttggtttcatgctccgttaagtcatagcgact
aatcgctagttcatttgctttgaaaacaactaattcagacatacatctcaattggtctaggtgattttaatcactataccaattgagatgg
gctagtcaatgataattactagtcctttttcctttgagttgtgggtatctgtaaattctgctagacctttgctggaaaacttgtaaattctgct
agaccctctgtaaattccgctagacctttgtgtgtttttttgtttatattcaagtggttataatttatagaataaagaaagaataaaaaaa
gataaaaagaatagatcccagccctgtgtataactcactactttagtcagttccgcagtattacaaaaggatgtcgcaaacgctgttt
gctcctctacaaaacagaccttaaaaccctaaaggcttaagtagcaccctcgcaagctcgggcaaatcgctgaatattccttttgtc
tccgaccatcaggcacctgagtcgctgtctttttcgtgacattcagttcgctgcgctcacggctctggcagtgaatgggggtaaatg
gcactacaggcgccttttatggattcatgcaaggaaactacccataatacaagaaaagcccgtcacgggcttctcagggcgtttta
tggcgggtctgctatgtggtgctatctgacttttttgctgttcagcagttcctgccctctgattttccagtctgaccacttcggattatccc
gtgacaggtcattcagactggctaatgcacccagtaaggcagcggtatcatcaacaggctta (SEQ ID NO:87)

Figure 108A

1- caagaaaaatgccccgcttacgcagggcatccatttattactcaaccgtaaccgattttgccaggttacgcggctggtcaacgtcg
gtgcctttgatcagcgcgacatggtaagccagcagctgcagcggaacggtgtagaagatcggtgcaatcacctcttccacatgc
ggcatctcgatgatgtgcatgttatcgctacttacaaaacccgcatcctgatcggcgaagacatacaactgaccgccacgcgcgc
gaacttcttcaatgttggatttcagtttttccagcaattcgttgttcggtgcaacaacaataaccggcatatcggcatcaattagcgcc
agcggaccgtgtttcagttcgccagcagcgtaggcttcagcgtgaatgtaagagatctctttcaacttcaatgcgccttccagcgc
gattgggtactgatcgccacggcccaggaacagcgcgtgatgtttgtcagagaaatcttctgccagcgcttcaatgcgtttgtcct
gagacagcatctgctcaatacggctcggcagcgcctgcagaccatgcacgatgtcatgttcaatggaggcatccagacctttca
ggcgagacagcttcgccaccagcatcaacagcacagttaactgagtggtgaatgctttagtggatgccacgccgatttctgtacc
cgcgttggtcattagcgccagatcggattcgcgcaccagagaagaacccggaacgttacagattgccagtgaaccaaggtaac
ccagctctttcgacagacgcaggccagccagggtatccgcggtttcgccagactgtgacacgatcgcccttcccaacagttgcg
cagcctatacgtacggcagtttaaggtttacacctataaaagagagagccgttatcgtctgtttgtggatgtacagagtgatattattg
acacgccggggcgacggatggtgatcccccctggccagtgcacgtctgctgtcagataaagtctcccgtgaactttacccggtgg
tgcatatcggggatgaaagctggcgcatgatgaccaccgatatggccagtgtgccggtctccgttatcggggaagaagtggctg
atctcagccaccgcgaaaatgacatcaaaaacgccattaacctgatgttctggggaatataaatgtcaggcatgagattatcaaaa
aggatcttcacctagatccttttcacgtagaaagccagtccgcagaaacggtgctgaccccggatgaatgtcagctactgggctat
ctggacaagggaaaacgcaagcgcaaagagaaagcaggtagcttgcagtgggcttacatggcgatagctagactgggcggttt
tatggacagcaagcgaaccggaattgccagctggggcgccctctggtaaggttgggaagccctgcaaagtaaactggatggct
ttctcgccgccaaggatctgatggcgcaggggatcaagctctgatcaagagacaggatgaggatcgtttcgcatgattgaacaa
gatggattgcacgcaggttctccggccgcttgggtggagaggctattcggctatgactgggcacaacagacaatcggctgctct
gatgccgccgtgttccggctgtcagcgcaggggcgcccggttctttttgtcaagaccgacctgtccggtgccctgaatgaactgc
aagacgaggcagcgcggctatcgtggctggccacgacgggcgttccttgcgcagctgtgctcgacgttgtcactgaagcggga
agggactggctgctattgggcgaagtgccggggcaggatctcctgtcatctcaccttgctcctgccgagaaagtatccatcatgg
ctgatgcaatgcggcggctgcatacgcttgatccggctacctgcccattcgaccaccaagcgaaacatcgcatcgagcgagca
cgtactcggatggaagccggtcttgtcgatcaggatgatctggacgaagagcatcaggggctcgcgccagccgaactgttcgc
caggctcaaggcgagcatgcccgacggcgaggatctcgtcgtgacccatggcgatgcctgcttgccgaatatcatggtggaaa
atggccgcttttctggattcatcgactgtggccggctgggtgtggcggaccgctatcaggacatagcgttggctacccgtgatatt
gctgaagagcttggcggcgaatgggctgaccgcttcctcgtgctttacggtatcgccgctcccgattcgcagcgcatcgccttcta
tcgccttcttgacgagttcttctgaattattaacgcttacaatttcctgatgcggtattttctccttacgcatctgtgcggtatttcacaccg
catacaggtggcacttttcggggaaatgtgcgcggaacccctatttgtttatttttctaaatacattcaaatatgtatccgctcatgaga
caataaccctgataaatgcttcaataatagcacgtgaggagggccaccatggccaagttgaccagtgccgttccggtgctcaccg
cgcgcgacgtcgccggagcggtcgagttctggaccgaccggctcgggttctcccctagtaacggccgccagtgtgctggaatt
caggcagttcaacctgttgatagtacgtactaagctctcatgtttcacgtactaagctctcatgtttaacgtactaagctctcatgtttaa
cgaactaaaccctcatggctaacgtactaagctctcatggctaacgtactaagctctcatgtttcacgtactaagctctcatgtttgaa
caataaaattaatataaatcagcaacttaaatagcctctaaggttttaagttttataagaaaaaaaagaatatataaggcttttaaagct
tttaaggtttaacggttgtggacaacaagccagggatgtaacgcactgagaagcccttagagcctctcaaagcaattttcagtgac
acaggaacacttaacggctgacagcctgaattctgcagatatctgtttttccactcttcgttcactttcgccaggtagctggtgaaga
cgaaggaagtcccggagccatctgcgcggcgtactacagcaatgttttgtgaaggcagtttcagacccggattcagtttggcgat
ggcttcatcatcccacttcttgattttgcccaggtagatgtcgccgagggttttaccatccagcaccagttcgccagacttcagccct
ggaatgttaaccgccagcaccacgccgccaatcacggtcgggaactggaacagaccttcctgagccagtttttcgtcagacagc
ggcgcgtcagaggcaccaaaatcaacggtattagcgataatctgttttacgccaccggaagaaccgataccctggtagttaacttt
attaccggtttctttctggtaagtgtcagcccatttggcatacaccggcgcagggaaggttgcacctgcacctgtcaggcttgcttct
gcaaacacagagaaagcactcatcgataaggtcgcggcgacaacagttgcgacggtggtacgcataactttcataatgtctcctg
ggaggattcataaagcattgtttgttggctacgagaagcaaaataggacaaacaggtgacagttatatgtaaggaatatgacagttt
tatgacagagagataaagtcttcagtctgatttaaataagcgttgatattcagtcaattacaaacattaataacg

Figure 108B aagagatgacagaaaaattttcattctgtgacagagaaaaagtagccgaagatgacggtttgtcacatggagttggcaggatgttt
gattaaaagcaattaaccctcactaaagggcggccgcgaagttcctattctctagaaagtataggaacttcattctaccgggtagg
ggaggcgcttttcccaaggcagtctggagcatgcgctttagcagccccgctgggcacttggcgctacacaagtggcctctggcc
tcgcacacattccacatccaccggtaggcgccaaccggctccgttctttggtggccccttcgcgccaccttccactcctcccctag
tcaggaagttcccccccgccccgcagctcgcgtcgtgcaggacgtgacaaatggaagtagcacgtctcactagtctcgtgcaga
tggacagcaccgctgagcaatggaagcgggtaggcctttggggcagcggccaatagcagctttgctccttcgctttctgggctca
gaggctgggaaggggtgggtccgggggcgggctcaggggcgggctcaggggcggggcgggcgcccgaaggtcctccgg
aggcccggcattctgcacgcttcaaaagcgcacgtctgccgcgctgttctcctcttcctcatctccgggcctttcgacctgcagca
gcacgtgttgacaattaatcatcggcatagtatatcggcatagtataatacgacaaggtgaggaactaaaccatggagaaaaaat
cactggatataccaccgttgatatatcccaatggcatcgtaaagaacattttgaggcatttcagtcagttgctcaatgtacctataacc
agaccgttcagctggatattacggcctttttaaagaccgtaaagaaaaataagcacaagttttatccggcctttattcacattcttgcc
cgcctgatgaatgctcatccggaattccgtatggcaatgaaagacggtgagctggtgatatgggatagtgttcacccttgttacacc
gttttccatgagcaaactgaaacgttttcatcgctctggagtgaataccacgacgatttccggcagtttctacacatatattcgcaaga
tgtggcgtgttacggtgaaaacctggcctatttccctaaagggtttattgagaatatgtttttcgtctcagccaatccctgggtgagttt
caccagttttgatttaaacgtggccaatatggacaacttcttcgcccccgttttcaccatgggcaaatattatacgcaaggcgacaa
ggtgctgatgccgctggcgattcaggttcatcatgccgtttgtgatggcttccatgtcggcagaatgcttaatgaattacaacagtac
tgcgatgagtggcagggcggggcgtaagcgggactctggggttcgaataaagaccgaccaagcgacgtctgagagctccctg
gcgaattcggtaccaataaaagagctttattttcatgatctgtgtgttggtttttgtgtgcggcgcggaagttcctattctctagaaagta
taggaacttcctcgagccctatagtgagtcgtattagcccttgacgatgccacatcctgagcaaataattcaaccactaattgtgag
cggataacacaaggaggaaacagctatgtcattaccgttcttaacttctgcaccgggaaaggttattattttggtgaacactctgct
gtgtacaacaagcctgccgtcgctgctagtgtgtctgcgttgagaacctacctgctaataagcgagtcatctgcaccagatactatt
gaattggacttcccggacattagctttaatcataagtggtccatcaatgatttcaatgccatcaccgaggatcaagtaaactcccaaa
aattggccaaggctcaacaagccaccgatggcttgtctcaggaactcgttagtcttttggatccgttgttagctcaactatccgaatc
cttccactaccatgcagcgttttgtttcctgtatatgtttgtttgcctatgcccccatgccaagaatattaagtttctttaaagtctacttta
cccatcggtgctgggttgggctcaagcgcctctatttctgtatcactggccttagctatggcctacttgggggggttaataggatcta
atgacttggaaaagctgtcagaaaacgataagcatatagtgaatcaatgggccttcataggtgaaaagtgtattcacggtaccctt
caggaatagataacgctgtggccacttatggtaatgccctgctatttgaaaaagactcacataatggaacaataaacacaaacaat
tttaagttcttagatgatttcccagccattccaatgatcctaacctatactagaattccaaggtctacaaaagatcttgttgctcgcgttc
gtgtgttggtcaccgagaaatttcctgaagttatgaagccaattctagatgccatgggtgaatgtgccctacaaggcttagagatca
tgactaagttaagtaaatgtaaaggcaccgatgacgaggctgtagaaactaataatgaactgtatgaacaactattggaattgataa
gaataaatcatggactgcttgtctcaatcggtgtttctcatcctggattagaacttattaaaaatctgagcgatgatttgagaattggct
ccacaaaacttaccggtgctggtggcggcggttgctctttgactttgttacgaagagacattactcaagagcaaattgacagcttca
aaaagaaattgcaagatgattttagttacgagacatttgaaacagacttgggtgggactggctgctgtttgttaagcgcaaaaaattt
gaataaagatcttaaaatcaaatccctagtattccaattatttgaaaataaaactaccacaaagcaacaaattgacgatctattattgc
caggaaacacgaatttaccatggacttcataagctaatttgcgataggcctgcacccttaaggaggaaaaaaacatgtcagagttg
agagccttcagtgccccagggaaagcgttactagctggtggatatttagttttagatacaaaatatgaagcatttgtagtcggattat
cggcaagaatgcatgctgtagcccatccttacggttcattgcaagggtctgataagtttgaagtgcgtgtgaaaagtaaacaattta
aagatggggagtggctgtaccatataagtcctaaaagtggcttcattcctgtttcgataggcggatctaagaaccctttcattgaaaa
agttatcgctaacgtatttagctactttaaacctaacatggacgactactgcaatagaaacttgttcgttattgatattttctctgatgatg
cctaccattctcaggaggatagcgttaccgaacatcgtggcaacagaagattgagttttcattcgcacagaattgaagaagttccc
aaaacagggctgggctcctcggcaggtttagtcacagttttaactacagctttggcctcctttttgtatcggacctggaaaataatgt
agacaaatatagagaagttattcataatttagcacaagttgctcattgtcaagctcagggtaaaattggaagcgggtttgatgtagcg
gcggcagcatatggatctatcagatatagaagattcccacccgcattaatctctaatttgccagatattggaagtgctacttacggca
gtaaactggcgcatttggttgatgaagaagactggaatattacgattaaaagtaaccatttaccttc

Figure 108C gggattaactttatggatgggcgatattaagaatggttcagaaacagtaaaactggtccagaaggtaaaaaattggtatgattcgc
atatgccagaaagcttgaaaatatatacagaactcgatcatgcaaattctagatttatggatggactatctaaactagatcgcttaca
cgagactcatgacgattacagcgatcagatatttgagtctcttgagaggaatgactgtacctgtcaaaagtatcctgaaatcacag
aagttagagatgcagttgccacaattagacgttcctttagaaaaataactaaagaatctggtgccgatatcgaacctcccgtacaa
actagcttattggatgattgccagaccttaaaaggagttcttacttgcttaatacctggtgctggtggttatgacgccattgcagtgat
tactaagcaagatgttgatcttagggctcaaaccgctaatgacaaaagattttctaaggttcaatggctggatgtaactcaggctga
ctggggtgttaggaaagaaaaagatccggaaacttatcttgataaataacttaaggtagctgcatgcagaattcgcccttaaggag
gaaaaaaaaatgaccgtttacacagcatccgttaccgcacccgtcaacatcgcaacccttaagtattgggggaaaagggacac
gaagttgaatctgcccaccaattcgtccatatcagtgactttatcgcaagatgacctcagaacgttgacctctgcggctactgcac
ctgagtttgaacgcgacactttgtggttaaatggagaaccacacagcatcgacaatgaaagaactcaaaattgtctgcgcgacct
acgccaattaagaaaggaaatggaatcgaaggacgcctcattgcccacattatctcaatggaaactccacattgtctccgaaaat
aactttcctacagcagctggtttagcttcctccgctgctggctttgctgcattggtctctgcaattgctaagttataccaattaccacag
tcaacttcagaaatatctagaatagcaagaaaggggtctggttcagcttgtagatcgttgtttggcggatacgtggcctgggaaat
gggaaaagctgaagatggtcatgattccatggcagtacaaatcgcagacagctctgactggcctcagatgaaagcttgtgtccta
gttgtcagcgatattaaaaaggatgtgagttccactcagggtatgcaattgaccgtggcaacctccgaactatttaaagaaagaatt
gaacatgtcgtaccaaagagatttgaagtcatgcgtaaagccattgttgaaaaagatttcgccacctttgcaaaggaaacaatgat
ggattccaactctttccatgccacatgtttggactctttccctccaatattctacatgaatgacacttccaagcgtatcatcagttggtg
ccacaccattaatcagttttacggagaaacaatcgttgcatacacgtttgatgcaggtccaaatgctgtgttgtactacttagctgaa
aatgagtcgaaactctttgcatttatctataaattgtttggctctgttcctggatgggacaagaaatttactactgagcagcttgaggct
ttcaaccatcaatttgaatcatctaactttactgcacgtgaattggatcttgagttgcaaaaggatgttgccagagtgattttaactcaa
gtcggttcaggcccacaagaaacaaacgaatctttgattgacgcaaagactggtctaccaaaggaataagatcaattcgctgcat
cgcccttaggaggtaaaaaaaaatgactgccgacaacaatagtatgccccatggtgcagtatctagttacgccaaattagtgcaa
aaccaaacacctgaagacattttggaagagtttcctgaaattattccattacaacaaagacctaatacccgatctagtgagacgtca
aatgacgaaagcggagaaacatgtttttctggtcatgatgaggagcaaattaagttaatgaatgaaaattgtattgttttggattggg
acgataatgctattggtgccggtaccaagaaagtttgtcatttaatggaaaatattgaaaagggtttactacatcgtgcattctccgtc
tttattttcaatgaacaaggtgaattacttttacaacaaagagccactgaaaaaataactttccctgatctttggactaacacatgctg
ctctcatccactatgtattgatgacgaattaggtttgaagggtaagctagacgataagattaagggcgctattactgcggcggtga
gaaaactagatcatgaattaggtattccagaagatgaaactaagacaaggggtaagtttcacttttaaacagaatccattacatgg
caccaagcaatgaaccatggggtgaacatgaaattgattacatcctattttataagatcaacgctaaagaaaacttgactgtcaac
ccaaacgtcaatgaagttagagacttcaaatgggtttcaccaaatgatttgaaaactatgtttgctgacccaagttacaagtttacgc
cttggtttaagattatttgcgagaattacttattcaactggtgggagcaattagatgacctttctgaagtggaaaatgacaggcaaatt
catagaatgctataacaacgcgtctacaaataaaaaaggcacgtcagatgacgtgccttttttcttggggcc (SEQ ID NO:90)

Figure 110A 1-
gtgcggccgcaagcttgtcgacggagctcgaattcggatccctgcagttagacatacatcagctggttaatcgggaaagggtca
atcagcagcagtttgatgcggttttcagtcgcgtagtctgggcgacccagaccatcgccatactggtaggtgcagtgggaaaca
cgtgccatgttaactgcgatttccatgaacgctttaggcagcagggtggagtcgctaacgcgttcacgattcatctttttccattcgg
cgtcgatcagtttacgcagttcttcgcgggcctgttcctcgctggtaccatcgttttcgtgcatgtagctaatgatagaattggtagtc
tcgccacgttccagctccgccgcagaggtggccagatcgttgcacaggcggaagataacgcagctagaacgcaccagaccat
ggaagtcggtcagggaacgcagcgcgtggtcggagatgtcttcctgctgctggcatacggaaaagtaagacggcgccagcag
cgctacaccggaggaggaaacgctggcgttttccaggtacttggagaaagccgggataatttgttgttggaccatttcgcctctt
gcagaaaggctttgcacagttcacgccagcttttcgtcagataggacaggttgttatgacctttctctttcagaatagaataggacgt
gtcgttaacggtgttgtacagtgccaggaaacacagtttcatatagtccggcagggtgttaatagcgttaacgtcccagcgctcta
cagcatcggtgaacagttgcagttcgtccagagtgccataaacgtcatacacgtcatcgatgatcgtcaccagaccaaacattta
gtaacagctttgcgacattcaccaaactgcgggtctggcgccatacccagtgcccagaaataaacttccatcaggcggtcgcgt
acaaaatccagtttgctagccaggcccatctcggtccaccagcgggacagatcttgcagctctttctggtgcagggtctgtaccat
gttaaaatccagcttcgccagctccagcagcagctggtgatgcggttctttcggttcgtatttatccaggaaccaacgtgcctccag
acggtgcagacgctggtgatatggcagttccagggcgtggctcacttgttctgcaaccttggtattaatgccttctttcaggttgttct
tcaggtgggtgatggaaaaggtacgcgcctcctccagcaggttctcaccctcgaaacccaggtaagacgcttcatacaggctca
gcaggccttggacgtcacctttcagttcaccgctgaaaccaccttctttatccttgaaacgctcaaaaacatcctgagaaacctcga
aaccgtgctgacgcagcagacggaaagacagagcggttgcgtgcaggtcagatttgttctttttgttttcgtccagcagtacgatg
ttttccagggctttaatgatgtctttttcaaatttgtaggtcagacccaggcgctgcacatcgtcgatcagctccagcagggacagc
ggctgggtgtctacacggttgatcatgcagcgaacttcttcctccagtttggtcgctttctcctccagcttttccactttcaggtcgttct
ccagggattgcaggaattcgaaattccacaggtttggctgatagtttgcggaacgacgggaattatgctcggtaatctgagtaaatt
gagaagaggtcgcacacatggtatatctccttcttaaagttaaacaaaattatttctagaggggaattgttatccgctcacaattccc
ctatagtgagtcgtattaatttcgcgggatcgagatctcgatcctctacgccggacgcatcgtggccggcatcaccggcgccaca
ggtgcggttgctggcgcctatatcgccgacatcaccgatggggaagatcgggctcgccacttcgggctcatgagcgcttgtttcg
gcgtgggtatggtggcaggccccgtggccgggggactgttgggcgccatctccttgcatgcaccattccttgcggcggcggtg
ctcaacggcctcaacctactactgggctgcttcctaatgcaggagtcgcataagggagagcgtcgagatcccggacaccatcg
aatggcgcaaaacctttcgcggtatggcatgatagcgcccggaagagagtcaattcagggtggtgaatgtgaaaccagtaacgt
tatacgatgtcgcagagtatgccggtgtctcttatcagaccgtttcccgcgtggtgaaccaggccagccacgtttctgcgaaaacg
cgggaaaaagtggaagcggcgatggcggagctgaattacattcccaaccgcgtggcacaacaactggcgggcaaacagtcg
ttgctgattggcgttgccacctccagtctggccctgcacgcgccgtcgcaaattgtcgcggcgattaaatctcgcgccgatcaact
gggtgccagcgtggtggtgtcgatggtagaacgaagcggcgtcgaagcctgtaaagcggcggtgcacaatcttctcgcgcaa
cgcgtcagtgggctgatcattaactatccgctggatgaccaggatgccattgctgtggaagctgcctgcactaatgttccggcgtt
atttcttgatgtctctgaccagacacccatcaacagtattattttctcccatgaagacggtacgcgactgggcgtggagcatctggt
cgcattgggtcaccagcaaatcgcgctgttagcgggcccattaagttctgtctcggcgcgtctgcgtctggctggctggcataaat
atctcactcgcaatcaaattcagccgatagcggaacgggaaggcgactggagtgccatgtccggttttcaacaaaccatgcaaa
tgctgaatgagggcatcgttcccactgcgatgctggttgccaacgatcagatggcgctgggcgcaatgcgcgccattaccgagt
ccgggctgcgcgttggtgcggatatctcggtagtgggatacgacgataccgaagacagctcatgttatatcccgccgttaaccac
catcaaacaggattttcgcctgctggggcaaaccagcgtggaccgcttgctgcaactctctcagggccaggcggtgaagggca
atcagctgttgcccgtctcactggtgaaaagaaaaaccaccctggcgcccaatacgcaaaccgcctctccccgcgcgttggcc
gattcattaatgcagctggcacgacaggtttcccgactggaaagcgggcagtgagcgcaacgcaattaatgtaagttagctcact
cattaggcaccgggatctcgaccgatgcccttgagagccttcaacccagtcagctccttccggtgggcgcggggcatgactatc
gtcgccgcacttatgactgtcttctttatcatgcaactcgtaggacaggtgccggcagcgctctgggtcatttcggcgaggaccg
ctttcgctggagcgcgacgatgatcggcctgtcgcttgcggtattcggaatcttgcacgccctcgctcaagccttcgtcactggtc
ccgccaccaaacgtttcggcgagaagcaggccattatcgccggcatggcggccccacgggtgcgcatgatcgtgctcctg

Figure 110B tcgttgaggacccggctaggctggcggggttgccttactggttagcagaatgaatcaccgatacgcgagcgaacgtgaagcga
ctgctgctgcaaaacgtctgcgacctgagcaacaacatgaatggtcttcggtttccgtgtttcgtaaagtctggaaacgcggaagt
cagcgccctgcaccattatgttccggatctgcatcgcaggatgctgctggctaccctgtggaacacctacatctgtattaacgaag
cgctggcattgaccctgagtgatttttctctggtcccgccgcatccataccgccagttgtttaccctcacaacgttccagtaaccggg
catgttcatcatcagtaacccgtatcgtgagcatcctctctcgtttcatcggtatcattacccccatgaacagaaatcccccttacacg
gaggcatcagtgaccaaacaggaaaaaaccgcccttaacatggcccgctttatcagaagccagacattaacgcttctggagaaa
ctcaacgagctggacgcggatgaacaggcagacatctgtgaatcgcttcacgaccacgctgatgagctttaccgcagctgcctc
gcgcgtttcggtgatgacggtgaaaacctctgacacatgcagctcccggagacggtcacagcttgtctgtaagcggatgccggg
agcagacaagcccgtcagggcgcgtcagcgggtgttggcgggtgtcggggcgcagccatgacccagtcacgtagcgatagc
ggagtgtatactggcttaactatgcggcatcagagcagattgtactgagagtgcaccatatatgcggtgtgaaataccgcacagat
gcgtaaggagaaaataccgcatcaggcgctcttccgcttcctcgctcactgactcgctgcgctcggtcgttcggctgcggcgagc
ggtatcagctcactcaaaggcggtaatacggttatccacagaatcaggggataacgcaggaaagaacatgtgagcaaaaggcc
agcaaaaggccaggaaccgtaaaaaggccgcgttgctggcgtttttccataggctccgcccccctgacgagcatcacaaaaatc
gacgctcaagtcagaggtggcgaaacccgacaggactataaagataccaggcgtttccccctggaagctccctcgtgcgctctc
ctgttccgaccctgccgcttaccggatacctgtccgcctttctcccttcgggaagcgtggcgctttctcatagctcacgctgtaggta
tctcagttcggtgtaggtcgttcgctccaagctgggctgtgtgcacgaaccccccgttcagcccgaccgctgcgccttatccggta
actatcgtcttgagtccaacccggtaagacacgacttatcgccactggcagcagccactggtaacaggattagcagagcgaggt
atgtaggcggtgctacagagttcttgaagtggtggcctaactacggctacactagaaggacagtatttggtatctgcgctctgctga
agccagttaccttcggaaaaagagttggtagctcttgatccggcaaacaaaccaccgctggtagcggtggtttttttgtttgcaagc
agcagattacgcgcagaaaaaaaggatctcaagaagatcctttgatcttttctacggggtctgacgctcagtggaacgaaaactc
acgttaagggattttggtcatgaacaataaaactgtctgcttacataaacagtaatacaaggggtgttatgagccatattcaacggg
aaacgtcttgctctaggccgcgattaaattccaacatggatgctgatttatatgggtataaatgggctcgcgataatgtcgggcaatc
aggtgcgacaatctatcgattgtatgggaagcccgatgcgccagagttgtttctgaaacatggcaaaggtagcgttgccaatgatg
ttacagatgagatggtcagactaaactggctgacggaatttatgcctcttccgaccatcaagcattttatccgtactcctgatgatgc
atggttactcaccactgcgatccccgggaaaacagcattccaggtattagaagaatatcctgattcaggtgaaaatattgttgatgc
gctggcagtgttcctgcgccggttgcattcgattcctgtttgtaattgtccttttaacagcgatcgcgtatttcgtctcgctcaggcgca
atcacgaatgaataacggtttggttgatgcgagtgattttgatgacgagcgtaatggctggcctgttgaacaagtctggaaagaaat
gcataaacttttgccattctcaccggattcagtcgtcactcatggtgatttctcacttgataaccttatttttgacgaggggaaattaata
ggttgtattgatgttggacgagtcggaatcgcagaccgataccaggatcttgccatcctatggaactgcctcggtgagttttctcctt
cattacagaaacggctttttcaaaaatatggtattgataatcctgatatgaataaattgcagtttcatttgatgctcgatgagtttttctaa
gaattaattcatgagcggatacatatttgaatgtatttagaaaaataaacaaataggggttccgcgcacatttccccgaaaagtgcc
acctgaaattgtaaacgttaatattttgttaaaattcgcgttaaatttttgttaaatcagctcattttttaaccaataggccgaaatcggca
aaatcccttataaatcaaaagaatagaccgagatagggttgagtgttgttccagtttggaacaagagtccactattaaagaacgtgg
actccaacgtcaaagggcgaaaaaccgtctatcagggcgatggcccactacgtgaaccatcaccctaatcaagttttttggggtc
gaggtgccgtaaagcactaaatcggaaccctaaagggagcccccgatttagagcttgacggggaaagccggcgaacgtggc
gagaaaggaagggaagaaagcgaaaggagcgggcgctagggcgctggcaagtgtagcggtcacgctgcgcgtaaccacc
acacccgccgcgcttaatgcgccgctacagggcgcgtcccattcgccaatccggatatagttcctcctttcagcaaaaaacccct
caagacccgtttagaggccccaaggggttatgctagttattgctcagcggtggcagcagccaactcagcttcctttcgggctttgtt
agcagccggatctcagtggtggtggtggtggtgctcga

A

B

C

D

E

I

J

K

O

| | | |
|---|---|---|
| MCM63 | Ptrc minus lacO forw | Tcatccggctcgtataatgtgtggtcacacaggaaacagcgccgctga (SEQ ID NO: 123) |
| MCM64 | Ptrc minus lacO rev | Tcagcggcgctgtttcctgtgtgaccacacattatacgagccggatga (SEQ ID NO: 124) |

P

Figure 112Q ttcacacaggaaacagcgccgctgagaaaaagcgaagcggcactgctctttaacaatttatcagacaatctgtgtgggcactcgaccggaa
ttatcgattaactttattattaaaaattaaagaggtatatattaatgtatcgattaaataaggaggaataaaccatggatccgagctcaggaggta
aaaaaacatgaaaacagtagttattattgatgcattacgaacaccaattggaaaatataaaggcagcttaagtcaagtaagtgccgtagactta
ggaacacatgttacaacacaacttttaaaaagacattccactatttctgaagaaattgatcaagtaatctttggaaatgttttacaagctggaaat
ggccaaaatcccgcacgacaaatagcaataaacagcggtttgtctcatgaaattcccgcaatgacggttaatgaggtctgcggatcaggaat
gaaggccgttatttggcgaaacaattgattcaattaggagaagcggaagttttaattgctggcgggattgagaatatgtcccaagcacctaaa
ttacaacgttttaattacgaaacagaaagctacgatgcgcctttttctagtatgatgtatgatggattaacggatgcctttagtggtcaggcaatg
ggcttaactgctgaaaatgtggccgaaaagtatcatgtaactagagaagagcaagatcaattttctgtacattcacaattaaaagcagctcaag
cacaagcagaagggatattcgctgacgaaatagccccattagaagtatcaggaacgcttgtggagaaagatgaagggattcgccctaattc
gagcgttgagaagctaggaacgcttaaaacagttttaaagaagacggtactgtaacagcagggaatgcatcaaccattaatgatggggctt
ctgctttgattattgcttcacaagaatatgccgaagcacacggtcttccttatttagctattattcgagacagtgtggaagtcggtattgatccagc
ctatatgggaatttcgccgattaaagccattcaaaaactgttagcgcgcaatcaacttactacggaagaaattgatctgtatgaaatcaacgaa
gcatttgcagcaacttcaatcgtggtccaaagagaactggctttaccagaggaaaaggtcaacatttatggtggcggtatttcattaggtcatg
cgattggtgccacaggtgctcgtttattaacgagtttaagttatcaattaaatcaaaaagaaaagaaatatggagtggcttctttatgtatcggcg
gtggcttaggactcgctatgctactagagagacctcagcaaaaaaaaaacagccgattttatcaaatgagtcctgaggaacgcctggcttctc
ttcttaatgaaggccagatttctgctgatacaaaaaaagaatttgaaaatacggctttatcttcgcagattgccaatcatatgattgaaaatcaaat
cagtgaaacagaagtgccgatgggcgttggcttacatttaacagtggacgaaactgattatttggtaccaatggcgacagaagagccctcag
ttattgcggctttgagtaatggtgcaaaaatagcacaaggatttaaaacagtgaatcaacaacgcttaatgcgtggacaaatcgtttttacgat
gttgcagatcccgagtcattgattgataaactacaagtaagagaagcggaagtttttcaacaagcagagttaagttatccatctatcgttaaacg
gggcggcggcttaagagatttgcaatatcgtacttttgatgaatcatttgtatctgtcgacttttagtagatgttaaggatgcaatgggggcaaat
atcgttaacgctatgttggaaggtgtggccgagttgttccgtgaatggtttgcggagcaaaagattttattcagtattttaagtaattatgccacgg
agtcggttgttacgatgaaaacggctattccagtttcacgtttaagtaaggggagcaatggccgggaaattgctgaaaaaattgttttagcttca
cgctatgcttcattagatccttatcgggcagtcacgcataacaaaggaatcatgaatggcattgaagctgtagttttagctacaggaaatgata
cacgcgctgttagcgcttcttgtcatgcttttgcggtgaaggaaggtcgctaccaaggcttgactagttggacgctggatggcgaacaactaa
ttggtgaaatttcagttccgcttgctttagccacggttggcggtgccacaaaagtcttacctaaatctcaagcagctgctgatttgttagcagtga
cggatgcaaaagaactaagtcgagtagtagcggctgttggtttggcacaaaatttagcggcgttacgggccttagtctctgaaggaattcaaa
aaggacacatggctctacaagcacgttctttagcgatgacggtcggagctactggtaaagaagttgaggcagtcgctcaacaattaaaacgt
caaaaaacgatgaaccaagaccgagccatggctattttaaatgatttaagaaaacaataaaggaggtaaaaaacatgacaattgggattga
taaaattagtttttttgtgcccccttattatattgatatgacggcactggctgaagccagaaatgtagaccctggaaaatttcatattggtattgggc
aagaccaaatggcggtgaacccaatcagccaagatattgtgacatttgcagccaatgccgcagaagcgatcttgaccaaagaagataaag
aggccattgatatggtgattgtcgggactgagtccagtatcgatgagtcaaaagcggccgcagttgtcttacatcgtttaatggggattcaacc
tttcgctcgctctttcgaaatcaaggaagcttgttacggagcaacagcaggcttacagttagctaagaatcacgtagccttacatccagataaa
aaagtcttggtcgtagcggcagatattgcaaaatatggcttaaattctggcggtgagcctacacaaggagctggggcggttgcaatgttagtt
gctagtgaaccgcgcattttggctttaaaagaggataatgtgatgctgacgcaagatatctatgacttttggcgtccaacaggccacccgtatc
ctatggtcgatggtcctttgtcaaacgaaacctacatccaatcttttgcccaagtctgggatgaacataaaaaacgaaccggtcttgattttgca
gattatgatgctttagcgttccatattccttacacaaaaatgggcaaaaaagccttattagcaaaaatctccgaccaaactgaagcagaacag
gaacgaattttagcccgttatgaagaaagtatcgtctatagtcgtcgcgtaggaaacttgtatacgggttcactttatctgggactcatttcccttt
agaaaatgcaacgactttaaccgcaggcaatcaaattggtttattcagttatggttctggtgctgtcgctgaattttcactggtgaattagtagct
ggttatcaaaatcatttacaaaaagaaactcatttagcactgctggataatcggacagaactttctatcgctgaatatgaagccatgtttgcaga
aactttagacacagacattgatcaaacgttagaagatgaattaaaatatagtatttctgctattaataataccgttcgttcttatcgaaactaagag
atctgcagctggtaccatatgggaattcgaagcttgggcccgaacaaaaactcatctcagaagaggatctgaatagcgccgtcgaccatcat
catcatcatcattgagtttaaacggtctccagcttggctgttttggcggatgagagaagattttcagcctgatacagattaaatcagaacgcaga
agcggtctgataaaacagaatttgcctggcggcagtagcgcggtggtcccacctgaccccatgccgaactcagaagtgaaacgccgtagc
gccgatggtagtgtggggtctccccatgcgagagtagggaactgccaggcatcaaataaaacgaaaggctcagtcgaaagactggg

Figure 112R cctttcgttttatctgttgtttgtcggtgaacgctctcctgagtaggacaaatccgccgggagcggatttgaacgttgcgaagcaacggcccgg
agggtggcgggcaggacgcccgccataaactgccaggcatcaaattaagcagaaggccatcctgacggatggcctttttgcgtttctacaa
actcttttgtttatttttctaaatacattcaaatatgtatccgctcatgagacaataaccctgataaatgcttcaataatctggcgtaatagcgaaga
ggcccgcaccgatcgcccttcccaacagttgcgcagcctgaatggcgaatggcgcctgatgcggtattttctccttacgcatctgtgcggtat
ttcacaccgcatatggtgcactctcagtacaatctgctctgatgccgcatagttaagccagccccgacacccgccaacacccgctgacgag
cttagtaaagccctcgctagattttaatgcggatgttgcgattacttcgccaactattgcgataacaagaaaaagccagcctttcatgatatatct
cccaatttgtgtagggcttattatgcacgcttaaaaataataaaagcagacttgacctgatagtttggctgtgagcaattatgtgcttagtgcatct
aacgcttgagttaagccgcgccgcgaagcggcgtcggcttgaacgaattgttagacattatttgccgactaccttggtgatctcgcctttcacg
tagtggacaaattcttccaactgatctgcgcgcgaggccaagcgatcttcttcttgtccaagataagcctgtctagcttcaagtatgacgggct
gatactgggccggcaggcgctccattgcccagtcggcagcgacatccttcggcgcgattttgccggttactgcgctgtaccaaatgcggga
caacgtaagcactacatttcgctcatcgccagcccagtcgggcggcgagttccatagcgttaaggtttcatttagcgcctcaaatagatcctgt
tcaggaaccggatcaaagagttcctccgccgctggacctaccaaggcaacgctatgttctcttgcttttgtcagcaagatagccagatcaatg
tcgatcgtggctggctcgaagatacctgcaagaatgtcattgcgctgccattctccaaattgcagttcgcgcttagctggataacgccacgga
atgatgtcgtcgtgcacaacaatggtgacttctacagcgcggagaatctcgctctctccaggggaagccgaagtttccaaaaggtcgttgat
caaagctcgccgcgttgtttcatcaagccttacggtcaccgtaaccagcaaatcaatatcactgtgtggcttcaggccgccatccactgcgga
gccgtacaaatgtacggccagcaacgtcggttcgagatggcgctcgatgacgccaactacctctgatagttgagtcgatacttcggcgatca
ccgcttccctcatgatgtttaactttgttttagggcgactgccctgctgcgtaacatcgttgctgctccataacatcaaacatcgacccacggcg
taacgcgcttgctgcttggatgcccgaggcatagactgtaccccaaaaaaacagtcataacaagccatgaaaaccgccactgcgccgttac
caccgctgcgttcggtcaaggttctggaccagttgcgtgagcgcatacgctacttgcattacagcttacgaaccgaacaggcttatgtccact
gggttcgtgccttcatccgtttccacggtgtgcgtcacccggcaaccttgggcagcagcgaagtcgaggcatttctgtcctggctggcgaac
gagcgcaaggtttcggtctccacgcatcgtcaggcattggcggccttgctgttcttctacggcaaggtgctgtgcacggatctgccctggctt
caggagatcggaagacctcggccgtcgcggcgcttgccggtggtgctgaccccggatgaagtggttcgcatcctcggttttctggaaggc
gagcatcgtttgttcgcccagcttctgtatggaacgggcatgcggatcagtgagggtttgcaactgcgggtcaaggatctggatttcgatcac
ggcacgatcatcgtgcgggagggcaagggctccaaggatcgggccttgatgttacccgagagcttggcacccagcctgcgcgagcagg
ggaattaattcccacgggttttgctgcccgcaaacgggctgttctggtgttgctagtttgttatcagaatcgcagatccggcttcagccggtttg
ccggctgaaagcgctatttcttccagaattgccatgatttttccccacgggaggcgtcactggctcccgtgttgtcggcagctttgattcgata
agcagcatcgcctgtttcaggctgtctatgtgtgactgttgagctgtaacaagttgtctcaggtgttcaatttcatgttctagttgctttgttttactg
gtttcacctgttctattaggtgttacatgctgttcatctgttacattgtcgatctgttcatggtgaacagctttgaatgcaccaaaaactcgtaaaag
ctctgatgtatctatcttttttacaccgttttcatctgtgcatatggacagttttccctttgatatgtaacggtgaacagttgttctacttttgtttgttagt
cttgatgcttcactgatagatacaagagccataagaacctcagatccttccgtatttagccagtatgttctctagtgtggttcgttgtttttgcgtga
gccatgagaacgaaccattgagatcatacttactttgcatgtcactcaaaaattttgcctcaaaactggtgagctgaatttttgcagttaaagcat
cgtgtagtgtttttcttagtccgttatgtaggtaggaatctgatgtaatggttgttggtattttgtcaccattcatttttatctggttgttctcaagttcggt
tacgagatccatttgtctatctagttcaacttggaaaatcaacgtatcagtcgggcggcctcgcttatcaaccaccaatttcatattgctgtaagt
gtttaaatctttacttattggtttcaaaacccattggttaagccttttaaactcatggtagttattttcaagcattaacatgaacttaaattcatcaagg
ctaatctctatatttgccttgtgagttttcttttgtgttagttcttttaataaccactcataaatcctcatagagtatttgttttcaaaagacttaacatgttc
cagattatattttatgaattttttaactggaaaagataaggcaatatctcttcactaaaaactaattctaatttttcgcttgagaacttggcatagtttg
tccactggaaaatctcaaagcctttaaccaaaggattcctgatttccacagttctcgtcatcagctctctggttgctttagctaatacaccataag
cattttccctactgatgttcatcatctgagcgtattggttataagtgaacgataccgtccgttctttccttgtagggttttcaatcgtggggttgagta
gtgccacacagcataaaattagcttggtttcatgctccgttaagtcatagcgactaatcgctagttcatttgctttgaaaacaactaattcagacat
acatctcaattggtctaggtgattttaatcactataccaattgagatgggctagtcaatgataattactagtcctttttcctttgagttgtgggtatctgt
aaattctgctagacctttgctggaaaacttgtaaattctgctagaccctctgtaaattccgctagacctttgtgtgttttttttgtttatattcaagtggt
tataatttatagaataaagaaagaataaaaaaagataaaaagaatagatcccagccctgtgtataactcactactttagtcagttccgcagtatt
acaaaaggatgtcgcaaacgctgtttgctcctctacaaaacagaccttaaaaccctaaaggcttaagtagcaccctcgcaagctcgggcaa
atcgctgaatattccttttgtctccgaccatcaggcacctgagtcgctgtctttttcgtgacattcagttcgctgcgctcacggctctggcagtg

Figure 112S

Aatgggggtaaatggcactacaggcgccttttatggattcatgcaaggaaactacccataatacaagaaaagcccgtcacgggcttctcag
ggcgttttatggcgggtctgctatgtggtgctatctgactttttgctgttcagcagttcctgccctctgattttccagtctgaccacttcggattatcc
cgtgacaggtcattcagactggctaatgcacccagtaaggcagcggtatcatcaacaggcttacccgtcttactgtcgggaattcgcgttgg
ccgattcattaatgcagattctgaaatgagctgttgacaattaatcatccggctcgtataatgtgtgga (SEQ ID NO:125)

T

EL-976 : (+) PCR of KKDI insertion into pCL vector (upstream of promoter region)
CTTCTCAGGGCGTTTTATGGC (SEQ ID NO:126)

EL-977 : (-) PCR of KKDI insertion into pCL vector (anneals to MVK gene)
GTTGAGCTAACAACGGATCC (SEQ ID NO:127)

EL-978 : (+) sequence from yeast IDI towards terminator
GACTGTCAACCCAAACGTCAATG (SEQ ID NO :128)

U

Figure 112V cccgtcttactgtcgggaattcgcgttggccgattcattaatgcagattctgaaatgagctgttgacaattaatcatccggctcgtataatgtgtg
gtcacacaggaaacagcgccgctgagaaaaagcgaagcggcactgctctttaacaatttatcagacaatctgtgtgggcactcgaccgga
attatcgattaactttattattaaaaattaaagaggtatatattaatgtatcgattaaataaggaggaataaaccatggatccgagctcggatccac
tagtaacggccgccagtgtgctggaattcgcccttaggaggtaaaaaaacatgtcattaccgttcttaacttctgcaccgggaaaggttattatt
tttggtgaacactctgctgtgtacaacaagcctgccgtcgctgctagtgtgtctgcgttgagaacctacctgctaataagcgagtcatctgcac
cagatactattgaattggacttcccggacattagctttaatcataagtggtccatcaatgatttcaatgccatcaccgaggatcaagtaaactccc
aaaaattggccaaggctcaacaagccaccgatggcttgtctcaggaactcgttagtcttttggatccgttgttagctcaactatccgaatccttc
cactaccatgcagcgttttgtttcctgtatatgtttgtttgcctatgcccccatgccaagaatattaagttttctttaaagtctactttacccatcggtg
ctgggttgggctcaagcgcctctatttctgtatcactggccttagctatggcctacttgggggggttaataggatctaatgacttggaaaagctg
tcagaaaacgataagcatatagtgaatcaatgggccttcataggtgaaaagtgtattcacggtaccccttcaggaatagataacgctgtggcc
acttatggtaatgccctgctatttgaaaaagactcacataatggaacaataaacacaaacaattttaagttcttagatgatttcccagccattcca
atgatcctaacctatactagaattccaaggtctacaaaagatcttgttgctcgcgttcgtgtgttggtcaccgagaaatttcctgaagttatgaag
ccaattctagatgccatgggtgaatgtgccctacaaggcttagagatcatgactaagttaagtaaatgtaaaggcaccgatgacgaggctgta
gaaactaataatgaactgtatgaacaactattggaattgataagaataaatcatggactgcttgtctcaatcggtgtttctcatcctggattagaa
cttattaaaaatctgagcgatgatttgagaattggctccacaaaacttaccggtgctggtggcggcggttgctctttgactttgttacgaagaga
cattactcaagagcaaattgacagcttcaaaaagaaattgcaagatgattttagttacgagacatttgaaacagacttgggtgggactggctgc
tgtttgttaagcgcaaaaaatttgaataaagatcttaaaatcaaatccctagtattccaattatttgaaaataaaactaccacaaagcaacaaattg
acgatctattattgccaggaaacacgaatttaccatggacttcataagctaatttgcgataggcctgcacccttaaggaggaaaaaaacatgtc
agagttgagagccttcagtgccccagggaaagcgttactagctggtggatatttagttttagatacaaaatatgaagcatttgtagtcggattat
cggcaagaatgcatgctgtagcccatccttacggttcattgcaagggtctgataagtttgaagtgcgtgtgaaaagtaaacaatttaaagatgg
ggagtggctgtaccatataagtcctaaaagtggcttcattcctgtttcgataggcggatctaagaaccctttcattgaaaaagttatcgctaacgt
atttagctactttaaacctaacatggacgactactgcaatagaaacttgttcgttattgatattttctctgatgatgcctaccattctcaggaggata
gcgttaccgaacatcgtggcaacagaagattgagttttcattcgcacagaattgaagaagttcccaaaacagggctgggctcctcggcaggt
ttagtcacagttttaactacagctttggcctcctttttgtatcggacctggaaaataatgtagacaaatatagagaagttattcataatttagcaca
agttgctcattgtcaagctcagggtaaaattggaagcgggtttgatgtagcggcggcagcatatggatctatcagatatagaagattcccacc
cgcattaatctctaatttgccagatattggaagtgctacttacggcagtaaactggcgcatttggttgatgaagaagactggaatattacgattaa
aagtaaccatttaccttcgggattaactttatggatgggcgatattaagaatggttcagaaacagtaaaactggtccagaaggtaaaaaattgg
tatgattcgcatatgccagaaagcttgaaaatatatacagaactcgatcatgcaaattctagatttatggatggactatctaaactagatcgctta
cacgagactcatgacgattacagcgatcagatatttgagtctcttgagaggaatgactgtacctgtcaaaagtatcctgaaatcacagaagtta
gagatgcagttgccacaattagacgttcctttagaaaaataactaaagaatctggtgccgatatcgaacctcccgtacaaactagcttattggat
gattgccagaccttaaaaggagttcttacttgcttaatacctggtgctggtggttatgacgccattgcagtgattactaagcaagatgttgatctta
gggctcaaaccgctaatgacaaaagattttctaaggttcaatggctggatgtaactcaggctgactggggtgttaggaaagaaaaagatccg
gaaacttatcttgataaataacttaaggtagctgcatgcagaattcgcccttaaggaggaaaaaaaatgaccgtttacacagcatccgttacc
gcacccgtcaacatcgcaacccttaagtattgggggaaaagggacacgaagttgaatctgcccaccaattcgtccatatcagtgactttatcg
caagatgacctcagaacgttgacctctgcggctactgcacctgagtttgaacgcgacactttgtggttaaatggagaaccacacagcatcga
caatgaaagaactcaaaattgtctgcgcgacctacgccaattaagaaaggaaatggaatcgaaggacgcctcattgcccacattatctcaat
ggaaactccacattgtctccgaaaataactttcctacagcagctggtttagcttcctccgctgctggctttgctgcattggtctctgcaattgctaa
gttataccaattaccacagtcaacttcagaaatatctagaatagcaagaaaggggtctggttcagcttgtagatcgttgtttggcggatacgtgg
cctgggaaatgggaaaagctgaagatggtcatgattccatggcagtacaaatcgcagacagctctgactggcctcagatgaaagcttgtgtc
ctagttgtcagcgatattaaaaaggatgtgagttccactcagggtatgcaattgaccgtggcaacctccgaactatttaaagaaagaattgaac
atgtcgtaccaaagagatttgaagtcatgcgtaaagccattgttgaaaaagatttcgccacctttgcaaaggaaacaatgatggattccaactc
tttccatgccacatgtttggactctttccctccaatattctacatgaatgacacttccaagcgtatcatcagttggtgccacaccattaatcagtttta
cggagaaacaatcgttgcatacacgtttgatgcaggtccaaatgctgtgttgtactacttagctgaaaatgagtcgaaactctttgcatttatctat
aaattgtttggctctgttcctggatgggacaagaaatttactactgagcagcttgaggctttcaaccatcaatttgaatcatctaacttta

Figure 112W ctgcacgtgaattggatcttgagttgcaaaaggatgttgccagagtgattttaactcaagtcggttcaggcccacaagaaacaaacgaatcttt
gattgacgcaaagactggtctaccaaaggaataagatcaattcgctgcatcgcccttaggaggtaaaaaaaaatgactgccgacaacaata
gtatgccccatggtgcagtatctagttacgccaaattagtgcaaaaccaaacacctgaagacattttggaagagtttcctgaaattattccatta
caacaaagacctaatacccgatctagtgagacgtcaaatgacgaaagcggagaaacatgtttttctggtcatgatgaggagcaaattaagtt
aatgaatgaaaattgtattgttttggattgggacgataatgctattggtgccggtaccaagaaagtttgtcatttaatggaaaatattgaaaaggg
tttactacatcgtgcattctccgtctttattttcaatgaacaaggtgaattacttttacaacaaagagccactgaaaaaataactttccctgatcttg
gactaacacatgctgctctcatccactatgtattgatgacgaattaggtttgaagggtaagctagacgataagattaagggcgctattactgcg
gcggtgagaaaactagatcatgaattaggtattccagaagatgaaactaagacaaggggtaagtttcacttttaaacagaatccattacatgg
caccaagcaatgaaccatggggtgaacatgaaattgattacatcctattttataagatcaacgctaaagaaaacttgactgtcaacccaaacgt
caatgaagttagagacttcaaatgggtttcaccaaatgatttgaaaactatgtttgctgacccaagttacaagtttacgccttggtttaagattattt
gcgagaattacttattcaactggtgggagcaattagatgacctttctgaagtggaaaatgacaggcaaattcatagaatgctataacaacgcgt
cctgcagctggtaccatatgggaattcgaagcttgggcccgaacaaaaactcatctcagaagaggatctgaatagcgccgtcgaccatcat
catcatcatcattgagtttaaacggtctccagcttggctgttttggcggatgagagaagattttcagcctgatacagattaaatcagaacgcaga
agcggtctgataaaacagaatttgcctggcggcagtagcgcggtggtcccacctgaccccatgccgaactcagaagtgaaacgccgtagc
gccgatggtagtgtggggtctccccatgcgagagtagggaactgccaggcatcaaataaaacgaaaggctcagtcgaaagactgggcctt
tcgttttatctgttgtttgtcggtgaacgctctcctgagtaggacaaatccgccgggagcggatttgaacgttgcgaagcaacggcccggagg
gtggcgggcaggacgcccgccataaactgccaggcatcaaattaagcagaaggccatcctgacggatggcctttttgcgtttctacaaact
ctttttgtttatttttctaaatacattcaaatatgtatccgctcatgagacaataaccctgataaatgcttcaataatctggcgtaatagcgaagagg
cccgcaccgatcgcccttcccaacagttgcgcagcctgaatggcgaatggcgcctgatgcggtattttctccttacgcatctgtgcggtatttc
acaccgcatatggtgcactctcagtacaatctgctctgatgccgcatagttaagccagccccgacacccgccaacacccgctgacgagctt
agtaaagccctcgctagatttaatgcggatgttgcgattacttcgccaactattgcgataacaagaaaaagccagcctttcatgatatatctcc
caatttgtgtagggcttattatgcacgcttaaaaataataaaagcagacttgacctgatagtttggctgtgagcaattatgtgcttagtgcatctaa
cgcttgagttaagccgcgccgcgaagcggcgtcggcttgaacgaattgttagacattatttgccgactaccttggtgatctcgcctttcacgta
gtggacaaattcttccaactgatctgcgcgcgaggccaagcgatcttcttcttgtccaagataagcctgtctagcttcaagtatgacgggctga
tactgggccggcaggcgctccattgcccagtcggcagcgacatccttcggcgcgattttgccggttactgcgctgtaccaaatgcgggaca
acgtaagcactacatttcgctcatcgccagcccagtcgggcggcgagttccatagcgttaaggtttcatttagcgcctcaaatagatcctgttc
aggaaccggatcaaagagttcctccgccgctggacctaccaaggcaacgctatgttctcttgcttttgtcagcaagatagccagatcaatgtc
gatcgtggctggctcgaagatacctgcaagaatgtcattgcgctgccattctccaaattgcagttcgcgcttagctggataacgccacggaat
gatgtcgtcgtgcacaacaatggtgacttctacagcgcggagaatctcgctctctccaggggaagccgaagtttccaaaaggtcgttgatca
aagctcgccgcgttgtttcatcaagccttacggtcaccgtaaccagcaaatcaatatcactgtgtggcttcaggccgccatccactgcggag
ccgtacaaatgtacggccagcaacgtcggttcgagatggcgctcgatgacgccaactacctctgatagttgagtcgatacttcggcgatcac
cgcttccctcatgatgtttaactttgttttagggcgactgccctgctgcgtaacatcgttgctgctccataacatcaaacatcgacccacggcgt
aacgcgcttgctgcttggatgcccgaggcatagactgtaccccaaaaaaacagtcataacaagccatgaaaaccgccactgcgccgttac
caccgctgcgttcggtcaaggttctggaccagttgcgtgagcgcatacgctacttgcattacagcttacgaaccgaacaggcttatgtccact
gggttcgtgccttcatccgtttccacggtgtgcgtcacccggcaaccttgggcagcagcgaagtcgaggcatttctgtcctggctggcgaac
gagcgcaaggtttcggtctccacgcatcgtcaggcattggcggccttgctgttcttctacggcaaggtgctgtgcacggatctgccctggctt
caggagatcggaagacctcggccgtcgcggcgcttgccggtggtgctgaccccggatgaagtggttcgcatcctcggttttctggaaggc
gagcatcgtttgttcgcccagcttctgtatggaacgggcatgcggatcagtgagggtttgcaactgcgggtcaaggatctggatttcgatcac
ggcacgatcatcgtgcgggagggcaagggctccaaggatcgggccttgatgttacccgagagcttggcacccagcctgcgcgagcagg
ggaattaattcccacgggttttgctgcccgcaaacgggctgttctggtgttgctagtttgttatcagaatcgcagatccggcttcagccggtttg
ccggctgaaagcgctatttcttccagaattgccatgatttttccccacgggaggcgtcactggctcccgtgttgtcggcagctttgattcgata
agcagcatcgcctgtttcaggctgtctatgtgtgactgttgagctgtaacaagttgtctcaggtgttcaatttcatgttctagttgctttgttttactg
gtttcacctgttctattaggtgttacatgctgttcatctgttacattgtcgatctgttcatggtgaacagctttgaatgcaccaaaaactcgtaaaag
ctctgatgtatctatctttttacaccgttttcatctgtgcatatggacagttttccctttgatatgtaacggtgaacagttgttctactttgtttgttagt
ctt

Figure 112X gatgcttcactgatagatacaagagccataagaacctcagatccttccgtatttagccagtatgttctctagtgtggttcgttgtttttgcgtgagc
catgagaacgaaccattgagatcatacttactttgcatgtcactcaaaaattttgcctcaaaactggtgagctgaatttttgcagttaaagcatcg
tgtagtgtttttcttagtccgttatgtaggtaggaatctgatgtaatggttgttggtattttgtcaccattcattttatctggttgttctcaagttcggtta
cgagatccatttgtctatctagttcaacttggaaaatcaacgtatcagtcgggcggcctcgcttatcaaccaccaatttcatattgctgtaagtgtt
taaatctttacttattggtttcaaaacccattggttaagccttttaaactcatggtagttattttcaagcattaacatgaacttaaattcatcaaggcta
atctctatatttgccttgtgagttttcttttgtgttagttcttttaataaccactcataaatcctcatagagtatttgttttcaaaagacttaacatgttcca
gattatattttatgaatttttttaactggaaaagataaggcaatatctcttcactaaaaactaattctaattttcgcttgagaacttggcatagtttgtc
cactggaaaatctcaaagcctttaaccaaaggattcctgatttccacagttctcgtcatcagctctctggttgctttagctaatacaccataagca
ttttccctactgatgttcatcatctgagcgtattggttataagtgaacgataccgtccgttctttccttgtagggttttcaatcgtggggttgagtagt
gccacacagcataaaattagcttggtttcatgctccgttaagtcatagcgactaatcgctagttcatttgctttgaaaacaactaattcagacata
catctcaattggtctaggtgattttaatcactataccaattgagatgggctagtcaatgataattactagtcctttcctttgagttgtgggtatctgt
aaattctgctagacctttgctggaaaacttgtaaattctgctagaccctctgtaaattccgctagacctttgtgtgtttttttgtttatattcaagtggt
tataatttatagaataaagaaagaataaaaaaagataaaaagaatagatcccagccctgtgtataactcactactttagtcagttccgcagtatt
acaaaaggatgtcgcaaacgctgtttgctcctctacaaaacagaccttaaaccctaaaggcttaagtagcaccctcgcaagctcgggcaa
atcgctgaatattcctttgtctccgaccatcaggcacctgagtcgctgtctttttcgtgacattcagttcgctgcgctcacggctctggcagtga
atgggggtaaatggcactacaggcgccttttatggattcatgcaaggaaactacccataatacaagaaaagcccgtcacgggcttctcagg
gcgttttatggcgggtctgctatgtggtgctatctgacttttgctgttcagcagttcctgccctctgattttccagtctgaccacttcggattatccc
gtgacaggtcattcagactggctaatgcacccagtaaggcagcggtatcatcaacaggctta (SEQ ID NO:129)

Figure 119B cattaagttctgtctcggcgcgtctgcgtctggctggctggcataaatatctcactcgcaatcaaattcagccgatagcggaacgg
gaaggcgactggagtgccatgtccggttttcaacaaaccatgcaaatgctgaatgagggcatcgttcccactgcgatgctggttg
ccaacgatcagatggcgctgggcgcaatgcgcgccattaccgagtccgggctgcgcgttggtgcggatatctcggtagtggga
tacgacgataccgaagacagctcatgttatatcccgccgtcaaccaccatcaaacaggattttcgcctgctggggcaaaccagcg
tggaccgcttgctgcaactctctcagggccaggcggtgaagggcaatcagctgttgcccgtctcactggtgaaaagaaaaacca
ccctggcgcccaatacgcaaaccgcctctccccgcgcgttggccgattcattaatgcagctggcacgacaggtttcccgactgg
aaagcgggcagtgagcgcaacgcaattaatgtgagttagcgcgaattgatctggtttgacagcttatcatcgactgcacggtgca
ccaatgcttctggcgtcaggcagccatcggaagctgtggtatggctgtgcaggtcgtaaatcactgcataattcgtgtcgctcaag
gcgcactcccgttctggataatgttttttgcgccgacatcataacggttctggcaaatattctgaaatgagctgttgacaattaatcatc
cggctcgtataatgtgtggaattgtgagcggataacaatttcacacaggaaacagcgccgctgagaaaaagcgaagcggcact
gctctttaacaatttatcagacaatctgtgtgggcactcgaccggaattatcgattaactttattattaaaaattaaagaggtatatatta
atgtatcgattaaataaggaggaataaaccatggatccgagctcgagatctgcagctggtaccatatgggaattcgaagctttcta
gaacaaaaactcatctcagaagaggatctgaatagcgccgtcgaccatcatcatcatcatcattgagtttaaacggtctccagcttg
gctgttttggcggatgagagaagattttcagcctgatacagattaaatcagaacgcagaagcggtctgataaaacagaatttgcct
ggcggcagtagcgcggtggtcccacctgaccccatgccgaactcagaagtgaaacgccgtagcgccgatggtagtgtggggt
ctccccatgcgagagtagggaactgccaggcatcaaataaaacgaaaggctcagtcgaaagactgggcctttcgttttatctgttg
tttgtcggtgaacgctctcctgagtaggacaaatccgccgggagcggatttgaacgttgcgaagcaacggcccggagggtggc
gggcaggacgcccgccataaactgccaggcatcaaattaagcagaaggccatcctgacggatggcctttttgcgtttctacaaac
tctttttgtttatttttctaaatacattcaaatatgtatccgcttaaccggaattgccagctggggcgccctctggtaaggttgggaagcc
ctgcaaagtaaactggatggctttctcgccgccaaggatctgatggcgcaggggatcaagctctgatcaagagacaggatgagg
atcgtttcgcatgattgaacaagatggattgcacgcaggttctccggccgcttgggtggagaggctattcggctatgactgggcac
aacagacaatcggctgctctgatgccgccgtgttccggctgtcagcgcaggggcgcccggttctttttgtcaagaccgacctgtc
cggtgccctgaatgaactgcaagacgaggcagcgcggctatcgtggctggccacgacgggcgttccttgcgcagctgtgctcg
acgttgtcactgaagcgggaagggactggctgctattgggcgaagtgccggggcaggatctcctgtcatctcaccttgctcctgc
cgagaaagtatccatcatggctgatgcaatgcggcggctgcatacgcttgatccggctacctgcccattcgaccaccaagcgaa
acatcgcatcgagcgagcacgtactcggatggaagccggtcttgtcgatcaggatgatctggacgaagagcatcaggggctcg
cgccagccgaactgttcgccaggctcaaggcgagcatgcccgacggcgaggatctcgtcgtgacccatggcgatgcctgcttg
ccgaatatcatggtggaaaatggccgcttttctggattcatcgactgtggccggctgggtgtggcggaccgctatcaggacatag
cgttggctacccgtgatattgctgaagagcttggcggcgaatgggctgaccgcttcctcgtgctttacggtatcgccgctcccgatt
cgcagcgcatcgccttctatcgccttcttgacgagttcttctgacgcatgaccaaaatcccttaacgtgagttttcgttccactgagc
gtcagaccccgtagaaaagatcaaaggatcttcttgagatcctttttttctgcgcgtaatctgctgcttgcaaacaaaaaaaccacc
gctaccagcggtggtttgtttgccggatcaagagctaccaactctttttccgaaggtaactggcttcagcagagcgcagataccaa
atactgtccttctagtgtagccgtagttaggccaccacttcaagaactctgtagcaccgcctacatacctcgctctgctaatcctgtta
ccagtggctgctgccagtggcgataagtcgtgtcttaccgggttggactcaagacgatagttaccggataaggcgcagcggtcg
ggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcac
gagggagcttccagggggaaacgcctggtatctttatagtcctgtcgggtttcgccacctctgacttgagcgtcgatttttgtgatgc
tcgtcaggggggcggagcctatggaaaaacgccagcaacgcggcctttttacggttcctggccttttgctggccttttgctcacat
gttctttcctgcgttatcccctgattctgtggataaccgtattaccgcctttgagtgagctgataccgctcgccgcagccgaacgacc
gagcgcagcgagtcagtgagcgaggaagcggaagagcgcctgatgcggtattttctccttacgcatctgtgcggtatttcacacc
gcatatggtgcactctcagtacaatctgctctgatgccgcatagttaagccagtatacactccgctatcgctacgtgactgggtcat
ggctgcgccccgacacccgccaacacccgctgacgcgccctgacgggcttgtctgctcccggcatccgcttacagacaagctg
tgaccgtctccgggagctgcatgtgtcagaggttttcaccgtcatcaccgaaacgcgcgaggcagcagatcaattcgcgcgcga
aggcgaagcggcatgcatttacgttgacaccatcgaatggtgcaaaacctttcgcggtatggcatgat

Figure 119C agcgcccggaagagagtcaattcagggtggtgaatgtgaaaccagtaacgttatacgatgtcgcagagtatgccggtgtctctta
tcagaccgtttcccgcgtggtgaaccaggccagccacgtttctgcgaaaacgcgggaaaaagtggaagcggcgatggcgga
gctgaattacattcccaaccgcgtggcacaacaactggcgggcaaacagtcgttgctgattggcgttgccacctccagtctggcc
ctgcacgcgccgtcgcaaattgtcgcggcgattaaatctcgcgccgatcaactgggtgccagcgtggtggtgtcgatggtagaa
cgaagcggcgtcgaagcctgtaaagcggcggtgcacaatcttctcgcgcaacgcgtcagtgggctgatcattaactatccgctg
gatgaccaggatgccattgctgtggaagctgcctgcactaatgttccggcgttatttcttgatgtctctgaccagacacccatcaac
agtattattttctcccatgaagacggtacgcgactgggcgtggagcatctggtcgcattgggtcaccagcaaatcgcgctgttagc
gggcc
(SEQ ID NO:107)

A

B

C

D

E

F

Figure 126A 1-
ttcttgaagacgaaagggcctcgtgatacgcctatttttataggttaatgtcatgataataatggtttcttagacgtcaggtggcacttt
tcggggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcattttgccttcctgtttt
tgctcacccagaaacgctggtgaaagtaaaagatgctgaagatcagttgggtgcacgagtgggttacatcgaactggatctcaa
cagcggtaagatccttgagagttttcgccccgaagaacgttttccaatgatgagcacttttaaagttctgctatgtggcgcggtatta
tcccgtgttgacgccgggcaagagcaactcggtcgccgcatacactattctcagaatgacttggttgagtactcaccagtcacag
aaaagcatcttacggatggcatgacagtaagagaattatgcagtgctgccataaccatgagtgataacactgcggccaacttactt
ctgacaacgatcggaggaccgaaggagctaaccgcttttttgcacaacatgggggatcatgtaactcgccttgatcgttgggaac
cggagctgaatgaagccataccaaacgacgagcgtgacaccacgatgcctgcagcaatggcaacaacgttgcgcaaactatt
aactggcgaactacttactctagcttcccggcaacaattaatagactggatggaggcggataaagttgcaggaccacttctgcgc
tcggcccttccggctggctggtttattgctgataaatctggagccggtgagcgtgggtctcgcggtatcattgcagcactggggcc
agatggtaagccctcccgtatcgtagttatctacacgacggggagtcaggcaactatggatgaacgaaatagacagatcgctga
gataggtgcctcactgattaagcattggtaactgtcagaccaagtttactcatatatactttagattgatttaaaacttcatttttaatttaa
aaggatctaggtgaagatcctttttgataatctcatgaccaaaatcccttaacgtgagttttcgttccactgagcgtcagaccccgta
gaaaagatcaaaggatcttcttgagatcctttttttctgcgcgtaatctgctgcttgcaaacaaaaaaaccaccgctaccagcggtg
gtttgtttgccggatcaagagctaccaactctttttccgaaggtaactggcttcagcagagcgcagataccaaatactgtccttctag
tgtagccgtagttaggccaccacttcaagaactctgtagcaccgcctacatacctcgctctgctaatcctgttaccagtggctgctg
ccagtggcgataagtcgtgtcttaccgggttggactcaagacgatagttaccggataaggcgcagcggtcgggctgaacgggg
ggttcgtgcacacagcccagcttggagcgaacgacctacaccgaactgagatacctacagcgtgagctatgagaaagcgcca
cgcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcaggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcatatatggtg
cactctcagtacaatctgctctgatgccgcatagttaagccagtatacactccgctatcgctacgtgactgggtcatggctgcgcc
ccgacacccgccaacacccgctgacgcgccctgacgggcttgtctgctcccggcatccgcttacagacaagctgtgaccgtct
ccgggagctgcatgtgtcagaggttttcaccgtcatcaccgaaacgcgcgaggcagctgcggtaaagctcatcagcgtggtcgt
gaagcgattcacagatgtctgcctgttcatccgcgtccagctcgttgagtttctccagaagcgttaatgtctggcttctgataaagcg
ggccatgttaagggcggttttttcctgtttggtcactgatgcctccgtgtaagggggatttctgttcatgggggtaatgataccgatg
aaacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtatagggcggcgcctacaatccatgcc
aacccgttccatgtgctcgccgaggcggcataaatcgccgtgacgatcagcggtccagtgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt
cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccc

Figure 126B accggaaggagctgactgggttgaaggctctcaagggcatcggtcgagatcccggtgcctaatgagtgagctaacttacattaa
ttgcgttgcgctcactgcccgctttccagtcgggaaacctgtcgtgccagctgcattaatgaatcggccaacgcgcggggagag
gcggtttgcgtattgggcgccagggtggtttttcttttcaccagtgagacgggcaacagctgattgcccttcaccgcctggccctg
agagagttgcagcaagcggtccacgctggtttgccccagcaggcgaaaatcctgtttgatggtggttaacggcgggatataaca
tgagctgtcttcggtatcgtcgtatcccactaccgagatatccgcaccaacgcgcagcccggactcggtaatggcgcgcattgc
gcccagcgccatctgatcgttggcaaccagcatcgcagtgggaacgatgccctcattcagcatttgcatggtttgttgaaaaccg
gacatggcactccagtcgccttcccgttccgctatcggctgaatttgattgcgagtgagatatttatgccagccagccagacgcag
acgcgccgagacagaacttaatgggcccgctaacagcgcgatttgctggtgacccaatgcgaccagatgctccacgcccagtc
gcgtaccgtcttcatgggagaaaataatactgttgatgggtgtctggtcagagacatcaagaaataacgccggaacattagtgca
ggcagcttccacagcaatggcatcctggtcatccagcggatagttaatgatcagcccactgacgcgttgcgcgagaagattgtg
caccgccgctttacaggcttcgacgccgcttcgttctaccatcgacaccaccacgctggcacccagttgatcggcgcgagattta
atcgccgcgacaatttgcgacggcgcgtgcagggccagactggaggtggcaacgccaatcagcaacgactgtttgcccgcca
gttgttgtgccacgcggttgggaatgtaattcagctccgccatcgccgcttccactttttcccgcgttttcgcagaaacgtggctgg
cctggttcaccacgcgggaaacggtctgataagagacaccggcatactctgcgacatcgtataacgttactggtttcacattcacc
accctgaattgactctcttccgggcgctatcatgccataccgcgaaaggttttgcgccattcgatggtgtccgggatctcgacgct
ctcccttatgcgactcctgcattaggaagcagcccagtagtaggttgaggccgttgagcaccgccgccgcaaggaatggtgcat
gcaaggagatggcgcccaacagtcccccggccacggggcctgccaccatacccacgccgaaacaagcgctcatgagcccg
aagtggcgagcccgatcttccccatcggtgatgtcggcgatataggcgccagcaaccgcacctgtggcgccggtgatgccgg
ccacgatgcgtccggcgtagaggatcgagatctcgatcccgcgaaattaatacgactcactataggggaattgtgagcggataa
caattcccctctagaaataattttgtttaactttaagaaggagatataccatgggccatcatcatcatcatcatcatcatcatcacagc
agcggccatatcgaaggtcgtcatatgtcattaccgttcttaacttctgcaccgggaaaggttattattttggtgaacactctgctgt
gtacaacaagcctgccgtcgctgctagtgtgtctgcgttgagaacctacctgctaataagcgagtcatctgcaccagatactattg
aattggacttcccggacattagctttaatcataagtggtccatcaatgatttcaatgccatcaccgaggatcaagtaaactcccaaa
aattggccaaggctcaacaagccaccgatggcttgtctcaggaactcgttagtcttttggatccgttgttagctcaactatccgaatc
cttccactaccatgcagcgttttgtttcctgtatatgtttgtttgcctatgcccccatgccaagaatattaagttttctttaaagtctacttta
cccatcggtgctgggttgggctcaagcgcctctatttctgtatcactggccttagctatggcctacttgggggggttaataggatcta
atgacttggaaaagctgtcagaaaacgataagcatatagtgaatcaatgggccttcataggtgaaaagtgtattcacggtacccct
tcaggaatagataacgctgtggccacttatggtaatgccctgctatttgaaaaagactcacataatggaacaataaacacaaacaa
ttttaagttcttagatgatttcccagccattccaatgatcctaacctatactagaattccaaggtctacaaaagatcttgttgctcgcgtt
cgtgtgttggtcaccgagaaatttcctgaagttatgaagccaattctagatgccatgggtgaatgtgccctacaaggcttagagatc
atgactaagttaagtaaatgtaaaggcaccgatgacgaggctgtagaaactaataatgaactgtatgaacaactattggaattgat
aagaataaatcatggactgcttgtctcaatcggtgtttctcatcctggattagaacttattaaaaatctgagcgatgatttgagaattgg
ctccacaaaacttaccggtgctggtggcggcggttgctctttgactttgttacgaagagacattactcaagagcaaattgacagctt
caaaaagaaattgcaagatgattttagttacgagacatttgaaacagacttgggtgggactggctgctgtttgttaagcgcaaaaa
atttgaataaagatcttaaaatcaaatccctagtattccaattatttgaaaataaaactaccacaaagcaacaaattgacgatctattat
tgccaggaaacacgaatttaccatggacttcataagctaatttgcgataggccatatgctcgaggatccggctgctaacaaagcc
cgaaaggaagctgagttggctgctgccaccgctgagcaataactagcataaccccttggggcctctaaacgggtcttgaggggt
tttttgctgaaaggaggaactatatccggatatcccgcaagaggcccggcagtaccggcataaccaagcctatgcctacagcat
ccagggtgacggtgccgaggatgacgatgagcgcattgttagatttcatacacggtgcctgactgcgttagcaatttaactgtgat
aaactaccgcattaaagcttatcgatgataagctgtcaaacatgagaa
(SEQ ID NO:108)

A

B

Figure 143A sequence of pDW02 – S. pneumoniae MVK in pET200D aagggcgagctcaacgatccggctgctaacaaagcccgaaaggaagctgagttggctgctgccaccgctgagcaataactagcataacc
ccttggggcctctaaacgggtcttgaggagttttttgctgaaaggaggaactatatccggatatcccgcaagaggcccggcagtaccggcat
aaccaagcctatgcctacagcatccagggtgacggtgccgaggatgacgatgagcgcattgttagatttcatacacggtgcctgactgcgtt
agcaatttaactgtgataaactaccgcattaaagcttatcgatgataagctgtcaaacatgagaattaattcttgaagacgaaagggcctcgtg
atacgcctatttttataggttaatgtcatgataataatggtttcttagacgtcaggtggcacttttcggggaaatgtgcgcggaacccctatttgttt
atttttctaaatacattcaaatatgtatccgctcatgagacaataaccctgataaatgcttcaataatattgaaaaaggaagagtatgattgaaca
agatggattgcacgcaggttctccggccgcttgggtggagaggctattcggctatgactgggcacaactgacaatcggctgctctgatgcc
gccgtgttccggctgtcagcgcaggggcgcccggttctttttgtcaagaccgacctgtccggtgccctgaatgaactgcaggacgaggcag
cgcggctatcgtggctggccacgacgggcgttccttgcgcagctgtgctcgacgttgtcactgaagcgggaagggactggctgctattggg
cgaagtgccggggcaggatctcctgtcatctcaccttgctcctgccgagaaagtatccatcatggctgatgcaatgcggcggctgcatacgc
ttgatccggctacctgcccattcgaccaccaagcgaaacatcgcatcgagcgggcacgtactcggatggaagccggtcttgtcgatcagg
atgatctggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtgtggcgg
accgctatcaggacatagcgttggctacccgtgatattgctgaagagcttggcggcgaatgggctgaccgcttcctcgtgctttacggtatcg
ccgctcccgattcgcagcgcatcgccttctatcgccttcttgacgagttcttctgagcgggactctggggttcgaaatgaccgaccaagcgac
gcctaactgtcagaccaagtttactcatatatactttagattgatttaaaacttcatttttaatttaaaaggatctaggtgaagatcctttttgataatct
catgaccaaaatcccttaacgtgagttttcgttccactgagcgtcagaccccgtagaaaagatcaaaggatcttcttgagatcctttttttctgcg
cgtaatctgctgcttgcaaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgtagcaccgcctacatac
ctcgctctgctaatcctgttaccagtggctgctgccagtggcgataagtcgtgtcttaccgggttggactcaagacgatagttaccggataag
gcgcagcggtcgggctgaacggggggttcgtgcacacagcccagcttggagcgaacgacctacaccgaactgagatacctacagcgtg
agctatgagaaagcgccacgcttcccgaagggagaaaggcggacaggtatccggtaagcggcagggtcggaacaggagagcgcacg
agggagcttccagggggaaacgcctggtatctttatagtcctgtcgggtttcgccacctctgacttgagcgtcgatttttgtgatgctcgtcagg
ggggcggagcctatggaaaaacgccagcaacgcggcctttttacggttcctggccttttgctggccttttgctcacatgttctttcctgcgttatc
ccctgattctgtggataaccgtattaccgcctttgagtgagctgataccgctcgccgcagccgaacgaccgagcgcagcgagtcagtgagc
gaggaagcggaagagcgcctgatgcggtattttctccttacgcatctgtgcggtatttcacaccgcaatggtgcactctcagtacaatctgctc
tgatgccgcatagttaagccagtatacactccgctatcgctacgtgactgggtcatggctgcgccccgacacccgccaacacccgctgacg
cgccctgacgggcttgtctgctcccggcatccgcttacagacaagctgtgaccgtctccgggagctgcatgtgtcagaggttttcaccgtcat
caccgaaacgcgcgaggcagctgcggtaaagctcatcagcgtggtcgtgaagcgattcacagatgtctgcctgttcatccgcgtccagctc
gttgagtttctccagaagcgttaatgtctggcttctgataaagcgggccatgttaagggcggttttttcctgtttggtcactgatgcctccgtgtaa
gggggatttctgttcatgggggtaatgataccgatgaaacgagagaggatgctcacgatacgggttactgatgatgaacatgcccggttact
ggaacgttgtgagggtaaacaactggcggtatggatgcggcgggaccagagaaaaatcactcagggtcaatgccagcgcttcgttaatac
agatgtaggtgttccacagggtagccagcagcatcctgcgatgcagatccggaacataatggtgcagggcgctgacttccgcgtttccaga
ctttacgaaacacggaaaccgaagaccattcatgttgttgctcaggtcgcagacgttttgcagcagcagtcgcttcacgttcgctcgcgtatc
ggtgattcattctgctaaccagtaaggcaaccccgccagcctagccgggtcctcaacgacaggagcacgatcatgcgcacccgtggcca
ggacccaacgctgcccgagatgcgccgcgtgcggctgctggagatggcggacgcgatggatatgttctgccaagggttggtttgcgcatt
cacagttctccgcaagaattgattggctccaattcttggagtggtgaatccgttagcgaggtgccgccggcttccattcaggtcgaggtggcc
cggctccatgcaccgcgacgcaacgcggggaggcagacaaggtatagggcggcgcctacaatccatgccaacccgttccatgtgctcg
ccgaggcggcataaatcgccgtgacgatcagcggtccaatgatcgaagttaggctggtaagagccgcgagcgatccttgaagctgtccct
gatggtcgtcatctacctgcctggacagcatggcctgcaacgcgggcatcccgatgccgccggaagcgagaagaatcataatggggaag
gccatccagcctcgcgtcgcgaacgccagcaagacgtagcccagcgcgtcggccgccatgccggcgataatggcctgcttctcgccga
aacgtttggtggcgggaccagtgacgaaggcttgagcgagggcgtgcaagattccgaataccgcaagcgacaggccgatcatcgtcgcg
ctccagcgaaagcggtcctcgccgaaaatgacccagagcgctgccggcacctgtcctacgagttgcatgataaagaagacagtcataagt
gcggcgacgatagtcatgccccgcgcccaccggaaggagctgactgggttgaaggctctcaagggcatcggtcgagatcccggtgcct

Figure 143B aatgagtgagctaacttacattaattgcgttgcgctcactgcccgctttccagtcgggaaacctgtcgtgccagctgcattaatgaatcgg
ccaacgcgcggggagaggcggtttgcgtattgggcgccagggtggtttttcttttcaccagtgagacgggcaacagctgattgcccttc
accgcctggccctgagagagttgcagcaagcggtccacgctggtttgccccagcaggcgaaaatcctgtttgatggtggttaacggcg
ggatataacatgagctgtcttcggtatcgtcgtatcccactaccgagatatccgcaccaacgcgcagcccggactcggtaatggcgcgc
attgcgcccagcgccatctgatcgttggcaaccagcatcgcagtgggaacgatgccctcattcagcatttgcatggtttgttgaaaaccg
gacatggcactccagtcgccttcccgttccgctatcggctgaatttgattgcgagtgagatatttatgccagccagccagacgcagacgc
gccgagacagaacttaatgggcccgctaacagcgcgatttgctggtgacccaatgcgaccagatgctccacgcccagtcgcgtaccg
tcttcatgggagaaaataatactgttgatgggtgtctggtcagagacatcaagaaataacgccggaacattagtgcaggcagcttccaca
gcaatggcatcctggtcatccagcggatagttaatgatcagcccactgacgcgttgcgcgagaagattgtgcaccgccgctttacaggc
ttcgacgccgcttcgttctaccatcgacaccaccacgctggcacccagttgatcggcgcgagatttaatcgccgcgacaatttgcgacg
gcgcgtgcagggccagactggaggtggcaacgccaatcagcaacgactgtttgcccgccagttgttgtgccacgcggttgggaatgt
aattcagctccgccatcgccgcttccactttttcccgcgttttcgcagaaacgtggctggcctggttcaccacgcgggaaacggtctgata
agagacaccggcatactctgcgacatcgtataacgttactggtttcacattcaccaccctgaattgactctcttccgggcgctatcatgcca
taccgcgaaaggttttgcgccattcgatggtgtccgggatctcgacgctctcccttatgcgactcctgcattaggaagcagcccagtagt
aggttgaggccgttgagcaccgccgccgcaaggaatggtgcatgcaaggagatggcgcccaacagtcccccggccacggggcctg
ccaccatacccacgccgaaacaagcgctcatgagcccgaagtggcgagcccgatcttccccatcggtgatgtcggcgatataggcgc
cagcaaccgcacctgtggcgccggtgatgccggccacgatgcgtccggcgtagaggatcgagatctcgatcccgcgaaattaatacg
actcactataggggaattgtgagcggataacaattcccctctagaaataattttgtttaactttaagaaggagatatacatatgcggggttct
catcatcatcatcatcatggtatggctagcatgactggtggacagcaaatgggtcgggatctgtacgacgatgacgataaggatcatccc
ttcaccatgacaaaaaaagttggtgtcggtcaggcacatagtaagataattttaataggggaacatgcggtcgtttacggttatcctgccat
ttccctgcctcttttggaagtggaggtgacctgtaaggtagttcctgcagagagtccttggcgcctttatgaggaggataccttgtccatgg
cggtttatgcctcactggagtatttgaatatcacagaagcctgcattcgttgtgagattgactcggctatccctgagaaacgggggatggg
ttcgtcagcggctatcagcatagcggccattcgtgcggtatttgactactatcaggctgatctgcctcatgatgtactagaaatcttggtcaa
tcgagctgaaatgattgcccatatgaatcctagtggtttggatgctaagacctgtctcagtgaccaacctattcgctttatcaagaacgtag
gatttacagaacttgagatggatttatccgcctatttggtgattgccgatacgggtgtttatggtcatactcgtgaagccatccaagtggttca
aaataagggcaaggatgccctaccgtttttgcatgccttgggagaattaacccagcaggcagaaattgcgatttcacaaaaagatgctg
aagggctgggacaaatcctcagtcaagcacatttacatttaaaagaaattggtgtcagtagccttgaggcagactctttggttgaaacagc
tcttagtcatggtgctctgggtgccaagatgagcggtggtgggctaggaggttgtatcatagccttggtaaccaatttgacacacgcaca
agaactagcagaaagattagaagagaaaggagctgttcagacatggatagagagcctgtgacag

INCREASED ISOPRENE PRODUCTION USING THE ARCHAEAL LOWER MEVALONATE PATHWAY

CROSS-REFERENCE TO RELATED APPLICATIONS

This application is a divisional patent application of U.S. patent application Ser. No. 12/560,390, now U.S. Pat. No. 8,361,762, filed on Sep. 15, 2009, which claims benefit of U.S. Provisional Patent Application No. 61/097,186, filed on Sep. 15, 2008, and U.S. Provisional Patent Application 61/187,876, filed on Jun. 17, 2009, the contents of which are hereby incorporated by reference in its entirety.

BACKGROUND OF THE INVENTION

Isoprene (2-methyl-1,3-butadiene) is the critical starting material for a variety of synthetic polymers, most notably synthetic rubbers. Isoprene is naturally produced by a variety of microbial, plant, and animal species. In particular, two pathways have been identified for the biosynthesis of isoprene: the mevalonate (MVA) pathway and the non-mevalonate (DXP) pathway (FIGS. 19A and 19B). However, the yield of isoprene from naturally-occurring organisms is commercially unattractive. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex.

Currently, the tire and rubber industry is based on the use of natural and synthetic rubber. Natural rubber is obtained from the milky juice of rubber trees or plants found in the rainforests of Africa. Synthetic rubber is based primarily on butadiene polymers. For these polymers, butadiene is obtained as a co-product from ethylene and propylene manufacture.

While isoprene can be obtained by fractionating petroleum, the purification of this material is expensive and time-consuming. Petroleum cracking of the C5 stream of hydrocarbons produces only about 15% isoprene. Thus, more economical methods for producing isoprene are needed. In particular, methods that produce isoprene at rates, titers, and purity that are sufficient to meet the demands of a robust commercial process are desirable. Also desired are systems for producing isoprene from inexpensive starting materials.

The invention provided herein fulfills these needs and provides additional benefits as well.

BRIEF SUMMARY OF THE INVENTION

The invention provides for, inter alia, compositions and methods for increasing the production of isoprene by using feedback-resistant mevalonate kinase, such as those found in archaeal organisms. In some embodiments, the invention provides for cells comprising (i) one or more non-modified nucleic acids encoding feedback-resistant mevalonate kinase polypeptides or (ii) one or more additional copies of an endogenous nucleic acid encoding a feedback-resistant mevalonate kinase polypeptide. In some embodiments, the feedback-resistant archaeal mevalonate kinase polypeptide is *M. mazei* mevalonate kinase. In some embodiments, the cells in culture comprise (i) a heterologous nucleic acid encoding a feedback-resistant mevalonate kinase polypeptide (e.g., a *Methanosarcina mazei* mevalonate kinase polypeptide or a homolog thereof) and/or (ii) a duplicate copy of an endogenous nucleic acid encoding a feedback-resistant mevalonate kinase polypeptide (e.g., a *Methanosarcina mazei* mevalonate kinase polypeptide or a homolog thereof). In some embodiments, the mevalonate kinase nucleic acid is operably linked to a promoter. In some embodiments, the feedback-resistant mevalonate kinase polypeptide is an archaeal mevalonate kinase polypeptide (e.g., a *Methanosarcina mazei* mevalonate kinase polypeptide). In some embodiments, concentrations of geranyl diphosphate (GPP) or farnesyl diphosphate (FPP) that are equal to or less than about any of 20, 30, 40, 50, 60, 70, 80, 90, or 100 μM do not substantially inhibit (e.g., inhibit by less than about any of 10, 8, 6, 4, 3, 2, 1%) the ability of the feedback-resistant mevalonate kinase polypeptide to bind ATP, bind mevalonate, or convert mevalonate to mevalonate-5-phosphate. In some embodiments, concentrations of 3,3-dimethylallyl diphosphate (DMAPP) that are equal to or less than about any of 20, 30, 40, 50, 60, 70, 80, 90, 100, 250, 500, 750, 1000, 2000, 3000, 4000, or 5000 μM do not substantially inhibit (e.g., inhibit by less than about any of 10, 8, 6, 4, 3, 2, 1%) the ability of the feedback-resistant mevalonate kinase polypeptide to bind ATP, bind mevalonate, or convert mevalonate to mevalonate-5-phosphate. In some embodiments, the cells express (i) a heterologous nucleic acid encoding a second mevalonate kinase polypeptide or (ii) a duplicate copy of a nucleic acid encoding a second mevalonate kinase polypeptide (such as a feedback-resistant or feedback-inhibited mevalonate kinase polypeptide). In some embodiments, the second mevalonate kinase polypeptide is a *Lactobacillus* mevalonate kinase polypeptide (e.g., a *Lactobacillus sakei* mevalonate kinase polypeptide), a yeast mevalonate kinase polypeptide (e.g., a *Saccharomyces cerevisia* mevalonate kinase polypeptide), a *Streptococcus* mevalonate kinase polypeptide (e.g., a *Streptococcus pneumoniae* mevalonate kinase polypeptide), or a *Streptomyces* mevalonate kinase polypeptide (e.g., a *Streptomyces* CL190 mevalonate kinase polypeptide). In some embodiments, the cells further comprise a heterologous nucleic acid or a duplicate copy of an endogenous nucleic acid encoding an isoprene synthase polypeptide. In some embodiments, the cells further comprise one or more heterologous nucleic acids or one or more additional copies of an endogenous nucleic acid encoding an isoprene synthase polypeptide. In some embodiments, the heterologous nucleic acid encodes for an MVA pathway enzyme or a DXP pathway enzyme. In some embodiments, the MVA pathway enzyme is mevalonate kinase. In some embodiments, the cells have a heterologous nucleic acid that (i) encodes an isoprene synthase polypeptide and (ii) is operably linked to a promoter. In some embodiments, the cells in culture produce greater than about 400 nmole/$g_{wcm}$/hr of isoprene. In some embodiments, the cells in culture convert more than about 0.002% of the carbon in a cell culture medium into isoprene.

In some embodiments of any of the cells, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions.

In another aspect, the invention provides for one or more compositions for producing isoprene comprising any of the cells described herein.

In one aspect, the invention features methods of producing isoprene, such as methods of using any of the cells described herein to produce isoprene. In some embodiments, the method involves culturing cells comprising (i) one or more non-modified nucleic acids encoding feedback-resistant mevalonate kinase polypeptides or (ii) one or more additional copies of an endogenous nucleic acid encoding a feedback-resistant mevalonate kinase polypeptide. In another embodiment, the method further comprises recovering the isoprene. In some embodiments, the method involves culturing cells comprising (i) a heterologous nucleic acid encoding a feedback-resistant mevalonate kinase polypeptide (e.g., a *Methanosarcina mazei* mevalonate kinase polypeptide or a homolog thereof) or (ii) a duplicate copy of an endogenous nucleic acid encoding a feedback-resistant mevalonate kinase polypeptide (e.g., a *Methanosarcina mazei* mevalonate kinase polypeptide or a homolog thereof). In some embodiments, the cells are cultured under suitable culture conditions for the production of isoprene, and isoprene is produced. In some embodiments, the mevalonate kinase nucleic acid is operably linked to a promoter. In some embodiments, the feedback-resistant mevalonate kinase polypeptide is an archaeal mevalonate kinase polypeptide (e.g., a *Methanosarcina mazei* mevalonate kinase polypeptide). In some embodiments, concentrations of geranyl diphosphate (GPP) or farnesyl diphosphate (FPP) that are equal to or less than about any of 20, 30, 40, 50, 60, 70, 80, 90, or 100 μM do not substantially inhibit (e.g., inhibit by less than about any of 10, 8, 6, 4, 3, 2, 1%) the ability of the feedback-resistant mevalonate kinase polypeptide to bind ATP, bind mevalonate, or convert mevalonate to mevalonate-5-phosphate. In some embodiments, concentrations of 3,3-dimethylallyl diphosphate (DMAPP) that are equal to or less than about any of 20, 30, 40, 50, 60, 70, 80, 90, 100, 250, 500, 750, 1000, 2000, 3000, 4000, or 5000 μM do not substantially inhibit (e.g., inhibit by less than about any of 10, 8, 6, 4, 3, 2, 1%) the ability of the feedback-resistant mevalonate kinase polypeptide to bind ATP, bind mevalonate, or convert mevalonate to mevalonate-5-phosphate.

The invention also provides for methods of increasing the rate or flux of production of 3,3-dimethylallyl diphosphate (DMAPP), isopentenyl diphosphate (IPP), or a product derived from 3,3-dimethylallyl diphosphate (DMAPP) or isopentenyl diphosphate (IPP) comprising: (a) culturing cells of claim 1 wherein the cells are cultured under suitable culture conditions for increasing the rate or flux of production of 3,3-dimethylallyl diphosphate (DMAPP), isopentenyl diphosphate (IPP), or a product derived from 3,3-dimethylallyl diphosphate (DMAPP) or isopentenyl diphosphate (IPP), and (b) producing 3,3-dimethylallyl diphosphate (DMAPP), isopentenyl diphosphate (IPP), or a product derived from 3,3-dimethylallyl diphosphate (DMAPP) or isopentenyl diphosphate (IPP). In one embodiment, the product derived from 3,3-dimethylallyl diphosphate (DMAPP) or isopentenyl diphosphate (IPP) is isoprene.

The invention also provides for methods of producing or increasing the production of 3,3-dimethylallyl diphosphate (DMAPP), isopentenyl diphosphate (IPP), or a product derived from 3,3-dimethylallyl diphosphate (DMAPP) or isopentenyl diphosphate (IPP) by (a) culturing cells comprising (i) a heterologous nucleic acid encoding a feedback-resistant archaeal mevalonate kinase polypeptide or (ii) a duplicate copy of an endogenous nucleic acid encoding a feedback-resistant archaeal mevalonate kinase polypeptide, wherein the cells are cultured under suitable culture conditions for the production of 3,3-dimethylallyl diphosphate (DMAPP), isopentenyl diphosphate (IPP), or a product derived from 3,3-dimethylallyl diphosphate (DMAPP) or isopentenyl diphosphate (IPP), and (b) producing 3,3-dimethylallyl diphosphate (DMAPP), isopentenyl diphosphate (IPP), or a product derived from 3,3-dimethylallyl diphosphate (DMAPP) or isopentenyl diphosphate (IPP). In some embodiments, the product derived from 3,3-dimethylallyl diphosphate (DMAPP) or isopentenyl diphosphate (IPP) is isoprene. In another embodiment, the feedback-resistant archaeal mevalonate kinase polypeptide is *M. Mazei* mevalonate kinase.

In some embodiments, the cells express (i) a heterologous nucleic acid encoding a second mevalonate kinase polypeptide or (ii) a duplicate copy of a nucleic acid encoding a second mevalonate kinase polypeptide (such as a feedback-resistant or feedback-inhibited mevalonate kinase polypeptide). In some embodiments, the second mevalonate kinase polypeptide is a *Lactobacillus* mevalonate kinase polypeptide (e.g., a *Lactobacillus sakei* mevalonate kinase polypeptide), a yeast mevalonate kinase polypeptide (e.g., a *Saccharomyces cerevisiae* mevalonate kinase polypeptide), a *Streptococcus* mevalonate kinase polypeptide (e.g., a *Streptococcus pneumoniae* mevalonate kinase polypeptide), or a *Streptomyces* mevalonate kinase polypeptide (e.g., a *Streptomyces* CL190 mevalonate kinase polypeptide). In some embodiments, the cells further comprise a heterologous nucleic acid or a duplicate copy of an endogenous nucleic acid encoding an isoprene synthase polypeptide. In some embodiments, the cells have a heterologous nucleic acid that (i) encodes an isoprene synthase polypeptide and (ii) is operably linked to a promoter. In some embodiments, the method involves culturing cells under conditions sufficient to produce greater than about 400 nmole/$g_{wcm}$/hr of isoprene. In some embodiments, the method includes culturing cells under conditions sufficient to convert more than about 0.002% of the carbon (mol/mol) in a cell culture medium into isoprene.

In some embodiments of the methods, the method also includes recovering isoprene produced by the cells. In some embodiments, the method includes purifying isoprene produced by the cells. In some embodiments, the method includes polymerizing the isoprene. In some embodiments, the cells are cultured in a culture medium that includes a carbon source, such as, but not limited to, a carbohydrate, glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, polypeptide (e.g., a microbial or plant protein or peptide), yeast extract, component from a yeast extract, or any combination of two or more of the foregoing. In some embodiments, the cells are cultured under limited glucose conditions. In various embodiments, the amount of isoprene produced (such as the total amount of isoprene produced or the amount of isoprene produced per liter of broth per hour per $OD_{600}$) during stationary phase is greater than or about 2 or more times the amount of isoprene produced during the growth phase for the same length of time. In some embodiments, the gas phase comprises greater than or about 9.5% (volume) oxygen, and the concentration of isoprene in the gas phase is less than the lower flammability limit or greater than the upper flammability limit. In particular embodiments, (i) the concentration of isoprene in the gas phase is less than the lower flammability limit or greater than the upper flammability limit, and (ii) the cells produce greater than about 400 nmole/$g_{wcm}$/hr of isoprene.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time.

In some embodiments, at least a portion of the isoprene is in a gas phase. In some embodiments, at least a portion of the isoprene is in a liquid phase (such as a condensate). In some embodiments, at least a portion of the isoprene is in a solid phase. In some embodiments, at least a portion of the isoprene is adsorbed to a solid support, such as a support that includes silica and/or activated carbon. In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments, the composition includes between about 4 to about 15% by weight of isoprene, such as between about 4 to about 8%, about 8 to about 12%, or about 12 to about 15% by weight of isoprene.

In some embodiments, the invention also features systems that include any of the cells and/or compositions described herein. In some embodiments, the system includes a reactor that chamber comprises cells in culture that produce greater than about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments, the system is not a closed system. In some embodiments, at least a portion of the isoprene is removed from the system. In some embodiments, the system includes a gas phase comprising isoprene. In various embodiments, the gas phase comprises any of the compositions described herein.

In one aspect, the invention provides a tire comprising polyisoprene. In some embodiments, the polyisoprene is produced by (i) polymerizing isoprene in any of the compositions described herein or (ii) polymerizing isoprene recovered from any of the compositions described herein. In some embodiments, the polyisoprene comprises cis-1,4-polyisoprene. In another aspect, the invention provides methods of manufacturing a tire wherein the improvement comprises using any one or more the compositions, cells, systems and/or methods described herein to produce isoprene for the manufacture of the tire.

In some embodiments of any of the compositions, systems, and methods of the invention, a nonflammable concentration of isoprene in the gas phase is produced. In some embodiments, the gas phase comprises less than about 9.5% (volume) oxygen. In some embodiments, the gas phase comprises greater than or about 9.5% (volume) oxygen, and the concentration of isoprene in the gas phase is less than the lower flammability limit or greater than the upper flammability limit. In some embodiments, the portion of the gas phase other than isoprene comprises between about 0% to about 100% (volume) oxygen, such as between about 10% to about 100% (volume) oxygen. In some embodiments, the portion of the gas phase other than isoprene comprises between about 0% to about 99% (volume) nitrogen. In some embodiments, the portion of the gas phase other than isoprene comprises between about 1% to about 50% (volume) $CO_2$.

In some embodiments of any of the aspects of the invention, the cells in culture produce isoprene at greater than or about 400, 500, 600, 700, 800, 900, 1,000, 1,250, 1,500, 1,750, 2,000, 2,500, 3,000, 4,000, 5,000, or more nmole/$g_{wcm}$/hr isoprene. In some embodiments of any of the aspects of the invention, the cells in culture convert greater than or about 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6%, or more of the carbon in the cell culture medium into isoprene. In some embodiments of any of the aspects of the invention, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments of any of the aspects of the invention, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). Other exemplary rates of isoprene production and total amounts of isoprene production are disclosed herein.

In some embodiments of any of the aspects of the invention, the cells further comprise a heterologous nucleic acid encoding an IDI polypeptide. In some embodiments of any of the aspects of the invention, the cells further comprise an insertion of a copy of an endogenous nucleic acid encoding an IDI polypeptide. In some embodiments of any of the aspects of the invention, the cells further comprise a heterologous nucleic acid encoding a DXS polypeptide. In some embodiments of any of the aspects of the invention, the cells further comprise an insertion of a copy of an endogenous nucleic acid encoding a 1-Deoxyxylulose-5-phosphate synthase (DXS) polypeptide. In some embodiments of any of the aspects of the invention, the cells further comprise one or more nucleic acids encoding an IDI (Isopentenyl-diphosphate delta-isomerase) polypeptide and a DXS polypeptide. In some embodiments of any of the aspects of the invention, one nucleic acid encodes the isoprene synthase polypeptide, IDI polypeptide, and DXS polypeptide. In some embodiments of any of the aspects of the invention, one vector encodes the isoprene synthase polypeptide, IDI polypeptide, and DXS polypeptide. In some embodiments, the vector comprises a selective marker, such as an antibiotic resistance nucleic acid.

In some embodiments of any of the aspects of the invention, the cells express a second MVA pathway polypeptide (other than the mevalonate kinase polypeptide). In some embodiments, the second MVA pathway polypeptide is an acetyl-CoA acetyltransferase polypeptide, 3-hydroxy-3-methylglutaryl-CoA synthase polypeptide, 3-hydroxy-3-methylglutaryl-CoA reductase polypeptide, phosphomevalonate kinase polypeptide, diphosphomevalonate decarboxylase polypeptide, or isopentenyl-diphosphate delta-isomerase polypeptide. In some embodiments, the cells express an entire MVA pathway.

In some embodiments of any of the aspects of the invention, the cells comprise a heterologous nucleic acid encoding an MVA pathway polypeptide (such as an MVA pathway polypeptide from *Saccharomyces cerevisia* or *Enterococcus faecalis*). In some embodiments of any of the aspects of the invention, the cells further comprise an insertion of a copy of an endogenous nucleic acid encoding an MVA pathway polypeptide (such as an MVA pathway polypeptide from *Saccharomyces cerevisia* or *Enterococcus faecalis*). In some embodiments of any of the aspects of the invention, the cells comprise an isoprene synthase, DXS, and MVA pathway nucleic acid. In some embodiments of any of the aspects of the invention, the cells comprise an isoprene synthase nucleic acid, a DXS nucleic acid, an IDI nucleic acid, and a MVA pathway nucleic (in addition to the IDI nucleic acid).

In some embodiments of any of the aspects of the invention, the isoprene synthase polypeptide is a polypeptide from a plant such as *Pueraria* (e.g., *Pueraria montana* or *Pueraria lobata*) or *Populus* (e.g., *Populus tremuloides, Populus alba, Populus nigra, Populus trichocarpa*, or the hybrid, *Populus alba* x *Populus tremula*).

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

In some embodiments of any of the aspects of the invention, the cells are bacterial cells, such as gram-positive bacterial cells (e.g., *Bacillus* cells such as *Bacillus subtilis* cells or *Streptomyces* cells such as *Streptomyces lividans, Streptomyces coelicolor*, or *Streptomyces griseus* cells). In some embodiments of any of the aspects of the invention, the cells are gram-negative bacterial cells (e.g., *Escherichia* cells such as *Escherichia coli* cells or *Pantoea* cells such as *Pantoea citrea* cells). In some embodiments of any of the aspects of the invention, the cells are fungal, cells such as filamentous fungal cells (e.g., *Trichoderma* cells such as *Trichoderma reesei* cells or *Aspergillus* cells such as *Aspergillus oryzae* and *Aspergillus niger*) or yeast cells (e.g., *Yarrowia* cells such as *Yarrowia lipolytica* cells).

In some embodiments of any of the aspects of the invention, the microbial polypeptide carbon source includes one or more polypeptides from yeast or bacteria. In some embodiments of any of the aspects of the invention, the plant polypeptide carbon source includes one or more polypeptides from soy, corn, canola, jatropha, palm, peanut, sunflower, coconut, mustard, rapeseed, cottonseed, palm kernel, olive, safflower, sesame, or linseed.

In one aspect, the invention features a product produced by any of the compositions or methods of the invention. It is to be understood that one, some, or all of the properties of the various embodiments described herein may be combined to form other embodiments of the present invention.

All publications, patents and patent applications referenced in this specification are incorporated by reference in their entirety.

BRIEF DESCRIPTION OF THE DRAWINGS

FIG. 1 is the nucleotide sequence of a kudzu isoprene synthase gene codon-optimized for expression in *E. coli* (SEQ ID NO:1). The atg start codon is in italics, the stop codon is in bold and the added PstI site is underlined.

FIGS. 3A-3C are the nucleotide sequence of pTrcKudzu (SEQ ID NO:2). The RBS is underlined, the kudzu isoprene synthase start codon is in bold capitol letters and the stop codon is in bold, capitol, italics letters. The vector backbone is pTrcHis2B.

FIGS. 5A-5C are the nucleotide sequence of pETNHisKudzu (SEQ ID NO:5).

FIGS. 7A-7C are the nucleotide sequence of pCL-lac-Kudzu (SEQ ID NO:7).

FIG. 9A is a graph showing OD over time of fermentation of *E. coli* BL21/pTrcKudzu in a 14 liter fed batch fermentation.

FIG. 9B is a graph showing isoprene production over time of fermentation of *E. coli* BL21/pTrcKudzu in a 14 liter fed batch fermentation.

FIGS. 12A-12C are the nucleotide sequence of pBS Kudzu #2 (SEQ ID NO:57).

FIG. 13 is the nucleotide sequence of kudzu isoprene synthase codon-optimized for expression in *Yarrowia* (SEQ ID NO:8).

FIGS. 15A-15C are the nucleotide sequence of vector pSPZ1(MAP29Spb) (SEQ ID NO:11).

FIG. 16 is the nucleotide sequence of the synthetic kudzu (*Pueraria montana*) isoprene gene codon-optimized for expression in *Yarrowia* (SEQ ID NO:12).

FIG. 17 is the nucleotide sequence of the synthetic hybrid poplar (*Populus alba* x *Populus tremula*) isoprene synthase gene (SEQ ID NO:13). The ATG start codon is in bold and the stop codon is underlined.

Assay: J. Bacteriol., 184: 2116-2122, 2002; MVK or MK; Mevalonate kinase, ERG12, EC 2.7.1.36. Assay: Curr Genet 19:9-14, 1991. PMK; Phosphomevalonate kinase, ERGS, EC 2.7.4.2, Assay: Mol Cell Biol., 11:620-631, 1991; DPMDC; Diphosphomevalonate decarboxylase, MVD1, EC 4.1.1.33. Assay: Biochemistry, 33:13355-13362, 1994; IDI; Isopentenyl-diphosphate delta-isomerase, IDI1, EC 5.3.3.2. Assay: J. Biol. Chem. 264:19169-19175, 1989. DXP Pathway: DXS; 1-Deoxyxylulose-5-phosphate synthase, dxs, EC 2.2.1.7. Assay: PNAS, 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay: PNAS, 97: 6451-6456, 2000; CMK; 4-Diphosphocytidyl-2-C-methyl-D-erythritol kinase, IspE, EC 2.7.1.148. Assay: PNAS, 97:1062-1067, 2000; MCS; 2C-Methyl-D-erythritol 2,4-cyclodiphosphate synthase, IspF, EC 4.6.1.12. Assay: PNAS, 96:11758-11763, 1999; HDS; 1-Hydroxy-2-methyl-2-(E)-butenyl 4-diphosphate synthase, ispG, EC 1.17.4.3. Assay: J. Org. Chem., 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

Figure 19A:
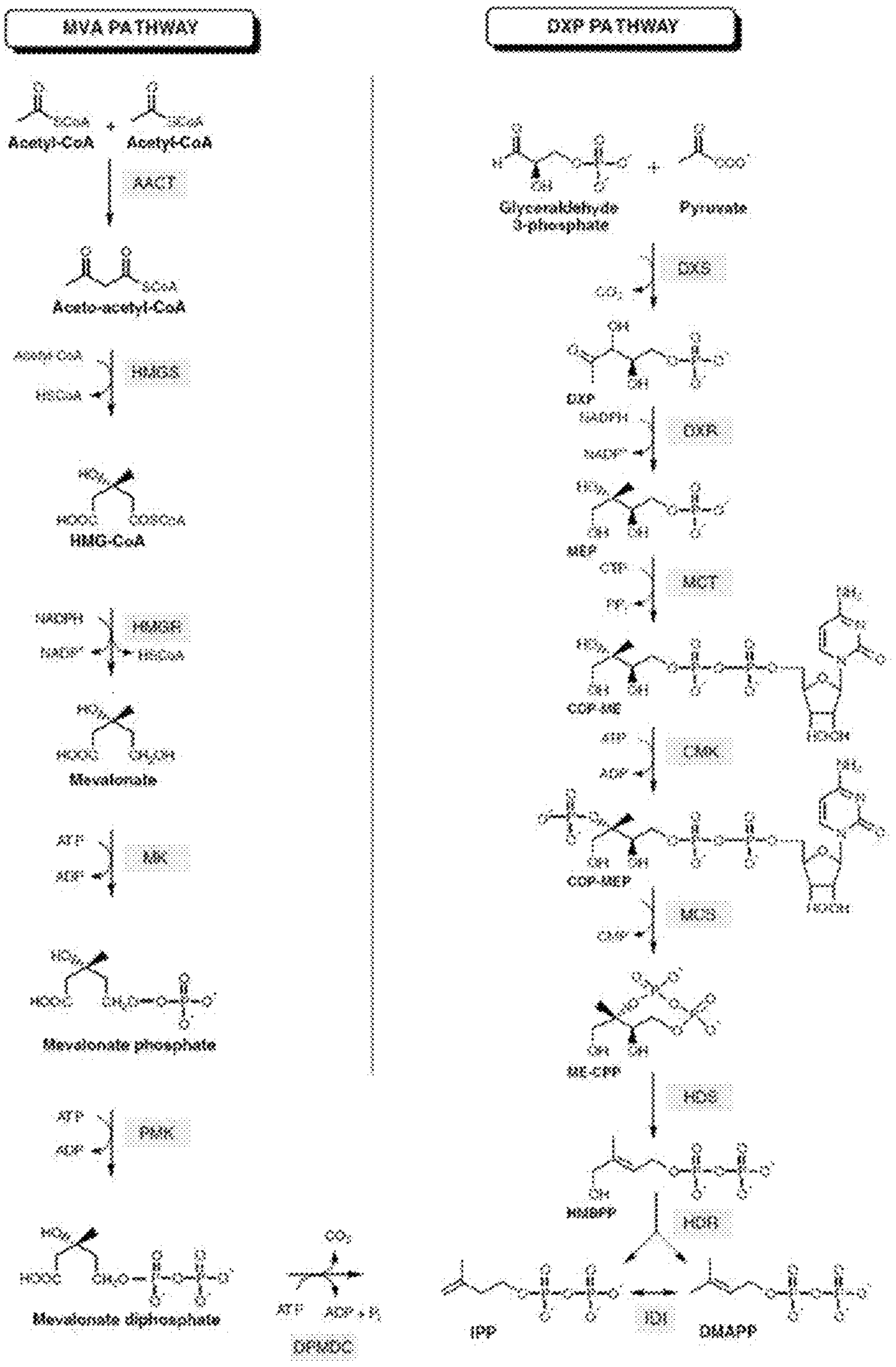
FIG. 19A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide (each of these references are each hereby incorporated by reference in their entireties, particularly with respect to assays for polypeptide activity for polypeptides in the MVA and DXP pathways). Mevalonate Pathway: AACT; Acetyl-CoA acetyltransferase, MvaE, EC 2.3.1.9. Assay: J. Bacteriol., 184: 2116-2122, 2002; HMGS; Hydroxymethylglutaryl-CoA synthase, MvaS, EC 2.3.3.10. Assay: J. Bacteriol., 184: 4065-4070, 2002; HMGR; 3-Hydroxy-3-methylglutaryl-CoA reductase, MvaE, EC 1.1.1.34.
Figure 19B:
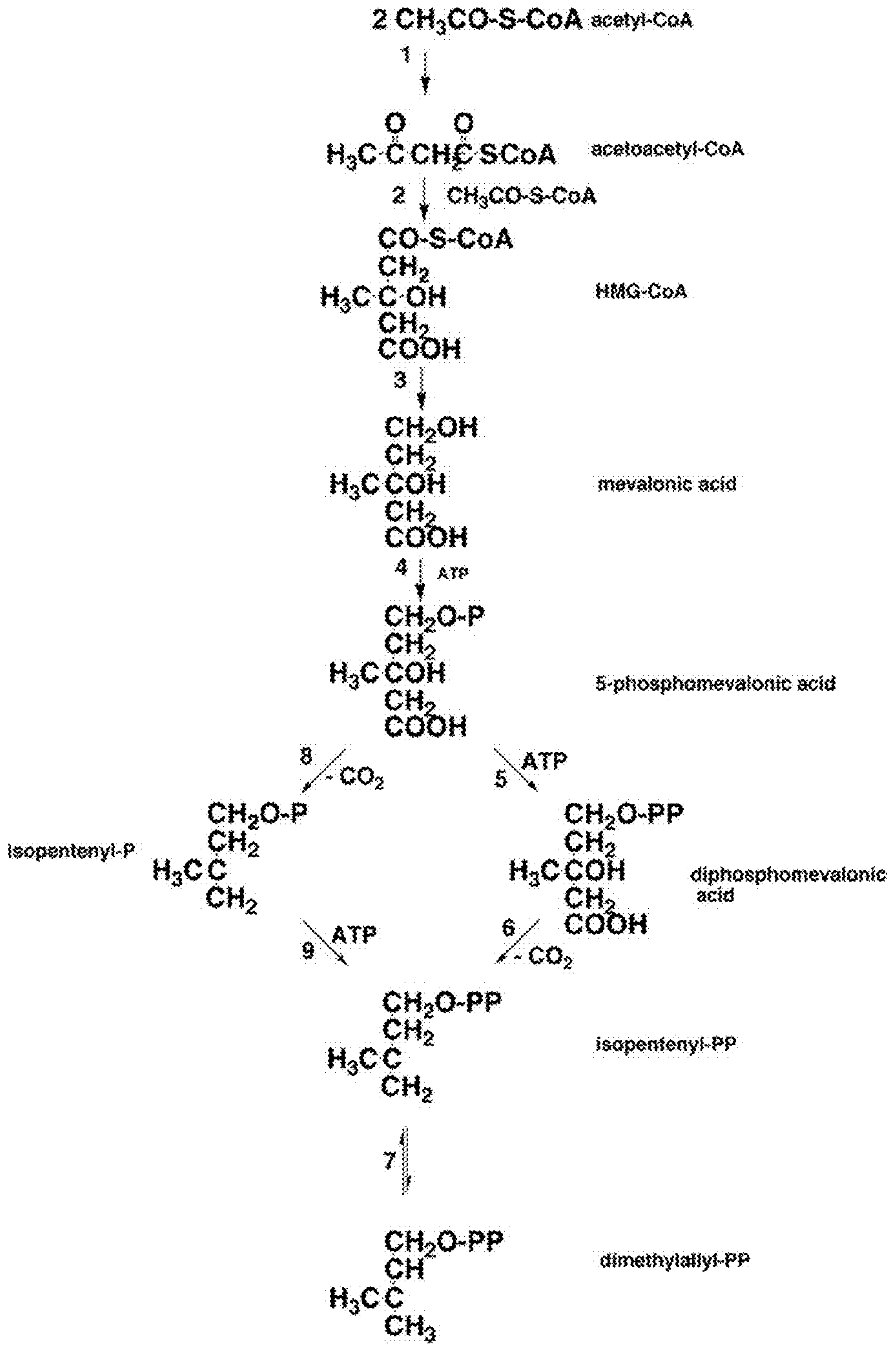

FIG. 19B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews,* 71:97-120, 2007, which is incorporated by reference in its entirety, particularly with respect to nucleic acids and polypeptides of the modified MVA pathway. The modified MVA pathway is present, for example, in some archaeal organisms, such as *Methanosarcina mazei.*

Figure 20:
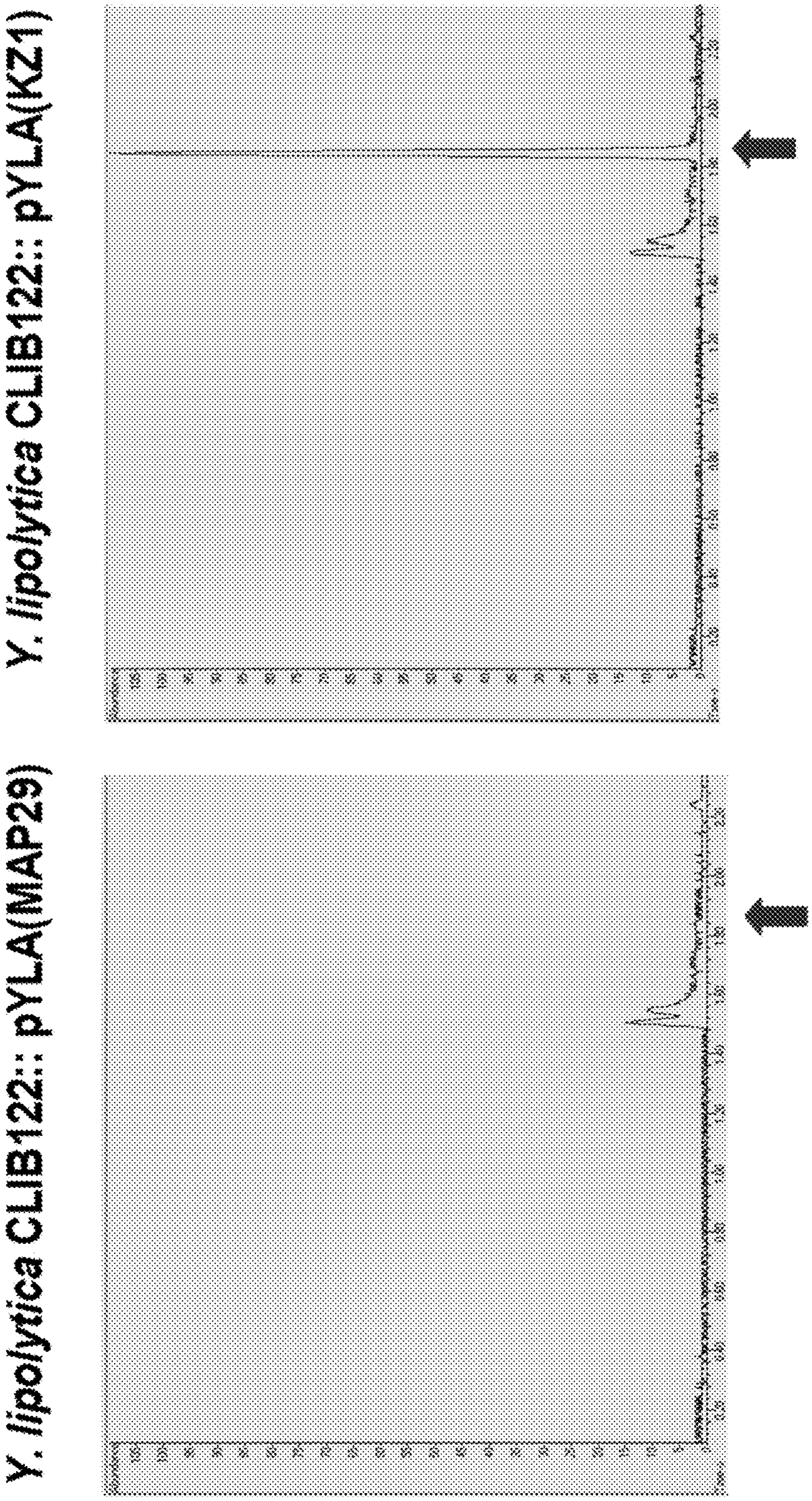

FIG. 20 shows graphs representing results of the GC-MS analysis of isoprene production by recombinant *Y. lipolytica* strains without (left) or with (right) a kudzu isoprene synthase gene. The arrows indicate the elution time of the authentic isoprene standard.

Figure 21:
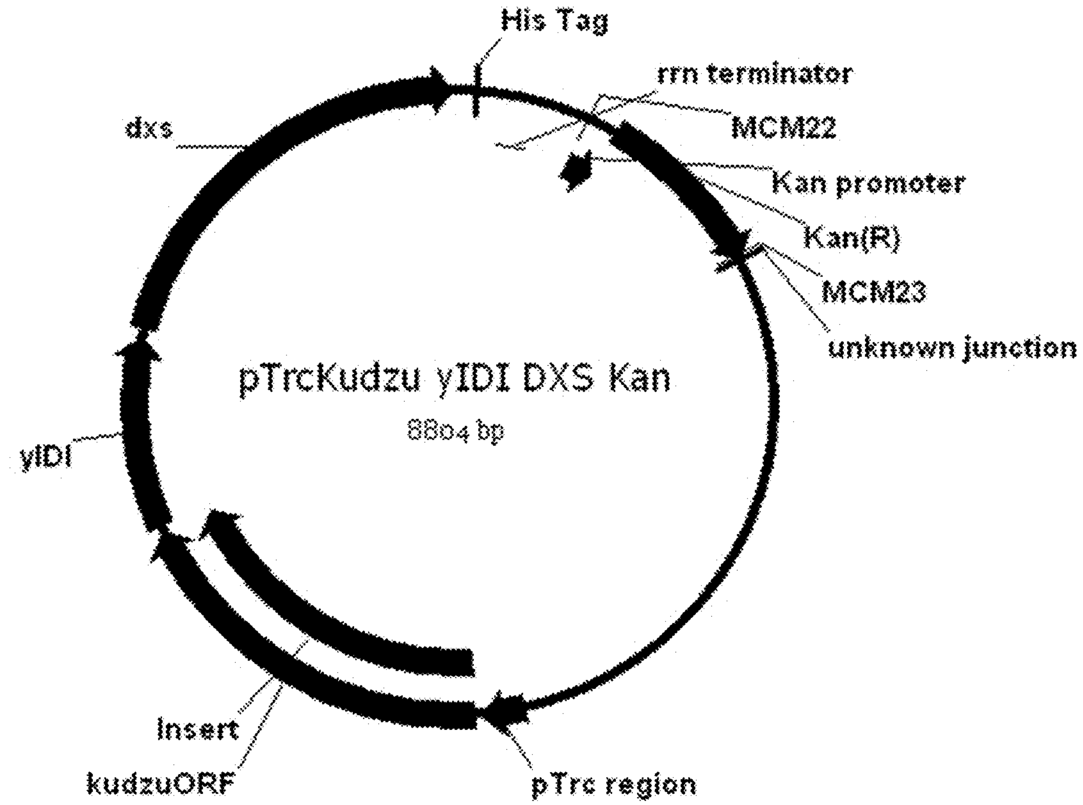

FIG. 21 is a map of pTrcKudzu yIDI DXS Kan.

FIGS. 22A-22D are the nucleotide sequence of pTrcKudzu yIDI DXS Kan (SEQ ID NO:20).

Figure 23A:
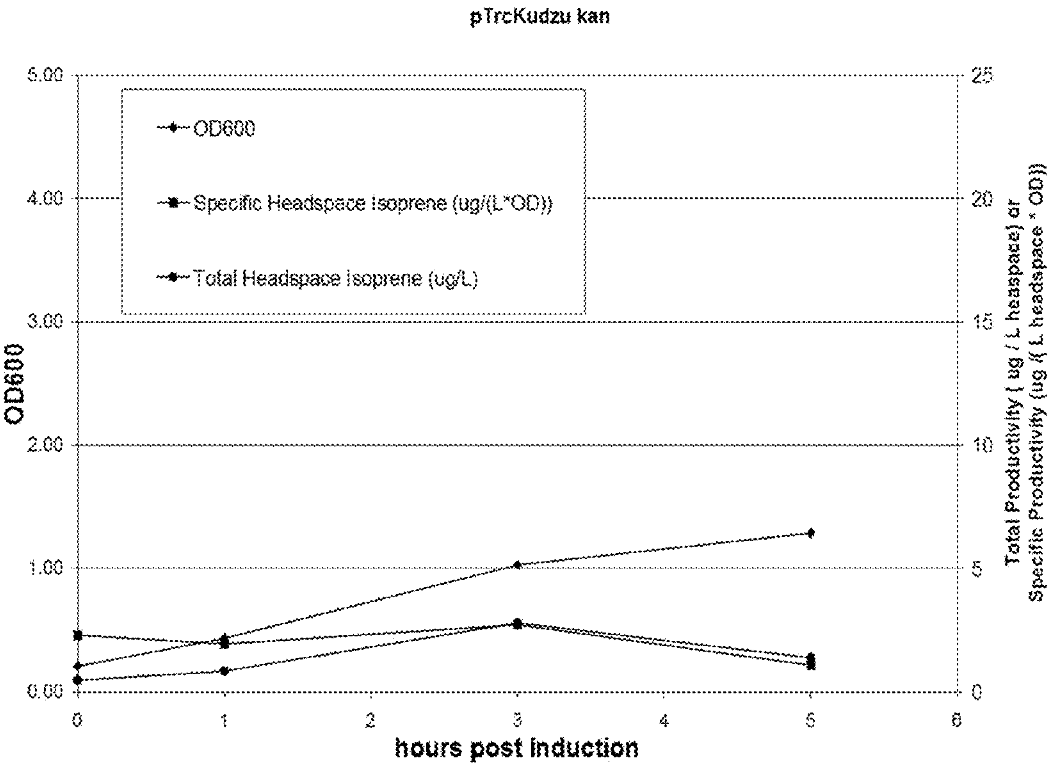

FIG. 23A is a graph showing production of isoprene from glucose in BL21/pTrcKudzukan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23B:
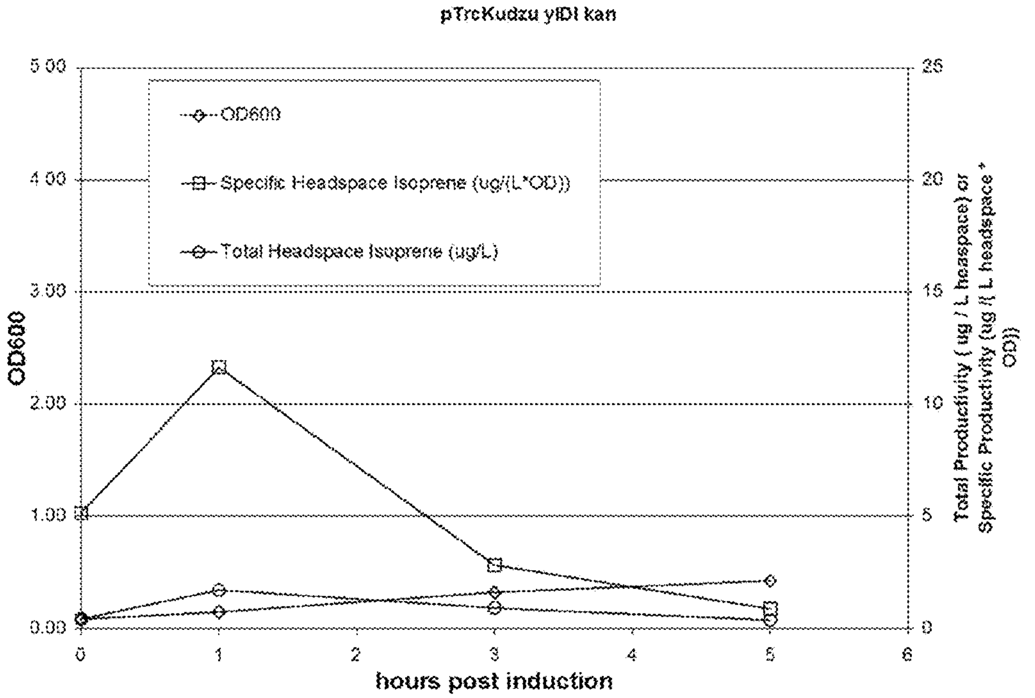

FIG. 23B is a graph showing production of isoprene from glucose in BL21/pTrcKudzu yIDI kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23C:
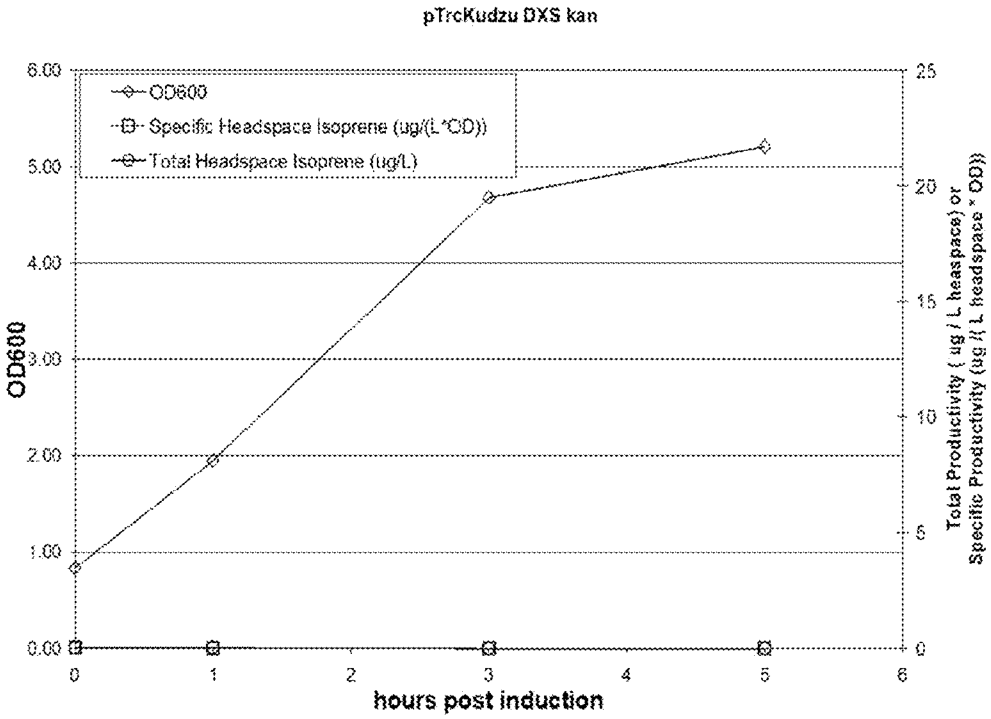

FIG. 23C is a graph showing production of isoprene from glucose in BL21/pTrcKudzu DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23D:
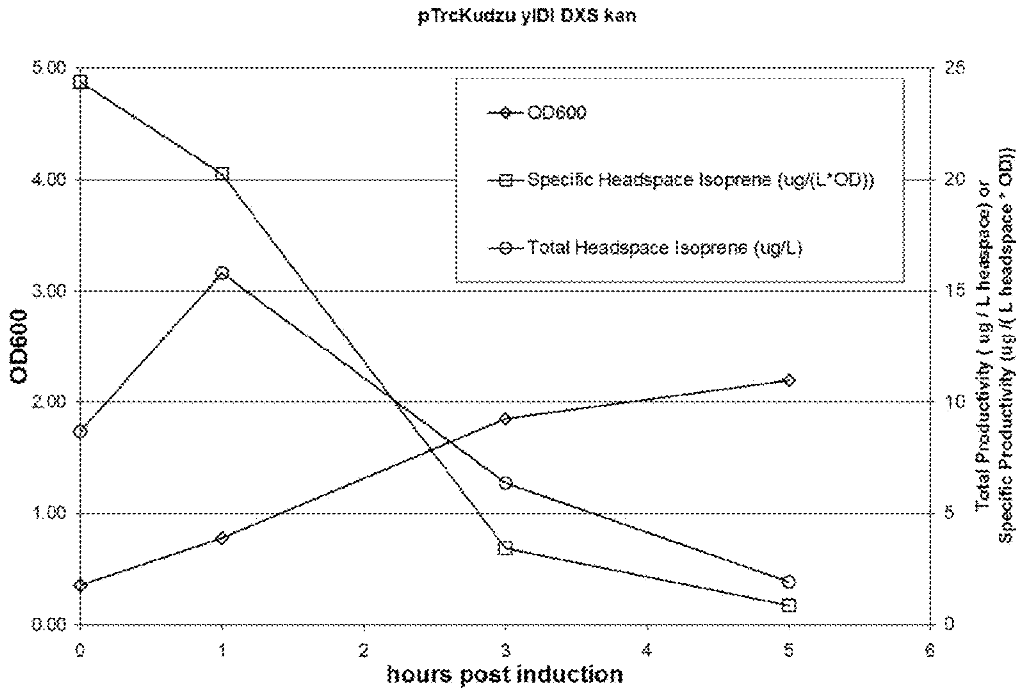

FIG. 23D is a graph showing production of isoprene from glucose in BL21/pTrcKudzu yIDI DXS kan. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23E:
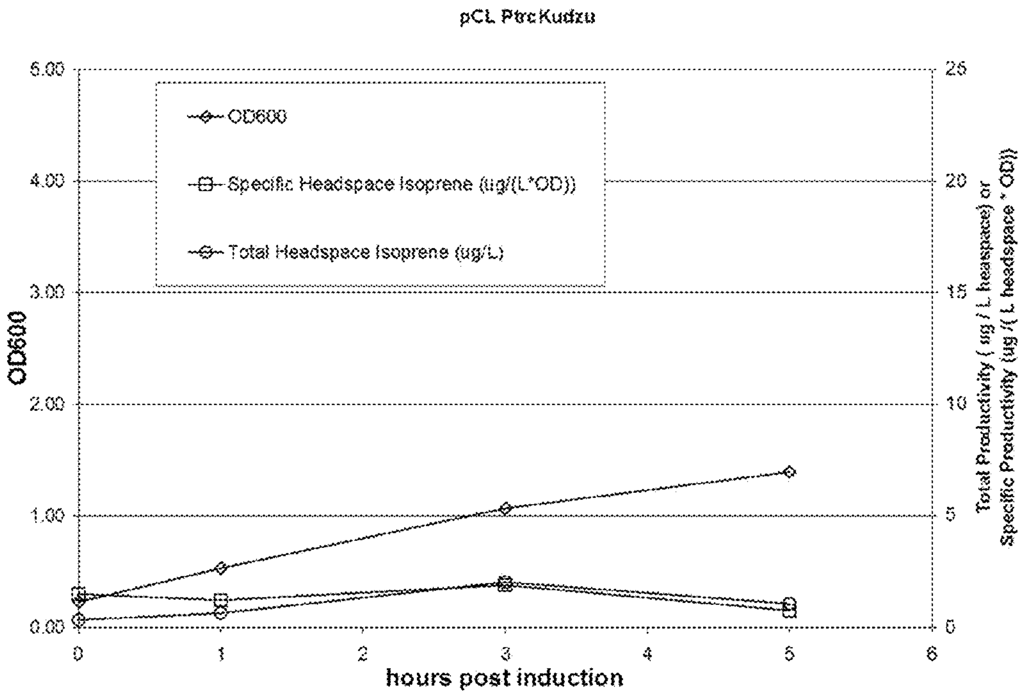

FIG. 23E is a graph showing production of isoprene from glucose in BL21/pCL PtrcKudzu. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23F:
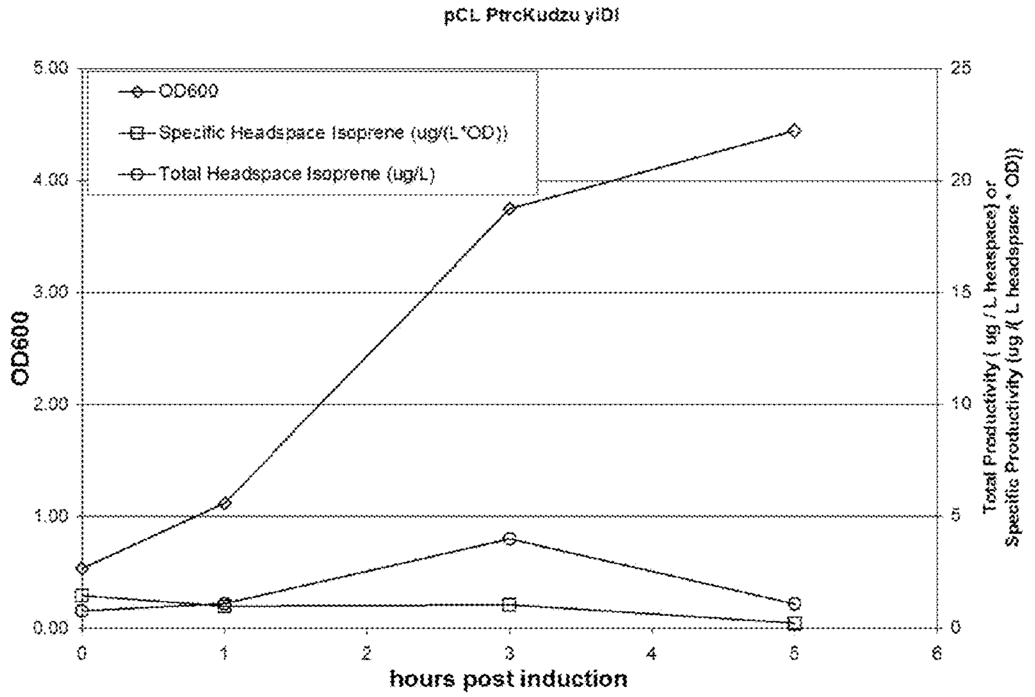

FIG. 23F is a graph showing production of isoprene from glucose in BL21/pCL PtrcKudzu yIDI. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23G:
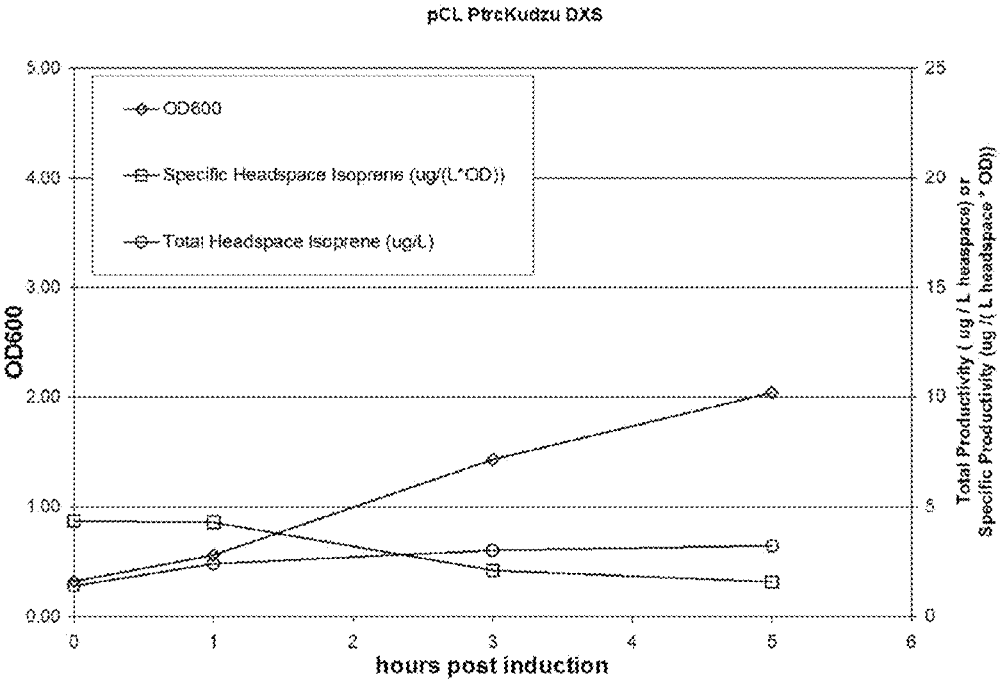

FIG. 23G is a graph showing production of isoprene from glucose in BL21/pCL PtrcKudzu DXS. Time 0 is the time of induction with IPTG (400 μmol). The x-axis is time after induction; the y-axis is $OD_{600}$ and the y2-axis is total productivity of isoprene (μg/L headspace or specific productivity (μg/L headspace/OD). Diamonds represent $OD_{600}$, circles represent total isoprene productivity (μg/L) and squares represent specific productivity of isoprene (μg/L/OD).

Figure 23H:
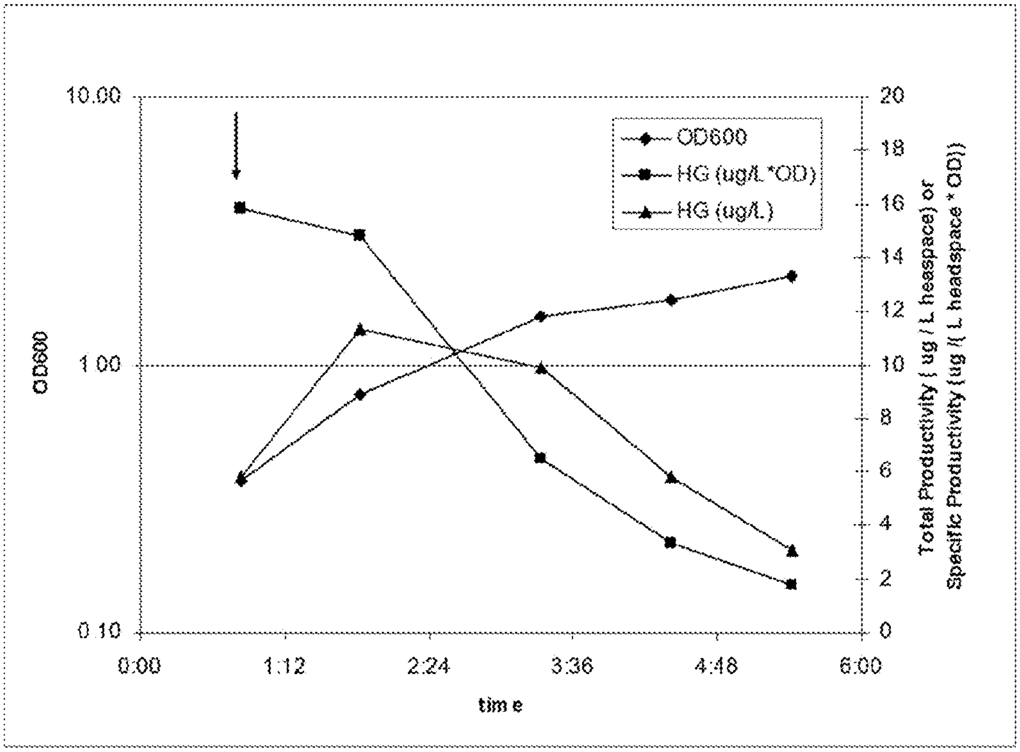

FIG. 23H is a graph showing production of isoprene from glucose in BL21/pTrcKudzuIDIDXSkan. The arrow indicates the time of induction with IPTG (400 μmol). The x-axis is time after inoculation; the y-axis is OD600 and the y2-axis is total productivity of isoprene (μg/L headspace or specific productivity (μg/L headspace/OD). Diamonds represent OD600, triangles represent total isoprene productivity (μg/L) and squares represent specific productivity of isoprene (μg/L/OD).

Figure 24:
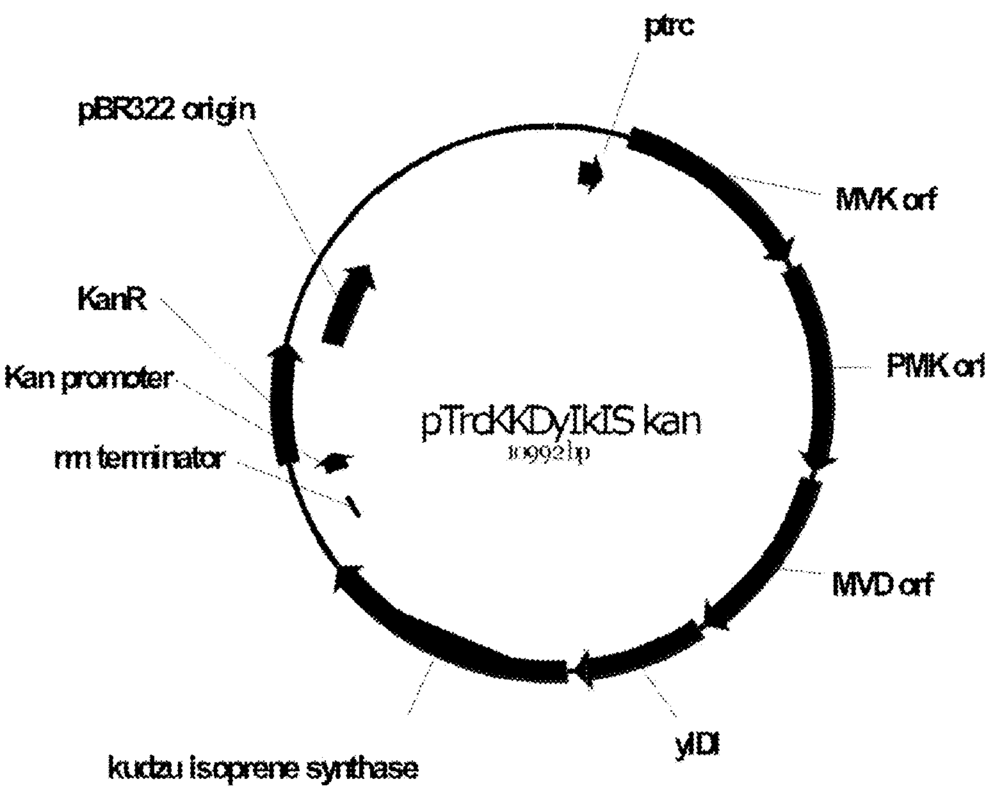

FIG. 24 is a map of pTrcKKDyIkIS kan.

FIGS. 25A-25D are the nucleotide sequence of pTrcKKDyIkIS kan (SEQ ID NO:33).

Figure 26:
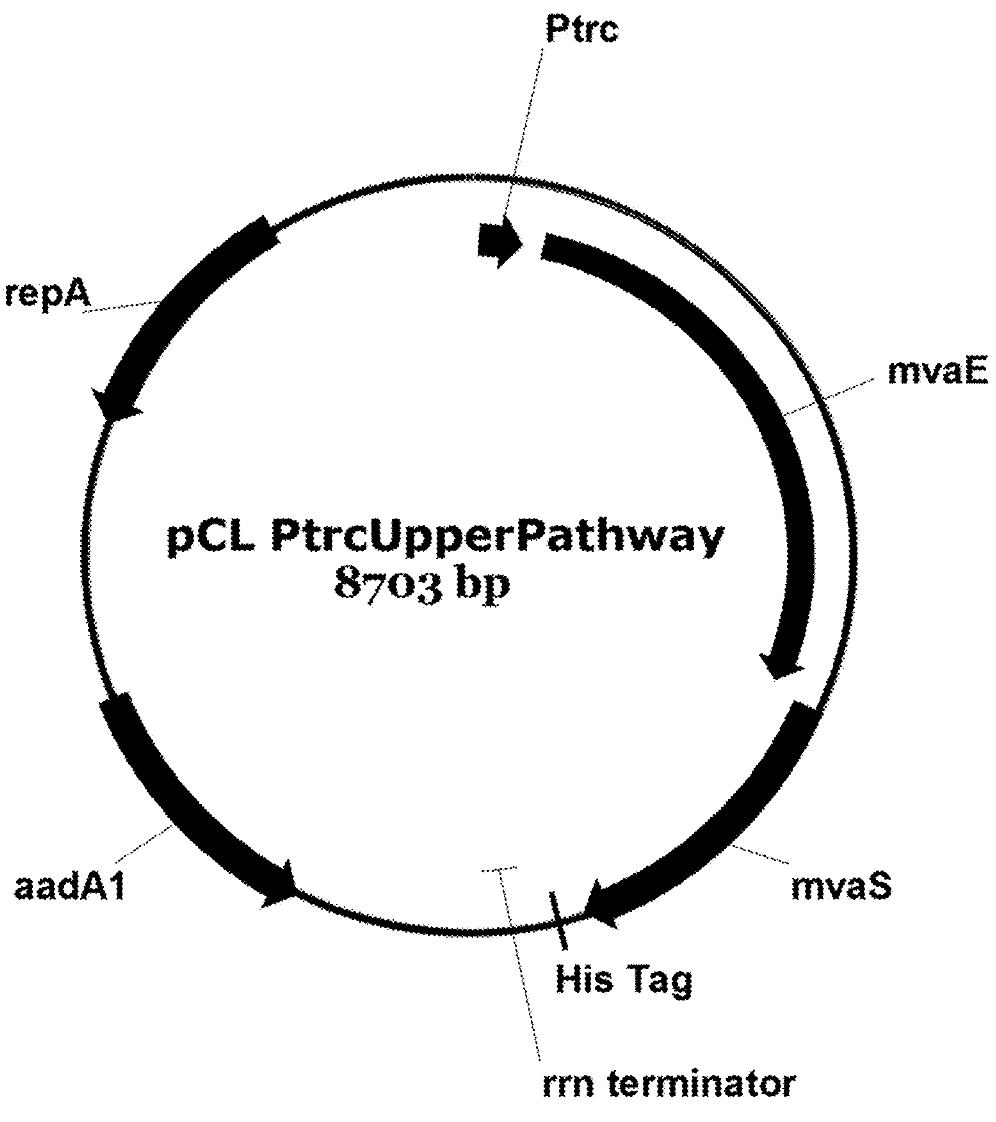

FIG. 26 is a map of pCL PtrcUpperPathway.

FIGS. 27A-27D are the nucleotide sequence of pCL PtrcUpperPathway (SEQ ID NO:46).

Figure 28:
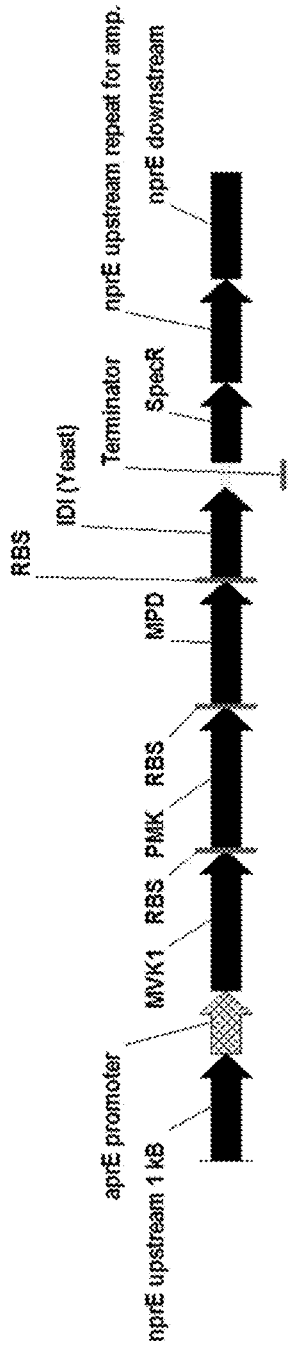

FIG. 28 shows a map of the cassette containing the lower MVA pathway and yeast idi for integration into the *B. subtilis* chromosome at the nprE locus. nprE upstream/downstream indicates 1 kb each of sequence from the nprE locus for integration. aprE promoter (alkaline serine protease promoter) indicates the promoter (−35, −10, +1 transcription start site, RBS) of the aprE gene. MVK1 indicates the yeast mevalonate kinase gene. RBS-PMK indicates the yeast phosphomevalonate kinase gene with a *Bacillus* RBS upstream of the start site. RBS-MPD indicates the yeast diphosphomevalonate decarboxylase gene with a *Bacillus* RBS upstream of the start site. RBS-IDI indicates the yeast idi gene with a *Bacillus* RBS upstream of the start site. Terminator indicates the terminator alkaline serine protease transcription terminator from *B. amyliquefaciens*. SpecR indicates the spectinomycin resistance marker. "nprE upstream repeat for amp." indicates a direct repeat of the upstream region used for amplification.

FIGS. 29A-29D are the nucleotide sequence of cassette containing the lower MVA pathway and yeast idi for integration into the *B. subtilis* chromosome at the nprE locus (SEQ ID NO:47).

Figure 30:
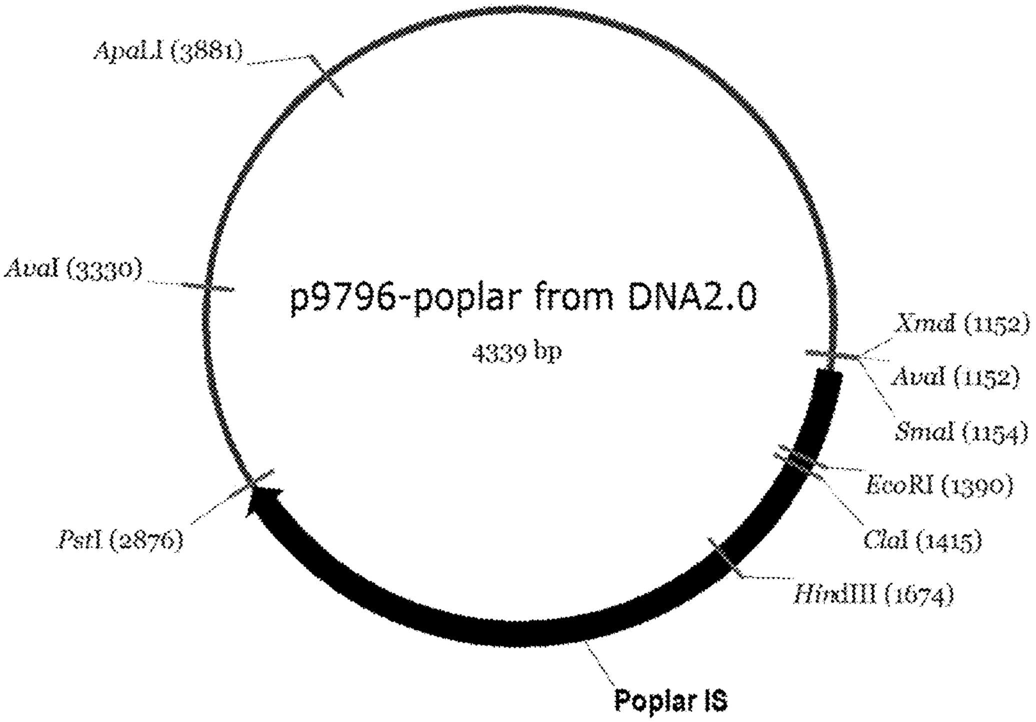

FIG. 30 is a map of p9796-poplar.

FIGS. 31A and 31B are the nucleotide sequence of p9796-poplar (SEQ ID NO:48).

Figure 32:
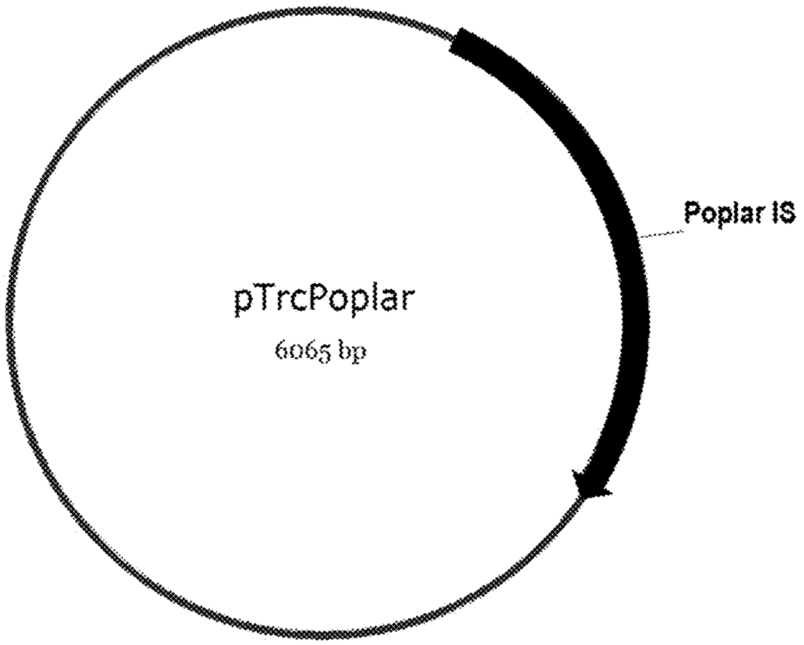

FIG. 32 is a map of pTrcPoplar.

FIGS. 33A-33C are the nucleotide sequence of pTrcPoplar (SEQ ID NO:49).

Figure 34:
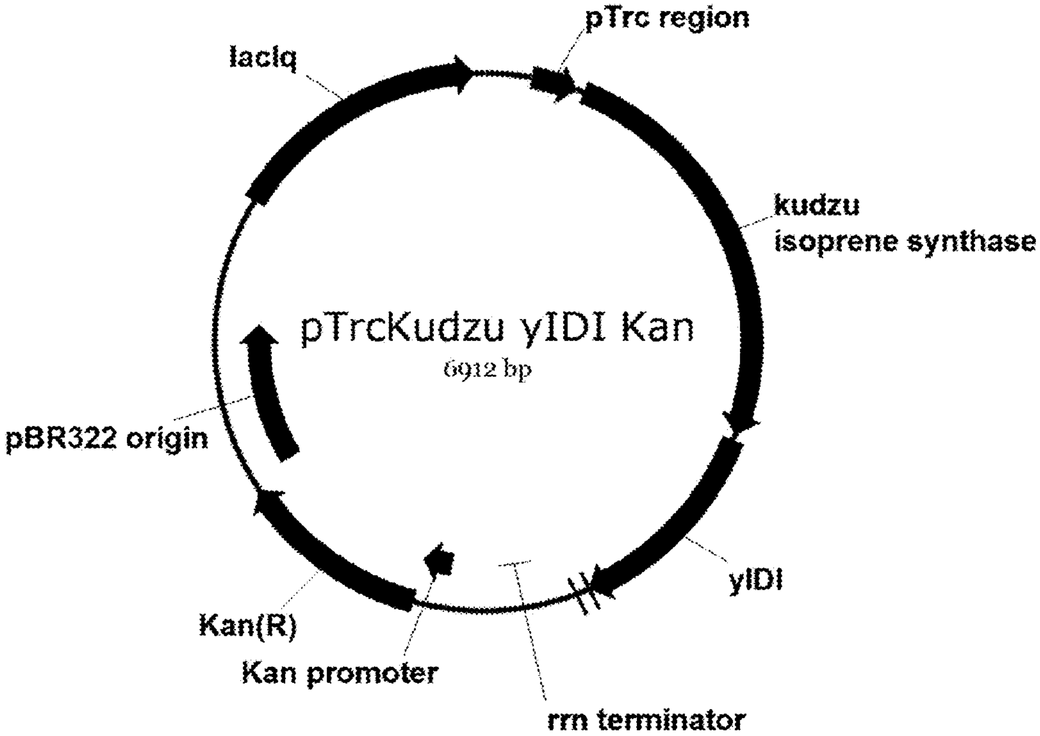

FIG. 34 is a map of pTrcKudzu yIDI Kan.

FIGS. 35A-35C are the nucleotide sequence of pTrcKudzu yIDI Kan (SEQ ID NO:50).

Figure 36:
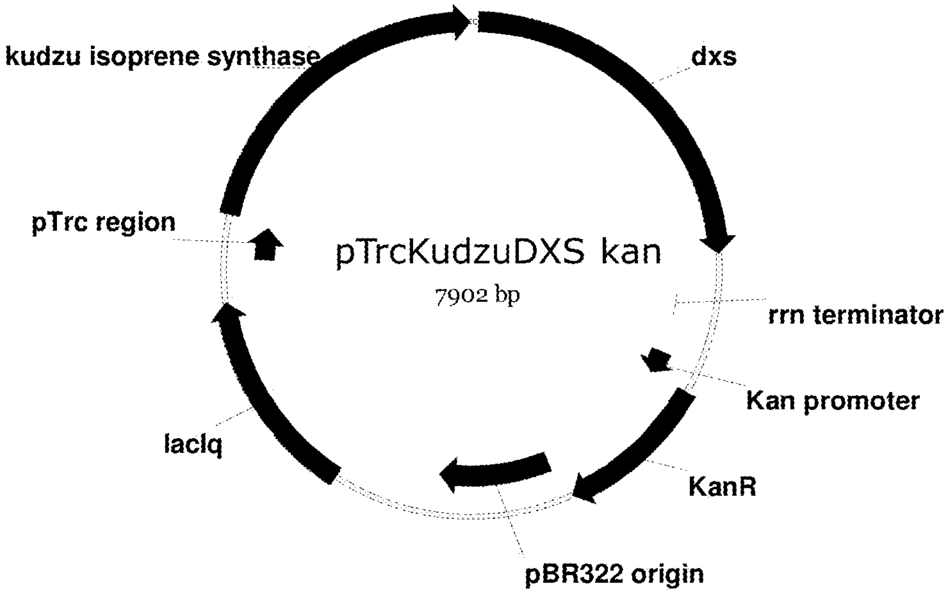

FIG. 36 is a map of pTrcKudzuDXS Kan.

FIGS. 37A-37C are the nucleotide sequence of pTrcKudzuDXS Kan (SEQ ID NO:51).

Figure 38:
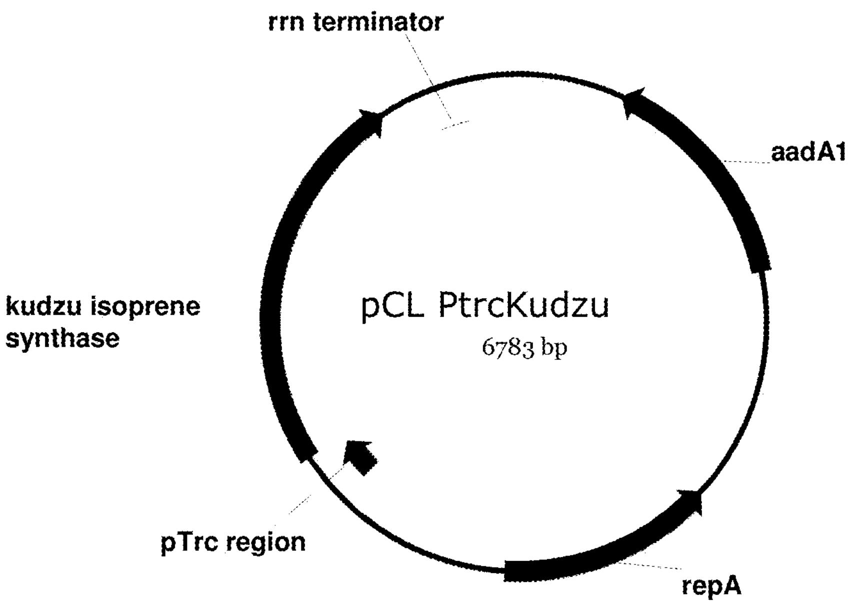

FIG. 38 is a map of pCL PtrcKudzu.

FIGS. 39A-39C are the nucleotide sequence of pCL PtrcKudzu (SEQ ID NO:52).

Figure 40:
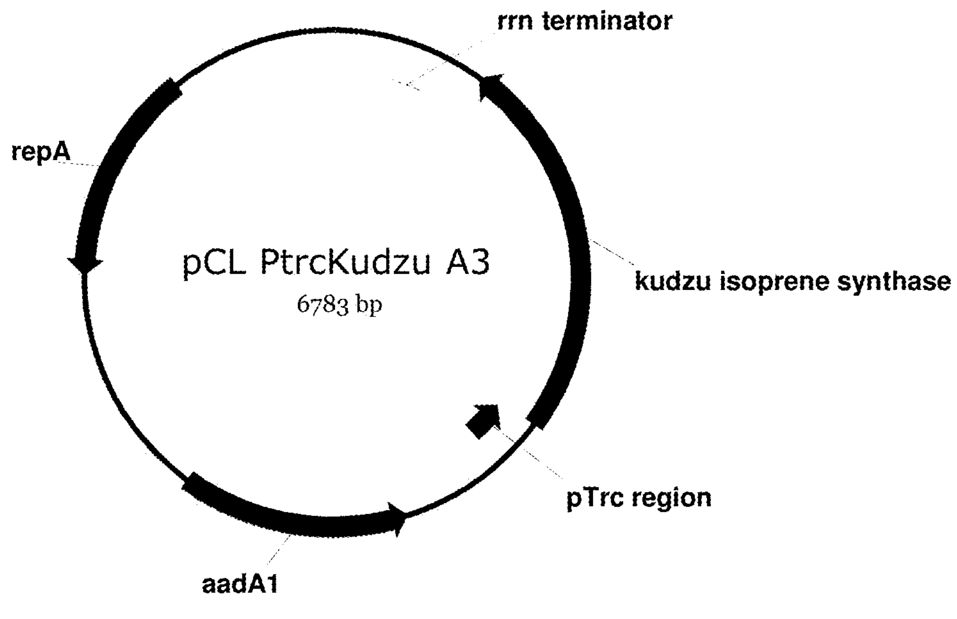

FIG. 40 is a map of pCL PtrcKudzu A3.

FIGS. 41A-41C are the nucleotide sequence of pCL PtrcKudzu A3 (SEQ ID NO:53).

Figure 42:
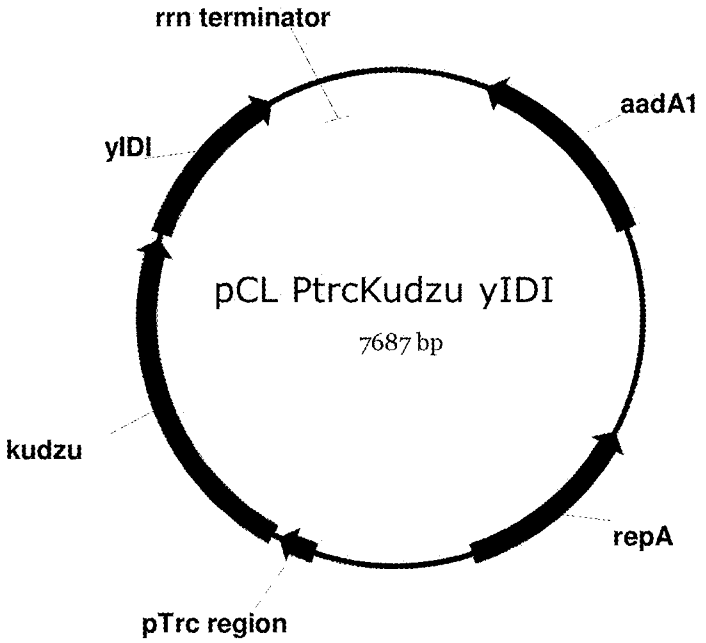

FIG. 42 is a map of pCL PtrcKudzu yIDI.

FIGS. 43A-43C are the nucleotide sequence of pCL PtrcKudzu yIDI (SEQ ID NO:54).

Figure 44:
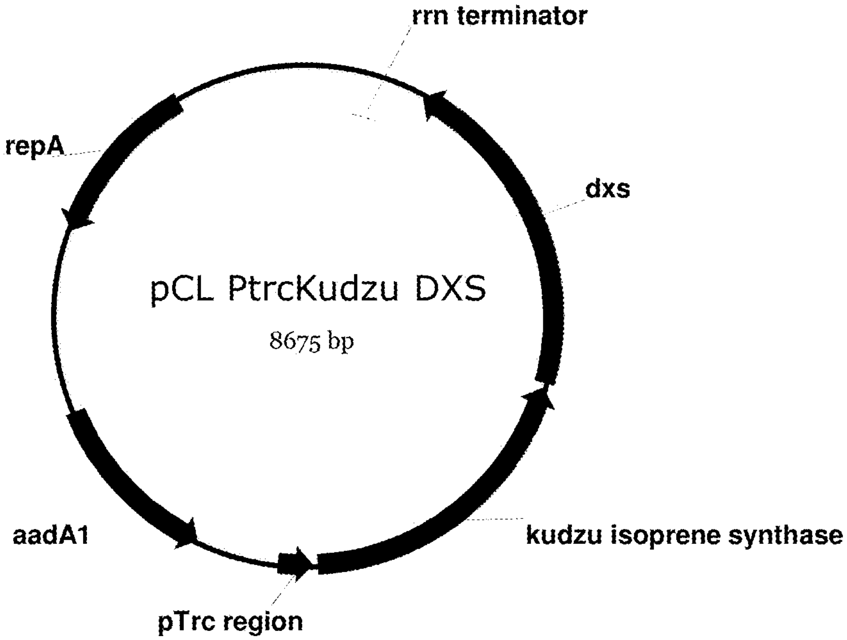

FIG. 44 is a map of pCL PtrcKudzu DXS.

FIGS. 45A-45D are the nucleotide sequence of pCL PtrcKudzu DXS (SEQ ID NO:55).

Figure 46A:
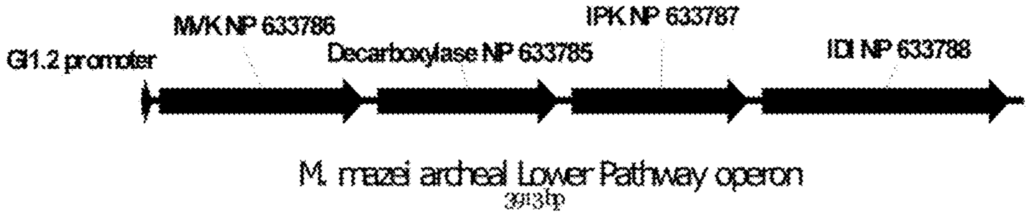

FIG. 46A is a map of the *M. mazei* archaeal Lower Pathway operon.

FIGS. 46B and 46C are the nucleotide sequence of the *M. mazei* archaeal lower Pathway operon (SEQ ID NO:102).

Figure 47A:
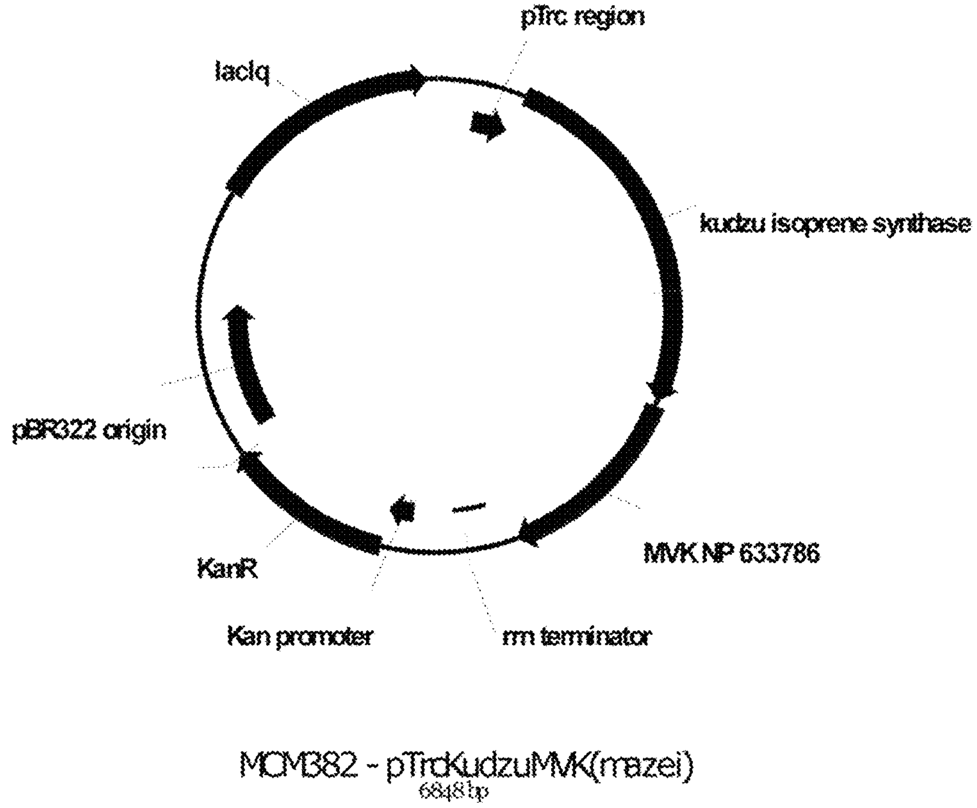

FIG. 47A is a map of MCM382-pTrcKudzuMVK(mazei).

FIGS. 47B and 47C are the nucleotide sequence of MCM382-pTrcKudzuMVK(mazei) (SEQ ID NO:103).

Figure 48A:
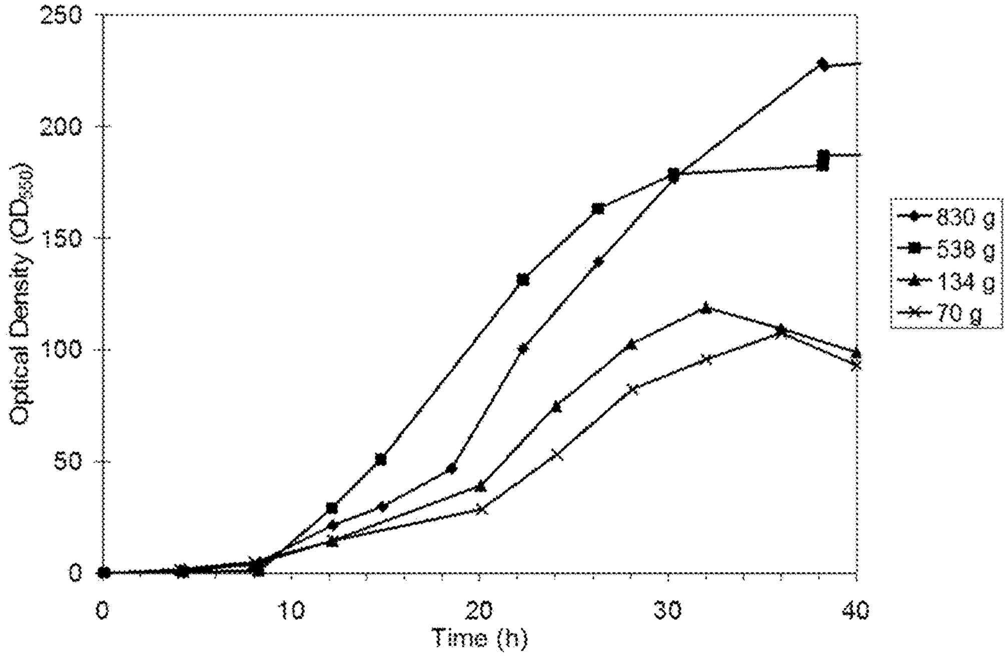
Figure 48B:
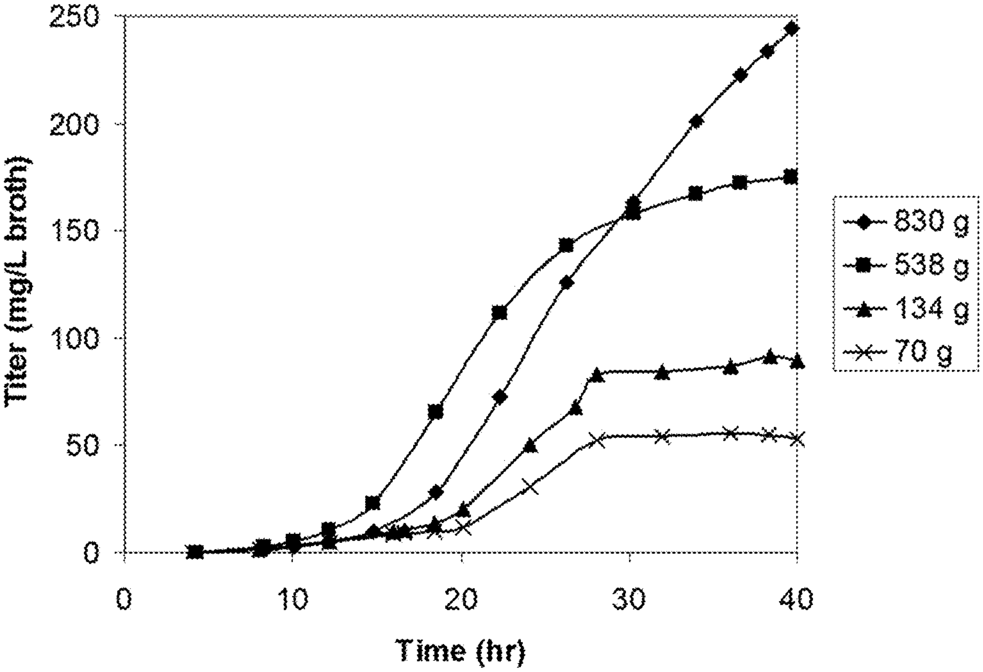
Figure 48C:
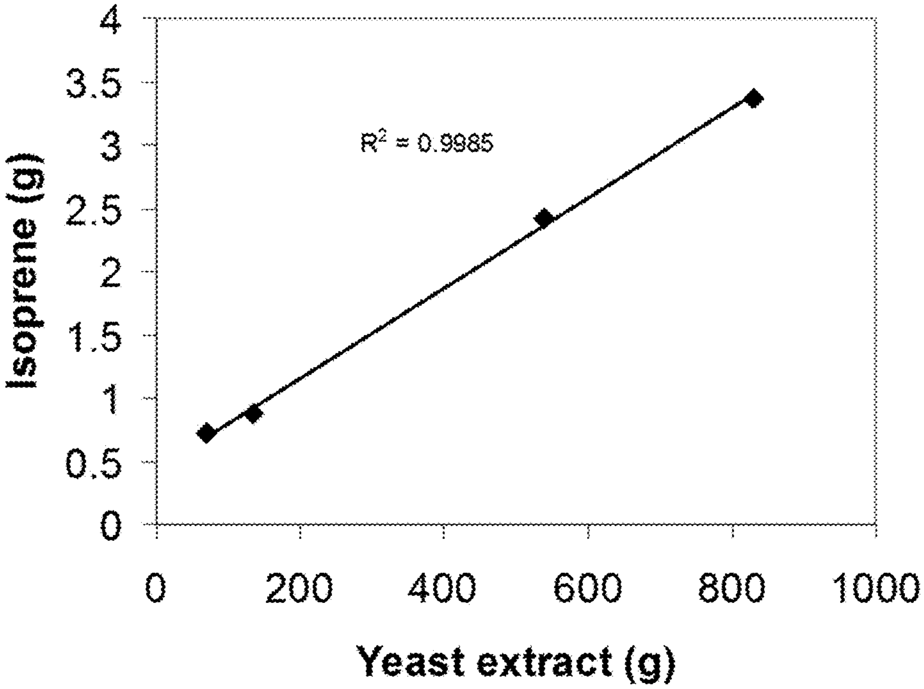

FIGS. 48A-48C are graphs demonstrating the effect of yeast extract of isoprene production. FIG. 48A is the time course of optical density within fermentors fed with varying amounts of yeast extract. FIG. 48B is the time course of isoprene titer within fermentors fed with varying amounts of yeast extract. The titer is defined as the amount of isoprene produced per liter of fermentation broth. FIG. 48C shows the effect of yeast extract on isoprene production in *E. coli* grown in fed-batch culture.

FIG. 49 shows graphs demonstrating isoprene production from a 500 L bioreactor with *E. coli* cells containing the pTrcKudzu+yIDI+DXS plasmid. Panel A shows the time course of optical density within the 500-L bioreactor fed with glucose and yeast extract. Panel B shows the time course of isoprene titer within the 500-L bioreactor fed with glucose and yeast extract. The titer is defined as the amount of isoprene produced per liter of fermentation broth. Panel C shows the time course of total isoprene produced from the 500-L bioreactor fed with glucose and yeast extract.

Figure 50:
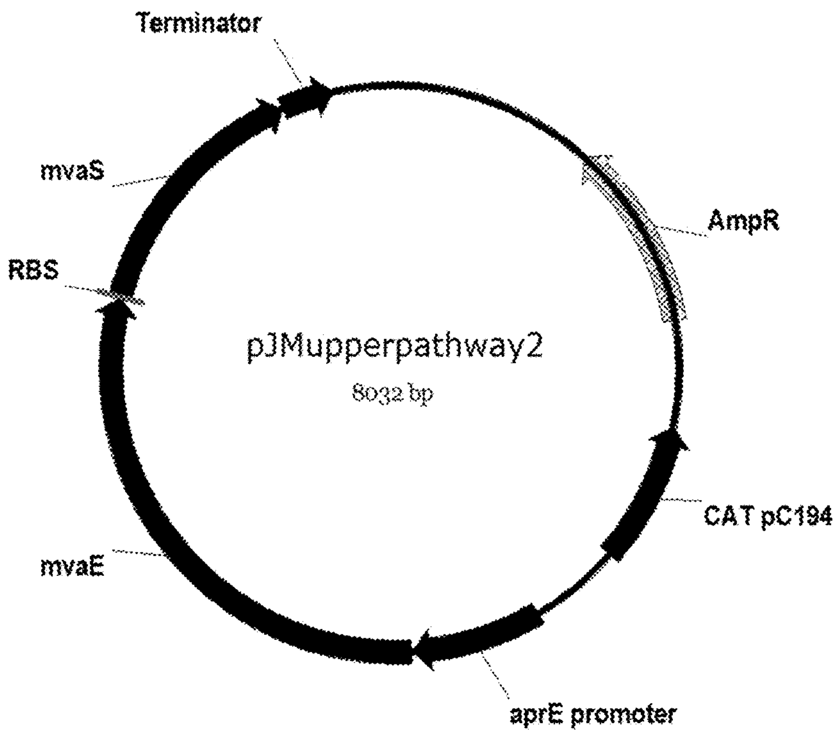

FIG. 50 is a map of pJMupperpathway2.

FIGS. 51A-51C are the nucleotide sequence of pJMupperpathway2 (SEQ ID NO:56).

Figure 52:
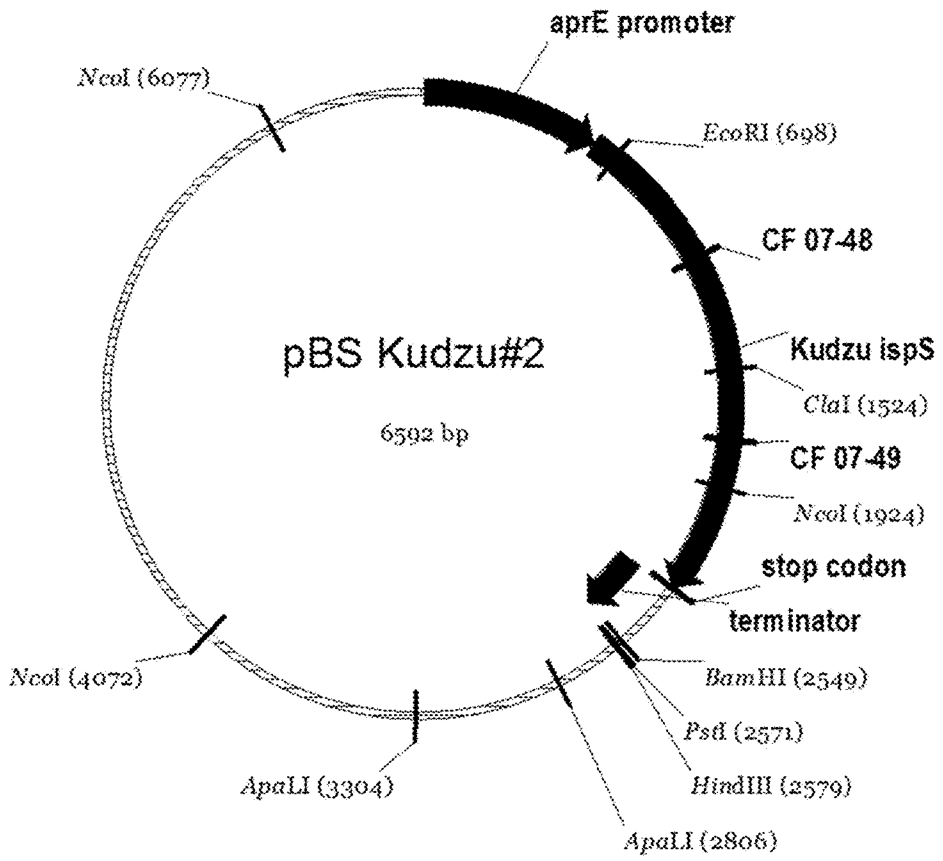

FIG. 52 is a map of pBS Kudzu #2.

Figure 53A:
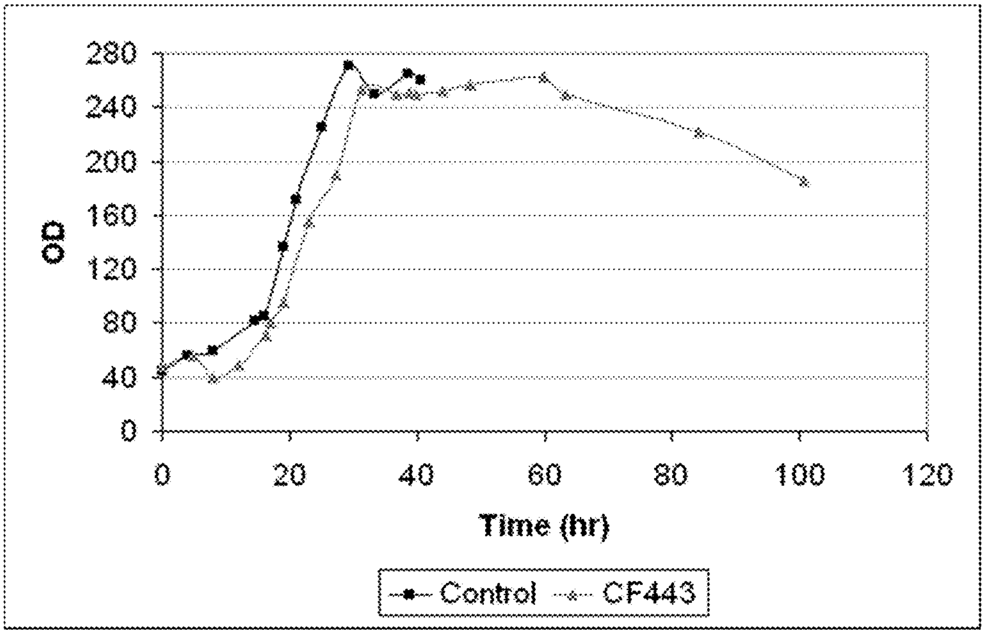

FIG. 53A is a graph showing growth during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Figure 53B:
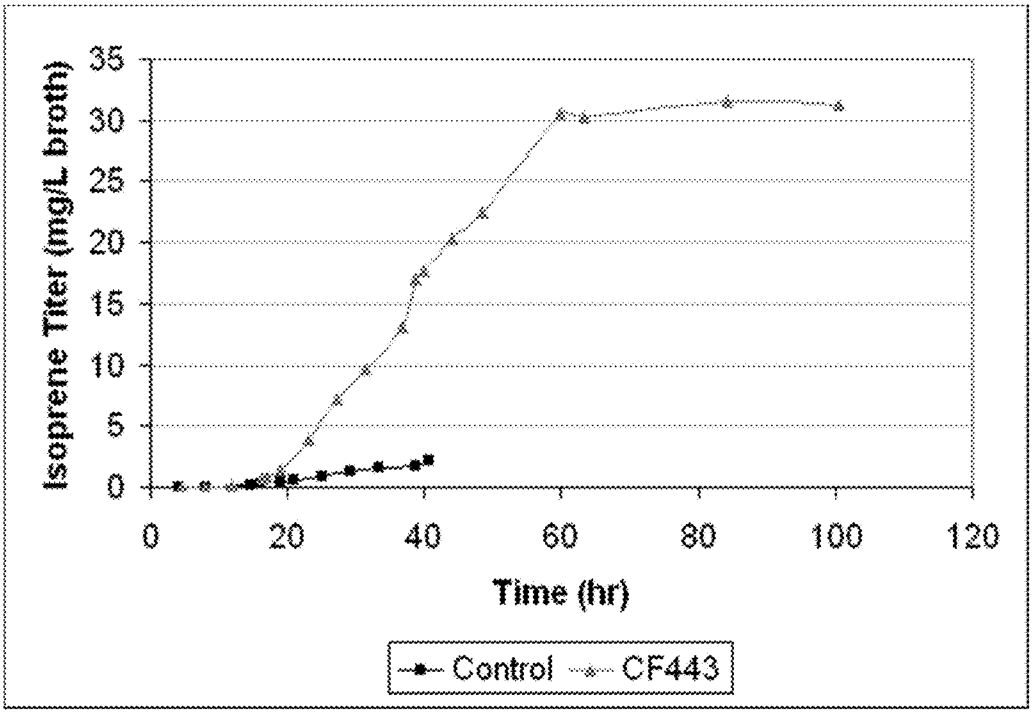

FIG. 53B is a graph showing isoprene production during fermentation time of *Bacillus* expressing recombinant kudzu isoprene synthase in 14 liter fed batch fermentation. Black diamonds represent a control strain (BG3594comK) without recombinant isoprene synthase (native isoprene production) and grey triangles represent *Bacillus* with pBSKudzu (recombinant isoprene production).

Figure 54:
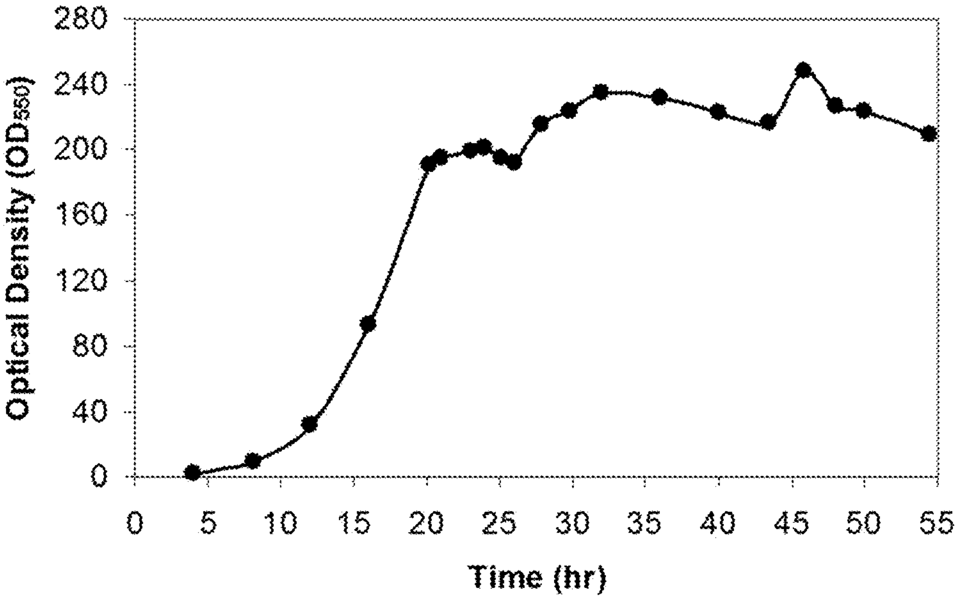

FIG. 54 is a time course of optical density within the 15-L bioreactor fed with glucose.

Figure 55:
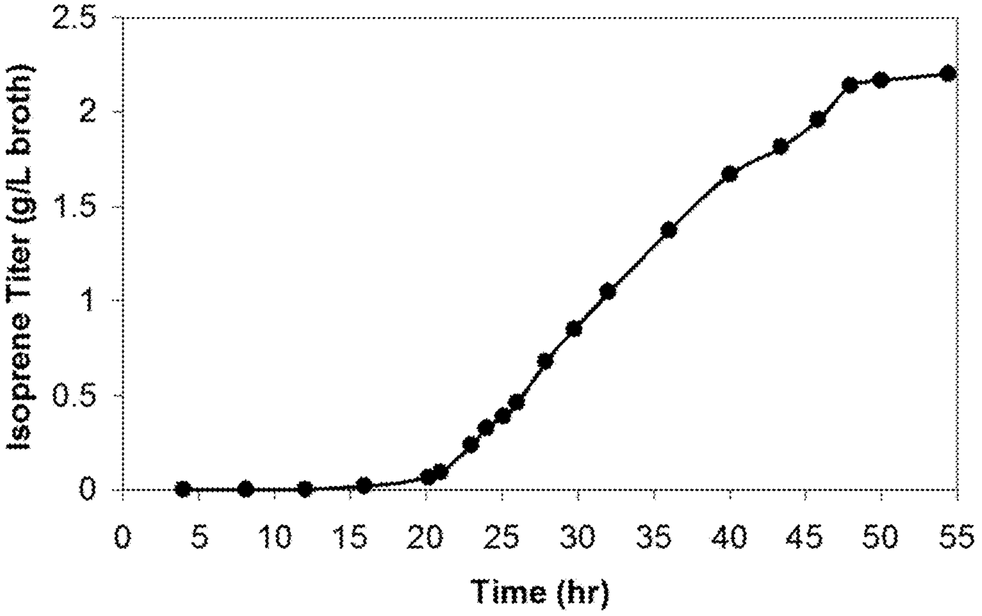

FIG. 55 is a time course of isoprene titer within the 15-L bioreactor fed with glucose. The titer is defined as the amount of isoprene produced per liter of fermentation broth.

Figure 56:
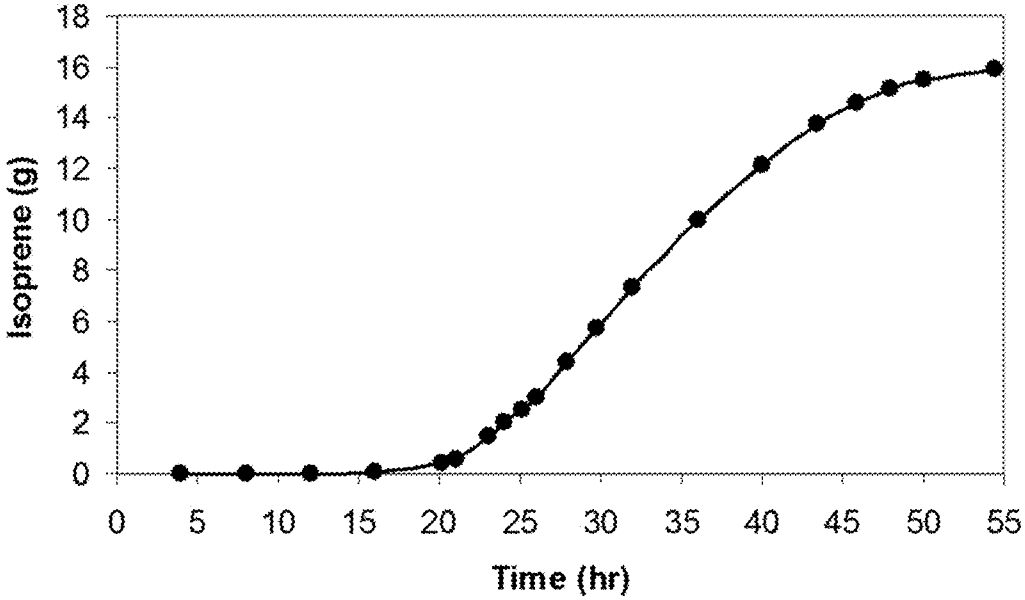

FIG. 56 is a time course of total isoprene produced from the 15-L bioreactor fed with glucose.

Figure 57A:
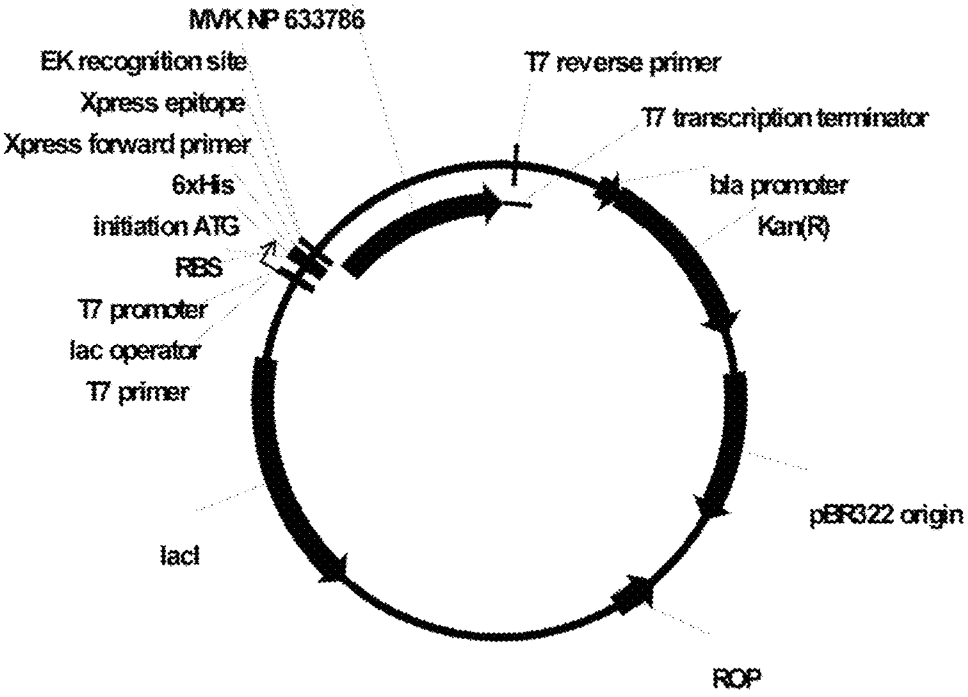

FIG. 57A is a map of MCM376-MVK from *M. mazei* archaeal Lowerin pET200D.

FIGS. 57B and 57C are the nucleotide sequence of MCM376-MVK from *M. mazei* archaeal Lowerin pET200D (SEQ ID NO:104).

Figure 58A:
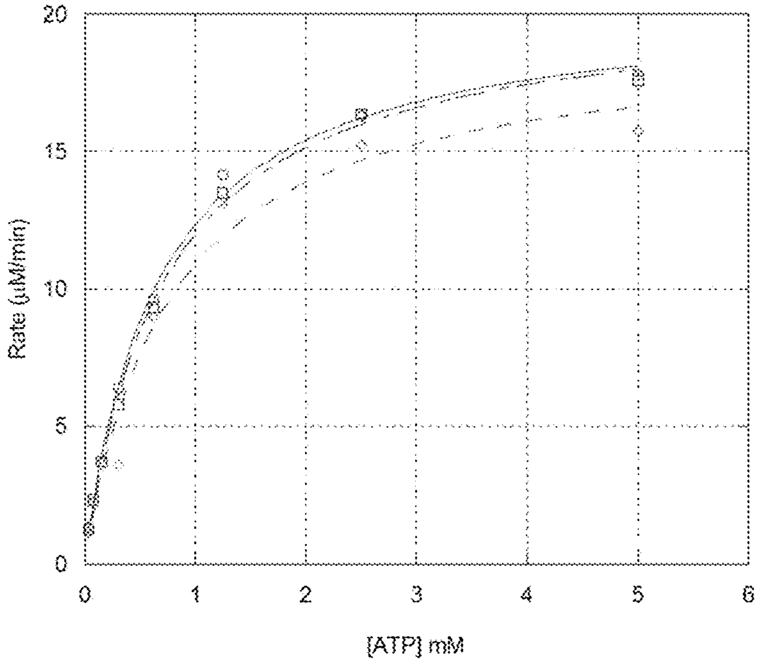
Figure 58B:
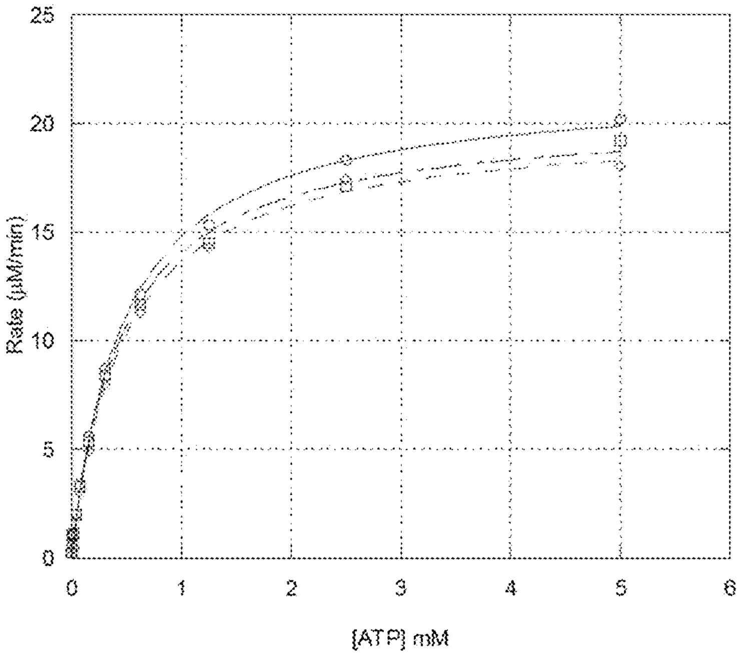
Figure 58C:
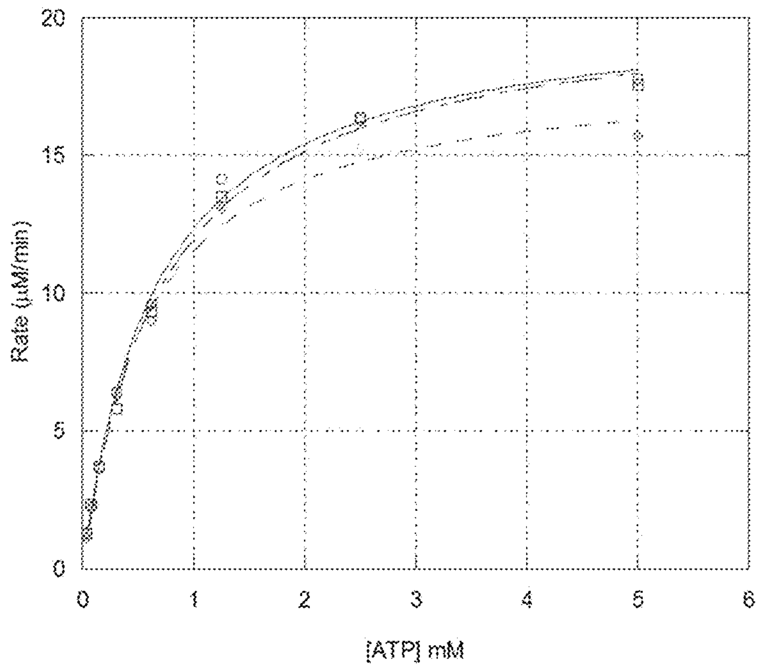
Figure 58D:
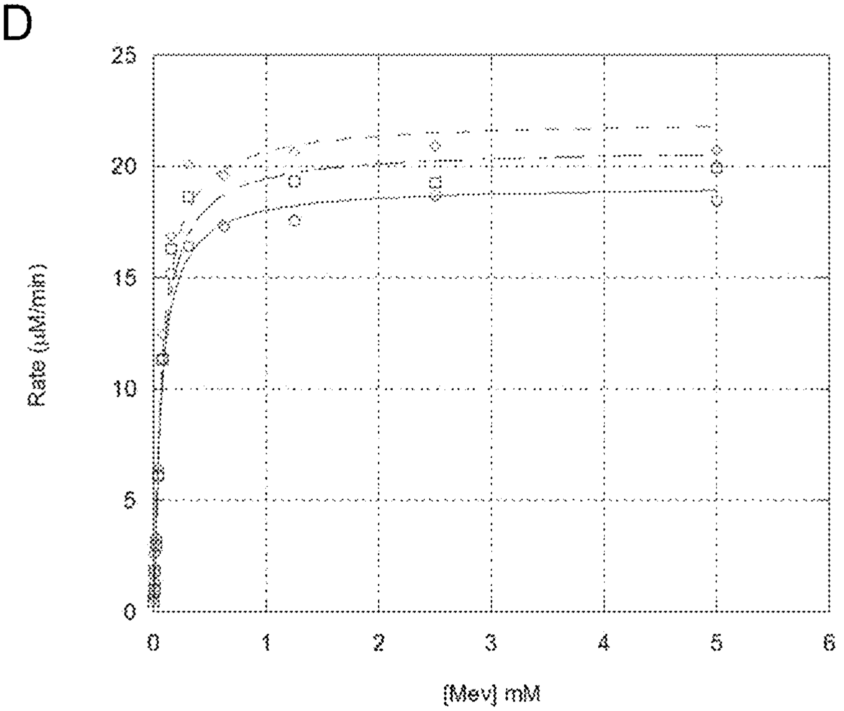

FIGS. 58A-58D are graphs showing the kinetics of yeast and *M. mazei* mevalonate kinases. FIG. 58A is a graph of the rate vs. [ATP] for yeast mevalonate kinase. FIG. 58B is a graph of the rate vs. [mevalonate] for yeast mevalonate kinase. FIG. 58C is a graph of the rate vs. [ATP] for *M. mazei* mevalonate kinase. FIG. 58D is a graph of the rate vs. [mevalonate] for *M. mazei* mevalonate kinase.

Figure 59A:
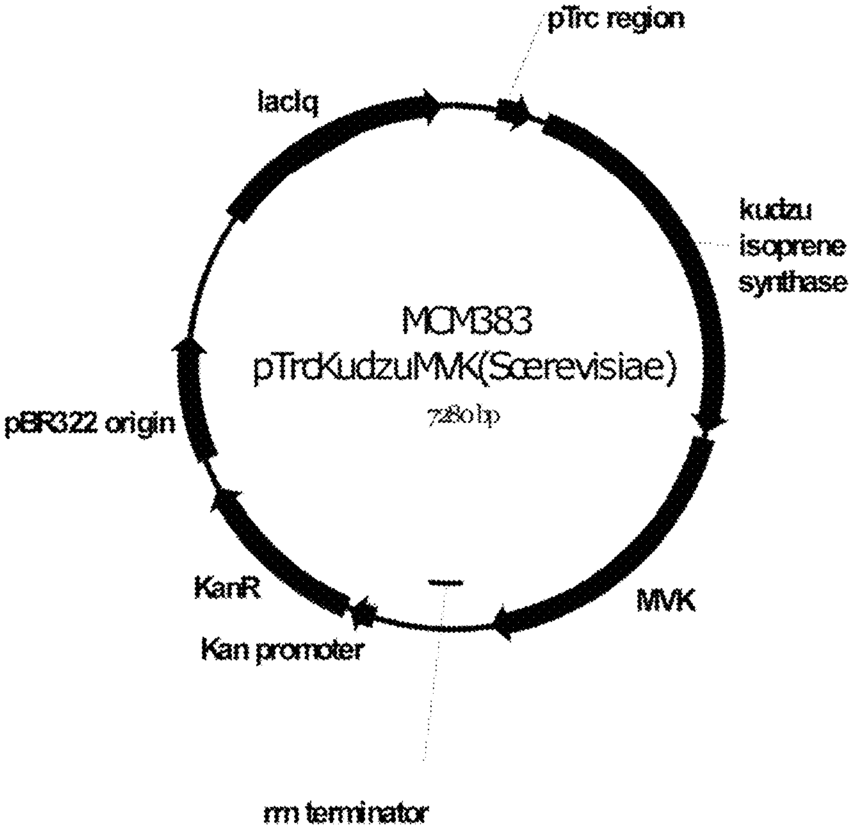

FIG. 59A is a map of MCM 383-pTrcKudzuMVK (*S. cerevisiae*).

FIGS. 59B and 59C are the nucleotide sequence of MCM 383-pTrcKudzuMVK (*S. cerevisiae*) (SEQ ID NO:105).

Figure 60A:
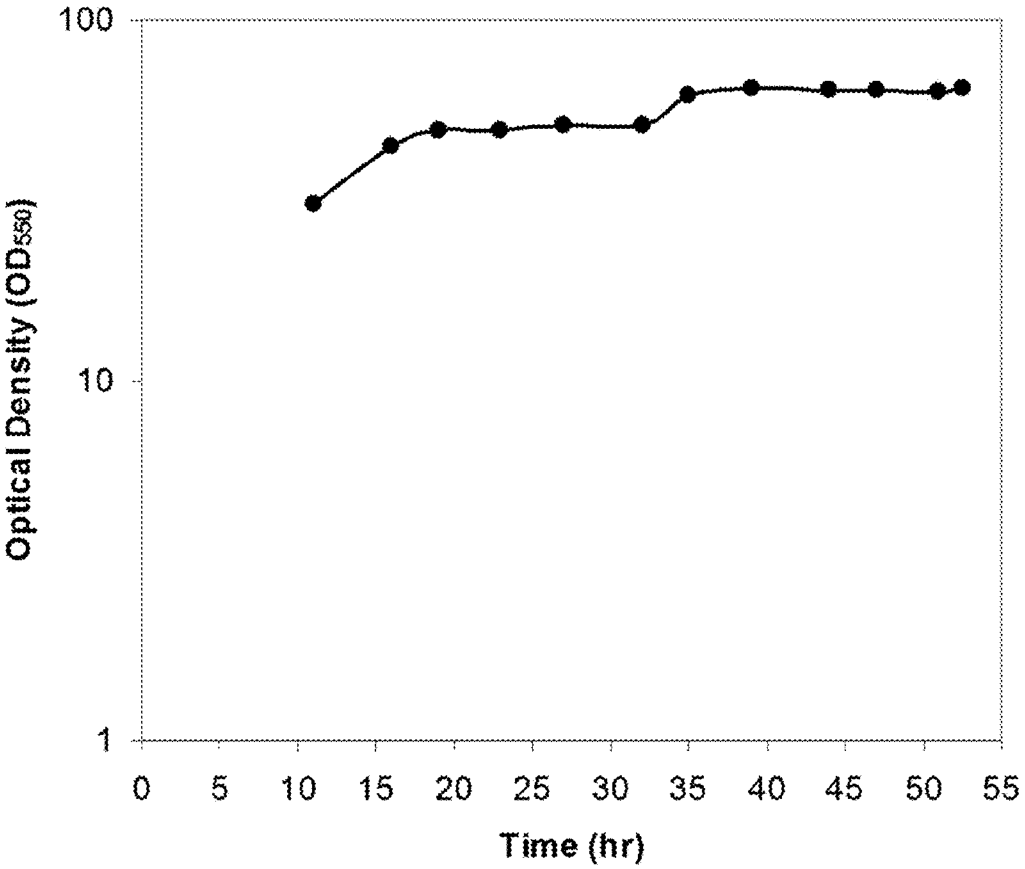
Figure 60B:
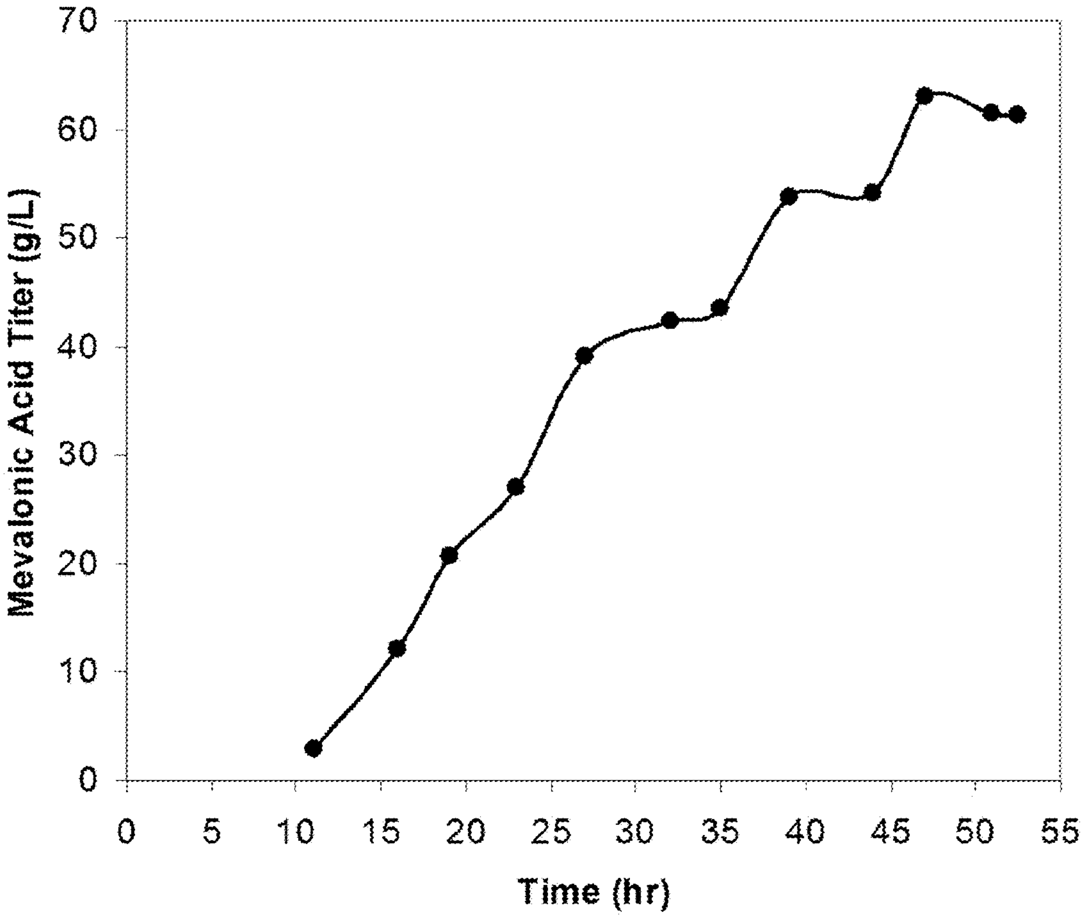
Figure 60C:
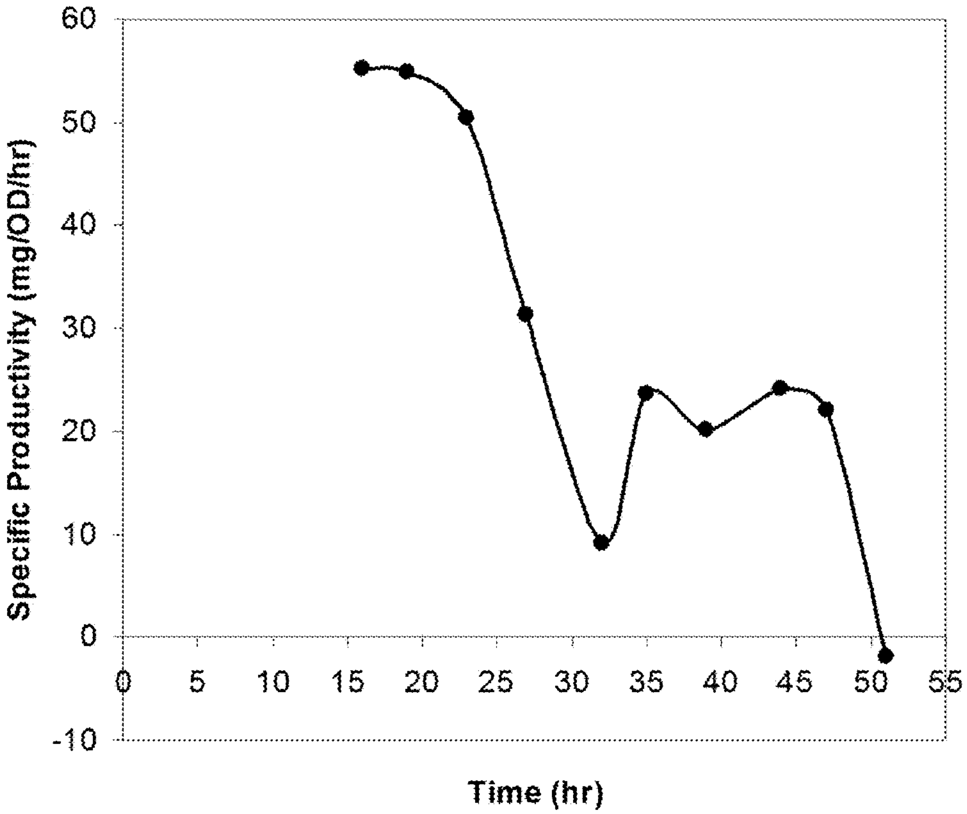

FIGS. 60A-60C are the time courses of optical density, mevalonic acid titer, and specific productivity within the 150-L bioreactor fed with glucose.

Figure 61A:
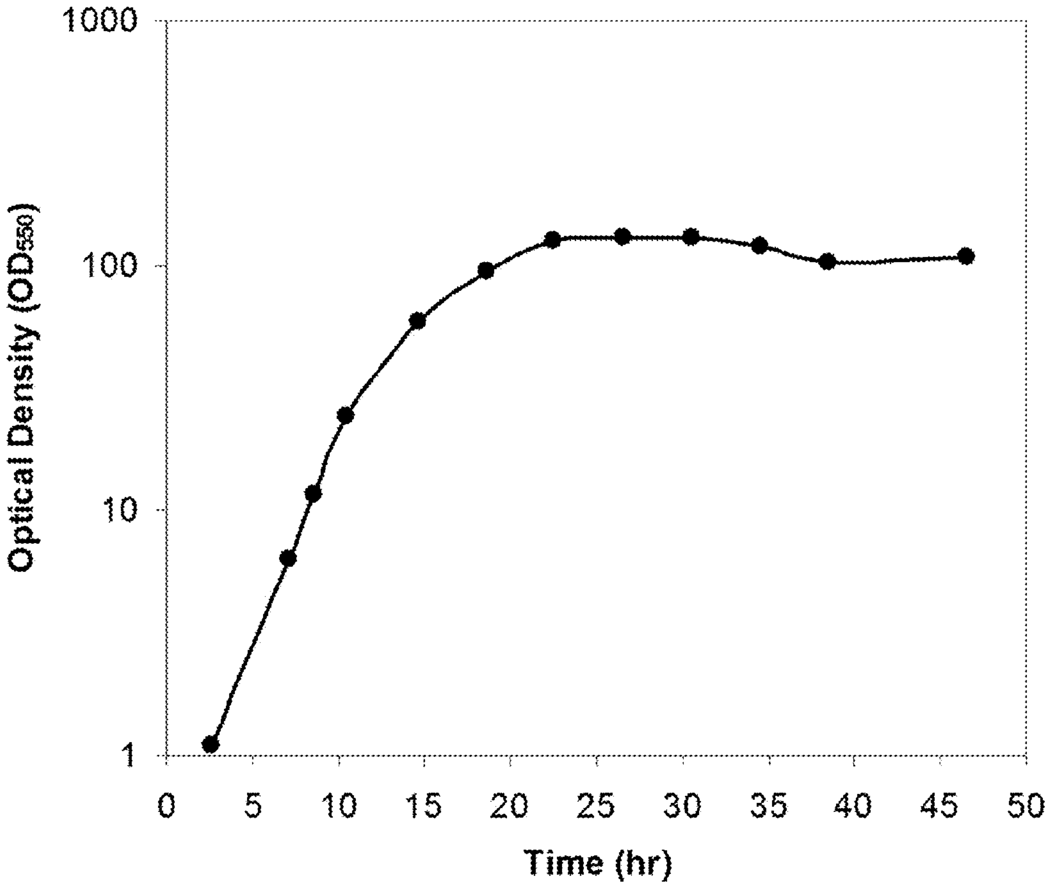
Figure 61B:
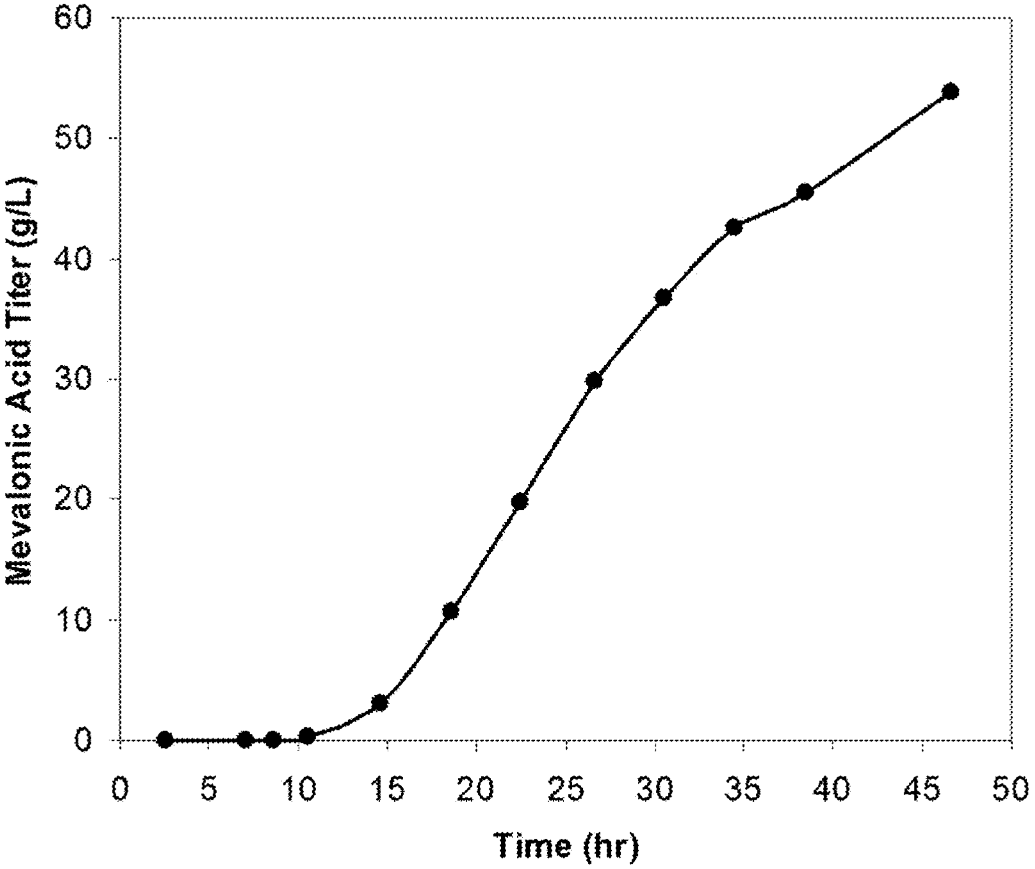
Figure 61C:
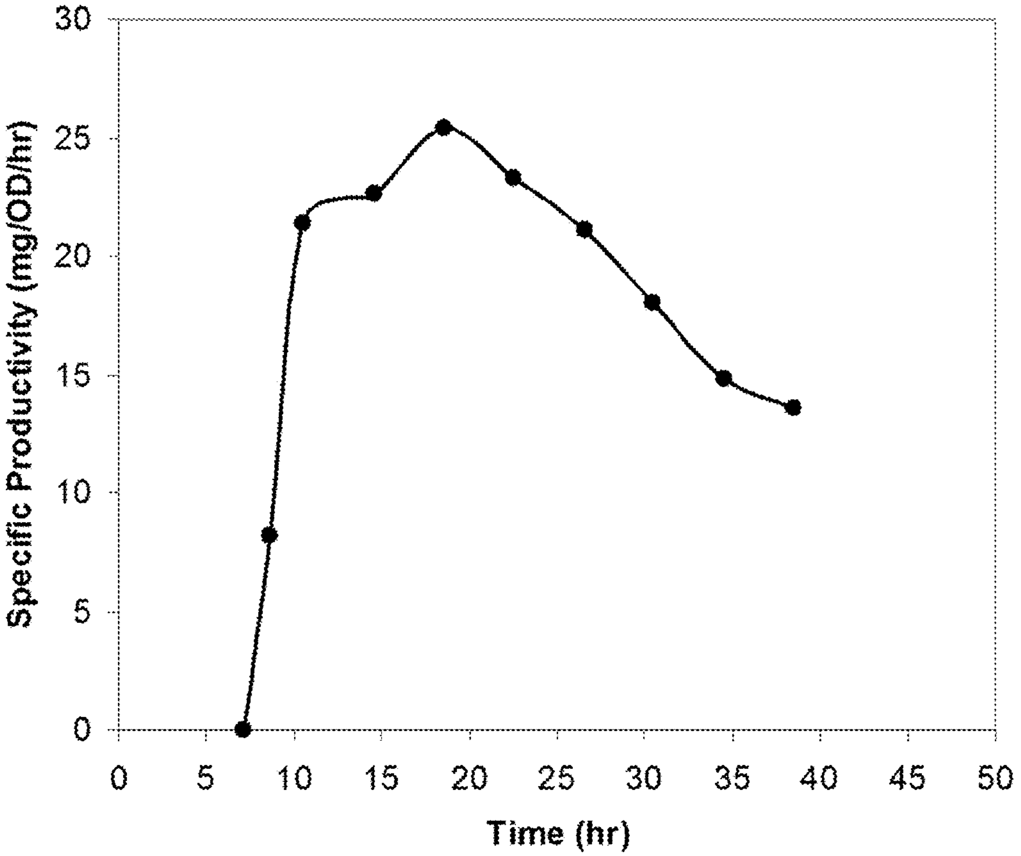

FIGS. 61A-61C are the time courses of optical density, mevalonic acid titer, and specific productivity within the 15-L bioreactor fed with glucose.

Figure 62A:
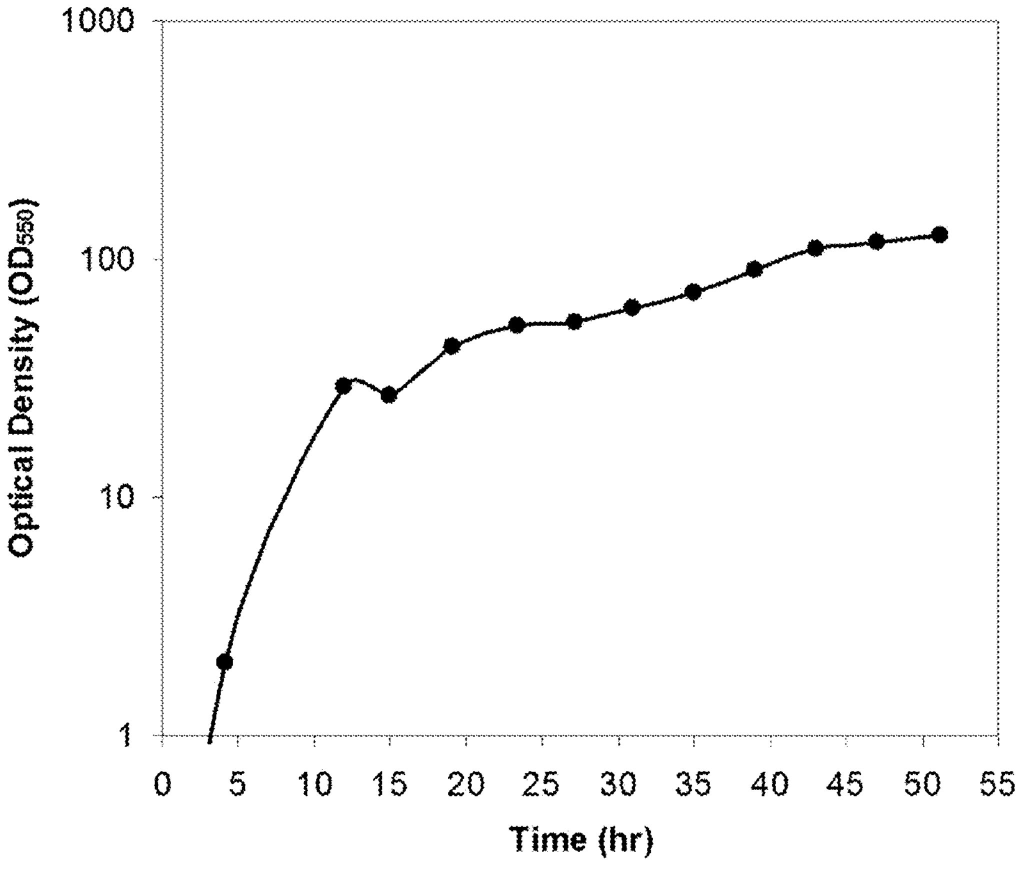
Figure 62B:
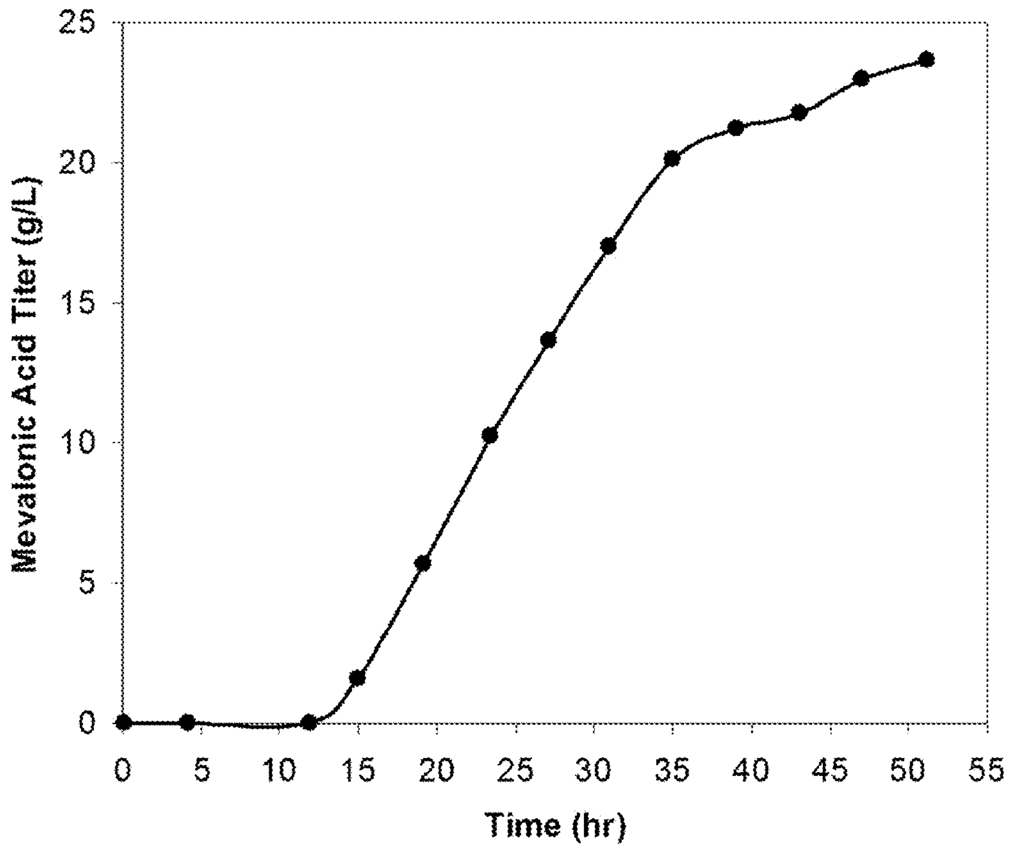
Figure 62C:
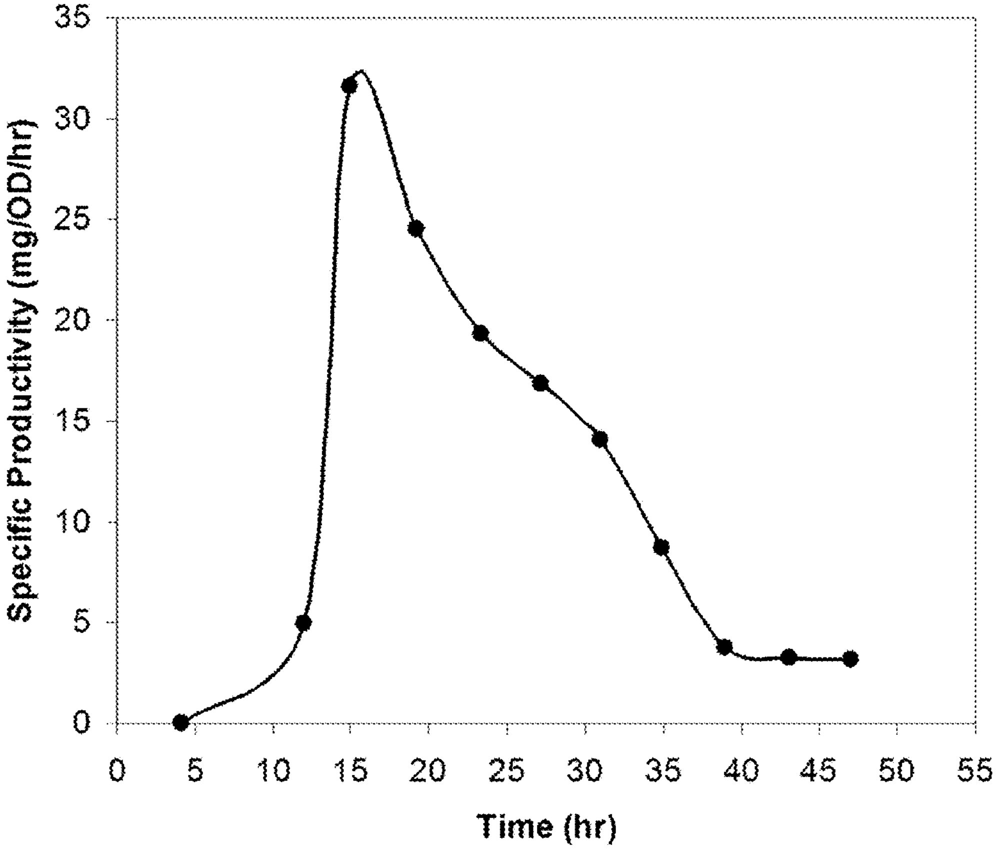

FIGS. 62A-62C are the time courses of optical density, mevalonic acid titer, and specific productivity within the 15-L bioreactor fed with glucose.

Figure 63A:
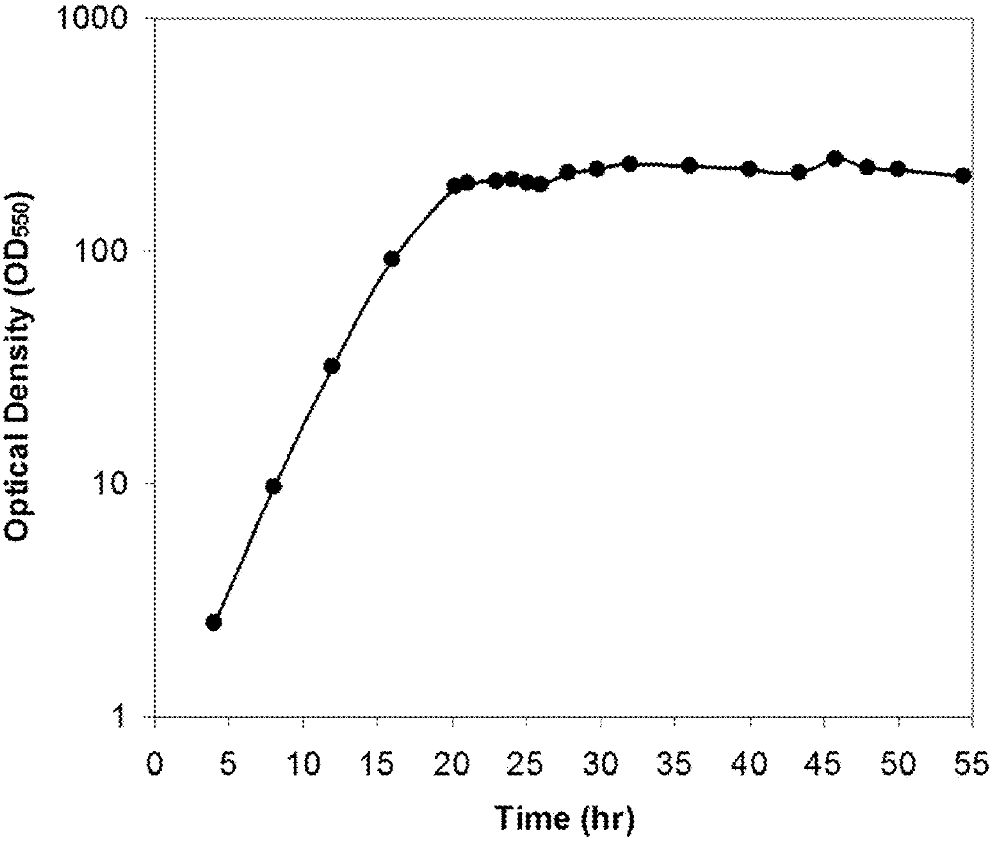
Figure 63B:
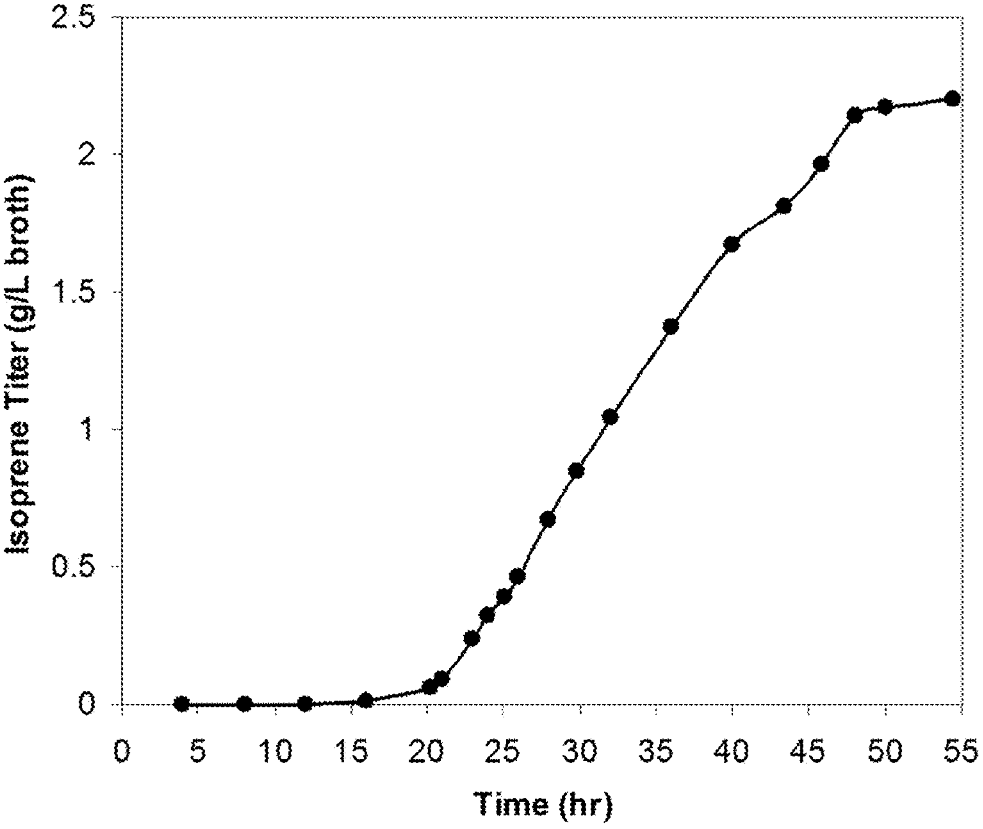
Figure 63C:
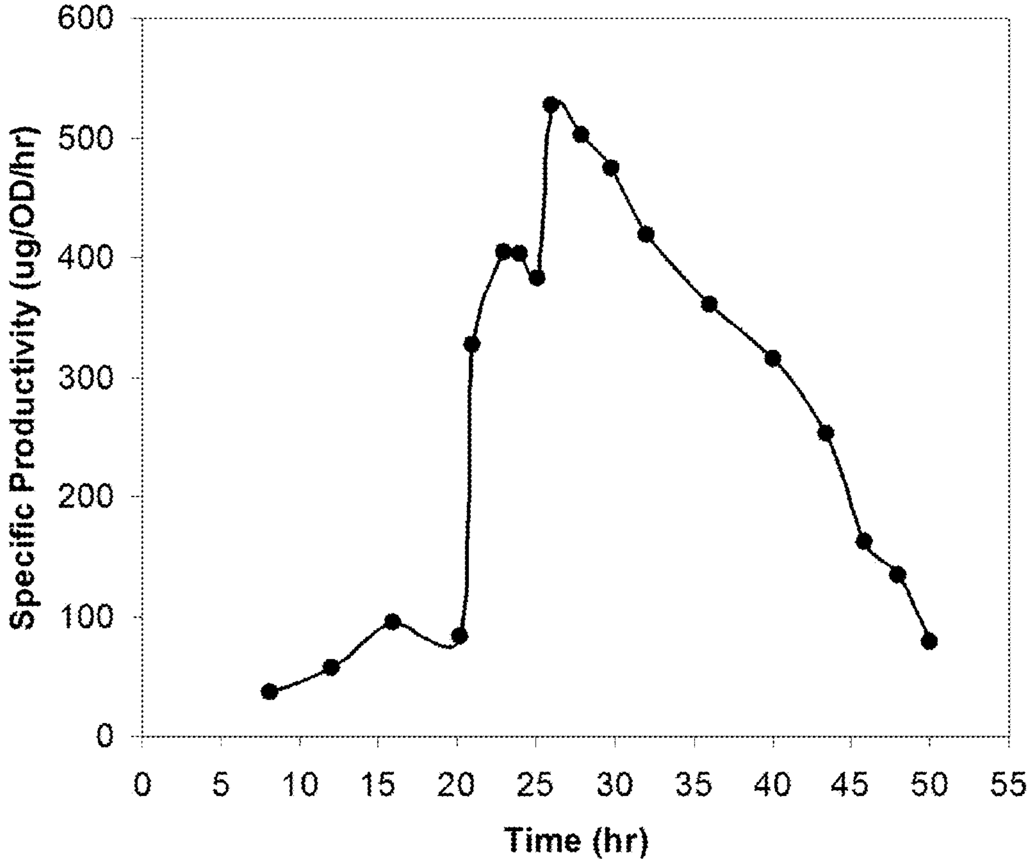

FIG. 63A-63C are the time courses of optical density, isoprene titer, and specific productivity within the 15-L bioreactor fed with glucose.

Figure 64A:
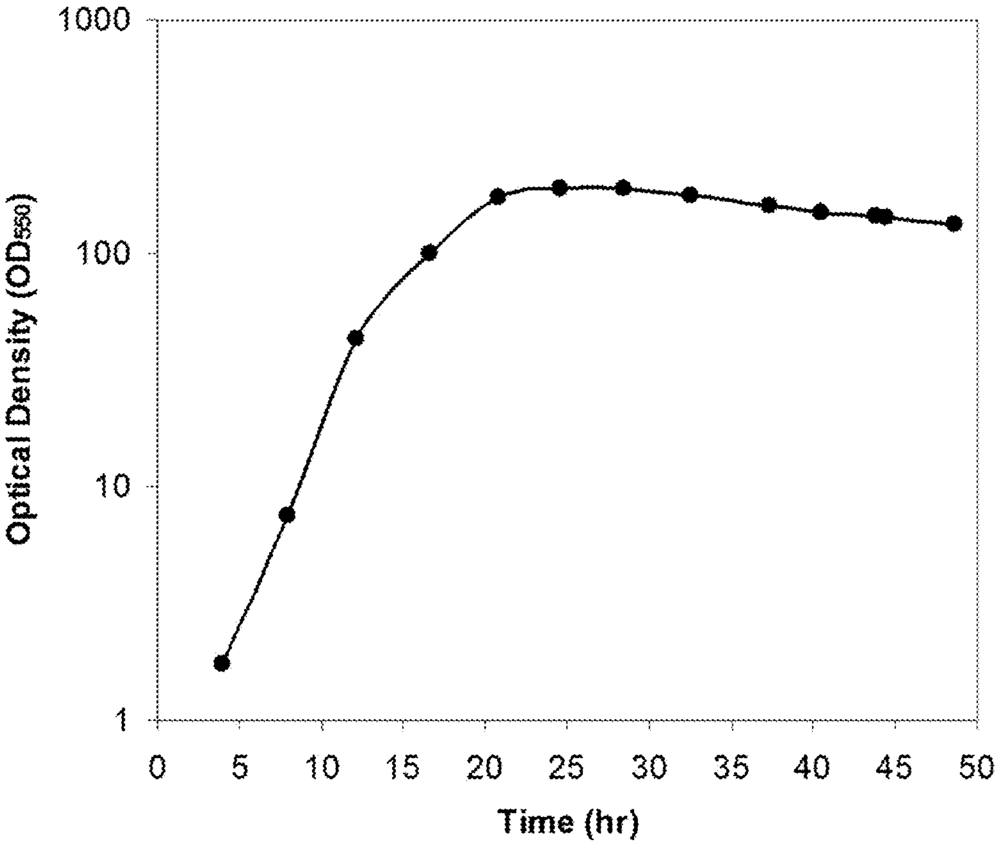
Figure 64B:
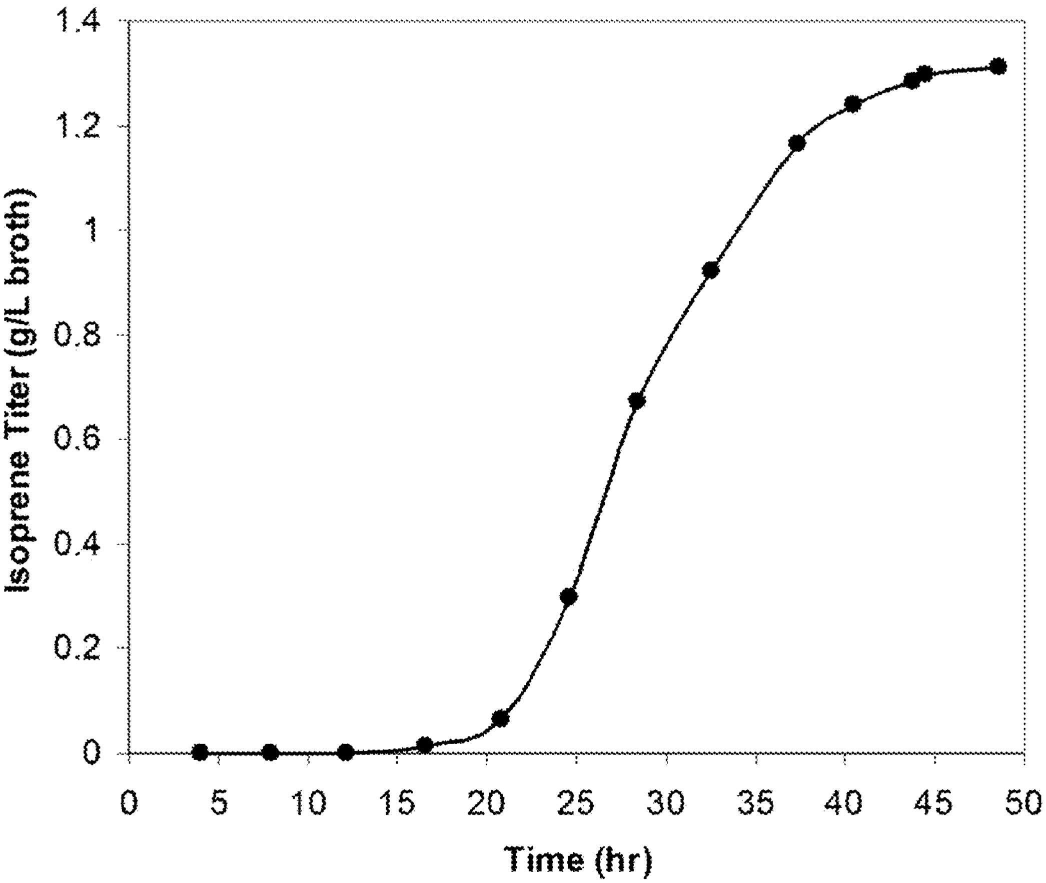
Figure 64C:
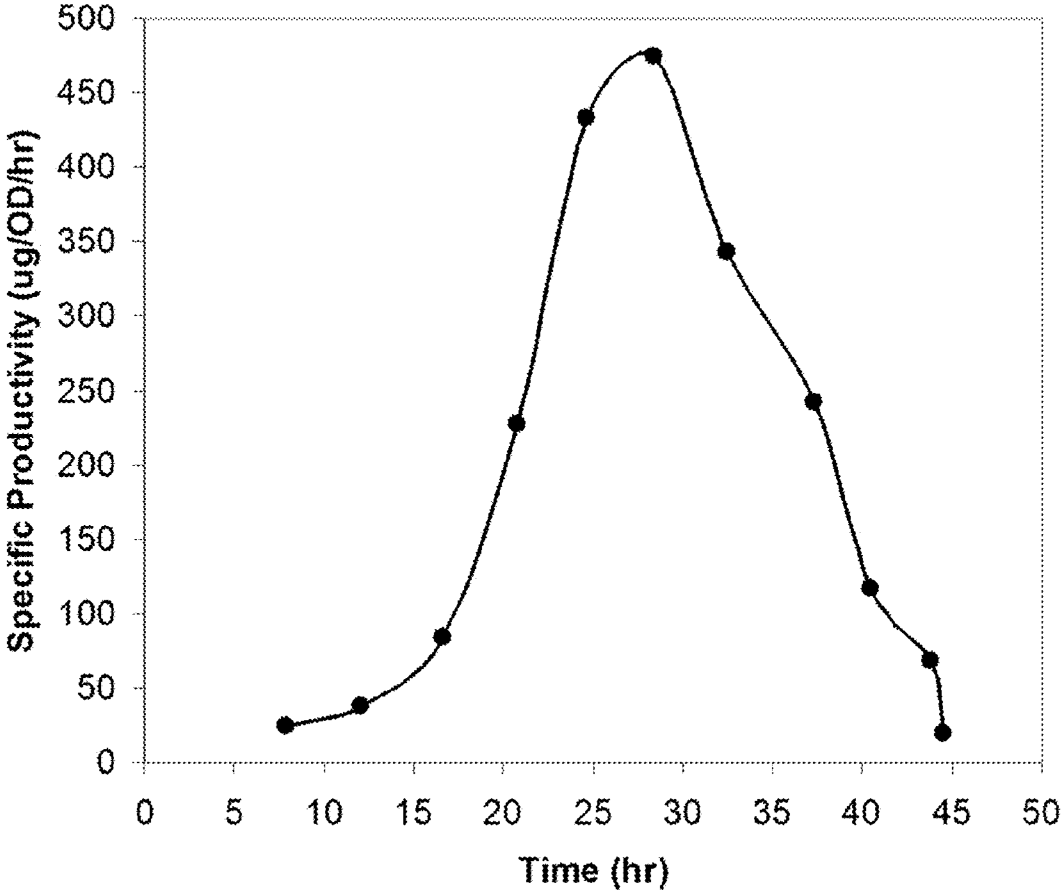

FIGS. 64A-64C are the time courses of optical density, isoprene titer, and specific productivity within the 15-L bioreactor fed with glucose.

Figure 65A:
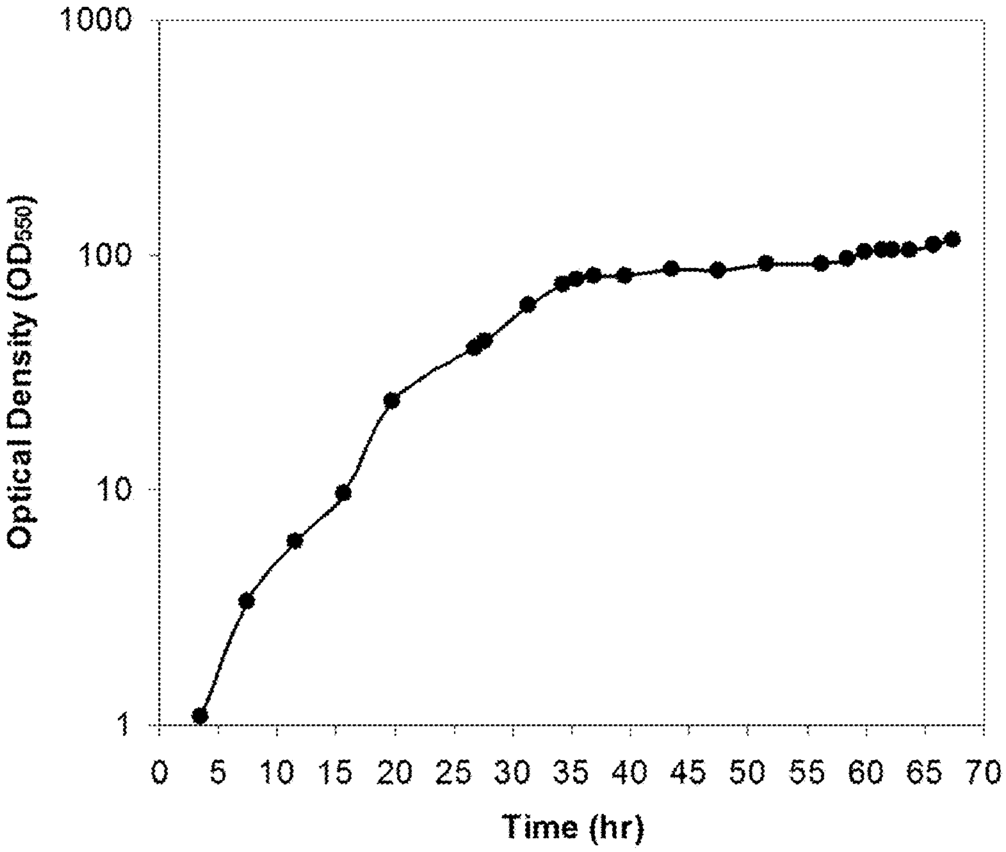
Figure 65B:
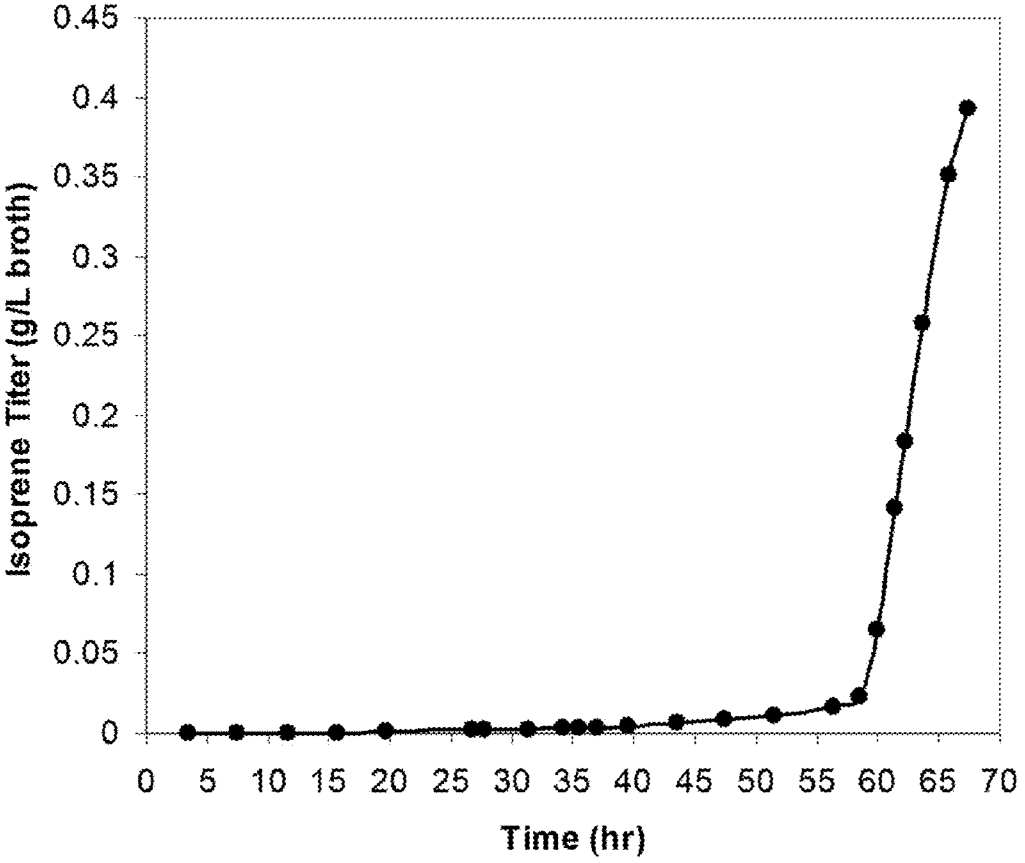
Figure 65C:
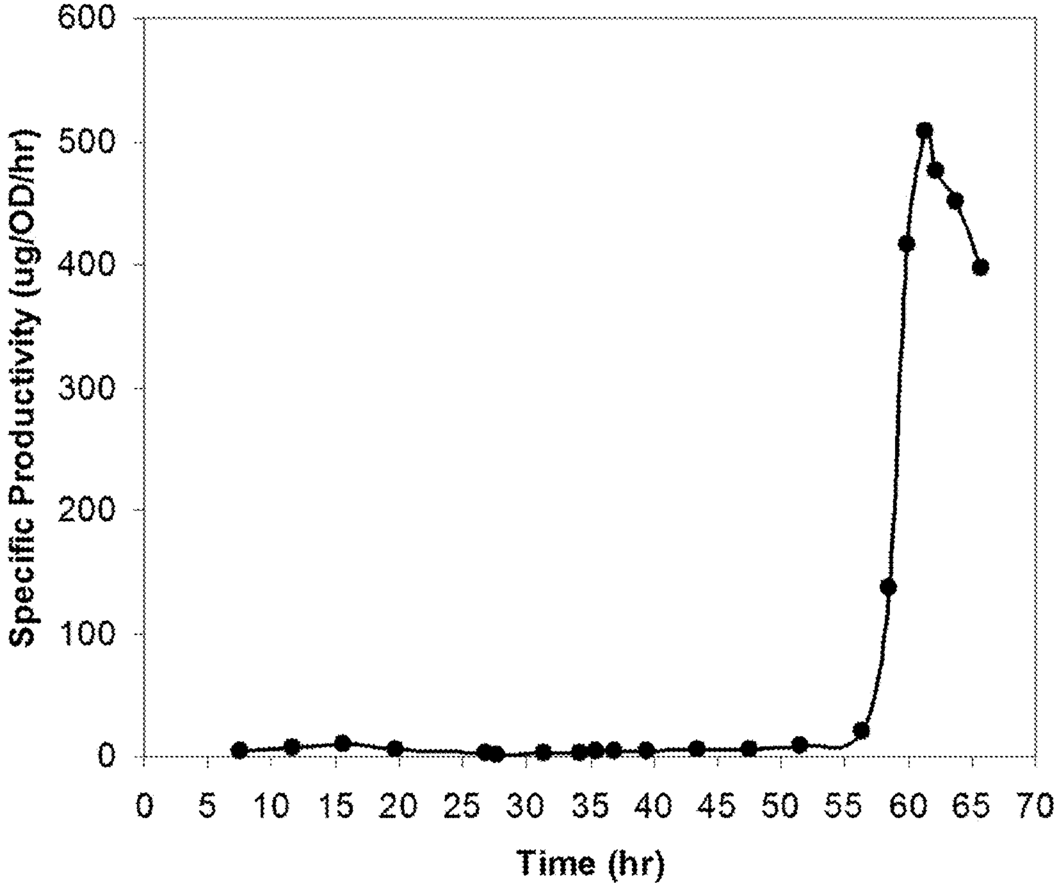

FIGS. 65A-65C are the time courses of optical density, isoprene titer, and specific productivity within the 15-L bioreactor fed with glucose.

Figure 66A:
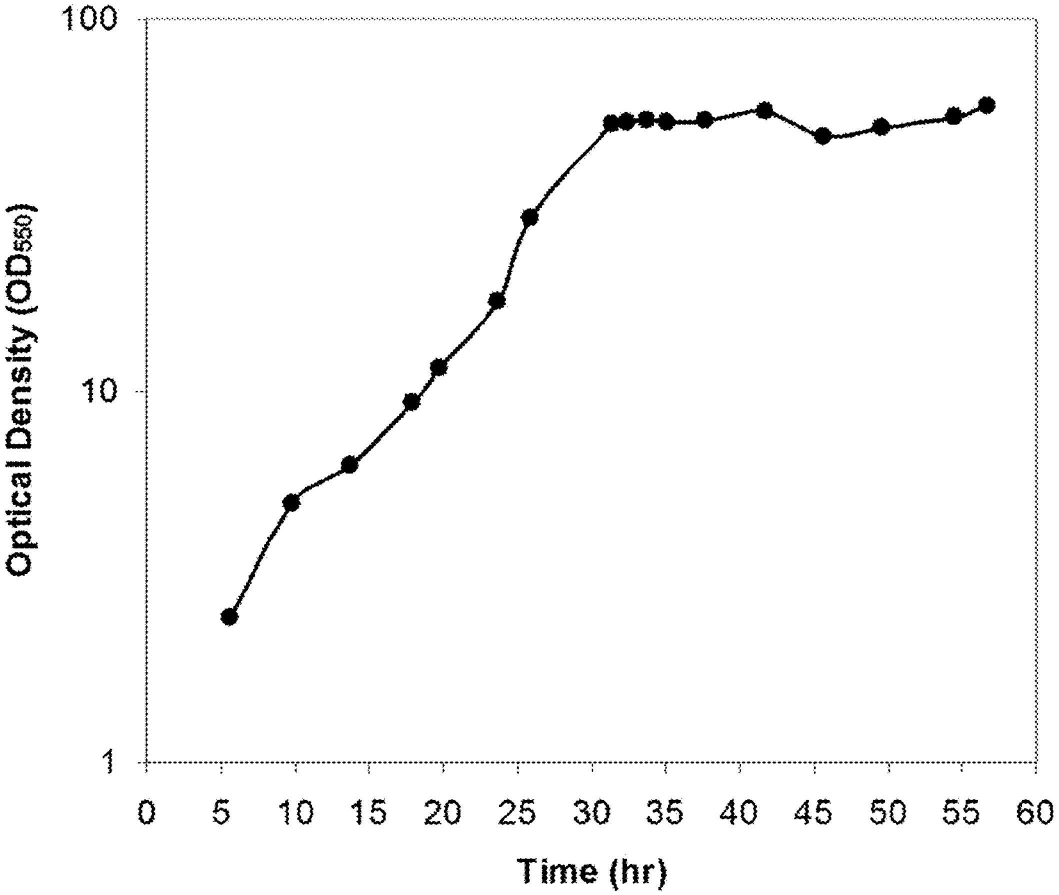
Figure 66B:
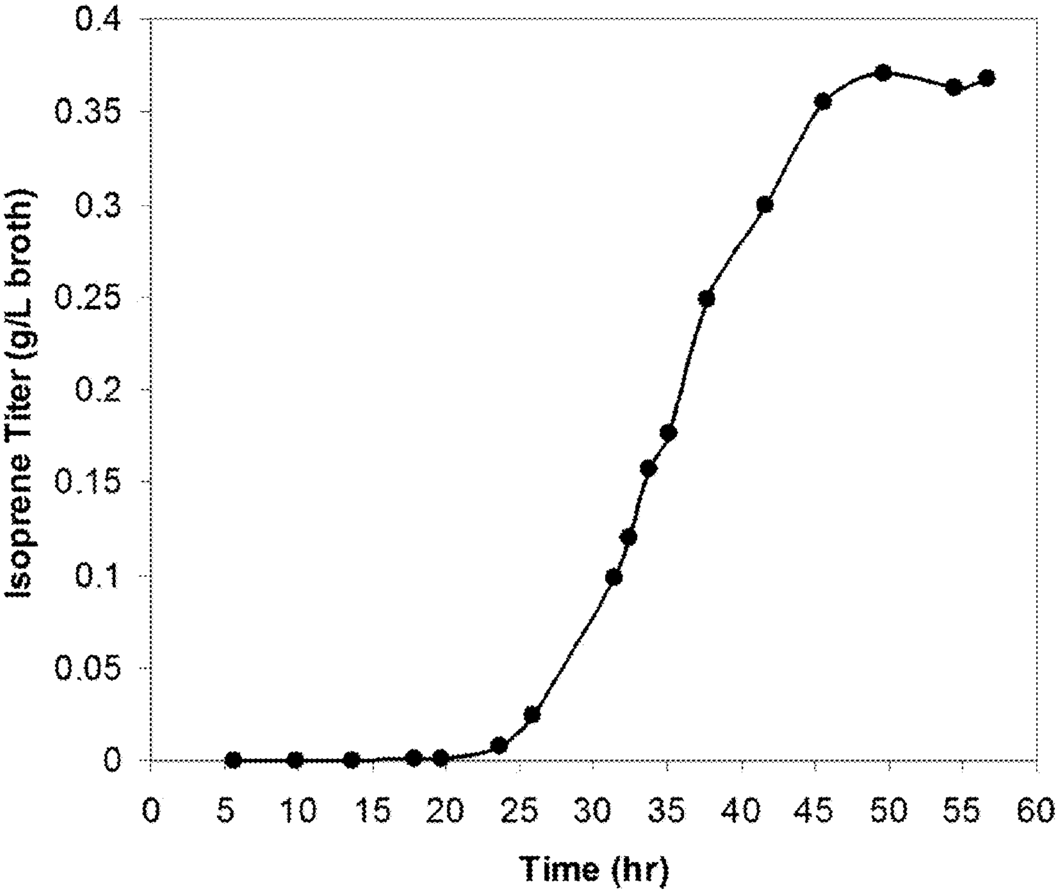
Figure 66C:
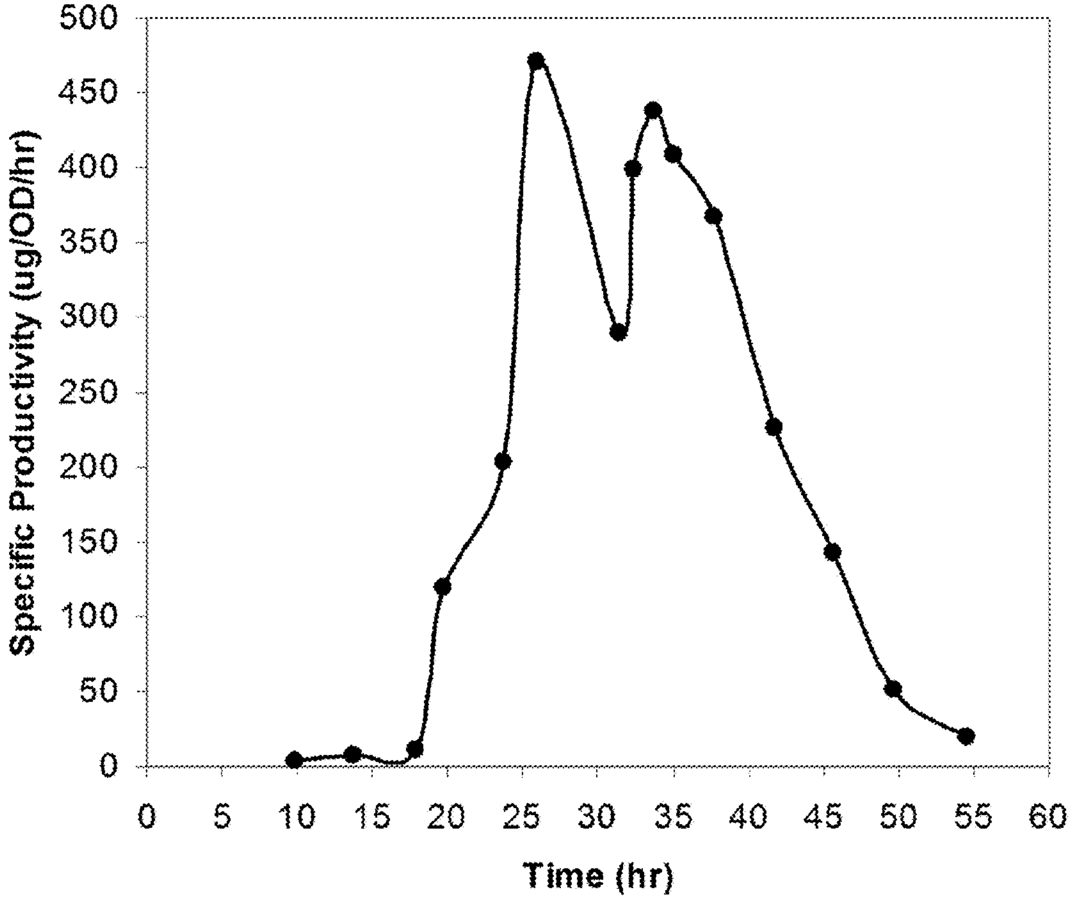

FIGS. 66A-66C are the time courses of optical density, isoprene titer, and specific productivity within the 15-L bioreactor fed with glucose.

Figure 67A:
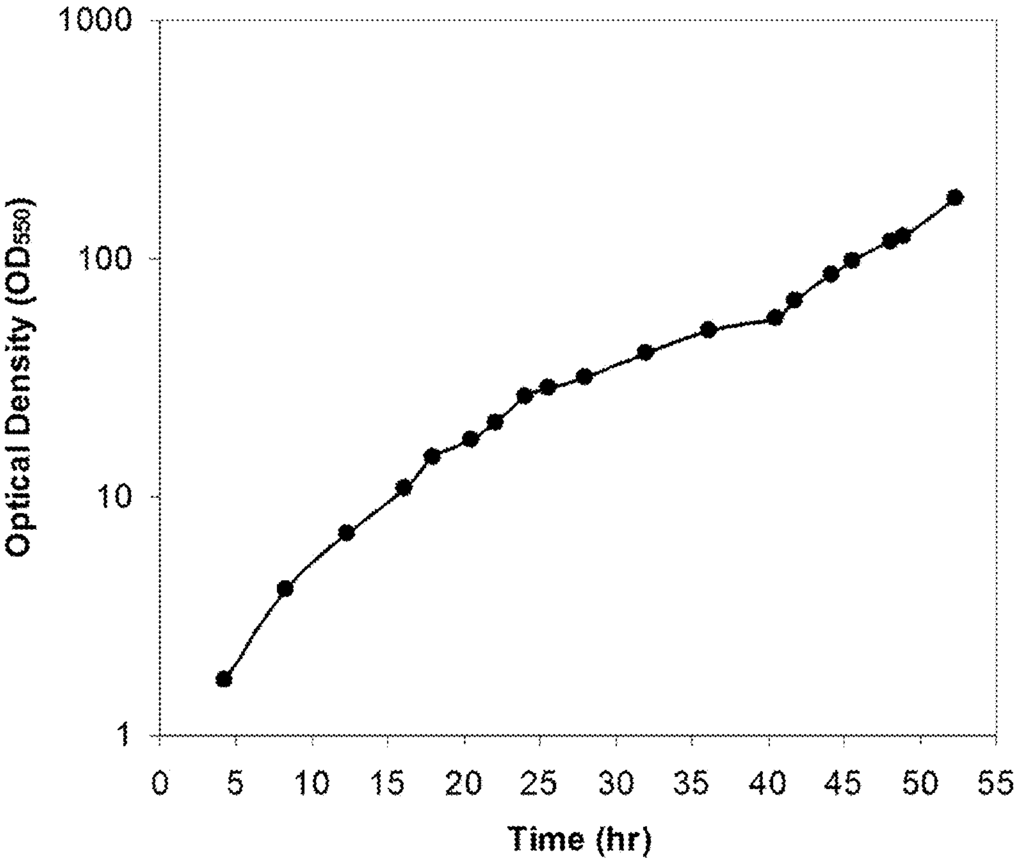
Figure 67B:
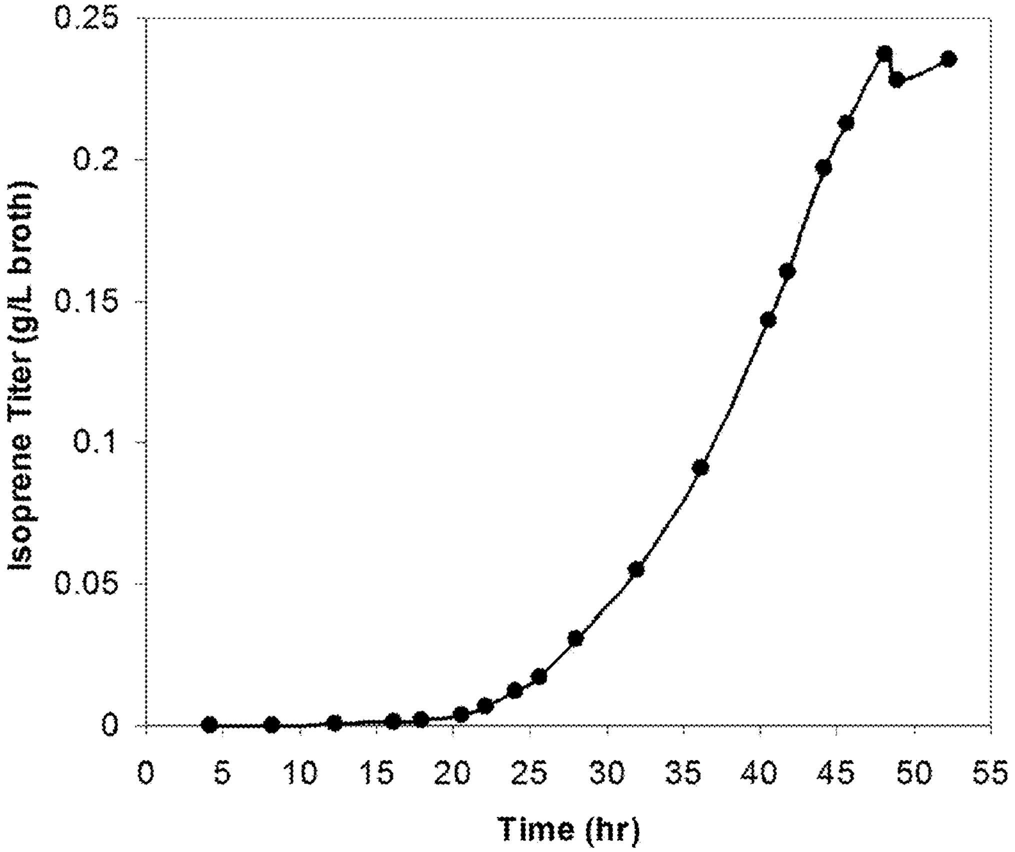
Figure 67C:
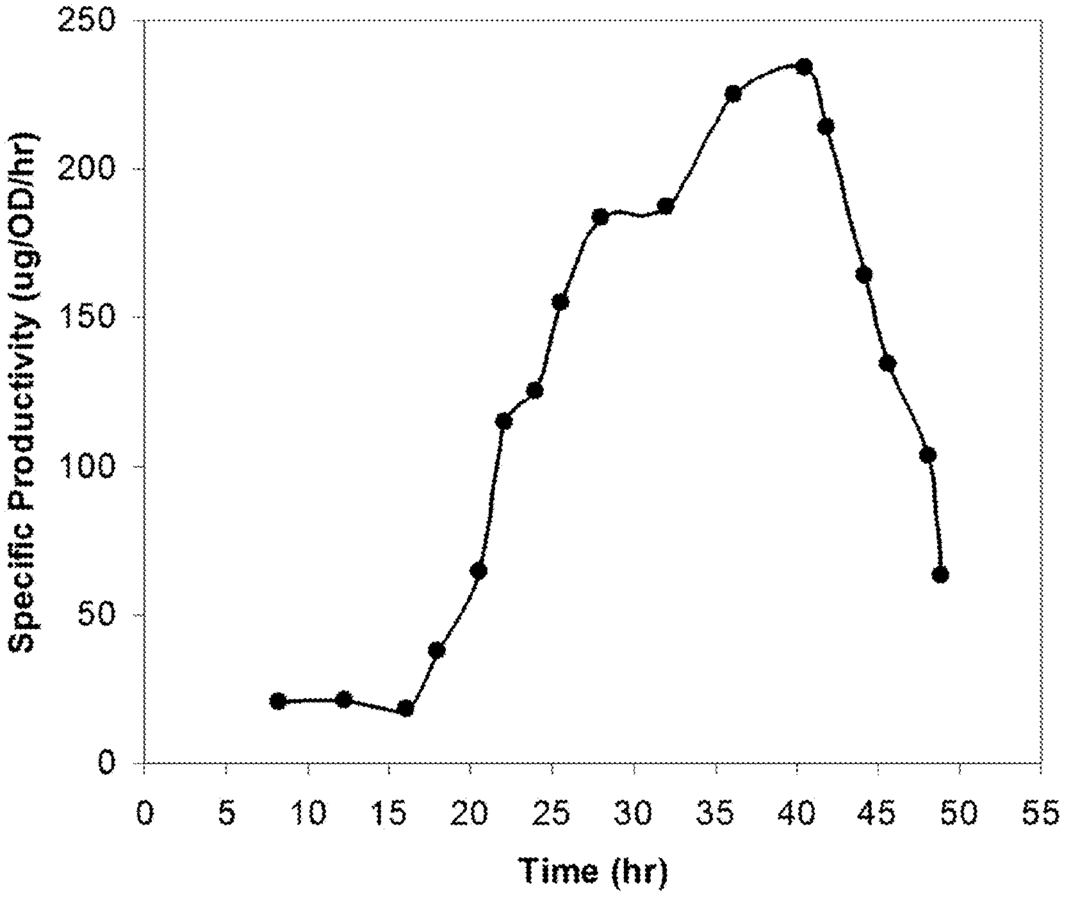

FIG. 67A-67C are the time courses of optical density, isoprene titer, and specific productivity within the 15-L bioreactor fed with glucose.

Figure 68:
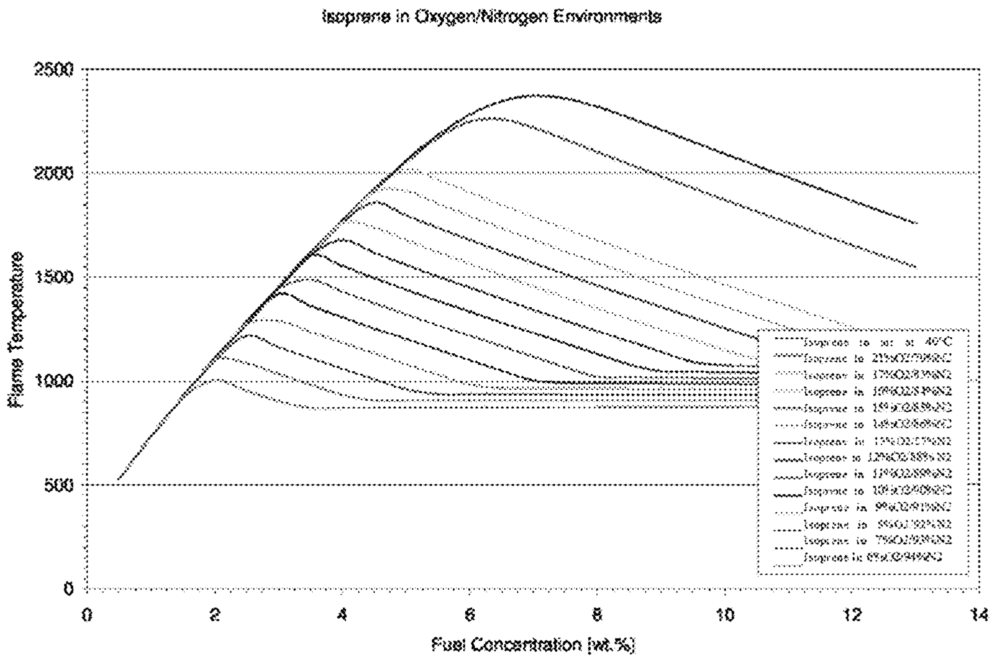

FIG. 68 is a graph of the calculated adiabatic flame temperatures for Series A as a function of fuel concentration for various oxygen levels. The figure legend lists the curves in the order in which they appear in the graph. For example, the first entry in the figure legend (isoprene in air at 40° C.) corresponds to the highest curve in the graph.

Figure 69:
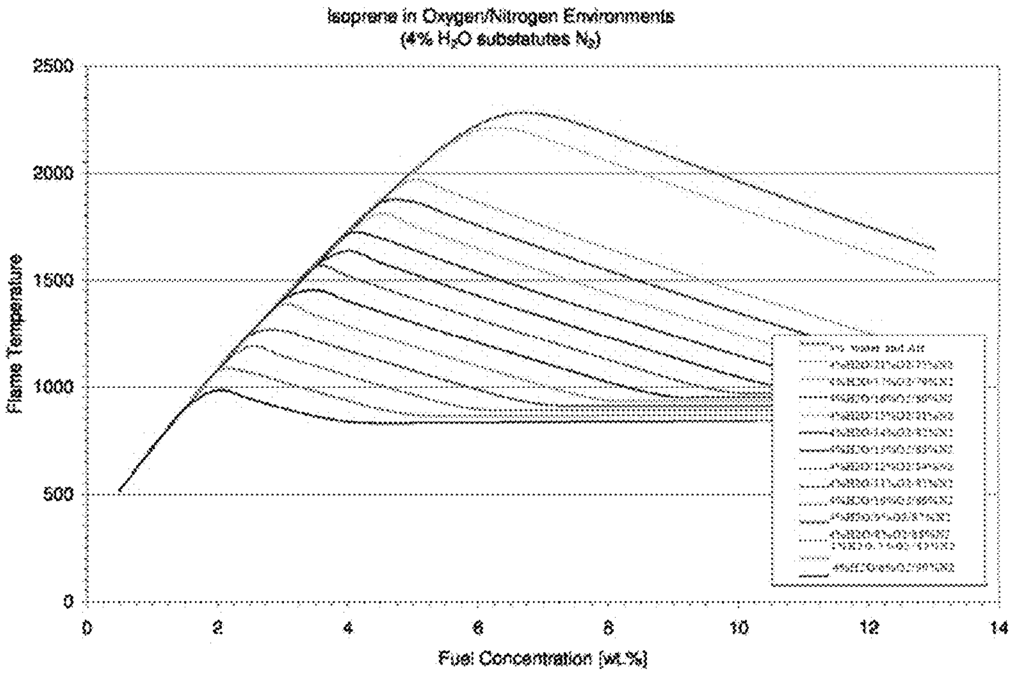

FIG. 69 is a graph of the calculated adiabatic flame temperatures for Series B as a function of fuel concentration for various oxygen levels with 4% water. The figure legend lists the curves in the order in which they appear in the graph.

Figure 70:
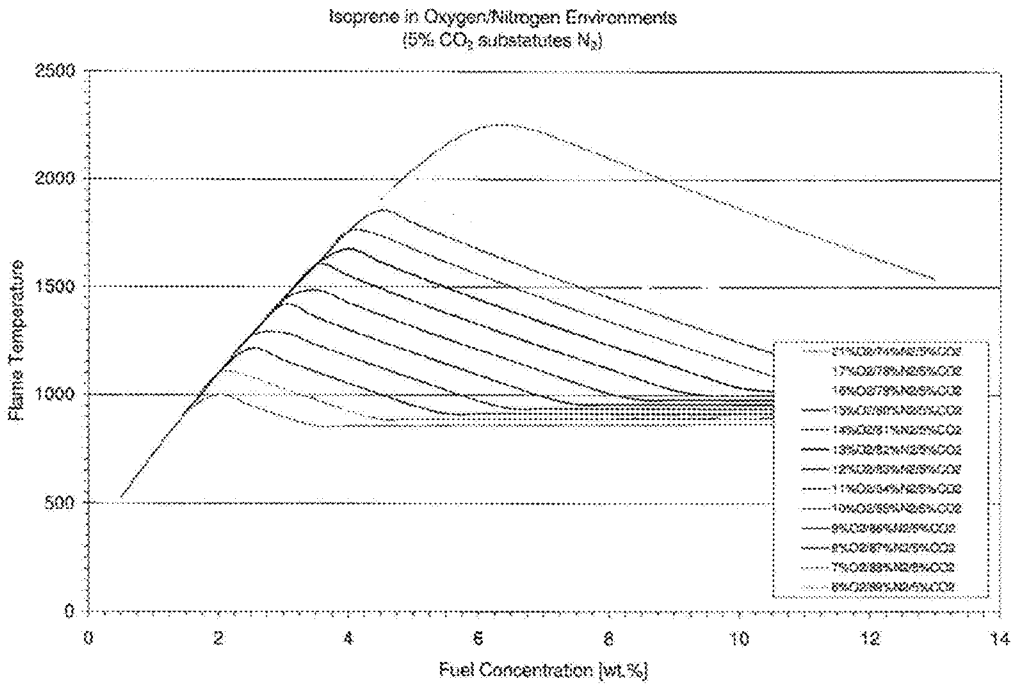

FIG. 70 is a graph of the calculated adiabatic flame temperatures for Series C as a function of fuel concentration for various oxygen levels with 5% $CO_2$. The figure legend lists the curves in the order in which they appear in the graph.

Figure 71:
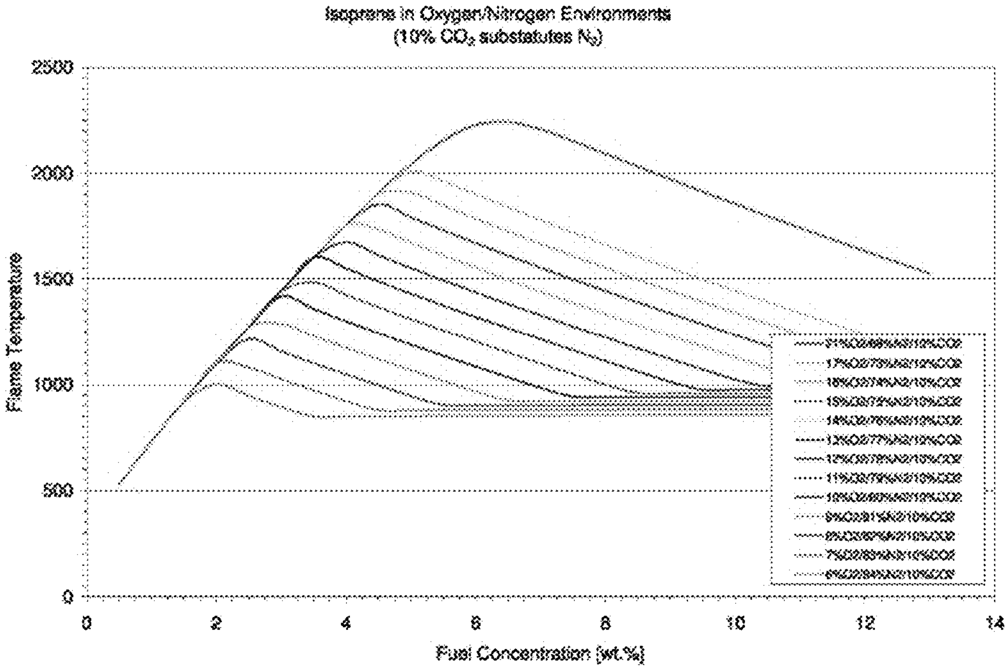

FIG. 71 is a graph of the calculated adiabatic flame temperatures for Series D as a function of fuel concentration for various oxygen levels with 10% $CO_2$. The figure legend lists the curves in the order in which they appear in the graph.

Figure 72:
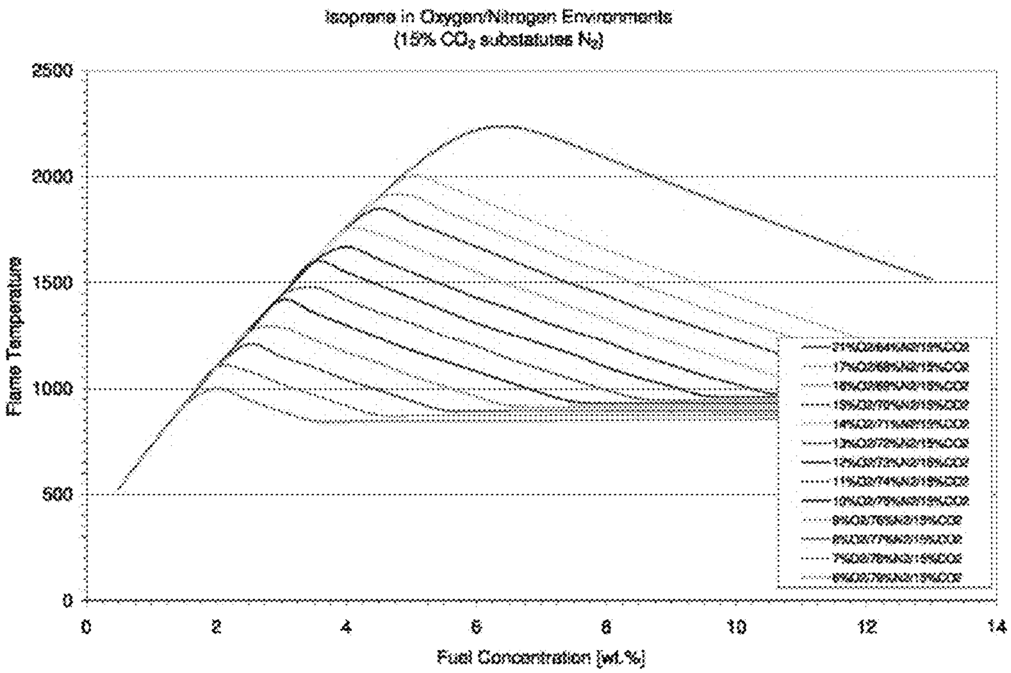

FIG. 72 is a graph of the calculated adiabatic flame temperatures for Series E as a function of fuel concentration for various oxygen levels with 15% $CO_2$. The figure legend lists the curves in the order in which they appear in the graph.

Figure 73:
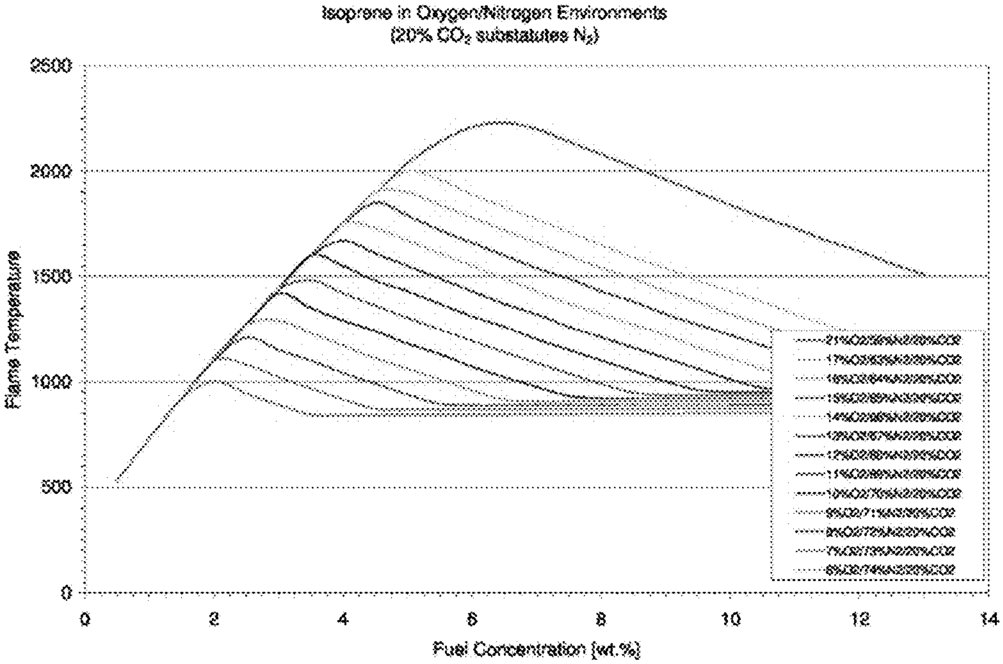

FIG. 73 is a graph of the calculated adiabatic flame temperatures for Series F as a function of fuel concentration for various oxygen levels with 20% $CO_2$. The figure legend lists the curves in the order in which they appear in the graph.

Figure 74:
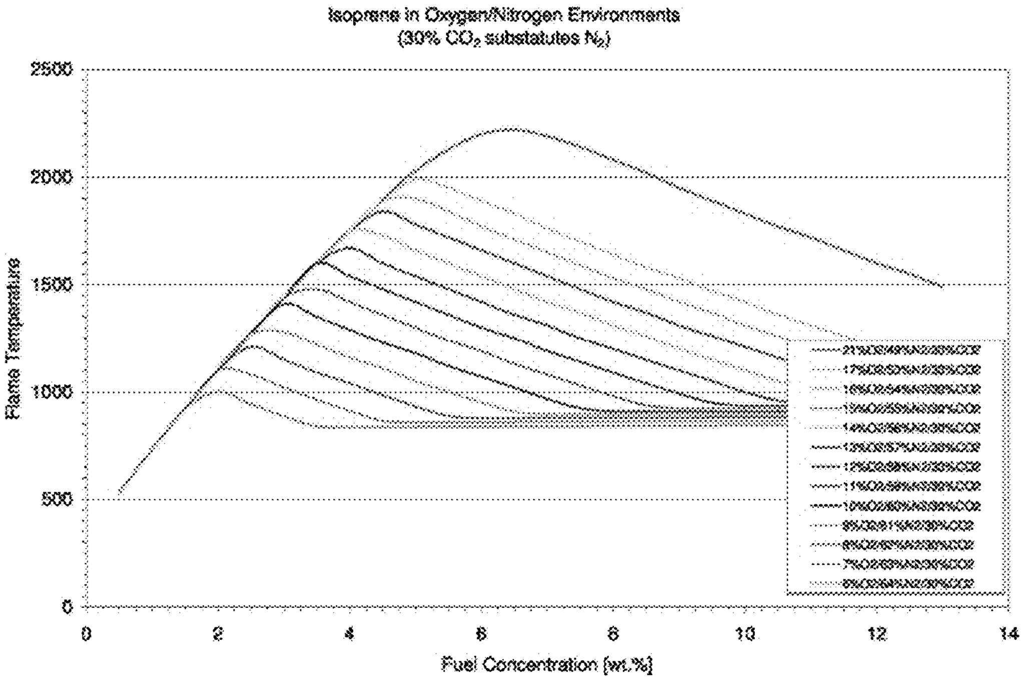

FIG. 74 is a graph of the calculated adiabatic flame temperatures for Series G as a function of fuel concentration for various oxygen levels with 30% $CO_2$. The figure legend lists the curves in the order in which they appear in the graph.

Figures 75A, 75B:
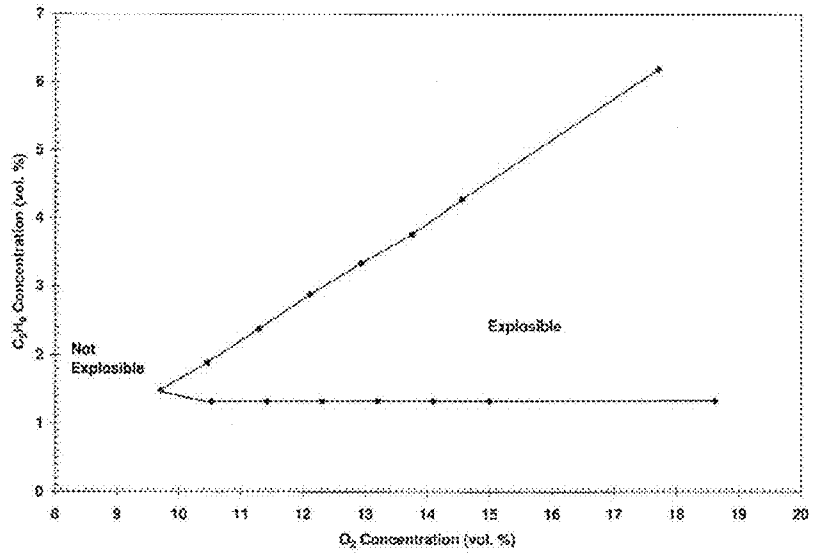

FIG. 75A is a table of the conversion of the CAFT Model results from weight percent to volume percent for series A.

FIG. 75B is a graph of the flammability results from the CAFT model for Series A in FIG. 68 plotted as volume percent.

Figures 76A, 76B:
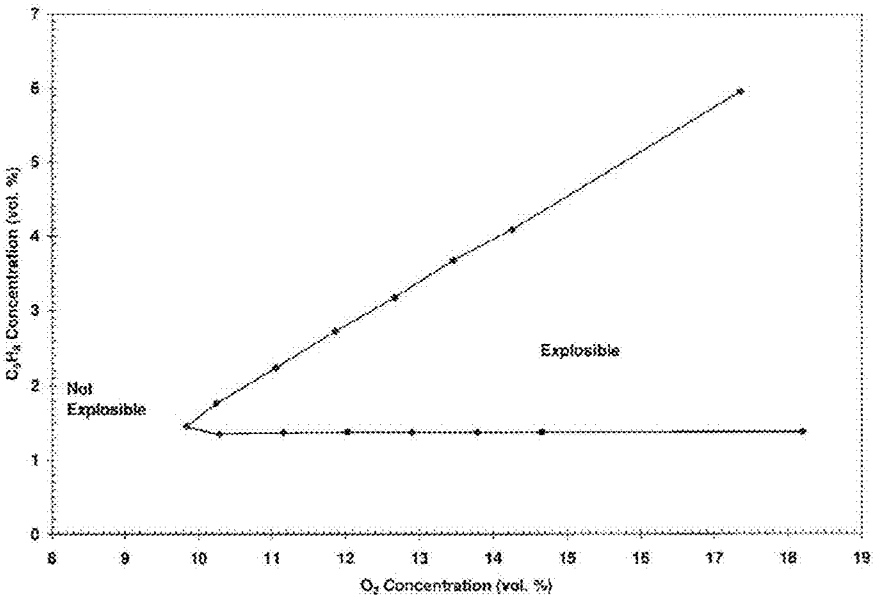

FIG. 76A is a table of the conversion of the CAFT Model results from weight percent to volume percent for series B.

FIG. 76B is a graph of the flammability results from the CAFT model for Series B in FIG. 69 plotted as volume percent.

Figure 77:
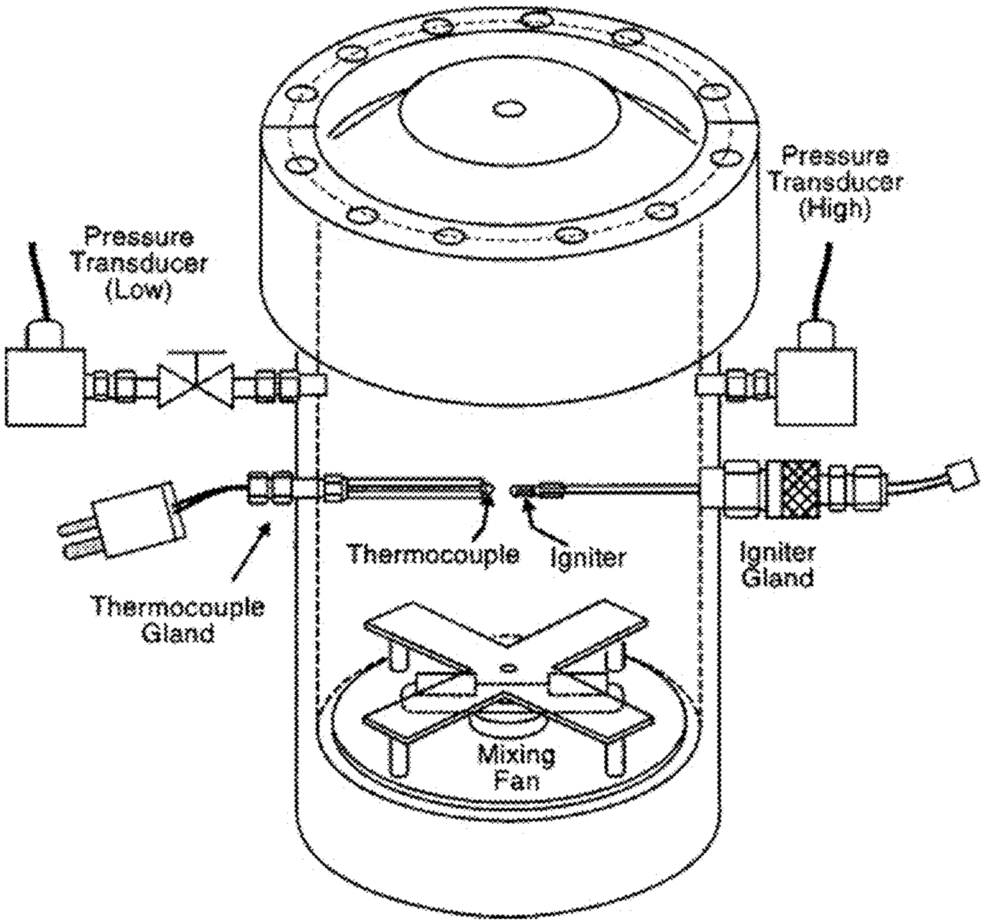

FIG. 77 is a figure of the flammability test vessel.

Figure 78A:
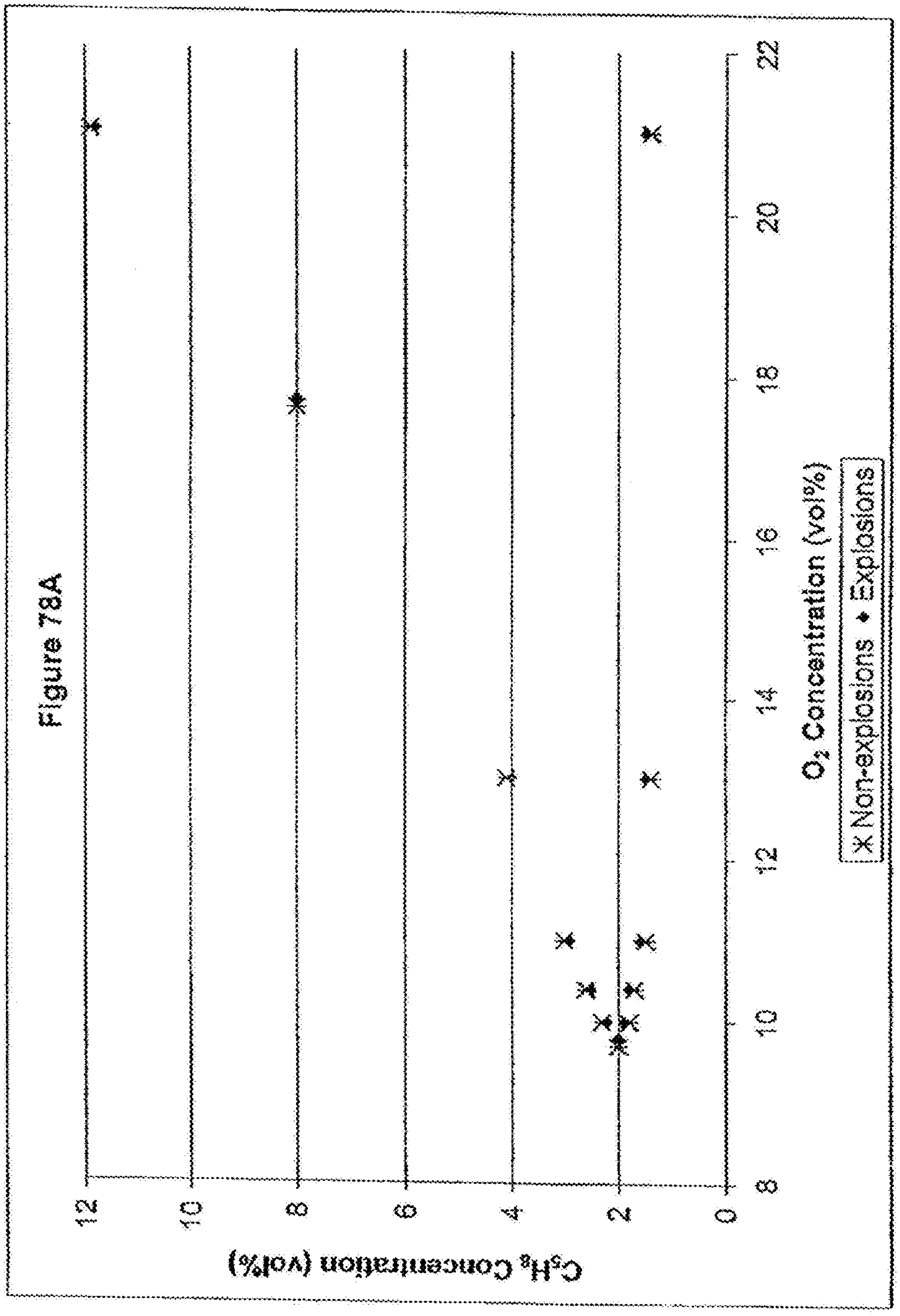

FIG. 78A is a graph of the flammability Curve for Test Series 1: 0% Steam, 0 psig, and 40° C.

FIG. 78B is a table summarizing the explosion and non-explosion data points for Test Series 1.

Figure 78C:
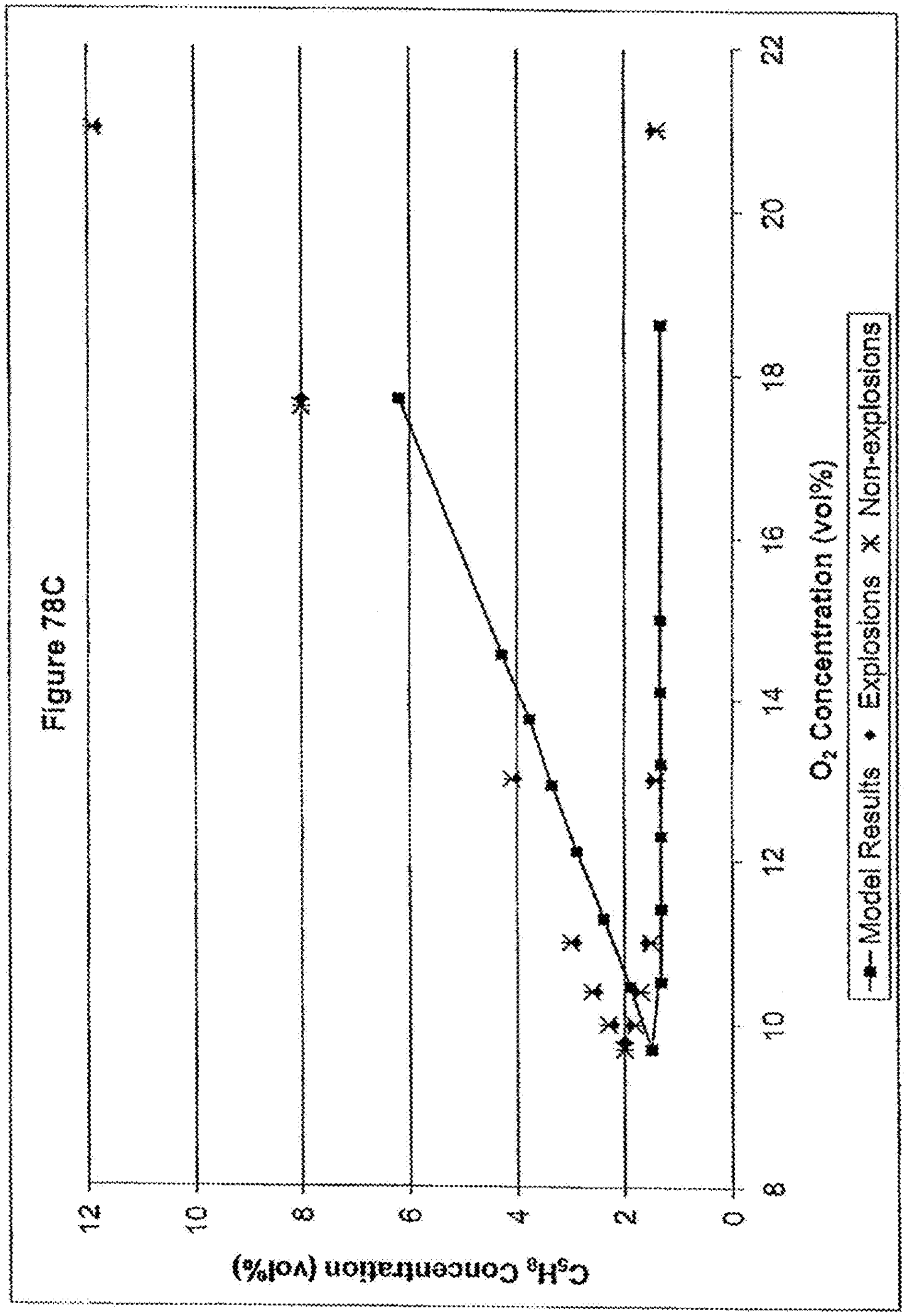

FIG. 78C is a graph of the flammability curve for Test Series 1 compared with the CAFT Model.

Figure 79A:
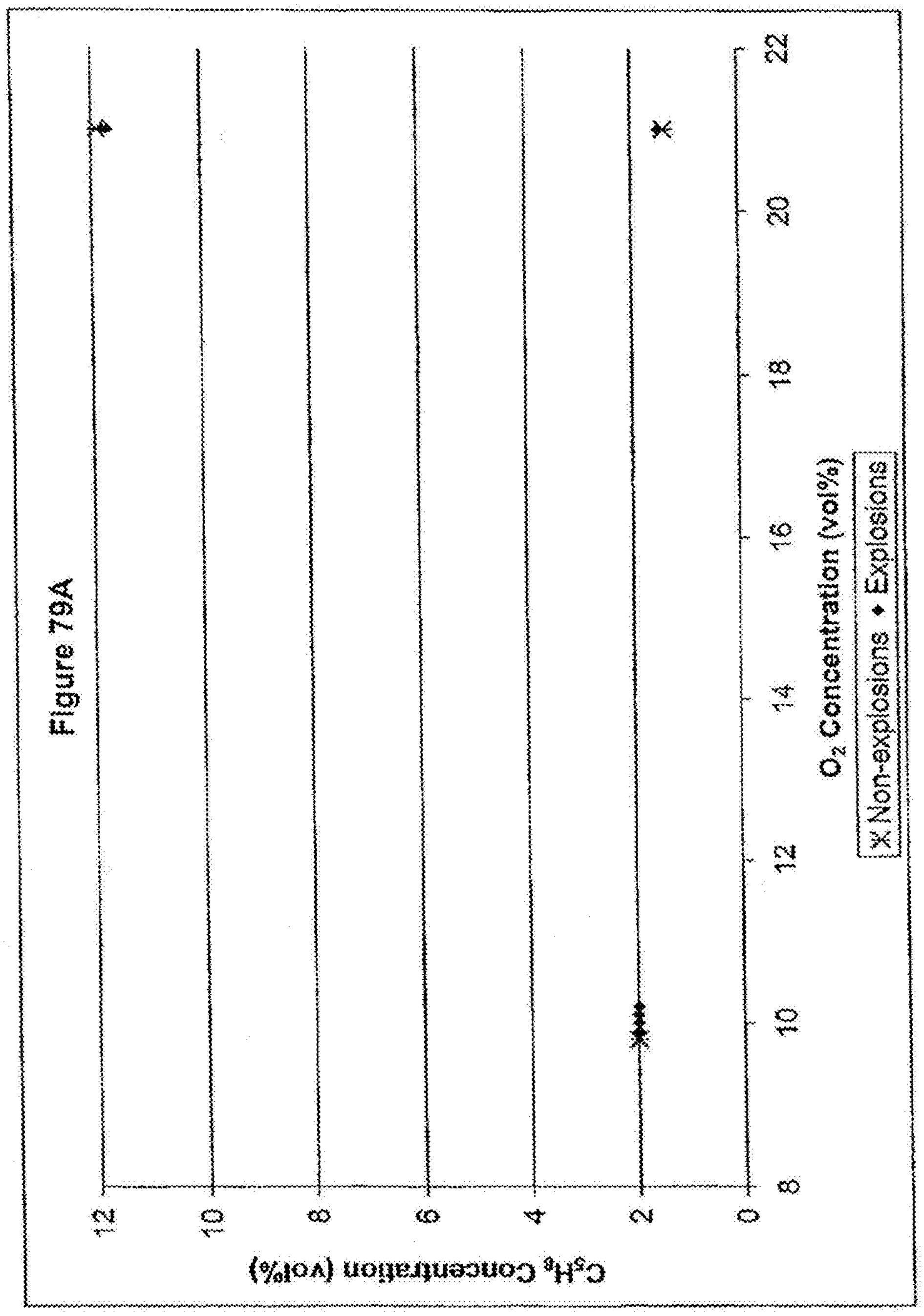

FIG. 79A is a graph of the flammability curve for Test Series 2: 4% Steam, 0 psig, and 40° C.

FIG. 79B is a table summarizing the explosion and non-explosion data points for Test Series 2.

Figure 79C:
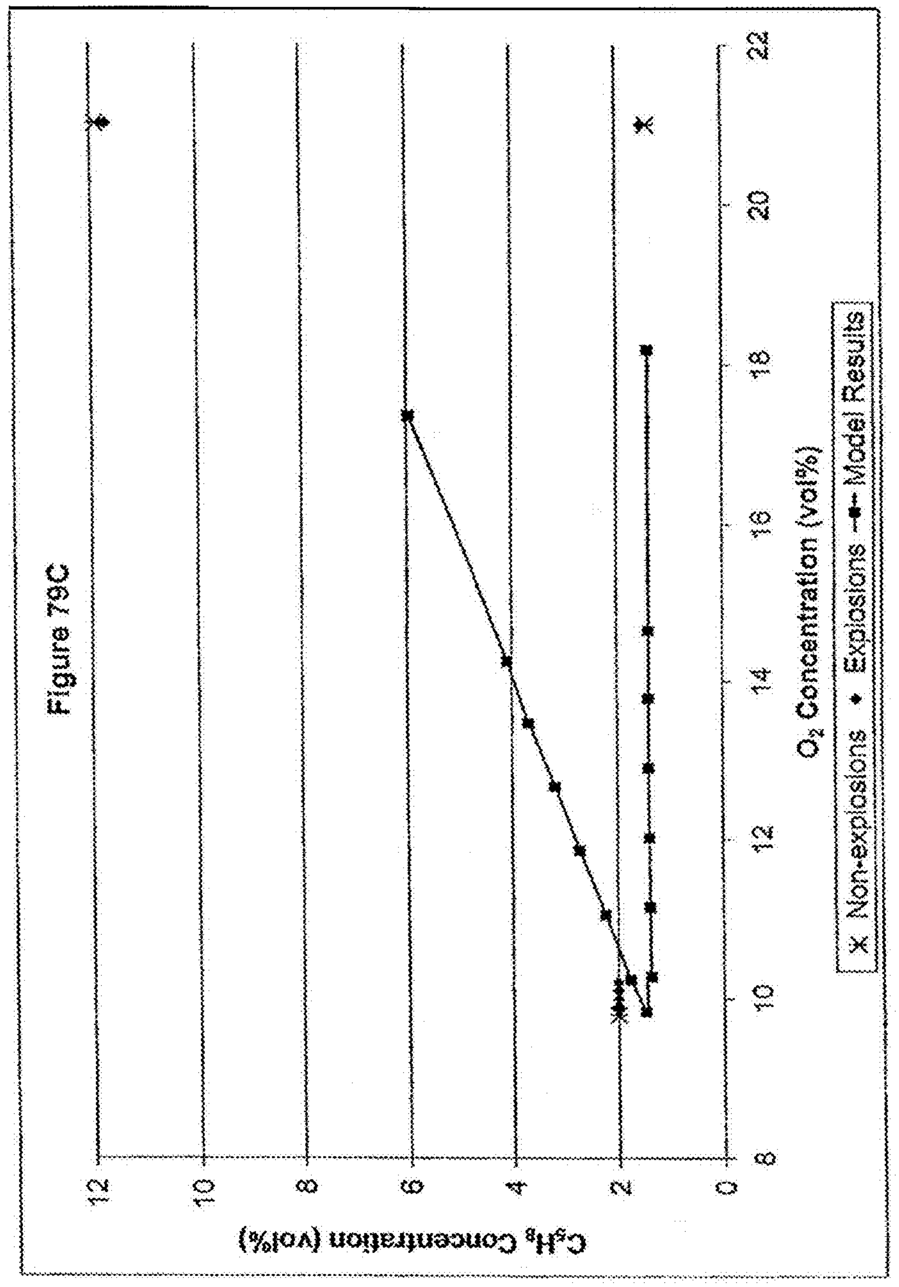

FIG. 79C is a graph of the flammability curve for Test Series 2 compared with the CAFT Model.

FIGS. 80A and 80B are a table of the detailed experimental conditions and results for Test Series 1.

FIG. 81 is a table of the detailed experimental conditions and results for Test Series 2.

Figure 82:
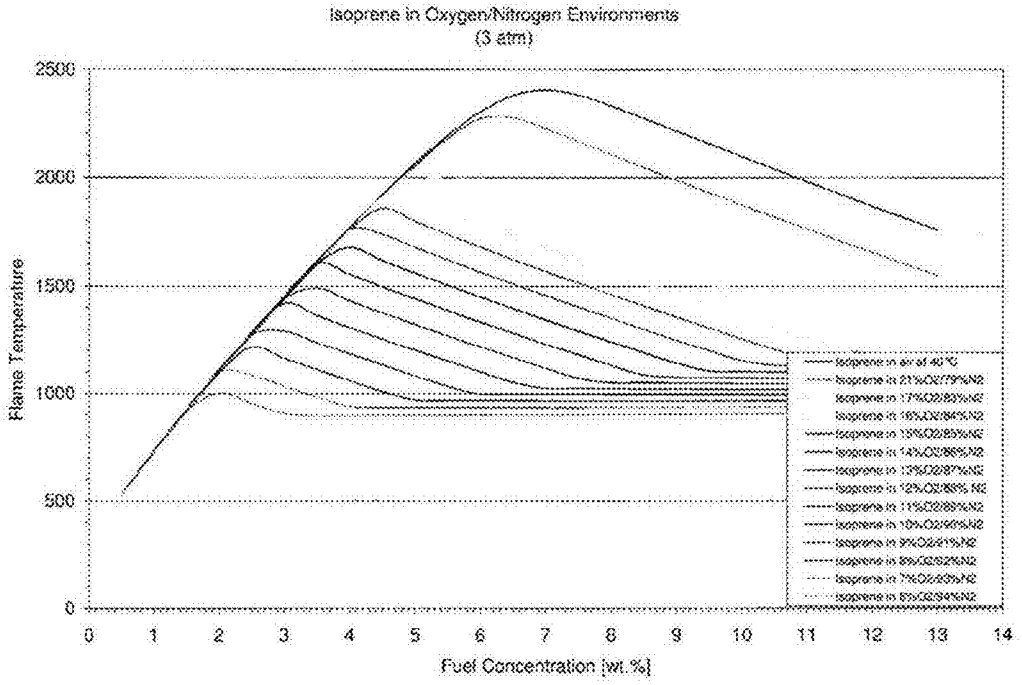

FIG. 82 is a graph of the calculated adiabatic flame temperature plotted as a function of fuel concentration for various nitrogen/oxygen ratios at 3 atmospheres of pressure.

Figure 83:
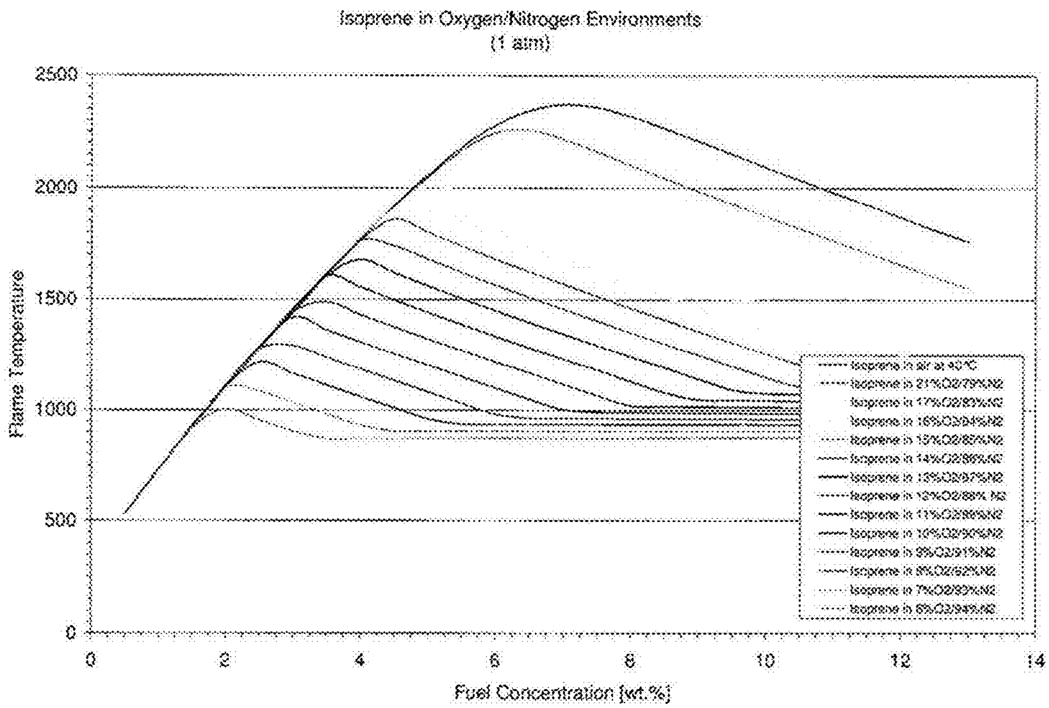

FIG. 83 is a graph of the calculated adiabatic flame temperature plotted as a function of fuel concentration for various nitrogen/oxygen ratios at 1 atmosphere of pressure.

Figure 84:
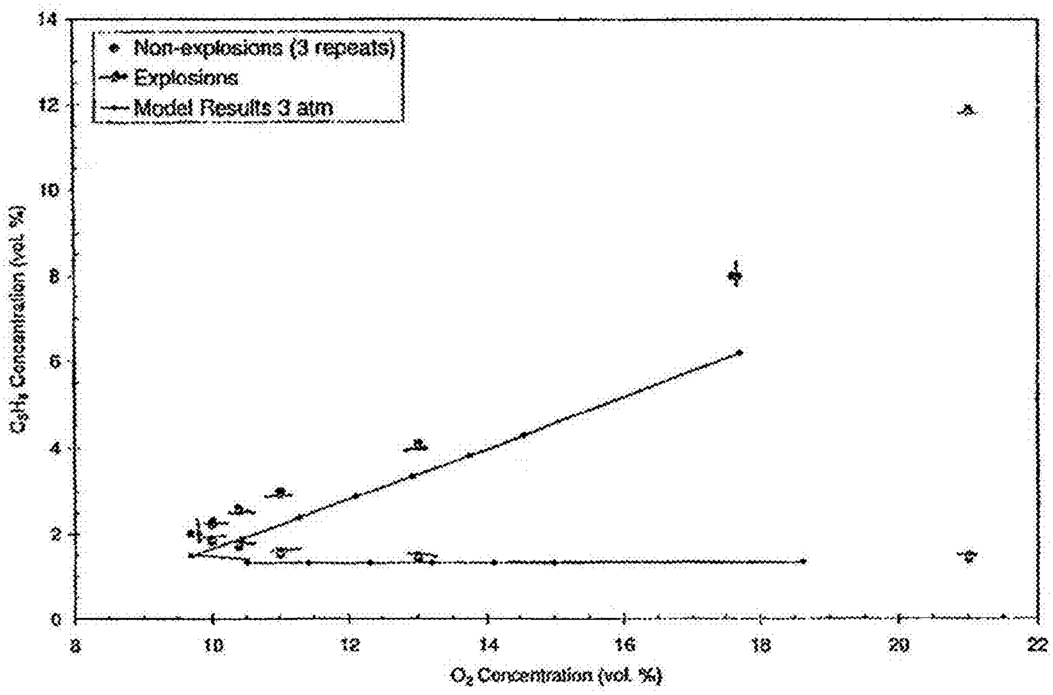

FIG. 84 is a graph of the flammability envelope constructed using data from FIG. 82 and following the methodology described in Example 21. The experimental data points (circles) are from tests described herein that were conducted at 1 atmosphere initial system pressure.

Figure 85:
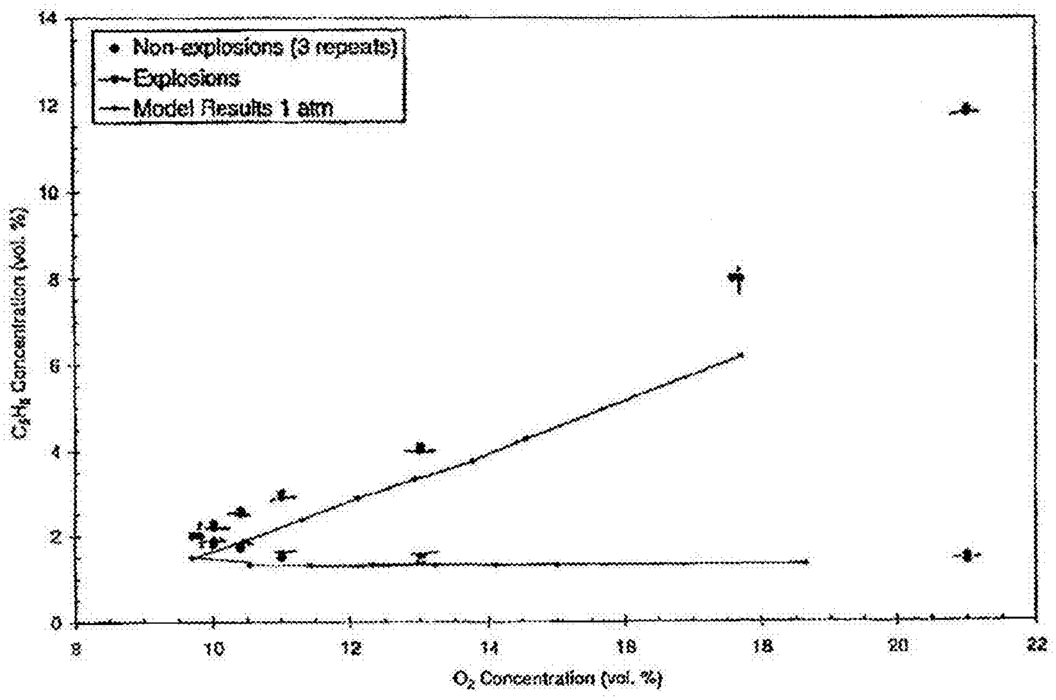

FIG. 85 is a graph of the flammability envelope constructed using data from FIG. 83 and following the methodology described in Example 21. The experimental data points (circles) are from tests described herein that were conducted at 1 atmosphere initial system pressure.

Figure 86A:
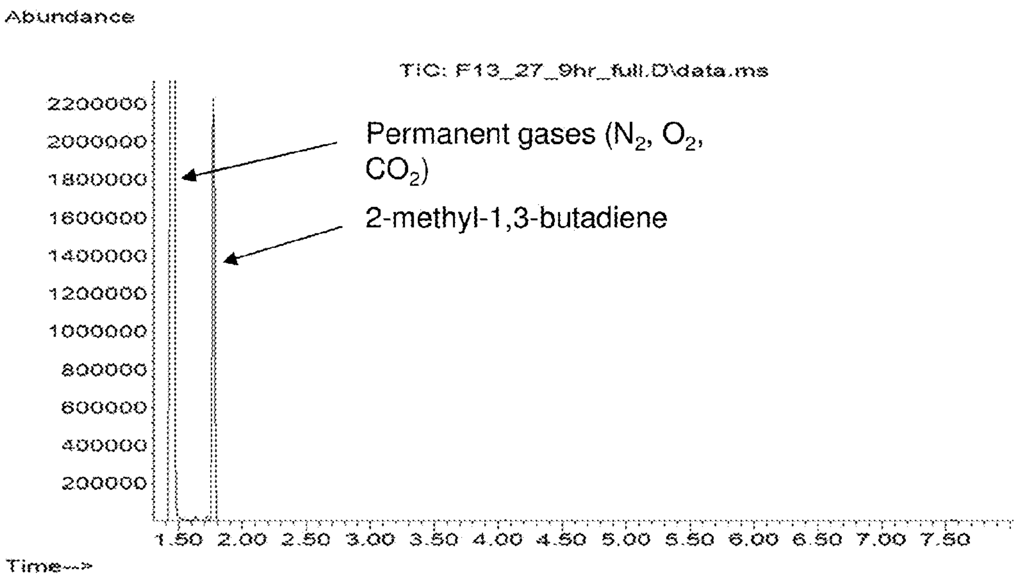

FIG. 86A is a GC/MS chromatogram of fermentation off-gas.

Figure 86B:
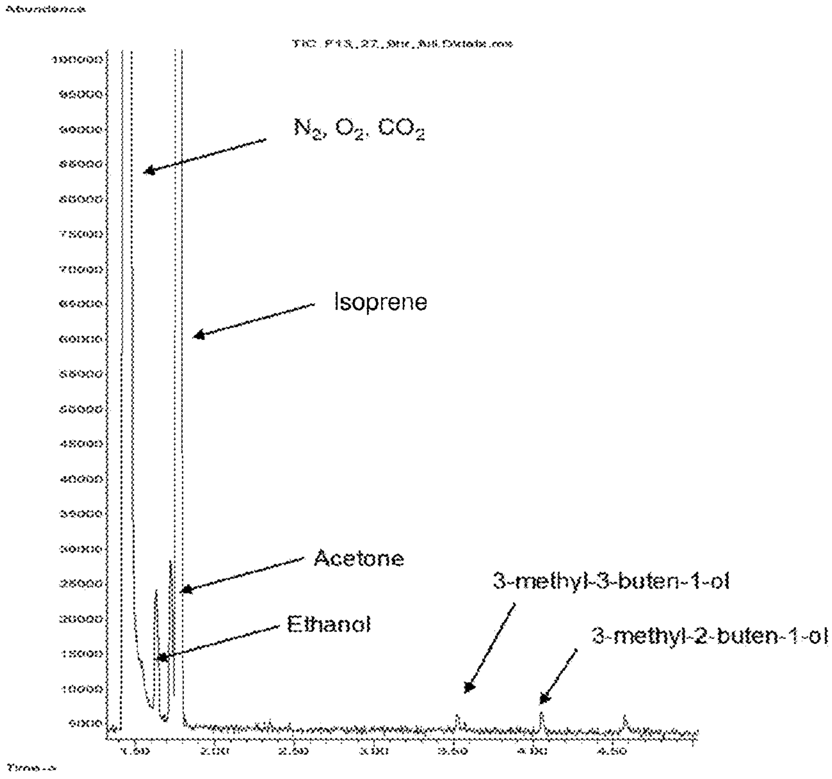

FIG. 86B is an expansion of FIG. 86A to show minor volatiles present in fermentation off-gas.

Figure 87A:
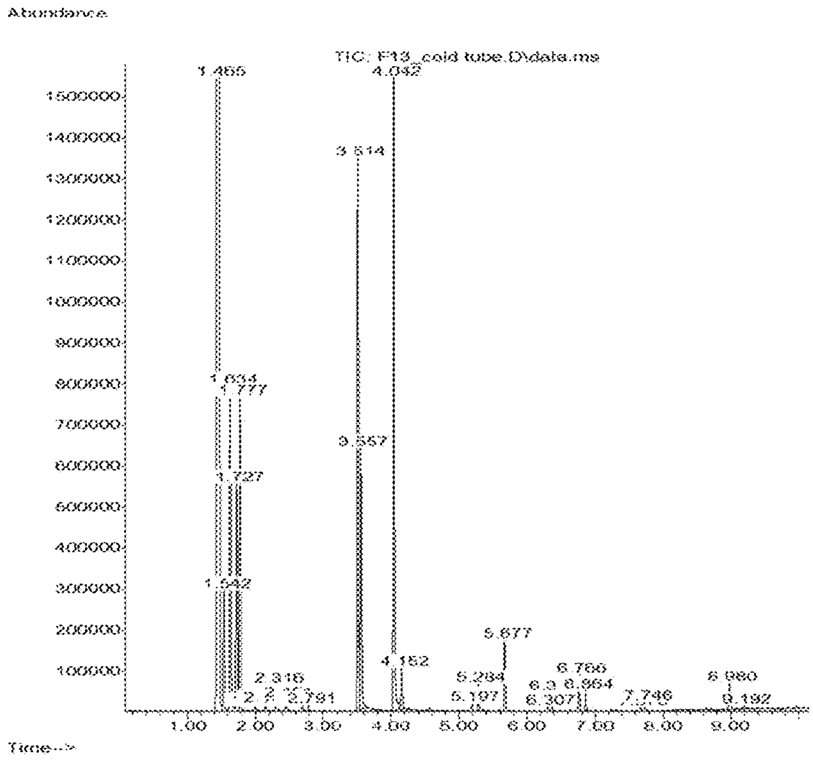

FIG. 87A is a GC/MS chromatogram of trace volatiles present in off-gas following cryo-trapping at −78° C.

Figure 87B:
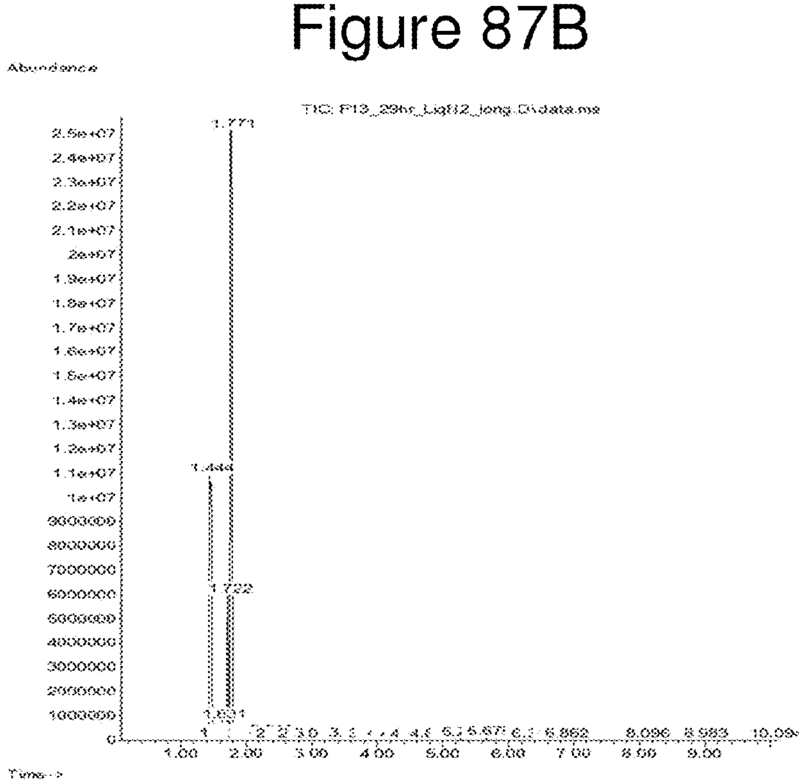

FIG. 87B is a GC/MS chromatogram of trace volatiles present in off-gas following cryo-trapping at −196° C.

Figure 87C:
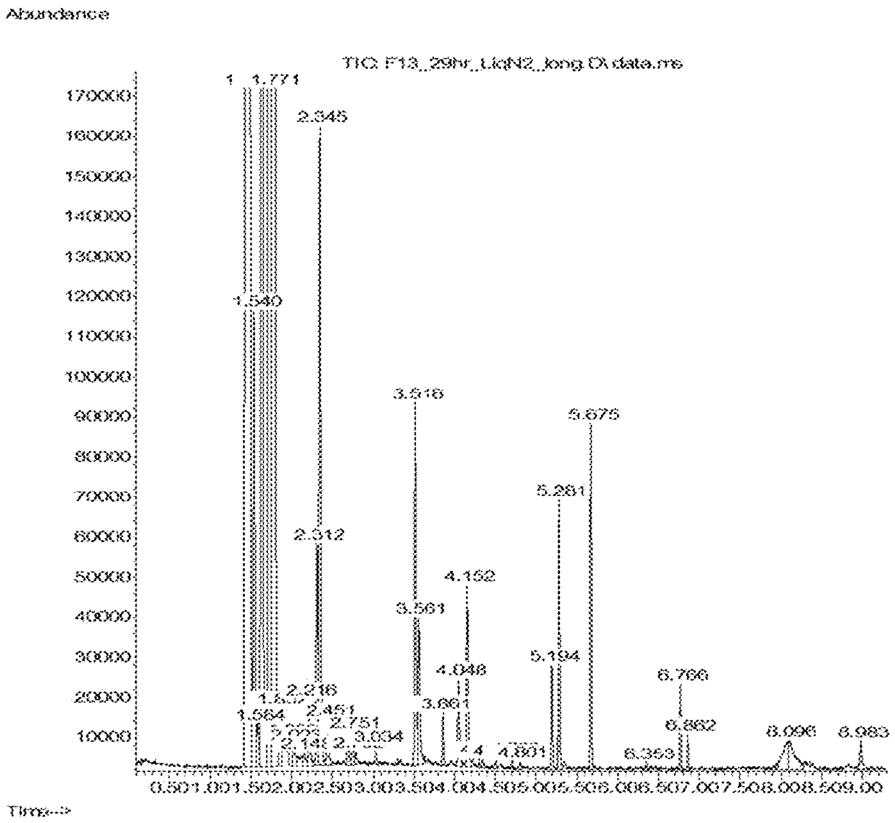

FIG. 87C is an expansion of FIG. 87B.

Figure 87D:
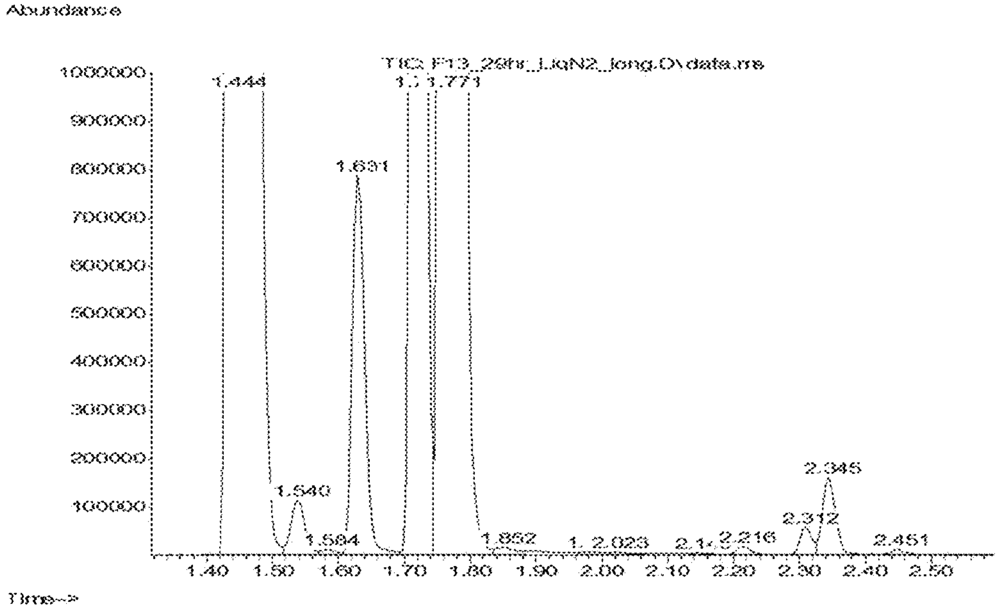

FIG. 87D is an expansion of FIG. 87C.

FIGS. 88A and 88B are GC/MS chromatogram comparing C5 hydrocarbons from petroleum-derived isoprene (FIG. 88A) and biologically produced isoprene (FIG. 88B). The standard contains three C5 hydrocarbon impurities eluting around the main isoprene peak (FIG. 88A). In contrast, biologically produced isoprene contains amounts of ethanol and acetone (run time of 3.41 minutes) (FIG. 88A).

FIG. 89 is a graph of the analysis of fermentation off-gas of an *E. coli* BL21 (DE3) pTrcIS strain expressing a Kudzu isoprene synthase and fed glucose with 3 g/L yeast extract.

FIG. 90 shows the structures of several impurities that are structurally similar to isoprene and may also act as polymerization catalyst poisons.

Figure 91:
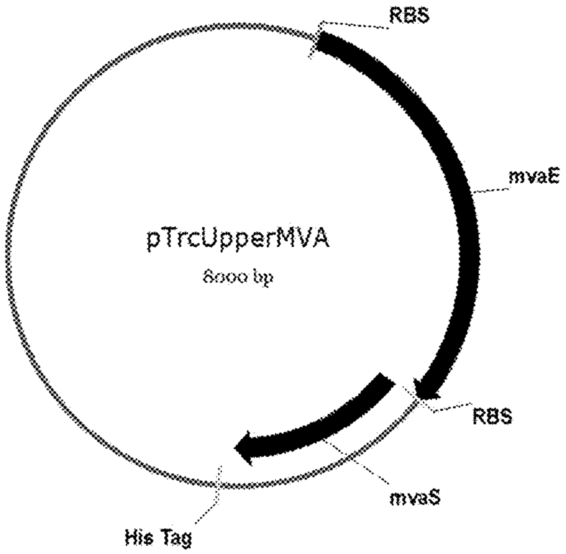

FIG. 91 is a map of pTrcHis2AUpperPathway (also called pTrcUpperMVA).

FIGS. 92A-92C are the nucleotide sequence of pTrcHis2AUpperPathway (also called pTrcUpperMVA) (SEQ ID NO:86).

Figure 93:
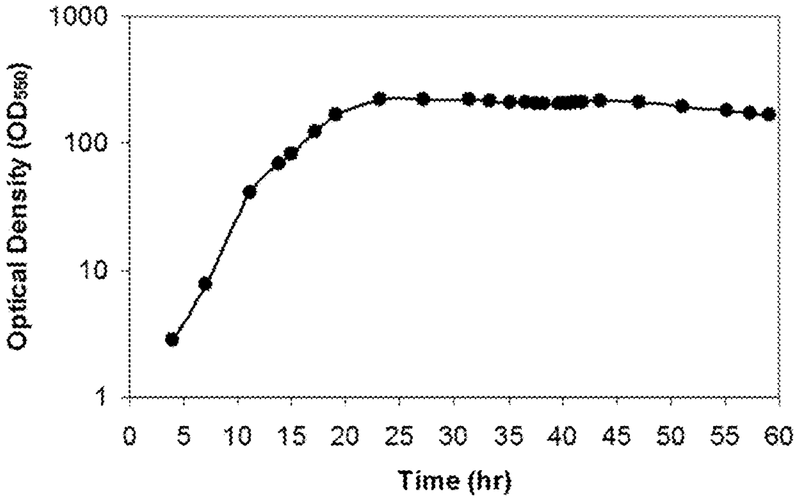

FIG. 93 is a time course of optical density within the 15-L bioreactor fed with glucose.

Figure 94:
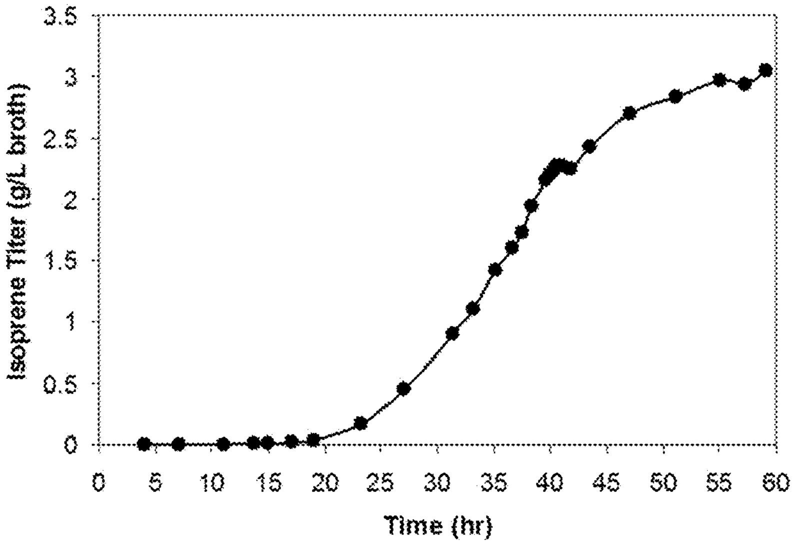

FIG. 94 is a time course of isoprene titer within the 15-L bioreactor fed with glucose. The titer is defined as the amount of isoprene produced per liter of fermentation broth.

Figure 95:
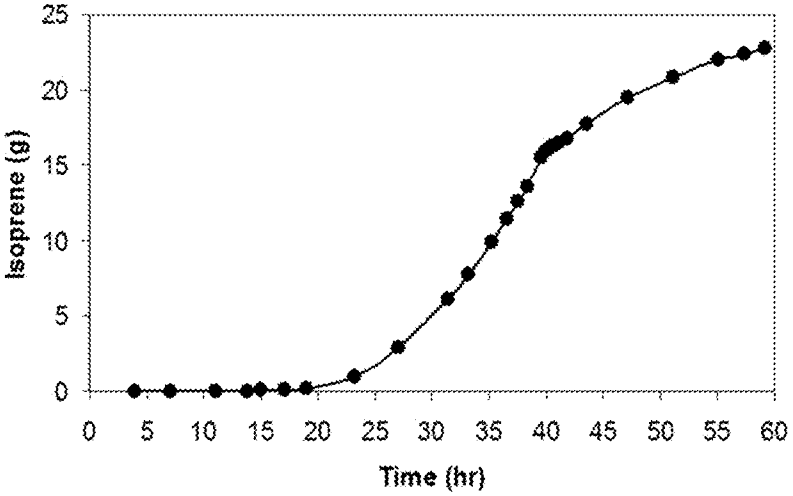

FIG. 95 is a time course of total isoprene produced from the 15-L bioreactor fed with glucose.

Figure 96A:
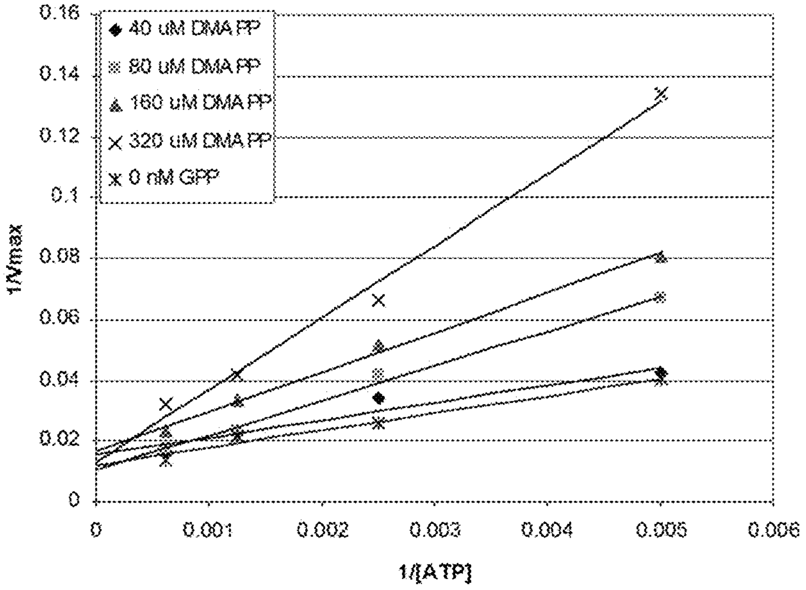
Figure 96B:
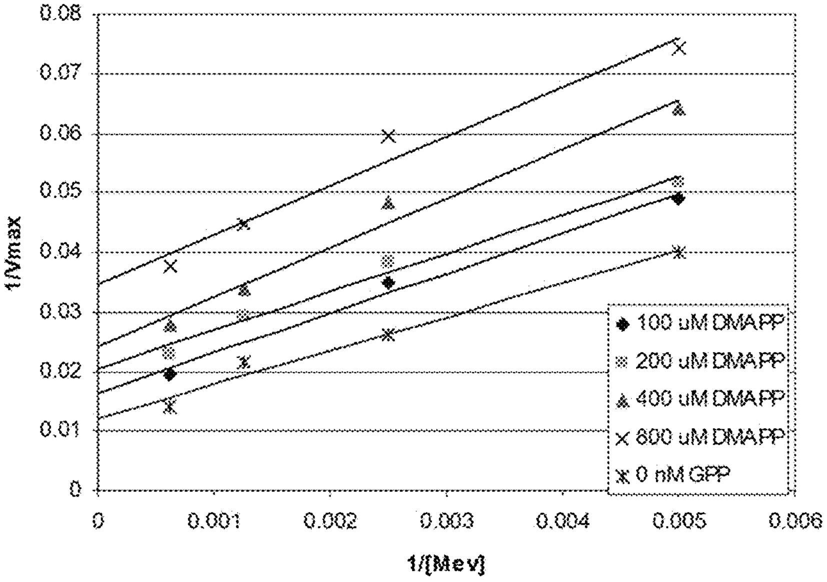

FIGS. 96A and 96B are Lineweaver-Burke plots for DMAPP inhibition of yeast mevalonate kinase. FIG. 96A shows that DMAPP displays competitive inhibition with respect to ATP. FIG. 96B shows that DMAPP displays uncompetitive inhibition with respect to mevalonate.

Figure 97A:
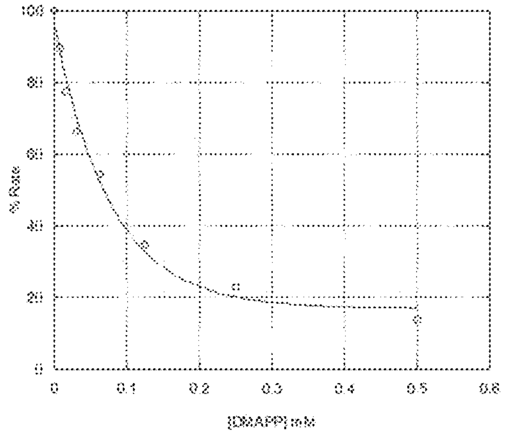
Figure 97B:
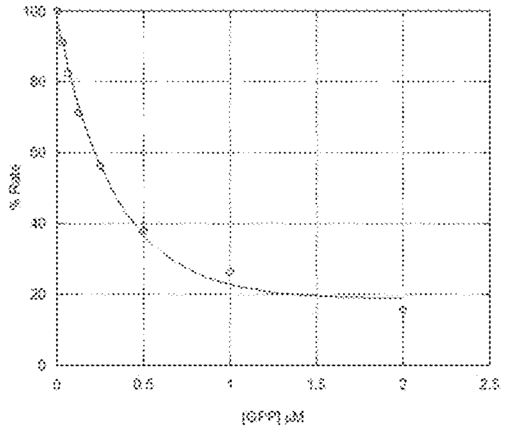
Figure 97C:
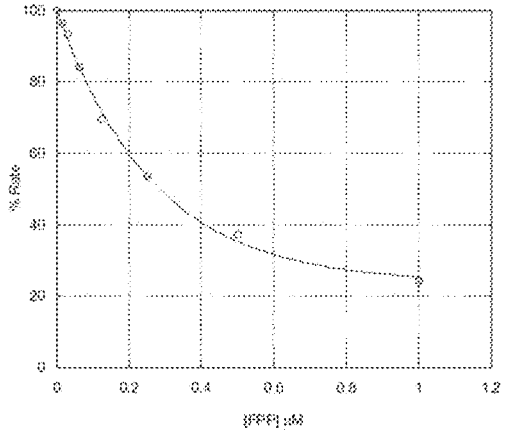

FIGS. 97A-97C are graphs showing the inhibition of yeast mevalonate kinase with respect to ATP. FIG. 97A shows the percent of activity without inhibitor vs. [DMAPP] at [ATP] equal to $K_{MappATP}$ FIG. 97B shows the percent of activity without inhibitor vs. [GPP] at [ATP] equal to $K_{MappATP}$ FIG. 97C shows the percent of activity without inhibitor vs. [FPP] at [ATP] equal to $K_{MappATP}$.

Figure 98A:
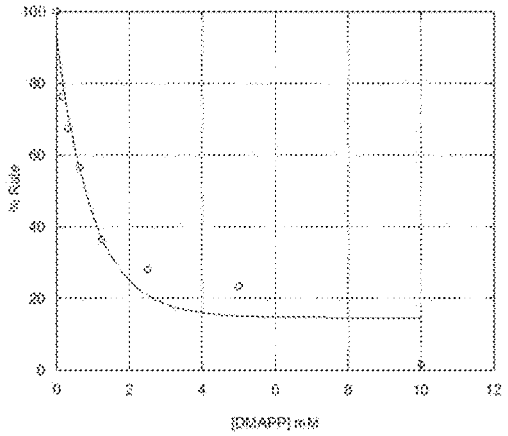
Figure 98B:
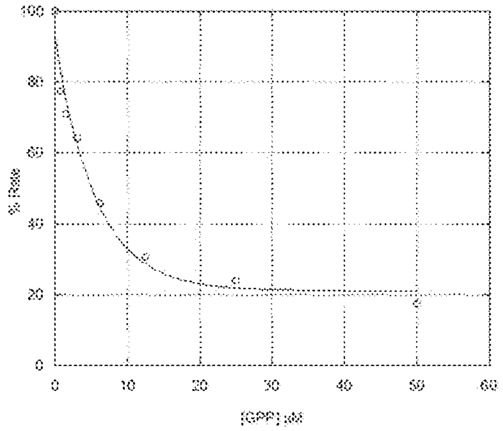
Figure 98C:
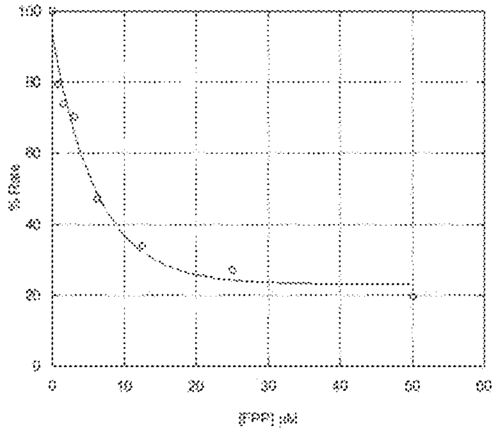

FIGS. 98A-98C are graphs showing the inhibition of yeast mevalonate kinase with respect to mevalonate. FIG. 98A shows the percent of activity without inhibitor vs. [DMAPP] at [mevalonate] equal to $K_{MappMev}$. FIG. 98B shows the percent of activity without inhibitor vs. [GPP] at [mevalonate] equal to $K_{MappMev}$. FIG. 98C shows the percent of activity without inhibitor vs. [FPP] at [mevalonate] equal to $K_{MappMev}$.

Figure 99:
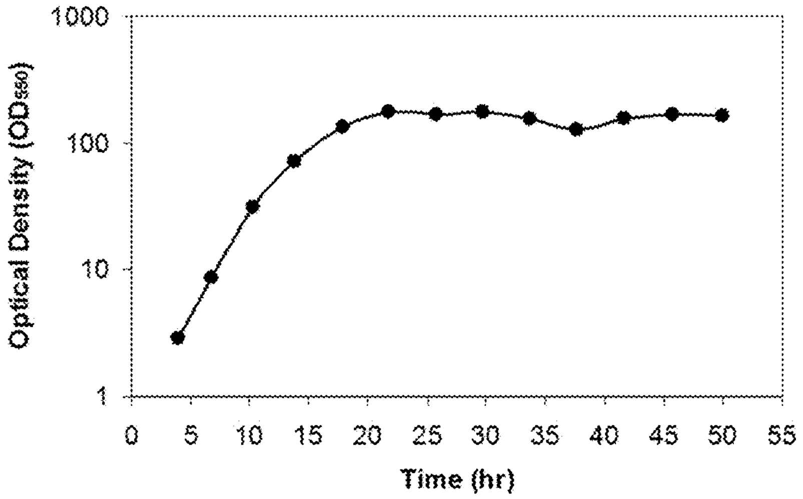

FIG. 99 is a time course of optical density within the 15-L bioreactor fed with glucose.

Figure 100:
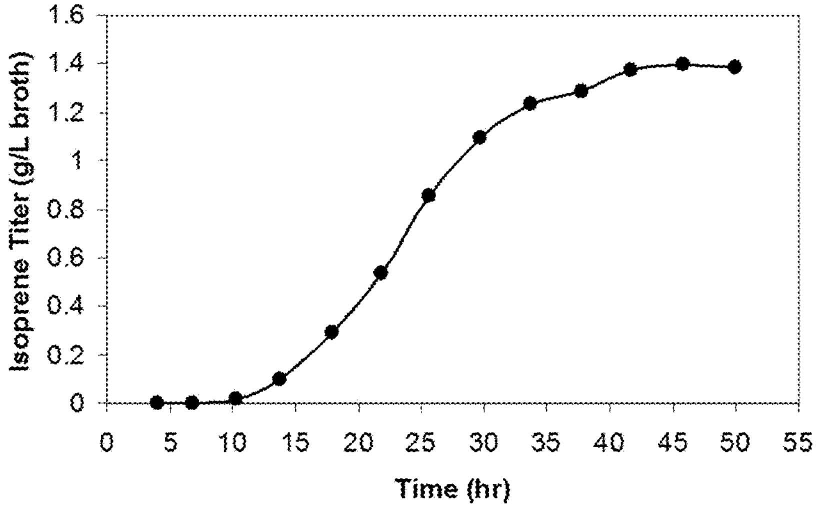

FIG. 100 is a time course of isoprene titer within the 15-L bioreactor fed with glucose. The titer is defined as the amount of isoprene produced per liter of fermentation broth.

Figure 101:
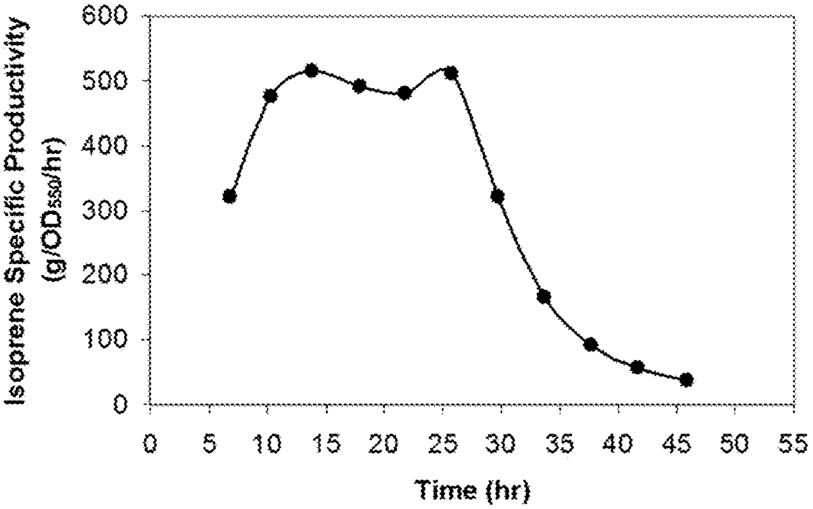

FIG. 101 is a time course of isoprene specific activity from the 15-L bioreactor fed with glucose.

Figure 102:
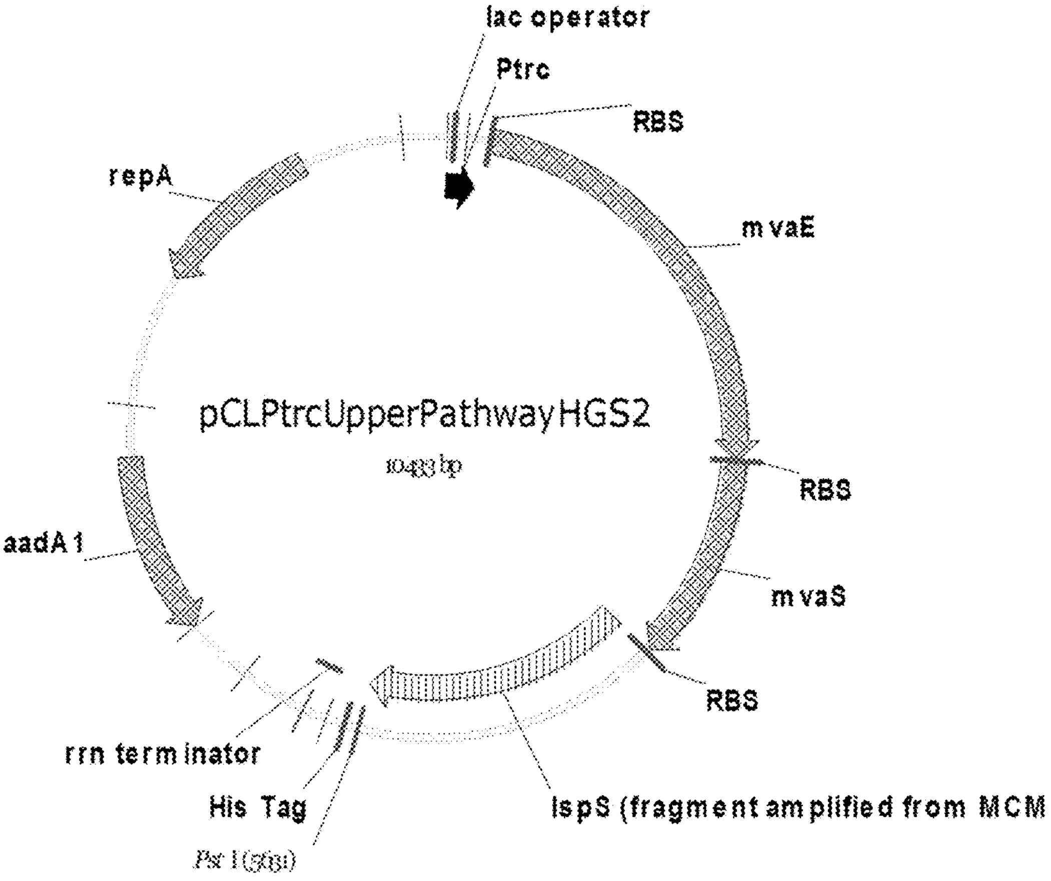

FIG. 102 is a map of pCLPtrcUpperPathwayHGS2 (also referred to as pCL UpperHGS2).

FIGS. 103A-103C are the nucleotide sequence of pCLPtrcUpperPathwayHGS2 (SEQ ID NO:87).

Figure 104:
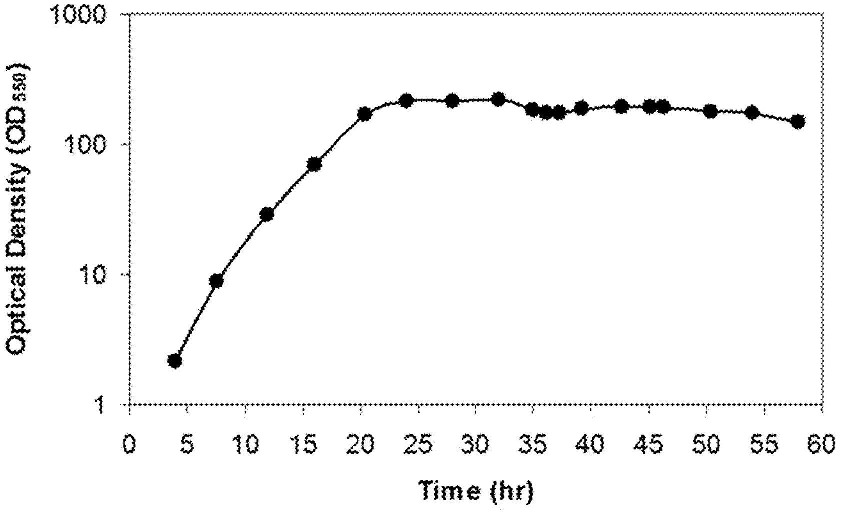

FIG. 104 is a time course of optical density within the 15-L bioreactor fed with glucose.

Figure 105:
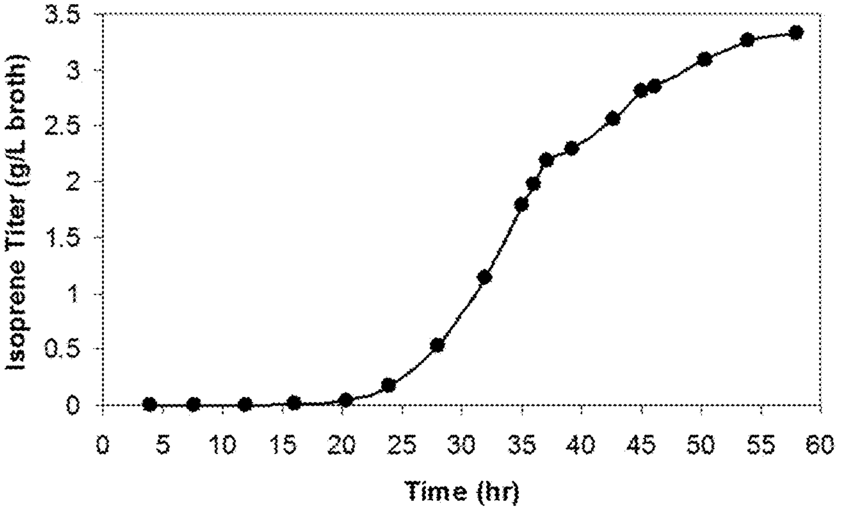

FIG. 105 is a time course of isoprene titer within the 15-L bioreactor fed with glucose. The titer is defined as the amount of isoprene produced per liter of fermentation broth.

Figure 106:
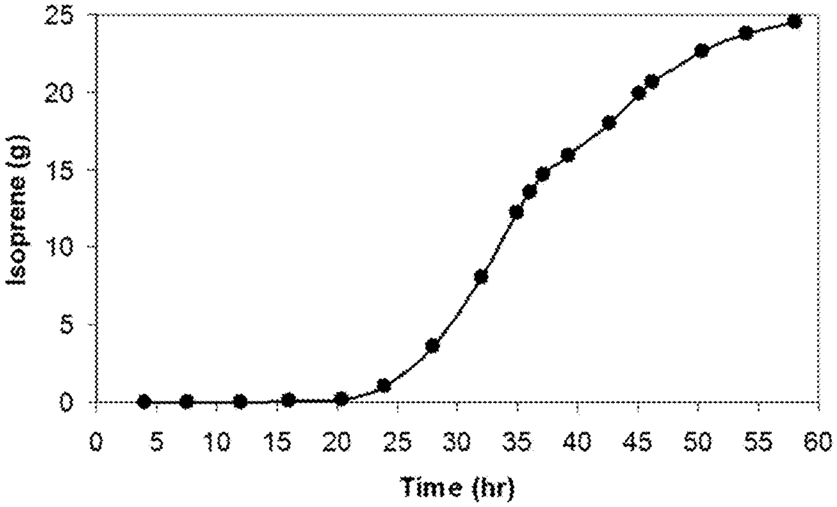

FIG. 106 is a time course of total isoprene produced from the 15-L bioreactor fed with glucose.

Figure 107:
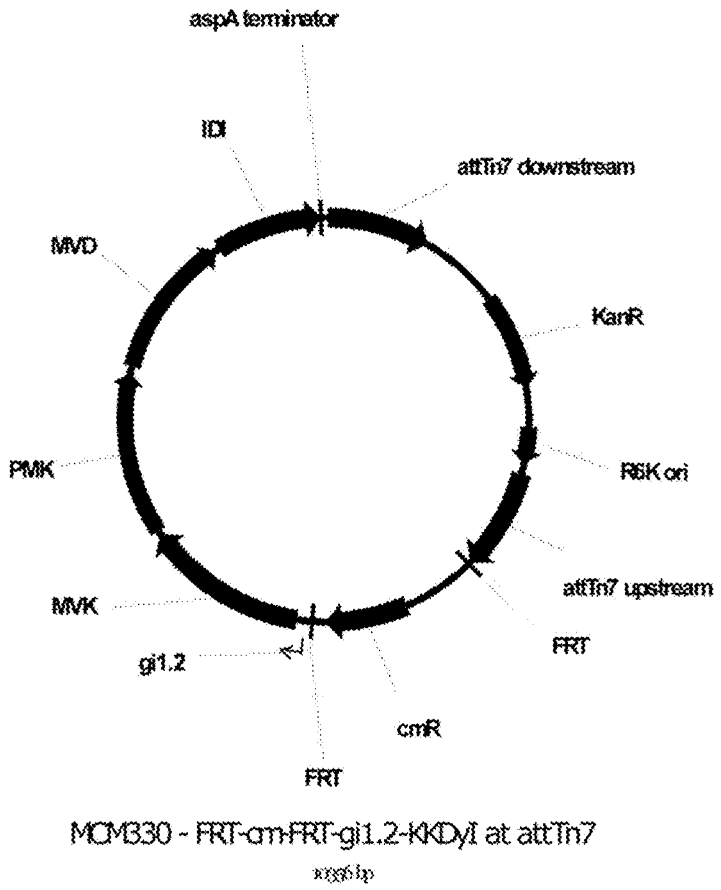

FIG. 107 is a map of plasmid MCM330.

FIGS. 108A-108C are the nucleotide sequence of plasmid MCM330 (SEQ ID NO:90).

Figure 109:
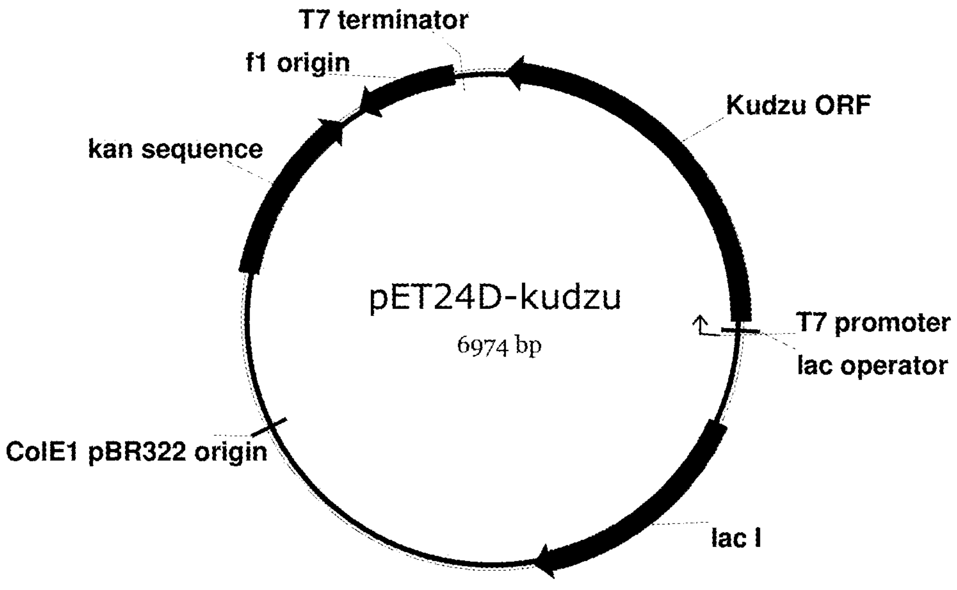

FIG. 109 is a map of pET24D-Kudzu.

FIGS. 110A and 110B are the nucleotide sequence of pET24D-Kudzu (SEQ ID NO:101).

Figure 111A:
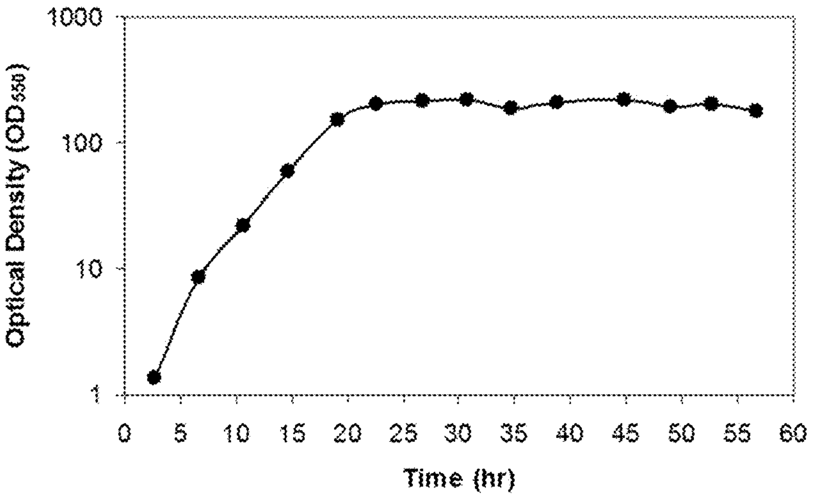

FIG. 111A is a time course of optical density within the 15-L bioreactor fed with glucose.

Figure 111B:
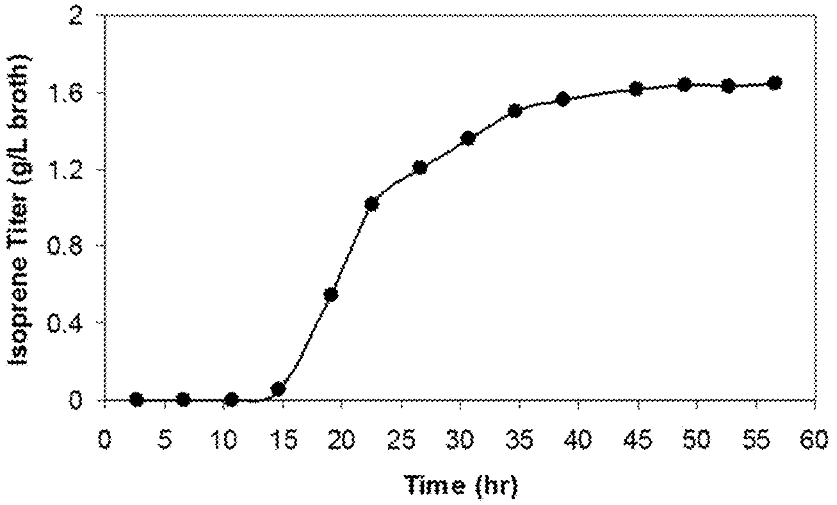

FIG. 111B is a time course of isoprene titer within the 15-L bioreactor fed with glucose. The titer is defined as the amount of isoprene produced per liter of fermentation broth.

Figure 111C:
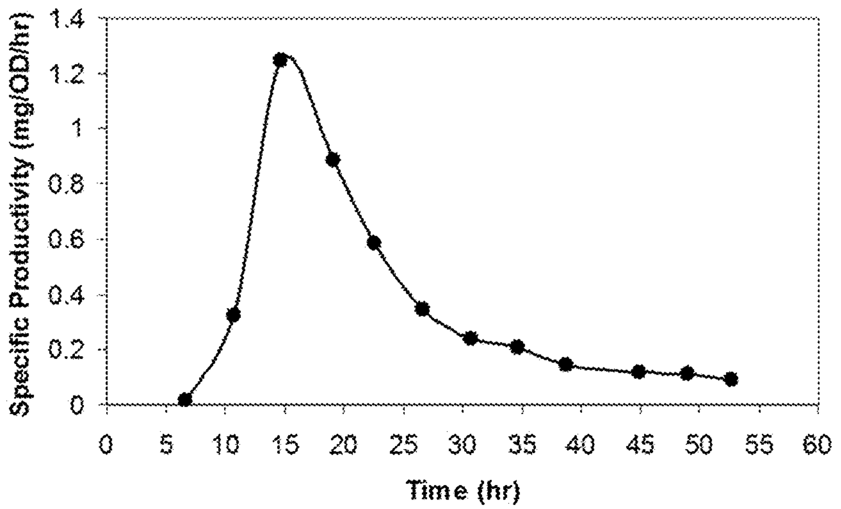

FIG. 111C is a time course of specific productivity of isoprene in the 15-L bioreactor fed with glucose.

Figure 112A:
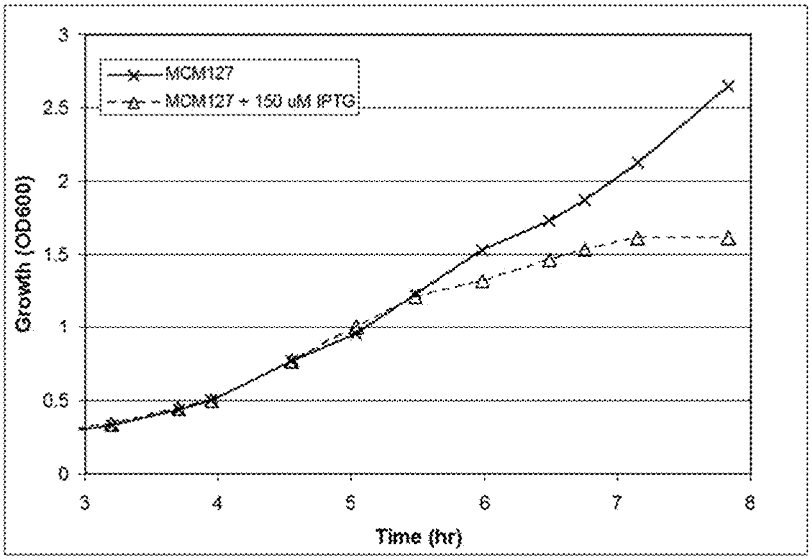

FIG. 112A is a graph of the growth of MCM127 in TM3 media at 30° C. measured as optical density (OD600). One culture was induced with 150 μM IPTG 4 hours after inoculation.

Figure 112B:
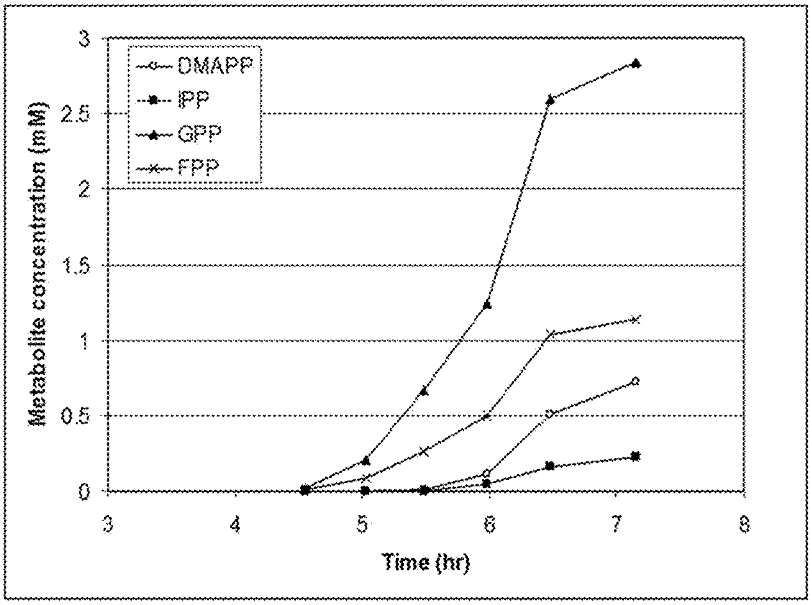

FIG. 112B is a graph of the accumulated key metabolic intermediates after induction of MCM127 with 150 μM IPTG. The culture was induced 4 hours after inoculation and samples were analyzed using LCMS.

Figure 112C:
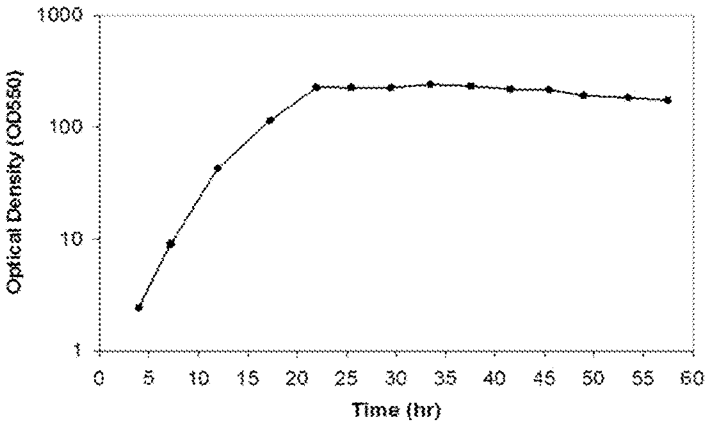
Figure 112D:
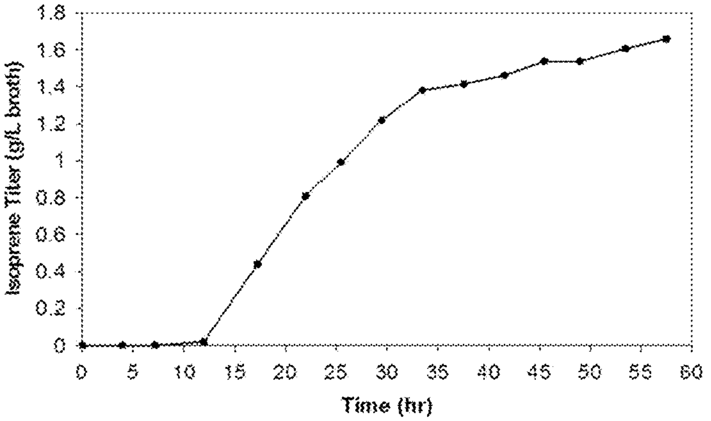
Figure 112E:
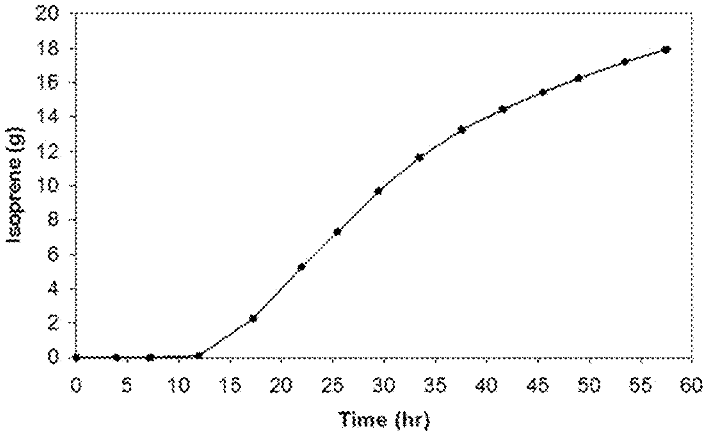
Figures 112F, 112G, 112H:
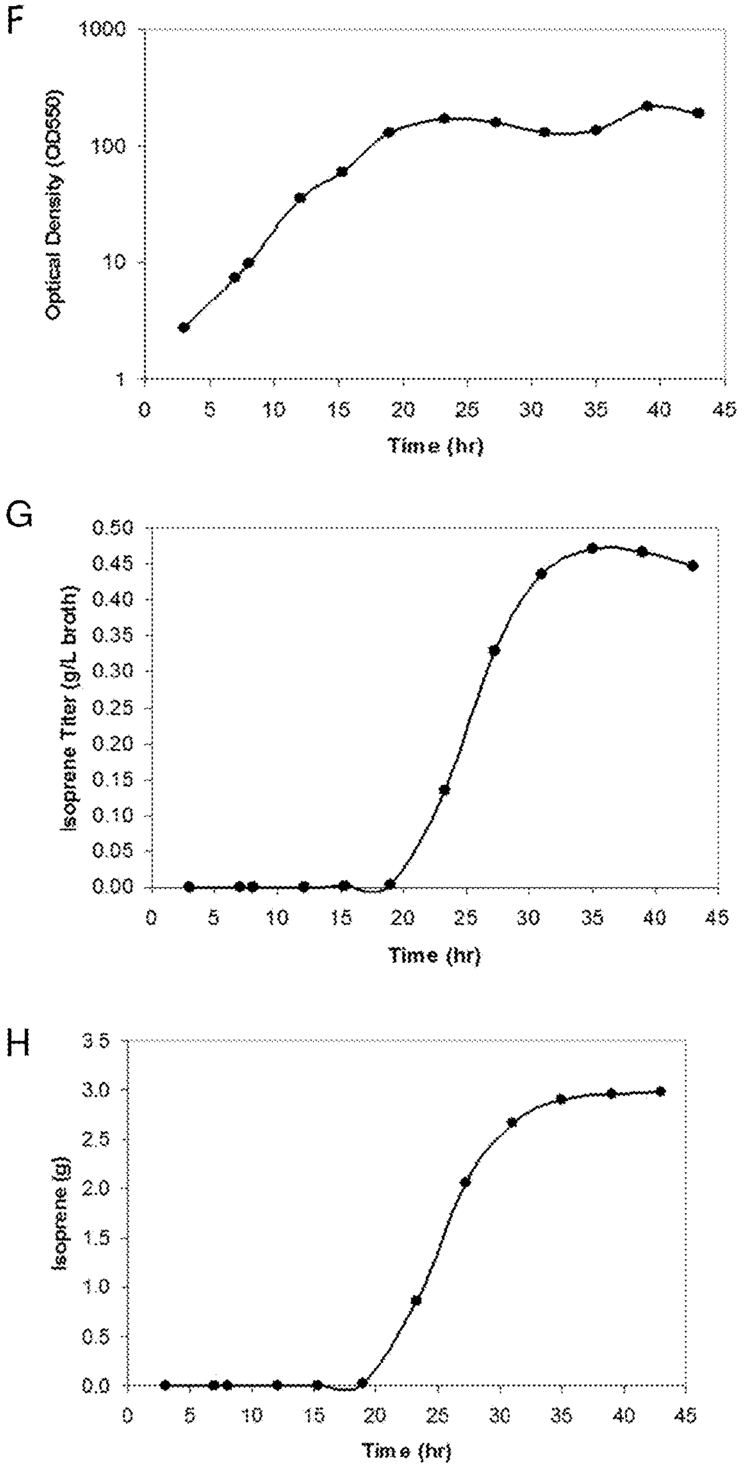
Figure 112I:
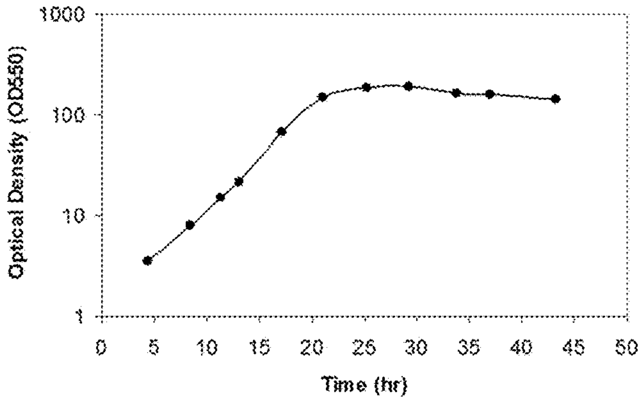
Figure 112J:
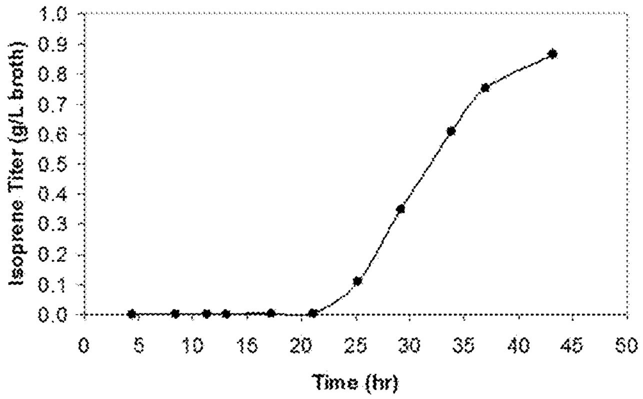
Figure 112K:
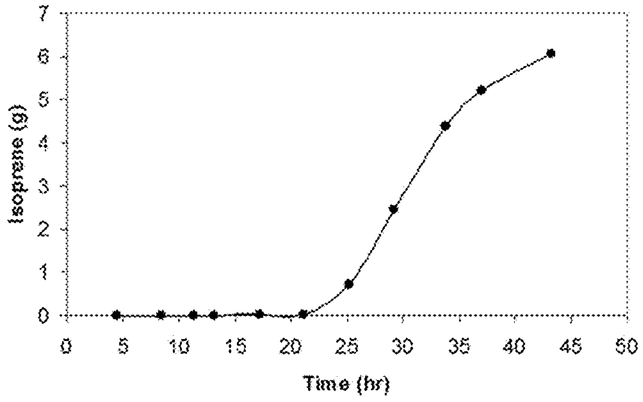

FIGS. 112C-112K are isoprene fermentation expressing genes from the MVA pathway and grown in fed-batch culture at the 15-L scale in different *E. coli* strains (MCM343 strain (FIGS. 112C-112E); MCM127 strain (FIGS. 112F-112H); dxr knock-out strain (FIGS. 112I-112K)). FIGS. 112C, 112F, and 112I show the time course of optical density within the 15-L bioreactor fed with glucose in MCM343 strain, MCM127 strain, and dxr knock-out strain, respectively. FIGS. 112D, 112G, and 112J are the time course of isoprene titer within the 15-L bioreactor fed with glucose in MCM343 strain, MCM127 strain, and dxr knock-out strain, respectively. The titer is defined as the amount of isoprene produced per liter of fermentation broth. FIGS. 112E, 112H, and 112K are the time course of total isoprene produced from the 15-L bioreactor fed with glucose in MCM343 strain, MCM127 strain, and dxr knock-out strain, respectively.

Figures 112L, 112M, 112N:
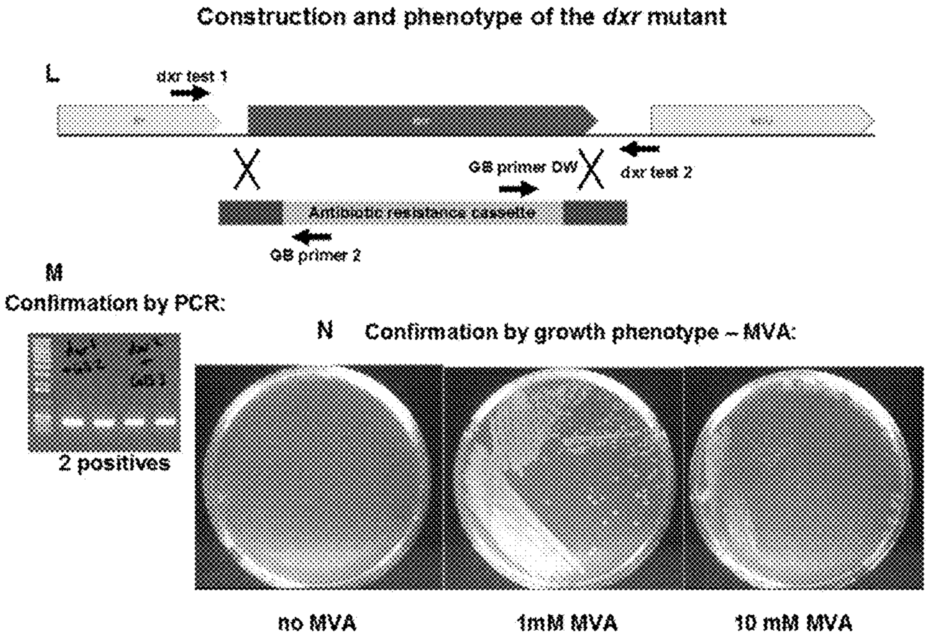

FIGS. 112L-112N depict the construction and phenotype of the dxr mutant in *E. coli.* 1-deoxy-D-xylulose 5-phosphate reductoisomerase (dxr) was deleted using the GeneBridges Quick & Easy *E. coli* Gene Deletion Kit. FIG. 112L shows the chromosomal location of dxr (from EcoCyc) and the approximate primer binding sites for testing the insertion of the GB resistance cassette. FIG. 112M is a PCR analysis of dxr deletion strains (in MG1655) using primers dxrTest1 and GBprimer2 (GB2), and dxrTest2 and GBprimerDW (GB3). PCR products were run on an Egel (Invitrogen) according to the manufacturer's protocol. FIG. 112N shows the inhibition of the growth of dxr deletion strains at 10 mM MVA. DW28 were grown overnight at 37° C. on LB medium plates containing spectinomycin 50 μg/ml, chloramphenicol 25 μg/ml, and the indicated concentrations of MVA.

Figures 112O, 112P:
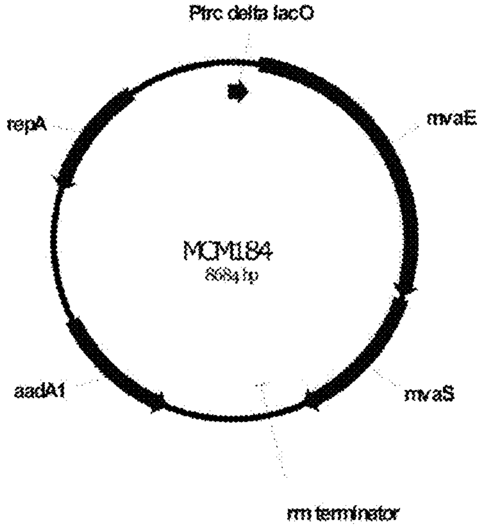

FIG. 112O lists forward and reverse primers for pCL Ptrc (minus lacO) UpperPathway: forward primer MCM63 (SEQ ID NO:123) and reverse primer MCM64 (SEQ ID NO:124).

FIG. 112P is a map of MCM184—pCL Ptrc(minus lacO) UpperPathway.

FIG. 112Q-112S are the nucleotide sequence of MCM184 (SEQ ID NO:125).

Figures 112T, 112U:
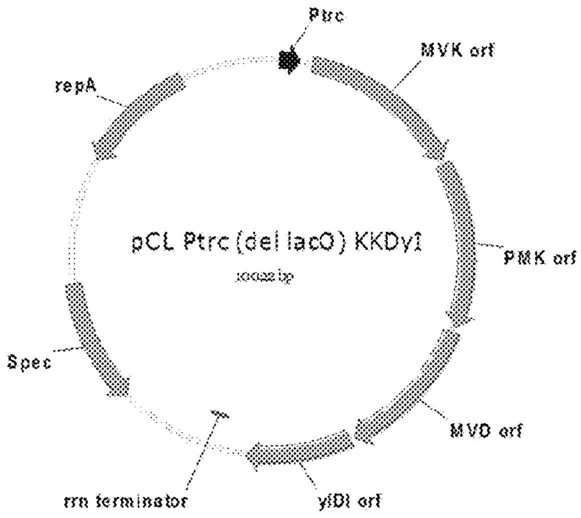

FIG. 112T lists PCR and sequencing primers for pCL Ptrc (ΔlacO)KKDyI: primer EL-976 (SEQ ID NO:126), primer EL-977 (SEQ ID NO:127), and primer EL-978 (SEQ ID NO:128).

FIG. 112U is a map of pCL Ptrc (ΔlacO)KKDyI.

FIGS. 112V-112X are the nucleotide sequence of pCL Ptrc (ΔlacO)KKDyI (SEQ ID NO:129).

Figures 113A, 113B, 113C, 113D:
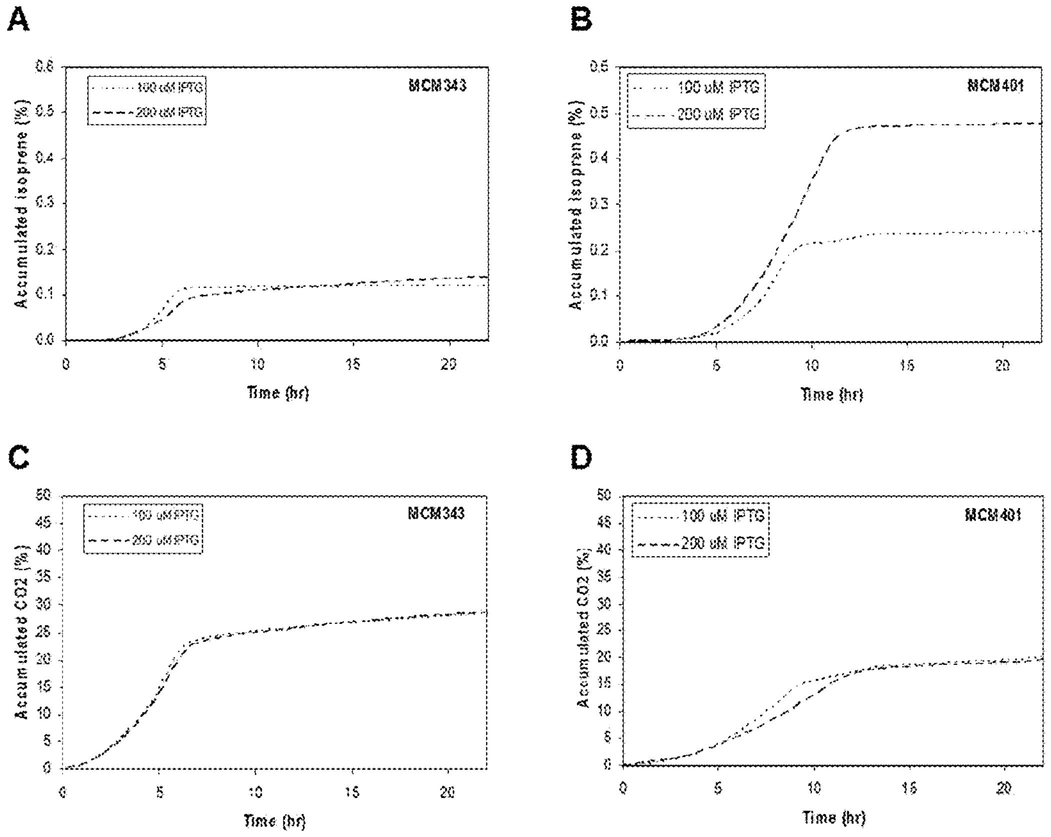

FIGS. 113A-113D demonstrate that over-expression of MVK and isoprene synthase results in increased isoprene production. Accumulated isoprene and $CO_2$ from MCM401 and MCM343 during growth on glucose in 100 mL bioreactors with 100 and 200 uM IPTG induction of isoprene production was measured over a 22 hour time course. FIG. 113A is a graph of the accumulated isoprene (%) from MCM343. FIG. 113B is a graph of the accumulated isoprene (%) from MCM401. FIG. 113C is a graph of the accumulated $CO_2$ (%) from MCM343. FIG. 113D is a graph of the accumulated $CO_2$ (%) from MCM401.

Figure 114:
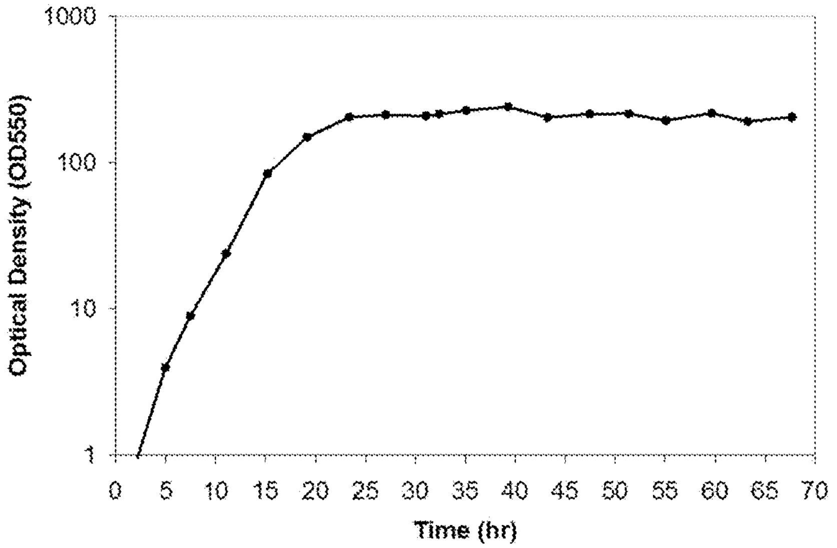

FIG. 114 is a time course of optical density within the 15-L bioreactor fed with glucose.

Figure 115:
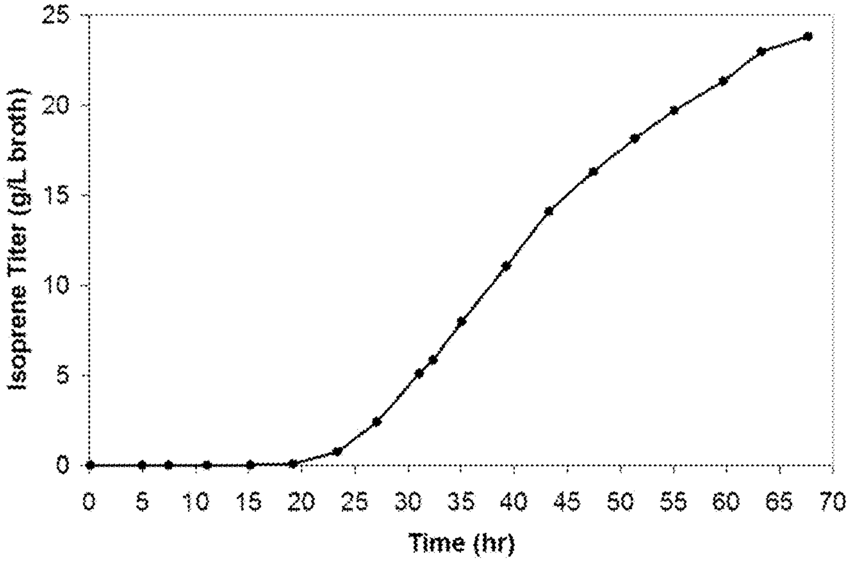

FIG. 115 is a time course of isoprene titer within the 15-L bioreactor fed with glucose. The titer is defined as the amount of isoprene produced per liter of fermentation broth.

Figure 116:
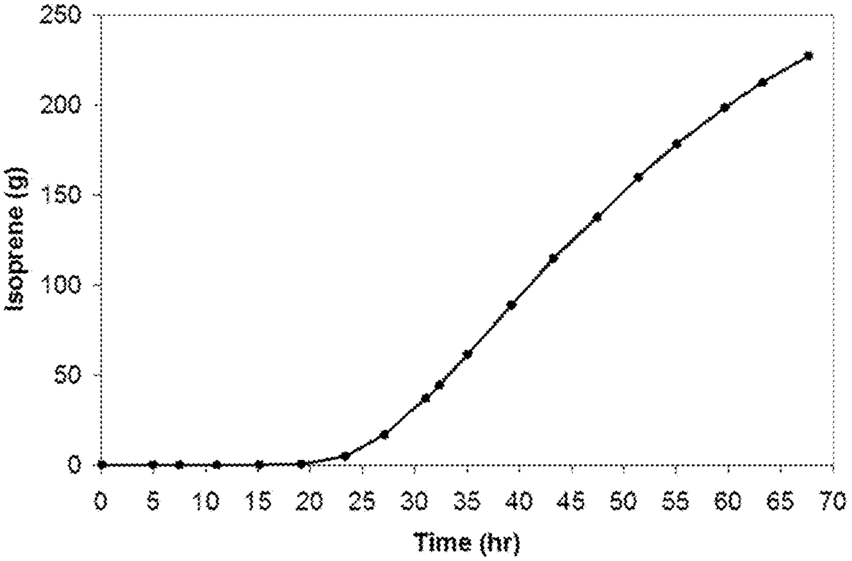

FIG. 116 is a time course of total isoprene produced from the 15-L bioreactor fed with glucose.

Figure 117:
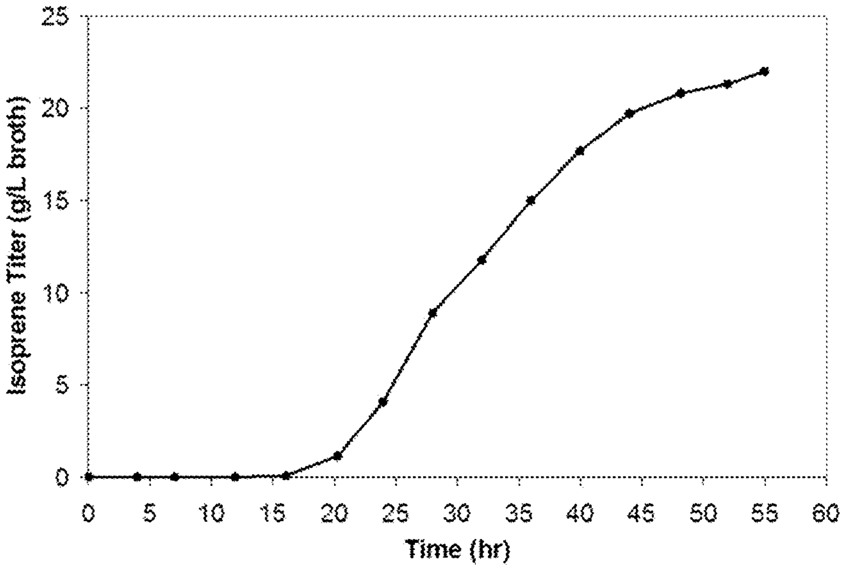

FIG. 117 is a time course of isoprene titer within the 15-L bioreactor fed with glucose. The titer is defined as the amount of isoprene produced per liter of fermentation broth.

Figure 118:
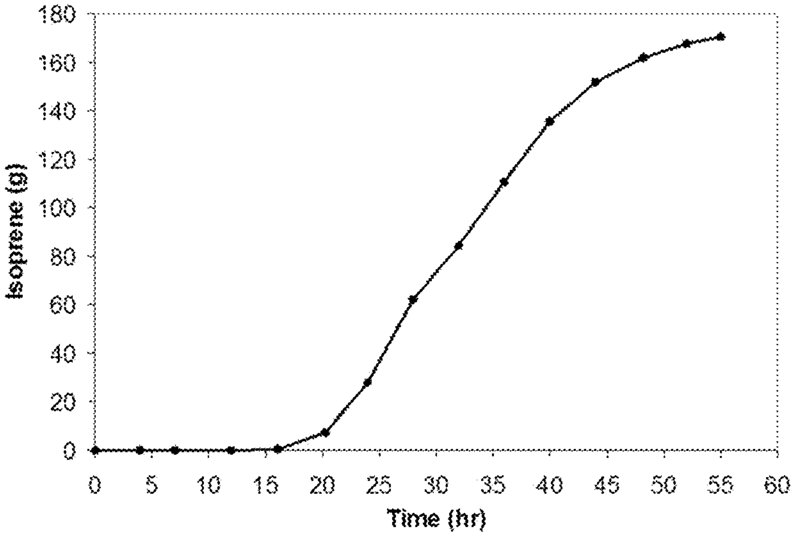

FIG. 118 is a time course of total isoprene produced from the 15-L bioreactor fed with glucose.

Figure 119A:
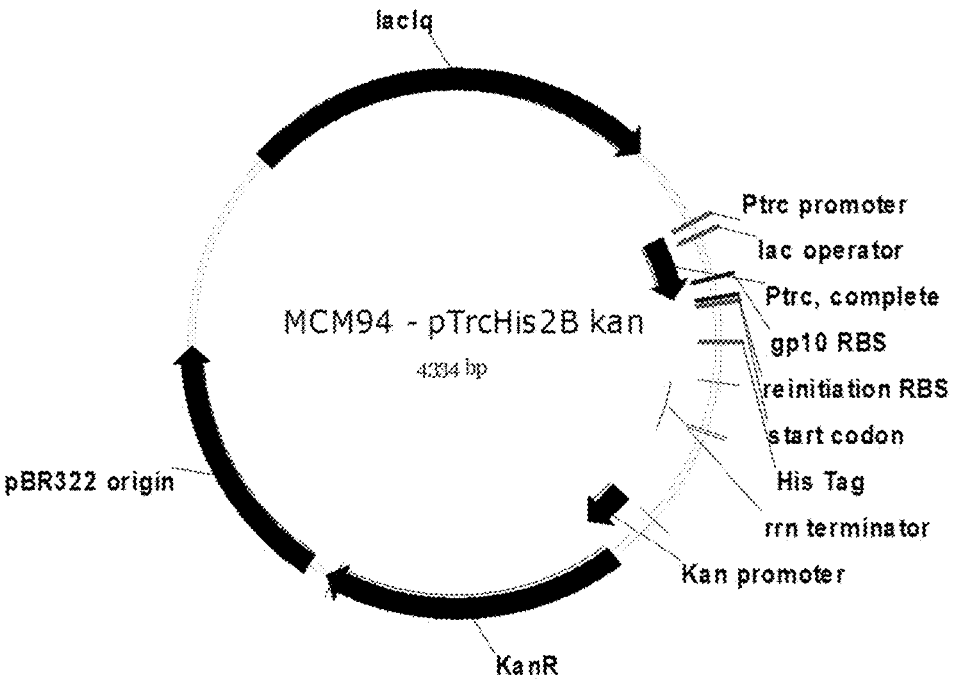

FIG. 119A is a map of plasmid MCM94-pTrcHis2B kan.

FIGS. 119B and 119C are the nucleotide sequence of plasmid MCM94-pTrcHis2B kan (SEQ ID NO: 107).

Figure 120:
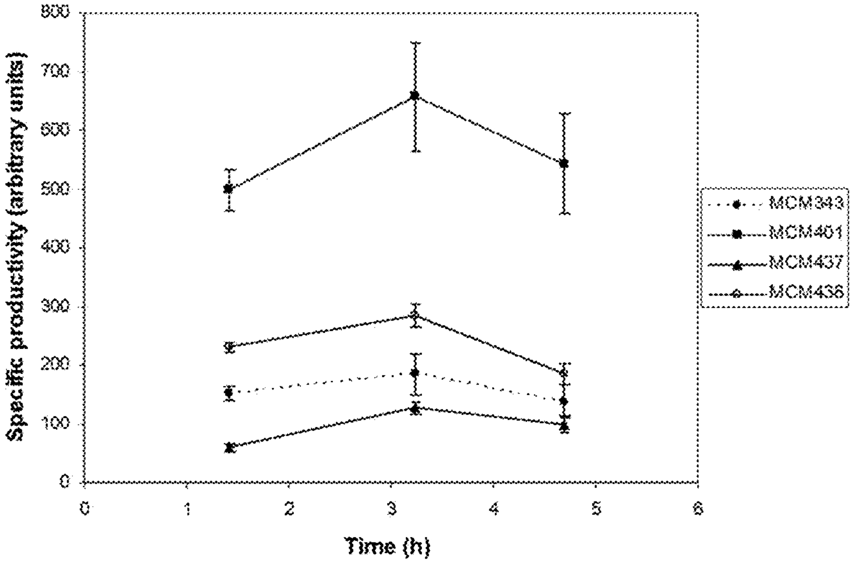

FIG. 120 is a graph showing that over-expression of both isoprene synthase and MVK results in an increased specific productivity of isoprene compared to over-expression of each of the enzymes alone, or low expression of both enzymes. The specific productivity of isoprene using MCM343, MCM401, MCM437, and MCM438 during growth on glucose in mini-fermentations with 200 μM IPTG induction was measured over time. Error bars represent one standard deviation.

Figure 121:
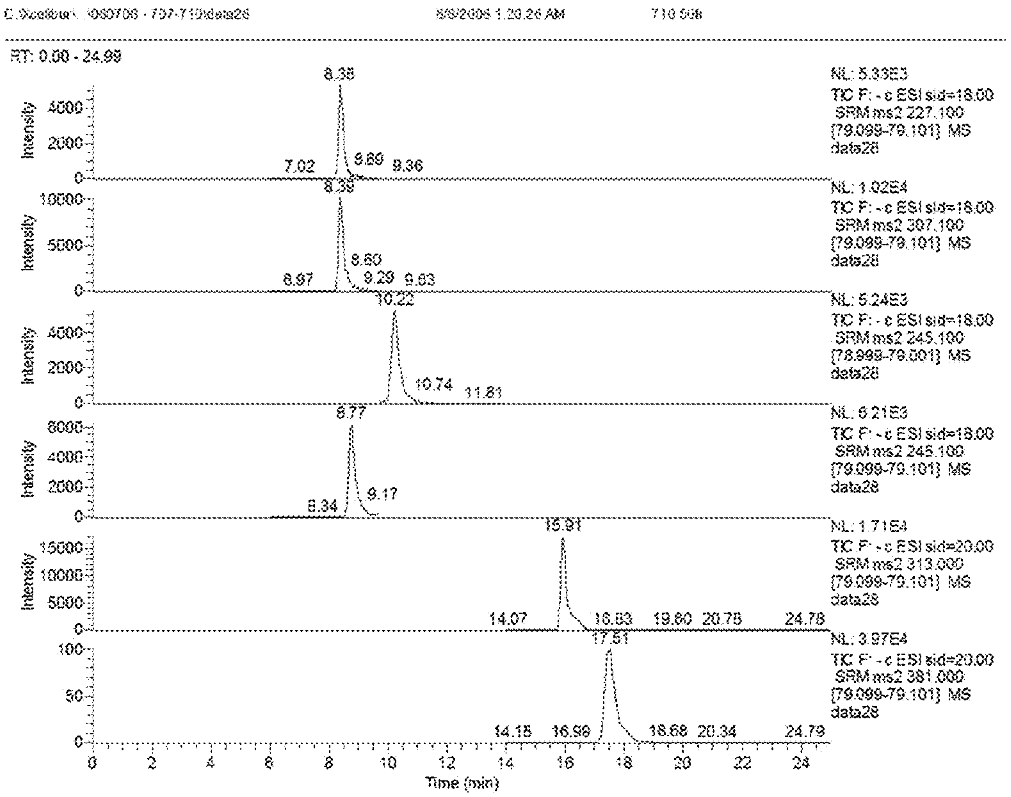

FIG. 121 is a typical elution profile of phosphorylated intermediates in the isoprenoid pathway extracted from the MCM391 strain of *E. coli* after 50 hours of fermentation and detected using LC-ESI-MS/MS.

Figure 122A:
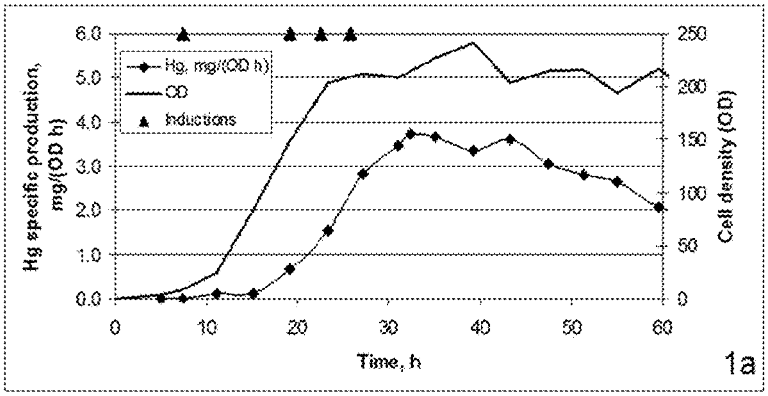
Figure 122B:
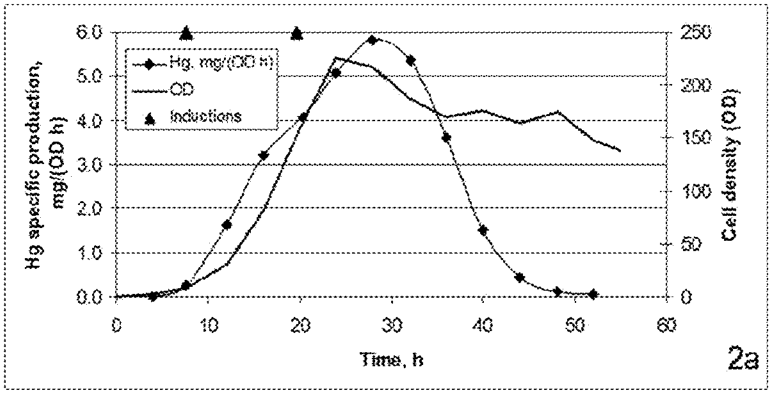
Figure 122C:
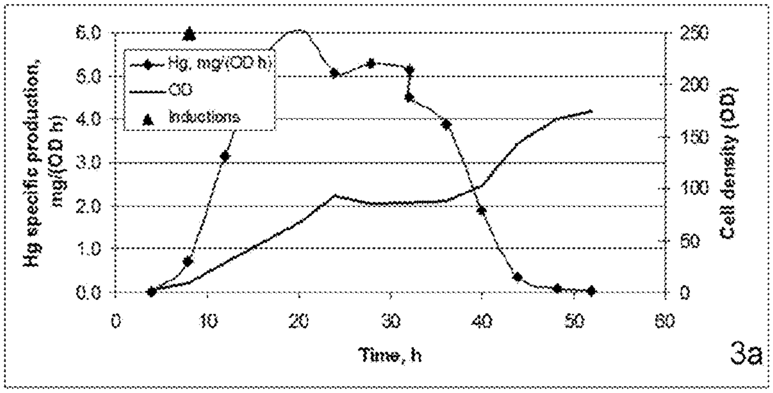
Figure 122D:
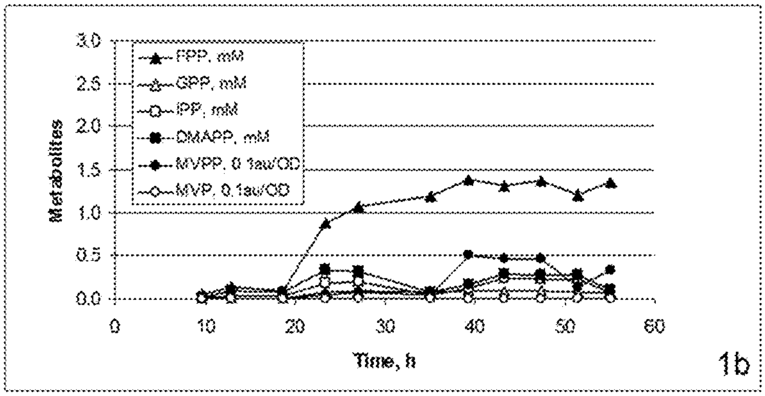
Figure 122E:
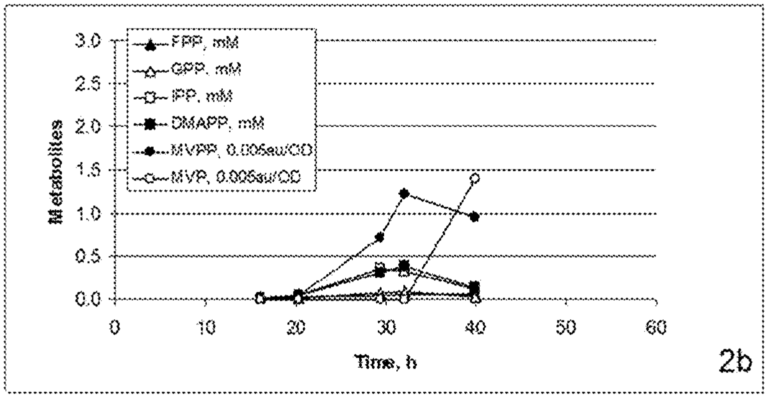
Figure 122F:
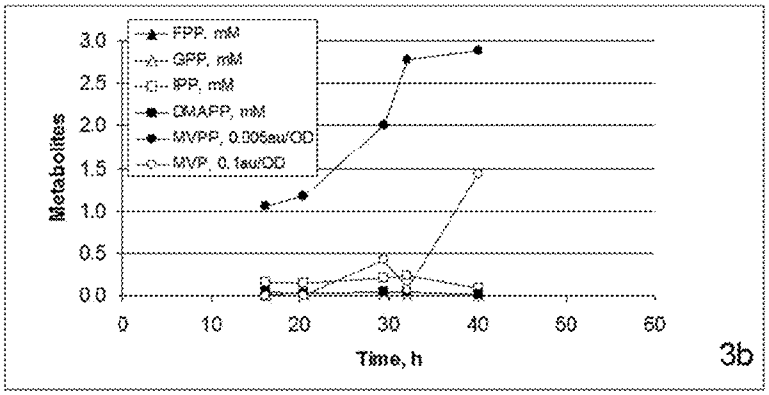

FIGS. 122A-122F are graphs showing the accumulation of isoprenoid pathway intermediates in MCM401 strain of *E. coli* containing MVK from *M. mazei* upon different levels of enzyme expression. FIGS. 122A-122C show ODs and specific isoprene production of the cultures grown in 14-L fermentors, and FIGS. 122D-122F show intracellular levels of isoprenoid metabolites. Arrows on top of the figures indicate the time points when IPTG was added to fermentors (1-4×50 μM; 2-2×100 μM and 3-1×200 μM).

Figure 123:
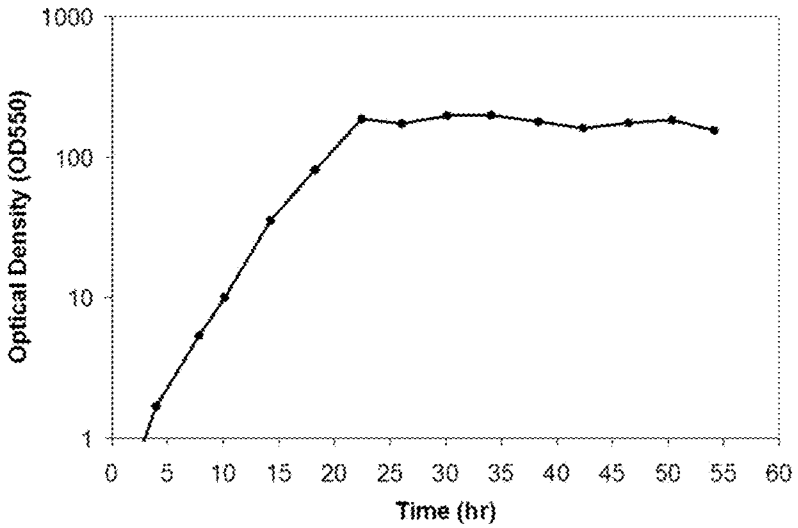

FIG. 123 is a time course of optical density within the 15-L bioreactor fed with glucose.

Figure 124:
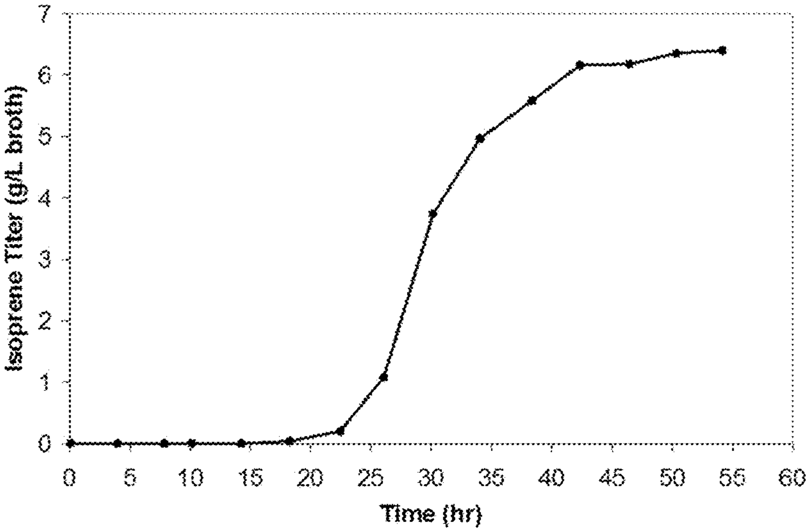

FIG. 124 is a time course of isoprene titer within the 15-L bioreactor fed with glucose. The titer is defined as the amount of isoprene produced per liter of fermentation broth.

Figure 125:
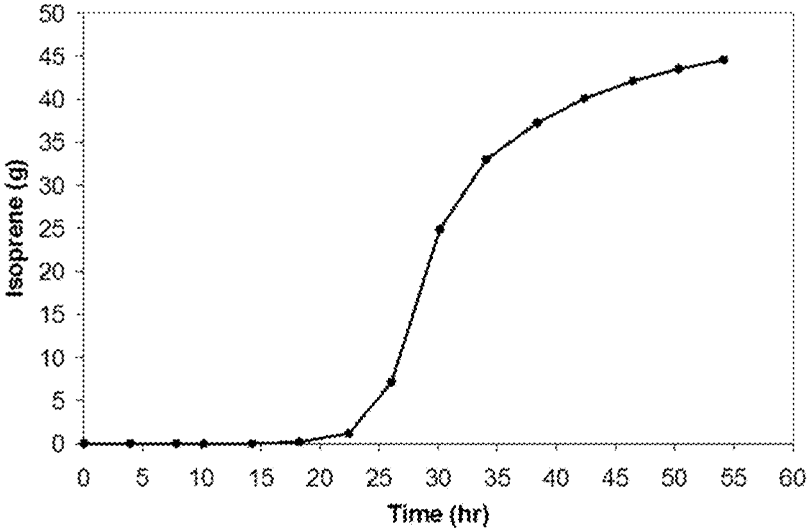

FIG. 125 is a time course of total isoprene produced from the 15-L bioreactor fed with glucose.

FIGS. 126A and 126B are the nucleotide sequence of pDU-5 MVK from *S. cerevsiae* in pET-16b (SEQ ID NO:108).

Figure 127A:
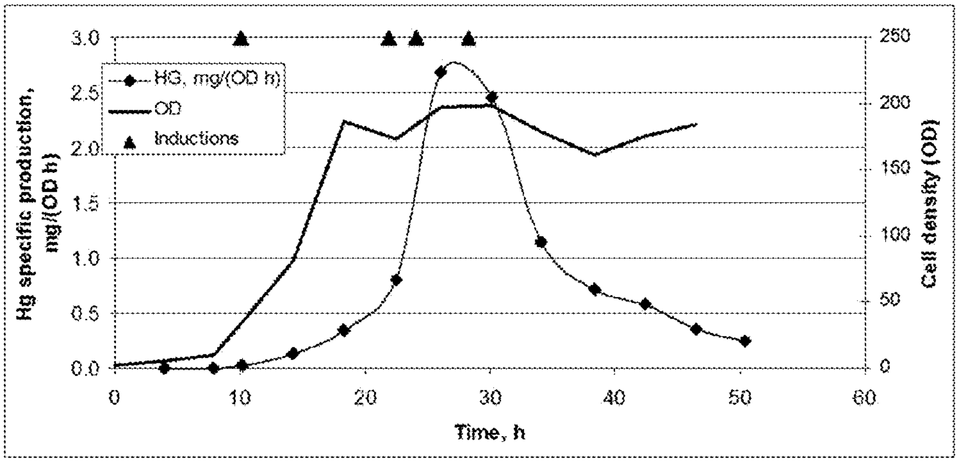
Figure 127B:
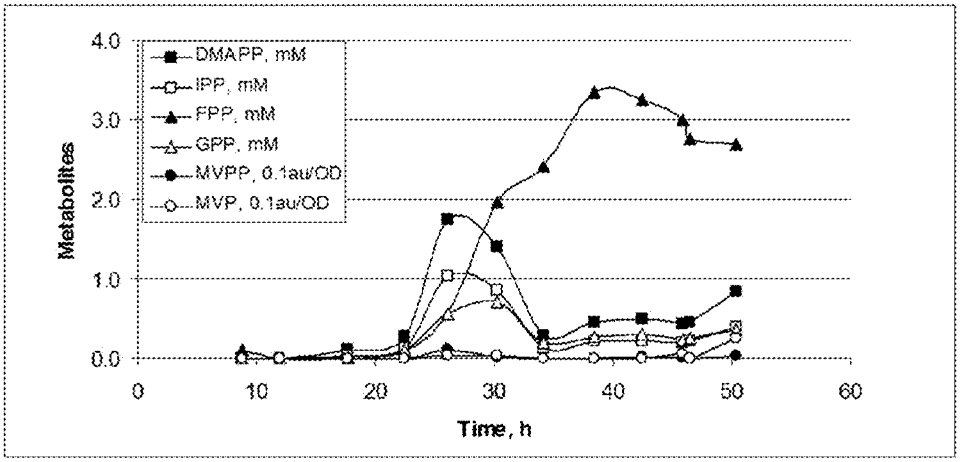

FIGS. 127A and 127B are graphs showing the accumulation of isoprenoid pathway intermediates in the MCM402 strain of *E. coli* containing MVK from yeast and grown in 14-L fermentors. Arrows on the top figure indicate the time points when 50 μM IPTG doses were added to fermentors.

Figures 128A, 128B:
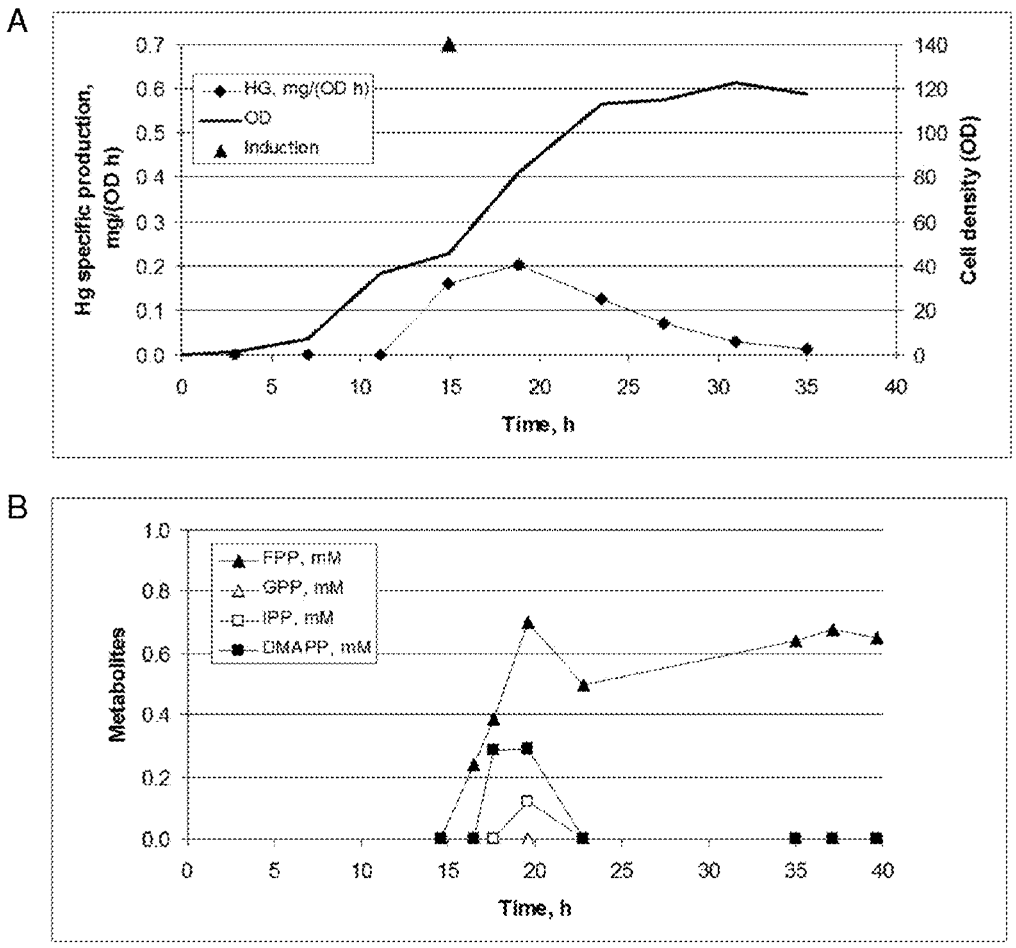

FIGS. 128A and 128B are graphs showing the accumulation of isoprenoid pathway intermediates in the MCM343 strain of *E. coli*. Arrows on the top figure indicate the time point when 100 μM IPTG dose was added to the fermentor.

Figure 129:
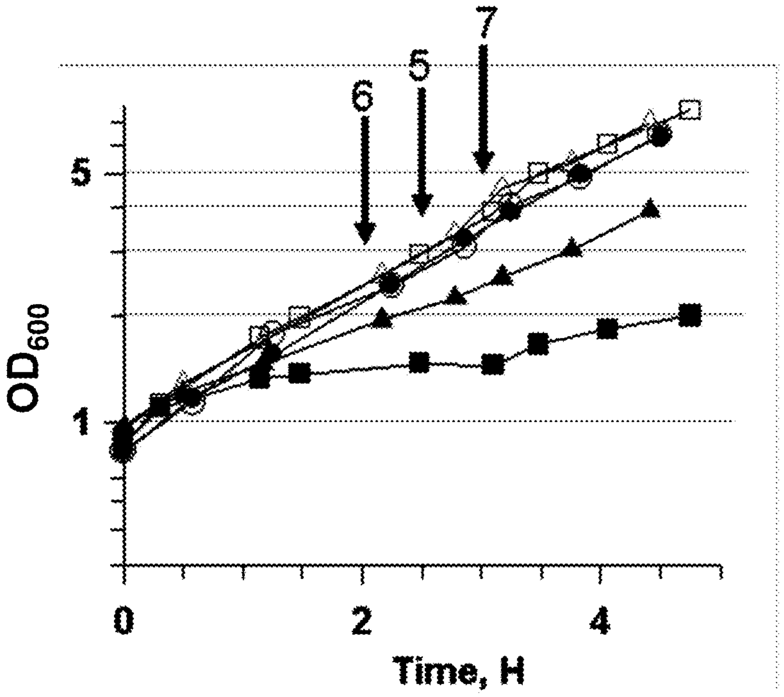

FIG. 129 is a graph of growth curves for cultures of BL21 expressing MVK, circles; MVK+PMV, triangles; MVK+PMV+MDD, squares. Cultures were either fed 5.8 mM MVA, filled symbols, or grown without addition of MVA, open symbols. Y-axis is $OD_{600}$. Samples were taken for analysis at times indicated by the arrow. Numbers above the arrows correspond to *E. coli* BL21 cells bearing pTrcK, representing a plasmid expressing MVK (#5), pTrcKK representing a plasmid expressing MVK plus PMK (#7), and pTrcKKD, representing a plasmid expressing MVK plus PMK plus MDD (#6) were grown.

Figure 130:
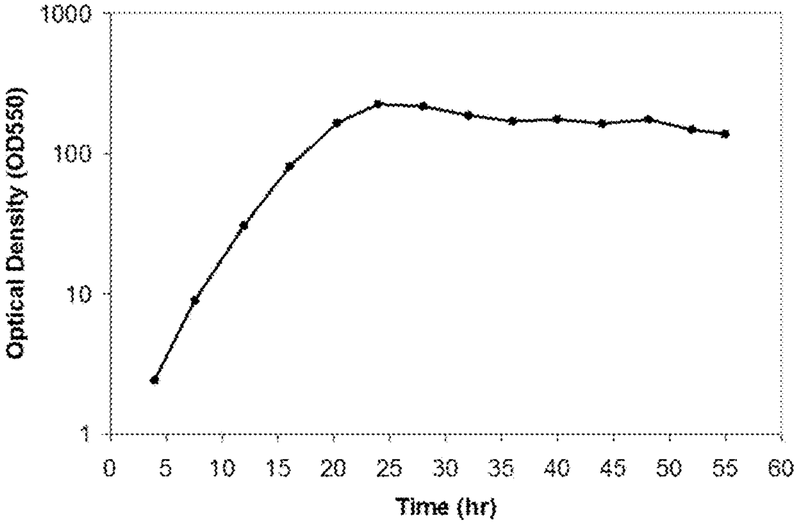

FIG. 130 is a time course of optical density within the 15-L bioreactor fed with glucose.

Figure 131:
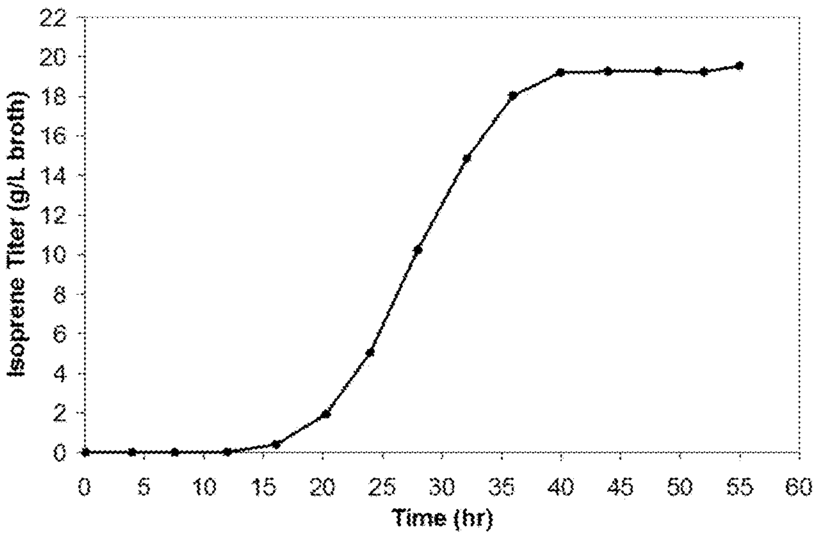

FIG. 131 is a time course of isoprene titer within the 15-L bioreactor fed with glucose. The titer is defined as the amount of isoprene produced per liter of fermentation broth.

Figure 132:
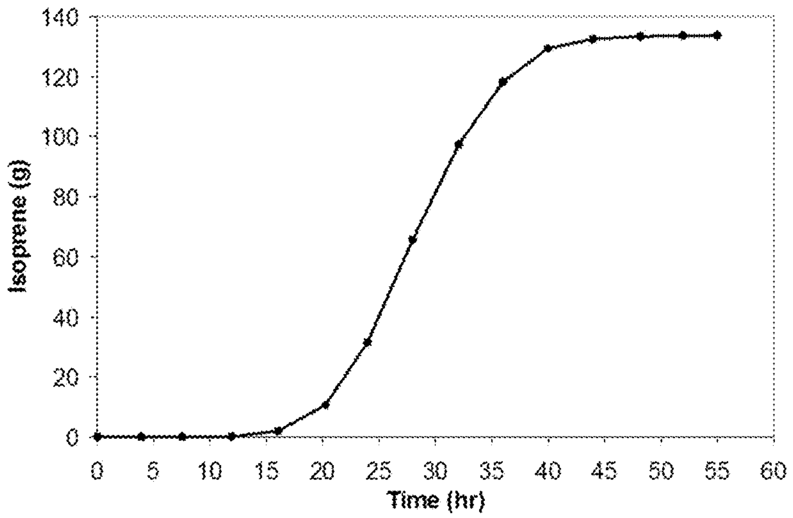

FIG. 132 is a time course of total isoprene produced from the 15-L bioreactor fed with glucose.

Figure 133:
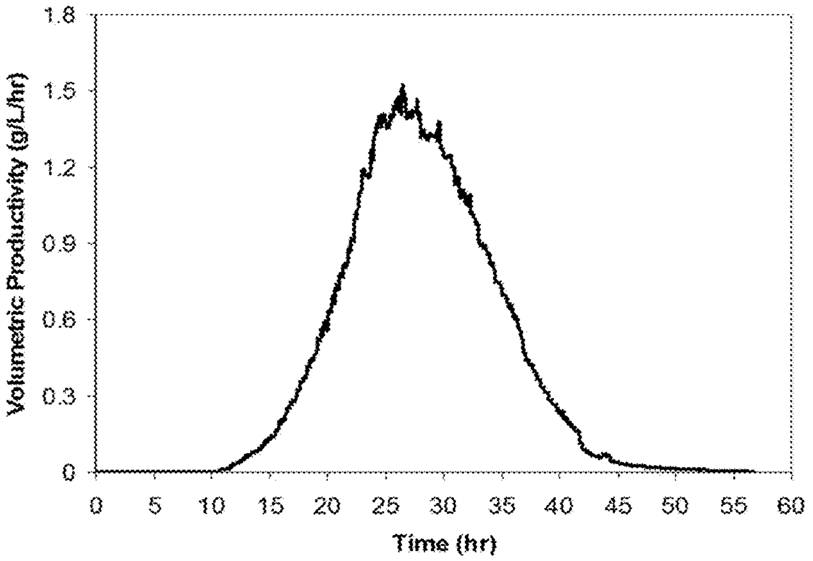

FIG. 133 is a time course of volumetric productivity within the 15-L bioreactor fed with glucose. The volumetric productivity is defined as the amount of isoprene produced per liter of broth per hour.

Figure 134:
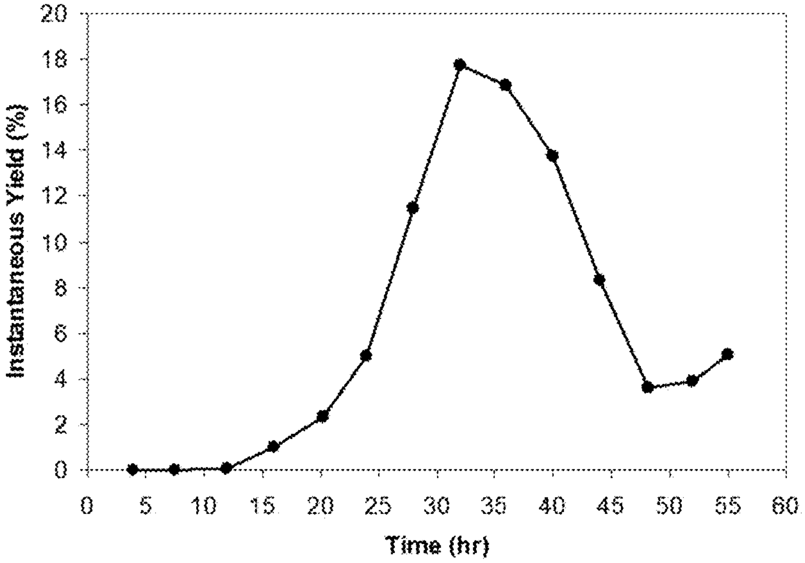

FIG. 134 is a time course of instantaneous yield within the 15-L bioreactor fed with glucose. The instantaneous yield is defined as the amount of isoprene (gram) produced per amount of glucose (gram) fed to the bioreactor (w/w) during the time interval between the data points.

Figure 135:
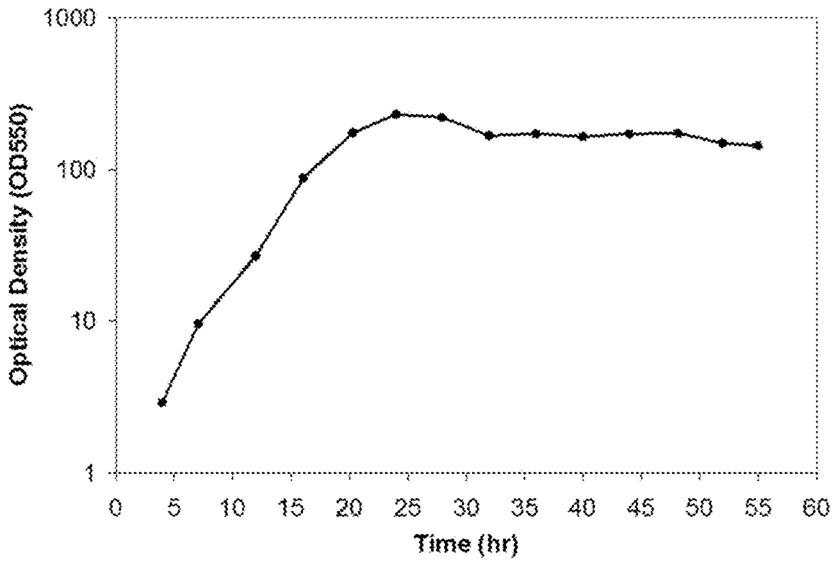

FIG. 135 is a time course of optical density within the 15-L bioreactor fed with glucose.

Figure 136:
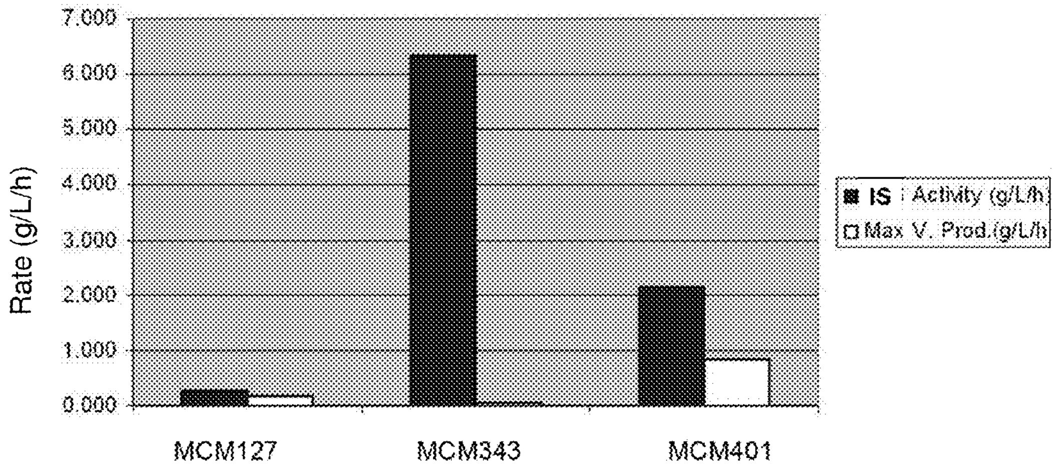

FIG. 136 is a graph of isoprene synthase (IS) activity versus volumetric productivity in strains MCM127, MCM343, and MCM401.

Figure 137:
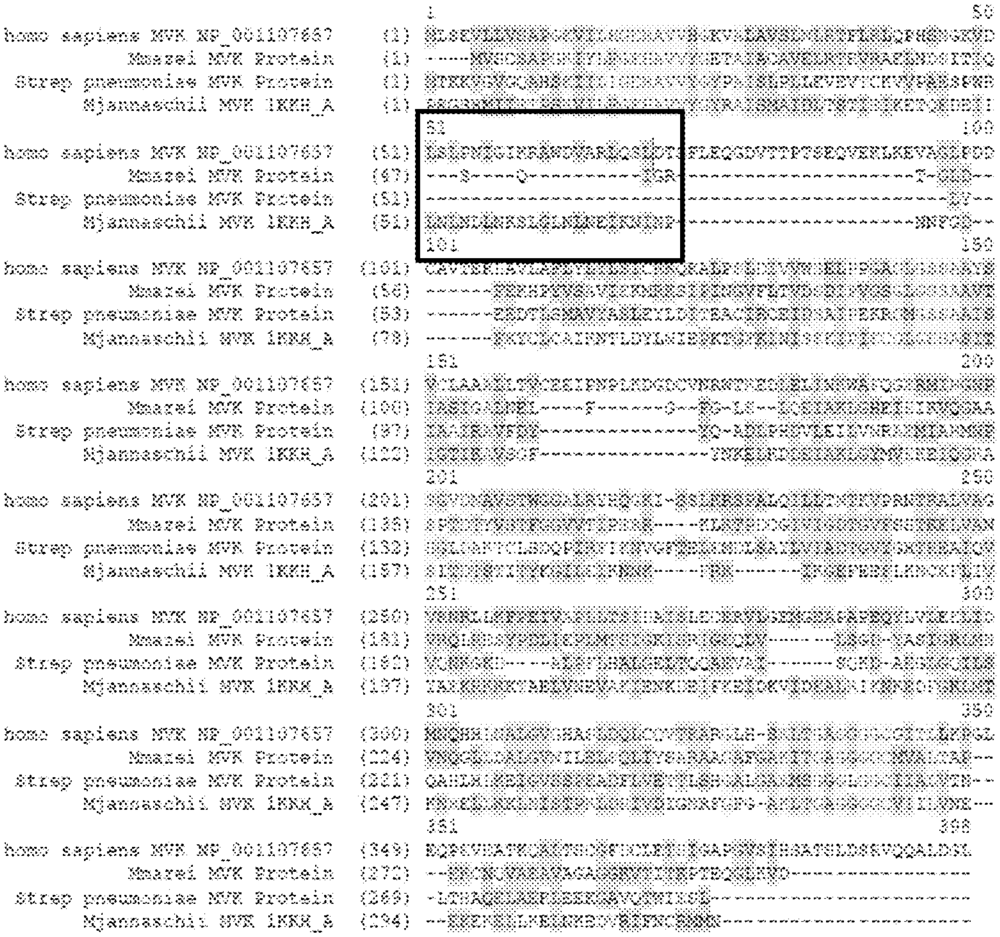

FIG. 137 is an alignment of the protein sequences for mevalonate kinases from *Homo sapiens, Methanosarcina mazei, Streptococcus pneumoniae*, and *Methanococcus jannaschii* (SEQ ID NOs:109-112, respectively). Alignments were generated using Vector Nti (Invitrogen). Light grey area highlighted amino acids are identical; dark grey highlighted amino acids are conserved in some of the mevalonate kinases. The boxed area represents the loop that is present in the mevalonate kinases from *Homo sapiens* and *M. jannaschii* (sensitive to feedback inhibition) but absent in *M. mazei* and *S. pneumoniae* (feedback inhibition resistant).

Figure 138:
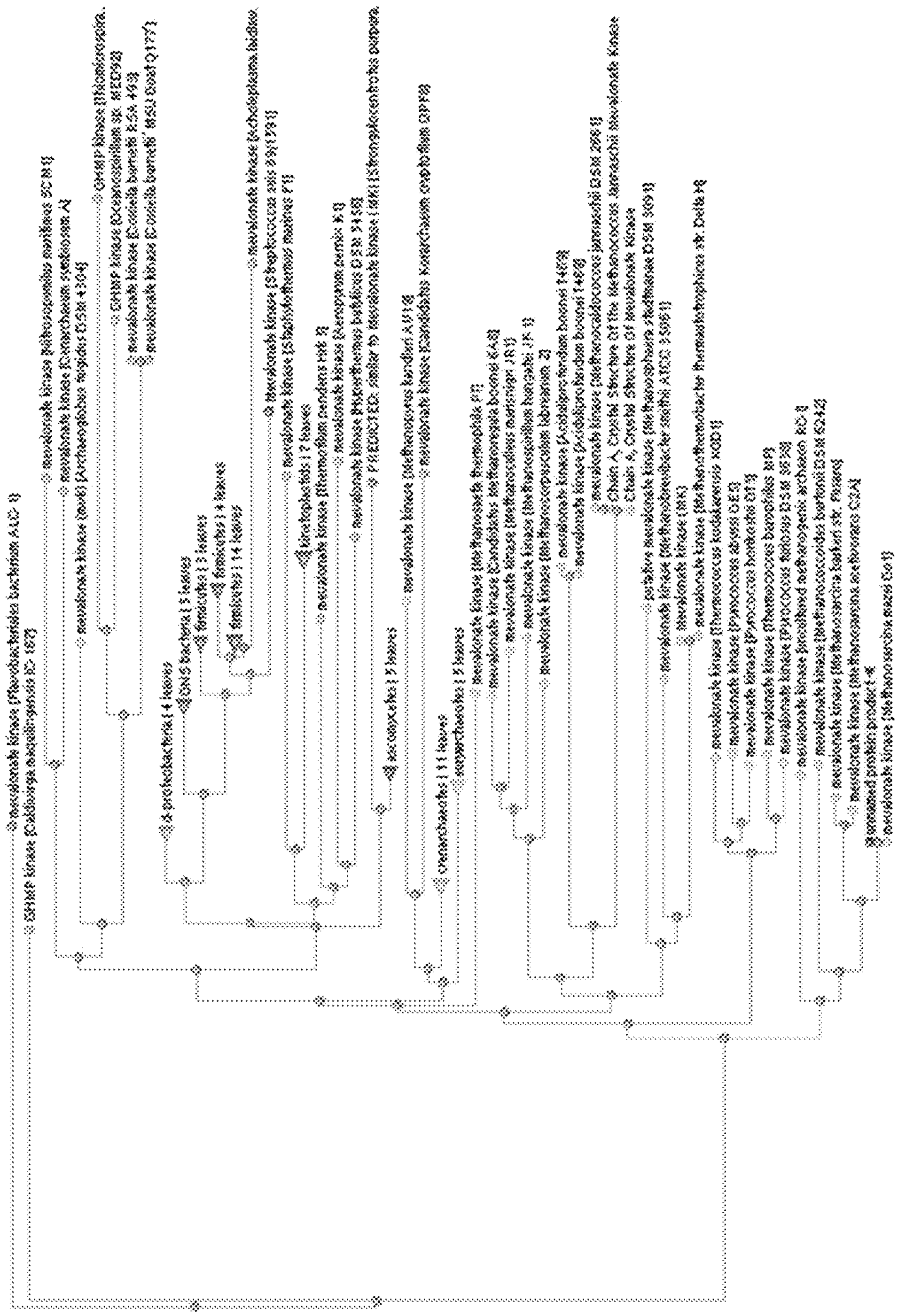

FIG. 138 is *M. mazei* mevalonate kinase BLAST search distance tree. Exemplary potential feedback resistant mevalonate kinase polypeptides are circled.

Figures 139A, 139B, 139C:

FIGS. 139A-139C are graphs of a model of *M. mazei* mevalonate kinase. FIG. 139A is a model of the *M. mazei* mevalonate kinase generated using PyMol based on the *Streptococcus pneumoniae* (pdb 2oi2) as the starting structure. FIG. 139B is a pictorial view of the active sites of the *M. mazei* mevalonate kinase, with Lys9, His16, Ser95, Ser135, Asp138, and Thr174 shown as sticks. FIG. 139C shows the conserved ATP binding motif of *M. mazei* mevalonate kinase, containing residues $^{87}$PVGSGKGSSAA$^{97}$.

Figure 140A:
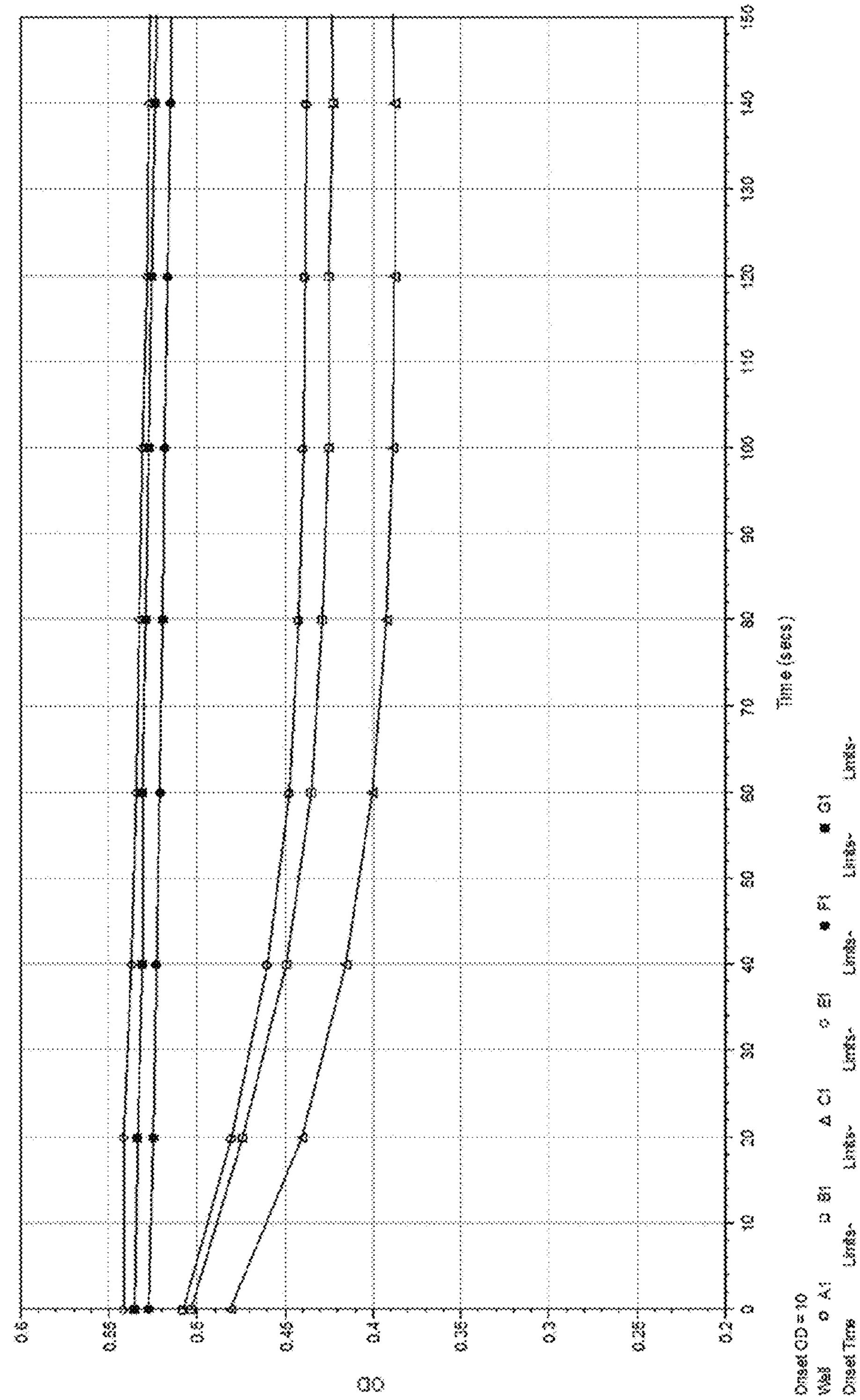
Figure 140B:
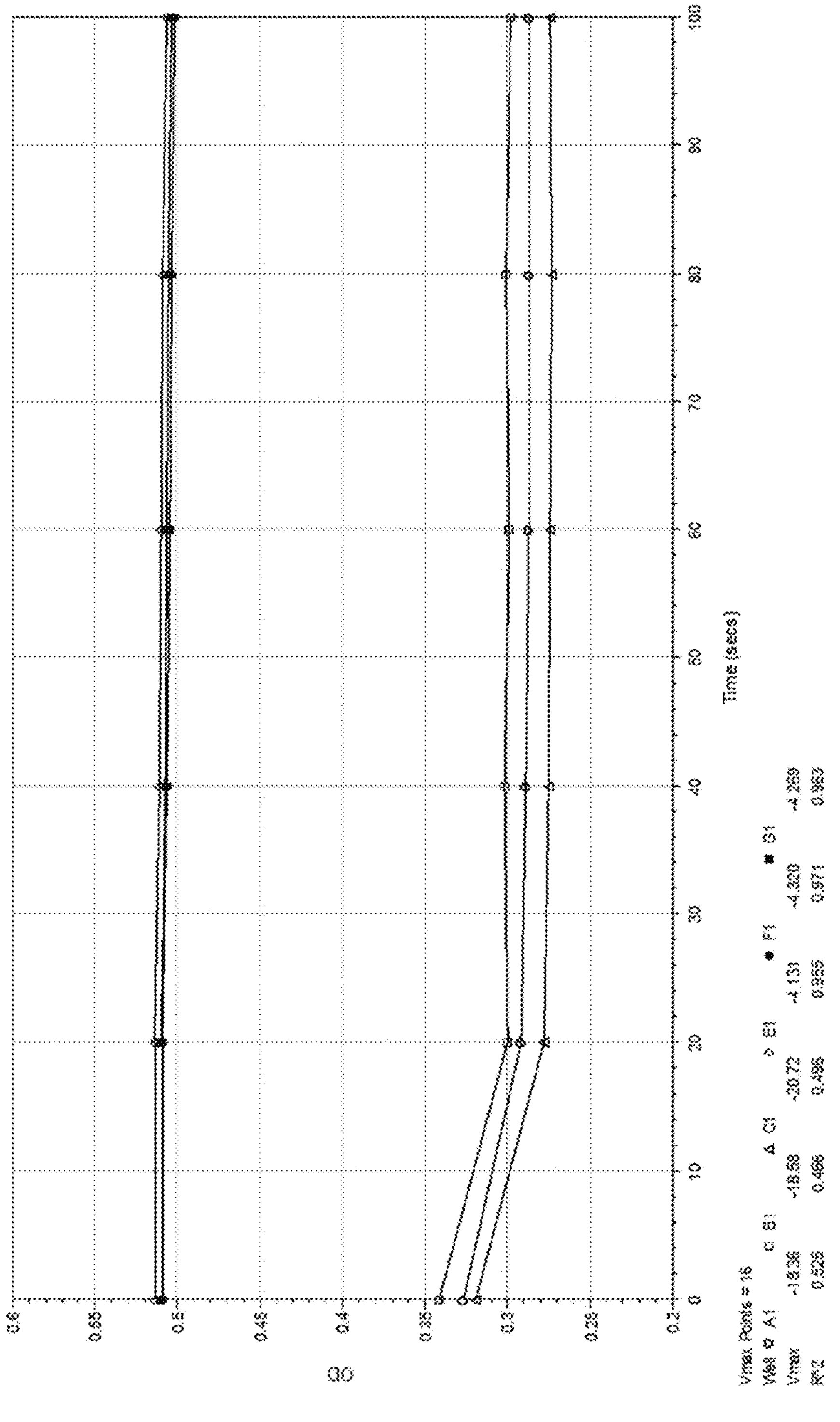
Figure 140C:
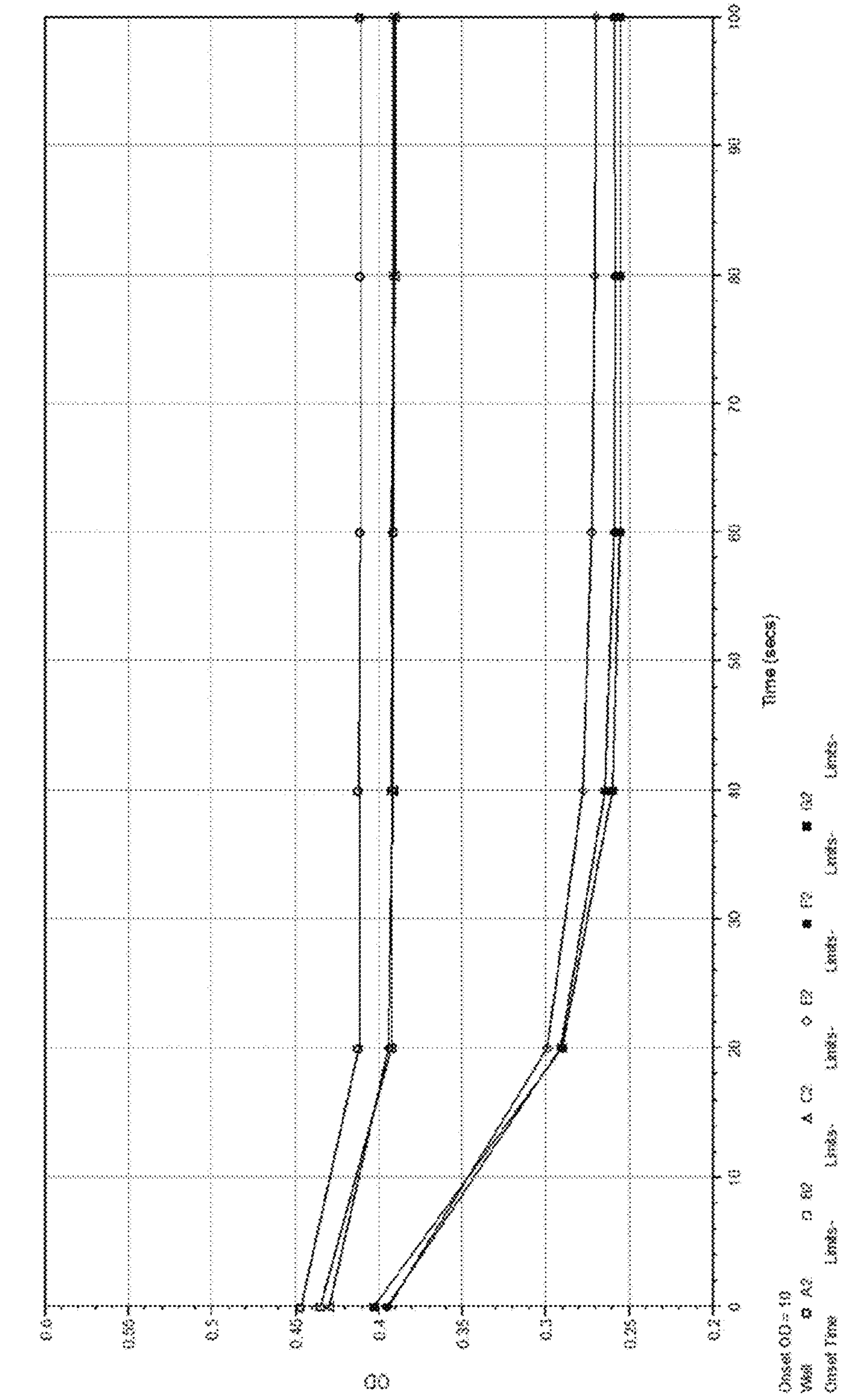
Figure 140D:
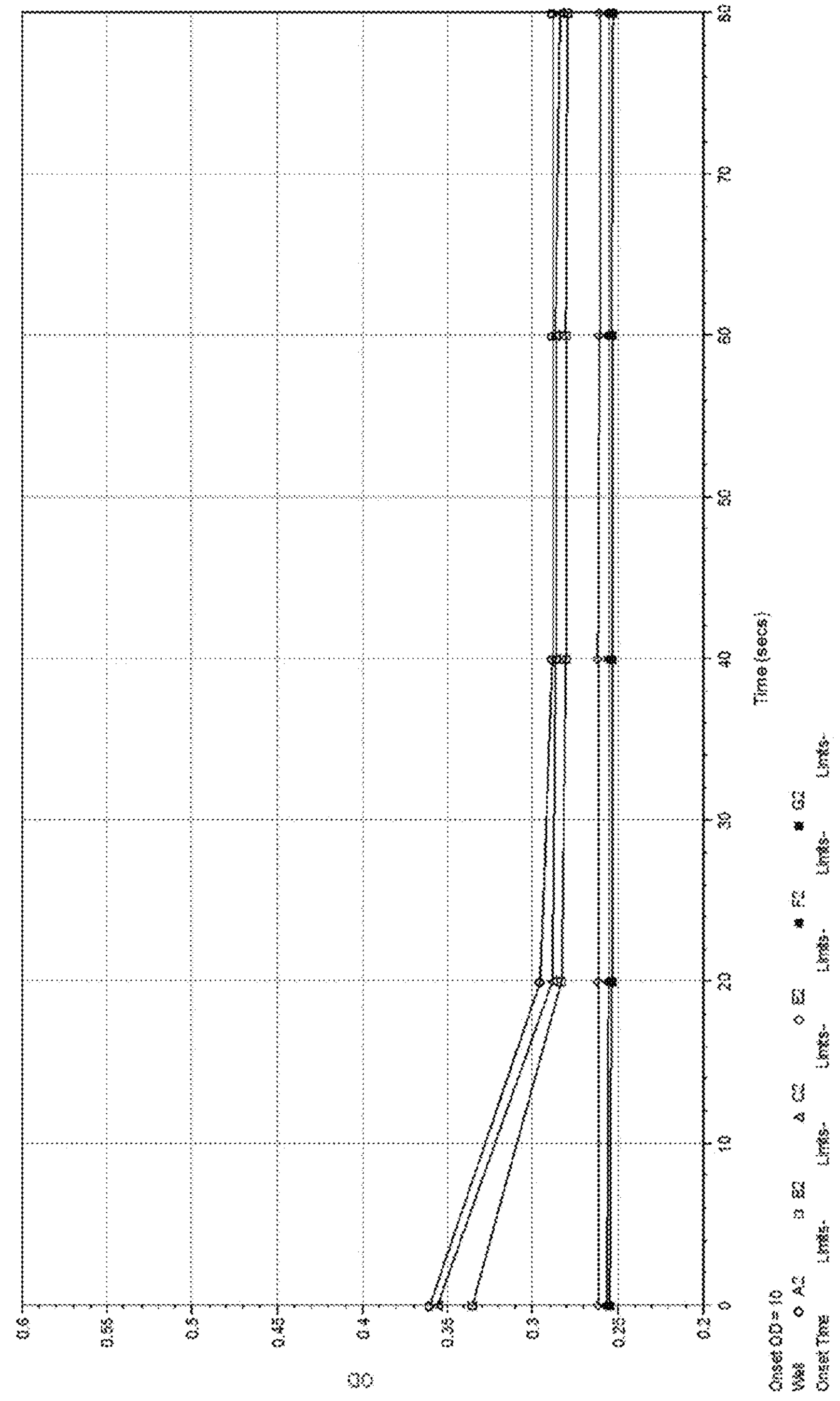
Figure 140E:
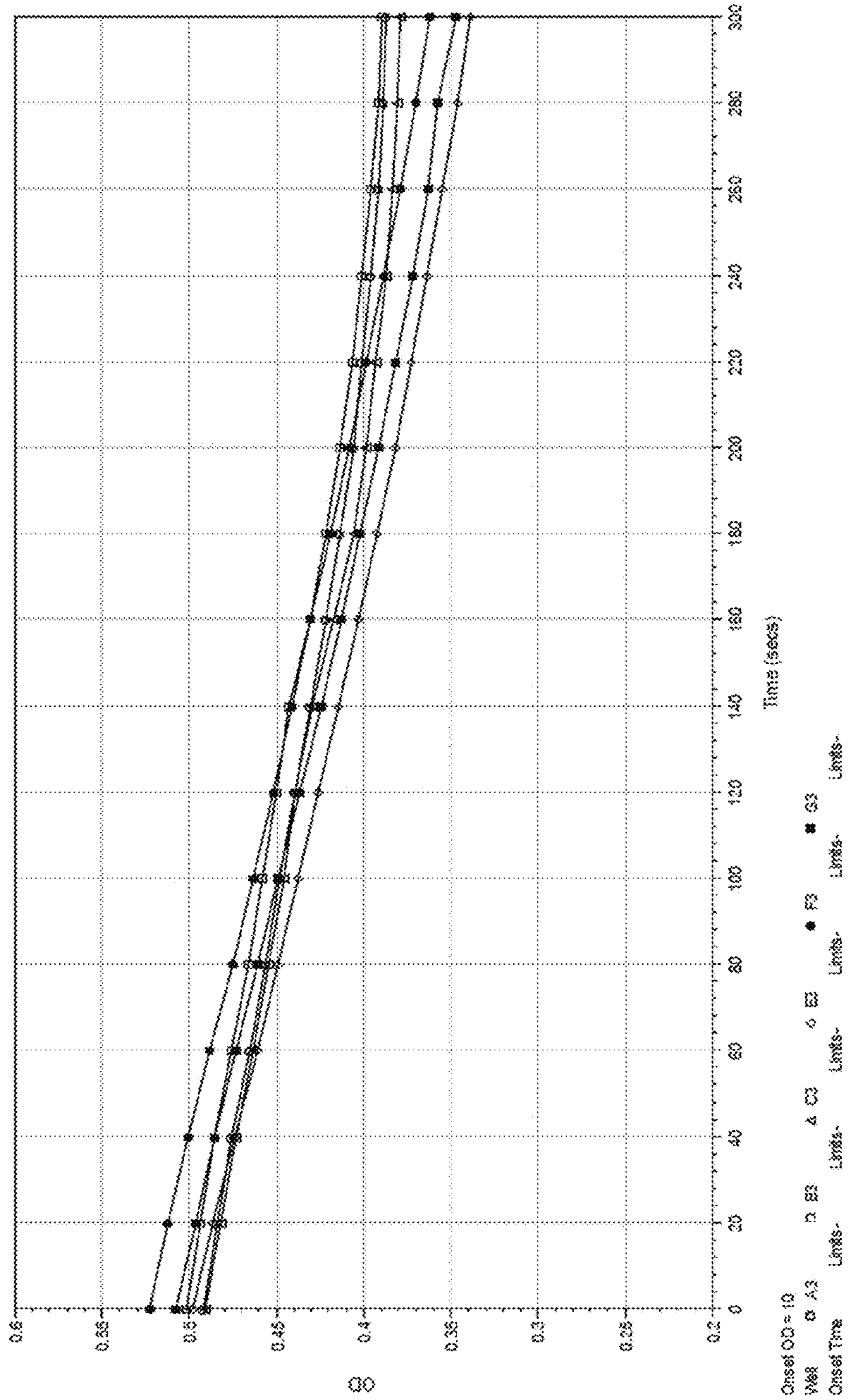
Figure 140F:
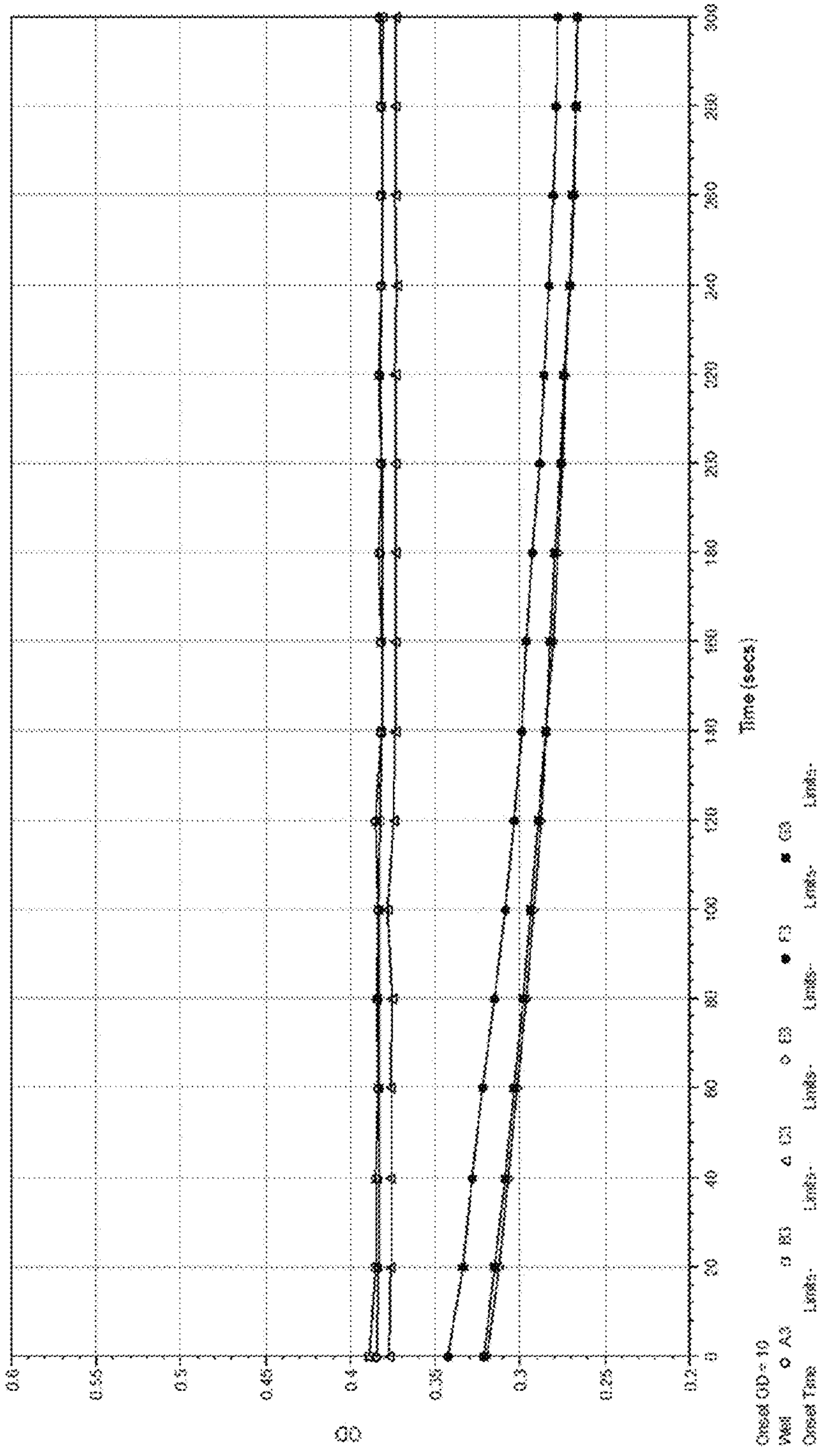
Figure 140G:
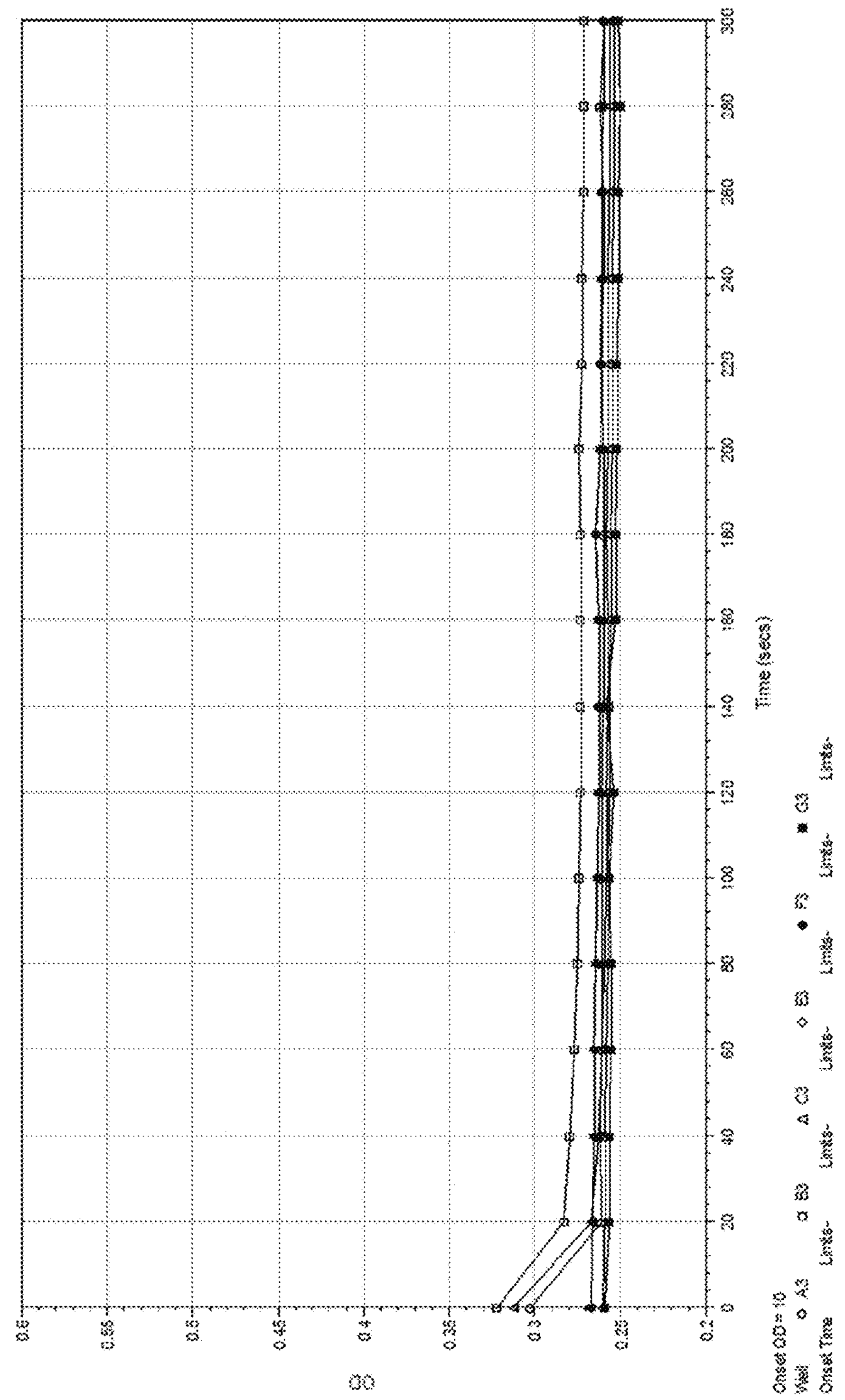

FIGS. 140A-140G are graphs showing the change in optical density (OD) over time correlating with diphosphomevalonate inhibition of *S. pneumoniae* mevalonate kinase (FIGS. 140A-140B), yeast mevalonate kinase (FIGS. 140C-140D), and *M. mazei* mevalonate kinase (FIGS. 140E-140G). FIGS. 140A, 140C, 140E, and 140F represent reactions A (open circle), B (open square), and C (open triangle) containing mevalonate kinase in 100 μM Tris and reactions E (open diamond), F (closed circle), and G (closed square) containing mevalonate kinase and phosphomevalonate kinase. FIGS. 140B, 140D, and 140G represent reactions A (open circle), B (open square), and C (open triangle) containing mevalonate kinase to which phosphomevalonate kinase has been added after the mevalonate kinase reaction is complete and reactions E (open diamond), F (closed circle), and G (closed square) containing mevalonate kinase and phosphomevalonate kinase.

Figure 141:
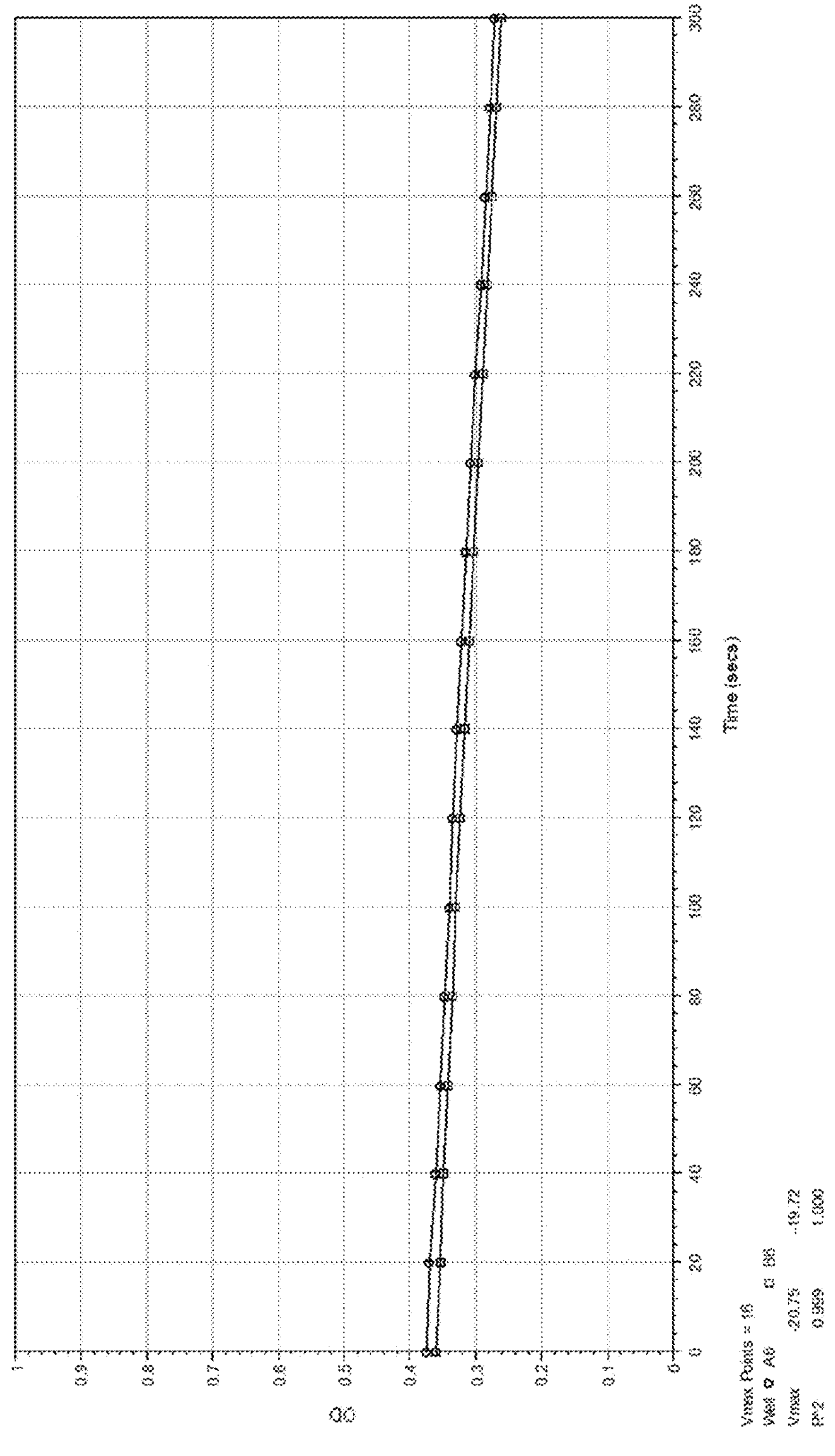

FIG. 141 is a graph showing the change in optical density over time correlating with isopentenyl monophosphate inhibition of *M. mazei* mevalonate kinase. Reaction A (open circle) contains *M. mazei* mevalonate kinase and all necessary cofactors. Reaction B (open square) contains *M. mazei* mevalonate kinase, all necessary cofactors, and 100 μM isopentenyl monophosphate.

Figure 142:
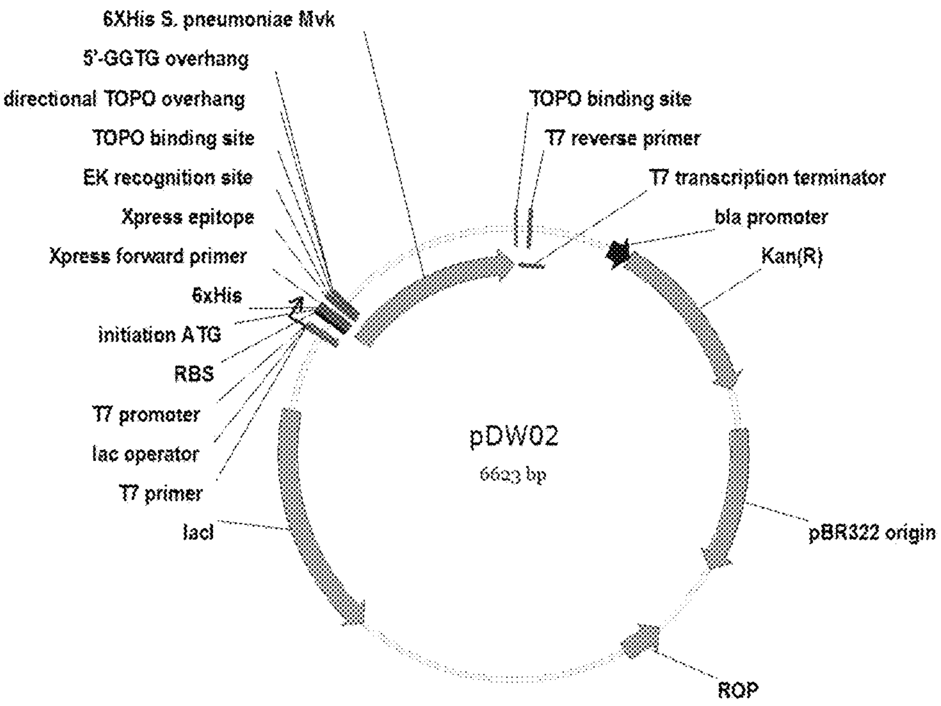

FIG. 142 is a map of pDW02 in pET200D MVK (*S. pneumoniae*).

FIGS. 143A and 143B are the nucleotide sequence of pDW02 in pET200D MVK (*S. pneumoniae*) (SEQ ID NO:106).

DETAILED DESCRIPTION OF THE INVENTION

The invention described herein provides for, inter alia, compositions and methods for producing and/or increasing the production of isoprene by utilizing a feedback resistant mevalonate kinase as part of the production process. Mevalonate kinase (MVK or MK) polypeptides phosphorylate mevalonate (MVA) to form mevalonate-5-phosphate (MVAP), as part of the MVA pathway for the biosynthesis of isoprene (FIGS. 19A and 19B). As used herein, the term "isoprene" or "2-methyl-1,3-butadiene" (CAS#78-79-5) refers to the direct and final volatile C5 hydrocarbon product from the elimination of pyrophosphate from 3,3-dimethylallyl pyrophosphate (DMAPP), and does not involve the linking or polymerization of one or more isopentenyl diphosphate (IPP) molecules to one or more DMAPP molecules.

The present invention is based in part on the surprising discovery that the MVK polypeptide from the archaeon *Methanosarcina mazei* is resistant to feedback inhibition. For example, this result is surprising in view of a prior report that the MVK from the archaeon *Methanococcus jannaschii* is feedback inhibited by GPP (geranyl pyrophosphate) and FPP (farnesyl pyrophosphate) (see, for example, Huang et al., *Protein Expression and Purification* 17(1):33-40, 1999; which is hereby incorporated by reference in its entirety, particularly with respect to feedback-inhibited MVK polypeptides). Additionally, the human MVK polypeptide is reported to be inhibited by GPP, FPP, and geranylgeranyl diphosphate (GGPP) with $K_i$ values in the nanomolar range, and MVK polypeptides from some bacterial sources are reported to be inhibited by FPP with $K_i$ values in the μM range.

As used herein, the term "enzyme inhibition" denotes the inhibition of enzymatic activity of an MVK polypeptide. Exemplary types of enzyme inhibition include substrate inhibition and feedback inhibition. In various embodiments, an enzymatic activity of a MVK polypeptide (such as the conversion of MVA to MVAP) is inhibited by less than about any of 90, 80, 70, 60, 50, 40, 30, 20, 10, or 5% by a compound (such as MVA) produced by the cells compared to the enzymatic activity of the MVK polypeptide in the absence of the compound.

As used herein, the term "substrate inhibition" refers to the inhibition of enzymatic activity of a mevalonate kinase polypeptide by the substrate MVA.

As used herein, the term "feedback inhibition" denotes the inhibition of enzymatic activity of a MVK polypeptide by a metabolite downstream of mevalonate in isoprenoid or isoprenoid biosynthesis. Metabolites downstream of mevalonate (MVA) in isoprenoid or isoprenoid biosynthesis include, but are not limited to, mevalonate-5-phosphate (MVAP), mevalonate-5-diphosphate (MVAPP), isopentenyl diphosphate (IPP), 3,3 dimethylallyl diphosphate (DMAPP), geranyl diphosphate (GPP), farnesyl diphosphate (FPP), geranylgeranyl diphosphate (GGPP), farnesol, dolichol phosphate, phytyl-pyrophosphate, diphosphomevalonate, and isopentenyl monophosphate (IP). While not intending to be bound by any particular theory, it is believed that feedback inhibition of MVK polypeptides is based on allosteric regulation of MVK polypeptides by binding to the MVK polypeptides of a metabolite downstream of mevalonate in isoprenoid biosynthesis (see, for example, WO/2004/111214 which is hereby incorporated by reference in its entirety, particularly with respect to feedback-inhibited and feedback-resistant MVK polypeptides).

Feedback inhibition of an MVK polypeptide can be analyzed using any standard method known to one skilled in the art. For example, MVK polypeptide feedback inhibition by the mevalonate downstream metabolite diphosphomevalonate can be measured using a two enzyme system employing the MVK polypeptide in question and PMK (see, e.g., Andreassi et al., *Biochemistry,* 43:16461-66, 2004, which is incorporated by reference in its entirety). In some embodiments, the feedback inhibition of an MVK polypeptide by a potential feedback inhibitor molecule (e.g., a metabolite downstream of mevalonate in isoprenoid or isoprenoid biosynthesis) is determined as described in Example 8, part IX (v).

By "feedback resistance" or "feedback-resistant" is meant any resistance to feedback inhibition. Feedback resistance can be analyzed using any standard method known to one skilled in the art. For example, MVK polypeptide activity can be measured in two different methods. In the first method, ATP (or another phosphate donor) concentration is around a non-saturating concentration (i.e., a concentration around which the reaction rate is sensitive to changes of these substrate concentrations (e.g., at concentrations around the respective Km values of the MVK polypeptide under investigation for these substrates concentration, see for example, WO/2004/111214, which is hereby incorporated by reference in its entirety, particularly with respect to feedback-inhibited and feedback-resistant MVK polypeptides)) and mevalonate (or mevalonate analogue) is around a saturating concentration. In the second method, ATP (or another phosphate donor) concentration is around a saturating concentration and mevalonate is around a non-saturating concentration (e.g., Km values). In some embodiments, the $K_i$ value for a potential feedback inhibitor molecule (e.g., a metabolite downstream of mevalonate in isoprenoid or isoprenoid biosynthesis) is determined as described in Example 8, part IX (i-iv).

In some embodiments in which a MVK polypeptide is feedback-resistant, concentrations of GPP or FPP that are equal to or less than about any of 20, 30, 40, 50, 60, 70, 80, 90, or 100 μM do not substantially inhibit (e.g., inhibit by less than about any of 10, 8, 6, 4, 3, 2, 1%) one or more of the following activities of a MVK polypeptide: the binding of ATP, the binding of mevalonate, and/or the conversion of MVA to MVAP. In some embodiments, concentrations of DMAPP that are equal to or less than about any of 20, 30, 40, 50, 60, 70, 80, 90, 100, 250, 500, 750, 1000, 2000, 3000, 4000, or 5000 μM do not substantially inhibit (e.g., inhibit by less than about any of 10, 8, 6, 4, 3, 2, 1%) one or more of the following activities of a MVK polypeptide: the binding of ATP, the binding of mevalonate, and/or the conversion of MVA to MVAP. In some embodiments, the $K_i$ value of a feedback-resistant MVK polypeptide for GPP or FPP is equal to or greater than about any of 10, 20, 30, 40, 50, 60, 70, 80, 90, 100, 125, 150, 175, 200, 225, 250, or 300 μM. In some embodiments, the $K_i$ value of a feedback-resistant MVK polypeptide for DMAPP is equal to or greater than about any of 0.8, 1.0, 2.0, 3.0, 4.0, 5.0, 6.0, 7.0, 8.0, 9.0, or 10.0 mM.

The use of a feedback-resistant MVK polypeptide for the production of isoprene is desirable because it results in increased MVK polypeptide activity, and thereby reduces the accumulation of MVA and increases the supply of MVAP for conversion to isoprene using the MVA pathway. Example 8 compares the ability of DMAPP, GPP, FPP, and GGPP to inhibit MVK polypeptides from the yeast *Sacharaomyces cerevisiae* and the archaeon *Methanosarcina mazei*. The conversion of mevalonate to phosphomevalonate catalyzed by the *M. mazei* MVK polypeptide was not inhibited by DMAPP, GPP, or FPP at concentrations up to 100 μM under the conditions tested, correlating to a $K_i$>200 μM. Additionally, the *M. mazei* MVK polypeptide was not inhibited by up to 5 mM DMAPP under the conditions tested. In contrast, DMAPP, GPP, and FPP are competitive inhibitors with respect to ATP for the *S. cerevisiae* MVK polypeptide with inhibition constants ($K_i$s) of 33.2 μM, 153.3 nM, and 138.5 nM, respectively. In addition, DMAPP, GPP, and FPP are uncompetitive inhibitors with respect to mevalonate for the *S. cerevisiae* MVK polypeptide with $K_i$s of 394.6 μM, 2.54 μM, and 2.98 μM, respectively.

Based on the discovery that the MVK polypeptide from the archaeon *M. mazei* is resistant to feedback inhibition, other MVK polypeptides (such as other archaeal MVK polypeptides) that are homologous to the *M. mazei* MVK polypeptide are predicted to be feedback-resistant as well. In particular, sequence alignments indicate that the *M. mazei* MVK polypeptide is missing a loop that is present in MVK polypeptides that are sensitive to feedback inhibition by downstream products such as FPP (e.g., MVK polypeptides from *Homo sapiens*, rat, and *Methanococcus jannaschii*). These MVK polypeptides from *H. sapiens*, rat, and *M. jannaschii* contain a loop that is absent in MVK polypeptides that are resistant to feedback inhibition (Fu et al., *Biochemistry* 47(12):3715-24, 2008; see, for example, FIG. 3; which is hereby incorporated by reference in its entirety, particularly with respect to feedback-inhibited and feedback-resistant MVK polypeptides). Further, modeling studies of the *M. mazei* MVK suggest that it folds in a similar way in comparison to *S. pneumoniae* MVK, including the active site and the ATP binding motif (Andreassi et al., *Protein Sci* 16(5): 983-989, 2007). The human MVK contains two additional loops (residues 59-85 and 93-121) that are not found in the *M. mazei* or *S. pneumoniae* MVKs. It has been shown that residues found in those loops contribute to feedback inhibition by farnesyl diphosphate (see supra Fu et al.). FIGS. 139A-139C show a model of *M. mazei* mevalonate kinase, its active site, and its conserved ATP binding motif, respectively. Any MVK polypeptide that is feedback-resistant can be used in the compositions and methods disclosed herein for the production of isoprene. Exemplary archaeal MVK polypeptides that are predicted to be feedback-resistant based on their homology to the *M. mazei* MVK polypeptide include YP_304960.1 mevalonate kinase *Methanosarcina barkeri* str. Fusaro, NP_615566.1 mevalonate kinase *Methanosarcina acetivorans* C2A, YP_566996.1 mevalonate kinase *Methanococcoides burtonii* DSM 6242, and YP_684687.1 mevalonate kinase uncultured methanogenic archaeon RC-I. For this prediction, the default parameters were used for a protein-protein BLAST search using the NCBI BLAST software currently publicly available on the world wide web. Additionally, FIG. 138 shows a *M. mazei* mevalonate kinase BLAST search distance tree that was created using the distance tree of results link on the NCBI BLAST results page. Exemplary potential feedback-resistant mevalonate kinase polypeptides that lack the loop disclosed by Fue et al. are circled. In some embodiments, any of the MVK nucleic acids and polypeptides listed in Appendix 1 in the section "Exemplary mevalonate kinase nucleic acids and polypeptides" that are feedback-resistant (e.g., MVK polypeptides that lack the loop denoted in FIG. 137) are used in the compositions or methods disclosed herein. In some embodiments, any of the mutated MVK polypeptides that are feedback-resistant and that are disclosed by WO 2004/111214 are used.

As used herein, "non-modified nucleic acids encoding feedback-resistant mevalonate kinase" refers to any mevalonate kinase which has not been manipulated to increase mevalonate kinase activity to a greater extent than if no manipulation has occurred. For example, mutation(s) to one or more nucleotide(s) or amino acids of a mevalonate kinase found in nature is considered to be a modified mevalonate kinase. Examples of modified mevalonate kinases are disclosed in WO 2004/111214 and WO 2006/063752. In some embodiments, the modified mevalonate kinases in WO 2004/111214 and WO 2006/063752 are excluded from the invention. In other embodiments, the feedback resistant mevalonate kinases of this invention do not include a modified mevalonate kinase wherein at least one mutation is at one or more amino acid position(s) selected from the group consisting of amino acid positions corresponding to positions 55, 59, 66, 83, 106, 111, 117, 142, 152, 158, 218, 231, 249, 367 and 375 of the amino acid sequence of *Saccharomyces cerevisiae* mevalonate kinase as shown in SEQ ID NO:1 in WO 2006/063752. In another embodiment, the feedback resistant mevalonate kinases of this invention do not include a modified mevalonate kinase having the nucleotide sequence SEQ ID NO: 5 in WO 2006/063752.

Thus, the MVK polypeptide from *M. mazei* or other feedback-resistant MVK polypeptides can be used to decrease feedback inhibition by downstream metabolites of the isoprene or isoprenoid pathways (such as DMAPP, GPP, and/or FPP) and increase the rate of production of DMAPP compared to MVK polypeptides that are more sensitive to feedback inhibition. If desired, a heterologous nucleic acid or a duplicate copy of an endogenous nucleic acid encoding an isoprene synthase polypeptide can be used to increase the conversion of DMAPP to isoprene.

In particular, both a high flux from central metabolism to DMAPP and a robust enzyme activity to catalyze the conversion of DMAPP to isoprene are desirable for the commercial scale production of isoprene in vivo. Since high concentrations of DMAPP are growth inhibitory, high flux through the MVA pathway is desirably accompanied by high isoprene synthase polypeptide activity to avoid accumulation of toxic amounts of DMAPP. Accordingly, in one aspect, the invention features a method of producing isoprene that involves increasing the expression and/or activity of (i) a MVK polypeptide (such as a feedback-resistant MVK polypeptide) and (ii) an isoprene synthase polypeptide compared to the expression level and/or activity level normally found in the cell. For example, overexpressing the MVK polypeptide from *M. mazei* and the isoprene synthase from kudzu supports high flux to DMAPP and simultaneous conversion of DMAPP to isoprene. Furthermore, by balancing the activity of the MVK polypeptide and the isoprene synthase polypeptide, we have generated cells which convert acetyl-CoA to isoprene at high flux and titer without the accumulation of DMAPP. The total activity level of an MVK polypeptide is influenced by both the level of protein expressed and the enzymatic characteristics of the specific MVK polypeptide used. Limiting the accumulation of DMAPP is valuable because it prevents DMAPP-associated growth inhibition and loss of metabolic activity.

As described further in the Examples, overexpression of the feedback-resistant *M. mazei* MVK polypeptide and the kudzu isoprene synthase polypeptide resulted in an eight-fold increase in isoprene titer compared to overexpression of isoprene synthase alone. As discussed in Examples 3-5, *E. coli* cells containing the MVA pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from kudzu (pTrcKudzuMVK(*M. mazei*)) were used to produce isoprene in 15-L bioreactors. Example 3 indicates that the total amount of isoprene produced during a 68 hour fermentation was 227.2 g. Instantaneous volumetric productivity levels reached values as high as 1.5 g isoprene/L broth/hr, and the instantaneous yield levels reached as high as 17.7% w/w (Example 4). Example 5 indicates that the molar yield of utilized carbon that went into producing isoprene during this fermentation was 16.6%, and the weight percent yield of isoprene from glucose over the entire fermentation was 7.7%. Example 9 indicates that overexpression of the feedback-inhibited *S. cerevisiae* MVK polypeptide produced less isoprene than overexpression of the feedback-resistant *M. mazei* MVK polypeptide.

Example 6 describes the comparison of four strains with different relative levels of isoprene synthase polypeptide activity and MVK polypeptide activity: (i) the MCM343 strain with low MVK polypeptide activity and high isoprene synthase polypeptide activity, (ii) the MCM401 strain with high MVK polypeptide activity and high isoprene synthase polypeptide activity, (iii) the MCM437 with low MVK polypeptide activity and low isoprene synthase, and (iv) the MCM438 strain with high MVK polypeptide activity and low isoprene synthase polypeptide activity. In particular, the specific productivity of isoprene from a strain expressing the full mevalonic acid pathway and kudzu isoprene synthase polypeptide at low levels (MCM437) was compared to a strain that in addition over-expressed MVK polypeptide from *M. mazei* and kudzu isoprene synthase polypeptide (MCM401), as well as strains that either over-expressed just MVK polypeptide (MCM438), or just kudzu isoprene synthase polypeptide (MCM343). The strain over-expressing both MVK polypeptide and isoprene synthase polypeptide (MCM401) had higher specific productivity of isoprene compared to the strain over-expressing just MVK polypeptide (MCM438) or just kudzu isoprene synthase polypeptide (MCM343). The strain with low activities of both MVK polypeptide and kudzu isoprene synthase polypeptide (MCM437) had the lowest specific productivity of isoprene overall.

Accordingly, in some embodiments, the cells overexpress both an MVK polypeptide (such as a feedback-resistant MVK polypeptide) and an isoprene synthase polypeptide. In the experiments described in Examples 2-5, *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from kudzu (pTrcKudzuM- VK(*M. mazei*)0 were used to produce isoprene. In these experiments, the *M. mazei* MVK polypeptide and kudzu isoprene synthase polypeptide were overexpressed from a high copy plasmid under the control of a strong promoter. In contrast, the *S. cerevisiae* lower MVA pathway nucleic acids (mevalonate kinase, mevalonate phosphate kinase, mevalonate pyrophosphate decarboxylase, and IPP isomerase) were present as a single copy of the nucleic acids integrated in the chromosome under the control of a weak promoter. The *E. faecalis* upper MVA pathway nucleic acids (mvaE encoding a naturally occurring fusion protein that has both acetyl-CoA acetyltransferase and 3-hydroxy-3-methylglutaryl-CoA reductase activities and mvaS encoding a 3-hydroxy-3-methylglutaryl-CoA synthase polypeptide) were overexpressed from a medium copy plasmid under the control of a strong promoter (the same promoter used to express the *M. mazei* MVK polypeptide and kudzu isoprene synthase polypeptide). Thus, the *M. mazei* MVK polypeptide and kudzu isoprene synthase polypeptide were expressed at a much higher level than the other MVA pathway polypeptides. Since the feedback-resistant *M. mazei* MVK polypeptide was expressed at a much higher level than the feedback-inhibited *S. cerevisiae* MVK polypeptide, most of the conversion of MVA to MVAP seems to be due to the *M. mazei* MVK polypeptide rather than the *S. cerevisiae* MVK polypeptide. If desired, the *S. cerevisiae* MVK nucleic acid can be removed from any of the cells disclosed herein using standard methods (such that the only heterologous MVK nucleic acid is the *M. mazei* MVK nucleic acid). If desired, the *S. cerevisiae* MVK nucleic acid can alternatively be replaced by any other MVK nucleic acid in any of the cells described herein.

Accordingly, in some embodiments, an MVK polypeptide (such as a feedback-resistant MVK polypeptide) and/or an isoprene synthase polypeptide is expressed at a level that is at least about any of 2, 5, 10, 20, 30, 40, 50, 60, 70, 80, 90, 100, 125, 150, 200, 225, 250, 275, 300, 350, 400, 450, or 500-fold (i) higher than the level of expression of a second MVA pathway polypeptide (such as an acetyl-CoA acetyltransferase (AACT) polypeptide, 3-hydroxy-3-methylglutaryl-CoA synthase (HMGS) polypeptide, 3-hydroxy-3-methylglutaryl-CoA reductase (HMGR) polypeptide, phosphomevalonate kinase (PMK) polypeptide, diphosphomevalonate decarboxylase (DPMDC) polypeptide, or isopentenyl-diphosphate delta-isomerase (IDI) polypeptide) or (ii) higher than the level of expression of all other MVA pathway polypeptides in the cell. In particular embodiments, the MVK polypeptide and/or an isoprene synthase polypeptide is expressed a level that is at least about any of 2, 5, 10, 12, 14, 16, 18, 20, 30, 40, 50, 60, 70, 80, 90, 100, 125, 150, 200, 225, 250, 275, 300, 350, 400, 450, or 500-fold higher than the level of expression of an AACT polypeptide, HMGS polypeptide, and HMGR polypeptide. In particular embodiments, the MVK polypeptide and/or an isoprene synthase polypeptide is expressed a level that is at least about any of 2, 5, 10, 20, 30, 40, 50, 60, 70, 80, 90, 100, 125, 150, 200, 225, 250, 275, 300, 350, 400, 450, or 500-fold higher than the level of expression of an PMK polypeptide, DPMDC polypeptide, and IDI polypeptide. In some embodiments, the total amount of MVK polypeptide is similar to the total amount of isoprene synthase polypeptide. For example, in some embodiments, the total amount of MVK polypeptide is within about any of 10, 8, 6, 4, 2, 1, or 0.5-fold higher or lower than the total amount of isoprene synthase polypeptide (e.g., the amount of MVK polypeptide may be between about 10-fold lower to about 10-fold higher than the amount of isoprene synthase polypeptide). Standard methods (such as western blotting) can be used to quantitate the amount of any of these polypeptides. Standard methods can be used to alter the relative amounts of expressed MVA pathway polypeptides, such as by using a stronger promoter or a plasmid with a higher copy number to express an MVK polypeptide and/or an isoprene synthase polypeptide compared to the promoter(s) and plasmid(s) used to express other MVA pathway polypeptides.

In some embodiments, an MVK RNA molecule (such as an RNA molecule encoding a feedback-resistant polypeptide) and/or an isoprene synthase RNA molecule is expressed at a level that is at least about any of 2, 5, 10, 20, 30, 40, 50, 60, 70, 80, 90, 100, 125, 150, 200, 225, 250, 275, 300, 350, 400, 450, or 500-fold (i) higher than the level of expression of a second MVA pathway RNA molecule (such as an AACT RNA molecule, HMGS RNA molecule, HMGR RNA molecule, PMK RNA molecule, DPMDC RNA molecule, or IDI RNA molecule) or (ii) higher than the level of expression of all other MVA pathway RNA molecules in the cell. In particular embodiments, the MVK RNA molecule and/or an isoprene synthase RNA molecule is expressed at a level that is at least about any of 2, 5, 10, 12, 14, 16, 18, 20, 30, 40, 50, 60, 70, 80, 90, 100, 125, 150, 200, 225, 250, 275, 300, 350, 400, 450, or 500-fold higher than the level of expression of an AACT RNA molecule, HMGS RNA molecule, and HMGR RNA molecule. In particular embodiments, the MVK RNA molecule and/or an isoprene synthase RNA molecule is expressed at a level that is at least about any of 2, 5, 10, 20, 30, 40, 50, 60, 70, 80, 90, 100, 125, 150, 200, 225, 250, 275, 300, 350, 400, 450, or 500-fold higher than the level of expression of an PMK RNA molecule, DPMDC RNA molecule, and IDI RNA molecule. In some embodiments, the total amount of MVK RNA is similar to the total amount of isoprene synthase RNA. For example, in some embodiments, the total amount of MVK RNA is within about any of 10, 8, 6, 4, 2, 1, or 0.5-fold higher or lower than the total amount of isoprene synthase RNA (e.g., the amount of MVK RNA may be between about 10-fold lower to about 10-fold higher than the amount of isoprene synthase RNA). Standard methods (such as northern blotting) can be used to quantitate the amount of any of these RNA molecules. Standard methods can be used to alter the relative amounts of expressed MVA pathway RNA molecules, such as by using a stronger promoter or a plasmid with a higher copy number to express an MVK RNA molecule and/or an isoprene synthase RNA molecule compared to the promoter(s) and plasmid(s) used to express other MVA pathway RNA molecules.

In some embodiments, the number of copies of an MVK DNA molecule (such as a DNA molecule encoding a feedback-resistant polypeptide) and/or an isoprene synthase DNA molecule is at least about any of 2, 5, 10, 20, 30, 40, 50, 60, 70, 80, 90, 100, 125, 150, 200, 225, 250, 275, 300, 350, 400, 450, or 500-fold (i) higher than the number of copies of a second MVA pathway DNA molecule (such as an AACT DNA molecule, HMGS DNA molecule, HMGR DNA molecule, PMK DNA molecule, DPMDC DNA molecule, or IDI DNA molecule) or (ii) higher than the number of copies of all other MVA pathway DNA molecules in the cell. In particular embodiments, the number of copies of an MVK DNA molecule and/or an isoprene synthase DNA molecule is at least about any of 2, 5, 10, 12, 14, 16, 18, 20, 30, 40, 50, 60, 70, 80, 90, 100, 125, 150, 200, 225, 250, 275, 300, 350, 400, 450, or 500-fold higher than the number of copies of an AACT DNA molecule, HMGS DNA molecule, and HMGR DNA molecule. In particular embodiments, the number of copies of a MVK DNA molecule and/or an isoprene synthase DNA molecule is at least about any of 2, 5, 10, 20, 30, 40, 50, 60, 70, 80, 90, 100, 125, 150, 200, 225, 250, 275, 300, 350, 400, 450, or 500-fold higher than the number of copies of an PMK DNA molecule, DPMDC DNA molecule, and IDI DNA molecule. In some embodiments, the number of copies of an MVK DNA molecule is similar to the number of copies of an isoprene synthase DNA molecule. For example, in some embodiments, the number of copies of an MVK DNA molecule is within about any of 10, 8, 6, 4, 2, 1, or 0.5-fold higher or lower than the number of copies of an isoprene synthase DNA molecule (e.g., the number of copies of a MVK DNA may be between about 10-fold lower to about 10-fold higher than the number of copies of an isoprene synthase DNA molecule). Standard methods (such as southern blotting) can be used to quantitate the amount of any of these DNA molecules. Standard methods can be used to alter the relative amounts of MVA pathway DNA molecules, such as by using a plasmid with a higher copy number to insert an MVK DNA molecule and/or an isoprene synthase DNA molecule compared to the plasmid(s) used to insert other MVA pathway DNA molecules.

As discussed above, using a feedback-resistant MVK polypeptide decreases that amount of MVA that accumulates in the cell medium since more MVA is converted to MVAP. Increasing the expression of an isoprene synthase polypeptide decreases the accumulation of DMAPP since more DMAPP is converted to isoprene. If desired, the expression of a PMK polypeptide, DPMDC polypeptide, IDI polypeptide, or any combination of two or more of the foregoing can also be increased to reduce the accumulation of MVA pathway intermediates and/or to increase the flux through the MVA pathway. In some embodiments, the amount of MVA, DMAPP, IPP, GPP, FPP, or any combination of two or more of the foregoing allows production of isoprene without causing undesirable amounts of growth inhibition, toxicity, or cell death. In some embodiments, the amount of MVA, DMAPP, and/or IPP is high enough to allow production of isoprene in any of the amounts or concentrations disclosed below in the "Exemplary Production of Isoprene" section. In some embodiments, a detectable amount of MVA, DMAPP, and/or IPP does not accumulate since the intermediate(s) are being converted to downstream molecules at a rate that does not allow a detectable amount of MVA, DMAPP, and/or IPP to accumulate. Example 8, parts IV and V indicate that overexpression of the feedback-inhibited *S. cerevisiae* MVK polypeptide is correlated with the accumulation of more DMAPP and IPP than overexpression of the feedback-resistant *M. mazei* MVK polypeptide. This accumulation of DMAPP can cause undesirable growth inhibition. A goal is therefore to achieve a pathway enzyme balance to minimize the accumulation of these metabolites for the relief of growth inhibition.

Tables 15A and 15B list exemplary desirable concentrations of DMAPP, IPP, GPP, and FPP as well as examples of relatively high concentrations of these metabolites that have been detected using the cells and methods described herein. Table 15B has the same data as Table 15A that has been normalized to grams of dry cell weight assuming that 1 liter of the culture at OD=1 has 0.33 grams dry cell weight ($g_{dcw}$). For these experiments, the quantitation limit is below 0.1 mM for the intracellular concentrations of DMAPP, FPP, GPP, and IPP. If desired, more sensitive equipment can be used to detect even smaller amounts of these compounds. The lowest absolute concentrations that were used as standards for the LCMS analysis were 3.4 uM DMAPP, 1.7 uM IPP, 0.9 uM GPP, and 2.3 uM FPP. Thus, absolute amounts that are equal to or greater than these standard amounts can be readily quantified.

In these experiments, there was a negligible amount of DMAPP, FPP, GPP, and IPP in the liquid cell medium (outside of the cells). Thus, the amounts listed in Tables 15A and 15B are representative of the intracellular concentrations of DMAPP, FPP, GPP, and IPP.

TABLE 15A

Exemplary metabolite concentrations

| | | Metabolite | | | |
|---|---|---|---|---|---|
| | | DMAPP | IPP | GPP | FPP |
| Intracellular concentration, mM | Exemplary desirable concentrations | 0.4 mM[1] | 0.3 mM[1] | 0.7 mM[2] | 1.4 mM[1] |
| | Exemplary detected concentrations | 9.2 mM[3]<br>15.3 mM[5] | 27-40 mM[4]<br>6.3 mM[5] | 2.8 mM[3]<br>3.3 mM[5] | 3.6 mM[3] |

[1]Example 3.
[2]Example 8, Part VII.
[3]Example 7, Part III.
[4]Example 8, Part VIII.
[5]Example 7, Part II.

TABLE 15B

Exemplary metabolite concentrations

| | | Metabolite | | | |
|---|---|---|---|---|---|
| | | DMAPP | IPP | GPP | FPP |
| Intracellular concentration, μmol/$g_{dcw}$[6] | Exemplary desirable concentrations | 0.3[1] | 0.2[1] | 0.5[2] | 1.1[1] |
| | Exemplary detected concentrations | 7.0[3]<br>11.6[5] | 20-30[4]<br>4.8[5] | 2.1[3]<br>3.3[5] | 2.0[3] |

[1]Example 3.
[2]Example 8, Part VII.
[3]Example 7, Part III.
[4]Example 8, Part VIII.
[5]Example 7, Part II.

In some embodiments, the intracellular concentration of DMAPP is between about 0 to about 25 μmol/$g_{dcw}$, such as between about 0.1 to about 20 μmol $g_{dcw}$, about 0.1 to about 15 μmol/$g_{dcw}$, about 0.1 to about 11 μmol/$g_{dcw}$, about 0.1 to about 7 μmol/$g_{dcw}$, about 0.1 to about 5 μmol/$g_{dcw}$, about 0.1 to about 2 μmol/$g_{dcw}$, about 0.1 to about 1 μmol/$g_{dcw}$, about 0.1 to about 0.8 μmol/$g_{dcw}$, about 0.1 to about 0.6 μmol/$g_{dcw}$, about 0.2 to about 15 μmol/$g_{dcw}$, about 0.2 to about 11 μmol/$g_{dcw}$, about 0.2 to about 7 μmol/$g_{dcw}$, about 0.2 to about 5 μmol/$g_{dcw}$, about 0.2 to about 2 μmol/$g_{dcw}$, about 0.3 to about 11 μmol/$g_{dcw}$, about 0.3 to about 7 μmol/$g_{dcw}$, about 0.3 to about 5 μmol/$g_{dcw}$, about 0.3 to about 2 μmol/$g_{dcw}$, about 0.3 to about 1 μmol/$g_{dcw}$, about 0.4 to about 11 μmol/$g_{dcw}$, about 0.4 to about 7 μmol/$g_{dcw}$, about 0.4 to about 5 μmol/$g_{dcw}$, about 0.4 to about 2 μmol/$g_{dcw}$, about 0.5 to about 7 μmol/$g_{dcw}$, about 0.5 to about 5 μmol/$g_{dcw}$, or about 0.5 to about 2 μmol/$g_{dcw}$. In some embodiments, the intracellular concentration of DMAPP is equal to or less than about any of 25, 20, 18, 16, 14, 12, 10, 8, 6, 4, 2, 1, 0.8, 0.6, 0.5, 0.4, 0.3, 0.2, or 0.1 μmol/$g_{dcw}$.

In some embodiments, the intracellular concentration of IPP is between about 0 to about 60 μmol/$g_{dcw}$, such as between about 0.1 to about 50 μmol/$g_{dcw}$, about 0.1 to about 40 μmol/$g_{dcw}$, about 0.1 to about 30 μmol/$g_{dcw}$, about 0.1 to about 20 μmol/$g_{dcw}$, about 0.1 to about 15 μmol/$g_{dcw}$, about 0.1 to about 11 μmol/$g_{dcw}$, about 0.1 to about 7 μmol/$g_{dcw}$, about 0.1 to about 5 μmol/$g_{dcw}$, about 0.1 to about 2 μmol/$g_{dcw}$, about 0.1 to about 1 μmol/$g_{dcw}$, about 0.1 to about 0.8 μmol/$g_{dcw}$, about 0.1 to about 0.6 μmol/$g_{dcw}$, about 0.2 to about 60 μmol/$g_{dcw}$, about 0.2 to about 50 μmol/$g_{dcw}$, about 0.2 to about 40 μmol/$g_{dcw}$, about 0.2 to about 30 μmol/$g_{dcw}$, about 0.2 to about 20 μmol/$g_{dcw}$, about 0.2 to about 15 μmol/$g_{dcw}$, about 0.2 to about 11 μmol/$g_{dcw}$, about 0.2 to about 7 μmol/$g_{dcw}$, about 0.2 to about 5 μmol/$g_{dcw}$, about 0.2 to about 2 μmol/$g_{dcw}$, about 0.3 to about 60 μmol/$g_{dcw}$, about 0.3 to about 50 μmol/$g_{dcw}$, about 0.3 to about 40 μmol/$g_{dcw}$, about 0.3 to about 30 μmol/$g_{dcw}$, about 0.3 to about 15 μmol/$g_{dcw}$, about 0.3 to about 11 μmol/$g_{dcw}$, about 0.3 to about 7 μmol/$g_{dcw}$, about 0.3 to about 5 μmol/$g_{dcw}$, about 0.3 to about 2 μmol/$g_{dcw}$, about 0.4 to about 60 μmol/$g_{dcw}$, about 0.4 to about 50 μmol/$g_{dcw}$, about 0.4 to about 40 μmol/$g_{dcw}$, about 0.4 to about 30 μmol/$g_{dcw}$, about 0.4 to about 15 μmol/$g_{dcw}$, about 0.4 to about 7 μmol/$g_{dcw}$, about 0.4 to about 5 μmol/$g_{dcw}$, about 0.4 to about 2 μmol/$g_{dcw}$, about 0.5 to about 60 μmol/$g_{dcw}$, about 0.5 to about 50 μmol/$g_{dcw}$, about 0.5 to about 40 μmol/$g_{dcw}$, about 0.5 to about 30 μmol/$g_{dcw}$, about 0.5 to about 15 μmol/$g_{dcw}$, about 0.5 to about 11 μmol/$g_{dcw}$, about 0.5 to about 7 μmol/$g_{dcw}$, about 0.5 to about 5 μmol/$g_{dcw}$, or about 0.5 to about 2 μmol/$g_{dcw}$. In some embodiments, the intracellular concentration of IPP is equal to or less than about any of 60, 50, 40, 30, 25, 20, 18, 16, 14, 12, 10, 8, 6, 4, 2, 1, 0.8, 0.6, 0.5, 0.4, 0.3, 0.2, or 0.1 μmol/$g_{dcw}$.

In some embodiments, the intracellular concentration of GPP is between about 0 to about 8 μmol/$g_{dcw}$, such as between about 0.1 to about 7 μmol/$g_{dcw}$, about 0.1 to about 6 μmol/$g_{dcw}$, about 0.1 to about 5 μmol/$g_{dcw}$, about 0.1 to about 4 μmol/$g_{dcw}$, about 0.1 to about 3 μmol/$g_{dcw}$, about 0.1 to about 2 μmol/$g_{dcw}$, about 0.1 to about 1 μmol/$g_{dcw}$, about 0.1 to about 0.8 μmol/$g_{dcw}$, about 0.1 to about 0.6 μmol/$g_{dcw}$, about 0.2 to about 7 μmol/$g_{dcw}$, about 0.2 to about 6 μmol/$g_{dcw}$, about 0.2 to about 5 μmol/$g_{dcw}$, about 0.2 to about 4 μmol/$g_{dcw}$, about 0.2 to about 3 μmol/$g_{dcw}$, about 0.2 to about 2 μmol/$g_{dcw}$, about 0.3 to about 7 μmol/$g_{dcw}$, about 0.3 to about 6 μmol/$g_{dcw}$, about 0.3 to about 5 μmol/$g_{dcw}$, about 0.3 to about 4 μmol/$g_{dcw}$, about 0.3 to about 3 μmol/$g_{dcw}$, about 0.3 to about 2 μmol/$g_{dcw}$, about 0.4 to about 7 μmol/$g_{dcw}$, about 0.4 to about 6 μmol/$g_{dcw}$, about 0.4 to about 5 μmol/$g_{dcw}$, about 0.4 to about 2 μmol/$g_{dcw}$, about 0.5 to about 7 μmol/$g_{dcw}$, about 0.5 to about 5 μmol/$g_{dcw}$, about 0.5 to about 2 μmol/$g_{dcw}$, about 0.6 to about 7 μmol/$g_{dcw}$, about 0.6 to about 5 μmol/$g_{dcw}$, about 0.6 to about 2 μmol/$g_{dcw}$, about 0.7 to about 7 μmol/$g_{dcw}$, about 0.7 to about 5 μmol/$g_{dcw}$, or about 0.7 to about 2 mmol/$g_{dcw}$. In some embodiments, the intracellular concentration of GPP is equal to or less than about any of 8, 6, 4, 2, 1, 0.8, 0.6, 0.5, 0.4, 0.3, 0.2, or 0.1 μmol/$g_{dcw}$.

In some embodiments, the intracellular concentration of FPP is between about 0 to about 6 μmol/$g_{dcw}$, such as between about 0.1 to about 6 μmol/$g_{dcw}$, about 0.1 to about 5 μmol/$g_{dcw}$, about 0.1 to about 4 μmol/$g_{dcw}$, about 0.1 to about 3 μmol/$g_{dcw}$, about 0.1 to about 2 μmol/$g_{dcw}$, about 0.1 to about 1 μmol/$g_{dcw}$, about 0.1 to about 0.8 μmol/$g_{dcw}$, about 0.1 to about 0.6 μmol/$g_{dcw}$, about 0.2 to about 6 μmol/$g_{dcw}$, about 0.2 to about 5 μmol/$g_{dcw}$, about 0.2 to about 4 μmol/$g_{dcw}$, about 0.2 to about 3 μmol/$g_{dcw}$, about 0.2 to about 2 μmol/$g_{dcw}$, about 0.3 to about 6 μmol/$g_{dcw}$, about 0.3 to about 5 μmol/$g_{dcw}$, about 0.3 to about 4 μmol/$g_{dcw}$, about 0.3 to about 3 μmol/$g_{dcw}$, about 0.3 to about 2 μmol/$g_{dcw}$, about 0.4 to about 6 μmol/$g_{dcw}$, about 0.4 to about 5 μmol/$g_{dcw}$, about 0.4 to about 2 μmol/$g_{dcw}$, about 0.5 to about 6 μmol/$g_{dcw}$, about 0.5 to about 5 μmol/$g_{dcw}$, about 0.5 to about 2 μmol/$g_{dcw}$, about 0.8 to about 6 μmol/$g_{dcw}$, about 0.8 to about 5 μmol/$g_{dcw}$, about 0.8 to about 2 μmol/$g_{dcw}$, about 1 to about 6 μmol/$g_{dcw}$, about 1 to about 5 μmol/$g_{dcw}$, about 1 to about 2 μmol/$g_{dcw}$, about 1.1 to about 6 μmol/$g_{dcw}$, about 1.1 to about 5 μmol/$g_{dcw}$, about 1.1 to about 2 μmol/$g_{dcw}$, about 1.1 to about 1.5 μmol/$g_{dcw}$, about 1.2 to about 6 μmol/$g_{dcw}$, about 1.2 to about 5 μmol/$g_{dcw}$, about 1.2 to about 2 μmol/$g_{dcw}$, or about 1.2 to about 1.5 μmol/$g_{dcw}$. In some embodiments, the intracellular concentration of FPP is equal to or less than about any of 6, 4, 2, 1.5, 1.4, 1.3, 1.2, 1.1, 1, 0.9, 0.8, 0.6, 0.5, 0.4, 0.3, 0.2, or 0.1 μmol/$g_{dcw}$.

In some embodiments, the concentration (e.g., concentration in the cell medium) of MVA is between about 0 to about 120 g/L, such as between about 0 to about 110 g/L, such as between about 0.1 to about 100 g/L, about 0.1 to about 75 g/L, about 0.1 to about 60 g/L, about 0.1 to about 50 g/L, about 0.1 to about 40 g/L, about 0.1 to about 30 g/L, about 0.1 to about 20 g/L, about 0.1 to about 15 g/L, about 0.1 to about 11 g/L, about 0.1 to about 7 g/L, about 0.1 to about 5 g/L, about 0.1 to about 2 g/L, about 0.1 to about 1 g/L, about 0.1 to about 0.8 g/L, about 0.1 to about 0.6 g/L, about 0.2 to about 120 g/L, about 0.2 to about 100 g/L, about 0.2 to about 75 g/L, about 0.2 to about 60 g/L, about 0.2 to about 50 g/L, about 0.2 to about 40 g/L, about 0.2 to about 30 g/L, about 0.2 to about 20 g/L, about 0.2 to about 15 g/L, about 0.2 to about 11 g/L, about 0.2 to about 7 g/L, about 0.2 to about 5 g/L, about 0.2 to about 2 g/L, about 0.3 to about 120 g/L, about 0.3 to about 100 g/L, about 0.3 to about 75 g/L, about 0.3 to about 60 g/L, about 0.3 to about 50 g/L, about 0.3 to about 40 g/L, about 0.3 to about 30 g/L, about 0.3 to about 15 g/L, about 0.3 to about 11 g/L, about 0.3 to about 7 g/L, about 0.3 to about 5 g/L, about 0.3 to about 2 g/L, about 0.4 to about 120 g/L, about 0.4 to about 100 g/L, about 0.4 to about 75 g/L, about 0.4 to about 60 g/L, about 0.4 to about 50 g/L, about 0.4 to about 40 g/L, about 0.4 to about 30 g/L, about 0.4 to about 15 g/L, about 0.4 to about 7 g/L, about 0.4 to about 5 g/L, about 0.4 to about 2 g/L, about 0.5 to about 1200 g/L, about 0.5 to about 100 g/L, about 0.5 to about 75 g/L, about 0.5 to about 60 g/L, about 0.5 to about 50 g/L, about 0.5 to about 40 g/L, about 0.5 to about 30 g/L, about 0.5 to about 15 g/L, about 0.5 to about 11 g/L, about 0.5 to about 7 g/L, about 0.5 to about 5 g/L, about 0.5 to about 2 g/L, about 50 to about 60 g/L, or about 1 g/L. In some embodiments, the concentration (e.g., concentration in the cell medium) of MVA is equal to or less than about any of 120, 100, 80, 70, 60, 50, 40, 30, 25, 20, 18, 16, 14, 12, 10, 8, 6, 4, 2, 1, 0.8, 0.6, 0.5, 0.4, 0.3, 0.2, or 0.1 g/L.

Examples 10-21 also support the use of the compositions and methods disclosed herein to produce large amounts of isoprene. The methods described herein can be used to modify any of the cells and methods of Examples 10-21 to express a feedback-resistant MVK polypeptide (such as a *M. mazei* MVK polypeptide) either as the only MVK polypeptide or as an additional MVK polypeptide. Additionally, methods described herein can be used to modify any of the cells and methods of U.S. Ser. No. 61/134,094, filed Jul. 2, 2008 (which is hereby incorporated by reference in its entirety, particularly with respect to methods of making isoprene and isoprene compositions) to express a feedback-resistant MVK polypeptide (such as a *M. mazei* MVK polypeptide) either as the only MVK polypeptide or as an additional MVK polypeptide. As discussed above, the use of a feedback-resistant MVK polypeptide may further increase the production of isoprene.

Summary of Exemplary Compositions and Methods for Producing Isoprene

This section summaries exemplary compositions and methods for producing isoprene that can be used with a feedback-resistant MVK polypeptide (such as a *M. mazei* MVK polypeptide). In one aspect, the invention features compositions and methods for the production of isoprene in increased amounts and/or purity. In one aspect, compositions and methods of the invention increase the rate of isoprene production and increase the total amount of isoprene that is produced. For example, cell culture systems that generate $4.8\times10^4$ nmole/$g_{wcm}$/hr of isoprene have been produced (Table 1). The efficiency of these systems is demonstrated by the conversion of about 2.2% of the carbon that the cells consume from a cell culture medium into isoprene. As shown in the Examples and Table 2, approximately 3 g of isoprene per liter of broth was generated. If desired, even greater amounts of isoprene can be obtained using other conditions, such as those described herein. In some embodiments, a renewable carbon source is used for the production of isoprene. In some embodiments, the production of isoprene is decoupled from the growth of the cells. In some embodiments, the concentrations of isoprene and any oxidants are within the nonflammable ranges to reduce or eliminate the risk that a fire may occur during production or recovery of isoprene. The compositions and methods of the present invention are desirable because they allow high isoprene yield per cell, high carbon yield, high isoprene purity, high productivity, low energy usage, low production cost and investment, and minimal side reactions. This efficient, large scale, biosynthetic process for isoprene production provides an isoprene source for synthetic isoprene-based rubber and provides a desirable, low-cost alternative to using natural rubber.

As discussed further herein, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethylallyl diphosphate (DMAPP) into isoprene. As shown in the Examples, a heterologous *Pueraria Montana* (kudzu) isoprene synthase polypeptide was expressed in a variety of host cells, such as *Escherichia coli, Panteoa citrea, Bacillus subtilis, Yarrowia lipolytica*, and *Trichoderma reesei*. All of these cells produced more isoprene than the corresponding cells without the heterologous isoprene synthase polypeptide. As illustrated in Tables 1 and 2, large amounts of isoprene are produced using the methods described herein. For example, *B. subtilis* cells with a heterologous isoprene synthase nucleic acid produced approximately 10-fold more isoprene in a 14 liter fermentor than the corresponding control *B. subtilis* cells without the heterologous nucleic acid (Table 2). The production of 300 mg of isoprene per liter of broth (mg/L, wherein the volume of broth includes both the volume of the cell medium and the volume of the cells) by *E. coli* and 30 mg/L by *B. subtilis* in fermentors indicates that significant amounts of isoprene can be generated (Table 2). If desired, isoprene can be produced on an even larger scale or other conditions described herein can be used to further increase the amount of isoprene. The vectors listed in Tables 1 and 2 and the experimental conditions are described in further detail below and in the Examples section.

TABLE 1

Exemplary yields of isoprene from a shake flask using the cell cultures and methods of the invention. The assay for measuring isoprene production is described in Example 10, part II. For this assay, a sample was removed at one or more time points from the shake flask and cultured for 30 minutes. The amount of isoprene produced in this sample was then measured. The headspace concentration and specific rate of isoprene production are listed in Table 1 and described further herein.

| | Isoprene Production in a Headspace vial* | |
|---|---|---|
| Strain | Headspace concentration μg/$L_{gas}$ | Specific Rate μg/$L_{broth}$/hr/OD (nmol/$g_{wcm}$/hr) |
| *E. coli* BL21/pTrcKudzu IS | 1.40 | 53.2 (781.2) |
| *E. coli* BL21/pCL DXS yidi Kudzu IS | 7.61 | 289.1 ($4.25\times10^3$) |
| *E. coli* BL21/MCM127 with kudzu IS and entire MVA pathway | 23.0 | 874.1 ($12.8\times10^3$) |
| *E. coli* BL21/pET N-HisKudzu IS | 1.49 | 56.6 (831.1) |
| *Pantoea citrea*/pTrcKudzu IS | 0.66 | 25.1 (368.6) |
| *E. coli* w/Poplar IS [Miller (2001)] | — | 5.6 (82.2) |
| *Bacillis licheniformis* Fall U.S. Pat. No. 5,849,970 | — | 4.2 (61.4) |
| *Yarrowia lipolytica* with kudzu isoprene synthase | ~0.05 μg/L | ~2 (~30) |
| *Trichoderma reesei* with kudzu isoprene synthase | ~0.05 μg/L | ~2 (~30) |
| *E. coli* BL21/pTrcKKD$_y$I$_k$IS with kudzu IS and lower MVA pathway | 85.9 | $3.2\times10^3$ ($4.8\times10^4$) |

*Normalized to 1 mL of 1 $OD_{600}$, cultured for 1 hour in a sealed headspace vial with a liquid to headspace volume ratio of 1:19.

TABLE 2

Exemplary yields of isoprene in a fermentor using the cell cultures and methods of the invention. The assay for measuring isoprene production is described in Example 10, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** (ug/$L_{gas}$) | Titer (mg/$L_{broth}$) | Peak Specific rate μg/$L_{broth}$/hr/OD (nmol/$g_{wcm}$/hr) |
| *E. coli* BL21/pTrcKudzu with Kudzu IS | 52 | 41.2 | 37 (543.3) |
| *E. coli* FM5/pTrcKudzu IS | 3 | 3.5 | 21.4 (308.1) |
| *E. coli* BL21/triple strain (DXS, yidi, IS) | 285 | 300 | 240 ($3.52\times10^3$) |
| *E. coli* FM5/triple strain (DXS, yidi, IS) | 50.8 | 29 | 180.8 ($2.65\times10^3$) |
| *E. coli*/MCM127 with Kudzu IS and entire MVA pathway | 3815 | 3044 | 992.5 ($1.46\times10^4$) |
| *E. coli* BL21/pCLPtrc UpperPathway gi1.2 integrated lower pathway pTrcKudzu | 2418 | 1640 | 1248 ($1.83\times10^4$) |

TABLE 2-continued

Exemplary yields of isoprene in a fermentor using the cell cultures and methods of the invention. The assay for measuring isoprene production is described in Example 10, part II. For this assay, a sample of the off-gas of the fermentor was taken and analyzed for the amount of isoprene. The peak headspace concentration (which is the highest headspace concentration during the fermentation), titer (which is the cumulative, total amount of isoprene produced per liter of broth), and peak specific rate of isoprene production (which is the highest specific rate during the fermentation) are listed in Table 2 and described further herein.

| | Isoprene Production in Fermentors | | |
|---|---|---|---|
| Strain | Peak Headspace concentration** ($ug/L_{gas}$) | Titer ($mg/L_{broth}$) | Peak Specific rate $\mu g/L_{broth}/hr/OD$ ($nmol/g_{wcm}/hr$) |
| *E. coli* BL21/MCM401 with 4 × 50 uM IPTG | 13991 | 23805 | 3733 ($5.49 \times 10^4$) |
| *E. coli* BL21/MCM401 with 2 × 100 uM IPTG | 22375 | 19541 | 5839.5 ($8.59 \times 10^4$) |
| *E. coli* BL21/pCLPtrc UpperPathwayHGS2-pTrcKKDyIkIS | 3500 | 3300 | 1088 ($1.60 \times 10^4$) |
| *Bacillus subtilis* wild-type | 1.5 | 2.5 | 0.8 (11.7) |
| *Bacillus* pBS Kudzu IS | 16.6 | ~30 (over 100 hrs) | 5 (73.4) |
| *Bacillus* Marburg 6051 [Wagner and Fall (1999)] | 2.04 | 0.61 | 24.5 (359.8) |
| *Bacillus* Marburg 6051 Fall U.S. Pat. No. 5,849,970 | 0.7 | 0.15 | 6.8 (100) |

**Normalized to an off-gas flow rate of 1 vvm (1 volume off-gas per 1 $L_{broth}$ per minute).

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells. For example, a DXS nucleic acid and/or an IDI nucleic acid can be introduced into the cells. The DXS nucleic acid may be a heterologous nucleic acid or a duplicate copy of an endogenous nucleic acid. Similarly, the IDI nucleic acid may be a heterologous nucleic acid or a duplicate copy of an endogenous nucleic acid. In some embodiments, the amount of DXS and/or IDI polypeptide is increased by replacing the endogenous DXS and/or IDI promoters or regulatory regions with other promoters and/or regulatory regions that result in greater transcription of the DXS and/or IDI nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

The encoded DXS and IDI polypeptides are part of the DXP pathway for the biosynthesis of isoprene (FIG. 19A). DXS polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production. IDI polypeptides catalyze the interconversion of isopentenyl diphosphate (IPP) and dimethylallyl diphosphate (DMAPP). While not intending to be bound by any particular theory, it is believed that increasing the amount of IDI polypeptide in cells increases the amount (and conversion rate) of IPP that is converted into DMAPP, which in turn is converted into isoprene.

For example, fermentation of *E. coli* cells with a kudzu isoprene synthase, S. cerevisia IDI, and *E. coli* DXS nucleic acids was used to produce isoprene. The levels of isoprene varied from 50 to 300 ⊠ g/L over a time period of 15 hours (Example 16, part VII).

In some embodiments, the presence of heterologous or extra endogenous isoprene synthase, IDI, and DXS nucleic acids causes cells to grow more reproducibly or remain viable for longer compared to the corresponding cell with only one or two of these heterologous or extra endogenous nucleic acids. For example, cells containing heterologous isoprene synthase, IDI, and DXS nucleic acids grew better than cells with only heterologous isoprene synthase and DXS nucleic acids or with only a heterologous isoprene synthase nucleic acid. Also, heterologous isoprene synthase, IDI, and DXS nucleic acids were successfully operably linked to a strong promoter on a high copy plasmid that was maintained by *E. coli* cells, suggesting that large amounts of these polypeptides could be expressed in the cells without causing an excessive amount of toxicity to the cells. While not intending to be bound to a particular theory, it is believed that the presence of heterologous or extra endogenous isoprene synthase and IDI nucleic acids may reduce the amount of one or more potentially toxic intermediates that would otherwise accumulate if only a heterologous or extra endogenous DXS nucleic acid was present in the cells.

In some embodiments, the production of isoprene by cells by cells that contain a heterologous isoprene synthase nucleic acid is augmented by increasing the amount of a MVA pathway polypeptide expressed by the cells (FIGS. 19A and 19B). Exemplary MVA pathways polypeptides include any of the following polypeptides: acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. For example, one or more MVA pathway nucleic acids can be introduced into the cells. In some embodiments, the cells contain the upper MVA pathway, which includes AA-CoA thiolase, HMG-CoA synthase, and HMG-CoA reductase nucleic acids. In some embodiments, the cells contain the lower MVA pathway, which includes MVK, PMK, MVD, and IDI nucleic acids. In some embodiments, the cells contain an entire MVA pathway that includes AA-CoA thiolase, HMG-CoA synthase, HMG-CoA reductase, MVK, PMK, MVD, and IDI nucleic acids. In some embodiments, the cells contain an entire MVA pathway that includes AA-CoA thiolase, HMG-CoA synthase, HMG-CoA reductase, MVK, PMDC, IPK, and IDI nucleic acids. The MVA pathway nucleic acids may be heterologous nucleic acids or duplicate copies of endogenous nucleic acids. In some embodiments, the amount of one or more MVA pathway polypeptides is increased by replacing the endogenous promoters or regulatory regions for the MVA pathway nucleic acids with other promoters and/or regulatory regions that result in greater transcription of the MVA pathway nucleic acids. In some embodiments, the cells contain both a heterologous nucleic acid encoding an isoprene synthase polypeptide (e.g., a plant isoprene synthase nucleic acid) and a duplicate copy of an endogenous nucleic acid encoding an isoprene synthase polypeptide.

For example, *E. coli* cells containing a nucleic acid encoding a kudzu isoprene synthase polypeptide and nucleic acids encoding *Saccharomyces* cerevisia MVK, PMK, MVD, and IDI polypeptides generated isoprene at a rate of $6.67\times10^{-4}$ mol/$L_{broth}$/$OD_{600}$/hr (see Example 17). Additionally, a 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid (an intermediate of the MVA pathway). A shake flask of these cells produced 2-4 grams of mevalonic acid per liter. These results indicate that heterologous MVA pathways nucleic acids are active in *E. coli*. *E. coli* cells that contain nucleic acids for both the upper MVA pathway and the lower MVA pathway as well as a kudzu isoprene synthase (strain MCM 127) produced significantly more isoprene (874 ug/L) compared to *E. coli* cells with nucleic acids for only the lower MVA pathway and the kudzu isoprene synthase (strain MCM 131) (see Table 10 and Example 17, part VIII).

In some embodiments, at least a portion of the cells maintain the heterologous isoprene synthase, DXS, IDI, and/or MVA pathway nucleic acid for at least about 5, 10, 20, 50, 75, 100, 200, 300, or more cell divisions in a continuous culture (such as a continuous culture without dilution). In some embodiments of any of the aspects of the invention, the nucleic acid comprising the heterologous or duplicate copy of an endogenous isoprene synthase, DXS, IDI, and/or MVA pathway nucleic acid also comprises a selective marker, such as a kanamycin, ampicillin, carbenicillin, gentamicin, hygromycin, phleomycin, bleomycin, neomycin, or chloramphenicol antibiotic resistance nucleic acid.

As indicated in Example 16, part VI, the amount of isoprene produced can be further increased by adding yeast extract to the cell culture medium. In this example, the amount of isoprene produced was linearly proportional to the amount of yeast extract in the cell medium for the concentrations tested (FIG. 48C). Additionally, approximately 0.11 grams of isoprene per liter of broth was produced from a cell medium with yeast extract and glucose (Example 16, part VIII). Both of these experiments used *E. coli* cells with kudzu isoprene synthase, S. cerevisia IDI, and *E. coli* DXS nucleic acids to produce isoprene. Increasing the amount of yeast extract in the presence of glucose resulted in more isoprene being produced than increasing the amount of glucose in the presence of yeast extract. Also, increasing the amount of yeast extract allowed the cells to produce a high level of isoprene for a longer length of time and improved the health of the cells.

Isoprene production was also demonstrated using three types of hydrolyzed biomass (bagasse, corn stover, and soft wood pulp) as the carbon source. *E. coli* cells with kudzu isoprene synthase, S. cerevisia IDI, and *E. coli* DXS nucleic acids produced as much isoprene from these hydrolyzed biomass carbon sources as from the equivalent amount of glucose (e.g., 1% glucose, w/v). If desired, any other biomass carbon source can be used in the compositions and methods of the invention. Biomass carbon sources are desirable because they are cheaper than many conventional cell mediums, thereby facilitating the economical production of isoprene.

Additionally, invert sugar was shown to function as a carbon source for the generation of isoprene. For example, 2.4 g/L of isoprene was produced from cells expressing MVA pathway polypeptides and a Kudzu isoprene synthase. Glycerol was as also used as a carbon source for the generation of 2.2 mg/L of isoprene from cells expressing a Kudzu isoprene synthase. Expressing a DXS nucleic acid, an IDI nucleic acid, and/or one or more MVA pathway nucleic acids (such as nucleic acids encoding the entire MVA pathway) in addition to an isoprene synthase nucleic acid may increase the production of isoprene from glycerol.

In some embodiments, an oil is included in the cell medium. For example, *B. subtilis* cells containing a kudzu isoprene synthase nucleic acid produced isoprene when cultured in a cell medium containing an oil and a source of glucose (Example 13, part III). In some embodiments, more than one oil (such as 2, 3, 4, 5, or more oils) is included in the cell medium. While not intending to be bound to any particular theory, it is believed that (i) the oil may increase the amount of carbon in the cells that is available for conversion to isoprene, (ii) the oil may increase the amount of acetyl-CoA in the cells, thereby increasing the carbon flow through the MVA pathway, and/or (ii) the oil may provide extra nutrients to the cells, which is desirable since a lot of the carbon in the cells is converted to isoprene rather than other products. In some embodiments, cells that are cultured in a cell medium containing oil naturally use the MVA pathway to produce isoprene or are genetically modified to contain nucleic acids for the entire MVA pathway. In some embodiments, the oil is partially or completely hydrolyzed before being added to the cell culture medium to facilitate the use of the oil by the host cells.

One of the major hurdles to commercial production of small molecules such as isoprene in cells (e.g., bacteria) is the decoupling of production of the molecule from growth of the cells. In some embodiments for the commercially viable production of isoprene, a significant amount of the carbon from the feedstock is converted to isoprene, rather than to the growth and maintenance of the cells ("carbon efficiency"). In various embodiments, the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In particular embodiments, a significant portion of the carbon from the feedstock that is converted to downstream products is converted to isoprene. As described further in Example 19, *E. coli* cells expressing MVA pathway and kudzu isoprene synthase nucleic acids exhibited decoupling of the production of isoprene or the intermediate mevalonic acid from growth, resulting in high carbon efficiency. In particular, mevalonic acid was formed from cells expressing the upper MVA pathway from *Enterococcus faecalis*. Isoprene was formed from cells expressing the upper MVA pathway from *Enterococcus faecalis*, the lower MVA pathway from *Saccharomyces cerevisiae*, and the isoprene synthase from *Pueraria montana* (Kudzu). This decoupling of isoprene or mevalonic acid production from growth was demonstrated in four different strains of *E. coli*: BL21(LDE3), BL21(LDE3) Tuner, FM5, and MG1655. The first two *E. coli* strains are B strains, and the latter two are K12 strains. Decoupling of production from growth was also demonstrated in a variant of MG1655 with ack and pta genes deleted. This variant also demonstrated less production of acetate.

The vast majority of isoprene is derived from petrochemical sources as an impure C5 hydrocarbon fraction which requires extensive purification before the material is suitable for polymerization. Several impurities are particularly problematic given their structural similarity to isoprene and the fact that they can act as polymerization catalyst poisons. Such compounds include 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, and cis-pent-3-ene-1-yne (FIG. 90). In other embodiments, the impurities can be 3-hexen-1-ol, 3-hexen- 1-yl acetate, limonene, geraniol (trans-3,7-dimethyl-2,6-octadien-1-ol) and citronellol (3,7-dimethyl-6-octen-1-ol). In some embodiments, the isoprene composition of the invention is substantially free of any contaminating unsaturated C5 hydrocarbons. No detectable amount of unsaturated C5 hydrocarbons other than isoprene (such as 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) was found in isoprene compositions produced using the methods described herein. Some isoprene compositions produced using the methods described herein contain ethanol, acetone, and C5 prenyl alcohols as determined by GC/MS analysis. All of these components are far more readily removed from the isoprene stream than the isomeric C5 hydrocarbon fractions that are present in isoprene compositions derived from petrochemical sources. Accordingly, in some embodiments, the isoprene compositions of the invention require minimal treatment in order to be of polymerization grade.

Exemplary Polypeptides and Nucleic Acids

Various isoprene synthase, DXS, IDI, and/or MVA pathway polypeptides and nucleic acids can be used in the compositions and methods of the invention.

As used herein, "polypeptides" includes polypeptides, proteins, peptides, fragments of polypeptides, and fusion polypeptides. In some embodiments, the fusion polypeptide includes part or all of a first polypeptide (e.g., an isoprene synthase, DXS, IDI, or MVA pathway polypeptide or catalytically active fragment thereof) and may optionally include part or all of a second polypeptide (e.g., a peptide that facilitates purification or detection of the fusion polypeptide, such as a His-tag). In some embodiments, the fusion polypeptide has an activity of two or more MVA pathway polypeptides (such as AA-CoA thiolase and HMG-CoA reductase polypeptides). In some embodiments, the polypeptide is a naturally-occurring polypeptide (such as the polypeptide encoded by an *Enterococcus faecalis* mvaE nucleic acid) that has an activity of two or more MVA pathway polypeptides.

In various embodiments, a polypeptide has at least or about 50, 100, 150, 175, 200, 250, 300, 350, 400, or more amino acids. In some embodiments, the polypeptide fragment contains at least or about 25, 50, 75, 100, 150, 200, 300, or more contiguous amino acids from a full-length polypeptide and has at least or about 5%, 10%, 20%, 30%, 40%, 50%, 60%, 70%, 80%, 90%, 95%, or 100% of an activity of a corresponding full-length polypeptide. In particular embodiments, the polypeptide includes a segment of or the entire amino acid sequence of any naturally-occurring isoprene synthase, DXS, IDI, or MVA pathway polypeptide. In some embodiments, the polypeptide has one or more mutations compared to the sequence of a wild-type (i.e., a sequence occurring in nature) isoprene synthase, DXS, IDI, or MVA pathway polypeptide.

In some embodiments, the polypeptide is an isolated polypeptide. As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

In some embodiments, the polypeptide is a heterologous polypeptide. By "heterologous polypeptide" is meant a polypeptide whose amino acid sequence is not identical to that of another polypeptide naturally expressed in the same host cell. In particular, a heterologous polypeptide is not identical to a wild-type nucleic acid that is found in the same host cell in nature.

As used herein, a "nucleic acid" refers to two or more deoxyribonucleotides and/or ribonucleotides in either single or double-stranded form. In some embodiments, the nucleic acid is a recombinant nucleic acid. By "recombinant nucleic acid" means a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In various embodiments, a nucleic acid is a recombinant nucleic acid. In some embodiments, an isoprene synthase, DXS, IDI, or MVA pathway nucleic acid is operably linked to another nucleic acid encoding all or a portion of another polypeptide such that the recombinant nucleic acid encodes a fusion polypeptide that includes an isoprene synthase, DXS, IDI, or MVA pathway polypeptide and all or part of another polypeptide (e.g., a peptide that facilitates purification or detection of the fusion polypeptide, such as a His-tag). In some embodiments, part or all of a recombinant nucleic acid is chemically synthesized. It is to be understood that mutations, including single nucleotide mutations, can occur within a nucleic acid as defined herein.

In some embodiments, the nucleic acid is a heterologous nucleic acid. By "heterologous nucleic acid" is meant a nucleic acid whose nucleic acid sequence is not identical to that of another nucleic acid naturally found in the same host cell.

In particular embodiments, the nucleic acid includes a segment of or the entire nucleic acid sequence of any naturally-occurring isoprene synthase, DXS, IDI, or MVA pathway nucleic acid. In some embodiments, the nucleic acid includes at least or about 50, 100, 150, 200, 300, 400, 500, 600, 700, 800, or more contiguous nucleotides from a naturally-occurring isoprene synthase nucleic acid DXS, IDI, or MVA pathway nucleic acid. In some embodiments, the nucleic acid has one or more mutations compared to the sequence of a wild-type (i.e., a sequence occurring in nature) isoprene synthase, DXS, IDI, or MVA pathway nucleic acid. In some embodiments, the nucleic acid has one or more mutations (e.g., a silent mutation) that increase the transcription or translation of isoprene synthase, DXS, IDI, or MVA pathway nucleic acid. In some embodiments, the nucleic acid is a degenerate variant of any nucleic acid encoding an isoprene synthase, DXS, IDI, or MVA pathway polypeptide.

"Codon degeneracy" refers to divergence in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a nucleic acid for improved expression in a host cell, it is desirable in some embodiments to design the nucleic acid such that its frequency of codon usage approaches the frequency of preferred codon usage of the host cell.

The accession numbers of exemplary isoprene synthase, DXS, IDI, and/or MVA pathway polypeptides and nucleic acids are listed in Appendix 1 (the accession numbers of Appendix 1 and their corresponding sequences are herein incorporated by reference in their entireties, particularly with respect to the amino acid and nucleic acid sequences of isoprene synthase, DXS, IDI, and/or MVA pathway polypeptides and nucleic acids). The Kegg database also contains the amino acid and nucleic acid sequences of numerous exemplary isoprene synthase, DXS, IDI, and/or MVA pathway polypeptides and nucleic acids (see, for example, the world-wide web at "genome.jp/kegg/pathway/map/map00100.html" and the sequences therein, which are each hereby incorporated by reference in their entireties, particularly with respect to the amino acid and nucleic acid sequences of isoprene synthase, DXS, IDI, and/or MVA pathway polypeptides and nucleic acids). In some embodiments, one or more of the isoprene synthase, DXS, IDI, and/or MVA pathway polypeptides and/or nucleic acids have a sequence identical to a sequence publicly available on Dec. 12, 2007 or Sep. 14, 2008, such as any of the sequences that correspond to any of the accession numbers in Appendix 1 or any of the sequences present in the Kegg database. Additional exemplary isoprene synthase, DXS, IDI, and/or MVA pathway polypeptides and nucleic acids are described further below.

Exemplary Isoprene Synthase Polypeptides and Nucleic Acids

As noted above, isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Standard methods can be used to determine whether a polypeptide has isoprene synthase polypeptide activity by measuring the ability of the polypeptide to convert DMAPP into isoprene in vitro, in a cell extract, or in vivo. In an exemplary assay, cell extracts are prepared by growing a strain (e.g., the *E. coli*/pTrcKudzu strain described herein) in the shake flask method as described in Example 10. After induction is complete, approximately 10 mL of cells are pelleted by centrifugation at 7000×g for 10 minutes and resuspended in 5 ml of PEB without glycerol. The cells are lysed using a French Pressure cell using standard procedures. Alternatively the cells are treated with lysozyme (Ready-Lyse lysozyme solution; EpiCentre) after a freeze/thaw at −80 C.

Isoprene synthase polypeptide activity in the cell extract can be measured, for example, as described in Silver et al., J. Biol. Chem. 270:13010-13016, 1995 and references therein, which are each hereby incorporated by reference in their entireties, particularly with respect to assays for isoprene synthase polypeptide activity. DMAPP (Sigma) is evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) is added to 25 μL of cell extract in a 20 ml Headspace vial with a metal screw cap and teflon coated silicon septum (Agilent Technologies) and cultured at 37° C. for 15 minutes with shaking. The reaction is quenched by adding 200 μL of 250 mM EDTA and quantified by GC/MS as described in Example 10, part II.

Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137: 700-712, 2005), *Pueraria lobata*, poplar (such as *Populus alba, Populus nigra, Populus trichocarpa*, or *Populus alba* x *tremula* (CAC35696) Miller et al., Planta 213: 483-487, 2001) aspen (such as *Populus tremuloides*) Silver et al., JBC 270(22): 13010-1316, 1995), or English Oak (*Quercus robur*) (Zimmer et al., WO 98/02550), which are each hereby incorporated by reference in their entireties, particularly with respect to isoprene synthase nucleic acids and the expression of isoprene synthase polypeptides. Suitable isoprene synthases include, but are not limited to, those identified by Genbank Accession Nos. AY341431, AY316691, AY279379, AJ457070, and AY182241, which are each hereby incorporated by reference in their entireties, particularly with respect to sequences of isoprene synthase nucleic acids and polypeptides. In some embodiments, the isoprene synthase polypeptide or nucleic acid is not a naturally-occurring polypeptide or nucleic acid from *Quercus robur* (i.e., the isoprene synthase polypeptide or nucleic acid is an isoprene synthase polypeptide or nucleic acid other than a naturally-occurring polypeptide or nucleic acid from *Quercus robur*). In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Exemplary DXS Polypeptides and Nucleic Acids

As noted above, 1-deoxy-D-xylulose-5-phosphate synthase (DXS) polypeptides convert pyruvate and D-glyceraldehyde-3-phosphate into 1-deoxy-D-xylulose-5-phosphate. Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein as well as mutant polypeptides and nucleic acids derived from any of the source organisms described herein.

In particular, acetyl-CoA acetyltransferase polypeptides (AA-CoA thiolase or AACT) convert two molecules of acetyl-CoA into acetoacetyl-CoA. Standard methods (such as those described herein) can be used to determine whether a polypeptide has AA-CoA thiolase polypeptide activity by measuring the ability of the polypeptide to convert two molecules of acetyl-CoA into acetoacetyl-CoA in vitro, in a cell extract, or in vivo.

3-hydroxy-3-methylglutaryl-CoA synthase (HMG-CoA synthase or HMGS) polypeptides convert acetoacetyl-CoA into 3-hydroxy-3-methylglutaryl-CoA. Standard methods (such as those described herein) can be used to determine whether a polypeptide has HMG-CoA synthase polypeptide activity by measuring the ability of the polypeptide to convert acetoacetyl-CoA into 3-hydroxy-3-methylglutaryl-CoA in vitro, in a cell extract, or in vivo.

3-hydroxy-3-methylglutaryl-CoA reductase (HMG-CoA reductase or HMGR) polypeptides convert 3-hydroxy-3-methylglutaryl-CoA into mevalonate. Standard methods (such as those described herein) can be used to determine whether a polypeptide has HMG-CoA reductase polypeptide activity by measuring the ability of the polypeptide to convert 3-hydroxy-3-methylglutaryl-CoA into mevalonate in vitro, in a cell extract, or in vivo.

Mevalonate kinase (MVK) polypeptides phosphorylates mevalonate to form mevalonate-5-phosphate. Standard methods (such as those described herein) can be used to determine whether a polypeptide has MVK polypeptide activity by measuring the ability of the polypeptide to convert mevalonate into mevalonate-5-phosphate in vitro, in a cell extract, or in vivo.

Phosphomevalonate kinase (PMK) polypeptides phosphorylates mevalonate-5-phosphate to form mevalonate-5-diphosphate. Standard methods (such as those described herein) can be used to determine whether a polypeptide has PMK polypeptide activity by measuring the ability of the polypeptide to convert mevalonate-5-phosphate into mevalonate-5-diphosphate in vitro, in a cell extract, or in vivo.

Diphosphomevalonate decarboxylase (MVD or DPMDC) polypeptides convert mevalonate-5-diphosphate into isopentenyl diphosphate (IPP). Standard methods (such as those described herein) can be used to determine whether a polypeptide has MVD polypeptide activity by measuring the ability of the polypeptide to convert mevalonate-5-diphosphate into IPP in vitro, in a cell extract, or in vivo.

Phosphomevalonate decarboxylase (PMDC) polypeptides convert mevalonate-5-phosphate into isopentenyl phosphate (IP). Standard methods (such as those described herein) can be used to determine whether a polypeptide has PMDC polypeptide activity by measuring the ability of the polypeptide to convert mevalonate-5-phosphate into IP in vitro, in a cell extract, or in vivo.

Isopentenyl phosphate kinase (IPK) polypeptides phosphorylate isopentyl phosphate (IP) to form isopentenyl diphosphate (IPP). Standard methods (such as those described herein) can be used to determine whether a polypeptide has IPK polypeptide activity by measuring the ability of the polypeptide to convert IP into IPP in vitro, in a cell extract, or in vivo.

Exemplary IDI polypeptides and nucleic acids are described above.

Exemplary Methods for Isolating Nucleic Acids

Isoprene synthase, DXS, IDI, and/or MVA pathway nucleic acids can be isolated using standard methods. Methods of obtaining desired nucleic acids from a source organism of interest (such as a bacterial genome) are common and well known in the art of molecular biology (see, for example, WO 2004/033646 and references cited therein, which are each hereby incorporated by reference in their entireties, particularly with respect to the isolation of nucleic acids of interest). For example, if the sequence of the nucleic acid is known (such as any of the known nucleic acids described herein), suitable genomic libraries may be created by restriction endonuclease digestion and may be screened with probes complementary to the desired nucleic acid sequence. Once the sequence is isolated, the DNA may be amplified using standard primer directed amplification methods such as polymerase chain reaction (PCR) (U.S. Pat. No. 4,683,202, which is incorporated by reference in its entirety, particularly with respect to PCR methods) to obtain amounts of DNA suitable for transformation using appropriate vectors.

Alternatively, isoprene synthase, DXS, IDI, and/or MVA pathway nucleic acids (such as any isoprene synthase, DXS, IDI, and/or MVA pathway nucleic acids with a known nucleic acid sequence) can be chemically synthesized using standard methods.

Additional isoprene synthase, DXS, IDI, or MVA pathway polypeptides and nucleic acids which may be suitable for use in the compositions and methods described herein can be identified using standard methods. For example, cosmid libraries of the chromosomal DNA of organisms known to produce isoprene naturally can be constructed in organisms such as *E. coli*, and then screened for isoprene production. In particular, cosmid libraries may be created where large segments of genomic DNA (35-45 kb) are packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the heterologous DNA. In addition to the cos sequence, these vectors also contain an origin of replication such as ColEI and drug resistance markers such as a nucleic acid resistant to ampicillin or neomycin. Methods of using cosmid vectors for the transformation of suitable bacterial hosts are well described in Sambrook et al., Molecular Cloning: A Laboratory Manual, $2^{nd}$ ed., Cold Spring Harbor, 1989, which is hereby incorporated by reference in its entirety, particularly with respect to transformation methods.

Typically to clone cosmids, heterologous DNA is isolated using the appropriate restriction endonucleases and ligated adjacent to the cos region of the cosmid vector using the appropriate ligases. Cosmid vectors containing the linearized heterologous DNA are then reacted with a DNA packaging vehicle such as bacteriophage. During the packaging process, the cos sites are cleaved and the heterologous DNA is packaged into the head portion of the bacterial viral particle. These particles are then used to transfect suitable host cells such as *E. coli*. Once injected into the cell, the heterologous DNA circularizes under the influence of the cos sticky ends. In this manner, large segments of heterologous DNA can be introduced and expressed in host cells.

Additional methods for obtaining isoprene synthase, DXS, IDI, and/or MVA pathway nucleic acids include screening a metagenomic library by assay (such as the headspace assay described herein) or by PCR using primers directed against nucleotides encoding for a length of conserved amino acids (for example, at least 3 conserved amino acids). Conserved amino acids can be identified by aligning amino acid sequences of known isoprene synthase, DXS, IDI, and/or MVA pathway polypeptides. Conserved amino acids for isoprene synthase polypeptides can be identified based on aligned sequences of known isoprene synthase polypeptides. An organism found to produce isoprene naturally can be subjected to standard protein purification methods (which are well known in the art) and the resulting purified polypeptide can be sequenced using standard methods. Other methods are found in the literature (see, for example, Julsing et al., *Applied. Microbiol. Biotechnol.* 75: 1377-84, 2007; Withers et al., *Appl Environ Microbiol.* 73(19):6277-83, 2007, which are each hereby incorporated by reference in their entireties, particularly with respect to identification of nucleic acids involved in the synthesis of isoprene).

Additionally, standard sequence alignment and/or structure prediction programs can be used to identify additional DXS, IDI, or MVA pathway polypeptides and nucleic acids based on the similarity of their primary and/or predicted polypeptide secondary structure with that of known DXS, IDI, or MVA pathway polypeptides and nucleic acids. Standard databases such as the swissprot-trembl database (world-wide web at "expasy.org", Swiss Institute of Bioinformatics Swiss-Prot group CMU—1 rue Michel Servet CH-1211 Geneva 4, Switzerland) can also be used to identify isoprene synthase, DXS, IDI, or MVA pathway polypeptides and nucleic acids. The secondary and/or tertiary structure of an isoprene synthase, DXS, IDI, or MVA pathway polypeptide can be predicted using the default settings of standard structure prediction programs, such as PredictProtein (630 West, 168 Street, BB217, New York, N.Y. 10032, USA). Alternatively, the actual secondary and/or tertiary structure of an isoprene synthase, DXS, IDI, or MVA pathway polypeptide can be determined using standard methods. Additional isoprene synthase, DXS, IDI, or MVA pathway nucleic acids can also be identified by hybridization to probes generated from known isoprene synthase, DXS, IDI, or MVA pathway nucleic acids.

Exemplary Promoters and Vectors

Any of the isoprene synthase, DXS, IDI, or MVA pathway nucleic acid described herein can be included in one or more vectors. Accordingly, the invention also features vectors with one more nucleic acids encoding any of the isoprene synthase, DXS, IDI, or MVA pathway polypeptides that are described herein. As used herein, a "vector" means a construct that is capable of delivering, and desirably expressing one or more nucleic acids of interest in a host cell. Examples of vectors include, but are not limited to, plasmids, viral vectors, DNA or RNA expression vectors, cosmids, and phage vectors. In some embodiments, the vector contains a nucleic acid under the control of an expression control sequence.

As used herein, an "expression control sequence" means a nucleic acid sequence that directs transcription of a nucleic acid of interest. An expression control sequence can be a promoter, such as a constitutive or an inducible promoter, or an enhancer. An "inducible promoter" is a promoter that is active under environmental or developmental regulation. The expression control sequence is operably linked to the nucleic acid segment to be transcribed.

In some embodiments, the vector contains a selective marker. The term "selective marker" refers to a nucleic acid capable of expression in a host cell that allows for ease of selection of those host cells containing an introduced nucleic acid or vector. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. Exemplary nutritional selective markers include those markers known in the art as amdS, argB, and pyr4. Markers useful in vector systems for transformation of *Trichoderma* are known in the art (see, e.g., Finkelstein, Chapter 6 in Biotechnology of Filamentous Fungi, Finkelstein et al., Eds. Butterworth-Heinemann, Boston, Mass., Chap. 6., 1992; and Kinghorn et al., Applied Molecular Genetics of Filamentous Fungi, Blackie Academic and Professional, Chapman and Hall, London, 1992, which are each hereby incorporated by reference in their entireties, particularly with respect to selective markers). In some embodiments, the selective marker is the amdS nucleic acid, which encodes the enzyme acetamidase, allowing transformed cells to grow on acetamide as a nitrogen source. The use of an *A. nidulans* amdS nucleic acid as a selective marker is described in Kelley et al., EMBO J. 4:475-479, 1985 and Penttila et al., *Gene* 61:155-164, 1987 (which are each hereby incorporated by reference in their entireties, particularly with respect to selective markers). In some embodiments, an isoprene synthase, DXS, IDI, or MVA pathway nucleic acid integrates into a chromosome of the cells without a selective marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Sambrook et al., Molecular Cloning: A Laboratory Manual, $2^{nd}$ ed., Cold Spring Harbor, 1989, which is hereby incorporated by reference in its entirety, particularly with respect to the use of vectors).

Promoters are well known in the art. Any promoter that functions in the host cell can be used for expression of an isoprene synthase, DXS, IDI, or MVA pathway nucleic acid in the host cell. Initiation control regions or promoters, which are useful to drive expression of isoprene synthase, DXS, IDI, or MVA pathway nucleic acids in various host cells are numerous and familiar to those skilled in the art (see, for example, WO 2004/033646 and references cited therein, which are each hereby incorporated by reference in their entireties, particularly with respect to vectors for the expression of nucleic acids of interest). Virtually any promoter capable of driving these nucleic acids is suitable for the present invention including, but not limited to, CYC1, HIS3, GAL1, GAL10, ADH1, PGK, PHO5, GAPDH, ADCI, TRP1, URA3, LEU2, ENO, and TPI (useful for expression in *Saccharomyces*); AOX1 (useful for expression in *Pichia*); and lac, trp, ⊠ $P_L$, ⊠ $P_R$, T7, tac, and trc (useful for expression in *E. coli*).

In some embodiments, a glucose isomerase promoter is used (see, for example, U.S. Pat. No. 7,132,527 and references cited therein, which are each hereby incorporated by reference in their entireties, particularly with respect promoters and plasmid systems for expressing polypeptides of interest). Reported glucose isomerase promoter mutants can be used to vary the level of expression of the polypeptide encoded by a nucleic acid operably linked to the glucose isomerase promoter (U.S. Pat. No. 7,132,527). In various embodiments, the glucose isomerase promoter is contained in a low, medium, or high copy plasmid (U.S. Pat. No. 7,132,527).

In various embodiments, an isoprene synthase, DXS, IDI, and/or MVA pathway nucleic acid is contained in a low copy plasmid (e.g., a plasmid that is maintained at about 1 to about 4 copies per cell), medium copy plasmid (e.g., a plasmid that is maintained at about 10 to about 15 copies per cell), or high copy plasmid (e.g., a plasmid that is maintained at about 50 or more copies per cell). In some embodiments, the heterologous or extra endogenous isoprene synthase, DXS, IDI, or MVA pathway nucleic acid is operably linked to a T7 promoter. In some embodiments, the heterologous or extra endogenous isoprene synthase, DXS, IDI, or MVA pathway nucleic acid operably linked to a T7 promoter is contained in a medium or high copy plasmid. In some embodiments, the heterologous or extra endogenous isoprene synthase, DXS, IDI, or MVA pathway nucleic acid is operably linked to a Trc promoter. In some embodiments, the heterologous or extra endogenous isoprene synthase, DXS, IDI, or MVA pathway nucleic acid operably linked to a Trc promoter is contained in a medium or high copy plasmid. In some embodiments, the heterologous or extra endogenous isoprene synthase, DXS, IDI, or MVA pathway nucleic acid is operably linked to a Lac promoter. In some embodiments, the heterologous or extra endogenous isoprene synthase, DXS, IDI, or MVA pathway nucleic acid operably linked to a Lac promoter is contained in a low copy plasmid. In some embodiments, the heterologous or extra endogenous isoprene synthase, DXS, IDI, or MVA pathway nucleic acid is operably linked to an endogenous promoter, such as an endogenous *Escherichia, Panteoa, Bacillus, Yarrowia, Streptomyces*, or *Trichoderma* promoter or an endogenous alkaline serine protease, isoprene synthase, DXS, IDI, or MVA pathway promoter. In some embodiments, the heterologous or extra endogenous isoprene synthase, DXS, IDI, or MVA pathway nucleic acid operably linked to an endogenous promoter is contained in a high copy plasmid. In some embodiments, the vector is a replicating plasmid that does not integrate into a chromosome in the cells. In some embodiments, part or all of the vector integrates into a chromosome in the cells.

In some embodiments, the vector is any vector which when introduced into a fungal host cell is integrated into the host cell genome and is replicated. Reference is made to the Fungal Genetics Stock Center Catalogue of Strains (FGSC, the world-wide web at "fgsc.net" and the references cited therein, which are each hereby incorporated by reference in their entireties, particularly with respect to vectors) for a list of vectors. Additional examples of suitable expression and/or integration vectors are provided in Sambrook et al., Molecular Cloning: A Laboratory Manual, $2^{nd}$ ed., Cold Spring Harbor, 1989, Current Protocols in Molecular Biology (F. M. Ausubel et al. (eds) 1987, Supplement 30, section 7.7.18); van den Hondel et al. in Bennett and Lasure (Eds.) More Gene Manipulations in Fungi, Academic Press pp. 396-428, 1991; and U.S. Pat. No. 5,874,276, which are each hereby incorporated by reference in their entireties, particularly with respect to vectors. Particularly useful vectors include pFB6, pBR322, PUC18, pUC100, and pENTR/D.

In some embodiments, an isoprene synthase, DXS, IDI, or MVA pathway nucleic acid is operably linked to a suitable promoter that shows transcriptional activity in a fungal host cell. The promoter may be derived from one or more nucleic acids encoding a polypeptide that is either endogenous or heterologous to the host cell. In some embodiments, the promoter is useful in a *Trichoderma* host. Suitable non-limiting examples of promoters include cbh1, cbh2, egl1, egl2, pepA, hfb1, hfb2, xyn1, and amy. In some embodiments, the promoter is one that is native to the host cell. For example, in some embodiments when *T. reesei* is the host, the promoter is a native *T. reesei* promoter. In some embodiments, the promoter is *T. reesei* cbh1, which is an inducible promoter and has been deposited in GenBank under Accession No. D86235, which is incorporated by reference in its entirety, particularly with respect to promoters. In some embodiments, the promoter is one that is heterologous to the fungal host cell. Other examples of useful promoters include promoters from the genes of *A. awamori* and *A. niger* glucoamylase (glaA) (Nunberg et al., Mol. Cell Biol. 4:2306-2315, 1984 and Boel et al., EMBO J. 3:1581-1585, 1984, which are each hereby incorporated by reference in their entireties, particularly with respect to promoters); *Aspergillus niger* alpha amylases, *Aspergillus oryzae* TAKA amylase, *T. reesei* xln1, and the *T. reesei* cellobiohydrolase 1 (EP 137280, which is incorporated by reference in its entirety, particularly with respect to promoters).

In some embodiments, the expression vector also includes a termination sequence. Termination control regions may also be derived from various genes native to the host cell. In some embodiments, the termination sequence and the promoter sequence are derived from the same source. In another embodiment, the termination sequence is endogenous to the host cell. A particularly suitable terminator sequence is cbh1 derived from a *Trichoderma* strain (such as *T. reesei*). Other useful fungal terminators include the terminator from an *A. niger* or *A. awamori* glucoamylase nucleic acid (Nunberg et al., *Mol. Cell Biol.* 4:2306-2315, 1984 and Boel et al., *EMBO J.* 3:1581-1585, 1984; which are each hereby incorporated by reference in their entireties, particularly with respect to fungal terminators). Optionally, a termination site may be included. For effective expression of the polypeptides, DNA encoding the polypeptide are linked operably through initiation codons to selected expression control regions such that expression results in the formation of the appropriate messenger RNA.

In some embodiments, the promoter, coding, region, and terminator all originate from the isoprene synthase, DXS, IDI, or MVA pathway nucleic acid to be expressed. In some embodiments, the coding region for an isoprene synthase, DXS, IDI, or MVA pathway nucleic acid is inserted into a general-purpose expression vector such that it is under the transcriptional control of the expression construct promoter and terminator sequences. In some embodiments, genes or part thereof are inserted downstream of the strong cbh1 promoter.

An isoprene synthase, DXS, IDI, or MVA pathway nucleic acid can be incorporated into a vector, such as an expression vector, using standard techniques (Sambrook et al., Molecular Cloning: A Laboratory Manual, Cold Spring Harbor, 1982, which is hereby incorporated by reference in its entirety, particularly with respect to the screening of appropriate DNA sequences and the construction of vectors). Methods used to ligate the DNA construct comprising a nucleic acid of interest (such as an isoprene synthase, DXS, IDI, or MVA pathway nucleic acid), a promoter, a terminator, and other sequences and to insert them into a suitable vector are well known in the art. For example, restriction enzymes can be used to cleave the isoprene synthase, DXS, IDI, or MVA pathway nucleic acid and the vector. Then, the compatible ends of the cleaved isoprene synthase, DXS, IDI, or MVA pathway nucleic acid and the cleaved vector can be ligated. Linking is generally accomplished by ligation at convenient restriction sites. If such sites do not exist, the synthetic oligonucleotide linkers are used in accordance with conventional practice (see, Sambrook et al., Molecular Cloning: A Laboratory Manual, $2^{nd}$ ed., Cold Spring Harbor, 1989, and Bennett and Lasure, More Gene Manipulations in Fungi, Academic Press, San Diego, pp 70-76, 1991, which are each hereby incorporated by reference in their entireties, particularly with respect to oligonucleotide linkers). Additionally, vectors can be constructed using known recombination techniques (e.g., Invitrogen Life Technologies, Gateway Technology).

In some embodiments, it may be desirable to over-express isoprene synthase, DXS, IDI, or MVA pathway nucleic acids at levels far higher than currently found in naturally-occurring cells. This result may be accomplished by the selective cloning of the nucleic acids encoding those polypeptides into multicopy plasmids or placing those nucleic acids under a strong inducible or constitutive promoter. Methods for over-expressing desired polypeptides are common and well known in the art of molecular biology and examples may be found in Sambrook et al., Molecular Cloning: A Laboratory Manual, $2^{nd}$ ed., Cold Spring Harbor, 1989, which is hereby incorporated by reference in its entirety, particularly with respect to cloning techniques.

The following resources include descriptions of additional general methodology useful in accordance with the invention: Kreigler, Gene Transfer and Expression; A Laboratory Manual, 1990 and Ausubel et al., Eds. Current Protocols in Molecular Biology, 1994, which are each hereby incorporated by reference in their entireties, particularly with respect to molecular biology and cloning techniques.

Exemplary Source Organisms

Isoprene synthase, DXS, IDI, or MVA pathway nucleic acids (and their encoded polypeptides) can be obtained from any organism that naturally contains isoprene synthase, DXS, IDI, and/or MVA pathway nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 19A and 19B). Thus, DXS nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways.

In some embodiments, the nucleic acid sequence of the isoprene synthase, DXS, IDI, or MVA pathway nucleic is identical to the sequence of a nucleic acid that is produced by any of the following organisms in nature. In some embodiments, the amino acid sequence of the isoprene synthase, DXS, IDI, or MVA pathway polypeptide is identical to the sequence of a polypeptide that is produced by any of the following organisms in nature. In some embodiments, the isoprene synthase, DXS, IDI, or MVA pathway nucleic acid or polypeptide is a mutant nucleic acid or polypeptide derived from any of the organisms described herein. As used herein, "derived from" refers to the source of the nucleic acid or polypeptide into which one or more mutations is introduced. For example, a polypeptide that is "derived from a plant polypeptide" refers to polypeptide of interest that results from introducing one or more mutations into the sequence of a wild-type (i.e., a sequence occurring in nature) plant polypeptide.

In some embodiments, the source organism is a fungus, examples of which are species of *Aspergillus* such as *A. oryzae* and *A. niger*, species of *Saccharomyces* such as *S. cerevisiae*, species of *Schizosaccharomyces* such as *S. pombe*, and species of *Trichoderma* such as *T. reesei*. In some embodiments, the source organism is a filamentous fungal cell. The term "filamentous fungi" refers to all filamentous forms of the subdivision Eumycotina (see, Alexopoulos, C. J. (1962), Introductory Mycology, Wiley, New York). These fungi are characterized by a vegetative mycelium with a cell wall composed of chitin, cellulose, and other complex polysaccharides. The filamentous fungi are morphologically, physiologically, and genetically distinct from yeasts. Vegetative growth by filamentous fungi is by hyphal elongation and carbon catabolism is obligatory aerobic. The filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., Appl. Microbiol. Biotechnol 20: 46-53, 1984; ATCC No. 56765 and ATCC No. 26921); *Penicillium* sp., *Humicola* sp. (e.g., *H. insolens, H. lanuginose*, or *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, or *A. awamori*) (Ward et al., Appl. Microbiol. Biotechnol. 39: 7380743, 1993 and Goedegebuur et al., Genet 41: 89-98, 2002), *Fusarium* sp., (e.g., *F. roseum, F. graminum F. cerealis, F. oxysporuim*, or *F. venenatum*), *Neurospora* sp., (e.g., *N. crassa*), *Hypocrea* sp., *Mucor* sp., (e.g., *M. miehei*), *Rhizopus* sp. and *Emericella* sp. (see also, Innis et al., Sci. 228: 21-26, 1985). The term "*Trichoderma*" or "*Trichoderma* sp." or "*Trichoderma* spp." refer to any fungal genus previously or currently classified as *Trichoderma*.

In some embodiments, the fungus is *A. nidulans, A. awamori, A. oryzae, A. aculeatus, A. niger, A. japonicus, T. reesei, T. viride, F. oxysporum*, or *F. solani*. *Aspergillus* strains are disclosed in Ward et al., Appl. Microbiol. Biotechnol. 39:738-743, 1993 and Goedegebuur et al., Curr Gene 41:89-98, 2002, which are each hereby incorporated by reference in their entireties, particularly with respect to fungi. In particular embodiments, the fungus is a strain of *Trichoderma*, such as a strain of *T. reesei*. Strains of *T. reesei* are known and non-limiting examples include ATCC No. 13631, ATCC No. 26921, ATCC No. 56764, ATCC No. 56765, ATCC No. 56767, and NRRL 15709, which are each hereby incorporated by reference in their entireties, particularly with respect to strains of *T. reesei*. In some embodiments, the host strain is a derivative of RL-P37. RL-P37 is disclosed in Sheir-Neiss et al., Appl. Microbiol. Biotechnology 20:46-53, 1984, which is hereby incorporated by reference in its entirety, particularly with respect to strains of *T. reesei.*

In some embodiments, the source organism is a yeast, such as *Saccharomyces* sp., *Schizosaccharomyces* sp., *Pichia* sp., or *Candida* sp.

In some embodiments, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, or strains of *Escherichia* such as *E. coli*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the source organism is a gram-positive bacterium. Non-limiting examples include strains of *Streptomyces* (e.g., *S. lividans, S. coelicolor*, or *S. griseus*) and *Bacillus*. In some embodiments, the source organism is a gram-negative bacterium, such as *E. coli* or *Pseudomonas* sp.

In some embodiments, the source organism is a plant, such as a plant from the family Fabaceae, such as the Faboideae subfamily. In some embodiments, the source organism is kudzu, poplar (such as *Populus alba* x *tremula* CAC35696), aspen (such as *Populus tremuloides*), or *Quercus robur*.

In some embodiments, the source organism is an algae, such as a green algae, red algae, glaucophytes, chlorarachniophytes, euglenids, chromista, or dinoflagellates.

In some embodiments, the source organism is a cyanobacteria, such as cyanobacteria classified into any of the following groups based on morphology: *Chroococcales, Pleurocapsales, Oscillatoriales, Nostocales*, or *Stigonematales*.

In some embodiments, the source organism is an archaeon, such as *Methanosarcina mazei*. Exemplary archaea include those disclosed by Koga and Morii (*Microbiology & Mol. Biology Reviews*, 71:97-120, 2007, which is hereby incorporated by reference in its entirety, particularly with respect to archaea (see Table 3)). Other exemplary archaea are hyperthermophilic archaea, such as *Methanococcus jannaschii* (Huang et al., *Protein Expression and Purification* 17(1):33-40, 1999) and halophilic archaea (such as *Halobacterium salanarium*).

TABLE 3

Exemplary archaea

| Original name | Exemplary Strain | Name most recently proposed |
|---|---|---|
| *Caldariella acidophila* | | *Sulfolobus solfataricus* |
| *Halobacterium cutirubrum* | | *Halobacterium salinarum* |
| *Halobacterium halobium* | | *Halobacterium salinarum* |
| *Halobacterium mediterranei* | | *Haloferax mediterranei* |
| *Halobacterium vallismortis* | | *Haloarcula vallismortis* |
| *Methanobacterium thermoautotrophicum* | ΔH | *Methanothermobacter thermautotrophicus* |
| *Methanobacterium thermoautotrophicum* | Marburg | *Methanothermobacter marburgensis* |
| *Methanobacterium thermoformicicum* | SF-4 | *Methanothermobacter wolfeii* |
| *Methanococcus igneus* | | *Methanotorris igneus* |

TABLE 3-continued

Exemplary archaea

| Original name | Exemplary Strain | Name most recently proposed |
|---|---|---|
| *Natronobacterium pharaonis* | | *Natronomonas pharaonis* |
| *Pseudomonas salinaria* | | *Halobacterium salinarum* |

Exemplary Host Cells

A variety of host cells can be used to express isoprene synthase, DXS, IDI, and/or MVA pathway polypeptides and to produce isoprene in the methods of the invention. Exemplary host cells include cells from any of the organisms listed in the prior section under the heading "Exemplary Source Organisms." The host cell may be a cell that naturally produces isoprene or a cell that does not naturally produce isoprene. In some embodiments, the host cell naturally produces isoprene using the DXP pathway, and an isoprene synthase, DXS, and/or IDI nucleic acid is added to enhance production of isoprene using this pathway. In some embodiments, the host cell naturally produces isoprene using the MVA pathway, and an isoprene synthase and/or one or more MVA pathway nucleic acids are added to enhance production of isoprene using this pathway. In some embodiments, the host cell naturally produces isoprene using the DXP pathway and one or more MVA pathway nucleic acids are added to produce isoprene using part or all of the MVA pathway as well as the DXP pathway. In some embodiments, the host cell naturally produces isoprene using both the DXP and MVA pathways and one or more isoprene synthase, DXS, IDI, or MVA pathway nucleic acids are added to enhance production of isoprene by one or both of these pathways.

Exemplary Transformation Methods

Isoprene synthase, DXS, IDI, and/or MVA pathway nucleic acids or vectors containing them can be inserted into a host cell (e.g., a plant cell, a fungal cell, a yeast cell, or a bacterial cell described herein) using standard techniques for expression of the encoded isoprene synthase, DXS, IDI, and/or MVA pathway polypeptide. Introduction of a DNA construct or vector into a host cell can be performed using techniques such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989, which are each hereby incorporated by reference in their entireties, particularly with respect to transformation methods). The expression of heterologous polypeptide in *Trichoderma* is described in U.S. Pat. No. 6,022,725; U.S. Pat. No. 6,268,328; U.S. Pat. No. 7,262,041; WO 2005/001036; Harkki et al.; *Enzyme Microb. Technol.* 13:227-233, 1991; Harkki et al., *Bio Technol.* 7:596-603, 1989; EP 244,234; EP 215,594; and Nevalainen et al., "*The Molecular Biology of Trichoderma and its Application to the Expression of Both Homologous and Heterologous Genes*," in Molecular Industrial Mycology, Eds. Leong and Berka, Marcel Dekker Inc., NY pp. 129-148, 1992, which are each hereby incorporated by reference in their entireties, particularly with respect to transformation and expression methods). Reference is also made to Cao et al., (*Sci.* 9:991-1001, 2000; EP 238023; and Yelton et al., *Proceedings. Natl. Acad. Sci. USA* 81:1470-1474, 1984 (which are each hereby incorporated by reference in their entireties, particularly with respect to transformation methods) for transformation of *Aspergillus* strains. The introduced nucleic acids may be integrated into chromosomal DNA or maintained as extrachromosomal replicating sequences.

Any method known in the art may be used to select transformants. In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability is conducted by growing the transformants on a solid non-selective medium (e.g., a medium that lacks acetamide), harvesting spores from this culture medium, and determining the percentage of these spores which subsequently germinate and grow on selective medium containing acetamide.

In some embodiments, fungal cells are transformed by a process involving protoplast formation and transformation of the protoplasts followed by regeneration of the cell wall in a known manner. In one specific embodiment, the preparation of *Trichoderma* sp. for transformation involves the preparation of protoplasts from fungal mycelia (see, Campbell et al., *Curr. Genet.* 16:53-56, 1989, which is incorporated by reference in its entirety, particularly with respect to transformation methods). In some embodiments, the mycelia are obtained from germinated vegetative spores. The mycelia are treated with an enzyme that digests the cell wall resulting in protoplasts. The protoplasts are then protected by the presence of an osmotic stabilizer in the suspending medium. These stabilizers include sorbitol, mannitol, potassium chloride, magnesium sulfate, and the like. Usually the concentration of these stabilizers varies between 0.8 M and 1.2 M. It is desirable to use about a 1.2 M solution of sorbitol in the suspension medium.

Uptake of DNA into the host *Trichoderma* sp. strain is dependent upon the calcium ion concentration. Generally, between about 10 mM $CaCl_2$ and 50 mM $CaCl_2$ is used in an uptake solution. In addition to the calcium ion in the uptake solution, other compounds generally included are a buffering system such as TE buffer (10 Mm Tris, pH 7.4; 1 mM EDTA) or 10 mM MOPS, pH 6.0 buffer (morpholinepropanesulfonic acid) and polyethylene glycol (PEG). While not intending to be bound to any particular theory, it is believed that the polyethylene glycol acts to fuse the cell membranes, thus permitting the contents of the medium to be delivered into the cytoplasm of the *Trichoderma* sp. strain and the plasmid DNA to be transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL (such as $2\times10^6$/mL) are used in the transformation. A volume of 100 μL of these protoplasts or cells in an appropriate solution (e.g., 1.2 M sorbitol and 50 mM $CaCl_2$) are mixed with the desired DNA. Generally, a high concentration of PEG is added to the uptake solution. From 0.1 to 1 volume of 25% PEG 4000 can be added to the protoplast suspension. In some embodiments, about 0.25 volumes are added to the protoplast suspension. Additives such as dimethyl sulfoxide, heparin, spermidine, potassium chloride, and the like may also be added to the uptake solution and aid in transformation. Similar procedures are available for other fungal host cells (see, e.g., U.S. Pat. Nos. 6,022,725 and 6,268,328, which are each hereby incorporated by reference in their entireties, particularly with respect to transformation methods).

Generally, the mixture is then cultured at approximately 0° C. for a period of between 10 to 30 minutes. Additional PEG is then added to the mixture to further enhance the uptake of the desired nucleic acid sequence. The 25% PEG 4000 is generally added in volumes of 5 to 15 times the volume of the transformation mixture; however, greater and lesser volumes may be suitable. The 25% PEG 4000 is desirably about 10 times the volume of the transformation mixture. After the PEG is added, the transformation mixture is then cultured either at room temperature or on ice before the addition of a sorbitol and $CaCl_2$ solution. The protoplast suspension is then further added to molten aliquots of a growth medium. When the growth medium includes a growth selection (e.g., acetamide or an antibiotic) it permits the growth of transformants only.

The transformation of bacterial cells may be performed according to conventional methods, e.g., as described in Sambrook et al., Molecular Cloning: A Laboratory Manual, Cold Spring Harbor, 1982, which is hereby incorporated by reference in its entirety, particularly with respect to transformation methods.

Exemplary Cell Culture Media

The invention also includes a cell or a population of cells in culture that produce isoprene. By "cells in culture" is meant two or more cells in a solution (e.g., a cell medium) that allows the cells to undergo one or more cell divisions. "Cells in culture" do not include plant cells that are part of a living, multicellular plant containing cells that have differentiated into plant tissues. In various embodiments, the cell culture includes at least or about 10, 20, 50, 100, 200, 500, 1,000, 5,000, 10,000 or more cells.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells.

In some embodiments, the carbon source is a carbohydrate (such as monosaccharide, disaccharide, oligosaccharide, or polysaccharide), invert sugar (e.g., enzymatically treated sucrose syrup), glycerol, glycerine (e.g., a glycerine byproduct of a biodiesel or soap-making process), dihydroxyacetone, one-carbon source, oil (e.g., a plant or vegetable oil such as corn, palm, or soybean oil), animal fat, animal oil, fatty acid (e.g., a saturated fatty acid, unsaturated fatty acid, or polyunsaturated fatty acid), lipid, phospholipid, glycerolipid, monoglyceride, diglyceride, triglyceride, polypeptide (e.g., a microbial or plant protein or peptide), renewable carbon source (e.g., a biomass carbon source such as a hydrolyzed biomass carbon source), yeast extract, component from a yeast extract, polymer, acid, alcohol, aldehyde, ketone, amino acid, succinate, lactate, acetate, ethanol, or any combination of two or more of the foregoing. In some embodiments, the carbon source is a product of photosynthesis, including, but not limited to, glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose). In some embodiments, the cell medium includes a carbohydrate as well as a carbon source other than a carbohydrate (e.g., glycerol, glycerine, dihydroxyacetone, one-carbon source, oil, animal fat, animal oil, fatty acid, lipid, phospholipid, glycerolipid, monoglyceride, diglyceride, triglyceride, renewable carbon source, or a component from a yeast extract). In some embodiments, the cell medium includes a carbohydrate as well as a polypeptide (e.g., a microbial or plant protein or peptide). In some embodiments, the microbial polypeptide is a polypeptide from yeast or bacteria. In some embodiments, the plant polypeptide is a polypeptide from soy, corn, canola, jatropha, palm, peanut, sunflower, coconut, mustard, rapeseed, cottonseed, palm kernel, olive, safflower, sesame, or linseed.

In some embodiments, the concentration of the carbohydrate is at least or about 5 grams per liter of broth (g/L, wherein the volume of broth includes both the volume of the cell medium and the volume of the cells), such as at least or about 10, 15, 20, 30, 40, 50, 60, 80, 100, 150, 200, 300, 400, or more g/L. In some embodiments, the concentration of the carbohydrate is between about 50 and about 400 g/L, such as between about 100 and about 360 g/L, between about 120 and about 360 g/L, or between about 200 and about 300 g/L. In some embodiments, this concentration of carbohydrate includes the total amount of carbohydrate that is added before and/or during the culturing of the host cells.

In some embodiments, the cells are cultured under limited glucose conditions. By "limited glucose conditions" is meant that the amount of glucose that is added is less than or about 105% (such as about 100%) of the amount of glucose that is consumed by the cells. In particular embodiments, the amount of glucose that is added to the culture medium is approximately the same as the amount of glucose that is consumed by the cells during a specific period of time. In some embodiments, the rate of cell growth is controlled by limiting the amount of added glucose such that the cells grow at the rate that can be supported by the amount of glucose in the cell medium. In some embodiments, glucose does not accumulate during the time the cells are cultured. In various embodiments, the cells are cultured under limited glucose conditions for greater than or about 1, 2, 3, 5, 10, 15, 20, 25, 30, 35, 40, 50, 60, or 70 hours. In various embodiments, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some embodiments, the cells are cultured in the presence of an excess of glucose. In particular embodiments, the amount of glucose that is added is greater than about 105% (such as about or greater than 110, 120, 150, 175, 200, 250, 300, 400, or 500%) or more of the amount of glucose that is consumed by the cells during a specific period of time. In some embodiments, glucose accumulates during the time the cells are cultured.

Exemplary lipids are any substance containing one or more fatty acids that are C4 and above fatty acids that are saturated, unsaturated, or branched.

Exemplary oils are lipids that are liquid at room temperature. In some embodiments, the lipid contains one or more C4 or above fatty acids (e.g., contains one or more saturated, unsaturated, or branched fatty acid with four or more carbons). In some embodiments, the oil is obtained from soy, corn, canola, jatropha, palm, peanut, sunflower, coconut, mustard, rapeseed, cottonseed, palm kernel, olive, safflower, sesame, linseed, oleagineous microbial cells, Chinese tallow, or any combination of two or more of the foregoing.

Exemplary fatty acids include compounds of the formula RCOOH, where "R" is a hydrocarbon. Exemplary unsaturated fatty acids include compounds where "R" includes at least one carbon-carbon double bond. Exemplary unsaturated fatty acids include, but are not limited to, oleic acid, vaccenic acid, linoleic acid, palmitelaidic acid, and arachidonic acid. Exemplary polyunsaturated fatty acids include compounds where "R" includes a plurality of carbon-carbon double bonds. Exemplary saturated fatty acids include compounds where "R" is a saturated aliphatic group. In some embodiments, the carbon source includes one or more $C_{12}$-$C_{22}$ fatty acids, such as a $C_{12}$ saturated fatty acid, a $C_{14}$ saturated fatty acid, a $C_{16}$ saturated fatty acid, a $C_{18}$ saturated fatty acid, a $C_{20}$ saturated fatty acid, or a $C_{22}$ saturated fatty acid. In an exemplary embodiment, the fatty acid is palmitic acid. In some embodiments, the carbon source is a salt of a fatty acid (e.g., an unsaturated fatty acid), a derivative of a fatty acid (e.g., an unsaturated fatty acid), or a salt of a derivative of fatty acid (e.g., an unsaturated fatty acid). Suitable salts include, but are not limited to, lithium salts, potassium salts, sodium salts, and the like. Di- and triglycerols are fatty acid esters of glycerol.

In some embodiments, the concentration of the lipid, oil, fat, fatty acid, monoglyceride, diglyceride, or triglyceride is at least or about 1 gram per liter of broth (g/L, wherein the volume of broth includes both the volume of the cell medium and the volume of the cells), such as at least or about 5, 10, 15, 20, 30, 40, 50, 60, 80, 100, 150, 200, 300, 400, or more g/L. In some embodiments, the concentration of the lipid, oil, fat, fatty acid, monoglyceride, diglyceride, or triglyceride is between about 10 and about 400 g/L, such as between about 25 and about 300 g/L, between about 60 and about 180 g/L, or between about 75 and about 150 g/L. In some embodiments, the concentration includes the total amount of the lipid, oil, fat, fatty acid, monoglyceride, diglyceride, or triglyceride that is added before and/or during the culturing of the host cells. In some embodiments, the carbon source includes both (i) a lipid, oil, fat, fatty acid, monoglyceride, diglyceride, or triglyceride and (ii) a carbohydrate, such as glucose. In some embodiments, the ratio of the lipid, oil, fat, fatty acid, monoglyceride, diglyceride, or triglyceride to the carbohydrate is about 1:1 on a carbon basis (i.e., one carbon in the lipid, oil, fat, fatty acid, monoglyceride, diglyceride, or triglyceride per carbohydrate carbon). In particular embodiments, the amount of the lipid, oil, fat, fatty acid, monoglyceride, diglyceride, or triglyceride is between about 60 and 180 g/L, and the amount of the carbohydrate is between about 120 and 360 g/L.

Exemplary microbial polypeptide carbon sources include one or more polypeptides from yeast or bacteria. Exemplary plant polypeptide carbon sources include one or more polypeptides from soy, corn, canola, jatropha, palm, peanut, sunflower, coconut, mustard, rapeseed, cottonseed, palm kernel, olive, safflower, sesame, or linseed.

Exemplary renewable carbon sources include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

In some embodiments, the renewable carbon source (such as biomass) is pretreated before it is added to the cell culture medium. In some embodiments, the pretreatment includes enzymatic pretreatment, chemical pretreatment, or a combination of both enzymatic and chemical pretreatment (see, for example, Farzaneh et al., *Bioresource Technology* 96 (18): 2014-2018, 2005; U.S. Pat. No. 6,176,176; U.S. Pat. No. 6,106,888; which are each hereby incorporated by reference in their entireties, particularly with respect to the pretreatment of renewable carbon sources). In some embodiments, the renewable carbon source is partially or completely hydrolyzed before it is added to the cell culture medium.

In some embodiments, the renewable carbon source (such as corn stover) undergoes ammonia fiber expansion (AFEX) pretreatment before it is added to the cell culture medium (see, for example, Farzaneh et al., *Bioresource Technology* 96 (18): 2014-2018, 2005). During AFEX pretreatment, a renewable carbon source is treated with liquid anhydrous ammonia at moderate temperatures (such as about 60 to about 100° C.) and high pressure (such as about 250 to about 300 psi) for about 5 minutes. Then, the pressure is rapidly released. In this process, the combined chemical and physical effects of lignin solubilization, hemicellulose hydrolysis, cellulose decrystallization, and increased surface area enables near complete enzymatic conversion of cellulose and hemicellulose to fermentable sugars. AFEX pretreatment has the advantage that nearly all of the ammonia can be recovered and reused, while the remaining serves as nitrogen source for microbes in downstream processes. Also, a wash stream is not required for AFEX pretreatment. Thus, dry matter recovery following the AFEX treatment is essentially 100%. AFEX is basically a dry to dry process. The treated renewable carbon source is stable for long periods and can be fed at very high solid loadings in enzymatic hydrolysis or fermentation processes. Cellulose and hemicellulose are well preserved in the AFEX process, with little or no degradation. There is no need for neutralization prior to the enzymatic hydrolysis of a renewable carbon source that has undergone AFEX pretreatment. Enzymatic hydrolysis of AFEX-treated carbon sources produces clean sugar streams for subsequent fermentation use.

In some embodiments, the concentration of the carbon source (e.g., a renewable carbon source) is equivalent to at least or about 0.1, 0.5, 1, 1.5 2, 3, 4, 5, 10, 15, 20, 30, 40, or 50% glucose (w/v). The equivalent amount of glucose can be determined by using standard HPLC methods with glucose as a reference to measure the amount of glucose generated from the carbon source. In some embodiments, the concentration of the carbon source (e.g., a renewable carbon source) is equivalent to between about 0.1 and about 20% glucose, such as between about 0.1 and about 10% glucose, between about 0.5 and about 10% glucose, between about 1 and about 10% glucose, between about 1 and about 5% glucose, or between about 1 and about 2% glucose.

In some embodiments, the carbon source includes yeast extract or one or more components of yeast extract. In some embodiments, the concentration of yeast extract is at least 1 gram of yeast extract per liter of broth (g/L, wherein the volume of broth includes both the volume of the cell medium and the volume of the cells), such at least or about 5, 10, 15, 20, 30, 40, 50, 60, 80, 100, 150, 200, 300, or more g/L. In some embodiments, the concentration of yeast extract is between about 1 and about 300 g/L, such as between about 1 and about 200 g/L, between about 5 and about 200 g/L, between about 5 and about 100 g/L, or between about 5 and about 60 g/L. In some embodiments, the concentration includes the total amount of yeast extract that is added before and/or during the culturing of the host cells. In some embodiments, the carbon source includes both yeast extract (or one or more components thereof) and another carbon source, such as glucose. In some embodiments, the ratio of yeast extract to the other carbon source is about 1:5, about 1:10, or about 1:20 (w/w).

Additionally the carbon source may also be one-carbon substrates such as carbon dioxide, or methanol. Glycerol production from single carbon sources (e.g., methanol, formaldehyde, or formate) has been reported in methylotrophic yeasts (Yamada et al., *Agric. Biol. Chem.,* 53(2) 541-543, 1989, which is hereby incorporated by reference in its entirety, particularly with respect to carbon sources) and in bacteria (Hunter et. al., *Biochemistry,* 24, 4148-4155, 1985, which is hereby incorporated by reference in its entirety, particularly with respect to carbon sources). These organisms can assimilate single carbon compounds, ranging in oxidation state from methane to formate, and produce glycerol. The pathway of carbon assimilation can be through ribulose monophosphate, through serine, or through xylulose-momophosphate (Gottschalk, *Bacterial Metabolism*, Second Edition, Springer-Verlag: New York, 1986, which is hereby incorporated by reference in its entirety, particularly with respect to carbon sources). The ribulose monophosphate pathway involves the condensation of formate with ribulose-5-phosphate to form a six carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates, methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl-Compd.*, [Int. Symp.], $7^{th}$ ed., 415-32. Editors: Murrell et al., Publisher: Intercept, Andover, UK, 1993, which is hereby incorporated by reference in its entirety, particularly with respect to carbon sources). Similarly, various species of *Candida* metabolize alanine or oleic acid (Sulter et al., *Arch. Microbiol.* 153(5), 485-9, 1990, which is hereby incorporated by reference in its entirety, particularly with respect to carbon sources).

In some embodiments, cells are cultured in a standard medium containing physiological salts and nutrients (see, e.g., Pourquie, J. et al., Biochemistry and Genetics of Cellulose Degradation, eds. Aubert et al., Academic Press, pp. 71-86, 1988 and Ilmen et al., *Appl. Environ. Microbiol.* 63:1298-1306, 1997, which are each hereby incorporated by reference in their entireties, particularly with respect to cell medias). Exemplary growth media are common commercially prepared media such as Luria Bertani (LB) broth, Sabouraud Dextrose (SD) broth, or Yeast medium (YM) broth. Other defined or synthetic growth media may also be used, and the appropriate medium for growth of particular host cells are known by someone skilled in the art of microbiology or fermentation science.

In addition to an appropriate carbon source, the cell medium desirably contains suitable minerals, salts, cofactors, buffers, and other components known to those skilled in the art suitable for the growth of the cultures or the enhancement of isoprene production (see, for example, WO 2004/033646 and references cited therein and WO 96/35796 and references cited therein, which are each hereby incorporated by reference in their entireties, particularly with respect cell medias and cell culture conditions). In some embodiments where an isoprene synthase, DXS, IDI, and/or MVA pathway nucleic acid is under the control of an inducible promoter, the inducing agent (e.g., a sugar, metal salt or antimicrobial), is desirably added to the medium at a concentration effective to induce expression of an isoprene synthase, DXS, IDI, and/or MVA pathway polypeptide. In some embodiments, cell medium has an antibiotic (such as kanamycin) that corresponds to the antibiotic resistance nucleic acid (such as a kanamycin resistance nucleic acid) on a vector that has one or more DXS, IDI, or MVA pathway nucleic acids.

Exemplary Cell Culture Conditions

Materials and methods suitable for the maintenance and growth of bacterial cultures are well known in the art. Exemplary techniques may be found in *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass., which are each hereby incorporated by reference in their entireties, particularly with respect to cell culture techniques. In some embodiments, the cells are cultured in a culture medium under conditions permitting the expression of one or more isoprene synthase, DXS, IDI, or MVA pathway polypeptides encoded by a nucleic acid inserted into the host cells.

Standard cell culture conditions can be used to culture the cells (see, for example, WO 2004/033646 and references cited therein, which are each hereby incorporated by reference in their entireties, particularly with respect to cell culture and fermentation conditions). Cells are grown and maintained at an appropriate temperature, gas mixture, and pH (such as at about 20 to about 37° C., at about 6% to about 84% $CO_2$, and at a pH between about 5 to about 9). In some embodiments, cells are grown at 35° C. in an appropriate cell medium. In some embodiments, e.g., cultures are cultured at approximately 28° C. in appropriate medium in shake cultures or fermentors until desired amount of isoprene production is achieved. In some embodiments, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells. Exemplary culture conditions for a given filamentous fungus are known in the art and may be found in the scientific literature and/or from the source of the fungi such as the American Type Culture Collection and Fungal Genetics Stock Center.

In various embodiments, the cells are grown using any known mode of fermentation, such as batch, fed-batch, or continuous processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., glucose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: *A Textbook of Industrial Microbiology*, Second Edition (1989) Sinauer Associates, Inc., which is hereby incorporated by reference in its entirety, particularly with respect to cell culture and fermentation conditions.

In some embodiments, cells are immobilized on a substrate as whole cell catalysts and subjected to fermentation conditions for isoprene production.

In some embodiments, bottles of liquid culture are placed in shakers in order to introduce oxygen to the liquid and maintain the uniformity of the culture. In some embodiments, an incubator is used to control the temperature, humidity, shake speed, and/or other conditions in which a culture is grown. The simplest incubators are insulated boxes with an adjustable heater, typically going up to ~65° C. More elaborate incubators can also include the ability to lower the temperature (via refrigeration), or the ability to control humidity or $CO_2$ levels. Most incubators include a timer; some can also be programmed to cycle through different temperatures, humidity levels, etc. Incubators can vary in size from tabletop to units the size of small rooms.

If desired, a portion or all of the cell medium can be changed to replenish nutrients and/or avoid the build up of potentially harmful metabolic byproducts and dead cells. In the case of suspension cultures, cells can be separated from the media by centrifuging or filtering the suspension culture and then resuspending the cells in fresh media. In the case of adherent cultures, the media can be removed directly by aspiration and replaced. In some embodiments, the cell medium allows at least a portion of the cells to divide for at least or about 5, 10, 20, 40, 50, 60, 65, or more cell divisions in a continuous culture (such as a continuous culture without dilution).

In some embodiments, a constitutive or leaky promoter (such as a Trc promoter) is used and a compound (such as IPTG) is not added to induce expression of the isoprene synthase, DXS, IDI, or MVA pathway nucleic acid(s) operably linked to the promoter. In some embodiments, a compound (such as IPTG) is added to induce expression of the isoprene synthase, DXS, IDI, or MVA pathway nucleic acid(s) operably linked to the promoter.

Exemplary Methods for Decoupling Isoprene Production from Cell Growth

Desirably, carbon from the feedstock is converted to isoprene rather than to the growth and maintenance of the cells. In some embodiments, the cells are grown to a low to medium $OD_{600}$, then production of isoprene is started or increased. This strategy permits a large portion of the carbon to be converted to isoprene.

In some embodiments, cells reach an optical density such that they no longer divide or divide extremely slowly, but continue to make isoprene for several hours (such as about 2, 4, 6, 8, 10, 15, 20, 25, 30, or more hours). For example, FIGS. 60A-67C illustrate that cells may continue to produce a substantial amount of mevalonic acid or isoprene after the cells reach an optical density such that they no longer divide or divide extremely slowly. In some cases, the optical density at 550 nm decreases over time (such as a decrease in the optical density after the cells are no longer in an exponential growth phase due to cell lysis), and the cells continue to produce a substantial amount of mevalonic acid or isoprene. In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr) during this time period. In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium) during this time period. In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some embodiments, the optical density at 550 nm of the cells increases by less than or about 50% (such as by less than or about 40, 30, 20, 10, 5, or 0%) over a certain time period (such as greater than or about 5, 10, 15, 20, 25, 30, 40, 50 or 60 hours), and the cells convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene during this time period. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

In some embodiments, isoprene is only produced in stationary phase. In some embodiments, isoprene is produced in both the growth phase and stationary phase. In various embodiments, the amount of isoprene produced (such as the total amount of isoprene produced or the amount of isoprene produced per liter of broth per hour per $OD_{600}$) during stationary phase is greater than or about 2, 3, 4, 5, 10, 20, 30, 40, 50, or more times the amount of isoprene produced during the growth phase for the same length of time. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells are in stationary phase. In various embodiments, greater than or about 5, 10, 20, 30, 40, 50, 60, 70, 80, 90, 95, 99% or more of the total amount of isoprene that is produced (such as the production of isoprene during a fermentation for a certain amount of time, such as 20 hours) is produced while the cells divide slowly or not at all such that the optical density at 550 nm of the cells increases by less than or about 50% (such as by less than or about 40, 30, 20, 10, 5, or 0%). In some embodiments, isoprene is only produced in the growth phase.

In some embodiments, one or more MVA pathway, IDI, DXP, or isoprene synthase nucleic acids are placed under the control of a promoter or factor that is more active in stationary phase than in the growth phase. For example, one or more MVA pathway, IDI, DXP, or isoprene synthase nucleic acids may be placed under control of a stationary phase sigma factor, such as RpoS. In some embodiments, one or more MVA pathway, IDI, DXP, or isoprene synthase nucleic acids are placed under control of a promoter inducible in stationary phase, such as a promoter inducible by a response regulator active in stationary phase.

Production of Isoprene within Safe Operating Ranges

The production of isoprene within safe operating levels according to its flammability characteristics simplifies the design and construction of commercial facilities, vastly improves the ability to operate safely, and limits the potential for fires to occur. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene).

Thus, computer modeling and experimental testing were used to determine the flammability limits of isoprene (such as isoprene in the presence of $O_2$, $N_2$, $CO_2$, or any combination of two or more of the foregoing gases) in order to ensure process safety. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment.

The following conditions were tested using computer simulation and mathematical analysis and experimental testing. If desired, other conditions (such as other temperature, pressure, and permanent gas compositions) may be tested using the methods described herein to determine the LFL, UFL, and LOC concentrations.

(1) Computer Simulation and Mathematical Analysis

Test Suite 1:
isoprene: 0 wt %-14 wt %
$O_2$: 6 wt %-21 wt %
$N_2$: 79 wt %-94 wt %

Test Suite 2:
isoprene: 0 wt %-14 wt %
$O_2$: 6 wt %-21 wt %
$N_2$: 79 wt %-94 wt %
Saturated with $H_2O$ Test Suite 3:
isoprene: 0 wt %-14 wt %
$O_2$: 6 wt %-21 wt %
$N_2$: 79 wt %-94 wt %
$CO_2$: 5 wt %-30 wt %

(2) Experimental Testing for Final Determination of Flammability Limits

Test Suite 1:
isoprene: 0 wt %-14 wt %
$O_2$: 6 wt %-21 wt %
$N_2$: 79 wt %-94 wt %

Test Suite 2:
isoprene: 0 wt %-14 wt %
$O_2$: 6 wt %-21 wt %
$N_2$: 79 wt %-94 wt %
Saturated with $H_2O$ Simulation software was used to give an estimate of the flammability characteristics of the system for several different testing conditions. $CO_2$ showed no significant affect on the system's flammability limits. Test suites 1 and 2 were confirmed by experimental testing. The modeling results were in-line with the experimental test results. Only slight variations were found with the addition of water.

The LOC was determined to be 9.5 vol % for an isoprene, $O_2$, $N_2$, and $CO_2$ mixture at 40° C. and 1 atmosphere. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems,* 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

Exemplary Production of Isoprene

In some embodiments, the cells are cultured in a culture medium under conditions permitting the production of isoprene by the cells. By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The specific productivity is determined by dividing the total productivity by the amount of cells, as determined by optical density at 600 nm (OD600). In some embodiments, the isoprene amount is measured at the peak specific productivity time point. In some embodiments, the peak specific productivity for the cells is about any of the isoprene amounts per cell disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

By "relative detector response" refers to the ratio between the detector response (such as the GC/MS area) for one compound (such as isoprene) to the detector response (such as the GC/MS area) of one or more compounds (such as all C5 hydrocarbons). The detector response may be measured as described herein, such as the GC/MS analysis performed with an Agilent 6890 GC/MS system fitted with an Agilent HP-5MS GC/MS column (30 m×250 μm; 0.25 μm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some embodiments, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 320 C with shaking at 200 rpm for approximately 3 hours) are analyzed for isoprene using a standard gas chromatography system, such as a system operated isothermally (850 C) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A: 2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some embodiments, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some embodiments, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h. The amount of isoprene in ng/$g_{wcm}$/h can be calculated by multiplying the value for isoprene production in the units of nmole/$g_{wcm}$/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some embodiments, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some embodiments, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace (as described, for example, in Example 10, part II). If the $OD_{600}$ value is not 1.0, then the measurement can be normalized to an $OD_{600}$ value of 1.0 by dividing by the $OD_{600}$ value. The value of mg isoprene/L headspace can be converted to mg/$L_{broth}$/hr/$OD_{600}$ of culture broth by multiplying by a factor of 38. The value in units of mg/$L_{broth}$/hr/$OD_{600}$ can be multiplied by the number of hours and the $OD_{600}$ value to obtain the cumulative titer in units of mg of isoprene/L of broth.

The instantaneous isoprene production rate in mg/$L_{broth}$/hr in a fermentor can be measured by taking a sample of the fermentor off-gas, analyzing it for the amount of isoprene (in units such as mg of isoprene per $L_{gas}$) as described, for example, in Example 10, part II and multiplying this value by the rate at which off-gas is passed though each liter of broth (e.g., at 1 vvm (volume of air/volume of broth/minute) this is 60 $L_{gas}$ per hour). Thus, an off-gas level of 1 mg/$L_{gas}$ corresponds to an instantaneous production rate of 60 mg/$L_{broth}$/hr at air flow of 1 vvm. If desired, the value in the units mg/$L_{broth}$/hr can be divided by the $OD_{600}$ value to obtain the specific rate in units of mg/$L_{broth}$/hr/OD. The average value of mg isoprene/$L_{gas}$ can be converted to the total product productivity (grams of isoprene per liter of fermentation broth, mg/$L_{broth}$) by multiplying this average off-gas isoprene concentration by the total amount of off-gas sparged per liter of fermentation broth during the fermentation. Thus, an average off-gas isoprene concentration of 0.5 mg/$L_{broth}$/hr over 10 hours at 1 vvm corresponds to a total product concentration of 300 mg isoprene/$L_{broth}$.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 5.0, 6.0, 7.0, or 8.0% of the carbon in the cell culture medium into isoprene. In some embodiments, the percent conversion of carbon into isoprene is between such as about 0.002 to about 4.0%, about 0.002 to about 3.0%, about 0.002 to about 2.0%, about 0.002 to about 1.6%, about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. In some embodiments, the percent conversion of carbon into isoprene is between about 0.002 to about 0.4%, 0.002 to about 0.16%, 0.04 to about 0.16%, about 0.005 to about 0.3%, about 0.01 to about 0.3%, or about 0.05 to about 0.3%.

The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100 Equation 1

For this calculation, yeast extract can be assumed to contain 50% w/w carbon. As an example, for the 500 liter described in Example 16, part VIII, the percent conversion of carbon into isoprene can be calculated as shown in Equation 2.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042% Equation 2

For the two 500 liter fermentations described herein (Example 16, parts VII and VIII), the percent conversion of carbon into isoprene was between 0.04-0.06%. A 0.11-0.16% carbon yield has been achieved using 14 liter systems as described herein. Example 19, part V describes the 1.53% conversion of carbon to isoprene using the methods described herein.

One skilled in the art can readily convert the rates of isoprene production or amount of isoprene produced into any other units. Exemplary equations are listed below for interconverting between units.

Units for Rate of Isoprene production (total and specific)

1 g isoprene/$L_{broth}$/hr=14.7 mmol isoprene/$L_{broth}$/hr (total volumetric rate) Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.) Equation 4

1 nmol isoprene/$g_{wcm}$/hr=68.1 ng isoprene/$g_{wcm}$/hr (given the molecular weight of isoprene) Equation 5

1 nmol isoprene/$L_{gas}$ $O_2$/hr=90 nmol isoprene/$L_{broth}$/hr (at an $O_2$ flow rate of 90 L/hr per L of culture broth) Equation 6

1 ug isoprene/$L_{gas}$ isoprene in off-gas=60 ug isoprene/$L_{broth}$/hr at a flow rate of 60 $L_{gas}$ per $L_{broth}$(1 vvm) Equation 7

Units for Titer (Total and Specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg) (specific productivity) Equation 8

1 g isoprene/$L_{broth}$=14.7 mmol isoprene/$L_{broth}$(total titer) Equation 9

If desired, Equation 10 can be used to convert any of the units that include the wet weight of the cells into the corresponding units that include the dry weight of the cells.

Dry weight of cells=(wet weight of cells)/3.3 Equation 10

If desired, Equation 11 can be used to convert between units of ppm and ug/L. In particular, "ppm" means parts per million defined in terms of ug/g (w/w). Concentrations of gases can also be expressed on a volumetric basis using "ppmv" (parts per million by volume), defined in terms of uL/L (vol/vol). Conversion of ug/L to ppm (e.g., ug of analyte per g of gas) can be performed by determining the mass per L of off-gas (i.e., the density of the gas). For example, a liter of air at standard temperature and pressure (STP; 101.3 kPa (1 bar) and 273.15K) has a density of approximately 1.29 g/L. Thus, a concentration of 1 ppm (ug/g) equals 1.29 ug/L at STP (equation 11). The conversion of ppm (ug/g) to ug/L is a function of both pressure, temperature, and overall composition of the off-gas.

1 ppm (ug/g) equals 0.83 ug/L at standard temperature and pressure (STP; 101.3 kPa (1 bar) and 273.15K) Equation 11

Conversion of ug/L to ppmv (e.g., uL of analyte per L of gas) can be performed using the Universal Gas Law (equation 12). For example, an off-gas concentration of 1000 ug/$L_{gas}$ corresponds to 14.7 umol/$L_{gas}$. The universal gas constant is 0.082057 L·atm $K^{-1}$ $mol^{-1}$, so using equation 12, the volume occupied by 14.7 umol of HG at STP is equal to 0.329 mL. Therefore, the concentration of 1000 ug/L HG is equal to 329 ppmv or 0.0329% (v/v) at STP.

PV=nRT, where "P" is pressure, "V" is volume, "n" is moles of gas, "R" is the Universal gas constant, and "T" is temperature in Kelvin Equation 12

The amount of impurities in isoprene compositions are typically measured herein on a weight per volume (w/v) basis in units such as ug/L. If desired, measurements in units of ug/L can be converted to units of mg/$m^3$ using equation 13.

1 ug/L=1 mg/$m^3$ Equation 13

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

In some embodiments, the isoprene composition comprises greater than or about 99.90, 99.92, 99.94, 99.96, 99.98, or 100% isoprene by weight compared to the total weight of all C5 hydrocarbons in the composition. In some embodiments, the composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the composition. In some embodiments, the isoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the composition.

In some embodiments, the isoprene composition comprises less than or about 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the composition. In some embodiments, the composition has a relative detector response of less than or about 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne compared to the detector response for all C5 hydrocarbons in the composition. In some embodiments, the isoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne) by weight compared to the total weight of all C5 hydrocarbons in the composition.

In some embodiments, the isoprene composition comprises less than or about 50, 40, 30, 20, 10, 5, 1, 0.5, 0.1, 0.05, 0.01, or 0.005 ug/L of a compound that inhibits the polymerization of isoprene for any compound in the composition that inhibits the polymerization of isoprene. In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a compound that inhibits the polymerization of isoprene for any compound in the composition that inhibits the polymerization of isoprene. In some embodiments, the isoprene composition comprises less than or about 50, 40, 30, 20, 10, 5, 1, 0.5, 0.1, 0.05, 0.01, or 0.005 ug/L of a hydrocarbon other than isoprene (such 1,3-cyclopentadiene, cis-1,3-pentadiene, trans-1,3-pentadiene, 1-pentyne, 2-pentyne, 1-pentene, 2-methyl-1-butene, 3-methyl-1-butyne, trans-piperylene, cis-piperylene, pent-4-ene-1-yne, trans-pent-3-ene-1-yne, or cis-pent-3-ene-1-yne). In some embodiments, the isoprene composition comprises between about 0.005 to about 50, such as about 0.01 to about 10, about 0.01 to about 5, about 0.01 to about 1, about 0.01 to about 0.5, or about 0.01 to about 0.005 ug/L of a hydrocarbon other than isoprene. In some embodiments, the isoprene composition comprises less than or about 50, 40, 30, 20, 10, 5, 1, 0.5, 0.1, 0.05, 0.01, or 0.005 ug/L of a protein or fatty acid (such as a protein or fatty acid that is naturally associated with natural rubber).

In some embodiments, the isoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the isoprene composition comprises less than or about 5, 1, 0.5, 0.1, 0.05, 0.01, or 0.005 ppm of sulfur or allenes. In some embodiments, the isoprene composition comprises less than or about 30, 20, 15, 10, 5, 1, 0.5, 0.1, 0.05, 0.01, or 0.005 ppm of all acetylenes (such as pentyne-1, butyne-2, 2MB1-3yne, and 1-pentyne-4-yne). In some embodiments, the isoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimmers (e.g., cyclic C10 compounds derived from the dimerization of two isoprene units).

In some embodiments, the composition comprises greater than about 2 mg of isoprene, such as greater than or about 5, 10, 20, 30, 40, 50, 60, 70, 80, 90, 100, 200, 300, 400, 500, 600, 700, 800, 900, or 1000 mg of isoprene. In some embodiments, the composition comprises greater than or about 2, 5, 10, 20, 30, 40, 50, 60, 70, 80, 90, 100 g of isoprene. In some embodiments, the amount of isoprene in the composition is between about 2 to about 5,000 mg, such as between about 2 to about 100 mg, about 100 to about 500 mg, about 500 to about 1,000 mg, about 1,000 to about 2,000 mg, or about 2,000 to about 5,000 mg. In some embodiments, the amount of isoprene in the composition is between about 20 to about 5,000 mg, about 100 to about 5,000 mg, about 200 to about 2,000 mg, about 200 to about 1,000 mg, about 300 to about 1,000 mg, or about 400 to about 1,000 mg. In some embodiments, greater than or about 20, 25, 30, 40, 50, 60, 70, 80, 90, or 95% by weight of the volatile organic fraction of the composition is isoprene.

In some embodiments, the composition includes ethanol. In some embodiments, the composition includes between about 75 to about 90% by weight of ethanol, such as between about 75 to about 80%, about 80 to about 85%, or about 85 to about 90% by weight of ethanol. In some embodiments in which the composition includes ethanol, the composition also includes between about 4 to about 15% by weight of isoprene, such as between about 4 to about 8%, about 8 to about 12%, or about 12 to about 15% by weight of isoprene.

Exemplary Isoprene Purification Methods

In some embodiments, any of the methods described herein further include recovering the isoprene. For example, the isoprene produced using the compositions and methods of the invention can be recovered using standard techniques. such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In particular, embodiments, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent.

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis.

In some embodiments, at least a portion of the gas phase remaining after one or more recovery steps for the removal of isoprene is recycled by introducing the gas phase into a cell culture system (such as a fermentor) for the production of isoprene.

In some embodiments, any of the methods described herein further include polymerizing the isoprene. For example, standard methods can be used to polymerize the purified isoprene to form cis-polyisoprene or other down stream products using standard methods. Accordingly, the invention also features a tire comprising polyisoprene, such as cis-1,4-polyisoprene and/or trans-1,4-polyisoprene made from any of the isoprene compositions disclosed herein.

The following Examples are provided to illustrate but not limit the invention.

EXAMPLES

The examples, which are intended to be purely exemplary of the invention and should therefore not be considered to limit the invention in any way, also describe and detail aspects and embodiments of the invention discussed above. Unless indicated otherwise, temperature is in degrees Centigrade and pressure is at or near atmospheric. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Example 1

Expression Constructs and Strains

I. Construction of Plasmids Encoding Mevalonate Kinase.

A construct encoding the *Methanosarcina mazei* lower MVA pathway (Accession numbers NC_003901.1, NC_003901.1, NC_003901.1, and NC_003901.1, which are each hereby incorporated by reference in their entireties) was synthesized with codon optimization for expression in *E. coli*. This construct is named *M. mazei* archaeal Lower Pathway operon (FIGS. 46A-46C) and encodes *M. mazei* MVK, a putative decarboxylase, IPK, and IDI enzymes. The gene encoding MVK (Accession number NC_003901.1) was PCR amplified using primers MCM165 and MCM177 (Table 4) using the Strategene Herculase II Fusion kit according to the manufacturer's protocol using 30 cycles with an annealing temperature of 55° C. and extension time of 60 seconds. This amplicon was purified using a Qiagen PCR column and then digested at 37° C. in a 10 uL reaction with PmeI (in the presence of NEB buffer 4 and BSA). After one hour, NsiI and Roche buffer H were added for an additional hour at 37° C. The digested DNA was purified over a Qiagen PCR column and ligated to a similarly digested and purified plasmid MCM29 in an 11 uL reaction 5 uL Roche Quick Ligase buffer 1, 1 uL buffer 2, 1 uL plasmid, 3 uL amplicon, and 1 uL ligase (1 hour at room temperature). MCM29 is pTrcKudzukan. The ligation reaction was introduced into Invitrogen TOP10 cells and transformants selected on LA/kan50 plates incubated at 37° C. overnight. The MVK insert in the resulting plasmid MCM382 was sequenced (FIGS. 47A-47C).

Using the method described above for plasmid MCM382, pTrcKudzu-MVK(mazei), additional plasmids were constructed with MVK genes from different source organisms (Table 5 and FIGS. 59A-59C).

TABLE 5

Plasmid encoding MVK from *Saccharomyces cerevisiae*.

| Source Organism | PCR Template | Forward Primer | Reverse Primer | Final Plasmid |
|---|---|---|---|---|
| *Saccharomyces cerevisiae* | pTrcKK (described herein) | MCM170 | MCM171 | MCM383 |

II. Creation of Strains Overexpressing Mevalonate Kinase and Isoprene Synthase.

Plasmid MCM382 was transformed into MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) that had been grown to midlog in LB medium and washed three times in iced, sterile water. 1 uL of DNA was added to 50 uL of cell suspension, and this mixture was electroporated in a 2 mm cuvette at 2.5 volts, 25 uFd followed immediately by recovery in 500 uL LB medium for one hour at 37° C. Transformant was selected on LA/kan50 and named MCM391. Plasmid MCM82 was introduced into this strain by the same electroporation protocol followed by selection on LA/kan50/spec50. The resulting strain MCM401 contains a cmp-marked chromosomal construct gi1.2KKDyI, kan-marked plasmid MCM382, and spec-marked plasmid MCM82 (which is pCL PtrcUpperPathway encoding *E. faecalis* mvaE and mvaS).

Production strains analogous to MCM401 were generated for each of the four plasmids detailed in Table 5 using the methods described above for MCM401. MCM331 was transformed with plasmid MCM379, 380, 381, or 383, and then selected on LA+kan50. The resulting strains were transformed with MCM82 and selected on LA+kan50+spec50.

TABLE 6

| Strains overexpressing mevalonate kinase and isoprene synthase | | | |
|---|---|---|---|
| MVK Source | Plasmid pTrcKudzu-MVK | Strain MCM331 transformed with pTrcKudzuMVK | Strain MCM331 transformed with pTrcKudzuMVK then transformed with MCM82 |
| *Methanosarcina mazei* | MCM382 | MCM391 | MCM401 |
| *Saccharomyces cerevisiae* | MCM383 | MCM392 | MCM402 |
| MVK Source | Plasmid pTrcKudzu-MVK | Strain MCM333 transformed with pTrcKudzuMVK | Strain MCM333 transformed with pTrcKudzuMVK then transformed with MCM82 |
| *Methanosarcina mazei* | MCM382 | MCM396 | MCM406 |
| *Saccharomyces cerevisiae* | MCM383 | MCM397 | MCM407 |

Additional strain information is provided below.

MCM382: *E. coli* BL21 (lambdaDE3) pTrcKudzuMVK(*M. mazei*)GI1.2KKDyI

MCM391: MCM331 pTrcKudzuMVK(*M. mazei*)

MCM401: MCM331pTrcKudzuMVK(*M. mazei*)pCLPtrcUpperpathway

MCM396: MCM333pTrcKudzuMVK(*M. mazei*)

MCM406: MCM333pTrcKudzuMVK(*M. mazei*)pCLPtrcUpperpathway

III. Construction of Plasmid MCM376-MVK from *M. mazei* Archaeal Lower in pET200D.

The MVK ORF from the *M. mazei* archaeal Lower Pathway operon (FIGS. 46A-46C) was PCR amplified using primers MCM161 and MCM162 (Table 4) using the Invitrogen Platinum HiFi PCR mix. 45 uL of PCR mix was combined with 1 uL template, 1 uL of each primer at 10 uM, and 2 uL water. The reaction was cycled as follows: 94° C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 uL of this PCR reaction was ligated to Invitrogen pET200D plasmid according to the manufacturer's protocol. 3 uL of this ligation was introduced into Invitrogen TOP10 cells, and transformants were selected on LA/kan50. A plasmid from a transformant was isolated and the insert sequenced, resulting in MCM376 (FIGS. 57A-57C).

VI. Construction of pDu5 Expressing *S. cerevisiae* MVK

The *S. cerevisiae* MVK was cloned into pET16b from Invitrogen as follows (Table 7). The MVK enzyme from *S. cerevisiae* was PCR amplified with Hg-MVK-F2-NdeI and Hg-MVK-R2-NdeI primers using Stratagene Pfu UltraII Fusion DNA Polymerase Kit according to manufacturer's protocol, and pMVK1 (described herein) as the template DNA. The following cycle parameter was used for the reaction (95° C. for 2 minutes, 29 cycles (95° C. for 20 seconds, 55° C. for 20 seconds, 72° C. for 21 seconds), 72° C. for 3 minutes, and 4° C. until cool) using an Eppendorf Mastercycler Gradient Machine).

As a result, a 1.352 kb MVK PCR fragment was obtained and was gel purified using Qiagen's gel purification kit. The purified PCR product was digested with NdeI restriction enzyme. The digested DNA was purified over Qiagen PCR column. 5 uL of purified PCR product was ligated to 1 uL of pET-16b vector that was previously digested with NdeI and then treated with SAP (Shrimp Alkaline Phosphatase). A New England BioLab (NEB) T4 ligase kit was used for ligation at approximately 16° C. overnight according to manufacturer's protocol.

5 uL of overnight ligation mixture was transformed into Invitrogen TOP10 cells. The transformation was carried on ice for a 30 minute incubation followed by a 30 second heat shock at approximately 42° C. and a 1 hour recovery in 1 ml LB at approximately 37° C. The transformation was selected on LA/Carb50 incubated at approximately 37° C. overnight. Plasmids from transformants were isolated and the insert sequenced with T7 promoter and T7 terminator using Quintara Bio Sequencing Service. The resulting plasmid for *S. cerevisiae* MVK in pET-16b vector is called pDu5 (FIGS. 126A and 126B).

Once the sequence is verified, 1 ul of plasmid (pDu5) is then transformed into BL21 pLysS host strain. Transformants are selected on LA/Carb50 plates and incubated at approximately 37° C. The resulting expression strain is called MD08-MVK.

TABLE 7

| Plasmid and Strain overexpressing mevalonate kinase | | | | | |
|---|---|---|---|---|---|
| | Template | For. Primer | Rev. Primer | Plasmid | Expression Strain |
| *S. cerevisiae* | pMVK1 | Hg-MVK-F2-NdeI | Hg-MVK-R2-NdeI | pDu5 | MD08-MVK |

V. Creation of Expression Strain MCM378.

Plasmid MCM376 was transformed into Invitrogen OneShot BL21 Star (DE3) cells according to the manufacturer's protocol. Transformant MCM378 was selected on LA/kan50. Additional strains were created using the same protocol and are listed in the Table 7. Invitrogen OneShot BL21(DE3) pLysS transformed with the indicated plasmid and selected on LA and carb50 cmp35 for MD08-MVK were used.

VI. Construction of Plasmid pCLPtrcUpperPathwayHGS2

The gene encoding isoprene synthase from *Pueraria lobata* was PCR-amplified using primers NsiI-RBS-HGS F (cttgATGCATCCTGCATTCGCCCTTAGGAGG, SEQ ID NO:113) and pTrcR (CCAGGCAAATTCTGTTTTATCAG, SEQ ID NO:114), and pTrcKKDyIkIS (MCM118) as a template. The resulting PCR product was restriction-digested with NsiI and PstI and gel-purified using the Qiagen QIAquick Gel Extraction kit using standard methods. MCM82 (pCL PtrcUpperPathway) was restriction-digested with PstI and dephosphorylated using rAPid alkaline phosphatase (Roche). These DNA pieces were ligated together using T4 ligase and the ligation reaction was transformed in

*E. coli* Top10 electrocompetent cells (Invitrogen). Plasmid was prepared from six clones using the Qiagen QiaPrep Spin MiniPrep kit. The plasmids were digested with restriction enzymes EcoRV and MluI, and a clone in which the insert had the right orientation (i.e., gene oriented in the same way as the pTrc promoter) was identified. The resulting plasmid pCLPtrcUpperPathwayHGS2 (FIGS. 112A-112D) was found to produce isoprene in *E. coli* Top10, using a headspace assay described herein, thus validating the functionality of the expression construct.

TABLE 4

| Oligonucleotides | |
|---|---|
| Hg-MVK-F2-NdeI | cagcagcagCATATGtcattaccgttcttaacttc (SEQ ID NO: 115) |
| Hg-MVK-R2-NdeI | cagcagcagCATATGgcctatcgcaaattagcttatg (SEQ ID NO: 116) |
| MCM161 *M. mazei* MVK for | CACCATGGTATCCTGTTCTGCG (SEQ ID NO: 117) |
| MCM162 *M. mazei* MVK rev | TTAATCTACTTTCAGACCTTGC (SEQ ID NO: 118) |
| MCM165 *M. mazei* MVK for w/RBS | gcgaacgATGCATaaaggaggtaaaaaaacATGGTATCCTGTTCTGCGCCGGGTA AGATTTACCTG (SEQ ID NO: 119) |
| MCM170 *S. cerevisiae* MVK for w/RBS | gcgaacgATGCATaaaggaggtaaaaaaacATGTCATTACCGTTCTTAACTTCTGCA (SEQ ID NO: 120) |
| MCM171 *S. cerevisiae* MVK rev | gggcccgtttaaactttaactagactCTGCAGTTATGAAGTCCATGGTAAATTCGTGT (SEQ ID NO: 121) |
| MCM177 *M. mazei* MVK rev Pst | gggcccgtttaaactttaactagactTTAATCTACTTTCAGACCTTGC (SEQ ID NO: 122) |

Example 2

Production of Isoprene by *E. Coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 20 mL Batch Scale Medium Recipe (Per Liter Fermentation Medium):

Each liter of fermentation medium contained $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, and 1000× Trace Metal Solution 1 ml. All of the components were added together and dissolved in $diH_2O$. The pH was adjusted to 6.8 with ammonium hydroxide (30%) and brought to volume. Media was filter sterilized with a 0.22 micron filter. Glucose 2.5 g and antibiotics were added after sterilization and pH adjustment.

1000× Trace Metal Solution:

1000× Trace Metal Solution contained citric Acids$*H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then brought to volume and filter sterilized with a 0.22 micron filter.

Strains:

MCM343 cells are BL21 (DE3) *E. coli* cells containing the upper mevalonic acid (MVA) pathway (pCL Upper), the integrated lower MVA pathway (gi1.2KKDyI), and isoprene synthase from Kudzu (pTrcKudzu). The *S. cerevisiae* MVK gene is present only as one copy on the chromosome of the MCM343 cells and is controlled by a weak promoter. The expression level of isoprene synthase may not be limiting in the MCM343 cells. The isoprene synthase gene has the same plasmid backbone and promoter as in the MCM401 cells.

MCM401 cells are BL21 (DE3) *E. coli* cells containing the upper mevalonic acid (MVA) pathway (pCL Upper), the integrated lower MVA pathway (gi1.2KKDyI), and high expression of mevalonate kinase from *M. mazei* and isoprene synthase from Kudzu (pTrcKudzuMVK(*M. mazei*)). The *M. mazei* MVK gene is present in multiple copies on a plasmid in the MCM401 cells (~30-50 copies/cell) and is under a stronger promoter than the *S. cerevisiae* MVK gene. Based on this information, the MVK protein level in the MCM401 cells is expected to be at least about 30 to 50 fold higher than the level in the MCM343 cells. The expression level of isoprene synthase may not be limiting in the MCM401 cells. The isoprene synthase gene shares the same plasmid backbone and promoter as the MCM343 cells. In addition, the amount of isoprene synthase made is higher in the MCM401 cells, and the protein level of the isoprene synthase was not dependent upon the inhibition of MVK.

Isoprene production was analyzed by growing the strains in 100 mL bioreactors with a 20 mL working volume at a temperature of 30° C. An inoculum of *E. coli* strain taken from a frozen vial was streaked onto an LB broth agar plate (with antibiotics) and incubated at 30° C. A single colony was inoculated into media and grown overnight. The bacteria were diluted into 20 mL of media to reach an optical density of 0.05 measured at 550 nm. The 100 mL bioreactors were sealed, and air was pumped through at a rate of 8 mL/min. Adequate agitation of the media was obtained by stirring at 600 rpm using magnetic stir bars. The off-gas from the bioreactors was analyzed using an on-line Hiden HPR-20 mass spectrometer. Masses corresponding to isoprene, $CO_2$, and other gasses naturally occurring in air were monitored. Accumulated isoprene and $CO_2$ production were calculated by summing the concentration (in percent) of the respective gasses over time. Atmospheric $CO_2$ was subtracted from the total in order to estimate the $CO_2$ released due to metabolic activity.

Isoprene production from a strain expressing the full mevalonic acid pathway and Kudzu isoprene synthase (MCM343) was compared to a strain that in addition over-expressed MVK from *M. mazei* and Kudzu isoprene synthase (MCM401) in 100 mL bioreactors. The bacteria were grown under identical conditions in defined media with glucose as carbon source. Induction of isoprene production was achieved by adding isopropyl-beta-D-1-thiogalactopyranoside (IPTG) to a final concentration of either 100 uM or 200 uM. Off-gas measurements revealed that the strain over-expressing both MVK and isoprene synthase (MCM401) produced significantly more isoprene compared to the strain expressing only the mevalonic acid pathway and Kudzu isoprene synthase (MCM343) as shown in FIGS. 113A-113D. At 100 uM induction, the MCM401 strain produced 2-fold more isoprene compared to the MCM343 strain. At 200 uM IPTG induction, the MCM401 strain produced 3.4-fold more isoprene when compared to the MCM343 strain. Analysis of $CO_2$ in the off-gas from the bioreactors, which is a measure of metabolic activity, indicates that metabolic activity was independent from IPTG induction and isoprene production.

Example 3

Production of Isoprene by *E. Coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to innoculate 5-L of cell medium in the 15-L bioreactor. In particular, the 15-L bioreactor had an initial working volume of 5 L. The liquid volume increases throughout the fermentation (such as to approximately 10 liters).

Glucose was fed at an exponential rate until cells reached the stationary phase. After this time, the glucose feed was decreased to meet metabolic demands. The total amount of glucose delivered to the bioreactor during the 68 hour fermentation was 3.8 kg. Induction was achieved by adding isopropyl-beta-D-1-thiogalactopyranoside (IPTG). The IPTG concentration was brought to 51 uM when the optical density at 550 nm ($OD_{550}$) reached a value of 9. The IPTG concentration was raised to 88 uM when $OD_{550}$ reached 149. Additional IPTG additions raised the concentration to 119 uM at $OD_{550}$=195 and 152 uM at $OD_{550}$=210. The $OD_{550}$ profile within the bioreactor over time is shown in FIG. 114. The isoprene level in the off gas from the bioreactor was determined using a Hiden mass spectrometer. The isoprene titer increased over the course of the fermentation to a final value of 23.8 g/L (FIG. 115). The total amount of isoprene produced during the 68 hour fermentation was 227.2 g and the time course of production is shown in FIG. 116. The molar yield of utilized carbon that went into producing isoprene during fermentation was 13.0%. The weight percent yield of isoprene from glucose was 6.3%.

Example 4

Production of Isoprene by *E. Coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to innoculate 5-L of cell medium in the 15-L bioreactor. The liquid volume increases throughout the fermentation (such as to approximately 10 liters).

Glucose was fed at an exponential rate until cells reached the stationary phase. After this time the glucose feed was decreased to meet metabolic demands. The total amount of glucose delivered to the bioreactor during the 55 hour fermentation was 1.9 kg. Induction was achieved by adding IPTG. The IPTG concentration was brought to 111 uM when the optical density at 550 nm ($OD_{550}$) reached a value of 9. The IPTG concentration was raised to 193 uM when $OD_{550}$ reached 155. The $OD_{550}$ profile within the bioreactor over time is shown in FIG. 130. The isoprene level in the off gas from the bioreactor was determined using a Hiden mass spectrometer. The isoprene titer increased over the course of the fermentation to a final value of 19.5 g/L (FIG. 131). The total amount of isoprene produced during the 55 hour fermentation was 133.8 g, and the time course of production is shown in FIG. 132. Instantaneous volumetric productivity levels reached values as high as 1.5 g isoprene/L broth/hr (FIG. 133). Instantaneous yield levels reached as high as 17.7% w/w (FIG. 134). The molar yield of utilized carbon that went into producing isoprene during fermentation was 15.8%. The weight percent yield of isoprene from glucose over the entire fermentation was 7.4%.

Example 5

Production of Isoprene by *E. Coli* Expressing the Upper Mevalonic Acid (MVA) Pathway, the Integrated Lower MVA Pathway (gi1.2KKDyI), Mevalonate Kinase from *M. mazei*, and Isoprene Synthase from Kudzu and Grown in Fed-Batch Culture at the 15-L Scale Medium Recipe (Per Liter Fermentation Medium):

Each liter of fermentation medium contained $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from *M. mazei* and isoprene synthase from Kudzu (pTrcKudzuMVK(*M. mazei*)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to innoculate 5-L of cell medium in the 15-L bioreactor. The liquid volume increases throughout the fermentation (such as to approximately 10 liters).

Glucose was fed at an exponential rate until cells reached the stationary phase. After this time the glucose feed was decreased to meet metabolic demands. The total amount of glucose delivered to the bioreactor during the 55 hour fermentation was 2.2 kg. Induction was achieved by adding IPTG. The IPTG concentration was brought to 51 uM when the optical density at 550 nm ($OD_{550}$) reached a value of 10. In addition to the IPTG spike, at $OD_{550}$=10 a constant feed began and delivered 164 mg of IPTG over 18 hours. The $OD_{550}$ profile within the bioreactor over time is shown in FIG. 135. The isoprene level in the off gas from the bioreactor was determined using a Hiden mass spectrometer. The isoprene titer increased over the course of the fermentation to a final value of 22.0 g/L (FIG. 117). The total amount of isoprene produced during the 55 hour fermentation was 170.5 g and the time course of production is shown in FIG. 118. The molar yield of utilized carbon that went into producing isoprene during fermentation was 16.6%. The weight percent yield of isoprene from glucose over the entire fermentation was 7.7%.

Example 6

Over-Expression of Mevalonate Kinase and Isoprene Synthase in *E. Coli* Harboring the MVA Pathway Over-expression of both mevalonate kinase and isoprene synthase results in high specific productivity of isoprene production by *E. coli* harboring the MVA pathway.

I. Construction of Plasmid MCM94

Plasmid pTrcHis2B (Invitrogen) was digested for 2 hours at 30° C. in 10 uL containing ApaI (Roche) and Roche BufferA. The reaction was brought to a total of 30 uL containing 1× Roche Buffer H and 2 uL PstI (Roche) and incubated for 1 hour at 37° C. The 996 bp fragment containing the pTrc promoter region was gel purified from an Invitrogen E-gel (1.2%) using a Qiagen Gel Purification spin column according to the manufacturer's protocol.

Plasmid MCM29 was digested as described above, and the 3338 bp fragment containing the origin and kanR genes was gel purified as described above. The two fragments (3 uL pTrcHis2B fragment, 1 uL MCM29 fragment) were ligated for 1 hour at room temperature in a 20 uL reaction following the Roche Rapid DNA Ligation kit protocol. 5 uL of this ligation reaction was used to transform Invitrogen TOP10 chemically competent cells according to the manufacturer's protocol. Transformants were selected on LA and kanamycin50 ppm. Plasmids were isolated by Qiagen Spin Miniprep from several colonies which had been grown overnight in 5 mL LB and kan50. A clone with the pTrc promoter but no kudzu isoprene synthase gene was frozen as MCM94 (FIGS. 119A-119C).

II. Construction of Strains MCM433, 437, and 438

Plasmid pCL PtrcUpperHGS2 (Construction of this plasmid is described in Example 1 part VI) was transformed into MCM331 by electroporation as described herein for expression strain MCM401. Transformant MCM433 was selected on LA and spectinomycin 50 ppm. Strain MCM433 was subsequently transformed with either plasmid MCM94 (described above) or MCM376 and selected on LA, spectinomycin 50 ppm, and kanamycin 50 ppm.

TABLE 8

| Strains MCM433, 437, and 438 | | | | | |
|---|---|---|---|---|---|
| Strain | Parent | Host Origin | Integrated | Plasmid(s) | Markers |
| MCM433 | MCM331 | BL21(DE3) | gi1.2KKDyI | pCLUpperHGS2 | cmp5, spec50 |
| MCM437 | MCM433 | BL21(DE3) | gi1.2KKDyI | pCLUpperHGS2 pTrcHis2B kan (MCM94) | cmp5, spec50. kan50 |
| MCM438 | MCM433 | BL21(DE3) | gi1.2KKDyI | pCLUpperHGS2 pTrcKudzuMVK(mazei) MCM376 | cmp5, spec50. kan50 |

III. Cell Fermentation

Medium Recipe (Per Liter Fermentation Medium):

Each liter of fermentation medium contained $K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 1 g, and 1000× Trace Metal Solution 1 ml. All of the components were added together and dissolved in $diH_2O$. The pH was adjusted to 6.8 with ammonium hydroxide (30%) and brought to volume. Media was filter sterilized with a 0.22 micron filter. Glucose 5.0 g and antibiotics were added after sterilization and pH adjustment.

1000× Trace Metal Solution (Per Liter Fermentation Media):

1000× Trace Metal Solution contained citric Acids$*H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in DI $H_2O$, pH to 3.0 with HCl/NaOH, then brought to volume and filter sterilized with a 0.22 micron filter.

Strains:

The MCM343 strain is BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and isoprene synthase from Kudzu (pTrcKudzu). This strain has low MVK polypeptide activity and high isoprene synthase polypeptide activity.

The MCM401 strain is BL21 (DE3) *E. coli* cells containing the upper MVA pathway (pCL PtrcUpperPathway), the integrated lower MVA pathway (gi1.2KKDyI), and high expression of MVK from *M. mazei* and IS from Kudzu (pTrcKudzuMVK(*M. mazei*). This strain has high MVK polypeptide activity and high isoprene synthase polypeptide activity.

The MCM437 strain is BL21 (DE3) *E. coli* cells containing the upper MVA pathway and low expression of IS from Kudzu (pCLPtrcUpperPathwayHGS2), the integrated lower MVA pathway (gi1.2KKDyI), and a control plasmid conferring kanamycin resistance (so that the growth media was identical in all cases). This strain has low MVK polypeptide activity and low isoprene synthase.

The MCM438 strain is BL21 (DE3) *E. coli* cells containing the upper MVA pathway and low expression of IS from Kudzu (pCLPtrcUpperPathwayHGS2), the integrated lower MVA pathway (gi1.2KKDyI), and strong expression of *M. mazei* MVK (*M. mazei* MVK in pET200). This strain has high MVK polypeptide activity and low isoprene synthase polypeptide activity.

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of *E. coli* strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 μL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (μg/L) by the OD reading. Samples were taken at three time points for each of the 24-wells over the course of the mini-fermentations. There were six replicates for each strain (4 strains×6 wells/strain).

Specific productivity of isoprene from a strain expressing the full mevalonic acid pathway and Kudzu isoprene synthase at low levels (MCM437) was compared to a strain that in addition over-expressed MVK from *M. mazei* and Kudzu isoprene synthase (MCM401), as well as strains that either over-expressed just MVK (MCM438), or just Kudzu isoprene synthase (MCM343). The bacteria were grown under identical conditions in defined media with glucose as a carbon source in mini-fermentations. Induction of isoprene production was achieved by adding IPTG to a final concentration of 200 μM at the start of the run. Headspace measurements over time (FIG. 120) revealed that the strain over-expressing both MVK and isoprene synthase (MCM401) had higher specific productivity of isoprene compared to the strain over-expressing just MVK (MCM438) or just Kudzu isoprene synthase (MCM343). The strain with low activities of both MVK and Kudzu isoprene synthase (MCM437) had the lowest specific productivity of isoprene overall.

IV. Determination of Isoprene Synthase Polypeptide Activity and Volumetric Productivity in Fermentation Runs.

Strain MCM401 that overexpresses both *M. mazei* MVK and isoprene synthase had a greater maximum volumetric productivity for isoprene than either strain MC343 or strain MCM127 that do not express *M. mazei* MVK.

(i). Isoprene Synthase DMAPP Activity from Lysate Protocol

For this assay, the following reagents were used: 50% glycerol in PEB containing 1 mg/mL lysozyme (Sigma) and 0.1 mg/mL DNAaseI (Sigma). 1 mL of fermentation broth was mixed with 1 mL of 50% glycerol in PEB containing 1 mg lysozyme and 0.1 mg DNAaseI. The mixture is passed through the french press one time. 25 μL of the mixture is then used for the DMAPP assay. The DMAPP assay contained the following components:

| DMAPP Assay | | |
|---|---|---|
| | 25 μL | lysate mixture |
| | 5 μL | $MgCl_2$ (1M) |
| | 5 μL | DMAPP (100 mM) |
| | 65 μL | 50 mM Tris pH 8 |
| Total volume: | 100 μL | |

The reaction is performed at 30° C. for 15 minutes in a gas tight 1.8 mL GC tube. Reactions are terminated by the addition of 100 μL 250 mM EDTA (pH 8).

The active protein concentration was measured using Equation 14.

mg/mL active isoprene synthase=(Dilution factor)*$X$ ug/L (DMAPP Assay reading)*0.0705/294(specific activity from 14-L) or 0.0002397*$X$ ug/L    Equation 14

The volumetric productivity was measured using Equation 15.

mg/L/h isoprene=(dilution factor)*0.288*$X$ ug/L (DMAPP Assay reading)    Equation 15

The maximum in vitro isoprene synthase polypeptide activity was compared with the maximum volumetric productivity for strains MCM401, MC343, and MCM127 (FIG. 136).

Example 7

Exemplary Methods for Producing Isoprene: Isoprene Fermentation from *E. Coli* Expressing Genes from the Mevalonic Acid Pathway and Grown in Fed-Batch Culture at the 15-L Scale Medium Recipe (Per Liter Fermentation Medium):

Each liter of fermentation medium contained $K_2HPO_4$ 7.5 g, $MgSO_4$*$7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in diH2O. This solution was autoclaved. The pH was adjusted to 7.0 with ammonium hydroxide (30%) and brought to volume. Glucose 10 g, thiamine*HCl 0.1 g, and antibiotics were added after sterilization and pH adjustment.

1000× Modified Trace Metal Solution:

1000× Trace Metal Solution contained citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, ZnSO*$7H_2O$ 1 g, CuSO4*$5H_2O$ 100 mg, $H_3BO_3$ 100 mg, $NaMoO_4$*$2H_2O$ 100 mg. Each component was dissolved one at a time in Di H2O, pH to 3.0 with HCl/NaOH, then brought to volume and filter sterilized with 0.22 micron filter.

I. MCM343 High Titer: Isoprene Fermentation from *E. coli* Expressing Genes from the Mevalonic Acid Pathway and Grown in Fed-Batch Culture at the 15-L Scale Fermentation was performed in a 15-L bioreactor with BL21 (DE3) *E. coli* cells containing the gi1.2 integrated lower MVA pathway and the pCL PtrcUpperMVA and pTrcKudzu plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time the glucose feed was decreased to meet metabolic demands. The total amount of glucose delivered to the bioreactor during the 58 hour fermentation was 4.5 kg. Induction was achieved by adding isopropyl-beta-D-1-thiogalactopyranoside (IPTG). The IPTG concentration was brought to 98 uM when the carbon dioxide evolution rate reached 25 mmol/L/hr ($OD_{550}$=9). The $OD_{550}$ profile within the bioreactor over time is shown in FIG. 112C. The isoprene level in the off gas from the bioreactor was determined using a Hiden mass spectrometer. The isoprene titer increased over the course of the fermentation to a final value of 1.6 g/L (FIG. 112D). The total amount of isoprene produced during the 58 hour fermentation was 17.9 g and the time course of production is shown in FIG. 112E. The molar yield of utilized carbon that went into producing isoprene during fermentation was 0.8%. The weight percent yield of isoprene from glucose was 0.4%.

II. MCM 127: Isoprene Fermentation from *E. coli* Expressing Genes from the Mevalonic Acid Pathway and Grown in Fed-Batch Culture at the 15-L Scale Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 5-L bioreactor.

Glucose was fed at an exponential rate until cells reached the stationary phase. After this time, the glucose feed was decreased to meet metabolic demands. The total amount of glucose delivered to the bioreactor during the 43 hour fermentation was 1.4 kg. Induction was achieved by adding isopropyl-beta-D-1-thiogalactopyranoside (IPTG). The IPTG concentration was brought to 23 uM when the carbon dioxide evolution rate reached 25 mmol/L/hr ($OD_{550}$=129). The $OD_{550}$ profile within the bioreactor over time is shown in FIG. 112F. The isoprene level in the off gas from the bioreactor was determined as previously described by measuring isoprene concentrations in the offgas by GC. The isoprene titer increased over the course of the fermentation to a final value of 0.4 g/L (FIG. 112G). The total amount of isoprene produced during the 43 hour fermentation was 3.0 g and the time course of production is shown in FIG. 112H. The molar yield of utilized carbon that went into producing isoprene during fermentation was 0.5%. The weight percent yield of isoprene from glucose was 0.3%.

III. dxr Knock-Out Strain: Isoprene Fermentation from *E. coli* Expressing Genes from the Mevalonic Acid Pathway and Grown in Fed-Batch Culture at the 15-L Scale.

Fermentation was performed in a 15-L bioreactor with BL21 (DE3) *E. coli* cells (Δdxr) containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial volume of 5-L.

Glucose was fed at an exponential rate until cells reached the stationary phase. After this time, the glucose feed was decreased to meet metabolic demands. The total amount of glucose delivered to the bioreactor during the 43 hour fermentation was 1.7 kg. Induction was achieved by adding isopropyl-beta-D-1-thiogalactopyranoside (IPTG). The IPTG concentration was brought to 25 uM when the optical density at 550 nm ($OD_{550}$) reached a value of 8. The IPTG concentration was raised to 40 uM when $OD_{550}$ reached 140. The $OD_{550}$ profile within the bioreactor over time is shown in FIG. 112I. The isoprene level in the off gas from the bioreactor was determined as previously described (GC of offgas samples). The isoprene titer increased over the course of the fermentation to a final value of 0.9 g/L (FIG. 112J). The total amount of isoprene produced during the 43 hour fermentation was 6.0 g and the time course of production is shown in FIG. 112K. The molar yield of utilized carbon that went into producing isoprene during fermentation was 0.8%. The weight percent yield of isoprene from glucose was 0.4%.

(i) Construction of the dxr Mutant in *E. coli*

To generate a deletion of dxr (1-deoxy-D-xylulose 5-phosphate reductoisomerase), the enzyme that encodes the first committed step in the deoxy-xylulose-phosphate (DXP) pathway in *Escherichia coli*, the GeneBridges Quick & Easy *E. coli* Gene Deletion Kit (GB) was used according to the manufacturer's recommended protocol. Briefly, GB insertion cassettes encoding either kanamycin (FRT-PGK-gb2-neo-FRT) or chloramphenicol (FRT-cm-FRT) resistance were PCR amplified using primers GBdxr1 and GBdxr2 (see below for primer sequences and cycling parameters). PCR products of the correct size (for the respective GB insertion cassette) were pooled, purified (Qiagen) and diluted to a concentration of approximately 300 ng/μl. The deletion of dxr was then carried out according to the protocol described in the GB manual. All replicating plasmids were introduced into *E. coli* strains via electroporation using standard molecular biology techniques (see Table 16 below for a complete strain list). LB medium containing ampicillin (50 μg/ml) and spectinomycin (50 μg/ml) was inoculated with *E. coli* strains (DW13 or DW38) harboring the pRed/ET plasmid (encoding ampicillin/carbenicillin resistance) and pCL Ptrc(minus lacO) KKDyI (from Edwin Lee, encoding spectinomycin resistance). These strains carried pCL Ptrc(minus lacO) KKDyI (see (iv) below) so that *E. coli*, in the absence of a functional DXP pathway, could convert mevalonic acid (MVA) through the MVA lower pathway to IPP/DMAPP as a source for all lower isoprenoid molecules. Cultures were grown overnight at 30° C. and diluted to an $OD_{600}$ of approximately 0.2 in 5 ml total volume with antibiotics the next morning. After several hours of growth at 30° C., strains were shifted to 37° C. and L-arabinose was added at a concentration of 0.4%. After 1 hour of induction, cells were washed multiple times in ice cold $H_2O$, and approximately 700 ng of the purified PCR product (described above) for each GB insertion template was introduced via electroporation (using standard techniques). Cells were recovered for 3 hours at 37° C. in LB with 1 mM MVA with no antibiotics, and then plated onto selective LB medium (MVA 1 mM and spectinomycin 50 μg/ml, with either kanamycin 15 μg/ml or chloramphenicol 25 μg/ml). The next day, positive colonies were tested by PCR, using the dxrTest1 and dxrTest2 primers, with either GBprimer2 or GBprimerDW (i.e. GB3, see FIG. 112M), respectively (see Table 16). Colonies that tested positive with these primer combinations were then tested for sensitivity to MVA at varying concentrations. FIG. 112J shows that in the absence of MVA, dxr deletion strains are unable to grow, whereas in the presence of 1 mM MVA, growth is robust. FIG. 112N also shows that at a concentration of 10 mM MVA, growth of dxr deletion strains appears to be inhibited, most likely because of the accumulation of isoprenoid molecules. To generate strain DW48, strain DW43 was electroporated with plasmids MCM82 (Sp) and MCM118 (Kan), which harbor the entire MVA pathway and HGS. Since MVA was omitted from recovery and on the selective plate (LB with Sp μg/ml and Kan μg/ml), strain DW48 was forced to lose plasmid pCL Ptrc(minus lacO) KKDyI and gain MCM82, which contains the MVA upper pathway. Thus, only cells harboring the entire MVA pathway to convert acetyl-CoA to IPP/DMAPP and lower isoprenoids were able to grow without exogenous MVA.

(ii) PCR Cycling Parameters

The Herculase II (Stratagene) DNA polymerase enzyme was used for amplification of all GB templates with oligonucleotide primer pairs at a concentration of 0.4 μM each in 50 μl total volume/reaction according to the manufacturer's protocol. All PCR products for generating dxr deletion strains via GB were of the expected size: approximately 1.6 kb (kanamycin), and 1.5 kb (chloramphenicol).

To test GB insertions at the dxr locus, illustra PuReTaq Ready-To-Go™ PCR Beads (GE Healthcare) were used with oligonucleotide primer pairs at a concentration of 0.4 μM each in 25 μl total volume/reaction.

1) 95° C. —4 min
2) 95° C. —20 sec
3) 55° C. —20 sec (52° C. for Beads)
4) 72° C. —2 min (30 sec for Beads)
5 cycles of steps 2 through 4
5) 95° C. —20 sec
6) 58° C. —20 sec (55° C. for Beads)
7) 72° C. —2 min (30 sec for Beads)
25 cycles of steps 5 through 7
72° C. —10 min
4° C.—end

TABLE 16

PCR primers, plasmids, and Strains

| Primer Name | Sequence (5' to 3') | Purpose |
|---|---|---|
| GBdxr1 | GGCTGGCGGCGTTTTGCTTTTTATT CTGTCTCAACTCTGGATGTTTCATG AATTAACCCTCACTAAAGGGCG (SEQ ID NO: 130) | dxr knock out GB - Forward primer for all templates |
| GBdxr2 | AAGCCCTACGCTAACAAATAGCGC GACTCTCTGTAGCCGGATTATCCTC ATAATACGACTCACTATAGGGCTC (SEQ ID NO: 131) | dxr knock out GB - Reverse primer for all GB templates |

TABLE 16-continued

| PCR primers, plasmids, and Strains | | |
|---|---|---|
| dxrTest1 | ACGCCGCTCAGTAGATCCTTGCGG AT (SEQ ID NO: 132) | 5' of 50 bp homology region (in GBdxr1) used for GB knock-out |
| dxrTest2 | CTACTTACGATCAGATGGCGCAGA CTA (SEQ ID NO: 133) | 3' of 50 bp homology region (in GBdxr2) used for GB knock-out |
| GBprimer2 | CGAGACTAGTGAGACGTGCTAC (SEQ ID NO: 134) | GB test primer all cassettes - amplifies towards 5' end |
| GBprimerDW | AAAGACCGACCAAGCGACGTCTGA (SEQ ID NO: 135) | GB test primer all cassettes - amplifies towards 3' end |
| **Plasmid** | **Resistance** | **purpose** |
| pCL Ptrc(minus lacO) KKDyI | Spectinomycin (sp) | Lower MVA pathway for conversion of MVA to IPP/DMAPP - lower isoprenoids |
| FRT-cm-FRT | Chloramphenicol (GBchlor) | GB template - chloramphenicol |
| FRT-PGK-gb2-neo-FRT | Kanamycin (GBkan) | GB template - kanamycin |
| pRedET | Ampicillin (amp) | GB L-arabinose inducible expression of Red/ET proteins |
| MCM82 | Spectinomycin (sp) | Upper MVA pathway |
| MCM118 | Kanamycin (kan) | Lower MVA pathway + HGS |
| **Strain** | **Genotype** | **purpose** |
| DW13 | MG1655 with pCL Ptrc(minus lacO) KKDyI and pRedET, sp, amp | Parent strain of dxr deletion - has entire MVA lower pathway |
| DW23 | MG1655 Δdxr::GBkan with pCL Ptrc(minus lacO) KKDyI, kan, sp | dxr delection (kan) in MG1655 |
| DW28 | MG1655 Δdxr::GBchlor with pCL Ptrc(minus lacO) KKDyI, chlor, sp | dxr delection (chlor) in MG1655 |
| DW38 | BL21 DE3 (Invitrogen) with pCL Ptrc(minus lacO) KKDyI and pRedET, sp, amp | Parent strain of dxr deletion - has entire MVA lower pathway |
| DW43 | BL21 DE3 Δdxr::GBchlor with pCL Ptrc(minus lacO) KKDyI, chlor, sp | dxr delection (chlor) in BL21 DE3 |
| DW48 | BL21 DE3 Δdxr::GBchlor with MCM82 and MCM118, sp, kan | dxr delection (chlor) in BL21 DE3 with entire MVA pathway - requires no MVA |

(iii) Construction of MCM184—pCL Ptrc(minus lacO) UpperPathway

Plasmid MCM82 was mutagenized using the Stratagene QuikChange XL II kit. A reaction consisting of 10 uL buffer, 1 uL 100 ng/uL MCM82 DNA, 2.5 uL 10 uM primer MCM63 (SEQ ID NO:123), 2.5 uL 10 uM primer MCM64 (SEQ ID NO:124), 2 uL dNTP mix, 6 uL QuikSolution, 76 uL ddH2O and 2 uL polymerase was combined and aliquotted to four PCR tubes. Tubes were cycled in columns 1, 4, 7 and 12 of a BioRad 96-well gradient block using 1×95 C for 1 minute, 18×95° C. for 50 seconds, 60-65° C. for 50 seconds, 68° C. for 10 minutes), 1×68° C. for 7 minutes, 1×4° C. until cool. 1 uL DpnI was added and reactions were incubated at 37° C. for 2 hr and then frozen overnight at −20° C. 5 uL was transformed into Invitrogen TOP10 OneShot cells according to the manufacturer's protocol. Transformants were selected on LA+50 ppm Spectinomycin. Several colonies were cultured in LB+spectinomycin50 and then used for plasmid purification. Clone 2 from reaction 3 (column 7 from gradient block PCR) had the expected sequence and was frozen as MCM 184.

(iv) Construction of pCL Ptrc(ΔlacO) KKDyI (As Referred to as pCL Ptrc (Minus lacO) KKDyI or pCL Ptrc (Minus lacO) Lower Pathway)

Plasmid MCM 184 (pCL Ptrc(minus lacO) UpperPathway) was digested sequentially with SacI and PstI restriction endonucleases to remove the Upper MVA Pathway. A reaction consisting of 8 uL MCM184 (80 ng/uL), 3 ul Roche 10× Buffer A, 2 uL SacI restriction endonuclease, and 17 uL $ddH_2O$ was prepared and incubated at 37° C. for 2 hours. The SacI restriction endonuclease was then inactivated by heating at 65° C. for 20 minutes. The DNA fragment was then purified by using a Qiagen PCR Purification column per manufacturer's protocol. The DNA fragment was then eluted from the column with a volume of 34 uL $ddH_2O$. The next (sequential) restriction digest reaction consisted of the 34 uL SacI digested eluant, 4 uL Roche 10× Buffer H, and 2 uL PstI restriction endonuclease. The reaction was incubated at 37° C. for 2 hours before being heat inactivated at 65° C. for 20 minutes. A dephosphorylation step was then performed by addition of 4.7 uL Roche 10× Shrimp Alkaline Phosphatase (SAP) buffer), and 2 uL SAP enzyme. The reaction was then incubated at 37° C. for 1 hour. The digested MCM184 vector backbone was then separated from the Upper MVA Pathway DNA fragment by electrophoresis on a 1.2% E-gel (Invitrogen).

The Lower MVA Pathway fragment (KKDyI) was digested sequentially with SacI and PstI restriction endonucleases from plasmid MCM107. A reaction consisting of 2 uL MCM107 (375 ng/uL), 3 uL Roche 10× Buffer A, 2 uL SacI restriction endonuclease, and 23 uL $ddH_2O$ was prepared and incubated at 37° C. for 3 hours. The SacI restriction endonuclease was then inactivated by heating at 65° C. for 20 minutes. The DNA fragment was then purified by using a Qiagen PCR Purification column per manufacturer's protocol. The DNA fragment was then eluted from the column with a volume of 34 uL $ddH_2O$. The sequential digest reaction consisted of the 34 uL SacI digested eluant, 4 uL Roche 10× Buffer H, and 2 uL PstI restriction endonuclease. The reaction was incubated at 37° C. for 2 hours before being heat inactivated at 65° C. for 20 minutes. The digested KKDyI fragment was then separated from the MCM107 vector backbone by electrophoresis on a 1.2% E-gel (Invitrogen).

A ligation reaction consisting of 3 uL MCM184 vector backbone, 6 uL KKDyI DNA fragment, 2 uL New England Biolabs (NEB) 10× T4 DNA Ligase Buffer, 1 ul T4 DNA ligase, and 8 uL $ddH_2O$ were incubated at room temperature for 20 minutes. The ligation reaction was then transformed into TOP10 chemically competent *E. coli* cells (Invitrogen) per manufacturer's protocol and plated on LA+50 ppm spectinomycin plates. To confirm that transformants had correct sized insert fragment, a PCR screen was performed. 50 uL $ddH_2O$ was inoculated with individual colonies from the transformation, boiled at 95° C. for 5 minutes, and microcentrifuged for 5 minutes to pellet cellular debri. PCR was performed using PuReTaq Ready-To-Go PCR beads (GE Healthcare). Individual reaction tubes contained 1 uL of boiled cell lysate, 1 uL 10 uM primer EL-976 (SEQ ID NO:126), 1 uL 10 uM primer EL-977 (SEQ ID NO:127), and 22 uL $ddH_2O$. PCR tubes were cycled 1×95° C. for 1 minute, 30× (95° C. for 30 seconds, 53° C. for 30 seconds, 72° C. for 45 seconds), 1×72° C. for 2 minutes. The PCR products were then analyzed on a 1.2% E-gel for an 840 bp fragment. Clones #2, #3, and #4 were contained the correct sized fragments and were DNA sequenced using primers EL-976 (SEQ ID NO:126) and EL-978 (SEQ ID NO:128). DNA sequencing confirmation showed that all 3 were correct.

Example 8

Metabolite Analysis, Growth Inhibition, and Feedback Inhibition

I. Metabolite Extraction from *E. coli*. Sampled from 14-L Fermentors.

The metabolism of bacterial cells grown in fermentors was rapidly inactivated by withdrawing approximately 4 mL of culture into a tube filled with 8 mL of dry ice-cold methanol. The resulting samples were weighed to calculate the amount of sampled broth and then put into −80° C. for storage until further analysis. For metabolite extraction and concentration, 1.5 to 4.0 mL aliquots of cell suspension were diluted with methanol/ammonium acetate buffer (5 mM, pH=8.0) mixture (6:1, v/v) to a final volume of 6 mL, and cell debris was pelleted by a 5 minute centrifugation. The supernatant was collected and loaded onto a Strata-X-AW column (Phenomenex) containing 30 mg of sorbent that selectively retains strong organic acids. The pellet was extracted two more times, first with 3 mL of the methanol/ammonium acetate buffer (5 mM, pH=8.0) mixture (6:1 v/v), and then with 6 mL of methanol/ammonium acetate buffer (5 mM, pH=8.0) mixture (1:1 v/v). Both times the cells were pelleted by centrifugation, and the resulting supernatants were consecutively loaded onto the same Strata-X-AW column. During the extraction-centrifugation, samples with cells were kept below 4° C. to minimize degradation of metabolites. After washing the columns with 1 mL of water and 1 mL of methanol, metabolites of interest were eluted from the columns first with 0.3 mL of concentrated $NH_4OH$/methanol (1:14, v/v) mixture and then with 0.3 mL of concentrated $NH_4OH$/methanol/water (1:12:2, v/v) mixture. The resulting eluant was neutralized by adding 20 μL of glacial acetic acid, and then cleared by centrifugation in a microcentrifuge.

II. Metabolite Extraction from *E. coli*. Grown in Shake Flasks.

To extract metabolites from shake flask-grown *E. coli*, methanol-quenched cells were pelleted by centrifugation, and the resulting supernatant was loaded onto Strata-X-AW anion exchange column (Phenomenex) containing 30 mg of sorbent. The pellet was re-extracted twice with several milliliters of 50%, v/v, aqueous methanol containing 20% ammonium bicarbonate buffer (pH=8.0) and then with 75%, v/v, aqueous bicarbonate-buffered methanol. After each extraction, cell debris was pelleted by centrifugation, and the supernatant was consecutively loaded onto the same anion exchange columns. During the extraction and centrifugation steps, the samples were kept at below +4° C. Prior to metabolite elution, the columns were washed with water and methanol (1 mL of each), and the analytes were eluted by adding 0.3 mL of concentrated $NH_4OH$/methanol (1:14, v/v) and then 0.3 mL of concentrated $NH_4OH$/water/methanol (1:2:12) mixtures. The eluant was neutralized with 40 μL of glacial acetic acid and then cleared by centrifugation in a microcentrifuge.

III. Metabolite Quantification

Analysis of metabolites was carried out using a Thermo Finnigan TSQ system (Thermo Electron Corporation, San Jose, Calif.). All system control, data acquisition, and mass spectral data evaluation were performed using XCalibur and LCQuan software (Thermo Electron Corp). For the LC-ESI-MS/MS method, a chiral Nucleodex β-OH 5 μM HPLC column (200×4 mm, Macherey-Nagel, Germany) was used with a CC 8/4 Nucleodex beta-OH guard cartridge. A mobile phase gradient (Table 9) was applied at a flow rate of 0.8 mL/min in which mobile phase A was MilliQ-grade water, mobile phase B was 100 mM ammonium acetate (SigmaUltra grade, Sigma) buffer (pH adjusted to 8.0 by ammonium hydroxide) in MilliQ-grade water and mobile phase C was LC-MS grade acetonitrile (Chromasolv, Riedel-de Haën). The column and sample tray temperatures were reduced to 5° C. and 4° C., respectively. The injection volume was 10 or 20 μL. FIG. 121 shows typical elution profiles of selected metabolites extracted from an isoprene-producing *E. coli* strain.

TABLE 9

HPLC gradient used to elute metabolites in the MVA pathway.

| Time, min | Mobile phase, % A (water) | B (100 mM ammonium acetate, pH = 8.0) | C (acetonitrile) |
|---|---|---|---|
| 0.0 | 0.0 | 20.0 | 80.0 |
| 1.0 | 0.0 | 20.0 | 80.0 |
| 8.0 | 0.0 | 50.0 | 50.0 |
| 11.0 | 0.0 | 50.0 | 50.0 |
| 13.0 | 46.0 | 4.0 | 50.0 |
| 19.0 | 49.6 | 0.4 | 50.0 |
| 22.5 | 49.6 | 0.4 | 50.0 |

TABLE 9-continued

HPLC gradient used to elute metabolites in the MVA pathway.

| | Mobile phase, % | | |
|---|---|---|---|
| Time, min | A (water) | B (100 mM ammonium acetate, pH = 8.0) | C (acetonitrile) |
| 23.0 | 0.0 | 20.0 | 80.0 |
| 25.0 | 0.0 | 20.0 | 80.0 |

Mass detection was carried out using electrospray ionization in the negative mode (ESI spray voltage of 2.5-3.0 kV and ion transfer tube temperature of 390° C.). The following m/z values for precursor ions were selected to detect the metabolites of interest in SRM mode: 245.0 for IPP and DMAPP, 313.1 for GPP, 381.1 for FPP, 227.0 for MVP, and 307.1 for MVPP. Concentrations of metabolites were determined based on the integrated intensities of peaks generated by $PO_3^-$ product ion (m/z=79.0). Calibration curves obtained by injection of standards (IPP, DMAPP, and GPP purchased from Sigma-Aldrich, and FPP purchased from Echelon Biosciences Inc.) were used to calculate concentrations of metabolites in cell extracts. Concentrations of MVP and MVPP were expressed in arbitrary units because of the absence of commercially available standards. Intracellular concentrations of metabolites were determined based on the assumption that in 1 mL of the culture at OD=200 the integrated volume of all cells is 50 μL.

IV. Intracellular Concentrations of Metabolites in the MCM401 Strain of *E. coli* Containing MVK from *M. mazei* Under Different Levels of Enzyme Expression Induced by Adding IPTG to the Fermentors.

FIG. 122A-122F provide an example of intracellular concentrations of metabolites in the MCM401 strain of *E. coli* containing MVK from *M. mazei* under different levels of enzyme expression induced by adding IPTG to the fermentors. Even though the final IPTG concentrations in all three fermentors were similar (~200 μM), cell response was very different depending on the IPTG feeding scheme. A single-shot addition of a high dose of IPTG (FIGS. 122C and 1224F) caused an instant increase in isoprene production and early accumulation of a significant level of MVPP. In contrast, concentrations of DMAPP, the immediate precursor of isoprene, as well as GPP and FPP, the products of IPP and DMAPP condensation, were low (below ~0.2 mM). Intracellular concentrations of IPP remained higher than the concentration of DMAPP during the analyzed fermentation period, indicating that DMAPP is synthesized from IPP slower than it is consumed in the isoprene biosynthesis reaction.

Although the maximum specific productivity of MCM401 cells reached about the same level upon adding IPTG in two steps (~100 μM each time; FIGS. 122B and 122E), the amount of MVPP accumulated in cells by the end of the production period was lower than in the single IPTG shot experiment and the buildup of MVPP pool started only after the second portion of IPTG was added to the fermentor. In both cases a decline in the isoprene production correlated with accumulation of MVP, which pool reached much higher concentrations in cells that had received two doses of IPTG. Moderate levels of IPP and DMAPP (~0.4 mM) were detected in the latter case around 30 hours of fermentation, which correlated in time with the maximum rate of isoprene biosynthesis by these cells. Notably, intracellular concentrations of GPP and FPP were low presumably due to a very high activity of the isoprene synthase.

Four IPTG shots of about 50 μM each resulted in the lowest specific productivity of the MCM401 strain; however, under these conditions the culture continued to synthesize isoprene at a significant rate for a longer period of time (FIGS. 122A and 122D). The maximum intracellular levels of IPP and DMAPP generally remained in the range of 0.2-0.4 mM during the production period, and FPP raised to 1.0-1.5 mM in response to the second 50 μM dose of IPTG. Notably, DMAPP concentration was slightly higher than the concentration of IPP likely due to the fact that DMAPP conversion into isoprene occurred slower in this case compared to the fermentations illustrated in FIGS. 122B, 122C, 122E, and 122F, and FPP biosynthesis did not consume significant amounts of DMAPP.

V. Intracellular Concentrations of Metabolites in the MCM402 Strain of *E. coli* Overexpressing MVK from *Saccharomyces cerevisiae*

FIGS. 127A and 127B illustrate the experiment with the MCM402 strain of *E. coli*, containing overexpressed MVK from *Saccharomyces cerevisiae*. As in the case with the MCM401 strain having MVK from *M. mazei* and grown under similar IPTG induction conditions (4×50 μM shots), isoprene production started after the second dose of IPTG has been added to the fermentor, which coincided in time with rapid accumulation of DMAPP and IPP to relatively high levels (up to 1.8 mM of DMAPP) in the MCM402 cells. However, in the MCM402 cells, the isoprene production period remained very short correlating with the drop in DMAPP and IPP pools. In contrast, FPP continued to accumulate up to the level of 2.6-3.5 mM even when DMAPP and IPP concentrations dropped to below 1 mM. Therefore, parts IV and V of this example emphasize superior properties of MVK from *M. mazei* as compared to yeast MVK.

VI. Intracellular Concentrations of Metabolites in the MCM343 Strain of *E. coli* Expressing the Full Mevalonic Acid Pathway and Kudzu Isoprene Synthase (without Overexpression of a Second Mevalonate Kinase)

FIGS. 128A and 128B depict changes in concentrations of selected intermediates in the isoprenoid pathway in the course of fermentation of MCM343 *E. coli* strain. This fermentation run was characterized by very low specific productivity and barely detectable concentrations of most of isoprenoid intermediates except for FPP, which intracellular level reached 0.7 mM, after 100 μM IPTG was added to the cells. IPP and DMAPP were detected shortly after the IPTG addition and then their level dropped below the detection limit. No MVP or MVPP were detected during the fermentation.

VII. Safe and Maximal Metabolite Concentrations During Isoprene Production Shake Flask Experiment with MCM 127

A shake flask experiment with MCM127 was performed to investigate the accumulation of key intermediates during strong induction of isoprene production. Strong induction of this strain resulted in growth inhibition most likely due to accumulation of toxic metabolic intermediates.

Medium Recipe (Per Liter Fermentation Medium):

Each liter of fermentation medium contained $K_2HPO_4$ 13.6 g, $KH_2PO_4$ 13.6 g, $MgSO_4$*$7H_2O$ 2 g, citric acid monohydrate 2 g, ferric ammonium citrate 0.3 g, $(NH_4)_2SO_4$ 3.2 g, yeast extract 1 g, 1000× Trace Metal Solution 1 ml. All of the components were added together and dissolved in $diH_2O$. The pH was adjusted to 6.8 with ammonium hydroxide (30%) and brought to volume. Medium was filter-sterilized with a 0.22 micron vacuum filter. Glucose was added to the medium to a final concentration of 0.5%. Antibiotics were added after sterilization and pH adjustment.

1000× Trace Metal Solution (Per Liter Fermentation Medium):

1000× trace metal solution contained citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in $diH_2O$, pH to 3.0 with HCl/NaOH, and then brought to volume and filter sterilized with 0.22 micron filter.

Strain:

The MCM127 strain is BL21 (DE3) *E. coli* cells containing the upper mevalonic acid (MVA pathway (pCL Upper) and the lower MVA pathway including isoprene synthase from kudzu (pTrcKKDyIkIS)

An inoculum of *E. coli* strain MCM127 taken from a frozen vial was streaked onto an LB broth agar plate (with antibiotics) and incubated at 30° C. A single colony was inoculated into media containing glucose as carbon source and grown overnight at 30° C. The bacteria were diluted into fermentation media to reach an optical density of 0.05 measured at 550 nm. A total of 150 mL of culture was dispensed into two 500 mL flasks that were then shaken at 170 rpm in a 30° C. incubator. When the cultures reached an optical density ($OD_{600}$) of 0.5, one of the flasks was induced with 150 μM isopropyl-beta-D-1-thiogalactopyranoside (IPTG). Samples of 20 mL from both the induced and non-induced culture were taken approximately every half hour for metabolite analysis after induction. The samples were quickly quenched in equal volume of methanol cooled on dry ice. After centrifugation, supernatant was loaded on Stata X-AW columns. The pellet was resuspended in 5 mL of Methanol-water (6:1, water contained 5 mM NH4Ac at pH=8.0), cell debris were separated by centrifugation, and the supernatant was loaded on the Stata X-AW columns. Metabolites were eluted with 0.30 mL ethanol:conc NH4OH (14:1 vol/vol), then with 0.3 mL methanol:water:conc NH4OH (12:2:1 vol/vol/vol), finally pH was adjusted by adding 40 uL of glacial acetic acid. Extracted metabolites were analyzed by LCMS using a standard cyclodextrin column protocol. To increase sensitivity, only ions corresponding to IPP, DMAPP, GPP, and FPP were detected. Injection volume was 20 uL/sample. Standards of all metabolites were used for calibration.

Upon induction of the MCM127 with 150 μM IPTG, the bacteria continued to grow identical to the non-induced strain for approximately one and a half hour. After this, the induced culture began to show signs of growth inhibition (FIG. 112A). Key metabolites were measured during the experiment and showed an increasing accumulation of FPP, GPP, DMAPP and IPP after induction. DMAPP and IPP only began to accumulate when the induced bacteria first showed signs of growth inhibition (FIG. 112B). None of the mentioned intermediates were detected in measurable amount in the non-induced culture. The experiment demonstrates that *E. coli* can tolerate significant intracellular concentrations of GPP and FPP (Tables 15A and 15B), while accumulation of DMAPP and IPP coincides with growth inhibition when cultures are grown in shake flasks. Data in Tables 15A and 15B were from the 5.5 hr time point, where growth was still normal in the induced culture.

VIII. Growth Inhibition i) Recovery of Mevalonic Acid from Fermentation Broth.

Mevalonic acid was obtained by a fed batch fermentation of *Escherichia coli* strain, BL21 harboring an expression plasmid bearing the genes mvaS and mvaE from *Enterococcus faecalis* (U.S. Appl. Pub. No. 2005/0287655, which is incorporated by reference in its entirety, particularly with respect to genes mvaS and mvaE). Fermentation of the strains was carried out in fed batch fermentation mode in a minimal medium with a glucose feed for 40 hours. Broth was harvested, mixed with diatomaceous earth (DE; Catalog #Celatom FW-12, American Tartaric Products Inc.), and filtered under vacuum through a Buchner funnel fitted with a filter pad. The filtrate was sterile filtered through a 10,000 MWCO membrane. Mevalonic acid was converted to the lactone by acidification and recovered by continuous organic solvent extraction; NMR analysis indicated a purity of 84%. All recovery steps are well known to those skilled in the art. When the free acid was required for experiments, the MVA lactone was hydrolyzed by the addition of 1 equivalent of base to a solution of lactone and allowed to stand for 1 hour prior to use. The sterile filtered solution can be stored for extended time at 4° C.

ii) Growth Inhibition of *Escherichia coli* BL21 by the Accumulation of Mevalonate Diphosphate, Isopentenyl Diphosphate (IPP), and Dimethylallyl Diphosphate (DMAPP).

The purpose of this experiment was to determine the effect of the expression of the proteins mevalonate kinase (MVK), phophomevalonate kinase (PMK), and diphosphomevalonate decarboxylase (MDD) on *Escherichia coli* cultures.

*E. coli* BL21 cells bearing pTrcK, representing a plasmid expressing MVK, pTrcKK representing a plasmid expressing MVK plus PMK, and pTrcKKD, representing a plasmid expressing MVK plus PMK plus MDD were grown at approximately 30° C. and 250 rpm in 250 mL flasks containing 25 mL of TM3 medium (13.6 g $K_2PO_4$, 13.6 g $KH_2PO_4$, 2.0 g $MgSO_4.7H_2O$) supplemented with 1% glucose and 0.8 g/L Biospringer yeast extract (1% Yeast extract final). When OD600 reached 0.8 to 0.9, 5.8 mM mevalonic acid was added to the cultures and incubation was continues for an additional 5 hours. $OD_{600}$ measurements were taken, and the cultures were sampled for metabolite analysis at 2 hours post MVA addition. Samples were collected into 100% MeOH pre-chilled in dry ice in a ratio of 1:1. Samples were stored at −80° C. until analyzed as follows. The methanol-quenched cells were pelleted by centrifugation and the resulting supernatant was loaded onto Strata-X-AW anion exchange column (Phenomenex) containing 30 mg of sorbent. The pellet was reextracted twice with several milliliters of 50%, v/v, aqueous methanol containing 20% ammonium bicarbonate buffer (pH=8.0) and then with 75%, v/v, aqueous bicarbonate-buffered methanol. After each extraction, cell debris were pelleted by centrifugation and the supernatant was consecutively loaded onto the same anion exchange columns. During the extraction and centrifugation steps, the samples were kept at below +4° C. Prior to metabolite elution, the columns were washed with water and methanol (1 mL of each) and the analytes were eluted by adding 0.3 mL of concentrated $NH_4OH$/methanol (1:14, v/v) and then 0.3 mL of concentrated $NH_4OH$/water/methanol (1:2:12) mixtures. The eluant was neutralized with 40 μL of glacial acetic acid and then cleared by centrifugation in microcentrifuge. Analysis of metabolites in these samples is as described above.

As is shown in FIG. 129, inhibition of growth was evident when the enzymes MVK and PMK are expressed (strain #7); additional inhibition is observed when MDD is added to the cloned pathway (strain #6). No growth inhibition was observed when MVK was the only enzyme expressed (strain #5). Analysis of MVA concentration at the time of collection of samples suggests that strain with MVK plus PMK plus MDD consumed 2.9 mM MVA while the other two strains consume lower quantities. The culture carrying MVK and PMV showed about 30 and 60-fold higher levels, respectively, of phosphomevalonate and diphosphomevalonate compared to the strain carrying MVK, PMK, and MDD. The latter strain accumulated surprisingly high levels of IPP and DMAPP on the order of 40 mM IPP and 320 uM DMAPP when calculated as an intracellular concentration. These measurements were conducted on whole cell broth; thus, some of the metabolites may have been excreted by the cells. While not intending to be bound by any particular theory, it is believed that the observed growth inhibition is due to the accumulation of one or more of these metabolites. A goal is therefore to achieve a pathway enzyme balance to minimize the accumulation of these metabolites for the relief of growth inhibition.

IX. Feedback Inhibition i) Methods and General Procedures

Geranyl-pyrophosphate (GPP), farnesyl-pyrophosphate (FPP), adenosine triphosphate (ATP), phosphoenolpyruvate (PEP), NADH, magnesium chloride, sodium chloride, Tris, HEPES, DNase I, and lysozyme were purchased from Sigma. Dithiothreitol (DTT) was purchased from Fluka. Lactate dehydrogenase was purchased from Calbiochem and pyruvate kinase was purchased from MD biomedicals. All columns used in purification were obtained from GE healthcare. Purity was analyzed by 4-12% SDS-Page gel electropheresis using precast gels and reagents purchased from Invitrogen. Protein concentration was determined by UV-absorbance at 280 nm using the following conversion factors: 0.597 OD/mg/mL for yeast mevalonate kinase and 0.343 OD/mg/mL for *M. mazei* mevalonate kinase (these were obtained using ExPASy ProtParam tool). Kinetics were performed using SpectraMax 190 platereader (Molecular Devices). All kinetic data were analyzed using Kaleidagraph 4.0 graphing program from Synergy software. Purified mevalonate was obtained using standard methods.

ii) Expression and Purification of Yeast Mevalonate Kinase and *M. mazei* Mevalonate Kinase Yeast and *M. mazei* mevalonate kinases were expressed as follows. *E. coli* strain MCM376 containing yeast MVK was grown at 37° C. in 2×1-L of LB media containing 50 mg/L carbenicillin and 30 mg/L chrolamphenicol. Cells were induced with 200 μM IPTG at $OD_{600}$=0.6-0.8. *E. coli* strain MD08-MVK containing *M. mazei* MVK was grown at 30° C. in 1-L of Terrific broth with 50 mg/L kannamycin and 30 mg/L chloramphenicol. Cells were induced with 500 uM IPTG at $OD_{600}$=0.5. Identical harvest and purification procedures were used for yeast and *M. mazei* mevalonate kinases. Cells were harvested by centrifugation approximately 15 hours after induction. Pelleted cells were resuspended in 15 mL Ni-binding buffer (50 mM sodium phosphate, 300 mM sodium chloride, 20 mM imidazole, pH 8.0) and containing ~1 mg/mL lysozyme and ~0.1 mg/mL DNase I and french-pressed two times at 20,000 psi. Lysate was then centrifuged at 229,000×g for one hour. Supernatant was loaded onto a Hi Trap IMAC HP column charged with $NiSO_4$ and equilibrated with Ni-binding buffer. Column was washed with 10 column volumes of Ni-binding buffer. Yeast and *M. mazei* mevalonate kinases were eluted with a 0.02-0.5 M gradient of imidizole. The buffer of fractions containing mevalonate kinase were exchanged with 50 mM HEPES, 50 mM sodium chloride, pH 7.4, containing 1 mM DTT using a Hi Prep 26/10 desalting column. Following desalting, mevalonate kinases were further purified over an anion exchange Hi Trap Q HP column. The column was washed with 50 mM Tris, 0.05 M sodium chloride pH 7.6 containing 1 mM DTT, and eluted with a 0.05-1.0 M salt gradient. Fractions containing mevalonate kinase were desalted as previously described to 50 mM HEPES, 50 mM sodium chloride, pH 7.4 containing 1 mM DTT to yield >95% pure yeast mevalonate kinase and *M. mazei* mevalonate kinase (as determined by SDS-PAGE and coomasie staining).

iii) Kinetics of Yeast Mevalonate Kinase and *M. mazei* Mevalonate Kinase

The catalytic activities of the mevalonate kinases were determined using a modified protocol (Beytia et al., (J. Biol. Chem. 245, 5450, 1970, which is incorporated by reference in its entirety, particularly with respect to kinase assays). The assay was performed in a 96-well plate format (Costar #9017) with a final reaction volume of 100 μl. Each reaction contained the following reagents: 0.4 mM PEP, 0.05 mM DTT, 0.32 mM NADH, 1 mM $MgCl_2$, 4 units of LDH and 4 units of PK in 50 mM Tris, 50 mM NaCl, pH 7.6. The $K_M$ value for yeast mevalonate kinase at the mevalonate binding site was determined by adding 5 mM ATP to the reaction to saturate the ATP binding site, followed by addition of mevalonate at concentrations ranging from 5 mM to 0.039 mM. The reaction was initiated with the addition of 10 nM (50.1 ng) purified mevalonate kinase from yeast. The $K_M$ value for yeast mevalonate kinase at the ATP binding site was similarly determined, by saturating with 5 mM mevalonate and titrating ATP at concentrations ranging from 5 mM to 0.039 mM. The $K_M$ values for *M. mazei* mevalonate kinase were determined using the same procedure with the following exceptions: substrate concentrations ranged from 0 mM to 5 mM, and the reaction was initiated by adding 80 nM (0.25 μg) purified mevalonate kinase from *M. mazei*. Reactions were monitored by a decrease in absorbance at 340 nm. The concentration of NADH was plotted against time to determine the rate of the reactions. Units of absorbance were converted to μM NADH using a conversion factor determined from the difference in absorbance at 340 nm of 320 μM NADH and 320 μM fully oxidized NADH ($NAD^+$) divided by the NADH concentration (320 μM). Reactions were conducted at 30° C. and data were collected every 10-15 seconds continuously over the course of the reactions.

Protein inhibition studies were performed using various concentrations of terpenyl diphosphates.

iv) Yeast and *M. mazei* Mevalonate Kinase Kinetic Properties and Inhibition Results Kinetic studies were conducted using yeast mevalonate kinase and *M. mazei* mevalonate kinase. The $K_{Mapp}$ of yeast mevalonate kinase was determined to be 714±49 μM for the ATP binding site and 131±8 μM for the mevalonate binding site with a turnover number ($k_{cat}$) of 38±5 $s^{-1}$ (FIGS. 58A and 58B). The $K_{Mapp}$ of *M. mazei* mevalonate kinase was determined to be 464±12 μM for the ATP binding site and 68±4 μM for the mevalonate binding site with $k_{cat}$ of 4.3±0.2 $s^{-1}$ (FIGS. 58C and 58D).

Inhibition studies were performed using DMAPP, GPP, and FPP. Lineweaver-Burke plots of the inhibition studies demonstrate that the inhibition of yeast mevalonate kinase is competitive with respect to ATP and uncompetitive with respect to mevalonate (FIGS. 96A and 96B). Therefore, the inhibition constants for the ATP and mevalonate sites were calculated by determining the $IC_{50}$ value followed by conversion to the $K_i$ value with Equation 16:

$$K_i = \frac{IC_{50}}{1 + \frac{[S]}{K_M}}. \quad \text{Equation 16}$$

The $K_i$s of DMAPP, GPP, and FPP for yeast mevalonate kinase ATP-binding site were determined to be 33.2 μM, 153.3 nM, and 138.5 nM, respectively (FIGS. 97A-97C). The $K_i$s of DMAPP, GPP, and FPP for yeast mevalonate kinase mevalonate-binding site were determined to be 394.6 μM, 2.54 μM, and 2.98 μM, respectively (FIGS. 98A-98C).

*M. mazei* mevalonate kinase was not inhibited at concentrations of DMAPP up to 5 mM and concentrations of GPP and FPP up to 100 μM.

v) Diphosphomevalonate and Isopentyl Phosphate Inhibition of Yeast MVK, *Streptococcus pneumoniae* MVK, and *Methanosarcina* MVK This experiment investigates the inhibitory effect of diphosphomevalonate and isopentyl monophosphate (IP) on MVK activity using MVK enzymes from *S. pneumoniae*, yeast, and *M. mazei*, respectively. Inhibition of MVK by diphosphomevalonate and IP was shown using a two enzyme system (Andreassi et al., *Biochemistry,* 43:16461-66, 2004, which is incorporated by reference in its entirety with particular emphasis on determination of inhibition of MVK by diphosphomevalonate). All reactions were performed in 96-well plates and were monitored by absorbance at 386 nm on a Molecular Devices Spectramax 190 UV-Vis 96-well spectrophotometer. All experiments were run as 100 μL reactions at 30° C. and contained 5 mM ATP, 3 mM $MgCl_2$, 2.9 mM NADH, 0.7 mM R-mevalonate (Genencor), 4 mM phosphoenolpyruvate, 10 U lactate dehydrogenase (MP Biomedicals LLC), 10 U pyruvate kinase (MP Biomedicals LLC), and 1 mM DTT. All chemical reagents were purchased from Sigma unless otherwise specified. Yeast and *M. mazei* MVK were obtained as described above and *S. pneumoniae* MVK and yeast phosphomevalonate kinase (PMK) were obtained as previously described (Andreassi et al., Biochemistry, 43:16461-66, 2004) from pDW02 in pET200D MVK (FIG. 142).

When 1 μM *S. pneumoniae* MVK and 1 μM PMK are incubated with mevalonate and all essential co-factors, the reaction does not progress at the same rate as a reaction containing only *S. pneumoniae* MVK (FIG. 140A). However, the reaction proceeds to completion when PMK is added to the MVK-only reaction after that half of the reaction is complete (i.e. the production of phosphomevalonate), indicating that production of diphosphomevalonate inhibits *S. pneumoniae* MVK (FIG. 140B). Conversely, a reaction containing 1 μM Yeast MVK proceeds to completion regardless of whether 1 μM PMK is present initially (FIG. 140C) or is added after yeast MVK conversion of mevalonate to phosphomevalonate is complete (FIG. 140D), indicating yeast MVK is not inhibited by diphosphomevalonate. Likewise, reactions containing 1 μM archaeal *M. mazei* MVK proceed to completion whether or not PMK is present initially (FIGS. 140E-140F) or added to the MVK-only reaction after that half of the reaction is complete (FIG. 140G).

Without being bound by theory, the archaeal mevalonate pathway has been postulated to contain an isopentyl monophosphate (IP) kinase that catalyzes the formation of isopentenyl diphosphate (IPP). Therefore, archaea may use an alternate mevalonate biosynthetic pathway to produce IPP and DMAPP. This putative pathway may contain a phosphomevalonate decarboxylase that catalyzes the formation of IP from phosphomevalonate. When 100 μM of IPP was added to a reaction containing 1 μM *M. mazei* MVK and all reagents listed above, the reaction was not inhibited compared to a control reaction containing all reagents listed above without the addition of IP (FIG. 141).

*S. pneumoniae* MVK was inhibited by diphosphomevalonate according to previously published results (FIGS. 140A-140B; Andreassi et al., *Biochemistry,* 43:16461-66, 2004). Neither yeast MVK nor *M. mazei* MVK was inhibited by diphosphomevalonate (FIGS. 140C-140G). *M. mazei* MVK was not inhibited by IP at concentrations up to 100 μM (FIG. 141). *M. mazei* MVK is thus the first described MVK that is not inhibited by diphosphomevalonate, DMAPP, IP, GPP, or FPP.

Example 9

Production of Isoprene by *E. coli* Expressing the Upper Mevalonic Acid (MVA) Pathway, the Integrated Lower MVA Pathway (gi1.2KKDyI), Mevalonate Kinase from Yeast, and Isoprene Synthase from Kudzu and Grown in Fed-Batch Culture at the 15-L Scale Medium Recipe (Per Liter Fermentation Medium):

Each liter of fermentation medium contained $K_2HPO_4$ 7.5 g, $MgSO_4$*7$H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

1000× Modified Trace Metal Solution contained citric Acids*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, and $NaMoO_4$*2$H_2O$ 100 mg. Each component was dissolved one at a time in DI $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the upper mevalonic acid (MVA) pathway (pCL PtrcUpperPathway encoding *E. faecalis* mvaE and mvaS), the integrated lower MVA pathway (gi1.2KKDyI encoding *S. cerevisiae* mevalonate kinase, mevalonate phosphate kinase, mevalonate pyrophosphate decarboxylase, and IPP isomerase), and high expression of mevalonate kinase from yeast and isoprene synthase from Kudzu (pTrcKudzuMVK(yeast)). This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to innoculate 5-L of cell medium in the 15-L bioreactor. The liquid volume increases throughout the fermentation (such as to approximately 10 liters).

Glucose was fed at an exponential rate until cells reached the stationary phase. After this time the glucose feed was decreased to meet metabolic demands. The total amount of glucose delivered to the bioreactor during the 54 hour fermentation was 1.6 kg. Induction was achieved by adding IPTG. The IPTG concentration was brought to 54 uM when the optical density at 550 nm ($OD_{550}$) reached a value of 10. The IPTG concentration was raised to 87 uM when $OD_{550}$ reached 175. Additional IPTG additions raised the concentration to 122 uM at $OD_{550}$=180 and 157 uM at $OD_{550}$=185. The $OD_{550}$ profile within the bioreactor over time is shown in FIG. 123. The isoprene level in the off gas from the bioreactor was determined using a Hiden mass spectrometer. The isoprene titer increased over the course of the fermentation to a final value of 6.4 g/L (FIG. 124). The total amount of isoprene produced during the 54 hour fermentation was 44.6 g and the time course of production is shown in FIG. 125. The molar yield of utilized carbon that went into producing isoprene during fermentation was 6.1%. The weight percent yield of isoprene from glucose was 2.8%.

Example 10

Production of Isoprene in *E. coli* Expressing Recombinant Kudzu Isoprene Synthase I. Construction of Vectors for Expression of the Kudzu Isoprene Synthase in *E. coli:*

Figure 2:
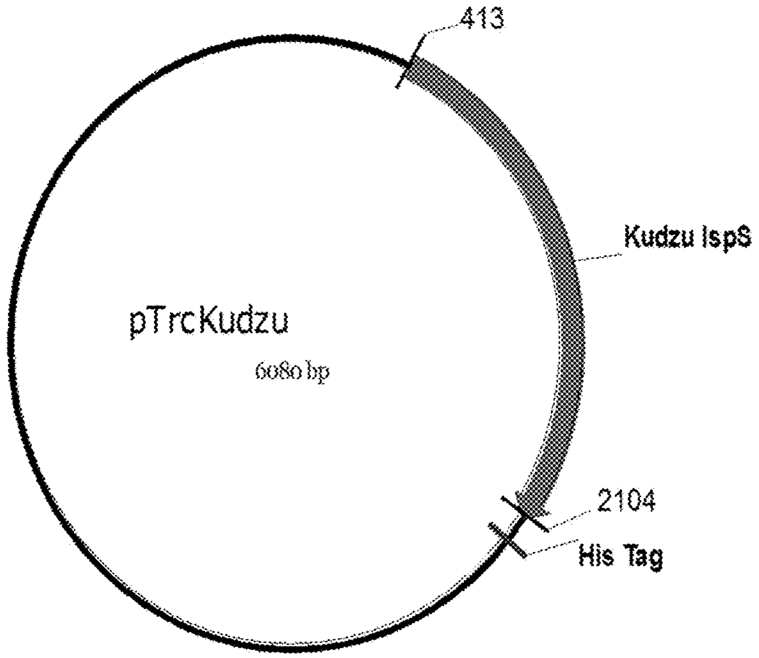
FIG. 2 is a map of pTrcKudzu.

The protein sequence for the kudzu (*Pueraria montana*) isoprene synthase gene (IspS) was obtained from GenBank (AAQ84170). A kudzu isoprene synthase gene, optimized for *E. coli* codon usage, was purchased from DNA2.0 (SEQ ID NO:1). The isoprene synthase gene was removed from the supplied plasmid by restriction endonuclease digestion with BspLU11I/PstI, gel-purified, and ligated into pTrcHis2B (Invitrogen) that had been digested with NcoI/PstI. The construct was designed such that the stop codon in the isoprene synthase gene 5' to the PstI site. As a result, when the construct was expressed the His-Tag is not attached to the isoprene synthase protein. The resulting plasmid, pTrcKudzu, was verified by sequencing (FIGS. 2 and 3).

Figure 4:
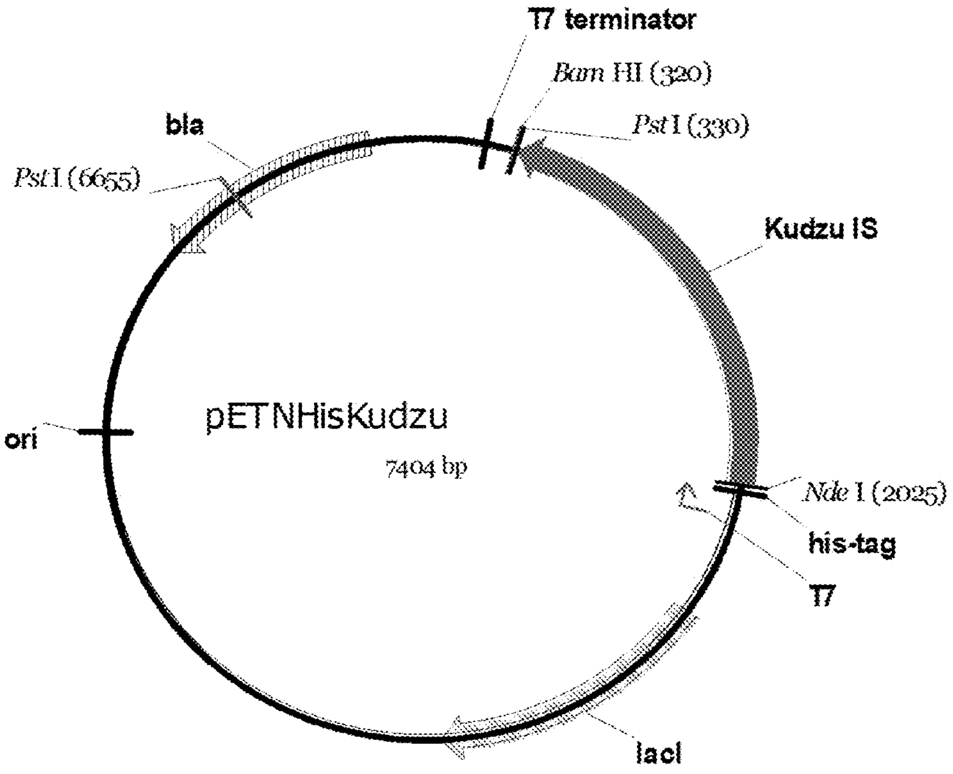
FIG. 4 is a map of pETNHisKudzu.
Figure 6:
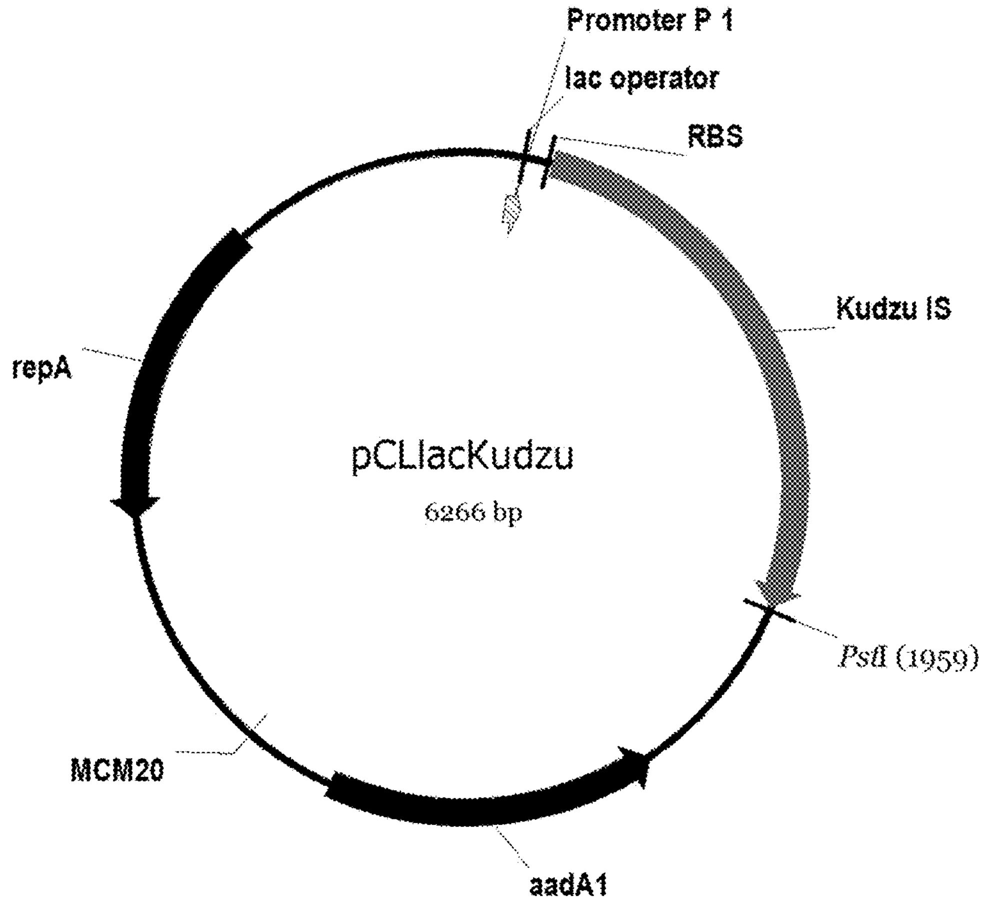
FIG. 6 is a map of pCL-lac-Kudzu.
Figure 8A:
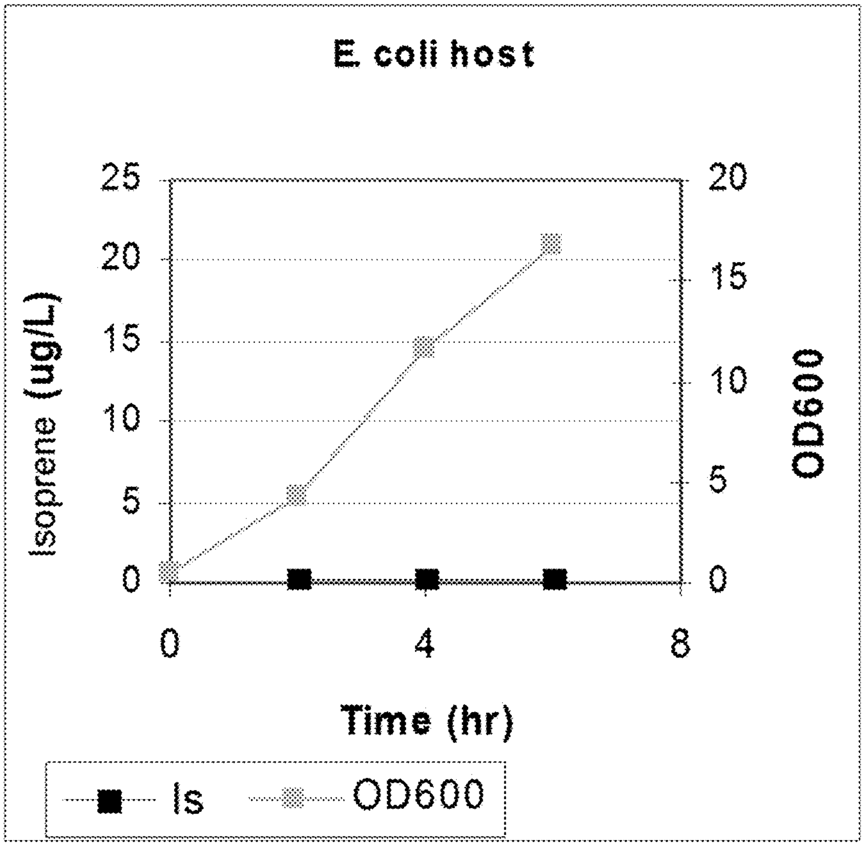
FIG. 8A is a graph showing the production of isoprene in *E. coli* BL21 cells with no vector.
Figure 8B:
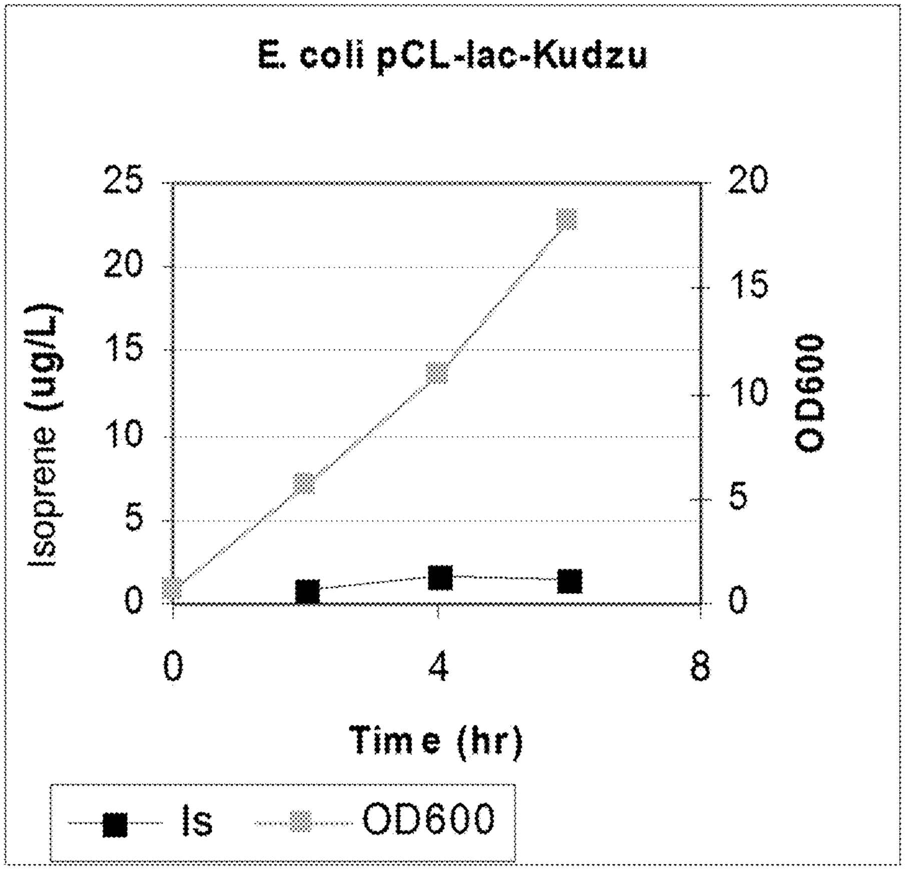
FIG. 8B is a graph showing the production of isoprene in *E. coli* BL21 cells with pCL-lac-Kudzu
Figure 8C:
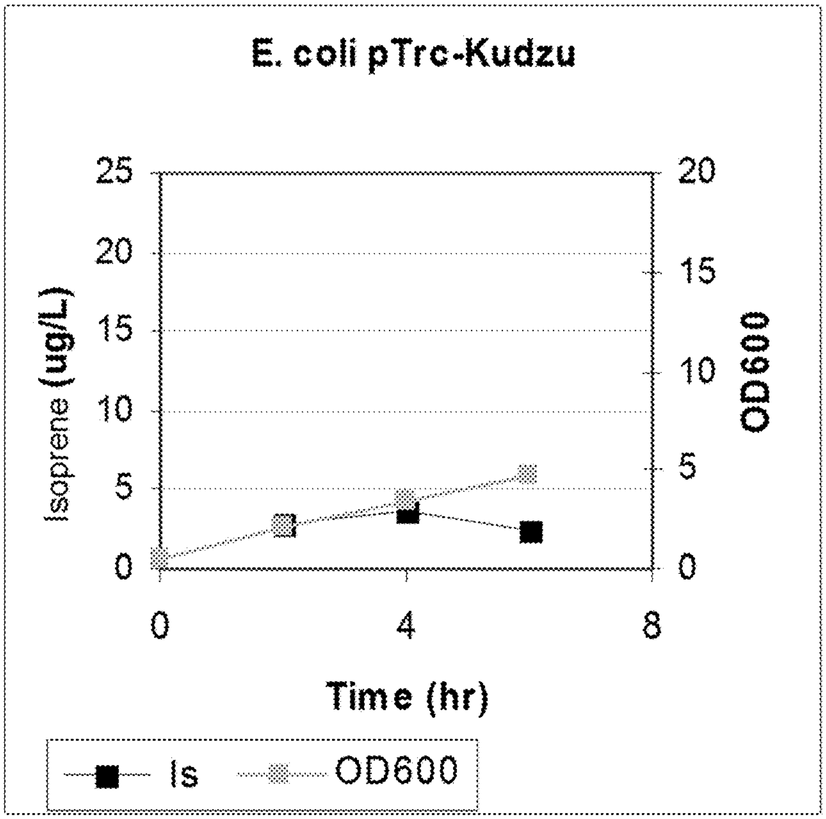
FIG. 8C is a graph showing the production of isoprene in *E. coli* BL21 cells with pTrcKudzu.
Figure 8D:
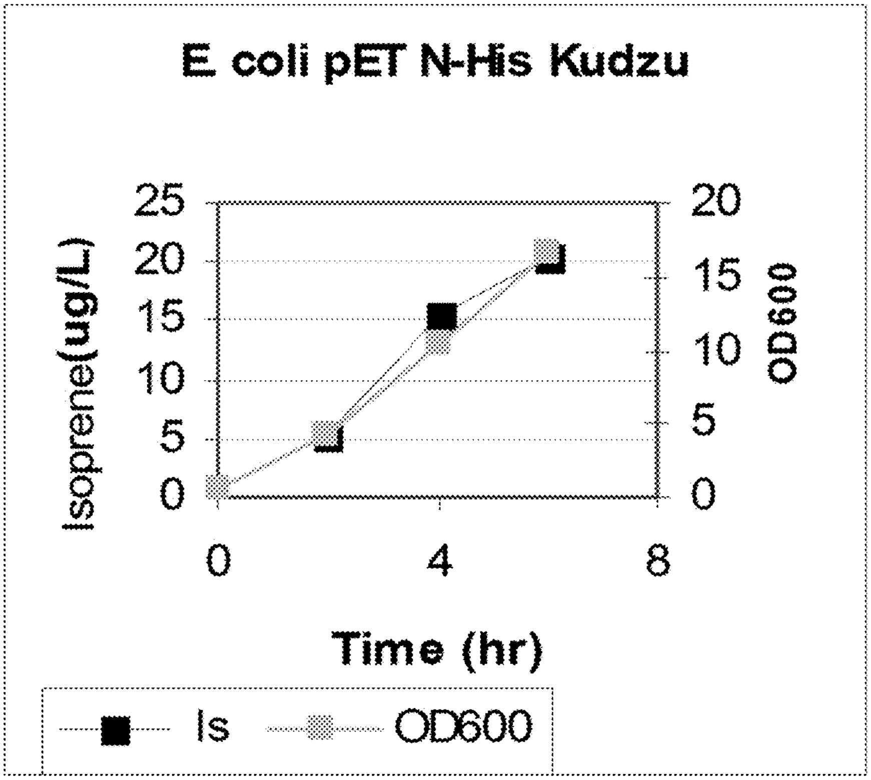
FIG. 8D is a graph showing the production of isoprene in *E. coli* BL21 cells with pETNHisKudzu.

The isoprene synthase gene was also cloned into pET16b (Novagen). In this case, the isoprene synthase gene was inserted into pET16b such that the recombinant isoprene synthase protein contained the N-terminal His tag. The isoprene synthase gene was amplified from pTrcKudzu by PCR using the primer set pET-His-Kudzu-2F: 5'-CGTGAGATCATATGTGTGCGACCTCTTCTCAATTTAC (SEQ ID NO:3) and pET-His-Kudzu-R: 5'-CGGTCGACGGATCCCTGCAGTTAGACATACATCAGCTG (SEQ ID NO:4). These primers added an NdeI site at the 5'-end and a BamH1 site at the 3' end of the gene respectively. The plasmid pTrcKudzu, described above, was used as template DNA, Herculase polymerase (Stratagene) was used according to manufacture's directions, and primers were added at a concentration of 10 pMols. The PCR was carried out in a total volume of 25 μl. The PCR product was digested with NdeI/BamH1 and cloned into pET16b digested with the same enzymes. The ligation mix was transformed into *E. coli* Top10 (Invitrogen) and the correct clone selected by sequencing. The resulting plasmid, in which the kudzu isoprene synthase gene was expressed from the T7 promoter, was designated pET-NHisKudzu (FIGS. 4 and 5).

The kudzu isoprene synthase gene was also cloned into the low copy number plasmid pCL1920. Primers were used to amplify the kudzu isoprene synthase gene from pTrcKudzu described above. The forward primer added a HindIII site and an *E. coli* consensus RBS to the 5' end. The PstI cloning site was already present in pTrcKudzu just 3' of the stop codon so the reverse primer was constructed such that the final PCR product includes the PstI site. The sequences of the primers were: HindIII-rbs-Kudzu F: 5'-CATATGAAAGCTTGTATCGATTAAATAAGGAGGAATAAACC (SEQ ID NO:6) and BamH1-Kudzu R:

5'-CGGTCGACGGATCCCTGCAGTTAGACATACATCAGCTG (SEQ ID NO:4). The PCR product was amplified using Herculase polymerase with primers at a concentration of 10 pmol and with 1 ng of template DNA (pTrcKudzu). The amplification protocol included 30 cycles of (95° C. for 1 minute, 60° C. for 1 minute, 72° C. for 2 minutes). The product was digested with HindIII and PstI and ligated into pCL1920 which had also been digested with HindIII and PstI. The ligation mix was transformed into *E. coli* Top10. Several transformants were checked by sequencing. The resulting plasmid was designated pCL-lac-Kudzu (FIGS. 6 and 7A-7C).

II. Determination of Isoprene Production

For the shake flask cultures, one ml of a culture was transferred from shake flasks to 20 ml CTC headspace vials (Agilent vial cat#5188 2753; cap cat#5188 2759). The cap was screwed on tightly and the vials incubated at the equivalent temperature with shaking at 250 rpm. After 30 minutes the vials were removed from the incubator and analyzed as described below (see Table 1 for some experimental values from this assay).

In cases where isoprene production in fermentors was determined, samples were taken from the off-gas of the fermentor and analyzed directly as described below (see Table 2 for some experimental values from this assay).

The analysis was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 μm film thickness) was used for separation of analytes. The sampler was set up to inject 500 μL of headspace gas. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 μg/L to 2000 μg/L. The limit of detection was estimated to be 50 to 100 ng/L using this method.

III. Production of Isoprene in Shake Flasks Containing *E. coli* Cells Expressing Recombinant Isoprene Synthase The vectors described above were introduced to *E. coli* strain BL21 (Novagen) to produce strains BL21/ptrcKudzu, BL21/pCL-lac-Kudzu and BL21/pETHisKudzu. The strains were spread for isolation onto LA (Luria agar)+carbenicillin (50 μg/ml) and incubated overnight at 37° C. Single colonies were inoculated into 250 ml baffled shake flasks containing 20 ml Luria Bertani broth (LB) and carbenicillin (100 μg/ml). Cultures were grown overnight at 20° C. with shaking at 200 rpm. The $OD_{600}$ of the overnight cultures were measured and the cultures were diluted into a 250 ml baffled shake flask containing 30 ml MagicMedia (Invitrogen)+carbenicillin (100 μg/ml) to an $OD_{600}$~0.05. The culture was incubated at 30° C. with shaking at 200 rpm. When the $OD_{600}$~0.5-0.8, 400 μM IPTG was added and the cells were incubated for a further 6 hours at 30° C. with shaking at 200 rpm. At 0, 2, 4 and 6 hours after induction with IPTG, 1 ml aliquots of the cultures were collected, the $OD_{600}$ was determined and the amount of isoprene produced was measured as described above. Results are shown in FIGS. 8A-8D.

IV. Production of Isoprene from BL21/ptrcKudzu in 14 Liter Fermentation

Large scale production of isoprene from *E. coli* containing the recombinant kudzu isoprene synthase gene was determined from a fed-batch culture. The recipe for the fermentation media (TM2) per liter of fermentation medium was as follows: $K_2HPO_4$ 13.6 g, $KH_2PO_4$ 13.6 g, MgSO4*7$H_2O$ 2 g, citric acid monohydrate 2 g, ferric ammonium citrate 0.3 g, $(NH_4)_2SO_4$ 3.2 g, yeast extract 5 g, 1000× Modified Trace Metal Solution 1 ml. All of the components were added together and dissolved in di$H_2O$. The pH was adjusted to 6.8 with potassium hydroxide (KOH) and q.s. to volume. The final product was filter sterilized with 0.22μ filter (only, do not autoclave). The recipe for 1000× Modified Trace Metal Solution was as follows: Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in $diH_2O$, pH to 3.0 with HCl/NaOH, then q.s. to volume and filter sterilized with a 0.22μ filter.

This experiment was carried out in 14 L bioreactor to monitor isoprene formation from glucose at the desired fermentation, pH 6.7 and temperature 34° C. An inoculum of *E. coli* strain BL21/ptrcKudzu taken from a frozen vial was prepared in soytone-yeast extract-glucose medium. After the inoculum grew to $OD_{550}$=0.6, two 600 ml flasks were centrifuged and the contents resuspended in 70 ml supernatant to transfer the cell pellet (70 ml of OD 3.1 material) to the bioreactor. At various times after inoculation, samples were removed and the amount of isoprene produced was determined as described above. Results are shown in FIGS. 9A and 9B.

Example 11

Production of Isoprene in *E. coli* Expressing Recombinant Poplar Isoprene Synthase The protein sequence for the poplar (*Populus alba* x *Populus tremula*) isoprene synthase (Schnitzler, J-P, et al. (2005) *Planta* 222:777-786) was obtained from GenBank (CAC35696). A gene, codon optimized for *E. coli*, was purchased from DNA2.0 (p9796-poplar, FIGS. 30 and 31A and 31B). The isoprene synthase gene was removed from the supplied plasmid by restriction endonuclease digestion with BspLU11I/PstI, gel-purified, and ligated into pTrcHis2B that had been digested with NcoI/PstI. The construct is cloned such that the stop codon in the insert is before the PstI site, which results in a construct in which the His-Tag is not attached to the isoprene synthase protein. The resulting plasmid pTrcPoplar (FIGS. 32 and 33A-33C), was verified by sequencing.

Example 12

Figure 10A:
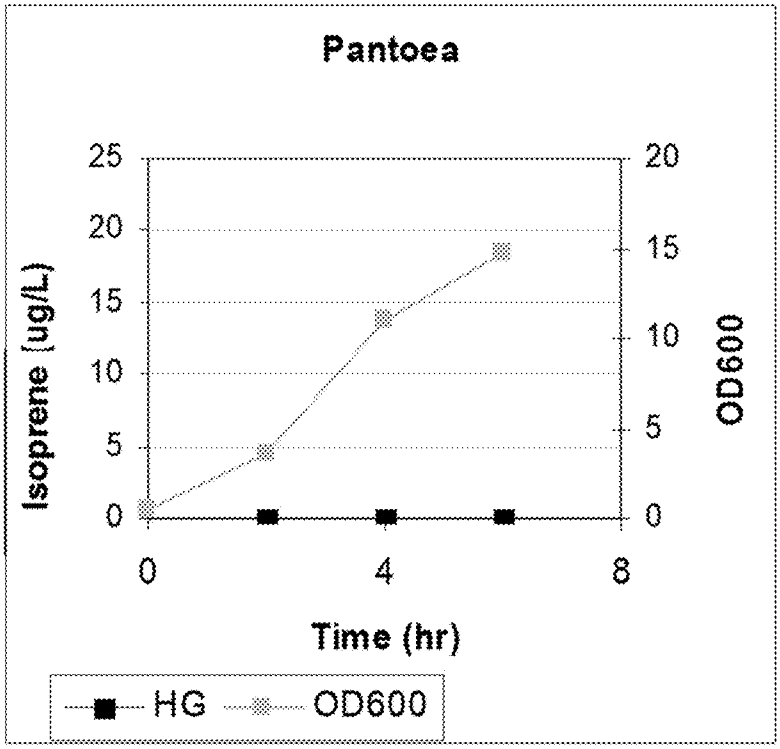
FIG. 10A is a graph showing the production of isoprene in *Panteoa citrea*. Control cells without recombinant kudzu isoprene synthase. Grey diamonds represent isoprene synthesis, black squares represent $OD_{600}$).
Figure 10B:
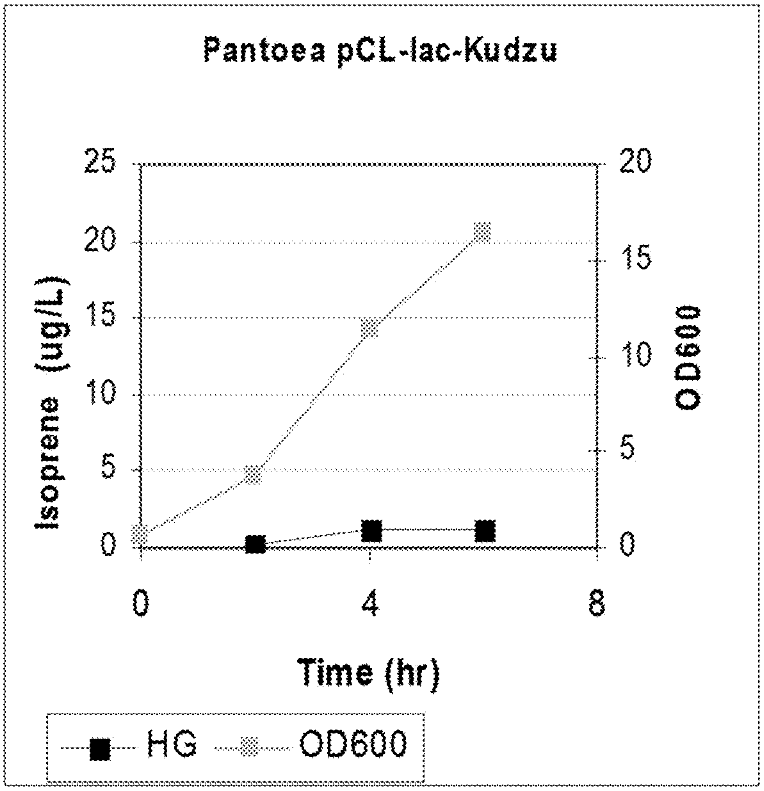
FIG. 10B is a graph showing the production of isoprene in *Panteoa citrea* expressing pCL-lac Kudzu. Grey diamonds represent isoprene synthesis, black squares represent $OD_{600}$.
Figure 10C:
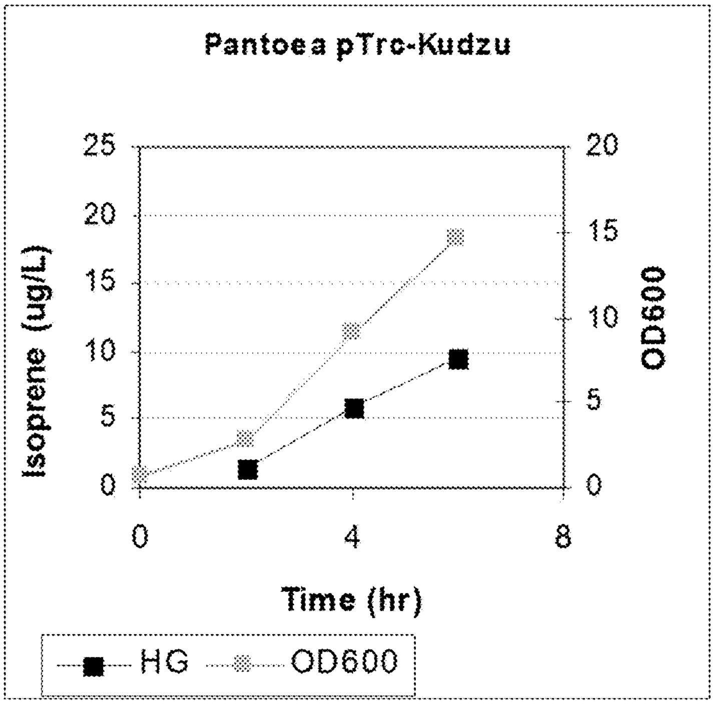
FIG. 10C is a graph showing the production of isoprene in *Panteoa citrea* expressing pTrcKudzu. Grey diamonds represent isoprene synthesis, black squares represent $OD_{600}$.

Production of Isoprene in *Panteoa citrea* Expressing Recombinant Kudzu Isoprene Synthase The pTrcKudzu and pCL-lac Kudzu plasmids described in Example 10 were electroporated into *P. citrea* (U.S. Pat. No. 7,241,587). Transformants were selected on LA containing carbenicillin (200 μg/ml) or spectinomycin (50 μg/ml) respectively. Production of isoprene from shake flasks and determination of the amount of isoprene produced was performed as described in Example 10 for *E. coli* strains expressing recombinant kudzu isoprene synthase. Results are shown in FIGS. 10A-10C.

Example 13

Production of Isoprene in *Bacillus subtilis* Expressing Recombinant Kudzu Isoprene Synthase I. Construction of a *B. subtilis* Replicating Plasmid for the Expression of Kudzu Isoprene Synthase The kudzu isoprene synthase gene was expressed in *Bacillus subtilis* aprEnprE Pxyl-comK strain (BG3594comK) using a replicating plasmid (pBS19 with a chloramphenicol resistance cassette) under control of the aprE promoter. The isoprene synthase gene, the aprE promoter and the transcription terminator were amplified separately and fused using PCR. The construct was then cloned into pBS 19 and transformed into *B. subtilis*.

a) Amplification of the aprE Promoter

The aprE promoter was amplified from chromosomal DNA from *Bacillus subtilis* using the following primers:

```
CF 797 (+) Start aprE promoter MfeI
                                    (SEQ ID NO: 58)
5'-GACATCAATTGCTCCATTTTCTTCTGCTATC

CF 07-43 (-) Fuse aprE promoter to Kudzu ispS
                                    (SEQ ID NO: 59)
5'-ATTGAGAAGAGGTCGCACACACTCTTTACCCTCTCCTTTTA
```

b) Amplification of the Isoprene Synthase Gene

The kudzu isoprene synthase gene was amplified from plasmid pTrcKudzu (SEQ ID NO:2). The gene had been codon optimized for *E. coli* and synthesized by DNA 2.0. The following primers were used:

```
CF 07-42 (+) Fuse the aprE promoter to kudzu
isoprene synthase gene (GTG start codon)
                                    (SEQ ID NO: 60)
5'-TAAAAGGAGAGGGTAAAGAGTGTGTGCGACCTCTTCTCAAT

CF 07-45 (-) Fuse the 3' end of kudzu isoprene
synthase gene to the terminator
                                    (SEQ ID NO: 61)
5'-CCAAGGCCGGTTTTTTTTAGACATACATCAGCTGGTTAATC
```

c) Amplification of the Transcription Terminator

The terminator from the alkaline serine protease of *Bacillus amyliquefaciens* was amplified from a previously sequenced plasmid pJHPms382 using the following primers:

```
CF 07-44 (+) Fuse the 3' end of kudzu isoprene
synthase to the terminator
                                    (SEQ ID NO: 62)
5'-GATTAACCAGCTGATGTATGTCTAAAAAAAACCGGCCTTGG

CF 07-46 (-) End of B. amyliquefaciens terminator
(BamHI)
                                    (SEQ ID NO: 63)
5'-GACATGACGGATCCGATTACGAATGCCGTCTC
```

The kudzu fragment was fused to the terminator fragment using PCR with the following primers:

```
CF 07-42 (+) Fuse the aprE promoter to kudzu
isoprene synthase gene (GTG start codon)
                                    (SEQ ID NO: 60)
5'-TAAAAGGAGAGGGTAAAGAGTGTGTGCGACCTCTTCTCAAT

CF 07-46 (-) End of B. amyliquefaciens terminator
(BamHI)
                                    (SEQ ID NO: 63)
5'-GACATGACGGATCCGATTACGAATGCCGTCTC
```

The kudzu-terminator fragment was fused to the promoter fragment using PCR with the following primers:

```
CF 797 (+) Start aprE promoter MfeI
                                    (SEQ ID NO: 64)
5'-GACATCAATTGCTCCATTTTCTTCTGCTATC

CF 07-46 (-) End of B. amyliquefaciens terminator
(BamHI)
                                    (SEQ ID NO: 63)
5'-GACATGACGGATCCGATTACGAATGCCGTCTC
```

The fusion PCR fragment was purified using a Qiagen kit and digested with the restriction enzymes MfeI and BamHI.

This digested DNA fragment was gel purified using a Qiagen kit and ligated to a vector known as pBS19, which had been digested with EcoRI and BamHI and gel purified.

The ligation mix was transformed into *E. coli* Top 10 cells and colonies were selected on LA+50 carbenicillin plates. A total of six colonies were chosen and grown overnight in LB+50 carbenicillin and then plasmids were isolated using a Qiagen kit. The plasmids were digested with EcoRI and BamHI to check for inserts and three of the correct plasmids were sent in for sequencing with the following primers:

```
CF 149 (+) EcoRI start of aprE promoter
                                         (SEQ ID NO: 65)
5'-GACATGAATTCCTCCATTTTCTTCTGC

CF 847 (+) Sequence in pXX 049 (end of aprE
promoter)
                                         (SEQ ID NO: 66)
5'-AGGAGAGGGTAAAGAGTGAG

CF 07-45 (-) Fuse the 3' end of kudzu isoprene
synthase to the terminator
                                         (SEQ ID NO: 61)
5'-CCAAGGCCGGTTTTTTTTAGACATACATCAGCTGGTTAATC

CF 07-48 (+) Sequencing primer for kudzu isoprene
synthase
                                         (SEQ ID NO: 67)
5'-CTTTTCCATCACCCACCTGAAG

CF 07-49 (+) Sequencing in kudzu isoprene synthase
                                         (SEQ ID NO: 68)
5'-GGCGAAATGGTCCAACAACAAAATTATC
```

The plasmid designated pBS Kudzu #2 (FIGS. 52 and 12A-12C) was correct by sequencing and was transformed into BG 3594 comK, a *Bacillus subtilis* host strain. Selection was done on LA+5 chloramphenicol plates. A transformant was chosen and struck to single colonies on LA+5 chloramphenicol, then grown in LB+5 chloramphenicol until it reached an $OD_{600}$ of 1.5. It was stored frozen in a vial at −80° C. in the presence of glycerol. The resulting strain was designated CF 443.

Figure 11:
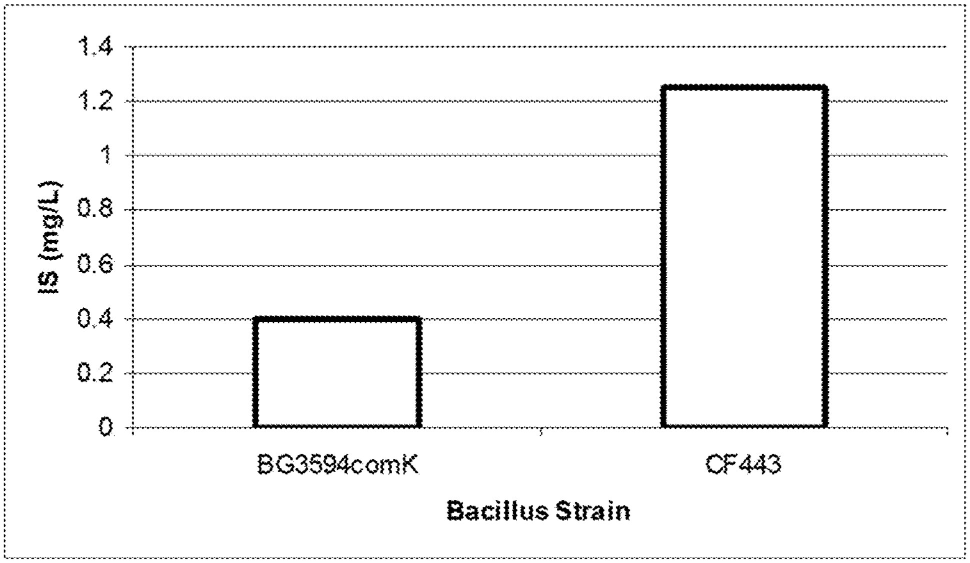
FIG. 11 is a graph showing the production of isoprene in *Bacillus subtilis* expressing recombinant isoprene synthase. BG3594comK is a *B. subtilis* strain without plasmid (native isoprene production). CF443-BG3594comK is a *B. subtilis* strain with pBSKudzu (recombinant isoprene production). IS on the y-axis indicates isoprene.

II. Production of Isoprene in Shake Flasks Containing *B. subtilis* Cells Expressing Recombinant Isoprene Synthase Overnight cultures were inoculated with a single colony of CF 443 from a LA+Chloramphenicol (Cm, 25 μg/ml). Cultures were grown in LB+Cm at 37° C. with shaking at 200 rpm. These overnight cultures (1 ml) were used to inoculate 250 ml baffled shake flasks containing 25 ml Grants II media and chloramphenicol at a final concentration of 25 μg/ml. Grants II Media recipe was 10 g soytone, 3 ml 1M $K_2HPO_4$, 75 g glucose, 3.6 g urea, 100 ml 10×MOPS, q.s. to 1 L with $H_2O$, pH 7.2; 10×MOPS recipe was 83.72 g MOPS, 7.17 g tricine, 12 g KOH pellets, 10 ml 0.276M $K_2SO_4$ solution, 10 ml 0.528M $MgCl_2$ solution, 29.22 g NaCl, 100 ml 100× micronutrients, q.s. to 1 L with $H_2O$; and 100× micronutrients recipe was 1.47 g $CaCl_2$*$2H_2O$, 0.4 g $FeSO_4.7H_2O$, 0.1 g $MnSO_4$*$H_2O$, 0.1 g $ZnSO_4$*$H_2O$, 0.05 g $CuCl_2$*$2H_2O$, 0.1 g $CoCl_2$*$6H_2O$, 0.1 g $Na_2MoO_4.2H_2O$, q.s. to 1 L with $H_2O$. Shake flasks were incubated at 37° C. and samples were taken at 18, 24, and 44 hours. At 18 hours the headspaces of CF443 and the control strain were sampled. This represented 18 hours of accumulation of isoprene. The amount of isoprene was determined by gas chromatography as described in Example 10. Production of isoprene was enhanced significantly by expressing recombinant isoprene synthase (FIG. 11).

III. Production of Isoprene by CF443 in 14 L Fermentation

Large scale production of isoprene from *B. subtilis* containing the recombinant kudzu isoprene synthase gene on a replication plasmid was determined from a fed-batch culture. *Bacillus* strain CF 443, expressing a kudzu isoprene synthase gene, or control stain which does not express a kudzu isoprene synthase gene were cultivated by conventional fed-batch fermentation in a nutrient medium containing soy meal (Cargill), sodium and potassium phosphate, magnesium sulfate and a solution of citric acid, ferric chloride and manganese chloride. Prior to fermentation the media is macerated for 90 minutes using a mixture of enzymes including cellulases, hemicellulases and pectinases (see, WO95/04134). 14-L batch fermentations are fed with 60% wt/wt glucose (Cargill DE99 dextrose, ADM Versadex greens or Danisco invert sugar) and 99% wt/wt oil (Western Family soy oil, where the 99% wt/wt is the concentration of oil before it was added to the cell culture medium). Feed was started when glucose in the batch was non-detectable. The feed rate was ramped over several hours and was adjusted to add oil on an equal carbon basis. The pH was controlled at 6.8-7.4 using 28% w/v ammonium hydroxide. In case of foaming, antifoam agent was added to the media. The fermentation temperature was controlled at 37° C. and the fermentation culture was agitated at 750 rpm. Various other parameters such as pH, DO %, airflow, and pressure were monitored throughout the entire process. The DO % is maintained above 20. Samples were taken over the time course of 36 hours and analyzed for cell growth ($OD_{550}$) and isoprene production. Results of these experiments are presented in FIGS. 53A and 53B.

IV. Integration of the Kudzu Isoprene Synthase (ispS) in *B. subtilis.*

The kudzu isoprene synthase gene was cloned in an integrating plasmid (pJH101-cmpR) under the control of the aprE promoter. Under the conditions tested, no isoprene was detected.

Example 14

Production of Isoprene in *Trichoderma*

I. Construction of Vectors for Expression of the Kudzu Isoprene Synthase in *Trichoderma reesei*

The *Yarrowia lipolytica* codon-optimized kudzu IS gene was synthesized by DNA 2.0 (SEQ ID NO:8) (FIG. 13). This plasmid served as the template for the following PCR amplification reaction: 1 μl plasmid template (20 ng/ul), 1 μl Primer EL-945 (10 uM) 5'-GCTTATGGATCCTCTAGACTATTACACGTACATCAATTGG (SEQ ID NO:9), 1 μl Primer EL-965 (10 uM) 5'-CACCATGTGTGCAACCTCCTCCCAGTTTAC (SEQ ID NO:10), 1 μl dNTP (10 mM), 5 μl 10×PfuUltra II Fusion HS DNA Polymerase Buffer, 1 μl PfuUltra II Fusion HS DNA Polymerase, 40 μl water in a total reaction volume of 50 μl. The forward primer contained an additional 4 nucleotides at the 5'-end that did not correspond to the *Y. lipolytica* codon-optimized kudzu isoprene synthase gene, but was required for cloning into the pENTR/D-TOPO vector. The reverse primer contained an additional 21 nucleotides at the 5'-end that did not correspond to the *Y. lipolytica* codon-optimized kudzu isoprene synthase gene, but were inserted for cloning into other vector backbones. Using the MJ Research PTC-200 Thermocycler, the PCR reaction was performed as follows: 95° C. for 2 minutes (first cycle only), 95° C. for 30 seconds, 55° C. for 30 seconds, 72° C. for 30 seconds (repeat for 27 cycles), 72° C. for 1 minute after the last cycle. The PCR product was analyzed on a 1.2% E-gel to confirm successful amplification of the *Y. lipolytica* codon-optimized kudzu isoprene synthase gene.

The PCR product was then cloned using the TOPO pENTR/D-TOPO Cloning Kit following manufacturer's protocol: 1 μl PCR reaction, 1 μl Salt solution, 1 μl TOPO pENTR/D-TOPO vector and 3 μl water in a total reaction volume of 6 μl. The reaction was incubated at room temperature for 5 minutes. One microliter of TOPO reaction was transformed into TOP10 chemically competent *E. coli* cells. The transformants were selected on LA+50 μg/ml kanamycin plates. Several colonies were picked and each was inoculated into a 5 ml tube containing LB+50 μg/ml kanamycin and the cultures grown overnight at 37° C. with shaking at 200 rpm. Plasmids were isolated from the overnight culture tubes using QIAprep Spin Miniprep Kit, following manufacturer's protocol. Several plasmids were sequenced to verify that the DNA sequence was correct.

A single pENTR/D-TOPO plasmid, encoding a *Y. lipolytica* codon-optimized kudzu isoprene synthase gene, was used for Gateway Cloning into a custom-made pTrex3g vector. Construction of pTrex3g is described in WO 2005/001036 A2. The reaction was performed following manufacturer's protocol for the Gateway LR Clonase II Enzyme Mix Kit (Invitrogen): 1 μl *Y. lipolytica* codon-optimized kudzu isoprene synthase gene pENTR/D-TOPO donor vector, 1 μl pTrex3g destination vector, 6 μl TE buffer, pH 8.0 in a total reaction volume of 8 μl. The reaction was incubated at room temperature for 1 hour and then 1 μl proteinase K solution was added and the incubation continued at 37° C. for 10 minutes. Then 1 μl of reaction was transformed into TOP10 chemically competent *E. coli* cells. The transformants were selected on LA+50 μg/ml carbenicillin plates. Several colonies were picked and each was inoculated into a 5 ml tube containing LB+50 μg/ml carbenicillin and the cultures were grown overnight at 37° C. with shaking at 200 rpm. Plasmids were isolated from the overnight culture tubes using QIAprep Spin Miniprep Kit (Qiagen, Inc.), following manufacturer's protocol. Several plasmids were sequenced to verify that the DNA sequence was correct.

Figure 14:
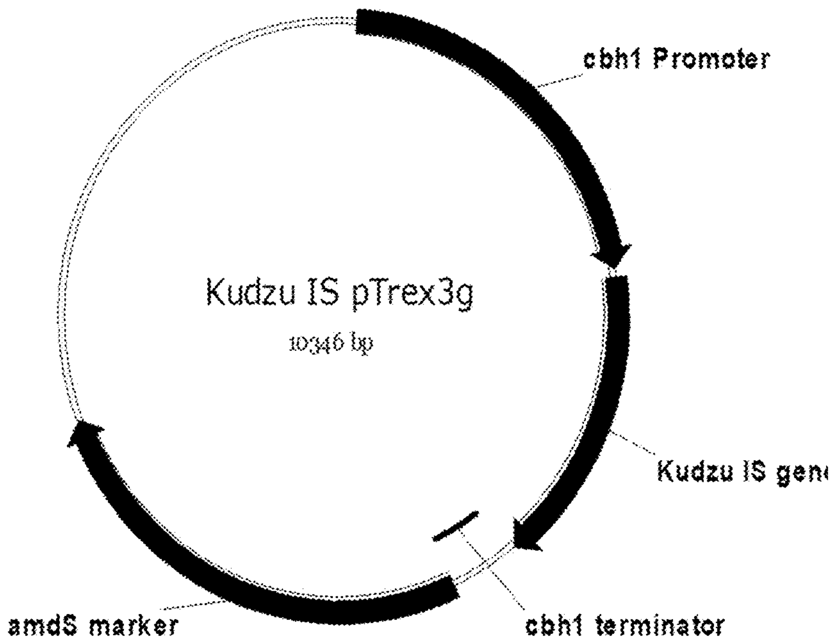
FIG. 14 is a map of pTrex3g comprising a kudzu isoprene synthase gene codon-optimized for expression in *Yarrowia.*

Biolistic transformation of *Y. lipolytica* codon-optimized kudzu isoprene synthase pTrex3g plasmid (FIG. 14) into a quad delete *Trichoderma reesei* strain was performed using the Biolistic PDS-1000/HE Particle Delivery System (see WO 2005/001036 A2). Isolation of stable transformants and shake flask evaluation was performed using protocol listed in Example 11 of patent publication WO 2005/001036 A2.

II. Production of Isoprene in Recombinant Strains of *T. reesei*

One ml of 15 and 36 hour old cultures of isoprene synthase transformants described above were transferred to head space vials. The vials were sealed and incubated for 5 hours at 30° C. Head space gas was measured and isoprene was identified by the method described in Example 10. Two of the transformants showed traces of isoprene. The amount of isoprene could be increased by a 14 hour incubation. The two positive samples showed isoprene at levels of about 0.5 μg/L for the 14 hour incubation. The untransformed control showed no detectable levels of isoprene. This experiment shows that *T. reesei* is capable of producing isoprene from endogenous precursor when supplied with an exogenous isoprene synthase.

Example 15

Production of Isoprene in *Yarrowia*

I. Construction of Vectors for Expression of the Kudzu Isoprene Synthase in *Yarrowia lipolytica.*

The starting point for the construction of vectors for the expression of the kudzu isoprene synthase gene in *Yarrowia lipolytica* was the vector pSPZ1(MAP29Spb). The complete sequence of this vector (SEQ ID No:11) is shown in FIGS. 15A-15C.

The following fragments were amplified by PCR using chromosomal DNA of a *Y. lipolytica* strain GICC 120285 as the template: a promotorless form of the URA3 gene, a fragment of 18S ribosomal RNA gene, a transcription terminator of the *Y. lipolytica* XPR2 gene and two DNA fragments containing the promoters of XPR2 and ICL1 genes. The following PCR primers were used:

```
ICL1 3
                                        (SEQ ID NO: 69)
5'-GGTGAATTCAGTCTACTGGGGATTCCCAAATCTATATATACTGCAG

GTGAC

ICL1 5
                                        (SEQ ID NO: 70)
5'-GCAGGTGGGAAACTATGCACTCC

XPR 3
                                        (SEQ ID NO: 71)
5'-CCTGAATTCTGTTGGATTGGAGGATTGGATAGTGGG

XPR 5
                                        (SEQ ID NO: 72)
5'-GGTGTCGACGTACGGTCGAGCTTATTGACC

XPRT3
                                        (SEQ ID NO: 73)
5'-GGTGGGCCCGCATTTTGCCACCTACAAGCCAG

XPRT 5
                                        (SEQ ID NO: 74)
5'-GGTGAATTCTAGAGGATCCCAACGCTGTTGCCTACAACGG

Y18S3
                                        (SEQ ID NO: 75)
5'-GGTGCGGCCGCTGTCTGGACCTGGTGAGTTTCCCCG

Y18S 5
                                        (SEQ ID NO: 76)
5'-GGTGGGCCCATTAAATCAGTTATCGTTTATTTGATAG

YURA3
                                        (SEQ ID NO: 77)
5'-GGTGACCAGCAAGTCCATGGGTGGTTTGATCATGG

YURA 50
                                        (SEQ ID NO: 78)
5'-GGTGCGGCCGCCTTTGGAGTACGACTCCAACTATG

YURA 51
                                        (SEQ ID NO: 79)
5'-GCGGCCGCAGACTAAATTTATTTCAGTCTCC
```

For PCR amplification the PfuUltraII polymerase (Stratagene), supplier-provided buffer and dNTPs, 2.5 μM primers and the indicated template DNA were used as per the manufacturer's instructions. The amplification was done using the following cycle: 95° C. for 1 min; 34× (95° C. for 30 sec; 55° C. for 30 sec; 72° C. for 3 min) and 10 min at 72° C. followed by a 4° C. incubation.

Figure 18A:
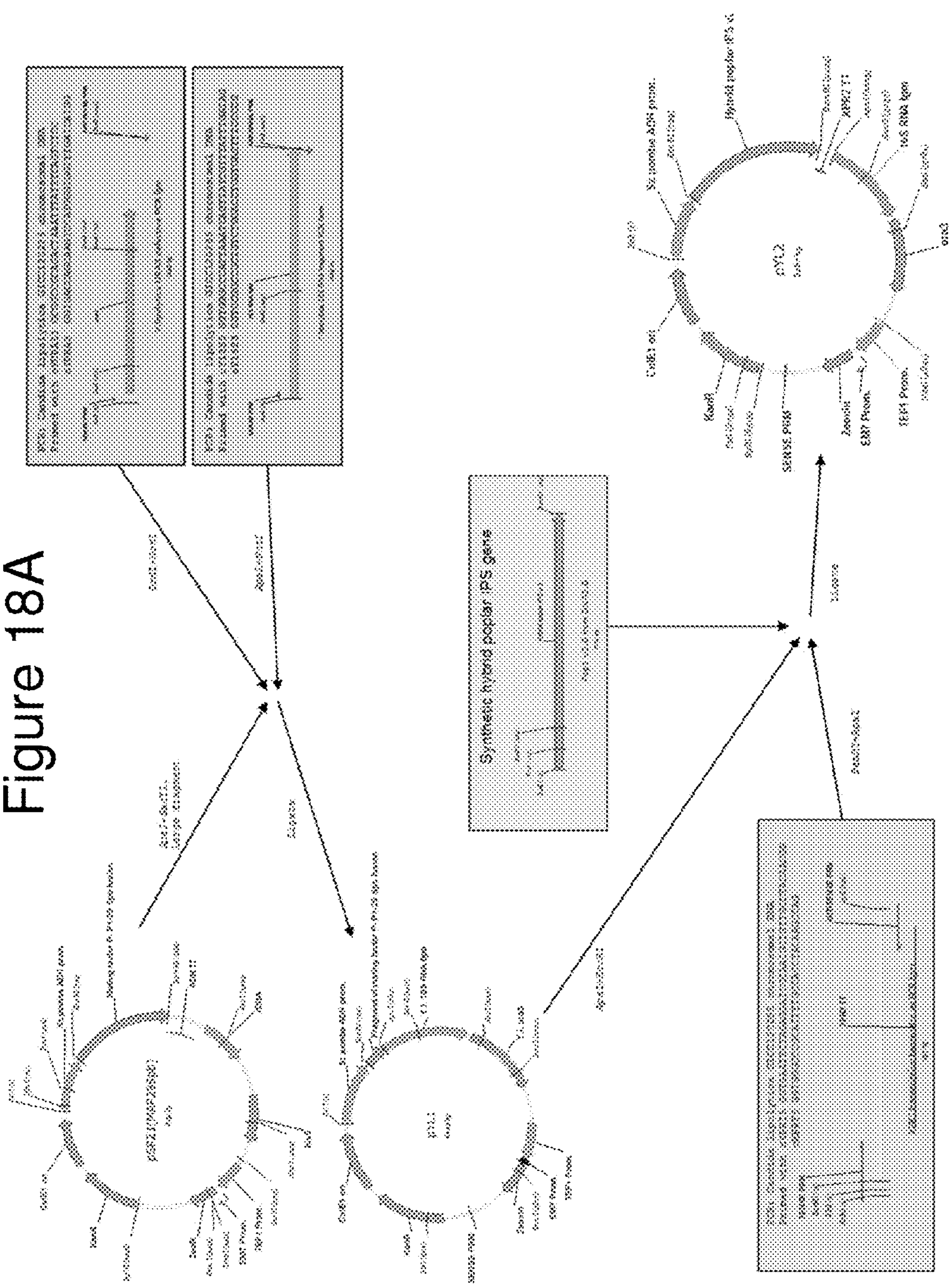
FIG. 18A shows a schematic outlining construction of vectors pYLA 1, pYL1 and pYL2 (SEQ ID NO:73-77, SEQ ID NO:79).
Figure 18B:
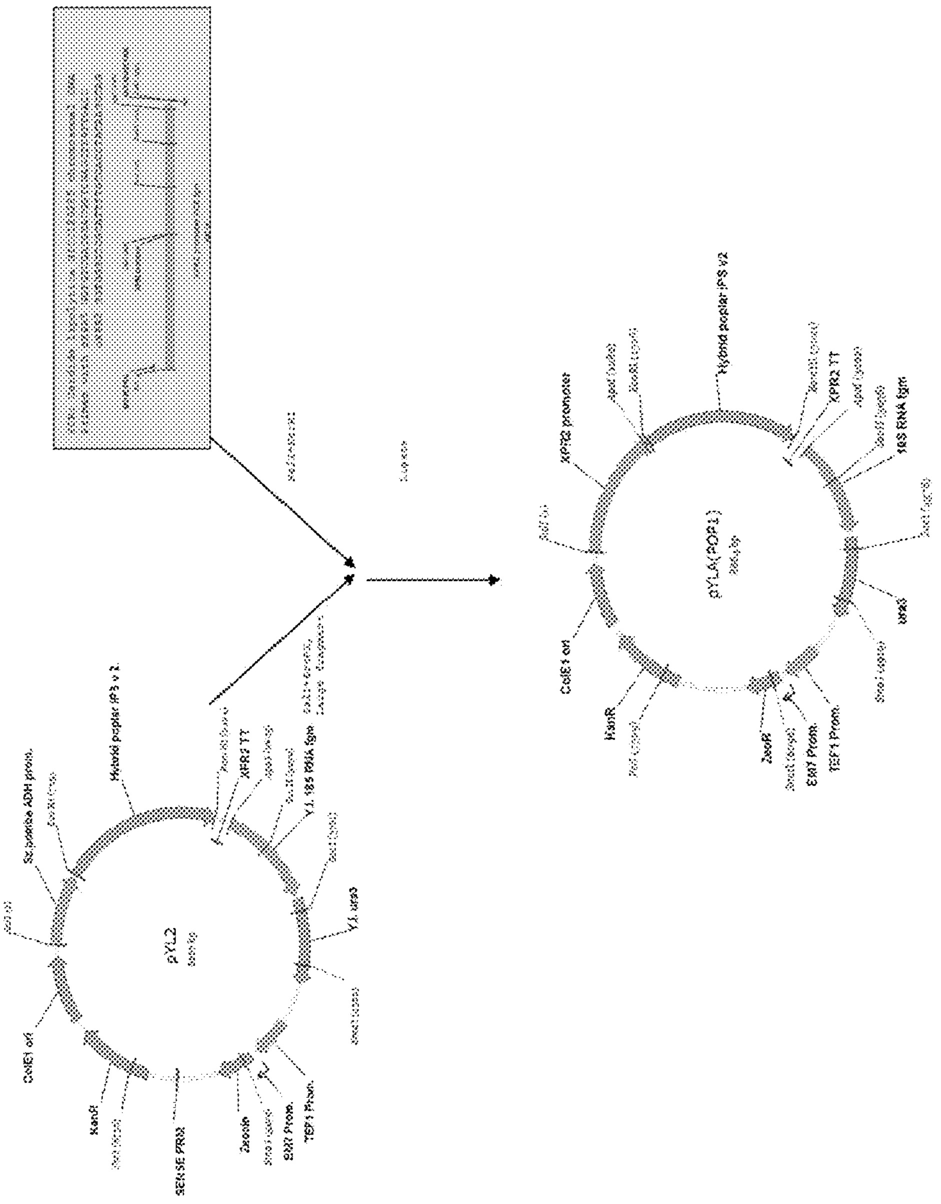
FIG. 18B shows a schematic outlining construction of the vector pYLA(POP1) (SEQ ID NO:72-73).
Figure 18C:
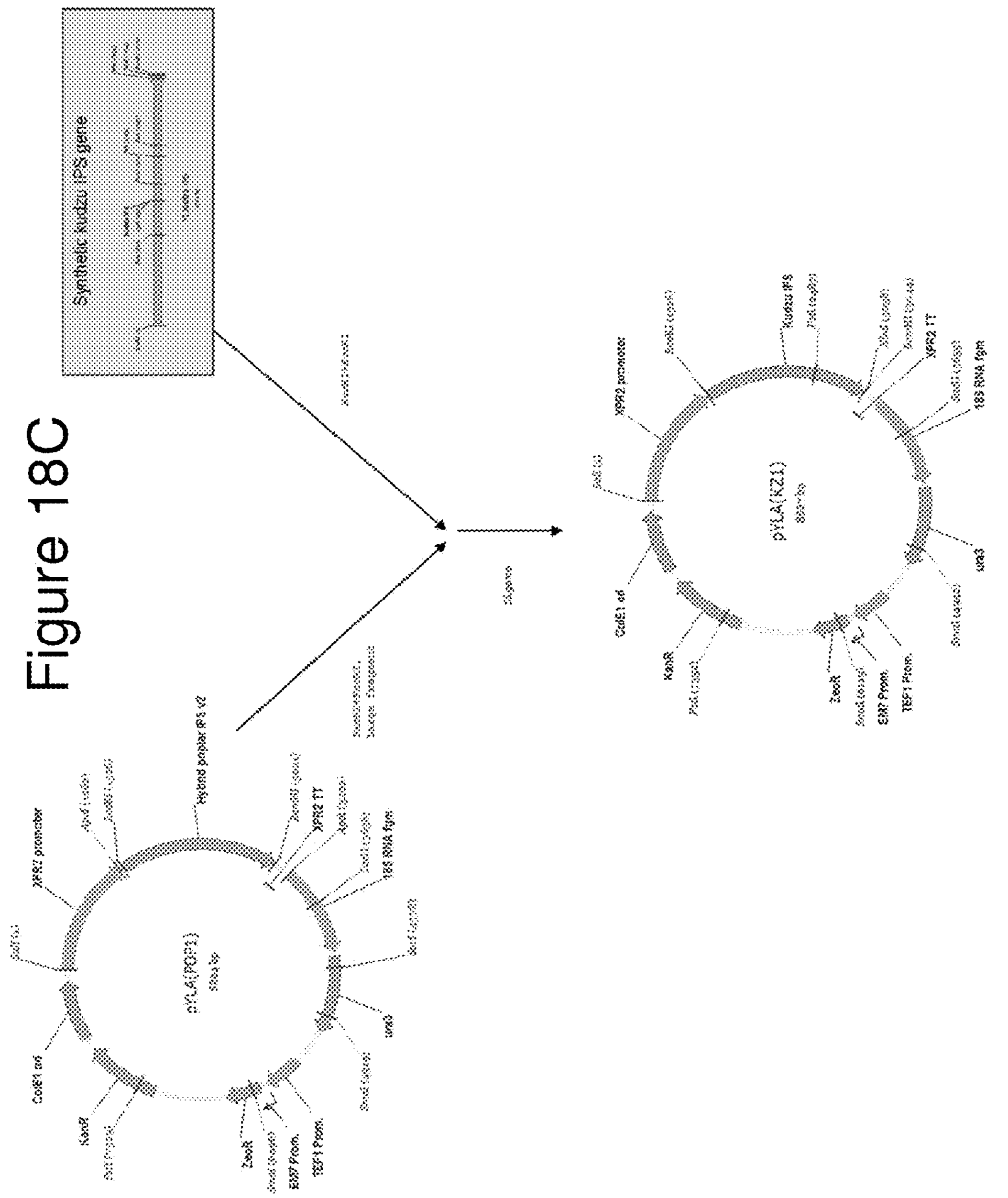
FIG. 18C shows a schematic outlining construction of the vector pYLA(KZ1) (SEQ ID NO:70-71).
Figure 18D:
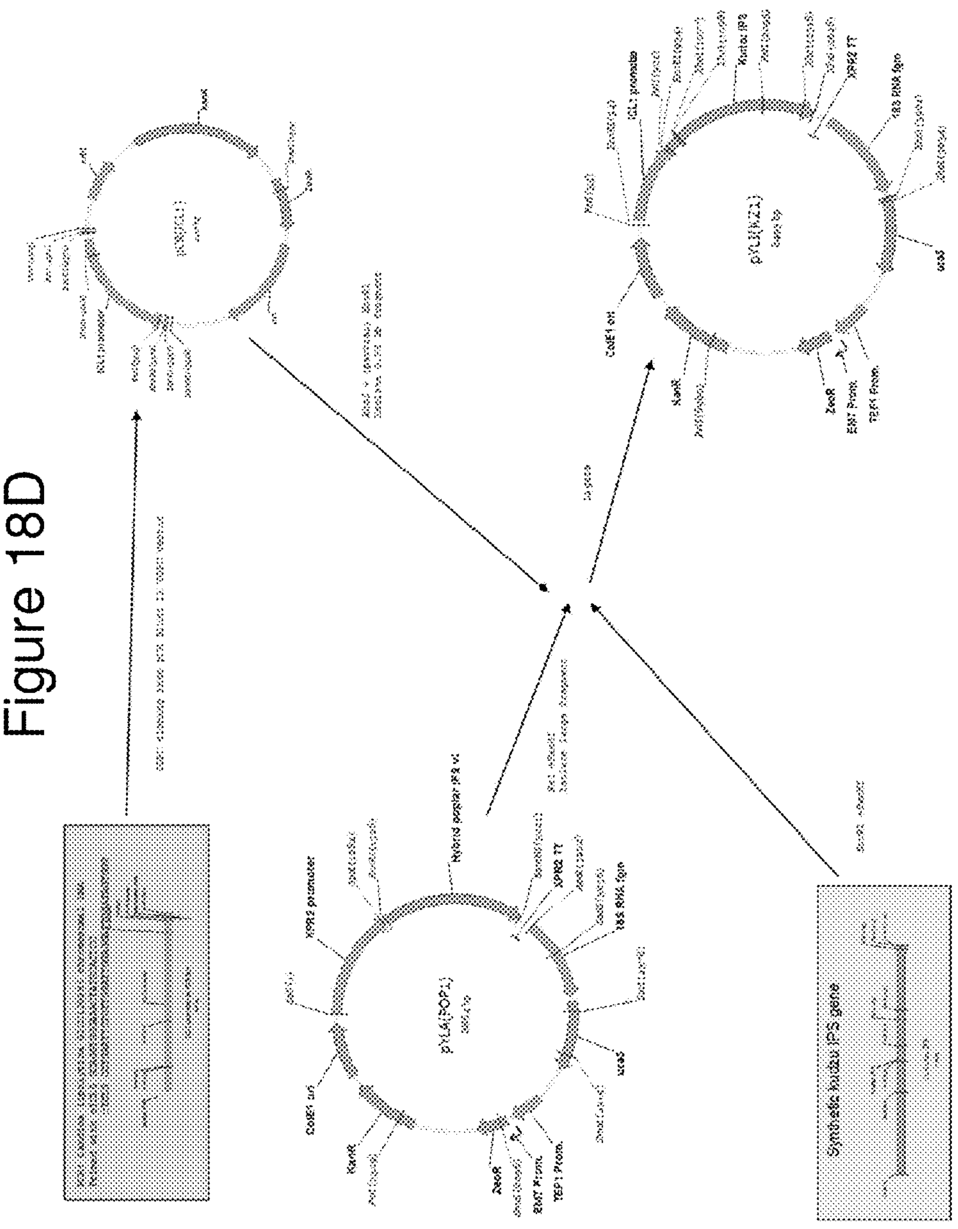
FIG. 18D shows a schematic outlining construction of the vector pYLI(KZ1)
Figure 18E:
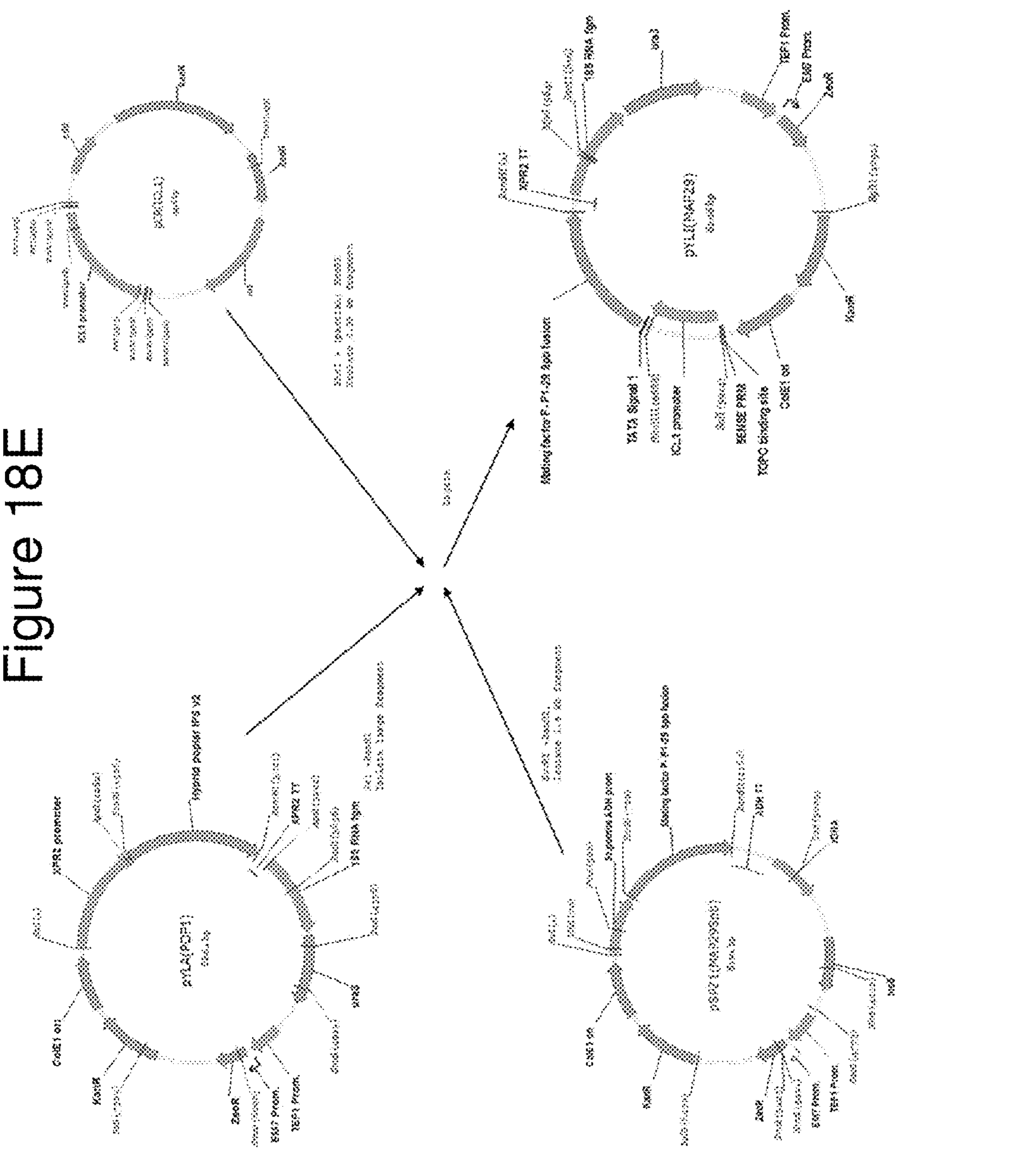
FIG. 18E shows a schematic outlining construction of the vector pYLI(MAP29)
Figure 18F:
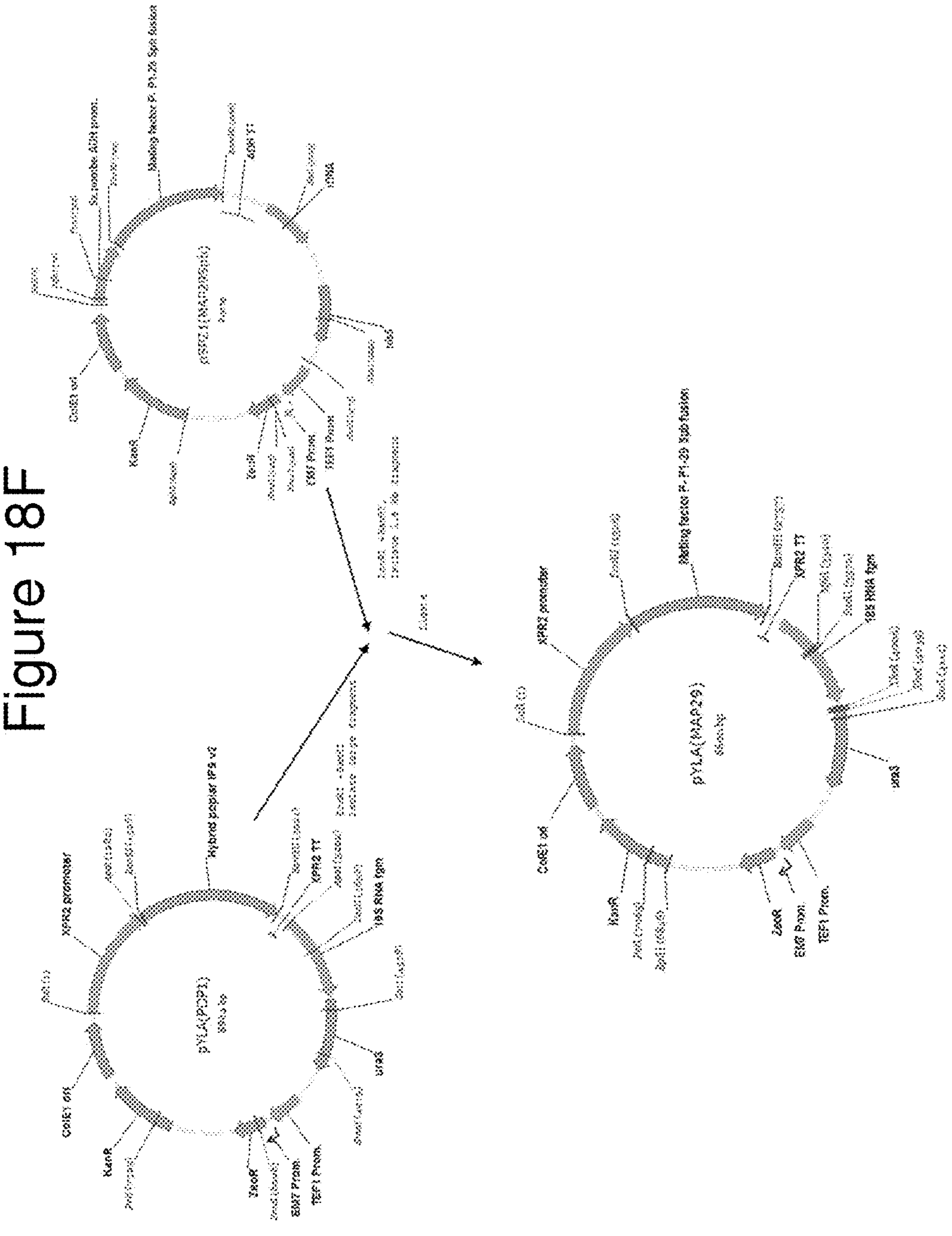
FIG. 18F shows a schematic outlining construction of the vector pYLA(MAP29)

Synthetic DNA molecules encoding the kudzu isoprene synthase gene, codon-optimized for expression in *Yarrowia*, was obtained from DNA 2.0 (FIG. 16; SEQ ID NO:12). Full detail of the construction scheme of the plasmids pYLA (KZ1) and pYLI(KZ1) carrying the synthetic kudzu isoprene synthase gene under control of XPR2 and ICL1 promoters respectively is presented in FIGS. 18A-18F. Control plasmids in which a mating factor gene (MAP29) is inserted in place of an isoprene synthase gene were also constructed (FIGS. 18E and 18F).

A similar cloning procedure can be used to express a poplar (*Populus alba* x *Populus tremula*) isoprene synthase gene.

The sequence of the poplar isoprene is described in Miller B. et al. (2001) *Planta* 213, 483-487 and shown in FIG. 17 (SEQ ID NO:13). A construction scheme for the generation the plasmids pYLA(POP1) and pYLI(POP1) carrying synthetic poplar isoprene synthase gene under control of XPR2 and ICL1 promoters respectively is presented in FIGS. 18A and B.

II. Production of Isoprene by Recombinant Strains of *Y. lipolytica*.

Vectors pYLA(KZ1), pYLI(KZ1), pYLA(MAP29) and pYLI(MAP29) were digested with SacII and used to transform the strain *Y. lipolytica* CLIB 122 by a standard lithium acetate/polyethylene glycol procedure to uridine prototrophy. Briefly, the yeast cells grown in YEPD (1% yeast extract, 2% peptone, 2% glucose) overnight, were collected by centrifugation (4000 rpm, 10 min), washed once with sterile water and suspended in 0.1 M lithium acetate, pH 6.0. Two hundred μl aliquots of the cell suspension were mixed with linearized plasmid DNA solution (10-20 μg), incubated for 10 minutes at room temperature and mixed with 1 ml of 50% PEG 4000 in the same buffer. The suspensions were further incubated for 1 hour at room temperature followed by a 2 minutes heat shock at 42° C. Cells were then plated on SC his leu plates (0.67% yeast nitrogen base, 2% glucose, 100 mg/L each of leucine and histidine). Transformants appeared after 3-4 days of incubation at 30° C.

Three isolates from the pYLA(KZ1) transformation, three isolates from the pYLI(KZ1) transformation, two isolates from the pYLA(MAP29) transformation and two isolates from the pYLI(MAP29) transformation were grown for 24 hours in YEP7 medium (1% yeast extract, 2% peptone, pH 7.0) at 30° C. with shaking. Cells from 10 ml of culture were collected by centrifugation, resuspended in 3 ml of fresh YEP7 and placed into 15 ml screw cap vials. The vials were incubated overnight at room temperature with gentle (60 rpm) shaking. Isoprene content in the headspace of these vials was analyzed by gas chromatography using mass-spectrometric detector as described in Example 10. All transformants obtained with pYLA(KZ1) and pYLI(KZ1) produced readily detectable amounts of isoprene (0.5 μg/L to 1 μg/L, FIG. 20). No isoprene was detected in the headspace of the control strains carrying phytase gene instead of an isoprene synthase gene.

Example 16

Production of Isoprene in *E. coli* Expressing Kudzu Isoprene Synthase and idi, or dxs, or idi and dxs I. Construction of Vectors Encoding Kudzu Isoprene Synthase and idi, or dxs, or idi and dxs for the Production of Isoprene in *E. coli* i) Construction of pTrcKudzuKan

The bla gene of pTrcKudzu (described in Example 10) was replaced with the gene conferring kanamycin resistance. To remove the bla gene, pTrcKudzu was digested with BspHI, treated with Shrimp Alkaline Phosphatase (SAP), heat killed at 65° C., then end-filled with Klenow fragment and dNTPs. The 5 kbp large fragment was purified from an agarose gel and ligated to the $kan^r$ gene which had been PCR amplified from pCR-Blunt-II-TOPO using primers MCM22 5'-GATCAAGCTTAACCGGAATTGCCAGCTG (SEQ ID NO:14) and MCM23 5'-GATCCGATCGTCAGAAGAACTCGTCAAGAAGGC (SEQ ID NO:15), digested with HindIII and PvuI, and end-filled. A transformant carrying a plasmid conferring kanamycin resistance (pTrcKudzuKan) was selected on LA containing kanamycin 50 μg/ml.

ii) Construction of pTrcKudzu yIDI Kan pTrcKudzuKan was digested with PstI, treated with SAP, heat killed and gel purified. It was ligated to a PCR product encoding idi from *S. cerevisiae* with a synthetic RBS. The primers for PCR were NsiI-YIDI 1 F 5'-CATCAATGCATCGCCCTTAGGAGGTAAAAAAAAATGAC (SEQ ID NO:16) and PstI-YIDI 1 R 5'-CCTTCTGCAGGACGCGTTGTTATAGC (SEQ ID NO:17); and the template was *S. cerevisiae* genomic DNA. The PCR product was digested with NsiI and PstI and gel purified prior to ligation. The ligation mixture was transformed into chemically competent TOP10 cells and selected on LA containing 50 μg/ml kanamycin. Several transformants were isolated and sequenced and the resulting plasmid was called pTrcKudzu-yIDI(kan) (FIGS. 34 and 35A-35C).

iii) Construction of pTrcKudzu DXS Kan

Plasmid pTrcKudzuKan was digested with PstI, treated with SAP, heat killed and gel purified. It was ligated to a PCR product encoding dxs from *E. coli* with a synthetic RBS. The primers for PCR were MCM 13 5'-GATCATGCATTCGCCCTTAGGAGGTAAAAAAACATGAGTTTTGATATTGCCAAATACCC G (SEQ ID NO:18) and MCM14 5'-CATGCTGCAGTTATGCCAGCCAGGCCTTGAT (SEQ ID NO:19); and the template was *E. coli* genomic DNA. The PCR product was digested with NsiI and PstI and gel purified prior to ligation. The resulting transformation reaction was transformed into TOP10 cells and selected on LA with kanamycin 50 μg/ml. Several transformants were isolated and sequenced and the resulting plasmid was called pTrcKudzu-DXS(kan) (FIGS. 36 and 37A-37C).

iv) Construction of pTrcKudzu-yIDI-dxs (kan)

pTrcKudzu-yIDI(kan) was digested with PstI, treated with SAP, heat killed and gel purified. It was ligated to a PCR product encoding *E. coli* dxs with a synthetic RBS (primers MCM13 5'-GATCATGCATTCGCCCTTAGGAGGTAAAAAAACATGAGTTTTGATATTGCCAAATACCC G (SEQ ID NO:18) and MCM14 5'-CATGCTGCAGTTATGCCAGCCAGGCCTTGAT (SEQ ID NO:19); template TOP10 cells) which had been digested with NsiI and PstI and gel purified. The final plasmid was called pTrcKudzu-yIDI-dxs (kan) (FIGS. 21 and 22A-22D).

v) Construction of pCL PtrcKudzu

A fragment of DNA containing the promoter, structural gene and terminator from Example 10 above was digested from pTrcKudzu using SspI and gel purified. It was ligated to pCL1920 which had been digested with PvuII, treated with SAP and heat killed. The resulting ligation mixture was transformed into TOP10 cells and selected in LA containing spectinomycin 50 μg/ml. Several clones were isolated and sequenced and two were selected. pCL PtrcKudzu and pCL PtrcKudzu (A3) have the insert in opposite orientations (FIGS. 38-41A-41C).

vi) Construction of pCL PtrcKudzu yIDI

The NsiI-PstI digested, gel purified, IDI PCR amplicon from (ii) above was ligated into pCL PtrcKudzu which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu yIDI (FIGS. 42 and 43A-43C).

vii) Construction of pCL PtrcKudzu DXS

The NsiI-PstI digested, gel purified, DXS PCR amplicon from (iii) above was ligated into pCL PtrcKudzu (A3) which had been digested with PstI, treated with SAP, and heat killed. The ligation mixture was transformed into TOP10 cells and selected in LA containing spectinomycin 50 μg/ml. Several clones were isolated and sequenced and the resulting plasmid is called pCL PtrcKudzu DXS (FIGS. 44 and 45A-45D).

II. Measurement of Isoprene in Headspace from Cultures Expressing Kudzu Isoprene Synthase, idi, and/or dxs at Different Copy Numbers.

Cultures of *E. coli* BL21(λDE3) previously transformed with plasmids pTrcKudzu(kan) (A), pTrcKudzu-yIDI kan (B), pTrcKudzu-DXS kan (C), pTrcKudzu-yIDI-DXS kan (D) were grown in LB kanamycin 50 μg/mL. Cultures of pCL PtrcKudzu (E), pCL PtrcKudzu, pCL PtrcKudzu-yIDI (F) and pCL PtrcKudzu-DXS (G) were grown in LB spectinomycin 50 μg/mL. Cultures were induced with 400 μM IPTG at time 0 ($OD_{600}$ approximately 0.5) and samples taken for isoprene headspace measurement (see Example 10). Results are shown in FIG. 23A-23G.

Plasmid pTrcKudzu-yIDI-dxs (kan) was introduced into *E. coli* strain BL21 by transformation. The resulting strain BL21/pTrc Kudzu IDI DXS was grown overnight in LB containing kanamycin (50 μg/ml) at 20° C. and used to inoculate shake flasks of TM3 (13.6 g $K_2PO_4$, 13.6 g $KH_2PO_4$, 2.0 g $MgSO_4.7H_2O$), 2.0 g citric acid monohydrate, 0.3 g ferric ammonium citrate, 3.2 g $(NH_4)_2SO_4$, 0.2 g yeast extract, 1.0 ml 1000× Modified Trace Metal Solution, adjusted to pH 6.8 and q.s. to $H_2O$, and filter sterilized) containing 1% glucose. Flasks were incubated at 30° C. until an $OD_{600}$ of 0.8 was reached, and then induced with 400 μM IPTG. Samples were taken at various times after induction and the amount of isoprene in the head space was measured as described in Example 10. Results are shown in FIG. 23H.

III. The Effect of Yeast Extract on Isoprene Production in *E. coli* Grown in Fed-Batch Culture Fermentation was performed at the 14-L scale as previously described with *E. coli* cells containing the pTrcKudzu yIDI DXS plasmid described above. Yeast extract (Bio Springer, Montreal, Quebec, Canada) was fed at an exponential rate. The total amount of yeast extract delivered to the fermentor was varied between 70-830 g during the 40 hour fermentation. Optical density of the fermentation broth was measured at a wavelength of 550 nm. The final optical density within the fermentors was proportional to the amount of yeast extract added (FIG. 48A). The isoprene level in the off-gas from the fermentor was determined as previously described. The isoprene titer increased over the course of the fermentation (FIG. 48B). The amount of isoprene produced was linearly proportional to the amount of fed yeast extract (FIG. 48C).

IV. Production of Isoprene in 500 L Fermentation of pTrcKudzu DXS yIDI

A 500 liter fermentation of *E. coli* cells with a kudzu isoprene synthase, *S. cerevisiae* IDI, and *E. coli* DXS nucleic acids (*E. coli* BL21 (λDE3) pTrc Kudzu dxs yidi) was used to produce isoprene. The levels of isoprene varied from 50 to 300 μg/L over a time period of 15 hours. On the basis of the average isoprene concentrations, the average flow through the device and the extent of isoprene breakthrough, the amount of isoprene collected was calculated to be approximately 17 g.

V. Production of Isoprene in 500 L Fermentation of *E. coli* Grown in Fed-Batch Culture Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium gas ($NH_3$) and q.s. to volume. Glucose 10 g, thiamine*HCl 0.1 g, and antibiotic were added after sterilization and pH adjustment.

1000× Modified Trace Metal Solution:

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in DI $H_2O$, pH to 3.0 with HCl/NaOH, then q.s. to volume and filter sterilized with 0.22 micron filter.

Fermentation was performed in a 500-L bioreactor with *E. coli* cells containing the pTrcKudzu yIDI DXS plasmid. This experiment was carried out to monitor isoprene formation from glucose and yeast extract at the desired fermentation pH 7.0 and temperature 30° C. An inoculum of *E. coli* strain taken from a frozen vial was prepared in soytone-yeast extract-glucose medium. After the inoculum grew to OD 0.15, measured at 550 nm, 20 ml was used to inoculate a bioreactor containing 2.5-L soytone-yeast extract-glucose medium. The 2.5-L bioreactor was grown at 30° C. to OD 1.0 and 2.0-L was transferred to the 500-L bioreactor.

Figure 49A:
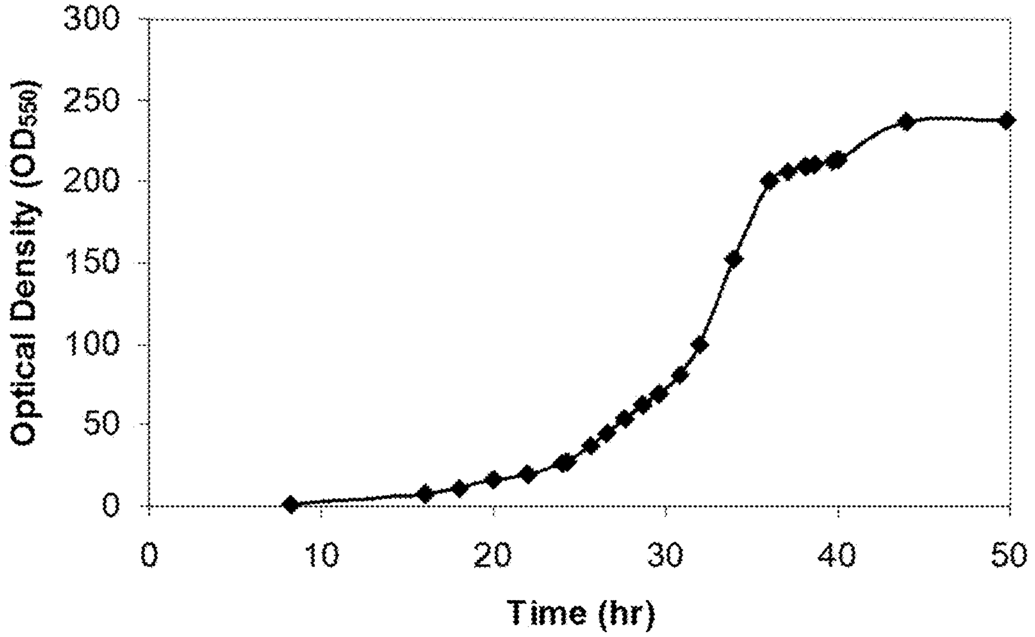
Figure 49B:
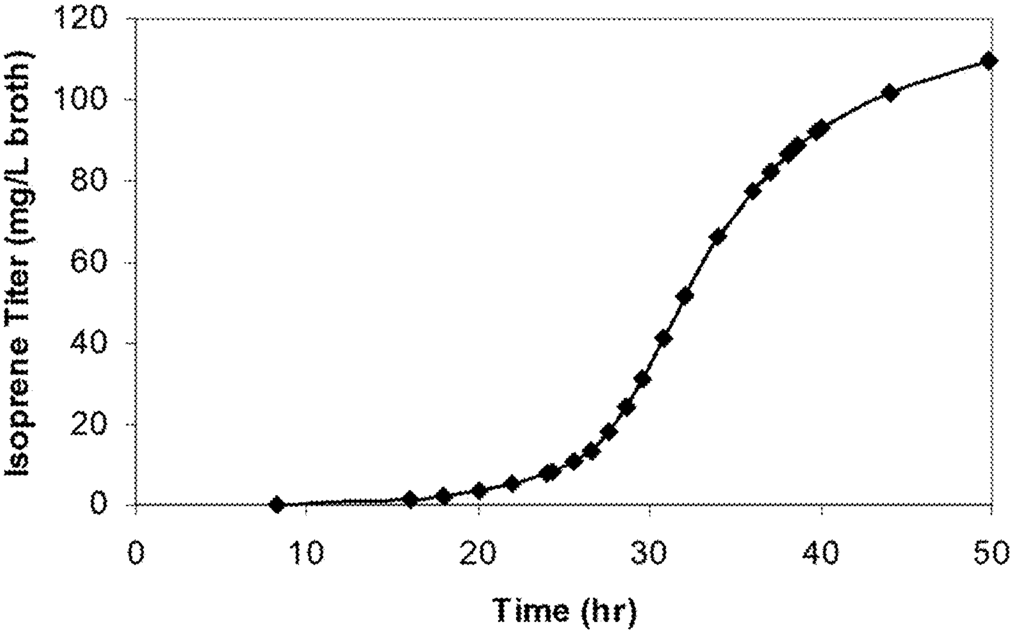
Figure 49C:
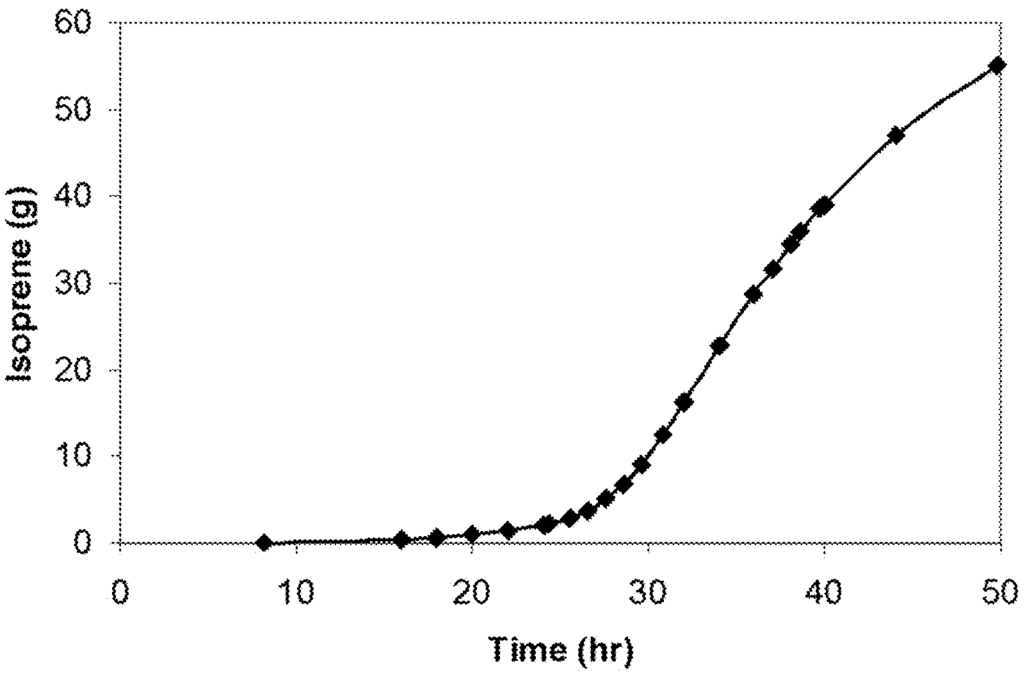

Yeast extract (Bio Springer, Montreal, Quebec, Canada) and glucose were fed at exponential rates. The total amount of glucose and yeast extract delivered to the bioreactor during the 50 hour fermentation was 181.2 kg and 17.6 kg, respectively. The optical density within the bioreactor over time is shown in FIG. 49A. The isoprene level in the off-gas from the bioreactor was determined as previously described. The isoprene titer increased over the course of the fermentation (FIG. 49B). The total amount of isoprene produced during the 50 hour fermentation was 55.1 g and the time course of production is shown in FIG. 49C.

Example 17

Production of Isoprene in *E. coli* Expressing Kudzu Isoprene Synthase and Recombinant Mevalonic Acid Pathway Genes I. Cloning the Lower MVA Pathway The strategy for cloning the lower mevalonic pathway was as follows. Four genes of the mevalonic acid biosynthesis pathway; mevalonate kinase (MVK), phosphomevalonate kinase (PMK), diphosphomevalonate decarboxylase (MVD) and isopentenyl diphosphate isomerase genes were amplified by PCR from *S. cerevisiae* chromosomal DNA and cloned individually into the pCR BluntII TOPO plasmid (Invitrogen). In some cases, the idi gene was amplified from *E. coli* chromosomal DNA. The primers were designed such that an *E. coli* consensus RBS (AGGAGGT (SEQ ID NO:80) or AAGGAGG (SEQ ID NO:81)) was inserted at the 5' end, 8 bp upstream of the start codon and a PstI site was added at the 3' end. The genes were then cloned one by one into the pTrcHis2B vector until the entire pathway was assembled.

Chromosomal DNA from *S. cerevisiae* S288C was obtained from ATCC (ATCC 204508D). The MVK gene was amplified from the chromosome of *S. cerevisiae* using primers MVKF (5'-AGGAGGTAAAAAAACATGTCATTACCGTTCTTAACTTCTGC, SEQ ID NO:21) and MVK-Pst1-R (5'-ATGGCTGCAGGCCTATCGCAAATTAGC TTATGAAGTCCATGGTAAATTCGTG, SEQ ID NO:22) using PfuTurbo as per manufacturer's instructions. The correct sized PCR product (1370 bp) was identified by electrophoresis through a 1.2% E-gel (Invitrogen) and cloned into pZeroBLUNT TOPO. The resulting plasmid was designated pMVK1. The plasmid pMVK1 was digested with SacI and Taq1 restriction endonucleases and the fragment was gel purified and ligated into pTrcHis2B digested with SacI and BstBI. The resulting plasmid was named pTrcMVK1 (also referred to as pTrcK).

The second gene in the mevalonic acid biosynthesis pathway, PMK, was amplified by PCR using primers: PstI-PMK1 R (5'-GAATTCGCCCTTCTGCAGCTACC, SEQ ID NO:23) and BsiHKA I-PMK1 F (5'-CGACTGGTGCACCCTTAAGGAGGAAAAAAACATGTCAG, SEQ ID NO:24). The PCR reaction was performed using Pfu Turbo polymerase (Stratagene) as per manufacturer's instructions. The correct sized product (1387 bp) was digested with PstI and BsiHKI and ligated into pTrcMVK1 digested with PstI. The resulting plasmid was named pTrcKK.

The MVD and the idi genes were cloned in the same manner. PCR was carried out using the primer pairs PstI-MVD 1 R (5'-GTGCTGGAATTCGCCCTTCTGCAGC, SEQ ID NO:25) and NsiI-MVD 1 F (5'-GTAGATGCATGCAGAATTCGCCCTTAAGGAGG, SEQ ID NO:26) to amplify the MVD gene and PstI-YIDI 1 R (5'-CCTTCTGCAGGACGCGTTGTTATAGC, SEQ ID NO:27) and NsiI-YIDI 1 F (5'-CATCAATGCATCGCCCTTAGGAGGTAAAAAAAAATGAC, SEQ ID NO:28) to amplify the yIDI gene. The plasmid with the MVK, PMK, and MVD genes inserted is named pTrcKKD. In some cases the IPP isomerase gene, idi from *E. coli* was used. To amplify idi from *E. coli* chromosomal DNA, the following primer set was used: PstI-CIDI 1 R (5'-GTGTGATGGATATCTGCAGAATTCG, SEQ ID NO:29) and NsiI-CIDI 1 F (5'-CATCAATGCATCGCCCTTAGGAGGTAAAAAAACATG, SEQ ID NO:30). Template DNA was chromosomal DNA isolated by standard methods from *E. coli* FM5 (WO 96/35796 and WO 2004/033646, which are each hereby incorporated by reference in their entireties, particularly with respect to isolation of nucleic acids). The final plasmids were named pKKDIy for the construct encoding the yeast idi gene or pKKDIc for the construct encoding the *E. coli* idi gene. The plasmids were transformed into *E. coli* hosts BL21 for subsequent analysis. In some cases the isoprene synthase from kudzu was cloned into pKKDIy yielding plasmid pKKDIyIS.

The lower MVA pathway was also cloned into pTrc containing a kanamycin antibiotic resistance marker. The plasmid pTrcKKDIy was digested with restriction endonucleases ApaI and PstI, the 5930 bp fragment was separated on a 1.2% agarose E-gel and purified using the Qiagen Gel Purification kit according to the manufacturer's instructions. The plasmid pTrcKudzuKan, described in Example 16, was digested with restriction endonucleases ApaI and PstI, and the 3338 bp fragment containing the vector was purified from a 1.2% E-gel using the Qiagen Gel Purification kit. The 3338 bp vector fragment and the 5930 bp lower MVA pathway fragment were ligated using the Roche Quick Ligation kit. The ligation mix was transformed into *E. coli* TOP10 cells and tranformants were grown at 37° C. overnight with selection on LA containing kanamycin (50 μg/ml). The transformants were verified by restriction enzyme digestion and one was frozen as a stock. The plasmid was designated pTrcKanKKDIy.

II. Cloning a Kudzu Isoprene Synthase Gene into pTrcKanKKDIy

The kudzu isoprene synthase gene was amplified by PCR from pTrcKudzu, described in Example 10, using primers MCM50 5'-GATCATGCATTCGCCCTTAGGAGGTAAAAAAACATGTGTGCGACCTCTTCTCAATTTAC T (SEQ ID NO:31) and MCM53 5'-CGGTCGACGGATCCCTGCAGTTAGACATACATCAGCTG (SEQ ID NO:32). The resulting PCR fragment was cloned into pCR2.1 and transformed into *E. coli* TOP10. This fragment contains the coding sequence for kudzu isoprene synthase and an upstream region containing a RBS from *E. coli*. Transformants were incubated overnight at 37° C. with selection on LA containing carbenicillin (50 μg/ml). The correct insertion of the fragment was verified by sequencing and this strain was designated MCM93.

The plasmid from strain MCM93 was digested with restriction endonucleases NsiI and PstI to liberate a 1724 bp insert containing the RBS and kudzu isoprene synthase. The 1724 bp fragment was separated on a 1.2% agarose E-gel and purified using the Qiagen Gel Purification kit according to the manufacturer's instructions. Plasmid pTrcKanKKDIy was digested with the restriction endonuclease PstI, treated with SAP for 30 minutes at 37° C. and purified using the Qiagen PCR cleanup kit. The plasmid and kudzu isoprene synthase encoding DNA fragment were ligated using the Roche Quick Ligation kit. The ligation mix was transformed into *E. coli* TOP10 cells and transformants were grown overnight at 37° C. with selection on LA containing Kanamycin at 50 μg/ml. The correct transformant was verified by restriction digestion and the plasmid was designated pTrcKKDyIkISKan (FIGS. 24 and 25A-25D). This plasmid was transformed into BL21 (λDE3) cells (Invitrogen).

III. Isoprene Production from Mevalonate in *E. coli* Expressing the Recombinant Lower Mevalonate Pathway and Isoprene Synthase from Kudzu.

Strain BL21/pTrcKKDyIkISKan was cultured in MOPS medium (Neidhardt et al., (1974) *J. Bacteriology* 119:736-747) adjusted to pH 7.1 and supplemented with 0.5% glucose and 0.5% mevalonic acid. A control culture was also set up using identical conditions but without the addition of 0.5% mevalonic acid. The culture was started from an overnight seed culture with a 1% inoculum and induced with 500 μM IPTG when the culture had reached an $OD_{600}$ of 0.3 to 0.5. The cultures were grown at 30° C. with shaking at 250 rpm. The production of isoprene was analyzed 3 hours after induction by using the head space assay described in Example 10. Maximum production of isoprene was $6.67\times10^{-4}$ mol/$L_{broth}$/$OD_{600}$/hr where $L_{broth}$ is the volume of broth and includes both the volume of the cell medium and the volume of the cells. The control culture not supplemented with mevalonic acid did not produce measurable isoprene.

IV. Cloning the Upper MVA Pathway

The upper mevalonate biosynthetic pathway, comprising two genes encoding three enzymatic activities, was cloned from *Enterococcus faecalis*. The mvaE gene encodes a protein with the enzymatic activities of both acetyl-CoA acetyltransferase and 3-hydroxy-3-methylglutaryl-CoA (HMG-CoA) reductase, the first and third proteins in the pathway, and the mvaS gene encodes second enzyme in the pathway, HMG-CoA synthase. The mvaE gene was amplified from *E. faecalis* genomic DNA (ATCC 700802D-5) with an *E. coli* ribosome binding site and a spacer in front using the following primers:

```
CF 07-60 (+) Start of mvaE w/RBS + ATG start
codon SacI
                                    (SEQ ID NO: 34)
5'-GAGACATGAGCTCAGGAGGTAAAAAAACATGAAAACAGTAGTTATT

ATTG

CF 07-62 (-) Fuse mvaE to mvaS with RBS in between
                                    (SEQ ID NO: 35)
5'-TTTATCAATCCCAATTGTCATGTTTTTTTACCTCCTTTATTGTTTT

CTTAAATC
```

The mvaS gene was amplified from *E. faecalis* genomic DNA (ATCC 700802D-5) with a RBS and spacer from *E. coli* in front using the following primers:

CF 07-61 (+) Fuse mvaE to mvaS with RBS in between
(SEQ ID NO: 36)
5'-GATTTAAGAAAACAATAAAGGAGGTAAAAAAACATGACAATTGGGA

TTGATAAA

CF 07-102 (-) End of mvaS gene BglII
(SEQ ID NO: 37)
5'-GACATGACATAGATCTTTAGTTTCGATAAGAACGAACGGT The PCR fragments were fused together with PCR using the following primers:

CF 07-60 (+) Start of mvaE w/RBS + ATG start codon SacI
(SEQ ID NO: 34)
5'-GAGACATGAGCTCAGGAGGTAAAAAAACATGAAAACAGTAGTTATT

ATTG

CF 07-102 (-) End of mvaS gene BglII
(SEQ ID NO: 37)
5'-GACATGACATAGATCTTTAGTTTCGATAAGAACGAACGGT The fusion PCR fragment was purified using a Qiagen kit and digested with the restriction enzymes SacI and BglII. This digested DNA fragment was gel purified using a Qiagen kit and ligated into the commercially available vector pTrcHis2A, which had been digested with SacI and BglII and gel purified.

The ligation mix was transformed into *E. coli* Top 10 cells and colonies were selected on LA+50 μg/ml carbenicillin plates. A total of six colonies were chosen and grown overnight in LB+50 μg/ml carbenicillin and plasmids were isolated using a Qiagen kit. The plasmids were digested with SacI and BglII to check for inserts and one correct plasmid was sequenced with the following primers:

CF 07-58 (+) Start of mvaE gene
(SEQ ID NO: 38)
5'-ATGAAAACAGTAGTTATTATTGATGC

CF 07-59 (-) End of mvaE gene
(SEQ ID NO: 39)
5'-ATGTTATTGTTTTCTTAAATCATTTAAAATAGC CF 07-82 (+) Start of mvaS gene
(SEQ ID NO: 40)
5'-ATGACAATTGGGATTGATAAAATTAG CF 07-83 (-) End of mvaS gene
(SEQ ID NO: 41)
5'-TTAGTTTCGATAAGAACGAACGGT CF 07-86 (+) Sequence in mvaE
(SEQ ID NO: 42)
5'-GAAATAGCCCCATTAGAAGTATC CF 07-87 (+) Sequence in mvaE
(SEQ ID NO: 43)
5'-TTGCCAATCATATGATTGAAAATC CF 07-88 (+) Sequence in mvaE
(SEQ ID NO: 44)
5'-GCTATGCTTCATTAGATCCTTATCG CF 07-89 (+) Sequence mvaS
(SEQ ID NO: 45)
5'-GAAACCTACATCCAATCTTTTGCCC The plasmid called pTrcHis2AUpperPathway#1 was correct by sequencing and was transformed into the commercially available *E. coli* strain BL21. Selection was done on LA+50 μg/ml carbenicillin. Two transformants were chosen and grown in LB+50 μg/ml carbenicillin until they reached an $OD_{600}$ of 1.5. Both strains were frozen in a vial at −80° C. in the presence of glycerol. Strains were designated CF 449 for pTrcHis2AUpperPathway#1 in BL21, isolate #1 and CF 450 for pTrcHis2AUpperPathway#1 in BL21, isolate #2. Both clones were found to behave identically when analyzed.

V. Cloning of UpperMVA Pathway into pCL1920

The plasmid pTrcHis2AUpperPathway was digested with the restriction endonuclease SspI to release a fragment containing pTrc-mvaE-mvaS-(His tag)-terminator. In this fragment, the his-tag was not translated. This blunt ended 4.5 kbp fragment was purified from a 1.2% E-gel using the Qiagen Gel Purification kit. A dephosphorylated, blunt ended 4.2 kbp fragment from pCL1920 was prepared by digesting the vector with the restriction endonuclease PvuII, treating with SAP and gel purifying from a 1.2% E-gel using the Qiagen Gel Purification kit. The two fragments were ligated using the Roche Quick Ligation Kit and transformed into TOP10 chemically competent cells. Transformants were selected on LA containing spectinomycin (50 μg/ml). A correct colony was identified by screening for the presence of the insert by PCR. The plasmid was designated pCL PtrcUpperPathway (FIGS. 26 and 27A-27D).

VI. Strains Expressing the Combined Upper and Lower Mevalonic Acid Pathways

To obtain a strain with a complete mevalonic acid pathway plus kudzu isoprene synthase, plasmids pTrcKKDyIkISkan and pCLpTrcUpperPathway were both transformed into BL21(λDE3) competent cells (Invitrogen) and transformants were selected on LA containing kanamycin (50 μg/ml) and Spectinomycin (50 μg/ml). The transformants were checked by plasmid prep to ensure that both plasmids were retained in the host. The strain was designated MCM127.

VII. Production of Mevalonic Acid from Glucose in *E. coli*/pUpperpathway

Single colonies of the BL21/pTrcHis2A-mvaE/mvaS or FM5/p pTrcHis2A-mvaE/mvaS are inoculated into LB+carbenicillin (100 μg/ml) and are grown overnight at 37° C. with shaking at 200 rpm. These cultures were diluted into 50 ml medium in 250 ml baffled flasks to an $OD_{600}$ of 0.1. The medium was TM3+1 or 2% glucose+carbenicillin (100 ug/ml) or TM3+1% glucose+hydrolyzed soy oil+carbenicillin (100 ug/ml) or TM3+biomass (prepared bagasse, corn stover or switchgrass). Cultures were grown at 30° C. with shaking at 200 rpm for approximately 2-3 hours until an $OD_{600}$ of 0.4 was reached. At this point the expression from the mvaE mvaS construct was induced by the addition of IPTG (400 μM). Cultures were incubated for a further 20 or 40 hours with samples taken at 2 hour intervals to 6 hour post induction and then at 24, 36 and 48 hours as needed. Sampling was done by removing 1 ml of culture, measuring the $OD_{600}$, pelleting the cells in a microfuge, removing the supernatant and analyzing it for mevalonic acid.

A 14 liter fermentation of *E. coli* cells with nucleic acids encoding *Enterococcus faecalis* AA-CoA thiolase, HMG-CoA synthase, and HMG-CoA reductase polypeptides produced 22 grams of mevalonic acid with TM3 medium and 2% glucose as the cell medium. A shake flask of these cells produced 2-4 grams of mevalonic acid per liter with LB medium and 1% glucose as the cell culture medium. The production of mevalonic acid in these strains indicated that the MVA pathway was functional in *E. coli.*

VIII. Production of Isoprene from *E. Coli* BL21 Containing the Upper and Lower MVA Pathway Plus Kudzu Isoprene Synthase.

The following strains were created by transforming in various combinations of plasmids containing the upper and lower MVA pathway and the kudzu isoprene synthase gene as described above and the plasmids containing the idi, dxs, and dxr and isoprene synthase genes described in Example 16. The host cells used were chemically competent BL21(λDE3) and the transformations were done by standard methods. Transformants were selected on L agar containing kanamycin (50 μg/ml) or kanamycin plus spectinomycin (both at a concentration of 50 μg/ml). Plates were grown at 37° C. The resulting strains were designated as follows:

Grown on Kanamycin plus Spectinomycin (50 μg/ml each)

MCM127—pCL Upper MVA+pTrcKKDyIkIS (kan) in BL21(λDE3)

MCM131—pCL1920+pTrcKKDyIkIS (kan) in BL21 (λDE3)

MCM125—pCL Upper MVA+pTrcHis2B (kan) in BL21 (λDE3)

Grown on Kanamycin (50 μg/ml)

MCM64—pTrcKudzu yIDI DXS (kan) in BL21(λDE3)

MCM50—pTrcKudzu (kan) in BL21(λDE3)

MCM123—pTrcKudzu yIDI DXS DXR (kan) in BL21 (λDE3)

The above strains were streaked from freezer stocks to LA+appropriate antibiotic and grown overnight at 37° C. A single colony from each plate was used to inoculate shake flasks (25 ml LB+the appropriate antibiotic). The flasks were incubated at 22° C. overnight with shaking at 200 rpm. The next morning the flasks were transferred to a 37° C. incubator and grown for a further 4.5 hours with shaking at 200 rpm. The 25 ml cultures were centrifuged to pellet the cells and the cells were resuspended in 5 ml LB+the appropriate antibiotic. The cultures were then diluted into 25 ml LB+1% glucose+ the appropriate antibiotic to an $OD_{600}$ of 0.1. Two flasks for each strain were set up, one set for induction with IPTG (800 μM) the second set was not induced. The cultures were incubated at 37° C. with shaking at 250 rpm. One set of the cultures were induced after 1.50 hours (immediately following sampling time point 1). At each sampling time point, the $OD_{600}$ was measured and the amount of isoprene determined as described in Example 10. Results are presented in Table 10. The amount of isoprene made is presented as the amount at the peak production for the particular strain.

TABLE 10

Production of isoprene in *E. coli* strains

| Strain | Isoprene (μg/liter/OD/hr |
|---|---|
| MCM50 | 23.8 |
| MCM64 | 289 |
| MCM125 | ND |
| MCM131 | Trace |
| MCM127 | 874 |

ND: not detected

Trace: peak present but not integrable.

IX. Analysis of mevalonic acid

Mevalonolactone (1.0 g, 7.7 mmol) (CAS#503-48-0) was supplied from Sigma-Aldrich (WI, USA) as a syrup that was dissolved in water (7.7 mL) and was treated with potassium hydroxide (7.7 mmol) in order to generate the potassium salt of mevalonic acid. The conversion to mevalonic acid was confirmed by $^1H$ NMR analysis. Samples for HPLC analysis were prepared by centrifugation at 14,000 rpm for 5 minutes to remove cells, followed by the addition of a 300 μl aliquot of supernatant to 900 μl of $H_2O$. Perchloric acid (36 μl of a 70% solution) was then added followed by mixing and cooling on ice for 5 minutes. The samples were then centrifuged again (14,000 rpm for 5 min) and the supernatant transferred to HPLC. Mevalonic acid standards (20, 10, 5, 1 and 0.5 g/L) were prepared in the same fashion. Analysis of mevalonic acid (20 uL injection volume) was performed by HPLC using a BioRad Aminex 87-H+ column (300 mm by 7.0 mm) eluted with 5 mM sulfuric acid at 0.6 mL/min with refractive index (R1) detection. Under these conditions mevalonic acid eluted as the lactone form at 18.5 minutes.

X. Production of Isoprene from *E. coli* BL21 Containing the Upper MVA Pathway Plus Kudzu Isoprene Synthase A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 2.2 g/L of isoprene.

Medium Recipe (Per Liter Fermentation Medium):

The medium was generated using the following components per liter fermentation medium: $K_2HPO_4$ 7.5 g, $MgSO_4$*7$H_2O$ 2 g, citric acid monohydrate 2 g, ferric ammonium citrate 0.3 g, yeast extract 0.5 g, and 1000× modified trace metal solution 1 ml. All of the components were added together and dissolved in di$H_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4$*$H_2O$ 30 g, NaCl 10 g, $FeSO_4$*7$H_2O$ 1 g, $CoCl_2$*6$H_2O$ 1 g, $ZnSO_4$*7$H_2O$ 1 g, $CuSO_4$*5$H_2O$ 100 mg, $H_3BO_3$ 100 mg, and $NaMoO_4$*2$H_2O$ 100 mg. Each component was dissolved one at a time in di$H_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperPathway (FIG. 26) and pTrcKKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into soytone-yeast extract-glucose medium. After the inoculum grew to OD 1.0 when measured at 550 nm, 500 mL was used to inoculate a 15-L bioreactor containing an initial working volume of 5 L.

Glucose was fed at an exponential rate until cells reached the stationary phase. After this time the glucose feed was decreased to meet metabolic demands. The total amount of glucose delivered to the bioreactor during the 54 hour fermentation was 3.7 kg. Induction was achieved by adding isopropyl-beta-D-1-thiogalactopyranoside (IPTG). The IPTG concentration was brought to 25 uM when the optical density at 550 nm ($OD_{550}$) reached a value of 10. The IPTG concentration was raised to 50 uM when $OD_{550}$ reached 190. IPTG concentration was raised to 100 uM at 38 hours of fermentation. The $OD_{550}$ profile within the bioreactor over time is shown in FIG. 54. The isoprene level in the off gas from the bioreactor was determined as described herein. The isoprene titer increased over the course of the fermentation to a final value of 2.2 g/L (FIG. 55). The total amount of isoprene produced during the 54 hour fermentation was 15.9 g, and the time course of production is shown in FIG. 56.

XI. Isoprene Fermentation from *E. Coli* Expressing Genes from the Mevalonic Acid Pathway and Grown in Fed-Batch Culture at the 15-L Scale A 15-L scale fermentation of *E. coli* expressing mevalonic acid pathway polypeptides and Kudzu isoprene synthase was used to produce isoprene from cells in fed-batch culture. This experiment demonstrates that growing cells under glucose limiting conditions resulted in the production of 3.0 g/L of isoprene.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in $diH_2O$, pH to 3.0 with HCl/NaOH, then q.s. to volume, and filter sterilized with a 0.22 micron filter.

Fermentation was performed in a 15-L bioreactor with BL21 (DE3) *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Glucose was fed at an exponential rate until cells reached the stationary phase. After this time, the glucose feed was decreased to meet metabolic demands. The total amount of glucose delivered to the bioreactor during the 59 hour fermentation was 2.2 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 93. The isoprene level in the off gas from the bioreactor was determined as described herein. The isoprene titer increased over the course of the fermentation to a final value of 3.0 g/L (FIG. 94). The total amount of isoprene produced during the 59 hour fermentation was 22.8 g, and the time course of production is shown in FIG. 95. The molar yield of utilized carbon that went into producing isoprene during fermentation was 2.2%. The weight percent yield of isoprene from glucose was 1.0%.

XII. Isoprene Fermentation from *E. coli* Expressing Genes from the Mevalonic Acid Pathway and Grown in Fed-Batch Culture at the 15-L Scale A 15-L scale fermentation of *E. coli* expressing mevalonic acid pathway polypeptides, *Pueraria lobata* isoprene synthase, and Kudzu isoprene synthase was used to produce isoprene from cells in fed-batch culture. This experiment demonstrates that growing cells under glucose limiting conditions resulted in the production of 3.3 g/L of isoprene.

i) Construction of pCLPtrcUpperPathwayHGS2

The gene encoding isoprene synthase from *Pueraria lobata* was PCR-amplified using primers NsiI-RBS-HGS F (CTTGATGCATCCTGCATTCGCCCTTAGGAGG, SEQ ID NO:88) and pTrcR (CCAGGCAAATTCTGTTTTATCAG, SEQ ID NO:89), and pTrcKKDyIkIS as a template. The PCR product thus obtained was restriction-digested with NsiI and PstI and gel-purified. The plasmid pCL PtrcUpperPathway was restriction-digested with PstI and dephosphorylated using rAPid alkaline phosphatase (Roche) according to manufacturer's instructions.

These DNA fragments were ligated together and the ligation reaction was transformed into *E. coli* Top10 chemically competent cells (Invitrogen), plated on L agar containing spectinomycin (50 ug/ml) and incubated overnight at 370 C. Plasmid DNA was prepared from 6 clones using the Qiaquick Spin Mini-prep kit. The plasmid DNA was digested with restriction enzymes EcoRV and MluI to identify a clone in which the insert had the right orientation (i.e., the gene oriented in the same way as the pTrc promoter).

The resulting correct plasmid was designated pCLPtrcUpperPathwayHGS2. This plasmid was assayed using the headspace assay described herein and found to produce isoprene in *E. coli* Top10, thus validating the functionality of the gene. The plasmid was transformed into BL21(LDE3) containing pTrcKKDyIkIS to yield the strain BL21/pCLPtrcUpperPathwayHGS2-pTrcKKDyIkIS This strain has an extra copy of the isoprene synthase compared to the BL21/pCL PtrcUpperMVA and pTrc KKDyIkIS strain (Example 17, part XI). This strain also had increased expression and activity of HMGS compared to the BL21/pCL PtrcUpperMVA and pTrc KKDyIkIS strain used in Example 17, part XI.

ii) Isoprene Fermentation from *E. coli* Expressing pCLPtrcUpperPathwayHGS2-pTrcKKDyIkIS and Grown in Fed-Batch Culture at the 15-L Scale Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with 0.22 micron filter.

Fermentation was performed in a 15-L bioreactor with BL21 (DE3) *E. coli* cells containing the pCLPtrcUpperPathwayHGS2 and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0 measured at 550 nm, 500 mL was used to inoculate a 15-L bioreactor containing an initial working volume of 5 L.

Glucose was fed at an exponential rate until cells reached the stationary phase. After this time the glucose feed was decreased to meet metabolic demands. The total amount of glucose delivered to the bioreactor during the 58 hour fermentation was 2.1 kg. Induction was achieved by adding IPTG. The IPTG concentration was brought to 25 uM when the optical density at 550 nm ($OD_{550}$) reached a value of 9. The IPTG concentration was raised to 50 uM when $OD_{550}$ reached 170. The $OD_{550}$ profile within the bioreactor over time is shown in FIG. 104. The isoprene level in the off gas from the bioreactor was determined as described herein. The isoprene titer increased over the course of the fermentation to a final value of 3.3 g/L (FIG. 105). The total amount of isoprene produced during the 58 hour fermentation was 24.5 g and the time course of production is shown in FIG. 106. The molar yield of utilized carbon that went into producing isoprene during fermentation was 2.5%. The weight percent yield of isoprene from glucose was 1.2%. Analysis showed that the activity of the isoprene synthase was increased by approximately 3-4 times that compared to BL21 expressing CL PtrcUpperMVA and pTrc KKDyIkIS plasmids (data not shown).

XIII. Chromosomal Integration of the Lower Mevalonate Pathway in *E. coli*.

A synthetic operon containing mevalonate kinase, mevalonate phosphate kinase, mevalonate pyrophosphate decarboxylase, and the IPP isomerase was integrated into the chromosome of *E. coli*. If desired, expression may be altered by integrating different promoters 5' of the operon.

Table 11 lists primers used for this experiment.

TABLE 11

| Primers | | |
|---|---|---|
| MCM78 | attTn7 up rev for integration construct | gcatgctcgagcggccgcTTTTAATCAAACATCCTGCCAACTC (SEQ ID NO: 91) |
| MCM79 | attTn7 down rev for integration construct | gatcgaagggcgatcgTGTCACAGTCTGGCGAAACCG (SEQ ID NO: 92) |
| MCM88 | attTn7 up forw for integration construct | ctgaattctgcagatatcTGTTTTTCCACTCTTCGTTCACTTT (SEQ ID NO: 93) |
| MCM89 | attTn7 down forw for integration construct | tctagagggcccAAGAAAAATGCCCCGCTTACG (SEQ ID NO: 94) |
| MCM104 | GI1.2 promoter - MVK | Gatcgcggccgcgcccttgacgatgccacatcctgagcaaataattcaaccactaa ttgtgagcggataacacaaggaggaaacagctatgtcattaccgttcttaacttc (SEQ ID NO: 95) |
| MCM105 | aspA terminator - yIDI | Gatcgggccccaagaaaaaaggcacgtcatctgacgtgcctttttttatttgtagacgc gttgttatagcattcta (SEQ ID NO: 96) |
| MCM120 | Forward of attTn7: attTn7 homology, GB marker homology | aaagtagccgaagatgacggtttgtcacatggagttggcaggatgtttgattaaaagc AATTAACCCTCACTAAAGGGCGG (SEQ ID NO: 97) |
| MCM127 | Rev complement of 1.2 GI: GB marker homology(extra long), promoter, RBS, ATG | AGAGTGTTCACCAAAAATAATAACCTTTCCCGGTGCAgaag ttaagaacggtaatgacatagctgtttcctccttgtgttatccgctcacaattagtggttga attatttgctcaggatgtggcatcgtcaagggcTAATACGACTCACTATAG GGCTCG (SEQ ID NO: 98) |

i) Target Vector Construction

The attTn7 site was selected for integration. Regions of homology upstream (attTn7 up) (primers MCM78 and MCM79) and downstream (attTn7 down) (primers MCM88 and MCM89) were amplified by PCR from MG1655 cells. A 50 uL reaction with 1 uL 10 uM primers, 3 uL ddH2O, 45 uL Invitrogen Platinum PCR Supermix High Fidelity, and a scraped colony of MG1655 was denatured for 2:00 at 940 C, cycled 25 times (2:00 at 940 C, 0:30 at 500 C, and 1:00 at 680 C), extended for 7:00 at 720 C, and cooled to 40 C. This resulting DNA was cloned into pCR2.1 (Invitrogen) according to the manufacturer's instructions, resulting in plasmids MCM278 (attTn7 up) and MCM252 (attTn7 down). The 832 bp ApaI-PvuI fragment digested and gel purified from MCM252 was cloned into ApaI-PvuI digested and gel purified plasmid pR6K, creating plasmid MCM276. The 825 bp PstI-NotI fragment digested and gel purified from MCM278 was cloned into PstI-NotI digested and gel purified MCM276, creating plasmid MCM281.

ii) Cloning of Lower Pathway and Promoter

MVK-PMK-MVD-IDI genes were amplified from pTrcKKDyIkIS with primers MCM104 and MCM105 using Roche Expand Long PCR System according to the manufacturer's instructions. This product was digested with NotI and ApaI and cloned into MCM281 which had been digested with NotI and ApaI and gel purified. Primers MCM 120 and MCM 127 were used to amplify CMR cassette from the GeneBridges FRT-gb2-Cm-FRT template DNA using Stratagene Pfu Ultra II. A PCR program of denaturing at 950 C for 4:00, 5 cycles of 950 C for 0:20, 550 C for 0:20, 720 C for 2:00, 25 cycles of 950 C for 0:20, 580 C for 0:20, 720 C for 2:00, 720 C for 10:00, and then cooling to 40 C was used with four 50 uL PCR reactions containing 1 uL~10 ng/uL template, 1 uL each primer, 1.25 uL 10 mM dNTPs, 5 uL 10× buffer, 1 uL enzyme, and 39.75 uL ddH20. Reactions were pooled, purified on a Qiagen PCR cleanup column, and used to electroporate water-washed Pir1 cells containing plasmid MCM296. Electroporation was carried out in 2 mM cuvettes at 2.5V and 200 ohms. Electroporation reactions were recovered in LB for 3 hr at 300 C. Transformant MCM330 was selected on LA with CMPS, Kan50 (FIGS. 107 and 108A-108C).

iii) Integration into *E. coli* Chromosome

Miniprepped DNA (Qiaquick Spin kit) from MCM330 was digested with SnaBI and used to electroporate BL21(DE3) (Novagen) or MG1655 containing GeneBridges plasmid pRedET Carb. Cells were grown at 300 C to ~OD1 then induced with 0.4% L-arabinose at 370 C for 1.5 hours. These cells were washed three times in 40 C ddH2O before electroporation with 2 uL of DNA. Integrants were selected on L agar with containing chloramphenicol (5 ug/ml) and subsequently confirmed to not grow on L agar+Kanamycin (50 ug/ml). BL21 integrant MCM331 and MG1655 integrant MCM333 were frozen.

iv) Construction of pET24D-Kudzu Encoding Kudzu Isoprene Synthase

The kudzu isoprene synthase gene was subcloned into the pET24d vector (Novagen) from the pCR2.1 vector (Invitrogen). In particular, the kudzu isoprene synthase gene was amplified from the pTrcKudzu template DNA using primers MCM50 5'-GATCATGCAT TCGCCCTTAG GAGGTAAAAA AACATGTGTG CGACCTCTTC TCAATTTACT (SEQ ID NO:99) and MCM53 5'-CGGTCGACGG ATCCCTGCAG TTAGACATAC ATCAGCTG (SEQ ID NO:100). PCR reactions were carried out using Taq DNA Polymerase (Invitrogen), and the resulting PCR product was cloned into pCR2.1-TOPO TA cloning vector (Invitrogen), and transformed into *E. coli* Top10 chemically competent cells (Invitrogen). Transformants were plated on L agar containing carbenicillin (50 μg/ml) and incubated overnight at 37° C. Five ml Luria Broth cultures containing carbenicillin 50 μg/ml were inoculated with single transformants and grown overnight at 37° C. Five colonies were screened for the correct insert by sequencing of plasmid DNA isolated from 1 ml of liquid culture (Luria Broth) and purified using the QIAprep Spin Mini-prep Kit (Qiagen). The resulting plasmid, designated MCM93, contains the kudzu isoprene synthase coding sequence in a pCR2.1 backbone.

The kudzu coding sequence was removed by restriction endonuclease digestion with PciI and BamH1 (Roche) and gel purified using the QIAquick Gel Extraction kit (Qiagen). The pET24d vector DNA was digested with NcoI and BamHI (Roche), treated with shrimp alkaline phosphatase (Roche), and purified using the QIAprep Spin Mini-prep Kit (Qiagen). The kudzu isoprene synthase fragment was ligated to the NcoI/BamH1 digested pET24d using the Rapid DNA Ligation Kit (Roche) at a 5:1 fragment to vector ratio in a total volume of 20 μl. A portion of the ligation mixture (5 μl) was transformed into *E. coli* Top 10 chemically competent cells and plated on L agar containing kanamycin (50 μg/ml). The correct transformant was confirmed by sequencing and transformed into chemically competent BL21(λDE3) pLysS cells (Novagen). A single colony was selected after overnight growth at 37° C. on L agar containing kanamycin (50 μg/ml). A map of the resulting plasmid designated as pET24D-Kudzu is shown in FIG. 109. The sequence of pET24D-Kudzu (SEQ ID NO:101) is shown in FIGS. 110A and 110B. Isoprene synthase polypeptide activity was confirmed using a headspace assay.

v) Production Strains

Strains MCM331 and MCM333 were cotransformed with plasmids pCLPtrcupperpathway and either pTrcKudzu or pETKudzu, resulting in the strains shown in Table 12.

TABLE 12

Production Strains

| Background | Integrated Lower | Upper MVA plasmid | Isoprene synthase plasmid | Production Stain |
|---|---|---|---|---|
| BL21(DE3) | MCM331 | pCLPtrcUpper Pathway | pTrcKudzu | MCM343 |
| BL21(DE3) | MCM331 | pCLPtrcUpper Pathway | pET24D-Kudzu | MCM335 |
| MG1655 | MCM333 | pCLPtrcUpper Pathway | pTrcKudzu | MCM345 |

vi) Isoprene Fermentation from *E. coli* Expressing Genes from the Mevalonic Acid Pathway and Grown in Fed-Batch Culture at the 15-L Scale.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di $H_2O$, pH to 3.0 with HCl/NaOH, then q.s. to volume and filter sterilized with a 0.22 micron filter.

Fermentation was performed in a 15-L bioreactor with BL21 (DE3) *E. coli* cells containing the gi1.2 integrated lower MVA pathway described above and the pCL PtrcUpperMVA and pTrcKudzu plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Glucose was fed at an exponential rate until cells reached the stationary phase. After this time, the glucose feed was decreased to meet metabolic demands. The total amount of glucose delivered to the bioreactor during the 57 hour fermentation was 3.9 kg. Induction was achieved by adding IPTG. The IPTG concentration was brought to 100 uM when the carbon dioxide evolution rate reached 100 mmol/L/hr. The $OD_{550}$ profile within the bioreactor over time is shown in FIG. 111A. The isoprene level in the off gas from the bioreactor was determined as described herein. The isoprene titer increased over the course of the fermentation to a final value of 1.6 g/L (FIG. 111B). The specific productivity of isoprene over the course of the fermentation is shown in FIG. 111C and peaked at 1.2 mg/OD/hr. The total amount of isoprene produced during the 57 hour fermentation was 16.2 g. The molar yield of utilized carbon that went into producing isoprene during fermentation was 0.9%. The weight percent yield of isoprene from glucose was 0.4%.

Example 18

Construction of the Upper and Lower MVA Pathway for Integration into *Bacillus subtilis*

I. Construction of the Upper MVA Pathway in *Bacillus subtilis*

The upper pathway from *Enterococcus faecalis* is integrated into *B. subtilis* under control of the aprE promoter. The upper pathway consists of two genes; mvaE, which encodes for AACT and HMGR, and mvaS, which encodes for HMGS. The two genes are fused together with a stop codon in between, an RBS site in front of mvaS, and are under the control of the aprE promoter. A terminator is situated after the mvaE gene. The chloramphenicol resistance marker is cloned after the mvaE gene and the construct is integrated at the aprE locus by double cross over using flanking regions of homology.

Four DNA fragments are amplified by PCR such that they contain overhangs that will allowed them to be fused together by a PCR reaction. PCR amplifications are carried out using Herculase polymerase according to manufacturer's instructions.

```
1. PaprE
CF 07-134 (+) Start of aprE promoter PstI
                                        (SEQ ID NO: 82)
5'-GACATCTGCAGCTCCATTTTCTTCTGC

CF 07-94 (-) Fuse PaprE to mvaE
                                        (SEQ ID NO: 83)
5'-CAATAATAACTACTGTTTTCACTCTTTACCCTCTCCTTTTAA
Template: Bacillus subtilis chromosomal DNA

2. mvaE
CF 07-93 (+) fuse mvaE to the aprE promoter
(GTG start codon)
                                        (SEQ ID NO: 84)
5'-TTAAAAGGAGAGGGTAAAGAGTGAAAACAGTAGTTATTATTG

CF 07-62 (-) Fuse mvaE to mvaS with RBS in between
                                        (SEQ ID NO: 35)
5'-TTTATCAATCCCAATTGTCATGTTTTTTTACCTCCTTTATTGTTTT

CTTAAATC
Template: Enterococcus faecalis chromosomal DNA
(from ATCC)

3. mvaS
CF 07-61 (+) Fuse mvaE to mvaS with RBS in between
                                        (SEQ ID NO: 36)
5'-GATTTAAGAAAACAATAAAGGAGGTAAAAAAACATGACAATTGGGA

TTGATAAA

CF 07-124 (-) Fuse the end of mvaS to the
terminator
                                        (SEQ ID NO: 85)
5'-CGGGGCCAAGGCCGGTTTTTTTTAGTTTCGATAAGAACGAACGGT
Template: Enterococcus faecalis chromosomal DNA

4. B. amyliquefaciens alkaline serine protease
terminator
CF 07-123 (+) Fuse the end of mvaS to the
terminator
                                       (SEQ ID NO: 136)
5'-ACCGTTCGTTCTTATCGAAACTAAAAAAAACCGGCCTTGGCCCCG

CF 07-46 (-) End of B. amyliquefaciens terminator
BamHI
                                        (SEQ ID NO: 63)
5'-GACATGACGGATCCGATTACGAATGCCGTCTC
Template: Bacillus amyliquefaciens chromosomal DNA

PCR Fusion Reactions
5. Fuse mvaE to mvaS
CF 07-93 (+) fuse mvaE to the aprE promoter
(GTG start codon)
                                        (SEQ ID NO: 84)
5'-TTAAAAGGAGAGGGTAAAGAGTGAAAACAGTAGTTATTATTG

CF 07-124 (-) Fuse the end of mvaS to the
terminator
                                        (SEQ ID NO: 85)
5'-CGGGGCCAAGGCCGGTTTTTTTTAGTTTCGATAAGAACGAACGGT
Template: #2 and 3 from above

6. Fuse mvaE-mvaS to aprE promoter
CF 07-134 (+) Start of aprE promoter PstI
                                        (SEQ ID NO: 82)
5'-GACATCTGCAGCTCCATTTTCTTCTGC

CF 07-124 (-) Fuse the end of mvaS to the
terminator
```

-continued

```
                                        (SEQ ID NO: 85)
5'-CGGGGCCAAGGCCGGTTTTTTTTAGTTTCGATAAGAACGAACGGT
Template #1 and #4 from above

7. Fuse PaprE-mvaE-mvaS to terminator
CF 07-134 (+) Start of aprE promoter PstI
                                        (SEQ ID NO: 82)
5'-GACATCTGCAGCTCCATTTTCTTCTGC

CF 07-46 (-) End of B. amyliquefaciens terminator
BamHI
                                        (SEQ ID NO: 63)
5'-GACATGACGGATCCGATTACGAATGCCGTCTC
```

Template: #4 and #6

The product is digested with restriction endonucleases PstI/BamHI and ligated to pJM102 (Perego, M. 1993. Integrational vectors for genetic manipulation in *Bacillus subtilis*, p. 615-624. In A. L. Sonenshein, J. A. Hoch, and R. Losick (ed.), *Bacillus subtilis* and other gram-positive bacteria: biochemistry, physiology, and molecular genetics. American Society for Microbiology, Washington, D.C.) which is digested with PstI/BamHI. The ligation is transformed into *E. coli* TOP 10 chemically competent cells and transformants are selected on LA containing carbenicillin (50 μg/ml). The correct plasmid is identified by sequencing and is designated pJMUpperpathway2 (FIGS. 50 and 51A-51C). Purified plasmid DNA is transformed into *Bacillus subtilis* aprEnprE Pxyl-comK and transformants are selected on L agar containing chloramphenicol (5 μg/ml). A correct colony is selected and is plated sequentially on L agar containing chloramphenicol 10, 15 and 25 μg/ml to amplify the number of copies of the cassette containing the upper pathway.

The resulting strain is tested for mevalonic acid production by growing in LB containing 1% glucose and 1%. Cultures are analyzed by GC for the production of mevalonic acid.

This strain is used subsequently as a host for the integration of the lower mevalonic acid pathway.

The following primers are used to sequence the various constructs above.

Sequencing Primers:

```
CF 07-134 (+) Start of aprE promoter PstI
                                        (SEQ ID NO: 82)
5'-GACATCTGCAGCTCCATTTTCTTCTGC

CF 07-58 (+) Start of mvaE gene
                                        (SEQ ID NO: 38)
5'-ATGAAAACAGTAGTTATTATTGATGC

CF 07-59 (-) End of mvaE gene
                                        (SEQ ID NO: 39)
5'-ATGTTATTGTTTTCTTAAATCATTTAAAATAGC

CF 07-82 (+) Start of mvaS gene
                                        (SEQ ID NO: 40)
5'-ATGACAATTGGGATTGATAAAATTAG

CF 07-83 (-) End of mvaS gene
                                        (SEQ ID NO: 41)
5'-TTAGTTTCGATAAGAACGAACGGT

CF 07-86 (+) Sequence in mvaE
                                        (SEQ ID NO: 42)
5'-GAAATAGCCCCATTAGAAGTATC

CF 07-87 (+) Sequence in mvaE
                                        (SEQ ID NO: 43)
5'-TTGCCAATCATATGATTGAAAATC

CF 07-88 (+) Sequence in mvaE
                                        (SEQ ID NO: 44)
5'-GCTATGCTTCATTAGATCCTTATCG
```

-continued

CF 07-89 (+) Sequence mvaS (SEQ ID NO: 45)

5'-GAAACCTACATCCAATCTTTTGCCC

Transformants are selected on LA containing chloramphenicol at a concentration of 5 μg/ml. One colony is confirmed to have the correct integration by sequencing and is plated on LA containing increasing concentrations of chloramphenicol over several days, to a final level of 25 μg/ml. This results in amplification of the cassette containing the genes of interest. The resulting strain is designated CF 455: pJMupperpathway#1×*Bacillus subtilis* aprEnprE Pxyl comK (amplified to grow on LA containing chloramphenicol 25 μg/ml).

II. Construction of the Lower MVA Pathway in *Bacillus subtilis*

The lower MVA pathway, consisting of the genes mvk1, pmk, mpd and idi are combined in a cassette consisting of flanking DNA regions from the nprE region of the *B. subtilis* chromosome (site of integration), the aprE promoter, and the spectinomycin resistance marker (see FIGS. 28 and 29A-29D). This cassette is synthesized by DNA2.0 and is integrated into the chromosome of *B. subtilis* containing the upper MVA pathway integrated at the aprE locus. The kudzu isoprene synthase gene is expressed from the replicating plasmid described in Example 13 and is transformed into the strain with both upper and lower pathways integrated.

Example 19

The De-Coupling of Growth and Production of Isoprene in *E. coli* Expressing Genes from the Mevalonic Acid Pathway and Fermented in a Fed-Batch Culture This example illustrates the de-coupling of cell growth from mevalonic acid and isoprene production.

I. Fermentation Conditions

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in diH2O. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component was dissolved one at a time in Di $H_2O$, pH to 3.0 with HCl/NaOH, then q.s. to volume, and filter sterilized with a 0.22 micron filter.

Fermentation was performed with *E. coli* cells containing the pTrcHis2AUpperPathway (also called pTrcUpperMVA, FIGS. 91 and 92A-92C) (50 μg/ml carbenicillin) or the pCL PtrcUpperMVA (also called pCL PtrcUpperPathway (FIG. 26)) (50 μg/ml spectinomycin) plasmids. For experiments in which isoprene was produced, the *E. coli* cells also contained the pTrc KKDyIkIS (50 μg/ml kanamycin) plasmid. These experiments were carried out to monitor mevalonic acid or isoprene formation from glucose at the desired fermentation pH 7.0 and temperature 30° C. An inoculum of an *E. coli* strain taken from a frozen vial was streaked onto an LA broth agar plate (with antibiotics) and incubated at 37° C. A single colony was inoculated into tryptone-yeast extract medium. After the inoculum grew to optical density 1.0 when measured at 550 nm, it was used to inoculate the bioreactor.

Glucose was fed at an exponential rate until cells reached the stationary phase. After this time the glucose feed was decreased to meet metabolic demands. Induction was achieved by adding IPTG. The mevalonic acid concentration in fermentation broth was determined by applying perchloric acid (Sigma-Aldrich #244252) treated samples (0.3 M incubated at 4° C. for 5 minutes) to an organic acids HPLC column (BioRad #125-0140). The concentration was determined by comparing the broth mevalonic acid peak size to a calibration curve generated from mevalonolacetone (Sigma-Aldrich #M4667) treated with perchloric acid to form D,L-mevalonate. The isoprene level in the off gas from the bioreactor was determined as described herein. The isoprene titer is defined as the amount of isoprene produced per liter of fermentation broth.

II. Mevalonic Acid Production from *E. coli* BL21 (DE3) Cells Expressing the pTrcUpperMVA Plasmid at a 150-L Scale BL21 (DE3) cells that were grown on a plate as explained above in Example 19, part I were inoculated into a flask containing 45 mL of tryptone-yeast extract medium and incubated at 30° C. with shaking at 170 rpm for 5 hours. This solution was transferred to a 5-L bioreactor of tryptone-yeast extract medium, and the cells were grown at 30° C. and 27.5 rpm until the culture reached an $OD_{550}$ of 1.0. The 5 L of inoculum was seeded into a 150-L bioreactor containing 45-kg of medium. The IPTG concentration was brought to 1.1 mM when the $OD_{550}$ reached a value of 10. The $OD_{550}$ profile within the bioreactor over time is shown in FIG. 60A. The mevalonic acid titer increased over the course of the fermentation to a final value of 61.3 g/L (FIG. 60B). The specific productivity profile throughout the fermentation is shown in FIG. 60C and a comparison to FIG. 60A illustrates the de-coupling of growth and mevalonic acid production. The total amount of mevalonic acid produced during the 52.5 hour fermentation was 4.0 kg from 14.1 kg of utilized glucose. The molar yield of utilized carbon that went into producing mevalonic acid during fermentation was 34.2%.

III. Mevalonic Acid Production from *E. coli* BL21 (DE3) Cells Expressing the pTrcUpperMVA Plasmid at a 15-L Scale BL21 (DE3) cells that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 10. The $OD_{550}$ profile within the bioreactor over time is shown in FIG. 61A. The mevalonic acid titer increased over the course of the fermentation to a final value of 53.9 g/L (FIG. 61B). The specific productivity profile throughout the fermentation is shown in FIG. 61C and a comparison to FIG. 61A illustrates the de-coupling of growth and mevalonic acid production. The total amount of mevalonic acid produced during the 46.6 hour fermentation was 491 g from 2.1 kg of utilized glucose. The molar yield of utilized carbon that went into producing mevalonic acid during fermentation was 28.8%.

IV. Mevalonic Acid Production from *E. coli* FM5 Cells Expressing the pTrcUpperMVA Plasmid at a 15-L Scale FM5 cells that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 1.0 mM when the $OD_{550}$ reached a value of 30. The $OD_{550}$ profile within the bioreactor over time is shown in FIG. 62A. The mevalonic acid titer increased over the course of the fermentation to a final value of 23.7 g/L (FIG. 62B). The specific productivity profile throughout the fermentation is shown in FIG. 62C and a comparison to FIG. 62A illustrates the de-coupling of growth and mevalonic acid production. The total amount of mevalonic acid produced during the 51.2 hour fermentation was 140 g from 1.1 kg of utilized glucose. The molar yield of utilized carbon that went into producing mevalonic acid during fermentation was 15.2%.

V. Isoprene Production from *E. coli* BL21 (DE3) Cells Expressing the pCL PtrcUpperMVA and pTrc KKDyIkIS Plasmids at a 15-L Scale BL21 (DE3) cells expressing the pCL PtrcUpperMVA and pTrc KKDyIkIS plasmids that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 25 μM when the $OD_{550}$ reached a value of 10. The IPTG concentration was raised to 50 uM when $OD_{550}$ reached 190. The IPTG concentration was raised to 100 uM at 38 hours of fermentation. The $OD_{550}$ profile within the bioreactor over time is shown in FIG. 63A. The isoprene titer increased over the course of the fermentation to a final value of 2.2 g/L broth (FIG. 63B). The specific productivity profile throughout the fermentation is shown in FIG. 63C and a comparison to FIG. 63A illustrates the de-coupling of growth and isoprene production. The total amount of isoprene produced during the 54.4 hour fermentation was 15.9 g from 2.3 kg of utilized glucose. The molar yield of utilized carbon that went into producing isoprene during fermentation was 1.53%.

VI. Isoprene Production from *E. coli* BL21 (DE3) Tuner Cells Expressing the pCL PtrcUpperMVA and pTrc KKDyIkIS Plasmids at a 15-L Scale BL21 (DE3) tuner cells expressing the pCL PtrcUpperMVA and pTrc KKDyIkIS plasmids that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 26 μM when the $OD_{550}$ reached a value of 10. The IPTG concentration was raised to 50 uM when $OD_{550}$ reached 175. The $OD_{550}$ profile within the bioreactor over time is shown in FIG. 64A. The isoprene titer increased over the course of the fermentation to a final value of 1.3 g/L broth (FIG. 64B). The specific productivity profile throughout the fermentation is shown in FIG. 64C and a comparison to FIG. 64A illustrates the de-coupling of growth and isoprene production. The total amount of isoprene produced during the 48.6 hour fermentation was 9.9 g from 1.6 kg of utilized glucose. The molar yield of utilized carbon that went into producing isoprene during fermentation was 1.34%.

VII. Isoprene Production from *E. coli* MG1655 Cells Expressing the pCL PtrcUpperMVA and pTrc KKDyIkIS Plasmids at a 15-L Scale MG1655 cells expressing the pCL PtrcUpperMVA and pTrc KKDyIkIS plasmids that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 24 μM when the $OD_{550}$ reached a value of 45. The $OD_{550}$ profile within the bioreactor over time is shown in FIG. 65A. The isoprene titer increased over the course of the fermentation to a final value of 393 mg/L broth (FIG. 65B). The specific productivity profile throughout the fermentation is shown in FIG. 65C and a comparison to FIG. 65A illustrates the de-coupling of growth and isoprene production. The total amount of isoprene produced during the 67.4 hour fermentation was 2.2 g from 520 g of utilized glucose. The molar yield of utilized carbon that went into producing isoprene during fermentation was 0.92%.

VIII. Isoprene Production from *E. coli* MG1655ack-pta Cells Expressing the pCL PtrcUpperMVA and pTrc KKDyIkIS Plasmids at a 15-L Scale MG1655ack-pta cells expressing the pCL PtrcUpperMVA and pTrc KKDyIkIS plasmids that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 30 μM when the $OD_{550}$ reached a value of 10. The $OD_{550}$ profile within the bioreactor over time is shown in FIG. 66A. The isoprene titer increased over the course of the fermentation to a final value of 368 mg/L broth (FIG. 66B). The specific productivity profile throughout the fermentation is shown in FIG. 66C and a comparison to FIG. 66A illustrates the de-coupling of growth and isoprene production. The total amount of isoprene produced during the 56.7 hour fermentation was 1.8 g from 531 g of utilized glucose. The molar yield of utilized carbon that went into producing isoprene during fermentation was 0.73%.

IX. Isoprene Production from *E. coli* FM5 Cells Expressing the pCL PtrcUpperMVA and pTrc KKDyIkIS Plasmids at a 15-L Scale FM5 cells expressing the pCL PtrcUpperMVA and pTrc KKDyIkIS plasmids that were grown on a plate as explained above in Example 19, part I were inoculated into a flask containing 500 mL of tryptone-yeast extract medium and grown at 30° C. at 160 rpm to $OD_{550}$ 1.0. This material was seeded into a 15-L bioreactor containing 4.5-kg of medium. The IPTG concentration was brought to 27 μM when the $OD_{550}$ reached a value of 15. The $OD_{550}$ profile within the bioreactor over time is shown in FIG. 67A. The isoprene titer increased over the course of the fermentation to a final value of 235 mg/L broth (FIG. 67B). The specific productivity profile throughout the fermentation is shown in FIG. 67C and a comparison to FIG. 67A illustrates the de-coupling of growth and isoprene production. The total amount of isoprene produced during the 52.3 hour fermentation was 1.4 g from 948 g of utilized glucose. The molar yield of utilized carbon that went into producing isoprene during fermentation was 0.32%.

Example 20

Production of Isoprene During the Exponential Growth Phase of *E. Coli* Expressing Genes from the Mevalonic Acid Pathway and Fermented in a Fed-Batch Culture This example illustrates the production of isoprene during the exponential growth phase of cells.

Medium Recipe (Per Liter Fermentation Medium):

The medium was generated using the following components per liter fermentation medium: $K_2HPO_4$ 7.5 g, $MgSO_4*7H_2O$ 2 g, citric acid monohydrate 2 g, ferric ammonium citrate 0.3 g, yeast extract 0.5 g, and 1000× modified trace metal solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified Trace Metal Solution:

The 1000× modified trace metal solution was generated using the following components: citric acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, and $NaMoO_4*2H_2O$ 100 mg. Each component is dissolved one at a time in Di H2O, pH to 3.0 with HCl/NaOH, then q.s. to volume and filter sterilized with 0.22 micron filter.

Fermentation was performed in a 15-L bioreactor with ATCC11303 *E. coli* cells containing the pCL PtrcUpperMVA and pTrc KKDyIkIS plasmids. This experiment was carried out to monitor isoprene formation from glucose at the desired fermentation pH 7.0 and temperature 30° C. An inoculum of *E. coli* strain taken from a frozen vial was streaked onto an LB broth agar plate (with antibiotics) and incubated at 37° C. A single colony was inoculated into tryptone-yeast extract medium. After the inoculum grew to OD 1.0, measured at 550 nm, 500 mL was used to inoculate a 15-L bioreactor containing an initial working volume of 5 L.

Glucose was fed at an exponential rate until cells reached the stationary phase. After this time the glucose feed was decreased to meet metabolic demands. The total amount of glucose delivered to the bioreactor during the 50 hour fermentation was 2.0 kg. Induction was achieved by adding IPTG. The IPTG concentration was brought to 25 uM when the optical density at 550 nm ($OD_{550}$) reached a value of 10. The IPTG concentration was raised to 50 uM when $OD_{550}$ reached 190. The $OD_{550}$ profile within the bioreactor over time is shown in FIG. 99. The isoprene level in the off gas from the bioreactor was determined as described herein. The isoprene titer increased over the course of the fermentation to a final value of 1.4 g/L (FIG. 100). The total amount of isoprene produced during the 50 hour fermentation was 10.0 g. The profile of the isoprene specific productivity over time within the bioreactor is shown in FIG. 101. The molar yield of utilized carbon that contributed to producing isoprene during fermentation was 1.1%. The weight percent yield of isoprene from glucose was 0.5%.

Example 21

Flammability Modeling and Testing of Isoprene

I. Summary of Flammability Modeling and Testing of Isoprene

Flammability modeling and experiments were performed for various hydrocarbon/oxygen/nitrogen/water/carbon dioxide mixtures. This modeling and experimental tested was aimed at defining isoprene and oxygen/nitrogen flammability curves under specified steam and carbon monoxide concentrations at a fixed pressure and temperature. A matrix of the model conditions is shown in Table 13, and a matrix of the experiments performed is shown in Table 14.

TABLE 13

Summary of Modeled Isoprene Flammability

| Series | Temperature (° C.) | Pressure (psig) | Steam Concentration (wt %) | Carbon Dioxide Concentration (wt. %) | Isoprene Concentration (vol. %) | Oxygen Concentration (vol. %) |
|---|---|---|---|---|---|---|
| A | 40 | 0 | 0 | 0 | Varying | Varying |
| B | 40 | 0 | 4 | 0 | Varying | Varying |
| C | 40 | 0 | 0 | 5 | Varying | Varying |
| D | 40 | 0 | 0 | 10 | Varying | Varying |
| E | 40 | 0 | 0 | 15 | Varying | Varying |
| F | 40 | 0 | 0 | 20 | Varying | Varying |
| G | 40 | 0 | 0 | 30 | Varying | Varying |

TABLE 14

Summary of Isoprene Flammability Tests

| Series Number | Temperature (° C.) | Pressure (psig) | Steam Concentration (vol. %) | Isoprene Concentration (vol. %) | Oxygen Concentration (vol. %) |
|---|---|---|---|---|---|
| 1 | 40 | 0 | 0 | Varying | Varying |
| 2 | 40 | 0 | 4 | Varying | Varying |

II. Description of Calculated Adiabatic Flame Temperature (CAFT) Model

Calculated adiabatic flame temperatures (CAFT) along with a selected limit flame temperature for combustion propagation were used to determine the flammability envelope for isoprene. The computer program used in this study to calculate the flame temperatures is the NASA Glenn Research Center CEA (Chemical Equilibrium with Applications) software.

There are five steps involved in determining the flammability envelope using an adiabatic flame temperature model for a homogeneous combustion mechanism (where both the fuel and oxidant are in the gaseous state): selection of the desired reactants, selection of the test condition, selection of the limit flame temperature, modification of the reactants, and construction of a flammability envelope from calculations.

In this first step, selection of desired reactants, a decision must be made as to the reactant species that will be present in the system and the quantities of each. In many cases the computer programs used for the calculations have a list of reactant and product species. If any of the data for the species to be studied are not found in the program, they may be obtained from other sources such as the JANAF tables or from the internet. In this current model data for water, nitrogen, oxygen and carbon dioxide were present in the program database. The program database did not have isoprene as a species; therefore thermodynamic properties were incorporated manually.

The next step is to decide whether the initial pressure and temperature conditions that the combustion process is taking place in. In this model the pressure was 1 atmosphere (absolute) and the temperature was 40° C., the boiling point of isoprene.

The limit flame temperature for combustion can be either selected based on theoretical principles or determined experimentally. Each method has its own limitations.

Based on prior studies, the limit flame temperatures of hydrocarbons fall in the range of 1000 K to 1500 K. For this model, the value of 1500 K was selected. This is the temperature at which the reaction of carbon monoxide to carbon dioxide (a highly exothermic reaction and constitutes a significant proportion of the flame energy) becomes self sustaining.

Once the limit flame temperature has been decided upon, model calculations are performed on the given reactant mixture (species concentrations) and the adiabatic flame temperature is determined. Flame propagation is considered to have occurred only if the temperature is greater than the limit flame temperature. The reactant mixture composition is then modified to create data sets for propagation and non-propagation mixtures.

This type of model shows good agreement with the experimentally determined flammability limits. Regions outside the derived envelope are nonflammable and regions within it are flammable. The shape of the envelope forms a nose. The nose of the envelope is related to the limiting oxygen concentration (LOC) for gaseous fuels.

III. Results from Calculated Adiabatic Flame Temperature (CAFT) Model

Plotted in FIGS. 68 through 74 are the CAFT model results for Series A to G, respectively. The figures plot the calculated adiabatic flame temperature (using the NASA CEA program) as a function of fuel concentration (by weight) for several oxygen/nitrogen ratios (by weight). The parts of the curve that are above 1500 K, the selected limit flame temperature, contain fuel levels sufficient for flame propagation. The results may be difficult to interpret in the form presented in FIGS. 68 through 74. Additionally, the current form is not conducive to comparison with experimental data which is generally presented in terms of volume percent.

Using Series A as an example the data in FIG. 68 can be plotted in the form of a traditional flammability envelope. Using FIG. 68 and reading across the 1500 K temperature line on the ordinate one can determine the fuel concentration for this limit flame temperature by dropping a tangent to the abscissa for each curve (oxygen to nitrogen ratio) that it intersects. These values can then be tabulated as weight percent of fuel for a given weight percent of oxidizer (FIG. 75A). Then knowing the composition of the fuel (100 wt. % isoprene) and the composition of the oxidizer (relative content of water, oxygen and nitrogen) molar quantities can be established.

From these molar quantities percentage volume concentrations can be calculated. The concentrations in terms of volume percent can then be plotted to generate a flammability envelope (FIG. 75B). The area bounded by the envelope is the explosible range and the area excluded is the non-explosible range. The “nose” of the envelope is the limiting oxygen concentration. FIGS. 76A and 76B contain the calculated volume concentrations for the flammability envelope for Series B generated from data presented in FIG. 69. A similar approach can be used on data presented in FIGS. 70-74.

IV. Flammability Testing Experimental Equipment and Procedure

Flammability testing was conducted in a 4 liter high pressure vessel. The vessel was cylindrical in shape with an inner diameter of 6" and an internal height of 8.625". The temperature of the vessel (and the gases inside) was maintained using external heaters that were controlled by a PID controller. To prevent heat losses, ceramic wool and reflective insulation were wrapped around the pressure vessel. Type K thermocouples were used the measure the temperature of the gas space as well as the temperature of the vessel itself. FIG. 77 illustrates the test vessel.

Before a test was ran, the vessel was evacuated and purged with nitrogen to ensure that any gases from previous tests were removed. A vacuum was then pulled on the vessel. The pressure after this had been done was typically around 0.06 bar(a). Due to the nitrogen purging, the gas responsible for this initial pressure was assumed to be nitrogen. Using partial pressures, water, isoprene, nitrogen, and oxygen were then added in the appropriate amounts to achieve the test conditions in question. A magnetically driven mixing fan within the vessel ensured mixing of the gaseous contents. The gases were allowed to mix for about 2 minutes with the fan being turned off approximately 1 minute prior to ignition.

The igniter was comprised of a 1.5 ohm nicrome coil and an AC voltage source on a timer circuit. Using an oscilloscope, it was determined that 34.4 VAC were delivered to the igniter for 3.2 seconds. A maximum current of 3.8 amps occurred approximately halfway into the ignition cycle. Thus, the maximum power was 131 W and the total energy provided over the ignition cycle was approximately 210 J.

Deflagration data was acquired using a variable reluctance Validyne DP215 pressure transducer connected to a data acquisition system. A gas mixture was considered to have deflagrated if the pressure rise was greater than or equal to 5%.

V. Results of Flammability Testing

The first experimental series (Series 1) was run at 40° C. and 0 psig with no steam. Running tests at varying concentrations of isoprene and oxygen produced the flammability curve shown in FIG. 78A. The data points shown in this curve are only those that border the curve. A detailed list of all the data points taken for this series is shown in FIGS. 80A and 80B.

FIG. 78B summarizes the explosibility data points shown in FIG. 78A. FIG. 78C is a comparison of the experimental data with the CAFT model predicted flammability envelope. The model agrees very well with the experimental data. Discrepancies may be due to the non-adiabatic nature of the test chamber and limitations of the model. The model looks at an infinite time horizon for the oxidation reaction and does not take into consideration any reaction kinetic limitation.

Additionally, the model is limited by the number of equilibrium chemical species that are in its database and thus may not properly predict pyrolytic species. Also, the flammability envelope developed by the model uses one value for a limit flame temperature (1500K). The limit flame temperature can be a range of values from 1,000K to 1,500K depending on the reacting chemical species. The complex nature of pyrolytic chemical species formed at fuel concentrations above the stoichiometric fuel/oxidizer level is one reason why the model may not accurately predict the upper flammable limit for this system.

The second experimental series (Series 2) was run at 40° C. and 0 psig with a fixed steam concentration of 4%. Running tests at varying concentrations of isoprene and oxygen produced the flammability curve shown in FIG. 79A. The data points shown in this curve are only those that border the curve. A detailed list of all the data points taken for this series is shown in FIG. 81. Due to the similarity between the data in Series 1 only the key points of lower flammable limit, limiting oxygen concentration, and upper flammable limits were tested. The addition of 4% steam to the test mixture did not significantly change the key limits of the flammability envelope. It should be noted that higher concentrations of steam/water and or other inertants may influence the flammability envelope.

FIG. 79B summarizes the explosibility data points shown in FIG. 79A. FIG. 79C is a comparison of the experimental data with the CAFT model predicted flammability envelope. The model agrees very well with the experimental data. Discrepancies may be due to the same factors described in Series 1

V. Calculation of Flammability Limits of Isoprene in Air at 3 Atmospheres of Pressure The methods described in Example 21, parts I to IV were also used to calculate the flammability limits of isoprene at an absolute system pressure of 3 atmospheres and 40° C. These results were compared to those of Example 21, parts I to IV at an absolute system pressure of 1 atmosphere and 40° C. This higher pressure was tested because the flammability envelope expands or grows larger as the initial system pressure is increased. The upper flammability limit is affected the most, followed by the limiting oxygen composition. The lower flammability limit is the least affected (see, for example, "Bulletin 627—Flammability Characteristics of Combustible Gases and Vapors" written by Michael G. Zabetakis and published by the former US Bureau of Mines (1965), which is hereby incorporated by reference in its entirety, particular with respect to the calculation of flammability limits).

In FIG. 82, the calculated adiabatic flame temperature is plotted as a function of isoprene (fuel) concentration, expressed in weight percent of the total fuel/nitrogen/oxygen, where the system pressure was initially 3 atmospheres. The calculated flame temperatures are very similar to those determined initially in the 1 atmosphere system (FIG. 83). As a result, when flammability envelopes are generated using the calculated adiabatic flammability data, the curves are very similar (see FIGS. 84 and 85). Therefore, based on these theoretical calculations, a system pressure increase from 1 atmosphere to 3 atmosphere does not result in a significant increase/broadening of the flammability envelope. If desired, these model results may be validated using experimental testing (such as the experimental testing described herein at a pressure of 1 atmosphere).

VII. Summary of Flammability Studies

A calculated adiabatic temperature model was developed for the flammability envelope of the isoprene/oxygen/nitrogen/water/carbon dioxide system at 40° C. and 0 psig. The CAFT model that was developed agreed well with the experimental data generated by the tests conducted in this work. The experimental results from Series 1 and 2 validated the model results from Series A and B.

Unless defined otherwise, the meanings of all technical and scientific terms used herein are those commonly understood by one of skill in the art to which this invention belongs. Singleton, et al., Dictionary of Microbiology and Molecular Biology, 2nd ed., John Wiley and Sons, New York (1994), and Hale & Marham, The Harper Collins Dictionary of Biology, Harper Perennial, N.Y. (1991) provide one of skill with a general dictionary of many of the terms used in this invention. It is to be understood that this invention is not limited to the particular methodology, protocols, and reagents described, as these may vary. One of skill in the art will also appreciate that any methods and materials similar or equivalent to those described herein can also be used to practice or test the invention.

The headings provided herein are not limitations of the various aspects or embodiments of the invention which can be had by reference to the specification as a whole.

For use herein, unless clearly indicated otherwise, use of the terms "a", "an," and the like refers to one or more.

Reference to "about" a value or parameter herein includes (and describes) embodiments that are directed to that value or parameter per se. For example, description referring to "about X" includes description of "X." Numeric ranges are inclusive of the numbers defining the range.

It is understood that aspects and embodiments of the invention described herein include "comprising," "consisting," and "consisting essentially of" aspects and embodiments.

APPENDIX 1

Exemplary 1-deoxy-D-xylulose-5-phosphate synthase nucleic acids and polypeptides ATH: AT3G21500(DXPS1) AT4G15560(CLA1) AT5G11380(DXPS3)
OSA: 4338768 4340090 4342614
CME: CMF089C
PFA: MAL13P1.186
TAN: TA20470
TPV: TP01_0516
ECO: b0420(dxs)
ECJ: JWO410(dxs)
ECE: Z0523(dxs)
ECS: ECs0474
ECC: c0531(dxs)
ECI: UTI89_CO443(dxs)
ECP: ECP_0479
ECV: APECO1_1590(dxs)
ECW: EcE24377A_0451(dxs)
ECX: EcHS_A0491
STY: STY0461(dxs)
STT: t2441(dxs)
SPT: SPA2301(dxs)
SEC: SC0463(dxs)
STM: STM0422(dxs)
YPE: YPO3177(dxs)
YPK: y1008(dxs)
YPM: YP_0754(dxs)
YPA: YPA 2671
YPN: YPN_0911
YPP: YPDSF_2812
YPS: YPTB0939(dxs)
YPI: YpsIP31758_3112(dxs)
SFL: SF0357(dxs)
SFX: S0365(dxs)
SFV: SFV_0385(dxs)
SSN: SSON_0397(dxs)
SBO: SBO_0314(dxs)
SDY: SDY_0310(dxs)
ECA: ECA1131(dxs)
PLU: plu3887(dxs)
BUC: BU464(dxs)
BAS: BUsg448(dxs)
WBR: WGLp144(dxs)
SGL: SG0656
KPN: KPN_00372(dxs)
BFL: Bfl238(dxs)
BPN: BPEN_244(dxs)
HIN: HI1439(dxs)

HIT: NTHI1691(dxs)
HIP: CGSHiEE_04795
HIQ: CGSHiGG_01080
HDU: HD0441(dxs)
HSO: HS_0905(dxs)
PMU: PM0532(dxs)
MSU: MS1059(dxs)
APL: APL_0207(dxs)
XFA: XF2249
XFT: PD1293(dxs)
XCC: XCC2434(dxs)
XCB: XC_1678
XCV: XCV2764(dxs)
XAC: XAC2565(dxs)
XOO: XOO2017(dxs)
XOM: XOO_1900(XOO1900)
VCH: VC0889
VVU: VV1_0315
VVY: VV0868
VPA: VP0686
VFI: VF0711
PPR: PBPRA0805
PAE: PA4044(dxs)
PAU: PA14_11550(dxs)
PAP: PSPA7_1057(dxs)
PPU: PP_0527(dxs)
PST: PSPTO_0698(dxs)
PSB: Psyr_0604
PSP: PSPPH_0599(dxs)
PFL: PFL_5510(dxs)
PFO: Pfl_5007
PEN: PSEEN0600(dxs)
PMY: Pmen_3844
PAR: Psyc_0221(dxs)
PCR: Pcryo_0245
ACI: ACIAD3247(dxs)
SON: SO_1525(dxs)
SDN: Sden_2571
SFR: Sfri_2790
SAZ: Sama_2436
SBL: Sbal_1357
SLO: Shew_2771
SHE: Shewmr4_2731
SHM: Shewmr7_2804
SHN: Shewana3_2901
SHW: Sputw3181_2831
ILO: IL2138(dxs)
CPS: CPS_1088(dxs)
PHA: PSHAa2366(dxs)
PAT: Patl_1319
SDE: Sde_3381
PIN: Ping_2240
MAQ: Maqu_2438
MCA: MCA0817(dxs)
FTU: FTT1018c(dxs)
FTF: FTF1018c(dxs)
FTW: FTW_0925(dxs)
FTL: FTL_1072
FTH: FTH_1047(dxs)
FTA: FTA_1131(dxs)
FTN: FTN_0896(dxs)
NOC: Noc_1743
AEH: Mlg_1381
HCH: HCH_05866(dxs)
CSA: Csal_0099
ABO: ABO_2166(dxs)
AHA: AHA_3321(dxs)
BCI: BCI_0275(dxs)
RMA: Rmag_0386
VOK: COSY_0360(dxs)
NME: NMB1867
NMA: NMA0589(dxs)
NMC: NMC0352(dxs)
NGO: NGO0036
CVI: CV_2692(dxs)
RSO: RSc2221(dxs)
REU: Reut_A0882
REH: H16_A2732(dxs)
RME: Rmet_2615
BMA: BMAA0330(dxs)
BMV: BMASAVP1_1512(dxs)
BML: BMA10299_1706(dxs)
BMN: BMA10247_A0364(dxs)
BXE: Bxe_B2827
BUR: Bcep18194_B2211
BCN: Bcen_4486
BCH: Bcen2424_3879
BAM: Bamb_3250
BPS: BPSS1762(dxs)
BPM: BURPS1710b_A0842(dxs)
BPL: BURPS1106A_A2392(dxs)
BPD: BURPS668_A2534(dxs)
BTE: BTH_II0614(dxs)
BPE: BP2798(dxs)
BPA: BPP2464(dxs)
BBR: BB1912(dxs)
RFR: Rfer_2875
POL: Bpro_1747
PNA: Pnap_1501
AJS: Ajs_1038
MPT: Mpe_A2631
HAR: HEAR0279(dxs)
MMS: mma_0331
NEU: NE1161(dxs)
NET: Neut_1501
NMU: Nmul_A0236
EBA: ebA4439(dxs)
AZO: azo1198(dxs)
DAR: Daro_3061
TBD: Tbd_0879
MFA: Mfla_2133
HPY: HP0354(dxs)
HPJ: jhp0328(dxs)
HPA: HPAG1_0349
HHE: HH0608(dxs)
HAC: Hac_0968(dxs)
WSU: WS1996
TDN: Tmden_0475
CJE: Cj0321(dxs)
CJR: CJE0366(dxs)
CJJ: CJJ81176_0343(dxs)
CJU: C8J_0298(dxs)
CJD: JJD26997_1642(dxs)
CFF: CFF8240_0264(dxs)
CCV: CCV52592_1671(dxs) CCV52592_1722
CHA: CHAB381_1297(dxs)
CCO: CCC13826_1594(dxs)
ABU: Abu_2139(dxs)
NIS: NIS_0391(dxs)
SUN: SUN_2055(dxs)
GSU: GSU0686(dxs-1) GSU1764(dxs-2)
GME: Gmet_1934 Gmet_2822
PCA: Pcar_1667
PPD: Ppro_1191 Ppro_2403

DVU: DVU1350(dxs)
DVL: Dvul_1718
DDE: Dde_2200
LIP: LI0408(dsx)
DPS: DP2700
ADE: Adeh_1097
MXA: MXAN_4643(dxs)
SAT: SYN_02456
SFU: Sfum_1418
PUB: SAR11_0611(dxs)
MLO: mlr7474
MES: Meso_0735
SME: SMc00972(dxs)
ATU: Atu0745(dxs)
ATC: AGR_C_1351
RET: RHE_CH00913(dxs)
RLE: RL0973(dxs)
BME: BMEI1498
BMF: BAB1_0462(dxs)
BMS: BR0436(dxs)
BMB: BruAb1_0458(dxs)
BOV: BOV_0443(dxs)
BJA: bll2651(dxs)
BRA: BRADO2161(dxs)
BBT: BBta_2479(dxs)
RPA: RPA0952(dxs)
RPB: RPB_4460
RPC: RPC_1149
RPD: RPD_4305
RPE: RPE_1067
NWI: Nwi_0633
NHA: Nham_0778
BHE: BH04350(dxs)
BQU: BQ03540(dxs)
BBK: BARBAKC583_0400(dxs)
CCR: CC_2068
SIL: SPO0247(dxs)
SIT: TM1040_2920
RSP: RSP_0254(dxsA) RSP_1134(dxs)
JAN: Jann_0088 Jann_0170
RDE: RD1_0101(dxs) RD1_0548(dxs)
MMR: Mmar10_0849
HNE: HNE_1838(dxs)
ZMO: ZMO1234(dxs) ZMO1598(dxs)
NAR: Saro_0161
SAL: Sala_2354
ELI: ELI_12520
GOX: GOX0252
GBE: GbCGDNIH1_0221 GbCGDNIH1_2404
RRU: Rru_A0054 Rru_A2619
MAG: amb2904
MGM: Mmc1_1048
SUS: Acid_1783
BSU: BG11715(dxs)
BHA: BH2779
BAN: BA4400(dxs)
BAR: GBAA4400(dxs)
BAA: BA_4853
BAT: BAS4081
BCE: BC4176(dxs)
BCA: BCE_4249(dxs)
BCZ: BCZK3930(dxs)
BTK: BT9727_3919(dxs)
BTL: BALH_3785(dxs)
BLI: BL01523(dxs)
BLD: BLi02598(dxs)
BCL: ABC2462(dxs)
BAY: RBAM_022600
BPU: BPUM_2159
GKA: GK2392
GTN: GTNG_2322
LMO: lmo1365(tktB)
LMF: LMOf2365_1382(dxs)
LIN: lin1402(tktB)
LWE: lwe1380(tktB)
LLA: L108911(dxsA) L123365(dxsB)
LLC: LACR_1572 LACR_1843
LLM: llmg_0749(dxsB)
SAK: SAK_0263
LPL: lp_2610(dxs)
LJO: LJ0406
LAC: LBA0356
LSL: LSL_0209(dxs)
LGA: LGAS_0350
STH: STH1842
CAC: CAC2077 CA_P0106(dxs)
CPE: CPE1819
CPF: CPF_2073(dxs)
CPR: CPR_1787(dxs)
CTC: CTC01575
CNO: NT01CX_1983
CTH: Cthe_0828
CDF: CD1207(dxs)
CBO: CBO1881(dxs)
CBA: CLB_1818(dxs)
CBH: CLC_1825(dxs)
CBF: CLI_1945(dxs)
CKL: CKL_1231(dxs)
CHY: CHY_1985(dxs)
DSY: DSY2348
DRM: Dred_1078
PTH: PTH_1196(dxs)
SWO: Swol_0582
CSC: Csac_1853
TTE: TTE1298(dxs)
MTA: Moth_1511
MPE: MYPE730
MGA: MGA_1268(dxs)
MTU: Rv2682c(dxs1) Rv3379c(dxs2)
MTC: MT2756(dxs)
MBO: Mb2701c(dxs1) Mb3413c(dxs2)
MLE: ML1038(dxs)
MPA: MAP2803c(dxs)
MAV: MAV_3577(dxs)
MSM: MSMEG_2776(dxs)
MMC: Mmcs_2208
CGL: NCgl1827(cgl1902)
CGB: cg2083(dxs)
CEF: CE1796
CDI: DIP1397(dxs)
CJK: jk1078(dxs)
NFA: nfa37410(dxs)
RHA: RHA1_ro06843
SCO: SCO6013(SC1C3.01) SCO6768(SC6A5.17)
SMA: SAV1646(dxs1) SAV2244(dxs2)
TWH: TWT484
TWS: TW280(Dxs)
LXX: Lxx10450(dxs)
CMI: CMM_1660(dxsA)
AAU: AAur_1790(dxs)
PAC: PPA1062
TFU: Tfu_1917
FRA: Francci3_1326
FAL: FRAAL2088(dxs)

ACE: Acel_1393
SEN: SACE_1815(dxs) SACE_4351
BLO: BL1132(dxs)
BAD: BAD_0513(dxs)
FNU: FN1208 FN1464
RBA: RB2143(dxs)
CTR: CT331(dxs)
CTA: CTA_0359(dxs)
CMU: TC0608
CPN: CPn1060(tktB_2)
CPA: CP0790
CPJ: CPj 1060(tktB_2)
CPT: CpB1102
CCA: CCA00304(dxs)
CAB: CAB301(dxs)
CFE: CF0699(dxs)
PCU: pc0619(dxs)
TPA: TP0824
TDE: TDE1910(dxs)
LIL: LA3285(dxs)
LIC: LIC10863(dxs)
LBJ: LBJ_0917(dxs)
LBL: LBL_0932(dxs)
SYN: sll1945(dxs)
SYW: SYNW1292(Dxs)
SYC: syc1087_c(dxs)
SYF: Synpcc7942_0430
SYD: Syncc9605_1430
SYE: Syncc9902_1069
SYG: sync_1410(dxs)
SYR: SynRCC307_1390(dxs)
SYX: SynWH7803_1223(dxs)
CYA: CYA_1701(dxs)
CYB: CYB_1983(dxs)
TEL: tll0623
GVI: gll0194
ANA: alr0599
AVA: Ava_4532
PMA: Pro0928(dxs)
PMM: PMM0907(Dxs)
PMT: PMT0685(dxs)
PMN: PMN2A_0300
PMI: PMT9312_0893
PMB: A9601_09541(dxs)
PMC: P9515_09901(dxs)
PMF: P9303_15371(dxs)
PMG: P9301_09521(dxs)
PMH: P9215_09851
PMJ: P9211_08521
PME: NATL1_09721(dxs)
TER: Tery_3042
BTH: BT_1403 BT_4099
BFR: BF0873 BF4306
BFS: BF0796(dxs) BF4114
PGI: PG2217(dxs)
CHU: CHU_3643(dxs)
GFO: GFO_3470(dxs)
FPS: FP0279(dxs)
CTE: CT0337(dxs)
CPH: Cpha266_0671
PVI: Cvib_0498
PLT: Plut_0450
DET: DET0745(dxs)
DEH: cbdb_A720(dxs)
DRA: DR_1475
DGE: Dgeo_0994
TTH: TTC1614
TTJ: TTHA0006
AAE: aq_881
TMA: TM1770
PMO: Pmob_1001

Exemplary acetyl-CoA-acetyltransferase nucleic acids and polypeptides

HSA: 38(ACAT1) 39(ACAT2)
PTR: 451528(ACAT1)
MCC: 707653(ACAT1) 708750(ACAT2)
MMU: 110446(Acat1) 110460(Acat2)
RNO: 25014(Acat1)
CFA: 484063(ACAT2) 489421(ACAT1)
GGA: 418968(ACAT1) 421587(RCJMB04_34i5)
XLA: 379569(MGC69098) 414622(MGC81403) 414639 (MGC81256) 444457(MGC83664)
XTR: 394562(acat2)
DRE: 30643(acat2)
SPU: 759502(LOC759502)
DME: Dmel_CG10932 Dmel_CG9149
CEL: T02G5.4 T02G5.7 T02G5.8(kat-1)
ATH: AT5G48230(ACAT2/EMB1276)
OSA: 4326136 4346520
CME: CMA042C CME087C
SCE: YPL028W(ERG10)
AGO: AGOS_ADR165c
PIC: PICST_31707(ERG10)
CAL: CaO19.1591(erg10)
CGR: CAGL0L12364g
SPO: SPBC215.09c
MGR: MGG_01755 MGG_13499
ANI: AN1409.2
AFM: AFUA_6G14200 AFUA_8G04000
AOR: AO090103000012 AO090103000406
CNE: CNC05280
UMA: UM03571.1
DDI: DDB_0231621
PFA: PF14_0484
TET: TTHERM_00091590 TTHERM_00277470 TTHERM_00926980
TCR: 511003.60
ECO: b2224(atoB)
ECJ: JW2218(atoB) JW5453(yqeF)
ECE: Z4164(yqeF)
ECS: ECs3701
ECC: c2767(atoB) c3441(yqeF)
ECI: UTI89_C2506(atoB) UTI89_C3247(yqeF)
ECP: ECP_2268 ECP_2857
ECV: APECO1_3662(yqeF) APECO1_4335(atoB) APECO1_43352(atoB)
ECX: EcHS_A2365
STY: STY3164(yqeF)
STT: t2929(yqeF)
SPT: SPA2886(yqeF)
SEC: SC2958(yqeF)
STM: STM3019(yqeF)
SFL: SF2854(yqeF)
SFX: 53052(yqeF)
SFV: SFV_2922(yqeF)
SSN: SSON_2283(atoB) SSON_3004(yqeF)
SBO: SBO_2736(yqeF)
ECA: ECA1282(atoB)
ENT: Ent638_3299
SPE: Spro_0592
HIT: NTHI0932(atoB)
XCC: XCC1297(atoB)
XCB: XC_2943
XCV: XCV1401(thlA)

XAC: XAC1348(atoB)
XOO: XOO1881(atoB)
XOM: XOO__1778(XOO1778)
VCH: VCA0690
VCO: VC0395__0630
VVU: VV2__0494 VV2__0741
VVY: VVA1043 VVA1210
VPA: VPA0620 VPA1123 VPA1204
PPR: PBPRB1112 PBPRB1840
PAE: PA2001(atoB) PA2553 PA3454 PA3589 PA3925
PAU: PA14__38630(atoB)
PPU: PP__2051(atoB) PP__2215(fadAx) PP__3754 PP__4636
PPF: Pput__2009 Pput__2403 Pput__3523 Pput__4498
PST: PSPTO__0957(phbA-1) PSPTO__3164(phbA-2)
PSB: Psyr__0824 Psyr__3031
PSP: PSPPH__0850(phbA1) PSPPH__2209(phbA2)
PFL: PFL__1478(atoB-2) PFL__2321 PFL__3066 PFL__4330 (atoB-2) PFL__5283
PFO: Pfl__1269 Pfl__1739 Pfl__2074 Pfl__2868
PEN: PSEEN3197 PSEEN3547(fadAx) PSEEN4635(phbA)
PMY: Pmen__1138 Pmen__2036 Pmen__3597 Pmen__3662 Pmen__3820
PAR: Psyc__0252 Psyc__1169
PCR: Pcryo__0278 Pcryo__1236 Pcryo__1260
PRW: PsycPRwf__2011
ACI: ACIAD0694 ACIAD1612 ACIAD2516(atoB)
SON: SO__1677(atoB)
SDN: Sden__1943
SFR: Sfri__1338 Sfri__2063
SAZ: Sama__1375
SBL: Sbal__1495
SBM: Shew185__1489
SBN: Sbal195__1525
SLO: Shew__1667 Shew__2858
SPC: Sputcn32__1397
SSE: Ssed__1473 Ssed__3533
SPL: Spea__2783
SHE: Shewmr4__2597
SHM: Shewmr7__2664
SHN: Shewana3__2771
SHW: Sputw3181__2704
ILO: IL0872
CPS: CPS__1605 CPS__2626
PHA: PSHAa0908 PSHAa1454(atoB) PSHAa1586(atoB)
PAT: Patl__2923
SDE: Sde__3149
PIN: Ping__0659 Ping__2401
MAQ: Maqu__2117 Maqu__2489 Maqu__2696 Maqu__3162
CBU: CBU__0974
LPN: lpg1825(atoB)
LPF: lpl1789
LPP: lpp1788
NOC: Noc__1891
AEH: Mlg__0688 Mlg__2706
HHA: Hhal__1685
HCH: HCH__05299
CSA: Csal__0301 Csal__3068
ABO: ABO__0648(fadAx)
MMW: Mmwyl1__0073 Mmwyl1__3021 Mmwyl1__3053 Mmwyl1__3097 Mmwyl1__4182
AHA: AHA__2143(atoB)
CVI: CV__2088(atoB) CV__2790(phaA)
RSO: RSc0276(atoB) RSc1632(phbA) RSc1637(bktB) RSc1761(RS02948)
REU: Reut_A0138 Reut_A1348 Reut_A1353 Reut_B4561 Reut_B4738 Reut_B5587 Reut_C5943 Reut_C6062
REH: H16_A0170 H16_A0867 H16_A0868 H16_A0872 H16_A1297 H16_A1438(phaA) H16_A1445(bktB) H16_A1528 H16_A1713 H16_A1720 H16_A1887 H16_A2148 H16_B0380 H16_B0381 H16_B0406 H16_B0662 H16_B0668 H16_B0759 H16_B1369 H16_B1771
RME: Rmet__0106 Rmet__1357 Rmet__1362 Rmet__5156
BMA: BMA1316 BMA1321(phbA) BMA1436
BMV: BMASAVP1_A1805(bktB) BMASAVP1_A1810 (phbA)
BML: BMA10299_A0086(phbA) BMA10299_A0091
BMN: BMA10247__1076(bktB) BMA10247__1081(phbA)
BXE: Bxe_A2273 Bxe_A2335 Bxe_A2342 Bxe_A4255 Bxe_B0377 Bxe_B0739 Bxe_C0332 Bxe_C0574 Bxe_C0915
BVI: Bcep1808__0519 Bcep1808__1717 Bcep1808__2877 Bcep1808__3594 Bcep1808__4015 Bcep1808__5507 Bcep1808__5644
BUR: Bcep18194_A3629 Bcep18194_A5080 Bcep18194_A5091 Bcep18194_A6102 Bcep18194_B0263 Bcep18194_B1439 Bcep18194_C6652 Bcep18194_C6802 Bcep18194_C6874 Bcep18194_C7118 Bcep18194_C7151 Bcep18194_C7332
BCN: Bcen__1553 Bcen__1599 Bcen__2158 Bcen__2563 Bcen__2998 Bcen__6289
BCH: Bcen2424__0542 Bcen2424__1790 Bcen2424__2772 Bcen2424__5368 Bcen2424__6232 Bcen2424__6276
BAM: Bamb__0447 Bamb__1728 Bamb__2824 Bamb__4717 Bamb__5771 Bamb__5969
BPS: BPSL1426 BPSL1535(phbA) BPSL1540
BPM: BURPS1710b__2325(bktB) BURPS1710b__2330 (phbA) BURPS1710b__2453(atoB-2)
BPL: BURPS1106A__2197(bktB) BURPS1106A__2202 (phbA)
BPD: BURPS668__2160(bktB) BURPS668__2165(phbA)
BTE: BTH__I2144 BTH__I2256 BTH__I2261
PNU: Pnuc__0927
BPE: BP0447 BP0668 BP2059
BPA: BPP0608 BPP1744 BPP3805 BPP4216 BPP4361
BBR: BB0614 BB3364 BB4250 BB4804 BB4947
RFR: Rfer__0272 Rfer__1000 Rfer__1871 Rfer__2273 Rfer__2561 Rfer__2594 Rfer__3839
POL: Bpro__1577 Bpro__2140 Bpro__3113 Bpro__4187
PNA: Pnap__0060 Pnap__0458 Pnap__0867 Pnap__1159 Pnap__2136 Pnap__2804
AAV: Aave__0031 Aave__2478 Aave__3944 Aave__4368
AJS: Ajs__0014 Ajs__0124 Ajs__1931 Ajs__2073 Ajs__2317 Ajs__3548 Ajs__3738 Ajs__3776
VEI: Veis__1331 Veis__3818 Veis__4193
DAC: Daci__0025 Daci__0192 Daci__3601 Daci__5988
MPT: Mpe_A1536 Mpe_A1776 Mpe_A1869 Mpe_A3367
HAR: HEAR0577(phbA)
MMS: mma__0555
NEU: NE2262(bktB)
NET: Neut__0610
EBA: ebA5202 p2A409(tioL)
AZO: azo0464(fadA1) azo0469(fadA2) azo2172(thlA)
DAR: Daro__0098 Daro__3022
HPA: HPAG1__0675
HAC: Hac__0958(atoB)
GME: Gmet__1719 Gmet__2074 Gmet__2213 Gmet__2268 Gmet__3302
GUR: Gura__3043
BBA: Bd0404(atoB) Bd2095
DOL: Dole__0671 Dole__1778 Dole__2160 Dole__2187
ADE: Adeh__0062 Adeh__2365

AFW: Anae109_0064 Anae109_1504
MXA: MXAN_3791
SAT: SYN_02642
SFU: Sfum_2280 Sfum_3582
RPR: RP737
RCO: RC1134 RC1135
RFE: RF_0163(paaJ)
RBE: RBE_0139(paaJ)
RAK: A1C_05820
RBO: A1I_07215
RCM: A1E_04760
PUB: SAR11_0428(thlA)
MLO: mlr3847
MES: Meso_3374
PLA: Plav_1573 Plav_2783
SME: SMa1450 SMc03879(phbA)
SMD: Smed_0499 Smed_3117 Smed_5094 Smed_5096
ATU: Atu2769(atoB) Atu3475
ATC: AGR_C_5022(phbA) AGR_L_2713
RET: RHE_CH04018(phbAch) RHE_PC00068(ypc00040) RHE_PF00014(phbAf)
RLE: RL4621(phaA) pRL100301 pRL120369
BME: BMEI0274 BMEII0817
BMF: BAB1_1783(phbA-1) BAB2_0790(phbA-2)
BMS: BR1772(phbA-1) BRA0448(phbA-2)
BMB: BruAb1_1756(phbA-1) BruAb2_0774(phbA-2)
BOV: BOV_1707(phbA-1)
OAN: Oant_1130 Oant_3107 Oant_3718 Oant_4020
BJA: bll0226(atoB) bll3949 bll7400 bll7819 blr3724(phbA)
BRA: BRADO0562(phbA) BRADO0983(pimB) BRADO3110 BRADO3134(atoB)
BBT: BBta_3558 BBta_3575(atoB) BBta_5147(pimB) BBta_7072(pimB) BBta_7614(phbA)
RPA: RPA0513(pcaF) RPA0531 RPA3715(pimB)
RPB: RPB_0509 RPB_0525 RPB_1748
RPC: RPC_0504 RPC_0636 RPC_0641 RPC_0832 RPC_1050 RPC_2005 RPC_2194 RPC_2228
RPD: RPD_0306 RPD_0320 RPD 3105 RPD_3306
RPE: RPE_0168 RPE_0248 RPE_3827
NWI: Nwi_3060
XAU: Xaut_3108 Xaut_4665
CCR: CC_0510 CC_0894 CC_3462
SIL: SPO0142(bktB) SPO0326(phbA) SPO0773 SPO3408
SIT: TM1040_0067 TM1040_2790 TM1040_3026 TM1040_3735
RSP: RSP_0745 RSP_1354 RSP 3184
RSH: Rsph17029_0022 Rsph17029_2401 Rsph17029_3179 Rsph17029_3921
RSQ: Rsph17025_0012 Rsph17025_2466 Rsph17025_2833
JAN: Jann_0262 Jann_0493 Jann_4050
RDE: RD1_0025 RD1_0201(bktB) RD1_3394(phbA)
PDE: Pden_2026 Pden_2663 Pden_2870 Pden_2907 Pden_4811 Pden_5022
DSH: Dshi_0074 Dshi_3066 Dshi_3331
MMR: Mmar10_0697
HNE: HNE_2706 HNE_3065 HNE 3133
NAR: Saro_0809 Saro_1069 Saro_1222 Saro_2306 Saro_2349
SAL: Sala_0781 Sala_1244 Sala_2896 Sala 3158
SWI: Swit_0632 Swit_0752 Swit_2893 Swit_3602 Swit_4887 Swit_5019 Swit_5309
ELI: ELI_01475 ELI_06705 ELI_12035
GBE: GbCGDNIH1_0447
ACR: Acry_1847 Acry_2256
RRU: Rru_A0274 Rru_A1380 Rru_A1469 Rru_A1946 Rru_A3387
MAG: amb0842
MGM: Mmc1_1165
ABA: Acid345_3239
BSU: BG11319(mmgA) BG13063(yhfS)
BHA: BH1997 BH2029 BH3801(mmgA)
BAN: BA3687 BA4240 BA5589
BAR: GBAA3687 GBAA4240 GBAA5589
BAA: BA_0445 BA_4172 BA_4700
BAT: BAS3418 BAS3932 BAS5193
BCE: BC3627 BC4023 BC5344
BCA: BCE_3646 BCE_4076 BCE_5475
BCZ: BCZK3329(mmgA) BCZK3780(thl) BCZK5044 (atoB)
BCY: Bcer98_2722 Bcer98_3865
BTK: BT9727_3379(mmgA) BT9727_3765(thl) BT9727_5028(atoB)
BTL: BALH_3262(mmgA) BALH_3642(fadA) BALH_4843(atoB)
BLI: BL03925(mmgA)
BLD: BLi03968(mmgA)
BCL: ABC0345 ABC2989 ABC3617 ABC3891(mmgA)
BAY: RBAM_022450
BPU: BPUM_2374(yhfS) BPUM_2941 BPUM_3373
OIH: OB06760B06890B26320B3013
GKA: GK1658 GK3397
SAU: SA0342 SA0534(vraB)
SAV: SAV0354 SAV0576(vraB)
SAM: MW0330 MW0531(vraB)
SAR: SAR0351(thl) SAR0581
SAS: SAS0330 SAS0534
SAC: SACOL0426 SACOL0622(atoB)
SAB: SAB0304(thl) SAB0526
SAA: SAUSA300_0355 SAUSA300_0560(vraB)
SAO: SAOUHSC_00336 SAOUHSC_00558
SAJ: SaurJH9_0402
SAH: SaurJH1_0412
SEP: SE0346 SE2384
SER: SERP0032 SERP0220
SHA: SH0510(mvaC) SH2417
SSP: SSP0325 SSP2145
LMO: lmo1414
LMF: LMOf2365_1433
LIN: lin1453
LWE: lwe1431
LLA: L11745(thiL) L25946(fadA)
LLC: LACR_1665 LACR_1956
LLM: llmg_0930(thiL)
SPY: SPy_0140 SPy_1637(atoB)
SPZ: M5005_Spy_0119 M5005_Spy_0432 M5005_Spy_1344(atoB)
SPM: spyM18_0136 spyM18_1645(atoB)
SPG: SpyM3_0108 SpyM3_1378(atoB)
SPS: SPs0110 SPs0484
SPH: MGAS10270_Spy0121 MGAS10270_Spy0433 MGAS10270_Spy1461(atoB)
SPI: MGAS10750_Spy0124 MGAS10750_Spy0452 MGAS10750_Spy1453(atoB)
SPJ: MGAS2096_Spy0123 MGAS2096_Spy0451 MGAS2096_Spy1365(atoB)
SPK: MGAS9429_Spy0121 MGAS9429_Spy0431 MGAS9429_Spy1339(atoB)
SPF: SpyM50447(atoB2)
SPA: M6_Spy0166 M6_Spy0466 M6_Spy1390
SPB: M28_Spy0117 M28_Spy0420 M28_Spy1385(atoB)
SAK: SAK_0568
LJO: LJ1609
LAC: LBA0626(thiL)

LSA: LSA1486
LDB: Ldb0879
LBU: LBUL_0804
LBR: LVIS_2218
LCA: LSEI_1787
LGA: LGAS_1374
LRE: Lreu_0052
EFA: EF1364
OOE: OEOE_0529
STH: STH2913 STH725 STH804
CAC: CAC2873 CA_P0078(thiL)
CPE: CPE2195(atoB)
CPF: CPF_2460
CPR: CPR_2170
CTC: CTC00312
CNO: NT01CX_0538 NT01CX_0603
CDF: CD1059(thlA1) CD2676(thlA2)
CBO: CBO3200(thl)
CBE: Cbei_0411 Cbei_3630
CKL: CKL_3696(thlA1) CKL_3697(thlA2) CKL_3698 (thlA3)
AMT: Amet_4630
AOE: Clos_0084 Clos_0258
CHY: CHY_1288 CHY_1355(atoB) CHY_1604 CHY_1738
DSY: DSY0632 DSY0639 DSY1567 DSY1710 DSY2402 DSY3302
DRM: Dred_0400 Dred_1491 Dred_1784 Dred_1892
SWO: Swol_0308 Swol_0675 Swol_0789 Swol_1486 Swol_1934 Swol_2051
TTE: TTE0549(paaJ)
MTA: Moth_1260
MTU: Rv1135A Rv1323(fadA4) Rv3546(fadA5)
MTC: MT1365(phbA)
MBO: Mb1167 Mb1358(fadA4) Mb3576(fadA5) Mb3586c (fadA6)
MBB: BCG_1197 BCG_1385(fadA4) BCG_3610(fadA5) BCG_3620c(fadA6)
MLE: ML1158(fadA4)
MPA: MAP2407c(fadA3) MAP2436c(fadA4)
MAV: MAV_1544 MAV_1573 MAV_1863 MAV_5081
MSM: MSMEG_2224 MSMEG_4920
MUL: MUL_0357
MVA: Mvan_1976 Mvan_1988 Mvan_4305 Mvan_4677 Mvan_4891
MGI: Mflv_1347 Mflv_1484 Mflv_2040 Mflv_2340 Mflv_4356 Mflv_4368
MMC: Mmcs_1758 Mmcs_1769 Mmcs_3796 Mmcs_3864
MKM: Mkms_0251 Mkms_1540 Mkms_1805 Mkms_1816 Mkms_2836 Mkms_3159 Mkms_3286 Mkms_3869 Mkms_3938 Mkms_4227 Mkms_4411 Mkms_4580 Mkms_4724 Mkms_4764 Mkms_4776
MJL: Mjls_0231 Mjls_1739 Mjls_1750 Mjls_2819 Mjls_3119 Mjls_3235 Mjls_3800 Mjls_3850 Mjls_4110 Mjls_4383 Mjls_4705 Mjls_4876 Mjls_5018 Mjls_5063 Mjls_5075
CGL: NCgl2309(cgl2392)
CGB: cg2625(pcaF)
CEF: CE0731 CE2295
CJK: jk1543(fadA3)
NFA: nfa10750(fadA4)
RHA: RHA1_ro01455 RHA1_ro01623 RHA1_ro01876 RHA1_ro02517(catF) RHA1_ro03022 RHA1_ro03024 RHA1_ro03391 RHA1_ro03892 RHA1_ro04599 RHA1_ro05257 RHA1_ro08871
SCO: SCO5399(SC8F4.03)
SMA: SAV1384(fadA5) SAV2856(fadA1)
ART: Arth_1160 Arth_2986 Arth_3268 Arth_4073
NCA: Noca_1371 Noca_1797 Noca_1828 Noca_2764 Noca_4142
TFU: Tfu_1520 Tfu_2394
FRA: Francci3_3687
FRE: Franean1_1044 Franean1_2711 Franean1_2726 Franean1_3929 Franean1_4037 Franean1_4577
FAL: FRAAL2514 FRAAL2618 FRAAL5910(atoB)
ACE: Acel_0626 Acel_0672
SEN: SACE_1192(mmgA) SACE_2736(fadA6) SACE_4011(catF) SACE_6236(fadA4)
STP: Strop_3610
SAQ: Sare_1316 Sare_3991
RXY: Rxyl_1582 Rxyl_1842 Rxyl_2389 Rxyl_2530
FNU: FN0495
BGA: BG0110(fadA)
BAF: BAPKO_0110(fadA)
LIL: LA0457(thiL1) LA0828(thiL2) LA4139(fadA)
LIC: LIC10396(phbA)
LBJ: LBJ_2862(paaJ-4)
LBL: LBL_0209(paaJ-4)
SYN: slr1993(phaA)
SRU: SRU_1211(atoB) SRU_1547
CHU: CHU_1910(atoB)
GFO: GFO_1507(atoB)
FJO: Fjoh_4612
FPS: FP0770 FP1586 FP1725
RRS: RoseRS_3911 RoseRS_4348
RCA: Rcas_0702 Rcas_3206
HAU: Haur_0522
DRA: DR_1072 DR_1428 DR_1960 DR_2480 DR_A0053
DGE: Dgeo_0755 Dgeo_1305 Dgeo_1441 Dgeo_1883
TTH: TTC0191 TTC0330
TTJ: TTHA0559
TME: Tmel_1134
FNO: Fnod_0314
PMO: Pmob_0515
HMA: rrnAC0896(acaB3) rrnAC2815(aca2) rrnAC3497 (yqeF) rrnB0240(aca1) rrnB0242(acaB2) rrnB0309 (acaB1)
TAC: Ta0582
TVO: TVN0649
PTO: PTO1505
APE: APE_2108
SSO: SSO2377(acaB-4)
STO: ST0514
SAI: Saci_0963 Saci_1361(acaB1)
MSE: Msed_0656
PAI: PAE1220
PIS: Pis1_0029 Pis1_1301
PCL: Pcal_0781
PAS: Pars_0309 Pars_1071
CMA: Cmaq_1941

Exemplary HMG-CoA synthase nucleic acids and polypeptides

HSA: 3157(HMGCS1) 3158(HMGCS2)
PTR: 457169(HMGCS2) 461892(HMGCS1)
MCC: 702553(HMGCS1) 713541(HMGCS2)
MMU: 15360(Hmgcs2) 208715(Hmgcs1)
RNO: 24450(Hmgcs2) 29637(Hmgcs1)
CFA: 479344(HMGCS1) 607923(HMGCS2)
BTA: 407767(HMGCS1)
SSC: 397673(CH242-38B5.1)
GGA: 396379(HMGCS1)
XLA: 380091(hmgcs1) 447204(MGC80816)

DRE: 394060(hmgcs1)
SPU: 578259(L00578259)
DME: Dmel_CG4311(Hmgs)
CEL: F25B4.6
ATH: AT4G11820(BAP1)
OSA: 4331418 4347614
CME: CMM189C
SCE: YML126C(ERG13)
AGO: AGOS_ADL356C
PIC: PICST__83020
CAL: CaO19__7312(CaO19.7312)
CGR: CAGL0H04081g
SPO: SPAC4F8.14c(hcs)
MGR: MGG__01026
ANI: AN4923.2
AFM: AFUA__3G10660 AFUA__8G07210
AOR: AO090003000611 AO090010000487
CNE: CNC05080 CNG02670
UMA: UM05362.1
ECU: ECU10__0510
DDI: DDBDRAFT__0217522 DDB__0219924(hgsA)
TET: TTHERM__00691190
TBR: Tb927.8.6110
YPE: YPO1457
YPK: y2712(pksG)
YPM: YP__1349(pksG)
YPA: YPA__0750
YPN: YPN__2521
YPP: YPDSF__1517
YPS: YPTB1475
CBD: COXBU7E912__1931
TCX: Tcr__1719
DNO: DNO__0799
BMA: BMAA1212
BPS: BPSS1002
BPM: BURPS1710b_A2613
BPL: BURPS1106A_A1384
BPD: BURPS668_A1470
BTE: BTH_II1670
MXA: MXAN__3948(tac) MXAN__4267(mvaS)
BSU: BG10926(pksG)
OIH: OB2248
SAU: SA2334(mvaS)
SAV: SAV2546(mvaS)
SAM: MW2467(mvaS)
SAR: SAR2626(mvaS)
SAS: SAS2432
SAC: SACOL2561
SAB: SAB2420(mvaS)
SAA: SAUSA300__2484
SAO: SAOUHSC__02860
SAJ: SaurJH9__2569
SAH: SaurJH1__2622
SEP: SE2110
SER: SERP2122
SHA: SH0508(mvaS)
SSP: SSP0324
LMO: lmo1415
LMF: LMOf2365__1434(mvaS)
LIN: lin1454
LWE: lwe1432(mvaS)
LLA: L13187(hmcM)
LLC: LACR__1666
LLM: llmg__0929(hmcM)
SPY: SPy__0881(mvaS.2)
SPZ: M5005_Spy__0687(mvaS.1)
SPM: spyM18__0942(mvaS2)
SPG: SpyM3__0600(mvaS.2)
SPS: SPs1253
SPH: MGAS10270_Spy0745(mvaS1)
SPI: MGAS10750_Spy0779(mvaS1)
SPJ: MGAS2096_Spy0759(mvaS1)
SPK: MGAS9429_Spy0743(mvaS1)
SPF: SpyM51121(mvaS)
SPA: M6_Spy0704
SPB: M28_Spy0667(mvaS.1)
SPN: SP__1727
SPR: spr1571(mvaS)
SPD: SPD__1537(mvaS)
SAG: SAG1316
SAN: gbs1386
SAK: SAK__1347
SMU: SMU.943c
STC: str0577(mvaS)
STL: stu0577(mvaS)
STE: STER__0621
SSA: SSA__0338(mvaS)
SSU: SSU05__1641
SSV: SSU98__1652
SGO: SGO__0244
LPL: lp__2067(mvaS)
LJO: LJ1607
LAC: LBA0628(hmcS)
LSA: LSA1484(mvaS)
LSL: LSL__0526
LDB: Ldb0881(mvaS)
LBU: LBUL__0806
LBR: LVIS__1363
LCA: LSEI__1785
LGA: LGAS__1372
LRE: Lreu__0676
PPE: PEPE__0868
EFA: EF1363
OOE: OEOE__0968
LME: LEUM__1184
NFA: nfa22120
SEN: SACE__4570(pksG)
BBU: BB0683
BGA: BG0706
BAF: BAPKO__0727
FJO: Fjoh__0678
HAL: VNG1615G(mvaB)
HMA: rrnAC1740(mvaS)
HWA: HQ2868A(mvaB)
NPH: NP2608A(mvaB__1) NP4836A(mvaB__2)

Exemplary hydroxymethylglutaryl-CoA reductase nucleic acids and polypeptides

HSA: 3156(HMGCR)
PTR: 471516(HMGCR)
MCC: 705479(HMGCR)
MMU: 15357(Hmgcr)
RNO: 25675(Hmgcr)
CFA: 479182(HMGCR)
BTA: 407159(HMGCR)
GGA: 395145(RCJMB04__14 m24)
SPU: 373355(LOC373355)
DME: Dmel_CG 10367 (Hmgcr)
CEL: F08F8.2
OSA: 4347443
SCE: YLR450W(HMG2) YML075C(HMG1)
AGO: AGOS_AER152W
CGR: CAGL0L11506g
SPO: SPCC162.09c(hmg1)
ANI: AN3817.2

AFM: AFUA_1G11230 AFUA_2G03700
AOR: AO090103000311 AO090120000217
CNE: CNF04830
UMA: UM03014.1
ECU: ECU10_1720
DDI: DDB_0191125(hmgA) DDB_0215357(hmgB)
TBR: Tb927.6.4540
TCR: 506831.40 509167.20
LMA: LmjF30.3190
VCH: VCA0723
VCO: VC0395_0662
VVU: VV2_0117
VVY: VVA0625
VPA: VPA0968
VFI: VFA0841
PAT: Patl_0427
CBU: CBU_0030 CBU_0610
CBD: COXBU7E912_0151 COXBU7E912_0622(hmgA)
TCX: Tcr_1717
DNO: DNO_0797
CVI: CV_1806
SUS: Acid_5728 Acid_6132
SAU: SA2333(mvaA)
SAV: SAV2545(mvaA)
SAM: MW2466(mvaA)
SAB: SAB2419c(mvaA)
SEP: SE2109
LWE: lwe0819(mvaA)
LLA: L10433(mvaA)
LLC: LACR_1664
LLM: llmg_0931(mvaA)
SPY: SPy_0880(mvaS.1)
SPM: spyM18_0941(mvaS1)
SPG: SpyM3_0599(mvaS.1)
SPS: SPs1254
SPH: MGAS10270_Spy0744
SPI: MGAS10750_Spy0778
SPJ: MGAS2096_Spy0758
SPK: MGAS9429_Spy0742
SPA: M6_Spy0703
SPN: SP_1726
SAG: SAG1317
SAN: gbs1387
STC: str0576(mvaA)
STL: stu0576(mvaA)
STE: STER_0620
SSA: SSA_0337(mvaA)
LPL: lp_0447(mvaA)
LJO: LJ1608
LSL: LSL_0224
LBR: LVIS_0450
LGA: LGAS_1373
EFA: EF1364
NFA: nfa22110
BGA: BG0708(mvaA)
SRU: SRU_2422
FPS: FP2341
MMP: MMP0087(hmgA)
MMQ: MmarC5_1589
MAC: MA3073(hmgA)
MBA: Mbar_A1972
MMA: MM_0335
MBU: Mbur_1098
MHU: Mhun_3004
MEM: Memar_2365
MBN: Mboo_0137
MTH: MTH562
MST: Msp_0584(hmgA)
MSI: Msm_0227
MKA: MK0355(HMG1)
AFU: AF1736(mvaA)
HAL: VNG1875G(mvaA)
HMA: rrnAC3412(mvaA)
HWA: HQ3215A(hmgR)
NPH: NP0368A(mvaA_2) NP2422A(mvaA_1)
TAC: Ta0406m
TVO: TVN1168
PTO: PTO1143
PAB: PAB2106(mvaA)
PFU: PF1848
TKO: TK0914
RCI: RCIX1027(hmgA) RCIX376(hmgA)
APE: APE_1869
IHO: Igni_0476
HBU: Hbut_1531
SSO: SSO0531
STO: ST1352
SAI: Saci_1359
PAI: PAE2182
PIS: Pis1_0814
PCL: Pcal_1085
PAS: Pars_0796

Exemplary mevalonate kinase nucleic acids and polypeptides

HSA: 4598(MVK)
MCC: 707645(MVK)
MMU: 17855(Mvk)
RNO: 81727(Mvk)
CFA: 486309(MVK)
BTA: 505792(MVK)
GGA: 768555(MVK)
DRE: 492477(zgc:103473)
SPU: 585785(L00585785)
DME: Dmel_CG33671
OSA: 4348331
SCE: YMR208W(ERG12)
AGO: AGOS_AER335W
PIC: PICST_40742(ERG12)
CGR: CAGL0F03861g
SPO: SPAC13G6.11c
MGR: MGG_06946
ANI: AN3869.2
AFM: AFUA_4G07780
AOR: AO090023000793
CNE: CNK01740
ECU: ECU09_1780
DDI: DDBDRAFT_0168621
TET: TTHERM_00637680
TBR: Tb927.4.4070
TCR: 436521.9 509237.10
LMA: LmjF31.0560
CBU: CBU_0608 CBU_0609
CBD: COXBU7E912_0620(mvk)
LPN: lpg2039
LPF: lpl2017
LPP: lpp2022
BBA: Bd1027(lmbP) Bd1630(mvk)
MXA: MXAN_5019(mvk)
OIH: OB0225
SAU: SA0547(mvaK1)
SAV: SAV0590(mvaK1)
SAM: MW0545(mvaK1)
SAR: SAR0596(mvaK1)
SAS: SAS0549
SAC: SACOL0636(mvk)

SAB: SAB0540(mvaK1)
SAA: SAUSA300_0572(mvk)
SAO: SAOUHSC_00577
SEP: SE0361
SER: SERP0238(mvk)
SHA: SH2402(mvaK1)
SSP: SSP2122
LMO: lmo0010
LMF: LMOf2365_0011
LIN: lin0010
LWE: lwe0011(mvk)
LLA: L7866(yeaG)
LLC: LACR_0454
LLM: llmg_0425(mvk)
SPY: SPy_0876(mvaK1)
SPZ: M5005_Spy_0682(mvaK1)
SPM: spyM18_0937(mvaK1)
SPG: SpyM3_0595(mvaK1)
SPS: SPs1258
SPH: MGAS10270_Spy0740(mvaK1)
SPI: MGAS10750_Spy0774(mvaK1)
SPJ: MGAS2096_Spy0753(mvaK1)
SPK: MGAS9429_Spy0737(mvaK1)
SPF: SpyM51126(mvaK1)
SPA: M6_Spy0699
SPB: M28_Spy0662(mvaK1)
SPN: SP_0381
SPR: spr0338(mvk)
SPD: SPD_0346(mvk)
SAG: SAG1326
SAN: gbs1396
SAK: SAK_1357(mvk)
SMU: SMU.181
STC: str0559(mvaK1)
STL: stu0559(mvaK1)
STE: STER_0598
SSA: SSA_0333(mvaK1)
SSU: SSU05_0289
SSV: SSU98_0285
SGO: SGO_0239(mvk)
LPL: lp_1735(mvaK1)
LJO: LJ11205
LAC: LBA1167(mvaK)
LSA: LSA0908(mvaK1)
LSL: LSL_0685(eRG)
LDB: Ldb0999(mvk)
LBU: LBUL_0906
LBR: LVIS_0858
LCA: LSEI_1491
LGA: LGAS_1033
LRE: Lreu_0915
PPE: PEPE_0927
EFA: EF0904(mvk)
OOE: OEOE_1100
LME: LEUM_1385
NFA: nfa22070
BGA: BG0711
BAF: BAPKO_0732
FPS: FP0313
MMP: MMP1335
MAE: Maeo_0775
MAC: MA0602(mvk)
MBA: Mbar_A1421
MMA: MM_1762
MBU: Mbur_2395
MHU: Mhun_2890
MEM: Memar_1812
MBN: Mboo_2213
MST: Msp_0858(mvk)
MSI: Msm_1439
MKA: MK0993(ERG12)
HAL: VNG1145G(mvk)
HMA: rrnAC0077(mvk)
HWA: HQ2925A(mvk)
NPH: NP2850A(mvk)
PTO: PTO1352
PHO: PH1625
PAB: PAB0372(mvk)
PFU: PF1637(mvk)
TKO: TK1474
RCI: LRC399(mvk)
APE: APE_2439
HBU: Hbut_0877
SSO: SSO0383
STO: ST2185
SAI: Saci_2365(mvk)
MSE: Msed_1602
PAI: PAE3108
PIS: Pisl_0467
PCL: Pcal_1835

Exemplary mevalonate kinase nucleic acids and polypeptides homologus to *Methanosarcina mazei* mevalonate kinase NP_633786.1 mevalonate kinase *Methanosarcina mazei* Go1

YP_304960.1 mevalonate kinase *Methanosarcina barkeri* str. Fusaro

NP 615566.1 mevalonate kinase *Methanosarcina acetivorans* C2A

YP_566996.1 mevalonate kinase *Methanococcoides burtonii* DSM 6242

YP_684687.1 mevalonate kinase uncultured methanogenic archaeon RC-I

YP_183887.1 mevalonate kinase *Thermococcus kodakarensis* KOD1

NP_126232.1 mevalonate kinase *Pyrococcus abyssi* GE5

NP_143478.1 mevalonate kinase *Pyrococcus horikoshii* OT3

NP_579366.1 mevalonate kinase *Pyrococcus furiosus* DSM 3638

YP_842907.1 mevalonate kinase *Methanosaeta thermophila* PT

YP_327075.1 mevalonate kinase *Natronomonas pharaonis* DSM 2160

YP_658630.1 mevalonate kinase *Haloquadratum walsbyi* DSM 16790

YP_134862.1 mevalonate kinase *Haloarcula marismortui* ATCC 43049

YP_001405370.1 mevalonate kinase *Candidatus Methanoregula boonei* 6A8

YP_001030120.1 mevalonate kinase *Methanocorpusculum labreanum* Z

YP_447890.1 putative mevalonate kinase *Methanosphaera stadtmanae* DSM 3091

YP_920295.1 mevalonate kinase *Thermofilum pendens* Hrk 5

ZP_02015315.1 mevalonate kinase *Halorubrum lacusprofundi* ATCC 49239

NP_280049.1 mevalonate kinase *Halobacterium* sp. NRC-1

YP_001274012.1 mevalonate kinase *Methanobrevibacter smithii* ATCC 35061

YP_001435347.1 mevalonate kinase *Ignicoccus hospitalis* KIN4/I

YP_001540788.1 mevalonate kinase *Caldivirga maquilingensis* IC-167

Q50559 KIME_METTH mevalonate kinase (MK)
NP_275189.1 mevalonate kinase *Methanothermobacter thermautotrophicus* str.
NP_071114.1 mevalonate kinase (mvk) *Archaeoglobus fulgidus* DSM 4304
YP_504301.1 mevalonate kinase *Methanospirillum hungatei* JF-1
YP_001040239.1 mevalonate kinase *Staphylothermus marinus* F1
YP_001047720.1 mevalonate kinase *Methanoculleus marisnigri* JR1
NP_614276.1 mevalonate kinase *Methanopyrus kandleri* AV19
YP_001737496.1 mevalonate kinase *Candidatus Korarchaeum* cryptofilum OPF8
YP_256937.1 mevalonate kinase *Sulfolobus acidocaldarius* DSM 639
NP 341921.1 mevalonate kinase *Sulfolobus solfataricus* P2
YP_001276466.1 mevalonate kinase *Roseiflexus* sp. RS-1
YP_001581649.1 mevalonate kinase *Nitrosopumilus maritimus* SCM1
NP_378182.1 hypothetical protein ST2185 *Sulfolobus tokodaii* str. 7
YP_001547075.1 mevalonate kinase *Herpetosiphon aurantiacus* ATCC 23779
YP_001056718.1 mevalonate kinase *Pyrobaculum calidifontis* JCM 11548
YP_001431846.1 mevalonate kinase *Roseiflexus castenholzii* DSM 13941
YP_001153805.1 mevalonate kinase *Pyrobaculum arsenaticum* DSM 13514
AAG02440.1AF290093_1 mevalonate kinase *Enterococcus faecalis*
NP_814642.1 mevalonate kinase *Enterococcus faecalis* V583
YP_001634502.1 mevalonate kinase *Chloroflexus aurantiacus* J-10-fl
XP_790690.1 similar to Mevalonate kinase (MK) *Strongylocentrotus purpuratus*
NP_560495.1 mevalonate kinase *Pyrobaculum aerophilum* str. IM2
YP_929988.1 mevalonate kinase *Pyrobaculum islandicum* DSM 4184
ZP_01465063.1 mevalonate kinase *Stigmatella aurantiaca* DW4/3-1
ZP_01906658.1 mevalonate kinase *Plesiocystis pacifica* SIR-1
NP_248080.1 mevalonate kinase *Methanocaldococcus jannaschii* DSM 2661
1KKHA chain A of the *Methanococcus jannaschii* mevalonate kinase Exemplary mevalonate kinase nucleic acids and polypeptides homologus to *Lactobacillus sakei* mevalonate kinase YP_395519.1 mevalonate kinase *Lactobacillus sakei* subsp. *sakei* 23K
YP_535578.1 mevalonate kinase *Lactobacillus salivarius* UCC118
YP_804427.1 mevalonate kinase *Pediococcus pentosaceus* ATCC 25745
YP_001271514.1 mevalonate kinase *Lactobacillus reuteri* F275
ZP_03073995.1 mevalonate kinase *Lactobacillus reuteri* 100-23
YP_795031.1 mevalonate kinase *Lactobacillus brevis* ATCC 367
ZP_02185318.1 mevalonate kinase *Carnobacterium* sp. AT7
YP_001844008.1 mevalonate kinase *Lactobacillus fermentum* IFO 3956
NP_266560.1 mevalonate kinase *Lactococcus lactis* subsp. *lactis* 111403
YP_818851.1 mevalonate kinase *Leuconostoc mesenteroides* subsp. *mesenteroides* ATCC 8293
NP_785308.1 mevalonate kinase *Lactobacillus plantarum* WCFS1
ZP_00604007.1 Mevalonate kinase *Enterococcus faecium* DO
YP_808480.1 mevalonate kinase *Lactococcus lactis* subsp. *cremoris* SK11
YP_001031775.1 mevalonate kinase *Lactococcus lactis* subsp. *cremoris* MG1363
NP_814642.1 mevalonate kinase *Enterococcus faecalis* V583
AAG02440.1 AF290093_1 mevalonate kinase *Enterococcus faecalis*

Exemplary mevalonate kinase nucleic acids and polypeptides homologus to *Streptomyces* sp. CL190 mevalonate kinase BAB07790.1 mevalonate kinase *Streptomyces* sp. CL190
BAD86800.1 mevalonate kinase *Streptomyces* sp. KO-3988
BAB07817.1 mevalonate kinase *Kitasatospora griseola*
ABS50475.1 NapT6 *Streptomyces* sp. CNQ525
ABS50448.1 NapT6 *Streptomyces aculeolatus*
BAE78977.1 mevalonate kinase *Streptomyces* sp. KO-3988
CAL34097.1 putative mevalonate kinase *Streptomyces cinnamonensis*
BAD07375.1 mevalonate kinase *Actinoplanes* sp. A40644
YP_118418.1 putative mevalonate kinase *Nocardia farcinica* IFM 10152
YP_818851.1 mevalonate kinase *Leuconostoc mesenteroides* subsp. *mesenteroides* ATCC 8293
YP_001620791.1 mevalonate kinase *Acholeplasma laidlawii* PG-8A
NP_720650.1 putative mevalonate kinase *Streptococcus mutans* UA159
YP_001031775.1 mevalonate kinase *Lactococcus lactis* subsp. *cremoris* MG1363
ZP_02689018.1 mevalonate kinase *Listeria monocytogenes* FSL J2-071
NP_266560.1 mevalonate kinase *Lactococcus lactis* subsp. *lactis* 111403
YP_395519.1 mevalonate kinase *Lactobacillus sakei* subsp. *sakei* 23K
YP_808480.1 mevalonate kinase *Lactococcus lactis* subsp. *cremoris* SK11
ZP_01926008.1 mevalonate kinase *Listeria monocytogenes* FSL N1-017
ZP_01942559.1 mevalonate kinase *Listeria monocytogenes* HPB2262
YP_012624.1 mevalonate kinase *Listeria monocytogenes* str. 4b F2365
YP_001727922.1 mevalonate kinase *Leuconostoc citreum* KM20
NP_469357.1 hypothetical protein lin0010 *Listeria innocua* Clip11262
ZP_00875673.1 Mevalonate kinase *Streptococcus suis* 89/1591
ZP_00604007.1 Mevalonate kinase *Enterococcus faecium* DO
ZP_00230799.1 mevalonate kinase *Listeria monocytogenes* str. 4b H7858
YP_139080.1 mevalonate kinase *Streptococcus thermophilus* LMG 18311
YP_140970.1 mevalonate kinase *Streptococcus thermophilus* CNRZ1066

ZP_01544345.1 mevalonate kinase *Oenococcus oeni* ATCC BAA-1163

YP_001197657.1 mevalonate kinase *Streptococcus suis* 05ZYH33

YP_810664.1 mevalonate kinase *Oenococcus oeni* PSU-1

NP_463543.1 hypothetical protein lmo0010 *Listeria monocytogenes* EGD-e

YP_848214.1 mevalonate kinase *Listeria welshimeri* serovar 6b str. SLCC5334

ZP_01695505.1 mevalonate kinase *Bacillus coagulans* 36D1

YP_804427.1 mevalonate kinase *Pediococcus pentosaceus* ATCC 25745

YP_820062.1 mevalonate kinase *Streptococcus thermophilus* LMD-9

NP_814642.1 mevalonate kinase *Enterococcus faecalis* V583

AAG02440.1 AF290093_1 mevalonate kinase *Enterococcus faecalis*

YP_598349.1 mevalonate kinase *Streptococcus pyogenes* MGAS10270

YP_535578.1 mevalonate kinase *Lactobacillus salivarius* UCC118

YP_001851498.1 mevalonate kinase, Erg12 *Mycobacterium marinum* M

ZP_01817104.1 mevalonate kinase *Streptococcus pneumoniae* SP3-BS71

YP_002037061.1 mevalonate kinase *Streptococcus pneumoniae* G54

NP_357932.1 mevalonate kinase *Streptococcus pneumoniae* R6

ZP_02710031.1 mevalonate kinase *Streptococcus pneumoniae* CDC1087-00

NP_344908.1 mevalonate kinase *Streptococcus pneumoniae* TIGR4

YP_001547075.1 mevalonate kinase *Herpetosiphon aurantiacus* ATCC 23779

AAG02455.1 AF290099_1 mevalonate kinase *Streptococcus pneumoniae*

ZP_01819603.1 mevalonate kinase *Streptococcus pneumoniae* SP6-BS73

YP_001271514.1 mevalonate kinase *Lactobacillus reuteri* F275

NP_965060.1 mevalonate kinase *Lactobacillus johnsonii* NCC 533

ZP_02919501.1 hypothetical protein STRINF_00343 *Streptococcus infantarius*

YP_001034340.1 mevalonate kinase, putative *Streptococcus sanguinis* SK36

YP_001844008.1 mevalonate kinase *Lactobacillus fermentum* IFO 3956

ZP_03073995.1 mevalonate kinase *Lactobacillus reuteri* 100-23

NP_688324.1 mevalonate kinase, putative *Streptococcus agalactiae* 2603V/R

YP_907150.1 mevalonate kinase, Erg12 *Mycobacterium ulcerans* Agy99

NP_691146.1 mevalonate kinase *Oceanobacillus iheyensis* HTE831

YP_795031.1 mevalonate kinase *Lactobacillus brevis* ATCC 367

YP_002123449.1 mevalonate kinase Mvk *Streptococcus equi* subsp. *zooepidemicus* str. MGCS10565

YP_001449558.1 mevalonate kinase *Streptococcus gordonii* str. Challis substr. CH1

ZP_02185318.1 mevalonate kinase *Carnobacterium* sp. AT7

YP_001634502.1 mevalonate kinase *Chloroflexus aurantiacus* J-10-fl

YP_812921.1 mevalonate kinase *Lactobacillus delbrueckii* subsp. *bulgaricus* ATCC BAA-365

YP_814846.1 mevalonate kinase *Lactobacillus gasseri* ATCC 33323

YP_001987652.1 Mevalonate kinase *Lactobacillus casei*

YP_618979.1 mevalonate kinase *Lactobacillus delbrueckii* subsp. *bulgaricus* ATCC 11842

NP_664399.1 mevalonate kinase *Streptococcus pyogenes* MGAS315

YP_806709.1 mevalonate kinase *Lactobacillus casei* ATCC 334

YP_060017.1 mevalonate kinase *Streptococcus pyogenes* MGAS10394

YP_280130.1 mevalonate kinase *Streptococcus pyogenes* MGAS6180

NP_269075.1 mevalonate kinase *Streptococcus pyogenes* M1 GAS

YP_001276466.1 mevalonate kinase *Roseiflexus* sp. RS-1

NP_607080.1 mevalonate kinase *Streptococcus pyogenes* MGAS8232

NP_785308.1 mevalonate kinase *Lactobacillus plantarum* WCFS1

ABH11598.1 GMP synthase, mevalonate kinase *Lactobacillus helveticus* CNRZ32

YP_001577580.1 mevalonate kinase *Lactobacillus helveticus* DPC 4571

YP_001431846.1 mevalonate kinase *Roseiflexus castenholzii* DSM 13941

YP_302212.1 mevalonate kinase *Staphylococcus saprophyticus* subsp. *saprophyticus* ATCC 15305

YP_040044.1 mevalonate kinase *Staphylococcus aureus* subsp. *aureus* MRSA252

AAG02424.1 AF290087_1 mevalonate kinase *Staphylococcus aureus*

NP_645362.1 mevalonate kinase *Staphylococcus aureus* subsp. *aureus* MW2

ZP_01514039.1 mevalonate kinase *Chloroflexus aggregans* DSM 9485

YP_194037.1 mevalonate kinase *Lactobacillus acidophilus* NCFM

YP_254317.1 mevalonate kinase *Staphylococcus haemolyticus* JCSC1435

YP_187834.1 mevalonate kinase *Staphylococcus epidermidis* RP62A

AAG02435.1 AF290091_1 mevalonate kinase *Staphylococcus epidermidis*

YP_183887.1 mevalonate kinase *Thermococcus kodakarensis* KOD1

NP_143478.1 mevalonate kinase *Pyrococcus horikoshii* OT3

ZP_00780842.1 mevalonate kinase *Streptococcus agalactiae* 18RS21

NP_579366.1 mevalonate kinase *Pyrococcus furiosus* DSM 3638

NP_126232.1 mevalonate kinase *Pyrococcus abyssi* GE5

NP_371114.1 mevalonate kinase *Staphylococcus aureus* subsp. *aureus* Mu50

YP_001040239.1 mevalonate kinase *Staphylothermus marinus* F1

NP_763916.1 mevalonate kinase *Staphylococcus epidermidis* ATCC 12228

YP_633174.1 mevalonate kinase *Myxococcus xanthus* DK 1622

YP_920295.1 mevalonate kinase *Thermofilum pendens* Hrk 5

NP_148611.1 mevalonate kinase *Aeropyrum pernix* K1
NP_633786.1 mevalonate kinase *Methanosarcina mazei* Go1

Exemplary phosphomevalonate kinase nucleic acids and polypeptides

HSA: 10654(PMVK)
PTR: 457350(PMVK)
MCC: 717014(PMVK)
MMU: 68603(Pmvk)
CFA: 612251(PMVK)
BTA: 513533(PMVK)
DME: Dmel_CG10268
ATH: AT1G31910
OSA: 4332275
SCE: YMR220W(ERG8)
AGO: AGOS_AER354W
PIC: PICST_52257(ERG8)
CGR: CAGL0F03993g
SPO: SPAC343.01c
MGR: MGG_05812
ANI: AN2311.2
AFM: AFUA_5G10680
AOR: AO090010000471
CNE: CNM00100
UMA: UM00760.1
DDI: DDBDRAFT_0184512
TBR: Tb09.160.3690
TCR: 507913.20 508277.140
LMA: LmjF15.1460
MXA: MXAN_5017
OIH: OB0227
SAU: SA0549(mvaK2)
SAV: SAV0592(mvaK2)
SAM: MW0547(mvaK2)
SAR: SAR0598(mvaK2)
SAS: SAS0551
SAC: SACOL0638
SAB: SAB0542(mvaK2)
SAA: SAUSA300_0574
SAO: SAOUHSC_00579
SAJ: SaurJH9_0615
SEP: SE0363
SER: SERP0240
SHA: SH2400(mvaK2)
SSP: SSP2120
LMO: lmo0012
LMF: LMOf2365_0013
LIN: lin0012
LWE: lwe0013
LLA: L10014(yebA)
LLC: LACR_0456
LLM: llmg_0427
SPY: SPy_0878(mvaK2)
SPZ: M5005_Spy_0684(mvaK2)
SPM: spyM18_0939
SPG: SpyM3_0597(mvaK2)
SPS: SPs1256
SPH: MGAS10270_Spy0742(mvaK2)
SPI: MGAS10750_Spy0776(mvaK2)
SPJ: MGAS2096_Spy0755(mvaK2)
SPK: MGAS9429_Spy0739(mvaK2)
SPF: SpyM51124(mvaK2)
SPA: M6_Spy0701
SPB: M28_Spy0664(mvaK2)
SPN: SP_0383
SPR: spr0340(mvaK2)
SPD: SPD_0348(mvaK2)
SAG: SAG1324
SAN: gbs1394
SAK: SAK_1355
SMU: SMU.938
STC: str0561(mvaK2)
STL: stu0561(mvaK2)
STE: STER_0600
SSA: SSA_0335(mvaK2)
SSU: SSU05_0291
SSV: SSU98_0287
SGO: SGO 0241
LPL: lp_1733(mvaK2)
LJO: 111207
LAC: LBA1169
LSA: LSA0906(mvaK2)
LSL: LSL_0683
LDB: Ldb0997(mvaK)
LBU: LBUL_0904
LBR: LVIS_0860
LCA: LSEI_1092
LGA: LGAS_1035
LRE: Lreu_0913
PPE: PEPE_0925
EFA: EF0902
NFA: nfa22090
BGA: BG0710
BAF: BAPKO_0731
NPH: NP2852A
SSO: SSO2988
STO: ST0978
SAI: Saci_1244

Exemplary diphosphomevalonate decarboxylase nucleic acids and polypeptides

HSA: 4597(MVD)
PTR: 468069(MVD)
MCC: 696865(MVD)
MMU: 192156(Mvd)
RNO: 81726(Mvd)
CFA: 489663(MVD)
GGA: 425359(MVD)
DME: Dmel_CG8239
SCE: YNR043W(MVD1)
AGO: AGOS_AGL232C
PIC: PICST_90752
CGR: CAGL0C03630g
SPO: SPAC24C9.03
MGR: MGG_09750
ANI: AN4414.2
AFM: AFUA_4G07130
AOR: AO090023000862
CNE: CNL04950
UMA: UM05179.1
DDI: DDBDRAFT_0218058
TET: TTHERM_00849200
TBR: Tb10.05.0010 Tb10.61.2745
TCR: 507993.330 511281.40
LMA: LmjF18.0020
CBU: CBU_0607(mvaD)
CBD: COXBU7E912_0619(mvaD)
LPN: lpg2040
LPF: lpl2018
LPP: lpp2023
TCX: Tcr_1734
DNO: DNO_0504(mvaD)
BBA: Bd1629
MXA: MXAN_5018(mvaD)
OIH: OB0226

SAU: SA0548(mvaD)
SAV: SAV0591(mvaD)
SAM: MW0546(mvaD)
SAR: SAR0597(mvaD)
SAS: SAS0550
SAC: SACOL0637(mvaD)
SAB: SAB0541(mvaD)
SAA: SAUSA300_0573(mvaD)
SAO: SAOUHSC_00578
SAJ: SaurJH9_0614
SAH: SaurJH1_0629
SEP: SE0362
SER: SERP0239(mvaD)
SHA: SH2401(mvaD)
SSP: SSP2121
LMO: lmo0011
LMF: LMOf2365_0012(mvaD)
LIN: lin0011
LWE: lwe0012(mvaD)
LLA: L9089(yeaH)
LLC: LACR_0455
LLM: llmg_0426(mvaD)
SPY: SPy_0877(mvaD)
SPZ: M5005_Spy_0683(mvaD)
SPM: spyM18_0938(mvd)
SPG: SpyM3_0596(mvaD)
SPS: SPs1257
SPH: MGAS10270_Spy0741(mvaD)
SPI: MGAS10750_Spy0775(mvaD)
SPJ: MGAS2096_Spy0754(mvaD)
SPK: MGAS9429_Spy0738(mvaD)
SPF: SpyM51125(mvaD)
SPA: M6_Spy0700
SPB: M28_Spy0663(mvaD)
SPN: SP_0382
SPR: spr0339(mvd1)
SPD: SPD_0347(mvaD)
SAG: SAG1325(mvaD)
SAN: gbs1395
SAK: SAK_1356(mvaD)
SMU: SMU.937
STC: str0560(mvaD)
STL: stu0560(mvaD)
STE: STER_0599
SSA: SSA_0334(mvaD)
SSU: SSU05_0290
SSV: SSU98_0286
SGO: SGO_0240(mvaD)
LPL: lp_1734(mvaD)
LJO: LJ1206
LAC: LBA1168(mvaD)
LSA: LSA0907(mvaD)
LSL: LSL_0684
LDB: Ldb0998(mvaD)
LBU: LBUL_0905
LBR: LVIS_0859
LCA: LSEI_1492
LGA: LGAS_1034
LRE: Lreu_0914
PPE: PEPE_0926
EFA: EF0903(mvaD)
LME: LEUM_1386
NFA: nfa22080
BBU: BB0686
BGA: BG0709
BAF: BAPKO_0730
GFO: GFO_3632
FPS: FP0310(mvaD)
HAU: Haur_1612
HAL: VNG0593G(dmd)
HMA: rrnAC1489(dmd)
HWA: HQ1525A(mvaD)
NPH: NP1580A(mvaD)
PTO: PTO0478 PTO1356
SSO: SSO2989
STO: ST0977
SAI: Saci_1245(mvd)
MSE: Msed_1576

Exemplary isopentenyl phosphate kinases (IPK) nucleic acids and polypeptides

*Methanobacterium thermoautotrophicum* gil2621082
*Methanococcus jannaschii* DSM 2661 gil1590842;
*Methanocaldococcus jannaschii* gil590842
*Methanothermobacter thermautotrophicus* gil2621082
*Picrophilus torridus* DSM9790 (IG-57) gil48477569
*Pyrococcus abyssi* gil4520758
*Pyrococcus horikoshii* OT3 gil3258052
*Archaeoglobus fulgidus* DSM4304 gil2648231

Exemplary isopentenyl-diphosphate Delta-isomerase (IDI) nucleic acids and polypeptides HSA: 3422(IDI1) 91734(IDI2)
PTR: 450262(IDI2) 450263(IDI1)
MCC: 710052(LOC710052) 721730(LOC721730)
MMU: 319554(Idi1)
RNO: 89784(Idi1)
GGA: 420459(IDI1)
XLA: 494671(LOC494671)
XTR: 496783(idi2)
SPU: 586184(L00586184)
CEL: K06H7.9(idi-1)
ATH: AT3G02780(IPP2)
OSA: 4338791 4343523
CME: CMB062C
SCE: YPL117C(IDI1)
AGO: AGOS_ADL268C
PIC: PICST_68990(IDI1)
CGR: CAGL0J06952g
SPO: SPBC106.15(idi1)
ANI: AN0579.2
AFM: AFUA_6G11160
AOR: AO090023000500
CNE: CNA02550
UMA: UM04838.1
ECU: ECU02_0230
DDI: DDB_0191342(ipi)
TET: TTHERM_00237280 TTHERM_00438860
TBR: Tb09.211.0700
TCR: 408799.19 510431.10
LMA: LmjF35.5330
EHI: 46.t00025
ECO: b2889(idi)
ECJ: JW2857(idi)
ECE: Z4227
ECS: ECs3761
ECC: c3467
ECI: UTI89_C3274
ECP: ECP_2882
ECV: APECO1_3638
ECW: EcE24377A_3215(idi)
ECX: EcHS_A3048
STY: STY3195
STT: t2957
SPT: SPA2907(idi)
SEC: SC2979(idi)

STM: STM3039(idi)
SFL: SF2875(idi)
SFX: S3074
SFV: SFV_2937
SSN: SSON_3042 SSON_3489(yhfK)
SBO: SBO 3103
SDY: SDY 3193
ECA: ECA2789
PLU: plu3987
ENT: Ent638_3307
SPE: Spro_2201
VPA: VPA0278
VFI: VF0403
PPR: PBPRA0469(mvaD)
PEN: PSEEN4850
CBU: CBU_0607(mvaD)
CBD: COXBU7E912_0619(mvaD)
LPN: lpg2051
LPF: lpl2029
LPP: lpp2034
TCX: Tcr_1718
HHA: Hhal_1623
DNO: DNO 0798
EBA: ebA5678 p2A143
DVU: DVU1679(idi)
DDE: Dde_1991
LIP: LI1134
BBA: Bd1626
AFW: Anae109_4082
MXA: MXAN_5021(fni)
RPR: RP452
RTY: RT0439(idi)
RCO: RC0744
RFE: RF_0785(fni)
RBE: RBE_0731(fni)
RAK: A1C_04190
RBO: A1I_04755
RCM: A1E_02555
RRI: A1G_04195
MLO: mlr6371
RET: RHE_PD00245(ypd00046)
XAU: Xaut_4134
SIL: SP00131
SIT: TM1040_3442
RSP: RSP_0276
RSH: Rsph17029_1919
RSQ: Rsph17025_1019
JAN: Jann_0168
RDE: RD1_0147(idi)
DSH: Dshi_3527
BSU: BG11440(ypgA)
BAN: BA1520
BAR: GBAA1520
BAA: BA_2041
BAT: BAS 1409
BCE: BC1499
BCA: BCE_1626
BCZ: BCZK1380(fni)
BCY: Bcer98_1222
BTK: BT9727_1381(fni)
BTL: BALH_1354
BLI: BL02217(fni)
BLD: BLi02426
BAY: RBAM_021020(fni)
BPU: BPUM_2020(fni)
OIH: OB0537
SAU: SA2136(fni)
SAV: SAV2346(fni)
SAM: MW2267(fni)
SAR: SAR2431(fni)
SAS: SAS2237
SAC: SACOL2341(fni)
SAB: SAB2225c(fni)
SAA: SAUSA300_2292(fni)
SAO: SAOUHSC_02623
SEP: SE1925
SER: SERP1937(fni-2)
SHA: SH0712(fni)
SSP: SSP0556
LMO: lmo1383
LMF: LMOf2365_1402(fni)
LIN: lin1420
LWE: lwe1399(fni)
LLA: L11083(yebB)
LLC: LACR_0457
LLM: llmg_0428(fni)
SPY: SPy_0879
SPZ: M5005_Spy_0685
SPM: spyM18_0940
SPG: SpyM3_0598
SPS: SPs1255
SPH: MGAS10270_Spy0743
SPI: MGAS10750_Spy0777
SPJ: MGAS2096_Spy0756
SPK: MGAS9429_Spy0740
SPF: SpyM51123(fni)
SPA: M6_Spy0702
SPB: M28_Spy0665
SPN: SP_0384
SPR: spr0341(fni)
SPD: SPD_0349(fni)
SAG: SAG1323
SAN: gbs1393
SAK: SAK_1354(fni)
SMU: SMU.939
STC: str0562(idi)
STL: stu0562(idi)
STE: STER_0601
SSA: SSA_0336
SGO: SGO_0242
LPL: lp_1732(idi1)
LJO: LJ1208
LAC: LBA1171
LSA: LSA0905(idi)
LSL: LSL_0682
LDB: Ldb0996(fni)
LBU: LBUL_0903
LBR: LVIS_0861
LCA: LSEI_1493
LGA: LGAS_1036
LRE: Lreu_0912
EFA: EF0901
OOE: OEOE_1103
STH: STH1674
CBE: Cbei_3081
DRM: Dred_0474
SWO: Swol_1341
MTA: Moth_1328
MTU: Rv1745c(idi)
MTC: MT1787(idi)
MBO: Mb1774c(idi)
MBB: BCG_1784c(idi)
MPA: MAP3079c
MAV: MAV_3894(fni)

MSM: MSMEG_1057(fni) MSMEG_2337(fni)
MUL: MUL_0380(idi2)
MVA: Mvan_1582 Mvan_2176
MGI: Mflv_1842 Mflv_4187
MMC: Mmcs_1954
MKM: Mkms_2000
MJL: Mjls_1934
CGL: NCgl2223(cg12305)
CGB: cg2531(idi)
CEF: CE2207
CDI: DIP1730(idi)
NFA: nfa19790 nfa22100
RHA: RHA1_ro00239
SCO: SCO6750(SC5F2A.33c)
SMA: SAV1663(idi)
LXX: Lxx23810(idi)
CMI: CMM_2889(idiA)
AAU: AAur_0321(idi)
PAC: PPA2115
FRA: Francci3_4188
FRE: Franean15570
FAL: FRAAL6504(idi)
KRA: Krad_3991
SEN: SACE_2627(idiB_2) SACE_5210(idi)
STP: Strop_4438
SAQ: Sare_4564 Sare_4928
RXY: Rxyl_0400
BBU: BB0684
BGA: BG0707
SYN: sll1556
SYC: syc2161_c
SYF: Synpcc7942_1933
CYA: CYA_2395(fni)
CYB: CYB_2691(fni)
TEL: tll1403
ANA: all4591
AVA: Ava_2461 Ava_B0346
TER: Tery_1589
SRU: SRU_1900(idi)
CHU: CHU_0674(idi)
GFO: GFO_2363(idi)
FJO: Fjoh_0269
FPS: FP1792(idi)
CTE: CT0257
CCH: Cag_1445
CPH: Cpha266_0385
PVI: Cvib_1545
PLT: Plut_1764
RRS: RoseRS_2437
RCA: Rcas_2215
HAU: Haur_4687
DRA: DR_1087
DGE: Dgeo_1381
TTH: TT_P0067
TTJ: TTHB 110
MJA: MJ0862
MMP: MMP0043
MMQ: MmarC5_1637
MMX: MmarC6_0906
MMZ: MmarC7_1040
MAE: Maeo_1184
MVN: Mevan_1058
MAC: MA0604(idi)
MBA: Mbar_A1419
MMA: MM_1764
MBU: Mbur_2397
MTP: Mthe_0474
MHU: Mhun_2888
MLA: Mlab_1665
MEM: Memar_1814
MBN: Mboo_2211
MTH: MTH48
MST: Msp_0856(fni)
MSI: Msm_1441
MKA: MK0776(lldD)
AFU: AF2287
HAL: VNG1818G(idi) VNG6081G(crt_1) VNG6445G (crt_2) VNG7060 VNG7149
HMA: rrnAC3484(idi)
HWA: HQ2772A(idiA) HQ2847A(idiB)
NPH: NP0360A(idiB_1) NP4826A(idiA) NP5124A(idiB_2)
TAC: Ta0102
TVO: TVN0179
PTO: PTO0496
PHO: PH1202
PAB: PAB1662
PFU: PF0856
TKO: TK1470
RCI: LRC397(fni)
APE: APE_1765.1
SMR: Smar_0822
IHO: Igni_0804
HBU: Hbut_0539
SSO: SSO0063
STO: ST2059
SAI: Saci_0091
MSE: Msed_2136
PAI: PAE0801
PIS: Pisl_1093
PCL: Pcal_0017
PAS: Pars_0051
TPE: Tpen_0272

Exemplary isoprene synthase nucleic acids and polypeptides Genbank Accession Nos.

AY341431
AY316691
AY279379
AJ457070
AY182241

What is claimed is:

1. A method of producing isoprene, the method comprising (a) culturing recombinant cells comprising (i) one or more heterologous nucleic acids encoding feedback-resistant mevalonate kinase polypeptides, (ii) one or more heterologous nucleic acids encoding an isoprene synthase polypeptide or one or more additional copies of an endogenous nucleic acid encoding an isoprene synthase polypeptide, and (iii) one or more nucleic acids encoding a mevalonate (MVA) pathway polypeptide under suitable culture conditions for the production of isoprene, and (b) producing isoprene.

2. The method of claim 1, wherein the cells further comprise (iv) one or more nucleic acids encoding a DXP pathway enzyme.

3. The method of claim 1, wherein the feedback-resistant mevalonate kinase is archaeal mevalonate kinase.

4. The method of claim 3, wherein the archaeal mevalonate kinase polypeptide is *M. mazei* mevalonate kinase.

5. The method of claim 1, wherein the cells in culture produce greater than about 400 nmole/$g_{wcm}$/hr of isoprene.

6. The method of claim 1, further comprising recovering the isoprene.

7. The method of claim 1, wherein the (iii) one or more nucleic acids encoding a mevalonate (MVA) pathway polypeptide is heterologous.

8. The method of claim 1, wherein the (iii) one or more nucleic acids encoding a mevalonate (MVA) pathway polypeptide is endogenous.

9. The method of claim 1, wherein the isoprene synthase polypeptide is from *Pueraria* or *Populus* or a hybrid, *Populus alba*x *Populus tremula*, or mutant thereof.

10. The method of claim 9, wherein the isoprene synthase polypeptide is selected from the group consisting of *Pueraria montana* or *Pueraria lobata, Populus tremuloides, Populus alba, Populus nigra*, and *Populus trichocarpa*, or mutant thereof.

11. The method of claim 1, wherein the cells are gram-positive bacterial cells, gram-negative bacterial cells, fungal cells, filamentous fungal cells, or yeast cells.

12. The method of claim 11, wherein the cells are *Streptomyces cells, Escherichia cells, Pantoea cells, Trichoderma* cells, or *Aspergillus* cells.

13. The method of claim 11, wherein the cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisieae* and *Yarrowia lipolytica.*

14. The method of claim 1, wherein the (iii) one or more nucleic acids encoding a mevalonate (MVA) pathway polypeptide is selected from the group consisting of acetyl-CoA acetyltransferase (AA-CoA thiolase) polypeptide, 3-hydroxy-3-methylglutaryl-CoA synthase (HMG-CoA synthase) polypeptide, 3-hydroxy-3-methylglutaryl-CoA reductase (HMG-CoA reductase) polypeptide, mevalonate kinase (MVK) polypeptide, phosphomevalonate kinase (PMK) polypeptide, diphosphomevalonate decarboxylase (MVD) polypeptide, phosphomevalonate decarboxylase (PMDC) polypeptide, isopentenyl phosphate kinase (IPK) polypeptide.

15. The method of claim 1, wherein the (iii) one or more nucleic acids encoding a mevalonate (MVA) pathway polypeptide encodes for upper MVA pathway polypeptide selected from the group consisting of AA-CoA thiolase, HMG-CoA synthase, and HMG-CoA reductase polypeptide.

16. The method of claim 1, wherein the (iii) one or more nucleic acids encoding a mevalonate (MVA) pathway polypeptide encodes for lower MVA pathway polypeptide selected from the group consisting of MVK, PMK, MVD, and IDI (Isopentenyl-diphosphate delta isomerase) polypeptide.

17. The method of claim 1, wherein the feedback-resistant mevalonate kinase polypeptide has a $K_i \geq 500$ μM DMAPP.

18. The method of claim 1, wherein the feedback-resistant mevalonate kinase polypeptide has a $K_i \geq 20$ μM GPP.

19. The method of claim 1, wherein the feedback-resistant mevalonate kinase polypeptide has a $K_i \geq 20$ μM FPP.

20. The method of claim 1, wherein the (i) one or more heterologous nucleic acids encoding feedback-resistant mevalonate kinase polypeptides are non-modified.

* * * * *

SEQUENCE LISTING

```
<160> NUMBER OF SEQ ID NOS: 136

<210> SEQ ID NO 1
<211> LENGTH: 1701
<212> TYPE: DNA
<213> ORGANISM: Artificial Sequence
<220> FEATURE:
<223> OTHER INFORMATION: Synthetic Construct
```

<400> SEQUENCE: 1
atgtgtgcga cctcttctca atttactcag attaccgagc ataattcccg tcgttccgca 60
aactatcagc caaacctgtg gaatttcgaa ttcctgcaat ccctggagaa cgacctgaaa 120
gtggaaaagc tggaggagaa agcgaccaaa ctggaggaag aagttcgctg catgatcaac 180
cgtgtagaca cccagccgct gtccctgctg gagctgatcg acgatgtgca gcgcctgggt 240
ctgacctaca aatttgaaaa agacatcatt aaagccctgg aaaacatcgt actgctggac 300
gaaaacaaaa agaacaaatc tgacctgcac gcaaccgctc tgtctttccg tctgctgcgt 360
cagcacggtt tcgaggtttc tcaggatgtt tttgagcgtt tcaaggataa agaaggtggt 420
ttcagcggtg aactgaaagg tgacgtccaa ggcctgctga gcctgtatga agcgtcttac 480
ctgggtttcg agggtgagaa cctgctggag gaggcgcgta ccttttccat cacccacctg 540
aagaacaacc tgaaagaagg cattaatacc aaggttgcag aacaagtgag ccacgccctg 600
gaactgccat atcaccagcg tctgcaccgt ctggaggcac gttggttcct ggataaatac 660
gaaccgaaag aaccgcatca ccagctgctg ctggagctgg cgaagctgga ttttaacatg 720
gtacagaccc tgcaccagaa agagctgcaa gatctgtccc gctggtggac cgagatgggc 780
ctggctagca aactggattt tgtacgcgac cgcctgatgg aagtttattt ctgggcactg 840
ggtatggcgc cagacccgca gtttggtgaa tgtcgcaaag ctgttactaa aatgtttggt 900
ctggtgacga tcatcgatga cgtgtatgac gtttatggca ctctggacga actgcaactg 960
ttcaccgatg ctgtagagcg ctgggacgtt aacgctatta acaccctgcc ggactatatg 1020
aaactgtgtt tcctggcact gtacaacacc gttaacgaca cgtcctattc tattctgaaa 1080
gagaaaggtc ataacaacct gtcctatctg acgaaaagct ggcgtgaact gtgcaaagcc 1140
tttctgcaag aggcgaaatg gtccaacaac aaaattatcc cggctttctc caagtacctg 1200
gaaaacgcca gcgtttcctc ctccggtgta gcgctgctgg cgccgtctta cttttccgta 1260
tgccagcagc aggaagacat ctccgaccac gcgctgcgtt ccctgaccga cttccatggt 1320
ctggtgcgtt ctagctgcgt tatcttccgc ctgtgcaacg atctggccac ctctgcggcg 1380
gagctggaac gtggcgagac taccaattct atcattagct acatgcacga aaacgatggt 1440
accagcgagg aacaggcccg cgaagaactg cgtaaactga tcgacgccga atggaaaaag 1500
atgaatcgtg aacgcgttag cgactccacc ctgctgccta aagcgttcat ggaaatcgca 1560
gttaacatgg cacgtgtttc ccactgcacc taccagtatg gcgatggtct gggtcgccca 1620
gactacgcga ctgaaaaccg catcaaactg ctgctgattg accctttccc gattaaccag 1680
ctgatgtatg tctaactgca g 1701

<210> SEQ ID NO 2
<211> LENGTH: 6080
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240

-continued

```
taacaatttc acacaggaaa cagcgccgct gagaaaaagc gaagcggcac tgctctttaa    300

caatttatca gacaatctgt gtgggcactc gaccggaatt atcgattaac tttattatta    360

aaaattaaag aggtatatat taatgtatcg attaaataag gaggaataaa ccatgtgtgc    420

gacctcttct caatttactc agattaccga gcataattcc cgtcgttccg caaactatca    480

gccaaacctg tggaatttcg aattcctgca atccctggag aacgacctga aagtggaaaa    540

gctggaggag aaagcgacca aactggagga agaagttcgc tgcatgatca accgtgtaga    600

cacccagccg ctgtccctgc tggagctgat cgacgatgtg cagcgcctgg gtctgaccta    660

caaatttgaa aaagacatca ttaaagccct ggaaaacatc gtactgctgg acgaaaacaa    720

aaagaacaaa tctgacctgc acgcaaccgc tctgtctttc cgtctgctgc gtcagcacgg    780

tttcgaggtt tctcaggatg tttttgagcg tttcaaggat aaagaaggtg gtttcagcgg    840

tgaactgaaa ggtgacgtcc aaggcctgct gagcctgtat gaagcgtctt acctgggttt    900

cgagggtgag aacctgctgg aggaggcgcg taccttttcc atcacccacc tgaagaacaa    960

cctgaaagaa ggcattaata ccaaggttgc agaacaagtg agccacgccc tggaactgcc   1020

atatcaccag cgtctgcacc gtctggaggc acgttggttc ctggataaat acgaaccgaa   1080

agaaccgcat caccagctgc tgctggagct ggcgaagctg gattttaaca tggtacagac   1140

cctgcaccag aaagagctgc aagatctgtc ccgctggtgg accgagatgg gcctggctag   1200

caaactggat tttgtacgcg accgcctgat ggaagtttat ttctgggcac tgggtatggc   1260

gccagacccg cagtttggtg aatgtcgcaa agctgttact aaaatgtttg gtctggtgac   1320

gatcatcgat gacgtgtatg acgtttatgg cactctggac gaactgcaac tgttcaccga   1380

tgctgtagag cgctgggacg ttaacgctat taacaccctg ccggactata tgaaactgtg   1440

tttcctggca ctgtacaaca ccgttaacga cacgtcctat tctattctga aagagaaagg   1500

tcataacaac ctgtcctatc tgacgaaaag ctggcgtgaa ctgtgcaaag cctttctgca   1560

agaggcgaaa tggtccaaca acaaaattat cccggctttc tccaagtacc tggaaaacgc   1620

cagcgtttcc tcctccggtg tagcgctgct ggcgccgtct tacttttccg tatgccagca   1680

gcaggaagac atctccgacc acgcgctgcg ttccctgacc gacttccatg gtctggtgcg   1740

ttctagctgc gttatcttcc gcctgtgcaa cgatctggcc acctctgcgg cggagctgga   1800

acgtggcgag actaccaatt ctatcattag ctacatgcac gaaaacgatg gtaccagcga   1860

ggaacaggcc cgcgaagaac tgcgtaaact gatcgacgcc gaatggaaaa agatgaatcg   1920

tgaacgcgtt agcgactcca ccctgctgcc taaagcgttc atggaaatcg cagttaacat   1980

ggcacgtgtt tcccactgca cctaccagta tggcgatggt ctgggtcgcc cagactacgc   2040

gactgaaaac cgcatcaaac tgctgctgat tgaccctttc ccgattaacc agctgatgta   2100

tgtctaactg cagctggtac catatgggaa ttcgaagctt tctagaacaa aaactcatct   2160

cagaagagga tctgaatagc gccgtcgacc atcatcatca tcatcattga gtttaaacgg   2220

tctccagctt ggctgttttg gcggatgaga gaagattttc agcctgatac agattaaatc   2280

agaacgcaga agcggtctga taaaacagaa tttgcctggc ggcagtagcg cggtggtccc   2340

acctgacccc atgccgaact cagaagtgaa acgccgtagc gccgatggta gtgtggggtc   2400

tccccatgcg agagtaggga actgccaggc atcaaataaa acgaaaggct cagtcgaaag   2460

actgggcctt tcgttttatc tgttgtttgt cggtgaacgc tctcctgagt aggacaaatc   2520

cgccgggagc ggatttgaac gttgcgaagc aacggcccgg agggtggcgg gcaggacgcc   2580

cgcccataaac tgccaggcat caaattaagc agaaggccat cctgacggat ggcctttttg   2640
```

-continued

```
cgtttctaca aactcttttt gtttattttt ctaaatacat tcaaatatgt atccgctcat   2700
gagacaataa ccctgataaa tgcttcaata atattgaaaa aggaagagta tgagtattca   2760
acatttccgt gtcgccctta ttcccttttt tgcggcattt tgccttcctg tttttgctca   2820
cccagaaacg ctggtgaaag taaaagatgc tgaagatcag ttgggtgcac gagtgggtta   2880
catcgaactg gatctcaaca gcggtaagat ccttgagagt tttcgccccg aagaacgttt   2940
tccaatgatg agcactttta aagttctgct atgtggcgcg gtattatccc gtgttgacgc   3000
cgggcaagag caactcggtc gccgcataca ctattctcag aatgacttgg ttgagtactc   3060
accagtcaca gaaaagcatc ttacggatgg catgacagta agagaattat gcagtgctgc   3120
cataaccatg agtgataaca ctgcggccaa cttacttctg acaacgatcg gaggaccgaa   3180
ggagctaacc gcttttttgc acaacatggg ggatcatgta actcgccttg atcgttggga   3240
accggagctg aatgaagcca taccaaacga cgagcgtgac accacgatgc ctgtagcaat   3300
ggcaacaacg ttgcgcaaac tattaactgg cgaactactt actctagctt cccggcaaca   3360
attaatagac tggatggagg cggataaagt tgcaggacca cttctgcgct cggcccttcc   3420
ggctggctgg tttattgctg ataaatctgg agccggtgag cgtgggtctc gcggtatcat   3480
tgcagcactg gggccagatg gtaagccctc ccgtatcgta gttatctaca cgacggggag   3540
tcaggcaact atggatgaac gaaatagaca gatcgctgag ataggtgcct cactgattaa   3600
gcattggtaa ctgtcagacc aagtttactc atatatactt tagattgatt taaaacttca   3660
tttttaattt aaaaggatct aggtgaagat cctttttgat aatctcatga ccaaaatccc   3720
ttaacgtgag ttttcgttcc actgagcgtc agaccccgta gaaaagatca aaggatcttc   3780
ttgagatcct ttttttctgc gcgtaatctg ctgcttgcaa acaaaaaaac caccgctacc   3840
agcggtggtt tgtttgccgg atcaagagct accaactctt tttccgaagg taactggctt   3900
cagcagagcg cagataccaa atactgtcct tctagtgtag ccgtagttag gccaccactt   3960
caagaactct gtagcaccgc ctacatacct cgctctgcta atcctgttac cagtggctgc   4020
tgccagtggc gataagtcgt gtcttaccgg gttggactca agacgatagt taccggataa   4080
ggcgcagcgg tcgggctgaa cggggggttc gtgcacacag cccagcttgg agcgaacgac   4140
ctacaccgaa ctgagatacc tacagcgtga gctatgagaa agcgccacgc ttcccgaagg   4200
gagaaaggcg gacaggtatc cggtaagcgg cagggtcgga acaggagagc gcacgaggga   4260
gcttccaggg ggaaacgcct ggtatcttta tagtcctgtc gggtttcgcc acctctgact   4320
tgagcgtcga tttttgtgat gctcgtcagg ggggcggagc ctatggaaaa acgccagcaa   4380
cgcggccttt ttacggttcc tggccttttg ctggcctttt gctcacatgt tctttcctgc   4440
gttatcccct gattctgtgg ataaccgtat taccgccttt gagtgagctg ataccgctcg   4500
ccgcagccga acgaccgagc gcagcgagtc agtgagcgag gaagcggaag agcgcctgat   4560
gcggtatttt ctccttacgc atctgtgcgg tatttcacac cgcatatggt gcactctcag   4620
tacaatctgc tctgatgccg catagttaag ccagtataca ctccgctatc gctacgtgac   4680
tgggtcatgg ctgcgccccg acacccgcca acacccgctg acgcgccctg acgggcttgt   4740
ctgctcccgg catccgctta cagacaagct gtgaccgtct ccgggagctg catgtgtcag   4800
aggttttcac cgtcatcacc gaaacgcgcg aggcagcaga tcaattcgcg cgcgaaggcg   4860
aagcggcatg catttacgtt gacaccatcg aatggtgcaa aacctttcgc ggtatggcat   4920
gatagcgccc ggaagagagt caattcaggg tggtgaatgt gaaaccagta acgttatacg   4980
```

-continued

```
atgtcgcaga gtatgccggt gtctcttatc agaccgtttc ccgcgtggtg aaccaggcca   5040

gccacgtttc tgcgaaaacg cgggaaaaag tggaagcggc gatggcggag ctgaattaca   5100

ttcccaaccg cgtggcacaa caactggcgg gcaaacagtc gttgctgatt ggcgttgcca   5160

cctccagtct ggccctgcac gcgccgtcgc aaattgtcgc ggcgattaaa tctcgcgccg   5220

atcaactggg tgccagcgtg gtggtgtcga tggtagaacg aagcggcgtc gaagcctgta   5280

aagcggcggt gcacaatctt ctcgcgcaac gcgtcagtgg gctgatcatt aactatccgc   5340

tggatgacca ggatgccatt gctgtggaag ctgcctgcac taatgttccg gcgttatttc   5400

ttgatgtctc tgaccagaca cccatcaaca gtattatttt ctcccatgaa gacggtacgc   5460

gactgggcgt ggagcatctg gtcgcattgg gtcaccagca aatcgcgctg ttagcgggcc   5520

cattaagttc tgtctcggcg cgtctgcgtc tggctggctg gcataaatat ctcactcgca   5580

atcaaattca gccgatagcg gaacgggaag gcgactggag tgccatgtcc ggttttcaac   5640

aaaccatgca aatgctgaat gagggcatcg ttcccactgc gatgctggtt gccaacgatc   5700

agatggcgct gggcgcaatg cgcgccatta ccgagtccgg gctgcgcgtt ggtgcggata   5760

tctcggtagt gggatacgac gataccgaag acagctcatg ttatatcccg ccgtcaacca   5820

ccatcaaaca ggattttcgc ctgctggggc aaaccagcgt ggaccgcttg ctgcaactct   5880

ctcagggcca ggcggtgaag ggcaatcagc tgttgcccgt ctcactggtg aaaagaaaaa   5940

ccaccctggc gcccaatacg caaaccgcct ctccccgcgc gttggccgat tcattaatgc   6000

agctggcacg acaggtttcc cgactggaaa gcgggcagtg agcgcaacgc aattaatgtg   6060

agttagcgcg aattgatctg                                               6080
```

<210> SEQ ID NO 3
<211> LENGTH: 37
<212> TYPE: DNA
<213> ORGANISM: Artificial Sequence
<220> FEATURE:
<223> OTHER INFORMATION: Synthetic Construct

<400> SEQUENCE: 3

```
cgtgagatca tatgtgtgcg acctcttctc aatttac                              37
```

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4

```
cggtcgacgg atccctgcag ttagacatac atcagctg                             38
```

<210> SEQ ID NO 5
<211> LENGTH: 7404
<212> TYPE: DNA
<213> ORGANISM: Artificial Sequence
<220> FEATURE:
<223> OTHER INFORMATION: Synthetic Construct

<400> SEQUENCE: 5

```
ttctcatgtt tgacagctta tcatcgataa gctttaatgc ggtagtttat cacagttaaa     60

ttgctaacgc agtcaggcac cgtgtatgaa atctaacaat gcgctcatcg tcatcctcgg    120

caccgtcacc ctggatgctg taggcatagg cttggttatg ccggtactgc cgggcctctt    180

gcgggatatc cggatatagt tcctcctttc agcaaaaaac ccctcaagac ccgtttagag    240
```

```
gccccaaggg gttatgctag ttattgctca gcggtggcag cagccaactc agcttccttt    300
cgggctttgt tagcagccgg atccctgcag ttagacatac atcagctggt taatcgggaa    360
agggtcaatc agcagcagtt tgatgcggtt ttcagtcgcg tagtctgggc gacccagacc    420
atcgccatac tggtaggtgc agtgggaaac acgtgccatg ttaactgcga tttccatgaa    480
cgctttaggc agcagggtgg agtcgctaac gcgttcacga ttcatctttt tccattcggc    540
gtcgatcagt ttacgcagtt cttcgcgggc ctgttcctcg ctggtaccat cgttttcgtg    600
catgtagcta atgatagaat tggtagtctc gccacgttcc agctccgccg cagaggtggc    660
cagatcgttg cacaggcgga agataacgca gctagaacgc accagaccat ggaagtcggt    720
cagggaacgc agcgcgtggt cggagatgtc ttcctgctgc tggcatacgg aaaagtaaga    780
cggcgccagc agcgctacac cggaggagga aacgctggcg ttttccaggt acttggagaa    840
agccgggata attttgttgt tggaccattt cgcctcttgc agaaaggctt tgcacagttc    900
acgccagctt ttcgtcagat aggacaggtt gttatgacct ttctctttca gaatagaata    960
ggacgtgtcg ttaacggtgt tgtacagtgc caggaaacac agtttcatat agtccggcag   1020
ggtgttaata gcgttaacgt cccagcgctc tacagcatcg gtgaacagtt gcagttcgtc   1080
cagagtgcca taaacgtcat acacgtcatc gatgatcgtc accagaccaa acattttagt   1140
aacagctttg cgacattcac caaactgcgg gtctggcgcc atacccagtg cccagaaata   1200
aacttccatc aggcggtcgc gtacaaaatc cagtttgcta gccaggccca tctcggtcca   1260
ccagcgggac agatcttgca gctctttctg gtgcagggtc tgtaccatgt taaaatccag   1320
cttcgccagc tccagcagca gctggtgatg cggttctttc ggttcgtatt tatccaggaa   1380
ccaacgtgcc tccagacggt gcagacgctg gtgatatggc agttccaggg cgtggctcac   1440
ttgttctgca accttggtat taatgccttc tttcaggttg ttcttcaggt gggtgatgga   1500
aaaggtacgc gcctcctcca gcaggttctc accctcgaaa cccaggtaag acgcttcata   1560
caggctcagc aggccttgga cgtcaccttt cagttcaccg ctgaaaccac cttctttatc   1620
cttgaaacgc tcaaaaacat cctgagaaac ctcgaaaccg tgctgacgca gcagacggaa   1680
agacagagcg gttgcgtgca ggtcagattt gttctttttg ttttcgtcca gcagtacgat   1740
gttttccagg gctttaatga tgtctttttc aaatttgtag gtcagaccca ggcgctgcac   1800
atcgtcgatc agctccagca gggacagcgg ctgggtgtct acacggttga tcatgcagcg   1860
aacttcttcc tccagtttgg tcgctttctc ctccagcttt tccactttca ggtcgttctc   1920
cagggattgc aggaattcga aattccacag gtttggctga tagtttgcgg aacgacggga   1980
attatgctcg gtaatctgag taaattgaga agaggtcgca cacatatgac gaccttcgat   2040
atggccgctg ctgtgatgat gatgatgatg atgatgatga tggcccatgg tatatctcct   2100
tcttaaagtt aaacaaaatt atttctagag gggaattgtt atccgctcac aattccccta   2160
tagtgagtcg tattaatttc gcgggatcga gatctcgatc ctctacgccg gacgcatcgt   2220
ggccggcatc accggcgcca caggtgcggt tgctggcgcc tatatcgccg acatcaccga   2280
tggggaagat cgggctcgcc acttcgggct catgagcgct tgtttcggcg tgggtatggt   2340
ggcaggcccc gtggccgggg gactgttggg cgccatctcc ttgcatgcac cattccttgc   2400
ggcggcggtg ctcaacggcc tcaacctact actgggctgc ttcctaatgc aggagtcgca   2460
taagggagag cgtcgagatc ccggacacca tcgaatggcg caaaaccttt cgcggtatgg   2520
catgatagcg cccggaagag agtcaattca gggtggtgaa tgtgaaacca gtaacgttat   2580
```

-continued

```
acgatgtcgc agagtatgcc ggtgtctctt atcagaccgt ttcccgcgtg gtgaaccagg   2640
ccagccacgt ttctgcgaaa acgcgggaaa aagtggaagc ggcgatggcg gagctgaatt   2700
acattcccaa ccgcgtggca caacaactgg cgggcaaaca gtcgttgctg attggcgttg   2760
ccacctccag tctggccctg cacgcgccgt cgcaaattgt cgcggcgatt aaatctcgcg   2820
ccgatcaact gggtgccagc gtggtggtgt cgatggtaga acgaagcggc gtcgaagcct   2880
gtaaagcggc ggtgcacaat cttctcgcgc aacgcgtcag tgggctgatc attaactatc   2940
cgctggatga ccaggatgcc attgctgtgg aagctgcctg cactaatgtt ccggcgttat   3000
ttcttgatgt ctctgaccag acacccatca acagtattat tttctcccat gaagacggta   3060
cgcgactggg cgtggagcat ctggtcgcat tgggtcacca gcaaatcgcg ctgttagcgg   3120
gcccattaag ttctgtctcg gcgcgtctgc gtctggctgg ctggcataaa tatctcactc   3180
gcaatcaaat tcagccgata gcggaacggg aaggcgactg gagtgccatg tccggttttc   3240
aacaaaccat gcaaatgctg aatgagggca tcgttcccac tgcgatgctg gttgccaacg   3300
atcagatggc gctgggcgca atgcgcgcca ttaccgagtc cgggctgcgc gttggtgcgg   3360
atatctcggt agtgggatac gacgataccg aagacagctc atgttatatc ccgccgttaa   3420
ccaccatcaa acaggatttt cgcctgctgg ggcaaaccag cgtggaccgc ttgctgcaac   3480
tctctcaggg ccaggcggtg aagggcaatc agctgttgcc cgtctcactg gtgaaaagaa   3540
aaaccaccct ggcgcccaat acgcaaaccg cctctccccg cgcgttggcc gattcattaa   3600
tgcagctggc acgacaggtt tcccgactgg aaagcgggca gtgagcgcaa cgcaattaat   3660
gtaagttagc tcactcatta ggcaccggga tctcgaccga tgcccttgag agccttcaac   3720
ccagtcagct ccttccggtg ggcgcggggc atgactatcg tcgccgcact tatgactgtc   3780
ttctttatca tgcaactcgt aggacaggtg ccggcagcgc tctgggtcat tttcggcgag   3840
gaccgctttc gctggagcgc gacgatgatc ggcctgtcgc ttgcggtatt cggaatcttg   3900
cacgccctcg ctcaagcctt cgtcactggt cccgccacca aacgtttcgg cgagaagcag   3960
gccattatcg ccggcatggc ggccgacgcg ctgggctacg tcttgctggc gttcgcgacg   4020
cgaggctgga tggccttccc cattatgatt cttctcgctt ccggcggcat cgggatgccc   4080
gcgttgcagg ccatgctgtc caggcaggta gatgacgacc atcagggaca gcttcaagga   4140
tcgctcgcgg ctcttaccag cctaacttcg atcactggac cgctgatcgt cacggcgatt   4200
tatgccgcct cggcgagcac atggaacggg ttggcatgga ttgtaggcgc cgccctatac   4260
cttgtctgcc tccccgcgtt gcgtcgcggt gcatggagcc gggccacctc gacctgaatg   4320
gaagccggcg gcacctcgct aacggattca ccactccaag aattggagcc aatcaattct   4380
tgcggagaac tgtgaatgcg caaaccaacc cttggcagaa catatccatc gcgtccgcca   4440
tctccagcag ccgcacgcgg cgcatctcgg gcagcgttgg gtcctggcca cgggtgcgca   4500
tgatcgtgct cctgtcgttg aggacccggc taggctggcg gggttgcctt actggttagc   4560
agaatgaatc accgatacgc gagcgaacgt gaagcgactg ctgctgcaaa acgtctgcga   4620
cctgagcaac aacatgaatg gtcttcggtt tccgtgtttc gtaaagtctg gaaacgcgga   4680
agtcagcgcc ctgcaccatt atgttccgga tctgcatcgc aggatgctgc tggctaccct   4740
gtggaacacc tacatctgta ttaacgaagc gctggcattg accctgagtg atttttctct   4800
ggtcccgccg catccatacc gccagttgtt taccctcaca acgttccagt aaccgggcat   4860
gttcatcatc agtaacccgt atcgtgagca tcctctctcg tttcatcggt atcattaccc   4920
ccatgaacag aaatccccct tacacggagg catcagtgac caaacaggaa aaaaccgccc   4980
```

ttaacatggc ccgctttatc agaagccaga cattaacgct tctggagaaa ctcaacgagc 5040
tggacgcgga tgaacaggca gacatctgtg aatcgcttca cgaccacgct gatgagcttt 5100
accgcagctg cctcgcgcgt ttcggtgatg acggtgaaaa cctctgacac atgcagctcc 5160
cggagacggt cacagcttgt ctgtaagcgg atgccgggag cagacaagcc cgtcagggcg 5220
cgtcagcggg tgttggcggg tgtcggggcg cagccatgac ccagtcacgt agcgatagcg 5280
gagtgtatac tggcttaact atgcggcatc agagcagatt gtactgagag tgcaccatat 5340
atgcggtgtg aaataccgca cagatgcgta aggagaaaat accgcatcag gcgctcttcc 5400
gcttcctcgc tcactgactc gctgcgctcg gtcgttcggc tgcggcgagc ggtatcagct 5460
cactcaaagg cggtaatacg gttatccaca gaatcagggg ataacgcagg aaagaacatg 5520
tgagcaaaag gccagcaaaa ggccaggaac cgtaaaaagg ccgcgttgct ggcgtttttc 5580
cataggctcc gcccccctga cgagcatcac aaaaatcgac gctcaagtca gaggtggcga 5640
aacccgacag gactataaag ataccaggcg tttccccctg gaagctccct cgtgcgctct 5700
cctgttccga ccctgccgct taccggatac ctgtccgcct ttctcccttc gggaagcgtg 5760
gcgctttctc atagctcacg ctgtaggtat ctcagttcgg tgtaggtcgt tcgctccaag 5820
ctgggctgtg tgcacgaacc ccccgttcag cccgaccgct gcgccttatc cggtaactat 5880
cgtcttgagt ccaacccggt aagacacgac ttatcgccac tggcagcagc cactggtaac 5940
aggattagca gagcgaggta tgtaggcggt gctacagagt tcttgaagtg gtggcctaac 6000
tacggctaca ctagaaggac agtatttggt atctgcgctc tgctgaagcc agttaccttc 6060
ggaaaaagag ttggtagctc ttgatccggc aaacaaacca ccgctggtag cggtggtttt 6120
tttgtttgca agcagcagat tacgcgcaga aaaaaaggat ctcaagaaga tcctttgatc 6180
ttttctacgg ggtctgacgc tcagtggaac gaaaactcac gttaagggat tttggtcatg 6240
agattatcaa aaaggatctt cacctagatc cttttaaatt aaaaatgaag ttttaaatca 6300
atctaaagta tatatgagta aacttggtct gacagttacc aatgcttaat cagtgaggca 6360
cctatctcag cgatctgtct atttcgttca tccatagttg cctgactccc cgtcgtgtag 6420
ataactacga tacgggaggg cttaccatct ggccccagtg ctgcaatgat accgcgagac 6480
ccacgctcac cggctccaga tttatcagca ataaaccagc cagccggaag ggccgagcgc 6540
agaagtggtc ctgcaacttt atccgcctcc atccagtcta ttaattgttg ccgggaagct 6600
agagtaagta gttcgccagt taatagtttg cgcaacgttg ttgccattgc tgcaggcatc 6660
gtggtgtcac gctcgtcgtt tggtatggct tcattcagct ccggttccca acgatcaagg 6720
cgagttacat gatcccccat gttgtgcaaa aaagcggtta gctccttcgg tcctccgatc 6780
gttgtcagaa gtaagttggc cgcagtgtta tcactcatgg ttatggcagc actgcataat 6840
tctcttactg tcatgccatc cgtaagatgc ttttctgtga ctggtgagta ctcaaccaag 6900
tcattctgag aatagtgtat gcggcgaccg agttgctctt gcccggcgtc aacacgggat 6960
aataccgcgc cacatagcag aactttaaaa gtgctcatca ttggaaaacg ttcttcgggg 7020
cgaaaactct caaggatctt accgctgttg agatccagtt cgatgtaacc cactcgtgca 7080
cccaactgat cttcagcatc ttttactttc accagcgttt ctgggtgagc aaaaacagga 7140
aggcaaaatg ccgcaaaaaa gggaataagg gcgacacgga aatgttgaat actcatactc 7200
ttcctttttc aatattattg aagcatttat cagggttatt gtctcatgag cggatacata 7260
tttgaatgta tttagaaaaa taaacaaata ggggttccgc gcacatttcc ccgaaaagtg 7320
ccacctgacg tctaagaaac cattattatc atgacattaa cctataaaaa taggcgtatc 7380
acgaggccct ttcgtcttca agaa 7404

<210> SEQ ID NO 6
<211> LENGTH: 41
<212> TYPE: DNA
<213> ORGANISM: Artificial Sequence
<220> FEATURE:
<223> OTHER INFORMATION: Synthetic Construct

<400> SEQUENCE: 6
catatgaaag cttgtatcga ttaaataagg aggaataaac c 41

<210> SEQ ID NO 7
<211> LENGTH: 6266
<212> TYPE: DNA
<213> ORGANISM: Artificial Sequence
<220> FEATURE:
<223> OTHER INFORMATION: Synthetic Construct

<400> SEQUENCE: 7
cccgtcttac tgtcgggaat tcgcgttggc cgattcatta atgcagctgg cacgacaggt 60
ttcccgactg gaaagcgggc agtgagcgca acgcaattaa tgtgagttag ctcactcatt 120
aggcacccca ggctttacac tttatgcttc cggctcgtat gttgtgtgga attgtgagcg 180
gataacaatt tcacacagga aacagctatg accatgatta cgccaagctt gtatcgatta 240
aataaggagg aataaaccat gtgtgcgacc tcttctcaat ttactcagat taccgagcat 300
aattcccgtc gttccgcaaa ctatcagcca aacctgtgga atttcgaatt cctgcaatcc 360
ctggagaacg acctgaaagt ggaaaagctg gaggagaaag cgaccaaact ggaggaagaa 420
gttcgctgca tgatcaaccg tgtagacacc cagccgctgt ccctgctgga gctgatcgac 480
gatgtgcagc gcctgggtct gacctacaaa tttgaaaaag acatcattaa agccctggaa 540
aacatcgtac tgctggacga aaacaaaaag aacaaatctg acctgcacgc aaccgctctg 600
tctttccgtc tgctgcgtca gcacggtttc gaggtttctc aggatgtttt tgagcgtttc 660
aaggataaag aaggtggttt cagcggtgaa ctgaaaggtg acgtccaagg cctgctgagc 720
ctgtatgaag cgtcttacct gggtttcgag ggtgagaacc tgctggagga ggcgcgtacc 780
ttttccatca cccacctgaa gaacaacctg aaagaaggca ttaataccaa ggttgcagaa 840
caagtgagcc acgccctgga actgccatat caccagcgtc tgcaccgtct ggaggcacgt 900
tggttcctgg ataaatacga accgaaagaa ccgcatcacc agctgctgct ggagctggcg 960
aagctggatt ttaacatggt acagaccctg caccagaaag agctgcaaga tctgtcccgc 1020
tggtggaccg agatgggcct ggctagcaaa ctggattttg tacgcgaccg cctgatggaa 1080
gtttatttct gggcactggg tatggcgcca gacccgcagt ttggtgaatg tcgcaaagct 1140
gttactaaaa tgtttggtct ggtgacgatc atcgatgacg tgtatgacgt ttatggcact 1200
ctggacgaac tgcaactgtt caccgatgct gtagagcgct gggacgttaa cgctattaac 1260
accctgccgg actatatgaa actgtgtttc ctggcactgt acaacaccgt taacgacacg 1320
tcctattcta ttctgaaaga gaaaggtcat aacaacctgt cctatctgac gaaaagctgg 1380
cgtgaactgt gcaaagcctt tctgcaagag gcgaaatggt ccaacaacaa aattatcccg 1440
gctttctcca agtacctgga aaacgccagc gtttcctcct ccggtgtagc gctgctggcg 1500
ccgtcttact tttccgtatg ccagcagcag gaagacatct ccgaccacgc gctgcgttcc 1560
ctgaccgact tccatggtct ggtgcgttct agctgcgtta tcttccgcct gtgcaacgat 1620

```
ctggccacct ctgcggcgga gctggaacgt ggcgagacta ccaattctat cattagctac   1680
atgcacgaaa acgatggtac cagcgaggaa caggcccgcg aagaactgcg taaactgatc   1740
gacgccgaat ggaaaaagat gaatcgtgaa cgcgttagcg actccaccct gctgcctaaa   1800
gcgttcatgg aaatcgcagt taacatggca cgtgtttccc actgcaccta ccagtatggc   1860
gatggtctgg gtcgcccaga ctacgcgact gaaaaccgca tcaaactgct gctgattgac   1920
cctttcccga ttaaccagct gatgtatgtc taactgcagg tcgactctag aggatccccg   1980
ggtaccgagc tcgaattcac tggccgtcgt tttacaacgt cgtgactggg aaaaccctgg   2040
cgttacccaa cttaatcgcc ttgcagcaca tccccctttc gccagctggc gtaatagcga   2100
agaggcccgc accgatcgcc cttcccaaca gttgcgcagc ctgaatggcg aatggcgcct   2160
gatgcggtat tttctcctta cgcatctgtg cggtatttca caccgcatat ggtgcactct   2220
cagtacaatc tgctctgatg ccgcatagtt aagccagccc cgacacccgc caacacccgc   2280
tgacgagctt agtaaagccc tcgctagatt ttaatgcgga tgttgcgatt acttcgccaa   2340
ctattgcgat aacaagaaaa agccagcctt tcatgatata tctcccaatt tgtgtagggc   2400
ttattatgca cgcttaaaaa taataaaagc agacttgacc tgatagtttg gctgtgagca   2460
attatgtgct tagtgcatct aacgcttgag ttaagccgcg ccgcgaagcg gcgtcggctt   2520
gaacgaattg ttagacatta tttgccgact accttggtga tctcgccttt cacgtagtgg   2580
acaaattctt ccaactgatc tgcgcgcgag gccaagcgat cttcttcttg tccaagataa   2640
gcctgtctag cttcaagtat gacgggctga tactgggccg gcaggcgctc cattgcccag   2700
tcggcagcga catccttcgg cgcgattttg ccggttactg cgctgtacca aatgcgggac   2760
aacgtaagca ctacatttcg ctcatcgcca gcccagtcgg gcggcgagtt ccatagcgtt   2820
aaggtttcat ttagcgcctc aaatagatcc tgttcaggaa ccggatcaaa gagttcctcc   2880
gccgctggac ctaccaaggc aacgctatgt tctcttgctt ttgtcagcaa gatagccaga   2940
tcaatgtcga tcgtggctgg ctcgaagata cctgcaagaa tgtcattgcg ctgccattct   3000
ccaaattgca gttcgcgctt agctggataa cgccacggaa tgatgtcgtc gtgcacaaca   3060
atggtgactt ctacagcgcg gagaatctcg ctctctccag gggaagccga agtttccaaa   3120
aggtcgttga tcaaagctcg ccgcgttgtt tcatcaagcc ttacggtcac cgtaaccagc   3180
aaatcaatat cactgtgtgg cttcaggccg ccatccactg cggagccgta caaatgtacg   3240
gccagcaacg tcggttcgag atggcgctcg atgacgccaa ctacctctga tagttgagtc   3300
gatacttcgg cgatcaccgc ttccctcatg atgtttaact ttgttttagg gcgactgccc   3360
tgctgcgtaa catcgttgct gctccataac atcaaacatc gacccacggc gtaacgcgct   3420
tgctgcttgg atgcccgagg catagactgt accccaaaaa aacagtcata acaagccatg   3480
aaaaccgcca ctgcgccgtt accaccgctg cgttcggtca aggttctgga ccagttgcgt   3540
gagcgcatac gctacttgca ttacagctta cgaaccgaac aggcttatgt ccactgggtt   3600
cgtgccttca tccgtttcca cggtgtgcgt cacccggcaa ccttgggcag cagcgaagtc   3660
gaggcatttc tgtcctggct ggcgaacgag cgcaaggttt cggtctccac gcatcgtcag   3720
gcattggcgg ccttgctgtt cttctacggc aaggtgctgt gcacggatct gccctggctt   3780
caggagatcg gaagacctcg gccgtcgcgg cgcttgccgg tggtgctgac cccggatgaa   3840
gtggttcgca tcctcggttt tctggaaggc gagcatcgtt tgttcgccca gcttctgtat   3900
ggaacgggca tgcggatcag tgagggtttg caactgcggg tcaaggatct ggatttcgat   3960
```

-continued

```
cacggcacga tcatcgtgcg ggagggcaag ggctccaagg atcgggcctt gatgttaccc   4020
gagagcttgg cacccagcct gcgcgagcag gggaattaat tcccacgggt tttgctgccc   4080
gcaaacgggc tgttctggtg ttgctagttt gttatcagaa tcgcagatcc ggcttcagcc   4140
ggtttgccgg ctgaaagcgc tatttcttcc agaattgcca tgattttttc cccacgggag   4200
gcgtcactgg ctcccgtgtt gtcggcagct ttgattcgat aagcagcatc gcctgtttca   4260
ggctgtctat gtgtgactgt tgagctgtaa caagttgtct caggtgttca atttcatgtt   4320
ctagttgctt tgttttactg gtttcacctg ttctattagg tgttacatgc tgttcatctg   4380
ttacattgtc gatctgttca tggtgaacag ctttgaatgc accaaaaact cgtaaaagct   4440
ctgatgtatc tatctttttt acaccgtttt catctgtgca tatggacagt tttccctttg   4500
atatgtaacg gtgaacagtt gttctacttt tgtttgttag tcttgatgct tcactgatag   4560
atacaagagc cataagaacc tcagatcctt ccgtatttag ccagtatgtt ctctagtgtg   4620
gttcgttgtt tttgcgtgag ccatgagaac gaaccattga gatcatactt actttgcatg   4680
tcactcaaaa attttgcctc aaaactggtg agctgaattt ttgcagttaa agcatcgtgt   4740
agtgtttttc ttagtccgtt atgtaggtag gaatctgatg taatggttgt tggtattttg   4800
tcaccattca tttttatctg gttgttctca agttcggtta cgagatccat ttgtctatct   4860
agttcaactt ggaaaatcaa cgtatcagtc gggcggcctc gcttatcaac caccaatttc   4920
atattgctgt aagtgtttaa atctttactt attggtttca aaacccattg gttaagcctt   4980
ttaaactcat ggtagttatt ttcaagcatt aacatgaact taaattcatc aaggctaatc   5040
tctatatttg ccttgtgagt tttcttttgt gttagttctt ttaataacca ctcataaatc   5100
ctcatagagt atttgttttc aaaagactta acatgttcca gattatattt tatgaatttt   5160
tttaactgga aaagataagg caatatctct tcactaaaaa ctaattctaa tttttcgctt   5220
gagaacttgg catagtttgt ccactggaaa atctcaaagc ctttaaccaa aggattcctg   5280
atttccacag ttctcgtcat cagctctctg gttgctttag ctaatacacc ataagcattt   5340
tccctactga tgttcatcat ctgagcgtat tggttataag tgaacgatac cgtccgttct   5400
ttccttgtag ggttttcaat cgtggggttg agtagtgcca cacagcataa aattagcttg   5460
gtttcatgct ccgttaagtc atagcgacta atcgctagtt catttgcttt gaaaacaact   5520
aattcagaca tacatctcaa ttggtctagg tgattttaat cactatacca attgagatgg   5580
gctagtcaat gataattact agtccttttc ctttgagttg tgggtatctg taaattctgc   5640
tagacctttg ctggaaaact tgtaaattct gctagaccct ctgtaaattc cgctagacct   5700
ttgtgtgttt tttttgttta tattcaagtg gttataattt atagaataaa gaaagaataa   5760
aaaaagataa aaagaataga tcccagccct gtgtataact cactacttta gtcagttccg   5820
cagtattaca aaaggatgtc gcaaacgctg tttgctcctc tacaaaacag accttaaaac   5880
cctaaaggct taagtagcac cctcgcaagc tcgggcaaat cgctgaatat tccttttgtc   5940
tccgaccatc aggcacctga gtcgctgtct ttttcgtgac attcagttcg ctgcgctcac   6000
ggctctggca gtgaatgggg gtaaatggca ctacaggcgc cttttatgga ttcatgcaag   6060
gaaactaccc ataatacaag aaaagcccgt cacgggcttc tcagggcgtt ttatggcggg   6120
tctgctatgt ggtgctatct gactttttgc tgttcagcag ttcctgccct ctgatttttcc  6180
agtctgacca cttcggatta tcccgtgaca ggtcattcag actggctaat gcacccagta   6240
aggcagcggt atcatcaaca ggctta                                        6266
```

<210> SEQ ID NO 8
<211> LENGTH: 1695
<212> TYPE: DNA
<213> ORGANISM: Artificial Sequence
<220> FEATURE:
<223> OTHER INFORMATION: Synthetic Construct

<400> SEQUENCE: 8

```
atgtgtgcaa cctcctccca gtttactcag attaccgagc ataattctcg acgatctgct     60
aactaccagc cgaacctttg gaactttgag tttctccagt ctctcgaaaa tgacctgaag    120
gtggaaaagc tcgaggagaa ggcgaccaaa ctcgaggagg aggtgcgatg tatgatcaac    180
agagttgaca cccaacccct gtctttgctg gagctgatcg acgatgtgca gcggttgggt    240
ttgacttata aattcgagaa ggacattatc aaggcactgg agaacattgt gctcctcgac    300
gagaacaaga agaacaagtc tgatcttcac gctaccgctc tctctttccg acttcttcga    360
caacacggct tcgaggtgtc gcaggacgtc ttcgagagat ttaaggacaa ggagggagga    420
tttagcggcg agctgaaggg agacgttcag ggtcttctct ccttgtacga ggcgtcctac    480
ctgggattcg agggagagaa cctcctggag gaagctcgta cattttccat cactcacctt    540
aagaataacc ttaaggaggg aattaacacc aaggtggccg agcaggtttc tcacgccctg    600
gagctcccct accaccaacg gctccataga ctggaggctc gttggttcct ggacaaatat    660
gagccaaagg agcctcatca tcagttgctg ttggagttgg ccaagctgga cttcaatatg    720
gttcagacgc tgcaccaaaa ggagttgcag gacctgtctc gatggtggac cgagatggga    780
ttggcctcga agctggattt tgtccgtgac cgacttatgg aggtctattt ttgggccctt    840
ggaatggcgc ctgaccccca gttcggagag tgccggaagg cggtgacgaa gatgttcggt    900
cttgtgacta tcatcgacga cgtctacgat gtctacggca cactcgacga gttgcagctg    960
ttcactgacg ccgtcgagcg atgggatgtg aacgccatta atactctccc tgactatatg   1020
aagctgtgct tcctggctct gtacaacact gtcaacgata cctcgtactc tatcctcaag   1080
gagaagggac acaacaatct ctcctacttg accaaatcct ggcgagaact gtgcaaggct   1140
ttctgcagg aggctaaatg gtccaataac aagatcattc ctgctttttc taaatacctg   1200
gaaaatgcct cggtgtcgag ctctggcgtc gcccttctgg ccccttccta cttctccgtc   1260
tgccagcagc aggaggatat ttccgatcat gctcttagat cgctgaccga ttttcacggc   1320
ctcgtgcgat cttcctgcgt gatttttcgg ttgtgtaatg accttgcgac ctctgctgct   1380
gagctggaac gaggcgagac tacaaattcc attatttctt acatgcacga aaacgatgga   1440
acatctgaag aacaggctag agaggaactg cgaaagttga tcgacgccga gtggaagaag   1500
atgaacagag agcgggtgtc cgactctacc ctgcttccca aggccttcat ggagatcgcc   1560
gtgaacatgg ctcgagtttc ccattgtact taccagtacg gtgacggcct gggtcgtccg   1620
gactacgcta cagagaaccg aatcaagctg ctgctcatcg acccccttccc tatcaaccaa   1680
ttgatgtacg tgtaa                                                    1695
```

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9

```
gcttatggat cctctagact attacacgta catcaattgg                          40
```

<210> SEQ ID NO 10
<211> LENGTH: 30
<212> TYPE: DNA
<213> ORGANISM: Artificial Sequence
<220> FEATURE:
<223> OTHER INFORMATION: Synthetic Construct

<400> SEQUENCE: 10
caccatgtgt gcaacctcct cccagtttac 30

<210> SEQ ID NO 11
<211> LENGTH: 8185
<212> TYPE: DNA
<213> ORGANISM: Artificial Sequence
<220> FEATURE:
<223> OTHER INFORMATION: Synthetic Construct

<400> SEQUENCE: 11
cgaccggtga gaagaacagc atcgggacaa gggaaggaag aacaaagaca aagaaaacaa 60
aagaaagcaa ttgaaaacaa aacaaaacaa ttttcattcc ttctcttatc attccttttc 120
ttttcttttc tctcattcaa cgcactccat cgtatccgta ttcctcttat tttttctctt 180
tctctatatc catttctttc tctctaggtg tgtcctctct ctctcttcaa tttctctact 240
ccgcattcca acgcatcctt cccccaacct cccatttcct ccttacggcc cgatagcgat 300
cgtctttccc tcgctatcac tcgctaccgg cccctcctct gcaccgtaac ctcctacgta 360
tttaccatat cataaagttt tttccgacgc ttatcgctga ccccctgtcg ccctcctatt 420
ggcttccgga ttatcttctt gtccataagg tgatccatgc ttcctgaaga ttcccgaaat 480
gtgtccactt tggcggggaa tcattccatc cacttctttc tctctcgctt tcctcattcg 540
gcgctcccct tccgcgtctc attggtcttc cgctccgttt ttgctttgcc gatgttactt 600
ggggagaggt gcgataatcc tttcgcaaaa actcggtttg acgcctccca tggtataaat 660
agtgggtggt ggacaggtgc cttcgctttt ctttaagcaa gagaatccca ttgtcttgac 720
tatcacgaat tcacatacat tatgaagatc accgctgtca ttgccctttt attctcactt 780
gctgctgcct cacctattcc agttgccgat cctggtgtgg tttcagttag caagtcatat 840
gctgatttcc ttcgtgttta ccaaagttgg aacacttttg ctaatcctga tagacccaac 900
cttaagaaga gaaatgatac acctgcaagt ggatatcaag ttgaaaaagt cgtaattttg 960
tcacgtcacg gtgttagggc ccctacaaaa atgactcaaa ccatgcgtga tgtcactcct 1020
aatacatggc cagaatggcc cgttaaatta ggatatatta caccaagagg tgaacacttg 1080
atatcactta tgggcggttt ttaccgtcaa aaattccagc aacaaggaat cctttctcag 1140
ggctcctgtc ctactcctaa ctccatatat gtctgggctg acgtcgatca gcgtacttta 1200
aaaactggtg aagcattcct tgctggtttg gcaccacaat gtggcttgac aattcatcac 1260
caacaaaatc ttgagaaagc tgatcctctt tttcatcccg ttaaagctgg aacctgctct 1320
atggataaaa ctcaagttca acaagctgtt gagaaggagg cacaaactcc tatagataat 1380
ttgaatcaac attacatccc ctttttagct ttaatgaata caacattaaa ttttagtact 1440
tctgcctggt gccaaaaaca ctctgctgat aaatcctgtg acctaggttt atccatgcct 1500
tctaaattgt ccataaaaga taatggtaac aaggtcgcat tggatggagc tattggtcta 1560
tcctctactt tggccgagat ttttcttctt gaatatgctc aaggcatgcc tcaagctgct 1620
tggggtaaca tccactcaga gcaagagtgg gcttccttgc taaagttgca taatgttcaa 1680
ttcgatttga tggcccgaac accttatatt gctcgacata acggtactcc tttattgcaa 1740

-continued

```
gctatatcaa atgcccttaa tcccaacgcc actgaatcaa aacttccaga tatttcacct   1800
gataacaaaa tattgttcat tgcaggtcat gacacaaata ttgctaatat agccggcatg   1860
ttaaatatgc gttggacatt accaggtcaa ccagataata ctcctccagg tggtgcccta   1920
gtatttgaac gtcttgctga taaaagtgga aaacaatatg tttctgtatc tatggtttat   1980
caaacactag aacaacttcg atcacagact cccctttctc taaatcagcc tgccggatct   2040
gttcaactta aaattccagg ttgcaatgat caaacagccg agggttactg tcctctttcc   2100
acttttacaa gagttgtttc ccaatctgtt gaacctggat gccaacttca ataatgagga   2160
tccaagtaag ggaatgagaa tgtgatccac ttttaattcc taatgaatac atgcctatag   2220
ttcttttctt ttgttcttta tgtcgttttt cgatggtacg gccgttgtca atctcagttt   2280
gtgtgcttgg ttgcagcttg gtttcaaatc tgttcatctc atgaatcttt taccatttca   2340
ccacacgttt ataccattct ctcatagaat cttcatcaaa ccatctcggg gttagagtgg   2400
aaagaaagtc ttgttctttt atttcctttt ttccatcttc aaggcttttc ttttcttcct   2460
cctcctcgtt catcttgagg tttgacgtgt ctgtttagaa ttttgagctg ttgcagcatc   2520
ttattttttg ttttgcgaaa acgaagcgct ttactctctt catcagttgg acgattgtac   2580
ctttgaaaac caactacttt tgcatgtttt gtatagaaat caatgatatt agaatcccat   2640
cctttaattt ctttcaaagt agttgagcta tagttaagtg taagggccct actgcgaaag   2700
catttgccaa ggatgtttc attaatcaag aacgaaagtt aggggatcga agacgatcag   2760
ataccgtcgt agtcttaacc ataaactatg ccgactaggg atcgggcaat gtttcattta   2820
tcgacttgct cggcacctta cgagaaatca aagtctttgg gttccggggg gagtatggtc   2880
gcaaggctga aacttaaagg aattgacgga agggcaccac aatggagtgg agcctgcggc   2940
ttaatttgac tcaacacggg gaaactcacc aggtccagac atagtaagga ttgacagatt   3000
gagagctctt tcttgattct atgggtggtg gtgcatggcc gttcttagtt ggtggagtga   3060
tttgtctgct taattgcgat aacgaacgag accttaacct gctaaatagc tggatcagcc   3120
attttggctg atcattagct tcttagaggg actattggca taaagccaat ggaagtttga   3180
ggcaataaca ggtctgtgat gcccttagat gttctgggcc gcacgcgcgc tacactgacg   3240
gagccaacga gttgaaaaaa atcttttgat tttttatcct tggccggaag gtctgggtaa   3300
tcttgttaaa ctccgtcgtg ctggggatag agcattgcaa ttattgcggc cgctcctcaa   3360
ttcgatgttg cagattttac aagtttttaa aatgtatttc attattactt tttatatgcc   3420
taataaaaaa gccatagttt aatctataga taacttttttt tccagtgcac taacggacgt   3480
tacattccca tacaaaactg cgtagttaaa gctaaggaaa agttaatatc atgttaatta   3540
aatacgctat ttacaataag acattgaact catttatatc gttgaatatg aataaccaat   3600
ttcagcgaat ttttaacaaa catcgttcac ctcgtttaag gatatcttgt gtatggggtg   3660
ttgacttgct ttatcgaata attaccgtac ctgtaattgg cttgctggat atagcggtag   3720
tctaatatct agcaaaaatc ttttgggtga aaaggcttgc aatttcacga caccgaacta   3780
tttgtcattt tttaataagg aagttttcca taaattcctg taattctcgg ttgatctaat   3840
tgaaaagagt agttttgcat cacgatgagg agggcttttg tagaaagaaa tacgaacgaa   3900
acgaaaatca gcgttgccat cgctttggac aaagctccct tacctgaaga gtcgaatttt   3960
attgatgaac ttataacttc caagcatgca aaccaaaagg gagaacaagt aatccaagta   4020
gacacgggaa ttggattctt ggatcacatg tatcatgcac tggctaaaca tgcaggctgg   4080
```

-continued

```
agcttacgac tttactcaag aggtgattta atcatcgatg atcatcacac tgcagaagat   4140
actgctattg cacttggtat tgcattcaag caggctatgg gtaactttgc cggcgttaaa   4200
agatttggac atgcttattg tccacttgac gaagctcttt ctagaagcgt agttgacttg   4260
tcgggacggc cctatgctgt tatcgatttg ggattaaagc gtgaaaaggt tggggaattg   4320
tcctgtgaaa tgatccctca cttactatat tccttttcgg tagcagctgg aattactttg   4380
catgttacct gcttatatgg tagtaatgac catcatcgtg ctgaaagcgc ttttaaatct   4440
ctggctgttg ccatgcgcgc ggctactagt cttactggaa gttctgaagt cccaagcacg   4500
aagggagtgt tgtaaagatg aattggatta tgtcaggaaa agaacgacaa ttttgcatcc   4560
aaattgtcta aattttagag ttgcttgaaa acaatagaac cttacttgct ttataattac   4620
gttaattaga agcgttatct cgtgaaggaa tatagtacgt agccgtataa attgaattga   4680
atgttcagct tatagaatag agacactttg ctgttcaatg cgtcgtcact taccatactc   4740
actttattat acgactttaa gtataaactc cgcggttatg gtaaaattaa tgatgcacaa   4800
acgtccgatt ccatatgggt acactacaat taaatacttt taagctgatc ccccacacac   4860
catagcttca aaatgtttct actccttttt tactcttcca gattttctcg gactccgcgc   4920
atcgccgtac cacttcaaaa cacccaagca cagcatacta aattttccct ctttcttcct   4980
ctagggtgtc gttaattacc cgtactaaag gtttggaaaa gaaaaaagag accgcctcgt   5040
ttcttttct tcgtcgaaaa aggcaataaa aatttttatc acgtttcttt ttcttgaaat   5100
ttttttttt agttttttc tctttcagtg acctccattg atatttaagt taataaacgg   5160
tcttcaattt ctcaagtttc agtttcattt ttcttgttct attacaactt tttttacttc   5220
ttgttcatta gaaagaaagc atagcaatct aatctaaggg cggtgttgac aattaatcat   5280
cggcatagta tatcggcata gtataatacg acaaggtgag gaactaaacc atggccaagt   5340
tgaccagtgc cgttccggtg ctcaccgcgc gcgacgtcgc cggagcggtc gagttctgga   5400
ccgaccggct cgggttctcc cgggacttcg tggaggacga cttcgccggt gtggtccggg   5460
acgacgtgac cctgttcatc agcgcggtcc aggaccaggt ggtgccggac aacaccctgg   5520
cctgggtgtg ggtgcgcggc ctggacgagc tgtacgccga gtggtcggag gtcgtgtcca   5580
cgaacttccg ggacgcctcc gggccggcca tgaccgagat cggcgagcag ccgtgggggc   5640
gggagttcgc cctgcgcgac ccggccggca actgcgtgca cttcgtggcc gaggagcagg   5700
actgacacgt ccgacggcgg cccacgggtc ccaggcctcg gagatccgtc cccctttcc    5760
tttgtcgata tcatgtaatt agttatgtca cgcttacatt cacgccctcc ccccacatcc   5820
gctctaaccg aaaaggaagg agttagacaa cctgaagtct aggtccctat ttattttttt   5880
atagttatgt tagtattaag aacgttattt atatttcaaa tttttctttt ttttctgtac   5940
agacgcgagc ttcccagtaa atgtgccatc tcgtaggcag aaaacggttc ccccgtaggg   6000
tctctctctt ggcctccttt ctaggtcggg ctgattgctc ttgaagctct ctagggggc    6060
tcacaccata ggcagataac gttccccacc ggctcgcctc gtaagcgcac aaggactgct   6120
cccaaagatc ctaggcggga ttttgccgat ttcggcctaa aggaaccgga acacgtagaa   6180
agccagtccg cagaaacggt gctgaccccg gatgaatgtc agctactggg ctatctggac   6240
aagggaaaac gcaagcgcaa agagaaagca ggtagcttgc agtgggctta catggcgata   6300
gctagactgg gcggttttat ggacagcaag cgaaccggaa ttgccagctg gggcgccctc   6360
tggtaaggtt gggaagccct gcaaagtaaa ctggatggct ttcttgccgc caaggatctg   6420
atggcgcagg ggatcaagat ctgatcaaga gacaggatga ggatcgtttc gcatgattga   6480
```

acaagatgga ttgcacgcag gttctccggc cgcttgggtg gagaggctat tcggctatga 6540
ctgggcacaa cagacaatcg gctgctctga tgccgccgtg ttccggctgt cagcgcaggg 6600
gcgcccggtt ctttttgtca agaccgacct gtccggtgcc ctgaatgaac tgcaggacga 6660
ggcagcgcgg ctatcgtggc tggccacgac gggcgttcct tgcgcagctg tgctcgacgt 6720
tgtcactgaa gcgggaaggg actggctgct attgggcgaa gtgccggggc aggatctcct 6780
gtcatctcgc cttgctcctg ccgagaaagt atccatcatg gctgatgcaa tgcggcggct 6840
gcatacgctt gatccggcta cctgcccatt cgaccaccaa gcgaaacatc gcatcgagcg 6900
agcacgtact cggatggaag ccggtcttgt cgatcaggat gatctggaca agagcatcag 6960
gggctcgcgc cagccgaact gttcgccagg ctcaaggccg catgcccgac ggcgaggatc 7020
tcgtcgtgat ccatggcgat gcctgctgcc gaatatcatg gtggaaaatg gccgcttttc 7080
tggattaacg actgtggccg gctgggtgtg gcggaccgct atcaggacat agcgtggata 7140
cccgtgatat tgctgaagag cttggcggcg aatgggctga ccgcttcctc gtgctttacg 7200
gtatcgccgc tcccgattcg cagcgcatcg ccttctatcg ccttcttgac gagttcttct 7260
gaattgaaaa aggtaccaag tttactcata tatactttag attgatttaa aacttcattt 7320
ttaatttaaa aggatctagg tgaagatcct ttttgataat ctcatgacca aaatccctta 7380
acgtgagttt tcgttccact gagcgtcaga ccccgtagaa aagatcaaag gatcttcttg 7440
agatcctttt tttctgcgcg taatctgctg cttgcaaaca aaaaaaccac cgctaccagc 7500
ggtggtttgt ttgccggatc aagagctacc aactcttttt ccgaaggtaa ctggcttcag 7560
cagagcgcag ataccaaata ctgtccttct agtgtagccg tagttaggcc accacttcaa 7620
gaactctgta gcaccgccta catacctcgc tctgctaatc ctgttaccag tggctgctgc 7680
cagtggcgat aagtcgtgtc ttaccgggtt ggactcaaga cgatagttac cggataaggc 7740
gcagcggtcg ggctgaacgg ggggttcgtg cacacagccc agcttggagc gaacgaccta 7800
caccgaactg agatacctac agcgtgagca ttgagaaagc gccacgcttc ccgaagggag 7860
aaaggcggac aggtatccgg taagcggcag ggtcggaaca ggagagcgca cgagggagct 7920
tccaggggga aacgcctggt atctttatag tcctgtcggg tttcgccacc tctgacttga 7980
gcgtcgattt ttgtgatgct cgtcaggggg gcggagccta tggaaaaacg ccagcaacgc 8040
ggccttttta cggttcctgg ccttttgctg gccttttgct cacatgttct ttcctgcgtt 8100
atcccctgat tctgtggata accgtattac cgcctttgag tgagctgata ccgctcgccg 8160
cagccgaacg accgagcgca gcgag 8185

<210> SEQ ID NO 12
<211> LENGTH: 1724
<212> TYPE: DNA
<213> ORGANISM: Artificial Sequence
<220> FEATURE:
<223> OTHER INFORMATION: Synthetic Construct

<400> SEQUENCE: 12
gaattcaaaa caaaatgtgt gcaacctcct cccagtttac tcagattacc gagcataatt 60
ctcgacgatc tgctaactac cagccgaacc tttggaactt tgagtttctc cagtctctcg 120
aaaatgacct gaaggtggaa aagctcgagg agaaggcgac caaactcgag gaggaggtgc 180
gatgtatgat caacagagtt gacacccaac ccctgtcttt gctggagctg atcgacgatg 240
tgcagcggtt gggtttgact tataaattcg agaaggacat tatcaaggca ctggagaaca 300

```
ttgtgctcct cgacgagaac aagaagaaca agtctgatct tcacgctacc gctctctctt    360
tccgacttct tcgacaacac ggcttcgagg tgtcgcagga cgtcttcgag agatttaagg    420
acaaggaggg aggatttagc ggcgagctga agggagacgt tcagggtctt ctctccttgt    480
acgaggcgtc ctacctggga ttcgagggag agaacctcct ggaggaagct cgtacatttt    540
ccatcactca ccttaagaat aaccttaagg agggaattaa caccaaggtg gccgagcagg    600
tttctcacgc cctggagctc ccctaccacc aacggctcca tagactggag gctcgttggt    660
tcctggacaa atatgagcca aaggagcctc atcatcagtt gctgttggag ttggccaagc    720
tggacttcaa tatggttcag acgctgcacc aaaaggagtt gcaggacctg tctcgatggt    780
ggaccgagat gggattggcc tcgaagctgg attttgtccg tgaccgactt atggaggtct    840
atttttgggc ccttggaatg gcgcctgacc cccagttcgg agagtgccgg aaggcggtga    900
cgaagatgtt cggtcttgtg actatcatcg acgacgtcta cgatgtctac ggcacactcg    960
acgagttgca gctgttcact gacgccgtcg agcgatggga tgtgaacgcc attaatactc   1020
tccctgacta tatgaagctg tgcttcctgg ctctgtacaa cactgtcaac gatacctcgt   1080
actctatcct caaggagaag ggacacaaca atctctccta cttgaccaaa tcctggcgag   1140
aactgtgcaa ggcttttctg caggaggcta aatggtccaa taacaagatc attcctgctt   1200
tttctaaata cctggaaaat gcctcggtgt cgagctctgg cgtcgccctt ctggcccctt   1260
cctacttctc cgtctgccag cagcaggagg atatttccga tcatgctctt agatcgctga   1320
ccgattttca cggcctcgtg cgatcttcct gcgtgatttt tcggttgtgt aatgaccttg   1380
cgacctctgc tgctgagctg gaacgaggcg agactacaaa ttccattatt tcttacatgc   1440
acgaaaacga tggaacatct gaagaacagg ctagagagga actgcgaaag ttgatcgacg   1500
ccgagtggaa gaagatgaac agagagcggg tgtccgactc taccctgctt cccaaggcct   1560
tcatggagat cgccgtgaac atggctcgag tttcccattg tacttaccag tacggtgacg   1620
gcctgggtcg tccggactac gctacagaga accgaatcaa gctgctgctc atcgacccct   1680
tccctatcaa ccaattgatg tacgtgtaat agtctagagg atcc                    1724
```

```
<210> SEQ ID NO 13
<211> LENGTH: 1701
<212> TYPE: DNA
<213> ORGANISM: Artificial Sequence
<220> FEATURE:
<223> OTHER INFORMATION: Synthetic Construct

<400> SEQUENCE: 13

gaattcaaca aaaatgtgct ctgtttccac tgagaacgtg tcctttactg agactgagac     60
tgaagcacgt agaagcgcca actacgaacc caactcctgg gattatgact ttctgctgtc    120
ttctgacacc gacgagtcga tcgaggttta taaggataag gccaagaaac ttgaggccga    180
ggtcagacga gagattaaca acgagaaggc cgagttcctg acccttcttg agctgatcga    240
caacgttcaa cgacttggtc ttggttaccg tttcgaatcc gatatccgac gtgcattgga    300
tcgatttgtc tcgtccggag gtttcgatgg tgtgactaag acgtcgctgc acgccacagc    360
tctttccttc agactgttgc ggcagcatgg atttgaggtt tcccaggaag ccttttctgg    420
tttcaaggat cagaacggaa actttttgga gaatctcaag gaggacacca aggccatcct    480
gtcgttgtat gaggcctcgt tcctggctct tgagggcgag aatattctgg atgaggctcg    540
ggttttcgct atttcgcacc tgaaggagtt gtcggaggaa aagatcggaa aggaactggc    600
cgagcaggtc aaccatgcac ttgaacttcc cctgcatcga cgtacccagc gactggaggc    660
```

cgtgtggagc atcgaggcgt acagaaaaaa ggaggatgct aatcaggttc tgctcgaact 720
cgctatcctc gactataaca tgattcagag cgtgtaccag cgtgacttgc gagagacaag 780
ccggtggtgg cgacgggtgg gactggccac gaagctccac tttgctaaag atcgattgat 840
tgagtcgttc tactgggcag tgggtgtggc ctttgagcct cagtactccg actgccgaaa 900
ctccgttgca aagatgtttt cttttgtcac tatcatcgac gacatctacg atgtttacgg 960
cactctcgat gaactcgaac tcttcacgga cgctgtcgag cgatgggatg tgaatgccat 1020
taatgatctg ccagattata tgaagttgtg tttcttggcg ctctacaaca caattaatga 1080
aattgcctac gacaacctca aggacaaggg agagaacatt ctgccctacc ttactaaagc 1140
ctgggccgac ctgtgtaacg ccttttgca ggaagccaag tggctctata acaaatctac 1200
tcctacattt gatgactact tcggcaacgc ttggaagtct tccagcggcc ctctccagtt 1260
gatcttcgct tactttgcag tggtccagaa catcaagaaa gaggagattg agaacctcca 1320
gaagtatcac gacatcatct cccgaccttc gcacatcttt cgactgtgca atgaccttgc 1380
ctccgcatcc gctgagattg cccgaggaga aacagccaat tctgtgtcgt gttacatgcg 1440
tacaaagggc atctccgagg agctggctac cgagtctgtg atgaacctga tcgatgaaac 1500
ctgtaagaag atgaacaaag agaaactggg cggttctctg ttcgccaaac catttgttga 1560
aaccgcgatc aatctggctc gtcagtctca ttgtacttac cataacggtg acgcgcacac 1620
ttcgccggac gaattgaccc gtaagcgtgt gctttcggtg attaccgagc cgatcctgcc 1680
gttcgaaaga taataggatc c 1701

<210> SEQ ID NO 14
<211> LENGTH: 28
<212> TYPE: DNA
<213> ORGANISM: Artificial Sequence
<220> FEATURE:
<223> OTHER INFORMATION: Synthetic Construct

<400> SEQUENCE: 14
gatcaagctt aaccggaatt gccagctg 28

<210> SEQ ID NO 15
<211> LENGTH: 33
<212> TYPE: DNA
<213> ORGANISM: Artificial Sequence
<220> FEATURE:
<223> OTHER INFORMATION: Synthetic Construct

<400> SEQUENCE: 15
gatccgatcg tcagaagaac tcgtcaagaa ggc 33

<210> SEQ ID NO 16
<211> LENGTH: 38
<212> TYPE: DNA
<213> ORGANISM: Artificial Sequence
<220> FEATURE:
<223> OTHER INFORMATION: Synthetic Construct

<400> SEQUENCE: 16
catcaatgca tcgcccttag gaggtaaaaa aaaatgac 38

<210> SEQ ID NO 17
<211> LENGTH: 26
<212> TYPE: DNA
<213> ORGANISM: Artificial Sequence
<220> FEATURE:

<223> OTHER INFORMATION: Synthetic Construct

<400> SEQUENCE: 17
ccttctgcag gacgcgttgt tatagc 26

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
gatcatgcat tcgcccttag gaggtaaaaa aacatgagtt ttgatattgc caaatacccg 60

<210> SEQ ID NO 19
<211> LENGTH: 31
<212> TYPE: DNA
<213> ORGANISM: Artificial Sequence
<220> FEATURE:
<223> OTHER INFORMATION: Synthetic Construct

<400> SEQUENCE: 19
catgctgcag ttatgccagc caggccttga t 31

<210> SEQ ID NO 20
<211> LENGTH: 8804
<212> TYPE: DNA
<213> ORGANISM: Artificial Sequence
<220> FEATURE:
<223> OTHER INFORMATION: Synthetic Construct

<400> SEQUENCE: 20
gctggtacca tatgggaatt cgaagctttc tagaacaaaa actcatctca gaagaggatc 60
tgaatagcgc cgtcgaccat catcatcatc atcattgagt ttaaacggtc tccagcttgg 120
ctgttttggc ggatgagaga agattttcag cctgatacag attaaatcag aacgcagaag 180
cggtctgata aaacagaatt tgcctggcgg cagtagcgcg gtggtcccac ctgaccccat 240
gccgaactca gaagtgaaac gccgtagcgc cgatggtagt gtggggtctc cccatgcgag 300
agtagggaac tgccaggcat caaataaaac gaaaggctca gtcgaaagac tgggcctttc 360
gttttatctg ttgtttgtcg gtgaacgctc tcctgagtag gacaaatccg ccgggagcgg 420
atttgaacgt tgcgaagcaa cggcccggag ggtggcgggc aggacgcccg ccataaactg 480
ccaggcatca aattaagcag aaggccatcc tgacggatgg cctttttgcg tttctacaaa 540
ctctttttgt ttatttttct aaatacattc aaatatgtat ccgcttaacc ggaattgcca 600
gctggggcgc cctctggtaa ggttgggaag ccctgcaaag taaactggat ggctttctcg 660
ccgccaagga tctgatggcg caggggatca agctctgatc aagagacagg atgaggatcg 720
tttcgcatga ttgaacaaga tggattgcac gcaggttctc cggccgcttg ggtggagagg 780
ctattcggct atgactgggc acaacagaca atcggctgct ctgatgccgc cgtgttccgg 840
ctgtcagcgc aggggcgccc ggttcttttt gtcaagaccg acctgtccgg tgccctgaat 900
gaactgcaag acgaggcagc gcggctatcg tggctggcca cgacgggcgt tccttgcgca 960
gctgtgctcg acgttgtcac tgaagcggga agggactggc tgctattggg cgaagtgccg 1020
gggcaggatc tcctgtcatc tcaccttgct cctgccgaga aagtatccat catggctgat 1080
gcaatgcggc ggctgcatac gcttgatccg gctacctgcc cattcgacca ccaagcgaaa 1140
catcgcatcg agcgagcacg tactcggatg gaagccggtc ttgtcgatca ggatgatctg 1200

-continued

```
gacgaagagc atcaggggct cgcgccagcc gaactgttcg ccaggctcaa ggcgagcatg   1260
cccgacggcg aggatctcgt cgtgacccat ggcgatgcct gcttgccgaa tatcatggtg   1320
gaaaatggcc gcttttctgg attcatcgac tgtggccggc tgggtgtggc ggaccgctat   1380
caggacatag cgttggctac ccgtgatatt gctgaagagc ttggcggcga atgggctgac   1440
cgcttcctcg tgctttacgg tatcgccgct cccgattcgc agcgcatcgc cttctatcgc   1500
cttcttgacg agttcttctg acatgaccaa aatcccttaa cgtgagtttt cgttccactg   1560
agcgtcagac cccgtagaaa agatcaaagg atcttcttga gatccttttt ttctgcgcgt   1620
aatctgctgc ttgcaaacaa aaaaaccacc gctaccagcg gtggtttgtt tgccggatca   1680
agagctacca actctttttc cgaaggtaac tggcttcagc agagcgcaga taccaaatac   1740
tgtccttcta gtgtagccgt agttaggcca ccacttcaag aactctgtag caccgcctac   1800
atacctcgct ctgctaatcc tgttaccagt ggctgctgcc agtggcgata agtcgtgtct   1860
taccgggttg gactcaagac gatagttacc ggataaggcg cagcggtcgg gctgaacggg   1920
gggttcgtgc acacagccca gcttggagcg aacgacctac accgaactga gatacctaca   1980
gcgtgagcta tgagaaagcg ccacgcttcc cgaagggaga aaggcggaca ggtatccggt   2040
aagcggcagg gtcggaacag gagagcgcac gagggagctt ccagggggaa acgcctggta   2100
tctttatagt cctgtcgggt ttcgccacct ctgacttgag cgtcgatttt tgtgatgctc   2160
gtcagggggg cggagcctat ggaaaaacgc cagcaacgcg gcctttttac ggttcctggc   2220
cttttgctgg ccttttgctc acatgttctt tcctgcgtta tcccctgatt ctgtggataa   2280
ccgtattacc gcctttgagt gagctgatac cgctcgccgc agccgaacga ccgagcgcag   2340
cgagtcagtg agcgaggaag cggaagagcg cctgatgcgg tattttctcc ttacgcatct   2400
gtgcggtatt tcacaccgca tatggtgcac tctcagtaca atctgctctg atgccgcata   2460
gttaagccag tatacactcc gctatcgcta cgtgactggg tcatggctgc gccccgacac   2520
ccgccaacac ccgctgacgc gccctgacgg gcttgtctgc tcccggcatc cgcttacaga   2580
caagctgtga ccgtctccgg gagctgcatg tgtcagaggt tttcaccgtc atcaccgaaa   2640
cgcgcgaggc agcagatcaa ttcgcgcgcg aaggcgaagc ggcatgcatt tacgttgaca   2700
ccatcgaatg gtgcaaaacc tttcgcggta tggcatgata gcgcccggaa gagagtcaat   2760
tcagggtggt gaatgtgaaa ccagtaacgt tatacgatgt cgcagagtat gccggtgtct   2820
cttatcagac cgtttcccgc gtggtgaacc aggccagcca cgtttctgcg aaaacgcggg   2880
aaaaagtgga agcggcgatg gcggagctga attacattcc caaccgcgtg gcacaacaac   2940
tggcgggcaa acagtcgttg ctgattggcg ttgccacctc cagtctggcc ctgcacgcgc   3000
cgtcgcaaat tgtcgcggcg attaaatctc gcgccgatca actgggtgcc agcgtggtgg   3060
tgtcgatggt agaacgaagc ggcgtcgaag cctgtaaagc ggcggtgcac aatcttctcg   3120
cgcaacgcgt cagtgggctg atcattaact atccgctgga tgaccaggat gccattgctg   3180
tggaagctgc ctgcactaat gttccggcgt tatttcttga tgtctctgac cagacaccca   3240
tcaacagtat tattttctcc catgaagacg gtacgcgact gggcgtggag catctggtcg   3300
cattgggtca ccagcaaatc gcgctgttag cgggcccatt aagttctgtc tcggcgcgtc   3360
tgcgtctggc tggctggcat aaatatctca ctcgcaatca aattcagccg atagcggaac   3420
gggaaggcga ctggagtgcc atgtccggtt ttcaacaaac catgcaaatg ctgaatgagg   3480
gcatcgttcc cactgcgatg ctggttgcca acgatcagat ggcgctgggc gcaatgcgcg   3540
```

-continued

```
ccattaccga gtccgggctg cgcgttggtg cggatatctc ggtagtggga tacgacgata   3600
ccgaagacag ctcatgttat atcccgccgt caaccaccat caaacaggat tttcgcctgc   3660
tggggcaaac cagcgtggac cgcttgctgc aactctctca gggccaggcg gtgaagggca   3720
atcagctgtt gcccgtctca ctggtgaaaa gaaaaaccac cctggcgccc aatacgcaaa   3780
ccgcctctcc ccgcgcgttg gccgattcat taatgcagct ggcacgacag gtttcccgac   3840
tggaaagcgg gcagtgagcg caacgcaatt aatgtgagtt agcgcgaatt gatctggttt   3900
gacagcttat catcgactgc acggtgcacc aatgcttctg gcgtcaggca gccatcggaa   3960
gctgtggtat ggctgtgcag gtcgtaaatc actgcataat tcgtgtcgct caaggcgcac   4020
tcccgttctg gataatgttt tttgcgccga catcataacg gttctggcaa atattctgaa   4080
atgagctgtt gacaattaat catccggctc gtataatgtg tggaattgtg agcggataac   4140
aatttcacac aggaaacagc gccgctgaga aaaagcgaag cggcactgct ctttaacaat   4200
ttatcagaca atctgtgtgg gcactcgacc ggaattatcg attaacttta ttattaaaaa   4260
ttaaagaggt atatattaat gtatcgatta aataaggagg aataaaccat gtgtgcgacc   4320
tcttctcaat ttactcagat taccgagcat aattcccgtc gttccgcaaa ctatcagcca   4380
aacctgtgga atttcgaatt cctgcaatcc ctggagaacg acctgaaagt ggaaaagctg   4440
gaggagaaag cgaccaaact ggaggaagaa gttcgctgca tgatcaaccg tgtagacacc   4500
cagccgctgt ccctgctgga gctgatcgac gatgtgcagc gcctgggtct gacctacaaa   4560
tttgaaaaag acatcattaa agccctggaa aacatcgtac tgctggacga aaacaaaaag   4620
aacaaatctg acctgcacgc aaccgctctg tctttccgtc tgctgcgtca gcacggtttc   4680
gaggtttctc aggatgtttt tgagcgtttc aaggataaag aaggtggttt cagcggtgaa   4740
ctgaaaggtg acgtccaagg cctgctgagc ctgtatgaag cgtcttacct gggtttcgag   4800
ggtgagaacc tgctggagga ggcgcgtacc ttttccatca cccacctgaa gaacaacctg   4860
aaagaaggca ttaataccaa ggttgcagaa caagtgagcc acgccctgga actgccatat   4920
caccagcgtc tgcaccgtct ggaggcacgt tggttcctgg ataaatacga accgaaagaa   4980
ccgcatcacc agctgctgct ggagctggcg aagctggatt ttaacatggt acagaccctg   5040
caccagaaag agctgcaaga tctgtcccgc tggtggaccg agatgggcct ggctagcaaa   5100
ctggattttg tacgcgaccg cctgatggaa gtttatttct gggcactggg tatggcgcca   5160
gacccgcagt ttggtgaatg tcgcaaagct gttactaaaa tgtttggtct ggtgacgatc   5220
atcgatgacg tgtatgacgt ttatggcact ctggacgaac tgcaactgtt caccgatgct   5280
gtagagcgct gggacgttaa cgctattaac accctgccgg actatatgaa actgtgtttc   5340
ctggcactgt acaacaccgt taacgacacg tcctattcta ttctgaaaga gaaaggtcat   5400
aacaacctgt cctatctgac gaaaagctgg cgtgaactgt gcaaagcctt tctgcaagag   5460
gcgaaatggt ccaacaacaa aattatcccg gctttctcca agtacctgga aaacgccagc   5520
gtttcctcct ccggtgtagc gctgctggcg ccgtcttact tttccgtatg ccagcagcag   5580
gaagacatct ccgaccacgc gctgcgttcc ctgaccgact tccatggtct ggtgcgttct   5640
agctgcgtta tcttccgcct gtgcaacgat ctggccacct ctgcggcgga gctggaacgt   5700
ggcgagacta ccaattctat cattagctac atgcacgaaa acgatggtac cagcgaggaa   5760
caggcccgcg aagaactgcg taaactgatc gacgccgaat ggaaaaagat gaatcgtgaa   5820
cgcgttagcg actccaccct gctgcctaaa gcgttcatgg aaatcgcagt taacatggca   5880
cgtgtttccc actgcaccta ccagtatggc gatggtctgg gtcgcccaga ctacgcgact   5940
```

```
gaaaaccgca tcaaactgct gctgattgac cctttcccga ttaaccagct gatgtatgtc   6000
taactgcatc gcccttagga ggtaaaaaaa aatgactgcc gacaacaata gtatgcccca   6060
tggtgcagta tctagttacg ccaaattagt gcaaaaccaa acacctgaag acattttgga   6120
agagtttcct gaaattattc cattacaaca aagacctaat acccgatcta gtgagacgtc   6180
aaatgacgaa agcggagaaa catgtttttc tggtcatgat gaggagcaaa ttaagttaat   6240
gaatgaaaat tgtattgttt tggattggga cgataatgct attggtgccg gtaccaagaa   6300
agtttgtcat ttaatggaaa atattgaaaa gggtttacta catcgtgcat tctccgtctt   6360
tattttcaat gaacaaggtg aattactttt acaacaaaga gccactgaaa aaataacttt   6420
ccctgatctt tggactaaca catgctgctc tcatccacta tgtattgatg acgaattagg   6480
tttgaagggt aagctagacg ataagattaa gggcgctatt actgcggcgg tgagaaaact   6540
agatcatgaa ttaggtattc cagaagatga aactaagaca aggggtaagt ttcacttttt   6600
aaacagaatc cattacatgg caccaagcaa tgaaccatgg ggtgaacatg aaattgatta   6660
catcctattt tataagatca acgctaaaga aaacttgact gtcaacccaa acgtcaatga   6720
agttagagac ttcaaatggg tttcaccaaa tgatttgaaa actatgtttg ctgacccaag   6780
ttacaagttt acgccttggt ttaagattat ttgcgagaat tacttattca actggtggga   6840
gcaattagat gacctttctg aagtggaaaa tgacaggcaa attcatagaa tgctataaca   6900
acgcgtcctg cattcgccct taggaggtaa aaaaacatga gttttgatat tgccaaatac   6960
ccgaccctgg cactggtcga ctccacccag gagttacgac tgttgccgaa agagagttta   7020
ccgaaactct gcgacgaact gcgccgctat ttactcgaca gcgtgagccg ttccagcggg   7080
cacttcgcct ccgggctggg cacggtcgaa ctgaccgtgg cgctgcacta tgtctacaac   7140
accccgtttg accaattgat ttgggatgtg gggcatcagg cttatccgca taaaattttg   7200
accggacgcc gcgacaaaat cggcaccatc cgtcagaaag gcggtctgca cccgttcccg   7260
tggcgcggcg aaagcgaata tgacgtatta agcgtcgggc attcatcaac ctccatcagt   7320
gccggaattg gtattgcggt tgctgccgaa aaagaaggca aaaatcgccg caccgtctgt   7380
gtcattggcg atggcgcgat taccgcaggc atggcgtttg aagcgatgaa tcacgcgggc   7440
gatatccgtc ctgatatgct ggtgattctc aacgacaatg aaatgtcgat ttccgaaaat   7500
gtcggcgcgc tcaacaacca tctggcacag ctgctttccg gtaagcttta ctcttcactg   7560
cgcgaaggcg ggaaaaaagt tttctctggc gtgccgccaa ttaaagagct gctcaaacgc   7620
accgaagaac atattaaagg catggtagtg cctggcacgt tgtttgaaga gctgggcttt   7680
aactacatcg gcccggtgga cggtcacgat gtgctggggc ttatcaccac gctaaagaac   7740
atgcgcgacc tgaaaggccc gcagttcctg catatcatga ccaaaaaagg tcgtggttat   7800
gaaccggcag aaaaagaccc gatcactttc cacgccgtgc ctaaatttga tccctccagc   7860
ggttgtttgc cgaaaagtag cggcggtttg ccgagctatt caaaaatctt tggcgactgg   7920
ttgtgcgaaa cggcagcgaa agacaacaag ctgatggcga ttactccggc gatgcgtgaa   7980
ggttccggca tggtcgagtt ttcacgtaaa ttcccggatc gctacttcga cgtggcaatt   8040
gccgagcaac acgcggtgac ctttgctgcg ggtctggcga ttggtgggta caaacccatt   8100
gtcgcgattt actccacttt cctgcaacgc gcctatgatc aggtgctgca tgacgtggcg   8160
attcaaaagc ttccggtcct gttcgccatc gaccgcgcgg gcattgttgg tgctgacggt   8220
caaacccatc agggtgcttt tgatctctct tacctgcgct gcataccgga aatggtcatt   8280
```

-continued atgaccccga gcgatgaaaa cgaatgtcgc cagatgctct ataccggcta tcactataac 8340
gatggcccgt cagcggtgcg ctacccgcgt ggcaacgcgg tcggcgtgga actgacgccg 8400
ctggaaaaac taccaattgg caaaggcatt gtgaagcgtc gtggcgagaa actggcgatc 8460
cttaactttg gtacgctgat gccagaagcg gcgaaagtcg ccgaatcgct gaacgccacg 8520
ctggtcgata tgcgttttgt gaaaccgctt gatgaagcgt taattctgga aatggccgcc 8580
agccatgaag cgctggtcac cgtagaagaa aacgccatta tgggcggcgc aggcagcggc 8640
gtgaacgaag tgctgatggc ccatcgtaaa ccagtacccg tgctgaacat tggcctgccg 8700
gacttcttta ttccgcaagg aactcaggaa gaaatgcgcg ccgaactcgg cctcgatgcc 8760
gctggtatgg aagccaaaat caaggcctgg ctggcataac tgca 8804

<210> SEQ ID NO 21
<211> LENGTH: 40
<212> TYPE: DNA
<213> ORGANISM: Artificial Sequence
<220> FEATURE:
<223> OTHER INFORMATION: Synthetic Construct

<400> SEQUENCE: 21
aggaggtaaa aaaacatgtc attaccgttc ttaacttctg 40

<210> SEQ ID NO 22
<211> LENGTH: 52
<212> TYPE: DNA
<213> ORGANISM: Artificial Sequence
<220> FEATURE:
<223> OTHER INFORMATION: Synthetic Construct

<400> SEQUENCE: 22
atggctgcag gcctatcgca aattagctta tgaagtccat ggtaaattcg tg 52

<210> SEQ ID NO 23
<211> LENGTH: 23
<212> TYPE: DNA
<213> ORGANISM: Artificial Sequence
<220> FEATURE:
<223> OTHER INFORMATION: Synthetic Construct

<400> SEQUENCE: 23
gaattcgccc ttctgcagct acc 23

<210> SEQ ID NO 24
<211> LENGTH: 38
<212> TYPE: DNA
<213> ORGANISM: Artificial Sequence
<220> FEATURE:
<223> OTHER INFORMATION: Synthetic Construct

<400> SEQUENCE: 24
cgactggtgc acccttaagg aggaaaaaaa catgtcag 38

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
gtgctggaat tcgcccttct gcagc 25

<210> SEQ ID NO 26
<211> LENGTH: 32
<212> TYPE: DNA
<213> ORGANISM: Artificial Sequence
<220> FEATURE:
<223> OTHER INFORMATION: Synthetic Construct

<400> SEQUENCE: 26
gtagatgcat gcagaattcg cccttaagga gg 32

<210> SEQ ID NO 27
<211> LENGTH: 26
<212> TYPE: DNA
<213> ORGANISM: Artificial Sequence
<220> FEATURE:
<223> OTHER INFORMATION: Synthetic Construct

<400> SEQUENCE: 27
ccttctgcag gacgcgttgt tatagc 26

<210> SEQ ID NO 28
<211> LENGTH: 38
<212> TYPE: DNA
<213> ORGANISM: Artificial Sequence
<220> FEATURE:
<223> OTHER INFORMATION: Synthetic Construct

<400> SEQUENCE: 28
catcaatgca tcgcccttag gaggtaaaaa aaaatgac 38

<210> SEQ ID NO 29
<211> LENGTH: 25
<212> TYPE: DNA
<213> ORGANISM: Artificial Sequence
<220> FEATURE:
<223> OTHER INFORMATION: Synthetic Construct

<400> SEQUENCE: 29
gtgtgatgga tatctgcaga attcg 25

<210> SEQ ID NO 30
<211> LENGTH: 36
<212> TYPE: DNA
<213> ORGANISM: Artificial Sequence
<220> FEATURE:
<223> OTHER INFORMATION: Synthetic Construct

<400> SEQUENCE: 30
catcaatgca tcgcccttag gaggtaaaaa aacatg 36

<210> SEQ ID NO 31
<211> LENGTH: 60
<212> TYPE: DNA
<213> ORGANISM: Artificial Sequence
<220> FEATURE:
<223> OTHER INFORMATION: Synthetic Construct

<400> SEQUENCE: 31
gatcatgcat tcgcccttag gaggtaaaaa aacatgtgtg cgacctcttc tcaatttact 60

<210> SEQ ID NO 32
<211> LENGTH: 38
<212> TYPE: DNA
<213> ORGANISM: Artificial Sequence
<220> FEATURE:
<223> OTHER INFORMATION: Synthetic Construct

<400> SEQUENCE: 32
cggtcgacgg atccctgcag ttagacatac atcagctg 38

<210> SEQ ID NO 33
<211> LENGTH: 10992
<212> TYPE: DNA
<213> ORGANISM: Artificial Sequence
<220> FEATURE:
<223> OTHER INFORMATION: Synthetic Construct

<400> SEQUENCE: 33
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatggatcc 420
gagctcggat ccactagtaa cggccgccag tgtgctggaa ttcgccctta ggaggtaaaa 480
aaacatgtca ttaccgttct taacttctgc accgggaaag gttattattt ttggtgaaca 540
ctctgctgtg tacaacaagc ctgccgtcgc tgctagtgtg tctgcgttga gaacctacct 600
gctaataagc gagtcatctg caccagatac tattgaattg gacttcccgg acattagctt 660
taatcataag tggtccatca atgatttcaa tgccatcacc gaggatcaag taaactccca 720
aaaattggcc aaggctcaac aagccaccga tggcttgtct caggaactcg ttagtctttt 780
ggatccgttg ttagctcaac tatccgaatc cttccactac catgcagcgt tttgtttcct 840
gtatatgttt gtttgcctat gcccccatgc caagaatatt aagttttctt taaagtctac 900
tttacccatc ggtgctgggt tgggctcaag cgcctctatt tctgtatcac tggccttagc 960
tatggcctac ttggggggggt taataggatc taatgacttg gaaaagctgt cagaaaacga 1020
taagcatata gtgaatcaat gggccttcat aggtgaaaag tgtattcacg gtacccccttc 1080 aggaatagat aacgctgtgg ccacttatgg taatgccctg ctatttgaaa aagactcaca 1140
taatggaaca ataaacacaa acaattttaa gttcttagat gatttcccag ccattccaat 1200
gatcctaacc tatactagaa ttccaaggtc tacaaaagat cttgttgctc gcgttcgtgt 1260
gttggtcacc gagaaatttc ctgaagttat gaagccaatt ctagatgcca tgggtgaatg 1320
tgccctacaa ggcttagaga tcatgactaa gttaagtaaa tgtaaaggca ccgatgacga 1380
ggctgtagaa actaataatg aactgtatga acaactattg gaattgataa gaataaatca 1440
tggactgctt gtctcaatcg gtgtttctca tcctggatta gaacttatta aaaatctgag 1500
cgatgatttg agaattggct ccacaaaact taccggtgct ggtggcggcg gttgctcttt 1560
gactttgtta cgaagagaca ttactcaaga gcaaattgac agcttcaaaa agaaattgca 1620
agatgatttt agttacgaga catttgaaac agacttgggt gggactggct gctgtttgtt 1680
aagcgcaaaa aatttgaata aagatcttaa aatcaaatcc ctagtattcc aattatttga 1740
aaataaaact accacaaagc aacaaattga cgatctatta ttgccaggaa acacgaattt 1800
accatggact tcataagcta atttgcgata ggcctgcacc cttaaggagg aaaaaaacat 1860
gtcagagttg agagccttca gtgccccagg gaaagcgtta ctagctggtg gatatttagt 1920
tttagataca aaatatgaag catttgtagt cggattatcg gcaagaatgc atgctgtagc 1980

```
ccatccttac ggttcattgc aagggtctga taagtttgaa gtgcgtgtga aaagtaaaca   2040
atttaaagat ggggagtggc tgtaccatat aagtcctaaa agtggcttca ttcctgtttc   2100
gataggcgga tctaagaacc ctttcattga aaaagttatc gctaacgtat ttagctactt   2160
taaacctaac atggacgact actgcaatag aaacttgttc gttattgata ttttctctga   2220
tgatgcctac cattctcagg aggatagcgt taccgaacat cgtggcaaca gaagattgag   2280
ttttcattcg cacagaattg aagaagttcc caaaacaggg ctgggctcct cggcaggttt   2340
agtcacagtt ttaactacag ctttggcctc ctttttttgta tcggacctgg aaaataatgt   2400
agacaaatat agagaagtta ttcataattt agcacaagtt gctcattgtc aagctcaggg   2460
taaaattgga agcgggtttg atgtagcggc ggcagcatat ggatctatca gatatagaag   2520
attcccaccc gcattaatct ctaatttgcc agatattgga agtgctactt acggcagtaa   2580
actggcgcat ttggttgatg aagaagactg gaatattacg attaaaagta accatttacc   2640
ttcgggatta actttatgga tgggcgatat taagaatggt tcagaaacag taaaactggt   2700
ccagaaggta aaaaattggt atgattcgca tatgccagaa agcttgaaaa tatatacaga   2760
actcgatcat gcaaattcta gatttatgga tggactatct aaactagatc gcttacacga   2820
gactcatgac gattacagcg atcagatatt tgagtctctt gagaggaatg actgtacctg   2880
tcaaaagtat cctgaaatca cagaagttag agatgcagtt gccacaatta gacgttcctt   2940
tagaaaaata actaaagaat ctggtgccga tatcgaacct cccgtacaaa ctagcttatt   3000
ggatgattgc cagaccttaa aaggagttct tacttgctta atacctggtg ctggtggtta   3060
tgacgccatt gcagtgatta ctaagcaaga tgttgatctt agggctcaaa ccgctaatga   3120
caaaagattt tctaaggttc aatggctgga tgtaactcag gctgactggg gtgttaggaa   3180
agaaaaagat ccggaaactt atcttgataa ataacttaag gtagctgcat gcagaattcg   3240
cccttaagga ggaaaaaaaa atgaccgttt acacagcatc cgttaccgca cccgtcaaca   3300
tcgcaaccct taagtattgg gggaaaaggg acacgaagtt gaatctgccc accaattcgt   3360
ccatatcagt gactttatcg caagatgacc tcagaacgtt gacctctgcg gctactgcac   3420
ctgagtttga acgcgacact ttgtggttaa atggagaacc acacagcatc gacaatgaaa   3480
gaactcaaaa ttgtctgcgc gacctacgcc aattaagaaa ggaaatggaa tcgaaggacg   3540
cctcattgcc cacattatct caatggaaac tccacattgt ctccgaaaat aactttccta   3600
cagcagctgg tttagcttcc tccgctgctg gctttgctgc attggtctct gcaattgcta   3660
agttatacca attaccacag tcaacttcag aaatatctag aatagcaaga aaggggtctg   3720
gttcagcttg tagatcgttg tttggcggat acgtggcctg ggaaatggga aaagctgaag   3780
atggtcatga ttccatggca gtacaaatcg cagacagctc tgactggcct cagatgaaag   3840
cttgtgtcct agttgtcagc gatattaaaa aggatgtgag ttccactcag ggtatgcaat   3900
tgaccgtggc aacctccgaa ctatttaaag aaagaattga acatgtcgta ccaaagagat   3960
ttgaagtcat gcgtaaagcc attgttgaaa aagatttcgc cacctttgca aaggaaacaa   4020
tgatggattc caactctttc catgccacat gtttggactc tttccctcca atattctaca   4080
tgaatgacac ttccaagcgt atcatcagtt ggtgccacac cattaatcag ttttacggag   4140
aaacaatcgt tgcatacacg tttgatgcag gtccaaatgc tgtgttgtac tacttagctg   4200
aaaatgagtc gaaactcttt gcatttatct ataaattgtt tggctctgtt cctggatggg   4260
acaagaaatt tactactgag cagcttgagg ctttcaacca tcaatttgaa tcatctaact   4320
```

-continued

```
ttactgcacg tgaattggat cttgagttgc aaaaggatgt tgccagagtg attttaactc   4380
aagtcggttc aggcccacaa gaaacaaacg aatctttgat tgacgcaaag actggtctac   4440
caaaggaata agatcaattc gctgcatcgc ccttaggagg taaaaaaaaa tgactgccga   4500
caacaatagt atgccccatg gtgcagtatc tagttacgcc aaattagtgc aaaaccaaac   4560
acctgaagac attttggaag agtttcctga aattattcca ttacaacaaa gacctaatac   4620
ccgatctagt gagacgtcaa atgacgaaag cggagaaaca tgtttttctg gtcatgatga   4680
ggagcaaatt aagttaatga atgaaaattg tattgttttg gattgggacg ataatgctat   4740
tggtgccggt accaagaaag tttgtcattt aatggaaaat attgaaaagg gtttactaca   4800
tcgtgcattc tccgtcttta ttttcaatga acaaggtgaa ttacttttac aacaaagagc   4860
cactgaaaaa ataactttcc ctgatctttg gactaacaca tgctgctctc atccactatg   4920
tattgatgac gaattaggtt tgaagggtaa gctagacgat aagattaagg gcgctattac   4980
tgcggcggtg agaaaactag atcatgaatt aggtattcca gaagatgaaa ctaagacaag   5040
gggtaagttt cactttttaa acagaatcca ttacatggca ccaagcaatg aaccatgggg   5100
tgaacatgaa attgattaca tcctatttta taagatcaac gctaaagaaa acttgactgt   5160
caacccaaac gtcaatgaag ttagagactt caaatgggtt tcaccaaatg atttgaaaac   5220
tatgtttgct gacccaagtt acaagtttac gccttggttt aagattattt gcgagaatta   5280
cttattcaac tggtgggagc aattagatga cctttctgaa gtggaaaatg acaggcaaat   5340
tcatagaatg ctataacaac gcgtcctgca ttcgccctta ggaggtaaaa aaacatgtgt   5400
gcgacctctt ctcaatttac tcagattacc gagcataatt cccgtcgttc cgcaaactat   5460
cagccaaacc tgtggaattt cgaattcctg caatccctgg agaacgacct gaaagtggaa   5520
aagctggagg agaaagcgac caaactggag gaagaagttc gctgcatgat caaccgtgta   5580
gacacccagc cgctgtccct gctggagctg atcgacgatg tgcagcgcct gggtctgacc   5640
tacaaatttg aaaaagacat cattaaagcc ctggaaaaca tcgtactgct ggacgaaaac   5700
aaaaagaaca aatctgacct gcacgcaacc gctctgtctt tccgtctgct gcgtcagcac   5760
ggtttcgagg tttctcagga tgtttttgag cgtttcaagg ataaagaagg tggtttcagc   5820
ggtgaactga aggtgacgt ccaaggcctg ctgagcctgt atgaagcgtc ttacctgggt   5880
ttcgagggtg agaacctgct ggaggaggcg cgtacctttt ccatcaccca cctgaagaac   5940
aacctgaaag aaggcattaa taccaaggtt gcagaacaag tgagccacgc cctggaactg   6000
ccatatcacc agcgtctgca ccgtctggag gcacgttggt tcctggataa atacgaaccg   6060
aaagaaccgc atcaccagct gctgctggag ctggcgaagc tggattttaa catggtacag   6120
accctgcacc agaaagagct gcaagatctg tcccgctggt ggaccgagat gggcctggct   6180
agcaaactgg attttgtacg cgaccgcctg atggaagttt atttctgggc actgggtatg   6240
gcgccagacc cgcagtttgg tgaatgtcgc aaagctgtta ctaaaatgtt tggtctggtg   6300
acgatcatcg atgacgtgta tgacgtttat ggcactctgg acgaactgca actgttcacc   6360
gatgctgtag agcgctggga cgttaacgct attaacaccc tgccggacta tatgaaactg   6420
tgtttcctgg cactgtacaa caccgttaac gacacgtcct attctattct gaaagagaaa   6480
ggtcataaca acctgtccta tctgacgaaa agctggcgtg aactgtgcaa agcctttctg   6540
caagaggcga aatggtccaa caacaaaatt atcccggctt tctccaagta cctggaaaac   6600
gccagcgttt cctcctccgg tgtagcgctg ctggcgccgt cttacttttc cgtatgccag   6660
cagcaggaag acatctccga ccacgcgctg cgttccctga ccgacttcca tggtctggtg   6720
```

cgttctagct gcgttatctt ccgcctgtgc aacgatctgg ccacctctgc ggcggagctg 6780
gaacgtggcg agactaccaa ttctatcatt agctacatgc acgaaaacga tggtaccagc 6840
gaggaacagg cccgcgaaga actgcgtaaa ctgatcgacg ccgaatggaa aaagatgaat 6900
cgtgaacgcg ttagcgactc caccctgctg cctaaagcgt tcatggaaat cgcagttaac 6960
atggcacgtg tttcccactg cacctaccag tatggcgatg gtctgggtcg cccagactac 7020
gcgactgaaa accgcatcaa actgctgctg attgaccctt tcccgattaa ccagctgatg 7080
tatgtctaac tgcagctggt accatatggg aattcgaagc tttctagaac aaaaactcat 7140
ctcagaagag gatctgaata gcgccgtcga ccatcatcat catcatcatt gagtttaaac 7200
ggtctccagc ttggctgttt tggcggatga gagaagattt tcagcctgat acagattaaa 7260
tcagaacgca gaagcggtct gataaaacag aatttgcctg gcggcagtag cgcggtggtc 7320
ccacctgacc ccatgccgaa ctcagaagtg aaacgccgta gcgccgatgg tagtgtgggg 7380
tctccccatg cgagagtagg gaactgccag gcatcaaata aaacgaaagg ctcagtcgaa 7440
agactgggcc tttcgtttta tctgttgttt gtcggtgaac gctctcctga gtaggacaaa 7500
tccgccggga gcggatttga acgttgcgaa gcaacggccc ggagggtggc gggcaggacg 7560
cccgccataa actgccaggc atcaaattaa gcagaaggcc atcctgacgg atggcctttt 7620
tgcgtttcta caaactcttt ttgtttattt ttctaaatac attcaaatat gtatccgctt 7680
aaccggaatt gccagctggg gcgccctctg gtaaggttgg gaagccctgc aaagtaaact 7740
ggatggcttt ctcgccgcca aggatctgat ggcgcagggg atcaagctct gatcaagaga 7800
caggatgagg atcgtttcgc atgattgaac aagatggatt gcacgcaggt tctccggccg 7860
cttgggtgga gaggctattc ggctatgact gggcacaaca gacaatcggc tgctctgatg 7920
ccgccgtgtt ccggctgtca gcgcaggggc gcccggttct ttttgtcaag accgacctgt 7980
ccggtgccct gaatgaactg caagacgagg cagcgcggct atcgtggctg gccacgacgg 8040
gcgttccttg cgcagctgtg ctcgacgttg tcactgaagc gggaagggac tggctgctat 8100
tgggcgaagt gccggggcag gatctcctgt catctcacct tgctcctgcc gagaaagtat 8160
ccatcatggc tgatgcaatg cggcggctgc atacgcttga tccggctacc tgcccattcg 8220
accaccaagc gaaacatcgc atcgagcgag cacgtactcg gatggaagcc ggtcttgtcg 8280
atcaggatga tctggacgaa gagcatcagg ggctcgcgcc agccgaactg ttcgccaggc 8340
tcaaggcgag catgcccgac ggcgaggatc tcgtcgtgac ccatggcgat gcctgcttgc 8400
cgaatatcat ggtggaaaat ggccgctttt ctggattcat cgactgtggc cggctgggtg 8460
tggcggaccg ctatcaggac atagcgttgg ctacccgtga tattgctgaa gagcttggcg 8520
gcgaatgggc tgaccgcttc ctcgtgcttt acggtatcgc cgctcccgat tcgcagcgca 8580
tcgccttcta tcgccttctt gacgagttct tctgacgcat gaccaaaatc ccttaacgtg 8640
agttttcgtt ccactgagcg tcagaccccg tagaaaagat caaaggatct tcttgagatc 8700 cttttttct gcgcgtaatc tgctgcttgc aaacaaaaaa accaccgcta ccagcggtgg 8760
tttgtttgcc ggatcaagag ctaccaactc tttttccgaa ggtaactggc ttcagcagag 8820
cgcagatacc aaatactgtc cttctagtgt agccgtagtt aggccaccac ttcaagaact 8880
ctgtagcacc gcctacatac ctcgctctgc taatcctgtt accagtggct gctgccagtg 8940
gcgataagtc gtgtcttacc gggttggact caagacgata gttaccggat aaggcgcagc 9000
ggtcgggctg aacggggggt tcgtgcacac agcccagctt ggagcgaacg acctacaccg 9060

-continued

```
aactgagata cctacagcgt gagctatgag aaagcgccac gcttcccgaa gggagaaagg   9120
cggacaggta tccggtaagc ggcagggtcg gaacaggaga gcgcacgagg gagcttccag   9180
ggggaaacgc ctggtatctt tatagtcctg tcgggtttcg ccacctctga cttgagcgtc   9240
gatttttgtg atgctcgtca ggggggcgga gcctatggaa aaacgccagc aacgcggcct   9300
ttttacggtt cctggccttt tgctggcctt ttgctcacat gttctttcct gcgttatccc   9360
ctgattctgt ggataaccgt attaccgcct ttgagtgagc tgataccgct cgccgcagcc   9420
gaacgaccga gcgcagcgag tcagtgagcg aggaagcgga agagcgcctg atgcggtatt   9480
ttctccttac gcatctgtgc ggtatttcac accgcatatg gtgcactctc agtacaatct   9540
gctctgatgc cgcatagtta agccagtata cactccgcta tcgctacgtg actgggtcat   9600
ggctgcgccc cgacacccgc caacacccgc tgacgcgccc tgacgggctt gtctgctccc   9660
ggcatccgct tacagacaag ctgtgaccgt ctccgggagc tgcatgtgtc agaggttttc   9720
accgtcatca ccgaaacgcg cgaggcagca gatcaattcg cgcgcgaagg cgaagcggca   9780
tgcatttacg ttgacaccat cgaatggtgc aaaacctttc gcggtatggc atgatagcgc   9840
ccggaagaga gtcaattcag ggtggtgaat gtgaaaccag taacgttata cgatgtcgca   9900
gagtatgccg gtgtctctta tcagaccgtt tcccgcgtgg tgaaccaggc cagccacgtt   9960
tctgcgaaaa cgcgggaaaa agtggaagcg gcgatggcgg agctgaatta cattcccaac  10020
cgcgtggcac aacaactggc gggcaaacag tcgttgctga ttggcgttgc cacctccagt  10080
ctggccctgc acgcgccgtc gcaaattgtc gcggcgatta aatctcgcgc cgatcaactg  10140
ggtgccagcg tggtggtgtc gatggtagaa cgaagcggcg tcgaagcctg taaagcggcg  10200
gtgcacaatc ttctcgcgca acgcgtcagt gggctgatca ttaactatcc gctggatgac  10260
caggatgcca ttgctgtgga agctgcctgc actaatgttc cggcgttatt tcttgatgtc  10320
tctgaccaga cacccatcaa cagtattatt ttctcccatg aagacggtac gcgactgggc  10380
gtggagcatc tggtcgcatt gggtcaccag caaatcgcgc tgttagcggg cccattaagt  10440
tctgtctcgg cgcgtctgcg tctggctggc tggcataaat atctcactcg caatcaaatt  10500
cagccgatag cggaacggga aggcgactgg agtgccatgt ccggttttca acaaaccatg  10560
caaatgctga atgagggcat cgttcccact gcgatgctgg ttgccaacga tcagatggcg  10620
ctgggcgcaa tgcgcgccat taccgagtcc gggctgcgcg ttggtgcgga tatctcggta  10680
gtgggatacg acgataccga agacagctca tgttatatcc cgccgtcaac caccatcaaa  10740
caggattttc gcctgctggg gcaaaccagc gtggaccgct tgctgcaact ctctcagggc  10800
caggcggtga agggcaatca gctgttgccc gtctcactgg tgaaaagaaa aaccaccctg  10860
gcgcccaata cgcaaaccgc ctctccccgc gcgttggccg attcattaat gcagctggca  10920
cgacaggttt cccgactgga aagcgggcag tgagcgcaac gcaattaatg tgagttagcg  10980
cgaattgatc tg                                                      10992
```

<210> SEQ ID NO 34
<211> LENGTH: 50
<212> TYPE: DNA
<213> ORGANISM: Artificial Sequence
<220> FEATURE:
<223> OTHER INFORMATION: Synthetic Construct

<400> SEQUENCE: 34

```
gagacatgag ctcaggaggt aaaaaaacat gaaaacagta gttattattg                50
```

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
tttatcaatc ccaattgtca tgttttttta cctcctttat tgttttctta aatc 54

<210> SEQ ID NO 36
<211> LENGTH: 54
<212> TYPE: DNA
<213> ORGANISM: Artificial Sequence
<220> FEATURE:
<223> OTHER INFORMATION: Synthetic Construct

<400> SEQUENCE: 36
gatttaagaa aacaataaag gaggtaaaaa aacatgacaa ttgggattga taaa 54

<210> SEQ ID NO 37
<211> LENGTH: 40
<212> TYPE: DNA
<213> ORGANISM: Artificial Sequence
<220> FEATURE:
<223> OTHER INFORMATION: Synthetic Construct

<400> SEQUENCE: 37
gacatgacat agatctttag tttcgataag aacgaacggt 40

<210> SEQ ID NO 38
<211> LENGTH: 26
<212> TYPE: DNA
<213> ORGANISM: Enterococcus faecalis

<400> SEQUENCE: 38
atgaaaacag tagttattat tgatgc 26

<210> SEQ ID NO 39
<211> LENGTH: 33
<212> TYPE: DNA
<213> ORGANISM: Enterococcus faecalis

<400> SEQUENCE: 39
atgttattgt tttcttaaat catttaaaat agc 33

<210> SEQ ID NO 40
<211> LENGTH: 26
<212> TYPE: DNA
<213> ORGANISM: Enterococcus faecalis

<400> SEQUENCE: 40
atgacaattg ggattgataa aattag 26

<210> SEQ ID NO 41
<211> LENGTH: 24
<212> TYPE: DNA
<213> ORGANISM: Enterococcus faecalis

<400> SEQUENCE: 41
ttagtttcga taagaacgaa cggt 24

<210> SEQ ID NO 42
<211> LENGTH: 23
<212> TYPE: DNA

<213> ORGANISM: Enterococcus faecalis

<400> SEQUENCE: 42
gaaatagccc cattagaagt atc 23

<210> SEQ ID NO 43
<211> LENGTH: 24
<212> TYPE: DNA
<213> ORGANISM: Enterococcus faecalis

<400> SEQUENCE: 43
ttgccaatca tatgattgaa aatc 24

<210> SEQ ID NO 44
<211> LENGTH: 25
<212> TYPE: DNA
<213> ORGANISM: Enterococcus faecalis

<400> SEQUENCE: 44
gctatgcttc attagatcct tatcg 25

<210> SEQ ID NO 45
<211> LENGTH: 25
<212> TYPE: DNA
<213> ORGANISM: Enterococcus faecalis

<400> SEQUENCE: 45
gaaacctaca tccaatcttt tgccc 25

<210> SEQ ID NO 46
<211> LENGTH: 8703
<212> TYPE: DNA
<213> ORGANISM: Artificial Sequence
<220> FEATURE:
<223> OTHER INFORMATION: Synthetic Construct

<400> SEQUENCE: 46
cccgtcttac tgtcgggaat tcgcgttggc cgattcatta atgcagattc tgaaatgagc 60
tgttgacaat taatcatccg gctcgtataa tgtgtggaat tgtgagcgga taacaatttc 120
acacaggaaa cagcgccgct gagaaaaagc gaagcggcac tgctctttaa caatttatca 180
gacaatctgt gtgggcactc gaccggaatt atcgattaac tttattatta aaaattaaag 240
aggtatatat taatgtatcg attaaataag gaggaataaa ccatggatcc gagctcagga 300
ggtaaaaaaa catgaaaaca gtagttatta ttgatgcatt acgaacacca attggaaaat 360
ataaaggcag cttaagtcaa gtaagtgccg tagacttagg aacacatgtt acaacacaac 420
ttttaaaaag acattccact atttctgaag aaattgatca agtaatcttt ggaaatgttt 480
tacaagctgg aaatggccaa aatcccgcac gacaaatagc aataaacagc ggtttgtctc 540
atgaaattcc cgcaatgacg gttaatgagg tctgcggatc aggaatgaag gccgttattt 600
tggcgaaaca attgattcaa ttaggagaag cggaagtttt aattgctggc gggattgaga 660
atatgtccca agcacctaaa ttacaacgtt ttaattacga aacagaaagc tacgatgcgc 720
ctttttctag tatgatgtat gatggattaa cggatgcctt tagtggtcag gcaatgggct 780
taactgctga aaatgtggcc gaaaagtatc atgtaactag agaagagcaa gatcaatttt 840
ctgtacattc acaattaaaa gcagctcaag cacaagcaga agggatattc gctgacgaaa 900
tagccccatt agaagtatca ggaacgcttg tggagaaaga tgaagggatt cgccctaatt 960
cgagcgttga gaagctagga acgcttaaaa cagtttttaa agaagacggt actgtaacag 1020

```
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagtttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
gccgggaaat tgctgaaaaa attgttttag cttcacgcta tgcttcatta gatccttatc   2220
gggcagtcac gcataacaaa ggaatcatga atggcattga agctgtagtt ttagctacag   2280
gaaatgatac acgcgctgtt agcgcttctt gtcatgcttt tgcggtgaag gaaggtcgct   2340
accaaggctt gactagttgg acgctggatg gcgaacaact aattggtgaa atttcagttc   2400
cgcttgcttt agccacggtt ggcggtgcca caaaagtctt acctaaatct caagcagctg   2460
ctgatttgtt agcagtgacg gatgcaaaag aactaagtcg agtagtagcg gctgttggtt   2520
tggcacaaaa tttagcggcg ttacgggcct tagtctctga aggaattcaa aaaggacaca   2580
tggctctaca agcacgttct ttagcgatga cggtcggagc tactggtaaa gaagttgagg   2640
cagtcgctca acaattaaaa cgtcaaaaaa cgatgaacca agaccgagcc atggctattt   2700
taaatgattt aagaaaacaa taaaggaggt aaaaaaacat gacaattggg attgataaaa   2760
ttagtttttt tgtgccccct tattatattg atatgacggc actggctgaa gccagaaatg   2820
tagaccctgg aaaatttcat attggtattg ggcaagacca aatggcggtg aacccaatca   2880
gccaagatat tgtgacattt gcagccaatg ccgcagaagc gatcttgacc aaagaagata   2940
aagaggccat tgatatggtg attgtcggga ctgagtccag tatcgatgag tcaaaagcgg   3000
ccgcagttgt cttacatcgt ttaatgggga ttcaaccttt cgctcgctct ttcgaaatca   3060
aggaagcttg ttacggagca acagcaggct tacagttagc taagaatcac gtagccttac   3120
atccagataa aaaagtcttg gtcgtagcgg cagatattgc aaaatatggc ttaaattctg   3180
gcggtgagcc tacacaagga gctggggcgg ttgcaatgtt agttgctagt gaaccgcgca   3240
ttttggcttt aaaagaggat aatgtgatgc tgacgcaaga tatctatgac ttttggcgtc   3300
caacaggcca cccgtatcct atggtcgatg gtcctttgtc aaacgaaacc tacatccaat   3360
```

-continued

```
cttttgccca agtctgggat gaacataaaa aacgaaccgg tcttgatttt gcagattatg   3420
atgctttagc gttccatatt ccttacacaa aaatgggcaa aaaagcctta ttagcaaaaa   3480
tctccgacca aactgaagca gaacaggaac gaattttagc ccgttatgaa gaaagtatcg   3540
tctatagtcg tcgcgtagga aacttgtata cgggttcact ttatctggga ctcatttccc   3600
ttttagaaaa tgcaacgact ttaaccgcag gcaatcaaat tggtttattc agttatggtt   3660
ctggtgctgt cgctgaattt ttcactggtg aattagtagc tggttatcaa aatcatttac   3720
aaaaagaaac tcatttagca ctgctggata atcggacaga actttctatc gctgaatatg   3780
aagccatgtt tgcagaaact ttagacacag acattgatca aacgttagaa gatgaattaa   3840
aatatagtat ttctgctatt aataataccg ttcgttctta tcgaaactaa gagatctgca   3900
gctggtacca tatgggaatt cgaagcttgg gcccgaacaa aaactcatct cagaagagga   3960
tctgaatagc gccgtcgacc atcatcatca tcatcattga gtttaaacgg tctccagctt   4020
ggctgttttg gcggatgaga gaagattttc agcctgatac agattaaatc agaacgcaga   4080
agcggtctga taaaacagaa tttgcctggc ggcagtagcg cggtggtccc acctgacccc   4140
atgccgaact cagaagtgaa acgccgtagc gccgatggta gtgtggggtc tccccatgcg   4200
agagtaggga actgccaggc atcaaataaa acgaaaggct cagtcgaaag actgggcctt   4260
tcgttttatc tgttgtttgt cggtgaacgc tctcctgagt aggacaaatc cgccgggagc   4320
ggatttgaac gttgcgaagc aacggcccgg agggtggcgg gcaggacgcc cgccataaac   4380
tgccaggcat caaattaagc agaaggccat cctgacggat ggcctttttg cgtttctaca   4440
aactcttttt gtttattttt ctaaatacat tcaaatatgt atccgctcat gagacaataa   4500
ccctgataaa tgcttcaata atctggcgta atagcgaaga ggcccgcacc gatcgccctt   4560
cccaacagtt gcgcagcctg aatggcgaat ggcgcctgat gcggtatttt ctccttacgc   4620
atctgtgcgg tatttcacac cgcatatggt gcactctcag tacaatctgc tctgatgccg   4680
catagttaag ccagccccga cacccgccaa cacccgctga cgagcttagt aaagccctcg   4740
ctagatttta atgcggatgt tgcgattact tcgccaacta ttgcgataac aagaaaaagc   4800
cagcctttca tgatatatct cccaatttgt gtagggctta ttatgcacgc ttaaaaataa   4860
taaaagcaga cttgacctga tagtttggct gtgagcaatt atgtgcttag tgcatctaac   4920
gcttgagtta agccgcgccg cgaagcggcg tcggcttgaa cgaattgtta gacattattt   4980
gccgactacc ttggtgatct cgcctttcac gtagtggaca aattcttcca actgatctgc   5040
gcgcgaggcc aagcgatctt cttcttgtcc aagataagcc tgtctagctt caagtatgac   5100
gggctgatac tgggccggca ggcgctccat tgcccagtcg gcagcgacat ccttcggcgc   5160
gattttgccg gttactgcgc tgtaccaaat gcgggacaac gtaagcacta catttcgctc   5220
atcgccagcc cagtcgggcg gcgagttcca tagcgttaag gtttcattta gcgcctcaaa   5280
tagatcctgt tcaggaaccg gatcaaagag ttcctccgcc gctggaccta ccaaggcaac   5340
gctatgttct cttgcttttg tcagcaagat agccagatca atgtcgatcg tggctggctc   5400
gaagatacct gcaagaatgt cattgcgctg ccattctcca aattgcagtt cgcgcttagc   5460
tggataacgc cacggaatga tgtcgtcgtg cacaacaatg gtgacttcta cagcgcggag   5520
aatctcgctc tctccagggg aagccgaagt ttccaaaagg tcgttgatca aagctcgccg   5580
cgttgtttca tcaagcctta cggtcaccgt aaccagcaaa tcaatatcac tgtgtggctt   5640
caggccgcca tccactgcgg agccgtacaa atgtacggcc agcaacgtcg gttcgagatg   5700
gcgctcgatg acgccaacta cctctgatag ttgagtcgat acttcggcga tcaccgcttc   5760
```

cctcatgatg tttaactttg ttttagggcg actgccctgc tgcgtaacat cgttgctgct 5820
ccataacatc aaacatcgac ccacggcgta acgcgcttgc tgcttggatg cccgaggcat 5880
agactgtacc ccaaaaaaac agtcataaca agccatgaaa accgccactg cgccgttacc 5940
accgctgcgt tcggtcaagg ttctggacca gttgcgtgag cgcatacgct acttgcatta 6000
cagcttacga accgaacagg cttatgtcca ctgggttcgt gccttcatcc gtttccacgg 6060
tgtgcgtcac ccggcaacct tgggcagcag cgaagtcgag gcatttctgt cctggctggc 6120
gaacgagcgc aaggtttcgg tctccacgca tcgtcaggca ttggcggcct tgctgttctt 6180
ctacggcaag gtgctgtgca cggatctgcc ctggcttcag gagatcggaa gacctcggcc 6240
gtcgcggcgc ttgccggtgg tgctgacccc ggatgaagtg gttcgcatcc tcggttttct 6300
ggaaggcgag catcgtttgt tcgcccagct tctgtatgga acgggcatgc ggatcagtga 6360
gggtttgcaa ctgcgggtca aggatctgga tttcgatcac ggcacgatca tcgtgcggga 6420
gggcaagggc tccaaggatc gggccttgat gttacccgag agcttggcac ccagcctgcg 6480
cgagcagggg aattaattcc cacgggtttt gctgcccgca aacgggctgt tctggtgttg 6540
ctagtttgtt atcagaatcg cagatccggc ttcagccggt ttgccggctg aaagcgctat 6600
ttcttccaga attgccatga tttttcccc acgggaggcg tcactggctc ccgtgttgtc 6660
ggcagctttg attcgataag cagcatcgcc tgtttcaggc tgtctatgtg tgactgttga 6720
gctgtaacaa gttgtctcag gtgttcaatt tcatgttcta gttgctttgt tttactggtt 6780
tcacctgttc tattaggtgt tacatgctgt tcatctgtta cattgtcgat ctgttcatgg 6840
tgaacagctt tgaatgcacc aaaaactcgt aaaagctctg atgtatctat cttttttaca 6900
ccgttttcat ctgtgcatat ggacagtttt ccctttgata tgtaacggtg aacagttgtt 6960
ctacttttgt ttgttagtct tgatgcttca ctgatagata caagagccat aagaacctca 7020
gatccttccg tatttagcca gtatgttctc tagtgtggtt cgttgttttt gcgtgagcca 7080
tgagaacgaa ccattgagat catacttact ttgcatgtca ctcaaaaatt ttgcctcaaa 7140
actggtgagc tgaatttttg cagttaaagc atcgtgtagt gtttttctta gtccgttatg 7200
taggtaggaa tctgatgtaa tggttgttgg tattttgtca ccattcattt ttatctggtt 7260
gttctcaagt tcggttacga gatccatttg tctatctagt tcaacttgga aaatcaacgt 7320
atcagtcggg cggcctcgct tatcaaccac caatttcata ttgctgtaag tgtttaaatc 7380
tttacttatt ggtttcaaaa cccattggtt aagcctttta aactcatggt agttattttc 7440
aagcattaac atgaacttaa attcatcaag gctaatctct atatttgcct tgtgagtttt 7500
cttttgtgtt agttctttta ataaccactc ataaatcctc atagagtatt tgttttcaaa 7560
agacttaaca tgttccagat tatattttat gaattttttt aactggaaaa gataaggcaa 7620
tatctcttca ctaaaaacta attctaattt ttcgcttgag aacttggcat agtttgtcca 7680
ctggaaaatc tcaaagcctt taaccaaagg attcctgatt tccacagttc tcgtcatcag 7740
ctctctggtt gctttagcta atacaccata agcattttcc ctactgatgt tcatcatctg 7800
agcgtattgg ttataagtga acgataccgt ccgttctttc cttgtagggt tttcaatcgt 7860
ggggttgagt agtgccacac agcataaaat tagcttggtt tcatgctccg ttaagtcata 7920
gcgactaatc gctagttcat ttgctttgaa aacaactaat tcagacatac atctcaattg 7980
gtctaggtga ttttaatcac tataccaatt gagatgggct agtcaatgat aattactagt 8040
ccttttcctt tgagttgtgg gtatctgtaa attctgctag acctttgctg gaaaacttgt 8100

```
aaattctgct agaccctctg taaattccgc tagacctttg tgtgtttttt ttgtttatat   8160
tcaagtggtt ataatttata gaataaagaa agaataaaaa aagataaaaa gaatagatcc   8220
cagccctgtg tataactcac tactttagtc agttccgcag tattacaaaa ggatgtcgca   8280
aacgctgttt gctcctctac aaaacagacc ttaaaaccct aaaggcttaa gtagcaccct   8340
cgcaagctcg ggcaaatcgc tgaatattcc ttttgtctcc gaccatcagg cacctgagtc   8400
gctgtctttt tcgtgacatt cagttcgctg cgctcacggc tctggcagtg aatgggggta   8460
aatggcacta caggcgcctt ttatggattc atgcaaggaa actacccata atacaagaaa   8520
agcccgtcac gggcttctca gggcgtttta tggcgggtct gctatgtggt gctatctgac   8580
tttttgctgt tcagcagttc ctgccctctg attttccagt ctgaccactt cggattatcc   8640
cgtgacaggt cattcagact ggctaatgca cccagtaagg cagcggtatc atcaacaggc   8700
tta                                                                 8703
```

```
<210> SEQ ID NO 47
<211> LENGTH: 9371
<212> TYPE: DNA
<213> ORGANISM: Artificial Sequence
<220> FEATURE:
<223> OTHER INFORMATION: Synthetic Construct

<400> SEQUENCE: 47

tgtaaccttt gctttcaaat gagtagaaat aatgcacatc catgtttgta tcgtgcaaat     60
aaagtgtttc atccgtagga aaaaatgact ttagtatctg ttccgctttt tctgatgaaa    120
tgtgctcccc gacaaaattg aatgaatcat ggacatttgc tggctttgat acagcgaaag    180
cagccgttcc tatgttatat atcggattta acagcaggac aaaaaacacc atgacagcca    240
tcgtcaccca cttattcaca cgcacataaa cctttcctga cttttggaac agatgatagc    300
tcatcaaaaa tcccgccatt gccaaataaa tcgtatatgg cattactgca ccataatctt    360
ttgagatttg attgggatat ggcgcaagca gcaagacaag cagtccgata atcagcgtat    420
aaaataagcc tagtaagatc ttatccgttc tccaatacag cttgaaaaac actacattca    480
acgcaatggg aagagtgatg atgaaaaaca gaaacacgaa tgcaatcggc tccatcccat    540
ccgggtattc cttccaatac gaaaagaaac taaaaatcat ttgtacgatc ggcaaactga    600
caacagcaag gtcgaacgta taaaacttac cctttccgcc atgatcacgc ggcatcagca    660
tatagtgaaa agccgtcagc agcacatatc cgtataacaa aaaatgcagc agcggcagca    720
gttcttttcc gtcctctctt aagtaagcgc tggtgaagtt tgttgattgc acctggtgaa    780
taagttcaac agacactccc gccagcagca caatccgcaa tataacaccc gccaagaaca    840
ttgtgcgctg ccggtttatt ttgggatgat gcaccaaaag atataagccc gccagaacaa    900
caattgacca ttgaatcagc agggtgcttt gtctgcttaa tataaaataa cgttcgaaat    960
gcaatacata atgactgaat aactccaaca cgaacaacaa ctccattttc ttctgctatc   1020
aaaataacag actcgtgatt ttccaaacga gctttcaaaa aagcctctgc cccttgcaaa   1080
tcggatgcct gtctataaaa ttcccgatat tggttaaaca gcggcgcaat ggcggccgca   1140
tctgatgtct ttgcttggcg aatgttcatc ttatttcttc ctccctctca ataatttttt   1200
cattctatcc cttttctgta aagtttattt ttcagaatac ttttatcatc atgctttgaa   1260
aaaatatcac gataatatcc attgttctca cggaagcaca cgcaggtcat ttgaacgaat   1320
tttttcgaca ggaatttgcc gggactcagg agcatttaac ctaaaaaagc atgacatttc   1380
agcataatga acatttactc atgtctattt tcgttctttt ctgtatgaaa atagttattt   1440
```

-continued

```
cgagtctcta cggaaatagc gagagatgat atacctaaat agagataaaa tcatctcaaa   1500
aaaatgggtc tactaaaata ttattccatc tattacaata aattcacaga atagtctttt   1560
aagtaagtct actctgaatt tttttaaaag gagagggtaa agagtgtcat taccgttctt   1620
aacttctgca ccgggaaagg ttattatttt tggtgaacac tctgctgtgt acaacaagcc   1680
tgccgtcgct gctagtgtgt ctgcgttgag aacctacctg ctaataagcg agtcatctgc   1740
accagatact attgaattgg acttcccgga cattagcttt aatcataagt ggtccatcaa   1800
tgatttcaat gccatcaccg aggatcaagt aaactcccaa aaattggcca aggctcaaca   1860
agccaccgat ggcttgtctc aggaactcgt tagtcttttg gatccgttgt tagctcaact   1920
atccgaatcc ttccactacc atgcagcgtt ttgtttcctg tatatgtttg tttgcctatg   1980
cccccatgcc aagaatatta agttttcttt aaagtctact ttacccatcg gtgctgggtt   2040
gggctcaagc gcctctattt ctgtatcact ggccttagct atggcctact tggggggtt    2100
aataggatct aatgacttgg aaaagctgtc agaaaacgat aagcatatag tgaatcaatg   2160
ggccttcata ggtgaaaagt gtattcacgg taccccttca ggaatagata acgctgtggc   2220
cacttatggt aatgccctgc tatttgaaaa agactcacat aatggaacaa taaacacaaa   2280
caattttaag ttcttagatg atttcccagc cattccaatg atcctaacct atactagaat   2340
tccaaggtct acaaaagatc ttgttgctcg cgttcgtgtg ttggtcaccg agaaatttcc   2400
tgaagttatg aagccaattc tagatgccat gggtgaatgt gccctacaag gcttagagat   2460
catgactaag ttaagtaaat gtaaaggcac cgatgacgag gctgtagaaa ctaataatga   2520
actgtatgaa caactattgg aattgataag aataaatcat ggactgcttg tctcaatcgg   2580
tgtttctcat cctggattag aacttattaa aaatctgagc gatgatttga gaattggctc   2640
cacaaaactt accggtgctg gtggcggcgg ttgctctttg actttgttac gaagagacat   2700
tactcaagag caaattgaca gcttcaaaaa gaaattgcaa gatgatttta gttacgagac   2760
atttgaaaca gacttgggtg ggactggctg ctgtttgtta agcgcaaaaa atttgaataa   2820
agatcttaaa atcaaatccc tagtattcca attatttgaa aataaaacta ccacaaagca   2880
acaaattgac gatctattat tgccaggaaa cacgaattta ccatggactt cataaaagga   2940
gagggtgtca gagttgagag ccttcagtgc cccagggaaa gcgttactag ctggtggata   3000
tttagtttta gatacaaaat atgaagcatt tgtagtcgga ttatcggcaa gaatgcatgc   3060
tgtagcccat ccttacggtt cattgcaagg gtctgataag tttgaagtgc gtgtgaaaag   3120
taaacaattt aaagatgggg agtggctgta ccatataagt cctaaaagtg gcttcattcc   3180
tgtttcgata ggcggatcta agaacccttt cattgaaaaa gttatcgcta acgtatttag   3240
ctactttaaa cctaacatgg acgactactg caatagaaac ttgttcgtta ttgatatttt   3300
ctctgatgat gcctaccatt ctcaggagga tagcgttacc gaacatcgtg gcaacagaag   3360
attgagtttt cattcgcaca gaattgaaga agttcccaaa acagggctgg gctcctcggc   3420
aggtttagtc acagttttaa ctacagcttt ggcctccttt tttgtatcgg acctggaaaa   3480
taatgtagac aaatatagag aagttattca taatttagca caagttgctc attgtcaagc   3540
tcagggtaaa attggaagcg ggtttgatgt agcggcggca gcatatggat ctatcagata   3600
tagaagattc ccacccgcat taatctctaa tttgccagat attggaagtg ctacttacgg   3660
cagtaaactg gcgcatttgg ttgatgaaga agactggaat attacgatta aaagtaacca   3720
tttaccttcg ggattaactt tatggatggg cgatattaag aatggttcag aaacagtaaa   3780
```

-continued

```
actggtccag aaggtaaaaa attggtatga ttcgcatatg ccagaaagct tgaaaatata   3840
tacagaactc gatcatgcaa attctagatt tatggatgga ctatctaaac tagatcgctt   3900
acacgagact catgacgatt acagcgatca gatatttgag tctcttgaga ggaatgactg   3960
tacctgtcaa aagtatcctg aaatcacaga agttagagat gcagttgcca caattagacg   4020
ttcctttaga aaaataacta aagaatctgg tgccgatatc gaacctcccg tacaaactag   4080
cttattggat gattgccaga ccttaaaagg agttcttact tgcttaatac ctggtgctgg   4140
tggttatgac gccattgcag tgattactaa gcaagatgtt gatcttaggg ctcaaaccgc   4200
taatgacaaa agattttcta aggttcaatg gctggatgta actcaggctg actggggtgt   4260
taggaaagaa aaagatccgg aaacttatct tgataaataa aaggagaggg tgaccgttta   4320
cacagcatcc gttaccgcac ccgtcaacat cgcaaccctt aagtattggg ggaaaaggga   4380
cacgaagttg aatctgccca ccaattcgtc catatcagtg actttatcgc aagatgacct   4440
cagaacgttg acctctgcgg ctactgcacc tgagtttgaa cgcgacactt tgtggttaaa   4500
tggagaacca cacagcatcg acaatgaaag aactcaaaat tgtctgcgcg acctacgcca   4560
attaagaaag gaaatggaat cgaaggacgc ctcattgccc acattatctc aatggaaact   4620
ccacattgtc tccgaaaata actttcctac agcagctggt ttagcttcct ccgctgctgg   4680
ctttgctgca ttggtctctg caattgctaa gttataccaa ttaccacagt caacttcaga   4740
aatatctaga atagcaagaa aggggtctgg ttcagcttgt agatcgttgt ttggcggata   4800
cgtggcctgg gaaatgggaa aagctgaaga tggtcatgat tccatggcag tacaaatcgc   4860
agacagctct gactggcctc agatgaaagc ttgtgtccta gttgtcagcg atattaaaaa   4920
ggatgtgagt tccactcagg gtatgcaatt gaccgtggca acctccgaac tatttaaaga   4980
aagaattgaa catgtcgtac caaagagatt tgaagtcatg cgtaaagcca ttgttgaaaa   5040
agatttcgcc acctttgcaa aggaaacaat gatggattcc aactctttcc atgccacatg   5100
tttggactct ttccctccaa tattctacat gaatgacact tccaagcgta tcatcagttg   5160
gtgccacacc attaatcagt tttacggaga aacaatcgtt gcatacacgt ttgatgcagg   5220
tccaaatgct gtgttgtact acttagctga aaatgagtcg aaactctttg catttatcta   5280
taaattgttt ggctctgttc ctggatggga caagaaattt actactgagc agcttgaggc   5340
tttcaaccat caatttgaat catctaactt tactgcacgt gaattggatc ttgagttgca   5400
aaaggatgtt gccagagtga ttttaactca agtcggttca ggcccacaag aaacaaacga   5460
atctttgatt gacgcaaaga ctggtctacc aaaggaataa aaggagaggg tgactgccga   5520
caacaatagt atgccccatg gtgcagtatc tagttacgcc aaattagtgc aaaaccaaac   5580
acctgaagac attttggaag agtttcctga aattattcca ttacaacaaa gacctaatac   5640
ccgatctagt gagacgtcaa atgacgaaag cggagaaaca tgtttttctg gtcatgatga   5700
ggagcaaatt aagttaatga atgaaaattg tattgttttg gattgggacg ataatgctat   5760
tggtgccggt accaagaaag tttgtcattt aatggaaaat attgaaaagg gtttactaca   5820
tcgtgcattc tccgtcttta ttttcaatga acaaggtgaa ttacttttac aacaaagagc   5880
cactgaaaaa ataactttcc ctgatctttg gactaacaca tgctgctctc atccactatg   5940
tattgatgac gaattaggtt tgaagggtaa gctagacgat aagattaagg gcgctattac   6000
tgcggcggtg agaaaactag atcatgaatt aggtattcca gaagatgaaa ctaagacaag   6060
gggtaagttt cactttttaa acagaatcca ttacatggca ccaagcaatg aaccatgggg   6120
tgaacatgaa attgattaca tcctatttta taagatcaac gctaaagaaa acttgactgt   6180
```

-continued

```
caacccaaac gtcaatgaag ttagagactt caaatgggtt tcaccaaatg atttgaaaac   6240
tatgtttgct gacccaagtt acaagtttac gccttggttt aagattattt gcgagaatta   6300
cttattcaac tggtgggagc aattagatga cctttctgaa gtggaaaatg acaggcaaat   6360
tcatagaatg ctataaaaaa aaccggcctt ggccccgccg gtttttttatt atttttcttc   6420
ctccgcatgt tcaatccgct ccataatcga cggatggctc cctctgaaaa ttttaacgag   6480
aaacggcggg ttgacccggc tcagtcccgt aacggccaag tcctgaaacg tctcaatcgc   6540
cgcttcccgg tttccggtca gctcaatgcc gtaacggtcg gcggcgtttt cctgataccg   6600
ggagacggca ttcgtaattt gaatacatac gaacaaatta ataaagtgaa aaaaatactt   6660
cggaaacatt taaaaaataa ccttattggt acttacatgt ttggatcagg agttgagagt   6720
ggactaaaac caaatagtga tcttgacttt ttagtcgtcg tatctgaacc attgacagat   6780
caaagtaaag aaatacttat acaaaaaatt agacctattt caaaaaaaat aggagataaa   6840
agcaacttac gatatattga attaacaatt attattcagc aagaaatggt accgtggaat   6900
catcctccca aacaagaatt tatttatgga gaatggttac aagagcttta tgaacaagga   6960
tacattcctc agaaggaatt aaattcagat ttaaccataa tgctttacca agcaaaacga   7020
aaaaataaaa gaatatacgg aaattatgac ttagaggaat tactacctga tattccattt   7080
tctgatgtga gaagagccat tatggattcg tcagaggaat taatagataa ttatcaggat   7140
gatgaaacca actctatatt aactttatgc cgtatgattt taactatgga cacgggtaaa   7200
atcataccaa aagatattgc gggaaatgca gtggctgaat cttctccatt agaacatagg   7260
gagagaattt tgttagcagt tcgtagttat cttggagaga atattgaatg gactaatgaa   7320
aatgtaaatt taactataaa ctatttaaat aacagattaa aaaaattata atgtaacctt   7380
tgctttcaaa tgagtagaaa taatgcacat ccatgtttgt atcgtgcaaa taaagtgttt   7440
catccgtagg aaaaaatgac tttagtatct gttccgcttt ttctgatgaa atgtgctccc   7500
cgacaaaatt gaatgaatca tggacatttg ctggctttga tacagcgaaa gcagccgttc   7560
ctatgttata tatcggattt aacagcagga caaaaaacac catgacagcc atcgtcaccc   7620
acttattcac acgcacataa acctttcctg acttttggaa cagatgatag ctcatcaaaa   7680
atcccgccat tgccaaataa atcgtatatg gcattactgc accataatct tttgagattt   7740
gattgggata tggcgcaagc agcaagacaa gcagtccgat aatcagcgta taaaataagc   7800
ctagtaagat cttatccgtt ctccaataca gcttgaaaaa cactacattc aacgcaatgg   7860
gaagagtgat gatgaaaaac agaaacacga atgcaatcgg ctccatccca tccgggtatt   7920
ccttccaata cgaaaagaaa ctaaaaatca tttgtacgat cggcaaactg acaacagcaa   7980
ggtcgaacgt ataaaactta ccctttccgc catgatcacg cggcatcagc atatagtgaa   8040
aagccgtcag cagcacatat ccgtataaca aaaaatgcag cagcggcagc agttcttttc   8100
cgtcctctct taagtaagcg ctggtgaagt ttgttgattg cacctggtga ataagttcaa   8160
cagacactcc cgccagcagc acaatccgca atataacacc cgccaagaac attgtgcgct   8220
gccggtttat tttgggatga tgcaccaaaa gatataagcc cgccagaaca acaattgacc   8280
attgaatcag cagggtgctt tgtctgctta atataaaata acgttcgaaa tgcaatacat   8340
aatgactgaa taactccaac acgaacaaca aaagtgcgca ttttataaaa gctaatgatt   8400
cagtccacat aattgataga cgaattctgc tacaggtcac gtggctatgt gaaggatcgc   8460
gcgtccagtt aagagcaaaa acattgacaa aaaaatttat ttatgctaaa atttactatt   8520
```

```
aatatatttg tatgtataat aagattctcc tggccagggg aatcttattt tttgtggagg   8580
atcatttcat gaggaaaaat gagtccagct taacgtctct aatttcagct tttgcccgtg   8640
catatcacag ccgatatgac acacctctta tttttgatga ttttatcgca aaagatctca   8700
ttaacgaaaa agagtttatc gacatcagta aaaatatgat tcaagaaata tcgtttttca   8760
acaaagagat cgccgaacgt cttcaaaatg atcctgaaaa aatattaaaa tgggttgcac   8820
aaatccagct gtctccaacg cccctagcac gtgcttctta ttgtgaaaaa gtcttgcaca   8880
acgaattaat cctgggggca aaacagtatg tcattcttgg agcgggactg gatactttct   8940
gctttcggca tccagaatta gaaaacagct tacaggtttt cgaggttgat catccggcca   9000
cacagcaatt gaaaaaaaat aagctgaagg atgcaaatct gacaattccg ggtcatcttc   9060
attttgttcc tatggatttc accaaaacgt tttcgtatga tcctctctta gatgaaggat   9120
ttaaaaacac aaaaacattc ttcagccttc tcggagtgtc ttattatgta acacgggaag   9180
aaaatgcaag cttgatcagc aatttatttt ctcatgtccc gcctggaagc tctattgttt   9240
ttgattatgc ggacgaaaca ctttttacag caaaagggac gtcgaatcga gttgaacata   9300
tggtgaagat ggctgccgca agcggggaac cgatgaaatc atgtttcact tatcaagaga   9360
ttgaacatct g                                                        9371
```

```
<210> SEQ ID NO 48
<211> LENGTH: 4339
<212> TYPE: DNA
<213> ORGANISM: Artificial Sequence
<220> FEATURE:
<223> OTHER INFORMATION: Synthetic Construct

<400> SEQUENCE: 48
```

```
tagaaaaact catcgagcat caaatgaaac tgcaatttat tcatatcagg attatcaata     60
ccatattttt gaaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa aataaggtta tcaagtgaga aatcaccatg agtgacgact    240
gaatccggtg agaatggcaa aagtttatgc atttctttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttta gtcgctgaac atgtgctctg   1200
```

```
tttctaccga gaacgtttcc ttcactgaga cggaaaccga ggcacgtcgt agcgcgaact   1260
acgagccgaa tagctgggac tacgatttcc tgctgtcttc cgatactgac gaatctattg   1320
aggtgtacaa agacaaagca aagaaactgg aggctgaagt gcgccgcgaa attaacaacg   1380
agaaagctga attcctgact ctgctggagc tgatcgataa cgtacagcgc ctgggtctgg   1440
gttaccgctt cgaatctgat atccgtcgcg cactggatcg tttcgtaagc agcggcggtt   1500
tcgatggcgt gaccaaaacg agcctgcacg ctaccgcgct gtccttccgt ctgctgcgtc   1560
agcacggctt cgaagtttct caggaagcat tctccggttt caaagatcaa aacggtaact   1620
tcctggaaaa cctgaaagaa gacactaagg cgatcctgag cctgtatgag gcaagctttc   1680
tggccctgga gggtgagaac atcctggatg aggcgcgcgt attcgccatc tcccatctga   1740
aagagctgtc tgaagagaaa atcggtaagg aactggcaga gcaggttaat cacgcactgg   1800
aactgccgct gcatcgtcgt acccagcgtc tggaggcggt ttggtccatc gaagcgtacc   1860
gcaaaaagga ggatgctaac caggttctgc tggaactggc catcctggac tacaacatga   1920
tccagtccgt ttaccagcgt gatctgcgtg aaacctcccg ttggtggcgc cgtgtgggcc   1980
tggcgaccaa actgcacttc gctaaggacc gcctgattga gtctttttac tgggcagtcg   2040
gcgttgcgtt cgaacctcag tattctgact gccgtaacag cgttgcgaaa atgttcagct   2100
tcgttactat tatcgacgac atctacgacg tttacggtac tctggacgag ctggaactgt   2160
ttaccgacgc tgtcgaacgt tgggatgtta acgccatcaa cgatctgcct gactacatga   2220
aactgtgctt cctggcactg tataacacga tcaacgaaat tgcatacgac aacctgaaag   2280
acaaaggtga aaacatcctg ccgtacctga ctaaagcgtg ggcggatctg tgtaacgctt   2340
ttctgcaaga agcgaaatgg ctgtataaca aatccactcc gacctttgac gattatttcg   2400
gcaatgcctg gaaatccagc tctggcccgc tgcaactgat cttcgcttat tttgcggttg   2460
tccaaaacat caaaaaggag gaaattgaaa acctgcaaaa ataccacgat atcattagcc   2520
gtccttctca tatctttcgc ctgtgcaacg acctggcaag cgcgtccgca gagatcgcac   2580
gtggcgaaac cgctaactct gtttcctgct acatgcgcac caagggcatt tccgaagagc   2640
tggcaaccga gagcgtaatg aatctgatcg acgaaacctg taagaaaatg aacaaagaaa   2700
aactgggtgg ctccctgttc gctaaaccgt tcgtagagac tgctattaac ctggcacgtc   2760
agagccactg cacctaccac aatggtgacg cacatactag cccggatgaa ctgactcgta   2820
aacgtgtact gtctgttatc accgaaccga ttctgccgtt cgaacgttaa ctgcagcgtc   2880
aatcgaaagg gcgacacaaa atttattcta aatgcataat aaatactgat aacatcttat   2940
agtttgtatt atattttgta ttatcgttga catgtataat tttgatatca aaaactgatt   3000
ttccctttat tattttcgag atttattttc ttaattctct ttaacaaact agaaatattg   3060
tatatacaaa aaatcataaa taatagatga atagtttaat tataggtgtt catcaatcga   3120
aaaagcaacg tatcttattt aaagtgcgtt gctttttct catttataag gttaaataat   3180
tctcatatat caagcaaagt gacaggcgcc cttaaatatt ctgacaaatg ctctttccct   3240
aaactccccc cataaaaaaa cccgccgaag cgggtttta cgttatttgc ggattaacga   3300
ttactcgtta tcagaaccgc ccagggggcc cgagcttaag actggccgtc gttttacaac   3360
acagaaagag tttgtagaaa cgcaaaaagg ccatccgtca ggggccttct gcttagtttg   3420
atgcctggca gttccctact ctcgccttcc gcttcctcgc tcactgactc gctgcgctcg   3480
gtcgttcggc tgcggcgagc ggtatcagct cactcaaagg cggtaatacg gttatccaca   3540
```

-continued gaatcagggg ataacgcagg aaagaacatg tgagcaaaag gccagcaaaa ggccaggaac 3600
cgtaaaaagg ccgcgttgct ggcgtttttc cataggctcc gcccccctga cgagcatcac 3660
aaaaatcgac gctcaagtca gaggtggcga aacccgacag gactataaag ataccaggcg 3720
tttccccctg gaagctccct cgtgcgctct cctgttccga ccctgccgct taccggatac 3780
ctgtccgcct ttctcccttc gggaagcgtg gcgctttctc atagctcacg ctgtaggtat 3840
ctcagttcgg tgtaggtcgt tcgctccaag ctgggctgtg tgcacgaacc ccccgttcag 3900
cccgaccgct gcgccttatc cggtaactat cgtcttgagt ccaacccggt aagacacgac 3960
ttatcgccac tggcagcagc cactggtaac aggattagca gagcgaggta tgtaggcggt 4020
gctacagagt tcttgaagtg gtgggctaac tacggctaca ctagaagaac agtatttggt 4080
atctgcgctc tgctgaagcc agttaccttc ggaaaaagag ttggtagctc ttgatccggc 4140
aaacaaacca ccgctggtag cggtggtttt tttgtttgca agcagcagat tacgcgcaga 4200
aaaaaaggat ctcaagaaga tcctttgatc ttttctacgg ggtctgacgc tcagtggaac 4260
gacgcgcgcg taactcacgt taagggattt tggtcatgag cttgcgccgt cccgtcaagt 4320
cagcgtaatg ctctgcttt 4339

<210> SEQ ID NO 49
<211> LENGTH: 6065
<212> TYPE: DNA
<213> ORGANISM: Artificial Sequence
<220> FEATURE:
<223> OTHER INFORMATION: Synthetic Construct

<400> SEQUENCE: 49
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgtgctc 420
tgtttctacc gagaacgttt ccttcactga gacggaaacc gaggcacgtc gtagcgcgaa 480
ctacgagccg aatagctggg actacgattt cctgctgtct tccgatactg acgaatctat 540
tgaggtgtac aaagacaaag caaagaaact ggaggctgaa gtgcgccgcg aaattaacaa 600
cgagaaagct gaattcctga ctctgctgga gctgatcgat aacgtacagc gcctgggtct 660
gggttaccgc ttcgaatctg atatccgtcg cgcactggat cgtttcgtaa gcagcggcgg 720
tttcgatggc gtgaccaaaa cgagcctgca cgctaccgcg ctgtccttcc gtctgctgcg 780
tcagcacggc ttcgaagttt ctcaggaagc attctccggt ttcaaagatc aaaacggtaa 840
cttcctggaa aacctgaaag aagacactaa ggcgatcctg agcctgtatg aggcaagctt 900
tctggccctg gagggtgaga acatcctgga tgaggcgcgc gtattcgcca tctcccatct 960
gaaagagctg tctgaagaga aaatcggtaa ggaactggca gagcaggtta atcacgcact 1020
ggaactgccg ctgcatcgtc gtacccagcg tctggaggcg gtttggtcca tcgaagcgta 1080
ccgcaaaaag gaggatgcta accaggttct gctggaactg gccatcctgg actacaacat 1140
gatccagtcc gtttaccagc gtgatctgcg tgaaacctcc cgttggtggc gccgtgtggg 1200
cctggcgacc aaactgcact tcgctaagga ccgcctgatt gagtcttttt actgggcagt 1260

```
cggcgttgcg ttcgaacctc agtattctga ctgccgtaac agcgttgcga aaatgttcag   1320
cttcgttact attatcgacg acatctacga cgtttacggt actctggacg agctggaact   1380
gtttaccgac gctgtcgaac gttgggatgt taacgccatc aacgatctgc ctgactacat   1440
gaaactgtgc ttcctggcac tgtataacac gatcaacgaa attgcatacg acaacctgaa   1500
agacaaaggt gaaaacatcc tgccgtacct gactaaagcg tgggcggatc tgtgtaacgc   1560
ttttctgcaa gaagcgaaat ggctgtataa caaatccact ccgacctttg acgattattt   1620
cggcaatgcc tggaaatcca gctctggccc gctgcaactg atcttcgctt attttgcggt   1680
tgtccaaaac atcaaaaagg aggaaattga aaacctgcaa aaataccacg atatcattag   1740
ccgtccttct catatctttc gcctgtgcaa cgacctggca agcgcgtccg cagagatcgc   1800
acgtggcgaa accgctaact ctgtttcctg ctacatgcgc accaagggca tttccgaaga   1860
gctggcaacc gagagcgtaa tgaatctgat cgacgaaacc tgtaagaaaa tgaacaaaga   1920
aaaactgggt ggctccctgt tcgctaaacc gttcgtagag actgctatta acctggcacg   1980
tcagagccac tgcacctacc acaatggtga cgcacatact agcccggatg aactgactcg   2040
taaacgtgta ctgtctgtta tcaccgaacc gattctgccg ttcgaacgtt aactgcagct   2100
ggtaccatat gggaattcga agctttctag aacaaaaact catctcagaa gaggatctga   2160
atagcgccgt cgaccatcat catcatcatc attgagttta aacggtctcc agcttggctg   2220
ttttggcgga tgagagaaga ttttcagcct gatacagatt aaatcagaac gcagaagcgg   2280
tctgataaaa cagaatttgc ctggcggcag tagcgcggtg gtcccacctg accccatgcc   2340
gaactcagaa gtgaaacgcc gtagcgccga tggtagtgtg gggtctcccc atgcgagagt   2400
agggaactgc caggcatcaa ataaaacgaa aggctcagtc gaaagactgg gcctttcgtt   2460
ttatctgttg tttgtcggtg aacgctctcc tgagtaggac aaatccgccg ggagcggatt   2520
tgaacgttgc gaagcaacgg cccggagggt ggcgggcagg acgcccgcca taaactgcca   2580
ggcatcaaat taagcagaag gccatcctga cggatggcct ttttgcgttt ctacaaactc   2640
tttttgttta tttttctaaa tacattcaaa tatgtatccg ctcatgagac aataaccctg   2700
ataaatgctt caataatatt gaaaaaggaa gagtatgagt attcaacatt tccgtgtcgc   2760
ccttattccc ttttttgcgg cattttgcct tcctgttttt gctcacccag aaacgctggt   2820
gaaagtaaaa gatgctgaag atcagttggg tgcacgagtg ggttacatcg aactggatct   2880
caacagcggt aagatccttg agagttttcg ccccgaagaa cgttttccaa tgatgagcac   2940
ttttaaagtt ctgctatgtg gcgcggtatt atcccgtgtt gacgccgggc aagagcaact   3000
cggtcgccgc atacactatt ctcagaatga cttggttgag tactcaccag tcacagaaaa   3060
gcatcttacg gatggcatga cagtaagaga attatgcagt gctgccataa ccatgagtga   3120
taacactgcg gccaacttac ttctgacaac gatcggagga ccgaaggagc taaccgcttt   3180
tttgcacaac atgggggatc atgtaactcg ccttgatcgt tgggaaccgg agctgaatga   3240
agccatacca aacgacgagc gtgacaccac gatgcctgta gcaatggcaa caacgttgcg   3300
caaactatta actggcgaac tacttactct agcttcccgg caacaattaa tagactggat   3360
ggaggcggat aaagttgcag gaccacttct gcgctcggcc cttccggctg gctggtttat   3420
tgctgataaa tctggagccg gtgagcgtgg gtctcgcggt atcattgcag cactggggcc   3480
agatggtaag ccctcccgta tcgtagttat ctacacgacg gggagtcagg caactatgga   3540
tgaacgaaat agacagatcg ctgagatagg tgcctcactg attaagcatt ggtaactgtc   3600
```

-continued

```
agaccaagtt tactcatata tactttagat tgatttaaaa cttcattttt aatttaaaag   3660
gatctaggtg aagatccttt ttgataatct catgaccaaa atcccttaac gtgagttttc   3720
gttccactga gcgtcagacc ccgtagaaaa gatcaaagga tcttcttgag atcctttttt   3780
tctgcgcgta atctgctgct tgcaaacaaa aaaaccaccg ctaccagcgg tggtttgttt   3840
gccggatcaa gagctaccaa ctctttttcc gaaggtaact ggcttcagca gagcgcagat   3900
accaaatact gtccttctag tgtagccgta gttaggccac cacttcaaga actctgtagc   3960
accgcctaca tacctcgctc tgctaatcct gttaccagtg gctgctgcca gtggcgataa   4020
gtcgtgtctt accgggttgg actcaagacg atagttaccg gataaggcgc agcggtcggg   4080
ctgaacgggg ggttcgtgca cacagcccag cttggagcga acgacctaca ccgaactgag   4140
atacctacag cgtgagctat gagaaagcgc cacgcttccc gaagggagaa aggcggacag   4200
gtatccggta agcggcaggg tcggaacagg agagcgcacg agggagcttc cagggggaaa   4260
cgcctggtat ctttatagtc ctgtcgggtt tcgccacctc tgacttgagc gtcgattttt   4320
gtgatgctcg tcaggggggc ggagcctatg gaaaaacgcc agcaacgcgg cctttttacg   4380
gttcctggcc ttttgctggc cttttgctca catgttcttt cctgcgttat cccctgattc   4440
tgtggataac cgtattaccg cctttgagtg agctgatacc gctcgccgca gccgaacgac   4500
cgagcgcagc gagtcagtga gcgaggaagc ggaagagcgc ctgatgcggt attttctcct   4560
tacgcatctg tgcggtattt cacaccgcat atggtgcact ctcagtacaa tctgctctga   4620
tgccgcatag ttaagccagt atacactccg ctatcgctac gtgactgggt catggctgcg   4680
ccccgacacc cgccaacacc cgctgacgcg ccctgacggg cttgtctgct cccggcatcc   4740
gcttacagac aagctgtgac cgtctccggg agctgcatgt gtcagaggtt ttcaccgtca   4800
tcaccgaaac gcgcgaggca gcagatcaat tcgcgcgcga aggcgaagcg gcatgcattt   4860
acgttgacac catcgaatgg tgcaaaacct ttcgcggtat ggcatgatag cgcccggaag   4920
agagtcaatt cagggtggtg aatgtgaaac cagtaacgtt atacgatgtc gcagagtatg   4980
ccggtgtctc ttatcagacc gtttcccgcg tggtgaacca ggccagccac gtttctgcga   5040
aaacgcggga aaaagtggaa gcggcgatgg cggagctgaa ttacattccc aaccgcgtgg   5100
cacaacaact ggcgggcaaa cagtcgttgc tgattggcgt tgccacctcc agtctggccc   5160
tgcacgcgcc gtcgcaaatt gtcgcggcga ttaaatctcg cgccgatcaa ctgggtgcca   5220
gcgtggtggt gtcgatggta gaacgaagcg gcgtcgaagc ctgtaaagcg gcggtgcaca   5280
atcttctcgc gcaacgcgtc agtgggctga tcattaacta tccgctggat gaccaggatg   5340
ccattgctgt ggaagctgcc tgcactaatg ttccggcgtt atttcttgat gtctctgacc   5400
agacacccat caacagtatt attttctccc atgaagacgg tacgcgactg ggcgtggagc   5460
atctggtcgc attgggtcac cagcaaatcg cgctgttagc gggcccatta agttctgtct   5520
cggcgcgtct gcgtctggct ggctggcata aatatctcac tcgcaatcaa attcagccga   5580
tagcggaacg ggaaggcgac tggagtgcca tgtccggttt tcaacaaacc atgcaaatgc   5640
tgaatgaggg catcgttccc actgcgatgc tggttgccaa cgatcagatg gcgctgggcg   5700
caatgcgcgc cattaccgag tccgggctgc gcgttggtgc ggatatctcg gtagtgggat   5760
acgacgatac cgaagacagc tcatgttata tcccgccgtc aaccaccatc aaacaggatt   5820
ttcgcctgct ggggcaaacc agcgtggacc gcttgctgca actctctcag ggccaggcgg   5880
tgaagggcaa tcagctgttg cccgtctcac tggtgaaaag aaaaaccacc ctggcgccca   5940
atacgcaaac cgcctctccc cgcgcgttgg ccgattcatt aatgcagctg gcacgacagg   6000
```

tttcccgact ggaaagcggg cagtgagcgc aacgcaatta atgtgagtta gcgcgaattg 6060
atctg 6065

<210> SEQ ID NO 50
<211> LENGTH: 6912
<212> TYPE: DNA
<213> ORGANISM: Artificial Sequence
<220> FEATURE:
<223> OTHER INFORMATION: Synthetic Construct

<400> SEQUENCE: 50
ttgtctgctc ccggcatccg cttacagaca agctgtgacc gtctccggga gctgcatgtg 60
tcagaggttt tcaccgtcat caccgaaacg cgcgaggcag cagatcaatt cgcgcgcgaa 120
ggcgaagcgg catgcattta cgttgacacc atcgaatggt gcaaaacctt tcgcggtatg 180
gcatgatagc gcccggaaga gagtcaattc agggtggtga atgtgaaacc agtaacgtta 240
tacgatgtcg cagagtatgc cggtgtctct tatcagaccg tttcccgcgt ggtgaaccag 300
gccagccacg tttctgcgaa aacgcgggaa aaagtggaag cggcgatggc ggagctgaat 360
tacattccca accgcgtggc acaacaactg gcgggcaaac agtcgttgct gattggcgtt 420
gccacctcca gtctggccct gcacgcgccg tcgcaaattg tcgcggcgat taaatctcgc 480
gccgatcaac tgggtgccag cgtggtggtg tcgatggtag aacgaagcgg cgtcgaagcc 540
tgtaaagcgg cggtgcacaa tcttctcgcg caacgcgtca gtgggctgat cattaactat 600
ccgctggatg accaggatgc cattgctgtg gaagctgcct gcactaatgt tccggcgtta 660
tttcttgatg tctctgacca gacacccatc aacagtatta ttttctccca tgaagacggt 720
acgcgactgg gcgtggagca tctggtcgca ttgggtcacc agcaaatcgc gctgttagcg 780
ggcccattaa gttctgtctc ggcgcgtctg cgtctggctg gctggcataa atatctcact 840
cgcaatcaaa ttcagccgat agcggaacgg gaaggcgact ggagtgccat gtccggtttt 900
caacaaacca tgcaaatgct gaatgagggc atcgttccca ctgcgatgct ggttgccaac 960
gatcagatgg cgctgggcgc aatgcgcgcc attaccgagt ccgggctgcg cgttggtgcg 1020
gatatctcgg tagtgggata cgacgatacc gaagacagct catgttatat cccgccgtca 1080
accaccatca aacaggattt tcgcctgctg gggcaaacca gcgtggaccg cttgctgcaa 1140
ctctctcagg gccaggcggt gaagggcaat cagctgttgc ccgtctcact ggtgaaaaga 1200
aaaaccaccc tggcgcccaa tacgcaaacc gcctctcccc gcgcgttggc cgattcatta 1260
atgcagctgg cacgacaggt ttcccgactg gaaagcgggc agtgagcgca acgcaattaa 1320
tgtgagttag cgcgaattga tctggtttga cagcttatca tcgactgcac ggtgcaccaa 1380
tgcttctggc gtcaggcagc catcggaagc tgtggtatgg ctgtgcaggt cgtaaatcac 1440
tgcataattc gtgtcgctca aggcgcactc ccgttctgga taatgttttt tgcgccgaca 1500
tcataacggt tctggcaaat attctgaaat gagctgttga caattaatca tccggctcgt 1560
ataatgtgtg gaattgtgag cggataacaa tttcacacag gaaacagcgc cgctgagaaa 1620
aagcgaagcg gcactgctct ttaacaattt atcagacaat ctgtgtgggc actcgaccgg 1680
aattatcgat taactttatt attaaaaatt aaagaggtat atattaatgt atcgattaaa 1740
taaggaggaa taaaccatgt gtgcgacctc ttctcaattt actcagatta ccgagcataa 1800
ttcccgtcgt tccgcaaact atcagccaaa cctgtggaat ttcgaattcc tgcaatccct 1860
ggagaacgac ctgaaagtgg aaaagctgga ggagaaagcg accaaactgg aggaagaagt 1920

-continued

```
tcgctgcatg atcaaccgtg tagacaccca gccgctgtcc ctgctggagc tgatcgacga   1980
tgtgcagcgc ctgggtctga cctacaaatt tgaaaaagac atcattaaag ccctggaaaa   2040
catcgtactg ctggacgaaa acaaaaagaa caaatctgac ctgcacgcaa ccgctctgtc   2100
tttccgtctg ctgcgtcagc acggtttcga ggtttctcag gatgtttttg agcgtttcaa   2160
ggataaagaa ggtggtttca gcggtgaact gaaaggtgac gtccaaggcc tgctgagcct   2220
gtatgaagcg tcttacctgg gtttcgaggg tgagaacctg ctggaggagg cgcgtacctt   2280
ttccatcacc cacctgaaga acaacctgaa agaaggcatt aataccaagg ttgcagaaca   2340
agtgagccac gccctggaac tgccatatca ccagcgtctg caccgtctgg aggcacgttg   2400
gttcctggat aaatacgaac cgaaagaacc gcatcaccag ctgctgctgg agctggcgaa   2460
gctggatttt aacatggtac agaccctgca ccagaaagag ctgcaagatc tgtcccgctg   2520
gtggaccgag atgggcctgg ctagcaaact ggattttgta cgcgaccgcc tgatggaagt   2580
ttatttctgg gcactgggta tggcgccaga cccgcagttt ggtgaatgtc gcaaagctgt   2640
tactaaaatg tttggtctgg tgacgatcat cgatgacgtg tatgacgttt atggcactct   2700
ggacgaactg caactgttca ccgatgctgt agagcgctgg gacgttaacg ctattaacac   2760
cctgccggac tatatgaaac tgtgtttcct ggcactgtac aacaccgtta acgacacgtc   2820
ctattctatt ctgaaagaga aaggtcataa caacctgtcc tatctgacga aaagctggcg   2880
tgaactgtgc aaagcctttc tgcaagaggc gaaatggtcc aacaacaaaa ttatcccggc   2940
tttctccaag tacctggaaa acgccagcgt ttcctcctcc ggtgtagcgc tgctggcgcc   3000
gtcttacttt tccgtatgcc agcagcagga agacatctcc gaccacgcgc tgcgttccct   3060
gaccgacttc catggtctgg tgcgttctag ctgcgttatc ttccgcctgt gcaacgatct   3120
ggccacctct gcggcggagc tggaacgtgg cgagactacc aattctatca ttagctacat   3180
gcacgaaaac gatggtacca gcgaggaaca ggcccgcgaa gaactgcgta aactgatcga   3240
cgccgaatgg aaaaagatga atcgtgaacg cgttagcgac tccaccctgc tgcctaaagc   3300
gttcatggaa atcgcagtta acatggcacg tgtttcccac tgcacctacc agtatggcga   3360
tggtctgggt cgcccagact acgcgactga aaaccgcatc aaactgctgc tgattgaccc   3420
tttcccgatt aaccagctga tgtatgtcta actgcatcgc ccttaggagg taaaaaaaaa   3480
tgactgccga caacaatagt atgccccatg gtgcagtatc tagttacgcc aaattagtgc   3540
aaaaccaaac acctgaagac attttggaag agtttcctga aattattcca ttacaacaaa   3600
gacctaatac ccgatctagt gagacgtcaa atgacgaaag cggagaaaca tgtttttctg   3660
gtcatgatga ggagcaaatt aagttaatga atgaaaattg tattgttttg gattgggacg   3720
ataatgctat tggtgccggt accaagaaag tttgtcattt aatggaaaat attgaaaagg   3780
gtttactaca tcgtgcattc tccgtcttta ttttcaatga acaaggtgaa ttacttttac   3840
aacaaagagc cactgaaaaa ataactttcc ctgatctttg gactaacaca tgctgctctc   3900
atccactatg tattgatgac gaattaggtt tgaagggtaa gctagacgat aagattaagg   3960
gcgctattac tgcggcggtg agaaaactag atcatgaatt aggtattcca gaagatgaaa   4020
ctaagacaag ggtaagttt cactttttaa acagaatcca ttacatggca ccaagcaatg   4080
aaccatgggg tgaacatgaa attgattaca tcctatttta taagatcaac gctaaagaaa   4140
acttgactgt caacccaaac gtcaatgaag ttagagactt caaatgggtt tcaccaaatg   4200
atttgaaaac tatgtttgct gacccaagtt acaagtttac gccttggttt aagattattt   4260
gcgagaatta cttattcaac tggtgggagc aattagatga cctttctgaa gtggaaaatg   4320
```

```
acaggcaaat tcatagaatg ctataacaac gcgtcctgca gctggtacca tatgggaatt   4380
cgaagctttc tagaacaaaa actcatctca gaagaggatc tgaatagcgc cgtcgaccat   4440
catcatcatc atcattgagt ttaaacggtc tccagcttgg ctgttttggc ggatgagaga   4500
agattttcag cctgatacag attaaatcag aacgcagaag cggtctgata aaacagaatt   4560
tgcctggcgg cagtagcgcg gtggtcccac ctgaccccat gccgaactca gaagtgaaac   4620
gccgtagcgc cgatggtagt gtggggtctc cccatgcgag agtagggaac tgccaggcat   4680
caaataaaac gaaaggctca gtcgaaagac tgggcctttc gttttatctg ttgtttgtcg   4740
gtgaacgctc tcctgagtag gacaaatccg ccgggagcgg atttgaacgt tgcgaagcaa   4800
cggcccggag ggtggcgggc aggacgcccg ccataaactg ccaggcatca aattaagcag   4860
aaggccatcc tgacggatgg cctttttgcg tttctacaaa ctctttttgt ttatttttct   4920
aaatacattc aaatatgtat ccgcttaacc ggaattgcca gctggggcgc cctctggtaa   4980
ggttgggaag ccctgcaaag taaactggat ggctttctcg ccgccaagga tctgatggcg   5040
caggggatca agctctgatc aagagacagg atgaggatcg tttcgcatga ttgaacaaga   5100
tggattgcac gcaggttctc cggccgcttg ggtggagagg ctattcggct atgactgggc   5160
acaacagaca atcggctgct ctgatgccgc cgtgttccgg ctgtcagcgc aggggcgccc   5220
ggttcttttt gtcaagaccg acctgtccgg tgccctgaat gaactgcaag acgaggcagc   5280
gcggctatcg tggctggcca cgacgggcgt tccttgcgca gctgtgctcg acgttgtcac   5340
tgaagcggga agggactggc tgctattggg cgaagtgccg gggcaggatc tcctgtcatc   5400
tcaccttgct cctgccgaga aagtatccat catggctgat gcaatgcggc ggctgcatac   5460
gcttgatccg gctacctgcc cattcgacca ccaagcgaaa catcgcatcg agcgagcacg   5520
tactcggatg gaagccggtc ttgtcgatca ggatgatctg gacgaagagc atcaggggct   5580
cgcgccagcc gaactgttcg ccaggctcaa ggcgagcatg cccgacggcg aggatctcgt   5640
cgtgacccat ggcgatgcct gcttgccgaa tatcatggtg gaaaatggcc gcttttctgg   5700
attcatcgac tgtggccggc tgggtgtggc ggaccgctat caggacatag cgttggctac   5760
ccgtgatatt gctgaagagc ttggcggcga atgggctgac cgcttcctcg tgctttacgg   5820
tatcgccgct cccgattcgc agcgcatcgc cttctatcgc cttcttgacg agttcttctg   5880
acatgaccaa aatcccttaa cgtgagtttt cgttccactg agcgtcagac cccgtagaaa   5940
agatcaaagg atcttcttga gatccttttt ttctgcgcgt aatctgctgc ttgcaaacaa   6000
aaaaaccacc gctaccagcg gtggtttgtt tgccggatca agagctacca actctttttc   6060
cgaaggtaac tggcttcagc agagcgcaga taccaaatac tgtccttcta gtgtagccgt   6120
agttaggcca ccacttcaag aactctgtag caccgcctac atacctcgct ctgctaatcc   6180
tgttaccagt ggctgctgcc agtggcgata agtcgtgtct taccgggttg gactcaagac   6240
gatagttacc ggataaggcg cagcggtcgg gctgaacggg gggttcgtgc acacagccca   6300
gcttggagcg aacgacctac accgaactga gatacctaca gcgtgagcta tgagaaagcg   6360
ccacgcttcc cgaagggaga aaggcggaca ggtatccggt aagcggcagg gtcggaacag   6420
gagagcgcac gagggagctt ccagggggaa acgcctggta tctttatagt cctgtcgggt   6480
ttcgccacct ctgacttgag cgtcgatttt tgtgatgctc gtcagggggg cggagcctat   6540
ggaaaaacgc cagcaacgcg gcctttttac ggttcctggc cttttgctgg ccttttgctc   6600
acatgttctt tcctgcgtta tcccctgatt ctgtggataa ccgtattacc gcctttgagt   6660
```

```
gagctgatac cgctcgccgc agccgaacga ccgagcgcag cgagtcagtg agcgaggaag   6720

cggaagagcg cctgatgcgg tattttctcc ttacgcatct gtgcggtatt tcacaccgca   6780

tatggtgcac tctcagtaca atctgctctg atgccgcata gttaagccag tatacactcc   6840

gctatcgcta cgtgactggg tcatggctgc gccccgacac ccgccaacac ccgctgacgc   6900

gccctgacgg gc                                                       6912


<210> SEQ ID NO 51
<211> LENGTH: 7902
<212> TYPE: DNA
<213> ORGANISM: Artificial Sequence
<220> FEATURE:
<223> OTHER INFORMATION: Synthetic Construct

<400> SEQUENCE: 51

ttgtctgctc ccggcatccg cttacagaca agctgtgacc gtctccggga gctgcatgtg     60

tcagaggttt tcaccgtcat caccgaaacg cgcgaggcag cagatcaatt cgcgcgcgaa    120

ggcgaagcgg catgcattta cgttgacacc atcgaatggt gcaaaacctt tcgcggtatg    180

gcatgatagc gcccggaaga gagtcaattc agggtggtga atgtgaaacc agtaacgtta    240

tacgatgtcg cagagtatgc cggtgtctct tatcagaccg tttcccgcgt ggtgaaccag    300

gccagccacg tttctgcgaa aacgcgggaa aaagtggaag cggcgatggc ggagctgaat    360

tacattccca accgcgtggc acaacaactg gcgggcaaac agtcgttgct gattggcgtt    420

gccacctcca gtctggccct gcacgcgccg tcgcaaattg tcgcggcgat taaatctcgc    480

gccgatcaac tgggtgccag cgtggtggtg tcgatggtag aacgaagcgg cgtcgaagcc    540

tgtaaagcgg cggtgcacaa tcttctcgcg caacgcgtca gtgggctgat cattaactat    600

ccgctggatg accaggatgc cattgctgtg gaagctgcct gcactaatgt tccggcgtta    660

tttcttgatg tctctgacca gacacccatc aacagtatta ttttctccca tgaagacggt    720

acgcgactgg gcgtggagca tctggtcgca ttgggtcacc agcaaatcgc gctgttagcg    780

ggcccattaa gttctgtctc ggcgcgtctg cgtctggctg gctggcataa atatctcact    840

cgcaatcaaa ttcagccgat agcggaacgg gaaggcgact ggagtgccat gtccggtttt    900

caacaaacca tgcaaatgct gaatgagggc atcgttccca ctgcgatgct ggttgccaac    960

gatcagatgg cgctgggcgc aatgcgcgcc attaccgagt ccgggctgcg cgttggtgcg   1020

gatatctcgg tagtgggata cgacgatacc gaagacagct catgttatat cccgccgtca   1080

accaccatca aacaggattt tcgcctgctg gggcaaacca gcgtggaccg cttgctgcaa   1140

ctctctcagg gccaggcggt gaagggcaat cagctgttgc ccgtctcact ggtgaaaaga   1200

aaaaccaccc tggcgcccaa tacgcaaacc gcctctcccc gcgcgttggc cgattcatta   1260

atgcagctgg cacgacaggt ttcccgactg gaaagcgggc agtgagcgca acgcaattaa   1320

tgtgagttag cgcgaattga tctggtttga cagcttatca tcgactgcac ggtgcaccaa   1380

tgcttctggc gtcaggcagc catcggaagc tgtggtatgg ctgtgcaggt cgtaaatcac   1440

tgcataattc gtgtcgctca aggcgcactc ccgttctgga taatgttttt tgcgccgaca   1500

tcataacggt tctggcaaat attctgaaat gagctgttga caattaatca tccggctcgt   1560

ataatgtgtg gaattgtgag cggataacaa tttcacacag gaaacagcgc cgctgagaaa   1620

aagcgaagcg gcactgctct ttaacaattt atcagacaat ctgtgtgggc actcgaccgg   1680

aattatcgat taactttatt attaaaaatt aaagaggtat atattaatgt atcgattaaa   1740

taaggaggaa taaaccatgt gtgcgacctc ttctcaattt actcagatta ccgagcataa   1800
```

ttcccgtcgt tccgcaaact atcagccaaa cctgtggaat ttcgaattcc tgcaatccct 1860
ggagaacgac ctgaaagtgg aaaagctgga ggagaaagcg accaaactgg aggaagaagt 1920
tcgctgcatg atcaaccgtg tagacaccca gccgctgtcc ctgctggagc tgatcgacga 1980
tgtgcagcgc ctgggtctga cctacaaatt tgaaaaagac atcattaaag ccctggaaaa 2040
catcgtactg ctggacgaaa acaaaaagaa caaatctgac ctgcacgcaa ccgctctgtc 2100
tttccgtctg ctgcgtcagc acggtttcga ggtttctcag gatgtttttg agcgtttcaa 2160
ggataaagaa ggtggtttca gcggtgaact gaaaggtgac gtccaaggcc tgctgagcct 2220
gtatgaagcg tcttacctgg gtttcgaggg tgagaacctg ctggaggagg cgcgtacctt 2280
ttccatcacc cacctgaaga acaacctgaa agaaggcatt aataccaagg ttgcagaaca 2340
agtgagccac gccctggaac tgccatatca ccagcgtctg caccgtctgg aggcacgttg 2400
gttcctggat aaatacgaac cgaaagaacc gcatcaccag ctgctgctgg agctggcgaa 2460
gctggatttt aacatggtac agaccctgca ccagaaagag ctgcaagatc tgtcccgctg 2520
gtggaccgag atgggcctgg ctagcaaact ggattttgta cgcgaccgcc tgatggaagt 2580
ttatttctgg gcactgggta tggcgccaga cccgcagttt ggtgaatgtc gcaaagctgt 2640
tactaaaatg tttggtctgg tgacgatcat cgatgacgtg tatgacgttt atggcactct 2700
ggacgaactg caactgttca ccgatgctgt agagcgctgg gacgttaacg ctattaacac 2760
cctgccggac tatatgaaac tgtgtttcct ggcactgtac aacaccgtta acgacacgtc 2820
ctattctatt ctgaaagaga aaggtcataa caacctgtcc tatctgacga aaagctggcg 2880
tgaactgtgc aaagcctttc tgcaagaggc gaaatggtcc aacaacaaaa ttatcccggc 2940
tttctccaag tacctggaaa acgccagcgt ttcctcctcc ggtgtagcgc tgctggcgcc 3000
gtcttacttt tccgtatgcc agcagcagga agacatctcc gaccacgcgc tgcgttccct 3060
gaccgacttc catggtctgg tgcgttctag ctgcgttatc ttccgcctgt gcaacgatct 3120
ggccacctct gcggcggagc tggaacgtgg cgagactacc aattctatca ttagctacat 3180
gcacgaaaac gatggtacca gcgaggaaca ggcccgcgaa gaactgcgta aactgatcga 3240
cgccgaatgg aaaaagatga atcgtgaacg cgttagcgac tccaccctgc tgcctaaagc 3300
gttcatggaa atcgcagtta acatggcacg tgtttcccac tgcacctacc agtatggcga 3360
tggtctgggt cgcccagact acgcgactga aaaccgcatc aaactgctgc tgattgaccc 3420
tttcccgatt aaccagctga tgtatgtcta actgcattcg cccttaggag gtaaaaaaac 3480
atgagttttg atattgccaa atacccgacc ctggcactgg tcgactccac ccaggagtta 3540
cgactgttgc cgaaagagag tttaccgaaa ctctgcgacg aactgcgccg ctatttactc 3600
gacagcgtga gccgttccag cggcacttc gcctccgggc tgggcacggt cgaactgacc 3660
gtggcgctgc actatgtcta caacaccccg tttgaccaat tgatttggga tgtggggcat 3720
caggcttatc cgcataaaat tttgaccgga cgccgcgaca aaatcggcac catccgtcag 3780
aaaggcggtc tgcacccgtt cccgtggcgc ggcgaaagcg aatatgacgt attaagcgtc 3840
gggcattcat caacctccat cagtgccgga attggtattg cggttgctgc cgaaaaagaa 3900
ggcaaaaatc gccgcaccgt ctgtgtcatt ggcgatggcg cgattaccgc aggcatggcg 3960
tttgaagcga tgaatcacgc gggcgatatc cgtcctgata tgctggtgat tctcaacgac 4020
aatgaaatgt cgatttccga aaatgtcggc gcgctcaaca accatctggc acagctgctt 4080
tccggtaagc tttactcttc actgcgcgaa ggcgggaaaa aagttttctc tggcgtgccg 4140

-continued

```
ccaattaaag agctgctcaa acgcaccgaa gaacatatta aaggcatggt agtgcctggc   4200
acgttgtttg aagagctggg ctttaactac atcggcccgg tggacggtca cgatgtgctg   4260
gggcttatca ccacgctaaa gaacatgcgc gacctgaaag gcccgcagtt cctgcatatc   4320
atgaccaaaa aaggtcgtgg ttatgaaccg gcagaaaaag acccgatcac tttccacgcc   4380
gtgcctaaat ttgatccctc cagcggttgt ttgccgaaaa gtagcggcgg tttgccgagc   4440
tattcaaaaa tctttggcga ctggttgtgc gaaacggcag cgaaagacaa caagctgatg   4500
gcgattactc cggcgatgcg tgaaggttcc ggcatggtcg agttttcacg taaattcccg   4560
gatcgctact tcgacgtggc aattgccgag caacacgcgg tgacctttgc tgcgggtctg   4620
gcgattggtg ggtacaaacc cattgtcgcg atttactcca ctttcctgca acgcgcctat   4680
gatcaggtgc tgcatgacgt ggcgattcaa aagcttccgg tcctgttcgc catcgaccgc   4740
gcgggcattg ttggtgctga cggtcaaacc catcagggtg cttttgatct ctcttacctg   4800
cgctgcatac cggaaatggt cattatgacc ccgagcgatg aaaacgaatg tcgccagatg   4860
ctctataccg gctatcacta taacgatggc ccgtcagcgg tgcgctaccc gcgtggcaac   4920
gcggtcggcg tggaactgac gccgctggaa aaactaccaa ttggcaaagg cattgtgaag   4980
cgtcgtggcg agaaactggc gatccttaac tttggtacgc tgatgccaga agcggcgaaa   5040
gtcgccgaat cgctgaacgc cacgctggtc gatatgcgtt ttgtgaaacc gcttgatgaa   5100
gcgttaattc tggaaatggc cgccagccat gaagcgctgg tcaccgtaga agaaaacgcc   5160
attatgggcg gcgcaggcag cggcgtgaac gaagtgctga tggcccatcg taaaccagta   5220
cccgtgctga acattggcct gccggacttc tttattccgc aaggaactca ggaagaaatg   5280
cgcgccgaac tcggcctcga tgccgctggt atggaagcca aaatcaaggc ctggctggca   5340
taactgcagc tggtaccata tgggaattcg aagctttcta gaacaaaaac tcatctcaga   5400
agaggatctg aatagcgccg tcgaccatca tcatcatcat cattgagttt aaacggtctc   5460
cagcttggct gttttggcgg atgagagaag attttcagcc tgatacagat taaatcagaa   5520
cgcagaagcg gtctgataaa acagaatttg cctggcggca gtagcgcggt ggtcccacct   5580
gaccccatgc cgaactcaga agtgaaacgc cgtagcgccg atggtagtgt ggggtctccc   5640
catgcgagag tagggaactg ccaggcatca aataaaacga aaggctcagt cgaaagactg   5700
ggcctttcgt tttatctgtt gtttgtcggt gaacgctctc ctgagtagga caaatccgcc   5760
gggagcggat ttgaacgttg cgaagcaacg gcccggaggg tggcgggcag gacgcccgcc   5820
ataaactgcc aggcatcaaa ttaagcagaa ggccatcctg acggatggcc tttttgcgtt   5880
tctacaaact ctttttgttt atttttctaa atacattcaa atatgtatcc gcttaaccgg   5940
aattgccagc tggggcgccc tctggtaagg ttgggaagcc ctgcaaagta aactggatgg   6000
ctttctcgcc gccaaggatc tgatggcgca ggggatcaag ctctgatcaa gagacaggat   6060
gaggatcgtt tcgcatgatt gaacaagatg gattgcacgc aggttctccg gccgcttggg   6120
tggagaggct attcggctat gactgggcac aacagacaat cggctgctct gatgccgccg   6180
tgttccggct gtcagcgcag gggcgcccgg ttctttttgt caagaccgac ctgtccggtg   6240
ccctgaatga actgcaagac gaggcagcgc ggctatcgtg gctggccacg acgggcgttc   6300
cttgcgcagc tgtgctcgac gttgtcactg aagcgggaag ggactggctg ctattgggcg   6360
aagtgccggg gcaggatctc ctgtcatctc accttgctcc tgccgagaaa gtatccatca   6420
tggctgatgc aatgcggcgg ctgcatacgc ttgatccggc tacctgccca ttcgaccacc   6480
aagcgaaaca tcgcatcgag cgagcacgta ctcggatgga agccggtctt gtcgatcagg   6540
```

```
atgatctgga cgaagagcat caggggctcg cgccagccga actgttcgcc aggctcaagg   6600
cgagcatgcc cgacggcgag gatctcgtcg tgacccatgg cgatgcctgc ttgccgaata   6660
tcatggtgga aaatggccgc ttttctggat tcatcgactg tggccggctg ggtgtggcgg   6720
accgctatca ggacatagcg ttggctaccc gtgatattgc tgaagagctt ggcggcgaat   6780
gggctgaccg cttcctcgtg ctttacggta tcgccgctcc cgattcgcag cgcatcgcct   6840
tctatcgcct tcttgacgag ttcttctgac gcatgaccaa aatcccttaa cgtgagtttt   6900
cgttccactg agcgtcagac cccgtagaaa agatcaaagg atcttcttga gatccttttt   6960
ttctgcgcgt aatctgctgc ttgcaaacaa aaaaaccacc gctaccagcg gtggtttgtt   7020
tgccggatca agagctacca actctttttc cgaaggtaac tggcttcagc agagcgcaga   7080
taccaaatac tgtccttcta gtgtagccgt agttaggcca ccacttcaag aactctgtag   7140
caccgcctac atacctcgct ctgctaatcc tgttaccagt ggctgctgcc agtggcgata   7200
agtcgtgtct taccgggttg gactcaagac gatagttacc ggataaggcg cagcggtcgg   7260
gctgaacggg gggttcgtgc acacagccca gcttggagcg aacgacctac accgaactga   7320
gatacctaca gcgtgagcta tgagaaagcg ccacgcttcc cgaagggaga aaggcggaca   7380
ggtatccggt aagcggcagg gtcggaacag gagagcgcac gagggagctt ccagggggaa   7440
acgcctggta tctttatagt cctgtcgggt ttcgccacct ctgacttgag cgtcgatttt   7500
tgtgatgctc gtcagggggg cggagcctat ggaaaaacgc cagcaacgcg gcctttttac   7560
ggttcctggc cttttgctgg ccttttgctc acatgttctt tcctgcgtta tcccctgatt   7620
ctgtggataa ccgtattacc gcctttgagt gagctgatac cgctcgccgc agccgaacga   7680
ccgagcgcag cgagtcagtg agcgaggaag cggaagagcg cctgatgcgg tattttctcc   7740
ttacgcatct gtgcggtatt tcacaccgca tatggtgcac tctcagtaca atctgctctg   7800
atgccgcata gttaagccag tatacactcc gctatcgcta cgtgactggg tcatggctgc   7860
gccccgacac ccgccaacac ccgctgacgc gccctgacgg gc                      7902
```

<210> SEQ ID NO 52
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 52

```
ctggcgtaat agcgaagagg cccgcaccga tcgcccttcc caacagttgc gcagcctgaa     60
tggcgaatgg cgcctgatgc ggtattttct ccttacgcat ctgtgcggta tttcacaccg    120
catatggtgc actctcagta caatctgctc tgatgccgca tagttaagcc agccccgaca    180
cccgccaaca cccgctgacg agcttagtaa agccctcgct agattttaat gcggatgttg    240
cgattacttc gccaactatt gcgataacaa gaaaaagcca gcctttcatg atatatctcc    300
caatttgtgt agggcttatt atgcacgctt aaaaataata aaagcagact tgacctgata    360
gtttggctgt gagcaattat gtgcttagtg catctaacgc ttgagttaag ccgcgccgcg    420
aagcggcgtc ggcttgaacg aattgttaga cattatttgc cgactacctt ggtgatctcg    480
cctttcacgt agtggacaaa ttcttccaac tgatctgcgc gcgaggccaa gcgatcttct    540
tcttgtccaa gataagcctg tctagcttca agtatgacgg gctgatactg ggccggcagg    600
cgctccattg cccagtcggc agcgacatcc ttcggcgcga ttttgccggt tactgcgctg    660
```

-continued

```
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
tacttacttt gcatgtcact caaaaatttt gcctcaaaac tggtgagctg aatttttgca   2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
aaccactcat aaatcctcat agagtatttg ttttcaaaag acttaacatg ttccagatta   3060
```

-continued

```
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat tttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
gtaccttttc catcacccac ctgaagaaca acctgaaaga aggcattaat accaaggttg   5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
aagctgttac taaaatgttt ggtctggtga cgatcatcga tgacgtgtat gacgtttatg   5400
```

```
gcactctgga cgaactgcaa ctgttcaccg atgctgtaga gcgctgggac gttaacgcta   5460

ttaacaccct gccggactat atgaaactgt gtttcctggc actgtacaac accgttaacg   5520

acacgtccta ttctattctg aaagagaaag gtcataacaa cctgtcctat ctgacgaaaa   5580

gctggcgtga actgtgcaaa gcctttctgc aagaggcgaa atggtccaac aacaaaatta   5640

tcccggcttt ctccaagtac ctggaaaacg ccagcgtttc ctcctccggt gtagcgctgc   5700

tggcgccgtc ttacttttcc gtatgccagc agcaggaaga catctccgac cacgcgctgc   5760

gttccctgac cgacttccat ggtctggtgc gttctagctg cgttatcttc cgcctgtgca   5820

acgatctggc cacctctgcg gcggagctgg aacgtggcga gactaccaat tctatcatta   5880

gctacatgca cgaaaacgat ggtaccagcg aggaacaggc ccgcgaagaa ctgcgtaaac   5940

tgatcgacgc cgaatggaaa aagatgaatc gtgaacgcgt tagcgactcc accctgctgc   6000

ctaaagcgtt catggaaatc gcagttaaca tggcacgtgt ttcccactgc acctaccagt   6060

atggcgatgg tctgggtcgc ccagactacg cgactgaaaa ccgcatcaaa ctgctgctga   6120

ttgacccttt cccgattaac cagctgatgt atgtctaact gcagctggta ccatatggga   6180

attcgaagct ttctagaaca aaaactcatc tcagaagagg atctgaatag cgccgtcgac   6240

catcatcatc atcatcattg agtttaaacg gtctccagct tggctgtttt ggcggatgag   6300

agaagatttt cagcctgata cagattaaat cagaacgcag aagcggtctg ataaaacaga   6360

atttgcctgg cggcagtagc gcggtggtcc cacctgaccc catgccgaac tcagaagtga   6420

aacgccgtag cgccgatggt agtgtggggt ctccccatgc gagagtaggg aactgccagg   6480

catcaaataa aacgaaaggc tcagtcgaaa gactgggcct ttcgttttat ctgttgtttg   6540

tcggtgaacg ctctcctgag taggacaaat ccgccgggag cggatttgaa cgttgcgaag   6600

caacggcccg gagggtggcg ggcaggacgc ccgccataaa ctgccaggca tcaaattaag   6660

cagaaggcca tcctgacgga tggccttttt gcgtttctac aaactctttt tgtttatttt   6720

tctaaataca ttcaaatatg tatccgctca tgagacaata accctgataa atgcttcaat   6780

aat                                                                 6783
```

<210> SEQ ID NO 53
<211> LENGTH: 6783
<212> TYPE: DNA
<213> ORGANISM: Artificial Sequence
<220> FEATURE:
<223> OTHER INFORMATION: Synthetic Construct

<400> SEQUENCE: 53

```
cccgtcttac tgtcgggaat tcgcgttggc cgattcatta atgcagatta ttgaagcatt     60

tatcagggtt attgtctcat gagcggatac atatttgaat gtatttagaa aaataaacaa    120

aaagagtttg tagaaacgca aaaaggccat ccgtcaggat ggccttctgc ttaatttgat    180

gcctggcagt ttatggcggg cgtcctgccc gccaccctcc gggccgttgc ttcgcaacgt    240

tcaaatccgc tcccggcgga tttgtcctac tcaggagagc gttcaccgac aaacaacaga    300

taaaacgaaa ggcccagtct ttcgactgag cctttcgttt tatttgatgc ctggcagttc    360

cctactctcg catggggaga ccccacacta ccatcggcgc tacggcgttt cacttctgag    420

ttcggcatgg ggtcaggtgg gaccaccgcg ctactgccgc caggcaaatt ctgttttatc    480

agaccgcttc tgcgttctga tttaatctgt atcaggctga aaatcttctc tcatccgcca    540

aaacagccaa gctggagacc gtttaaactc aatgatgatg atgatgatgg tcgacggcgc    600

tattcagatc ctcttctgag atgagttttt gttctagaaa gcttcgaatt cccatatggt    660
```

accagctgca gttagacata catcagctgg ttaatcggga aagggtcaat cagcagcagt 720
ttgatgcggt tttcagtcgc gtagtctggg cgacccagac catcgccata ctggtaggtg 780
cagtgggaaa cacgtgccat gttaactgcg atttccatga acgctttagg cagcagggtg 840
gagtcgctaa cgcgttcacg attcatcttt ttccattcgg cgtcgatcag tttacgcagt 900
tcttcgcggg cctgttcctc gctggtacca tcgttttcgt gcatgtagct aatgatagaa 960
ttggtagtct cgccacgttc cagctccgcc gcagaggtgg ccagatcgtt gcacaggcgg 1020
aagataacgc agctagaacg caccagacca tggaagtcgg tcagggaacg cagcgcgtgg 1080
tcggagatgt cttcctgctg ctggcatacg gaaaagtaag acggcgccag cagcgctaca 1140
ccggaggagg aaacgctggc gttttccagg tacttggaga aagccgggat aattttgttg 1200
ttggaccatt tcgcctcttg cagaaaggct ttgcacagtt cacgccagct tttcgtcaga 1260
taggacaggt tgttatgacc tttctctttc agaatagaat aggacgtgtc gttaacggtg 1320
ttgtacagtg ccaggaaaca cagtttcata tagtccggca gggtgttaat agcgttaacg 1380
tcccagcgct ctacagcatc ggtgaacagt tgcagttcgt ccagagtgcc ataaacgtca 1440
tacacgtcat cgatgatcgt caccagacca aacattttag taacagcttt gcgacattca 1500
ccaaactgcg ggtctggcgc catacccagt gcccagaaat aaacttccat caggcggtcg 1560
cgtacaaaat ccagtttgct agccaggccc atctcggtcc accagcggga cagatcttgc 1620
agctctttct ggtgcagggt ctgtaccatg ttaaaatcca gcttcgccag ctccagcagc 1680
agctggtgat gcggttcttt cggttcgtat ttatccagga accaacgtgc ctccagacgg 1740
tgcagacgct ggtgatatgg cagttccagg gcgtggctca cttgttctgc aaccttggta 1800
ttaatgcctt ctttcaggtt gttcttcagg tgggtgatgg aaaaggtacg cgcctcctcc 1860
agcaggttct caccctcgaa acccaggtaa gacgcttcat acaggctcag caggccttgg 1920
acgtcacctt tcagttcacc gctgaaacca ccttctttat ccttgaaacg ctcaaaaaca 1980
tcctgagaaa cctcgaaacc gtgctgacgc agcagacgga aagacagagc ggttgcgtgc 2040
aggtcagatt tgttcttttt gttttcgtcc agcagtacga tgttttccag ggctttaatg 2100
atgtcttttt caaatttgta ggtcagaccc aggcgctgca catcgtcgat cagctccagc 2160
agggacagcg gctgggtgtc tacacggttg atcatgcagc gaacttcttc ctccagtttg 2220
gtcgctttct cctccagctt ttccactttc aggtcgttct ccagggattg caggaattcg 2280
aaattccaca ggtttggctg atagtttgcg gaacgacggg aattatgctc ggtaatctga 2340
gtaaattgag aagaggtcgc acacatggtt tattcctcct tatttaatcg atacattaat 2400
atatacctct ttaattttta ataataaagt taatcgataa ttccggtcga gtgcccacac 2460
agattgtctg ataaattgtt aaagagcagt gccgcttcgc tttttctcag cggcgctgtt 2520
tcctgtgtga aattgttatc cgctcacaat tccacacatt atacgagccg gatgattaat 2580
tgtcaacagc tcatttcaga atctggcgta atagcgaaga ggcccgcacc gatcgccctt 2640
cccaacagtt gcgcagcctg aatggcgaat ggcgcctgat gcggtatttt ctccttacgc 2700
atctgtgcgg tatttcacac cgcatatggt gcactctcag tacaatctgc tctgatgccg 2760
catagttaag ccagccccga cacccgccaa cacccgctga cgagcttagt aaagccctcg 2820
ctagatttta atgcggatgt tgcgattact tcgccaacta ttgcgataac aagaaaaagc 2880
cagcctttca tgatatatct cccaatttgt gtagggctta ttatgcacgc ttaaaaataa 2940
taaaagcaga cttgacctga tagtttggct gtgagcaatt atgtgcttag tgcatctaac 3000

-continued

```
gcttgagtta agccgcgccg cgaagcggcg tcggcttgaa cgaattgtta gacattattt   3060
gccgactacc ttggtgatct cgcctttcac gtagtggaca aattcttcca actgatctgc   3120
gcgcgaggcc aagcgatctt cttcttgtcc aagataagcc tgtctagctt caagtatgac   3180
gggctgatac tgggccggca ggcgctccat tgcccagtcg gcagcgacat ccttcggcgc   3240
gattttgccg gttactgcgc tgtaccaaat gcgggacaac gtaagcacta catttcgctc   3300
atcgccagcc cagtcgggcg gcgagttcca tagcgttaag gtttcattta gcgcctcaaa   3360
tagatcctgt tcaggaaccg gatcaaagag ttcctccgcc gctggaccta ccaaggcaac   3420
gctatgttct cttgcttttg tcagcaagat agccagatca atgtcgatcg tggctggctc   3480
gaagatacct gcaagaatgt cattgcgctg ccattctcca aattgcagtt cgcgcttagc   3540
tggataacgc cacggaatga tgtcgtcgtg cacaacaatg gtgacttcta cagcgcggag   3600
aatctcgctc tctccagggg aagccgaagt ttccaaaagg tcgttgatca aagctcgccg   3660
cgttgtttca tcaagcctta cggtcaccgt aaccagcaaa tcaatatcac tgtgtggctt   3720
caggccgcca tccactgcgg agccgtacaa atgtacggcc agcaacgtcg gttcgagatg   3780
gcgctcgatg acgccaacta cctctgatag ttgagtcgat acttcggcga tcaccgcttc   3840
cctcatgatg tttaactttg ttttagggcg actgccctgc tgcgtaacat cgttgctgct   3900
ccataacatc aaacatcgac ccacggcgta acgcgcttgc tgcttggatg cccgaggcat   3960
agactgtacc ccaaaaaaac agtcataaca agccatgaaa accgccactg cgccgttacc   4020
accgctgcgt tcggtcaagg ttctggacca gttgcgtgag cgcatacgct acttgcatta   4080
cagcttacga accgaacagg cttatgtcca ctgggttcgt gccttcatcc gtttccacgg   4140
tgtgcgtcac ccggcaacct tgggcagcag cgaagtcgag gcatttctgt cctggctggc   4200
gaacgagcgc aaggtttcgg tctccacgca tcgtcaggca ttggcggcct tgctgttctt   4260
ctacggcaag gtgctgtgca cggatctgcc ctggcttcag gagatcggaa gacctcggcc   4320
gtcgcggcgc ttgccggtgg tgctgacccc ggatgaagtg gttcgcatcc tcggttttct   4380
ggaaggcgag catcgtttgt tcgcccagct tctgtatgga acgggcatgc ggatcagtga   4440
gggtttgcaa ctgcgggtca aggatctgga tttcgatcac ggcacgatca tcgtgcggga   4500
gggcaagggc tccaaggatc gggccttgat gttacccgag agcttggcac ccagcctgcg   4560
cgagcagggg aattaattcc cacgggtttt gctgcccgca aacgggctgt tctggtgttg   4620
ctagtttgtt atcagaatcg cagatccggc ttcagccggt ttgccggctg aaagcgctat   4680
ttcttccaga attgccatga ttttttcccc acgggaggcg tcactggctc ccgtgttgtc   4740
ggcagctttg attcgataag cagcatcgcc tgtttcaggc tgtctatgtg tgactgttga   4800
gctgtaacaa gttgtctcag gtgttcaatt tcatgttcta gttgctttgt tttactggtt   4860
tcacctgttc tattaggtgt tacatgctgt tcatctgtta cattgtcgat ctgttcatgg   4920
tgaacagctt tgaatgcacc aaaaactcgt aaaagctctg atgtatctat cttttttaca   4980
ccgttttcat ctgtgcatat ggacagtttt ccctttgata tgtaacggtg aacagttgtt   5040
ctacttttgt ttgttagtct tgatgcttca ctgatagata caagagccat aagaacctca   5100
gatccttccg tatttagcca gtatgttctc tagtgtggtt cgttgttttt gcgtgagcca   5160
tgagaacgaa ccattgagat catacttact ttgcatgtca ctcaaaaatt ttgcctcaaa   5220
actggtgagc tgaatttttg cagttaaagc atcgtgtagt gtttttctta gtccgttatg   5280
taggtaggaa tctgatgtaa tggttgttgg tattttgtca ccattcattt ttatctggtt   5340
gttctcaagt tcggttacga gatccatttg tctatctagt tcaacttgga aaatcaacgt   5400
```

```
atcagtcggg cggcctcgct tatcaaccac caatttcata ttgctgtaag tgtttaaatc   5460

tttacttatt ggtttcaaaa cccattggtt aagcctttta aactcatggt agttattttc   5520

aagcattaac atgaacttaa attcatcaag gctaatctct atatttgcct tgtgagtttt   5580

cttttgtgtt agttctttta ataaccactc ataaatcctc atagagtatt tgttttcaaa   5640

agacttaaca tgttccagat tatattttat gaattttttt aactggaaaa gataaggcaa   5700

tatctcttca ctaaaaacta attctaattt ttcgcttgag aacttggcat agtttgtcca   5760

ctggaaaatc tcaaagcctt taaccaaagg attcctgatt tccacagttc tcgtcatcag   5820

ctctctggtt gctttagcta atacaccata agcattttcc ctactgatgt tcatcatctg   5880

agcgtattgg ttataagtga acgataccgt ccgttctttc cttgtagggt tttcaatcgt   5940

ggggttgagt agtgccacac agcataaaat tagcttggtt tcatgctccg ttaagtcata   6000

gcgactaatc gctagttcat ttgctttgaa aacaactaat tcagacatac atctcaattg   6060

gtctaggtga ttttaatcac tataccaatt gagatgggct agtcaatgat aattactagt   6120

ccttttcctt tgagttgtgg gtatctgtaa attctgctag acctttgctg gaaaacttgt   6180

aaattctgct agaccctctg taaattccgc tagacctttg tgtgtttttt ttgtttatat   6240

tcaagtggtt ataatttata gaataaagaa agaataaaaa aagataaaaa gaatagatcc   6300

cagccctgtg tataactcac tactttagtc agttccgcag tattacaaaa ggatgtcgca   6360

aacgctgttt gctcctctac aaaacagacc ttaaaaccct aaaggcttaa gtagcaccct   6420

cgcaagctcg ggcaaatcgc tgaatattcc ttttgtctcc gaccatcagg cacctgagtc   6480

gctgtctttt tcgtgacatt cagttcgctg cgctcacggc tctggcagtg aatgggggta   6540

aatggcacta caggcgcctt ttatggattc atgcaaggaa actacccata atacaagaaa   6600

agcccgtcac gggcttctca gggcgtttta tggcgggtct gctatgtggt gctatctgac   6660

tttttgctgt tcagcagttc ctgccctctg attttccagt ctgaccactt cggattatcc   6720

cgtgacaggt cattcagact ggctaatgca cccagtaagg cagcggtatc atcaacaggc   6780

tta                                                                 6783
```

<210> SEQ ID NO 54
<211> LENGTH: 7687
<212> TYPE: DNA
<213> ORGANISM: Artificial Sequence
<220> FEATURE:
<223> OTHER INFORMATION: Synthetic Construct

<400> SEQUENCE: 54

```
ctggcgtaat agcgaagagg cccgcaccga tcgcccttcc caacagttgc gcagcctgaa     60

tggcgaatgg cgcctgatgc ggtattttct ccttacgcat ctgtgcggta tttcacaccg    120

catatggtgc actctcagta caatctgctc tgatgccgca tagttaagcc agccccgaca    180

cccgccaaca cccgctgacg agcttagtaa agccctcgct agattttaat gcggatgttg    240

cgattacttc gccaactatt gcgataacaa gaaaaagcca gcctttcatg atatatctcc    300

caatttgtgt agggcttatt atgcacgctt aaaaataata aaagcagact tgacctgata    360

gtttggctgt gagcaattat gtgcttagtg catctaacgc ttgagttaag ccgcgccgcg    420

aagcggcgtc ggcttgaacg aattgttaga cattatttgc cgactacctt ggtgatctcg    480

cctttcacgt agtggacaaa ttcttccaac tgatctgcgc gcgaggccaa gcgatcttct    540

tcttgtccaa gataagcctg tctagcttca agtatgacgg gctgatactg ggccggcagg    600
```

-continued

```
cgctccattg cccagtcggc agcgacatcc ttcggcgcga ttttgccggt tactgcgctg    660
taccaaatgc gggacaacgt aagcactaca tttcgctcat cgccagccca gtcgggcggc    720
gagttccata gcgttaaggt ttcatttagc gcctcaaata gatcctgttc aggaaccgga    780
tcaaagagtt cctccgccgc tggacctacc aaggcaacgc tatgttctct tgcttttgtc    840
agcaagatag ccagatcaat gtcgatcgtg gctggctcga agatacctgc aagaatgtca    900
ttgcgctgcc attctccaaa ttgcagttcg cgcttagctg gataacgcca cggaatgatg    960
tcgtcgtgca caacaatggt gacttctaca gcgcggagaa tctcgctctc tccaggggaa   1020
gccgaagttt ccaaaaggtc gttgatcaaa gctcgccgcg ttgtttcatc aagccttacg   1080
gtcaccgtaa ccagcaaatc aatatcactg tgtggcttca ggccgccatc cactgcggag   1140
ccgtacaaat gtacggccag caacgtcggt tcgagatggc gctcgatgac gccaactacc   1200
tctgatagtt gagtcgatac ttcggcgatc accgcttccc tcatgatgtt taactttgtt   1260
ttagggcgac tgccctgctg cgtaacatcg ttgctgctcc ataacatcaa acatcgaccc   1320
acggcgtaac gcgcttgctg cttggatgcc cgaggcatag actgtacccc aaaaaaacag   1380
tcataacaag ccatgaaaac cgccactgcg ccgttaccac cgctgcgttc ggtcaaggtt   1440
ctggaccagt tgcgtgagcg catacgctac ttgcattaca gcttacgaac cgaacaggct   1500
tatgtccact gggttcgtgc cttcatccgt ttccacggtg tgcgtcaccc ggcaaccttg   1560
ggcagcagcg aagtcgaggc atttctgtcc tggctggcga acgagcgcaa ggtttcggtc   1620
tccacgcatc gtcaggcatt ggcggccttg ctgttcttct acggcaaggt gctgtgcacg   1680
gatctgccct ggcttcagga gatcggaaga cctcggccgt cgcggcgctt gccggtggtg   1740
ctgaccccgg atgaagtggt tcgcatcctc ggttttctgg aaggcgagca tcgtttgttc   1800
gcccagcttc tgtatggaac gggcatgcgg atcagtgagg gtttgcaact gcgggtcaag   1860
gatctggatt tcgatcacgg cacgatcatc gtgcgggagg gcaagggctc caaggatcgg   1920
gccttgatgt tacccgagag cttggcaccc agcctgcgcg agcaggggaa ttaattccca   1980
cgggttttgc tgcccgcaaa cgggctgttc tggtgttgct agtttgttat cagaatcgca   2040
gatccggctt cagccggttt gccggctgaa agcgctattt cttccagaat tgccatgatt   2100
ttttccccac gggaggcgtc actggctccc gtgttgtcgg cagctttgat tcgataagca   2160
gcatcgcctg tttcaggctg tctatgtgtg actgttgagc tgtaacaagt tgtctcaggt   2220
gttcaatttc atgttctagt tgctttgttt tactggtttc acctgttcta ttaggtgtta   2280
catgctgttc atctgttaca ttgtcgatct gttcatggtg aacagctttg aatgcaccaa   2340
aaactcgtaa aagctctgat gtatctatct tttttacacc gttttcatct gtgcatatgg   2400
acagttttcc ctttgatatg taacggtgaa cagttgttct acttttgttt gttagtcttg   2460
atgcttcact gatagataca agagccataa gaacctcaga tccttccgta tttagccagt   2520
atgttctcta gtgtggttcg ttgtttttgc gtgagccatg agaacgaacc attgagatca   2580
tacttacttt gcatgtcact caaaaatttt gcctcaaaac tggtgagctg aatttttgca   2640
gttaaagcat cgtgtagtgt ttttcttagt ccgttatgta ggtaggaatc tgatgtaatg   2700
gttgttggta ttttgtcacc attcattttt atctggttgt tctcaagttc ggttacgaga   2760
tccatttgtc tatctagttc aacttggaaa atcaacgtat cagtcgggcg gcctcgctta   2820
tcaaccacca atttcatatt gctgtaagtg tttaaatctt tacttattgg tttcaaaacc   2880
cattggttaa gccttttaaa ctcatggtag ttattttcaa gcattaacat gaacttaaat   2940
tcatcaaggc taatctctat atttgccttg tgagttttct tttgtgttag ttcttttaat   3000
```

-continued

```
aaccactcat aaatcctcat agagtatttg ttttcaaaag acttaacatg ttccagatta   3060
tattttatga attttttaa ctggaaaaga taaggcaata tctcttcact aaaaactaat   3120
tctaattttt cgcttgagaa cttggcatag tttgtccact ggaaaatctc aaagccttta   3180
accaaaggat tcctgatttc cacagttctc gtcatcagct ctctggttgc tttagctaat   3240
acaccataag cattttccct actgatgttc atcatctgag cgtattggtt ataagtgaac   3300
gataccgtcc gttctttcct tgtagggttt tcaatcgtgg ggttgagtag tgccacacag   3360
cataaaatta gcttggtttc atgctccgtt aagtcatagc gactaatcgc tagttcattt   3420
gctttgaaaa caactaattc agacatacat ctcaattggt ctaggtgatt ttaatcacta   3480
taccaattga gatgggctag tcaatgataa ttactagtcc ttttcctttg agttgtgggt   3540
atctgtaaat tctgctagac ctttgctgga aaacttgtaa attctgctag accctctgta   3600
aattccgcta gacctttgtg tgtttttttt gtttatattc aagtggttat aatttataga   3660
ataaagaaag aataaaaaaa gataaaaaga atagatccca gccctgtgta taactcacta   3720
ctttagtcag ttccgcagta ttacaaaagg atgtcgcaaa cgctgtttgc tcctctacaa   3780
aacagacctt aaaaccctaa aggcttaagt agcaccctcg caagctcggg caaatcgctg   3840
aatattcctt ttgtctccga ccatcaggca cctgagtcgc tgtctttttc gtgacattca   3900
gttcgctgcg ctcacggctc tggcagtgaa tgggggtaaa tggcactaca ggcgcctttt   3960
atggattcat gcaaggaaac tacccataat acaagaaaag cccgtcacgg gcttctcagg   4020
gcgttttatg gcgggtctgc tatgtggtgc tatctgactt tttgctgttc agcagttcct   4080
gccctctgat ttccagtct gaccacttcg gattatcccg tgacaggtca ttcagactgg   4140
ctaatgcacc cagtaaggca gcggtatcat caacaggctt acccgtctta ctgtcgggaa   4200
ttcgcgttgg ccgattcatt aatgcagatt ctgaaatgag ctgttgacaa ttaatcatcc   4260
ggctcgtata atgtgtggaa ttgtgagcgg ataacaattt cacacaggaa acagcgccgc   4320
tgagaaaaag cgaagcggca ctgctcttta acaatttatc agacaatctg tgtgggcact   4380
cgaccggaat tatcgattaa ctttattatt aaaaattaaa gaggtatata ttaatgtatc   4440
gattaaataa ggaggaataa accatgtgtg cgacctcttc tcaatttact cagattaccg   4500
agcataattc ccgtcgttcc gcaaactatc agccaaacct gtggaatttc gaattcctgc   4560
aatccctgga gaacgacctg aaagtggaaa agctggagga gaaagcgacc aaactggagg   4620
aagaagttcg ctgcatgatc aaccgtgtag acacccagcc gctgtccctg ctggagctga   4680
tcgacgatgt gcagcgcctg ggtctgacct acaaatttga aaaagacatc attaaagccc   4740
tggaaaacat cgtactgctg gacgaaaaca aaaagaacaa atctgacctg cacgcaaccg   4800
ctctgtcttt ccgtctgctg cgtcagcacg gtttcgaggt ttctcaggat gtttttgagc   4860
gtttcaagga taaagaaggt ggtttcagcg gtgaactgaa aggtgacgtc caaggcctgc   4920
tgagcctgta tgaagcgtct tacctgggtt tcgagggtga gaacctgctg gaggaggcgc   4980
gtacctttc catcacccac ctgaagaaca acctgaaaga aggcattaat accaaggttg   5040
cagaacaagt gagccacgcc ctggaactgc catatcacca gcgtctgcac cgtctggagg   5100
cacgttggtt cctggataaa tacgaaccga aagaaccgca tcaccagctg ctgctggagc   5160
tggcgaagct ggattttaac atggtacaga ccctgcacca gaaagagctg caagatctgt   5220
cccgctggtg gaccgagatg ggcctggcta gcaaactgga ttttgtacgc gaccgcctga   5280
tggaagttta tttctgggca ctgggtatgg cgccagaccc gcagtttggt gaatgtcgca   5340
```

-continued

```
aagctgttac taaaatgttt ggtctggtga cgatcatcga tgacgtgtat gacgtttatg   5400
gcactctgga cgaactgcaa ctgttcaccg atgctgtaga gcgctgggac gttaacgcta   5460
ttaacaccct gccggactat atgaaactgt gtttcctggc actgtacaac accgttaacg   5520
acacgtccta ttctattctg aaagagaaag gtcataacaa cctgtcctat ctgacgaaaa   5580
gctggcgtga actgtgcaaa gcctttctgc aagaggcgaa atggtccaac aacaaaatta   5640
tcccggcttt ctccaagtac ctggaaaacg ccagcgtttc ctcctccggt gtagcgctgc   5700
tggcgccgtc ttacttttcc gtatgccagc agcaggaaga catctccgac cacgcgctgc   5760
gttccctgac cgacttccat ggtctggtgc gttctagctg cgttatcttc cgcctgtgca   5820
acgatctggc cacctctgcg gcggagctgg aacgtggcga gactaccaat tctatcatta   5880
gctacatgca cgaaaacgat ggtaccagcg aggaacaggc ccgcgaagaa ctgcgtaaac   5940
tgatcgacgc cgaatggaaa aagatgaatc gtgaacgcgt tagcgactcc accctgctgc   6000
ctaaagcgtt catggaaatc gcagttaaca tggcacgtgt ttcccactgc acctaccagt   6060
atggcgatgg tctgggtcgc ccagactacg cgactgaaaa ccgcatcaaa ctgctgctga   6120
ttgacccttt cccgattaac cagctgatgt atgtctaact gcatcgccct taggaggtaa   6180
aaaaaaatga ctgccgacaa caatagtatg ccccatggtg cagtatctag ttacgccaaa   6240
ttagtgcaaa accaaacacc tgaagacatt ttggaagagt ttcctgaaat tattccatta   6300
caacaaagac ctaatacccg atctagtgag acgtcaaatg acgaaagcgg agaaacatgt   6360
ttttctggtc atgatgagga gcaaattaag ttaatgaatg aaaattgtat tgttttggat   6420
tgggacgata atgctattgg tgccggtacc aagaaagttt gtcatttaat ggaaaatatt   6480
gaaaagggtt tactacatcg tgcattctcc gtctttattt tcaatgaaca aggtgaatta   6540
cttttacaac aaagagccac tgaaaaaata actttccctg atctttggac taacacatgc   6600
tgctctcatc cactatgtat tgatgacgaa ttaggtttga agggtaagct agacgataag   6660
attaagggcg ctattactgc ggcggtgaga aaactagatc atgaattagg tattccagaa   6720
gatgaaacta agacaagggg taagtttcac tttttaaaca gaatccatta catggcacca   6780
agcaatgaac catggggtga acatgaaatt gattacatcc tattttataa gatcaacgct   6840
aaagaaaact tgactgtcaa cccaaacgtc aatgaagtta gagacttcaa atgggtttca   6900
ccaaatgatt tgaaaactat gtttgctgac ccaagttaca agtttacgcc ttggtttaag   6960
attatttgcg agaattactt attcaactgg tgggagcaat tagatgacct ttctgaagtg   7020
gaaaatgaca ggcaaattca tagaatgcta taacgacgcg tcctgcagct ggtaccatat   7080
gggaattcga agctttctag aacgaaaact catctcagaa gaggatctga atagcgccgt   7140
cgaccatcat catcatcatc attgagttta aacggtctcc agcttggctg ttttggcgga   7200
tgagagaaga ttttcagcct gatacagatt aaatcagaac gcagaagcgg tctgataaaa   7260
cagaatttgc ctggcggcag tagcgcggtg gtcccacctg accccatgcc gaactcagaa   7320
gtgaaacgcc gtagcgccga tggtagtgtg gggtctcccc atgcgagagt agggaactgc   7380
caggcatcaa ataaaacgaa aggctcagtc gaaagactgg gcctttcgtt ttatctgttg   7440
tttgtcggtg aacgctctcc tgagtaggac aaatccgccg ggagcggatt tgaacgttgc   7500
gaagcaacgg cccggagggt ggcgggcagg acgcccgcca taaactgcca ggcatcaaat   7560
taagcagaag gccatcctga cggatggcct ttttgcgttt ctacaaactc tttttgttta   7620
tttttctaaa tacattcaaa tatgtatccg ctcatgagac aataaccctg ataaatgctt   7680
caataat                                                             7687
```

<210> SEQ ID NO 55
<211> LENGTH: 8675
<212> TYPE: DNA
<213> ORGANISM: Artificial Sequence
<220> FEATURE:
<223> OTHER INFORMATION: Synthetic Construct

<400> SEQUENCE: 55
cccgtcttac tgtcgggaat tcgcgttggc cgattcatta atgcagatta ttgaagcatt 60
tatcagggtt attgtctcat gagcggatac atatttgaat gtatttagaa aaataaacaa 120
aaagagtttg tagaaacgca aaaaggccat ccgtcaggat ggccttctgc ttaatttgat 180
gcctggcagt ttatggcggg cgtcctgccc gccaccctcc gggccgttgc ttcgcaacgt 240
tcaaatccgc tcccggcgga tttgtcctac tcaggagagc gttcaccgac aaacaacaga 300
taaaacgaaa ggcccagtct ttcgactgag cctttcgttt tatttgatgc ctggcagttc 360
cctactctcg catggggaga ccccacacta ccatcggcgc tacggcgttt cacttctgag 420
ttcggcatgg ggtcaggtgg gaccaccgcg ctactgccgc caggcaaatt ctgttttatc 480
agaccgcttc tgcgttctga tttaatctgt atcaggctga aatcttctc tcatccgcca 540 aaacagccaa gctggagacc gtttaaactc aatgatgatg atgatgatgg tcgacggcgc 600
tattcagatc ctcttctgag atgagttttt gttctagaaa gcttcgaatt cccatatggt 660
accagctgca gttatgccag ccaggccttg attttggctt ccataccagc ggcatcgagg 720
ccgagttcgg cgcgcatttc ttcctgagtt ccttgcggaa taaagaagtc cggcaggcca 780
atgttcagca cgggtactgg tttacgatgg gccatcagca cttcgttcac gccgctgcct 840
gcgccgccca taatggcgtt ttcttctacg gtgaccagcg cttcatggct ggcggccatt 900
tccagaatta acgcttcatc aagcggtttc acaaaacgca tatcgaccag cgtggcgttc 960
agcgattcgg cgactttcgc cgcttctggc atcagcgtac caaagttaag gatcgccagt 1020
ttctcgccac gacgcttcac aatgcctttg ccaattggta gtttttccag cggcgtcagt 1080
tccacgccga ccgcgttgcc acgcgggtag cgcaccgctg acgggccatc gttatagtga 1140
tagccggtat agagcatctg gcgacattcg ttttcatcgc tcggggtcat aatgaccatt 1200
tccggtatgc agcgcaggta agagagatca aaagcaccct gatgggtttg accgtcagca 1260
ccaacaatgc ccgcgcggtc gatggcgaac aggaccggaa gcttttgaat cgccacgtca 1320
tgcagcacct gatcataggc gcgttgcagg aaagtggagt aaatcgcgac aatgggtttg 1380
tacccaccaa tcgccagacc cgcagcaaag gtcaccgcgt gttgctcggc aattgccacg 1440
tcgaagtagc gatccgggaa tttacgtgaa aactcgacca tgccggaacc ttcacgcatc 1500
gccggagtaa tcgccatcag cttgttgtct ttcgctgccg tttcgcacaa ccagtcgcca 1560
aagatttttg aatagctcgg caaaccgccg ctacttttcg gcaaacaacc gctggaggga 1620
tcaaatttag gcacggcgtg gaaagtgatc gggtcttttt ctgccggttc ataaccacga 1680
cctttttggg tcatgatatg caggaactgc gggcctttca ggtcgcgcat gttctttagc 1740
gtggtgataa gccccagcac atcgtgaccg tccaccgggc cgatgtagtt aaagcccagc 1800
tcttcaaaca acgtgccagg cactaccatg cctttaatat gttcttcggt gcgtttgagc 1860
agctctttaa ttggcggcac gccagagaaa acttttttcc cgccttcgcg cagtgaagag 1920
taaagcttac cggaaagcag ctgtgccaga tggttgttga gcgcgccgac attttcggaa 1980
atcgacattt cattgtcgtt gagaatcacc agcatatcag gacggatatc gcccgcgtga 2040

-continued

```
ttcatcgctt caaacgccat gcctgcggta atcgcgccat cgccaatgac acagacggtg   2100
cggcgatttt tgccttcttt ttcggcagca accgcaatac caattccggc actgatggag   2160
gttgatgaat gcccgacgct taatacgtca tattcgcttt cgccgcgcca cgggaacggg   2220
tgcagaccgc ctttctgacg gatggtgccg attttgtcgc ggcgtccggt caaaatttta   2280
tgcggataag cctgatgccc cacatcccaa atcaattggt caaacggggt gttgtagaca   2340
tagtgcagcg ccacggtcag ttcgaccgtg cccagcccgg aggcgaagtg cccgctggaa   2400
cggctcacgc tgtcgagtaa atagcggcgc agttcgtcgc agagtttcgg taaactctct   2460
ttcggcaaca gtcgtaactc ctgggtggag tcgaccagtg ccagggtcgg gtatttggca   2520
atatcaaaac tcatgttttt ttacctccta agggcgaatg cagttagaca tacatcagct   2580
ggttaatcgg gaaagggtca atcagcagca gtttgatgcg gttttcagtc gcgtagtctg   2640
ggcgacccag accatcgcca tactggtagg tgcagtggga aacacgtgcc atgttaactg   2700
cgatttccat gaacgcttta ggcagcaggg tggagtcgct aacgcgttca cgattcatct   2760
ttttccattc ggcgtcgatc agtttacgca gttcttcgcg ggcctgttcc tcgctggtac   2820
catcgttttc gtgcatgtag ctaatgatag aattggtagt ctcgccacgt tccagctccg   2880
ccgcagaggt ggccagatcg ttgcacaggc ggaagataac gcagctagaa cgcaccagac   2940
catggaagtc ggtcagggaa cgcagcgcgt ggtcggagat gtcttcctgc tgctggcata   3000
cggaaaagta agacggcgcc agcagcgcta caccggagga ggaaacgctg gcgttttcca   3060
ggtacttgga gaaagccggg ataattttgt tgttggacca tttcgcctct tgcagaaagg   3120
ctttgcacag ttcacgccag cttttcgtca gataggacag gttgttatga cctttctctt   3180
tcagaataga ataggacgtg tcgttaacgg tgttgtacag tgccaggaaa cacagtttca   3240
tatagtccgg cagggtgtta atagcgttaa cgtcccagcg ctctacagca tcggtgaaca   3300
gttgcagttc gtccagagtg ccataaacgt catacacgtc atcgatgatc gtcaccagac   3360
caaacatttt agtaacagct ttgcgacatt caccaaactg cgggtctggc gccataccca   3420
gtgcccagaa ataaacttcc atcaggcggt cgcgtacaaa atccagtttg ctagccaggc   3480
ccatctcggt ccaccagcgg gacagatctt gcagctcttt ctggtgcagg gtctgtacca   3540
tgttaaaatc cagcttcgcc agctccagca gcagctggtg atgcggttct ttcggttcgt   3600
atttatccag gaaccaacgt gcctccagac ggtgcagacg ctggtgatat ggcagttcca   3660
gggcgtggct cacttgttct gcaaccttgg tattaatgcc ttctttcagg ttgttcttca   3720
ggtgggtgat ggaaaaggta cgcgcctcct ccagcaggtt ctcaccctcg aaacccaggt   3780
aagacgcttc atacaggctc agcaggcctt ggacgtcacc tttcagttca ccgctgaaac   3840
caccttcttt atccttgaaa cgctcaaaaa catcctgaga aacctcgaaa ccgtgctgac   3900
gcagcagacg gaaagacaga gcggttgcgt gcaggtcaga tttgttcttt ttgttttcgt   3960
ccagcagtac gatgttttcc agggctttaa tgatgtcttt ttcaaatttg taggtcagac   4020
ccaggcgctg cacatcgtcg atcagctcca gcagggacag cggctgggtg tctacacggt   4080
tgatcatgca gcgaacttct tcctccagtt tggtcgcttt ctcctccagc ttttccactt   4140
tcaggtcgtt ctccagggat tgcaggaatt cgaaattcca caggtttggc tgatagtttg   4200
cggaacgacg ggaattatgc tcggtaatct gagtaaattg agaagaggtc gcacacatgg   4260
tttattcctc cttatttaat cgatacatta atatatacct ctttaatttt taataataaa   4320
gttaatcgat aattccggtc gagtgcccac acagattgtc tgataaattg ttaaagagca   4380
gtgccgcttc gctttttctc agcggcgctg tttcctgtgt gaaattgtta tccgctcaca   4440
```

-continued

```
attccacaca ttatacgagc cggatgatta attgtcaaca gctcatttca gaatctggcg   4500
taatagcgaa gaggcccgca ccgatcgccc ttcccaacag ttgcgcagcc tgaatggcga   4560
atggcgcctg atgcggtatt ttctccttac gcatctgtgc ggtatttcac accgcatatg   4620
gtgcactctc agtacaatct gctctgatgc cgcatagtta agccagcccc gacacccgcc   4680
aacacccgct gacgagctta gtaaagccct cgctagattt taatgcggat gttgcgatta   4740
cttcgccaac tattgcgata acaagaaaaa gccagccttt catgatatat ctcccaattt   4800
gtgtagggct tattatgcac gcttaaaaat aataaaagca gacttgacct gatagtttgg   4860
ctgtgagcaa ttatgtgctt agtgcatcta acgcttgagt taagccgcgc cgcgaagcgg   4920
cgtcggcttg aacgaattgt tagacattat ttgccgacta ccttggtgat ctcgcctttc   4980
acgtagtgga caaattcttc caactgatct gcgcgcgagg ccaagcgatc ttcttcttgt   5040
ccaagataag cctgtctagc ttcaagtatg acgggctgat actgggccgg caggcgctcc   5100
attgcccagt cggcagcgac atccttcggc gcgattttgc cggttactgc gctgtaccaa   5160
atgcgggaca acgtaagcac tacatttcgc tcatcgccag cccagtcggg cggcgagttc   5220
catagcgtta aggtttcatt tagcgcctca aatagatcct gttcaggaac cggatcaaag   5280
agttcctccg ccgctggacc taccaaggca acgctatgtt ctcttgcttt tgtcagcaag   5340
atagccagat caatgtcgat cgtggctggc tcgaagatac ctgcaagaat gtcattgcgc   5400
tgccattctc caaattgcag ttcgcgctta gctggataac gccacggaat gatgtcgtcg   5460
tgcacaacaa tggtgacttc tacagcgcgg agaatctcgc tctctccagg ggaagccgaa   5520
gtttccaaaa ggtcgttgat caaagctcgc cgcgttgttt catcaagcct tacggtcacc   5580
gtaaccagca aatcaatatc actgtgtggc ttcaggccgc catccactgc ggagccgtac   5640
aaatgtacgg ccagcaacgt cggttcgaga tggcgctcga tgacgccaac tacctctgat   5700
agttgagtcg atacttcggc gatcaccgct tccctcatga tgtttaactt tgttttaggg   5760
cgactgccct gctgcgtaac atcgttgctg ctccataaca tcaaacatcg acccacggcg   5820
taacgcgctt gctgcttgga tgcccgaggc atagactgta ccccaaaaaa acagtcataa   5880
caagccatga aaaccgccac tgcgccgtta ccaccgctgc gttcggtcaa ggttctggac   5940
cagttgcgtg agcgcatacg ctacttgcat tacagcttac gaaccgaaca ggcttatgtc   6000
cactgggttc gtgccttcat ccgtttccac ggtgtgcgtc acccggcaac cttgggcagc   6060
agcgaagtcg aggcatttct gtcctggctg gcgaacgagc gcaaggtttc ggtctccacg   6120
catcgtcagg cattggcggc cttgctgttc ttctacggca aggtgctgtg cacggatctg   6180
ccctggcttc aggagatcgg aagacctcgg ccgtcgcggc gcttgccggt ggtgctgacc   6240
ccggatgaag tggttcgcat cctcggtttt ctggaaggcg agcatcgttt gttcgcccag   6300
cttctgtatg gaacgggcat gcggatcagt gagggtttgc aactgcgggt caaggatctg   6360
gatttcgatc acggcacgat catcgtgcgg gagggcaagg gctccaagga tcgggccttg   6420
atgttacccg agagcttggc acccagcctg cgcgagcagg ggaattaatt cccacgggtt   6480
ttgctgcccg caaacgggct gttctggtgt tgctagtttg ttatcagaat cgcagatccg   6540
gcttcagccg gtttgccggc tgaaagcgct atttcttcca gaattgccat gatttttttcc  6600
ccacgggagg cgtcactggc tcccgtgttg tcggcagctt tgattcgata agcagcatcg   6660
cctgtttcag gctgtctatg tgtgactgtt gagctgtaac aagttgtctc aggtgttcaa   6720
tttcatgttc tagttgcttt gttttactgg tttcacctgt tctattaggt gttacatgct   6780
```

gttcatctgt tacattgtcg atctgttcat ggtgaacagc tttgaatgca ccaaaaactc 6840
gtaaaagctc tgatgtatct atcttttta caccgttttc atctgtgcat atggacagtt 6900
ttccctttga tatgtaacgg tgaacagttg ttctactttt gtttgttagt cttgatgctt 6960
cactgataga tacaagagcc ataagaacct cagatccttc cgtatttagc cagtatgttc 7020
tctagtgtgg ttcgttgttt ttgcgtgagc catgagaacg aaccattgag atcatactta 7080
ctttgcatgt cactcaaaaa ttttgcctca aaactggtga gctgaatttt tgcagttaaa 7140
gcatcgtgta gtgtttttct tagtccgtta tgtaggtagg aatctgatgt aatggttgtt 7200
ggtattttgt caccattcat ttttatctgg ttgttctcaa gttcggttac gagatccatt 7260
tgtctatcta gttcaacttg gaaaatcaac gtatcagtcg ggcggcctcg cttatcaacc 7320
accaatttca tattgctgta agtgtttaaa tctttactta ttggtttcaa aacccattgg 7380
ttaagccttt taaactcatg gtagttattt tcaagcatta acatgaactt aaattcatca 7440
aggctaatct ctatatttgc cttgtgagtt ttcttttgtg ttagttcttt taataaccac 7500
tcataaatcc tcatagagta tttgttttca aaagacttaa catgttccag attatatttt 7560
atgaattttt ttaactggaa aagataaggc aatatctctt cactaaaaac taattctaat 7620
ttttcgcttg agaacttggc atagtttgtc cactggaaaa tctcaaagcc tttaaccaaa 7680
ggattcctga tttccacagt tctcgtcatc agctctctgg ttgctttagc taatacacca 7740
taagcatttt ccctactgat gttcatcatc tgagcgtatt ggttataagt gaacgatacc 7800
gtccgttctt tccttgtagg gttttcaatc gtggggttga gtagtgccac acagcataaa 7860
attagcttgg tttcatgctc cgttaagtca tagcgactaa tcgctagttc atttgctttg 7920
aaaacaacta attcagacat acatctcaat tggtctaggt gattttaatc actataccaa 7980
ttgagatggg ctagtcaatg ataattacta gtccttttcc tttgagttgt gggtatctgt 8040
aaattctgct agacctttgc tggaaaactt gtaaattctg ctagaccctc tgtaaattcc 8100
gctagacctt tgtgtgtttt ttttgtttat attcaagtgg ttataattta tagaataaag 8160
aaagaataaa aaaagataaa aagaatagat cccagccctg tgtataactc actactttag 8220
tcagttccgc agtattacaa aaggatgtcg caaacgctgt ttgctcctct acaaaacaga 8280
ccttaaaacc ctaaaggctt aagtagcacc ctcgcaagct cgggcaaatc gctgaatatt 8340
ccttttgtct ccgaccatca ggcacctgag tcgctgtctt tttcgtgaca ttcagttcgc 8400
tgcgctcacg gctctggcag tgaatggggg taaatggcac tacaggcgcc ttttatggat 8460
tcatgcaagg aaactaccca taatacaaga aaagcccgtc acgggcttct cagggcgttt 8520
tatggcgggt ctgctatgtg gtgctatctg actttttgct gttcagcagt tcctgccctc 8580
tgatttccca gtctgaccac ttcggattat cccgtgacag gtcattcaga ctggctaatg 8640
cacccagtaa ggcagcggta tcatcaacag gctta 8675

<210> SEQ ID NO 56
<211> LENGTH: 8032
<212> TYPE: DNA
<213> ORGANISM: Artificial Sequence
<220> FEATURE:
<223> OTHER INFORMATION: Synthetic Construct

<400> SEQUENCE: 56
tcgctgcgct cggtcgttcg gctgcggcga gcggtatcag ctcactcaaa ggcggtaata 60
cggttatcca cagaatcagg ggataacgca ggaaagaaca tgtgagcaaa aggccagcaa 120
aaggccagga accgtaaaaa ggccgcgttg ctggcgtttt tccataggct ccgcccccct 180
gacgagcatc acaaaaatcg acgctcaagt cagaggtggc gaaacccgac aggactataa 240
agataccagg cgtttccccc tggaagctcc ctcgtgcgct ctcctgttcc gaccctgccg 300
cttaccggat acctgtccgc ctttctccct tcgggaagcg tggcgctttc tcatagctca 360
cgctgtaggt atctcagttc ggtgtaggtc gttcgctcca agctgggctg tgtgcacgaa 420
ccccccgttc agcccgaccg ctgcgcctta tccggtaact atcgtcttga gtccaacccg 480
gtaagacacg acttatcgcc actggcagca gccactggta acaggattag cagagcgagg 540
tatgtaggcg gtgctacaga gttcttgaag tggtggccta actacggcta cactagaaga 600
acagtatttg gtatctgcgc tctgctgaag ccagttacct tcggaaaaag agttggtagc 660
tcttgatccg gcaaacaaac caccgctggt agcggtggtt tttttgtttg caagcagcag 720
attacgcgca gaaaaaaagg atctcaagaa gatcctttga tcttttctac ggggtctgac 780
gctcagtgga acgaaaactc acgttaaggg attttggtca tgagattatc aaaaaggatc 840
ttcacctaga tccttttaaa ttaaaaatga agttttaaat caatctaaag tatatatgag 900
taaacttggt ctgacagtta ccaatgctta atcagtgagg cacctatctc agcgatctgt 960
ctatttcgtt catccatagt tgcctgactc cccgtcgtgt agataactac gatacgggag 1020
ggcttaccat ctggccccag tgctgcaatg ataccgcgag acccacgctc accggctcca 1080
gatttatcag caataaacca gccagccgga agggccgagc gcagaagtgg tcctgcaact 1140
ttatccgcct ccatccagtc tattaattgt tgccgggaag ctagagtaag tagttcgcca 1200
gttaatagtt tgcgcaacgt tgttgccatt gctacaggca tcgtggtgtc acgctcgtcg 1260
tttggtatgg cttcattcag ctccggttcc caacgatcaa ggcgagttac atgatccccc 1320
atgttgtgca aaaaagcggt tagctccttc ggtcctccga tcgttgtcag aagtaagttg 1380
gccgcagtgt tatcactcat ggttatggca gcactgcata attctcttac tgtcatgcca 1440
tccgtaagat gcttttctgt gactggtgag tactcaacca agtcattctg agaatagtgt 1500
atgcggcgac cgagttgctc ttgcccggcg tcaatacggg ataataccgc gccacatagc 1560
agaactttaa aagtgctcat cattggaaaa cgttcttcgg ggcgaaaact ctcaaggatc 1620
ttaccgctgt tgagatccag ttcgatgtaa cccactcgtg cacccaactg atcttcagca 1680
tcttttactt tcaccagcgt ttctgggtga gcaaaaacag gaaggcaaaa tgccgcaaaa 1740
aagggaataa gggcgacacg gaaatgttga atactcatac tcttcctttt tcaatattat 1800
tgaagcattt atcagggtta ttgtctcatg agcggataca tatttgaatg tatttagaaa 1860
aataaacaaa taggggttcc gcgcacattt ccccgaaaag tgccacctga cgtctaagaa 1920
accattatta tcatgacatt aacctataaa aataggcgta tcacgaggcc ctttcgtctc 1980
gcgcgtttcg gtgatgacgg tgaaaacctc tgacacatgc agctcccgga gacggtcaca 2040
gcttgtctgt aagcggatgc cgggagcaga caagcccgtc agggcgcgtc agcgggtgtt 2100
ggcgggtgtc ggggctggct taactatgcg gcatcagagc agattgtact gagagtgcac 2160
catagatctg gagctgtaat ataaaaacct tcttcaacta acggggcagg ttagtgacat 2220
tagaaaaccg actgtaaaaa gtacagtcgg cattatctca tattataaaa gccagtcatt 2280
aggcctatct gacaattcct gaatagagtt cataaacaat cctgcatgat aaccatcaca 2340
aacagaatga tgtacctgta aagatagcgg taaatatatt gaattacctt tattaatgaa 2400
ttttcctgct gtaataatgg gtagaaggta attactatta ttattgatat ttaagttaaa 2460
cccagtaaat gaagtccatg gaataataga aagagaaaaa gcattttcag gtataggtgt 2520

-continued

```
tttgggaaac aatttccccg aaccattata tttctctaca tcagaaaggt ataaatcata   2580
aaactctttg aagtcattct ttacaggagt ccaaatacca gagaatgttt tagatacacc   2640
atcaaaaatt gtataaagtg gctctaactt atcccaataa cctaactctc cgtcgctatt   2700
gtaaccagtt ctaaaagctg tatttgagtt tatcaccctt gtcactaaga aaataaatgc   2760
agggtaaaat ttatatcctt cttgttttat gtttcggtat aaaacactaa tatcaatttc   2820
tgtggttata ctaaaagtcg tttgttggtt caaataatga ttaaatatct cttttctctt   2880
ccaattgtct aaatcaattt tattaaagtt catttgatat gcctcctaaa tttttatcta   2940
aagtgaattt aggaggctta cttgtctgct ttcttcatta gaatcaatcc tttttttaaaa   3000
gtcaatatta ctgtaacata aatatatatt ttaaaaatat cccactttat ccaattttcg   3060
tttgttgaac taatgggtgc tttagttgaa gaataaaaga cctatgcggt gtgaaatacc   3120
gcacagatgc gtaaggagaa aataccgcat caggcgccat tcgccattca ggctgcgcaa   3180
ctgttgggaa gggcgatcgg tgcgggcctc ttcgctatta cgccagctgg cgaaaggggg   3240
atgtgctgca aggcgattaa gttgggtaac gccagggttt tcccagtcac gacgttgtaa   3300
aacgacggcc agtgccaagc ttgcatgcct gcactccatt ttcttctgct atcaaaataa   3360
cagactcgtg attttccaaa cgagctttca aaaaagcctc tgccccttgc aaatcggatg   3420
cctgtctata aaattcccga tattggttaa acagcggcgc aatggcggcc gcatctgatg   3480
tctttgcttg gcgaatgttc atcttatttc ttcctccctc tcaataattt tttcattcta   3540
tccctttctt gtaaagttta tttttcagaa tacttttatc atcatgcttt gaaaaaatat   3600
cacgataata tccattgttc tcacggaagc acacgcaggt catttgaacg aatttttttcg   3660
acaggaattt gccgggactc aggagcattt aacctaaaaa agcatgacat ttcagcataa   3720
tgaacattta ctcatgtcta ttttcgttct tttctgtatg aaaatagtta tttcgagtct   3780
ctacggaaat agcgagagat gatataccta aatagagata aaatcatctc aaaaaaatgg   3840
gtctactaaa atattattcc atctattaca ataaattcac agaatagtct tttaagtaag   3900
tctactctga attttttttaa aaggagaggg taaagagtga aaacagtagt tattattgat   3960
gcattacgaa caccaattgg aaaatataaa ggcagcttaa gtcaagtaag tgccgtagac   4020
ttaggaacac atgttacaac acaactttta aaaagacatt ccactatttc tgaagaaatt   4080
gatcaagtaa tctttggaaa tgttttacaa gctggaaatg gccaaaatcc cgcacgacaa   4140
atagcaataa acagcggttt gtctcatgaa attcccgcaa tgacggttaa tgaggtctgc   4200
ggatcaggaa tgaaggccgt tattttggcg aaacaattga ttcaattagg agaagcggaa   4260
gttttaattg ctggcgggat tgagaatatg tcccaagcac ctaaattaca acgttttaat   4320
tacgaaacag aaagctacga tgcgcctttt tctagtatga tgtatgatgg attaacggat   4380
gcctttagtg gtcaggcaat gggcttaact gctgaaaatg tggccgaaaa gtatcatgta   4440
actagagaag agcaagatca attttctgta cattcacaat taaaagcagc tcaagcacaa   4500
gcagaaggga tattcgctga cgaaatagcc ccattagaag tatcaggaac gcttgtggag   4560
aaagatgaag ggattcgccc taattcgagc gttgagaagc taggaacgct taaaacagtt   4620
tttaaagaag acggtactgt aacagcaggg aatgcatcaa ccattaatga tggggcttct   4680
gctttgatta ttgcttcaca agaatatgcc gaagcacacg gtcttcctta tttagctatt   4740
attcgagaca gtgtggaagt cggtattgat ccagcctata tgggaatttc gccgattaaa   4800
gccattcaaa aactgttagc gcgcaatcaa cttactacgg aagaaattga tctgtatgaa   4860
atcaacgaag catttgcagc aacttcaatc gtggtccaaa gagaactggc tttaccagag   4920
```

gaaaaggtca acatttatgg tggcggtatt tcattaggtc atgcgattgg tgccacaggt 4980
gctcgtttat taacgagttt aagttatcaa ttaaatcaaa aagaaaagaa atatggagtg 5040
gcttctttat gtatcggcgg tggcttagga ctcgctatgc tactagagag acctcagcaa 5100
aaaaaaaaca gccgatttta tcaaatgagt cctgaggaac gcctggcttc tcttcttaat 5160
gaaggccaga tttctgctga tacaaaaaaa gaatttgaaa atacggcttt atcttcgcag 5220
attgccaatc atatgattga aaatcaaatc agtgaaacag aagtgccgat gggcgttggc 5280
ttacatttaa cagtggacga aactgattat ttggtaccaa tggcgacaga agagccctca 5340
gttattgcgg ctttgagtaa tggtgcaaaa atagcacaag gatttaaaac agtgaatcaa 5400
caacgcttaa tgcgtggaca aatcgttttt tacgatgttg cagatcccga gtcattgatt 5460
gataaactac aagtaagaga agcggaagtt tttcaacaag cagagttaag ttatccatct 5520
atcgttaaac ggggcggcgg cttaagagat ttgcaatatc gtacttttga tgaatcattt 5580
gtatctgtcg actttttagt agatgttaag gatgcaatgg gggcaaatat cgttaacgct 5640
atgttggaag gtgtggccga gttgttccgt gaatggtttg cggagcaaaa gattttattc 5700
agtattttaa gtaattatgc cacggagtcg gttgttacga tgaaaacggc tattccagtt 5760
tcacgtttaa gtaaggggag caatggccgg gaaattgctg aaaaaattgt tttagcttca 5820
cgctatgctt cattagatcc ttatcgggca gtcacgcata acaaaggaat catgaatggc 5880
attgaagctg tagttttagc tacaggaaat gatacacgcg ctgttagcgc ttcttgtcat 5940
gcttttgcgg tgaaggaagg tcgctaccaa ggcttgacta gttggacgct ggatggcgaa 6000
caactaattg gtgaaatttc agttccgctt gctttagcca cggttggcgg tgccacaaaa 6060
gtcttaccta aatctcaagc agctgctgat ttgttagcag tgacggatgc aaaagaacta 6120
agtcgagtag tagcggctgt tggtttggca caaaatttag cggcgttacg ggccttagtc 6180
tctgaaggaa ttcaaaaagg acacatggct ctacaagcac gttctttagc gatgacggtc 6240
ggagctactg gtaaagaagt tgaggcagtc gctcaacaat taaaacgtca aaaaacgatg 6300
aaccaagacc gagccatggc tattttaaat gatttaagaa aacaataaaa ggagagggtg 6360
acaattggga ttgataaaat tagttttttt gtgccccctt attatattga tatgacggca 6420
ctggctgaag ccagaaatgt agaccctgga aaatttcata ttggtattgg gcaagaccaa 6480
atggcggtga acccaatcag ccaagatatt gtgacatttg cagccaatgc cgcagaagcg 6540
atcttgacca aagaagataa agaggccatt gatatggtga ttgtcgggac tgagtccagt 6600
atcgatgagt caaaagcggc cgcagttgtc ttacatcgtt taatggggat tcaacctttc 6660
gctcgctctt tcgaaatcaa ggaagcttgt tacggagcaa cagcaggctt acagttagct 6720
aagaatcacg tagccttaca tccagataaa aaagtcttgg tcgtagcggc agatattgca 6780
aaatatggct taaattctgg cggtgagcct acacaaggag ctggggcggt tgcaatgtta 6840
gttgctagtg aaccgcgcat tttggcttta aaagaggata atgtgatgct gacgcaagat 6900
atctatgact tttggcgtcc aacaggccac ccgtatccta tggtcgatgg tcctttgtca 6960
aacgaaacct acatccaatc ttttgcccaa gtctgggatg aacataaaaa acgaaccggt 7020
cttgattttg cagattatga tgctttagcg ttccatattc cttacacaaa aatgggcaaa 7080
aaagccttat tagcaaaaat ctccgaccaa actgaagcag aacaggaacg aattttagcc 7140
cgttatgaag aaagtatcgt ctatagtcgt cgcgtaggaa acttgtatac gggttcactt 7200
tatctgggac tcatttccct tttagaaaat gcaacgactt taaccgcagg caatcaaatt 7260
ggtttattca gttatggttc tggtgctgtc gctgaatttt tcactggtga attagtagct 7320
ggttatcaaa atcatttaca aaaagaaact catttagcac tgctggataa tcggacagaa 7380
ctttctatcg ctgaatatga agccatgttt gcagaaactt tagacacaga cattgatcaa 7440
acgttagaag atgaattaaa atatagtatt tctgctatta ataataccgt tcgttcttat 7500
cgaaactaaa aaaaaccggc cttggccccg ccggtttttt attattttc ttcctccgca 7560 tgttcaatcc gctccataat cgacggatgg ctccctctga aattttaac gagaaacggc 7620 gggttgaccc ggctcagtcc cgtaacggcc aagtcctgaa acgtctcaat cgccgcttcc 7680
cggtttccgg tcagctcaat gccgtaacgg tcggcggcgt tttcctgata ccgggagacg 7740
gcattcgtaa tcgggatccc cgggtaccga gctcgaattc gtaatcatgt catagctgtt 7800
tcctgtgtga aattgttatc cgctcacaat tccacacaac atacgagccg gaagcataaa 7860
gtgtaaagcc tggggtgcct aatgagtgag ctaactcaca ttaattgcgt tgcgctcact 7920
gcccgctttc cagtcgggaa acctgtcgtg ccagctgcat taatgaatcg gccaacgcgc 7980
ggggagaggc ggtttgcgta ttgggcgctc ttccgcttcc tcgctcactg ac 8032

<210> SEQ ID NO 57
<211> LENGTH: 6592
<212> TYPE: DNA
<213> ORGANISM: Artificial Sequence
<220> FEATURE:
<223> OTHER INFORMATION: Synthetic Construct

<400> SEQUENCE: 57
gaattgctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaaagag tgtgtgcgac ctcttctcaa tttactcaga ttaccgagca taattcccgt 660
cgttccgcaa actatcagcc aaacctgtgg aatttcgaat tcctgcaatc cctggagaac 720
gacctgaaag tggaaaagct ggaggagaaa gcgaccaaac tggaggaaga agttcgctgc 780
atgatcaacc gtgtagacac ccagccgctg tccctgctgg agctgatcga cgatgtgcag 840
cgcctgggtc tgacctacaa atttgaaaaa gacatcatta aagccctgga aaacatcgta 900
ctgctggacg aaaacaaaaa gaacaaatct gacctgcacg caaccgctct gtctttccgt 960
ctgctgcgtc agcacggttt cgaggtttct caggatgttt ttgagcgttt caaggataaa 1020
gaaggtggtt tcagcggtga actgaaaggt gacgtccaag gcctgctgag cctgtatgaa 1080
gcgtcttacc tgggtttcga gggtgagaac ctgctggagg aggcgcgtac cttttccatc 1140
acccacctga agaacaacct gaaagaaggc attaatacca aggttgcaga acaagtgagc 1200
cacgccctgg aactgccata tcaccagcgt ctgcaccgtc tggaggcacg ttggttcctg 1260
gataaatacg aaccgaaaga accgcatcac cagctgctgc tggagctggc gaagctggat 1320

-continued

```
tttaacatgg tacagaccct gcaccagaaa gagctgcaag atctgtcccg ctggtggacc   1380
gagatgggcc tggctagcaa actggatttt gtacgcgacc gcctgatgga agtttatttc   1440
tgggcactgg gtatggcgcc agacccgcag tttggtgaat gtcgcaaagc tgttactaaa   1500
atgtttggtc tggtgacgat catcgatgac gtgtatgacg tttatggcac tctggacgaa   1560
ctgcaactgt tcaccgatgc tgtagagcgc tgggacgtta acgctattaa caccctgccg   1620
gactatatga aactgtgttt cctggcactg tacaacaccg ttaacgacac gtcctattct   1680
attctgaaag agaaaggtca taacaacctg tcctatctga cgaaaagctg gcgtgaactg   1740
tgcaaagcct ttctgcaaga ggcgaaatgg tccaacaaca aaattatccc ggctttctcc   1800
aagtacctgg aaaacgccag cgtttcctcc tccggtgtag cgctgctggc gccgtcttac   1860
ttttccgtat gccagcagca ggaagacatc tccgaccacg cgctgcgttc cctgaccgac   1920
ttccatggtc tggtgcgttc tagctgcgtt atcttccgcc tgtgcaacga tctggccacc   1980
tctgcggcgg agctggaacg tggcgagact accaattcta tcattagcta catgcacgaa   2040
aacgatggta ccagcgagga acaggcccgc gaagaactgc gtaaactgat cgacgccgaa   2100
tggaaaaaga tgaatcgtga acgcgttagc gactccaccc tgctgcctaa agcgttcatg   2160
gaaatcgcag ttaacatggc acgtgtttcc cactgcacct accagtatgg cgatggtctg   2220
ggtcgcccag actacgcgac tgaaaaccgc atcaaactgc tgctgattga ccctttcccg   2280
attaaccagc tgatgtatgt ctaaaaaaaa ccggccttgg ccccgccggt tttttattat   2340
ttttcttcct ccgcatgttc aatccgctcc ataatcgacg gatggctccc tctgaaaatt   2400
ttaacgagaa acggcgggtt gacccggctc agtcccgtaa cggccaagtc ctgaaacgtc   2460
tcaatcgccg cttcccggtt tccggtcagc tcaatgccgt aacggtcggc ggcgttttcc   2520
tgataccggg agacggcatt cgtaatcgga tcctctagag tcgacctgca ggcatgcaag   2580
ctttgcctcg cgcgtttcgg tgatgacggt gaaaacctct gacacatgca gctcccggag   2640
acggtcacag cttgtctgta agcggatgcc gggagcagac aagcccgtca gggcgcgtca   2700
gcgggtgttg gcgggtgtcg gggcgcagcc atgacccagt cacgtagcga tagcggagtg   2760
tatactggct taactatgcg gcatcagagc agattgtact gagagtgcac catatgcggt   2820
gtgaaatacc gcacagatgc gtaaggagaa aataccgcat caggcgctct tccgcttcct   2880
cgctcactga ctcgctgcgc tcggtcgttc ggctgcggcg agcggtatca gctcactcaa   2940
aggcggtaat acggttatcc acagaatcag gggataacgc aggaaagaac atgtgagcaa   3000
aaggccagca aaaggccagg aaccgtaaaa aggccgcgtt gctggcgttt ttccataggc   3060
tccgcccccc tgacgagcat cacaaaaatc gacgctcaag tcagaggtgg cgaaacccga   3120
caggactata aagataccag gcgtttcccc ctggaagctc cctcgtgcgc tctcctgttc   3180
cgaccctgcc gcttaccgga tacctgtccg cctttctccc ttcgggaagc gtggcgcttt   3240
ctcaatgctc acgctgtagg tatctcagtt cggtgtaggt cgttcgctcc aagctgggct   3300
gtgtgcacga accccccgtt cagcccgacc gctgcgcctt atccggtaac tatcgtcttg   3360
agtccaaccc ggtaagacac gacttatcgc cactggcagc agccactggt aacaggatta   3420
gcagagcgag gtatgtaggc ggtgctacag agttcttgaa gtggtggcct aactacggct   3480
acactagaag gacagtattt ggtatctgcg ctctgctgaa gccagttacc ttcggaaaaa   3540
gagttggtag ctcttgatcc ggcaaacaaa ccaccgctgg tagcggtggt ttttttgttt   3600
gcaagcagca gattacgcgc agaaaaaaag gatctcaaga agatcctttg atcttttcta   3660
```

cggggtctga cgctcagtgg aacgaaaact cacgttaagg gattttggtc atgagattat 3720
caaaaaggat cgaagtcggt tcagaaaaag aaggatatgg atctggagct gtaatataaa 3780
aaccttcttc aactaacggg gcaggttagt gacattagaa aaccgactgt aaaaagtaca 3840
gtcggcatta tctcatatta taaaagccag tcattaggcc tatctgacaa ttcctgaata 3900
gagttcataa acaatcctgc atgataacca tcacaaacag aatgatgtac ctgtaaagat 3960
agcggtaaat atattgaatt acctttatta atgaattttc ctgctgtaat aatgggtaga 4020
aggtaattac tattattatt gatatttaag ttaaacccag taaatgaagt ccatggaata 4080
atagaaagag aaaaagcatt ttcaggtata ggtgttttgg gaaacaattt aaaagaacca 4140
ttatatttct ctacatcaga aaggtataaa tcataaaact ctttgaagtc attctttaca 4200
ggagtccaaa taccagagaa tgttttagat acaccatcaa aaattgtata aagtggctct 4260
aacttatccc aataacctaa ctctccgtcg ctattgtaac cagttctaaa agctgtattt 4320
gagtttatca cccttgtcac taagaaaata aatgcagggt aaaatttata tccttcttgt 4380
tttatgtttc ggtataaaac actaatatca atttctgtgg ttatactaaa agtcgtttgt 4440
tggttcaaat aatgattaaa tatctctttt ctcttccaat tgtctaaatc aattttatta 4500
aagttcattt gatatgcctc ctaaattttt atctaaagtg aatttaggag gcttacttgt 4560
ctgctttctt cattagaatc aatccttttt taaagtcaat attactgtaa cataaatata 4620
tattttaaaa atatcccact ttatccaatt ttcgtttgtt gaactaatgg gtgctttagt 4680
tgaagaataa agaccacatt aaaaaatgtg gtcttttgtg ttttttttaaa ggatttgagc 4740
gtacgcgaaa aatccttttc tttctttctt atcttgataa taagggtaac tattgccggt 4800
tgtccattca tggctgaact ctgcttcctc tgttgacatg acacacatca tctcaatatc 4860
cgaatagggc ccatcagtct gacgaccaag agagccataa acaccaatag ccttaacatc 4920
atccccatat ttatccaata ttcgttcctt aatttcatga acaatcttca ttctttcttc 4980
tctagtcatt attattggtc cattcactat tctcattccc ttttcagata attttagatt 5040
tgcttttcta aataagaata tttggagagc accgttctta ttcagctatt aataactcgt 5100
cttcctaagc atccttcaat ccttttaata acaattatag catctaatct tcaacaaact 5160
ggcccgtttg ttgaactact ctttaataaa ataattttc cgttcccaat tccacattgc 5220
aataatagaa aatccatctt catcggcttt ttcgtcatca tctgtatgaa tcaaatcgcc 5280
ttcttctgtg tcatcaaggt ttaatttttt atgtatttct tttaacaaac caccatagga 5340
gattaacctt ttacggtgta aaccttcctc caaatcagac aaacgtttca aattcttttc 5400
ttcatcatcg gtcataaaat ccgtatcctt tacaggatat tttgcagttt cgtcaattgc 5460
cgattgtata tccgatttat atttattttt cggtcgaatc atttgaactt ttacatttgg 5520
atcatagtct aatttcattg ccttttttcca aaattgaatc cattgttttt gattcacgta 5580
gttttctgtt attctaaaat aagttggttc cacacatacc attacatgca tgtgctgatt 5640
ataagaatta tctttattat ttattgtcac atccgttgca cgcataaaac caacaagatt 5700
tttattaatt tttttatatt gcatcattcg gcgaaatcct tgagccatat ctgtcaaact 5760
cttatttaat tcttcgccat cataaacatt tttaactgtt aatgtgagaa acaaccaacg 5820
aactgttggc ttttgtttaa taacttcagc aacaaccttt tgtgactgaa tgccatgttt 5880
cattgctctc ctccagttgc acattggaca aagcctggat ttgcaaaacc acactcgata 5940
ccactttctt tcgcctgttt cacgattttg tttatactct aatatttcag cacaatcttt 6000
tactctttca gccttttttaa attcaagaat atgcagaagt tcaaagtaat caacattagc 6060
gattttcttt tctctccatg gtctcacttt tccacttttt gtcttgtcca ctaaaaccct 6120
tgatttttca tctgaataaa tgctactatt aggacacata atattaaaag aaaccccccat 6180 ctatttagtt atttgtttag tcacttataa ctttaacaga tggggttttt ctgtgcaacc 6240
aattttaagg gttttcaata ctttaaaaca catacatacc aacacttcaa cgcacctttc 6300
agcaactaaa ataaaaatga cgttatttct atatgtatca agataagaaa gaacaagttc 6360
aaaaccatca aaaaaagaca ccttttcagg tgcttttttt attttataaa ctcattccct 6420
gatctcgact tcgttctttt tttacctctc ggttatgagt tagttcaaat tcgttctttt 6480
taggttctaa atcgtgtttt tcttggaatt gtgctgtttt atcctttacc ttgtctacaa 6540 acccccttaaa aacgttttta aaggctttta agccgtctgt acgttcctta ag 6592

<210> SEQ ID NO 58
<211> LENGTH: 31
<212> TYPE: DNA
<213> ORGANISM: Artificial Sequence
<220> FEATURE:
<223> OTHER INFORMATION: Synthetic Construct

<400> SEQUENCE: 58
gacatcaatt gctccatttt cttctgctat c 31

<210> SEQ ID NO 59
<211> LENGTH: 41
<212> TYPE: DNA
<213> ORGANISM: Artificial Sequence
<220> FEATURE:
<223> OTHER INFORMATION: Synthetic Construct

<400> SEQUENCE: 59
attgagaaga ggtcgcacac actctttacc ctctcctttt a 41

<210> SEQ ID NO 60
<211> LENGTH: 41
<212> TYPE: DNA
<213> ORGANISM: Artificial Sequence
<220> FEATURE:
<223> OTHER INFORMATION: Synthetic Construct

<400> SEQUENCE: 60
taaaaggaga gggtaaagag tgtgtgcgac ctcttctcaa t 41

<210> SEQ ID NO 61
<211> LENGTH: 41
<212> TYPE: DNA
<213> ORGANISM: Artificial Sequence
<220> FEATURE:
<223> OTHER INFORMATION: Synthetic Construct

<400> SEQUENCE: 61
ccaaggccgg tttttttag acatacatca gctggttaat c 41

<210> SEQ ID NO 62
<211> LENGTH: 41
<212> TYPE: DNA
<213> ORGANISM: Artificial Sequence
<220> FEATURE:
<223> OTHER INFORMATION: Synthetic Construct

<400> SEQUENCE: 62
gattaaccag ctgatgtatg tctaaaaaaa accggccttg g 41

<210> SEQ ID NO 63
<211> LENGTH: 32
<212> TYPE: DNA
<213> ORGANISM: Artificial Sequence
<220> FEATURE:
<223> OTHER INFORMATION: Synthetic Construct

<400> SEQUENCE: 63
gacatgacgg atccgattac gaatgccgtc tc 32

<210> SEQ ID NO 64
<211> LENGTH: 31
<212> TYPE: DNA
<213> ORGANISM: Artificial Sequence
<220> FEATURE:
<223> OTHER INFORMATION: Synthetic Construct

<400> SEQUENCE: 64
gacatcaatt gctccatttt cttctgctat c 31

<210> SEQ ID NO 65
<211> LENGTH: 27
<212> TYPE: DNA
<213> ORGANISM: Artificial Sequence
<220> FEATURE:
<223> OTHER INFORMATION: Synthetic Construct

<400> SEQUENCE: 65
gacatgaatt cctccatttt cttctgc 27

<210> SEQ ID NO 66
<211> LENGTH: 20
<212> TYPE: DNA
<213> ORGANISM: Artificial Sequence
<220> FEATURE:
<223> OTHER INFORMATION: Synthetic Construct

<400> SEQUENCE: 66
aggagagggt aaagagtgag 20

<210> SEQ ID NO 67
<211> LENGTH: 22
<212> TYPE: DNA
<213> ORGANISM: Pueraria montana

<400> SEQUENCE: 67
cttttccatc acccacctga ag 22

<210> SEQ ID NO 68
<211> LENGTH: 28
<212> TYPE: DNA
<213> ORGANISM: Pueraria montana

<400> SEQUENCE: 68
ggcgaaatgg tccaacaaca aaattatc 28

<210> SEQ ID NO 69
<211> LENGTH: 51
<212> TYPE: DNA
<213> ORGANISM: Artificial Sequence
<220> FEATURE:
<223> OTHER INFORMATION: Synthetic Construct

<400> SEQUENCE: 69
ggtgaattca gtctactggg gattcccaaa tctatatata ctgcaggtga c 51

<210> SEQ ID NO 70
<211> LENGTH: 23
<212> TYPE: DNA
<213> ORGANISM: Artificial Sequence
<220> FEATURE:
<223> OTHER INFORMATION: Synthetic Construct

<400> SEQUENCE: 70
gcaggtggga aactatgcac tcc 23

<210> SEQ ID NO 71
<211> LENGTH: 36
<212> TYPE: DNA
<213> ORGANISM: Artificial Sequence
<220> FEATURE:
<223> OTHER INFORMATION: Synthetic Construct

<400> SEQUENCE: 71
cctgaattct gttggattgg aggattggat agtggg 36

<210> SEQ ID NO 72
<211> LENGTH: 30
<212> TYPE: DNA
<213> ORGANISM: Artificial Sequence
<220> FEATURE:
<223> OTHER INFORMATION: Synthetic Construct

<400> SEQUENCE: 72
ggtgtcgacg tacggtcgag cttattgacc 30

<210> SEQ ID NO 73
<211> LENGTH: 32
<212> TYPE: DNA
<213> ORGANISM: Artificial Sequence
<220> FEATURE:
<223> OTHER INFORMATION: Synthetic Construct

<400> SEQUENCE: 73
ggtgggcccg cattttgcca cctacaagcc ag 32

<210> SEQ ID NO 74
<211> LENGTH: 40
<212> TYPE: DNA
<213> ORGANISM: Artificial Sequence
<220> FEATURE:
<223> OTHER INFORMATION: Synthetic Construct

<400> SEQUENCE: 74
ggtgaattct agaggatccc aacgctgttg cctacaacgg 40

<210> SEQ ID NO 75
<211> LENGTH: 36
<212> TYPE: DNA
<213> ORGANISM: Artificial Sequence
<220> FEATURE:
<223> OTHER INFORMATION: Synthetic Construct

<400> SEQUENCE: 75
ggtgcggccg ctgtctggac ctggtgagtt tccccg 36

<210> SEQ ID NO 76
<211> LENGTH: 37
<212> TYPE: DNA
<213> ORGANISM: Artificial Sequence
<220> FEATURE:

<223> OTHER INFORMATION: Synthetic Construct

<400> SEQUENCE: 76
ggtgggccca ttaaatcagt tatcgtttat ttgatag 37

<210> SEQ ID NO 77
<211> LENGTH: 35
<212> TYPE: DNA
<213> ORGANISM: Artificial Sequence
<220> FEATURE:
<223> OTHER INFORMATION: Synthetic Construct

<400> SEQUENCE: 77
ggtgaccagc aagtccatgg gtggtttgat catgg 35

<210> SEQ ID NO 78
<211> LENGTH: 35
<212> TYPE: DNA
<213> ORGANISM: Artificial Sequence
<220> FEATURE:
<223> OTHER INFORMATION: Synthetic Construct

<400> SEQUENCE: 78
ggtgcggccg cctttggagt acgactccaa ctatg 35

<210> SEQ ID NO 79
<211> LENGTH: 31
<212> TYPE: DNA
<213> ORGANISM: Artificial Sequence
<220> FEATURE:
<223> OTHER INFORMATION: Synthetic Construct

<400> SEQUENCE: 79
gcggccgcag actaaattta tttcagtctc c 31

<210> SEQ ID NO 80
<211> LENGTH: 7
<212> TYPE: DNA
<213> ORGANISM: Artificial Sequence
<220> FEATURE:
<223> OTHER INFORMATION: Synthetic Construct

<400> SEQUENCE: 80 aggaggt 7

<210> SEQ ID NO 81
<211> LENGTH: 7
<212> TYPE: DNA
<213> ORGANISM: Artificial Sequence
<220> FEATURE:
<223> OTHER INFORMATION: Synthetic Construct

<400> SEQUENCE: 81 aaggagg 7

<210> SEQ ID NO 82
<211> LENGTH: 27
<212> TYPE: DNA
<213> ORGANISM: Artificial Sequence
<220> FEATURE:
<223> OTHER INFORMATION: Synthetic Construct

<400> SEQUENCE: 82
gacatctgca gctccatttt cttctgc 27

<210> SEQ ID NO 83
<211> LENGTH: 42
<212> TYPE: DNA
<213> ORGANISM: Artificial Sequence
<220> FEATURE:
<223> OTHER INFORMATION: Synthetic Construct

<400> SEQUENCE: 83
caataataac tactgttttc actctttacc ctctcctttt aa 42

<210> SEQ ID NO 84
<211> LENGTH: 42
<212> TYPE: DNA
<213> ORGANISM: Artificial Sequence
<220> FEATURE:
<223> OTHER INFORMATION: Synthetic Construct

<400> SEQUENCE: 84
ttaaaaggag agggtaaaga gtgaaaacag tagttattat tg 42

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
cggggccaag gccggttttt tttagtttcg ataagaacga acggt 45

<210> SEQ ID NO 86
<211> LENGTH: 8000
<212> TYPE: DNA
<213> ORGANISM: Artificial Sequence
<220> FEATURE:
<223> OTHER INFORMATION: Synthetic Construct

<400> SEQUENCE: 86
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatggatcc 420
gagctcagga ggtaaaaaaa catgaaaaca gtagttatta ttgatgcatt acgaacacca 480
attggaaaat ataaaggcag cttaagtcaa gtaagtgccg tagacttagg aacacatgtt 540
acaacacaac ttttaaaaag acattccact atttctgaag aaattgatca agtaatcttt 600
ggaaatgttt tacaagctgg aaatggccaa aatcccgcac gacaaatagc aataaacagc 660
ggtttgtctc atgaaattcc cgcaatgacg gttaatgagg tctgcggatc aggaatgaag 720
gccgttattt tggcgaaaca attgattcaa ttaggagaag cggaagtttt aattgctggc 780
gggattgaga atatgtccca agcacctaaa ttacaacgtt ttaattacga aacagaaagc 840
tacgatgcgc ctttttctag tatgatgtat gatggattaa cggatgcctt tagtggtcag 900
gcaatgggct taactgctga aaatgtggcc gaaaagtatc atgtaactag agaagagcaa 960
gatcaatttt ctgtacattc acaattaaaa gcagctcaag cacaagcaga agggatattc 1020

-continued

```
gctgacgaaa tagccccatt agaagtatca ggaacgcttg tggagaaaga tgaagggatt   1080
cgccctaatt cgagcgttga gaagctagga acgcttaaaa cagtttttaa agaagacggt   1140
actgtaacag cagggaatgc atcaaccatt aatgatgggg cttctgcttt gattattgct   1200
tcacaagaat atgccgaagc acacggtctt ccttatttag ctattattcg agacagtgtg   1260
gaagtcggta ttgatccagc ctatatggga atttcgccga ttaaagccat tcaaaaactg   1320
ttagcgcgca atcaacttac tacggaagaa attgatctgt atgaaatcaa cgaagcattt   1380
gcagcaactt caatcgtggt ccaaagagaa ctggctttac cagaggaaaa ggtcaacatt   1440
tatggtggcg gtatttcatt aggtcatgcg attggtgcca caggtgctcg tttattaacg   1500
agtttaagtt atcaattaaa tcaaaaagaa aagaaatatg gagtggcttc tttatgtatc   1560
ggcggtggct taggactcgc tatgctacta gagagacctc agcaaaaaaa aaacagccga   1620
ttttatcaaa tgagtcctga ggaacgcctg gcttctcttc ttaatgaagg ccagatttct   1680
gctgatacaa aaaaagaatt tgaaaatacg gctttatctt cgcagattgc caatcatatg   1740
attgaaaatc aaatcagtga aacagaagtg ccgatgggcg ttggcttaca tttaacagtg   1800
gacgaaactg attatttggt accaatggcg acagaagagc cctcagttat tgcggctttg   1860
agtaatggtg caaaaatagc acaaggattt aaaacagtga atcaacaacg cttaatgcgt   1920
ggacaaatcg tttttacga tgttgcagat cccgagtcat tgattgataa actacaagta   1980
agagaagcgg aagtttttca acaagcagag ttaagttatc catctatcgt taaacggggc   2040
ggcggcttaa gagatttgca atatcgtact tttgatgaat catttgtatc tgtcgacttt   2100
ttagtagatg ttaaggatgc aatgggggca aatatcgtta acgctatgtt ggaaggtgtg   2160
gccgagttgt tccgtgaatg gtttgcggag caaaagattt tattcagtat tttaagtaat   2220
tatgccacgg agtcggttgt tacgatgaaa acggctattc cagtttcacg tttaagtaag   2280
gggagcaatg gccgggaaat tgctgaaaaa attgttttag cttcacgcta tgcttcatta   2340
gatccttatc gggcagtcac gcataacaaa ggaatcatga atggcattga agctgtagtt   2400
ttagctacag gaaatgatac acgcgctgtt agcgcttctt gtcatgcttt tgcggtgaag   2460
gaaggtcgct accaaggctt gactagttgg acgctggatg gcgaacaact aattggtgaa   2520
atttcagttc cgcttgcttt agccacggtt ggcggtgcca caaaagtctt acctaaatct   2580
caagcagctg ctgatttgtt agcagtgacg gatgcaaaag aactaagtcg agtagtagcg   2640
gctgttggtt tggcacaaaa tttagcggcg ttacgggcct tagtctctga aggaattcaa   2700
aaaggacaca tggctctaca agcacgttct ttagcgatga cggtcggagc tactggtaaa   2760
gaagttgagg cagtcgctca acaattaaaa cgtcaaaaaa cgatgaacca agaccgagcc   2820
atggctattt taaatgattt aagaaaacaa taaaggaggt aaaaaaacat gacaattggg   2880
attgataaaa ttagtttttt tgtgcccccc tattatattg atatgacggc actggctgaa   2940
gccagaaatg tagaccctgg aaaatttcat attggtattg ggcaagacca aatggcggtg   3000
aacccaatca gccaagatat tgtgacattt gcagccaatg ccgcagaagc gatcttgacc   3060
aaagaagata aagaggccat tgatatggtg attgtcggga ctgagtccag tatcgatgag   3120
tcaaaagcgg ccgcagttgt cttacatcgt ttaatgggga ttcaaccttt cgctcgctct   3180
ttcgaaatca aggaagcttg ttacggagca acagcaggct tacagttagc taagaatcac   3240
gtagccttac atccagataa aaaagtcttg gtcgtagcgg cagatattgc aaaatatggc   3300
ttaaattctg gcggtgagcc tacacaagga gctggggcgg ttgcaatgtt agttgctagt   3360
gaaccgcgca ttttggcttt aaaagaggat aatgtgatgc tgacgcaaga tatctatgac   3420
```

ttttggcgtc caacaggcca cccgtatcct atggtcgatg gtcctttgtc aaacgaaacc 3480
tacatccaat cttttgccca agtctgggat gaacataaaa aacgaaccgg tcttgatttt 3540
gcagattatg atgctttagc gttccatatt ccttacacaa aaatgggcaa aaaagcctta 3600
ttagcaaaaa tctccgacca aactgaagca gaacaggaac gaattttagc ccgttatgaa 3660
gaaagtatcg tctatagtcg tcgcgtagga aacttgtata cgggttcact ttatctggga 3720
ctcatttccc ttttagaaaa tgcaacgact ttaaccgcag gcaatcaaat tggtttattc 3780
agttatggtt ctggtgctgt cgctgaattt ttcactggtg aattagtagc tggttatcaa 3840
aatcatttac aaaaagaaac tcatttagca ctgctggata atcggacaga actttctatc 3900
gctgaatatg aagccatgtt tgcagaaact ttagacacag acattgatca aacgttagaa 3960
gatgaattaa aatatagtat ttctgctatt aataataccg ttcgttctta tcgaaactaa 4020
gagatctgca gctggtacca tatgggaatt cgaagcttgg gcccgaacaa aaactcatct 4080
cagaagagga tctgaatagc gccgtcgacc atcatcatca tcatcattga gtttaaacgg 4140
tctccagctt ggctgttttg gcggatgaga gaagattttc agcctgatac agattaaatc 4200
agaacgcaga agcggtctga taaaacagaa tttgcctggc ggcagtagcg cggtggtccc 4260
acctgacccc atgccgaact cagaagtgaa acgccgtagc gccgatggta gtgtggggtc 4320
tccccatgcg agagtaggga actgccaggc atcaaataaa acgaaaggct cagtcgaaag 4380
actgggcctt tcgttttatc tgttgtttgt cggtgaacgc tctcctgagt aggacaaatc 4440
cgccgggagc ggatttgaac gttgcgaagc aacggcccgg agggtggcgg gcaggacgcc 4500
cgccataaac tgccaggcat caaattaagc agaaggccat cctgacggat ggcctttttg 4560
cgtttctaca aactcttttt gtttattttt ctaaatacat tcaaatatgt atccgctcat 4620
gagacaataa ccctgataaa tgcttcaata atattgaaaa aggaagagta tgagtattca 4680
acatttccgt gtcgccctta ttcccttttt tgcggcattt tgccttcctg tttttgctca 4740
cccagaaacg ctggtgaaag taaaagatgc tgaagatcag ttgggtgcac gagtgggtta 4800
catcgaactg gatctcaaca gcggtaagat ccttgagagt tttcgccccg aagaacgttt 4860
tccaatgatg agcactttta aagttctgct atgtggcgcg gtattatccc gtgttgacgc 4920
cgggcaagag caactcggtc gccgcataca ctattctcag aatgacttgg ttgagtactc 4980
accagtcaca gaaaagcatc ttacggatgg catgacagta agagaattat gcagtgctgc 5040
cataaccatg agtgataaca ctgcggccaa cttacttctg acaacgatcg gaggaccgaa 5100
ggagctaacc gcttttttgc acaacatggg ggatcatgta actcgccttg atcgttggga 5160
accggagctg aatgaagcca taccaaacga cgagcgtgac accacgatgc ctgtagcaat 5220
ggcaacaacg ttgcgcaaac tattaactgg cgaactactt actctagctt cccggcaaca 5280
attaatagac tggatggagg cggataaagt tgcaggacca cttctgcgct cggcccttcc 5340
ggctggctgg tttattgctg ataaatctgg agccggtgag cgtgggtctc gcggtatcat 5400
tgcagcactg gggccagatg gtaagccctc ccgtatcgta gttatctaca cgacggggag 5460
tcaggcaact atggatgaac gaaatagaca gatcgctgag ataggtgcct cactgattaa 5520
gcattggtaa ctgtcagacc aagtttactc atatatactt tagattgatt taaaacttca 5580
tttttaattt aaaaggatct aggtgaagat cctttttgat aatctcatga ccaaaatccc 5640
ttaacgtgag ttttcgttcc actgagcgtc agaccccgta gaaaagatca aaggatcttc 5700
ttgagatcct ttttttctgc gcgtaatctg ctgcttgcaa acaaaaaaac caccgctacc 5760

```
agcggtggtt tgtttgccgg atcaagagct accaactctt tttccgaagg taactggctt   5820
cagcagagcg cagataccaa atactgtcct tctagtgtag ccgtagttag gccaccactt   5880
caagaactct gtagcaccgc ctacatacct cgctctgcta atcctgttac cagtggctgc   5940
tgccagtggc gataagtcgt gtcttaccgg gttggactca agacgatagt taccggataa   6000
ggcgcagcgg tcgggctgaa cggggggttc gtgcacacag cccagcttgg agcgaacgac   6060
ctacaccgaa ctgagatacc tacagcgtga gctatgagaa agcgccacgc ttcccgaagg   6120
gagaaaggcg gacaggtatc cggtaagcgg cagggtcgga acaggagagc gcacgaggga   6180
gcttccaggg ggaaacgcct ggtatcttta tagtcctgtc gggtttcgcc acctctgact   6240
tgagcgtcga tttttgtgat gctcgtcagg ggggcggagc ctatggaaaa acgccagcaa   6300
cgcggccttt ttacggttcc tggccttttg ctggcctttt gctcacatgt tctttcctgc   6360
gttatcccct gattctgtgg ataaccgtat taccgccttt gagtgagctg ataccgctcg   6420
ccgcagccga acgaccgagc gcagcgagtc agtgagcgag gaagcggaag agcgcctgat   6480
gcggtatttt ctccttacgc atctgtgcgg tatttcacac cgcatatggt gcactctcag   6540
tacaatctgc tctgatgccg catagttaag ccagtataca ctccgctatc gctacgtgac   6600
tgggtcatgg ctgcgccccg acacccgcca acacccgctg acgcgccctg acgggcttgt   6660
ctgctcccgg catccgctta cagacaagct gtgaccgtct ccgggagctg catgtgtcag   6720
aggttttcac cgtcatcacc gaaacgcgcg aggcagcaga tcaattcgcg cgcgaaggcg   6780
aagcggcatg catttacgtt gacaccatcg aatggtgcaa aacctttcgc ggtatggcat   6840
gatagcgccc ggaagagagt caattcaggg tggtgaatgt gaaaccagta acgttatacg   6900
atgtcgcaga gtatgccggt gtctcttatc agaccgtttc ccgcgtggtg aaccaggcca   6960
gccacgtttc tgcgaaaacg cgggaaaaag tggaagcggc gatggcggag ctgaattaca   7020
ttcccaaccg cgtggcacaa caactggcgg gcaaacagtc gttgctgatt ggcgttgcca   7080
cctccagtct ggccctgcac gcgccgtcgc aaattgtcgc ggcgattaaa tctcgcgccg   7140
atcaactggg tgccagcgtg gtggtgtcga tggtagaacg aagcggcgtc gaagcctgta   7200
aagcggcggt gcacaatctt ctcgcgcaac gcgtcagtgg gctgatcatt aactatccgc   7260
tggatgacca ggatgccatt gctgtggaag ctgcctgcac taatgttccg gcgttatttc   7320
ttgatgtctc tgaccagaca cccatcaaca gtattatttt ctcccatgaa gacggtacgc   7380
gactgggcgt ggagcatctg gtcgcattgg gtcaccagca aatcgcgctg ttagcgggcc   7440
cattaagttc tgtctcggcg cgtctgcgtc tggctggctg gcataaatat ctcactcgca   7500
atcaaattca gccgatagcg gaacgggaag gcgactggag tgccatgtcc ggttttcaac   7560
aaaccatgca aatgctgaat gagggcatcg ttcccactgc gatgctggtt gccaacgatc   7620
agatggcgct gggcgcaatg cgcgccatta ccgagtccgg gctgcgcgtt ggtgcggata   7680
tctcggtagt gggatacgac gataccgaag acagctcatg ttatatcccg ccgtcaacca   7740
ccatcaaaca ggattttcgc ctgctggggc aaaccagcgt ggaccgcttg ctgcaactct   7800
ctcagggcca ggcggtgaag ggcaatcagc tgttgcccgt ctcactggtg aaaagaaaaa   7860
ccaccctggc gcccaatacg caaaccgcct ctccccgcgc gttggccgat tcattaatgc   7920
agctggcacg acaggtttcc cgactggaaa gcgggcagtg agcgcaacgc aattaatgtg   7980
agttagcgcg aattgatctg                                               8000
```

<210> SEQ ID NO 87
<211> LENGTH: 10433

<212> TYPE: DNA
<213> ORGANISM: Artificial Sequence
<220> FEATURE:
<223> OTHER INFORMATION: Synthetic Construct

<400> SEQUENCE: 87

```
cccgtcttac tgtcgggaat tcgcgttggc cgattcatta atgcagattc tgaaatgagc     60
tgttgacaat taatcatccg gctcgtataa tgtgtggaat tgtgagcgga taacaatttc    120
acacaggaaa cagcgccgct gagaaaaagc gaagcggcac tgctctttaa caatttatca    180
gacaatctgt gtgggcactc gaccggaatt atcgattaac tttattatta aaaattaaag    240
aggtatatat taatgtatcg attaaataag gaggaataaa ccatggatcc gagctcagga    300
ggtaaaaaaa catgaaaaca gtagttatta ttgatgcatt acgaacacca attggaaaat    360
ataaaggcag cttaagtcaa gtaagtgccg tagacttagg aacacatgtt acaacacaac    420
ttttaaaaag acattccact atttctgaag aaattgatca agtaatcttt ggaaatgttt    480
tacaagctgg aaatggccaa aatcccgcac gacaaatagc aataaacagc ggtttgtctc    540
atgaaattcc cgcaatgacg gttaatgagg tctgcggatc aggaatgaag gccgttattt    600
tggcgaaaca attgattcaa ttaggagaag cggaagtttt aattgctggc gggattgaga    660
atatgtccca agcacctaaa ttacaacgtt ttaattacga aacagaaagc tacgatgcgc    720
ctttttctag tatgatgtat gatggattaa cggatgcctt tagtggtcag gcaatgggct    780
taactgctga aaatgtggcc gaaaagtatc atgtaactag agaagagcaa gatcaatttt    840
ctgtacattc acaattaaaa gcagctcaag cacaagcaga agggatattc gctgacgaaa    900
tagccccatt agaagtatca ggaacgcttg tggagaaaga tgaagggatt cgccctaatt    960
cgagcgttga gaagctagga acgcttaaaa cagtttttaa agaagacggt actgtaacag   1020
cagggaatgc atcaaccatt aatgatgggg cttctgcttt gattattgct tcacaagaat   1080
atgccgaagc acacggtctt ccttatttag ctattattcg agacagtgtg gaagtcggta   1140
ttgatccagc ctatatggga atttcgccga ttaaagccat tcaaaaactg ttagcgcgca   1200
atcaacttac tacggaagaa attgatctgt atgaaatcaa cgaagcattt gcagcaactt   1260
caatcgtggt ccaaagagaa ctggctttac cagaggaaaa ggtcaacatt tatggtggcg   1320
gtatttcatt aggtcatgcg attggtgcca caggtgctcg tttattaacg agtttaagtt   1380
atcaattaaa tcaaaaagaa aagaaatatg gagtggcttc tttatgtatc ggcggtggct   1440
taggactcgc tatgctacta gagagacctc agcaaaaaaa aaacagccga ttttatcaaa   1500
tgagtcctga ggaacgcctg gcttctcttc ttaatgaagg ccagatttct gctgatacaa   1560
aaaaagaatt tgaaaatacg gctttatctt cgcagattgc caatcatatg attgaaaatc   1620
aaatcagtga aacagaagtg ccgatgggcg ttggcttaca tttaacagtg gacgaaactg   1680
attatttggt accaatggcg acagaagagc cctcagttat tgcggctttg agtaatggtg   1740
caaaaatagc acaaggattt aaaacagtga atcaacaacg cttaatgcgt ggacaaatcg   1800
ttttttacga tgttgcagat cccgagtcat tgattgataa actacaagta agagaagcgg   1860
aagtttttca acaagcagag ttaagttatc catctatcgt taaacggggc ggcggcttaa   1920
gagatttgca atatcgtact tttgatgaat catttgtatc tgtcgacttt ttagtagatg   1980
ttaaggatgc aatgggggca aatatcgtta acgctatgtt ggaaggtgtg gccgagttgt   2040
tccgtgaatg gtttgcggag caaaagattt tattcagtat tttaagtaat tatgccacgg   2100
agtcggttgt tacgatgaaa acggctattc cagtttcacg tttaagtaag gggagcaatg   2160
```

gccgggaaat tgctgaaaaa attgttttag cttcacgcta tgcttcatta gatccttatc 2220
gggcagtcac gcataacaaa ggaatcatga atggcattga agctgtagtt ttagctacag 2280
gaaatgatac acgcgctgtt agcgcttctt gtcatgcttt tgcggtgaag gaaggtcgct 2340
accaaggctt gactagttgg acgctggatg gcgaacaact aattggtgaa atttcagttc 2400
cgcttgcttt agccacggtt ggcggtgcca caaaagtctt acctaaatct caagcagctg 2460
ctgatttgtt agcagtgacg gatgcaaaag aactaagtcg agtagtagcg gctgttggtt 2520
tggcacaaaa tttagcggcg ttacgggcct tagtctctga aggaattcaa aaaggacaca 2580
tggctctaca agcacgttct ttagcgatga cggtcggagc tactggtaaa gaagttgagg 2640
cagtcgctca acaattaaaa cgtcaaaaaa cgatgaacca agaccgagcc atggctattt 2700
taaatgattt aagaaaacaa taaaggaggt aaaaaaacat gacaattggg attgataaaa 2760
ttagtttttt tgtgcccccct tattatattg atatgacggc actggctgaa gccagaaatg 2820
tagaccctgg aaaatttcat attggtattg ggcaagacca aatggcggtg aacccaatca 2880
gccaagatat tgtgacattt gcagccaatg ccgcagaagc gatcttgacc aaagaagata 2940
aagaggccat tgatatggtg attgtcggga ctgagtccag tatcgatgag tcaaaagcgg 3000
ccgcagttgt cttacatcgt ttaatgggga ttcaaccttt cgctcgctct ttcgaaatca 3060
aggaagcttg ttacggagca acagcaggct tacagttagc taagaatcac gtagccttac 3120
atccagataa aaaagtcttg gtcgtagcgg cagatattgc aaaatatggc ttaaattctg 3180
gcggtgagcc tacacaagga gctggggcgg ttgcaatgtt agttgctagt gaaccgcgca 3240
ttttggcttt aaaagaggat aatgtgatgc tgacgcaaga tatctatgac ttttggcgtc 3300
caacaggcca cccgtatcct atggtcgatg gtcctttgtc aaacgaaacc tacatccaat 3360
cttttgccca agtctgggat gaacataaaa aacgaaccgg tcttgatttt gcagattatg 3420
atgctttagc gttccatatt ccttacacaa aaatgggcaa aaaagcctta ttagcaaaaa 3480
tctccgacca aactgaagca gaacaggaac gaattttagc ccgttatgaa gaaagtatcg 3540
tctatagtcg tcgcgtagga aacttgtata cgggttcact ttatctggga ctcatttccc 3600
ttttagaaaa tgcaacgact ttaaccgcag gcaatcaaat tggtttattc agttatggtt 3660
ctggtgctgt cgctgaattt ttcactggtg aattagtagc tggttatcaa aatcatttac 3720
aaaaagaaac tcatttagca ctgctggata atcggacaga actttctatc gctgaatatg 3780
aagccatgtt tgcagaaact ttagacacag acattgatca aacgttagaa gatgaattaa 3840
aatatagtat ttctgctatt aataataccg ttcgttctta tcgaaactaa agatctgcat 3900
cctgcattcg cccttaggag gtaaaaaaac atgtgtgcga cctcttctca atttactcag 3960
attaccgagc ataattcccg tcgttccgca aactatcagc caaacctgtg gaatttcgaa 4020
ttcctgcaat ccctggagaa cgacctgaaa gtggaaaagc tggaggagaa agcgaccaaa 4080
ctggaggaag aagttcgctg catgatcaac cgtgtagaca cccagccgct gtccctgctg 4140
gagctgatcg acgatgtgca gcgcctgggt ctgacctaca aatttgaaaa agacatcatt 4200
aaagccctgg aaaacatcgt actgctggac gaaaacaaaa agaacaaatc tgacctgcac 4260
gcaaccgctc tgtctttccg tctgctgcgt cagcacggtt tcgaggtttc tcaggatgtt 4320
tttgagcgtt tcaaggataa agaaggtggt ttcagcggtg aactgaaagg tgacgtccaa 4380
ggcctgctga gcctgtatga agcgtcttac ctgggtttcg agggtgagaa cctgctggag 4440
gaggcgcgta ccttttccat cacccacctg aagaacaacc tgaaagaagg cattaatacc 4500
aaggttgcag aacaagtgag ccacgccctg gaactgccat atcaccagcg tctgcaccgt 4560

-continued

```
ctggaggcac gttggttcct ggataaatac gaaccgaaag aaccgcatca ccagctgctg   4620
ctggagctgg cgaagctgga ttttaacatg gtacagaccc tgcaccagaa agagctgcaa   4680
gatctgtccc gctggtggac cgagatgggc ctggctagca aactggattt tgtacgcgac   4740
cgcctgatgg aagtttattt ctgggcactg ggtatggcgc cagacccgca gtttggtgaa   4800
tgtcgcaaag ctgttactaa aatgtttggt ctggtgacga tcatcgatga cgtgtatgac   4860
gtttatggca ctctggacga actgcaactg ttcaccgatg ctgtagagcg ctgggacgtt   4920
aacgctatta acaccctgcc ggactatatg aaactgtgtt tcctggcact gtacaacacc   4980
gttaacgaca cgtcctattc tattctgaaa gagaaaggtc ataacaacct gtcctatctg   5040
acgaaaagct ggcgtgaact gtgcaaagcc tttctgcaag aggcgaaatg gtccaacaac   5100
aaaattatcc cggctttctc caagtacctg gaaaacgcca gcgtttcctc ctccggtgta   5160
gcgctgctgg cgccgtctta cttttccgta tgccagcagc aggaagacat ctccgaccac   5220
gcgctgcgtt ccctgaccga cttccatggt ctggtgcgtt ctagctgcgt tatcttccgc   5280
ctgtgcaacg atctggccac ctctgcggcg gagctggaac gtggcgagac taccaattct   5340
atcattagct acatgcacga aaacgatggt accagcgagg aacaggcccg cgaagaactg   5400
cgtaaactga tcgacgccga atggaaaaag atgaatcgtg aacgcgttag cgactccacc   5460
ctgctgccta aagcgttcat ggaaatcgca gttaacatgg cacgtgtttc ccactgcacc   5520
taccagtatg gcgatggtct gggtcgccca gactacgcga ctgaaaaccg catcaaactg   5580
ctgctgattg accctttccc gattaaccag ctgatgtatg tctaactgca gctggtacca   5640
tatgggaatt cgaagcttgg gcccgaacaa aaactcatct cagaagagga tctgaatagc   5700
gccgtcgacc atcatcatca tcatcattga gtttaaacgg tctccagctt ggctgttttg   5760
gcggatgaga gaagattttc agcctgatac agattaaatc agaacgcaga agcggtctga   5820
taaaacagaa tttgcctggc ggcagtagcg cggtggtccc acctgacccc atgccgaact   5880
cagaagtgaa acgccgtagc gccgatggta gtgtggggtc tccccatgcg agagtaggga   5940
actgccaggc atcaaataaa acgaaaggct cagtcgaaag actgggcctt tcgttttatc   6000
tgttgtttgt cggtgaacgc tctcctgagt aggacaaatc cgccgggagc ggatttgaac   6060
gttgcgaagc aacggcccgg agggtggcgg gcaggacgcc cgccataaac tgccaggcat   6120
caaattaagc agaaggccat cctgacggat ggcctttttg cgtttctaca aactcttttt   6180
gtttattttt ctaaatacat tcaaatatgt atccgctcat gagacaataa ccctgataaa   6240
tgcttcaata atctggcgta atagcgaaga ggcccgcacc gatcgccctt cccaacagtt   6300
gcgcagcctg aatggcgaat ggcgcctgat gcggtatttt ctccttacgc atctgtgcgg   6360
tatttcacac cgcatatggt gcactctcag tacaatctgc tctgatgccg catagttaag   6420
ccagccccga cacccgccaa cacccgctga cgagcttagt aaagccctcg ctagatttta   6480
atgcggatgt tgcgattact tcgccaacta ttgcgataac aagaaaaagc cagcctttca   6540
tgatatatct cccaatttgt gtagggctta ttatgcacgc ttaaaaataa taaaagcaga   6600
cttgacctga tagtttggct gtgagcaatt atgtgcttag tgcatctaac gcttgagtta   6660
agccgcgccg cgaagcggcg tcggcttgaa cgaattgtta gacattattt gccgactacc   6720
ttggtgatct cgcctttcac gtagtggaca aattcttcca actgatctgc gcgcgaggcc   6780
aagcgatctt cttcttgtcc aagataagcc tgtctagctt caagtatgac gggctgatac   6840
tgggccggca ggcgctccat tgcccagtcg gcagcgacat ccttcggcgc gattttgccg   6900
```

-continued

```
gttactgcgc tgtaccaaat gcgggacaac gtaagcacta catttcgctc atcgccagcc   6960
cagtcgggcg gcgagttcca tagcgttaag gtttcattta gcgcctcaaa tagatcctgt   7020
tcaggaaccg gatcaaagag ttcctccgcc gctggaccta ccaaggcaac gctatgttct   7080
cttgcttttg tcagcaagat agccagatca atgtcgatcg tggctggctc gaagatacct   7140
gcaagaatgt cattgcgctg ccattctcca aattgcagtt cgcgcttagc tggataacgc   7200
cacggaatga tgtcgtcgtg cacaacaatg gtgacttcta cagcgcggag aatctcgctc   7260
tctccagggg aagccgaagt ttccaaaagg tcgttgatca aagctcgccg cgttgtttca   7320
tcaagcctta cggtcaccgt aaccagcaaa tcaatatcac tgtgtggctt caggccgcca   7380
tccactgcgg agccgtacaa atgtacggcc agcaacgtcg gttcgagatg gcgctcgatg   7440
acgccaacta cctctgatag ttgagtcgat acttcggcga tcaccgcttc cctcatgatg   7500
tttaactttg ttttagggcg actgccctgc tgcgtaacat cgttgctgct ccataacatc   7560
aaacatcgac ccacggcgta acgcgcttgc tgcttggatg cccgaggcat agactgtacc   7620
ccaaaaaaac agtcataaca agccatgaaa accgccactg cgccgttacc accgctgcgt   7680
tcggtcaagg ttctggacca gttgcgtgag cgcatacgct acttgcatta cagcttacga   7740
accgaacagg cttatgtcca ctgggttcgt gccttcatcc gtttccacgg tgtgcgtcac   7800
ccggcaacct tgggcagcag cgaagtcgag gcatttctgt cctggctggc gaacgagcgc   7860
aaggtttcgg tctccacgca tcgtcaggca ttggcggcct tgctgttctt ctacggcaag   7920
gtgctgtgca cggatctgcc ctggcttcag gagatcggaa gacctcggcc gtcgcggcgc   7980
ttgccggtgg tgctgacccc ggatgaagtg gttcgcatcc tcggttttct ggaaggcgag   8040
catcgtttgt tcgcccagct tctgtatgga acgggcatgc ggatcagtga gggtttgcaa   8100
ctgcgggtca aggatctgga tttcgatcac ggcacgatca tcgtgcggga gggcaagggc   8160
tccaaggatc gggccttgat gttacccgag agcttggcac ccagcctgcg cgagcagggg   8220
aattaattcc cacgggtttt gctgcccgca aacgggctgt tctggtgttg ctagtttgtt   8280
atcagaatcg cagatccggc ttcagccggt ttgccggctg aaagcgctat ttcttccaga   8340
attgccatga tttttcccc acgggaggcg tcactggctc ccgtgttgtc ggcagctttg   8400
attcgataag cagcatcgcc tgtttcaggc tgtctatgtg tgactgttga gctgtaacaa   8460
gttgtctcag gtgttcaatt tcatgttcta gttgctttgt tttactggtt tcacctgttc   8520
tattaggtgt tacatgctgt tcatctgtta cattgtcgat ctgttcatgg tgaacagctt   8580
tgaatgcacc aaaaactcgt aaaagctctg atgtatctat cttttttaca ccgttttcat   8640
ctgtgcatat ggacagtttt ccctttgata tgtaacggtg aacagttgtt ctacttttgt   8700
ttgttagtct tgatgcttca ctgatagata caagagccat aagaacctca gatccttccg   8760
tatttagcca gtatgttctc tagtgtggtt cgttgttttt gcgtgagcca tgagaacgaa   8820
ccattgagat catacttact ttgcatgtca ctcaaaaatt ttgcctcaaa actggtgagc   8880
tgaatttttg cagttaaagc atcgtgtagt gtttttctta gtccgttatg taggtaggaa   8940
tctgatgtaa tggttgttgg tattttgtca ccattcattt ttatctggtt gttctcaagt   9000
tcggttacga gatccatttg tctatctagt tcaacttgga aaatcaacgt atcagtcggg   9060
cggcctcgct tatcaaccac caatttcata ttgctgtaag tgtttaaatc tttacttatt   9120
ggtttcaaaa cccattggtt aagcctttta aactcatggt agttattttc aagcattaac   9180
atgaacttaa attcatcaag gctaatctct atatttgcct tgtgagtttt cttttgtgtt   9240
agttctttta ataaccactc ataaatcctc atagagtatt tgttttcaaa agacttaaca   9300
```

tgttccagat tatattttat gaattttttt aactggaaaa gataaggcaa tatctcttca 9360
ctaaaaacta attctaattt ttcgcttgag aacttggcat agtttgtcca ctggaaaatc 9420
tcaaagcctt taaccaaagg attcctgatt tccacagttc tcgtcatcag ctctctggtt 9480
gctttagcta atacaccata agcattttcc ctactgatgt tcatcatctg agcgtattgg 9540
ttataagtga acgataccgt ccgttctttc cttgtagggt tttcaatcgt ggggttgagt 9600
agtgccacac agcataaaat tagcttggtt tcatgctccg ttaagtcata gcgactaatc 9660
gctagttcat ttgctttgaa aacaactaat tcagacatac atctcaattg gtctaggtga 9720
ttttaatcac tataccaatt gagatgggct agtcaatgat aattactagt ccttttcctt 9780
tgagttgtgg gtatctgtaa attctgctag acctttgctg gaaaacttgt aaattctgct 9840
agaccctctg taaattccgc tagacctttg tgtgtttttt ttgtttatat tcaagtggtt 9900
ataatttata gaataaagaa agaataaaaa aagataaaaa gaatagatcc cagccctgtg 9960
tataactcac tactttagtc agttccgcag tattacaaaa ggatgtcgca aacgctgttt 10020
gctcctctac aaaacagacc ttaaaaccct aaaggcttaa gtagcaccct cgcaagctcg 10080
ggcaaatcgc tgaatattcc ttttgtctcc gaccatcagg cacctgagtc gctgtctttt 10140
tcgtgacatt cagttcgctg cgctcacggc tctggcagtg aatgggggta aatggcacta 10200
caggcgcctt ttatggattc atgcaaggaa actacccata atacaagaaa agcccgtcac 10260
gggcttctca gggcgtttta tggcgggtct gctatgtggt gctatctgac tttttgctgt 10320
tcagcagttc ctgccctctg attttccagt ctgaccactt cggattatcc cgtgacaggt 10380
cattcagact ggctaatgca cccagtaagg cagcggtatc atcaacaggc tta 10433

<210> SEQ ID NO 88
<211> LENGTH: 31
<212> TYPE: DNA
<213> ORGANISM: Artificial Sequence
<220> FEATURE:
<223> OTHER INFORMATION: Synthetic Construct

<400> SEQUENCE: 88
cttgatgcat cctgcattcg cccttaggag g 31

<210> SEQ ID NO 89
<211> LENGTH: 23
<212> TYPE: DNA
<213> ORGANISM: Artificial Sequence
<220> FEATURE:
<223> OTHER INFORMATION: Synthetic Construct

<400> SEQUENCE: 89
ccaggcaaat tctgttttat cag 23

<210> SEQ ID NO 90
<211> LENGTH: 10356
<212> TYPE: DNA
<213> ORGANISM: Artificial Sequence
<220> FEATURE:
<223> OTHER INFORMATION: Synthetic Construct

<400> SEQUENCE: 90
caagaaaaat gccccgctta cgcagggcat ccatttatta ctcaaccgta accgattttg 60
ccaggttacg cggctggtca acgtcggtgc ctttgatcag cgcgacatgg taagccagca 120
gctgcagcgg aacggtgtag aagatcggtg caatcacctc ttccacatgc ggcatctcga 180

-continued

```
tgatgtgcat gttatcgcta cttacaaaac ccgcatcctg atcggcgaag acatacaact    240
gaccgccacg cgcgcgaact tcttcaatgt tggatttcag tttttccagc aattcgttgt    300
tcggtgcaac aacaataacc ggcatatcgg catcaattag cgccagcgga ccgtgtttca    360
gttcgccagc agcgtaggct tcagcgtgaa tgtaagagat ctctttcaac ttcaatgcgc    420
cttccagcgc gattgggtac tgatcgccac ggcccaggaa cagcgcgtga tgtttgtcag    480
agaaatcttc tgccagcgct tcaatgcgtt tgtcctgaga cagcatctgc tcaatacggc    540
tcggcagcgc ctgcagacca tgcacgatgt catgttcaat ggaggcatcc agacctttca    600
ggcgagacag cttcgccacc agcatcaaca gcacagttaa ctgagtggtg aatgctttag    660
tggatgccac gccgatttct gtacccgcgt tggtcattag cgccagatcg gattcgcgca    720
ccagagaaga acccggaacg ttacagattg ccagtgaacc aaggtaaccc agctctttcg    780
acagacgcag gccagccagg gtatccgcgg tttcgccaga ctgtgacacg atcgcccttc    840
ccaacagttg cgcagcctat acgtacggca gtttaaggtt tacacctata aaagagagag    900
ccgttatcgt ctgtttgtgg atgtacagag tgatattatt gacacgccgg ggcgacggat    960
ggtgatcccc ctggccagtg cacgtctgct gtcagataaa gtctcccgtg aactttaccc   1020
ggtggtgcat atcggggatg aaagctggcg catgatgacc accgatatgg ccagtgtgcc   1080
ggtctccgtt atcggggaag aagtggctga tctcagccac cgcgaaaatg acatcaaaaa   1140
cgccattaac ctgatgttct ggggaatata aatgtcaggc atgagattat caaaaaggat   1200
cttcacctag atccttttca cgtagaaagc cagtccgcag aaacggtgct gaccccggat   1260
gaatgtcagc tactgggcta tctggacaag ggaaaacgca agcgcaaaga gaaagcaggt   1320
agcttgcagt gggcttacat ggcgatagct agactgggcg gttttatgga cagcaagcga   1380
accggaattg ccagctgggg cgccctctgg taaggttggg aagccctgca aagtaaactg   1440
gatggctttc tcgccgccaa ggatctgatg gcgcagggga tcaagctctg atcaagagac   1500
aggatgagga tcgtttcgca tgattgaaca agatggattg cacgcaggtt ctccggccgc   1560
ttgggtggag aggctattcg gctatgactg ggcacaacag acaatcggct gctctgatgc   1620
cgccgtgttc cggctgtcag cgcaggggcg cccggttctt tttgtcaaga ccgacctgtc   1680
cggtgccctg aatgaactgc aagacgaggc agcgcggcta tcgtggctgg ccacgacggg   1740
cgttccttgc gcagctgtgc tcgacgttgt cactgaagcg ggaagggact ggctgctatt   1800
gggcgaagtg ccggggcagg atctcctgtc atctcacctt gctcctgccg agaaagtatc   1860
catcatggct gatgcaatgc ggcggctgca tacgcttgat ccggctacct gcccattcga   1920
ccaccaagcg aaacatcgca tcgagcgagc acgtactcgg atggaagccg gtcttgtcga   1980
tcaggatgat ctggacgaag agcatcaggg gctcgcgcca gccgaactgt tcgccaggct   2040
caaggcgagc atgcccgacg gcgaggatct cgtcgtgacc catggcgatg cctgcttgcc   2100
gaatatcatg gtggaaaatg gccgcttttc tggattcatc gactgtggcc ggctgggtgt   2160
ggcggaccgc tatcaggaca tagcgttggc tacccgtgat attgctgaag agcttggcgg   2220
cgaatgggct gaccgcttcc tcgtgcttta cggtatcgcc gctcccgatt cgcagcgcat   2280
cgccttctat cgccttcttg acgagttctt ctgaattatt aacgcttaca atttcctgat   2340
gcggtatttt ctccttacgc atctgtgcgg tatttcacac cgcatacagg tggcactttt   2400
cggggaaatg tgcgcggaac ccctatttgt ttatttttct aaatacattc aaatatgtat   2460
ccgctcatga gacaataacc ctgataaatg cttcaataat agcacgtgag gagggccacc   2520
atggccaagt tgaccagtgc cgttccggtg ctcaccgcgc gcgacgtcgc cggagcggtc   2580
```

-continued

```
gagttctgga ccgaccggct cgggttctcc cctagtaacg gccgccagtg tgctggaatt   2640
caggcagttc aacctgttga tagtacgtac taagctctca tgtttcacgt actaagctct   2700
catgtttaac gtactaagct ctcatgttta acgaactaaa ccctcatggc taacgtacta   2760
agctctcatg gctaacgtac taagctctca tgtttcacgt actaagctct catgtttgaa   2820
caataaaatt aatataaatc agcaacttaa atagcctcta aggttttaag ttttataaga   2880
aaaaaaagaa tatataaggc ttttaaagct tttaaggttt aacggttgtg gacaacaagc   2940
cagggatgta acgcactgag aagcccttag agcctctcaa agcaattttc agtgacacag   3000
gaacacttaa cggctgacag cctgaattct gcagatatct gtttttccac tcttcgttca   3060
ctttcgccag gtagctggtg aagacgaagg aagtcccgga gccatctgcg cggcgtacta   3120
cagcaatgtt ttgtgaaggc agtttcagac ccggattcag tttggcgatg gcttcatcat   3180
cccacttctt gattttgccc aggtagatgt cgccgagggt tttaccatcc agcaccagtt   3240
cgccagactt cagccctgga atgttaaccg ccagcaccac gccgccaatc acggtcggga   3300
actggaacag accttcctga gccagttttt cgtcagacag cggcgcgtca gaggcaccaa   3360
aatcaacggt attagcgata atctgtttta cgccaccgga agaaccgata ccctggtagt   3420
taactttatt accggtttct ttctggtaag tgtcagccca tttggcatac accggcgcag   3480
ggaaggttgc acctgcacct gtcaggcttg cttctgcaaa cacagagaaa gcactcatcg   3540
ataaggtcgc ggcgacaaca gttgcgacgg tggtacgcat aactttcata atgtctcctg   3600
ggaggattca taaagcattg tttgttggct acgagaagca aaataggaca aacaggtgac   3660
agttatatgt aaggaatatg acagttttat gacagagaga taaagtcttc agtctgattt   3720
aaataagcgt tgatattcag tcaattacaa acattaataa cgaagagatg acagaaaaat   3780
tttcattctg tgacagagaa aaagtagccg aagatgacgg tttgtcacat ggagttggca   3840
ggatgtttga ttaaaagcaa ttaaccctca ctaaagggcg gccgcgaagt tcctattctc   3900
tagaaagtat aggaacttca ttctaccggg taggggaggc gcttttccca aggcagtctg   3960
gagcatgcgc tttagcagcc ccgctgggca cttggcgcta cacaagtggc ctctggcctc   4020
gcacacattc cacatccacc ggtaggcgcc aaccggctcc gttctttggt ggccccttcg   4080
cgccaccttc cactcctccc ctagtcagga agttcccccc cgccccgcag ctcgcgtcgt   4140
gcaggacgtg acaaatggaa gtagcacgtc tcactagtct cgtgcagatg gacagcaccg   4200
ctgagcaatg gaagcgggta ggcctttggg gcagcggcca atagcagctt tgctccttcg   4260
ctttctgggc tcagaggctg ggaaggggtg ggtccggggg cgggctcagg ggcgggctca   4320
ggggcggggc gggcgcccga aggtcctccg gaggcccggc attctgcacg cttcaaaagc   4380
gcacgtctgc cgcgctgttc tcctcttcct catctccggg cctttcgacc tgcagcagca   4440
cgtgttgaca attaatcatc ggcatagtat atcggcatag tataatacga caaggtgagg   4500
aactaaacca tggagaaaaa aatcactgga tataccaccg ttgatatatc ccaatggcat   4560
cgtaaagaac attttgaggc atttcagtca gttgctcaat gtacctataa ccagaccgtt   4620
cagctggata ttacggcctt tttaaagacc gtaaagaaaa ataagcacaa gttttatccg   4680
gcctttattc acattcttgc ccgcctgatg aatgctcatc cggaattccg tatggcaatg   4740
aaagacggtg agctggtgat atgggatagt gttcaccctt gttacaccgt tttccatgag   4800
caaactgaaa cgttttcatc gctctggagt gaataccacg acgatttccg gcagtttcta   4860
cacatatatt cgcaagatgt ggcgtgttac ggtgaaaacc tggcctattt ccctaaaggg   4920
```

-continued

```
tttattgaga atatgttttt cgtctcagcc aatccctggg tgagtttcac cagttttgat   4980
ttaaacgtgg ccaatatgga caacttcttc gcccccgttt tcaccatggg caaatattat   5040
acgcaaggcg acaaggtgct gatgccgctg gcgattcagg ttcatcatgc cgtttgtgat   5100
ggcttccatg tcggcagaat gcttaatgaa ttacaacagt actgcgatga gtggcagggc   5160
ggggcgtaag cgggactctg gggttcgaat aaagaccgac caagcgacgt ctgagagctc   5220
cctggcgaat tcggtaccaa taaaagagct ttattttcat gatctgtgtg ttggtttttg   5280
tgtgcggcgc ggaagttcct attctctaga aagtatagga acttcctcga gccctatagt   5340
gagtcgtatt agcccttgac gatgccacat cctgagcaaa taattcaacc actaattgtg   5400
agcggataac acaaggagga aacagctatg tcattaccgt tcttaacttc tgcaccggga   5460
aaggttatta tttttggtga acactctgct gtgtacaaca agcctgccgt cgctgctagt   5520
gtgtctgcgt tgagaaccta cctgctaata agcgagtcat ctgcaccaga tactattgaa   5580
ttggacttcc cggacattag ctttaatcat aagtggtcca tcaatgattt caatgccatc   5640
accgaggatc aagtaaactc ccaaaaattg gccaaggctc aacaagccac cgatggcttg   5700
tctcaggaac tcgttagtct tttggatccg ttgttagctc aactatccga atccttccac   5760
taccatgcag cgttttgttt cctgtatatg tttgtttgcc tatgccccca tgccaagaat   5820
attaagtttt ctttaaagtc tactttaccc atcggtgctg ggttgggctc aagcgcctct   5880
atttctgtat cactggcctt agctatggcc tacttggggg ggttaatagg atctaatgac   5940
ttggaaaagc tgtcagaaaa cgataagcat atagtgaatc aatgggcctt cataggtgaa   6000
aagtgtattc acggtacccc ttcaggaata gataacgctg tggccactta tggtaatgcc   6060
ctgctatttg aaaaagactc acataatgga acaataaaca caaacaattt taagttctta   6120
gatgatttcc cagccattcc aatgatccta acctatacta gaattccaag gtctacaaaa   6180
gatcttgttg ctcgcgttcg tgtgttggtc accgagaaat ttcctgaagt tatgaagcca   6240
attctagatg ccatgggtga atgtgcccta caaggcttag agatcatgac taagttaagt   6300
aaatgtaaag gcaccgatga cgaggctgta gaaactaata atgaactgta tgaacaacta   6360
ttggaattga taagaataaa tcatggactg cttgtctcaa tcggtgtttc tcatcctgga   6420
ttagaactta ttaaaaatct gagcgatgat ttgagaattg gctccacaaa acttaccggt   6480
gctggtggcg gcggttgctc tttgactttg ttacgaagag acattactca agagcaaatt   6540
gacagcttca aaaagaaatt gcaagatgat tttagttacg agacatttga aacagacttg   6600
ggtgggactg gctgctgttt gttaagcgca aaaaatttga ataaagatct taaaatcaaa   6660
tccctagtat tccaattatt tgaaaataaa actaccacaa agcaacaaat tgacgatcta   6720
ttattgccag gaaacacgaa tttaccatgg acttcataag ctaatttgcg ataggcctgc   6780
acccttaagg aggaaaaaaa catgtcagag ttgagagcct tcagtgcccc agggaaagcg   6840
ttactagctg gtggatattt agttttagat acaaaatatg aagcatttgt agtcggatta   6900
tcggcaagaa tgcatgctgt agcccatcct tacggttcat tgcaagggtc tgataagttt   6960
gaagtgcgtg tgaaaagtaa acaatttaaa gatggggagt ggctgtacca tataagtcct   7020
aaaagtggct tcattcctgt ttcgataggc ggatctaaga accctttcat tgaaaaagtt   7080
atcgctaacg tatttagcta ctttaaacct aacatggacg actactgcaa tagaaacttg   7140
ttcgttattg atattttctc tgatgatgcc taccattctc aggaggatag cgttaccgaa   7200
catcgtggca acagaagatt gagttttcat tcgcacagaa ttgaagaagt tcccaaaaca   7260
gggctgggct cctcggcagg tttagtcaca gttttaacta cagctttggc ctcctttttt   7320
```

```
gtatcggacc tggaaaataa tgtagacaaa tatagagaag ttattcataa tttagcacaa   7380
gttgctcatt gtcaagctca gggtaaaatt ggaagcgggt ttgatgtagc ggcggcagca   7440
tatggatcta tcagatatag aagattccca cccgcattaa tctctaattt gccagatatt   7500
ggaagtgcta cttacggcag taaactggcg catttggttg atgaagaaga ctggaatatt   7560
acgattaaaa gtaaccattt accttcggga ttaactttat ggatgggcga tattaagaat   7620
ggttcagaaa cagtaaaact ggtccagaag gtaaaaaatt ggtatgattc gcatatgcca   7680
gaaagcttga aaatatatac agaactcgat catgcaaatt ctagatttat ggatggacta   7740
tctaaactag atcgcttaca cgagactcat gacgattaca gcgatcagat atttgagtct   7800
cttgagagga atgactgtac ctgtcaaaag tatcctgaaa tcacagaagt tagagatgca   7860
gttgccacaa ttagacgttc ctttagaaaa ataactaaag aatctggtgc cgatatcgaa   7920
cctcccgtac aaactagctt attggatgat tgccagacct taaaaggagt tcttacttgc   7980
ttaatacctg gtgctggtgg ttatgacgcc attgcagtga ttactaagca agatgttgat   8040
cttagggctc aaaccgctaa tgacaaaaga ttttctaagg ttcaatggct ggatgtaact   8100
caggctgact ggggtgttag gaaagaaaaa gatccggaaa cttatcttga taaataactt   8160
aaggtagctg catgcagaat tcgcccttaa ggaggaaaaa aaaatgaccg tttacacagc   8220
atccgttacc gcacccgtca acatcgcaac ccttaagtat tggggggaaaa gggacacgaa   8280
gttgaatctg cccaccaatt cgtccatatc agtgacttta tcgcaagatg acctcagaac   8340
gttgacctct gcggctactg cacctgagtt tgaacgcgac actttgtggt taaatggaga   8400
accacacagc atcgacaatg aaagaactca aaattgtctg cgcgacctac gccaattaag   8460
aaaggaaatg gaatcgaagg acgcctcatt gcccacatta tctcaatgga aactccacat   8520
tgtctccgaa aataactttc ctacagcagc tggtttagct tcctccgctg ctggctttgc   8580
tgcattggtc tctgcaattg ctaagttata ccaattacca cagtcaactt cagaaatatc   8640
tagaatagca agaaaggggt ctggttcagc ttgtagatcg ttgtttggcg gatacgtggc   8700
ctgggaaatg ggaaaagctg aagatggtca tgattccatg gcagtacaaa tcgcagacag   8760
ctctgactgg cctcagatga aagcttgtgt cctagttgtc agcgatatta aaaaggatgt   8820
gagttccact cagggtatgc aattgaccgt ggcaacctcc gaactattta aagaaagaat   8880
tgaacatgtc gtaccaaaga gatttgaagt catgcgtaaa gccattgttg aaaaagattt   8940
cgccaccttt gcaaaggaaa caatgatgga ttccaactct ttccatgcca catgtttgga   9000
ctctttccct ccaatattct acatgaatga cacttccaag cgtatcatca gttggtgcca   9060
caccattaat cagttttacg gagaaacaat cgttgcatac acgtttgatg caggtccaaa   9120
tgctgtgttg tactacttag ctgaaaatga gtcgaaactc tttgcattta tctataaatt   9180
gtttggctct gttcctggat gggacaagaa atttactact gagcagcttg aggctttcaa   9240
ccatcaattt gaatcatcta actttactgc acgtgaattg gatcttgagt tgcaaaagga   9300
tgttgccaga gtgattttaa ctcaagtcgg ttcaggccca caagaaacaa acgaatcttt   9360
gattgacgca aagactggtc taccaaagga ataagatcaa ttcgctgcat cgcccttagg   9420
aggtaaaaaa aaatgactgc cgacaacaat agtatgcccc atggtgcagt atctagttac   9480
gccaaattag tgcaaaacca aacacctgaa gacattttgg aagagtttcc tgaaattatt   9540
ccattacaac aaagacctaa tacccgatct agtgagacgt caaatgacga aagcggagaa   9600
acatgttttt ctggtcatga tgaggagcaa attaagttaa tgaatgaaaa ttgtattgtt   9660
```

-continued

```
ttggattggg acgataatgc tattggtgcc ggtaccaaga aagtttgtca tttaatggaa   9720

aatattgaaa agggtttact acatcgtgca ttctccgtct ttattttcaa tgaacaaggt   9780

gaattacttt tacaacaaag agccactgaa aaaataactt tccctgatct ttggactaac   9840

acatgctgct ctcatccact atgtattgat gacgaattag gtttgaaggg taagctagac   9900

gataagatta agggcgctat tactgcggcg gtgagaaaac tagatcatga attaggtatt   9960

ccagaagatg aaactaagac aaggggtaag tttcactttt taaacagaat ccattacatg  10020

gcaccaagca atgaaccatg gggtgaacat gaaattgatt acatcctatt ttataagatc  10080

aacgctaaag aaaacttgac tgtcaaccca aacgtcaatg aagttagaga cttcaaatgg  10140

gtttcaccaa atgatttgaa aactatgttt gctgacccaa gttacaagtt tacgccttgg  10200

tttaagatta tttgcgagaa ttacttattc aactggtggg agcaattaga tgacctttct  10260

gaagtggaaa atgacaggca aattcataga atgctataac aacgcgtcta caaataaaaa  10320

aggcacgtca gatgacgtgc ctttttcttt ggggcc                             10356
```

```
<210> SEQ ID NO 91
<211> LENGTH: 43
<212> TYPE: DNA
<213> ORGANISM: Artificial Sequence
<220> FEATURE:
<223> OTHER INFORMATION: Synthetic Construct

<400> SEQUENCE: 91

gcatgctcga gcggccgctt ttaatcaaac atcctgccaa ctc                       43


<210> SEQ ID NO 92
<211> LENGTH: 37
<212> TYPE: DNA
<213> ORGANISM: Artificial Sequence
<220> FEATURE:
<223> OTHER INFORMATION: Synthetic Construct

<400> SEQUENCE: 92

gatcgaaggg cgatcgtgtc acagtctggc gaaaccg                              37


<210> SEQ ID NO 93
<211> LENGTH: 43
<212> TYPE: DNA
<213> ORGANISM: Artificial Sequence
<220> FEATURE:
<223> OTHER INFORMATION: Synthetic Construct

<400> SEQUENCE: 93

ctgaattctg cagatatctg tttttccact cttcgttcac ttt                       43


<210> SEQ ID NO 94
<211> LENGTH: 33
<212> TYPE: DNA
<213> ORGANISM: Artificial Sequence
<220> FEATURE:
<223> OTHER INFORMATION: Synthetic Construct

<400> SEQUENCE: 94

tctagagggc ccaagaaaaa tgccccgctt acg                                  33


<210> SEQ ID NO 95
<211> LENGTH: 111
<212> TYPE: DNA
<213> ORGANISM: Artificial Sequence
<220> FEATURE:
<223> OTHER INFORMATION: Synthetic Construct
```

<400> SEQUENCE: 95
gatcgcggcc gcgcccttga cgatgccaca tcctgagcaa ataattcaac cactaattgt 60
gagcggataa cacaaggagg aaacagctat gtcattaccg ttcttaactt c 111

<210> SEQ ID NO 96
<211> LENGTH: 75
<212> TYPE: DNA
<213> ORGANISM: Artificial Sequence
<220> FEATURE:
<223> OTHER INFORMATION: Synthetic Construct

<400> SEQUENCE: 96
gatcgggccc caagaaaaaa ggcacgtcat ctgacgtgcc ttttttattt gtagacgcgt 60
tgttatagca ttcta 75

<210> SEQ ID NO 97
<211> LENGTH: 81
<212> TYPE: DNA
<213> ORGANISM: Artificial Sequence
<220> FEATURE:
<223> OTHER INFORMATION: Synthetic Construct

<400> SEQUENCE: 97
aaagtagccg aagatgacgg tttgtcacat ggagttggca ggatgtttga ttaaaagcaa 60
ttaaccctca ctaaagggcg g 81

<210> SEQ ID NO 98
<211> LENGTH: 160
<212> TYPE: DNA
<213> ORGANISM: Artificial Sequence
<220> FEATURE:
<223> OTHER INFORMATION: Synthetic Construct

<400> SEQUENCE: 98
agagtgttca ccaaaaataa taacctttcc cggtgcagaa gttaagaacg gtaatgacat 60
agctgtttcc tccttgtgtt atccgctcac aattagtggt tgaattattt gctcaggatg 120
tggcatcgtc aagggctaat acgactcact atagggctcg 160

<210> SEQ ID NO 99
<211> LENGTH: 60
<212> TYPE: DNA
<213> ORGANISM: Artificial Sequence
<220> FEATURE:
<223> OTHER INFORMATION: Synthetic Construct

<400> SEQUENCE: 99
gatcatgcat tcgcccttag gaggtaaaaa aacatgtgtg cgacctcttc tcaatttact 60

<210> SEQ ID NO 100
<211> LENGTH: 38
<212> TYPE: DNA
<213> ORGANISM: Artificial Sequence
<220> FEATURE:
<223> OTHER INFORMATION: Synthetic Construct

<400> SEQUENCE: 100
cggtcgacgg atccctgcag ttagacatac atcagctg 38

<210> SEQ ID NO 101
<211> LENGTH: 6974
<212> TYPE: DNA

<213> ORGANISM: Artificial Sequence
<220> FEATURE:
<223> OTHER INFORMATION: Synthetic Construct

<400> SEQUENCE: 101
gtgcggccgc aagcttgtcg acggagctcg aattcggatc cctgcagtta gacatacatc 60
agctggttaa tcgggaaagg gtcaatcagc agcagtttga tgcggttttc agtcgcgtag 120
tctgggcgac ccagaccatc gccatactgg taggtgcagt gggaaacacg tgccatgtta 180
actgcgattt ccatgaacgc tttaggcagc agggtggagt cgctaacgcg ttcacgattc 240
atctttttcc attcggcgtc gatcagttta cgcagttctt cgcgggcctg ttcctcgctg 300
gtaccatcgt tttcgtgcat gtagctaatg atagaattgg tagtctcgcc acgttccagc 360
tccgccgcag aggtggccag atcgttgcac aggcggaaga taacgcagct agaacgcacc 420
agaccatgga agtcggtcag ggaacgcagc gcgtggtcgg agatgtcttc ctgctgctgg 480
catacggaaa agtaagacgg cgccagcagc gctacaccgg aggaggaaac gctggcgttt 540
tccaggtact tggagaaagc cgggataatt ttgttgttgg accatttcgc ctcttgcaga 600
aaggctttgc acagttcacg ccagcttttc gtcagatagg acaggttgtt atgacctttc 660
tctttcagaa tagaatagga cgtgtcgtta acggtgttgt acagtgccag gaaacacagt 720
ttcatatagt ccggcagggt gttaatagcg ttaacgtccc agcgctctac agcatcggtg 780
aacagttgca gttcgtccag agtgccataa acgtcataca cgtcatcgat gatcgtcacc 840
agaccaaaca ttttagtaac agctttgcga cattcaccaa actgcgggtc tggcgccata 900
cccagtgccc agaaataaac ttccatcagg cggtcgcgta caaaatccag tttgctagcc 960
aggcccatct cggtccacca gcgggacaga tcttgcagct ctttctggtg cagggtctgt 1020
accatgttaa aatccagctt cgccagctcc agcagcagct ggtgatgcgg ttctttcggt 1080
tcgtatttat ccaggaacca acgtgcctcc agacggtgca gacgctggtg atatggcagt 1140
tccagggcgt ggctcacttg ttctgcaacc ttggtattaa tgccttcttt caggttgttc 1200
ttcaggtggg tgatggaaaa ggtacgcgcc tcctccagca ggttctcacc ctcgaaaccc 1260
aggtaagacg cttcatacag gctcagcagg ccttggacgt cacctttcag ttcaccgctg 1320
aaaccacctt ctttatcctt gaaacgctca aaaacatcct gagaaacctc gaaaccgtgc 1380
tgacgcagca gacggaaaga cagagcggtt gcgtgcaggt cagatttgtt ctttttgttt 1440
tcgtccagca gtacgatgtt ttccagggct ttaatgatgt ctttttcaaa tttgtaggtc 1500
agacccaggc gctgcacatc gtcgatcagc tccagcaggg acagcggctg ggtgtctaca 1560
cggttgatca tgcagcgaac ttcttcctcc agtttggtcg ctttctcctc cagcttttcc 1620
actttcaggt cgttctccag ggattgcagg aattcgaaat tccacaggtt tggctgatag 1680
tttgcggaac gacgggaatt atgctcggta atctgagtaa attgagaaga ggtcgcacac 1740
atggtatatc tccttcttaa agttaaacaa aattatttct agaggggaat tgttatccgc 1800
tcacaattcc cctatagtga gtcgtattaa tttcgcggga tcgagatctc gatcctctac 1860
gccggacgca tcgtggccgg catcaccggc gccacaggtg cggttgctgg cgcctatatc 1920
gccgacatca ccgatgggga agatcgggct cgccacttcg ggctcatgag cgcttgtttc 1980
ggcgtgggta tggtggcagg ccccgtggcc gggggactgt tgggcgccat ctccttgcat 2040
gcaccattcc ttgcggcggc ggtgctcaac ggcctcaacc tactactggg ctgcttccta 2100
atgcaggagt cgcataaggg agagcgtcga gatcccggac accatcgaat ggcgcaaaac 2160
ctttcgcggt atggcatgat agcgcccgga agagagtcaa ttcagggtgg tgaatgtgaa 2220

-continued

```
accagtaacg ttatacgatg tcgcagagta tgccggtgtc tcttatcaga ccgtttcccg   2280
cgtggtgaac caggccagcc acgtttctgc gaaaacgcgg gaaaaagtgg aagcggcgat   2340
ggcggagctg aattacattc ccaaccgcgt ggcacaacaa ctggcgggca aacagtcgtt   2400
gctgattggc gttgccacct ccagtctggc cctgcacgcg ccgtcgcaaa ttgtcgcggc   2460
gattaaatct cgcgccgatc aactgggtgc cagcgtggtg gtgtcgatgg tagaacgaag   2520
cggcgtcgaa gcctgtaaag cggcggtgca caatcttctc gcgcaacgcg tcagtgggct   2580
gatcattaac tatccgctgg atgaccagga tgccattgct gtggaagctg cctgcactaa   2640
tgttccggcg ttatttcttg atgtctctga ccagacaccc atcaacagta ttattttctc   2700
ccatgaagac ggtacgcgac tgggcgtgga gcatctggtc gcattgggtc accagcaaat   2760
cgcgctgtta gcgggcccat taagttctgt ctcggcgcgt ctgcgtctgg ctggctggca   2820
taaatatctc actcgcaatc aaattcagcc gatagcggaa cgggaaggcg actggagtgc   2880
catgtccggt tttcaacaaa ccatgcaaat gctgaatgag ggcatcgttc ccactgcgat   2940
gctggttgcc aacgatcaga tggcgctggg cgcaatgcgc gccattaccg agtccgggct   3000
gcgcgttggt gcggatatct cggtagtggg atacgacgat accgaagaca gctcatgtta   3060
tatcccgccg ttaaccacca tcaaacagga ttttcgcctg ctggggcaaa ccagcgtgga   3120
ccgcttgctg caactctctc agggccaggc ggtgaagggc aatcagctgt tgcccgtctc   3180
actggtgaaa agaaaaacca ccctggcgcc caatacgcaa accgcctctc cccgcgcgtt   3240
ggccgattca ttaatgcagc tggcacgaca ggtttcccga ctggaaagcg ggcagtgagc   3300
gcaacgcaat taatgtaagt tagctcactc attaggcacc gggatctcga ccgatgccct   3360
tgagagcctt caacccagtc agctccttcc ggtgggcgcg gggcatgact atcgtcgccg   3420
cacttatgac tgtcttcttt atcatgcaac tcgtaggaca ggtgccggca gcgctctggg   3480
tcattttcgg cgaggaccgc tttcgctgga gcgcgacgat gatcggcctg tcgcttgcgg   3540
tattcggaat cttgcacgcc ctcgctcaag ccttcgtcac tggtcccgcc accaaacgtt   3600
tcggcgagaa gcaggccatt atcgccggca tggcggcccc acgggtgcgc atgatcgtgc   3660
tcctgtcgtt gaggacccgg ctaggctggc ggggttgcct tactggttag cagaatgaat   3720
caccgatacg cgagcgaacg tgaagcgact gctgctgcaa aacgtctgcg acctgagcaa   3780
caacatgaat ggtcttcggt ttccgtgttt cgtaaagtct ggaaacgcgg aagtcagcgc   3840
cctgcaccat tatgttccgg atctgcatcg caggatgctg ctggctaccc tgtggaacac   3900
ctacatctgt attaacgaag cgctggcatt gaccctgagt gatttttctc tggtcccgcc   3960
gcatccatac cgccagttgt ttaccctcac aacgttccag taaccgggca tgttcatcat   4020
cagtaacccg tatcgtgagc atcctctctc gtttcatcgg tatcattacc cccatgaaca   4080
gaaatccccc ttacacggag gcatcagtga ccaaacagga aaaaaccgcc cttaacatgg   4140
cccgctttat cagaagccag acattaacgc ttctggagaa actcaacgag ctggacgcgg   4200
atgaacaggc agacatctgt gaatcgcttc acgaccacgc tgatgagctt taccgcagct   4260
gcctcgcgcg tttcggtgat gacggtgaaa acctctgaca catgcagctc ccggagacgg   4320
tcacagcttg tctgtaagcg gatgccggga gcagacaagc ccgtcagggc gcgtcagcgg   4380
gtgttggcgg gtgtcggggc gcagccatga cccagtcacg tagcgatagc ggagtgtata   4440
ctggcttaac tatgcggcat cagagcagat tgtactgaga gtgcaccata tatgcggtgt   4500
gaaataccgc acagatgcgt aaggagaaaa taccgcatca ggcgctcttc cgcttcctcg   4560
```

-continued ctcactgact cgctgcgctc ggtcgttcgg ctgcggcgag cggtatcagc tcactcaaag 4620
gcggtaatac ggttatccac agaatcaggg gataacgcag gaaagaacat gtgagcaaaa 4680
ggccagcaaa aggccaggaa ccgtaaaaag gccgcgttgc tggcgttttt ccataggctc 4740
cgcccccctg acgagcatca caaaaatcga cgctcaagtc agaggtggcg aaacccgaca 4800
ggactataaa gataccaggc gtttccccct ggaagctccc tcgtgcgctc tcctgttccg 4860
accctgccgc ttaccggata cctgtccgcc tttctccctt cgggaagcgt ggcgctttct 4920
catagctcac gctgtaggta tctcagttcg gtgtaggtcg ttcgctccaa gctgggctgt 4980
gtgcacgaac cccccgttca gcccgaccgc tgcgccttat ccggtaacta tcgtcttgag 5040
tccaacccgg taagacacga cttatcgcca ctggcagcag ccactggtaa caggattagc 5100
agagcgaggt atgtaggcgg tgctacagag ttcttgaagt ggtggcctaa ctacggctac 5160
actagaagga cagtatttgg tatctgcgct ctgctgaagc cagttacctt cggaaaaaga 5220
gttggtagct cttgatccgg caaacaaacc accgctggta gcggtggttt ttttgtttgc 5280
aagcagcaga ttacgcgcag aaaaaaagga tctcaagaag atcctttgat cttttctacg 5340
gggtctgacg ctcagtggaa cgaaaactca cgttaaggga ttttggtcat gaacaataaa 5400
actgtctgct tacataaaca gtaatacaag gggtgttatg agccatattc aacgggaaac 5460
gtcttgctct aggccgcgat taaattccaa catggatgct gatttatatg ggtataaatg 5520
ggctcgcgat aatgtcgggc aatcaggtgc gacaatctat cgattgtatg ggaagcccga 5580
tgcgccagag ttgtttctga aacatggcaa aggtagcgtt gccaatgatg ttacagatga 5640
gatggtcaga ctaaactggc tgacggaatt tatgcctctt ccgaccatca agcattttat 5700
ccgtactcct gatgatgcat ggttactcac cactgcgatc cccgggaaaa cagcattcca 5760
ggtattagaa gaatatcctg attcaggtga aaatattgtt gatgcgctgg cagtgttcct 5820
gcgccggttg cattcgattc ctgtttgtaa ttgtcctttt aacagcgatc gcgtatttcg 5880
tctcgctcag gcgcaatcac gaatgaataa cggtttggtt gatgcgagtg attttgatga 5940
cgagcgtaat ggctggcctg ttgaacaagt ctggaaagaa atgcataaac ttttgccatt 6000
ctcaccggat tcagtcgtca ctcatggtga tttctcactt gataacctta tttttgacga 6060
ggggaaatta ataggttgta ttgatgttgg acgagtcgga atcgcagacc gataccagga 6120
tcttgccatc ctatggaact gcctcggtga gttttctcct tcattacaga aacggctttt 6180
tcaaaaatat ggtattgata atcctgatat gaataaattg cagtttcatt tgatgctcga 6240
tgagtttttc taagaattaa ttcatgagcg gatacatatt tgaatgtatt tagaaaaata 6300
aacaaatagg ggttccgcgc acatttcccc gaaaagtgcc acctgaaatt gtaaacgtta 6360
atattttgtt aaaattcgcg ttaaattttt gttaaatcag ctcatttttt aaccaatagg 6420
ccgaaatcgg caaaatccct tataaatcaa aagaatagac cgagataggg ttgagtgttg 6480
ttccagtttg gaacaagagt ccactattaa agaacgtgga ctccaacgtc aaagggcgaa 6540
aaaccgtcta tcagggcgat ggcccactac gtgaaccatc accctaatca agttttttgg 6600
ggtcgaggtg ccgtaaagca ctaaatcgga accctaaagg gagcccccga tttagagctt 6660
gacggggaaa gccggcgaac gtggcgagaa aggaagggaa gaaagcgaaa ggagcgggcg 6720
ctagggcgct ggcaagtgta gcggtcacgc tgcgcgtaac caccacaccc gccgcgctta 6780
atgcgccgct acagggcgcg tcccattcgc caatccggat atagttcctc ctttcagcaa 6840
aaaacccctc aagacccgtt tagaggcccc aaggggttat gctagttatt gctcagcggt 6900
ggcagcagcc aactcagctt cctttcgggc tttgttagca gccggatctc agtggtggtg 6960
gtggtggtgc tcga 6974

<210> SEQ ID NO 102
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 102
gcggccgcgc ccttgacgat gccacatcct gagcaaataa ttcaaccact aattgtgagc 60
ggataacaca aggaggaaac agccatggta tcctgttctg cgccgggtaa gatttacctg 120
ttcggtgaac acgccgtagt ttatggcgaa actgcaattg cgtgtgcggt ggaactgcgt 180
acccgtgttc gcgcggaact caatgactct atcactattc agagccagat cggccgcacc 240
ggtctggatt tcgaaaagca cccttatgtg tctgcggtaa ttgagaaaat gcgcaaatct 300
attcctatta acggtgtttt cttgaccgtc gattccgaca tcccggtggg ctccggtctg 360
ggtagcagcg cagccgttac tatcgcgtct attggtgcgc tgaacgagct gttcggcttt 420
ggcctcagcc tgcaagaaat cgctaaactg ggccacgaaa tcgaaattaa agtacagggt 480
gccgcgtccc caaccgatac gtatgtttct accttcggcg gcgtggttac catcccggaa 540
cgtcgcaaac tgaaaactcc ggactgcggc attgtgattg gcgataccgg cgttttctcc 600
tccaccaaag agttagtagc taacgtacgt cagctgcgcg aaagctaccc ggatttgatc 660
gaaccgctga tgacctctat tggcaaaatc tctcgtatcg gcgaacaact ggttctgtct 720
ggcgactacg catccatcgg ccgcctgatg aacgtcaacc agggtctcct ggacgccctg 780
ggcgttaaca tcttagaact gagccagctg atctattccg ctcgtgcggc aggtgcgttt 840
ggcgctaaaa tcacgggcgc tggcggcggt ggctgtatgg ttgcgctgac cgctccggaa 900
aaatgcaacc aagtggcaga agcggtagca ggcgctggcg gtaaagtgac tatcactaaa 960
ccgaccgagc aaggtctgaa agtagattaa gccttgactt aatagctgct tatttcgccc 1020
ttatggtacc tagtaggagg aaaaaaacat ggaaatgcgt caaccggctg tcgcaggtca 1080
attctaccca ctgcgttgcg agaacctgga aaacgaactg aaacgctgct tcgaaggcct 1140
ggagatccgc gaacaagaag tgctgggcgc agtctgtccg cacgccggtt atatgtactc 1200
tggcaaagtt gcggcgcacg tctatgccac tctgccggaa gctgatacct acgtaatctt 1260
cggcccgaac cacaccggct acggtagccc tgtctctgtg agccgtgaaa cttggaagac 1320
cccgttgggc aatatcgatg ttgacctgga actggcggac ggcttcctgg gttccatcgt 1380
agatgcggat gaactcggtc acaaatacga acactctatc gaagttcagc tgccgtttct 1440
gcaataccgt tttgaacgcg atttcaaaat tctgccaatc tgcatgggta tgcaagacga 1500
agaaaccgcg gtcgaagtag gtaacctgct ggcggatctg atcagcgagt ccggtaaacg 1560
tgctgtgatc atcgcaagct ctgatttcac ccactatgag acggctgaac gtgccaaaga 1620
aatcgattcc gaagttattg attctatcct gaactttgac atctctggca tgtacgatcg 1680
cctgtatcgc cgtaacgcct ctgtttgcgg ttacggcccg atcaccgcta tgctgacggc 1740
aagcaaaaag ctgggcggct ctcgtgcgac tttgctgaaa tacgcaaaca gcggtgacgt 1800
gtccggtgat aaagacgctg tggtgggcta cgccgccatc atcgttgagt aagctgatta 1860
aaggttgaac agataggatt tcgtcatgga tcctacaagg aggaaaaaaa catgaatgct 1920
tctaatgaac cggtgattct gaaactgggt ggctctgcta ttaccgacaa aggtgcctac 1980
gaaggcgtag ttaaggaagc tgatttgctg cgcatcgcac aggaagttag cggtttccgt 2040
ggcaagatga tcgtggttca tggtgctggt agcttcggcc atacgtacgc gaagaaatac 2100
ggcctggacc gtaccttcga cccagagggc gcaattgtta ctcatgaatc tgttaaaaag 2160
ctcgcctcca aagttgtagg tgctctgaat agcttcggcg tgcgtgctat cgcggtgcat 2220
cctatggact gcgcagtatg ccgtaacggt cgtatcgaaa cgatgtatct ggactccatc 2280
aagttaatgc tggaaaaagg tctggtgccg gttctgcacg gcgacgtcgc aatggatatt 2340
gaactgggca cttgtatcct gtccggtgat caaatcgttc cttacctggc caaagaactg 2400
ggtatctccc gcctcggcct gggcagcgca gaggatggtg tgctggatat ggagggcaaa 2460
cctgtaccgg aaatcacccc agaaactttc gaagagttcc gccactgcat cggtggttct 2520
ggttctactg atgtaaccgg tggcatgctg ggcaaagtgc tggaacttct ggaattgagc 2580
aaaaattctt ccattactag ctacattttc aacgctggta aagcagacaa catctaccgc 2640
tttctgaatg gtgagtccat cggcactcgc atcagcccgg acaagcgtgt ttaagctagt 2700
tattaaccta aatgctctaa accagttatg agctctacaa ggaggaaaaa aacatgatta 2760
acactaccag ccgccgcaaa attgaacacc tgaaactctg cgcagaatcc ccggttgaag 2820
cgcgtcaggt atctgccggc tttgaagacg ttactctgat ccaccgcgct ttaccggagc 2880
tgaacatgga tgaactggac ctcagcgttg atttcctggg taaacgcatc aaagcgccgt 2940
tcctgattgc gtctatcacg ggtggtcacc cagataccat cccggttaac gctgcgctgg 3000
cagctgctgc tgaggagctg ggtgttggca tcggcgttgg ctctcagcgc gcggccattg 3060
atgatccgag ccaggaagac agcttccgtg tagtgcgtga tgaagcccca gatgcgtttg 3120
tttatggcaa cgtcggcgca gcacagatcc gtcagtatgg tgttgaaggt gttgaaaaac 3180
tgatcgaaat gattgacgca gatgccttgg caatccacct gaactttctg caagaagcgg 3240
tccaaccgga aggtgaccgc gacgcgaccg gttgcctgga catgattacc gaaatttgct 3300
ctcagattaa aactccggta atcgtgaaag aaaccggtgc aggcattagc cgtgaagatg 3360
cgattctgtt ccagaaagct ggcgtgagcg caatcgacgt tggcggcgcg ggcggcacct 3420
cctgggctgg cgtcgaggtc taccgtgcta aagaaagccg tgactctgtt agcgagcgtt 3480
taggtgagct gttttgggat ttcggcattc cgacggtagc ttctctgatt gaatcccgcg 3540
tttccttgcc gctgatcgca accggcggta tccgtaacgg tctggacatt gctaaaagca 3600
ttgctctcgg cgcaagcgct gccagcgccg ctctgccgtt cgttggtccg tccctggagg 3660
gcaaagaatc cgttgtacgt gtgctgagct gcatgctgga agaatttaaa gcagcaatgt 3720
ttttgtgcgg ttgcggcaac atcaaagacc tgcacaactc tccagtagtg gtaactggtt 3780
ggacccgcga atacctggag cagcgcggtt ttaacgttaa ggacctctcc ctgccgggca 3840
acgctctgta agcttcaacg cgtctacaaa taaaaaaggc acgtcagatg acgtgccttt 3900
tttcttgtct aga 3913

<210> SEQ ID NO 103
<211> LENGTH: 6848
<212> TYPE: DNA
<213> ORGANISM: Artificial Sequence
<220> FEATURE:
<223> OTHER INFORMATION: Synthetic Construct

<400> SEQUENCE: 103
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120

-continued

```
gcactcccgt tctggataat gtttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga aagtggaaaa    540
gctggaggag aaagcgacca aactggagga agaagttcgc tgcatgatca accgtgtaga    600
cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720
aaagaacaaa tctgacctgc acgcaaccgc tctgtctttc cgtctgctgc gtcagcacgg    780
tttcgaggtt tctcaggatg tttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg tacctttttcc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga aagagaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgtttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc cagactacgc   2040
gactgaaaac cgcatcaaac tgctgctgat tgaccctttc ccgattaacc agctgatgta   2100
tgtctaactg cataaaggag gtaaaaaaac atggtatcct gttctgcgcc gggtaagatt   2160
tacctgttcg gtgaacacgc cgtagtttat ggcgaaactg caattgcgtg tgcggtggaa   2220
ctgcgtaccc gtgttcgcgc ggaactcaat gactctatca ctattcagag ccagatcggc   2280
cgcaccggtc tggatttcga aaagcaccct tatgtgtctg cggtaattga gaaaatgcgc   2340
aaatctattc ctattaacgg tgttttcttg accgtcgatt ccgacatccc ggtgggctcc   2400
ggtctgggta gcagcgcagc cgttactatc gcgtctattg gtgcgctgaa cgagctgttc   2460
```

```
ggctttggcc tcagcctgca agaaatcgct aaactgggcc acgaaatcga aattaaagta   2520
cagggtgccg cgtccccaac cgatacgtat gtttctacct tcggcggcgt ggttaccatc   2580
ccggaacgtc gcaaactgaa aactccggac tgcggcattg tgattggcga taccggcgtt   2640
ttctcctcca ccaaagagtt agtagctaac gtacgtcagc tgcgcgaaag ctacccggat   2700
ttgatcgaac cgctgatgac ctctattggc aaaatctctc gtatcggcga acaactggtt   2760
ctgtctggcg actacgcatc catcggccgc ctgatgaacg tcaaccaggg tctcctggac   2820
gccctgggcg ttaacatctt agaactgagc cagctgatct attccgctcg tgcggcaggt   2880
gcgtttggcg ctaaaatcac gggcgctggc ggcggtggct gtatggttgc gctgaccgct   2940
ccggaaaaat gcaaccaagt ggcagaagcg gtagcaggcg ctggcggtaa agtgactatc   3000
actaaaccga ccgagcaagg tctgaaagta gattaaagtc tagttaaagt ttaaacggtc   3060
tccagcttgg ctgttttggc ggatgagaga agattttcag cctgatacag attaaatcag   3120
aacgcagaag cggtctgata aaacagaatt tgcctggcgg cagtagcgcg gtggtcccac   3180
ctgaccccat gccgaactca gaagtgaaac gccgtagcgc cgatggtagt gtggggtctc   3240
cccatgcgag agtagggaac tgccaggcat caaataaaac gaaaggctca gtcgaaagac   3300
tgggcctttc gttttatctg ttgtttgtcg gtgaacgctc tcctgagtag gacaaatccg   3360
ccgggagcgg atttgaacgt tgcgaagcaa cggcccggag ggtggcgggc aggacgcccg   3420
ccataaactg ccaggcatca aattaagcag aaggccatcc tgacggatgg cctttttgcg   3480
tttctacaaa ctctttttgt ttatttttct aaatacattc aaatatgtat ccgcttaacc   3540
ggaattgcca gctggggcgc cctctggtaa ggttgggaag ccctgcaaag taaactggat   3600
ggctttctcg ccgccaagga tctgatggcg caggggatca agctctgatc aagagacagg   3660
atgaggatcg tttcgcatga ttgaacaaga tggattgcac gcaggttctc cggccgcttg   3720
ggtggagagg ctattcggct atgactgggc acaacagaca atcggctgct ctgatgccgc   3780
cgtgttccgg ctgtcagcgc aggggcgccc ggttcttttt gtcaagaccg acctgtccgg   3840
tgccctgaat gaactgcaag acgaggcagc gcggctatcg tggctggcca cgacgggcgt   3900
tccttgcgca gctgtgctcg acgttgtcac tgaagcggga agggactggc tgctattggg   3960
cgaagtgccg gggcaggatc tcctgtcatc tcaccttgct cctgccgaga aagtatccat   4020
catggctgat gcaatgcggc ggctgcatac gcttgatccg gctacctgcc cattcgacca   4080
ccaagcgaaa catcgcatcg agcgagcacg tactcggatg gaagccggtc ttgtcgatca   4140
ggatgatctg gacgaagagc atcaggggct cgcgccagcc gaactgttcg ccaggctcaa   4200
ggcgagcatg cccgacggcg aggatctcgt cgtgacccat ggcgatgcct gcttgccgaa   4260
tatcatggtg gaaaatggcc gcttttctgg attcatcgac tgtggccggc tgggtgtggc   4320
ggaccgctat caggacatag cgttggctac ccgtgatatt gctgaagagc ttggcggcga   4380
atgggctgac cgcttcctcg tgctttacgg tatcgccgct cccgattcgc agcgcatcgc   4440
cttctatcgc cttcttgacg agttcttctg acgcatgacc aaaatccctt aacgtgagtt   4500
ttcgttccac tgagcgtcag accccgtaga aaagatcaaa ggatcttctt gagatccttt   4560
ttttctgcgc gtaatctgct gcttgcaaac aaaaaaacca ccgctaccag cggtggtttg   4620
tttgccggat caagagctac caactctttt tccgaaggta actggcttca gcagagcgca   4680
gataccaaat actgtccttc tagtgtagcc gtagttaggc caccacttca agaactctgt   4740
agcaccgcct acatacctcg ctctgctaat cctgttacca gtggctgctg ccagtggcga   4800
taagtcgtgt cttaccgggt tggactcaag acgatagtta ccggataagg cgcagcggtc   4860
```

gggctgaacg gggggttcgt gcacacagcc cagcttggag cgaacgacct acaccgaact 4920
gagataccta cagcgtgagc tatgagaaag cgccacgctt cccgaaggga gaaaggcgga 4980
caggtatccg gtaagcggca gggtcggaac aggagagcgc acgagggagc ttccaggggg 5040
aaacgcctgg tatctttata gtcctgtcgg gtttcgccac ctctgacttg agcgtcgatt 5100
tttgtgatgc tcgtcagggg ggcggagcct atggaaaaac gccagcaacg cggccttttt 5160
acggttcctg gccttttgct ggccttttgc tcacatgttc tttcctgcgt tatcccctga 5220
ttctgtggat aaccgtatta ccgcctttga gtgagctgat accgctcgcc gcagccgaac 5280
gaccgagcgc agcgagtcag tgagcgagga agcggaagag cgcctgatgc ggtattttct 5340
ccttacgcat ctgtgcggta tttcacaccg catatggtgc actctcagta caatctgctc 5400
tgatgccgca tagttaagcc agtatacact ccgctatcgc tacgtgactg ggtcatggct 5460
gcgccccgac acccgccaac acccgctgac gcgccctgac gggcttgtct gctcccggca 5520
tccgcttaca gacaagctgt gaccgtctcc gggagctgca tgtgtcagag gttttcaccg 5580
tcatcaccga aacgcgcgag gcagcagatc aattcgcgcg cgaaggcgaa gcggcatgca 5640
tttacgttga caccatcgaa tggtgcaaaa cctttcgcgg tatggcatga tagcgcccgg 5700
aagagagtca attcagggtg gtgaatgtga aaccagtaac gttatacgat gtcgcagagt 5760
atgccggtgt ctcttatcag accgtttccc gcgtggtgaa ccaggccagc cacgtttctg 5820
cgaaaacgcg ggaaaaagtg gaagcggcga tggcggagct gaattacatt cccaaccgcg 5880
tggcacaaca actggcgggc aaacagtcgt tgctgattgg cgttgccacc tccagtctgg 5940
ccctgcacgc gccgtcgcaa attgtcgcgg cgattaaatc tcgcgccgat caactgggtg 6000
ccagcgtggt ggtgtcgatg gtagaacgaa gcggcgtcga agcctgtaaa gcggcggtgc 6060
acaatcttct cgcgcaacgc gtcagtgggc tgatcattaa ctatccgctg gatgaccagg 6120
atgccattgc tgtggaagct gcctgcacta atgttccggc gttatttctt gatgtctctg 6180
accagacacc catcaacagt attattttct cccatgaaga cggtacgcga ctgggcgtgg 6240
agcatctggt cgcattgggt caccagcaaa tcgcgctgtt agcgggccca ttaagttctg 6300
tctcggcgcg tctgcgtctg gctggctggc ataaatatct cactcgcaat caaattcagc 6360
cgatagcgga acgggaaggc gactggagtg ccatgtccgg ttttcaacaa accatgcaaa 6420
tgctgaatga gggcatcgtt cccactgcga tgctggttgc caacgatcag atggcgctgg 6480
gcgcaatgcg cgccattacc gagtccgggc tgcgcgttgg tgcggatatc tcggtagtgg 6540
gatacgacga taccgaagac agctcatgtt atatcccgcc gtcaaccacc atcaaacagg 6600
attttcgcct gctggggcaa accagcgtgg accgcttgct gcaactctct cagggccagg 6660
cggtgaaggg caatcagctg ttgcccgtct cactggtgaa aagaaaaacc accctggcgc 6720
ccaatacgca aaccgcctct ccccgcgcgt tggccgattc attaatgcag ctggcacgac 6780
aggtttcccg actggaaagc gggcagtgag cgcaacgcaa ttaatgtgag ttagcgcgaa 6840
ttgatctg 6848

<210> SEQ ID NO 104
<211> LENGTH: 6646
<212> TYPE: DNA
<213> ORGANISM: Artificial Sequence
<220> FEATURE:
<223> OTHER INFORMATION: Synthetic Construct

<400> SEQUENCE: 104

-continued

```
aagggcgagc tcaacgatcc ggctgctaac aaagcccgaa aggaagctga gttggctgct     60
gccaccgctg agcaataact agcataaccc cttggggcct ctaaacgggt cttgaggagt    120
tttttgctga aaggaggaac tatatccgga tatcccgcaa gaggcccggc agtaccggca    180
taaccaagcc tatgcctaca gcatccaggg tgacggtgcc gaggatgacg atgagcgcat    240
tgttagattt catacacggt gcctgactgc gttagcaatt taactgtgat aaactaccgc    300
attaaagctt atcgatgata agctgtcaaa catgagaatt aattcttgaa gacgaaaggg    360
cctcgtgata cgcctatttt tataggttaa tgtcatgata ataatggttt cttagacgtc    420
aggtggcact tttcggggaa atgtgcgcgg aacccctatt tgtttatttt tctaaataca    480
ttcaaatatg tatccgctca tgagacaata accctgataa atgcttcaat aatattgaaa    540
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
```

-continued

```
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgcggccg ccatgccggc gataatggcc tgcttctcgc cgaaacgttt   3780
ggtggcggga ccagtgacga aggcttgagc gagggcgtgc aagattccga ataccgcaag   3840
cgacaggccg atcatcgtcg cgctccagcg aaagcggtcc tcgccgaaaa tgacccagag   3900
cgctgccggc acctgtccta cgagttgcat gataaagaag acagtcataa gtgcggcgac   3960
gatagtcatg ccccgcgccc accggaagga gctgactggg ttgaaggctc tcaagggcat   4020
cggtcgagat cccggtgcct aatgagtgag ctaacttaca ttaattgcgt tgcgctcact   4080
gcccgctttc cagtcgggaa acctgtcgtg ccagctgcat taatgaatcg gccaacgcgc   4140
ggggagaggc ggtttgcgta ttgggcgcca gggtggtttt tcttttcacc agtgagacgg   4200
gcaacagctg attgcccttc accgcctggc cctgagagag ttgcagcaag cggtccacgc   4260
tggtttgccc cagcaggcga aaatcctgtt tgatggtggt taacggcggg atataacatg   4320
agctgtcttc ggtatcgtcg tatcccacta ccgagatatc cgcaccaacg cgcagcccgg   4380
actcggtaat ggcgcgcatt gcgcccagcg ccatctgatc gttggcaacc agcatcgcag   4440
tgggaacgat gccctcattc agcatttgca tggtttgttg aaaaccggac atggcactcc   4500
agtcgccttc ccgttccgct atcggctgaa tttgattgcg agtgagatat ttatgccagc   4560
cagccagacg cagacgcgcc gagacagaac ttaatgggcc cgctaacagc gcgatttgct   4620
ggtgacccaa tgcgaccaga tgctccacgc ccagtcgcgt accgtcttca tgggagaaaa   4680
taatactgtt gatgggtgtc tggtcagaga catcaagaaa taacgccgga acattagtgc   4740
```

aggcagcttc cacagcaatg gcatcctggt catccagcgg atagttaatg atcagcccac 4800
tgacgcgttg cgcgagaaga ttgtgcaccg ccgctttaca ggcttcgacg ccgcttcgtt 4860
ctaccatcga caccaccacg ctggcaccca gttgatcggc gcgagattta atcgccgcga 4920
caatttgcga cggcgcgtgc agggccagac tggaggtggc aacgccaatc agcaacgact 4980
gtttgcccgc cagttgttgt gccacgcggt tgggaatgta attcagctcc gccatcgccg 5040
cttccacttt ttcccgcgtt ttcgcagaaa cgtggctggc ctggttcacc acgcgggaaa 5100
cggtctgata agagacaccg gcatactctg cgacatcgta taacgttact ggtttcacat 5160
tcaccaccct gaattgactc tcttccgggc gctatcatgc cataccgcga aaggttttgc 5220
gccattcgat ggtgtccggg atctcgacgc tctcccttat gcgactcctg cattaggaag 5280
cagcccagta gtaggttgag gccgttgagc accgccgccg caaggaatgg tgcatgcaag 5340
gagatggcgc ccaacagtcc cccggccacg gggcctgcca ccatacccac gccgaaacaa 5400
gcgctcatga gcccgaagtg gcgagcccga tcttccccat cggtgatgtc ggcgatatag 5460
gcgccagcaa ccgcacctgt ggcgccggtg atgccggcca cgatgcgtcc ggcgtagagg 5520
atcgagatct cgatcccgcg aaattaatac gactcactat aggggaattg tgagcggata 5580
acaattcccc tctagaaata attttgttta actttaagaa ggagatatac atatgcgggg 5640
ttctcatcat catcatcatc atggtatggc tagcatgact ggtggacagc aaatgggtcg 5700
ggatctgtac gacgatgacg ataaggatca tcccttcacc atggtatcct gttctgcgcc 5760
gggtaagatt tacctgttcg gtgaacacgc cgtagtttat ggcgaaactg caattgcgtg 5820
tgcggtggaa ctgcgtaccc gtgttcgcgc ggaactcaat gactctatca ctattcagag 5880
ccagatcggc cgcaccggtc tggatttcga aaagcaccct tatgtgtctg cggtaattga 5940
gaaaatgcgc aaatctattc ctattaacgg tgttttcttg accgtcgatt ccgacatccc 6000
ggtgggctcc ggtctgggta gcagcgcagc cgttactatc gcgtctattg gtgcgctgaa 6060
cgagctgttc ggctttggcc tcagcctgca agaaatcgct aaactgggcc acgaaatcga 6120
aattaaagta cagggtgccg cgtccccaac cgatacgtat gtttctacct tcggcggcgt 6180
ggttaccatc ccggaacgtc gcaaactgaa aactccggac tgcggcattg tgattggcga 6240
taccggcgtt ttctcctcca ccaaagagtt agtagctaac gtacgtcagc tgcgcgaaag 6300
ctacccggat ttgatcgaac cgctgatgac ctctattggc aaaatctctc gtatcggcga 6360
acaactggtt ctgtctggcg actacgcatc catcggccgc ctgatgaacg tcaaccaggg 6420
tctcctggac gccctgggcg ttaacatctt agaactgagc cagctgatct attccgctcg 6480
tgcggcaggt gcgtttggcg ctaaaatcac gggcgctggc ggcggtggct gtatggttgc 6540
gctgaccgct ccggaaaaat gcaaccaagt ggcagaagcg gtagcaggcg ctggcggtaa 6600
agtgactatc actaaaccga ccgagcaagg tctgaaagta gattaa 6646

<210> SEQ ID NO 105
<211> LENGTH: 7280
<212> TYPE: DNA
<213> ORGANISM: Artificial Sequence
<220> FEATURE:
<223> OTHER INFORMATION: Synthetic Construct

<400> SEQUENCE: 105
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180

```
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgtgtgc    420
gacctcttct caatttactc agattaccga gcataattcc cgtcgttccg caaactatca    480
gccaaacctg tggaatttcg aattcctgca atccctggag aacgacctga aagtggaaaa    540
gctggaggag aaagcgacca aactggagga agaagttcgc tgcatgatca accgtgtaga    600
cacccagccg ctgtccctgc tggagctgat cgacgatgtg cagcgcctgg gtctgaccta    660
caaatttgaa aaagacatca ttaaagccct ggaaaacatc gtactgctgg acgaaaacaa    720
aaagaacaaa tctgacctgc acgcaaccgc tctgtctttc cgtctgctgc gtcagcacgg    780
tttcgaggtt tctcaggatg tttttgagcg tttcaaggat aaagaaggtg gtttcagcgg    840
tgaactgaaa ggtgacgtcc aaggcctgct gagcctgtat gaagcgtctt acctgggttt    900
cgagggtgag aacctgctgg aggaggcgcg taccttttcc atcacccacc tgaagaacaa    960
cctgaaagaa ggcattaata ccaaggttgc agaacaagtg agccacgccc tggaactgcc   1020
atatcaccag cgtctgcacc gtctggaggc acgttggttc ctggataaat acgaaccgaa   1080
agaaccgcat caccagctgc tgctggagct ggcgaagctg gattttaaca tggtacagac   1140
cctgcaccag aaagagctgc aagatctgtc ccgctggtgg accgagatgg gcctggctag   1200
caaactggat tttgtacgcg accgcctgat ggaagtttat ttctgggcac tgggtatggc   1260
gccagacccg cagtttggtg aatgtcgcaa agctgttact aaaatgtttg gtctggtgac   1320
gatcatcgat gacgtgtatg acgtttatgg cactctggac gaactgcaac tgttcaccga   1380
tgctgtagag cgctgggacg ttaacgctat taacaccctg ccggactata tgaaactgtg   1440
tttcctggca ctgtacaaca ccgttaacga cacgtcctat tctattctga aagagaaagg   1500
tcataacaac ctgtcctatc tgacgaaaag ctggcgtgaa ctgtgcaaag cctttctgca   1560
agaggcgaaa tggtccaaca acaaaattat cccggctttc tccaagtacc tggaaaacgc   1620
cagcgtttcc tcctccggtg tagcgctgct ggcgccgtct tacttttccg tatgccagca   1680
gcaggaagac atctccgacc acgcgctgcg ttccctgacc gacttccatg gtctggtgcg   1740
ttctagctgc gttatcttcc gcctgtgcaa cgatctggcc acctctgcgg cggagctgga   1800
acgtggcgag actaccaatt ctatcattag ctacatgcac gaaaacgatg gtaccagcga   1860
ggaacaggcc cgcgaagaac tgcgtaaact gatcgacgcc gaatggaaaa agatgaatcg   1920
tgaacgcgtt agcgactcca ccctgctgcc taaagcgttc atggaaatcg cagttaacat   1980
ggcacgtgtt tcccactgca cctaccagta tggcgatggt ctgggtcgcc cagactacgc   2040
gactgaaaac cgcatcaaac tgctgctgat tgaccctttc ccgattaacc agctgatgta   2100
tgtctaactg cataaaggag gtaaaaaaac atgtcattac cgttcttaac ttctgcaccg   2160
ggaaaggtta ttatttttgg tgaacactct gctgtgtaca acaagcctgc cgtcgctgct   2220
agtgtgtctg cgttgagaac ctacctgcta ataagcgagt catctgcacc agatactatt   2280
gaattggact tcccggacat tagctttaat cataagtggt ccatcaatga tttcaatgcc   2340
atcaccgagg atcaagtaaa ctcccaaaaa ttggccaagg ctcaacaagc caccgatggc   2400
ttgtctcagg aactcgttag tcttttggat ccgttgttag ctcaactatc cgaatccttc   2460
cactaccatg cagcgttttg tttcctgtat atgtttgttt gcctatgccc ccatgccaag   2520
```

-continued

```
aatattaagt tttctttaaa gtctacttta cccatcggtg ctgggttggg ctcaagcgcc   2580
tctatttctg tatcactggc cttagctatg gcctacttgg gggggttaat aggatctaat   2640
gacttggaaa agctgtcaga aaacgataag catatagtga atcaatgggc cttcataggt   2700
gaaaagtgta ttcacggtac cccttcagga atagataacg ctgtggccac ttatggtaat   2760
gccctgctat ttgaaaaaga ctcacataat ggaacaataa acacaaacaa ttttaagttc   2820
ttagatgatt tcccagccat tccaatgatc ctaacctata ctagaattcc aaggtctaca   2880
aaagatcttg ttgctcgcgt tcgtgtgttg gtcaccgaga aatttcctga agttatgaag   2940
ccaattctag atgccatggg tgaatgtgcc ctacaaggct tagagatcat gactaagtta   3000
agtaaatgta aaggcaccga tgacgaggct gtagaaacta ataatgaact gtatgaacaa   3060
ctattggaat tgataagaat aaatcatgga ctgcttgtct caatcggtgt ttctcatcct   3120
ggattagaac ttattaaaaa tctgagcgat gatttgagaa ttggctccac aaaacttacc   3180
ggtgctggtg gcggcggttg ctctttgact ttgttacgaa gagacattac tcaagagcaa   3240
attgacagct tcaaaaagaa attgcaagat gattttagtt acgagacatt tgaaacagac   3300
ttgggtggga ctggctgctg tttgttaagc gcaaaaaatt tgaataaaga tcttaaaatc   3360
aaatccctag tattccaatt atttgaaaat aaaactacca caaagcaaca aattgacgat   3420
ctattattgc caggaaacac gaatttacca tggacttcat aactgcagag tctagttaaa   3480
gtttaaacgg tctccagctt ggctgttttg gcggatgaga gaagattttc agcctgatac   3540
agattaaatc agaacgcaga agcggtctga taaaacagaa tttgcctggc ggcagtagcg   3600
cggtggtccc acctgacccc atgccgaact cagaagtgaa acgccgtagc gccgatggta   3660
gtgtggggtc tccccatgcg agagtaggga actgccaggc atcaaataaa acgaaaggct   3720
cagtcgaaag actgggcctt tcgttttatc tgttgtttgt cggtgaacgc tctcctgagt   3780
aggacaaatc cgccgggagc ggatttgaac gttgcgaagc aacggcccgg agggtggcgg   3840
gcaggacgcc cgccataaac tgccaggcat caaattaagc agaaggccat cctgacggat   3900
ggcctttttg cgtttctaca aactcttttt gtttattttt ctaaatacat tcaaatatgt   3960
atccgcttaa ccggaattgc cagctggggc gccctctggt aaggttggga agccctgcaa   4020
agtaaactgg atggctttct cgccgccaag gatctgatgg cgcaggggat caagctctga   4080
tcaagagaca ggatgaggat cgtttcgcat gattgaacaa gatggattgc acgcaggttc   4140
tccggccgct tgggtggaga ggctattcgg ctatgactgg gcacaacaga caatcggctg   4200
ctctgatgcc gccgtgttcc ggctgtcagc gcaggggcgc ccggttcttt ttgtcaagac   4260
cgacctgtcc ggtgccctga atgaactgca agacgaggca gcgcggctat cgtggctggc   4320
cacgacgggc gttccttgcg cagctgtgct cgacgttgtc actgaagcgg gaagggactg   4380
gctgctattg ggcgaagtgc cggggcagga tctcctgtca tctcaccttg ctcctgccga   4440
gaaagtatcc atcatggctg atgcaatgcg gcggctgcat acgcttgatc cggctacctg   4500
cccattcgac caccaagcga aacatcgcat cgagcgagca cgtactcgga tggaagccgg   4560
tcttgtcgat caggatgatc tggacgaaga gcatcagggg ctcgcgccag ccgaactgtt   4620
cgccaggctc aaggcgagca tgcccgacgg cgaggatctc gtcgtgaccc atggcgatgc   4680
ctgcttgccg aatatcatgg tggaaaatgg ccgcttttct ggattcatcg actgtggccg   4740
gctgggtgtg gcggaccgct atcaggacat agcgttggct acccgtgata ttgctgaaga   4800
gcttggcggc gaatgggctg accgcttcct cgtgctttac ggtatcgccg ctcccgattc   4860
gcagcgcatc gccttctatc gccttcttga cgagttcttc tgacgcatga ccaaaatccc   4920
```

ttaacgtgag ttttcgttcc actgagcgtc agaccccgta gaaaagatca aaggatcttc 4980
ttgagatcct ttttttctgc gcgtaatctg ctgcttgcaa acaaaaaaac caccgctacc 5040
agcggtggtt tgtttgccgg atcaagagct accaactctt tttccgaagg taactggctt 5100
cagcagagcg cagataccaa atactgtcct tctagtgtag ccgtagttag gccaccactt 5160
caagaactct gtagcaccgc ctacatacct cgctctgcta atcctgttac cagtggctgc 5220
tgccagtggc gataagtcgt gtcttaccgg gttggactca agacgatagt taccggataa 5280
ggcgcagcgg tcgggctgaa cggggggttc gtgcacacag cccagcttgg agcgaacgac 5340
ctacaccgaa ctgagatacc tacagcgtga gctatgagaa agcgccacgc ttcccgaagg 5400
gagaaaggcg gacaggtatc cggtaagcgg cagggtcgga acaggagagc gcacgaggga 5460
gcttccaggg ggaaacgcct ggtatcttta tagtcctgtc gggtttcgcc acctctgact 5520
tgagcgtcga tttttgtgat gctcgtcagg ggggcggagc ctatggaaaa acgccagcaa 5580
cgcggccttt ttacggttcc tggccttttg ctggcctttt gctcacatgt tctttcctgc 5640
gttatcccct gattctgtgg ataaccgtat taccgccttt gagtgagctg ataccgctcg 5700
ccgcagccga acgaccgagc gcagcgagtc agtgagcgag gaagcggaag agcgcctgat 5760
gcggtatttt ctccttacgc atctgtgcgg tatttcacac cgcatatggt gcactctcag 5820
tacaatctgc tctgatgccg catagttaag ccagtataca ctccgctatc gctacgtgac 5880
tgggtcatgg ctgcgccccg acacccgcca acacccgctg acgcgccctg acgggcttgt 5940
ctgctcccgg catccgctta cagacaagct gtgaccgtct ccgggagctg catgtgtcag 6000
aggttttcac cgtcatcacc gaaacgcgcg aggcagcaga tcaattcgcg cgcgaaggcg 6060
aagcggcatg catttacgtt gacaccatcg aatggtgcaa aacctttcgc ggtatggcat 6120
gatagcgccc ggaagagagt caattcaggg tggtgaatgt gaaaccagta acgttatacg 6180
atgtcgcaga gtatgccggt gtctcttatc agaccgtttc ccgcgtggtg aaccaggcca 6240
gccacgtttc tgcgaaaacg cgggaaaaag tggaagcggc gatggcggag ctgaattaca 6300
ttcccaaccg cgtggcacaa caactggcgg gcaaacagtc gttgctgatt ggcgttgcca 6360
cctccagtct ggccctgcac gcgccgtcgc aaattgtcgc ggcgattaaa tctcgcgccg 6420
atcaactggg tgccagcgtg gtggtgtcga tggtagaacg aagcggcgtc gaagcctgta 6480
aagcggcggt gcacaatctt ctcgcgcaac gcgtcagtgg gctgatcatt aactatccgc 6540
tggatgacca ggatgccatt gctgtggaag ctgcctgcac taatgttccg gcgttatttc 6600
ttgatgtctc tgaccagaca cccatcaaca gtattatttt ctcccatgaa gacggtacgc 6660
gactgggcgt ggagcatctg gtcgcattgg gtcaccagca aatcgcgctg ttagcgggcc 6720
cattaagttc tgtctcggcg cgtctgcgtc tggctggctg gcataaatat ctcactcgca 6780
atcaaattca gccgatagcg gaacgggaag gcgactggag tgccatgtcc ggttttcaac 6840
aaaccatgca aatgctgaat gagggcatcg ttcccactgc gatgctggtt gccaacgatc 6900
agatggcgct gggcgcaatg cgcgccatta ccgagtccgg gctgcgcgtt ggtgcggata 6960
tctcggtagt gggatacgac gataccgaag acagctcatg ttatatcccg ccgtcaacca 7020
ccatcaaaca ggattttcgc ctgctggggc aaaccagcgt ggaccgcttg ctgcaactct 7080
ctcagggcca ggcggtgaag ggcaatcagc tgttgcccgt ctcactggtg aaaagaaaaa 7140
ccaccctggc gcccaatacg caaaccgcct ctccccgcgc gttggccgat tcattaatgc 7200
agctggcacg acaggtttcc cgactggaaa gcgggcagtg agcgcaacgc aattaatgtg 7260
agttagcgcg aattgatctg 7280

<210> SEQ ID NO 106
<211> LENGTH: 6623
<212> TYPE: DNA
<213> ORGANISM: Artificial Sequence
<220> FEATURE:
<223> OTHER INFORMATION: Synthetic Construct

<400> SEQUENCE: 106
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540
aaggaagagt atgattgaac aagatggatt gcacgcaggt tctccggccg cttgggtgga 600
gaggctattc ggctatgact gggcacaact gacaatcggc tgctctgatg ccgccgtgtt 660
ccggctgtca gcgcaggggc gcccggttct ttttgtcaag accgacctgt ccggtgccct 720
gaatgaactg caggacgagg cagcgcggct atcgtggctg gccacgacgg gcgttccttg 780
cgcagctgtg ctcgacgttg tcactgaagc gggaagggac tggctgctat tgggcgaagt 840
gccggggcag gatctcctgt catctcacct tgctcctgcc gagaaagtat ccatcatggc 900
tgatgcaatg cggcggctgc atacgcttga tccggctacc tgcccattcg accaccaagc 960
gaaacatcgc atcgagcggg cacgtactcg gatggaagcc ggtcttgtcg atcaggatga 1020
tctggacgaa gagcatcagg ggctcgcgcc agccgaactg ttcgccaggc tcaaggcgcg 1080
catgcccgac ggcgaggatc tcgtcgtgac acatggcgat gcctgcttgc cgaatatcat 1140
ggtggaaaat ggccgctttt ctggattcat cgactgtggc cggctgggtg tggcggaccg 1200
ctatcaggac atagcgttgg ctacccgtga tattgctgaa gagcttggcg gcgaatgggc 1260
tgaccgcttc ctcgtgcttt acggtatcgc cgctcccgat tcgcagcgca tcgccttcta 1320
tcgccttctt gacgagttct tctgagcggg actctggggt tcgaaatgac cgaccaagcg 1380
acgcctaact gtcagaccaa gtttactcat atatacttta gattgattta aaacttcatt 1440
tttaatttaa aaggatctag gtgaagatcc tttttgataa tctcatgacc aaaatccctt 1500
aacgtgagtt ttcgttccac tgagcgtcag accccgtaga aaagatcaaa ggatcttctt 1560
gagatccttt ttttctgcgc gtaatctgct gcttgcaaac aaaaaaacca ccgctaccag 1620
cggtggtttg tttgccggat caagagctac caactctttt tccgaaggta actggcttca 1680
gcagagcgca gataccaaat actgtccttc tagtgtagcc gtagttaggc caccacttca 1740
agaactctgt agcaccgcct acatacctcg ctctgctaat cctgttacca gtggctgctg 1800
ccagtggcga taagtcgtgt cttaccgggt tggactcaag acgatagtta ccggataagg 1860
cgcagcggtc gggctgaacg gggggttcgt gcacacagcc cagcttggag cgaacgacct 1920
acaccgaact gagataccta cagcgtgagc tatgagaaag cgccacgctt cccgaaggga 1980
gaaaggcgga caggtatccg gtaagcggca gggtcggaac aggagagcgc acgagggagc 2040

-continued

```
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
```

-continued

```
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
gcagcccagt agtaggttga ggccgttgag caccgccgcc gcaaggaatg gtgcatgcaa   5340
ggagatggcg cccaacagtc ccccggccac ggggcctgcc accataccca cgccgaaaca   5400
agcgctcatg agcccgaagt ggcgagcccg atcttcccca tcggtgatgt cggcgatata   5460
ggcgccagca accgcacctg tggcgccggt gatgccggcc acgatgcgtc cggcgtagag   5520
gatcgagatc tcgatcccgc gaaattaata cgactcacta taggggaatt gtgagcggat   5580
aacaattccc ctctagaaat aattttgttt aactttaaga aggagatata catatgcggg   5640
gttctcatca tcatcatcat catggtatgg ctagcatgac tggtggacag caaatgggtc   5700
gggatctgta cgacgatgac gataaggatc atcccttcac catgacaaaa aaagttggtg   5760
tcggtcaggc acatagtaag ataattttaa taggggaaca tgcggtcgtt tacggttatc   5820
ctgccatttc cctgcctctt ttggaagtgg aggtgacctg taaggtagtt cctgcagaga   5880
gtccttggcg cctttatgag gaggatacct tgtccatggc ggtttatgcc tcactggagt   5940
atttgaatat cacagaagcc tgcattcgtt gtgagattga ctcggctatc cctgagaaac   6000
gggggatggg ttcgtcagcg gctatcagca tagcggccat tcgtgcggta tttgactact   6060
atcaggctga tctgcctcat gatgtactag aaatcttggt caatcgagct gaaatgattg   6120
cccatatgaa tcctagtggt ttggatgcta agacctgtct cagtgaccaa cctattcgct   6180
ttatcaagaa cgtaggattt acagaacttg agatggattt atccgcctat ttggtgattg   6240
ccgatacggg tgtttatggt catactcgtg aagccatcca agtggttcaa aataagggca   6300
aggatgccct accgtttttg catgccttgg gagaattaac ccagcaggca gaaattgcga   6360
tttcacaaaa agatgctgaa gggctgggac aaatcctcag tcaagcacat ttacatttaa   6420
aagaaattgg tgtcagtagc cttgaggcag actctttggt tgaaacagct cttagtcatg   6480
gtgctctggg tgccaagatg agcggtggtg ggctaggagg ttgtatcata gccttggtaa   6540
ccaatttgac acacgcacaa gaactagcag aaagattaga agagaaagga gctgttcaga   6600
catggataga gagcctgtga cag                                           6623
```

<210> SEQ ID NO 107
<211> LENGTH: 4334

<212> TYPE: DNA
<213> ORGANISM: Artificial Sequence
<220> FEATURE:
<223> OTHER INFORMATION: Synthetic Construct

<400> SEQUENCE: 107
cattaagttc tgtctcggcg cgtctgcgtc tggctggctg gcataaatat ctcactcgca 60
atcaaattca gccgatagcg gaacgggaag gcgactggag tgccatgtcc ggttttcaac 120
aaaccatgca aatgctgaat gagggcatcg ttcccactgc gatgctggtt gccaacgatc 180
agatggcgct gggcgcaatg cgcgccatta ccgagtccgg gctgcgcgtt ggtgcggata 240
tctcggtagt gggatacgac gataccgaag acagctcatg ttatatcccg ccgtcaacca 300
ccatcaaaca ggattttcgc ctgctggggc aaaccagcgt ggaccgcttg ctgcaactct 360
ctcagggcca ggcggtgaag ggcaatcagc tgttgcccgt ctcactggtg aaaagaaaaa 420
ccaccctggc gcccaatacg caaaccgcct ctccccgcgc gttggccgat tcattaatgc 480
agctggcacg acaggtttcc cgactggaaa gcgggcagtg agcgcaacgc aattaatgtg 540
agttagcgcg aattgatctg gtttgacagc ttatcatcga ctgcacggtg caccaatgct 600
tctggcgtca ggcagccatc ggaagctgtg gtatggctgt gcaggtcgta aatcactgca 660
taattcgtgt cgctcaaggc gcactcccgt tctggataat gttttttgcg ccgacatcat 720
aacggttctg gcaaatattc tgaaatgagc tgttgacaat taatcatccg gctcgtataa 780
tgtgtggaat tgtgagcgga taacaatttc acacaggaaa cagcgccgct gagaaaaagc 840
gaagcggcac tgctctttaa caatttatca gacaatctgt gtgggcactc gaccggaatt 900
atcgattaac tttattatta aaaattaaag aggtatatat taatgtatcg attaaataag 960
gaggaataaa ccatggatcc gagctcgaga tctgcagctg gtaccatatg ggaattcgaa 1020
gctttctaga acaaaaactc atctcagaag aggatctgaa tagcgccgtc gaccatcatc 1080
atcatcatca ttgagtttaa acggtctcca gcttggctgt tttggcggat gagagaagat 1140
tttcagcctg atacagatta aatcagaacg cagaagcggt ctgataaaac agaatttgcc 1200
tggcggcagt agcgcggtgg tcccacctga ccccatgccg aactcagaag tgaaacgccg 1260
tagcgccgat ggtagtgtgg ggtctcccca tgcgagagta gggaactgcc aggcatcaaa 1320
taaaacgaaa ggctcagtcg aaagactggg cctttcgttt tatctgttgt ttgtcggtga 1380
acgctctcct gagtaggaca aatccgccgg gagcggattt gaacgttgcg aagcaacggc 1440
ccggagggtg gcgggcagga cgcccgccat aaactgccag gcatcaaatt aagcagaagg 1500
ccatcctgac ggatggcctt tttgcgtttc tacaaactct tttgtttat ttttctaaat 1560 acattcaaat atgtatccgc ttaaccggaa ttgccagctg gggcgccctc tggtaaggtt 1620
gggaagccct gcaaagtaaa ctggatggct ttctcgccgc caaggatctg atggcgcagg 1680
ggatcaagct ctgatcaaga gacaggatga ggatcgtttc gcatgattga acaagatgga 1740
ttgcacgcag gttctccggc cgcttgggtg gagaggctat tcggctatga ctgggcacaa 1800
cagacaatcg gctgctctga tgccgccgtg ttccggctgt cagcgcaggg gcgcccggtt 1860
ctttttgtca agaccgacct gtccggtgcc ctgaatgaac tgcaagacga ggcagcgcgg 1920
ctatcgtggc tggccacgac gggcgttcct tgcgcagctg tgctcgacgt tgtcactgaa 1980
gcgggaaggg actggctgct attgggcgaa gtgccggggc aggatctcct gtcatctcac 2040
cttgctcctg ccgagaaagt atccatcatg gctgatgcaa tgcggcggct gcatacgctt 2100
gatccggcta cctgcccatt cgaccaccaa gcgaaacatc gcatcgagcg agcacgtact 2160

-continued

```
cggatggaag ccggtcttgt cgatcaggat gatctggacg aagagcatca ggggctcgcg   2220
ccagccgaac tgttcgccag gctcaaggcg agcatgcccg acggcgagga tctcgtcgtg   2280
acccatggcg atgcctgctt gccgaatatc atggtggaaa atggccgctt ttctggattc   2340
atcgactgtg gccggctggg tgtggcggac cgctatcagg acatagcgtt ggctacccgt   2400
gatattgctg aagagcttgg cggcgaatgg gctgaccgct tcctcgtgct ttacggtatc   2460
gccgctcccg attcgcagcg catcgccttc tatcgccttc ttgacgagtt cttctgacgc   2520
atgaccaaaa tcccttaacg tgagttttcg ttccactgag cgtcagaccc cgtagaaaag   2580
atcaaaggat cttcttgaga tccttttttt ctgcgcgtaa tctgctgctt gcaaacaaaa   2640
aaaccaccgc taccagcggt ggtttgtttg ccggatcaag agctaccaac tctttttccg   2700
aaggtaactg gcttcagcag agcgcagata ccaaatactg tccttctagt gtagccgtag   2760
ttaggccacc acttcaagaa ctctgtagca ccgcctacat acctcgctct gctaatcctg   2820
ttaccagtgg ctgctgccag tggcgataag tcgtgtctta ccgggttgga ctcaagacga   2880
tagttaccgg ataaggcgca gcggtcgggc tgaacggggg gttcgtgcac acagcccagc   2940
ttggagcgaa cgacctacac cgaactgaga tacctacagc gtgagctatg agaaagcgcc   3000
acgcttcccg aagggagaaa ggcggacagg tatccggtaa gcggcagggt cggaacagga   3060
gagcgcacga gggagcttcc agggggaaac gcctggtatc tttatagtcc tgtcgggttt   3120
cgccacctct gacttgagcg tcgatttttg tgatgctcgt caggggggcg gagcctatgg   3180
aaaaacgcca gcaacgcggc ctttttacgg ttcctggcct tttgctggcc ttttgctcac   3240
atgttctttc ctgcgttatc ccctgattct gtggataacc gtattaccgc ctttgagtga   3300
gctgataccg ctcgccgcag ccgaacgacc gagcgcagcg agtcagtgag cgaggaagcg   3360
gaagagcgcc tgatgcggta ttttctcctt acgcatctgt gcggtatttc acaccgcata   3420
tggtgcactc tcagtacaat ctgctctgat gccgcatagt taagccagta tacactccgc   3480
tatcgctacg tgactgggtc atggctgcgc cccgacaccc gccaacaccc gctgacgcgc   3540
cctgacgggc ttgtctgctc ccggcatccg cttacagaca agctgtgacc gtctccggga   3600
gctgcatgtg tcagaggttt tcaccgtcat caccgaaacg cgcgaggcag cagatcaatt   3660
cgcgcgcgaa ggcgaagcgg catgcattta cgttgacacc atcgaatggt gcaaaacctt   3720
tcgcggtatg gcatgatagc gcccggaaga gagtcaattc agggtggtga atgtgaaacc   3780
agtaacgtta tacgatgtcg cagagtatgc cggtgtctct tatcagaccg tttcccgcgt   3840
ggtgaaccag gccagccacg tttctgcgaa aacgcgggaa aaagtggaag cggcgatggc   3900
ggagctgaat tacattccca accgcgtggc acaacaactg gcgggcaaac agtcgttgct   3960
gattggcgtt gccacctcca gtctggccct gcacgcgccg tcgcaaattg tcgcggcgat   4020
taaatctcgc gccgatcaac tgggtgccag cgtggtggtg tcgatggtag aacgaagcgg   4080
cgtcgaagcc tgtaaagcgg cggtgcacaa tcttctcgcg caacgcgtca gtgggctgat   4140
cattaactat ccgctggatg accaggatgc cattgctgtg gaagctgcct gcactaatgt   4200
tccggcgtta tttcttgatg tctctgacca gacacccatc aacagtatta ttttctccca   4260
tgaagacggt acgcgactgg gcgtggagca tctggtcgca ttgggtcacc agcaaatcgc   4320
gctgttagcg ggcc                                                     4334
```

<210> SEQ ID NO 108
<211> LENGTH: 7063
<212> TYPE: DNA
<213> ORGANISM: Artificial Sequence
<220> FEATURE:
<223> OTHER INFORMATION: Synthetic Construct

<400> SEQUENCE: 108

```
ttcttgaaga cgaaagggcc tcgtgatacg cctattttta taggttaatg tcatgataat     60
aatggtttct tagacgtcag gtggcacttt tcggggaaat gtgcgcggaa cccctatttg    120
tttatttttc taaatacatt caaatatgta tccgctcatg agacaataac cctgataaat    180
gcttcaataa tattgaaaaa ggaagagtat gagtattcaa catttccgtg tcgcccttat    240
tccctttttt gcggcatttt gccttcctgt ttttgctcac ccagaaacgc tggtgaaagt    300
aaaagatgct gaagatcagt tgggtgcacg agtgggttac atcgaactgg atctcaacag    360
cggtaagatc cttgagagtt ttcgccccga agaacgtttt ccaatgatga gcacttttaa    420
agttctgcta tgtggcgcgg tattatcccg tgttgacgcc gggcaagagc aactcggtcg    480
ccgcatacac tattctcaga atgacttggt tgagtactca ccagtcacag aaaagcatct    540
tacggatggc atgacagtaa gagaattatg cagtgctgcc ataaccatga gtgataacac    600
tgcggccaac ttacttctga caacgatcgg aggaccgaag gagctaaccg cttttttgca    660
caacatgggg gatcatgtaa ctcgccttga tcgttgggaa ccggagctga atgaagccat    720
accaaacgac gagcgtgaca ccacgatgcc tgcagcaatg gcaacaacgt tgcgcaaact    780
attaactggc gaactactta ctctagcttc ccggcaacaa ttaatagact ggatggaggc    840
ggataaagtt gcaggaccac ttctgcgctc ggcccttccg gctggctggt ttattgctga    900
taaatctgga gccggtgagc gtgggtctcg cggtatcatt gcagcactgg ggccagatgg    960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc ctttttgata atctcatgac caaaatccct taacgtgagt tttcgttcca   1200
ctgagcgtca gaccccgtag aaaagatcaa aggatcttct tgagatcctt tttttctgcg   1260
cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct tcccgaaggg agaaaggcgg acaggtatcc   1680
ggtaagcggc agggtcggaa caggagagcg cacgagggag cttccagggg gaaacgcctg   1740
gtatctttat agtcctgtcg ggtttcgcca cctctgactt gagcgtcgat ttttgtgatg   1800
ctcgtcaggg gggcggagcc tatggaaaaa cgccagcaac gcggcctttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
```

-continued

```
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg tttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag ggcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga gaagaatcat   3360
aatggggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag ggcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gaggcggttt   3840
gcgtattggg cgccagggtg gtttttcttt tcaccagtga gacgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaaataata ctgttgatgg   4380
gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctggc acccagttga tcggcgcgag atttaatcgc cgcgacaatt tgcgacggcg   4620
```

-continued

```
cgtgcagggc cagactggag gtggcaacgc caatcagcaa cgactgtttg cccgccagtt   4680
gttgtgccac gcggttggga atgtaattca gctccgccat cgccgcttcc actttttccc   4740
gcgttttcgc agaaacgtgg ctggcctggt tcaccacgcg ggaaacggtc tgataagaga   4800
caccggcata ctctgcgaca tcgtataacg ttactggttt cacattcacc accctgaatt   4860
gactctcttc cgggcgctat catgccatac cgcgaaaggt tttgcgccat tcgatggtgt   4920
ccgggatctc gacgctctcc cttatgcgac tcctgcatta ggaagcagcc cagtagtagg   4980
ttgaggccgt tgagcaccgc cgccgcaagg aatggtgcat gcaaggagat ggcgcccaac   5040
agtcccccgg ccacggggcc tgccaccata cccacgccga aacaagcgct catgagcccg   5100
aagtggcgag cccgatcttc cccatcggtg atgtcggcga tataggcgcc agcaaccgca   5160
cctgtggcgc cggtgatgcc ggccacgatg cgtccggcgt agaggatcga gatctcgatc   5220
ccgcgaaatt aatacgactc actatagggg aattgtgagc ggataacaat tcccctctag   5280
aaataatttt gtttaacttt aagaaggaga tataccatgg gccatcatca tcatcatcat   5340
catcatcatc acagcagcgg ccatatcgaa ggtcgtcata tgtcattacc gttcttaact   5400
tctgcaccgg gaaaggttat tatttttggt gaacactctg ctgtgtacaa caagcctgcc   5460
gtcgctgcta gtgtgtctgc gttgagaacc tacctgctaa taagcgagtc atctgcacca   5520
gatactattg aattggactt cccggacatt agctttaatc ataagtggtc catcaatgat   5580
ttcaatgcca tcaccgagga tcaagtaaac tcccaaaaat tggccaaggc tcaacaagcc   5640
accgatggct tgtctcagga actcgttagt cttttggatc cgttgttagc tcaactatcc   5700
gaatccttcc actaccatgc agcgttttgt ttcctgtata tgtttgtttg cctatgcccc   5760
catgccaaga atattaagtt ttctttaaag tctactttac ccatcggtgc tgggttgggc   5820
tcaagcgcct ctatttctgt atcactggcc ttagctatgg cctacttggg ggggttaata   5880
ggatctaatg acttggaaaa gctgtcagaa aacgataagc atatagtgaa tcaatgggcc   5940
ttcataggtg aaaagtgtat tcacggtacc ccttcaggaa tagataacgc tgtggccact   6000
tatggtaatg ccctgctatt tgaaaaagac tcacataatg gaacaataaa cacaaacaat   6060
tttaagttct tagatgattt cccagccatt ccaatgatcc taacctatac tagaattcca   6120
aggtctacaa aagatcttgt tgctcgcgtt cgtgtgttgg tcaccgagaa atttcctgaa   6180
gttatgaagc caattctaga tgccatgggt gaatgtgccc tacaaggctt agagatcatg   6240
actaagttaa gtaaatgtaa aggcaccgat gacgaggctg tagaaactaa taatgaactg   6300
tatgaacaac tattggaatt gataagaata aatcatggac tgcttgtctc aatcggtgtt   6360
tctcatcctg gattagaact tattaaaaat ctgagcgatg atttgagaat tggctccaca   6420
aaacttaccg gtgctggtgg cggcggttgc tctttgactt tgttacgaag agacattact   6480
caagagcaaa ttgacagctt caaaaagaaa ttgcaagatg attttagtta cgagacattt   6540
gaaacagact tgggtgggac tggctgctgt ttgttaagcg caaaaaattt gaataaagat   6600
cttaaaatca aatccctagt attccaatta tttgaaaata aaactaccac aaagcaacaa   6660
attgacgatc tattattgcc aggaaacacg aatttaccat ggacttcata agctaatttg   6720
cgataggcca tatgctcgag gatccggctg ctaacaaagc ccgaaaggaa gctgagttgg   6780
ctgctgccac cgctgagcaa taactagcat aaccccttgg ggcctctaaa cgggtcttga   6840
ggggtttttt gctgaaagga ggaactatat ccggatatcc cgcaagaggc ccggcagtac   6900
cggcataacc aagcctatgc ctacagcatc cagggtgacg gtgccgagga tgacgatgag   6960
```

```
cgcattgtta gatttcatac acggtgcctg actgcgttag caatttaact gtgataaact   7020

accgcattaa agcttatcga tgataagctg tcaaacatga gaa                     7063


<210> SEQ ID NO 109
<211> LENGTH: 396
<212> TYPE: PRT
<213> ORGANISM: Artificial Sequence
<220> FEATURE:
<223> OTHER INFORMATION: Synthetic Construct

<400> SEQUENCE: 109

Met Leu Ser Glu Val Leu Leu Val Ser Ala Pro Gly Lys Val Ile Leu
 1               5                  10                  15

His Gly Glu His Ala Val Val His Gly Lys Val Ala Leu Ala Val Ser
            20                  25                  30

Leu Asn Leu Arg Thr Phe Leu Arg Leu Gln Pro His Ser Asn Gly Lys
        35                  40                  45

Val Asp Leu Ser Leu Pro Asn Ile Gly Ile Lys Arg Ala Trp Asp Val
    50                  55                  60

Ala Arg Leu Gln Ser Leu Asp Thr Ser Phe Leu Glu Gln Gly Asp Val
65                  70                  75                  80

Thr Thr Pro Thr Ser Glu Gln Val Glu Lys Leu Lys Glu Val Ala Gly
                85                  90                  95

Leu Pro Asp Asp Cys Ala Val Thr Glu Arg Leu Ala Val Leu Ala Phe
            100                 105                 110

Leu Tyr Leu Tyr Leu Ser Ile Cys Arg Lys Gln Arg Ala Leu Pro Ser
        115                 120                 125

Leu Asp Ile Val Val Trp Ser Glu Leu Pro Pro Gly Ala Gly Leu Gly
    130                 135                 140

Ser Ser Ala Ala Tyr Ser Val Cys Leu Ala Ala Ala Leu Leu Thr Val
145                 150                 155                 160

Cys Glu Glu Ile Pro Asn Pro Leu Lys Asp Gly Asp Cys Val Asn Arg
                165                 170                 175

Trp Thr Lys Glu Asp Leu Glu Leu Ile Asn Lys Trp Ala Phe Gln Gly
            180                 185                 190

Glu Arg Met Ile His Gly Asn Pro Ser Gly Val Asp Asn Ala Val Ser
        195                 200                 205

Thr Trp Gly Gly Ala Leu Arg Tyr His Gln Gly Lys Ile Ser Ser Leu
    210                 215                 220

Lys Arg Ser Pro Ala Leu Gln Ile Leu Leu Thr Asn Thr Lys Val Pro
225                 230                 235                 240

Arg Asn Thr Arg Ala Leu Val Ala Gly Val Arg Asn Arg Leu Leu Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Gly Glu Ala Pro Ala Pro
        275                 280                 285

Glu Gln Tyr Leu Val Leu Glu Glu Leu Ile Asp Met Asn Gln His His
    290                 295                 300

Leu Asn Ala Leu Gly Val Gly His Ala Ser Leu Asp Gln Leu Cys Gln
305                 310                 315                 320

Val Thr Arg Ala Arg Gly Leu His Ser Lys Leu Thr Gly Ala Gly Gly
                325                 330                 335

Gly Gly Cys Gly Ile Thr Leu Leu Lys Pro Gly Leu Glu Gln Pro Glu
            340                 345                 350
```

```
Val Glu Ala Thr Lys Gln Ala Leu Thr Ser Cys Gly Phe Asp Cys Leu
        355                 360                 365

Glu Thr Ser Ile Gly Ala Pro Gly Val Ser Ile His Ser Ala Thr Ser
    370                 375                 380

Leu Asp Ser Arg Val Gln Gln Ala Leu Asp Gly Leu
385                 390                 395


<210> SEQ ID NO 110
<211> LENGTH: 301
<212> TYPE: PRT
<213> ORGANISM: Artificial Sequence
<220> FEATURE:
<223> OTHER INFORMATION: Synthetic Construct

<400> SEQUENCE: 110

Met Val Ser Cys Ser Ala Pro Gly Lys Ile Tyr Leu Phe Gly Glu His
 1               5                  10                  15

Ala Val Val Tyr Gly Glu Thr Ala Ile Ala Cys Ala Val Glu Leu Arg
            20                  25                  30

Thr Arg Val Arg Ala Glu Leu Asn Asp Ser Ile Thr Ile Gln Ser Gln
        35                  40                  45

Ile Gly Arg Thr Gly Leu Asp Phe Glu Lys His Pro Tyr Val Ser Ala
    50                  55                  60

Val Ile Glu Lys Met Arg Lys Ser Ile Pro Ile Asn Gly Val Phe Leu
65                  70                  75                  80

Thr Val Asp Ser Asp Ile Pro Val Gly Ser Gly Leu Gly Ser Ser Ala
                85                  90                  95

Ala Val Thr Ile Ala Ser Ile Gly Ala Leu Asn Glu Leu Phe Gly Phe
            100                 105                 110

Gly Leu Ser Leu Gln Glu Ile Ala Lys Leu Gly His Glu Ile Glu Ile
        115                 120                 125

Lys Val Gln Gly Ala Ala Ser Pro Thr Asp Thr Tyr Val Ser Thr Phe
    130                 135                 140

Gly Gly Val Val Thr Ile Pro Glu Arg Arg Lys Leu Lys Thr Pro Asp
145                 150                 155                 160

Cys Gly Ile Val Ile Gly Asp Thr Gly Val Phe Ser Ser Thr Lys Glu
                165                 170                 175

Leu Val Ala Asn Val Arg Gln Leu Arg Glu Ser Tyr Pro Asp Leu Ile
            180                 185                 190

Glu Pro Leu Met Thr Ser Ile Gly Lys Ile Ser Arg Ile Gly Glu Gln
        195                 200                 205

Leu Val Leu Ser Gly Asp Tyr Ala Ser Ile Gly Arg Leu Met Asn Val
    210                 215                 220

Asn Gln Gly Leu Leu Asp Ala Leu Gly Val Asn Ile Leu Glu Leu Ser
225                 230                 235                 240

Gln Leu Ile Tyr Ser Ala Arg Ala Ala Gly Ala Phe Gly Ala Lys Ile
                245                 250                 255

Thr Gly Ala Gly Gly Gly Gly Cys Met Val Ala Leu Thr Ala Pro Glu
            260                 265                 270

Lys Cys Asn Gln Val Ala Glu Ala Val Ala Gly Ala Gly Gly Lys Val
        275                 280                 285

Thr Ile Thr Lys Pro Thr Glu Gln Gly Leu Lys Val Asp
    290                 295                 300


<210> SEQ ID NO 111
```

<211> LENGTH: 292
<212> TYPE: PRT
<213> ORGANISM: Artificial Sequence
<220> FEATURE:
<223> OTHER INFORMATION: Synthetic Construct

<400> SEQUENCE: 111

Met Thr Lys Lys Val Gly Val Gly Gln Ala His Ser Lys Ile Ile Leu
1 5 10 15

Ile Gly Glu His Ala Val Val Tyr Gly Tyr Pro Ala Ile Ser Leu Pro
20 25 30

Leu Leu Glu Val Glu Val Thr Cys Lys Val Val Pro Ala Glu Ser Pro
35 40 45

Trp Arg Leu Tyr Glu Glu Asp Thr Leu Ser Met Ala Val Tyr Ala Ser
50 55 60

Leu Glu Tyr Leu Asp Ile Thr Glu Ala Cys Ile Arg Cys Glu Ile Asp
65 70 75 80

Ser Ala Ile Pro Glu Lys Arg Gly Met Gly Ser Ser Ala Ala Ile Ser
85 90 95

Ile Ala Ala Ile Arg Ala Val Phe Asp Tyr Tyr Gln Ala Asp Leu Pro
100 105 110

His Asp Val Leu Glu Ile Leu Val Asn Arg Ala Glu Met Ile Ala His
115 120 125

Met Asn Pro Ser Gly Leu Asp Ala Lys Thr Cys Leu Ser Asp Gln Pro
130 135 140

Ile Arg Phe Ile Lys Asn Val Gly Phe Thr Glu Leu Glu Met Asp Leu
145 150 155 160

Ser Ala Tyr Leu Val Ile Ala Asp Thr Gly Val Tyr Gly His Thr Arg
165 170 175

Glu Ala Ile Gln Val Val Gln Asn Lys Gly Lys Asp Ala Leu Pro Phe
180 185 190

Leu His Ala Leu Gly Glu Leu Thr Gln Gln Ala Glu Val Ala Ile Ser
195 200 205

Gln Lys Asp Ala Glu Gly Leu Gly Gln Ile Leu Ser Gln Ala His Leu
210 215 220

His Leu Lys Glu Ile Gly Val Ser Ser Pro Glu Ala Asp Phe Leu Val
225 230 235 240

Glu Thr Thr Leu Ser His Gly Ala Leu Gly Ala Lys Met Ser Gly Gly
245 250 255

Gly Leu Gly Gly Cys Ile Ile Ala Leu Val Thr Asn Leu Thr His Ala
260 265 270

Gln Glu Leu Ala Glu Arg Leu Glu Glu Lys Gly Ala Val Gln Thr Trp
275 280 285

Ile Glu Ser Leu
290

<210> SEQ ID NO 112
<211> LENGTH: 317
<212> TYPE: PRT
<213> ORGANISM: Artificial Sequence
<220> FEATURE:
<223> OTHER INFORMATION: Synthetic Construct

<400> SEQUENCE: 112

Pro Arg Gly Ser His Met Ile Ile Glu Thr Pro Ser Lys Val Ile Leu
1 5 10 15

Phe Gly Glu His Ala Val Val Tyr Gly Tyr Arg Ala Ile Ser Met Ala

```
            20                  25                  30

Ile Asp Leu Thr Ser Thr Ile Glu Ile Lys Glu Thr Gln Glu Asp Glu
        35                  40                  45

Ile Ile Leu Asn Leu Asn Asp Leu Asn Lys Ser Leu Gly Leu Asn Leu
    50                  55                  60

Asn Glu Ile Lys Asn Ile Asn Pro Asn Asn Phe Gly Asp Phe Lys Tyr
65                  70                  75                  80

Cys Leu Cys Ala Ile Lys Asn Thr Leu Asp Tyr Leu Asn Ile Glu Pro
                85                  90                  95

Lys Thr Gly Phe Lys Ile Asn Ile Ser Ser Lys Ile Pro Ile Ser Cys
            100                 105                 110

Gly Leu Gly Ser Ser Ala Ser Ile Thr Ile Gly Thr Ile Lys Ala Val
        115                 120                 125

Ser Gly Phe Tyr Asn Lys Glu Leu Lys Asp Asp Glu Ile Ala Lys Leu
    130                 135                 140

Gly Tyr Met Val Glu Lys Glu Ile Gln Gly Lys Ala Ser Ile Thr Asp
145                 150                 155                 160

Thr Ser Thr Ile Thr Tyr Lys Gly Ile Leu Glu Ile Lys Asn Asn Lys
                165                 170                 175

Phe Arg Lys Ile Lys Gly Glu Phe Glu Glu Phe Leu Lys Asn Cys Lys
            180                 185                 190

Phe Leu Ile Val Tyr Ala Glu Lys Arg Lys Lys Lys Thr Ala Glu Leu
        195                 200                 205

Val Asn Glu Val Ala Lys Ile Glu Asn Lys Asp Glu Ile Phe Lys Glu
    210                 215                 220

Ile Asp Lys Val Ile Asp Glu Ala Leu Lys Ile Lys Asn Lys Glu Asp
225                 230                 235                 240

Phe Gly Lys Leu Met Thr Lys Asn His Glu Leu Leu Lys Lys Leu Asn
                245                 250                 255

Ile Ser Thr Pro Lys Leu Asp Arg Ile Val Asp Ile Gly Asn Arg Phe
            260                 265                 270

Gly Phe Gly Ala Lys Leu Thr Gly Ala Gly Gly Gly Gly Cys Val Ile
        275                 280                 285

Ile Leu Val Asn Glu Glu Lys Glu Lys Glu Leu Leu Lys Glu Leu Asn
    290                 295                 300

Lys Glu Asp Val Arg Ile Phe Asn Cys Arg Met Met Asn
305                 310                 315
```

<210> SEQ ID NO 113
<211> LENGTH: 31
<212> TYPE: DNA
<213> ORGANISM: Artificial Sequence
<220> FEATURE:
<223> OTHER INFORMATION: Synthetic Construct

<400> SEQUENCE: 113
cttgatgcat cctgcattcg cccttaggag g 31

<210> SEQ ID NO 114
<211> LENGTH: 23
<212> TYPE: DNA
<213> ORGANISM: Artificial Sequence
<220> FEATURE:
<223> OTHER INFORMATION: Synthetic Construct

<400> SEQUENCE: 114
ccaggcaaat tctgttttat cag 23

<210> SEQ ID NO 115
<211> LENGTH: 35
<212> TYPE: DNA
<213> ORGANISM: Artificial Sequence
<220> FEATURE:
<223> OTHER INFORMATION: Synthetic Construct

<400> SEQUENCE: 115
cagcagcagc atatgtcatt accgttctta acttc 35

<210> SEQ ID NO 116
<211> LENGTH: 37
<212> TYPE: DNA
<213> ORGANISM: Artificial Sequence
<220> FEATURE:
<223> OTHER INFORMATION: Synthetic Construct

<400> SEQUENCE: 116
cagcagcagc atatggccta tcgcaaatta gcttatg 37

<210> SEQ ID NO 117
<211> LENGTH: 22
<212> TYPE: DNA
<213> ORGANISM: Artificial Sequence
<220> FEATURE:
<223> OTHER INFORMATION: Synthetic Construct

<400> SEQUENCE: 117
caccatggta tcctgttctg cg 22

<210> SEQ ID NO 118
<211> LENGTH: 22
<212> TYPE: DNA
<213> ORGANISM: Artificial Sequence
<220> FEATURE:
<223> OTHER INFORMATION: Synthetic Construct

<400> SEQUENCE: 118
ttaatctact ttcagacctt gc 22

<210> SEQ ID NO 119
<211> LENGTH: 66
<212> TYPE: DNA
<213> ORGANISM: Artificial Sequence
<220> FEATURE:
<223> OTHER INFORMATION: Synthetic Construct

<400> SEQUENCE: 119
gcgaacgatg cataaaggag gtaaaaaaac atggtatcct gttctgcgcc gggtaagatt 60
tacctg 66

<210> SEQ ID NO 120
<211> LENGTH: 57
<212> TYPE: DNA
<213> ORGANISM: Artificial Sequence
<220> FEATURE:
<223> OTHER INFORMATION: Synthetic Construct

<400> SEQUENCE: 120
gcgaacgatg cataaaggag gtaaaaaaac atgtcattac cgttcttaac ttctgca 57

<210> SEQ ID NO 121
<211> LENGTH: 58
<212> TYPE: DNA

<213> ORGANISM: Artificial Sequence
<220> FEATURE:
<223> OTHER INFORMATION: Synthetic Construct

<400> SEQUENCE: 121
gggcccgttt aaactttaac tagactctgc agttatgaag tccatggtaa attcgtgt 58

<210> SEQ ID NO 122
<211> LENGTH: 48
<212> TYPE: DNA
<213> ORGANISM: Artificial Sequence
<220> FEATURE:
<223> OTHER INFORMATION: Synthetic Construct

<400> SEQUENCE: 122
gggcccgttt aaactttaac tagactttaa tctactttca gaccttgc 48

<210> SEQ ID NO 123
<211> LENGTH: 48
<212> TYPE: DNA
<213> ORGANISM: Artificial Sequence
<220> FEATURE:
<223> OTHER INFORMATION: Synthetic Construct

<400> SEQUENCE: 123
tcatccggct cgtataatgt gtggtcacac aggaaacagc gccgctga 48

<210> SEQ ID NO 124
<211> LENGTH: 48
<212> TYPE: DNA
<213> ORGANISM: Artificial Sequence
<220> FEATURE:
<223> OTHER INFORMATION: Synthetic Construct

<400> SEQUENCE: 124
tcagcggcgc tgtttcctgt gtgaccacac attatacgag ccggatga 48

<210> SEQ ID NO 125
<211> LENGTH: 8684
<212> TYPE: DNA
<213> ORGANISM: Artificial Sequence
<220> FEATURE:
<223> OTHER INFORMATION: Synthetic Construct

<400> SEQUENCE: 125
ttcacacagg aaacagcgcc gctgagaaaa agcgaagcgg cactgctctt taacaattta 60
tcagacaatc tgtgtgggca ctcgaccgga attatcgatt aactttatta ttaaaaatta 120
aagaggtata tattaatgta tcgattaaat aaggaggaat aaaccatgga tccgagctca 180
ggaggtaaaa aaacatgaaa acagtagtta ttattgatgc attacgaaca ccaattggaa 240
aatataaagg cagcttaagt caagtaagtg ccgtagactt aggaacacat gttacaacac 300
aacttttaaa aagacattcc actatttctg aagaaattga tcaagtaatc tttggaaatg 360
ttttacaagc tggaaatggc caaaatcccg cacgacaaat agcaataaac agcggtttgt 420
ctcatgaaat tcccgcaatg acggttaatg aggtctgcgg atcaggaatg aaggccgtta 480
ttttggcgaa acaattgatt caattaggag aagcggaagt tttaattgct ggcgggattg 540
agaatatgtc ccaagcacct aaattacaac gttttaatta cgaaacagaa agctacgatg 600 cgccttttc tagtatgatg tatgatggat taacggatgc ctttagtggt caggcaatgg 660
gcttaactgc tgaaaatgtg gccgaaaagt atcatgtaac tagagaagag caagatcaat 720
tttctgtaca ttcacaatta aaagcagctc aagcacaagc agaagggata ttcgctgacg 780

-continued

```
aaatagcccc attagaagta tcaggaacgc ttgtggagaa agatgaaggg attcgcccta    840
attcgagcgt tgagaagcta ggaacgctta aaacagtttt taaagaagac ggtactgtaa    900
cagcagggaa tgcatcaacc attaatgatg ggcttctgc tttgattatt gcttcacaag    960
aatatgccga agcacacggt cttccttatt tagctattat tcgagacagt gtggaagtcg   1020
gtattgatcc agcctatatg ggaatttcgc cgattaaagc cattcaaaaa ctgttagcgc   1080
gcaatcaact tactacggaa gaaattgatc tgtatgaaat caacgaagca tttgcagcaa   1140
cttcaatcgt ggtccaaaga gaactggctt taccagagga aaaggtcaac atttatggtg   1200
gcggtatttc attaggtcat gcgattggtg ccacaggtgc tcgtttatta acgagtttaa   1260
gttatcaatt aaatcaaaaa gaaaagaaat atggagtggc ttctttatgt atcggcggtg   1320
gcttaggact cgctatgcta ctagagagac ctcagcaaaa aaaaaacagc cgattttatc   1380
aaatgagtcc tgaggaacgc ctggcttctc ttcttaatga aggccagatt tctgctgata   1440
caaaaaaaga atttgaaaat acggctttat cttcgcagat tgccaatcat atgattgaaa   1500
atcaaatcag tgaaacagaa gtgccgatgg gcgttggctt acatttaaca gtggacgaaa   1560
ctgattattt ggtaccaatg gcgacagaag agccctcagt tattgcggct ttgagtaatg   1620
gtgcaaaaat agcacaagga tttaaaacag tgaatcaaca acgcttaatg cgtggacaaa   1680
tcgtttttta cgatgttgca gatcccgagt cattgattga taaactacaa gtaagagaag   1740
cggaagtttt tcaacaagca gagttaagtt atccatctat cgttaaacgg ggcggcggct   1800
taagagattt gcaatatcgt acttttgatg aatcatttgt atctgtcgac tttttagtag   1860
atgttaagga tgcaatgggg gcaaatatcg ttaacgctat gttggaaggt gtggccgagt   1920
tgttccgtga atggtttgcg gagcaaaaga ttttattcag tattttaagt aattatgcca   1980
cggagtcggt tgttacgatg aaaacggcta ttccagtttc acgtttaagt aaggggagca   2040
atggccggga aattgctgaa aaaattgttt tagcttcacg ctatgcttca ttagatcctt   2100
atcgggcagt cacgcataac aaaggaatca tgaatggcat tgaagctgta gttttagcta   2160
caggaaatga tacacgcgct gttagcgctt cttgtcatgc ttttgcggtg aaggaaggtc   2220
gctaccaagg cttgactagt tggacgctgg atggcgaaca actaattggt gaaatttcag   2280
ttccgcttgc tttagccacg gttggcggtg ccacaaaagt cttacctaaa tctcaagcag   2340
ctgctgattt gttagcagtg acggatgcaa aagaactaag tcgagtagta gcggctgttg   2400
gtttggcaca aaatttagcg gcgttacggg ccttagtctc tgaaggaatt caaaaaggac   2460
acatggctct acaagcacgt tctttagcga tgacggtcgg agctactggt aaagaagttg   2520
aggcagtcgc tcaacaatta aaacgtcaaa aaacgatgaa ccaagaccga gccatggcta   2580
ttttaaatga tttaagaaaa caataaagga ggtaaaaaaa catgacaatt gggattgata   2640
aaattagttt ttttgtgccc ccttattata ttgatatgac ggcactggct gaagccagaa   2700
atgtagaccc tggaaaattt catattggta ttgggcaaga ccaaatggcg gtgaacccaa   2760
tcagccaaga tattgtgaca tttgcagcca atgccgcaga agcgatcttg accaaagaag   2820
ataaagaggc cattgatatg gtgattgtcg ggactgagtc cagtatcgat gagtcaaaag   2880
cggccgcagt tgtcttacat cgtttaatgg ggattcaacc tttcgctcgc tctttcgaaa   2940
tcaaggaagc ttgttacgga gcaacagcag gcttacagtt agctaagaat cacgtagcct   3000
tacatccaga taaaaaagtc ttggtcgtag cggcagatat tgcaaaatat ggcttaaatt   3060
ctggcggtga gcctacacaa ggagctgggg cggttgcaat gttagttgct agtgaaccgc   3120
```

gcattttggc tttaaaagag gataatgtga tgctgacgca agatatctat gacttttggc 3180
gtccaacagg ccacccgtat cctatggtcg atggtccttt gtcaaacgaa acctacatcc 3240
aatcttttgc ccaagtctgg gatgaacata aaaaacgaac cggtcttgat tttgcagatt 3300
atgatgcttt agcgttccat attccttaca caaaaatggg caaaaaagcc ttattagcaa 3360
aaatctccga ccaaactgaa gcagaacagg aacgaatttt agcccgttat gaagaaagta 3420
tcgtctatag tcgtcgcgta ggaaacttgt atacgggttc actttatctg ggactcattt 3480
ccctttttaga aaatgcaacg actttaaccg caggcaatca aattggttta ttcagttatg 3540
gttctggtgc tgtcgctgaa tttttcactg gtgaattagt agctggttat caaaatcatt 3600
tacaaaaaga aactcattta gcactgctgg ataatcggac agaactttct atcgctgaat 3660
atgaagccat gtttgcagaa actttagaca cagacattga tcaaacgtta gaagatgaat 3720
taaaatatag tatttctgct attaataata ccgttcgttc ttatcgaaac taagagatct 3780
gcagctggta ccatatggga attcgaagct tgggcccgaa caaaaactca tctcagaaga 3840
ggatctgaat agcgccgtcg accatcatca tcatcatcat tgagtttaaa cggtctccag 3900
cttggctgtt ttggcggatg agagaagatt ttcagcctga tacagattaa atcagaacgc 3960
agaagcggtc tgataaaaca gaatttgcct ggcggcagta gcgcggtggt cccacctgac 4020
cccatgccga actcagaagt gaaacgccgt agcgccgatg gtagtgtggg gtctccccat 4080
gcgagagtag ggaactgcca ggcatcaaat aaaacgaaag gctcagtcga aagactgggc 4140
ctttcgtttt atctgttgtt tgtcggtgaa cgctctcctg agtaggacaa atccgccggg 4200
agcggatttg aacgttgcga agcaacggcc cggagggtgg cgggcaggac gcccgccata 4260
aactgccagg catcaaatta agcagaaggc catcctgacg gatggccttt ttgcgtttct 4320
acaaactctt tttgtttatt tttctaaata cattcaaata tgtatccgct catgagacaa 4380
taaccctgat aaatgcttca ataatctggc gtaatagcga agaggcccgc accgatcgcc 4440
cttcccaaca gttgcgcagc ctgaatggcg aatggcgcct gatgcggtat tttctcctta 4500
cgcatctgtg cggtatttca caccgcatat ggtgcactct cagtacaatc tgctctgatg 4560
ccgcatagtt aagccagccc cgacacccgc caacacccgc tgacgagctt agtaaagccc 4620
tcgctagatt ttaatgcgga tgttgcgatt acttcgccaa ctattgcgat aacaagaaaa 4680
agccagcctt tcatgatata tctcccaatt tgtgtagggc ttattatgca cgcttaaaaa 4740
taataaaagc agacttgacc tgatagtttg gctgtgagca attatgtgct tagtgcatct 4800
aacgcttgag ttaagccgcg ccgcgaagcg gcgtcggctt gaacgaattg ttagacatta 4860
tttgccgact accttggtga tctcgccttt cacgtagtgg acaaattctt ccaactgatc 4920
tgcgcgcgag gccaagcgat cttcttcttg tccaagataa gcctgtctag cttcaagtat 4980
gacgggctga tactgggccg gcaggcgctc cattgcccag tcggcagcga catccttcgg 5040
cgcgattttg ccggttactg cgctgtacca aatgcgggac aacgtaagca ctacatttcg 5100
ctcatcgcca gcccagtcgg gcggcgagtt ccatagcgtt aaggtttcat ttagcgcctc 5160
aaatagatcc tgttcaggaa ccggatcaaa gagttcctcc gccgctggac ctaccaaggc 5220
aacgctatgt tctcttgctt ttgtcagcaa gatagccaga tcaatgtcga tcgtggctgg 5280
ctcgaagata cctgcaagaa tgtcattgcg ctgccattct ccaaattgca gttcgcgctt 5340
agctggataa cgccacggaa tgatgtcgtc gtgcacaaca atggtgactt ctacagcgcg 5400
gagaatctcg ctctctccag ggaagccgaa agtttccaaa aggtcgttga tcaaagctcg 5460
ccgcgttgtt tcatcaagcc ttacggtcac cgtaaccagc aaatcaatat cactgtgtgg 5520

-continued cttcaggccg ccatccactg cggagccgta caaatgtacg gccagcaacg tcggttcgag 5580
atggcgctcg atgacgccaa ctacctctga tagttgagtc gatacttcgg cgatcaccgc 5640
ttccctcatg atgtttaact ttgttttagg gcgactgccc tgctgcgtaa catcgttgct 5700
gctccataac atcaaacatc gacccacggc gtaacgcgct tgctgcttgg atgcccgagg 5760
catagactgt accccaaaaa aacagtcata acaagccatg aaaaccgcca ctgcgccgtt 5820
accaccgctg cgttcggtca aggttctgga ccagttgcgt gagcgcatac gctacttgca 5880
ttacagctta cgaaccgaac aggcttatgt ccactgggtt cgtgccttca tccgtttcca 5940
cggtgtgcgt cacccggcaa ccttgggcag cagcgaagtc gaggcatttc tgtcctggct 6000
ggcgaacgag cgcaaggttt cggtctccac gcatcgtcag gcattggcgg ccttgctgtt 6060
cttctacggc aaggtgctgt gcacggatct gccctggctt caggagatcg gaagacctcg 6120
gccgtcgcgg cgcttgccgg tggtgctgac cccggatgaa gtggttcgca tcctcggttt 6180
tctggaaggc gagcatcgtt tgttcgccca gcttctgtat ggaacgggca tgcggatcag 6240
tgagggtttg caactgcggg tcaaggatct ggatttcgat cacggcacga tcatcgtgcg 6300
ggagggcaag ggctccaagg atcgggcctt gatgttaccc gagagcttgg cacccagcct 6360
gcgcgagcag gggaattaat tcccacgggt tttgctgccc gcaaacgggc tgttctggtg 6420
ttgctagttt gttatcagaa tcgcagatcc ggcttcagcc ggtttgccgg ctgaaagcgc 6480
tatttcttcc agaattgcca tgatttttc cccacgggag gcgtcactgg ctcccgtgtt 6540
gtcggcagct ttgattcgat aagcagcatc gcctgtttca ggctgtctat gtgtgactgt 6600
tgagctgtaa caagttgtct caggtgttca atttcatgtt ctagttgctt tgttttactg 6660
gtttcacctg ttctattagg tgttacatgc tgttcatctg ttacattgtc gatctgttca 6720
tggtgaacag ctttgaatgc accaaaaact cgtaaaagct ctgatgtatc tatcttttt 6780 acaccgtttt catctgtgca tatggacagt tttccctttg atatgtaacg gtgaacagtt 6840
gttctacttt tgtttgttag tcttgatgct tcactgatag atacaagagc cataagaacc 6900
tcagatcctt ccgtatttag ccagtatgtt ctctagtgtg gttcgttgtt tttgcgtgag 6960
ccatgagaac gaaccattga gatcatactt actttgcatg tcactcaaaa attttgcctc 7020
aaaactggtg agctgaattt ttgcagttaa agcatcgtgt agtgtttttc ttagtccgtt 7080
atgtaggtag gaatctgatg taatggttgt tggtattttg tcaccattca tttttatctg 7140
gttgttctca agttcggtta cgagatccat ttgtctatct agttcaactt ggaaaatcaa 7200
cgtatcagtc gggcggcctc gcttatcaac caccaatttc atattgctgt aagtgtttaa 7260
atctttactt attggtttca aaacccattg gttaagcctt ttaaactcat ggtagttatt 7320
ttcaagcatt aacatgaact taaattcatc aaggctaatc tctatatttg ccttgtgagt 7380
tttcttttgt gttagttctt ttaataacca ctcataaatc ctcatagagt atttgttttc 7440
aaaagactta acatgttcca gattatattt tatgaatttt tttaactgga aaagataagg 7500
caatatctct tcactaaaaa ctaattctaa tttttcgctt gagaacttgg catagtttgt 7560
ccactggaaa atctcaaagc ctttaaccaa aggattcctg atttccacag ttctcgtcat 7620
cagctctctg gttgctttag ctaatacacc ataagcattt tccctactga tgttcatcat 7680
ctgagcgtat tggttataag tgaacgatac cgtccgttct ttccttgtag ggttttcaat 7740
cgtggggttg agtagtgcca cacagcataa aattagcttg gtttcatgct ccgttaagtc 7800
atagcgacta atcgctagtt catttgcttt gaaaacaact aattcagaca tacatctcaa 7860
ttggtctagg tgattttaat cactatacca attgagatgg gctagtcaat gataattact 7920
agtccttttc ctttgagttg tgggtatctg taaattctgc tagacctttg ctggaaaact 7980
tgtaaattct gctagaccct ctgtaaattc cgctagacct ttgtgtgttt tttttgttta 8040
tattcaagtg gttataattt atagaataaa gaaagaataa aaaaagataa aaagaataga 8100
tcccagccct gtgtataact cactacttta gtcagttccg cagtattaca aaaggatgtc 8160
gcaaacgctg tttgctcctc tacaaaacag accttaaaac cctaaaggct taagtagcac 8220
cctcgcaagc tcgggcaaat cgctgaatat tccttttgtc tccgaccatc aggcacctga 8280
gtcgctgtct ttttcgtgac attcagttcg ctgcgctcac ggctctggca gtgaatgggg 8340
gtaaatggca ctacaggcgc cttttatgga ttcatgcaag gaaactaccc ataatacaag 8400
aaaagcccgt cacgggcttc tcagggcgtt ttatggcggg tctgctatgt ggtgctatct 8460
gactttttgc tgttcagcag ttcctgccct ctgattttcc agtctgacca cttcggatta 8520
tcccgtgaca ggtcattcag actggctaat gcacccagta aggcagcggt atcatcaaca 8580
ggcttacccg tcttactgtc gggaattcgc gttggccgat tcattaatgc agattctgaa 8640
atgagctgtt gacaattaat catccggctc gtataatgtg tgga 8684

<210> SEQ ID NO 126
<211> LENGTH: 21
<212> TYPE: DNA
<213> ORGANISM: Artificial Sequence
<220> FEATURE:
<223> OTHER INFORMATION: Synthetic Construct

<400> SEQUENCE: 126
cttctcaggg cgttttatgg c 21

<210> SEQ ID NO 127
<211> LENGTH: 20
<212> TYPE: DNA
<213> ORGANISM: Artificial Sequence
<220> FEATURE:
<223> OTHER INFORMATION: Synthetic Construct

<400> SEQUENCE: 127
gttgagctaa caacggatcc 20

<210> SEQ ID NO 128
<211> LENGTH: 23
<212> TYPE: DNA
<213> ORGANISM: Artificial Sequence
<220> FEATURE:
<223> OTHER INFORMATION: Synthetic Construct

<400> SEQUENCE: 128
gactgtcaac ccaaacgtca atg 23

<210> SEQ ID NO 129
<211> LENGTH: 10022
<212> TYPE: DNA
<213> ORGANISM: Artificial Sequence
<220> FEATURE:
<223> OTHER INFORMATION: Synthetic Construct

<400> SEQUENCE: 129
cccgtcttac tgtcgggaat tcgcgttggc cgattcatta atgcagattc tgaaatgagc 60
tgttgacaat taatcatccg gctcgtataa tgtgtggtca cacaggaaac agcgccgctg 120
agaaaaagcg aagcggcact gctctttaac aatttatcag acaatctgtg tgggcactcg 180

-continued

```
accggaatta tcgattaact ttattattaa aaattaaaga ggtatatatt aatgtatcga   240
ttaaataagg aggaataaac catggatccg agctcggatc cactagtaac ggccgccagt   300
gtgctggaat tcgcccttag gaggtaaaaa aacatgtcat taccgttctt aacttctgca   360
ccgggaaagg ttattatttt tggtgaacac tctgctgtgt acaacaagcc tgccgtcgct   420
gctagtgtgt ctgcgttgag aacctacctg ctaataagcg agtcatctgc accagatact   480
attgaattgg acttcccgga cattagcttt aatcataagt ggtccatcaa tgatttcaat   540
gccatcaccg aggatcaagt aaactcccaa aaattggcca aggctcaaca agccaccgat   600
ggcttgtctc aggaactcgt tagtcttttg gatccgttgt tagctcaact atccgaatcc   660
ttccactacc atgcagcgtt ttgtttcctg tatatgtttg tttgcctatg cccccatgcc   720
aagaatatta agttttcttt aaagtctact ttacccatcg gtgctgggtt gggctcaagc   780
gcctctattt ctgtatcact ggccttagct atggcctact tggggggggtt aataggatct   840
aatgacttgg aaaagctgtc agaaaacgat aagcatatag tgaatcaatg ggccttcata   900
ggtgaaaagt gtattcacgg taccccttca ggaatagata acgctgtggc cacttatggt   960
aatgccctgc tatttgaaaa agactcacat aatggaacaa taaacacaaa caattttaag  1020
ttcttagatg atttcccagc cattccaatg atcctaacct atactagaat tccaaggtct  1080
acaaaagatc ttgttgctcg cgttcgtgtg ttggtcaccg agaaatttcc tgaagttatg  1140
aagccaattc tagatgccat gggtgaatgt gccctacaag gcttagagat catgactaag  1200
ttaagtaaat gtaaaggcac cgatgacgag gctgtagaaa ctaataatga actgtatgaa  1260
caactattgg aattgataag aataaatcat ggactgcttg tctcaatcgg tgtttctcat  1320
cctggattag aacttattaa aaatctgagc gatgatttga gaattggctc cacaaaactt  1380
accggtgctg gtggcggcgg ttgctctttg actttgttac gaagagacat tactcaagag  1440
caaattgaca gcttcaaaaa gaaattgcaa gatgatttta gttacgagac atttgaaaca  1500
gacttgggtg ggactggctg ctgtttgtta agcgcaaaaa atttgaataa agatcttaaa  1560
atcaaatccc tagtattcca attatttgaa aataaaacta ccacaaagca acaaattgac  1620
gatctattat tgccaggaaa cacgaattta ccatggactt cataagctaa tttgcgatag  1680
gcctgcaccc ttaaggagga aaaaaacatg tcagagttga gagccttcag tgccccaggg  1740
aaagcgttac tagctggtgg atatttagtt ttagatacaa aatatgaagc atttgtagtc  1800
ggattatcgg caagaatgca tgctgtagcc catccttacg gttcattgca agggtctgat  1860
aagtttgaag tgcgtgtgaa aagtaaacaa tttaaagatg gggagtggct gtaccatata  1920
agtcctaaaa gtggcttcat tcctgtttcg ataggcggat ctaagaaccc tttcattgaa  1980
aaagttatcg ctaacgtatt tagctacttt aaacctaaca tggacgacta ctgcaataga  2040
aacttgttcg ttattgatat tttctctgat gatgcctacc attctcagga ggatagcgtt  2100
accgaacatc gtggcaacag aagattgagt tttcattcgc acagaattga agaagttccc  2160
aaaacagggc tgggctcctc ggcaggttta gtcacagttt taactacagc tttggcctcc  2220
ttttttgtat cggacctgga aaataatgta gacaaatata gagaagttat tcataattta  2280
gcacaagttg ctcattgtca agctcagggt aaaattggaa gcgggtttga tgtagcggcg  2340
gcagcatatg gatctatcag atatagaaga ttcccacccg cattaatctc taatttgcca  2400
gatattggaa gtgctactta cggcagtaaa ctggcgcatt tggttgatga agaagactgg  2460
aatattacga ttaaaagtaa ccatttacct tcgggattaa ctttatggat gggcgatatt  2520
```

-continued

```
aagaatggtt cagaaacagt aaaactggtc cagaaggtaa aaaattggta tgattcgcat   2580
atgccagaaa gcttgaaaat atatacagaa ctcgatcatg caaattctag atttatggat   2640
ggactatcta aactagatcg cttacacgag actcatgacg attacagcga tcagatattt   2700
gagtctcttg agaggaatga ctgtacctgt caaaagtatc ctgaaatcac agaagttaga   2760
gatgcagttg ccacaattag acgttccttt agaaaaataa ctaaagaatc tggtgccgat   2820
atcgaacctc ccgtacaaac tagcttattg gatgattgcc agaccttaaa aggagttctt   2880
acttgcttaa tacctggtgc tggtggttat gacgccattg cagtgattac taagcaagat   2940
gttgatctta gggctcaaac cgctaatgac aaaagatttt ctaaggttca atggctggat   3000
gtaactcagg ctgactgggg tgttaggaaa gaaaaagatc cggaaactta tcttgataaa   3060
taacttaagg tagctgcatg cagaattcgc ccttaaggag gaaaaaaaaa tgaccgttta   3120
cacagcatcc gttaccgcac ccgtcaacat cgcaaccctt aagtattggg ggaaaaggga   3180
cacgaagttg aatctgccca ccaattcgtc catatcagtg actttatcgc aagatgacct   3240
cagaacgttg acctctgcgg ctactgcacc tgagtttgaa cgcgacactt tgtggttaaa   3300
tggagaacca cacagcatcg acaatgaaag aactcaaaat tgtctgcgcg acctacgcca   3360
attaagaaag gaaatggaat cgaaggacgc ctcattgccc acattatctc aatggaaact   3420
ccacattgtc tccgaaaata actttcctac agcagctggt ttagcttcct ccgctgctgg   3480
ctttgctgca ttggtctctg caattgctaa gttataccaa ttaccacagt caacttcaga   3540
aatatctaga atagcaagaa aggggtctgg ttcagcttgt agatcgttgt ttggcggata   3600
cgtggcctgg gaaatgggaa aagctgaaga tggtcatgat tccatggcag tacaaatcgc   3660
agacagctct gactggcctc agatgaaagc ttgtgtccta gttgtcagcg atattaaaaa   3720
ggatgtgagt tccactcagg gtatgcaatt gaccgtggca acctccgaac tatttaaaga   3780
aagaattgaa catgtcgtac caaagagatt tgaagtcatg cgtaaagcca ttgttgaaaa   3840
agatttcgcc acctttgcaa aggaaacaat gatggattcc aactctttcc atgccacatg   3900
tttggactct ttccctccaa tattctacat gaatgacact tccaagcgta tcatcagttg   3960
gtgccacacc attaatcagt tttacggaga aacaatcgtt gcatacacgt ttgatgcagg   4020
tccaaatgct gtgttgtact acttagctga aaatgagtcg aaactctttg catttatcta   4080
taaattgttt ggctctgttc ctggatggga caagaaattt actactgagc agcttgaggc   4140
tttcaaccat caatttgaat catctaactt tactgcacgt gaattggatc ttgagttgca   4200
aaaggatgtt gccagagtga ttttaactca agtcggttca ggcccacaag aaacaaacga   4260
atctttgatt gacgcaaaga ctggtctacc aaaggaataa gatcaattcg ctgcatcgcc   4320
cttaggaggt aaaaaaaaat gactgccgac aacaatagta tgccccatgg tgcagtatct   4380
agttacgcca aattagtgca aaaccaaaca cctgaagaca ttttggaaga gtttcctgaa   4440
attattccat tacaacaaag acctaatacc cgatctagtg agacgtcaaa tgacgaaagc   4500
ggagaaacat gtttttctgg tcatgatgag gagcaaatta agttaatgaa tgaaaattgt   4560
attgttttgg attgggacga taatgctatt ggtgccggta ccaagaaagt ttgtcattta   4620
atggaaaata ttgaaaaggg tttactacat cgtgcattct ccgtctttat tttcaatgaa   4680
caaggtgaat tacttttaca acaaagagcc actgaaaaaa taactttccc tgatctttgg   4740
actaacacat gctgctctca tccactatgt attgatgacg aattaggttt gaagggtaag   4800
ctagacgata agattaaggg cgctattact gcggcggtga gaaaactaga tcatgaatta   4860
ggtattccag aagatgaaac taagacaagg ggtaagtttc actttttaaa cagaatccat   4920
```

-continued

```
tacatggcac caagcaatga accatggggt gaacatgaaa ttgattacat cctattttat   4980
aagatcaacg ctaaagaaaa cttgactgtc aacccaaacg tcaatgaagt tagagacttc   5040
aaatgggttt caccaaatga tttgaaaact atgtttgctg acccaagtta caagtttacg   5100
ccttggttta agattatttg cgagaattac ttattcaact ggtgggagca attagatgac   5160
ctttctgaag tggaaaatga caggcaaatt catagaatgc tataacaacg cgtcctgcag   5220
ctggtaccat atgggaattc gaagcttggg cccgaacaaa aactcatctc agaagaggat   5280
ctgaatagcg ccgtcgacca tcatcatcat catcattgag tttaaacggt ctccagcttg   5340
gctgttttgg cggatgagag aagattttca gcctgataca gattaaatca gaacgcagaa   5400
gcggtctgat aaaacagaat ttgcctggcg gcagtagcgc ggtggtccca cctgacccca   5460
tgccgaactc agaagtgaaa cgccgtagcg ccgatggtag tgtggggtct ccccatgcga   5520
gagtagggaa ctgccaggca tcaaataaaa cgaaaggctc agtcgaaaga ctgggccttt   5580
cgttttatct gttgtttgtc ggtgaacgct ctcctgagta ggacaaatcc gccgggagcg   5640
gatttgaacg ttgcgaagca acggcccgga gggtggcggg caggacgccc gccataaact   5700
gccaggcatc aaattaagca gaaggccatc ctgacggatg gcctttttgc gtttctacaa   5760
actctttttg tttatttttc taaatacatt caaatatgta tccgctcatg agacaataac   5820
cctgataaat gcttcaataa tctggcgtaa tagcgaagag gcccgcaccg atcgcccttc   5880
ccaacagttg cgcagcctga atggcgaatg gcgcctgatg cggtattttc tccttacgca   5940
tctgtgcggt atttcacacc gcatatggtg cactctcagt acaatctgct ctgatgccgc   6000
atagttaagc cagccccgac acccgccaac acccgctgac gagcttagta aagccctcgc   6060
tagattttaa tgcggatgtt gcgattactt cgccaactat tgcgataaca agaaaaagcc   6120
agcctttcat gatatatctc ccaatttgtg tagggcttat tatgcacgct taaaaataat   6180
aaaagcagac ttgacctgat agtttggctg tgagcaatta tgtgcttagt gcatctaacg   6240
cttgagttaa gccgcgccgc gaagcggcgt cggcttgaac gaattgttag acattatttg   6300
ccgactacct tggtgatctc gcctttcacg tagtggacaa attcttccaa ctgatctgcg   6360
cgcgaggcca agcgatcttc ttcttgtcca agataagcct gtctagcttc aagtatgacg   6420
ggctgatact gggccggcag gcgctccatt gcccagtcgg cagcgacatc cttcggcgcg   6480
attttgccgg ttactgcgct gtaccaaatg cgggacaacg taagcactac atttcgctca   6540
tcgccagccc agtcgggcgg cgagttccat agcgttaagg tttcatttag cgcctcaaat   6600
agatcctgtt caggaaccgg atcaaagagt tcctccgccg ctggacctac caaggcaacg   6660
ctatgttctc ttgcttttgt cagcaagata gccagatcaa tgtcgatcgt ggctggctcg   6720
aagatacctg caagaatgtc attgcgctgc cattctccaa attgcagttc gcgcttagct   6780
ggataacgcc acggaatgat gtcgtcgtgc acaacaatgg tgacttctac agcgcggaga   6840
atctcgctct ctccagggga agccgaagtt tccaaaaggt cgttgatcaa agctcgccgc   6900
gttgtttcat caagccttac ggtcaccgta accagcaaat caatatcact gtgtggcttc   6960
aggccgccat ccactgcgga gccgtacaaa tgtacggcca gcaacgtcgg ttcgagatgg   7020
cgctcgatga cgccaactac ctctgatagt tgagtcgata cttcggcgat caccgcttcc   7080
ctcatgatgt ttaactttgt tttagggcga ctgccctgct gcgtaacatc gttgctgctc   7140
cataacatca aacatcgacc cacggcgtaa cgcgcttgct gcttggatgc ccgaggcata   7200
gactgtaccc caaaaaaaca gtcataacaa gccatgaaaa ccgccactgc gccgttacca   7260
```

-continued

```
ccgctgcgtt cggtcaaggt tctggaccag ttgcgtgagc gcatacgcta cttgcattac   7320
agcttacgaa ccgaacaggc ttatgtccac tgggttcgtg ccttcatccg tttccacggt   7380
gtgcgtcacc cggcaacctt gggcagcagc gaagtcgagg catttctgtc ctggctggcg   7440
aacgagcgca aggtttcggt ctccacgcat cgtcaggcat tggcggcctt gctgttcttc   7500
tacggcaagg tgctgtgcac ggatctgccc tggcttcagg agatcggaag acctcggccg   7560
tcgcggcgct tgccggtggt gctgaccccg gatgaagtgg ttcgcatcct cggttttctg   7620
gaaggcgagc atcgtttgtt cgcccagctt ctgtatggaa cgggcatgcg gatcagtgag   7680
ggtttgcaac tgcgggtcaa ggatctggat ttcgatcacg gcacgatcat cgtgcgggag   7740
ggcaagggct ccaaggatcg ggccttgatg ttacccgaga gcttggcacc cagcctgcgc   7800
gagcagggga attaattccc acgggttttg ctgcccgcaa acgggctgtt ctggtgttgc   7860
tagtttgtta tcagaatcgc agatccggct tcagccggtt tgccggctga aagcgctatt   7920
tcttccagaa ttgccatgat tttttcccca cgggaggcgt cactggctcc cgtgttgtcg   7980
gcagctttga ttcgataagc agcatcgcct gtttcaggct gtctatgtgt gactgttgag   8040
ctgtaacaag ttgtctcagg tgttcaattt catgttctag ttgctttgtt ttactggttt   8100
cacctgttct attaggtgtt acatgctgtt catctgttac attgtcgatc tgttcatggt   8160
gaacagcttt gaatgcacca aaaactcgta aaagctctga tgtatctatc ttttttacac   8220
cgttttcatc tgtgcatatg gacagttttc cctttgatat gtaacggtga acagttgttc   8280
tacttttgtt tgttagtctt gatgcttcac tgatagatac aagagccata agaacctcag   8340
atccttccgt atttagccag tatgttctct agtgtggttc gttgtttttg cgtgagccat   8400
gagaacgaac cattgagatc atacttactt tgcatgtcac tcaaaaattt tgcctcaaaa   8460
ctggtgagct gaatttttgc agttaaagca tcgtgtagtg tttttcttag tccgttatgt   8520
aggtaggaat ctgatgtaat ggttgttggt attttgtcac cattcatttt tatctggttg   8580
ttctcaagtt cggttacgag atccatttgt ctatctagtt caacttggaa aatcaacgta   8640
tcagtcgggc ggcctcgctt atcaaccacc aatttcatat tgctgtaagt gtttaaatct   8700
ttacttattg gtttcaaaac ccattggtta agccttttaa actcatggta gttattttca   8760
agcattaaca tgaacttaaa ttcatcaagg ctaatctcta tatttgcctt gtgagttttc   8820
ttttgtgtta gttcttttaa taaccactca taaatcctca tagagtattt gttttcaaaa   8880
gacttaacat gttccagatt atattttatg aattttttta actggaaaag ataaggcaat   8940
atctcttcac taaaaactaa ttctaatttt tcgcttgaga acttggcata gtttgtccac   9000
tggaaaatct caaagccttt aaccaaagga ttcctgattt ccacagttct cgtcatcagc   9060
tctctggttg ctttagctaa tacaccataa gcattttccc tactgatgtt catcatctga   9120
gcgtattggt tataagtgaa cgataccgtc cgttctttcc ttgtagggtt ttcaatcgtg   9180
gggttgagta gtgccacaca gcataaaatt agcttggttt catgctccgt taagtcatag   9240
cgactaatcg ctagttcatt tgctttgaaa acaactaatt cagacataca tctcaattgg   9300
tctaggtgat tttaatcact ataccaattg agatgggcta gtcaatgata attactagtc   9360
cttttccttt gagttgtggg tatctgtaaa ttctgctaga cctttgctgg aaaacttgta   9420
aattctgcta gaccctctgt aaattccgct agacctttgt gtgttttttt tgtttatatt   9480
caagtggtta taatttatag aataaagaaa gaataaaaaa agataaaaag aatagatccc   9540
agccctgtgt ataactcact actttagtca gttccgcagt attacaaaag gatgtcgcaa   9600
acgctgtttg ctcctctaca aaacagacct taaaacccta aaggcttaag tagcaccctc   9660
```

gcaagctcgg gcaaatcgct gaatattcct tttgtctccg accatcaggc acctgagtcg 9720
ctgtcttttt cgtgacattc agttcgctgc gctcacggct ctggcagtga atgggggtaa 9780
atggcactac aggcgccttt tatggattca tgcaaggaaa ctacccataa tacaagaaaa 9840
gcccgtcacg ggcttctcag ggcgttttat ggcgggtctg ctatgtggtg ctatctgact 9900
ttttgctgtt cagcagttcc tgccctctga ttttccagtc tgaccacttc ggattatccc 9960
gtgacaggtc attcagactg gctaatgcac ccagtaaggc agcggtatca tcaacaggct 10020
ta 10022

<210> SEQ ID NO 130
<211> LENGTH: 72
<212> TYPE: DNA
<213> ORGANISM: Artificial Sequence
<220> FEATURE:
<223> OTHER INFORMATION: Synthetic Construct

<400> SEQUENCE: 130
ggctggcggc gttttgcttt ttattctgtc tcaactctgg atgtttcatg aattaaccct 60
cactaaaggg cg 72

<210> SEQ ID NO 131
<211> LENGTH: 73
<212> TYPE: DNA
<213> ORGANISM: Artificial Sequence
<220> FEATURE:
<223> OTHER INFORMATION: Synthetic Construct

<400> SEQUENCE: 131
aagccctacg ctaacaaata gcgcgactct ctgtagccgg attatcctca taatacgact 60
cactataggg ctc 73

<210> SEQ ID NO 132
<211> LENGTH: 26
<212> TYPE: DNA
<213> ORGANISM: Artificial Sequence
<220> FEATURE:
<223> OTHER INFORMATION: Synthetic Construct

<400> SEQUENCE: 132
acgccgctca gtagatcctt gcggat 26

<210> SEQ ID NO 133
<211> LENGTH: 27
<212> TYPE: DNA
<213> ORGANISM: Artificial Sequence
<220> FEATURE:
<223> OTHER INFORMATION: Synthetic Construct

<400> SEQUENCE: 133
ctacttacga tcagatggcg cagacta 27

<210> SEQ ID NO 134
<211> LENGTH: 22
<212> TYPE: DNA
<213> ORGANISM: Artificial Sequence
<220> FEATURE:
<223> OTHER INFORMATION: Synthetic Construct

<400> SEQUENCE: 134
cgagactagt gagacgtgct ac 22

-continued

```
<210> SEQ ID NO 135
<211> LENGTH: 24
<212> TYPE: DNA
<213> ORGANISM: Artificial Sequence
<220> FEATURE:
<223> OTHER INFORMATION: Synthetic Construct

<400> SEQUENCE: 135

aaagaccgac caagcgacgt ctga                                   24


<210> SEQ ID NO 136
<211> LENGTH: 45
<212> TYPE: DNA
<213> ORGANISM: Artificial Sequence
<220> FEATURE:
<223> OTHER INFORMATION: Synthetic Construct

<400> SEQUENCE: 136

accgttcgtt cttatcgaaa ctaaaaaaaa ccggccttgg ccccg            45
```